(12) United States Patent
Forsell

(10) Patent No.: US 8,992,409 B2
(45) Date of Patent: *Mar. 31, 2015

(54) METHOD FOR CONTROLLING FLOW IN A BODILY ORGAN

(76) Inventor: Peter Forsell, Bouveret (CH)

( * ) Notice: Subject to any disclaimer, the term of this patent is extended or adjusted under 35 U.S.C. 154(b) by 660 days.

This patent is subject to a terminal disclaimer.

(21) Appl. No.: 12/758,694

(22) Filed: Apr. 12, 2010

(65) Prior Publication Data

US 2011/0066254 A1 Mar. 17, 2011

Related U.S. Application Data

(63) Continuation-in-part of application No. PCT/SE2008/000594, filed on Oct. 13, 2008, and a continuation-in-part of application No. 12/285,794, filed on Oct. 14, 2008, now Pat. No. 8,696,543, and a (Continued)

(30) Foreign Application Priority Data

Oct. 10, 2008 (SE) ........................ 0802137
Oct. 10, 2008 (SE) ........................ 0802162

(51) Int. Cl.
*A61F 2/04* (2013.01)
*A61M 1/10* (2006.01)
(Continued)

(52) U.S. Cl.
CPC ........... *A61M 1/1068* (2013.01); *A61N 1/0507* (2013.01); *A61N 1/0517* (2013.01);
(Continued)

(58) Field of Classification Search
CPC ........... A61F 6/20; A61F 2/02; A61F 5/0079; A61B 17/12022; A61B 17/42; A61B 2017/4233; A61B 2018/00559; A61B 2017/00557; A61B 5/4325; A61B 17/1204; A61B 17/12109; A61B 5/489; A61N 1/3605; A61N 1/0507; A61N 1/0517; A61N 1/0521; A61N 2007/0026
USPC ................ 600/30, 37; 128/897–899; 607/151
See application file for complete search history.

(56) References Cited

U.S. PATENT DOCUMENTS 3,357,432 A 12/1967 Sparks
3,626,931 A 12/1971 Bysakh
(Continued)

FOREIGN PATENT DOCUMENTS

CN 104 74 47 12/1990
CN 227 58 59 3/1998
(Continued)

OTHER PUBLICATIONS

Anand Sneh. "Electrical pacing of the ampullary isthmic junction for contraception." IEEE Engineering in Medicine and Biology Society 10th annual international conference. 1988.*

(Continued)

*Primary Examiner* — Christine Matthews
*Assistant Examiner* — Joshua D Lannu

(57) ABSTRACT

There is provided a method for controlling a flow of fluid and/or other bodily matter in a lumen formed by a tissue wall of a patient's organ. The method comprises gently constricting (i.e., without substantially hampering the blood circulation in the tissue wall) at least one portion of the tissue wall to influence the flow in the lumen, and stimulating the constricted wall portion to cause contraction of the wall portion to further influence the flow in the lumen. The method can be used for restricting or stopping the flow in the lumen, or for actively moving the fluid in the lumen, with a low risk of injuring the organ. Such an organ may be the esophagus, stomach, intestines, urine bladder, urethra, ureter, renal pelvis, aorta, corpus cavernosum, exit veins of erectile tissue, uterine tube, vas deferens or bile duct, or a blood vessel.

33 Claims, 190 Drawing Sheets

Related U.S. Application Data continuation-in-part of application No. 12/285,809, filed on Oct. 14, 2008, application No. 12/758,694, which is a continuation-in-part of application No. PCT/SE2008/000592, filed on Oct. 13, 2008, application No. 12/758,694, which is a continuation-in-part of application No. PCT/SE2008/000590, filed on Oct. 13, 2008, application No. 12/758,694, which is a continuation-in-part of application No. 12/285,791, filed on Oct. 14, 2008, and a continuation-in-part of application No. 12/285,792, filed on Oct. 14, 2008, now Pat. No. 8,795,153, and a continuation-in-part of application No. 12/285,793, filed on Oct. 14, 2008, and a continuation-in-part of application No. 12/285,808, filed on Oct. 14, 2008, and a continuation-in-part of application No. PCT/SE2008/000589, filed on Oct. 13, 2008, application No. 12/758,694, which is a continuation-in-part of application No. PCT/SE2008/000595, filed on Oct. 13, 2008, application No. 12/758,694, which is a continuation-in-part of application No. PCT/SE2008/000579, filed on Oct. 10, 2008, application No. 12/758,694, which is a continuation-in-part of application No. 12/285,810, filed on Oct. 14, 2008, now abandoned, and a continuation-in-part of application No. PCT/SE2008/000570, filed on Oct. 10, 2008, application No. 12/758,694, which is a continuation-in-part of application No. PCT/SE2008/000577, filed on Oct. 10, 2008, application No. 12/758,694, which is a continuation-in-part of application No. PCT/SE2008/000583, filed on Oct. 10, 2008, application No. 12/758,694, which is a continuation-in-part of application No. PCT/SE2009/051127, filed on Oct. 9, 2009, and a continuation-in-part of application No. PCT/SE2008/000572, filed on Oct. 10, 2008, application No. 12/758,694, which is a continuation-in-part of application No. PCT/EP2008/008587, filed on Oct. 10, 2008, application No. 12/758,694, which is a continuation-in-part of application No. PCT/EP2008/008588, filed on Oct. 10, 2008, application No. 12/758,694, which is a continuation-in-part of application No. PCT/EP2008/008589, filed on Oct. 10, 2008, application No. 12/758,694, which is a continuation-in-part of application No. PCT/SE2008/000584, filed on Oct. 10, 2008, application No. 12/758,694, which is a continuation-in-part of application No. PCT/SE2008/000573, filed on Oct. 10, 2008, application No. 12/758,694, which is a continuation-in-part of application No. PCT/EP2008/008586, filed on Oct. 10, 2008, application No. 12/758,694, which is a continuation-in-part of application No. PCT/EP2008/008590, filed on Oct. 10, 2008, application No. 12/758,694, which is a continuation-in-part of application No. PCT/SE2009/051130, filed on Oct. 9, 2009.

(60) Provisional application No. 60/960,716, filed on Oct. 11, 2007, provisional application No. 60/960,715, filed on Oct. 11, 2007, provisional application No. 60/960,918, filed on Oct. 19, 2007, provisional application No. 60/960,916, filed on Oct. 19, 2007, provisional application No. 60/960,764, filed on Oct. 12, 2007, provisional application No. 60/960,765, filed on Oct. 12, 2007, provisional application No. 60/960,767, filed on Oct. 12, 2007, provisional application No. 60/960,766, filed on Oct. 12, 2007, provisional application No. 60/960,791, filed on Oct. 15, 2007, provisional application No. 61/227,810, filed on Jul. 23, 2009.

(51) Int. Cl.
  A61N 1/05   (2006.01)
  A61N 1/36   (2006.01)
  A61N 1/365  (2006.01)
  A61M 1/12   (2006.01)
  A61N 1/40   (2006.01)

(52) U.S. Cl.
  CPC .............. *A61N1/0521* (2013.01); *A61N 1/056* (2013.01); *A61N 1/36007* (2013.01); *A61N 1/3605* (2013.01); *A61N 1/36514* (2013.01); *A61M 1/122* (2013.01); *A61N 1/36564* (2013.01); *A61N 1/36578* (2013.01); *A61N 1/403* (2013.01); *A61N 1/36085* (2013.01); *A61N 1/36107* (2013.01)
  USPC ......... 600/30; 607/2; 607/39; 607/40; 607/41

(56) References Cited

U.S. PATENT DOCUMENTS

| | | |
|---|---|---|
| 3,699,957 A | 10/1972 | Robinson |
| 3,705,575 A | 12/1972 | Edwards |
| 3,750,194 A | 8/1973 | Summers |
| 3,817,237 A | 6/1974 | Bolduc |
| 3,863,622 A | 2/1975 | Buuck |
| 3,875,928 A | 4/1975 | Angelchik |
| 3,926,195 A | 12/1975 | Bleier et al. |
| 4,026,305 A | 5/1977 | Brownlee et al. |
| 4,050,449 A | 9/1977 | Castellana et al. |
| 4,146,029 A | 3/1979 | Ellinwood, Jr. |
| 4,153,059 A | 5/1979 | Fravel et al. |
| 4,190,040 A | 2/1980 | Schulte |
| 4,245,623 A | 1/1981 | Erb |
| 4,246,893 A | 1/1981 | Berson |
| 4,342,308 A | 8/1982 | Trick |
| 4,399,809 A | 8/1983 | Baro et al. |
| 4,408,597 A | 10/1983 | Tenney, Jr. |
| 4,419,985 A | 12/1983 | Trick et al. |
| 4,538,607 A | 9/1985 | Saul |
| 4,559,931 A | 12/1985 | Fischell |
| 4,580,578 A | 4/1986 | Barsom |
| 4,584,994 A | 4/1986 | Bamberger et al. |
| 4,587,954 A | 5/1986 | Haber |
| 4,592,355 A | 6/1986 | Antebi |
| 4,602,625 A | 7/1986 | Yachia et al. |
| 4,634,443 A | 1/1987 | Haber |
| 4,696,288 A | 9/1987 | Kuzmak et al. |
| 4,711,231 A | 12/1987 | Finegold et al. |
| 4,723,538 A | 2/1988 | Stewart et al. |
| 4,728,328 A | 3/1988 | Hughes et al. |
| 4,773,403 A | 9/1988 | Daly |
| 4,780,064 A | 10/1988 | Olsen |
| 4,786,276 A | 11/1988 | Haber |
| 4,822,341 A | 4/1989 | Colone |
| 4,822,348 A * | 4/1989 | Casey ........................ 604/346 |
| 4,828,544 A | 5/1989 | Lane et al. |
| 4,829,990 A | 5/1989 | Thuroff et al. |
| 4,878,889 A | 11/1989 | Polyak |
| 4,958,630 A | 9/1990 | Rosenbluth et al. |
| 4,982,731 A | 1/1991 | Lue et al. |
| 4,983,177 A | 1/1991 | Wolf |
| 5,048,511 A | 9/1991 | Rosenbluth et al. |
| 5,065,751 A | 11/1991 | Wolf |
| 5,074,868 A | 12/1991 | Kuzmak |
| 5,078,676 A | 1/1992 | Bailly |
| 5,123,428 A | 6/1992 | Schwarz |
| 5,160,338 A | 11/1992 | Vincent |
| 5,226,429 A | 7/1993 | Kuzmak |
| 5,261,898 A | 11/1993 | Polin et al. |
| 5,304,206 A | 4/1994 | Baker, Jr. et al. |
| 5,324,263 A | 6/1994 | Kraus et al. |

(56) References Cited

U.S. PATENT DOCUMENTS

| | | |
|---|---|---|
| 5,352,183 A | 10/1994 | Jonsson et al. |
| 5,435,230 A | 7/1995 | Phillips |
| 5,437,605 A | 8/1995 | Helmy |
| 5,449,368 A | 9/1995 | Kuzmak |
| 5,453,079 A | 9/1995 | Schwaninger |
| 5,454,840 A | 10/1995 | Krakovsky et al. |
| 5,509,888 A | 4/1996 | Miller |
| 5,518,504 A | 5/1996 | Polyak |
| 5,531,684 A | 7/1996 | Ensminger et al. |
| 5,562,598 A | 10/1996 | Whalen et al. |
| 5,632,753 A | 5/1997 | Loeser |
| 5,690,691 A | 11/1997 | Chen et al. |
| 5,702,431 A | 12/1997 | Wang et al. |
| 5,704,893 A | 1/1998 | Timm |
| 5,704,915 A | 1/1998 | Melsky et al. |
| 5,769,877 A | 6/1998 | Barreras |
| 5,836,935 A | 11/1998 | Ashton et al. |
| 5,876,425 A | 3/1999 | Gord et al. |
| 5,910,149 A | 6/1999 | Kuzmak |
| 5,938,669 A | 8/1999 | Klaiber et al. |
| 5,954,715 A | 9/1999 | Harrington et al. |
| 5,964,789 A | 10/1999 | Karsdon |
| 5,978,712 A | 11/1999 | Suda et al. |
| 5,995,874 A | 11/1999 | Borza |
| 6,039,748 A | 3/2000 | Savage et al. |
| 6,050,982 A | 4/2000 | Wheeler |
| 6,067,991 A | 5/2000 | Forsell |
| 6,074,341 A | 6/2000 | Anderson et al. |
| 6,102,922 A | 8/2000 | Jakobsson et al. |
| 6,116,193 A | 9/2000 | Goeckner |
| 6,117,067 A | 9/2000 | Gil-Vernet |
| 6,135,945 A | 10/2000 | Sultan |
| 6,145,505 A | 11/2000 | Nikolchev et al. |
| 6,170,484 B1 | 1/2001 | Feng |
| 6,185,452 B1 | 2/2001 | Schulman et al. |
| 6,210,347 B1 | 4/2001 | Forsell |
| 6,266,560 B1 | 7/2001 | Zhang et al. |
| 6,302,910 B1 | 10/2001 | Yamazaki et al. |
| 6,332,466 B1 * | 12/2001 | Yoon ........................ 128/830 |
| 6,400,988 B1 | 6/2002 | Gurewitsch |
| 6,402,767 B1 | 6/2002 | Nash et al. |
| 6,450,173 B1 | 9/2002 | Forsell |
| 6,450,946 B1 | 9/2002 | Forsell |
| 6,453,907 B1 | 9/2002 | Forsell |
| 6,454,698 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,460,543 B1 | 10/2002 | Forsell |
| 6,461,292 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,464,653 B1 | 10/2002 | Hovland et al. |
| 6,470,892 B1 | 10/2002 | Forsell |
| 6,471,635 B1 | 10/2002 | Forsell |
| 6,475,136 B1 | 11/2002 | Forsell |
| 6,482,145 B1 * | 11/2002 | Forsell ........................ 600/30 |
| 6,503,189 B1 | 1/2003 | Forsell |
| 6,571,127 B1 | 5/2003 | Ben-Haim et al. |
| 6,576,010 B2 | 6/2003 | Ulert et al. |
| 6,600,953 B2 | 7/2003 | Flesler et al. |
| 6,650,943 B1 | 11/2003 | Whitehurst et al. |
| 6,659,936 B1 | 12/2003 | Furness et al. |
| 6,709,385 B2 | 3/2004 | Forsell |
| 6,862,479 B1 | 3/2005 | Whitehurst et al. |
| 6,895,280 B2 | 5/2005 | Meadows et al. |
| 6,896,651 B2 | 5/2005 | Gross et al. |
| 6,915,165 B2 | 7/2005 | Forsell |
| 6,953,429 B2 | 10/2005 | Forsell |
| 6,979,351 B2 | 12/2005 | Forsell |
| 6,988,983 B2 | 1/2006 | Connors et al. |
| 7,011,624 B2 | 3/2006 | Forsell |
| 7,017,583 B2 | 3/2006 | Forsell |
| 7,207,936 B2 | 4/2007 | Forsell |
| 7,235,044 B2 | 6/2007 | Forsell |
| 7,338,437 B2 | 3/2008 | Forsell |
| 7,367,938 B2 | 5/2008 | Forsell |
| 7,407,481 B2 | 8/2008 | Forsell |
| 7,442,165 B2 | 10/2008 | Forsell |
| 7,621,863 B2 | 11/2009 | Forsell |
| 7,648,455 B2 | 1/2010 | Forsell |
| 7,666,132 B2 | 2/2010 | Forsell |
| 7,669,601 B2 | 3/2010 | Tal |
| 7,670,280 B2 | 3/2010 | Gloth |
| 7,846,160 B2 | 12/2010 | Payne et al. |
| 7,931,582 B2 | 4/2011 | Forsell |
| 7,972,354 B2 | 7/2011 | Prestezog et al. |
| 7,987,853 B2 | 8/2011 | Swann et al. |
| 7,988,616 B2 | 8/2011 | Forsell |
| 7,991,476 B2 | 8/2011 | Nachum |
| 8,126,558 B2 | 2/2012 | Forsell |
| 8,195,296 B2 | 6/2012 | Longhini et al. |
| 8,287,444 B2 | 10/2012 | Forsell |
| 8,290,594 B2 | 10/2012 | Forsell |
| 8,313,423 B2 | 11/2012 | Forsell |
| 2001/0016738 A1 | 8/2001 | Harrington et al. |
| 2002/0028846 A1 | 3/2002 | Yeager et al. |
| 2002/0032462 A1 | 3/2002 | Houser |
| 2002/0072759 A1 | 6/2002 | Fry |
| 2002/0111577 A1 | 8/2002 | Sirimanne et al. |
| 2002/0120219 A1 | 8/2002 | Hovland et al. |
| 2003/0009201 A1 | 1/2003 | Forsell |
| 2003/0009221 A1 | 1/2003 | Forsell |
| 2003/0032857 A1 | 2/2003 | Forsell |
| 2003/0040804 A1 | 2/2003 | Stack et al. |
| 2003/0060814 A1 | 3/2003 | Capuano et al. |
| 2003/0060893 A1 | 3/2003 | Forsell |
| 2003/0066536 A1 | 4/2003 | Forsell |
| 2003/0088148 A1 | 5/2003 | Forsell |
| 2003/0092962 A1 | 5/2003 | Forsell |
| 2003/0105385 A1 | 6/2003 | Forsell |
| 2003/0109771 A1 | 6/2003 | Forsell |
| 2003/0114729 A1 | 6/2003 | Forsell |
| 2003/0125605 A1 | 7/2003 | Forsell |
| 2003/0144575 A1 | 7/2003 | Forsell |
| 2003/0220621 A1 | 11/2003 | Arkinstall |
| 2004/0006291 A1 | 1/2004 | Rehrig |
| 2004/0024419 A1 | 2/2004 | Slepian et al. |
| 2004/0034275 A1 | 2/2004 | Forsell |
| 2004/0098113 A1 | 5/2004 | Forsell et al. |
| 2004/0122527 A1 | 6/2004 | Imran |
| 2004/0172141 A1 | 9/2004 | Stack et al. |
| 2004/0186344 A1 | 9/2004 | Jannuzzi |
| 2004/0215159 A1 | 10/2004 | Forsell |
| 2004/0215283 A1 | 10/2004 | Camps et al. |
| 2004/0220516 A1 | 11/2004 | Solomon et al. |
| 2004/0242956 A1 | 12/2004 | Scorvo |
| 2005/0192642 A1 | 9/2005 | Forsell |
| 2005/0209633 A1 | 9/2005 | Callister et al. |
| 2005/0209652 A1 | 9/2005 | Whitehurst et al. |
| 2005/0240229 A1 | 10/2005 | Whitehurst |
| 2005/0256587 A1 | 11/2005 | Egan |
| 2005/0266042 A1 | 12/2005 | Tseng |
| 2006/0030887 A1 | 2/2006 | Letort et al. |
| 2006/0047180 A1 | 3/2006 | Hegde et al. |
| 2006/0149129 A1 | 7/2006 | Watts et al. |
| 2006/0173238 A1 | 8/2006 | Starkebaum |
| 2006/0195139 A1 | 8/2006 | Gertner |
| 2006/0200194 A1 | 9/2006 | Yun |
| 2006/0206001 A1 | 9/2006 | Matsumura |
| 2006/0212055 A1 | 9/2006 | Karabey et al. |
| 2006/0247719 A1 | 11/2006 | Maschino et al. |
| 2006/0247721 A1 | 11/2006 | Maschino et al. |
| 2006/0247722 A1 | 11/2006 | Maschino et al. |
| 2007/0092862 A1 | 4/2007 | Gerber |
| 2007/0255335 A1 | 11/2007 | Herbert et al. |
| 2007/0255336 A1 | 11/2007 | Herbert et al. |
| 2007/0265675 A1 | 11/2007 | Lund et al. |
| 2008/0065167 A1 | 3/2008 | Boggs et al. |
| 2008/0103544 A1 | 5/2008 | Weiner |
| 2008/0139980 A1 | 6/2008 | Fladl et al. |
| 2008/0154256 A1 | 6/2008 | Payne et al. |
| 2008/0178889 A1 | 7/2008 | Tal |

(56) References Cited

U.S. PATENT DOCUMENTS

| | | |
|---|---|---|
| 2008/0195228 A1 | 8/2008 | Uno et al. |
| 2008/0245371 A1 | 10/2008 | Gruber |
| 2008/0275296 A1 | 11/2008 | Forsell |
| 2009/0024108 A1 | 1/2009 | Lee-Sepsick et al. |
| 2009/0054725 A1 | 2/2009 | Forsell |
| 2009/0082705 A1 | 3/2009 | Asfora |
| 2009/0131959 A1 | 5/2009 | Rolland |
| 2009/0216076 A1 | 8/2009 | Kain |
| 2009/0240100 A1 | 9/2009 | Forsell |
| 2009/0240294 A1 | 9/2009 | Forsell |
| 2009/0247817 A1 | 10/2009 | Forsell |
| 2009/0247818 A1 | 10/2009 | Forsell |
| 2009/0248033 A1 | 10/2009 | Forsell |
| 2009/0248109 A1 | 10/2009 | Forsell |
| 2009/0250068 A1 | 10/2009 | Forsell |
| 2009/0254106 A1 | 10/2009 | Forsell |
| 2009/0266366 A1 | 10/2009 | Swann et al. |
| 2010/0016657 A1 | 1/2010 | Robertson et al. |
| 2010/0145139 A1 | 6/2010 | Forsell |
| 2010/0210955 A1 | 8/2010 | Forsell |
| 2010/0211091 A1 | 8/2010 | Forsell |
| 2010/0211092 A1 | 8/2010 | Forsell |
| 2010/0217067 A1 | 8/2010 | Forsell |
| 2010/0217289 A1 | 8/2010 | Forsell |
| 2010/0217295 A1 | 8/2010 | Forsell |
| 2010/0222894 A1 | 9/2010 | Forsell |
| 2010/0286735 A1 | 11/2010 | Garfield et al. |
| 2011/0066254 A1 | 3/2011 | Forsell |
| 2011/0087337 A1 | 4/2011 | Forsell |
| 2011/0144468 A1 | 6/2011 | Boggs et al. |
| 2011/0184230 A1 | 7/2011 | Forsell |
| 2011/0192402 A1 | 8/2011 | Forsell |
| 2011/0196271 A1 | 8/2011 | Forsell |
| 2011/0196466 A1 | 8/2011 | Forsell |
| 2011/0208231 A1 | 8/2011 | Forsell |
| 2011/0230930 A1 | 9/2011 | Forsell |
| 2011/0288499 A1 | 11/2011 | Forsell |
| 2012/0209341 A1 | 8/2012 | Forsell |

FOREIGN PATENT DOCUMENTS

| | | |
|---|---|---|
| DE | 15 41 262 | 6/1969 |
| DE | 199 09 427 | 5/2000 |
| DE | 101 04 806 | 8/2002 |
| EP | 0 200 286 | 11/1986 |
| EP | 0 252 258 | 1/1988 |
| EP | 0 348 114 | 12/1989 |
| EP | 0 372 311 | 6/1990 |
| EP | 0 393 714 | 10/1990 |
| EP | 0 532 162 | 3/1993 |
| EP | 0 626 154 | 11/1994 |
| EP | 1 275 344 | 1/2003 |
| EP | 1 563 814 | 8/2005 |
| EP | 1 600 183 | 11/2005 |
| EP | 1 602 334 | 12/2005 |
| FR | 2 248 015 | 5/1975 |
| FR | 2 688 693 | 9/1993 |
| FR | 2 692 777 | 12/1993 |
| FR | 2 756 485 | 6/1998 |
| GB | 1174814 | 12/1969 |
| GB | 2021956 | 12/1979 |
| JP | 58-190437 | 11/1983 |
| JP | 62-8752 | 1/1987 |
| JP | 63-18177 | 7/1988 |
| JP | 1-305945 | 12/1989 |
| JP | 2-211170 | 8/1990 |
| JP | 3-63047 | 3/1991 |
| JP | 3-158154 | 7/1991 |
| JP | 2002-517277 | 6/2002 |
| SU | 1 635 980 | 3/1991 |
| WO | WO 96/01597 | 1/1996 |
| WO | WO 97/03616 | 2/1997 |
| WO | WO 97/41799 | 11/1997 |
| WO | WO 99/63907 | 12/1999 |
| WO | WO 00/09048 | 2/2000 |
| WO | WO 00/15158 | 3/2000 |
| WO | WO 00/21606 | 4/2000 |
| WO | WO 01/12075 | 2/2001 |
| WO | WO 01/12108 | 2/2001 |
| WO | WO 01/45486 | 6/2001 |
| WO | WO 01/47434 | 7/2001 |
| WO | WO 01/47435 | 7/2001 |
| WO | WO 01/47575 | 7/2001 |
| WO | WO 01/50832 | 7/2001 |
| WO | WO 01/54615 | 8/2001 |
| WO | WO 01/58391 | 8/2001 |
| WO | WO 02/39959 | 5/2002 |
| WO | WO 02/058563 | 8/2002 |
| WO | WO 03/002192 | 1/2003 |
| WO | WO 03/086507 | 10/2003 |
| WO | WO 2004/012806 | 2/2004 |
| WO | WO 2004/087233 | 10/2004 |
| WO | WO 2005/084730 | 9/2005 |
| WO | WO 2006/014496 | 2/2006 |
| WO | WO 2006/044194 | 4/2006 |
| WO | WO 2006/114004 | 11/2006 |
| WO | WO 2007/106303 | 9/2007 |
| WO | WO 2007/121525 | 11/2007 |
| WO | WO 2007/124128 | 11/2007 |
| WO | WO 2008/100390 | 8/2008 |
| WO | WO 2009/046994 | 4/2009 |
| WO | WO 2009/046995 | 4/2009 |
| WO | WO 2009/046996 | 4/2009 |
| WO | WO 2009/046997 | 4/2009 |
| WO | WO 2009/046998 | 4/2009 |
| WO | WO 2009/048367 | 4/2009 |
| WO | WO 2009/048368 | 4/2009 |
| WO | WO 2009/048370 | 4/2009 |
| WO | WO 2009/048374 | 4/2009 |
| WO | WO 2009/048375 | 4/2009 |
| WO | WO 2009/048376 | 4/2009 |
| WO | WO 2009/048378 | 4/2009 |
| WO | WO 2009/048379 | 4/2009 |
| WO | WO 2009/048380 | 4/2009 |
| WO | WO 2009/048381 | 4/2009 |
| WO | WO 2009/048382 | 4/2009 |
| WO | WO 2009/048383 | 4/2009 |
| WO | WO 2009/048384 | 4/2009 |
| WO | WO 2009/048387 | 4/2009 |
| WO | WO 2009/048388 | 4/2009 |
| WO | WO 2009/048389 | 4/2009 |
| WO | WO 2009/048391 | 4/2009 |
| WO | WO 2009/048392 | 4/2009 |
| WO | WO 2009/048393 | 4/2009 |
| WO | WO 2009/048394 | 4/2009 |
| WO | WO 2009/048395 | 4/2009 |
| WO | WO 2009/048398 | 4/2009 |
| WO | WO 2009/048399 | 4/2009 |
| WO | WO 2009/048400 | 4/2009 |
| WO | WO 2009/048401 | 4/2009 |
| WO | WO 2009/648396 | 4/2009 |
| WO | WO 2010/042045 | 4/2010 |
| WO | WO 2010/047644 | 4/2010 |

OTHER PUBLICATIONS

Notification of Office action in corresponding Chinese Application No. 200880119934.X, mailed Nov. 23, 2011.
English translation of Notification of Office action in corresponding Chinese Application No. 200880119934.X, mailed Nov. 23, 2011.
U.S. Appl. No. 12/285,791 (Forsell) filed Oct. 14, 2008.
U.S. Appl. No. 12/285,792 (Forsell) filed Oct. 14, 2008.
U.S. Appl. No. 12/285,793 (Forsell) filed Oct. 14, 2008.
U.S. Appl. No. 12/285,794 (Forsell) filed Oct. 14, 2008.
U.S. Appl. No. 12/285,807 (Forsell) filed Oct. 14, 2008.
U.S. Appl. No. 12/285,808 (Forsell) filed Oct. 14, 2008.
U.S. Appl. No. 12/285,809 (Forsell) filed Oct. 14, 2008.
U.S. Appl. No. 12/285,810 (Forsell) filed Oct. 14, 2008.
U.S. Appl. No. 12/682,462 (Forsell) filed Apr. 9, 2010.
U.S. Appl. No. 12/682,501 (Forsell) filed Apr. 9, 2010.
U.S. Appl. No. 12/682,491 (Forsell) filed Apr. 9, 2010.
U.S. Appl. No. 12/682,334 (Forsell) filed Apr. 9, 2010.

(56) References Cited

OTHER PUBLICATIONS

U.S. Appl. No. 12/758,684 (Forsell) filed Apr. 12, 2010.
U.S. Appl. No. 13/367,002 (Forsell) filed Feb. 6, 2012.
U.S. Appl. No. 12/758,694 (Forsell) filed Apr. 12, 2010.
U.S. Appl. No. 12/149,020 (Forsell) filed Apr. 25, 2008.
U.S. Appl. No. 13/122,907 (Forsell) filed Apr. 6, 2011.
U.S. Appl. No. 13/123,330 (Forsell) filed Apr. 8, 2011.
U.S. Appl. No. 13/123,145 (Forsell) filed Apr. 7, 2011.
U.S. Appl. No. 13/123,425 (Forsell) filed Apr. 8, 2011.
U.S. Appl. No. 12/682,523 (Forsell) filed Apr. 9, 2010.
U.S. Appl. No. 12/682,533 (Forsell) filed Apr. 9, 2010.
U.S. Appl. No. 12/656,513 (Forsell) filed Feb. 1, 2010.
U.S. Appl. No. 12/688,375 (Forsell) filed Jan. 15, 2010.
U.S. Appl. No. 13/080,118 (Forsell) filed Apr. 5, 2011.
International Search Report in International Application No. PCT/SE2008/000579 mailed Feb. 25, 2009.
International Search Report in International Application No. PCT/SE2008/000570 mailed Mar. 30, 2009.
International Search Report in International Application No. PCT/SE2008/000577 mailed Apr. 3, 2009.
International Search Report in International Application No. PCT/SE2008/000583 mailed Feb. 5, 2009.
International Search Report in International Application No. PCT/SE2009/051127 mailed Mar. 8, 2010.
International Search Report in International Application No. PCT/SE2008/000572 mailed Mar. 5, 2009.
International Search Report in International Application No. PCT/EP2008/008587 mailed Mar. 4, 2009.
International Search Report in International Application No. PCT/EP2008/008588 mailed Jun. 24, 2009.
International Search Report in International Application No. PCT/EP2008/008589 mailed Jun. 17, 2009.
International Search Report in International Application No. PCT/SE2008/000584 mailed Mar. 4, 2009.
International Search Report in International Application No. PCT/SE2008/000573 mailed Jan. 28, 2009.
International Search Report in International Application No. PCT/EP2008/008586 mailed May 27, 2009.
International Search Report in International Application No. PCT/EP2008/008590 mailed May 27, 2009.
International Search Report in International Application No. PCT/SE2009/051130 mailed Jan. 8, 2010.
International Search Report in International Application No. PCT/SE2008/000568 mailed Apr. 3, 2009 (published as WO 2009/048379 A3 Apr. 16, 2009).
International Search Report in International Application No. PCT/SE2008/000582 mailed Apr. 21, 2009 (published as WO 2009/048391 A3 Apr. 16, 2009).
International Search Report in International Application No. PCT/SE2008/000564 mailed Mar. 12, 2009.
International Search Report in International Application No. PCT/SE2008/000555 mailed Feb. 18, 2009.
International Search Report in International Application No. PCT/SE2008/000569 mailed Feb. 20, 2009.
International Search Report in International Application No. PCT/SE2008/000565 mailed Feb. 5, 2009.
International Search Report in International Application No. PCT/SE2008/000571 mailed Feb. 5, 2009.
International Search Report in International Application No. PCT/SE2008/000557 mailed Mar. 12, 2009.
International Search Report in International Application No. PCT/SE2008/000593 mailed Mar. 9, 2009.
International Search Report in International Application No. PCT/SE2008/000586 mailed Mar. 17, 2009 (published as WO 2009/048394 A3 Apr. 16, 2009).
International Search Report in International Application No. PCT/SE2008/000567 mailed Feb. 5, 2009.
International Search Report in International Application No. PCT/SE2008/000553 mailed Feb. 5, 2009.
International Search Report in International Application No. PCT/SE2008/000580 mailed Feb. 25, 2009.
International Search Report in International Application No. PCT/SE2008/000562 mailed Feb. 24, 2009.
International Search Report in International Application No. PCT/SE2008/000589 mailed Feb. 13, 2009.
International Search Report in International Application No. PCT/SE2008/000590 mailed Feb. 18, 2009.
International Search Report in International Application No. PCT/SE2008/000592 mailed Feb. 18, 2009.
International Search Report in International Application No. PCT/SE2008/000594 mailed Mar. 3, 2009.
International Search Report in International Application No. PCT/SE2008/000595 mailed Feb. 5, 2009.
International Preliminary Report on Patentability in International Application No. PCT/SE2008/000579 dated Apr. 13, 2010.
International Preliminary Report on Patentability in International Application No. PCT/SE2008/000570 dated Apr. 13, 2010.
International Preliminary Report on Patentability in International Application No. PCT/SE2008/000577 dated Apr. 13, 2010.
International Preliminary Report on Patentability in International Application No. PCT/SE2008/000583 dated Apr. 13, 2010.
International Preliminary Report on Patentability in International Application No. PCT/SE2009/051127 dated Apr. 12, 2011.
International Preliminary Report on Patentability in International Application No. PCT/SE2008/000572 dated Apr. 13, 2010.
International Preliminary Report on Patentability in International Application No. PCT/EP2008/008587 dated Apr. 13, 2010.
International Preliminary Report on Patentability in International Application No. PCT/EP2008/008588 dated Apr. 13, 2010.
International Preliminary Report on Patentability in International Application No. PCT/EP2008/008589 dated Apr. 13, 2010.
International Preliminary Report on Patentability in International Application No. PCT/SE2008/000584 dated Apr. 13, 2010.
International Preliminary Report on Patentability in International Application No. PCT/SE2008/000573 dated Oct. 16, 2012.
International Preliminary Report on Patentability in International Application No. PCT/EP2008/008586 dated Apr. 13, 2010.
International Preliminary Report on Patentability in International Application No. PCT/EP2008/008590 dated Apr. 13, 2010.
International Preliminary Report on Patentability in International Application No. PCT/SE2009/051130 dated Apr. 12, 2011.
International Preliminary Report on Patentability in International Application No. PCT/SE2008/000568 dated Apr. 13, 2010.
International Preliminary Report on Patentability in International Application No. PCT/SE2008/000582 dated Apr. 13, 2010.
International Preliminary Report on Patentability in International Application No. PCT/SE2008/000564 dated Apr. 13, 2010.
International Preliminary Report on Patentability in International Application No. PCT/SE2008/000555 dated Apr. 13, 2010.
International Preliminary Report on Patentability in International Application No. PCT/SE2008/000569 dated Apr. 13, 2010.
International Preliminary Report on Patentability in International Application No. PCT/SE2008/000565 dated Apr. 13, 2010.
International Preliminary Report on Patentability in International Application No. PCT/SE2008/000571 dated Apr. 13, 2010.
International Preliminary Report on Patentability in International Application No. PCT/SE2008/000557 dated Apr. 13, 2010.
International Preliminary Report on Patentability in International Application No. PCT/SE2008/000593 dated Apr. 13, 2010.
International Preliminary Report on Patentability in International Application No. PCT/SE2008/000586 dated Apr. 13, 2010.
International Preliminary Report on Patentability in International Application No. PCT/SE2008/000567 dated Apr. 13, 2010.
International Preliminary Report on Patentability in International Application No. PCT/SE2008/000553 dated Apr. 13, 2010.
International Preliminary Report on Patentability in International Application No. PCT/SE2008/000580 dated Apr. 13, 2010.
International Preliminary Report on Patentability in International Application No. PCT/SE2008/000562 dated Apr. 13, 2010.
International Preliminary Report on Patentability in International Application No. PCT/SE2008/000589 dated Apr. 13, 2010.

(56) References Cited

OTHER PUBLICATIONS

International Preliminary Report on Patentability in International Application No. PCT/SE2008/000590 dated Apr. 13, 2010.
International Preliminary Report on Patentability in International Application No. PCT/SE2008/000592 dated Apr. 13, 2010.
International Preliminary Report on Patentability in International Application No. PCT/SE2008/000594 dated Apr. 13, 2010.
International Preliminary Report on Patentability in International Application No. PCT/SE2008/000595 dated Apr. 13, 2010.
S. K. Guha et al., "Feasibility study of the reversible occlusion device for the vas deferens," Medical and Biological Engineering and Computing, vol. 14, No. 1, Jan. 1976, pp. 15-18.
Enclyclopedia Britannica definition of "ductus deferens" (retrieved from the Internet May 22, 2013: URL:http://www.britannica.com/EBchecked/topic/173003/ductus-deferens?sections=173003main&view=print).
"The human isolated vas deference: its response to electrical stimulation and to drugs." Br J Pharmacol. 1968,34(3):692P-693P ("*Pharmacaf*").
"Sperm transport in the human female genital tract and its modulation by oxytocin as assessed by hysterosalpingoscintigraphy, hysterotonography, electrohysterography and Doppler sonography," Human Reproduction Update 1998, vol. 4, No. 5, pp. 655-666.

\* cited by examiner

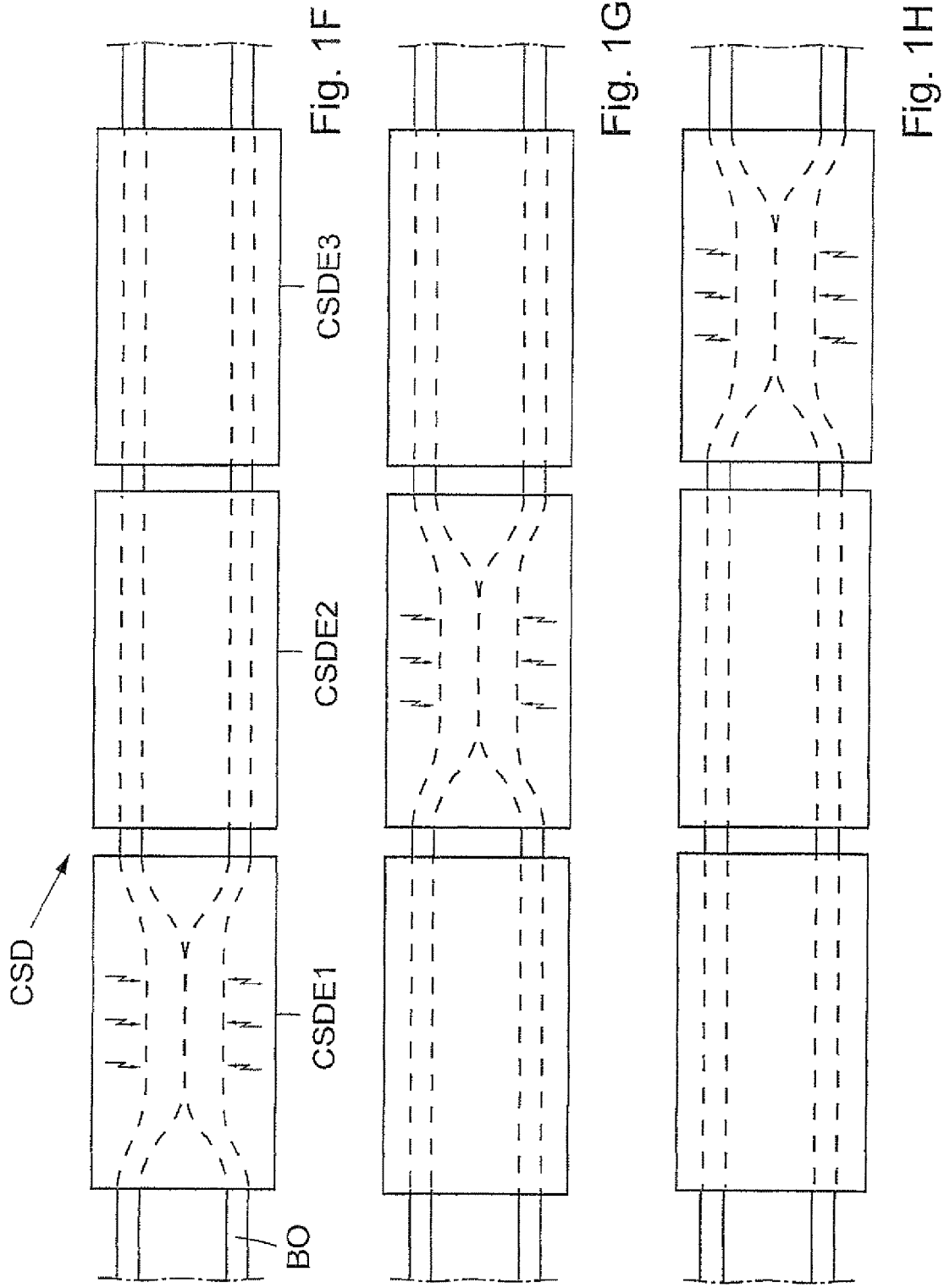

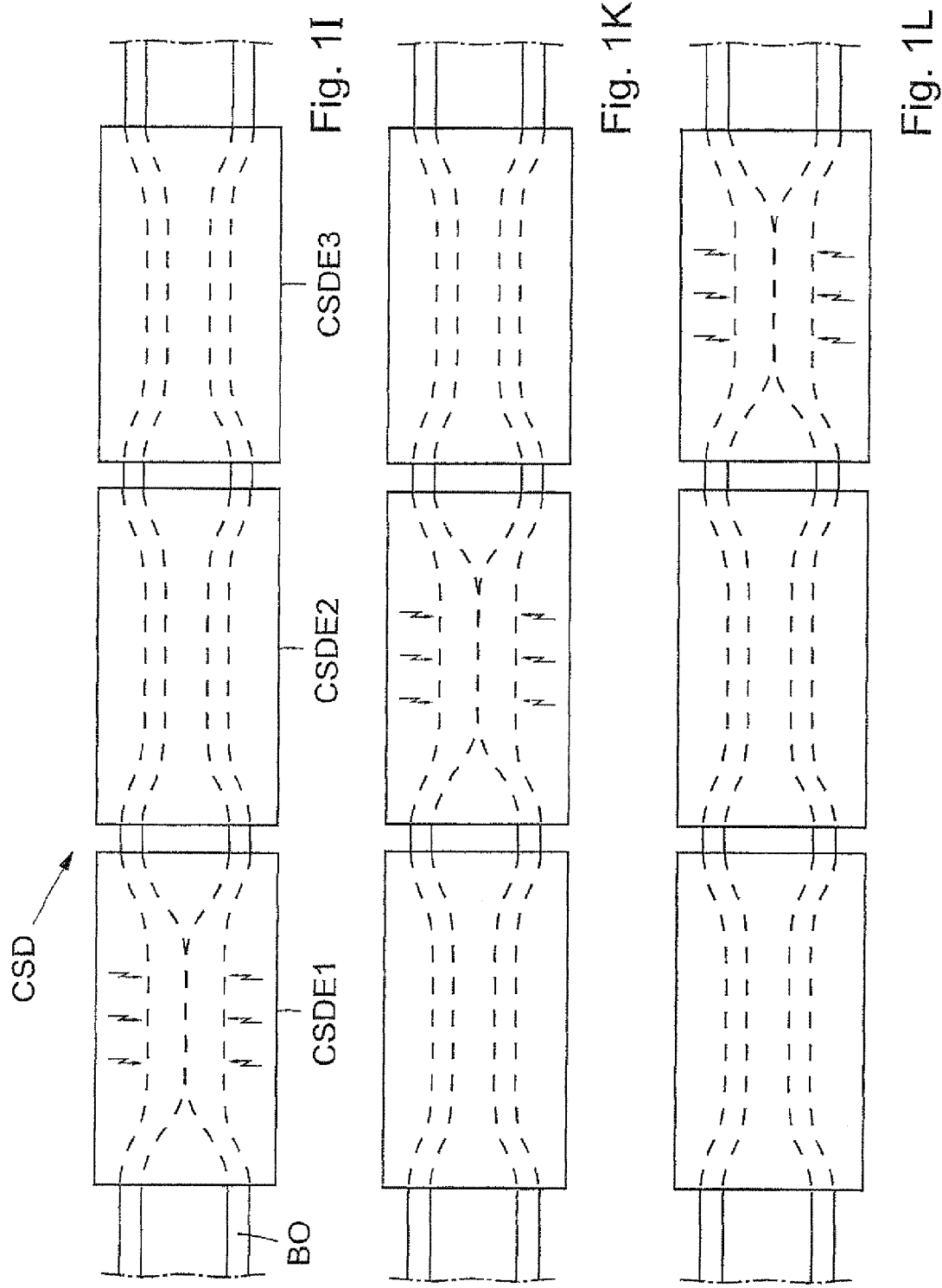

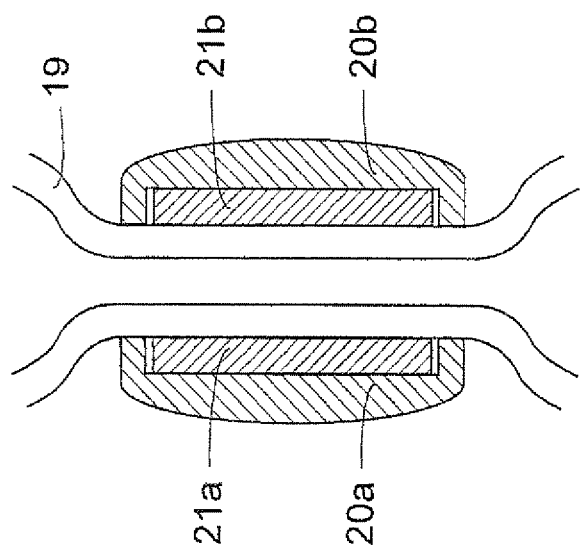
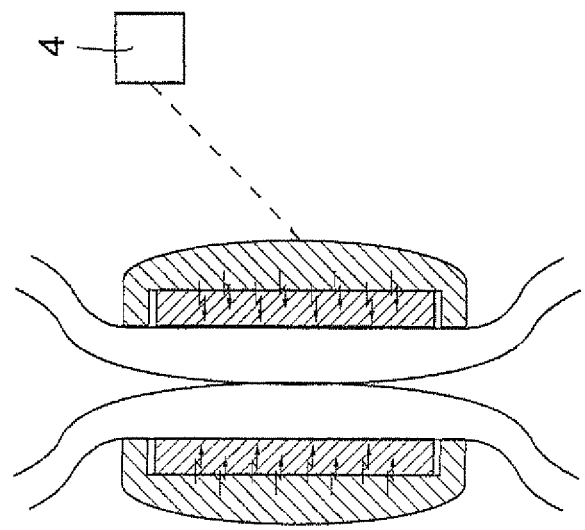
Fig. 11A
Fig. 11B

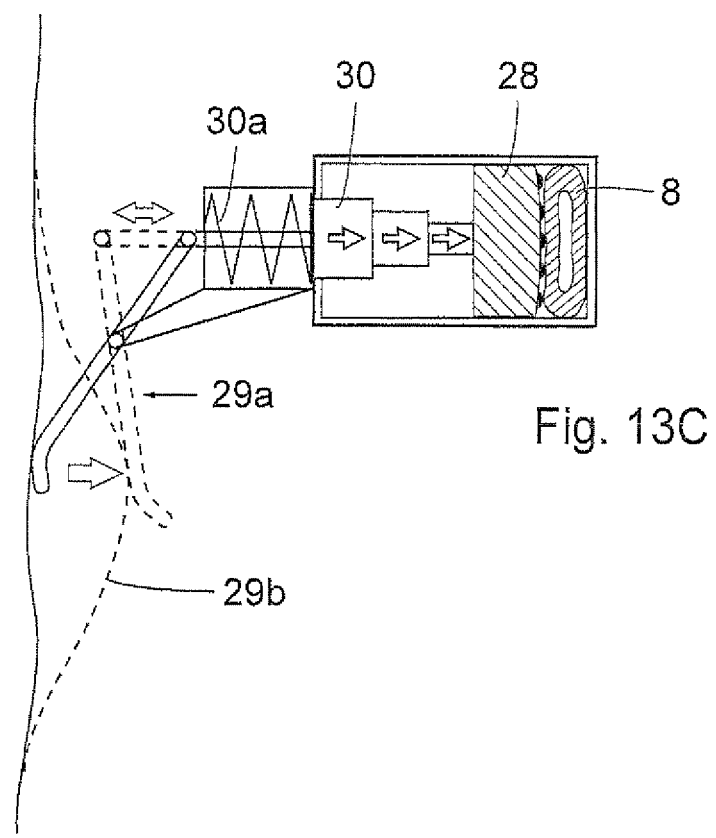

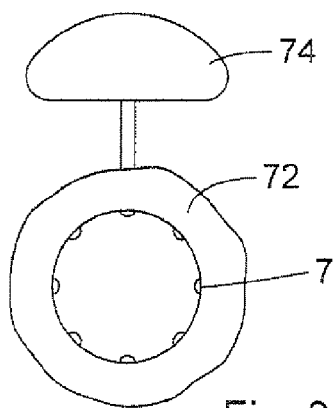 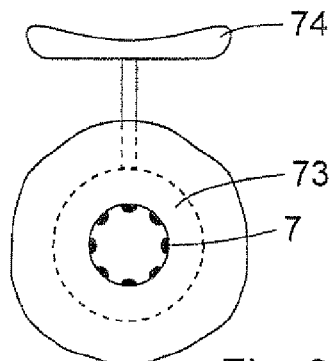
Fig. 30A    Fig. 30B
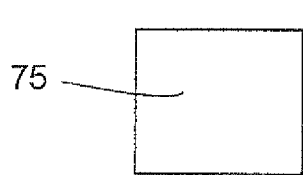
Fig. 31A
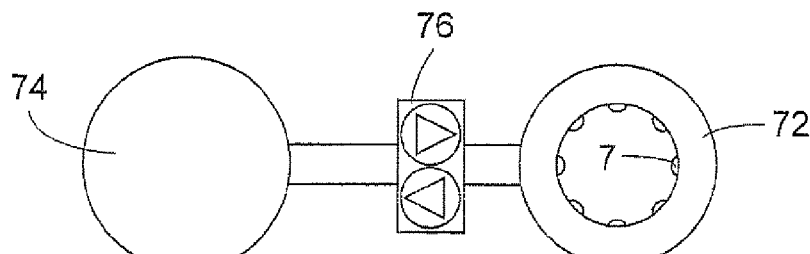
Fig. 31B
Fig. 31C
Fig. 31D 2a 2b 2c 2d 2e 2f 2g 2h 2i 2j 2k 2l 2m 2n

1000

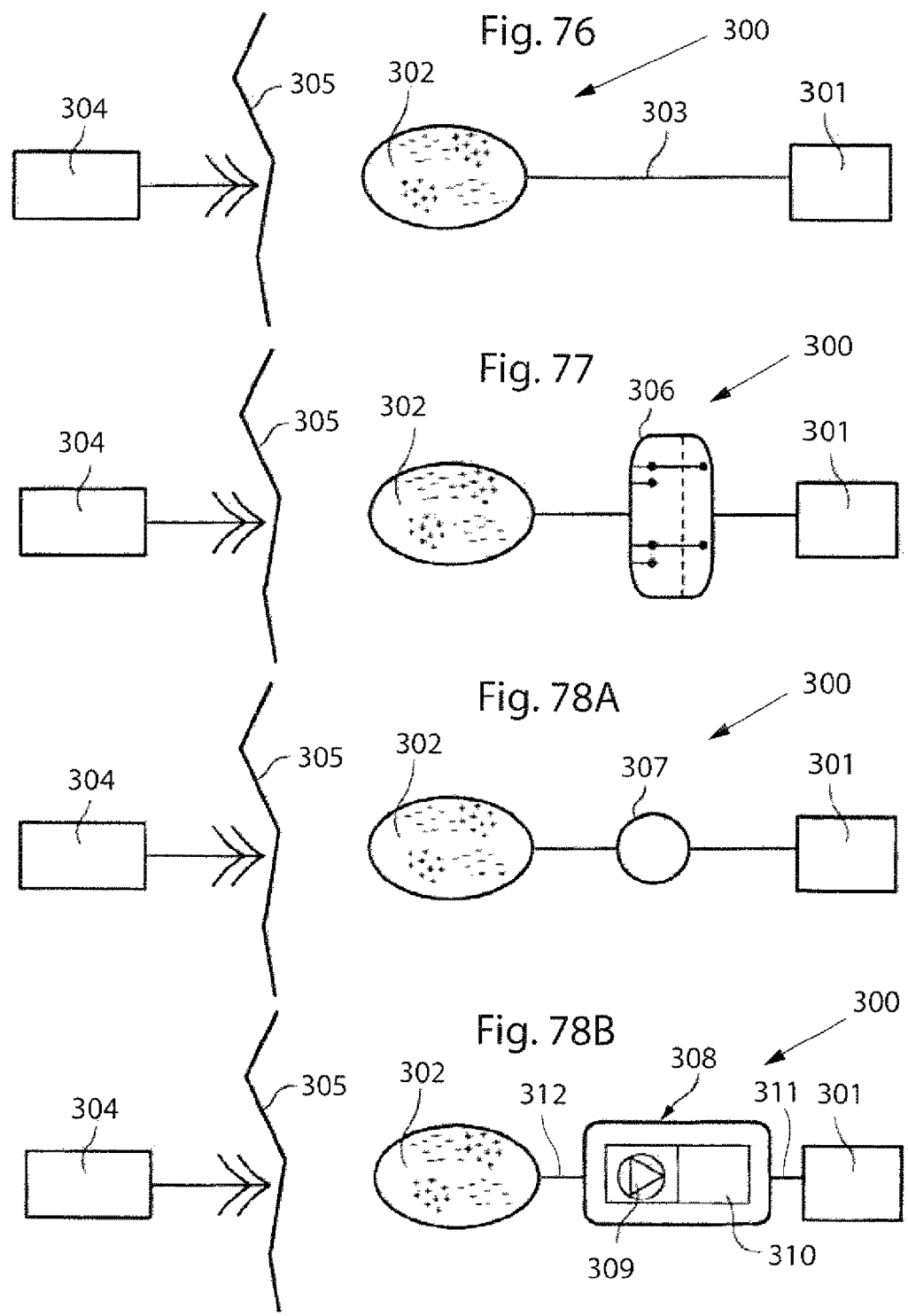

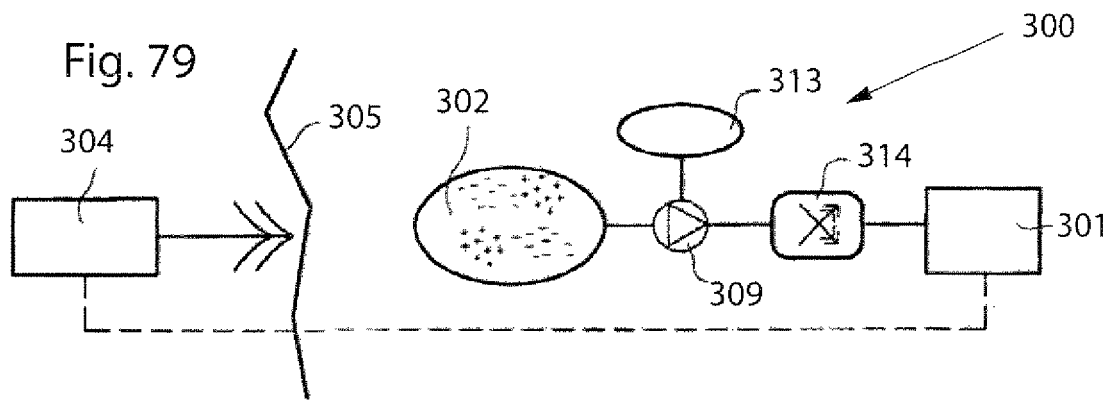
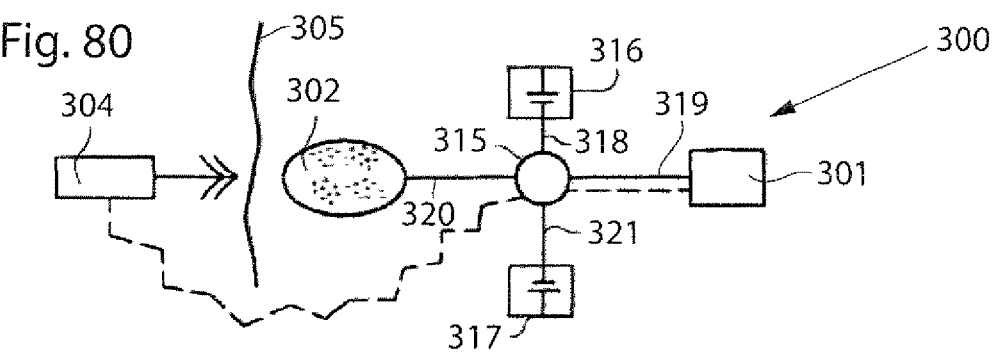
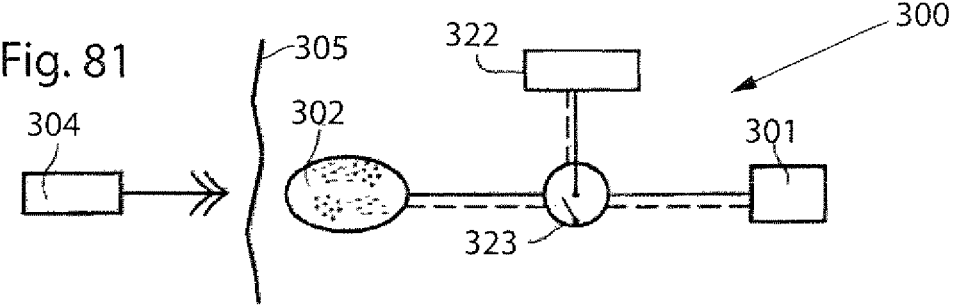
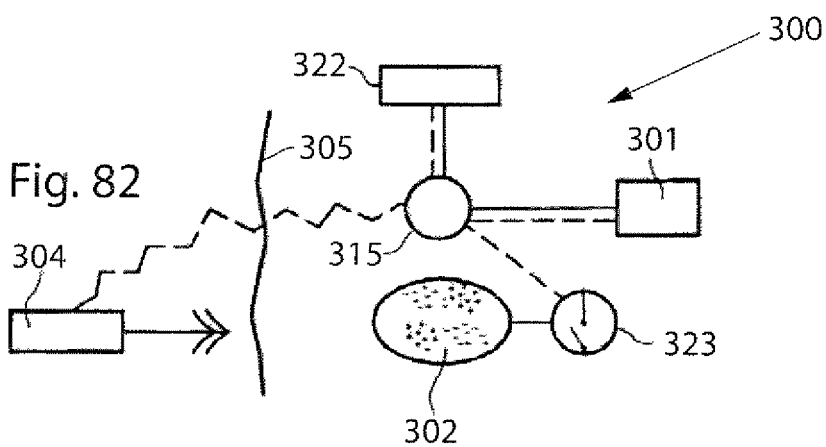

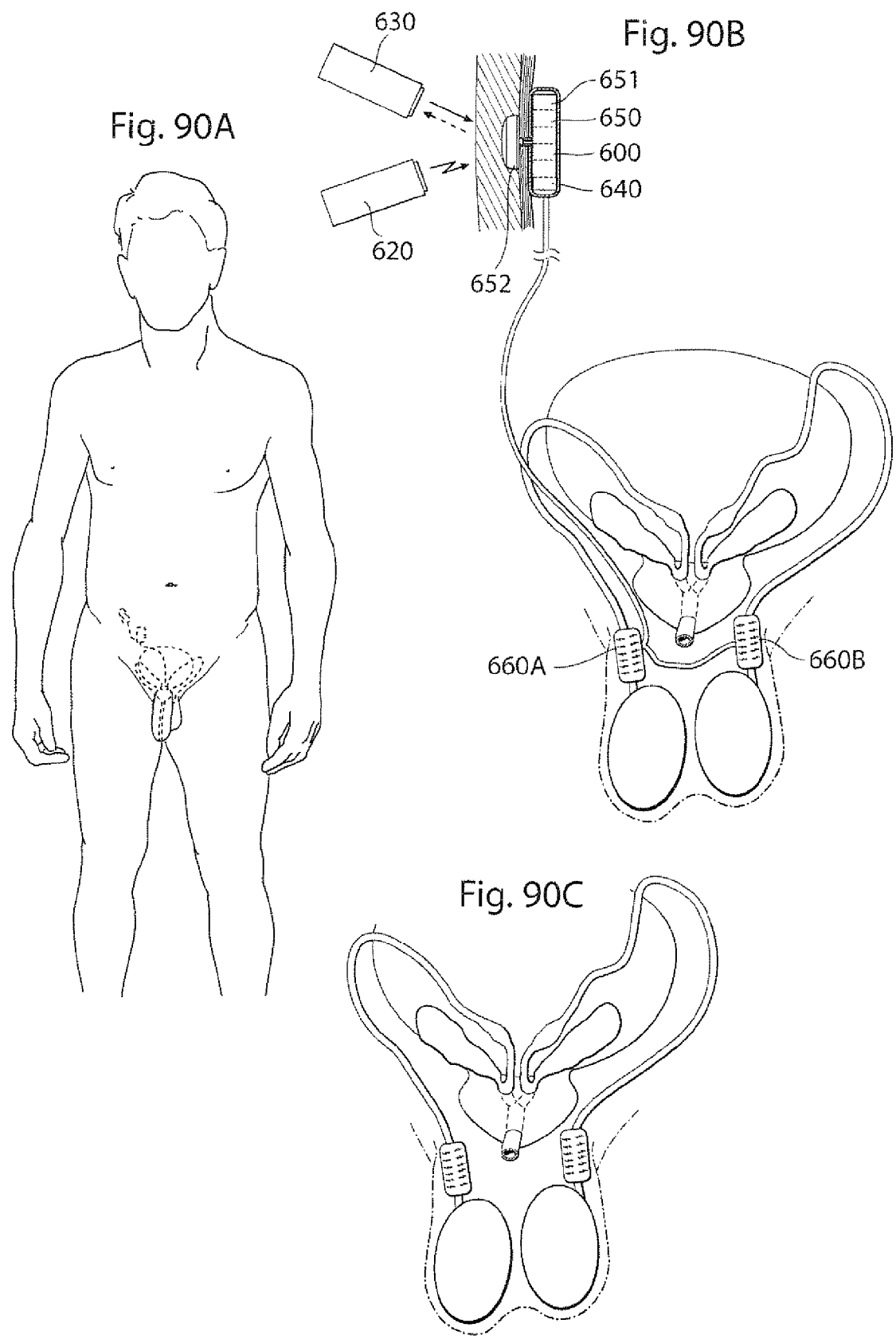

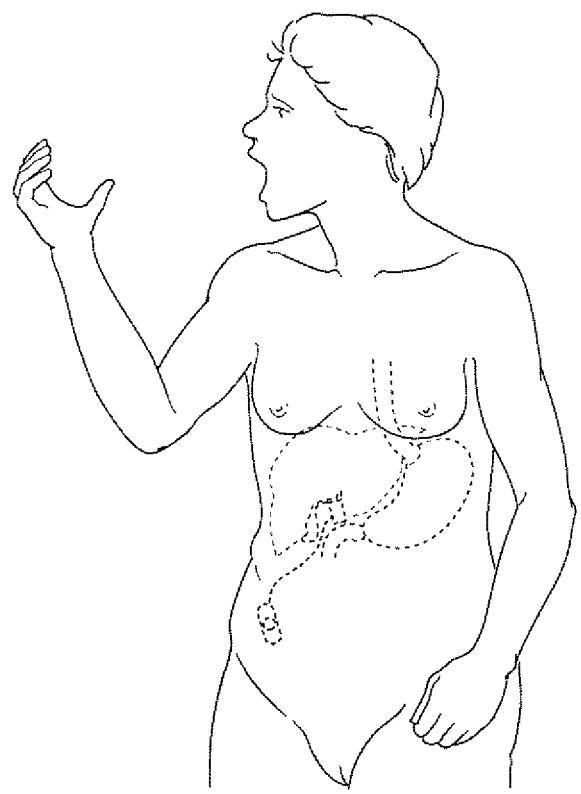
Fig.92
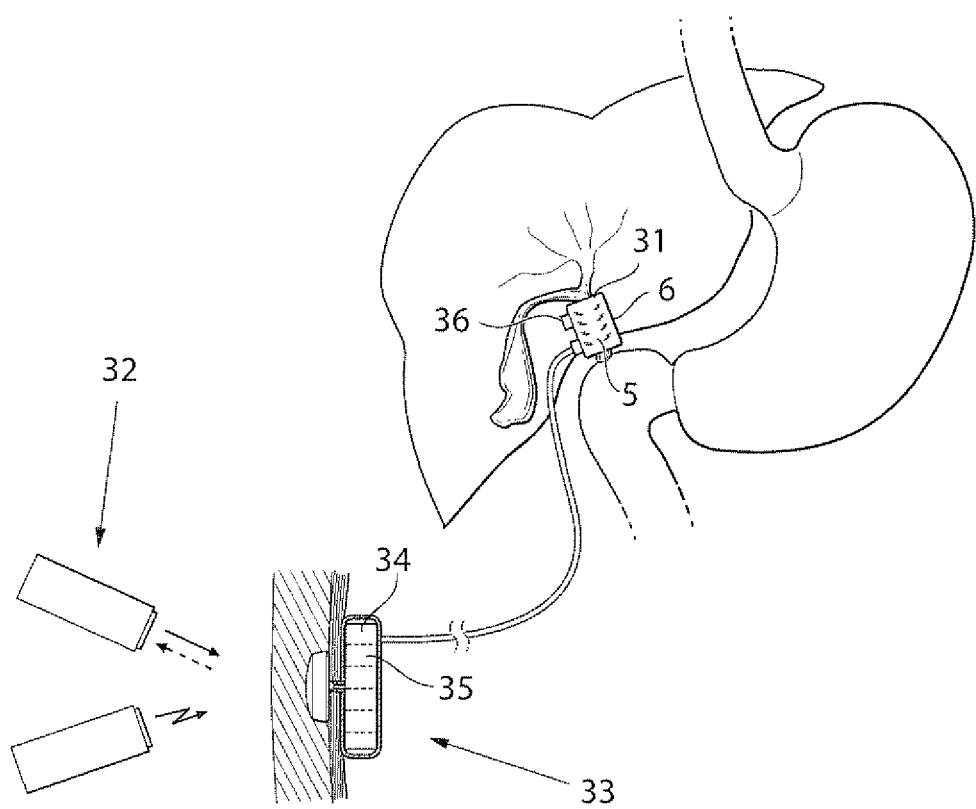

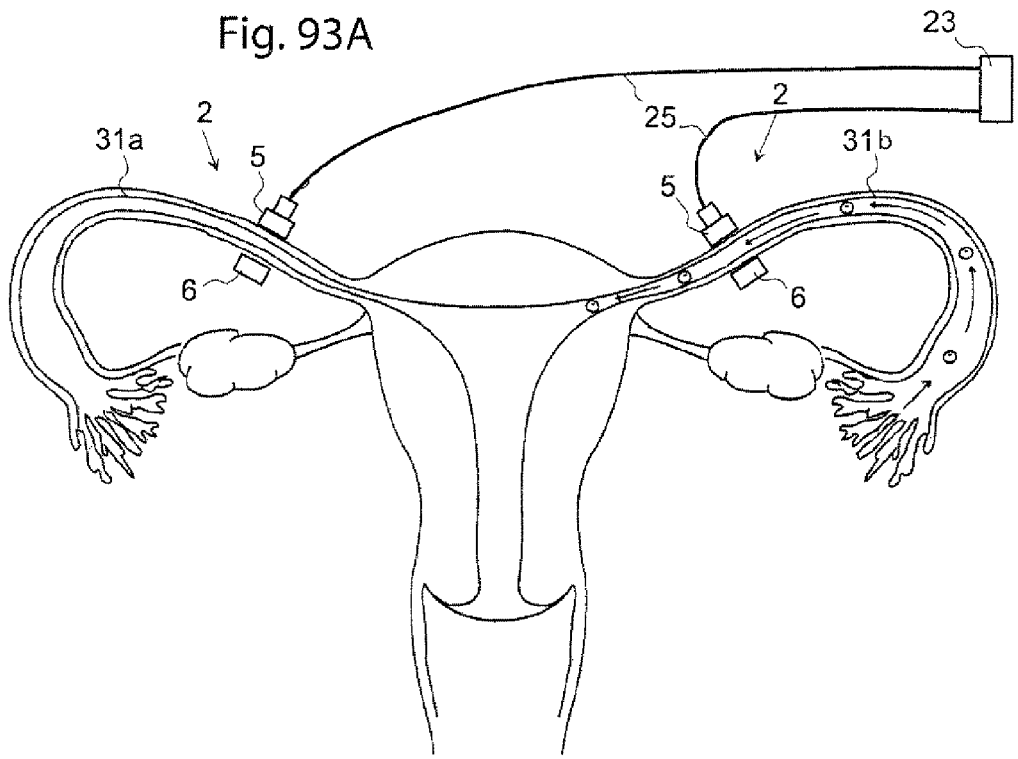
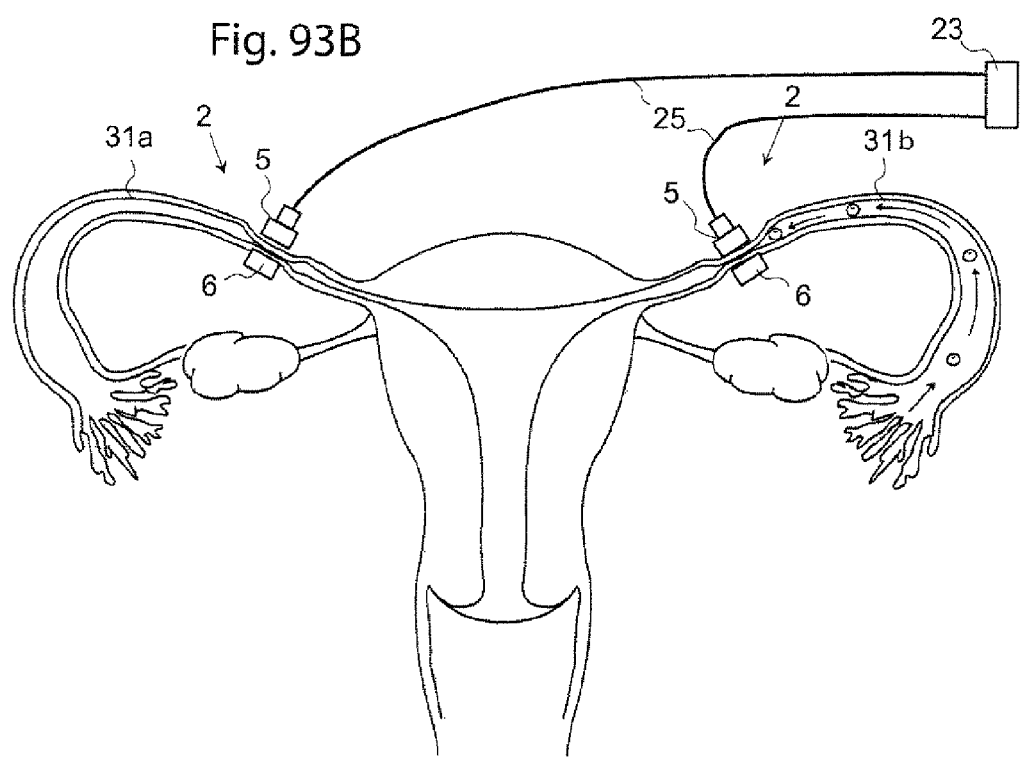

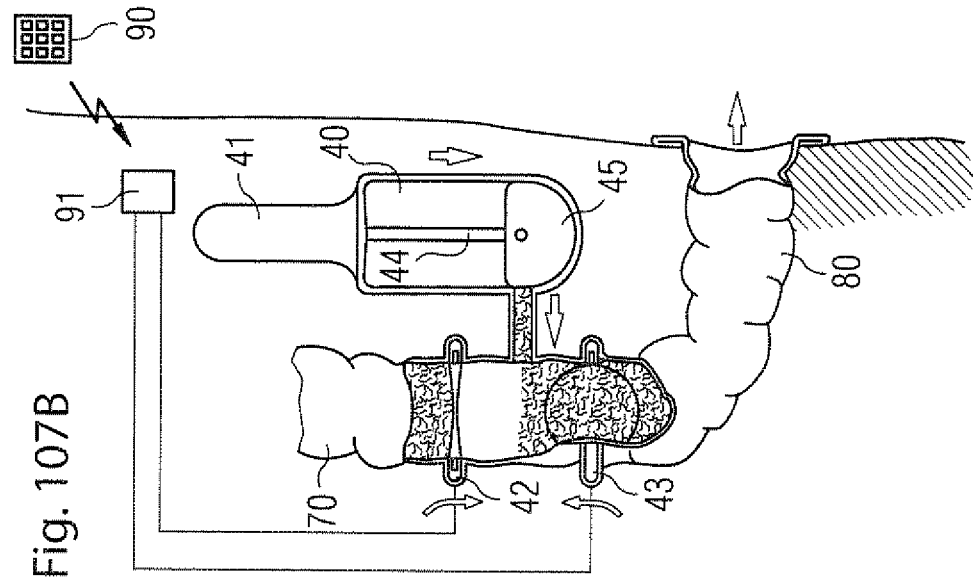
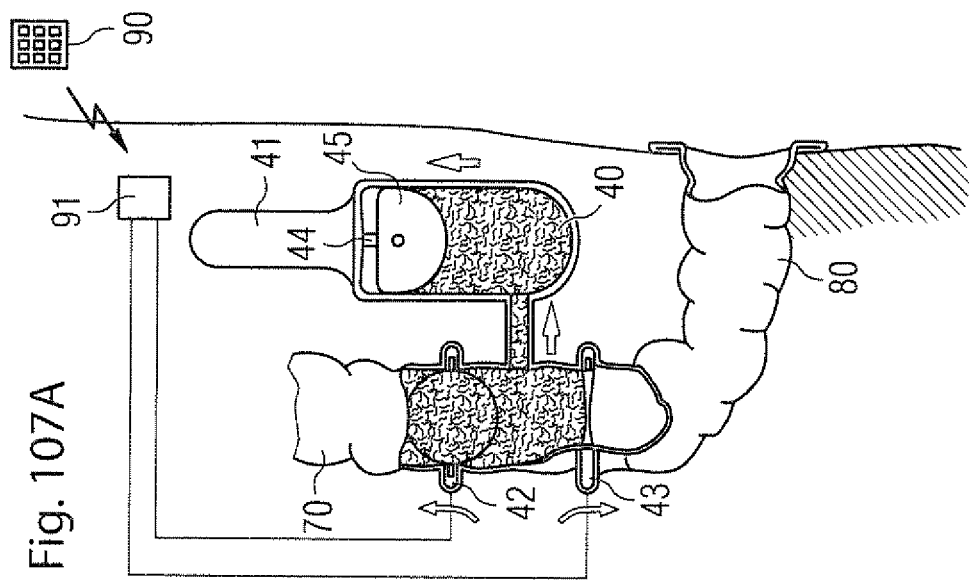

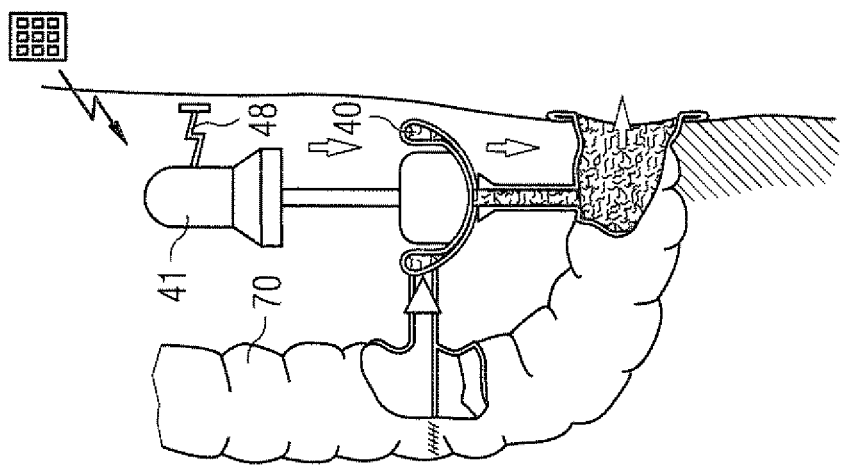
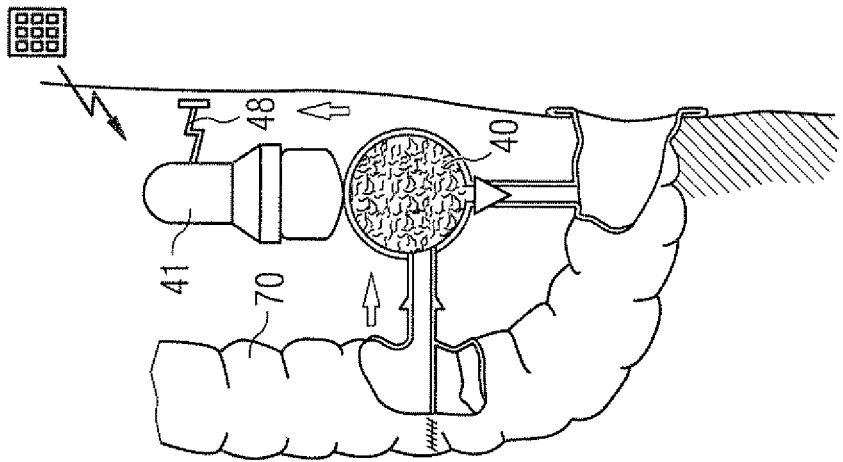
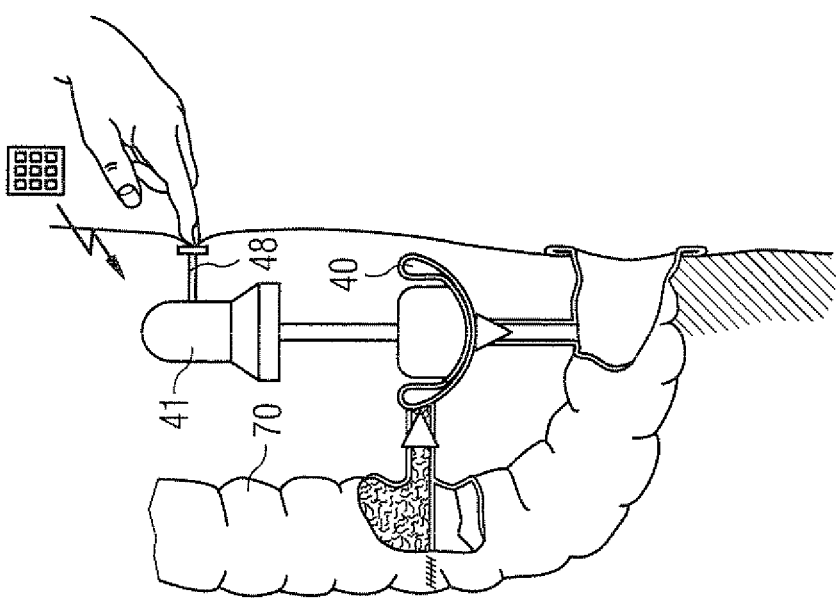

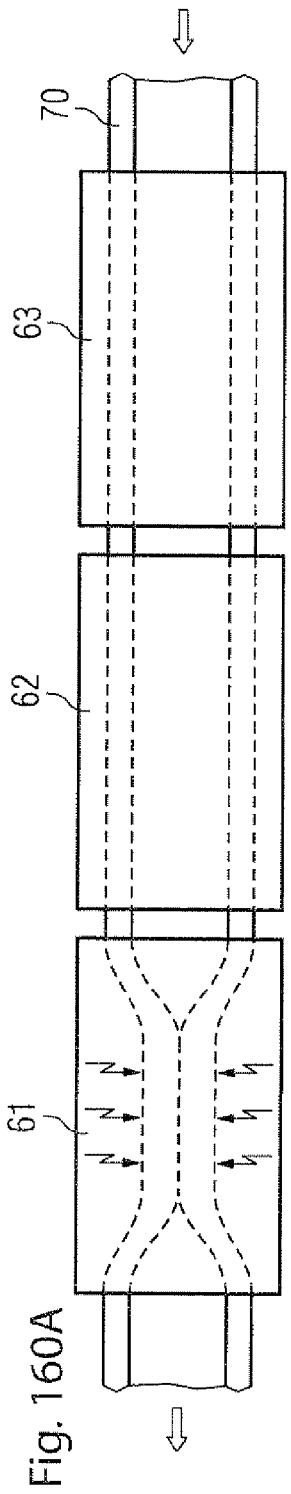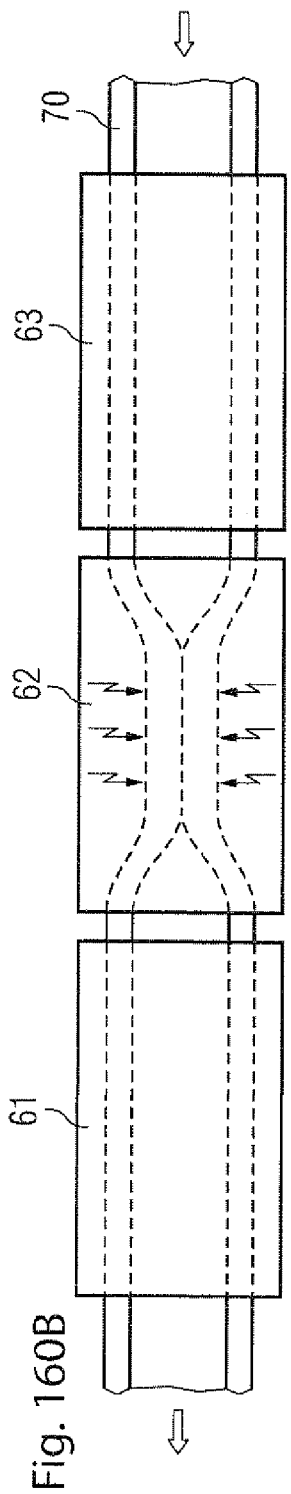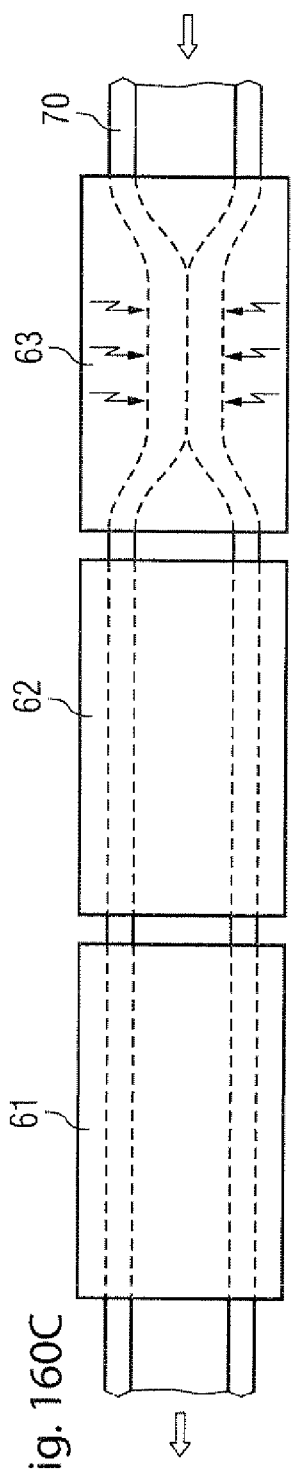

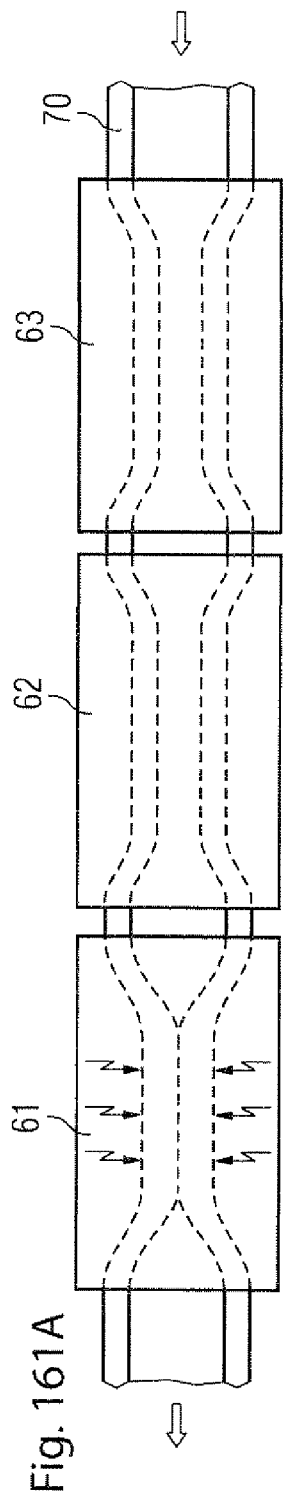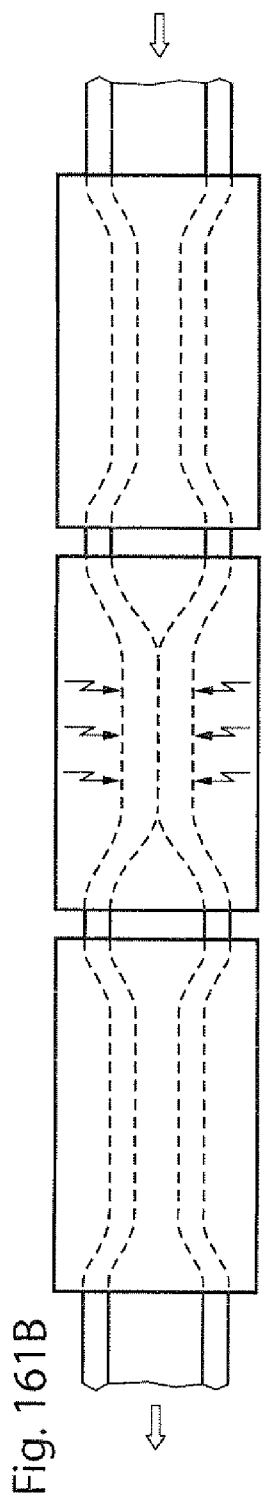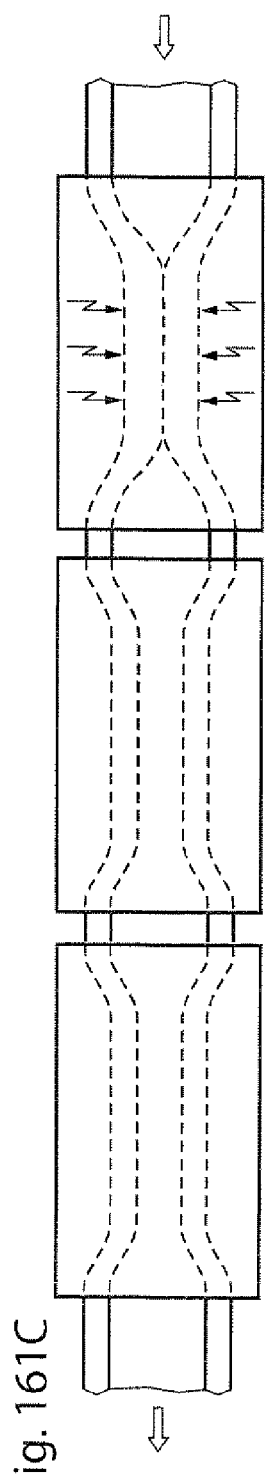

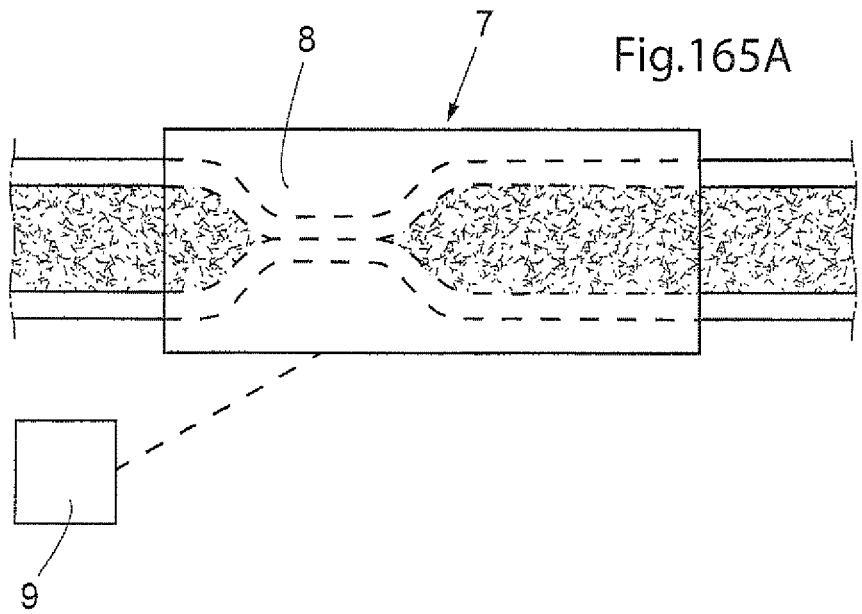
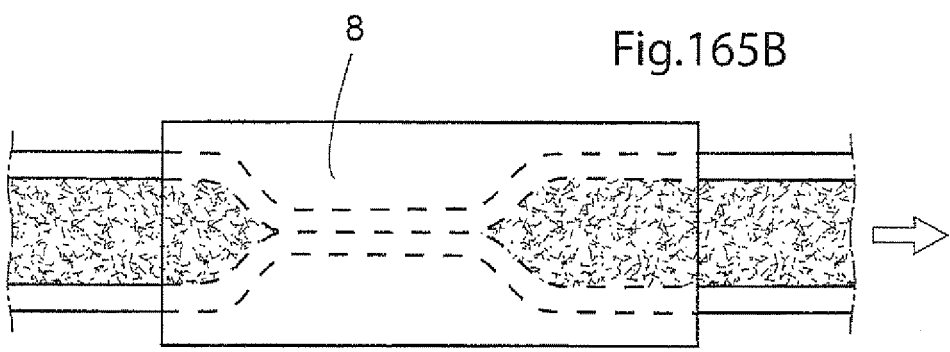
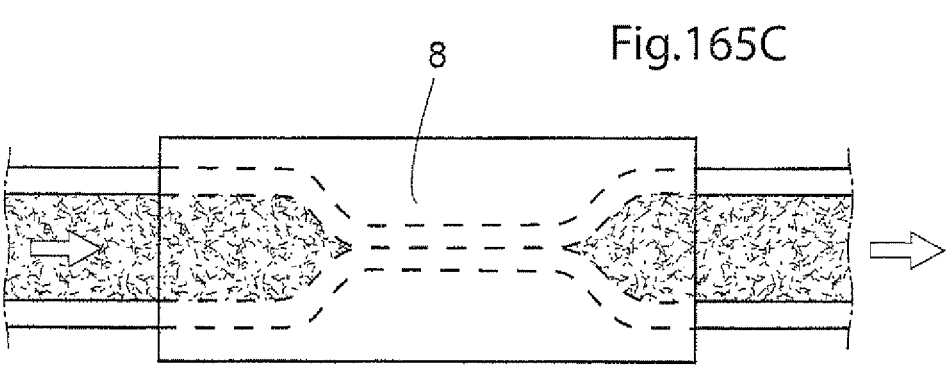

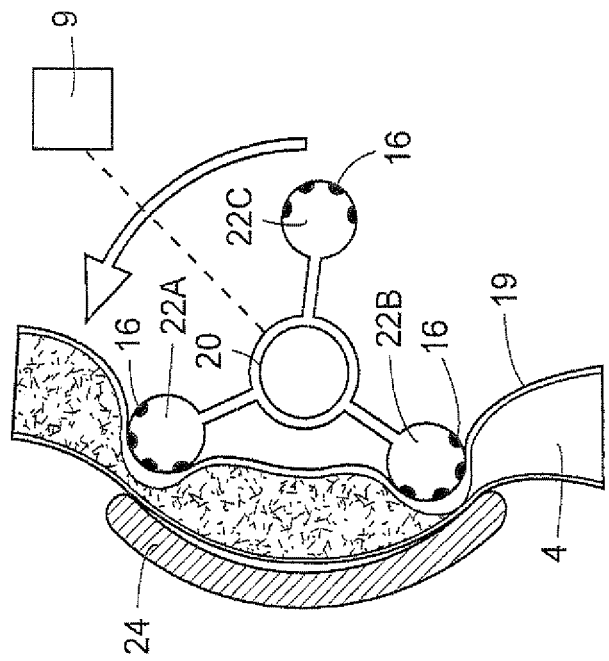
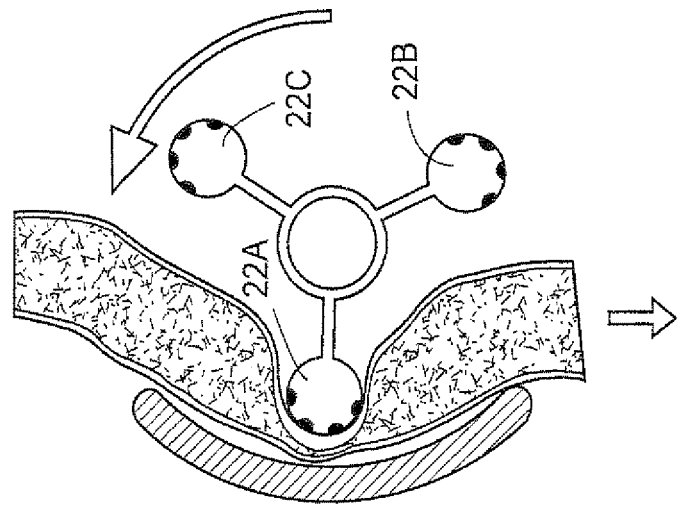
Fig.174A
Fig.174B

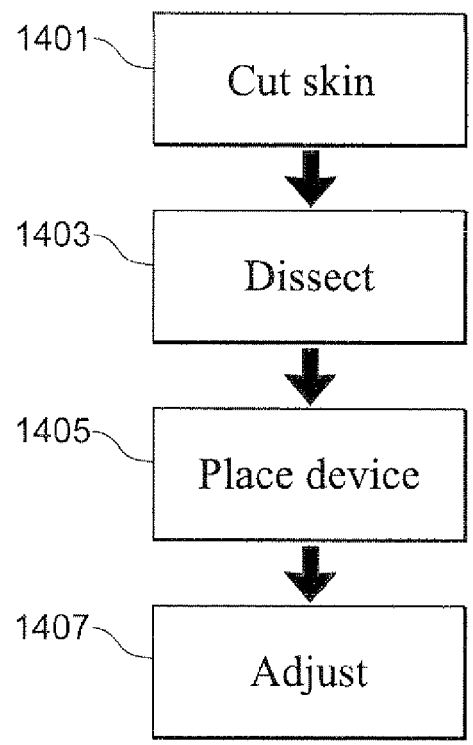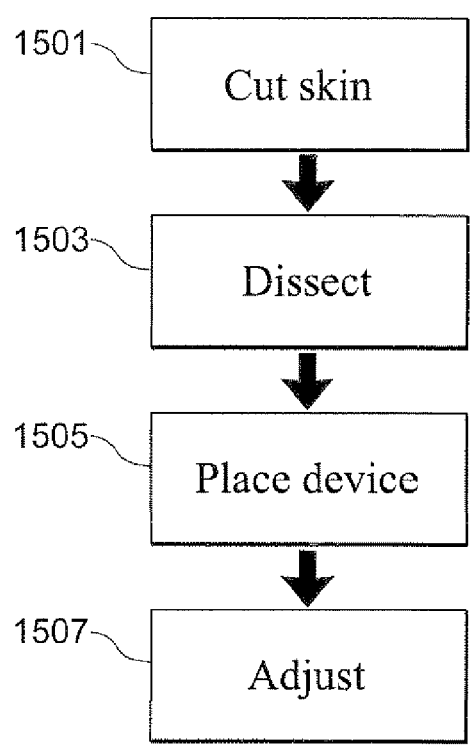

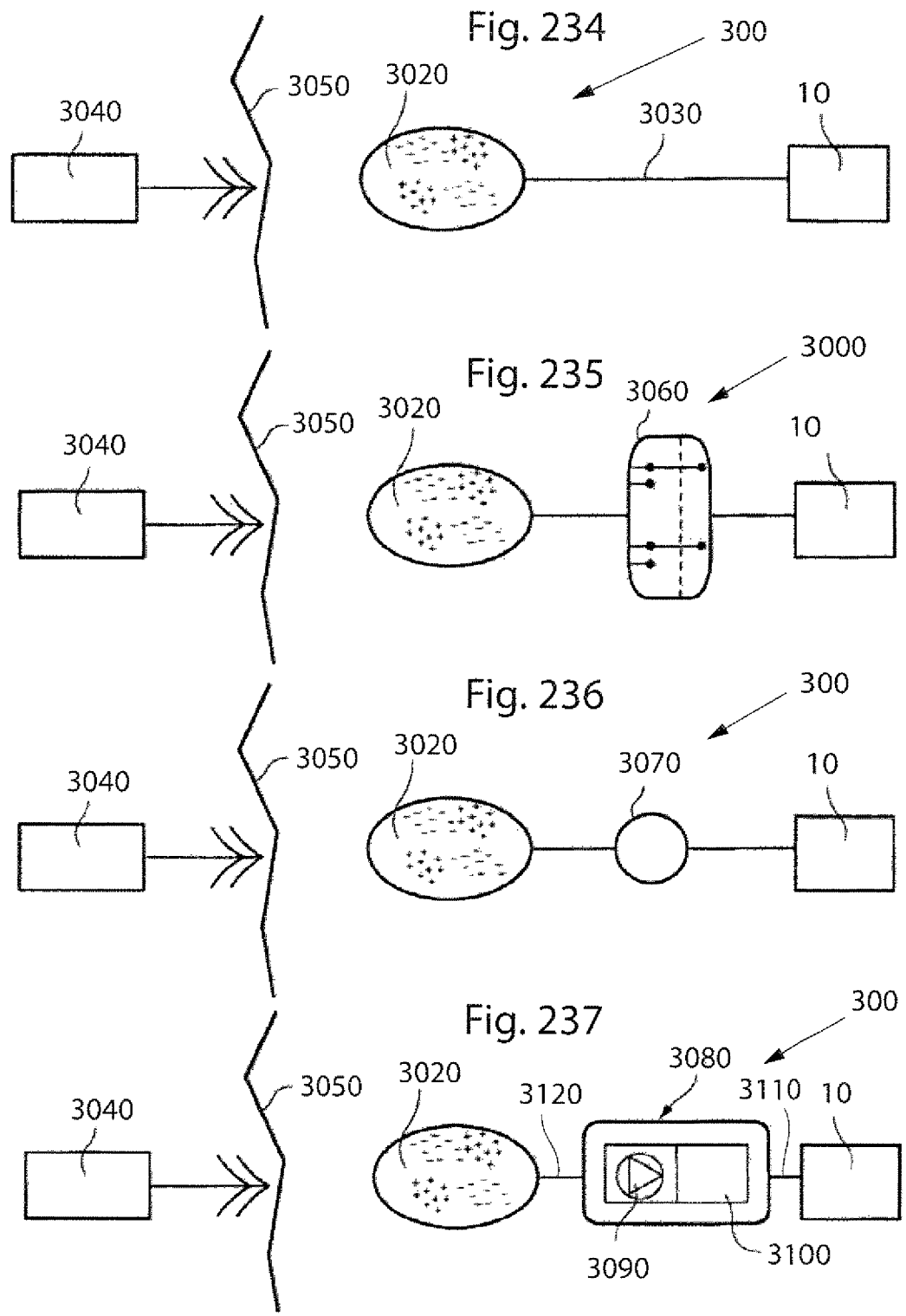

METHOD FOR CONTROLLING FLOW IN A BODILY ORGAN

This application is a continuation-in-part of International Application No. PCT/SE2008/000594, filed on Oct. 13, 2008, which claims the benefit of U.S. Provisional Application No. 60/960,716, filed on Oct. 11, 2007, and U.S. Regular application Ser. No. 12/285,794 now U.S. Pat. No. 8,696,543, filed Oct. 14, 2008, which claims the benefit of U.S. Provisional Application No. 60/960,716, filed on Oct. 11, 2007, and U.S. Regular application Ser. No. 12/285,809, filed on Oct. 14, 2008 which claims the benefit of U.S. Provisional Application No. 60/960,716, filed on Oct. 11, 2007, and International Application No. PCT/SE2008/000592, filed on Oct. 13, 2008, which claims the benefit of U.S. Provisional Application No. 60/960,716, filed on Oct. 11, 2007, and International Application No. PCT/SE2008/000590, filed on Oct. 13, 2008, which claims the benefit of U.S. Provisional Application No. 60/960,716, filed on Oct. 11, 2007, and U.S. Regular application Ser. No. 12/285,791, filed on Oct. 14, 2008, which claims the benefit of U.S. Provisional Application No. 60/960,716, filed on Oct. 11, 2007, and U.S. Regular application Ser. No. 12/285,792, filed on Oct. 14, 2008 now U.S. Pat. No. 8,795,153, which claims the benefit of U.S. Provisional Application No. 60/960,716, filed on Oct. 11, 2007, and U.S. Regular application Ser. No. 12/285,793, filed on Oct. 14, 2008, which claims the benefit of U.S. Provisional Application No. 60/960,716, filed Oct. 11, 2007, and U.S. Regular application Ser. No. 12/285,808, filed on Oct. 14, 2008, which claims the benefit of U.S. Provisional Application No. 60/960,716, filed Oct. 11, 2007, and International Application No. PCT/SE2008/000589, filed on Oct. 13, 2008, which claims the benefit of U.S. Provisional Application No. 60/960,716, filed Oct. 11, 2007, and International Application No. PCT/SE2008/000595, filed on Oct. 13, 2008, which claims the benefit of U.S. Provisional Application No. 60/960,716, filed Oct. 11, 2007, and International Application No. PCT/SE2008/000579, filed on Oct. 10, 2008, which claims the benefit of U.S. Provisional Application No. 60/960,716, filed Oct. 11, 2007 and U.S. Provisional Application No. 60/960,715, filed on Oct. 11, 2007 and U.S. Regular application Ser. No. 12/285,810, filed on Oct. 14, 2008 now abandoned, which claims the benefit of U.S. Provisional Application No. 60/960,716, filed Oct. 11, 2007, and International Application No. PCT/SE2008/000570, filed Oct. 10, 2008, which claims the benefit of U.S. Provisional Application No. Provisional Application No. 60/960,715, filed Oct. 11, 2007, and U.S. Provisional Application No. 60/960,716, filed on Oct. 11, 2007, and 60/960,918 filed on Oct. 19, 2007, and International Application No. PCT/SE2008/000577, filed on Oct. 10, 2008, which claims the benefit of U.S. Provisional Application No. 60/960,715, filed Oct. 11, 2007, and U.S. Provisional Application No. 60/960,716, filed on Oct. 11, 2007, and 60/960,918 filed on Oct. 19, 2007, and International Application No. PCT/SE2008/000583, filed on Oct. 10, 2008, which claims the benefit of U.S. Provisional Application No. 60/960,715, filed on Oct. 11, 2007, and U.S. Provisional Application No. 60/960,716, filed on Oct. 11, 2007, and International Application No. PCT/SE2009/051127, filed on Oct. 9, 2009, which claims the benefit of Swedish Regular Application No. 0802162-8, filed on Oct. 10, 2008, and International Application No. PCT/SE2008/000572, filed on Oct. 10, 2008, which claims the benefit of U.S. Provisional Application No. 60/960,715, filed Oct. 11, 2007, and U.S. Provisional Application No. 60/960,716, filed on Oct. 11, 2007, and International Application No. PCT/EP2008/008587, filed on Oct. 10, 2008, which claims the benefit of U.S. Provisional Application No. 60/960,715, filed Oct. 11, 2007, and U.S. Provisional Application No. 60/960,716, filed on Oct. 11, 2007, and U.S. Provisional Application No. 60/960,766, filed Oct. 12, 2007, and International Application No. PCT/EP2008/008588, filed on Oct. 10, 2008, which claims the benefit of U.S. Provisional Application No. 60/960,715, filed Oct. 11, 2007, and U.S. Provisional Application No. 60/960,716, filed on Oct. 11, 2007, and U.S. Provisional Application No. 60/960,764, filed Oct. 12, 2007, and International Application No. PCT/EP2008/008589, filed on Oct. 10, 2008, which claims the benefit of U.S. Provisional Application No. 60/960,715, filed Oct. 11, 2007, and U.S. Provisional Application No. 60/960,716, filed on Oct. 11, 2007, and U.S. Provisional Application No. 60/960,765, filed Oct. 12, 2007, and International Application No. PCT/SE2008/000584, filed on Oct. 10, 2008, which claims the benefit of U.S. Provisional Application No. 60/960,767, filed Oct. 12, 2007, and International Application No. PCT/SE2008/000573, filed on Oct. 10, 2008, which claims the benefit of U.S. Provisional Application No. 60/960,715, filed Oct. 11, 2007, and U.S. Provisional Application No. 60/960,716, filed on Oct. 11, 2007, and 60/960,918 filed on Oct. 19, 2007, and International Application No. PCT/EP2008/008586, filed on Oct. 10, 2008, which claims the benefit of U.S. Provisional Application No. 60/960,715, filed on Oct. 11, 2007, and U.S. Provisional Application No. 60/960,716, filed on Oct. 11, 2007, and U.S. Provisional Application No. 60/960,764, filed on Oct. 12, 2007, and U.S. Provisional Application No. 60/960,765, filed on Oct. 12, 2007, and U.S. Provisional Application No. 60/960,766, filed on Oct. 12, 2007, and U.S. Provisional Application No. 60/960,767, filed on Oct. 12, 2007, and U.S. Provisional Application No. 60/960,791, filed on 2007-10-15, and International Application No. PCT/EP2008/008590, filed on Oct. 10, 2008, which claims the benefit of U.S. Provisional Application No. 60/960,715, filed on Oct. 11, 2007, and U.S. Provisional Application No. 60/960,716, filed on Oct. 11, 2007, and U.S. Provisional Application No. 60/960,764, filed on Oct. 12, 2007, and U.S. Provisional Application No. 60/960,765, filed on Oct. 12, 2007, and U.S. Provisional Application No. 60/960,766, filed on Oct. 12, 2007, and U.S. Provisional Application No. 60/960,767, filed on Oct. 12, 2007, and U.S. Provisional Application No. 60/960,791, filed on Oct. 15, 2007, and International Application No. PCT/SE2009/051130, filed Oct. 9, 2009, which claims the benefit of Swedish Regular Application No. 0802137-0, filed on Oct. 10, 2008, and U.S. Provisional Application No. 61/227,810, filed on Jul. 23, 2007, each of which is incorporated herein by reference.

FIELD OF THE INVENTION

The present invention relates to controlling the flow of fluids and/or other bodily matter in bodily organs, and in particular, to methods for controlling the flow of fluids and/or other bodily matter in lumens formed by tissue walls of bodily organs, such as (but not limited to) the esophagus, stomach, intestines, urine bladder, urethra, ureter, renal pelvis, blood vessels, aorta, corpus cavernosum, exit veins of erectile tissue, uterine tube, vas deferens and bile duct.

BACKGROUND OF THE INVENTION

There are diseases that prevent a patient from maintaining normal control of the flow of fluids and/or other bodily matter in a lumen of a bodily organ. (The term "patient" generally includes human beings, but may also include animals.) For example, a patient suffering from urinary incontinence, which is a common disease that is very embarrassing to a patient, typically occurs where the patient has lost full control of urine flow in the urethra because of a malfunctioning of the urethral sphincter. Anal incontinence often occurs because of a malfunctioning of the anal sphincter, which causes an uncontrolled drainage of fecal matter through the anus. Impotence is typically due to an inability to sufficiently reduce blood flow from the penis so that an erection can be achieved. Reflux disease is typically due to a malfunctioning of the cardia, which causes stomach acids to be regurgitated into the esophagus when the stomach wall moves during digestion.

One prior solution to the problem of malfunctioning sphincters has been to implant an artificial sphincter that replaces a malfunctioning sphincter. A variety of artificial sphincters have been used in the past. These artificial sphincters have included cuffs, clamping elements or inflatable bands that are applied externally around the bodily organ that is connected to the malfunctioning sphincter.

For example, U.S. Pat. No. 3,750,194 discloses a hydraulic cuff applied around the urethra of a patient suffering from urinary incontinence Hydraulic fluid flowing to the hydraulic cuff causes the cuff to squeeze the urethra and restrict fluid flow through it.

U.S. Pat. No. 6,074,341 discloses a mechanical device in the form of a loop member that is applied around a bodily organ to replace the organ's missing or damaged sphincter. The loop member includes a wire which is used to constrict the organ in question to close the lumen therein.

A disadvantage common to all prior artificial sphincters is that hard fibrosis may form around the artificial sphincter over time and may cause malfunction of the artificial sphincter. Thus, the formed fibrosis may sooner or later become a hard fibrotic layer which may make it difficult for the artificial sphincter to work.

Another more serious disadvantage is that the element that constricts, clamps or restricts a bodily organ may injure the tissue wall of the organ. Thus, a consequence of the element's constricting action on the organ is that the element might erode into the organ over time, and in a worst case, penetrate the constricted wall portion of the organ. In addition, blood circulation in the constricted tissue wall portion of the organ is eventually hampered by the pressure exerted by the element, so that poor blood circulation, or worse, no blood circulation results in deterioration of the constricted tissue.

One solution to prevent tissue deterioration due to poor blood circulation could be to apply two or more separately operating constricting elements along respective tissue wall portions of the organ and operate the elements sequentially, whereby each tissue wall portion would have time to recover, i.e., restore normal blood circulation while one of the other tissue wall portions is constricted. However, an apparatus devised in accordance with this solution would have several disadvantages. First, the apparatus would require a large amount of space, making it impractical to implant. Second, the operation of the apparatus in moving the constricting elements between constricting and non-constricting positions day and night would require a large power supply. Such a large power supply would necessitate the implantation of a very large, high capacity battery and/or a sophisticated system for continuous wireless transmission of energy from outside the patient's body for frequent charging of an implanted rechargeable battery. Thus, because of its large size and high power consumption, the apparatus would be impractical or even unrealistic. Third, a sophisticated control system would be necessary to control the moving elements. Finally, such a complicated apparatus of the type described above would significantly add to the costs of treating a malfunctioning sphincter.

Another solution to the problem of malfunctioning sphincters that has been previously used has been the electrical stimulation of the sphincter, to restore its normal function, i.e., the contraction and closing of its associated lumen. This solution would work where the normal sphincteric function is somewhat reduced and has not completely ceased. European Patent EP 1004330 A1 discloses an example of such a solution, in which electric pulses are delivered to the lower esophageal sphincter of a patient suffering from reflux disease to minimize reflux. However, the esophageal sphincter has to be continuously stimulated with electric pulses to keep it closed, except when the patient eats, which may result in a decreased stimulation effect over time. An even more serious drawback to this solution is that the continuous stimulation over time might cause tissue deterioration due to poor blood circulation.

The use of electric stimula to restore the sphincteric function of a malfunctioning sphincter is only possible if the sphincter responds sufficiently to the stimula, i.e., closes the organ lumen in question. In cases where the sphincteric function of a sphincter has completely ceased, or the sphincter has been removed from the patient's body, electric stimulation cannot be employed.

Electric stimulation of bodily organs other than sphincters can only insignificantly affect the flow in the organ in question. For example, where the organ is the small intestine of an anal incontinent patient, electric stimulation of the small intestine affects fecal flow but could not possibly fully close the fecal passageway, at least not by employing the necessary low stimulation intensities that are harmless to the human body.

Intestinal Dysfunction

There are diseases that prevent a patient from maintaining normal control of the flow of intestinal contents in the patient's intestines, such as anal incontinence, reduced peristaltic function of the intestines and constipation intestines. (The term "patient" generally includes human beings, but may also include animals. Also, the term "intestines" generally includes small bowel, large bowel, and anus. This means that the term "intestinal passageway" includes the entire passage from the stomach to the anal orifice.) In particular, anal incontinence is a widespread disease and often occurs because of a malfunctioning of the anal sphincter, which causes an uncontrolled drainage of fecal matter through the anus.

Several kinds of sphincter plastic surgery are used today to remedy anal incontinence, i.e disability to close the anal sphincter. There is a prior manually operated sphincter system in an initial clinical trial phase where a hydraulic sphincter system connected to an elastic reservoir (balloon) placed in the scrotum is developed. A disadvantage of this system is that thick, hard fibrosis is created around the reservoir by pump movements making the system useless sooner or later. Another disadvantage is that the use of hydraulic fluid always entails a risk of fluid leaking from the implanted hydraulic system.

Furthermore, it is a rather complicated task to manually pump the reservoir when defecation is needed. U.S. Pat. No. 5,593,443 discloses hydraulic anal sphincter under both reflex and voluntary control. An inflatable artificial sphincter with the pump system in scrotum is disclosed in U.S. Pat. No. 4,222,377.

U.S. Pat. No. 4,739,764 discloses a method for treating anal incontinence by electric stimulation of nerves connected to muscles controlling the anal sphincter. The function of the anal sphincter is affected by applying electric pulse trains on the nerves. One general prior solution to the problem of malfunctioning sphincters of a human body has been to implant an artificial sphincter that replaces a malfunctioning sphincter. A variety of artificial sphincters have been used in the past. These artificial sphincters have included cuffs, clamping elements or inflatable bands that are applied externally around the bodily organ that is connected to the malfunctioning sphincter.

For example, U.S. Pat. No. 6,074,341 discloses a mechanical device in the form of a loop member that is applied around a bodily organ to replace the organ's missing or damaged sphincter. The loop member includes a wire which is used to constrict the organ in question to close the lumen therein.

A disadvantage common to all prior artificial sphincters is that hard fibrosis may form around the artificial sphincter over time and may cause malfunction of the artificial sphincter. Thus, the formed fibrosis may sooner or later become a hard fibrotic layer which may make it difficult for the artificial sphincter to work.

Another more serious disadvantage of the prior artificial sphincters if used for replacing malfunctioning anal sphincters is that the element of the artificial sphincter that constricts, clamps or restricts the intestines may injure the tissue wall of the intestines. Thus, a consequence of the element's constricting action on the intestines is that the element might erode into the intestines over time, and in a worst case, penetrate the constricted wall portion of the intestines. In addition, blood circulation in the constricted tissue wall portion of the intestines is eventually hampered by the pressure exerted by the element, so that poor blood circulation, or worse, no blood circulation results in deterioration of the constricted tissue.

One solution to prevent tissue deterioration due to poor blood circulation could be to apply two or more separately operating constricting elements along respective tissue wall portions of the intestines and operate the elements sequentially, whereby each tissue wall portion would have time to recover, i.e., restore normal blood circulation while one of the other tissue wall portions is constricted. However, an apparatus devised in accordance with this solution would have several disadvantages. First, the apparatus would require a large amount of space, making it impractical to implant. Second, the operation of the apparatus in moving the constricting elements between constricting and non-constricting positions day and night would require a large power supply. Such a large power supply would necessitate the implantation of a very large, high capacity battery and/or a sophisticated system for continuous wireless transmission of energy from outside the patient's body for frequent charging of an implanted rechargeable battery. Thus, because of its large size and high power consumption, the apparatus would be impractical or even unrealistic. Third, a sophisticated control system would be necessary to control the moving elements. Finally, such a complicated apparatus of the type described above would significantly add to the costs of treating a malfunctioning sphincter.

Another solution to the problem of malfunctioning sphincters that has been previously used has been the electric stimulation of the sphincter, to restore its normal function, i.e., the contraction and closing of its associated lumen. This solution would work where the normal sphincteric function is somewhat reduced and has not completely ceased. European patent application 1004330 A1 discloses an example of such a solution, in which electric pulses are delivered to the lower esophageal sphincter of a patient suffering from reflux disease to minimize reflux. However, the esophageal sphincter has to be continuously stimulated with electric pulses to keep it closed, except when the patient eats, which may result in a decreased stimulation effect over time. An even more serious drawback to this solution is that the continuous stimulation over time might cause tissue deterioration due to poor blood circulation.

The use of electric stimula to restore the sphincteric function of a malfunctioning anal sphincter is only possible if the anal sphincter responds sufficiently to the stimula, i.e., closes the intestinal passageway of the intestines. In cases where the sphincteric function of an anal sphincter has completely ceased, or the anal sphincter has been removed from the patient's body, electric stimulation cannot be employed.

Electric stimulation of intestinal organs other than anal sphincters can only insignificantly affect the flow of intestinal contents. For example, it is true that electric stimulation of the small intestine of an anal incontinent patient affects flow of intestinal contents, but could not possibly fully close the intestinal passageway, at least not by employing the necessary low stimulation intensities that are harmless to the human body.

Intestinal dysfunction may also involve disability of controlling the muscle that contracts the bowels, colon or rectum to provide transportation of the content thereof. Such a disability usually causes constipation. In particular paralysed patients may suffer from constipation.

Urinary Dysfunction

There are different kinds of urinary dysfunction that prevent a patient from maintaining normal control of the flow of urine in the patient's urethra, ureter, renal pelvis or bladder. For example, overflow incontinence, stress incontinence and urge incontinence. (The term "patient" generally includes human beings, but may also include animals.)

Overflow incontinence involves disability of controlling the muscle that contracts the urine bladder. In particular partially paralysed patients may suffer from this condition. Stress incontinence involves disability to keep the urethral sphincter completely closed. In a urinary stress incontinent patient the urethral sphincter is unable to prevent urine from being expelled from the bladder during transient increase in intra-abdominal pressure, which can be caused by sneezing, coughing or laughing, or by lifting heavy goods. Urge incontinence involves spontaneous activity of the bladder causing a compelling feeling of the patient that the bladder needs to be emptied, although the bladder maybe contains little urine.

Urinary stress and urge incontinences are widespread diseases. Although some people suffering from these diseases are helped through training of the muscles in the pelvic floor, too many have severe problems with urine leakage. Many different implant devices have been tried to remedy this kind of urinary incontinence. For example, there is a prior manually operated urinary incontinence treatment apparatus having an artificial hydraulic sphincter device engaging the urethra and connected to an elastic reservoir implanted in the scrotum or in the region of the labia majora. A disadvantage of this prior apparatus is that over time hard fibrosis is developed around the reservoir, which may cause malfunction of pumping components. Furthermore, it is a rather complicated task to manually squeeze the elastic implanted reservoir to pump hydraulic fluid to open the sphincter device when the patient needs to urinate. In particular women can get their fingers wet. The created fibrosis will sooner or later become a hard fibrotic layer, which may make it even more difficult to pump the reservoir. Yet a further disadvantage is that the use of hydraulic fluid always entails a risk of fluid leaking from implanted hydraulic components.

A prior hydraulic apparatus designed to compress the urethra is disclosed in U.S. Pat. No. 5,520,606. A prosthetic sphincter with an inflatable cuff, which surrounds the urethra or encloses it on two sides, is disclosed in for example U.S. Pat. Nos. 4,571,749 and 4,222,377. U.S. Pat. No. 4,969,474 discloses a hydraulic method for treating both men and women having urinary stress incontinence in the same way. The apparatus of U.S. Pat. No. 4,969,474 includes a reservoir containing fluid and an inflatable compression means designed to compress the urethra without risking tissue loss or necrosis to occur. An artificial hydraulically operated urethral sphincter employing an external magnet to achieve closure of the urethral cuff is disclosed in U.S. Pat. No. 5,562,598.

A prior mechanical prosthetic sphincter disclosed in U.S. Pat. No. 4,619,245 comprises a manually controllable actuating component for implanting at a convenient location in the patient's body.

U.S. Pat. No. 4,739,764 discloses a method for treating urinary stress incontinence by electric stimulation of an inferior somatic nerve connected to the urethral sphincter. The function of the urethral sphincter is affected by applying electric pulse trains on the somatic nerve.

U.S. Pat. No. 6.061,596 discloses a system for regularly conditioning and training the pelvic muscles of a urinary stress or urge incontinent patient with electric stimulation so as to restore voluntary control to the patient. The pelvic muscles are stimulated, i.e. conditioned, for 15-60 minutes each day using intermittent trains of electrical pulses. Accordingly, during the rest of each day, i.e. at least 23 hours, the pelvic muscles are not stimulated.

U.S. Pat. Appl. Publication No. 2002/0062060 A1 discloses a urinary stress or urge incontinence treatment device, which is sensor controlled and is normally not in operation unless signals from the sensors indicate a condition that is likely to cause involuntary urine flow. The sensors generate signals responsive to motion or to intravesical or abdominal pressure, or to urine volume in the bladder. The signals from the sensors are indicative of possible incontinence that may occur due to coughing, laughing, or other strain or motion of abdominal muscles.

One general prior solution to the problem of malfunctioning sphincters of a human body has been to implant an artificial sphincter that replaces a malfunctioning sphincter. A variety of artificial sphincters have been used in the past. These artificial sphincters have included cuffs, clamping elements or inflatable bands that are applied externally around the bodily organ that is connected to the malfunctioning sphincter.

For example, U.S. Pat. No. 3,750,194 discloses a hydraulic cuff applied around the urethra of a patient suffering from urinary incontinence. Hydraulic fluid flowing to the hydraulic cuff causes the cuff to squeeze the urethra and restrict fluid flow through it.

U.S. Pat. No. 6,074,341 discloses a mechanical device in the form of a loop member that is applied around a bodily organ to replace the organ's missing or damaged sphincter. The loop member includes a wire which is used to constrict the organ in question to close the lumen therein.

A disadvantage common to all prior artificial sphincters is that hard fibrosis may form around the artificial sphincter over time and may cause malfunction of the artificial sphincter. Thus, the formed fibrosis may sooner or later become a hard fibrotic layer which may make it difficult for the artificial sphincter to work.

Another more serious disadvantage of the prior artificial sphincters if used for replacing malfunctioning urethral sphincters is that the element that constricts, clamps or restricts the urethra may injure the tissue wall of the urethra. Thus, a consequence of the element's constricting action on the urethra is that the element might erode into the urethra over time, and in a worst case, penetrate the constricted wall portion of the urethra. In addition, blood circulation in the constricted tissue wall portion of the urethra is eventually hampered by the pressure exerted by the element, so that poor blood circulation, or worse, no blood circulation results in deterioration of the constricted tissue.

One solution to prevent tissue deterioration due to poor blood circulation could be to apply two or more separately operating constricting elements along respective tissue wall portions of the urethra and operate the elements sequentially, whereby each tissue wall portion would have time to recover, i.e., restore normal blood circulation while one of the other tissue wall portions is constricted. However, an apparatus devised in accordance with this solution would have several disadvantages. First, the apparatus would require a large amount of space, making it impractical to implant. Second, the operation of the apparatus in moving the constricting elements between constricting and non-constricting positions day and night would require a large power supply. Such a large power supply would necessitate the implantation of a very large, high capacity battery and/or a sophisticated system for continuous wireless transmission of energy from outside the patient's body for frequent charging of an implanted rechargeable battery. Thus, because of its large size and high power consumption, the apparatus would be impractical or even unrealistic. Third, a sophisticated control system would be necessary to control the moving elements. Finally, such a complicated apparatus of the type described above would significantly add to the costs of treating a malfunctioning sphincter.

Another solution to the problem of malfunctioning sphincters that has been previously used has been the electric stimulation of the sphincter, to restore its normal function, i.e., the contraction and closing of its associated lumen. This solution would work where the normal sphincteric function is somewhat reduced and has not completely ceased. European patent application 1004330 A1 discloses an example of such a solution, in which electric pulses are delivered to the lower esophageal sphincter of a patient suffering from reflux disease to minimize reflux. However, the esophageal sphincter has to be continuously stimulated with electric pulses to keep it closed, except when the patient eats, which may result in a decreased stimulation effect over time. An even more serious drawback to this solution is that the continuous stimulation over time might cause tissue deterioration due to poor blood circulation.

The use of electric stimula to restore the sphincteric function of a malfunctioning urethral sphincter is only possible if the sphincter responds sufficiently to the stimula, i.e., closes the urethra. In cases where the sphincteric function of a urethral sphincter has completely ceased, or the urethral sphincter has been removed from the patient's body, electric stimulation cannot be employed.

Electric stimulation of urinary organs other than urethral sphincters can only insignificantly affect the flow of urine. For example, it is true that electric stimulation of the urethra affects flow of urine, but could not possibly fully close the relatively stiff urethra, at least not by employing the necessary low stimulation intensities that are harmless to the human body.

Obesity

In the past, obese patients have been treated by gastric reduction surgery to restrict the food intake of the patient. At present, two gastric restriction procedures for treating obesity are most commonly performed, namely Adjustable Gastric Banding (AGB) and Vertical Banded Gastroplasty (VBG).

In AGB, a constricting band is placed completely around an obese patient's surgically intact stomach near the upper end thereof, just below the junction of stomach and esophagus, to restrict the food intake of the patient. As the band constricts the stomach, a small gastric pouch, or smaller compartment of the stomach, is formed above the band and a reduced permanent stoma in the stomach. The idea being that a small amount of food filling the small pouch causes the patient to sense fullness, i.e., satiety. An adjustment means enables a minor post-operation adjustment of the band and a corresponding adjustment of the size of the stoma opening. Typically the adjustment means includes an inflatable cavity in the band and a subcutaneously implanted injection port in fluid connection with the inflatable cavity. When needed an injection needle may penetrate the patient's skin and pass into the injection port to add fluid to the cavity to reduce the stoma, or withdraw fluid from the cavity to enlarge the stoma. Examples of AGB are disclosed in U.S. Pat. No. 4,592,339 and European Pat. No. 0611561, In VBG, typically the stomach is stapled vertically with four rows of linear staples, which compartmentalize the stomach into an elongate proximal smaller compartment adjacent the esophagus and a distal larger compartment, so that the volume of the smaller compartment is about 10% of the volume of the stomach. A circular hole is punched-out in the stomach at the lower end of the rows of linear staples and several circular rows of staples are placed on the stomach around the circular hole. A band is placed through the circular hole and is secured around the stomach, whereby the band defines a narrow outlet opening from the smaller compartment into the larger compartment of the stomach. Once secured, the band prevents the stomach from stretching at the outlet opening, which results in that the outlet opening over time maintains its initial small diameter. Food that the patient takes in is held up in the smaller compartment causing the sensation of fullness. Then, the food empties slowly through the outlet opening into the larger compartment where digestion takes place normally. Examples of VBG are disclosed in U.S. Pat. Nos. 5,345,949 and 5,549,621.

The operation described above called "VBG" encompasses a group of operation variants. Thus, the staples may be replaced by stitches or any other suitable means that secure the front and back walls of the stomach together, such as clamping bars. The stomach may be cut between the four rows of linear staples, which eliminates the need for punching out a circular hole for the band, because the band can be placed through the cut at the lower end of the of the staple rows. Also, the cut between the four rows of linear staples may expand into a small hole for receiving the band at the lower end of the of the staple rows. Alternatively, the band may not be placed through any cut or punched-out hole in the stomach, but may be attached to the front and back walls of the stomach by means of stitches or the like.

There are few complications associated with VBG. However, it is important that the patient very carefully chews food completely before swallowing it, so that food pieces collected in the smaller compartment of the stomach are able to pass through the narrow outlet opening of the smaller compartment. If food pieces were stuck in the outlet opening it might cause the patient to vomit and feel sick. In such a case the patient should have to visit a doctor or nurse. Another complication associated with VBG is that the patient may suffer from acid stomach reflux at night. These complications are also experienced with AGB.

Sexual Dysfunction

Male sexual impotence is a widespread problem. Many different solutions to this problem have been tried. A main solution currently practiced and disclosed in for instance U.S. Pat. Nos. 5,437,605 and 4,841,461 is to implant a hydraulic inflatable/contractible silicon prosthesis in the cavities of the corpora cavernosa of the patient's penis. In fluid connection with this prosthesis is a reservoir implanted in the scrotum. By manual pumping action the prosthesis is filled with fluid from the reservoir to effect erect condition or is emptied of fluid, which returns to the reservoir, to effect flaccid condition.

However, there are several more or less severe disadvantages of this main solution. Above all, the penis is more or less damaged by the operation and it is practically impossible to reverse the operation. Another disadvantage is that rather strong forces act against this implanted prosthesis resulting in a significant risk of the prosthesis being broken. A further disadvantage is that hard fibrosis created around the reservoir over time may cause malfunction of pumping components. Thus, the created fibrosis will sooner or later become a hard fibrotic layer which may make it difficult to pump the reservoir. Yet a further disadvantage is that the use of hydraulic fluid always entails a risk of fluid leaking from the prosthesis. Furthermore, it is a rather complicated task to manually pump the reservoir when erection is desired.

Another solution is to inject a substance in the vein system to achieve erection. However, injections are painful and complicated for the patient.

Yet another solution to achieve erection is to restrict the blood flow leaving the penis. For example, U.S. Pat. No. 4,829,990 discloses two hydraulically operated inflatable cuffs wrapped around the respective crura. Again, a disadvantage of such a solution is that it entails a risk of hydraulic fluid leaking from the cuffs.

Another example of the solution to restrict the penile blood flow is found in U.S. Pat. No. 4,828,544, which discloses an artificial fistula system surgically implanted and providing a primary fistula between the femoral artery and the femoral vein and a secondary fistula for leading blood from the the primary fistula to the penis. An inflatable balloon engages the primary fistula between the secondary fistula and the vein. The balloon is in fluid connection with a manually compressible reservoir implanted in the scrotum. Besides the risk of fluid leaking from the balloon, a further disadvantage of this latter example is that it requires delicate surgery.

Yet another example of the solution to restrict the penile blood flow is found in EP 1253877 B1, which discloses an adjustable restriction device that directly clamps a portion of the normal penile tissue or the prolongation thereof of the patient. There is an adjustment device that mechanically adjusts the restriction device to temporarily contract the portion of the normal penile tissue or the prolongation thereof to restrict the blood flow leaving the penis, when the patient desires to achieve erection.

A serious disadvantage of the prior art devices that constrict clamp the patient's penile tissue to restrict the exit penile blood flow is that the element that constricts, clamps or restricts the penile portion may injure the tissue wall of the penile portion. Thus, a consequence of the element's constricting action on the penile portion is that the element might erode into the penile portion over time, and in a worst case, penetrate the constricted penile portion of the penile portion.

A lot of attention has been given to male sexual disorders including impotence. This has lead to the availability of a number of treatment options for males, including pharmaceuticals such as Viagra.

In contrast, there is a lack of therapies for treating Female Sexual Dysfunction (FSD). Female sexual dysfunction such as disorders of sexual desire, arousal or orgasm is a common problem, affecting up to 43% of all women (Pauls et al, Obstret Gynecol Surv, 2005 60(3):3196-205). Both biological and psychological factors contribute to FSD.

Available treatments include psychological counselling to pairs or individuals. Where side effects of medication contribute to FSD, altering medication or dosage may help. However, there is a need for improved treatment of FSD.

During sexual arousal of the female, vasocongestion of the pelvic region leads to engorgement of the genitalia with blood leading to swelling of the external genitalia and erection of the clitoris. This is accompanied by lubrication of the vagina. In the female, the corpus cavernosa are two paired symmetrical extensions of the clitoris and engorgement of these is an important step during sexual arousal of the female.

Female sexual arousal is enhanced by stimulation of the vulva, by touching or caressing the clitoris, which for example contributes to arousal.

Hand held or other external devices that stimulate the clitoris are well-known. For example U.S. Pat. No. 7,081,087B2 discloses a sexual aid that vibrates. There has been proposed a device for treating FSD that applies a vacuum or suction to the clitoris. This will create a negative pressure that promotes the engorgement of the clitoris with blood (Hovland Claire, U.S. Pat. No. 6,464,653B1). The proposed device is implanted. An advantage with the implantation of a stimulating device is that it is always at hand and can conveniently be switched on before sexual intercourse. Hand held devices are more likely to cause embarrassment.

The local administration of prostaglandins to the female genitalia in order to treat FSD has been described in U.S. Pat. No. 6,486,207. The implantation of an electrode that stimulates the peripheral nerves of the vulva has been described (US 2008/0103544).

Pregnancy Control

Many women have difficulties getting pregnant. Old age when trying to get pregnant with lower fertility rate is one main reason. Artificial insemination is one way of promoting pregnancy that has increased dramatically in recent years. However, this method is not always easy and safe and is furthermore very expensive, particularly when repeated, which often is the case. Although uterus is prepared to accommodate an embryo for as long as approximately three days it seems that the right timing is of outmost importance when fertility goes down. Conceptive drugs may cause blood clots and other serious complications.

On the other hand pregnancy may be undesired. In this case, a women may choose among a variety of known birth control devices, for example contraceptive or antifertility agents, or pessaries.

Blood Flow Control

There are diseases that prevent a patient from maintaining normal control of the flow of blood in the vascular system. One example is a patient suffering from high blood pressure in the lungs. This state may if untreated cause gradual degradation of the normal lung function. Another example is a patient with an abnormal distribution of the blood flow. Treating high blood pressure locally or redistributing blood may be useful in many applications.

A disadvantage common to all prior artificial moving implants is that hard fibrosis may form around the artificial moving implant over time and may cause malfunction of the artificial moving implant. Thus, the formed fibrosis may sooner or later become a hard fibrotic layer which may make it difficult for the artificial moving implant to work.

Another more serious disadvantage is that elements of the artificial moving implants that constricts, clamps or constricts a blood vessel may injure the wall of the blood vessel. Thus, a consequence of the element's constricting action on the blood vessel is that the element might erode into the blood vessel over time, and in a worst case, penetrate the constricted wall portion of the blood vessel.

One solution to prevent harmful effects from the pressure of the artificial implant is to apply two or more separately operating constricting elements along the blood vessel and operate the elements sequentially on respective wall portions of the blood vessel, whereby each blood vessel portion would have time to recover, while one of the other part of the blood vessel is constricted. However, an apparatus devised in accordance with this solution would have several disadvantages. First, the apparatus would require a large amount of space, making it impractical to implant. Second, the operation of the apparatus in moving the constricting elements between constricting and non-constricting positions day and night would require a large power supply. Such a large power supply would necessitate the implantation of a very large, high capacity battery and/or a sophisticated system for wireless transmission of energy from outside the patient's body for frequent charging of an implanted rechargeable battery. Thus, because of its large size and high power consumption, the apparatus would be impractical or even unrealistic. Third, a sophisticated control system would be necessary to control the moving elements. Finally, such a complicated apparatus of the type described above would significantly add to the costs of treatment by an artificial implant.

Vascular Aneurysm

An aneurysm (or aneurysm) is a localized, blood-filled dilation (balloon-like bulge) of a blood vessel caused by disease or weakening of the vessel wall. Aneurysms most commonly occur in arteries at the base of the brain (the circle of Willis) and in the aorta (the main artery coming out of the heart), a so-called aortic aneurysm. The bulge in a blood vessel can burst and lead to severe internal hemorrhage and death at any time. The larger an aneurysm becomes, the more likely it is to burst and since aneurysms naturally grow, given enough time they will inevitably reach the bursting point if undetected.

Given the severe consequences of an aneurysm, screening is now commonly performed in order to early detect the presence of an aneurysm. In case of an aortic aneurysm the blood-filled dilation is commonly located in the abdomen close to the Y-bifurcation extending to the legs. At this location the aorta is typically about 2.5 centimeters wide, which can be measured for example using ultra-sonic or X-ray based measuring devices.

Existing treatment when detecting an aortic aneurysm includes implantation of a stent around the vessel using open surgery. An alternative surgical procedure is to implant a tube from the groin and guide the stent via arterial femoralis into position where the blood flow can by-pass the aortic aneurysm via the tube. The latter treatment has the drawback that an embolism is easily formed when alien material is introduced into the bloodstream.

Hence, there exists a need for a treatment of aortic aneurysm that is more robust and which brings about fewer complications.

Male Contraception

A common route of male contraception is occlusion of vas deferens (the sperm transporting duct). Vasectomy is a surgical intervention to cut vas deferens and is most frequently a confinement to permanent sterility. More recently, other alternatives have become available by the provision of devices to be inserted into vas deferens and obtain a sealing effect. One such technique is described in U.S. Pat. No. 6,513,528 that relates to a set of silicone plugs for insertion into vas deferens. However, even if this technology represents a possibility to reverse the individual to fertility, it is also associated with side effects, such as sperm antibody formation. It is therefore a need for a more gentle technique to obtain controlled male contraception which admits reversibility with minimal affection of body functions.

Gallstones

Cholelithiasis (gallstones) is the presence or formation of gallstones in the biliary tract. It can cause intense pain and is potentially dangerous. It is a common medical problem, affecting 10 to 15 percent of the population.

Bile is formed in the gallbladder and consists of water, cholesterol, fats, bile salts, proteins, and bilirubin. The main function is to secrete bile salts that emulsify dietary fats and to secrete bilirubin, which is a waste product. Bile is produced by hepatocytes of the liver and transported to the gall bladder were it is stored for release into the duodenum. Bile is transported through a system of ducts. The ducts include the hepatic ducts, which carry bile out of the liver, the cystic duct, which takes bile to and from the gallbladder, and the common bile duct, which takes bile from the cystic and hepatic ducts to the small intestine. These three ducts together with the sphincters that control them are referred to herein as the "biliary duct" or the "biliary ducts". Biliary ducts has smooth muscle tissue, that enables the ducts to contract.

Gallstones may form when cholesterol or bilirubin precipitates into hard aggregates. Gallstones can block the normal flow of bile if they move from the gallbladder and lodge in any of the ducts that carry bile from the liver to the small intestine Symptoms of blocked bile ducts include intense pain and are often referred to as a gallbladder "attack" because they occur suddenly. If any of the biliary ducts remain blocked by gallstones for a significant period of time, severe damage or infection can occur in the gallbladder, liver, or pancreas. Left untreated, the condition can be fatal.

The most common treatment for gallstones is the complete removal of the gallbladder (cholecystectomy). Present data suggest that the gallbladder is a nonessential organ and that patient can live a normal life without the gallbladder, as bile can instead reach the intestines via direct flow from the liver through the hepatic ducts into the common bile duct and into the small intestine, instead of being stored in the gallbladder.

Removal of the call bladder is usually performed using laparascopical procedures. However, open surgery is necessary in about 5 percent of gallbladder operations. Recovery from open surgery usually requires 3 to 5 days in the hospital and several weeks at home.

A serious disadvantage with the current treatment is the risk for serious damage to the the bile duct during surgery. This is a serious problem and requires additional surgery.

Another disadvantage is that a high percentage of patients suffer from diarrhea permanently or for a long time after removal of the gall bladder.

BRIEF SUMMARY OF THE INVENTION

The object of the present invention is to provide a method for controlling the flow of fluids and/or other bodily matter in lumens formed by tissue walls of bodily organs so as to at least substantially or even completely eliminate the injured tissue wall problems that have resulted from implanted prior art devices that constrict such bodily organs. The term "bodily organ" includes (but not limited to) the esophagus, stomach, intestines, urine bladder, urethra, ureter, renal pelvis, blood vessels, aorta, corpus cavernosum, exit veins of erectile tissue, uterine tube, vas deferens and bile duct.

In accordance with this object of the present invention, there is provided a method for controlling the flow of fluids and/or other bodily matter in a lumen that is formed by the tissue wall of a bodily organ, the method comprising:

a) gently constricting at least one portion of the tissue wall to influence the flow in the lumen, or b) stimulating at least one portion of the tissue wall to cause contraction of the wall portion to further influence the flow in the lumen.

In accordance with a most beneficial embodiment of the invention, the method comprises:

a) gently constricting the tissue wall portion to influence the flow in the lumen, and b) stimulating the constricted wall portion to cause contraction of the wall portion to further influence the flow in the lumen.

The present invention provides an advantageous combination of the method steps (a) and (b), which results in a two-stage influence on the flow of fluids and/or other bodily matter in the lumen of a bodily organ. Thus, applying a relatively weak force against the wall portion gently constricts the tissue wall and the constricted wall portion is stimulated to achieve the desired final influence on the flow in the lumen. The phrase "gently constricts a portion of the tissue wall" is to be understood as constricting the wall portion without substantially hampering the blood circulation in the tissue wall.

Preferably, step (b) is performed by intermittently and individually stimulating different areas of the wall portion. Such an intermittent and individual stimulation of different areas of the wall portion of the organ allows tissue of the wall portion to maintain over time substantially normal blood circulation.

The method of the present invention can be practiced on any place on any kind of bodily organs, in particular, but not limited to, tubular bodily organs, which is a significant advance in the art, as compared with prior stimulation devices that are confined to electric stimulation of malfunctioning sphincters. Preferably, the constriction step (a) and stimulation step (b) are performed independently of each other. Steps (a) and (b) may be performed simultaneously. Optionally, step (b) may or may not be performed while step (a) is performed.

Initially, the constriction of the wall portion can be calibrated by stimulating the wall portion while adjusting the constriction of the wall portion until the desired restriction of the flow in the lumen is obtained.

Flow Restriction

It should be understood that any embodiment or part of embodiment disclosed below in connection with flow restriction for the constriction and stimulation devices combined in the constriction/stimulation unit could be used for the separate constriction device and separate stimulation device, where applicable. The method of the present invention is well suited for restricting the flow of fluids and/or other bodily matter in the lumen of a bodily organ. Thus, in a principal embodiment of the invention, the wall portion is constricted, so that the flow in the lumen at least is restricted and the constricted wall portion is stimulated to at least further restrict the flow in the lumen. Specifically, the wall portion is constricted to a constricted state, in which the blood circulation in the constricted wall portion is substantially unrestricted and the flow in the lumen is at least restricted, and the constricted wall portion is stimulated when it is in the constricted state to at least further restrict the flow in the lumen.

The constriction step (a) and stimulation step (b) are suitably performed to constrict and stimulate the wall portion to an extent that depends on the flow restriction that is desired to be achieved in a specific application of the method of the invention. Thus, in accordance with a first flow restriction option, step (a) is performed by constricting the wall portion, so that the flow in the lumen is restricted but not stopped, and step (b) is performed by stimulating the constricted wall portion to cause contraction thereof, so that the flow in the lumen is further restricted but not stopped. The method may further comprise sensing a physical parameter of the patient and adjusting the intensity of the stimulation of the wall portion in response to the sensed parameter.

In accordance with a second flow restriction option, step (a) is performed by constricting the wall portion, so that the flow in the lumen is restricted but not stopped, and step (b) is performed by stimulating the constricted wall portion to cause contraction thereof, so that the flow in the lumen is stopped.

When using the method of the invention in accordance with the first or second options, the method may further comprise (c) ceasing stimulating the wall portion to increase or allow the flow in the lumen and (d) releasing the wall portion to restore the flow in the lumen.

In accordance with a third flow restriction option, step (a) is performed by constricting the wall portion, so that the flow in the lumen is substantially stopped, and step (b) is performed by stimulating the constricted wall portion to cause contraction thereof, so that the flow in the lumen is completely stopped. The method may further comprise (c) ceasing stimulating the wall portion to allow the flow in the lumen and (d) releasing the wall portion to restore the flow in the lumen.

For example, the third flow restriction option may be applied where the invention is used for controlling fecal flow of an anal incontinent patient. Between defecations, any portion of the incontinent patient's large or small intestines is gently constricted into a flattened shape to at least almost stop the fecal flow in the intestines, and the flattened portion of the intestines is stimulated to insure that the fecal flow is completely stopped. By intermittently and individually stimulating different areas of the wall portion the risk of injuring the intestines over time is significantly reduced or even eliminated, which insures that the effect of the stimulation is maintained over time. When the patient wants to defecate, the stimulation is ceased and the portion of the intestines is released, whereby fecal matter may pass the portion of the intestines. However, it should be noted that in some other applications of the present invention, for example where the invention is used for controlling urine flow of a urinary incontinent patient, it may suffice to just cease the stimulation to achieve fluid flow through the organ in question.

Where the constricted wall portion is stimulated to contract, so that the flow in the lumen is stopped, a first length of the constricted wall portion and a second length of the constricted wall portion, which is located downstream of the first length, are suitably simultaneously and cyclically stimulated, wherein the first length is progressively stimulated in the upstream direction of the lumen and the second length is progressively stimulated in the downstream direction of the lumen.

Furthermore, when using the method of the invention in accordance with the second and third options, the method may further comprise sensing a physical parameter of the patient or functional parameter of implanted components and adjusting the stimulation of the wall portion in response to the sensed parameter. For example, the intensity of the stimulation of the wall portion may be increased in response to a sensed pressure increase in the lumen, so that the flow in the lumen remains stopped when a pressure increase occurs in the lumen. In particular, the method may comprise sensing a physical parameter of the patient's that relates to the pressure in the lumen, and controlling the stimulation of the wall portion in response to the sensed parameter. Any sensor for sensing a physical parameter of the patient, such as a pressure in the patient's body that relates to the pressure in the lumen may be provided, wherein the stimulation is controlled in response to signals from the sensor. Such a sensor may for example sense the pressure in the patient's abdomen, the pressure against the implanted constriction device or the pressure on the tissue wall of the bodily organ. For example, a pressure sensor may be applied where the present invention is used for controlling urine flow of a urinary incontinent patient. Thus, the patient's urethra or urine bladder is constricted, so that the urine flow is substantially stopped, and the constricted urethra or urine bladder is stimulated to cause contraction thereof to completely stop the urine flow. The stimulation intensity is increased in response to signals from the pressure sensor sensing a sudden increase in the pressure in the patient's bladder or abdominal cavity, whereby the urine flow remains stopped and the patient maintains continence. In this manner, the present invention insures that the patient even is continent when he or she sneezes or coughs, or performs other physical activity that causes a sudden pressure increase in the patient's bladder/urinary tract.

In accordance with a fourth restriction option, step (a) is performed by constricting the wall portion, so that the flow in the lumen is stopped. When needed, the wall portion is released to restore the flow in the lumen. Step (b) is only performed by stimulating the constricted wall portion to cause contraction thereof, so that the flow in the lumen remains stopped when a pressure increase occurs in the lumen. The method may further comprise sensing a physical parameter of the patient's body, such as a pressure in the patient's body that relates to the pressure in the lumen, and controlling the stimulation of the wall portion in response to the sensed parameter. Such a physical parameter may be a pressure in the patient's abdomen and the sensor may be a pressure sensor.

For example, the fourth flow restriction option may be applied where the present invention is used for controlling urine flow of a urinary incontinent patient in a manner similar to the situation described in the foregoing paragraph 0027. However, in this example stimulation is only applied when necessary to maintain continence, Thus, the urethra or urine bladder is stimulated to cause contraction thereof in response to signals from the pressure sensor sensing a sudden increase in the pressure in the patient's bladder or abdominal cavity, when the patient sneezes or coughs, or performs other physical activity. As a result, the urine flow remains stopped and the patient maintains continence.

In some applications of the method of the invention, continuous stimulation may over time change the physical properties of the tissue so that the tissue might be injured. Also, the effect of a continuous stimulation of the tissue wall may decrease over time. Therefore, step (b) is preferably performed by intermittently and individually stimulating different areas of the wall portion so that the flow in the lumen continues to be restricted as desired and each area of the wall portion essentially maintains its natural physical properties over time to prevent the area from being injured. Advantageously, each area of the wall portion is stimulated during successive time periods, each time period being short enough to maintain over time satisfactory blood circulation in the area. Thus, the areas are stimulated so that an area that currently is not stimulated will have time to restore substantially normal blood circulation before it is stimulated again.

To maintain satisfactory blood circulation in the tissue wall of the patient's organ stimulation step (b) is suitably performed by stimulating one or more of different areas of the wall portion at a time, preferably by sequentially stimulating the different areas of the wall portion or by shifting the stimulation from one area to another over time. Preferably, stimulation step (b) is performed by cyclically propagating the stimulation of the areas along the wall portion, for example in accordance with a determined stimulation pattern.

The method of the invention may further comprise controlling, preferably by the patient, the constriction and/or stimulation of the wall portion from outside the patient's body.

Generally, the method of the invention comprises sensing a physical parameter of the patient and controlling, preferably automatically, the constriction and/or stimulation of the wall portion in response to the sensed parameter.

The constriction step (a) may be performed by constricting any wall portions of a series of wall portions of the organ's tissue wall, respectively, either in random or in accordance with a predetermined sequence. The stimulation step (b) may be performed by stimulating any of the constricted wall portions of the series of wall portions. Specifically, step (a) may be performed by constricting all of the wall portions of the series of wall portions, and step (b) may be performed by stimulating any constricted wall portions in random or in accordance with a predetermined sequence to close the organ's lumen.

Moving Fluid and/or Other Bodily Matter in the Lumen or Preventing the Movement of Fluid and/or Other Bodily Matters in the Lumen in a Similar Way It should be understood that any embodiment or part of embodiment disclosed below in connection with moving fluid or other bodily matter in the lumen, or preventing the move of fluid or any bodily matter in the lumen, for the constriction and stimulation devices combined in the constriction/stimulation unit could be used for the separate constriction device and separate stimulation device, where applicable. The method of the present invention can be practiced for actively moving the fluid and/or other bodily matter in lumen of a patient's organ. Thus, in the embodiments of the invention listed below, steps (a) and (b) are co-operated to move the fluid and/or other bodily matter in the lumen.

1) Step (a) is performed by constricting the wall portion to restrict the flow in the lumen, and step (b) is performed by stimulating the constricted wall portion to close the lumen either at an upstream end or a downstream end of the constricted wall portion. The method further comprises (c) increasing the constriction of the wall portion to move the fluid and/or other bodily matter in the lumen.

2) Step (a) is performed by constricting the wall portion to restrict the flow in the lumen, and step (b) is performed by progressively stimulating the constricted wall portion to cause progressive contraction of the wall portion to move the fluid and/or other bodily matter in the lumen. The constricted wall portion is progressively stimulated in the downstream or upstream direction of the lumen.

3) Step (a) is performed by varyingly constricting the wall portion to vary the flow in the lumen, and step (b) is performed by progressively stimulating the constricted wall portion to cause progressive contraction of the wall portion to move the fluid and/or other bodily matter in the lumen. The constricted wall portion is progressively stimulated in the downstream or upstream direction of the lumen.

4) Step (a) is performed by varyingly constricting different areas of the wall portion to cause progressive constriction of the wall portion in the downstream or upstream direction of the lumen, and the constricted wall portion is progressively stimulated to cause progressive contraction thereof in harmony with the progressive constriction of the wall portion. The method may further comprise providing at least one elongated constriction element extending along the wall portion, and controlling the elongated constriction element to progressively constrict the wall portion in the downstream or upstream direction of the lumen. The elongated constriction element suitably comprises contact surfaces dimensioned to contact a length of wall portion, and the method may further comprise providing a plurality of stimulation elements distributed along the contact surfaces, and controlling the stimulation elements to stimulate the different areas of the wall portion along the length of the wall portion.

5) Step (a) is performed by constricting any one of a series of wall portions of the tissue wall to at least restrict the flow in the lumen, and step (b) is performed by stimulating the constricted wall portion to close the lumen. The method further comprises successively constricting the wall portions of the series of wall portions to move the fluid and/or other bodily matter in the lumen in a peristaltic manner.

5a) In accordance with an alternative, the method further comprises providing at least one constriction element and at least one stimulation element positioned on the constriction element, moving the constriction element along the organ in the flow direction in the lumen to successively constrict the wall portions of the series of wall portions, and using the stimulation element to stimulate the wall portion constricted by the constriction element to close the lumen. Suitably, the method further comprises cyclically moving the constriction element along the wall portions of the series of wall portions.

5b) In accordance with another alternative, the method further comprises providing a plurality of constriction elements and stimulation elements positioned on the constriction elements, moving each constriction element along the organ to successively constrict the wall portions of the series of wall portions, and using the stimulation elements to stimulate the wall portion constricted by any one of the constriction elements to close the lumen. Suitably, the method further comprises cyclically moving the constriction elements one after the other along the wall portions of the series of wall portions. Specifically, the method further comprises providing a rotor carrying the constriction elements, and rotating the rotor so that each constriction element cyclically constricts the wall portions of the series of wall portions. Each constriction element suitably comprises a roller that rolls on the organ to constrict the latter.

6) Step (a) is performed by constricting any wall portions of a series of wall portions of the organ's tissue wall, respectively, wherein the wall portions of the series of wall portions are successively constricted along the organ to move the fluid and/or other bodily matter in the lumen of the patient's organ. The stimulation step (b) is performed by stimulating any constricted wall portions of the series of wall portions.

7) Step (a) is performed by constricting wall portions of a series of wall portions without completely closing the organ's lumen, and step (b) is performed by stimulating the constricted wall portions one after the other, so that the wall portions of the series of wall portions are successively contracted along the organ to move the fluid and/or other bodily matter in the lumen of the patient's organ.

8) Step (a) is performed by constricting the wall portion at an upstream or downstream end thereof to close the lumen. The method further comprises (c) constricting the wall portion between the upstream and downstream ends thereof, to move the fluid or other bodily matter contained in the wall portion between the upstream and downstream ends thereof downstream or upstream in the lumen. Optionally, the method further comprises stimulating the wall portion between the upstream and downstream ends thereof, as (c) is performed.

8a) In accordance with an alternative, step (a) is performed by constricting the wall portion at the upstream end thereof to restrict the flow in the lumen, and step (b) is performed by stimulating the constricted wall portion at the upstream end to close the lumen, whereby the fluid and/or other bodily matter contained in the wall portion between the upstream and downstream ends thereof is moved downstream in the lumen, as step (c) is performed.

8b) In accordance with another alternative, step (a) is performed by constricting the wall portion at the downstream end thereof to restrict the flow in the lumen, and step (b) is performed by stimulating the constricted wall portion at the downstream end to close the lumen, whereby the fluid and/or other bodily matter contained in the wall portion between the upstream and downstream ends thereof is moved upstream in the lumen, as step (c) is performed.

Where the organ is tubular in shape, such as the small intestines, a particularly long wall portion of the tubular organ may be surgically prepared to extend in zigzag with adjacent walls stitched together by two parallel rows of stitches and with the adjacent walls cut through between the two rows of stitches. As a result, the lumen of this long wall portion of the organ can be significantly expanded. In this case, a considerably larger volume of fluid is moved in the organ each time step (a) and/or step (b) is performed.

To summarize a few preferred embodiments see below:

In accordance with an alternative, step (a) is performed by constricting any wall portions of a series of wall portions of the organ's tissue wall, respectively. In accordance with an alternative, the wall portions of the series of wall portions are constricted in random or in accordance with a predetermined sequence. In accordance with an alternative, the wall portions of the series of wall portions are successively constricted along the organ to move the fluid and/or other bodily matter in the lumen of the patient's organ or to prevent the fluid and/or other bodily matter to move in the lumen of the patient's organ.

In accordance with an alternative, step (b) is performed by stimulating any constricted wall portions of the series of wall portions. In accordance with an alternative, the wall portions of the series of wall portions are constricted in random or in accordance with a predetermined sequence. In accordance with an alternative, wherein the wall portions of the series of wall portions are successively constricted along the organ to move the fluid and/or other bodily matter in the lumen of the patient's organ or to prevent the fluid and/or other bodily matter to move in the lumen of the patient's organ.

In accordance with an alternative, step (a) is performed by constricting any wall portions of a series of wall portions of the organ's tissue wall, respectively, wherein the wall portions of the series of wall portions are successively constricted without completely closing the organ's lumen, and step (b) is performed by stimulating the constricted wall portions, so that the wall portions of the series of wall portions are further constricted. In accordance with an alternative, the wall portions of the series of wall portions are constricted in random or in accordance with a predetermined sequence.

In accordance with an alternative, wherein the wall portions of the series of wall portions are successively constricted along the organ to move the fluid and/or other bodily matter in the lumen of the patient's organ or to prevent the fluid and/or other bodily matter to move in the lumen of the patient's organ.

In accordance with an alternative, step (a) is performed by constricting all of the wall portions of the series of wall portions, and step (b) is performed by stimulating any constricted wall portions so that the wall portions of the series of wall portions are further constricted.

In accordance with an alternative, the wall portions of the series of wall portions are further constricted by the stimulation device in random or in accordance with a predetermined sequence.

In accordance with an alternative, the wall portions of the series of wall portions are successively further constricted by the stimulation device along the organ to move the fluid and/or other bodily matter in the lumen of the patient's organ or to prevent the fluid and/or other bodily matter to move in the lumen of the patient's organ.

In accordance with an alternative for all applicable alternatives, step (a) and step (b) are performed independently of each other or in accordance with an alternative, step (a) and step (b) are performed simultaneously.

In any of the above noted embodiments (1) to (8b), step (b) may be performed by stimulating the wall portion with electric pulses.

Stimulation Modes

When stimulating neural or muscular tissue there is a risk of injuring or deteriorating the tissue over time if the stimulation is not properly performed. The method of the present invention is performed to reduce or even eliminate that risk. Thus, step (b) is performed by intermittently stimulating different areas of the wall portion so that at least two of the areas are stimulated at different points of time. I.e., the stimulation is shifted from one area to another area over time. In addition, step (b) is performed by intermittently stimulating the areas of the wall portion so that an area of the different areas that currently is not stimulated has time to restore substantially normal blood circulation before it is stimulated again. Furthermore, step (b) is performed by intermittently stimulating the areas during successive time periods, wherein each time period is short enough to maintain satisfactory blood circulation in the area until the laps of the time period. This gives the advantage that the method of the present invention provides continuous stimulation of the wall portion of the organ to achieve the desired flow control while essentially maintaining over time the natural physical properties of the organ without risk of injuring the organ.

Also, by physically changing the places of stimulation on the organ over time as described above it is possible to create an advantageous changing stimulation pattern on the organ, in order to achieve a desired flow control.

To achieve the desired reaction of the tissue wall during the stimulation thereof, step (b) may be performed by stimulating the wall portion with, preferably cyclically, varying stimulation intensity.

In a main embodiment of the invention, step (b) is performed by intermittently stimulating the wall portion with pulses, preferably in the form of pulse trains. The pulse trains can be configured in many different ways by varying pulse parameters. Thus, the pulse amplitudes of the pulses of the pulse trains, the off time periods between the individual pulses of each pulse train and the width and repetition frequency of each pulse may be varied. Also the off time periods between the pulse trains may be varied, wherein each off time period between the pulse trains is kept long enough to restore substantially normal blood circulation in each area of the wall portion, when the area is not stimulated during the off time periods. Furthermore, the repetition frequency of the pulses of the pulse trains and the length and number of pulses of each pulse train may be varied.

As mentioned above, for reasons of maintaining over time the effect of stimulation, it is preferable that different areas of the wall portion are intermittently and individually stimulated. In consequence, step (b) may be performed by stimulating one or more of the areas at a time with pulses, by cyclically propagating the stimulation of the areas with pulses along the wall portion, and/or by propagating the stimulation of the areas with pulses in accordance with a determined stimulation pattern. In case the off time periods between pulse trains that stimulate the respective area of the wall portion are varied, it is preferable that each off time period between the pulse trains is controlled to last long enough to restore substantially normal blood circulation in the area when the latter is not stimulated during the off time periods.

Electric Stimulation

In accordance with a preferred embodiment of the invention, step (b) is performed by electrically stimulating the wall portion, preferably with electric pulses to cause contraction of the wall portion. This embodiment is particularly suited for applications in which the patient's wall portion includes muscle fibers that react to electrical stimula. Thus, the wall portion that includes the muscle fibers is stimulated with such electric pulses, preferably in the form of electric pulse trains, when the wall portion is in the constricted state, to cause contraction of the wall portion. Of course, the configuration of the electric pulse trains may be similar to the above described pulse trains and different areas of the wall portion may be electrically stimulated in the same manner as described above.

In accordance with the preferred embodiment, the method of the invention comprises providing at least one, preferably a plurality of electrical elements, such as electrodes, engaging and stimulating the wall portion with electric pulses. Optionally, the electrical elements may be placed in a fixed orientation relative to one another. The method comprises electrically energizing the electrical elements, preferably by cyclically energizing each element with electric pulses. The electrical elements may be energized so that the electrical elements are energized one at a time in sequence, or so that a number or groups of the electrical elements are energized at a time. Also, groups of electrical elements may be sequentially energized, either randomly or in accordance with a predetermined pattern.

The method may further comprise applying the electrical elements on the patient's wall portion so that the electrical elements form any pattern of electrical elements, preferably an elongate pattern of electrical elements extending lengthwise along the wall portion and the elements abut the respective areas of the wall portion. The electrical elements may be successively energized along the elongate pattern of electrical elements in a direction opposite to or in the same direction as that of the flow in the patient's lumen. Optionally, the electrical elements may be successively energized along the elongate pattern of electrical elements from a position substantially at the center of the constricted wall portion towards both ends of the elongate pattern of electrical elements. Where the lumen of the organ is to be kept closed for a relatively long time, the electrical elements may be energized so that energized electrical elements form two waves of energized electrical elements that simultaneously advance from the center of the constricted wall portion in two opposite directions towards both ends of the elongate pattern of electrical elements. Such waves of energized electrical elements can be repeated over and over again without harming the organ and without moving fluid or gas in any direction in the lumen of the organ.

The elongate pattern of electrical elements may include one or more rows of electrical elements extending lengthwise along the organ. Each row of electrical elements may form a straight, helical or zig-zag path of electrical elements, or any form of path. The electrical elements may be energized so that the electrical elements currently energized form at least one group of adjacent energized electrical elements, wherein the elements in the group of energized electrical elements form a path of energized electrical elements extending at least in part around the patient's organ, preferably completely around the patient's organ. Alternatively, the elements in the group of energized electrical elements form two paths of energized electrical elements extending on mutual sides of the patient's organ or more than two paths of energized electrical elements extending on different sides of the patient's organ, preferably at least substantially transverse to the flow direction in the lumen of the organ.

In an embodiment of the invention, the electrical elements form a plurality of groups of elements, wherein the groups form a series of groups extending along the patient's organ in the flow direction in the patient's lumen. The electrical elements of each group of electrical elements may form a path of elements extending at least in part around the patient's organ. In a first alternative, the electrical elements of each group of electrical elements may form more than two paths of elements extending on different sides of the patient's organ, preferably substantially transverse to the flow direction in the patient's lumen. The groups of electrical elements in the series of groups may be energized in random or in accordance with a predetermined pattern. Alternatively, the groups of electrical elements in the series of groups may be successively energized in a direction opposite to or in the same direction as that of the flow in the patient's lumen, or in both said directions starting from a position substantially at the center of the constricted wall portion. For example, groups of energized electrical elements may form advancing waves of energized electrical elements, as described above. I.e., the groups of electrical elements may be energized so that energized electrical elements form two waves of energized electrical elements that simultaneously advance from the center of the constricted wall portion in two opposite directions towards both ends of the elongate pattern of electrical elements.

Thermal Stimulation

In accordance with an embodiment of the invention, stimulation step (b) is performed by thermally stimulating the wall portion. Thus, the wall portion may be cooled, when the wall portion is constricted, to cause contraction of the wall portion. For example, the wall portion may be constricted to at least restrict the flow in the lumen, and the constricted wall portion may be cooled to cause contraction thereof, so that the flow in the lumen is at least further restricted, or further restricted but not stopped, or stopped. Alternatively, the wall portion may be heated, when the wall portion is constricted and contracted, to cause expansion of the wall portion. Where the wall portion includes a blood vessel, the blood vessel may be cooled to cause contraction thereof, or heated to cause expansion thereof. Where applicable, thermal stimulation may be practiced in any of the embodiments of the present invention. Where applicable, thermal stimulation may be practiced in any of the embodiments of the present invention, and the thermal stimulation may be controlled in response to various sensors, for example strain, motion or pressure sensors.

Constriction and Stimulation Devices

It should be understood that any embodiment or part of embodiment for the combined stimulation device and constriction device, could be used, if applicable, for any one of the devices as a stand alone device. Generally, the method of the invention comprises providing a constriction device that constricts the wall portion, a stimulation device that stimulates the constricted wall portion and a control device that controls the constriction device and/or the stimulation device. The method comprises operating the control device from outside the patient's body, preferably by using the control device to wirelessly control the constriction device and/or stimulation device. The wireless control is preferably performed in a non-magnetic manner, whereby implanted magnetic devices can be avoided. Suitably, the control device comprises a hand-held wireless remote control operated by the patient.

Alternatively, the control device comprises a manually operable switch for switching on and off the constriction device and/or stimulation device. In this case, the method comprises subcutaneously implanting the switch in the patient and manually operating the the implanted switch from outside the patient's body.

In an embodiment of the invention, the control device comprises a programmable internal control unit, such as a microprocessor, and the method comprises implanting in the patient the internal control unit and controlling by the internal control unit the constriction device and/or stimulation device. The control device may also comprise an external control unit outside the patient's body. In this case, the method comprises controlling by the external control unit the constriction device and/or stimulation device and, optionally, using the external control unit to program the implanted internal control unit. The internal control unit may be programmable for controlling the constriction device and/or stimulation device over time, for example in accordance with an activity schedule program.

The constriction of the wall portion can be calibrated by using the control device to control the stimulation device to stimulate the wall portion while controlling the constriction device to adjust the constriction of the wall portion until the desired restriction of the flow in the lumen is obtained.

Sensor Controlled Constriction and/or Stimulation

It should be understood that any embodiment or part of embodiment disclosed below in connection with sensor control of the constriction and stimulation devices combined in the constriction/stimulation unit could be used for the separate constriction device and separate stimulation device, where applicable. In an embodiment of the invention, the method comprises implanting at least one sensor and controlling by the control device the constriction device and/or the stimulation device in response to signals from the sensor. Generally, the sensor directly or indirectly senses at least one physical parameter of the patient, functional parameter of the apparatus, or functional parameter of a medical implant in the patient.

Many different kinds of sensor for sensing physical parameters may be used. For example motion sensors for sensing organ motion, i.e. natural contractions, such as stomach or intestinal contractions, pressure sensors for sensing pressure in the organ, strain sensors for sensing strain of the organ, flow sensors for sensing fluid flow in the lumen of the organ, spectro-photometrical sensors, Ph-sensors for acidity or alkalinity of the fluid in the lumen of the organ, oxygen-sensors sensors for sensing the oxygen content of the fluid in the lumen of the organ, or sensors for sensing the distribution of the stimulation on the stimulated organ. Any conceivable sensors for sensing any other kind of useful physical parameter may be used.

Many different kinds of sensors that sense functional parameters of implanted components may also be used for the control of the constriction device and/or the stimulation device. For example sensors for sensing electric parameters of implanted electric components, or sensors for sensing the performance of implanted motors or the like.

The sensor may comprise a pressure sensor for sensing as the physical parameter a pressure in the patient's body that relates to the pressure in the lumen of the patient's bodily organ. In this case, the method suitably comprises operating the control device to control the constriction device to change the constriction of the patient's wall portion in response to the pressure sensor sensing a predetermined value of measured pressure.

Alternatively, or in combination with the pressure sensor, a position sensor may be provided for sensing as the physical parameter the orientation of the patient with respect to the horizontal. The position sensor may be a biocompatible version of what is shown in U.S. Pat. Nos. 4,942,668 and 5,900,909. For example, the control device may control the constriction device and/or stimulation device to change the constriction of the patient's wall portion in response to the position sensor sensing that the patient has assumed a substantially horizontal orientation, i.e. that the patient is lying down.

The above described sensors may be used in any of the embodiments of the invention, where applicable.

The control device may control the constriction device and/or stimulation device to change the constriction of the patient's wall portion in response to the time of day. For that purpose the control device may include a clock mechanism for controlling the constriction device and/or stimulation device to change the constriction of the patient's wall portion to increase or decrease the influence on the flow in the lumen during different time periods of the day. In case a sensor of any of the above-described types for sensing a physical or functional parameter is provided, either the clock mechanism is used for controlling the constriction device and/or stimulation device provided that the parameter sensed by the sensor does not override the clock mechanism, or the sensor is used for controlling the constriction device and/or stimulation device provided that the clock mechanism does not override the sensor. Suitably, the control device produces an indication, such as a sound signal or displayed information, in response to signals from the sensor.

The control device may comprise an implantable internal control unit that directly controls the constriction device and/or stimulation device in response to signals from the sensor. The control device may further comprise a wireless remote control adapted to set control parameters of the internal control unit from outside the patient without mechanically penetrating the patient. At least one of the control parameters, which is settable by the wireless remote control, is the physical or functional parameter. Suitably, the internal control unit includes the above mentioned clock mechanism, wherein the wireless remote control also is adapted to set the clock mechanism.

Alternatively, the control device may comprise an external control unit outside the patient's body for controlling the constriction device and/or stimulation device in response to signals from the sensor.

Constriction of Patient's Organ

It should be understood that any embodiment or part of embodiment disclosed below in connection with constricting the patient's organ could be used for the separate constriction device and separate stimulation device, where applicable. Method step (a) may be performed in many different ways. Thus, step (a) may be performed by:
  (1)- constricting the wall portion so that the through-flow area of the lumen assumes a size in the constricted state small enough to cause the constricted wall portion to contract to stop the flow in the lumen when step (b) is performed;
  (2)- bending the wall portion;
  (3)- clamping the wall portion between at least two elements positioned on different sides of the organ;
  (4)-clamping the organ between an element and the bone or tissue of the patient;
  (5)- rotating at least two elements positioned on different sides of the organ;
  (6) or
  (7)-clamping the organ between at least two articulated clamping elements positioned on different sides of the organ.

In the above noted alternatives (1) to (6) of method step (a), the constriction of the wall portion of the organ may be changed either mechanically or hydraulically. For many applications of the present invention, step (a) is suitably performed so that the through-flow area of the lumen assumes a size in the constricted state that is small enough to enable the stimulation during step (b) to contract the wall portion of the organ to stop the flow in the lumen.

Where the constriction of the wall portion is hydraulically changed, the method of the invention may further comprise implanting in the patient a reservoir containing a predetermined amount of hydraulic fluid, and a constriction device engaging the wall portion and having an expandable/contractible cavity, wherein step (a) is performed by distributing hydraulic fluid from the reservoir to increase the volume of the cavity to constrict the wall portion, and by distributing hydraulic fluid from the cavity to the reservoir to decrease the volume of the cavity to release the wall portion. The cavity may be defined by a balloon of the constriction device that abuts the tissue wall portion of the patient's organ, so that the patient's wall portion is constricted upon expansion of the cavity and released upon contraction of the cavity.

Alternatively, the cavity may be defined by a bellows that displaces a relatively large contraction element of the constriction device, for example a large balloon that abuts the wall portion, so that the patient's wall portion is constricted upon contraction of the bellows and released upon expansion of the bellows. Thus, a relatively small addition of hydraulic fluid to the bellows causes a relatively large increase in the constriction of the wall portion. Such a bellows may also be replaced by a suitably designed piston/cylinder mechanism.

Where the hydraulic means comprises a cavity in the constriction device, the following embodiments of the invention are conceivable.

1) The reservoir comprises first and second wall portions, and step (a) is performed by displacing the first and second wall portions relative to each other to change the volume of the reservoir, so that fluid is distributed from the reservoir to the cavity, or from the cavity to the reservoir.

1a) At least one of a magnetic device, a hydraulic device or an electric control device displaces the first and second wall portions of the reservoir.

2) A pump is provided for pumping fluid between the reservoir and the cavity.

2a) The pump comprises a first activation member for activating the pump to pump fluid from the reservoir to the cavity and a second activation member for activating the pump to pump fluid from the cavity to the reservoir.

2a1) The first and second activation members are operable by manual manipulation thereof.

2a2) At least one of the activation members operates when subjected to an external predetermined pressure.

2a3) At least one of the first and second activating members is operable by magnetic means, hydraulic means, or electric control means.

2b) A fluid conduit between the pump and the cavity is provided, wherein the reservoir forms part of the conduit. The conduit and pump are devoid of any non-return valve. The reservoir forms a fluid chamber with a variable volume, and the pump distributes fluid from the chamber to the cavity by a reduction in the volume of the chamber and withdraws fluid from the cavity by an expansion of the volume of the chamber. A motor is provided for driving the pump, wherein the pump comprises a movable wall of the reservoir for changing the volume of the chamber.

In all of the above noted embodiments 1 to 2b where the hydraulic means comprises an expandable cavity in the constriction device, the cavity can be exchanged by a cylinder/piston mechanism for adjusting the constriction device. In this case, hydraulic fluid is distributed between the reservoir and the cylinder/piston mechanism to adjust the constriction device.

3) The method further comprises implanting a reverse servo operatively connected to the hydraulic means. The term "reverse servo" is to be understood as a mechanism that transfers a strong force acting on a moving element having a short stroke into a weak force acting on another moving element having a long stroke; i.e., the reverse function of a normal servo mechanism. Thus, minor changes in the amount of fluid in a smaller reservoir could be transferred by the reverse servo into major changes in the amount of fluid in a larger reservoir.

Preferably, the reverse servo comprises an expandable servo reservoir containing servo fluid and a fluid supply reservoir hydraulically connected to the servo reservoir to form a closed conduit system for the servo fluid. The expandable servo reservoir has first and second wall portions, which are displaceable relative to each other in response to a change in the volume of the expandable servo reservoir.

In accordance with a first alternative, the first and second wall portions of the servo reservoir are operatively connected to the hydraulic means. The reverse servo distributes fluid between the fluid supply reservoir and the expandable servo reservoir to change the volume of the servo reservoir, whereby the hydraulic means is operated to adjust the constriction device.

In accordance with a second alternative, there is provided an implantable main reservoir containing a predetermined amount of hydraulic fluid, wherein the reverse servo is operated to distribute hydraulic fluid between the main reservoir and the hydraulic means to adjust the constriction device. More specifically, the main reservoir is provided with first and second wall portions operatively connected to the first and second wall portions of the expandable servo reservoir, so that the volume of the main reservoir is changed when the volume of the expandable servo reservoir is changed. Thus, when the reverse servo distributes servo fluid between the fluid supply reservoir and the expandable servo reservoir to change the volume of the main reservoir, hydraulic fluid is distributed from the main reservoir to the hydraulic means, or from the hydraulic means to the main reservoir. Advantageously, the method comprises dimensioning the servo and main reservoirs, so that when the volume of the servo reservoir is changed by a relatively small amount of servo fluid, the volume of the main reservoir is changed by a relatively large amount of hydraulic fluid.

In both of the above-described alternatives, the fluid supply reservoir may have first and second wall portions, which are displaceable relative to each other to change the volume of the fluid supply reservoir to distribute servo fluid between the fluid supply reservoir and the expandable servo reservoir. The first and second wall portions of the fluid supply reservoir may be displaced relative to each other by manual manipulation, a magnetic device, a hydraulic device, or an electric control device to change the volume of the fluid supply reservoir to distribute servo fluid between the fluid supply reservoir and the expandable servo reservoir.

In all of the above noted embodiments 1 to 2b where the hydraulic means comprises an expandable cavity in the constriction device, or in embodiments where the hydraulic means includes a hydraulically operable mechanical construction, the reverse servo described above may be used. In a further embodiment of the invention, the hydraulic means include first and second hydraulically interconnected expandable/contractible reservoirs. The first reservoir is operatively connected to the constriction device, so that the constriction device changes the constriction of the patient's wall portion upon expansion or contraction of the first reservoir. By changing the volume of the second reservoir hydraulic fluid is distributed between the two reservoirs, so that the first reservoir is either expanded or contracted. This embodiment requires no non-return valve in the fluid communication conduits between the two reservoirs, which is beneficial to long-term operation of the hydraulic means.

Alternatively, the hydraulic means may include first and second hydraulically interconnected piston/cylinder mechanisms instead of the first and second reservoirs described above. The first piston/cylinder mechanism is operatively connected to the constriction device, so that the constriction device changes the constriction of the patient's wall portion upon operation of the first piston/cylinder mechanism. By operating the second piston/cylinder mechanism hydraulic fluid is distributed between the two piston/cylinder mechanisms, so that the first piston/cylinder mechanism adjusts the constriction device.

Where the constriction device does not include an expandable/contractible cavity, the constriction device may comprise at least two elongated clamping elements extending along the wall portion on different sides of the organ. The hydraulic means, which may include the reverse servo described above, hydraulically moves the elongated clamping elements towards the organ to constrict the wall portion of the organ. For example, the constriction device may have hydraulic chambers in which the clamping elements slide back and forth, and the hydraulic means may also include a pump and an implantable reservoir containing hydraulic fluid. The pump distributes hydraulic fluid from the reservoir to the chambers to move the clamping elements against the wall portion, and distributes hydraulic fluid from the chambers to the reservoir to move the clamping elements away from the wall portion.

Energy Supply

It should be understood that any embodiment or part of embodiment disclosed below in connection with the power of the constriction and stimulation devices combined in the constriction/stimulation unit could be used for the separate constriction device and separate stimulation device, where applicable. Generally, method step (a) is performed by using the constriction device and step (b) is performed by using the stimulation device, wherein the method further comprises forming the constriction and stimulation devices in an operable constriction/stimulation unit.

In a simple form of the invention, the method comprises implanting a source of energy, such as a battery, rechargeable battery or accumulator, releasing energy from the source of energy and using the released energy in connection with the operation of the constriction/stimulation unit.

In a more sophisticated form of the invention, which is preferable, the method comprises transmitting wireless energy from outside the patient's body to inside the patient's body and using the transmitted wireless energy in connection with the operation of the constriction/stimulation unit.

Transmission of Wireless Energy

It should be understood that any embodiment or part of embodiment disclosed below in connection with wireless control or power of the constriction and stimulation devices combined in the constriction/stimulation unit could be used for the separate constriction device and separate stimulation device, where applicable. The wireless energy may be directly used in connection with the operation of the constriction/stimulation unit, as the wireless energy is being transmitted. For example, the wireless energy may be transmitted in the form of an electric, an electromagnetic or a magnetic field, or a combination thereof, or electromagnetic waves for direct power of the constriction/stimulation unit. For example, where an electric motor or pump operates the constriction device of the constriction/stimulation unit, wireless energy in the form of a magnetic or an electromagnetic field may be used for direct power of the motor or pump.

Thus, the motor or pump is running directly during transmission of the wireless energy. This may be achieved in two different ways: a) using a transforming device implanted in the patient to transform the wireless energy into energy of a different form, preferably electric energy, and powering the motor or pump with the transformed energy, or b) using the wirelessly transmitted energy to directly power the motor or pump. Preferably wireless energy in the form of an electromagnetic or magnetic field is used to directly influence specific components of the motor or pump to create kinetic energy. Such components may include coils integrated in the motor or pump.

The wireless energy is suitably transmitted in pulses or digital pulses, or a combination of pulses and digital pulses.

Preferably, the wireless energy is transmitted in at least one wireless signal, suitably a wave signal. The wave signal may comprise an electromagnetic wave signal including one of an infrared light signal, a visible light signal, an ultra violet light signal, a laser signal, a microwave signal, a radio wave signal, an x-ray radiation signal, and a gamma radiation signal. Alternatively, the wave signal may comprise a sound or an ultrasound wave signal. The wireless signal may be a digital or analogue signal, or a combination of a digital and analogue signal.

In accordance with a particular embodiment of the invention, the wireless energy is not for direct use in connection with the operation of the constriction/stimulation unit. In this embodiment the wireless energy comprises energy of a first form, which is transmitted into energy of a second form suited to operate the constriction/stimulation unit. Typically, the energy of the second form is different from the energy of the first form. For example, the wireless energy of the first form may comprise sound waves, whereas the energy of the second form may comprise electric energy. Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

Transforming Wireless Energy

It should be understood that any embodiment or part of embodiment disclosed below in connection with the control or energizing of the constriction and stimulation devices combined in the constriction/stimulation unit could be used for the separate constriction device and separate stimulation device, where applicable. In accordance with a particular embodiment of the invention, an implantable energy-transforming device is provided for transforming wireless energy of a first form transmitted by the energy-transmission device into energy of a second form, which typically is different from the energy of the first form. The constriction/stimulation unit is operable in response to the energy of the second form. For example, the wireless energy of the first form may comprise sound waves, whereas the energy of the second form may comprise electric energy. Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transforming device may function different from or similar to the energy-transmission device. Advantageously, the energy-transforming device comprises at least one element, such as at least one semiconductor, having a positive region and a negative region, when exposed to the energy of the first form transmitted by the energy-transmission device, wherein the element is capable of creating an energy field between the positive and negative regions, and the energy field produces the energy of the second form. More specifically, the element may comprise an electrical junction element, which is capable of inducing an electric field between the positive and negative regions when exposed to the energy of the first form transmitted by the energy-transmission device, whereby the energy of the second form comprises electric energy.

The energy of the first form may directly or indirectly be transformed into the energy of the second form. The method of the invention may comprise providing a motor for operating the constriction device and powering the motor with the energy of the second form. The constriction device may be operable to perform at least one reversible function and the method may comprise reversing the function by using the motor. For example, the method may comprise shifting the polarity of the energy of the second form to reverse the motor.

The motor may be directly powered with the transformed energy, as the energy of the second form is being transformed from the energy of the first form. Preferably, the constriction/stimulation unit is directly operated with the energy of the second form in a non-magnetic, non-thermal or non-mechanical manner.

Normally, the implanted constriction/stimulation unit comprises electric components that are energized with electrical energy. Therefore, the energy of the first form may be transformed into a direct current or pulsating direct current, or a combination of a direct current and pulsating direct current. Alternatively, the energy of the first form may be transformed into an alternating current or a combination of a direct and alternating current.

The method of the invention may comprise implanting in the patient an internal source of energy, and supplying energy from the internal source of energy for the operation of the constriction/stimulation unit. The method may further comprise implanting in the patient a switch operable to switch from an "off" mode, in which the internal source of energy is not in use, to an "on" mode, in which the internal source of energy supplies energy for the operation of the constriction/stimulation unit, and/or for energizing implanted electronic components of the constriction/stimulation unit. The switch may be operated by the energy of the first form or by the energy of the second form. The described switch arrangement reduces power consumption of the constriction/stimulation unit between operations.

The internal source of energy may store the energy of the second form. In this case, the internal source of energy suitably comprises an accumulator, such as at least one capacitor or at least one rechargeable battery, or a combination of at least one capacitor and at least one rechargeable battery. Where the internal source of energy is a rechargeable battery it may be charged only at times convenient for the patient, for example when the patient is sleeping. Alternatively, the internal source of energy may supply energy for the operation of the constriction/stimulation unit but not be used for storing the energy of the second form. In this alternative, the internal source of energy may be a battery and the switch described above may or may not be provided.

Suitably, the method of the invention may comprise implanting a stabilizer for stabilizing the energy of the second form. Where the energy of the second form comprises electric energy the stabilizer suitably comprises at least one capacitor.

The energy-transforming device may be designed for implantation subcutaneously in the abdomen, thorax or cephalic region of the patient. Alternatively, it may be designed for implantation in an orifice of the patient's body and under the mucosa or intramuscularly outside the mucosa of the orifice.

Control of Constriction/Stimulation Unit

It should be understood that any embodiment or part of embodiment disclosed below in connection with the control of the constriction and stimulation devices combined in the constriction/stimulation unit could be used for the separate constriction device and separate stimulation device, where applicable. Although the constriction device of the constriction/stimulation unit may normally keep the patient's wall portion in the constricted state, in most applications using the present invention there will be daily adjustments of the constriction device. Therefore, in a preferred embodiment of the invention, the constriction device is adjustable to enable changing the constriction of the patient's wall portion as desired and the control device controls the constriction device to change the constriction of the wall portion.

The method of the invention suitably comprises operating the control device by the patient. In a simple form the control device comprises a manually operable switch for switching on and off the constriction/stimulation unit, and the method further comprises subcutaneously implanting the switch in the patient. It is preferable, however, that the control device comprises a hand-held wireless remote control operable by the patient from outside the patient's body to control the constriction/stimulation unit to adjust the stimulation intensity and/or adjust the constriction of the wall portion. The wireless remote control is suitably designed for application on the patient's body like a wristwatch.

In some applications of the invention, the constriction device of the constriction/stimulation unit may be designed to normally keep the patient's wall portion in the constricted state. I.e., after implantation the constriction device all the time keeps the wall portion constricted. In this case, the control device may be used when needed, conveniently by the patient, to control the stimulation device of the constriction/stimulation unit to stimulate the constricted tissue wall portion, preferably while adjusting the stimulation intensity, to cause contraction of the wall portion, so that the flow in the lumen is at least further restricted or stopped, and to control the stimulation device to cease the stimulation. More precisely, the method of the invention may comprise operating the control device by the patient to a) control the stimulation device in a first mode to stimulate the constricted wall portion to further restrict the flow in the lumen and control the stimulation device in a second mode to cease the stimulation of the wall portion to increase the flow in the lumen; or b) control the stimulation device in a first mode to stimulate the constricted wall portion to stop the flow in the lumen and control the stimulation device in a second mode to cease the stimulation of the wall portion to allow flow in the lumen.

Either the first mode or the second mode may be temporary.

The wireless remote control preferably transmits at least one wireless control signal for controlling the constriction/stimulation unit. The control signal may comprise a frequency, amplitude, phase modulated signal or a combination thereof, and may be an analogue or a digital signal, or a combination of an analogue and digital signal. The remote control may transmit an electromagnetic carrier wave signal for carrying the digital or analogue control signal. Also the carrier signal may comprise digital, analogue or a combination of digital and analogue signals.

Any of the above signals may comprise wave signals, such as a sound wave signal, an ultrasound wave signal, an electromagnetic wave signal, an infrared light signal, a visible light signal, an ultra violet light signal, a laser light signal, a micro wave signal, a radio wave signal, an x-ray radiation signal or a gamma radiation signal.

Alternatively, the control signal may comprise an electric or magnetic field, or a combined electric and magnetic field.

Operation of Constriction/Stimulation Unit

It should be understood that any embodiment or part of embodiment for operating the combined stimulation device and constriction device, could be used, if applicable, for any one of the devices as a stand alone device. The method of the invention may comprise implanting in the patient an operation device, and operating the constriction/stimulation unit with the operation device. A magnet may be provided, wherein the method comprises using the magnet to activate the operation device from outside the patient's body. The operation device suitably comprises a motor which is powered with energy released from a source of energy, such as a battery. Although the constriction/stimulation unit in embodiments described above suitably is designed as a single piece, which is most practical for implantation, it should be noted that as an alternative the constriction device and stimulation device of the constriction/stimulation unit could be designed as separate pieces.

Laparoscopic Method

The present invention also provides a first method for controlling a flow of fluid and/or other bodily matter in a lumen formed by a tissue wall of a patient's organ. The method comprises the steps of:
inserting a needle like tube into the cavity of the patients body,
filling the cavity with gas thereby expanding the abdominal cavity,
placing at least two laparascopical trocars in the patient's body,
inserting a camera through one of the trocars into the cavity,
inserting a dissecting tool through any of the trocar and dissecting an area of at least one portion of the tissue wall of the organ,
placing a constriction device and a stimulation device in the dissected area in operative engagement with the organ,
using the constriction device to gently constrict the wall portion of the organ to influence the flow in the lumen, and
using the stimulation device to stimulate the constricted wall portion to cause contraction of the wall portion to further influence the flow in the lumen.

The present invention also provides a second method for controlling a flow of fluid and/or other bodily matter in a lumen formed by a tissue wall of a patient's organ. The method comprises the steps of:
inserting a needle like tube into a cavity of the patients body,
using the needle like tube to fill the cavity with gas thereby expanding the cavity,
placing at least two laparascopical trocars in the patient's body,
inserting a camera through one of the trocars into the cavity,
inserting a dissecting tool through any of the trocar and dissecting an area of at least one portion of the tissue wall of the organ,
placing a stimulation device in the dissected area in operative engagement with the organ, and
using the stimulation device to stimulate the wall portion to cause contraction of the wall portion to influence the flow in the lumen.

The present invention also provides a third method for controlling a flow of fluid and/or other bodily matter in a lumen formed by a tissue wall of a patient's organ. The method comprises the steps of:
inserting a needle like tube into a cavity of the patients body,
using the needle like tube to fill the cavity with gas thereby expanding the cavity, placing at least two laparascopical trocars in the patient's body, inserting a camera through one of the trocars into the cavity, inserting a dissecting tool through any of the trocar and dissecting an area of at least one portion of the tissue wall of the organ, placing a constriction device in the dissected area in operative engagement with the organ, using the constriction device to constrict the wall portion of the organ to influence the flow in the lumen.

The present invention also provides a fourth method for controlling a flow of fluid and/or other bodily matter in a lumen formed by a tissue wall of a patient's organ. The method comprises the steps of:

cutting the skin of the patient, inserting a dissecting tool and dissecting an area of at least one portion of the tissue wall of the organ, placing a constriction device and a stimulation device in the dissected area in operative engagement with the organ, using the constriction device to gently constrict the wall portion of the organ to influence the flow in the lumen, and using the stimulation device to stimulate the constricted wall portion to cause contraction of the wall portion to further influence the flow in the lumen.

The present invention also provides a fifth method for controlling a flow of fluid and/or other bodily matter in a lumen formed by a tissue wall of a patient's organ. The method comprises the steps of:

cutting the skin of the patient, inserting a dissecting tool and dissecting an area of at least one portion of the tissue wall of the organ, placing a stimulation device in the dissected area in operative engagement with the organ, and using the stimulation device to stimulate the wall portion to cause contraction of the wall portion to influence the flow in the lumen.

The present invention also provides a sixth method for controlling a flow of fluid and/or other bodily matter in a lumen formed by a tissue wall of a patient's organ. The method comprises the steps of:

cutting the skin of the patient, inserting a dissecting tool and dissecting an area of at least one portion of the tissue wall of the organ, placing a constriction device in the dissected area in operative engagement with the organ, and using the constriction device to constrict the wall portion of the organ to influence the flow in the lumen.

In all of the above-noted methods 1-6 the cavity may constitute at least one of an abdominal cavity, a cavity in the pelvic region, a thoraxial cavity, a cavity in a limb, a cavity in human soft tissue such as muscle, fat and fibrotic tissue.

The method further comprises implanting a powered operation device for operating the constriction device. The operation device may comprise a powered hydraulic operation device or an electrically powered operation device, such as an electric motor.

The method further comprises transmitting wireless energy for powering the operation device, and when desired to influence the flow in the patient's organ, powering the operation device with the transmitted energy to operate the constriction device.

The method further comprises implanting a source of energy in the patient, providing an external source of energy, controlling the external source of energy to release wireless energy, transforming the wireless energy into storable energy, such as electric energy, non-invasively charging the implanted source of energy with the transformed energy, and controlling the implanted source of energy from outside the patient's body to release energy for use in connection with the operation of the constriction device and/or stimulation device. The wireless energy is transformed into a storable energy different from the wireless energy.

Alternatively, the method further comprises providing a source of energy outside the patient's body, controlling the external source of energy from outside the patient's body to release wireless energy, and using the released wireless energy for operating the constriction device and/or stimulation device. The wireless energy may be transformed into electrical energy inside the patient's body by an implanted energy-transforming device, wherein the electrical energy is used in connection with the operation of the constriction device and/or stimulation device. The electrical energy may be directly used in connection with the operation of the constriction device and/or stimulation device, as the transforming device transforms the wireless energy into the electrical energy. The external source of energy may be controlled from outside the patient's body to release non-magnetic wireless energy, wherein the released non-magnetic wireless energy is used for operating the constriction device and/or stimulation device. Alternatively, the external source of energy may be controlled from outside the patient's body to release electromagnetic wireless energy, wherein the released electromagnetic wireless energy is used for operating the constriction device and/or stimulation device.

The above-described methods of the present invention may be practiced for treating dysfunctions of an organ of a human being or an animal.

Feed Back Related to the Wireless Energy

The following embodiments are related to feed back information related to an energy balance either comparing;

a) the amount of energy received by the internal energy source compared to the energy used by the constriction device and/or stimulation device, or b) the amount of energy received by the internal energy source and the amount of energy transmitted by the external energy source.

Several alternatives of the method of the present invention are disclosed below and may except being correlated directly to the constriction device and/or stimulation device also be included in the operating method. These methods are valid for use both with the stimulation device and constriction device separate or in combination.

A method for controlling the transmission of wireless energy comprising an internal energy source, wherein said wireless energy is transmitted from an external energy source located outside the patient and is received by the internal energy source located inside the patient, the internal energy source being connected to the constriction device and/or stimulation device for directly or indirectly supplying received energy thereto, the method comprising the steps of:

determining an energy balance between the energy received by the internal energy source and the energy used for the constriction device and/or stimulation device, and controlling the transmission of wireless energy from the external energy source, based on the determined energy balance.

A method, wherein the wireless energy is transmitted inductively from a primary coil in the external energy source to a secondary coil in the internal energy receiver.

A method, wherein a change in said energy balance is detected, and the transmission of wireless energy is controlled based on said detected energy balance change.

A method, wherein a difference is detected between energy received by said internal energy receiver and energy used for a medical device, and the transmission of wireless energy is controlled based on said detected energy difference.

A method, wherein the amount of transmitted wireless energy is decreased if the detected energy balance change implies that the energy balance is increasing, or vice versa.

A method, wherein the decrease/increase of energy transmission corresponds to a detected change rate.

A method, wherein the amount of transmitted wireless energy is decreased if the detected energy difference implies that the received energy is greater than the used energy, or vice versa.

A method, wherein the decrease/increase of energy transmission corresponds to the magnitude of said detected energy difference.

A method, wherein the energy used for the constriction device and/or stimulation device is stored in at least one energy storage device of the device.

A method, wherein substantially all the energy used for the constriction device and/or stimulation device device i is consumed to operate the device.

A method, wherein the energy is consumed after being stabilised in at least one energy stabilising unit of the device.

A method, wherein the energy used for the constriction device and/or stimulation device device is stored in at least one energy storage device of the device.

A method, wherein substantially all the energy used for the constriction device and/or stimulation device i is consumed to operate the device.

A method, wherein the energy is consumed after being stabilised in at least one energy stabilising unit of the device.

A method of controlling transmission of wireless energy supplied to at least one of the constriction and stimulation devices, comprising an internal energy source located inside the patient, connected to the constriction device and/or stimulation device for directly or indirectly supplying received energy thereto, the method comprising the steps of:
determining an energy balance between the energy sent by the
    external energy source and the energy received by the
    internal energy source, and
controlling the transmission of wireless energy from the
    external energy source, based on the determined energy
    balance.

A method, wherein the wireless energy is transmitted inductively from a primary coil in the external energy source to a secondary coil in the internal energy receiver.

A method, wherein a change in said energy balance is detected, and the transmission of wireless energy is controlled based on said detected energy balance change.

A method, wherein a difference is detected between the energy sent by the external energy source and the energy received by said internal energy receiver, and the transmission of wireless energy is controlled based on said detected energy difference.

A method, wherein the amount of transmitted wireless energy is decreased if the detected energy balance change implies that the energy balance is increasing, or vice versa.

A method, wherein the decrease/increase of energy transmission corresponds to a detected change rate.

A method, wherein the amount of transmitted wireless energy is decreased if the detected energy difference implies that the received energy is greater than the used energy, or vice versa.

A method, wherein the decrease/increase of energy transmission corresponds to the magnitude of said detected energy difference.

A method of controlling transmission of wireless energy, wherein said wireless energy being transmitted by means of a primary coil in the external energy source and received inductively by means of a secondary coil in an internal energy source, the internal energy source being connected to the medical device for directly or indirectly supplying received energy thereto, wherein feedback control information (S) is transferred from the secondary coil to the primary coil by switching the secondary coil on and off to induce a detectable impedance load variation in the primary coil encoding the feedback control information, wherein the feedback control information relates to the energy received by the internal energy source and is used for controlling the transmission of wireless energy from the external energy source.

The method, wherein the electronic circuit comprises an analyzer analyzing the amount of energy being transmitted and receiving the feedback information related to the amount of energy received in the receiver, and determining the energy balance by comparing the amount of transmitted energy and the feedback information related to the amount of received energy.

The method, wherein the external energy source is adapted to use said feedback information adjusting the level of said transmitted energy.

A method of controlling transmission of wireless energy, wherein said wireless energy being transmitted by means of a primary coil in an external energy source and received inductively by means of a secondary coil in an internal energy source, the internal energy receiver being connected to the medical device for directly or indirectly supplying received energy thereto, wherein feedback control information (S) is transferred from the secondary coil to the primary coil by switching the secondary coil on and off to induce a detectable impedance load variation in the primary coil encoding the feedback control information, where the feedback control information relates to said energy balance.

Intestinal Dysfunction

Another object of the present invention is to provide a method for controlling the flow of intestinal contents in the intestinal passageway formed by the tissue walls of a patient's intestines, so as to at least substantially or even completely eliminate the injured tissue wall problems that have resulted from implanted prior art devices that constrict similar bodily organs formed by tissue walls of bodily organs so as to at least substantially or even completely eliminate the injured tissue wall problems that have resulted from implanted prior art devices that constrict such bodily organs.

In accordance with this object of the present invention, there is provided a method for controlling the flow of intestinal contents in the intestinal passageway that is formed by the tissue wall of a patient's intestines, the method comprising:

a) gently constricting a portion of the tissue wall of the intestines wall to influence the flow in the intestinal passageway, and b) stimulating the constricted wall portion to cause contraction of the wall portion to further influence the flow in the intestinal passageway.

The present invention provides an advantageous combination of the method steps (a) and (b), which results in a two-stage influence on the flow of intestinal contents in the intestinal passageway of a patient's intestines. Thus, applying a relatively weak force against the wall portion gently constricts the tissue wall and the constricted wall portion is stimulated to achieve the desired final influence on the flow in the intestinal passageway. The phrase "gently constricts a portion of the tissue wall" is to be understood as constricting the wall portion without substantially hampering the blood circulation in the tissue wall.

Preferably, step (b) is performed by intermittently and individually stimulating different areas of the wall portion. Such an intermittent and individual stimulation of different areas of the wall portion of the intestines allows tissue of the wall portion to maintain over time substantially normal blood circulation.

The method of the present invention can be practiced on any place on the intestines, which is a significant advance in the art, as compared with prior stimulation devices that are confined to electric stimulation of malfunctioning sphincters.

Preferably, the constriction step (a) and stimulation step (b) may be performed independently of each other or. Steps (a) and (b) may be performed simultaneously. Optionally, step (b) may or may not be performed while step (a) is performed.

Initially, the constriction of the wall portion can be calibrated by stimulating the wall portion while adjusting the constriction of the wall portion until the desired restriction of the flow in the intestinal passageway is obtained.

Flow Restriction

It should be understood that any embodiment or part of embodiment disclosed below in connection with flow restriction for the constriction and stimulation devices combined in the constriction/stimulation unit could be used for the separate constriction device and separate stimulation device, where applicable.

The method of the present invention is well suited for restricting the flow of intestinal contents in the intestinal passageway of a patient's intestines. Thus, in a principal embodiment of the invention, the wall portion is constricted, so that the flow in the intestinal passageway at least is restricted and the constricted wall portion is stimulated to at least further restrict the flow in the intestinal passageway. Specifically, the wall portion is constricted to a constricted state, in which the blood circulation in the constricted wall portion is substantially unrestricted and the flow in the intestinal passageway is at least restricted, and the constricted wall portion is stimulated when it is in the constricted state to at least further restrict the flow in the intestinal passageway.

The constriction step (a) and stimulation step (b) are suitably performed to constrict and stimulate the wall portion to an extent that depends on the flow restriction that is desired to be achieved in a specific application of the method of the invention. Thus, in accordance with a first flow restriction option, step (a) is performed by constricting the wall portion, so that the flow in the intestinal passageway is restricted but not stopped, and step (b) is performed by stimulating the constricted wall portion to cause contraction thereof, so that the flow in the intestinal passageway is further restricted but not stopped. The method may further comprise sensing a physical parameter of the patient and adjusting the intensity of the stimulation of the wall portion in response to the sensed parameter.

In accordance with a second flow restriction option, step (a) is performed by constricting the wall portion, so that the flow in the intestinal passageway is restricted but not stopped, and step (b) is performed by stimulating the constricted wall portion to cause contraction thereof, so that the flow in the intestinal passageway is stopped.

When using the method of the invention in accordance with the first or second options, the method may further comprise (c) ceasing stimulating the wall portion to increase or allow the flow in the intestinal passageway and (d) releasing the wall portion to restore the flow in the intestinal passageway.

In accordance with a third flow restriction option, step (a) is performed by constricting the wall portion, so that the flow in the intestinal passageway is substantially stopped, and step (b) is performed by stimulating the constricted wall portion to cause contraction thereof, so that the flow in the intestinal passageway is completely stopped. The method may further comprise (c) ceasing stimulating the wall portion to allow the flow in the intestinal passageway and (d) releasing the wall portion to restore the flow in the intestinal passageway.

For example, the third flow restriction option may be applied where the invention is used for controlling fecal flow of an anal incontinent patient. Between defecations, any portion of the incontinent patient's large or small intestines is gently constricted into a flattened shape to at least almost stop the fecal flow in the intestines, and the flattened portion of the intestines is stimulated to insure that the fecal flow is completely stopped. By intermittently and individually stimulating different areas of the wall portion the risk of injuring the intestines over time is significantly reduced or even eliminated, which insures that the effect of the stimulation is maintained over time. When the patient wants to defecate, the stimulation is ceased and the portion of the intestines is released, whereby fecal matter may pass the portion of the intestines.

Where the constricted wall portion is stimulated to contract, so that the flow in the intestinal passageway is stopped, a first length of the constricted wall portion and a second length of the constricted wall portion, which is located downstream of the first length, are suitably simultaneously and cyclically stimulated, wherein the first length is progressively stimulated in the upstream direction of the intestinal passageway and the second length is progressively stimulated in the downstream direction of the intestinal passageway.

Furthermore, when using the method of the invention in accordance with the second and third options, the method may further comprise sensing a physical parameter of the patient or functional parameter of implanted components and adjusting the stimulation of the wall portion in response to the sensed parameter. For example, the intensity of the stimulation of the wall portion may be increased in response to a sensed pressure increase in the intestinal passageway, so that the flow in the intestinal passageway remains stopped when a pressure increase occurs in the intestinal passageway. In particular, the method may comprise sensing a physical parameter of the patient's that relates to the pressure in the intestinal passageway, and controlling the stimulation of the wall portion in response to the sensed parameter. Any sensor for sensing a physical parameter of the patient, such as a pressure in the patient's body that relates to the pressure in the intestinal passageway may be provided, wherein the stimulation is controlled in response to signals from the sensor. Such a sensor may for example sense the pressure in the patient's abdomen, the pressure against the implanted constriction device or the pressure on the tissue wall of the intestines.

In accordance with a fourth restriction option, step (a) is performed by constricting the wall portion, so that the flow in the intestinal passageway is stopped. When needed, the wall portion is released to restore the flow in the intestinal passageway. Step (b) is only performed by stimulating the constricted wall portion to cause contraction thereof, so that the flow in the intestinal passageway remains stopped when a pressure increase occurs in the intestinal passageway. The method may further comprise sensing a physical parameter of the patient's body, such as a pressure in the patient's body that relates to the pressure in the intestinal passageway, and controlling the stimulation of the wall portion in response to the sensed parameter. Such a physical parameter may be a pressure in the patient's abdomen and the sensor may be a pressure sensor.

In some applications of the method of the invention, continuous stimulation may over time change the physical properties of the tissue so that the tissue might be injured. Also, the effect of a continuous stimulation of the tissue wall may decrease over time. Therefore, step (b) is preferably performed by intermittently and individually stimulating different areas of the wall portion of the intestines so that the flow in the intestinal passageway continues to be restricted as desired and each area of the wall portion essentially maintains its natural physical properties over time to prevent the area from being injured. Advantageously, each area of the wall portion is stimulated during successive time periods, each time period being short enough to maintain over time satisfactory blood circulation in the area. Thus, the areas are stimulated so that an area that currently is not stimulated will have time to restore substantially normal blood circulation before it is stimulated again.

To maintain satisfactory blood circulation in the tissue wall of the patient's intestines stimulation step (b) is suitably performed by stimulating one or more of different areas of the wall portion at a time, preferably by sequentially stimulating the different areas of the wall portion or by shifting the stimulation from one area to another over time. Preferably, stimulation step (b) is performed by cyclically propagating the stimulation of the areas along the wall portion, for example in accordance with a determined stimulation pattern.

The method of the invention may further comprise controlling, preferably by the patient, the constriction and/or stimulation of the wall portion from outside the patient's body.

Generally, the method of the invention comprises sensing a physical parameter of the patient and controlling, preferably automatically, the constriction and/or stimulation of the wall portion in response to the sensed parameter.

The constriction step (a) may be performed by constricting any wall portions of a series of wall portions of the intestines, respectively, either in random or in accordance with a predetermined sequence. The stimulation step (b) may be performed by stimulating any of the constricted wall portions of the series of wall portions. Specifically, step (a) may be performed by constricting all of the wall portions of the series of wall portions, and step (b) may be performed by stimulating any constricted wall portions in random or in accordance with a predetermined sequence to close the intestinal passageway.

Moving Intestinal Contents in the Intestinal Passageway or Preventing Movement of Intestinal Contents in the Intestinal Passageway It should be understood that any embodiment or part of embodiment disclosed below in connection with moving intestinal contents, or preventing the intestinal contents from moving, for the constriction and stimulation devices combined in the constriction/stimulation unit could be used for the separate constriction device and separate stimulation device, where applicable.

The method of the present invention can be practiced for actively moving the intestinal contents in the intestinal passageway of a patient's intestines. Thus, in the embodiments of the invention listed below, steps (a) and (b) are co-operated to move the intestinal contents in the intestinal passageway.

1) Step (a) is performed by constricting the wall portion to restrict the flow in the intestinal passageway, and step (b) is performed by stimulating the constricted wall portion to close the intestinal passageway either at an upstream end or a downstream end of the constricted wall portion. The method further comprises (c) increasing the constriction of the wall portion to move the intestinal contents in the intestinal passageway.

2) Step (a) is performed by constricting the wall portion to restrict the flow in the intestinal passageway, and step (b) is performed by progressively stimulating the constricted wall portion to cause progressive contraction of the wall portion to move the intestinal contents in the intestinal passageway. The constricted wall portion is progressively stimulated in the downstream or upstream direction of the intestinal passageway.

3) Step (a) is performed by varyingly constricting the wall portion to vary the flow in the intestinal passageway, and step (b) is performed by progressively stimulating the constricted wall portion to cause progressive contraction of the wall portion to move the intestinal contents in the intestinal passageway. The constricted wall portion is progressively stimulated in the downstream or upstream direction of the intestinal passageway.

4) Step (a) is performed by varyingly constricting different areas of the wall portion to cause progressive constriction of the wall portion in the downstream or upstream direction of the intestinal passageway, and the constricted wall portion is progressively stimulated to cause progressive contraction thereof in harmony with the progressive constriction of the wall portion. The method may further comprise providing at least one elongated constriction element extending along the wall portion, and controlling the elongated constriction element to progressively constrict the wall portion in the downstream or upstream direction of the intestinal passageway. The elongated constriction element suitably comprises contact surfaces dimensioned to contact a length of wall portion, and the method may further comprise providing a plurality of stimulation elements distributed along the contact surfaces, and controlling the stimulation elements to stimulate the different areas of the wall portion along the length of the wall portion.

5) Step (a) is performed by constricting any one of a series of wall portions of the tissue wall to at least restrict the flow in the intestinal passageway, and step (b) is performed by stimulating the constricted wall portion to close the intestinal passageway. The method further comprises successively constricting the wall portions of the series of wall portions to move the intestinal contents in the intestinal passageway in a peristaltic manner.

5a) In accordance with an alternative, the method further comprises providing at least one constriction element and at least one stimulation element positioned on the constriction element, moving the constriction element along the intestines in the flow direction in the intestinal passageway to successively constrict the wall portions of the series of wall portions, and using the stimulation element to stimulate the wall portion constricted by the constriction element to close the intestinal passageway. Suitably, the method further comprises cyclically moving the constriction element along the wall portions of the series of wall portions.

5b) In accordance with another alternative, the method further comprises providing a plurality of constriction elements and stimulation elements positioned on the constriction elements, moving each constriction element along the intestines to successively constrict the wall portions of the series of wall portions, and using the stimulation elements to stimulate the wall portion constricted by any one of the constriction elements to close the intestinal passageway. Suitably, the method further comprises cyclically moving the constriction elements one after the other along the wall portions of the series of wall portions. Specifically, the method further comprises providing a rotor carrying the constriction elements, and rotating the rotor so that each constriction element cyclically constricts the wall portions of the series of wall portions. Each constriction element suitably comprises a roller that rolls on the intestines to constrict the latter.

6) Step (a) is performed by constricting any wall portions of a series of wall portions of the intestines, respectively, wherein the wall portions of the series of wall portions are successively constricted along the intestines to move the intestinal contents in the intestinal passageway of the patient's intestines. The stimulation step (b) is performed by stimulating any constricted wall portions of the series of wall portions.

7) Step (a) is performed by constricting wall portions of a series of wall portions without completely closing the intestinal passageway, and step (b) is performed by stimulating the constricted wall portions one after the other, so that the wall portions of the series of wall portions are successively contracted along the intestines to move the intestinal contents in the intestinal passageway of the patient's intestines.

8) Step (a) is performed by constricting the wall portion at an upstream or downstream end thereof to close the intestinal passageway. The method further comprises (c) constricting the wall portion between the upstream and downstream ends thereof, to move the fluid or other bodily matter contained in the wall portion between the upstream and downstream ends thereof downstream or upstream in the intestinal passageway. Optionally, the method further comprises stimulating the wall portion between the upstream and downstream ends thereof, as (c) is performed.

8a) In accordance with an alternative, step (a) is performed by constricting the wall portion at the upstream end thereof to restrict the flow in the intestinal passageway, and step (b) is performed by stimulating the constricted wall portion at the upstream end to close the intestinal passageway, whereby the intestinal contents contained in the wall portion between the upstream and downstream ends thereof is moved downstream in the intestinal passageway, as step (c) is performed.

8b) In accordance with another alternative, step (a) is performed by constricting the wall portion at the downstream end thereof to restrict the flow in the intestinal passageway, and step (b) is performed by stimulating the constricted wall portion at the downstream end to close the intestinal passageway, whereby the intestinal contents contained in the wall portion between the upstream and downstream ends thereof is moved upstream in the intestinal passageway, as step (c) is performed.

Where the intestines are tubular in shape, such as the small intestines, a particularly long wall portion of the tubular intestines may be surgically prepared to extend in zigzag with adjacent walls stitched together by two parallel rows of stitches and with the adjacent walls cut through between the two rows of stitches. As a result, the intestinal passageway of this long wall portion of the intestines can be significantly expanded. In this case, a considerably larger volume of fluid is moved in the intestines each time step (a) and/or step (b) is performed.

To summarize a few preferred embodiments see below:

In accordance with an alternative, step (a) is performed by constricting any wall portions of a series of wall portions of the tissue wall of the intestines, respectively. In accordance with an alternative, the wall portions of the series of wall portions are constricted in random or in accordance with a predetermined sequence. In accordance with an alternative, the wall portions of the series of wall portions are successively constricted along the intestines to move the intestinal contents in the intestinal passageway of the patient's intestines or to prevent the intestinal contents from moving in the intestinal passageway.

In accordance with an alternative, step (b) is performed by stimulating any constricted wall portions of the series of wall portions. In accordance with an alternative, the wall portions of the series of wall portions are constricted in random or in accordance with a predetermined sequence. In accordance with an alternative, wherein the wall portions of the series of wall portions are successively constricted along the intestines to move the intestinal contents in the intestinal passageway of the patient's intestines or to prevent the intestinal contents to move in the from moving in the patient's intestines.

In accordance with an alternative, step (a) is performed by constricting any wall portions of a series of wall portions of the tissue wall of the intestines, respectively, wherein the wall portions of the series of wall portions are successively constricted without completely closing the intestinal passageway, and step (b) is performed by stimulating the constricted wall portions, so that the wall portions of the series of wall portions are further constricted. In accordance with an alternative, the wall portions of the series of wall portions are constricted in random or in accordance with a predetermined sequence.

In accordance with an alternative, wherein the wall portions of the series of wall portions are successively constricted along the intestines to move the intestinal contents in the intestinal passageway of the patient's intestines or to prevent the intestinal contents from moving in the patient's intestines.

In accordance with an alternative, step (a) is performed by constricting all of the wall portions of the series of wall portions, and step (b) is performed by stimulating any constricted wall portions so that the wall portions of the series of wall portions are further constricted.

In accordance with an alternative, the wall portions of the series of wall portions are further constricted by the stimulation device in random or in accordance with a predetermined sequence.

In accordance with an alternative, the wall portions of the series of wall portions are successively further constricted by the stimulation device along the intestines to move the intestinal contents in the intestinal passageway of the patient's intestines or to prevent the intestinal contents from moving in the patient's intestines.

In accordance with an alternative for all applicable alternatives, step (a) and step (b) are performed independently of each other or in accordance with an alternative, step (a) and step (b) are performed simultaneously.

In any of the above noted embodiments (1) to (86b), step (b) may be performed by stimulating the wall portion with electric pulses.

Stimulation Modes

When stimulating neural or muscular tissue there is a risk of injuring or deteriorating the tissue over time if the stimulation is not properly performed. The method of the present invention is performed to reduce or even eliminate that risk. Thus, step (b) is performed by intermittently stimulating different areas of the wall portion so that at least two of the areas are stimulated at different points of time. I.e., the stimulation is shifted from one area to another area over time. In addition, step (b) is performed by intermittently stimulating the areas of the wall portion so that an area of the different areas that currently is not stimulated has time to restore substantially normal blood circulation before it is stimulated again. Furthermore, step (b) is performed by intermittently stimulating the areas during successive time periods, wherein each time period is short enough to maintain satisfactory blood circulation in the area until the laps of the time period. This gives the advantage that the method of the present invention provides continuous stimulation of the wall portion of the intestines to achieve the desired flow control while essentially maintaining over time the natural physical properties of the intestines without risk of injuring the intestines.

Also, by physically changing the places of stimulation on the intestines over time as described above it is possible to create an advantageous changing stimulation pattern on the intestines, in order to achieve a desired flow control.

To achieve the desired reaction of the tissue wall during the stimulation thereof, step (b) may be performed by stimulating the wall portion with, preferably cyclically, varying stimulation intensity.

In a main embodiment of the invention, step (b) is performed by intermittently stimulating the wall portion with pulses, preferably in the form of pulse trains. The pulse trains can be configured in many different ways by varying pulse parameters. Thus, the pulse amplitudes of the pulses of the pulse trains, the off time periods between the individual pulses of each pulse train and the width and repetition frequency of each pulse may be varied. Also the off time periods between the pulse trains may be varied, wherein each off time period between the pulse trains is kept long enough to restore substantially normal blood circulation in each area of the wall portion, when the area is not stimulated during the off time periods. Furthermore, the repetition frequency of the pulses of the pulse trains and the length and number of pulses of each pulse train may be varied.

As mentioned above, for reasons of maintaining over time the effect of stimulation, it is preferable that different areas of the wall portion are intermittently and individually stimulated. In consequence, step (b) may be performed by stimulating one or more of the areas at a time with pulses, by cyclically propagating the stimulation of the areas with pulses along the wall portion, and/or by propagating the stimulation of the areas with pulses in accordance with a determined stimulation pattern. In case the off time periods between pulse trains that stimulate the respective area of the wall portion are varied, it is preferable that each off time period between the pulse trains is controlled to last long enough to restore substantially normal blood circulation in the area when the latter is not stimulated during the off time periods.

Electric Stimulation

In accordance with a preferred embodiment of the invention, step (b) is performed by electrically stimulating the wall portion, preferably with electric pulses to cause contraction of the wall portion. This embodiment is particularly suited for applications in which the patient's wall portion includes muscle fibers that react to electrical stimula. Thus, the wall portion that includes the muscle fibers is stimulated with such electric pulses, preferably in the form of electric pulse trains, when the wall portion is in the constricted state, to cause contraction of the wall portion. Of course, the configuration of the electric pulse trains may be similar to the above described pulse trains and different areas of the wall portion may be electrically stimulated in the same manner as described above.

In accordance with the preferred embodiment, the method of the invention comprises providing at least one, preferably a plurality of electrical elements, such as electrodes, engaging and stimulating the wall portion with electric pulses. Optionally, the electrical elements may be placed in a fixed orientation relative to one another. The method comprises electrically energizing the electrical elements, preferably by cyclically energizing each element with electric pulses. The electrical elements may be energized so that the electrical elements are energized one at a time in sequence, or so that a number or groups of the electrical elements are energized at a time. Also, groups of electrical elements may be sequentially energized, either randomly or in accordance with a predetermined pattern.

The method may further comprise applying the electrical elements on the patient's wall portion so that the electrical elements form any pattern of electrical elements, preferably an elongate pattern of electrical elements extending lengthwise along the wall portion and the elements abut the respective areas of the wall portion. The electrical elements may be successively energized along the elongate pattern of electrical elements in a direction opposite to or in the same direction as that of the flow in the patient's intestinal passageway. Optionally, the electrical elements may be successively energized along the elongate pattern of electrical elements from a position substantially at the center of the constricted wall portion towards both ends of the elongate pattern of electrical elements. Where the intestinal passageway of the intestines is to be kept closed for a relatively long time, the electrical elements may be energized so that energized electrical elements form two waves of energized electrical elements that simultaneously advance from the center of the constricted wall portion in two opposite directions towards both ends of the elongate pattern of electrical elements. Such waves of energized electrical elements can be repeated over and over again without harming the intestines and without moving fluid or gas in any direction in the intestinal passageway of the intestines.

The elongate pattern of electrical elements may include one or more rows of electrical elements extending lengthwise along the intestines. Each row of electrical elements may form a straight, helical or zig-zag path of electrical elements, or any form of path. The electrical elements may be energized so that the electrical elements currently energized form at least one group of adjacent energized electrical elements, wherein the elements in the group of energized electrical elements form a path of energized electrical elements extending at least in part around the patient's intestines, preferably completely around the patient's intestines. Alternatively, the elements in the group of energized electrical elements form two paths of energized electrical elements extending on mutual sides of the patient's intestines or more than two paths of energized electrical elements extending on different sides of the patient's intestines, preferably at least substantially transverse to the flow direction in the intestinal passageway of the intestines.

In an embodiment of the invention, the electrical elements form a plurality of groups of elements, wherein the groups form a series of groups extending along the patient's intestines in the flow direction in the patient's intestinal passageway. The electrical elements of each group of electrical elements may form a path of elements extending at least in part around the patient's intestines. In a first alternative, the electrical elements of each group of electrical elements may form more than two paths of elements extending on different sides of the patient's intestines, preferably substantially transverse to the flow direction in the patient's intestinal passageway. The groups of electrical elements in the series of groups may be energized in random or in accordance with a predetermined pattern. Alternatively, the groups of electrical elements in the series of groups may be successively energized in a direction opposite to or in the same direction as that of the flow in the patient's intestinal passageway, or in both said directions starting from a position substantially at the center of the constricted wall portion. For example, groups of energized electrical elements may form advancing waves of energized electrical elements, as described above. I.e., the groups of electrical elements may be energized so that energized electrical elements form two waves of energized electrical elements that simultaneously advance from the center of the constricted wall portion in two opposite directions towards both ends of the elongate pattern of electrical elements.

Thermal Stimulation

In accordance with an embodiment of the invention, stimulation step (b) is performed by thermally stimulating the wall portion. Thus, the wall portion may be cooled, when the wall portion is constricted, to cause contraction of the wall portion. For example, the wall portion may be constricted to at least restrict the flow in the intestinal passageway, and the constricted wall portion may be cooled to cause contraction thereof, so that the flow in the intestinal passageway is at least further restricted, or further restricted but not stopped, or stopped. Alternatively, the wall portion may be heated, when the wall portion is constricted and contracted, to cause expansion of the wall portion. Where the wall portion includes a blood vessel, the blood vessel may be cooled to cause contraction thereof, or heated to cause expansion thereof. Where applicable, thermal stimulation may be practiced in any of the embodiments of the present invention. Where applicable, thermal stimulation may be practiced in any of the embodiments of the present invention, and the thermal stimulation may be controlled in response to various sensors, for example strain, motion or pressure sensors.

Constriction and Stimulation Devices

It should be understood that any embodiment or part of embodiment for the combined stimulation device and constriction device, could be used, where applicable, for any one of the devices as a stand alone device.

Generally, the method of the invention comprises providing a constriction device that constricts the wall portion, a stimulation device that stimulates the constricted wall portion and a control device that controls the constriction device and/or the stimulation device. The method comprises operating the control device from outside the patient's body, preferably by using the control device to wirelessly control the constriction device and/or stimulation device. The wireless control is preferably performed in a non-magnetic manner, whereby implanted magnetic devices can be avoided. Suitably, the control device comprises a hand-held wireless remote control operated by the patient.

Alternatively, the control device comprises a manually operable switch for switching on and off the constriction device and/or stimulation device. In this case, the method comprises subcutaneously implanting the switch in the patient and manually operating the the implanted switch from outside the patient's body.

In an embodiment of the invention, the control device comprises a programmable internal control unit, such as a microprocessor, and the method comprises implanting in the patient the internal control unit and controlling by the internal control unit the constriction device and/or stimulation device. The control device may also comprise an external control unit outside the patient's body. In this case, the method comprises controlling by the external control unit the constriction device and/or stimulation device and, optionally, using the external control unit to program the implanted internal control unit. The internal control unit may be programmable for controlling the constriction device and/or stimulation device over time, for example in accordance with an activity schedule program.

The constriction of the wall portion can be calibrated by using the control device to control the stimulation device to stimulate the wall portion while controlling the constriction device to adjust the constriction of the wall portion until the desired restriction of the flow in the intestinal passageway is obtained.

Sensor Controlled Constriction and/or Stimulation

It should be understood that any embodiment or part of embodiment disclosed below in connection with sensor control of the constriction and stimulation devices combined in the constriction/stimulation unit could be used for the separate constriction device and separate stimulation device, where applicable.

In an embodiment of the invention, the method comprises implanting at least one sensor and controlling by the control device the constriction device and/or the stimulation device in response to signals from the sensor. Generally, the sensor directly or indirectly senses at least one physical parameter of the patient, functional parameter of the apparatus, or functional parameter of a medical implant in the patient.

Many different kinds of sensor for sensing physical parameters may be used. For example motion sensors for sensing intestinal motion, i.e. natural contractions, such as stomach or intestinal contractions, pressure sensors for sensing pressure in the intestines, strain sensors for sensing strain of the intestines, flow sensors for sensing fluid flow in the intestinal passageway of the intestines, spectro-photometrical sensors, Ph-sensors for acidity or alkalinity of the fluid in the intestinal passageway of the intestines, oxygen-sensors sensors for sensing the oxygen content of the fluid in the intestinal passageway of the intestines, or sensors for sensing the distribution of the stimulation on the stimulated intestines. Any conceivable sensors for sensing any other kind of useful physical parameter may be used.

Many different kinds of sensors that sense functional parameters of implanted components may also be used for the control of the constriction device and/or the stimulation device. For example sensors for sensing electric parameters of implanted electric components, or sensors for sensing the performance of implanted motors or the like.

The sensor may comprise a pressure sensor for sensing as the physical parameter a pressure in the patient's body that relates to the pressure in the intestinal passageway of the patient's intestines. In this case, the method suitably comprises operating the control device to control the constriction device to change the constriction of the patient's wall portion in response to the pressure sensor sensing a predetermined value of measured pressure.

Alternatively, or in combination with the pressure sensor, a position sensor may be provided for sensing as the physical parameter the orientation of the patient with respect to the horizontal. The position sensor may be a biocompatible version of what is shown in U.S. Pat. Nos. 4,942,668 and 5,900,909. For example, the control device may control the constriction device and/or stimulation device to change the constriction of the patient's wall portion in response to the position sensor sensing that the patient has assumed a substantially horizontal orientation, i.e. that the patient is lying down.

The above described sensors may be used in any of the embodiments of the invention, where applicable.

The control device may control the constriction device and/or stimulation device to change the constriction of the patient's wall portion in response to the time of day. For that purpose the control device may include a clock mechanism for controlling the constriction device and/or stimulation device to change the constriction of the patient's wall portion to increase or decrease the influence on the flow in the intestinal passageway during different time periods of the day. In case a sensor of any of the above-described types for sensing a physical or functional parameter is provided, either the clock mechanism is used for controlling the constriction device and/or stimulation device provided that the parameter sensed by the sensor does not override the clock mechanism, or the sensor is used for controlling the constriction device and/or stimulation device provided that the clock mechanism does not override the sensor. Suitably, the control device produces an indication, such as a sound signal or displayed information, in response to signals from the sensor.

The control device may comprise an implantable internal control unit that directly controls the constriction device and/or stimulation device in response to signals from the sensor. The control device may further comprise a wireless remote control adapted to set control parameters of the internal control unit from outside the patient without mechanically penetrating the patient. At least one of the control parameters, which is settable by the wireless remote control, is the physical or functional parameter. Suitably, the internal control unit includes the above mentioned clock mechanism, wherein the wireless remote control also is adapted to set the clock mechanism.

Alternatively, the control device may comprise an external control unit outside the patient's body for controlling the constriction device and/or stimulation device in response to signals from the sensor.

Constriction of Patient's Intestines

It should be understood that any embodiment or part of embodiment disclosed below in connection with constricting the patient's intestines could be used for the separate constriction device and separate stimulation device, where applicable.

Method step (a) may be performed in many different ways. Thus, step (a) may be performed by:
(1)—constricting the wall portion so that the through-flow area of the intestinal passageway assumes a size in the constricted state small enough to cause the constricted wall portion to contract to stop the flow in the intestinal passageway when step (b) is performed;
(2)—bending the wall portion;
(3)—clamping the wall portion between at least two elements positioned on different sides of the intestines;
(4)—clamping the intestines between an element and the bone or tissue of the patient;
(5)—rotating at least two elements positioned on different sides of the intestines; or
(6)—clamping the intestines between at least two articulated clamping elements positioned on different sides of the intestines.

In the above noted alternatives (1) to (6) of method step (a), the constriction of the wall portion of the intestines may be changed either mechanically or hydraulically. For many applications of the present invention, step (a) is suitably performed so that the through-flow area of the intestinal passageway assumes a size in the constricted state that is small enough to enable the stimulation during step (b) to contract the wall portion of the intestines to stop the flow in the intestinal passageway.

Where the constriction of the wall portion is hydraulically changed, the method of the invention may further comprise implanting in the patient a reservoir containing a predetermined amount of hydraulic fluid, and a constriction device engaging the wall portion and having an expandable/contractible cavity, wherein step (a) is performed by distributing hydraulic fluid from the reservoir to increase the volume of the cavity to constrict the wall portion, and by distributing hydraulic fluid from the cavity to the reservoir to decrease the volume of the cavity to release the wall portion. The cavity may be defined by a balloon of the constriction device that abuts the tissue wall portion of the patient's intestines, so that the patient's wall portion is constricted upon expansion of the cavity and released upon contraction of the cavity.

Alternatively, the cavity may be defined by a bellows that displaces a relatively large contraction element of the constriction device, for example a large balloon that abuts the wall portion, so that the patient's wall portion is constricted upon contraction of the bellows and released upon expansion of the bellows. Thus, a relatively small addition of hydraulic fluid to the bellows causes a relatively large increase in the constriction of the wall portion. Such a bellows may also be replaced by a suitably designed piston/cylinder mechanism.

Where the hydraulic means comprises a cavity in the constriction device, the following embodiments of the invention are conceivable.

1) The reservoir comprises first and second wall portions, and step (a) is performed by displacing the first and second wall portions relative to each other to change the volume of the reservoir, so that fluid is distributed from the reservoir to the cavity, or from the cavity to the reservoir.

1a) At least one of a magnetic device, a hydraulic device or an electric control device displaces the first and second wall portions of the reservoir.

2) A pump is provided for pumping fluid between the reservoir and the cavity.

2a) The pump comprises a first activation member for activating the pump to pump fluid from the reservoir to the cavity and a second activation member for activating the pump to pump fluid from the cavity to the reservoir.

2a1) The first and second activation members are operable by manual manipulation thereof.

2a2) At least one of the activation members operates when subjected to an external predetermined pressure.

2a3) At least one of the first and second activating members is operable by magnetic means, hydraulic means, or electric control means.

2b) A fluid conduit between the pump and the cavity is provided, wherein the reservoir forms part of the conduit. The conduit and pump are devoid of any non-return valve. The reservoir forms a fluid chamber with a variable volume, and the pump distributes fluid from the chamber to the cavity by a reduction in the volume of the chamber and withdraws fluid from the cavity by an expansion of the volume of the chamber. A motor is provided for driving the pump, wherein the pump comprises a movable wall of the reservoir for changing the volume of the chamber.

In all of the above noted embodiments 1 to 2b where the hydraulic means comprises an expandable cavity in the constriction device, the cavity can be exchanged by a cylinder/ piston mechanism for adjusting the constriction device. In this case, hydraulic fluid is distributed between the reservoir and the cylinder/piston mechanism to adjust the constriction device.

3) The method further comprises implanting a reverse servo operatively connected to the hydraulic means. The term "reverse servo" is to be understood as a mechanism that transfers a strong force acting on a moving element having a short stroke into a weak force acting on another moving element having a long stroke; i.e., the reverse function of a normal servo mechanism. Thus, minor changes in the amount of fluid in a smaller reservoir could be transferred by the reverse servo into major changes in the amount of fluid in a larger reservoir.

Preferably, the reverse servo comprises an expandable servo reservoir containing servo fluid and a fluid supply reservoir hydraulically connected to the servo reservoir to form a closed conduit system for the servo fluid. The expandable servo reservoir has first and second wall portions, which are displaceable relative to each other in response to a change in the volume of the expandable servo reservoir.

In accordance with a first alternative, the first and second wall portions of the servo reservoir are operatively connected to the hydraulic means. The reverse servo distributes fluid between the fluid supply reservoir and the expandable servo reservoir to change the volume of the servo reservoir, whereby the hydraulic means is operated to adjust the constriction device.

In accordance with a second alternative, there is provided an implantable main reservoir containing a predetermined amount of hydraulic fluid, wherein the reverse servo is operated to distribute hydraulic fluid between the main reservoir and the hydraulic means to adjust the constriction device. More specifically, the main reservoir is provided with first and second wall portions operatively connected to the first and second wall portions of the expandable servo reservoir, so that the volume of the main reservoir is changed when the volume of the expandable servo reservoir is changed. Thus, when the reverse servo distributes servo fluid between the fluid supply reservoir and the expandable servo reservoir to change the volume of the main reservoir, hydraulic fluid is distributed from the main reservoir to the hydraulic means, or from the hydraulic means to the main reservoir. Advantageously, the method comprises dimensioning the servo and main reservoirs, so that when the volume of the servo reservoir is changed by a relatively small amount of servo fluid, the volume of the main reservoir is changed by a relatively large amount of hydraulic fluid.

In both of the above-described alternatives, the fluid supply reservoir may have first and second wall portions, which are displaceable relative to each other to change the volume of the fluid supply reservoir to distribute servo fluid between the fluid supply reservoir and the expandable servo reservoir. The first and second wall portions of the fluid supply reservoir may be displaced relative to each other by manual manipulation, a magnetic device, a hydraulic device, or an electric control device to change the volume of the fluid supply reservoir to distribute servo fluid between the fluid supply reservoir and the expandable servo reservoir.

In all of the above noted embodiments 1 to 2b where the hydraulic means comprises an expandable cavity in the constriction device, or in embodiments where the hydraulic means includes a hydraulically operable mechanical construction, the reverse servo described above may be used. In a further embodiment of the invention, the hydraulic means include first and second hydraulically interconnected expandable/contractible reservoirs. The first reservoir is operatively connected to the constriction device, so that the constriction device changes the constriction of the patient's wall portion upon expansion or contraction of the first reservoir. By changing the volume of the second reservoir hydraulic fluid is distributed between the two reservoirs, so that the first reservoir is either expanded or contracted. This embodiment requires no non-return valve in the fluid communication conduits between the two reservoirs, which is beneficial to long-term operation of the hydraulic means.

Alternatively, the hydraulic means may include first and second hydraulically interconnected piston/cylinder mechanisms instead of the first and second reservoirs described above. The first piston/cylinder mechanism is operatively connected to the constriction device, so that the constriction device changes the constriction of the patient's wall portion upon operation of the first piston/cylinder mechanism. By operating the second piston/cylinder mechanism hydraulic fluid is distributed between the two piston/cylinder mechanisms, so that the first piston/cylinder mechanism adjusts the constriction device.

Where the constriction device does not include an expandable/contractible cavity, the constriction device may comprise at least two elongated clamping elements extending along the wall portion on different sides of the intestines. The hydraulic means, which may include the reverse servo described above, hydraulically moves the elongated clamping elements towards the intestines to constrict the wall portion of the intestines. For example, the constriction device may have hydraulic chambers in which the clamping elements slide back and forth, and the hydraulic means may also include a pump and an implantable reservoir containing hydraulic fluid. The pump distributes hydraulic fluid from the reservoir to the chambers to move the clamping elements against the wall portion, and distributes hydraulic fluid from the chambers to the reservoir to move the clamping elements away from the wall portion.

Energy Supply

It should be understood that any embodiment or part of embodiment disclosed below in connection with the power of the constriction and stimulation devices combined in the constriction/stimulation unit could be used for the separate constriction device and separate stimulation device, where applicable.

Generally, method step (a) is performed by using the constriction device and step (b) is performed by using the stimulation device, wherein the method further comprises forming the constriction and stimulation devices in an operable constriction/stimulation unit.

In a simple form of the invention, the method comprises implanting a source of energy, such as a battery, rechargeable battery or accumulator, releasing energy from the source of energy and using the released energy in connection with the operation of the constriction/stimulation unit.

In a more sophisticated form of the invention, which is preferable, the method comprises transmitting wireless energy from outside the patient's body to inside the patient's body and using the transmitted wireless energy in connection with the operation of the constriction/stimulation unit.

Transmission of Wireless Energy

It should be understood that any embodiment or part of embodiment disclosed below in connection with wireless control or power of the constriction and stimulation devices combined in the constriction/stimulation unit could be used for the separate constriction device and separate stimulation device, where applicable.

The wireless energy may be directly used in connection with the operation of the constriction/stimulation unit, as the wireless energy is being transmitted. For example, the wireless energy may be transmitted in the form of an electric, an electromagnetic or a magnetic field, or a combination thereof, or electromagnetic waves for direct power of the constriction/stimulation unit. For example, where an electric motor or pump operates the constriction device of the constriction/stimulation unit, wireless energy in the form of a magnetic or an electromagnetic field may be used for direct power of the motor or pump.

Thus, the motor or pump is running directly during transmission of the wireless energy. This may be achieved in two different ways: a) using a transforming device implanted in the patient to transform the wireless energy into energy of a different form, preferably electric energy, and powering the motor or pump with the transformed energy, or b) using the wirelessly transmitted energy to directly power the motor or pump. Preferably wireless energy in the form of an electromagnetic or magnetic field is used to directly influence specific components of the motor or pump to create kinetic energy. Such components may include coils integrated in the motor or pump.

The wireless energy is suitably transmitted in pulses or digital pulses, or a combination of pulses and digital pulses.

Preferably, the wireless energy is transmitted in at least one wireless signal, suitably a wave signal. The wave signal may comprise an electromagnetic wave signal including one of an infrared light signal, a visible light signal, an ultra violet light signal, a laser signal, a microwave signal, a radio wave signal, an x-ray radiation signal, and a gamma radiation signal. Alternatively, the wave signal may comprise a sound or an ultrasound wave signal. The wireless signal may be a digital or analogue signal, or a combination of a digital and analogue signal.

In accordance with a particular embodiment of the invention, the wireless energy is not for direct use in connection with the operation of the constriction/stimulation unit. In this embodiment the wireless energy comprises energy of a first form, which is transmitted into energy of a second form suited to operate the constriction/stimulation unit. Typically, the energy of the second form is different from the energy of the first form. For example, the wireless energy of the first form may comprise sound waves, whereas the energy of the second form may comprise electric energy. Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

Transforming Wireless Energy

It should be understood that any embodiment or part of embodiment disclosed below in connection with the control or energizing of the constriction and stimulation devices combined in the constriction/stimulation unit could be used for the separate constriction device and separate stimulation device, where applicable.

In accordance with a particular embodiment of the invention, an implantable energy-transforming device is provided for transforming wireless energy of a first form transmitted by the energy-transmission device into energy of a second form, which typically is different from the energy of the first form. The constriction/stimulation unit is operable in response to the energy of the second form. For example, the wireless energy of the first form may comprise sound waves, whereas the energy of the second form may comprise electric energy. Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transforming device may function different from or similar to the energy-transmission device. Advantageously, the energy-transforming device comprises at least one element, such as at least one semiconductor, having a positive region and a negative region, when exposed to the energy of the first form transmitted by the energy-transmission device, wherein the element is capable of creating an energy field between the positive and negative regions, and the energy field produces the energy of the second form. More specifically, the element may comprise an electrical junction element, which is capable of inducing an electric field between the positive and negative regions when exposed to the energy of the first form transmitted by the energy-transmission device, whereby the energy of the second form comprises electric energy.

The energy of the first form may directly or indirectly be transformed into the energy of the second form. The method of the invention may comprise providing a motor for operating the constriction device and powering the motor with the energy of the second form. The constriction device may be operable to perform at least one reversible function and the method may comprise reversing the function by using the motor. For example, the method may comprise shifting the polarity of the energy of the second form to reverse the motor.

The motor may be directly powered with the transformed energy, as the energy of the second form is being transformed from the energy of the first form. Preferably, the constriction/stimulation unit is directly operated with the energy of the second form in a non-magnetic, non-thermal or non-mechanical manner.

Normally, the implanted constriction/stimulation unit comprises electric components that are energized with electrical energy. Therefore, the energy of the first form may be transformed into a direct current or pulsating direct current, or a combination of a direct current and pulsating direct current. Alternatively, the energy of the first form may be transformed into an alternating current or a combination of a direct and alternating current.

The method of the invention may comprise implanting in the patient an internal source of energy, and supplying energy from the internal source of energy for the operation of the constriction/stimulation unit. The method may further comprise implanting in the patient a switch operable to switch from an "off" mode, in which the internal source of energy is not in use, to an "on" mode, in which the internal source of energy supplies energy for the operation of the constriction/stimulation unit, and/or for energizing implanted electronic components of the constriction/stimulation unit. The switch may be operated by the energy of the first form or by the energy of the second form. The described switch arrangement reduces power consumption of the constriction/stimulation unit between operations.

The internal source of energy may store the energy of the second form. In this case, the internal source of energy suitably comprises an accumulator, such as at least one capacitor or at least one rechargeable battery, or a combination of at least one capacitor and at least one rechargeable battery. Where the internal source of energy is a rechargeable battery it may be charged only at times convenient for the patient, for example when the patient is sleeping. Alternatively, the internal source of energy may supply energy for the operation of the constriction/stimulation unit but not be used for storing the energy of the second form. In this alternative, the internal source of energy may be a battery and the switch described above may or may not be provided.

Suitably, the method of the invention may comprise implanting a stabilizer for stabilizing the energy of the second form. Where the energy of the second form comprises electric energy the stabilizer suitably comprises at least one capacitor.

The energy-transforming device may be designed for implantation subcutaneously in the abdomen, thorax or cephalic region of the patient. Alternatively, it may be designed for implantation in an orifice of the patient's body and under the mucosa or intramuscularly outside the mucosa of the orifice.

Control of Constriction/Stimulation Unit

It should be understood that any embodiment or part of embodiment disclosed below in connection with the control of the constriction and stimulation devices combined in the constriction/stimulation unit could be used for the separate constriction device and separate stimulation device, where applicable.

Although the constriction device of the constriction/stimulation unit may normally keep the patient's wall portion in the constricted state, in most applications using the present invention there will be daily adjustments of the constriction device. Therefore, in a preferred embodiment of the invention, the constriction device is adjustable to enable changing the constriction of the patient's wall portion as desired and the control device controls the constriction device to change the constriction of the wall portion.

The method of the invention suitably comprises operating the control device by the patient. In a simple form the control device comprises a manually operable switch for switching on and off the constriction/stimulation unit, and the method further comprises subcutaneously implanting the switch in the patient. It is preferable, however, that the control device comprises a hand-held wireless remote control operable by the patient from outside the patient's body to control the constriction/stimulation unit to adjust the stimulation intensity and/or adjust the constriction of the wall portion. The wireless remote control is suitably designed for application on the patient's body like a wristwatch.

In some applications of the invention, the constriction device of the constriction/stimulation unit may be designed to normally keep the patient's wall portion in the constricted state. I.e., after implantation the constriction device all the time keeps the wall portion constricted. In this case, the control device may be used when needed, conveniently by the patient, to control the stimulation device of the constriction/stimulation unit to stimulate the constricted tissue wall portion, preferably while adjusting the stimulation intensity, to cause contraction of the wall portion, so that the flow in the intestinal passageway is at least further restricted or stopped, and to control the stimulation device to cease the stimulation. More precisely, the method of the invention may comprise operating the control device by the patient to a) control the stimulation device in a first mode to stimulate the constricted wall portion to further restrict the flow in the intestinal passageway and control the stimulation device in a second mode to cease the stimulation of the wall portion to increase the flow in the intestinal passageway; or b) control the stimulation device in a first mode to stimulate the constricted wall portion to stop the flow in the intestinal passageway and control the stimulation device in a second mode to cease the stimulation of the wall portion to allow flow in the intestinal passageway.

Either the first mode or the second mode may be temporary.

The wireless remote control preferably transmits at least one wireless control signal for controlling the constriction/stimulation unit. The control signal may comprise a frequency, amplitude, phase modulated signal or a combination thereof, and may be an analogue or a digital signal, or a combination of an analogue and digital signal. The remote control may transmit an electromagnetic carrier wave signal for carrying the digital or analogue control signal. Also the carrier signal may comprise digital, analogue or a combination of digital and analogue signals.

Any of the above signals may comprise wave signals, such as a sound wave signal, an ultrasound wave signal, an electromagnetic wave signal, an infrared light signal, a visible light signal, an ultra violet light signal, a laser light signal, a micro wave signal, a radio wave signal, an x-ray radiation signal or a gamma radiation signal.

Alternatively, the control signal may comprise an electric or magnetic field, or a combined electric and magnetic field.

Operation of Constriction/Stimulation Unit

It should be understood that any embodiment or part of embodiment for operating the combined stimulation device and constriction device, could be used, if applicable, for any one of the devices as a stand alone device.

The method of the invention may comprise implanting in the patient an operation device, and operating the constriction/stimulation unit with the operation device. A magnet may be provided, wherein the method comprises using the magnet to activate the operation device from outside the patient's body. The operation device suitably comprises a motor which is powered with energy released from a source of energy, such as a battery. Although the constriction/stimulation unit in embodiments described above suitably is designed as a single piece, which is most practical for implantation, it should be noted that as an alternative the constriction device and stimulation device of the constriction/stimulation unit could be designed as separate pieces.

Laparoscopic Method

The present invention also provides a first method for controlling a flow of intestinal contents in the intestinal passageway formed by a tissue wall of a patient's intestines. The method comprises the steps of:
inserting a needle like tube into the cavity of the patients body,
filling the cavity with gas thereby expanding the abdominal cavity,
placing at least two laparascopical trocars in the patient's body,
inserting a camera through one of the trocars into the cavity,
inserting a dissecting tool through any of the trocar and dissecting an area of at least one portion of the tissue wall of the intestines,
placing a constriction device and a stimulation device in the dissected area in operative engagement with the intestines, using the constriction device to gently constrict the wall portion of the intestines to influence the flow in the intestines, and using the stimulation device to stimulate the constricted wall portion to cause contraction of the wall portion to further influence the flow in the intestines.

The present invention also provides a second method for controlling a flow of intestinal contents in the intestinal passageway formed by a tissue wall of a patient's intestines. The method comprises the steps of:

inserting a needle like tube into a cavity of the patients body, using the needle like tube to fill the cavity with gas thereby expanding the cavity, placing at least two laparascopical trocars in the patient's body, inserting a camera through one of the trocars into the cavity, inserting a dissecting tool through any of the trocar and dissecting an area of at least one portion of the tissue wall of the intestines, placing a stimulation device in the dissected area in operative engagement with the intestines, and using the stimulation device to stimulate the wall portion to cause contraction of the wall portion to influence the flow in the intestines.

The present invention also provides a third method for controlling a flow of intestinal contents in the intestinal passageway formed by a tissue wall of a patient's intestines. The method comprises the steps of:

inserting a needle like tube into a cavity of the patients body, using the needle like tube to fill the cavity with gas thereby expanding the cavity, placing at least two laparascopical trocars in the patient's body, inserting a camera through one of the trocars into the cavity, inserting a dissecting tool through any of the trocar and dissecting an area of at least one portion of the tissue wall of the intestines, placing a constriction device in the dissected area in operative engagement with the intestines, using the constriction device to constrict the wall portion of the intestines to influence the flow in the intestines.

The present invention also provides a fourth method for controlling a flow of intestinal contents in the intestinal passageway formed by a tissue wall of a patient's intestines. The method comprises the steps of:

cutting the skin of the patient, inserting a dissecting tool and dissecting an area of at least one portion of the tissue wall of the intestines, placing a constriction device and a stimulation device in the dissected area in operative engagement with the intestines, using the constriction device to gently constrict the wall portion of the intestines to influence the flow in the intestines, and using the stimulation device to stimulate the constricted wall portion to cause contraction of the wall portion to further influence the flow in the intestines.

The present invention also provides a fifth method for controlling a flow of intestinal contents in the intestinal passageway formed by a tissue wall of a patient's intestines. The method comprises the steps of:

cutting the skin of the patient, inserting a dissecting tool and dissecting an area of at least one portion of the tissue wall of the intestines, placing a stimulation device in the dissected area in operative engagement with the intestines, and using the stimulation device to stimulate the wall portion to cause contraction of the wall portion to influence the flow in the intestines.

The present invention also provides a sixth method for controlling a flow of intestinal contents in the intestinal passageway formed by a tissue wall of a patient's intestines. The method comprises the steps of:

cutting the skin of the patient, inserting a dissecting tool and dissecting an area of at least one portion of the tissue wall of the intestines, placing a constriction device in the dissected area in operative engagement with the intestines, and using the constriction device to constrict the wall portion of the intestines to influence the flow in the intestines.

In all of the above-noted methods 1-6 the cavity may constitute at least one of an abdominal cavity, or, a cavity in the pelvic region, a retroperitoneal cavity, a thoraxial cavity, a cavity in a limb, a cavity in human soft tissue such as muscle, fat and fibrotic tissue.

The present invention also provides another laparoscopic method. Accordingly, there is provided a method for controlling a flow of intestinal contents in the intestinal passageway formed by a tissue wall of a patient's intestines. The method comprises the steps of:

inserting a needle like tube into the abdomen of the patients body, filling the abdomen with gas thereby expanding the abdominal cavity, placing at least two laparascopical trocars in the patient's body, inserting a camera through one of the trocars into the abdomen, inserting a dissecting tool through any of the trocars and dissecting an area of at least one portion of the tissue wall of the intestines, placing a constriction device and a stimulation device in the dissected area in operative engagement with the intestines, using the constriction device to gently constrict the wall portion of the intestines to influence the flow in the intestinal passageway, and using the stimulation device to stimulate the constricted wall portion to cause contraction of the wall portion to further influence the flow in the intestinal passageway.

The method further comprises implanting a powered operation device for operating the constriction device. The operation device may comprise a powered hydraulic operation device or an electrically powered operation device, such as an electric motor.

The method further comprises transmitting wireless energy for powering the operation device, and when desired to influence the flow in the patient's intestines, powering the operation device with the transmitted energy to operate the constriction device.

Urinary Dysfunction

Another object of the present invention is to provide a method for controlling the flow of urine in urinary passageways formed by tissue walls of the urethra, ureter, renal pelvis or bladder, so as to at least substantially or even completely eliminate the injured tissue wall problems that have resulted from implanted prior art devices that constrict such bodily organs.

In accordance with this object of the present invention, there is provided a method for controlling the flow of urine in a urinary passageway formed by the tissue wall of a patient's urethra, ureter, renal pelvis or bladder, the method comprising
a) gently constricting a portion of the tissue wall of the urethra, ureter, renal pelvis or bladder to influence the flow in the urinary passageway, and b) stimulating the constricted wall portion to cause contraction of the wall portion to further influence the flow in the urinary passageway.

The present invention provides an advantageous combination of the method steps (a) and (b), which results in a two-stage influence on the flow of urine in the urinary passageway of a patient's urethra, ureter, renal pelvis or bladder. Thus, applying a relatively weak force against the wall portion gently constricts the tissue wall and the constricted wall portion is stimulated to achieve the desired final influence on the flow in the urinary passageway. The phrase "gently constricts a portion of the tissue wall" is to be understood as constricting the wall portion without substantially hampering the blood circulation in the tissue wall.

Preferably, step (b) is performed by intermittently and individually stimulating different areas of the wall portion. Such an intermittent and individual stimulation of different areas of the wall portion of the urethra, ureter, renal pelvis or bladder allows tissue of the wall portion to maintain over time substantially normal blood circulation.

The method of the present invention can be practiced on any place on the urethra, ureter, renal pelvis or bladder, which is a significant advance in the art, as compared with prior stimulation devices that are confined to electric stimulation of malfunctioning sphincters.

The constriction step (a) and stimulation step (b) may be performed independently of each other or simultaneously. Optionally, step (b) may or may not be performed while step (a) is performed.

Initially, the constriction of the wall portion can be calibrated by stimulating the wall portion while adjusting the constriction of the wall portion until the desired restriction of the flow in the urinary passageway is obtained.

Flow Restriction

It should be understood that any embodiment or part of embodiment disclosed below in connection with flow restriction for the constriction and stimulation devices combined in a constriction/stimulation unit could be used for the separate constriction device and separate stimulation device, where applicable.

The method of the present invention is well suited for restricting the flow of urine in the urinary passageway of a patient's urethra, ureter, renal pelvis or bladder. Thus, in a principal embodiment of the invention, the wall portion is constricted, so that the flow in the urinary passageway at least is restricted and the constricted wall portion is stimulated to at least further restrict the flow in the urinary passageway. Specifically, the wall portion is constricted to a constricted state, in which the blood circulation in the constricted wall portion is substantially unrestricted and the flow in the urinary passageway is at least restricted, and the constricted wall portion is stimulated when it is in the constricted state to at least further restrict the flow in the urinary passageway.

The constriction step (a) and stimulation step (b) are suitably performed to constrict and stimulate the wall portion to an extent that depends on the flow restriction that is desired to be achieved in a specific application of the method of the invention. Thus, in accordance with a first flow restriction option, step (a) is performed by constricting the wall portion, so that the flow in the urinary passageway is restricted but not stopped, and step (b) is performed by stimulating the constricted wall portion to cause contraction thereof, so that the flow in the urinary passageway is further restricted but not stopped. The method may further comprise sensing a physical parameter of the patient and adjusting the intensity of the stimulation of the wall portion in response to the sensed parameter.

In accordance with a second flow restriction option, step (a) is performed by constricting the wall portion, so that the flow in the urinary passageway is restricted but not stopped, and step (b) is performed by stimulating the constricted wall portion to cause contraction thereof, so that the flow in the urinary passageway is stopped.

When using the method of the invention in accordance with the first or second options, the method may further comprise (c) ceasing stimulating the wall portion to increase or allow the flow in the urinary passageway and (d) releasing the wall portion to restore the flow in the urinary passageway.

In accordance with a third flow restriction option, step (a) is performed by constricting the wall portion, so that the flow in the urinary passageway is substantially stopped, and step (b) is performed by stimulating the constricted wall portion to cause contraction thereof, so that the flow in the urinary passageway is completely stopped. The method may further comprise (c) ceasing stimulating the wall portion to allow the flow in the urinary passageway and (d) releasing the wall portion to restore the flow in the urinary passageway.

The third flow restriction option is well suited for treating a urinary stress incontinent patient. Thus, between urinations, a portion of the urethra, ureter, renal pelvis or bladder is gently flattened to at least almost completely stop the flow of urine and the flattened portion is stimulated to insure that the flow of urine is completely stopped. Since the areas of the wall portion are intermittently and individually stimulate, the risk of injuring the urethra, ureter, renal pelvis or bladder over time is significantly reduced or even eliminated, and it is insured that the effect of the stimulation is maintained over time. When the patient wants to urinate, the portion of the urethra, ureter, renal pelvis or bladder is released and the stimulation is ceased, whereby urine may pass through the urethra, ureter, renal pelvis or bladder. However, it should be noted that in some cases it may suffice to just cease the stimulation to achieve flow of urine through the urethra, ureter, renal pelvis or bladder.

Where the constricted wall portion is stimulated to contract, so that the flow in the urinary passageway is stopped, a first length of the constricted wall portion and a second length of the constricted wall portion, which is located downstream of the first length, are suitably simultaneously and cyclically stimulated, wherein the first length is progressively stimulated in the upstream direction of the urinary passageway and the second length is progressively stimulated in the downstream direction of the urinary passageway.

Furthermore, when using the method of the invention in accordance with the second and third options, the method may further comprise sensing a physical parameter of the patient or functional parameter of implanted components and adjusting the stimulation of the wall portion in response to the sensed parameter. For example, the intensity of the stimulation of the wall portion may be increased in response to a sensed pressure increase in the urinary passageway, so that the flow in the urinary passageway remains stopped when a pressure increase occurs in the urinary passageway. In particular, the method may comprise sensing a physical parameter of the patient's that relates to the pressure in the urinary passageway, and controlling the stimulation of the wall portion in response to the sensed parameter. Any sensor for sensing a physical parameter of the patient, such as a pressure in the patient's body that relates to the pressure in the urinary passageway may be provided, wherein the stimulation is controlled in response to signals from the sensor. Such a sensor may for example sense the pressure in the patient's abdomen, the pressure against the implanted constriction device or the pressure on the urethra, ureter, renal pelvis or bladder. For example, a pressure sensor may be provided for controlling the urine flow. Thus, the patient's urethra, ureter, renal pelvis or bladder is constricted, so that the urine flow is substantially stopped, and the constricted urethra, ureter, renal pelvis or bladder is stimulated to cause contraction thereof to completely stop the urine flow. The stimulation intensity is increased in response to signals from the pressure sensor sensing a sudden increase in the pressure in the patient's bladder or abdominal cavity, whereby the urine flow remains stopped and the patient maintains continence. In this manner, the present invention insures that the patient even is continent when he or she sneezes or coughs, or performs other physical activity that causes a sudden pressure increase in the patient's bladder/urinary tract.

In accordance with a fourth restriction option, step (a) is performed by constricting the wall portion, so that the flow in the urinary passageway is stopped. When needed, the wall portion is released to restore the flow in the urinary passageway. Step (b) is only performed by stimulating the constricted wall portion to cause contraction thereof, so that the flow in the urinary passageway remains stopped when a pressure increase occurs in the urinary passageway. The method may further comprise sensing a physical parameter of the patient's body, such as a pressure in the patient's body that relates to the pressure in the urinary passageway, and controlling the stimulation of the wall portion in response to the sensed parameter. Such a physical parameter may be a pressure in the patient's abdomen and the sensor may be a pressure sensor.

For example, the fourth flow restriction option may be applied for controlling urine flow of a urinary incontinent patient in a manner similar to the situation described above. However, in this example stimulation is only applied when necessary to maintain continence, Thus, the urethra is stimulated to cause contraction thereof in response to signals from the pressure sensor sensing a sudden increase in the pressure in the patient's bladder or abdominal cavity, when the patient sneezes or coughs, or performs other physical activity. As a result, the urine flow remains stopped and the patient maintains continence.

In some applications of the method of the invention, continuous stimulation may over time change the physical properties of the tissue so that the tissue might be injured. Also, the effect of a continuous stimulation of the tissue wall may decrease over time. Therefore, step (b) is preferably performed by intermittently and individually stimulating different areas of the wall portion of the urethra, ureter, renal pelvis or bladder so that the flow in the urinary passageway continues to be restricted as desired and each area of the wall portion essentially maintains its natural physical properties over time to prevent the area from being injured. Advantageously, each area of the wall portion is stimulated during successive time periods, each time period being short enough to maintain over time satisfactory blood circulation in the area. Thus, the areas are stimulated so that an area that currently is not stimulated will have time to restore substantially normal blood circulation before it is stimulated again.

To maintain satisfactory blood circulation in the tissue wall of the patient's urethra, ureter, renal pelvis or bladder stimulation step (b) is suitably performed by stimulating one or more of different areas of the wall portion at a time, preferably by sequentially stimulating the different areas of the wall portion or by shifting the stimulation from one area to another over time. Preferably, stimulation step (b) is performed by cyclically propagating the stimulation of the areas along the wall portion, for example in accordance with a determined stimulation pattern.

The method of the invention may further comprise controlling, preferably by the patient, the constriction and/or stimulation of the wall portion from outside the patient's body.

Generally, the method of the invention comprises sensing a physical parameter of the patient and controlling, preferably automatically, the constriction and/or stimulation of the wall portion in response to the sensed parameter.

The constriction step (a) may be performed by constricting any wall portions of a series of wall portions of the tissue wall of the urethra, ureter, renal pelvis or bladder, respectively, either in random or in accordance with a predetermined sequence. The stimulation step (b) may be performed by stimulating any of the constricted wall portions of the series of wall portions. Specifically, step (a) may be performed by constricting all of the wall portions of the series of wall portions, and step (b) may be performed by stimulating any constricted wall portions in random or in accordance with a predetermined sequence to close the urinary passageway.

Moving Urine in the Urinary Passageway or Preventing Movement of Urine in the Urinary Passageway It should be understood that any embodiment or part of embodiment disclosed below in connection with moving urine in the urinary passageway, or preventing the move of urine in the urinary passageway, for the constriction and stimulation devices combined in the constriction/stimulation unit could be used for the separate constriction device and separate stimulation device, where applicable.

The method of the present invention can be practiced for actively moving the urine in the urinary passageway of a patient's urethra, ureter, renal pelvis or bladder. Thus, in the embodiments of the invention listed below, steps (a) and (b) are co-operated to move the urine in the urinary passageway.

1) Step (a) is performed by constricting the wall portion to restrict the flow in the urinary passageway, and step (b) is performed by stimulating the constricted wall portion to close the urinary passageway either at an upstream end or a downstream end of the constricted wall portion. The method further comprises (c) increasing the constriction of the wall portion to move the urine in the urinary passageway.

2) Step (a) is performed by constricting the wall portion to restrict the flow in the urinary passageway, and step (b) is performed by progressively stimulating the constricted wall portion to cause progressive contraction of the wall portion to move the urine in the urinary passageway. The constricted wall portion is progressively stimulated in the downstream or upstream direction of the urinary passageway.

3) Step (a) is performed by varyingly constricting the wall portion to vary the flow in the urinary passageway, and step (b) is performed by progressively stimulating the constricted wall portion to cause progressive contraction of the wall portion to move the urine in the urinary passageway. The constricted wall portion is progressively stimulated in the downstream or upstream direction of the urinary passageway.

4) Step (a) is performed by varyingly constricting different areas of the wall portion to cause progressive constriction of the wall portion in the downstream or upstream direction of the urinary passageway, and the constricted wall portion is progressively stimulated to cause progressive contraction thereof in harmony with the progressive constriction of the wall portion. The method may further comprise providing at least one elongated constriction element extending along the wall portion, and controlling the elongated constriction element to progressively constrict the wall portion in the downstream or upstream direction of the urinary passageway. The elongated constriction element suitably comprises contact surfaces dimensioned to contact a length of wall portion, and the method may further comprise providing a plurality of stimulation elements distributed along the contact surfaces, and controlling the stimulation elements to stimulate the different areas of the wall portion along the length of the wall portion.

5) Step (a) is performed by constricting any one of a series of wall portions of the tissue wall to at least restrict the flow in the urinary passageway, and step (b) is performed by stimulating the constricted wall portion to close the urinary passageway. The method further comprises successively constricting the wall portions of the series of wall portions to move the urine in the urinary passageway in a peristaltic manner.

5a) In accordance with an alternative, the method further comprises providing at least one constriction element and at least one stimulation element positioned on the constriction element, moving the constriction element along the urethra, ureter, renal pelvis or bladder in the flow direction in the urinary passageway to successively constrict the wall portions of the series of wall portions, and using the stimulation element to stimulate the wall portion constricted by the constriction element to close the urinary passageway. Suitably, the method further comprises cyclically moving the constriction element along the wall portions of the series of wall portions.

5b) In accordance with another alternative, the method further comprises providing a plurality of constriction elements and stimulation elements positioned on the constriction elements, moving each constriction element along the urethra, ureter, renal pelvis or bladder to successively constrict the wall portions of the series of wall portions, and using the stimulation elements to stimulate the wall portion constricted by any one of the constriction elements to close the urinary passageway. Suitably, the method further comprises cyclically moving the constriction elements one after the other along the wall portions of the series of wall portions. Specifically, the method further comprises providing a rotor carrying the constriction elements, and rotating the rotor so that each constriction element cyclically constricts the wall portions of the series of wall portions. Each constriction element suitably comprises a roller that rolls on the urethra, ureter, renal pelvis or bladder to constrict the latter.

6) Step (a) is performed by constricting any wall portions of a series of wall portions of the tissue wall, respectively, wherein the wall portions of the series of wall portions are successively constricted along the urethra, ureter, renal pelvis or bladder to move the urine in the urinary passageway of the patient's urethra, ureter, renal pelvis or bladder. The stimulation step (b) is performed by stimulating any constricted wall portions of the series of wall portions.

7) Step (a) is performed by constricting wall portions of a series of wall portions without completely closing the urinary passageway, and step (b) is performed by stimulating the constricted wall portions one after the other, so that the wall portions of the series of wall portions are successively contracted along the urethra, ureter, renal pelvis or bladder to move the urine in the urinary passageway of the patient's urethra, ureter, renal pelvis or bladder.

8) Step (a) is performed by constricting the wall portion at an upstream or downstream end thereof to close the urinary passageway. The method further comprises (c) constricting the wall portion between the upstream and downstream ends thereof, to move the fluid or other urine contained in the wall portion between the upstream and downstream ends thereof downstream or upstream in the urinary passageway. Optionally, the method further comprises stimulating the wall portion between the upstream and downstream ends thereof, as (c) is performed.

8a) In accordance with an alternative, step (a) is performed by constricting the wall portion at the upstream end thereof to restrict the flow in the urinary passageway, and step (b) is performed by stimulating the constricted wall portion at the upstream end to close the urinary passageway, whereby the urine contained in the wall portion between the upstream and downstream ends thereof is moved downstream in the urinary passageway, as step (c) is performed.

8b) In accordance with another alternative, step (a) is performed by constricting the wall portion at the downstream end thereof to restrict the flow in the urinary passageway, and step (b) is performed by stimulating the constricted wall portion at the downstream end to close the urinary passageway, whereby the urine contained in the wall portion between the upstream and downstream ends thereof is moved upstream in the urinary passageway, as step (c) is performed.

Where the urethra, ureter, renal pelvis or bladder are the small urethra, ureter, renal pelvis or bladder, a particularly long wall portion of the urethra, ureter, renal pelvis or bladder may be surgically prepared to extend in zigzag with adjacent walls stitched together by two parallel rows of stitches and with the adjacent walls cut through between the two rows of stitches. As a result, the urinary passageway of this long wall portion of the urethra, ureter, renal pelvis or bladder can be significantly expanded. In this case, a considerably larger volume of fluid is moved in the urethra, ureter, renal pelvis or bladder each time step (a) and/or step (b) is performed.

To Summarize a Few Preferred Embodiments See Below

In accordance with an alternative, step (a) is performed by constricting any wall portions of a series of wall portions of the tissue wall of the urethra, ureter, renal pelvis or bladder, respectively. In accordance with an alternative, the wall portions of the series of wall portions are constricted in random or in accordance with a predetermined sequence. In accordance with an alternative, the wall portions of the series of wall portions are successively constricted along the urethra, ureter, renal pelvis or bladder to move the urine in the urinary passageway of the patient's urethra, ureter, renal pelvis or bladder or to prevent the urine to move in the lumen of the patient's urethra, ureter, renal pelvis or bladder.

In accordance with an alternative, step (b) is performed by stimulating any constricted wall portions of the series of wall portions. In accordance with an alternative, the wall portions of the series of wall portions are constricted in random or in accordance with a predetermined sequence. In accordance with an alternative, wherein the wall portions of the series of wall portions are successively constricted along the urethra, ureter, renal pelvis or bladder to move the urine in the urinary passageway of the patient's urethra, ureter, renal pelvis or bladder or to prevent the urine to move in the lumen of the patient's urethra, ureter, renal pelvis or bladder.

In accordance with an alternative, step (a) is performed by constricting any wall portions of a series of wall portions of the tissue wall of the urethra, ureter, renal pelvis or bladder, respectively, wherein the wall portions of the series of wall portions are successively constricted without completely closing the urinary passageway, and step (b) is performed by stimulating the constricted wall portions, so that the wall portions of the series of wall portions are further constricted. In accordance with an alternative, the wall portions of the series of wall portions are constricted in random or in accordance with a predetermined sequence.

In accordance with an alternative, wherein the wall portions of the series of wall portions are successively constricted along the urethra, ureter, renal pelvis or bladder to move the urine in the urinary passageway of the patient's urethra, ureter, renal pelvis or bladder or to prevent the urine to move in the lumen of the patient's urethra, ureter, renal pelvis or bladder.

In accordance with an alternative, step (a) is performed by constricting all of the wall portions of the series of wall portions, and step (b) is performed by stimulating any constricted wall portions so that the wall portions of the series of wall portions are further constricted.

In accordance with an alternative, the wall portions of the series of wall portions are further constricted by the stimulation device in random or in accordance with a predetermined sequence.

In accordance with an alternative, the wall portions of the series of wall portions are successively further constricted by the stimulation device along the urethra, ureter, renal pelvis or bladder to move the urine in the urinary passageway of the patient's urethra, ureter, renal pelvis or bladder or to prevent the urine to move in the lumen of the patient's urethra, ureter, renal pelvis or bladder.

In accordance with an alternative for all applicable alternatives, step (a) and step (b) are performed independently of each other or in accordance with an alternative, step (a) and step (b) are performed simultaneously.

In any of the above noted embodiments (1) to (8b), step (b) may be performed by stimulating the wall portion with electric pulses.

Stimulation Modes

When stimulating neural or muscular tissue there is a risk of injuring or deteriorating the tissue over time if the stimulation is not properly performed. The method of the present invention is performed to reduce or even eliminate that risk. Thus, step (b) is performed by intermittently stimulating different areas of the wall portion so that at least two of the areas are stimulated at different points of time. I.e., the stimulation is shifted from one area to another area over time. In addition, step (b) is performed by intermittently stimulating the areas of the wall portion so that an area of the different areas that currently is not stimulated has time to restore substantially normal blood circulation before it is stimulated again. Furthermore, step (b) is performed by intermittently stimulating the areas during successive time periods, wherein each time period is short enough to maintain satisfactory blood circulation in the area until the laps of the time period. This gives the advantage that the method of the present invention provides continuous stimulation of the wall portion of the urethra, ureter, renal pelvis or bladder to achieve the desired flow control while essentially maintaining over time the natural physical properties of the urethra, ureter, renal pelvis or bladder without risk of injuring the urethra, ureter, renal pelvis or bladder.

Also, by physically changing the places of stimulation on the urethra, ureter, renal pelvis or bladder over time as described above it is possible to create an advantageous changing stimulation pattern on the urethra, ureter, renal pelvis or bladder, in order to achieve a desired flow control.

To achieve the desired reaction of the tissue wall during the stimulation thereof, step (b) may be performed by stimulating the wall portion with, preferably cyclically, varying stimulation intensity.

In a main embodiment of the invention, step (b) is performed by intermittently stimulating the wall portion with pulses, preferably in the form of pulse trains. The pulse trains can be configured in many different ways by varying pulse parameters. Thus, the pulse amplitudes of the pulses of the pulse trains, the off time periods between the individual pulses of each pulse train and the width and repetition frequency of each pulse may be varied. Also the off time periods between the pulse trains may be varied, wherein each off time period between the pulse trains is kept long enough to restore substantially normal blood circulation in each area of the wall portion, when the area is not stimulated during the off time periods. Furthermore, the repetition frequency of the pulses of the pulse trains and the length and number of pulses of each pulse train may be varied.

As mentioned above, for reasons of maintaining over time the effect of stimulation, it is preferable that different areas of the wall portion are intermittently and individually stimulated. In consequence, step (b) may be performed by stimulating one or more of the areas at a time with pulses, by cyclically propagating the stimulation of the areas with pulses along the wall portion, and/or by propagating the stimulation of the areas with pulses in accordance with a determined stimulation pattern. In case the off time periods between pulse trains that stimulate the respective area of the wall portion are varied, it is preferable that each off time period between the pulse trains is controlled to last long enough to restore substantially normal blood circulation in the area when the latter is not stimulated during the off time periods.

Electric Stimulation

In accordance with a preferred embodiment of the invention, step (b) is performed by electrically stimulating the wall portion, preferably with electric pulses to cause contraction of the wall portion. This embodiment is particularly suited for applications in which the patient's wall portion includes muscle fibers that react to electrical stimula. Thus, the wall portion that includes the muscle fibers is stimulated with such electric pulses, preferably in the form of electric pulse trains, when the wall portion is in the constricted state, to cause contraction of the wall portion. Of course, the configuration of the electric pulse trains may be similar to the above described pulse trains and different areas of the wall portion may be electrically stimulated in the same manner as described above.

In accordance with the preferred embodiment, the method of the invention comprises providing at least one, preferably a plurality of electrical elements, such as electrodes, engaging and stimulating the wall portion with electric pulses. Optionally, the electrical elements may be placed in a fixed orientation relative to one another. The method comprises electrically energizing the electrical elements, preferably by cyclically energizing each element with electric pulses. The electrical elements may be energized so that the electrical elements are energized one at a time in sequence, or so that a number or groups of the electrical elements are energized at a time. Also, groups of electrical elements may be sequentially energized, either randomly or in accordance with a predetermined pattern.

The method may further comprise applying the electrical elements on the patient's wall portion so that the electrical elements form any pattern of electrical elements, preferably an elongate pattern of electrical elements extending lengthwise along the wall portion and the elements abut the respective areas of the wall portion. The electrical elements may be successively energized along the elongate pattern of electrical elements in a direction opposite to or in the same direction as that of the flow in the patient's urinary passageway. Optionally, the electrical elements may be successively energized along the elongate pattern of electrical elements from a position substantially at the center of the constricted wall portion towards both ends of the elongate pattern of electrical elements. Where the urinary passageway of the urethra, ureter, renal pelvis or bladder is to be kept closed for a relatively long time, the electrical elements may be energized so that energized electrical elements form two waves of energized electrical elements that simultaneously advance from the center of the constricted wall portion in two opposite directions towards both ends of the elongate pattern of electrical elements. Such waves of energized electrical elements can be repeated over and over again without harming the urethra, ureter, renal pelvis or bladder and without moving fluid or gas in any direction in the urinary passageway of the urethra, ureter, renal pelvis or bladder.

The elongate pattern of electrical elements may include one or more rows of electrical elements extending lengthwise along the urethra, ureter, renal pelvis or bladder. Each row of electrical elements may form a straight, helical or zig-zag path of electrical elements, or any form of path. The electrical elements may be energized so that the electrical elements currently energized form at least one group of adjacent energized electrical elements, wherein the elements in the group of energized electrical elements form a path of energized electrical elements extending at least in part around the patient's urethra, ureter, renal pelvis or bladder, preferably completely around the patient's urethra, ureter, renal pelvis or bladder. Alternatively, the elements in the group of energized electrical elements form two paths of energized electrical elements extending on mutual sides of the patient's urethra, ureter, renal pelvis or bladder or more than two paths of energized electrical elements extending on different sides of the patient's urethra, ureter, renal pelvis or bladder, preferably at least substantially transverse to the flow direction in the urinary passageway of the urethra, ureter, renal pelvis or bladder.

In an embodiment of the invention, the electrical elements form a plurality of groups of elements, wherein the groups form a series of groups extending along the patient's urethra, ureter, renal pelvis or bladder in the flow direction in the patient's urinary passageway. The electrical elements of each group of electrical elements may form a path of elements extending at least in part around the patient's urethra, ureter, renal pelvis or bladder. In a first alternative, the electrical elements of each group of electrical elements may form more than two paths of elements extending on different sides of the patient's urethra, ureter, renal pelvis or bladder, preferably substantially transverse to the flow direction in the patient's urinary passageway. The groups of electrical elements in the series of groups may be energized in random or in accordance with a predetermined pattern. Alternatively, the groups of electrical elements in the series of groups may be successively energized in a direction opposite to or in the same direction as that of the flow in the patient's urinary passageway, or in both said directions starting from a position substantially at the center of the constricted wall portion. For example, groups of energized electrical elements may form advancing waves of energized electrical elements, as described above. I.e., the groups of electrical elements may be energized so that energized electrical elements form two waves of energized electrical elements that simultaneously advance from the center of the constricted wall portion in two opposite directions towards both ends of the elongate pattern of electrical elements.

Thermal Stimulation

In accordance with an embodiment of the invention, stimulation step (b) is performed by thermally stimulating the wall portion. Thus, the wall portion may be cooled, when the wall portion is constricted, to cause contraction of the wall portion. For example, the wall portion may be constricted to at least restrict the flow in the urinary passageway, and the constricted wall portion may be cooled to cause contraction thereof, so that the flow in the urinary passageway is at least further restricted, or further restricted but not stopped, or stopped. Alternatively, the wall portion may be heated, when the wall portion is constricted and contracted, to cause expansion of the wall portion. Where applicable, thermal stimulation may be practised in any of the embodiments of the present invention, and the thermal stimulation may be controlled in response to various sensors, for example strain, motion or pressure sensors.

Constriction and Stimulation Devices

It should be understood that any embodiment or part of embodiment for a combined stimulation device and constriction device, could be used, where applicable, for any one of the devices as a stand alone device.

Generally, the method of the invention comprises providing a constriction device that constricts the wall portion, a stimulation device that stimulates the constricted wall portion and a control device that controls the constriction device and/or the stimulation device. The method comprises operating the control device from outside the patient's body, preferably by using the control device to wirelessly control the constriction device and/or stimulation device. The wireless control is preferably performed in a non-magnetic manner, whereby implanted magnetic devices can be avoided. Suitably, the control device comprises a hand-held wireless remote control operated by the patient.

Alternatively, the control device comprises a manually operable switch for switching on and off the constriction device and/or stimulation device. In this case, the method comprises subcutaneously implanting the switch in the patient and manually operating the the implanted switch from outside the patient's body.

In an embodiment of the invention, the control device comprises a programmable internal control unit, such as a microprocessor, and the method comprises implanting in the patient the internal control unit and controlling by the internal control unit the constriction device and/or stimulation device. The control device may also comprise an external control unit outside the patient's body. In this case, the method comprises controlling by the external control unit the constriction device and/or stimulation device and, optionally, using the external control unit to program the implanted internal control unit. The internal control unit may be programmable for controlling the constriction device and/or stimulation device over time, for example in accordance with an activity schedule program.

The constriction of the wall portion can be calibrated by using the control device to control the stimulation device to stimulate the wall portion while controlling the constriction device to adjust the constriction of the wall portion until the desired restriction of the flow in the urinary passageway is obtained.

Sensor Controlled Constriction and/or Stimulation

It should be understood that any embodiment or part of embodiment disclosed below in connection with sensor control of the constriction and stimulation devices combined in the constriction/stimulation unit could be used for the separate constriction device and separate stimulation device, where applicable.

In an embodiment of the invention, the method comprises implanting at least one sensor and controlling by the control device the constriction device and/or the stimulation device in response to signals from the sensor. Generally, the sensor directly or indirectly senses at least one physical parameter of the patient, functional parameter of the apparatus, or functional parameter of a medical implant in the patient.

Many different kinds of sensor for sensing physical parameters may be used. For example motion sensors for sensing urinary motion, i.e. natural contractions, such as urinary contractions, pressure sensors for sensing pressure in the urethra, ureter, renal pelvis or bladder, strain sensors for sensing strain of the urethra, ureter, renal pelvis or bladder, flow sensors for sensing fluid flow in the urinary passageway of the urethra, ureter, renal pelvis or bladder, spectro-photometrical sensors, Ph-sensors for acidity or alkalinity of the fluid in the urinary passageway of the urethra, ureter, renal pelvis or bladder, oxygen-sensors sensors for sensing the oxygen content of the fluid in the urinary passageway of the urethra, ureter, renal pelvis or bladder, or sensors for sensing the distribution of the stimulation on the stimulated urethra, ureter, renal pelvis or bladder. Any conceivable sensors for sensing any other kind of useful physical parameter may be used.

Many different kinds of sensors that sense functional parameters of implanted components may also be used for the control of the constriction device and/or the stimulation device. For example sensors for sensing electric parameters of implanted electric components, or sensors for sensing the performance of implanted motors or the like.

The sensor may comprise a pressure sensor for sensing as the physical parameter a pressure in the patient's body that relates to the pressure in the urinary passageway of the patient's bodily urethra, ureter, renal pelvis or bladder. In this case, the method suitably comprises operating the control device to control the constriction device to change the constriction of the patient's wall portion in response to the pressure sensor sensing a predetermined value of measured pressure.

Alternatively, or in combination with the pressure sensor, a position sensor may be provided for sensing as the physical parameter the orientation of the patient with respect to the horizontal. The position sensor may be a biocompatible version of what is shown in U.S. Pat. Nos. 4,942,668 and 5,900,909. For example, the control device may control the constriction device and/or stimulation device to change the constriction of the patient's wall portion in response to the position sensor sensing that the patient has assumed a substantially horizontal orientation, i.e. that the patient is lying down.

The above described sensors may be used in any of the embodiments of the invention, where applicable.

The control device may control the constriction device and/or stimulation device to change the constriction of the patient's wall portion in response to the time of day. For that purpose the control device may include a clock mechanism for controlling the constriction device and/or stimulation device to change the constriction of the patient's wall portion to increase or decrease the influence on the flow in the urinary passageway during different time periods of the day. In case a sensor of any of the above-described types for sensing a physical or functional parameter is provided, either the clock mechanism is used for controlling the constriction device and/or stimulation device provided that the parameter sensed by the sensor does not override the clock mechanism, or the sensor is used for controlling the constriction device and/or stimulation device provided that the clock mechanism does not override the sensor. Suitably, the control device produces an indication, such as a sound signal or displayed information, in response to signals from the sensor.

The control device may comprise an implantable internal control unit that directly controls the constriction device and/or stimulation device in response to signals from the sensor. The control device may further comprise a wireless remote control adapted to set control parameters of the internal control unit from outside the patient without mechanically penetrating the patient. At least one of the control parameters, which is settable by the wireless remote control, is the physical or functional parameter. Suitably, the internal control unit includes the above mentioned clock mechanism, wherein the wireless remote control also is adapted to set the clock mechanism.

Alternatively, the control device may comprise an external control unit outside the patient's body for controlling the constriction device and/or stimulation device in response to signals from the sensor.

Constriction of Patient's Urethra, Ureter, Renal pelvis or Bladder

It should be understood that any embodiment or part of embodiment disclosed below in connection with constricting the patient's urethra, ureter, renal pelvis or bladder could be used for a separate constriction device and a separate stimulation device, where applicable.

Method step (a) may be performed in many different ways. Thus, step (a) may be performed by:
constricting the wall portion so that the through-flow area of the urinary passageway assumes a size in the constricted state small enough to cause the constricted wall portion to contract to stop the flow in the urinary passageway when step (b) is performed;
bending the wall portion;
clamping the wall portion between at least two elements positioned on different sides of the urethra, ureter, renal pelvis or bladder;
clamping the urethra, ureter, renal pelvis or bladder between an element and the bone or tissue of the patient;
rotating at least two elements positioned on different sides of the urethra, ureter, renal pelvis or bladder;
or
clamping the urethra, ureter, renal pelvis or bladder between at least two articulated clamping elements positioned on different sides of the urethra, ureter, renal pelvis or bladder.

In the above noted alternatives (1) to (6) of method step (a), the constriction of the wall portion of the urethra, ureter, renal pelvis or bladder may be changed either mechanically or hydraulically. For many applications of the present invention, step (a) is suitably performed so that the through-flow area of the urinary passageway assumes a size in the constricted state that is small enough to enable the stimulation during step (b)

to contract the wall portion of the urethra, ureter, renal pelvis or bladder to stop the flow in the urinary passageway.

Where the constriction of the wall portion is hydraulically changed, the method of the invention may further comprise implanting in the patient a reservoir containing a predetermined amount of hydraulic fluid, and a constriction device engaging the wall portion and having an expandable/contractible cavity, wherein step (a) is performed by distributing hydraulic fluid from the reservoir to increase the volume of the cavity to constrict the wall portion, and by distributing hydraulic fluid from the cavity to the reservoir to decrease the volume of the cavity to release the wall portion. The cavity may be defined by a balloon of the constriction device that abuts the tissue wall portion of the patient's urethra, ureter, renal pelvis or bladder, so that the patient's wall portion is constricted upon expansion of the cavity and released upon contraction of the cavity.

Alternatively, the cavity may be defined by a bellows that displaces a relatively large contraction element of the constriction device, for example a large balloon that abuts the wall portion, so that the patient's wall portion is constricted upon contraction of the bellows and released upon expansion of the bellows. Thus, a relatively small addition of hydraulic fluid to the bellows causes a relatively large increase in the constriction of the wall portion. Such a bellows may also be replaced by a suitably designed piston/cylinder mechanism.

Where the hydraulic means comprises a cavity in the constriction device, the following embodiments of the invention are conceivable.

1) The reservoir comprises first and second wall portions, and step (a) is performed by displacing the first and second wall portions relative to each other to change the volume of the reservoir, so that fluid is distributed from the reservoir to the cavity, or from the cavity to the reservoir.

1a) At least one of a magnetic device, a hydraulic device or an electric control device displaces the first and second wall portions of the reservoir.

2) A pump is provided for pumping fluid between the reservoir and the cavity.

2a) The pump comprises a first activation member for activating the pump to pump fluid from the reservoir to the cavity and a second activation member for activating the pump to pump fluid from the cavity to the reservoir.

2a1) The first and second activation members are operable by manual manipulation thereof.

2a2) At least one of the activation members operates when subjected to an external predetermined pressure.

2a3) At least one of the first and second activating members is operable by magnetic means, hydraulic means, or electric control means.

2b) A fluid conduit between the pump and the cavity is provided, wherein the reservoir forms part of the conduit. The conduit and pump are devoid of any non-return valve. The reservoir forms a fluid chamber with a variable volume, and the pump distributes fluid from the chamber to the cavity by a reduction in the volume of the chamber and withdraws fluid from the cavity by an expansion of the volume of the chamber. A motor is provided for driving the pump, wherein the pump comprises a movable wall of the reservoir for changing the volume of the chamber.

In all of the above noted embodiments 1 to 2b where the hydraulic means comprises an expandable cavity in the constriction device, the cavity can be exchanged by a cylinder/piston mechanism for adjusting the constriction device. In this case, hydraulic fluid is distributed between the reservoir and the cylinder/piston mechanism to adjust the constriction device.

3) The method further comprises implanting a reverse servo operatively connected to the hydraulic means. The term "reverse servo" is to be understood as a mechanism that transfers a strong force acting on a moving element having a short stroke into a weak force acting on another moving element having a long stroke; i.e., the reverse function of a normal servo mechanism. Thus, minor changes in the amount of fluid in a smaller reservoir could be transferred by the reverse servo into major changes in the amount of fluid in a larger reservoir.

Preferably, the reverse servo comprises an expandable servo reservoir containing servo fluid and a fluid supply reservoir hydraulically connected to the servo reservoir to form a closed conduit system for the servo fluid. The expandable servo reservoir has first and second wall portions, which are displaceable relative to each other in response to a change in the volume of the expandable servo reservoir.

In accordance with a first alternative, the first and second wall portions of the servo reservoir are operatively connected to the hydraulic means. The reverse servo distributes fluid between the fluid supply reservoir and the expandable servo reservoir to change the volume of the servo reservoir, whereby the hydraulic means is operated to adjust the constriction device.

In accordance with a second alternative, there is provided an implantable main reservoir containing a predetermined amount of hydraulic fluid, wherein the reverse servo is operated to distribute hydraulic fluid between the main reservoir and the hydraulic means to adjust the constriction device. More specifically, the main reservoir is provided with first and second wall portions operatively connected to the first and second wall portions of the expandable servo reservoir, so that the volume of the main reservoir is changed when the volume of the expandable servo reservoir is changed. Thus, when the reverse servo distributes servo fluid between the fluid supply reservoir and the expandable servo reservoir to change the volume of the main reservoir, hydraulic fluid is distributed from the main reservoir to the hydraulic means, or from the hydraulic means to the main reservoir. Advantageously, the method comprises dimensioning the servo and main reservoirs, so that when the volume of the servo reservoir is changed by a relatively small amount of servo fluid, the volume of the main reservoir is changed by a relatively large amount of hydraulic fluid.

In both of the above-described alternatives, the fluid supply reservoir may have first and second wall portions, which are displaceable relative to each other to change the volume of the fluid supply reservoir to distribute servo fluid between the fluid supply reservoir and the expandable servo reservoir. The first and second wall portions of the fluid supply reservoir may be displaced relative to each other by manual manipulation, a magnetic device, a hydraulic device, or an electric control device to change the volume of the fluid supply reservoir to distribute servo fluid between the fluid supply reservoir and the expandable servo reservoir.

In all of the above noted embodiments 1 to 2b where the hydraulic means comprises an expandable cavity in the constriction device, or in embodiments where the hydraulic means includes a hydraulically operable mechanical construction, the reverse servo described above may be used. In a further embodiment of the invention, the hydraulic means include first and second hydraulically interconnected expandable/contractible reservoirs. The first reservoir is operatively connected to the constriction device, so that the constriction device changes the constriction of the patient's wall portion upon expansion or contraction of the first reservoir. By changing the volume of the second reservoir hydraulic fluid is distributed between the two reservoirs, so that the first reservoir is either expanded or contracted. This embodiment requires no non-return valve in the fluid communication conduits between the two reservoirs, which is beneficial to long-term operation of the hydraulic means.

Alternatively, the hydraulic means may include first and second hydraulically interconnected piston/cylinder mechanisms instead of the first and second reservoirs described above. The first piston/cylinder mechanism is operatively connected to the constriction device, so that the constriction device changes the constriction of the patient's wall portion upon operation of the first piston/cylinder mechanism. By operating the second piston/cylinder mechanism hydraulic fluid is distributed between the two piston/cylinder mechanisms, so that the first piston/cylinder mechanism adjusts the constriction device.

Where the constriction device does not include an expandable/contractible cavity, the constriction device may comprise at least two elongated clamping elements extending along the wall portion on different sides of the urethra, ureter, renal pelvis or bladder. The hydraulic means, which may include the reverse servo described above, hydraulically moves the elongated clamping elements towards the urethra, ureter, renal pelvis or bladder to constrict the wall portion of the urethra, ureter, renal pelvis or bladder. For example, the constriction device may have hydraulic chambers in which the clamping elements slide back and forth, and the hydraulic means may also include a pump and an implantable reservoir containing hydraulic fluid. The pump distributes hydraulic fluid from the reservoir to the chambers to move the clamping elements against the wall portion, and distributes hydraulic fluid from the chambers to the reservoir to move the clamping elements away from the wall portion.

Energy Supply

It should be understood that any embodiment or part of embodiment disclosed below in connection with the power of the constriction and stimulation devices combined in a constriction/stimulation unit could be used for the separate constriction device and separate stimulation device, where applicable.

Generally, method step (a) is performed by using the constriction device and step (b) is performed by using the stimulation device, wherein the method further comprises forming the constriction and stimulation devices in an operable constriction/stimulation unit.

In a simple form of the invention, the method comprises implanting a source of energy, such as a battery, rechargeable battery or accumulator, releasing energy from the source of energy and using the released energy in connection with the operation of the constriction/stimulation unit.

In a more sophisticated form of the invention, which is preferable, the method comprises transmitting wireless energy from outside the patient's body to inside the patient's body and using the transmitted wireless energy in connection with the operation of the constriction/stimulation unit.

Transmission of Wireless Energy

It should be understood that any embodiment or part of embodiment disclosed below in connection with wireless control or power of the constriction and stimulation devices combined in a constriction/stimulation unit could be used for the separate constriction device and separate stimulation device, where applicable.

The wireless energy may be directly used in connection with the operation of the constriction/stimulation unit, as the wireless energy is being transmitted. For example, the wireless energy may be transmitted in the form of an electric, an electromagnetic or a magnetic field, or a combination thereof, or electromagnetic waves for direct power of the constriction/stimulation unit. For example, where an electric motor or pump operates the constriction device of the constriction/stimulation unit, wireless energy in the form of a magnetic or an electromagnetic field may be used for direct power of the motor or pump.

Thus, the motor or pump is running directly during transmission of the wireless energy. This may be achieved in two different ways: a) using a transforming device implanted in the patient to transform the wireless energy into energy of a different form, preferably electric energy, and powering the motor or pump with the transformed energy, or b) using the wirelessly transmitted energy to directly power the motor or pump. Preferably wireless energy in the form of an electromagnetic or magnetic field is used to directly influence specific components of the motor or pump to create kinetic energy. Such components may include coils integrated in the motor or pump.

The wireless energy is suitably transmitted in pulses or digital pulses, or a combination of pulses and digital pulses.

Preferably, the wireless energy is transmitted in at least one wireless signal, suitably a wave signal. The wave signal may comprise an electromagnetic wave signal including one of an infrared light signal, a visible light signal, an ultra violet light signal, a laser signal, a microwave signal, a radio wave signal, an x-ray radiation signal, and a gamma radiation signal. Alternatively, the wave signal may comprise a sound or an ultrasound wave signal. The wireless signal may be a digital or analogue signal, or a combination of a digital and analogue signal.

In accordance with a particular embodiment of the invention, the wireless energy is not for direct use in connection with the operation of the constriction/stimulation unit. In this embodiment the wireless energy comprises energy of a first form, which is transmitted into energy of a second form suited to operate the constriction/stimulation unit. Typically, the energy of the second form is different from the energy of the first form. For example, the wireless energy of the first form may comprise sound waves, whereas the energy of the second form may comprise electric energy. Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

Transforming Wireless Energy

It should be understood that any embodiment or part of embodiment disclosed below in connection with the control or energizing of the constriction and stimulation devices combined in a constriction/stimulation unit could be used for the separate constriction device and separate stimulation device, where applicable.

In accordance with a particular embodiment of the invention, an implantable energy-transforming device is provided for transforming wireless energy of a first form transmitted by the energy-transmission device into energy of a second form, which typically is different from the energy of the first form. The constriction/stimulation unit is operable in response to the energy of the second form. For example, the wireless energy of the first form may comprise sound waves, whereas the energy of the second form may comprise electric energy. Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transforming device may function different from or similar to the energy-transmission device. Advantageously, the energy-transforming device comprises at least one element, such as at least one semiconductor, having a positive region and a negative region, when exposed to the energy of the first form transmitted by the energy-transmission device, wherein the element is capable of creating an energy field between the positive and negative regions, and the energy field produces the energy of the second form. More specifically, the element may comprise an electrical junction element, which is capable of inducing an electric field between the positive and negative regions when exposed to the energy of the first form transmitted by the energy-transmission device, whereby the energy of the second form comprises electric energy.

The energy of the first form may directly or indirectly be transformed into the energy of the second form. The method of the invention may comprise providing a motor for operating the constriction device and powering the motor with the energy of the second form. The constriction device may be operable to perform at least one reversible function and the method may comprise reversing the function by using the motor. For example, the method may comprise shifting the polarity of the energy of the second form to reverse the motor.

The motor may be directly powered with the transformed energy, as the energy of the second form is being transformed from the energy of the first form. Preferably, the constriction/stimulation unit is directly operated with the energy of the second form in a non-magnetic, non-thermal or non-mechanical manner.

Normally, the implanted constriction/stimulation unit comprises electric components that are energized with electrical energy. Therefore, the energy of the first form may be transformed into a direct current or pulsating direct current, or a combination of a direct current and pulsating direct current. Alternatively, the energy of the first form may be transformed into an alternating current or a combination of a direct and alternating current.

The method of the invention may comprise implanting in the patient an internal source of energy, and supplying energy from the internal source of energy for the operation of the constriction/stimulation unit. The method may further comprise implanting in the patient a switch operable to switch from an "off" mode, in which the internal source of energy is not in use, to an "on" mode, in which the internal source of energy supplies energy for the operation of the constriction/stimulation unit, and/or for energizing implanted electronic components of the constriction/stimulation unit. The switch may be operated by the energy of the first form or by the energy of the second form. The described switch arrangement reduces power consumption of the constriction/stimulation unit between operations.

The internal source of energy may store the energy of the second form. In this case, the internal source of energy suitably comprises an accumulator, such as at least one capacitor or at least one rechargeable battery, or a combination of at least one capacitor and at least one rechargeable battery. Where the internal source of energy is a rechargeable battery it may be charged only at times convenient for the patient, for example when the patient is sleeping. Alternatively, the internal source of energy may supply energy for the operation of the constriction/stimulation unit but not be used for storing the energy of the second form. In this alternative, the internal source of energy may be a battery and the switch described above may or may not be provided.

Suitably, the method of the invention may comprise implanting a stabilizer for stabilizing the energy of the second form. Where the energy of the second form comprises electric energy the stabilizer suitably comprises at least one capacitor.

The energy-transforming device may be designed for implantation subcutaneously in the abdomen, thorax or cephalic region of the patient. Alternatively, it may be designed for implantation in an orifice of the patient's body and under the mucosa or intramuscularly outside the mucosa of the orifice.

Control of Constriction/Stimulation Unit

It should be understood that any embodiment or part of embodiment disclosed below in connection with the control of the constriction and stimulation devices combined in a constriction/stimulation unit could be used for the separate constriction device and separate stimulation device, where applicable.

Although the constriction device of the constriction/stimulation unit may normally keep the patient's wall portion in the constricted state, in most applications using the present invention there will be daily adjustments of the constriction device. Therefore, in a preferred embodiment of the invention, the constriction device is adjustable to enable changing the constriction of the patient's wall portion as desired and the control device controls the constriction device to change the constriction of the wall portion.

The method of the invention suitably comprises operating the control device by the patient. In a simple form the control device comprises a manually operable switch for switching on and off the constriction/stimulation unit, and the method further comprises subcutaneously implanting the switch in the patient. It is preferable, however, that the control device comprises a hand-held wireless remote control operable by the patient from outside the patient's body to control the constriction/stimulation unit to adjust the stimulation intensity and/or adjust the constriction of the wall portion. The wireless remote control is suitably designed for application on the patient's body like a wristwatch.

In some applications of the invention, the constriction device of the constriction/stimulation unit may be designed to normally keep the patient's wall portion in the constricted state. I.e., after implantation the constriction device all the time keeps the wall portion constricted. In this case, the control device may be used when needed, conveniently by the patient, to control the stimulation device of the constriction/stimulation unit to stimulate the constricted tissue wall portion, preferably while adjusting the stimulation intensity, to cause contraction of the wall portion, so that the flow in the urinary passageway is at least further restricted or stopped, and to control the stimulation device to cease the stimulation. More precisely, the method of the invention may comprise operating the control device by the patient to
a) control the stimulation device in a first mode to stimulate the constricted wall portion to further restrict the flow in the urinary passageway and control the stimulation device in a second mode to cease the stimulation of the wall portion to increase the flow in the urinary passageway; or b) control the stimulation device in a first mode to stimulate the constricted wall portion to stop the flow in the urinary passageway and control the stimulation device in a second mode to cease the stimulation of the wall portion to allow flow in the urinary passageway.

Either the first mode or the second mode may be temporary.

The wireless remote control preferably transmits at least one wireless control signal for controlling the constriction/stimulation unit. The control signal may comprise a frequency, amplitude, phase modulated signal or a combination thereof, and may be an analogue or a digital signal, or a combination of an analogue and digital signal. The remote control may transmit an electromagnetic carrier wave signal for carrying the digital or analogue control signal. Also the carrier signal may comprise digital, analogue or a combination of digital and analogue signals.

Any of the above signals may comprise wave signals, such as a sound wave signal, an ultrasound wave signal, an electromagnetic wave signal, an infrared light signal, a visible light signal, an ultra violet light signal, a laser light signal, a micro wave signal, a radio wave signal, an x-ray radiation signal or a gamma radiation signal.

Alternatively, the control signal may comprise an electric or magnetic field, or a combined electric and magnetic field.

Operation of Constriction/Stimulation Unit

It should be understood that any embodiment or part of embodiment for operating the combined stimulation device and constriction device, could be used, if applicable, for any one of the devices as a stand alone device.

The method of the invention may comprise implanting in the patient an operation device, and operating the constriction/stimulation unit with the operation device. A magnet may be provided, wherein the method comprises using the magnet to activate the operation device from outside the patient's body. The operation device suitably comprises a motor which is powered with energy released from a source of energy, such as a battery. Although the constriction/stimulation unit in embodiments described above suitably is designed as a single piece, which is most practical for implantation, it should be noted that as an alternative the constriction device and stimulation device of the constriction/stimulation unit could be designed as separate pieces.

Laparoscopic Method

The present invention also provides a first method for controlling a flow of urine in the urinary passageway formed by a tissue wall of a patient's urethra, ureter, renal pelvis or bladder. The method comprises the steps of:
inserting a needle like tube into the cavity of the patients body,
filling the cavity with gas thereby expanding the abdominal cavity,
placing at least two laparoscopical trocars in the patient's body,
inserting a camera through one of the trocars into the cavity,
inserting a dissecting tool through any of the trocar and dissecting an area of at least one portion of the tissue wall of the urethra, ureter, renal pelvis or bladder,
placing a constriction device and a stimulation device in the dissected area in operative engagement with the urethra, ureter, renal pelvis or bladder,
using the constriction device to gently constrict the wall portion of the urethra, ureter, renal pelvis or bladder to influence the flow in the urethra, ureter, renal pelvis or bladder, and
using the stimulation device to stimulate the constricted wall portion to cause contraction of the wall portion to further influence the flow in the urethra, ureter, renal pelvis or bladder.

The present invention also provides a second method for controlling a flow of urine in the urinary passageway formed by a tissue wall of a patient's urethra, ureter, renal pelvis or bladder. The method comprises the steps of:
inserting a needle like tube into a cavity of the patients body,
using the needle like tube to fill the cavity with gas thereby expanding the cavity,
placing at least two laparoscopical trocars in the patient's body,
inserting a camera through one of the trocars into the cavity,
inserting a dissecting tool through any of the trocar and dissecting an area of at least one portion of the tissue wall of the urethra, ureter, renal pelvis or bladder,
placing a stimulation device in the dissected area in operative engagement with the urethra, ureter, renal pelvis or bladder, and
using the stimulation device to stimulate the wall portion to cause contraction of the wall portion to influence the flow in the urethra, ureter, renal pelvis or bladder.

The present invention also provides a third method for controlling a flow of urine in the urinary passageway formed by a tissue wall of a patient's urethra, ureter, renal pelvis or bladder. The method comprises the steps of:
inserting a needle like tube into a cavity of the patients body,
using the needle like tube to fill the cavity with gas thereby expanding the cavity,
placing at least two laparoscopical trocars in the patient's body,
inserting a camera through one of the trocars into the cavity,
inserting a dissecting tool through any of the trocar and dissecting an area of at least one portion of the tissue wall of the urethra, ureter, renal pelvis or bladder,
placing a constriction device in the dissected area in operative engagement with the urethra, ureter, renal pelvis or bladder,
using the constriction device to constrict the wall portion of the urethra, ureter, renal pelvis or bladder to influence the flow in the urethra, ureter, renal pelvis or bladder.

The present invention also provides a fourth method for controlling a flow of urine in the urinary passageway formed by a tissue wall of a patient's urethra, ureter, renal pelvis or bladder. The method comprises the steps of:
cutting the skin of the patient,
inserting a dissecting tool and dissecting an area of at least one portion of the tissue wall of the urethra, ureter, renal pelvis or bladder,
placing a constriction device and a stimulation device in the dissected area in operative engagement with the urethra, ureter, renal pelvis or bladder,
using the constriction device to gently constrict the wall portion of the urethra, ureter, renal pelvis or bladder to influence the flow in the urethra, ureter, renal pelvis or bladder, and
using the stimulation device to stimulate the constricted wall portion to cause contraction of the wall portion to further influence the flow in the urethra, ureter, renal pelvis or bladder.

The present invention also provides a fifth method for controlling a flow of urine in the urinary passageway formed by a tissue wall of a patient's urethra, ureter, renal pelvis or bladder. The method comprises the steps of:
cutting the skin of the patient, inserting a dissecting tool and dissecting an area of at least one portion of the tissue wall of the urethra, ureter, renal pelvis or bladder, placing a stimulation device in the dissected area in operative engagement with the urethra, ureter, renal pelvis or bladder, and using the stimulation device to stimulate the wall portion to cause contraction of the wall portion to influence the flow in the urethra, ureter, renal pelvis or bladder.

The present invention also provides a sixth method for controlling a flow of urine in the urinary passageway formed by a tissue wall of a patient's urethra, ureter, renal pelvis or bladder. The method comprises the steps of:

cutting the skin of the patient, inserting a dissecting tool and dissecting an area of at least one portion of the tissue wall of the urethra, ureter, renal pelvis or bladder, placing a constriction device in the dissected area in operative engagement with the urethra, ureter, renal pelvis or bladder, and using the constriction device to constrict the wall portion of the urethra, ureter, renal pelvis or bladder to influence the flow in the urethra, ureter, renal pelvis or bladder.

In all of the above-noted methods 1-6 the cavity may constitute at least one of an abdominal cavity, a cavity in the pelvic region, a retroperitoneal cavity, a cavity in human soft tissue such as muscle, fat and fibrotic tissue.

The present invention also provides another laparoscopic method. Accordingly, there is provided a method for controlling a flow of urine in the urinary passageway of a patient's urethra, ureter, renal pelvis or bladder formed by a tissue wall of a patient's urethra, ureter, renal pelvis or bladder. The method comprises the steps of:

inserting a needle like tube into the abdomen of the patients body, filling the abdomen with gas thereby expanding the abdominal cavity, placing at least two laparoscopical trocars in the patient's body, inserting a camera through one of the trocars into the abdomen, inserting a dissecting tool through any of the trocar and dissecting an area of at least one portion of the tissue wall of the urethra, ureter, renal pelvis or bladder, placing a constriction device and a stimulation device in the dissected area in operative engagement with the urethra, ureter, renal pelvis or bladder, using the constriction device to gently constrict the wall portion of the urethra, ureter, renal pelvis or bladder to influence the flow in the urinary passageway, and using the stimulation device to stimulate the constricted wall portion to cause contraction of the wall portion to further influence the flow in the urinary passageway.

The method further comprises implanting a powered operation device for operating the constriction device. The operation device may comprise a powered hydraulic operation device or an electrically powered operation device, such as an electric motor.

The method further comprises transmitting wireless energy for powering the operation device, and when desired to influence the flow in the patient's urethra, ureter, renal pelvis or bladder, powering the operation device with the transmitted energy to operate the constriction device.

Obesity, AGB

Another object of the present invention is to provide a versatile careful method for controlling the food flow in the stomach of an obese patient surgically modified by AGB, so as to reduce the patient's weight while minimizing the complications previously associated with gastric restriction surgery.

In accordance with this object of the present invention, there is provided a method for controlling the food flow in a patient's stomach, the method comprising:

gently constricting at least one portion of the stomach tissue wall to influence the flow in the stomach, and stimulating at least one portion of the stomach tissue wall to cause contraction of the wall portion to further influence the flow in the stomach.

The present invention provides an advantageous combination of the method steps (a) and (b), which results in a two-stage influence on the food flow in the stomach. Thus, applying a relatively weak force against the wall portion gently constricts the tissue wall and the constricted wall portion is stimulated to achieve the desired final influence on the flow in the stomach. The phrase "gently constricts a portion of the tissue wall" is to be understood as constricting the wall portion without substantially hampering the blood circulation in the tissue wall.

Preferably, step (b) is performed by intermittently and individually stimulating different areas of the wall portion. Such an intermittent and individual stimulation of different areas of the wall portion of the stomach allows tissue of the wall portion to maintain over time substantially normal blood circulation.

Preferably, the constriction step (a) and stimulation step (b) are performed independently of each other. Steps (a) and (b) may be performed simultaneously. Optionally, step (b) may or may not be performed while step (a) is performed.

Initially, the constriction of the wall portion can be calibrated by stimulating the wall portion while adjusting the constriction of the wall portion until the desired restriction of the flow in the stomach is obtained.

Flow Restriction

It should be understood that any embodiment or part of embodiment disclosed below in connection with flow restriction for the constriction and stimulation devices combined in a constriction/stimulation unit could be used for the separate constriction device and separate stimulation device, where applicable.

The method of the present invention is well suited for restricting the food flow in the stomach. Thus, in a principal embodiment of the invention, the wall portion is constricted, so that the flow in the stomach at least is restricted and the constricted wall portion is stimulated to at least further restrict the flow in the stomach. Specifically, the wall portion is constricted to a constricted state, in which the blood circulation in the constricted wall portion is substantially unrestricted and the flow in the stomach is at least restricted, and the constricted wall portion is stimulated when it is in the constricted state to at least further restrict the flow in the stomach.

The constriction step (a) and stimulation step (b) are suitably performed to constrict and stimulate the wall portion to an extent that depends on the flow restriction that is desired to be achieved in a specific application of the method of the invention. Thus, in accordance with a first flow restriction option, step (a) is performed by constricting the wall portion, so that the flow in the stomach is restricted but not stopped, and step (b) is performed by stimulating the constricted wall portion to cause contraction thereof, so that the flow in the stomach is further restricted but not stopped. The method may further comprise sensing a physical parameter of the patient and adjusting the intensity of the stimulation of the wall portion in response to the sensed parameter.

In accordance with a second flow restriction option, step (a) is performed by constricting the wall portion, so that the flow in the stomach is restricted but not stopped, and step (b) is performed by stimulating the constricted wall portion to cause contraction thereof, so that the flow in the stomach is stopped.

When using the method of the invention in accordance with the first or second options, the method may further comprise (c) ceaseing stimulating the wall portion to increase or allow the flow in the stomach and (d) releasing the wall portion to restore the flow in the stomach.

In accordance with a third flow restriction option, step (a) is performed by constricting the wall portion, so that the flow in the stomach is substantially stopped, and step (b) is performed by stimulating the constricted wall portion to cause contraction thereof, so that the flow in the stomach is completely stopped. The method may further comprise (c) ceaseing stimulating the wall portion to allow the flow in the stomach and (d) releasing the wall portion to restore the flow in the stomach.
 stomach Where the constricted wall portion is stimulated to contract, so that the flow in the stomach is stopped, a first length of the constricted wall portion and a second length of the constricted wall portion, which is located downstream of the first length, are suitably simultaneously and cyclically stimulated, wherein the first length is progressively stimulated in the upstream direction of the stomach and the second length is progressively stimulated in the downstream direction of the stomach.

Furthermore, when using the method of the invention in accordance with the second and third options, the method may further comprise sensing a physical parameter of the patient or functional parameter of implanted components and adjusting the stimulation of the wall portion in response to the sensed parameter. For example, the intensity of the stimulation of the wall portion may be increased in response to a sensed pressure increase in the stomach, so that the flow in the stomach remains stopped when a pressure increase occurs in the stomach. In particular, the method may comprise sensing a physical parameter of the patient's that relates to the pressure in the stomach, and controlling the stimulation of the wall portion in response to the sensed parameter. Any sensor for sensing a physical parameter of the patient, such as a pressure in the patient's body that relates to the pressure in the stomach may be provided, wherein the stimulation is controlled in response to signals from the sensor. Such a sensor may for example sense the pressure in the patient's abdomen, the pressure against the implanted constriction device or the pressure on the tissue wall of the stomach. In accordance with a fourth restriction option, step (a) is performed by constricting the wall portion, so that the flow in the stomach is stopped. When needed, the wall portion is released to restore the flow in the stomach. Step (b) is only performed by stimulating the constricted wall portion to cause contraction thereof, so that the flow in the stomach remains stopped when a pressure increase occurs in the stomach. The method may further comprise sensing a physical parameter of the patient's body, such as a pressure in the patient's body that relates to the pressure in the stomach, and controlling the stimulation of the wall portion in response to the sensed parameter. Such a physical parameter may be a pressure in the patient's abdomen and the sensor may be a pressure sensor.

In some applications of the method of the invention, continuous stimulation may over time change the physical properties of the tissue so that the tissue might be injured. Also, the effect of a continuous stimulation of the tissue wall may decrease over time. Therefore, step (b) is preferably performed by intermittently and individually stimulating different areas of the wall portion so that the flow in the stomach continues to be restricted as desired and each area of the wall portion essentially maintains its natural physical properties over time to prevent the area from being injured. Advantageously, each area of the wall portion is stimulated during successive time periods, each time period being short enough to maintain over time satisfactory blood circulation in the area. Thus, the areas are stimulated so that an area that currently is not stimulated will have time to restore substantially normal blood circulation before it is stimulated again.

To maintain satisfactory blood circulation in the tissue wall of the patient's stomach stimulation step (b) is suitably performed by stimulating one or more of different areas of the wall portion at a time, preferably by sequentially stimulating the different areas of the wall portion or by shifting the stimulation from one area to another over time. Preferably, stimulation step (b) is performed by cyclically propagating the stimulation of the areas along the wall portion, for example in accordance with a determined stimulation pattern.

The method of the invention may further comprise controlling, preferably by the patient, the constriction and/or stimulation of the wall portion from outside the patient's body.

Generally, the method of the invention comprises sensing a physical parameter of the patient and controlling, preferably automatically, the constriction and/or stimulation of the wall portion in response to the sensed parameter.

The constriction step (a) may be performed by constricting any wall portions of a series of wall portions of the stomach's tissue wall, respectively, either in random or in accordance with a predetermined sequence. The stimulation step (b) may be performed by stimulating any of the constricted wall portions of the series of wall portions. Specifically, step (a) may be performed by constricting all of the wall portions of the series of wall portions, and step (b) may be performed by stimulating any constricted wall portions in random or in accordance with a predetermined sequence to close the stomach.

Moving Fluid in the Stomach or Preventing the Movement of Fluids in the Stomach in a Similar Way It should be understood that any embodiment or part of embodiment disclosed below in connection with moving fluid in the stomach, or preventing the move of fluid or any matter in the stomach, for a constriction and stimulation devices combined in the constriction/stimulation unit could be used for the separate constriction device and separate stimulation device, where applicable. The method of the present invention can be practised for actively moving the fluid in stomach of a patient's stomach. Thus, in the embodiments of the invention listed below, steps (a) and (b) are co-operated to move the fluid in the stomach.

1) Step (a) is performed by constricting the wall portion to restrict the flow in the stomach, and step (b) is performed by stimulating the constricted wall portion to close the stomach either at an upstream end or a downstream end of the constricted wall portion. The method further comprises (c) increasing the constriction of the wall portion to move the fluid in the stomach.

2) Step (a) is performed by constricting the wall portion to restrict the flow in the stomach, and step (b) is performed by progressively stimulating the constricted wall portion to cause progressive contraction of the wall portion to move the fluid in the stomach. The constricted wall portion is progressively stimulated in the downstream or upstream direction of the stomach.

3) Step (a) is performed by varyingly constricting the wall portion to vary the flow in the stomach, and step (b) is performed by progressively stimulating the constricted wall portion to cause progressive contraction of the wall portion to move the fluid in the stomach. The constricted wall portion is progressively stimulated in the downstream or upstream direction of the stomach.

4) Step (a) is performed by varyingly constricting different areas of the wall portion to cause progressive constriction of the wall portion in the downstream or upstream direction of the stomach, and the constricted wall portion is progressively stimulated to cause progressive contraction thereof in harmony with the progressive constriction of the wall portion. The method may further comprise providing at least one elongated constriction element extending along the wall portion, and controlling the elongated constriction element to progressively constrict the wall portion in the downstream or upstream direction of the stomach. The elongated constriction element suitably comprises contact surfaces dimensioned to contact a length of wall portion, and the method may further comprise providing a plurality of stimulation elements distributed along the contact surfaces, and controlling the stimulation elements to stimulate the different areas of the wall portion along the length of the wall portion.

5) Step (a) is performed by constricting any one of a series of wall portions of the tissue wall to at least restrict the flow in the stomach, and step (b) is performed by stimulating the constricted wall portion to close the stomach. The method further comprises successively constricting the wall portions of the series of wall portions to move the fluid in the stomach in a peristaltic manner.

5a) In accordance with an alternative, the method further comprises providing at least one constriction element and at least one stimulation element positioned on the constriction element, moving the constriction element along the stomach in the flow direction in the stomach to successively constrict the wall portions of the series of wall portions, and using the stimulation element to stimulate the wall portion constricted by the constriction element to close the stomach. Suitably, the method further comprises cyclically moving the constriction element along the wall portions of the series of wall portions.

5b) In accordance with another alternative, the method further comprises providing a plurality of constriction elements and stimulation elements positioned on the constriction elements, moving each constriction element along the stomach to successively constrict the wall portions of the series of wall portions, and using the stimulation elements to stimulate the wall portion constricted by any one of the constriction elements to close the stomach. Suitably, the method further comprises cyclically moving the constriction elements one after the other along the wall portions of the series of wall portions. Specifically, the method further comprises providing a rotor carrying the constriction elements, and rotating the rotor so that each constriction element cyclically constricts the wall portions of the series of wall portions. Each constriction element suitably comprises a roller that rolls on the stomach to constrict the latter.

6) Step (a) is performed by constricting any wall portions of a series of wall portions of the stomach's tissue wall, respectively, wherein the wall portions of the series of wall portions are successively constricted along the stomach to move the fluid in the stomach of the patient's stomach. The stimulation step (b) is performed by stimulating any constricted wall portions of the series of wall portions.

7) Step (a) is performed by constricting wall portions of a series of wall portions without completely closing the stomach's stomach, and step (b) is performed by stimulating the constricted wall portions one after the other, so that the wall portions of the series of wall portions are successively contracted along the stomach to move the fluid in the stomach of the patient's stomach.

8) Step (a) is performed by constricting the wall portion at an upstream or downstream end thereof to close the stomach. The method further comprises (c) constricting the wall portion between the upstream and downstream ends thereof, to move the fluid contained in the wall portion between the upstream and downstream ends thereof downstream or upstream in the stomach. Optionally, the method further comprises stimulating the wall portion between the upstream and downstream ends thereof, as (c) is performed.

8a) In accordance with an alternative, step (a) is performed by constricting the wall portion at the upstream end thereof to restrict the flow in the stomach, and step (b) is performed by stimulating the constricted wall portion at the upstream end to close the stomach, whereby the fluid contained in the wall portion between the upstream and downstream ends thereof is moved downstream in the stomach, as step (c) is performed.

8b) In accordance with another alternative, step (a) is performed by constricting the wall portion at the downstream end thereof to restrict the flow in the stomach, and step (b) is performed by stimulating the constricted wall portion at the downstream end to close the stomach, whereby the fluid contained in the wall portion between the upstream and downstream ends thereof is moved upstream in the stomach, as step (c) is performed.

To summarize a few preferred embodiments see below:

In accordance with an alternative, step (a) is performed by constricting any wall portions of a series of wall portions of the stomach's tissue wall, respectively. In accordance with an alternative, the wall portions of the series of wall portions are constricted in random or in accordance with a predetermined sequence. In accordance with an alternative, the wall portions of the series of wall portions are successively constricted along the stomach to move the fluid in the stomach or to prevent the fluid to move in the patient's stomach.

In accordance with an alternative, step (b) is performed by stimulating any constricted wall portions of the series of wall portions. In accordance with an alternative, the wall portions of the series of wall portions are constricted in random or in accordance with a predetermined sequence. In accordance with an alternative, wherein the wall portions of the series of wall portions are successively constricted along the stomach to move the fluid in the the patient's stomach or to prevent the fluid to move in the stomach of the patient's stomach.

In accordance with an alternative, step (a) is performed by constricting any wall portions of a series of wall portions of the stomach's tissue wall, respectively, wherein the wall portions of the series of wall portions are successively constricted without completely closing the stomach', and step (b) is performed by stimulating the constricted wall portions, so that the wall portions of the series of wall portions are further constricted. In accordance with an alternative, the wall portions of the series of wall portions are constricted in random or in accordance with a predetermined sequence.

In accordance with an alternative, wherein the wall portions of the series of wall portions are successively constricted along the stomach to move the fluid in the patient's stomach or to prevent the fluid to move in the patient's stomach.

In accordance with an alternative, step (a) is performed by constricting all of the wall portions of the series of wall portions, and step (b) is performed by stimulating any constricted wall portions so that the wall portions of the series of wall portions are further constricted.

In accordance with an alternative, the wall portions of the series of wall portions are further constricted by the stimulation device in random or in accordance with a predetermined sequence.

In accordance with an alternative, the wall portions of the series of wall portions are successively further constricted by the stimulation device along the stomach to move the fluid in the patient's stomach or to prevent the fluid to move in the patient's stomach.

In accordance with an alternative for all applicable alternatives, step (a) and step (b) are performed independently of each other or in accordance with an alternative, step (a) and step (b) are performed simultaneously.

In any of the above noted embodiments (1) to (8b), step (b) may be performed by stimulating the wall portion with electric pulses.

Stimulation Modes

When stimulating neural or muscular tissue there is a risk of injuring or deteriorating the tissue over time if the stimulation is not properly performed. The method of the present invention is performed to reduce or even eliminate that risk. Thus, step (b) is performed by intermittently stimulating different areas of the wall portion so that at least two of the areas are stimulated at different points of time. I.e., the stimulation is shifted from one area to another area over time. In addition, step (b) is performed by intermittently stimulating the areas of the wall portion so that an area of the different areas that currently is not stimulated has time to restore substantially normal blood circulation before it is stimulated again. Furthermore, step (b) is performed by intermittently stimulating the areas during successive time periods, wherein each time period is short enough to maintain satisfactory blood circulation in the area until the laps of the time period. This gives the advantage that the method of the present invention provides continuous stimulation of the wall portion of the stomach to achieve the desired flow control while essentially maintaining over time the natural physical properties of the stomach without risk of injuring the stomach.

Also, by physically changing the places of stimulation on the stomach over time as described above it is possible to create an advantageous changing stimulation pattern on the stomach, in order to achieve a desired flow control.

To achieve the desired reaction of the tissue wall during the stimulation thereof, step (b) may be performed by stimulating the wall portion with, preferably cyclically, varying stimulation intensity.

In a main embodiment of the invention, step (b) is performed by intermittently stimulating the wall portion with pulses, preferably in the form of pulse trains. The pulse trains can be configured in many different ways by varying pulse parameters. Thus, the pulse amplitudes of the pulses of the pulse trains, the off time periods between the individual pulses of each pulse train and the width and repetition frequency of each pulse may be varied. Also the off time periods between the pulse trains may be varied, wherein each off time period between the pulse trains is kept long enough to restore substantially normal blood circulation in each area of the wall portion, when the area is not stimulated during the off time periods. Furthermore, the repetition frequency of the pulses of the pulse trains and the length and number of pulses of each pulse train may be varied.

As mentioned above, for reasons of maintaining over time the effect of stimulation, it is preferable that different areas of the wall portion are intermittently and individually stimulated. In consequence, step (b) may be performed by stimulating one or more of the areas at a time with pulses, by cyclically propagating the stimulation of the areas with pulses along the wall portion, and/or by propagating the stimulation of the areas with pulses in accordance with a determined stimulation pattern. In case the off time periods between pulse trains that stimulate the respective area of the wall portion are varied, it is preferable that each off time period between the pulse trains is controlled to last long enough to restore substantially normal blood circulation in the area when the latter is not stimulated during the off time periods.

Electric Stimulation

In accordance with a preferred embodiment of the invention, step (b) is performed by electrically stimulating the wall portion, preferably with electric pulses to cause contraction of the wall portion. This embodiment is particularly suited for applications in which the patient's wall portion includes muscle fibers that react to electrical stimula. Thus, the wall portion that includes the muscle fibers is stimulated with such electric pulses, preferably in the form of electric pulse trains, when the wall portion is in the constricted state, to cause contraction of the wall portion. Of course, the configuration of the electric pulse trains may be similar to the above described pulse trains and different areas of the wall portion may be electrically stimulated in the same manner as described above.

In accordance with the preferred embodiment, the method of the invention comprises providing at least one, preferably a plurality of electrical elements, such as electrodes, engaging and stimulating the wall portion with electric pulses. Optionally, the electrical elements may be placed in a fixed orientation relative to one another. The method comprises electrically energizing the electrical elements, preferably by cyclically energizing each element with electric pulses. The electrical elements may be energized so that the electrical elements are energized one at a time in sequence, or so that a number or groups of the electrical elements are energized at a time. Also, groups of electrical elements may be sequentially energized, either randomly or in accordance with a predetermined pattern.

The method may further comprise applying the electrical elements on the patient's wall portion so that the electrical elements form any pattern of electrical elements, preferably an elongate pattern of electrical elements extending lengthwise along the wall portion and the elements abut the respective areas of the wall portion. The electrical elements may be successively energized along the elongate pattern of electrical elements in a direction opposite to or in the same direction as that of the flow in the patient's stomach. Optionally, the electrical elements may be successively energized along the elongate pattern of electrical elements from a position substantially at the center of the constricted wall portion towards both ends of the elongate pattern of electrical elements. Where the food passageway of the stomach is to be kept closed for a relatively long time, the electrical elements may be energized so that energized electrical elements form two waves of energized electrical elements that simultaneously advance from the center of the constricted wall portion in two opposite directions towards both ends of the elongate pattern of electrical elements. Such waves of energized electrical elements can be repeated over and over again without harming the stomach and without moving fluid or gas in any direction in the stomach.

The elongate pattern of electrical elements may include one or more rows of electrical elements extending lengthwise along the stomach. Each row of electrical elements may form a straight, helical or zig-zag path of electrical elements, or any form of path. The electrical elements may be energized so that the electrical elements currently energized form at least one group of adjacent energized electrical elements, wherein the elements in the group of energized electrical elements form a path of energized electrical elements extending at least in part around the patient's stomach, preferably completely around the patient's stomach. Alternatively, the elements in the group of energized electrical elements form two paths of energized electrical elements extending on mutual sides of the patient's stomach or more than two paths of energized electrical elements extending on different sides of the patient's stomach, preferably at least substantially transverse to the flow direction in the stomach of the stomach.

In an embodiment of the invention, the electrical elements form a plurality of groups of elements, wherein the groups form a series of groups extending along the patient's stomach in the flow direction in the patient's stomach. The electrical elements of each group of electrical elements may form a path of elements extending at least in part around the patient's stomach. In a first alternative, the electrical elements of each group of electrical elements may form more than two paths of elements extending on different sides of the patient's stomach, preferably substantially transverse to the flow direction in the patient's stomach. The groups of electrical elements in the series of groups may be energized in random or in accordance with a predetermined pattern. Alternatively, the groups of electrical elements in the series of groups may be successively energized in a direction opposite to or in the same direction as that of the flow in the patient's stomach, or in both said directions starting from a position substantially at the center of the constricted wall portion. For example, groups of energized electrical elements may form advancing waves of energized electrical elements, as described above. I.e., the groups of electrical elements may be energized so that energized electrical elements form two waves of energized electrical elements that simultaneously advance from the center of the constricted wall portion in two opposite directions towards both ends of the elongate pattern of electrical elements.

Thermal Stimulation

In accordance with an embodiment of the invention, stimulation step (b) is performed by thermally stimulating the wall portion. Thus, the wall portion may be cooled, when the wall portion is constricted, to cause contraction of the wall portion. For example, the wall portion may be constricted to at least restrict the flow in the stomach, and the constricted wall portion may be cooled to cause contraction thereof, so that the flow in the stomach is at least further restricted, or further restricted but not stopped, or stopped. Alternatively, the wall portion may be heated, when the wall portion is constricted and contracted, to cause expansion of the wall portion. Where applicable, thermal stimulation may be practised in any of the embodiments of the present invention, and the thermal stimulation may be controlled in response to various sensors, for example strain, motion or pressure sensors.

Constriction and Stimulation Devices

It should be understood that any embodiment or part of embodiment for the combined stimulation device and constriction device, could be used, if applicable, for any one of the devices as a stand alone device. Generally, the method of the invention comprises providing a constriction device that constricts the wall portion, a stimulation device that stimulates the constricted wall portion and a control device that controls the constriction device and/or the stimulation device. The method comprises operating the control device from outside the patient's body, preferably by using the control device to wirelessly control the constriction device and/or stimulation device. The wireless control is preferably performed in a non-magnetic manner, whereby implanted magnetic devices can be avoided. Suitably, the control device comprises a hand-held wireless remote control operated by the patient.

Alternatively, the control device comprises a manually operable switch for switching on and off the constriction device and/or stimulation device. In this case, the method comprises subcutaneously implanting the switch in the patient and manually operating the the implanted switch from outside the patient's body.

In an embodiment of the invention, the control device comprises a programmable internal control unit, such as a microprocessor, and the method comprises implanting in the patient the internal control unit and controlling by the internal control unit the constriction device and/or stimulation device. The control device may also comprise an external control unit outside the patient's body. In this case, the method comprises controlling by the external control unit the constriction device and/or stimulation device and, optionally, using the external control unit to program the implanted internal control unit. The internal control unit may be programmable for controlling the constriction device and/or stimulation device over time, for example in accordance with an activity schedule program.

The constriction of the wall portion can be calibrated by using the control device to control the stimulation device to stimulate the wall portion while controlling the constriction device to adjust the constriction of the wall portion until the desired restriction of the flow in the stomach is obtained.

Sensor Controlled Constriction and/or Stimulation

It should be understood that any embodiment or part of embodiment disclosed below in connection with sensor control of the constriction and stimulation devices combined in the constriction/stimulation unit could be used for the separate constriction device and separate stimulation device, where applicable. In an embodiment of the invention, the method comprises implanting at least one sensor and controlling by the control device the constriction device and/or the stimulation device in response to signals from the sensor. Generally, the sensor directly or indirectly senses at least one physical parameter of the patient, functional parameter of the apparatus, or functional parameter of a medical implant in the patient.

Many different kinds of sensor for sensing physical parameters may be used. For example motion sensors for sensing stomach motion, i.e. natural stomach contractions, pressure sensors for sensing pressure in the stomach, strain sensors for sensing strain of the stomach, flow sensors for sensing fluid flow in the stomach, spectro-photometrical sensors, Ph-sensors for acidity or alkalinity of the fluid in the stomach, oxygen-sensors sensors for sensing the oxygen content of the fluid in the stomach, or sensors for sensing the distribution of the stimulation on the stimulated stomach. Any conceivable sensors for sensing any other kind of useful physical parameter may be used.

Many different kinds of sensors that sense functional parameters of implanted components may also be used for the control of the constriction device and/or the stimulation device. For example sensors for sensing electric parameters of implanted electric components, or sensors for sensing the performance of implanted motors or the like.

The sensor may comprise a pressure sensor for sensing as the physical parameter a pressure in the patient's body that relates to the pressure in the stomach of the patient's stomach. In this case, the method suitably comprises operating the control device to control the constriction device to change the constriction of the patient's wall portion in response to the pressure sensor sensing a predetermined value of measured pressure.

Alternatively, or in combination with the pressure sensor, a position sensor may be provided for sensing as the physical parameter the orientation of the patient with respect to the horizontal. The position sensor may be a biocompatible version of what is shown in U.S. Pat. Nos. 4,942,668 and 5,900,909. For example, the control device may control the constriction device and/or stimulation device to change the constriction of the patient's wall portion in response to the position sensor sensing that the patient has assumed a substantially horizontal orientation, i.e. that the patient is lying down.

The above described sensors may be used in any of the embodiments of the invention, where applicable.

The control device may control the constriction device and/or stimulation device to change the constriction of the patient's wall portion in response to the time of day. For that purpose the control device may include a clock mechanism for controlling the constriction device and/or stimulation device to change the constriction of the patient's wall portion to increase or decrease the influence on the flow in the stomach during different time periods of the day. In case a sensor of any of the above-described types for sensing a physical or functional parameter is provided, either the clock mechanism is used for controlling the constriction device and/or stimulation device provided that the parameter sensed by the sensor does not override the clock mechanism, or the sensor is used for controlling the constriction device and/or stimulation device provided that the clock mechanism does not override the sensor. Suitably, the control device produces an indication, such as a sound signal or displayed information, in response to signals from the sensor.

The control device may comprise an implantable internal control unit that directly controls the constriction device and/or stimulation device in response to signals from the sensor. The control device may further comprise a wireless remote control adapted to set control parameters of the internal control unit from outside the patient without mechanically penetrating the patient. At least one of the control parameters, which is settable by the wireless remote control, is the physical or functional parameter. Suitably, the internal control unit includes the above mentioned clock mechanism, wherein the wireless remote control also is adapted to set the clock mechanism.

Alternatively, the control device may comprise an external control unit outside the patient's body for controlling the constriction device and/or stimulation device in response to signals from the sensor.

Constriction of Patient's Stomach

It should be understood that any embodiment or part of embodiment disclosed below in connection with constricting the patient's stomach could be used for the separate constriction device and separate stimulation device, where applicable.

Method step (a) may be performed in many different ways. Thus, step (a) may be performed by:
  constricting the wall portion so that the through-flow area of the stomach assumes a size in the constricted state small enough to cause the constricted wall portion to contract to stop the flow in the stomach when step (b) is performed;
  bending the wall portion;
  clamping the wall portion between at least two elements positioned on different sides of the stomach;
  clamping the stomach between an element and the bone or tissue of the patient;
  rotating at least two elements positioned on different sides of the stomach; or
(6)—clamping the stomach between at least two articulated clamping elements positioned on different sides of the stomach.

In the above noted alternatives (1) to (6) of method step (a), the constriction of the wall portion of the stomach may be changed either mechanically or hydraulically. For many applications of the present invention, step (a) is suitably performed so that the through-flow area of the stomach assumes a size in the constricted state that is small enough to enable the stimulation during step (b) to contract the wall portion of the stomach to stop the flow in the stomach.

Where the constriction of the wall portion is hydraulically changed, the method of the invention may further comprise implanting in the patient a reservoir containing a predetermined amount of hydraulic fluid, and a constriction device engaging the wall portion and having an expandable/contractible cavity, wherein step (a) is performed by distributing hydraulic fluid from the reservoir to increase the volume of the cavity to constrict the wall portion, and by distributing hydraulic fluid from the cavity to the reservoir to decrease the volume of the cavity to release the wall portion. The cavity may be defined by a balloon of the constriction device that abuts the tissue wall portion of the patient's stomach, so that the patient's wall portion is constricted upon expansion of the cavity and released upon contraction of the cavity.

Alternatively, the cavity may be defined by a bellows that displaces a relatively large contraction element of the constriction device, for example a large balloon that abuts the wall portion, so that the patient's wall portion is constricted upon contraction of the bellows and released upon expansion of the bellows. Thus, a relatively small addition of hydraulic fluid to the bellows causes a relatively large increase in the constriction of the wall portion. Such a bellows may also be replaced by a suitably designed piston/cylinder mechanism.

Where the hydraulic means comprises a cavity in the constriction device, the following embodiments of the invention are conceivable.

1) The reservoir comprises first and second wall portions, and step (a) is performed by displacing the first and second wall portions relative to each other to change the volume of the reservoir, so that fluid is distributed from the reservoir to the cavity, or from the cavity to the reservoir.

1a) At least one of a magnetic device, a hydraulic device or an electric control device displaces the first and second wall portions of the reservoir.

2) A pump is provided for pumping fluid between the reservoir and the cavity.

2a) The pump comprises a first activation member for activating the pump to pump fluid from the reservoir to the cavity and a second activation member for activating the pump to pump fluid from the cavity to the reservoir.

2a1) The first and second activation members are operable by manual manipulation thereof.

2a2) At least one of the activation members operates when subjected to an external predetermined pressure.

2a3) At least one of the first and second activating members is operable by magnetic means, hydraulic means, or electric control means.

2b) A fluid conduit between the pump and the cavity is provided, wherein the reservoir forms part of the conduit. The conduit and pump are devoid of any non-return valve. The reservoir forms a fluid chamber with a variable volume, and the pump distributes fluid from the chamber to the cavity by a reduction in the volume of the chamber and withdraws fluid from the cavity by an expansion of the volume of the chamber. A motor is provided for driving the pump, wherein the pump comprises a movable wall of the reservoir for changing the volume of the chamber.

In all of the above noted embodiments 1 to 2b where the hydraulic means comprises an expandable cavity in the constriction device, the cavity can be exchanged by a cylinder/piston mechanism for adjusting the constriction device. In this case, hydraulic fluid is distributed between the reservoir and the cylinder/piston mechanism to adjust the constriction device.

3) The method further comprises implanting a reverse servo operatively connected to the hydraulic means. The term "reverse servo" is to be understood as a mechanism that transfers a strong force acting on a moving element having a short stroke into a weak force acting on another moving element having a long stroke; i.e., the reverse function of a normal servo mechanism. Thus, minor changes in the amount of fluid in a smaller reservoir could be transferred by the reverse servo into major changes in the amount of fluid in a larger reservoir.

Preferably, the reverse servo comprises an expandable servo reservoir containing servo fluid and a fluid supply reservoir hydraulically connected to the servo reservoir to form a closed conduit system for the servo fluid. The expandable servo reservoir has first and second wall portions, which are displaceable relative to each other in response to a change in the volume of the expandable servo reservoir.

In accordance with a first alternative, the first and second wall portions of the servo reservoir are operatively connected to the hydraulic means. The reverse servo distributes fluid between the fluid supply reservoir and the expandable servo reservoir to change the volume of the servo reservoir, whereby the hydraulic means is operated to adjust the constriction device.

In accordance with a second alternative, there is provided an implantable main reservoir containing a predetermined amount of hydraulic fluid, wherein the reverse servo is operated to distribute hydraulic fluid between the main reservoir and the hydraulic means to adjust the constriction device. More specifically, the main reservoir is provided with first and second wall portions operatively connected to the first and second wall portions of the expandable servo reservoir, so that the volume of the main reservoir is changed when the volume of the expandable servo reservoir is changed. Thus, when the reverse servo distributes servo fluid between the fluid supply reservoir and the expandable servo reservoir to change the volume of the main reservoir, hydraulic fluid is distributed from the main reservoir to the hydraulic means, or from the hydraulic means to the main reservoir. Advantageously, the method comprises dimensioning the servo and main reservoirs, so that when the volume of the servo reservoir is changed by a relatively small amount of servo fluid, the volume of the main reservoir is changed by a relatively large amount of hydraulic fluid.

In both of the above-described alternatives, the fluid supply reservoir may have first and second wall portions, which are displaceable relative to each other to change the volume of the fluid supply reservoir to distribute servo fluid between the fluid supply reservoir and the expandable servo reservoir. The first and second wall portions of the fluid supply reservoir may be displaced relative to each other by manual manipulation, a magnetic device, a hydraulic device, or an electric control device to change the volume of the fluid supply reservoir to distribute servo fluid between the fluid supply reservoir and the expandable servo reservoir.

In all of the above noted embodiments 1 to 2b where the hydraulic means comprises an expandable cavity in the constriction device, or in embodiments where the hydraulic means includes a hydraulically operable mechanical construction, the reverse servo described above may be used. In a further embodiment of the invention, the hydraulic means include first and second hydraulically interconnected expandable/contractible reservoirs. The first reservoir is operatively connected to the constriction device, so that the constriction device changes the constriction of the patient's wall portion upon expansion or contraction of the first reservoir. By changing the volume of the second reservoir hydraulic fluid is distributed between the two reservoirs, so that the first reservoir is either expanded or contracted. This embodiment requires no non-return valve in the fluid communication conduits between the two reservoirs, which is beneficial to long-term operation of the hydraulic means.

Alternatively, the hydraulic means may include first and second hydraulically interconnected piston/cylinder mechanisms instead of the first and second reservoirs described above. The first piston/cylinder mechanism is operatively connected to the constriction device, so that the constriction device changes the constriction of the patient's wall portion upon operation of the first piston/cylinder mechanism. By operating the second piston/cylinder mechanism hydraulic fluid is distributed between the two piston/cylinder mechanisms, so that the first piston/cylinder mechanism adjusts the constriction device.

Where the constriction device does not include an expandable/contractible cavity, the constriction device may comprise at least two elongated clamping elements extending along the wall portion on different sides of the stomach. The hydraulic means, which may include the reverse servo described above, hydraulically moves the elongated clamping elements towards the stomach to constrict the wall portion of the stomach. For example, the constriction device may have hydraulic chambers in which the clamping elements slide back and forth, and the hydraulic means may also include a pump and an implantable reservoir containing hydraulic fluid. The pump distributes hydraulic fluid from the reservoir to the chambers to move the clamping elements against the wall portion, and distributes hydraulic fluid from the chambers to the reservoir to move the clamping elements away from the wall portion.

Energy Supply

It should be understood that any embodiment or part of embodiment disclosed below in connection with the power of the constriction and stimulation devices combined in the constriction/stimulation unit could be used for the separate constriction device and separate stimulation device, where applicable. Generally, method step (a) is performed by using the constriction device and step (b) is performed by using the stimulation device, wherein the method further comprises forming the constriction and stimulation devices in an operable constriction/stimulation unit.

In a simple form of the invention, the method comprises implanting a source of energy, such as a battery, rechargeable battery or accumulator, releasing energy from the source of energy and using the released energy in connection with the operation of the constriction/stimulation unit.

In a more sophisticated form of the invention, which is preferable, the method comprises transmitting wireless energy from outside the patient's body to inside the patient's body and using the transmitted wireless energy in connection with the operation of the constriction/stimulation unit.

Transmission of Wireless Energy

It should be understood that any embodiment or part of embodiment disclosed below in connection with wireless control or power of the constriction and stimulation devices combined in the constriction/stimulation unit could be used for the separate constriction device and separate stimulation device, where applicable. The wireless energy may be directly used in connection with the operation of the constriction/stimulation unit, as the wireless energy is being transmitted. For example, the wireless energy may be transmitted in the form of an electric, an electromagnetic or a magnetic field, or a combination thereof, or electromagnetic waves for direct power of the constriction/stimulation unit. For example, where an electric motor or pump operates the constriction device of the constriction/stimulation unit, wireless energy in the form of a magnetic or an electromagnetic field may be used for direct power of the motor or pump.

Thus, the motor or pump is running directly during transmission of the wireless energy. This may be achieved in two different ways: a) using a transforming device implanted in the patient to transform the wireless energy into energy of a different form, preferably electric energy, and powering the motor or pump with the transformed energy, or b) using the wirelessly transmitted energy to directly power the motor or pump. Preferably wireless energy in the form of an electromagnetic or magnetic field is used to directly influence specific components of the motor or pump to create kinetic energy. Such components may include coils integrated in the motor or pump.

The wireless energy is suitably transmitted in pulses or digital pulses, or a combination of pulses and digital pulses.

Preferably, the wireless energy is transmitted in at least one wireless signal, suitably a wave signal. The wave signal may comprise an electromagnetic wave signal including one of an infrared light signal, a visible light signal, an ultra violet light signal, a laser signal, a microwave signal, a radio wave signal, an x-ray radiation signal, and a gamma radiation signal. Alternatively, the wave signal may comprise a sound or an ultrasound wave signal. The wireless signal may be a digital or analogue signal, or a combination of a digital and analogue signal.

In accordance with a particular embodiment of the invention, the wireless energy is not for direct use in connection with the operation of the constriction/stimulation unit. In this embodiment the wireless energy comprises energy of a first form, which is transmitted into energy of a second form suited to operate the constriction/stimulation unit. Typically, the energy of the second form is different from the energy of the first form. For example, the wireless energy of the first form may comprise sound waves, whereas the energy of the second form may comprise electric energy. Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

Transforming Wireless Energy

It should be understood that any embodiment or part of embodiment disclosed below in connection with the control or energizing of the constriction and stimulation devices combined in the constriction/stimulation unit could be used for the separate constriction device and separate stimulation device, where applicable. In accordance with a particular embodiment of the invention, an implantable energy-transforming device is provided for transforming wireless energy of a first form transmitted by the energy-transmission device into energy of a second form, which typically is different from the energy of the first form. The constriction/stimulation unit is operable in response to the energy of the second form. For example, the wireless energy of the first form may comprise sound waves, whereas the energy of the second form may comprise electric energy. Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transforming device may function different from or similar to the energy-transmission device. Advantageously, the energy-transforming device comprises at least one element, such as at least one semiconductor, having a positive region and a negative region, when exposed to the energy of the first form transmitted by the energy-transmission device, wherein the element is capable of creating an energy field between the positive and negative regions, and the energy field produces the energy of the second form. More specifically, the element may comprise an electrical junction element, which is capable of inducing an electric field between the positive and negative regions when exposed to the energy of the first form transmitted by the energy-transmission device, whereby the energy of the second form comprises electric energy.

The energy of the first form may directly or indirectly be transformed into the energy of the second form. The method of the invention may comprise providing a motor for operating the constriction device and powering the motor with the energy of the second form. The constriction device may be operable to perform at least one reversible function and the method may comprise reversing the function by using the motor. For example, the method may comprise shifting the polarity of the energy of the second form to reverse the motor.

The motor may be directly powered with the transformed energy, as the energy of the second form is being transformed from the energy of the first form. Preferably, the constriction/stimulation unit is directly operated with the energy of the second form in a non-magnetic, non-thermal or non-mechanical manner.

Normally, the implanted constriction/stimulation unit comprises electric components that are energized with electrical energy. Therefore, the energy of the first form may be transformed into a direct current or pulsating direct current, or a combination of a direct current and pulsating direct current.

Alternatively, the energy of the first form may be transformed into an alternating current or a combination of a direct and alternating current.

The method of the invention may comprise implanting in the patient an internal source of energy, and supplying energy from the internal source of energy for the operation of the constriction/stimulation unit. The method may further comprise implanting in the patient a switch operable to switch from an "off" mode, in which the internal source of energy is not in use, to an "on" mode, in which the internal source of energy supplies energy for the operation of the constriction/stimulation unit, and/or for energizing implanted electronic components of the constriction/stimulation unit. The switch may be operated by the energy of the first form or by the energy of the second form. The described switch arrangement reduces power consumption of the constriction/stimulation unit between operations.

The internal source of energy may store the energy of the second form. In this case, the internal source of energy suitably comprises an accumulator, such as at least one capacitor or at least one rechargeable battery, or a combination of at least one capacitor and at least one rechargeable battery. Where the internal source of energy is a rechargeable battery it may be charged only at times convenient for the patient, for example when the patient is sleeping. Alternatively, the internal source of energy may supply energy for the operation of the constriction/stimulation unit but not be used for storing the energy of the second form. In this alternative, the internal source of energy may be a battery and the switch described above may or may not be provided.

Suitably, the method of the invention may comprise implanting a stabilizer for stabilizing the energy of the second form. Where the energy of the second form comprises electric energy the stabilizer suitably comprises at least one capacitor.

The energy-transforming device may be designed for implantation subcutaneously in the abdomen, thorax or cephalic region of the patient. Alternatively, it may be designed for implantation in an orifice of the patient's body and under the mucosa or intramuscularly outside the mucosa of the orifice.

Control of Constriction/stimulation Unit

It should be understood that any embodiment or part of embodiment disclosed below in connection with the control of the constriction and stimulation devices combined in the constriction/stimulation unit could be used for the separate constriction device and separate stimulation device, where applicable. Although the constriction device of the constriction/stimulation unit may normally keep the patient's wall portion in the constricted state, in most applications using the present invention there will be daily adjustments of the constriction device. Therefore, in a preferred embodiment of the invention, the constriction device is adjustable to enable changing the constriction of the patient's wall portion as desired and the control device controls the constriction device to change the constriction of the wall portion.

The method of the invention suitably comprises operating the control device by the patient. In a simple form the control device comprises a manually operable switch for switching on and off the constriction/stimulation unit, and the method further comprises subcutaneously implanting the switch in the patient. It is preferable, however, that the control device comprises a hand-held wireless remote control operable by the patient from outside the patient's body to control the constriction/stimulation unit to adjust the stimulation intensity and/or adjust the constriction of the wall portion. The wireless remote control is suitably designed for application on the patient's body like a wristwatch.

In some applications of the invention, the constriction device of the constriction/stimulation unit may be designed to normally keep the patient's wall portion in the constricted state. I.e., after implantation the constriction device all the time keeps the wall portion constricted. In this case, the control device may be used when needed, conveniently by the patient, to control the stimulation device of the constriction/stimulation unit to stimulate the constricted tissue wall portion, preferably while adjusting the stimulation intensity, to cause contraction of the wall portion, so that the flow in the stomach is at least further restricted or stopped, and to control the stimulation device to cease the stimulation. More precisely, the method of the invention may comprise operating the control device by the patient to a) control the stimulation device in a first mode to stimulate the constricted wall portion to further restrict the flow in the stomach and control the stimulation device in a second mode to cease the stimulation of the wall portion to increase the flow in the stomach; or b) control the stimulation device in a first mode to stimulate the constricted wall portion to stop the flow in the stomach and control the stimulation device in a second mode to cease the stimulation of the wall portion to allow flow in the stomach.

Either the first mode or the second mode may be temporary.

The wireless remote control preferably transmits at least one wireless control signal for controlling the constriction/stimulation unit. The control signal may comprise a frequency, amplitude, phase modulated signal or a combination thereof, and may be an analogue or a digital signal, or a combination of an analogue and digital signal. The remote control may transmit an electromagnetic carrier wave signal for carrying the digital or analogue control signal. Also the carrier signal may comprise digital, analogue or a combination of digital and analogue signals.

Any of the above signals may comprise wave signals, such as a sound wave signal, an ultrasound wave signal, an electromagnetic wave signal, an infrared light signal, a visible light signal, an ultra violet light signal, a laser light signal, a micro wave signal, a radio wave signal, an x-ray radiation signal or a gamma radiation signal.

Alternatively, the control signal may comprise an electric or magnetic field, or a combined electric and magnetic field.

Operation of Constriction/stimulation Unit

It should be understood that any embodiment or part of embodiment for operating the combined stimulation device and constriction device, could be used, if applicable, for any one of the devices as a stand alone device. The method of the invention may comprise implanting in the patient an operation device, and operating the constriction/stimulation unit with the operation device. A magnet may be provided, wherein the method comprises using the magnet to activate the operation device from outside the patient's body. The operation device suitably comprises a motor which is powered with energy released from a source of energy, such as a battery. Although the constriction/stimulation unit in embodiments described above suitably is designed as a single piece, which is most practical for implantation, it should be noted that as an alternative the constriction device and stimulation device of the constriction/stimulation unit could be designed as separate pieces.

Laparoscopic Method

The present invention also provides a first method for controlling a flow of fluid in a patient's stomach. The method comprises the steps of:
inserting a needle like tube into the cavity of the patients body,
filling the cavity with gas thereby expanding the abdominal cavity,
placing at least two laparoscopical trocars in the patient's body,
inserting a camera through one of the trocars into the cavity,
inserting a dissecting tool through any of the trocar and dissecting an area of at least one portion of the tissue wall of the stomach,
placing a constriction device and a stimulation device in the dissected area in operative engagement with the stomach,
using the constriction device to gently constrict the wall portion of the stomach to influence the flow in the stomach, and
using the stimulation device to stimulate the constricted wall portion to cause contraction of the wall portion to further influence the flow in the stomach.

The present invention also provides a second method for controlling a flow of fluid in a patient's stomach. The method comprises the steps of: inserting a needle like tube into a cavity of the patients body, using the needle like tube to fill the cavity with gas thereby expanding the cavity, placing at least two laparoscopical trocars in the patient's body, inserting a camera through one of the trocars into the cavity, inserting a dissecting tool through any of the trocar and dissecting an area of at least one portion of the tissue wall of the stomach, placing a stimulation device in the dissected area in operative engagement with the stomach, and using the stimulation device to stimulate the wall portion to cause contraction of the wall portion to influence the flow in the stomach.

The present invention also provides a third method for controlling a flow of fluid in a patient's stomach. The method comprises the steps of: inserting a needle like tube into a cavity of the patients body, using the needle like tube to fill the cavity with gas thereby expanding the cavity, placing at least two laparoscopical trocars in the patient's body, inserting a camera through one of the trocars into the cavity, inserting a dissecting tool through any of the trocar and dissecting an area of at least one portion of the tissue wall of the stomach, placing a constriction device in the dissected area in operative engagement with the stomach, using the constriction device to constrict the wall portion of the stomach to influence the flow in the stomach.

The present invention also provides a fourth method for controlling a flow of fluid in a patient's stomach. The method comprises the steps of: cutting the skin of the patient, inserting a dissecting tool and dissecting an area of at least one portion of the tissue wall of the stomach, placing a constriction device and a stimulation device in the dissected area in operative engagement with the stomach, using the constriction device to gently constrict the wall portion of the stomach to influence the flow in the stomach, and using the stimulation device to stimulate the constricted wall portion to cause contraction of the wall portion to further influence the flow in the stomach.

The present invention also provides a fifth method for controlling a flow of fluid in a patient's stomach. The method comprises the steps of: cutting the skin of the patient, inserting a dissecting tool and dissecting an area of at least one portion of the tissue wall of the stomach, placing a stimulation device in the dissected area in operative engagement with the stomach, and using the stimulation device to stimulate the wall portion to cause contraction of the wall portion to influence the flow in the stomach.

The present invention also provides a sixth method for controlling a flow of fluid in a a patient's stomach. The method comprises the steps of:
cutting the skin of the patient,
inserting a dissecting tool and dissecting an area of at least one portion of the tissue wall of the stomach, placing a constriction device in the dissected area in operative engagement with the stomach, and using the constriction device to constrict the wall portion of the stomach to influence the flow in the stomach.

In all of the above-noted methods 1-6 the cavity may constitute the abdominal cavity.

The method further comprises implanting a powered operation device for operating the constriction device. The operation device may comprise a powered hydraulic operation device or an electrically powered operation device, such as an electric motor.

The method further comprises transmitting wireless energy for powering the operation device, and when desired to influence the flow in the patient's stomach, powering the operation device with the transmitted energy to operate the constriction device.

The method further comprises implanting a source of energy in the patient, providing an external source of energy, controlling the external source of energy to release wireless energy, transforming the wireless energy into storable energy, such as electric energy, non-invasively charging the implanted source of energy with the transformed energy, and controlling the implanted source of energy from outside the patient's body to release energy for use in connection with the operation of the constriction device and/or stimulation device. The wireless energy is transformed into a storable energy different from the wireless energy.

Alternatively, the method further comprises providing a source of energy outside the patient's body, controlling the external source of energy from outside the patient's body to release wireless energy, and using the released wireless energy for operating the constriction device and/or stimulation device. The wireless energy may be transformed into electrical energy inside the patient's body by an implanted energy-transforming device, wherein the electrical energy is used in connection with the operation of the constriction device and/or stimulation device. The electrical energy may be directly used in connection with the operation of the constriction device and/or stimulation device, as the transforming device transforms the wireless energy into the electrical energy. The external source of energy may be controlled from outside the patient's body to release non-magnetic wireless energy, wherein the released non-magnetic wireless energy is used for operating the constriction device and/or stimulation device. Alternatively, the external source of energy may be controlled from outside the patient's body to release electromagnetic wireless energy, wherein the released electromagnetic wireless energy is used for operating the constriction device and/or stimulation device.

Obesity, VBG

Another object of the present invention is to provide a versatile careful method for controlling the food flow in the stomach of an obese patient surgically modified by VBG, so as to reduce the patient's weight while minimizing the complications previously associated with gastric restriction surgery.

In accordance with this object of the present invention, there is provided a method for controlling the food flow in the stomach of an obese patient surgically modified by any one of the group of operations called Vertical Banded Gastroplasty, wherein the stomach is compartmentalized into a smaller proximal compartment adjacent the esophagus and a larger distal compartment, the smaller proximal compartment communicating with the larger distal compartment via a narrow outlet opening stomach. The method comprises:

gently constricting at least one portion of the stomach tissue wall to influence the flow in a food passageway extending in the smaller proximal compartment through the narrow outlet opening, and stimulating at least one portion of the stomach tissue wall to cause contraction of the wall portion to further influence the flow in the stomach.

The present invention provides an advantageous combination of the method steps (a) and (b), which results in a two-stage influence on the food flow in the smaller compartment of the stomach. Thus, applying a relatively weak force against the wall portion gently constricts the tissue wall and the constricted wall portion is stimulated to achieve the desired final influence on the flow in the stomach. The phrase "gently constricts a portion of the tissue wall" is to be understood as constricting the wall portion without substantially hampering the blood circulation in the tissue wall.

Preferably, step (b) is performed by intermittently and individually stimulating different areas of the wall portion of the smaller compartment. Such an intermittent and individual stimulation of different areas of the wall portion of the stomach allows tissue of the wall portion to maintain over time substantially normal blood circulation.

Preferably, the constriction step (a) and stimulation step (b) are performed independently of each other. Steps (a) and (b) may be performed simultaneously. Optionally, step (b) may or may not be performed while step (a) is performed.

Initially, the constriction of the wall portion can be calibrated by stimulating the wall portion while adjusting the constriction of the wall portion until the desired restriction of the flow in the stomach is obtained.

Flow restriction

It should be understood that any embodiment or part of embodiment disclosed below in connection with flow restriction for the constriction and stimulation devices combined in a constriction/stimulation unit could be used for the separate constriction device and separate stimulation device, where applicable.

The method of the present invention is well suited for restricting the food flow in the food passageway of the smaller compartment of the stomach of an obese VBG treated patient. Thus, in a principal embodiment of the invention, the wall portion is constricted, so that the smaller compartment form a size of the outlet opening that at least restricts the flow in the stomach and the constricted wall portion is stimulated to at least further restrict the flow in the stomach. Specifically, the wall portion is constricted to a constricted state, in which the blood circulation in the constricted wall portion is substantially unrestricted and the flow in the stomach is at least restricted, and the constricted wall portion is stimulated when it is in the constricted state to at least further restrict the flow in the stomach.

The constriction step (a) and stimulation step (b) are suitably performed to constrict and stimulate the wall portion to an extent that depends on the flow restriction that is desired to be achieved in a specific application of the method of the invention. Thus, in accordance with a first flow restriction option, step (a) is performed by constricting the wall portion, so that the flow in the stomach is restricted but not stopped, and step (b) is performed by stimulating the constricted wall portion to cause contraction thereof, so that the flow in the stomach is further restricted but not stopped. In this condition the outlet opening should be small enough to cause rapid filling of the proximal smaller compartment with a small amount of food, so that the patient senses fullness and stops to eat. The method may further comprise sensing a physical parameter of the patient and adjusting the intensity of the stimulation of the wall portion in response to the sensed parameter.

In accordance with a second flow restriction option, step (a) is performed by constricting the wall portion, so that the flow in the stomach is restricted but not stopped, and step (b) is performed by stimulating the constricted wall portion to cause contraction thereof, so that the flow in the stomach is stopped.

When using the method of the invention in accordance with the first or second options, the method may further comprise (c) ceaseing stimulating the wall portion to increase or allow the flow in the stomach and (d) releasing the wall portion to restore the flow in the stomach.

In accordance with a third flow restriction option, step (a) is performed by constricting the wall portion, so that the flow in the stomach is substantially stopped, and step (b) is performed by stimulating the constricted wall portion to cause contraction thereof, so that the flow in the stomach is completely stopped. The method may further comprise (c) ceaseing stimulating the wall portion to allow the flow in the stomach and (d) releasing the wall portion to restore the flow in the stomach.

Where the constricted wall portion is stimulated to contract, so that the flow in the stomach is stopped, a first length of the constricted wall portion and a second length of the constricted wall portion, which is located downstream of the first length, are suitably simultaneously and cyclically stimulated, wherein the first length is progressively stimulated in the upstream direction of the stomach and the second length is progressively stimulated in the downstream direction of the stomach.

Furthermore, when using the method of the invention in accordance with the second and third options, the method may further comprise sensing a physical parameter of the patient or functional parameter of implanted components and adjusting the stimulation of the wall portion in response to the sensed parameter. For example, the intensity of the stimulation of the wall portion may be increased in response to a sensed pressure increase in the stomach, so that the flow in the stomach remains stopped when a pressure increase occurs in the stomach. In particular, the method may comprise sensing a physical parameter of the patient's that relates to the pressure in the stomach, and controlling the stimulation of the wall portion in response to the sensed parameter. Any sensor for sensing a physical parameter of the patient, such as a pressure in the patient's body that relates to the pressure in the stomach may be provided, wherein the stimulation is controlled in response to signals from the sensor. Such a sensor may for example sense the pressure in the patient's abdomen, the pressure against the implanted constriction device or the pressure on the tissue wall of the stomach. In accordance with a fourth restriction option, step (a) is performed by constricting the wall portion, so that the flow in the stomach is stopped. When needed, the wall portion is released to restore the flow in the stomach. Step (b) is only performed by stimulating the constricted wall portion to cause contraction thereof, so that the flow in the stomach remains stopped when a pressure increase occurs in the stomach. The method may further comprise sensing a physical parameter of the patient's body, such as a pressure in the patient's body that relates to the pressure in the stomach, and controlling the stimulation of the wall portion in response to the sensed parameter. Such a physical parameter may be a pressure in the patient's abdomen and the sensor may be a pressure sensor.

In some applications of the method of the invention, continuous stimulation may over time change the physical properties of the tissue so that the tissue might be injured. Also, the effect of a continuous stimulation of the tissue wall may decrease over time. Therefore, step (b) is preferably performed by intermittently and individually stimulating different areas of the wall portion so that the flow in the stomach continues to be restricted as desired and each area of the wall portion essentially maintains its natural physical properties over time to prevent the area from being injured. Advantageously, each area of the wall portion is stimulated during successive time periods, each time period being short enough to maintain over time satisfactory blood circulation in the area. Thus, the areas are stimulated so that an area that currently is not stimulated will have time to restore substantially normal blood circulation before it is stimulated again.

To maintain satisfactory blood circulation in the tissue wall of the patient's stomach stimulation step (b) is suitably performed by stimulating one or more of different areas of the wall portion at a time, preferably by sequentially stimulating the different areas of the wall portion or by shifting the stimulation from one area to another over time. Preferably, stimulation step (b) is performed by cyclically propagating the stimulation of the areas along the wall portion, for example in accordance with a determined stimulation pattern.

The method of the invention may further comprise controlling, preferably by the patient, the constriction and/or stimulation of the wall portion from outside the patient's body.

Generally, the method of the invention comprises sensing a physical parameter of the patient and controlling, preferably automatically, the constriction and/or stimulation of the wall portion in response to the sensed parameter.

The constriction step (a) may be performed by constricting any wall portions of a series of wall portions of the stomach's tissue wall, respectively, either in random or in accordance with a predetermined sequence. The stimulation step (b) may be performed by stimulating any of the constricted wall portions of the series of wall portions. Specifically, step (a) may be performed by constricting all of the wall portions of the series of wall portions, and step (b) may be performed by stimulating any constricted wall portions in random or in accordance with a predetermined sequence to close the stomach.

Moving Fluid in the Stomach or Preventing the Movement of Fluids in the Stomach in a Similar Way It should be understood that any embodiment or part of embodiment disclosed below in connection with moving fluid in the stomach, or preventing the move of fluid or any matter in the stomach, for a constriction and stimulation devices combined in the constriction/stimulation unit could be used for the separate constriction device and separate stimulation device, where applicable.

For some individual obese patients treated with VBG it may be beneficial to temporarily aid the transportation of food through the food passageway of the proximal smaller compartment. In such a case the method of the present invention can be practised for actively moving the fluid in stomach of a patient's stomach. Thus, in the embodiments of the invention listed below, steps (a) and (b) are co-operated to move the fluid in the stomach.

1) Step (a) is performed by constricting the wall portion to restrict the flow in the stomach, and step (b) is performed by stimulating the constricted wall portion to close the stomach either at an upstream end or a downstream end of the constricted wall portion. The method further comprises (c) increasing the constriction of the wall portion to move the fluid in the stomach.

2) Step (a) is performed by constricting the wall portion to restrict the flow in the stomach, and step (b) is performed by progressively stimulating the constricted wall portion to cause progressive contraction of the wall portion to move the fluid in the stomach. The constricted wall portion is progressively stimulated in the downstream or upstream direction of the stomach.

3) Step (a) is performed by varyingly constricting the wall portion to vary the flow in the stomach, and step (b) is performed by progressively stimulating the constricted wall portion to cause progressive contraction of the wall portion to move the fluid in the stomach. The constricted wall portion is progressively stimulated in the downstream or upstream direction of the stomach.

4) Step (a) is performed by varyingly constricting different areas of the wall portion to cause progressive constriction of the wall portion in the downstream or upstream direction of the stomach, and the constricted wall portion is progressively stimulated to cause progressive contraction thereof in harmony with the progressive constriction of the wall portion. The method may further comprise providing at least one elongated constriction element extending along the wall portion, and controlling the elongated constriction element to progressively constrict the wall portion in the downstream or upstream direction of the stomach. The elongated constriction element suitably comprises contact surfaces dimensioned to contact a length of wall portion, and the method may further comprise providing a plurality of stimulation elements distributed along the contact surfaces, and controlling the stimulation elements to stimulate the different areas of the wall portion along the length of the wall portion.

5) Step (a) is performed by constricting any one of a series of wall portions of the tissue wall to at least restrict the flow in the stomach, and step (b) is performed by stimulating the constricted wall portion to close the stomach. The method further comprises successively constricting the wall portions of the series of wall portions to move the fluid in the stomach in a peristaltic manner.

5a) In accordance with an alternative, the method further comprises providing at least one constriction element and at least one stimulation element positioned on the constriction element, moving the constriction element along the stomach in the flow direction in the stomach to successively constrict the wall portions of the series of wall portions, and using the stimulation element to stimulate the wall portion constricted by the constriction element to close the stomach. Suitably, the method further comprises cyclically moving the constriction element along the wall portions of the series of wall portions.

5b) In accordance with another alternative, the method further comprises providing a plurality of constriction elements and stimulation elements positioned on the constriction elements, moving each constriction element along the stomach to successively constrict the wall portions of the series of wall portions, and using the stimulation elements to stimulate the wall portion constricted by any one of the constriction elements to close the stomach. Suitably, the method further comprises cyclically moving the constriction elements one after the other along the wall portions of the series of wall portions. Specifically, the method further comprises providing a rotor carrying the constriction elements, and rotating the rotor so that each constriction element cyclically constricts the wall portions of the series of wall portions. Each constriction element suitably comprises a roller that rolls on the stomach to constrict the latter.

6) Step (a) is performed by constricting any wall portions of a series of wall portions of the stomach's tissue wall, respectively, wherein the wall portions of the series of wall portions are successively constricted along the stomach to move the fluid in the stomach of the patient's stomach. The stimulation step (b) is performed by stimulating any constricted wall portions of the series of wall portions.

7) Step (a) is performed by constricting wall portions of a series of wall portions without completely closing the stomach's stomach, and step (b) is performed by stimulating the constricted wall portions one after the other, so that the wall portions of the series of wall portions are successively contracted along the stomach to move the fluid in the stomach of the patient's stomach.

8) Step (a) is performed by constricting the wall portion at an upstream or downstream end thereof to close the stomach. The method further comprises (c) constricting the wall portion between the upstream and downstream ends thereof, to move the fluid contained in the wall portion between the upstream and downstream ends thereof downstream or upstream in the stomach. Optionally, the method further comprises stimulating the wall portion between the upstream and downstream ends thereof, as (c) is performed.

8a) In accordance with an alternative, step (a) is performed by constricting the wall portion at the upstream end thereof to restrict the flow in the stomach, and step (b) is performed by stimulating the constricted wall portion at the upstream end to close the stomach, whereby the fluid contained in the wall portion between the upstream and downstream ends thereof is moved downstream in the stomach, as step (c) is performed.

8b) In accordance with another alternative, step (a) is performed by constricting the wall portion at the downstream end thereof to restrict the flow in the stomach, and step (b) is performed by stimulating the constricted wall portion at the downstream end to close the stomach, whereby the fluid contained in the wall portion between the upstream and downstream ends thereof is moved upstream in the stomach, as step (c) is performed.

To summarize a few preferred embodiments see below:

In accordance with an alternative, step (a) is performed by constricting any wall portions of a series of wall portions of the stomach's tissue wall, respectively. In accordance with an alternative, the wall portions of the series of wall portions are constricted in random or in accordance with a predetermined sequence. In accordance with an alternative, the wall portions of the series of wall portions are successively constricted along the stomach to move the fluid in the stomach or to prevent the fluid to move in the patient's stomach.

In accordance with an alternative, step (b) is performed by stimulating any constricted wall portions of the series of wall portions. In accordance with an alternative, the wall portions of the series of wall portions are constricted in random or in accordance with a predetermined sequence. In accordance with an alternative, wherein the wall portions of the series of wall portions are successively constricted along the stomach to move the fluid in the the patient's stomach or to prevent the fluid to move in the stomach of the patient's stomach.

In accordance with an alternative, step (a) is performed by constricting any wall portions of a series of wall portions of the stomach's tissue wall, respectively, wherein the wall portions of the series of wall portions are successively constricted without completely closing the stomach', and step (b) is performed by stimulating the constricted wall portions, so that the wall portions of the series of wall portions are further constricted. In accordance with an alternative, the wall portions of the series of wall portions are constricted in random or in accordance with a predetermined sequence.

In accordance with an alternative, wherein the wall portions of the series of wall portions are successively constricted along the stomach to move the fluid in the patient's stomach or to prevent the fluid to move in the patient's stomach.

In accordance with an alternative, step (a) is performed by constricting all of the wall portions of the series of wall portions, and step (b) is performed by stimulating any constricted wall portions so that the wall portions of the series of wall portions are further constricted.

In accordance with an alternative, the wall portions of the series of wall portions are further constricted by the stimulation device in random or in accordance with a predetermined sequence.

In accordance with an alternative, the wall portions of the series of wall portions are successively further constricted by the stimulation device along the stomach to move the fluid in the patient's stomach or to prevent the fluid to move in the patient's stomach.

In accordance with an alternative for all applicable alternatives, step (a) and step (b) are performed independently of each other or in accordance with an alternative, step (a) and step (b) are performed simultaneously.

In any of the above noted embodiments (1) to (8b), step (b) may be performed by stimulating the wall portion with electric pulses.

Stimulation Modes

When stimulating neural or muscular tissue there is a risk of injuring or deteriorating the tissue over time if the stimulation is not properly performed. The method of the present invention is performed to reduce or even eliminate that risk. Thus, step (b) is performed by intermittently stimulating different areas of the wall portion so that at least two of the areas are stimulated at different points of time. I.e., the stimulation is shifted from one area to another area over time. In addition, step (b) is performed by intermittently stimulating the areas of the wall portion so that an area of the different areas that currently is not stimulated has time to restore substantially normal blood circulation before it is stimulated again. Furthermore, step (b) is performed by intermittently stimulating the areas during successive time periods, wherein each time period is short enough to maintain satisfactory blood circulation in the area until the laps of the time period. This gives the advantage that the method of the present invention provides continuous stimulation of the wall portion of the stomach to achieve the desired flow control while essentially maintaining over time the natural physical properties of the stomach without risk of injuring the stomach.

Also, by physically changing the places of stimulation on the stomach over time as described above it is possible to create an advantageous changing stimulation pattern on the stomach, in order to achieve a desired flow control.

To achieve the desired reaction of the tissue wall during the stimulation thereof, step (b) may be performed by stimulating the wall portion with, preferably cyclically, varying stimulation intensity.

In a main embodiment of the invention, step (b) is performed by intermittently stimulating the wall portion with pulses, preferably in the form of pulse trains. The pulse trains can be configured in many different ways by varying pulse parameters. Thus, the pulse amplitudes of the pulses of the pulse trains, the off time periods between the individual pulses of each pulse train and the width and repetition frequency of each pulse may be varied. Also the off time periods between the pulse trains may be varied, wherein each off time period between the pulse trains is kept long enough to restore substantially normal blood circulation in each area of the wall portion, when the area is not stimulated during the off time periods. Furthermore, the repetition frequency of the pulses of the pulse trains and the length and number of pulses of each pulse train may be varied.

As mentioned above, for reasons of maintaining over time the effect of stimulation, it is preferable that different areas of the wall portion are intermittently and individually stimulated. In consequence, step (b) may be performed by stimulating one or more of the areas at a time with pulses, by cyclically propagating the stimulation of the areas with pulses along the wall portion, and/or by propagating the stimulation of the areas with pulses in accordance with a determined stimulation pattern. In case the off time periods between pulse trains that stimulate the respective area of the wall portion are varied, it is preferable that each off time period between the pulse trains is controlled to last long enough to restore substantially normal blood circulation in the area when the latter is not stimulated during the off time periods.

Electric Stimulation

In accordance with a preferred embodiment of the invention, step (b) is performed by electrically stimulating the wall portion, preferably with electric pulses to cause contraction of the wall portion. This embodiment is particularly suited for applications in which the patient's wall portion includes muscle fibers that react to electrical stimula. Thus, the wall portion that includes the muscle fibers is stimulated with such electric pulses, preferably in the form of electric pulse trains, when the wall portion is in the constricted state, to cause contraction of the wall portion. Of course, the configuration of the electric pulse trains may be similar to the above described pulse trains and different areas of the wall portion may be electrically stimulated in the same manner as described above.

In accordance with the preferred embodiment, the method of the invention comprises providing at least one, preferably a plurality of electrical elements, such as electrodes, engaging and stimulating the wall portion with electric pulses. Optionally, the electrical elements may be placed in a fixed orientation relative to one another. The method comprises electrically energizing the electrical elements, preferably by cyclically energizing each element with electric pulses. The electrical elements may be energized so that the electrical elements are energized one at a time in sequence, or so that a number or groups of the electrical elements are energized at a time. Also, groups of electrical elements may be sequentially energized, either randomly or in accordance with a predetermined pattern.

The method may further comprise applying the electrical elements on the patient's wall portion so that the electrical elements form any pattern of electrical elements, preferably an elongate pattern of electrical elements extending lengthwise along the wall portion and the elements abut the respective areas of the wall portion. The electrical elements may be successively energized along the elongate pattern of electrical elements in a direction opposite to or in the same direction as that of the flow in the patient's stomach. Optionally, the electrical elements may be successively energized along the elongate pattern of electrical elements from a position substantially at the center of the constricted wall portion towards both ends of the elongate pattern of electrical elements. Where the food passageway of the stomach is to be kept closed for a relatively long time, the electrical elements may be energized so that energized electrical elements form two waves of energized electrical elements that simultaneously advance from the center of the constricted wall portion in two opposite directions towards both ends of the elongate pattern of electrical elements. Such waves of energized electrical elements can be repeated over and over again without harming the stomach and without moving fluid or gas in any direction in the stomach.

The elongate pattern of electrical elements may include one or more rows of electrical elements extending lengthwise along the stomach. Each row of electrical elements may form a straight, helical or zig-zag path of electrical elements, or any form of path. The electrical elements may be energized so that the electrical elements currently energized form at least one group of adjacent energized electrical elements, wherein the elements in the group of energized electrical elements form a path of energized electrical elements extending at least in part around the patient's stomach, preferably completely around the patient's stomach. Alternatively, the elements in the group of energized electrical elements form two paths of energized electrical elements extending on mutual sides of the patient's stomach or more than two paths of energized electrical elements extending on different sides of the patient's stomach, preferably at least substantially transverse to the flow direction in the stomach of the stomach.

In an embodiment of the invention, the electrical elements form a plurality of groups of elements, wherein the groups form a series of groups extending along the patient's stomach in the flow direction in the patient's stomach. The electrical elements of each group of electrical elements may form a path of elements extending at least in part around the patient's stomach. In a first alternative, the electrical elements of each group of electrical elements may form more than two paths of elements extending on different sides of the patient's stomach, preferably substantially transverse to the flow direction in the patient's stomach. The groups of electrical elements in the series of groups may be energized in random or in accordance with a predetermined pattern. Alternatively, the groups of electrical elements in the series of groups may be successively energized in a direction opposite to or in the same direction as that of the flow in the patient's stomach, or in both said directions starting from a position substantially at the center of the constricted wall portion. For example, groups of energized electrical elements may form advancing waves of energized electrical elements, as described above. I.e., the groups of electrical elements may be energized so that energized electrical elements form two waves of energized electrical elements that simultaneously advance from the center of the constricted wall portion in two opposite directions towards both ends of the elongate pattern of electrical elements.

Thermal Stimulation

In accordance with an embodiment of the invention, stimulation step (b) is performed by thermally stimulating the wall portion. Thus, the wall portion may be cooled, when the wall portion is constricted, to cause contraction of the wall portion. For example, the wall portion may be constricted to at least restrict the flow in the stomach, and the constricted wall portion may be cooled to cause contraction thereof, so that the flow in the stomach is at least further restricted, or further restricted but not stopped, or stopped. Alternatively, the wall portion may be heated, when the wall portion is constricted and contracted, to cause expansion of the wall portion. Where applicable, thermal stimulation may be practised in any of the embodiments of the present invention, and the thermal stimulation may be controlled in response to various sensors, for example strain, motion or pressure sensors.

Constriction and Stimulation Devices

It should be understood that any embodiment or part of embodiment for the combined stimulation device and constriction device, could be used, if applicable, for any one of the devices as a stand alone device. Generally, the method of the invention comprises providing a constriction device that constricts the wall portion, a stimulation device that stimulates the constricted wall portion and a control device that controls the constriction device and/or the stimulation device. The method comprises operating the control device from outside the patient's body, preferably by using the control device to wirelessly control the constriction device and/or stimulation device. The wireless control is preferably performed in a non-magnetic manner, whereby implanted magnetic devices can be avoided. Suitably, the control device comprises a hand-held wireless remote control operated by the patient.

Alternatively, the control device comprises a manually operable switch for switching on and off the constriction device and/or stimulation device. In this case, the method comprises subcutaneously implanting the switch in the patient and manually operating the the implanted switch from outside the patient's body.

In an embodiment of the invention, the control device comprises a programmable internal control unit, such as a microprocessor, and the method comprises implanting in the patient the internal control unit and controlling by the internal control unit the constriction device and/or stimulation device. The control device may also comprise an external control unit outside the patient's body. In this case, the method comprises controlling by the external control unit the constriction device and/or stimulation device and, optionally, using the external control unit to program the implanted internal control unit. The internal control unit may be programmable for controlling the constriction device and/or stimulation device over time, for example in accordance with an activity schedule program.

The constriction of the wall portion can be calibrated by using the control device to control the stimulation device to stimulate the wall portion while controlling the constriction device to adjust the constriction of the wall portion until the desired restriction of the flow in the stomach is obtained.

Sensor Controlled Constriction and/or Stimulation

It should be understood that any embodiment or part of embodiment disclosed below in connection with sensor control of the constriction and stimulation devices combined in the constriction/stimulation unit could be used for the separate constriction device and separate stimulation device, where applicable. In an embodiment of the invention, the method comprises implanting at least one sensor and controlling by the control device the constriction device and/or the stimulation device in response to signals from the sensor. Generally, the sensor directly or indirectly senses at least one physical parameter of the patient, functional parameter of the apparatus, or functional parameter of a medical implant in the patient.

Many different kinds of sensor for sensing physical parameters may be used. For example motion sensors for sensing stomach motion, i.e. natural stomach contractions, pressure sensors for sensing pressure in the stomach, strain sensors for sensing strain of the stomach, flow sensors for sensing fluid flow in the stomach, spectro-photometrical sensors, Ph-sensors for acidity or alkalinity of the fluid in the stomach, oxygen-sensors sensors for sensing the oxygen content of the fluid in the stomach, or sensors for sensing the distribution of the stimulation on the stimulated stomach. Any conceivable sensors for sensing any other kind of useful physical parameter may be used.

Many different kinds of sensors that sense functional parameters of implanted components may also be used for the control of the constriction device and/or the stimulation device. For example sensors for sensing electric parameters of implanted electric components, or sensors for sensing the performance of implanted motors or the like.

The sensor may comprise a pressure sensor for sensing as the physical parameter a pressure in the patient's body that relates to the pressure in the stomach of the patient's stomach. In this case, the method suitably comprises operating the control device to control the constriction device to change the constriction of the patient's wall portion in response to the pressure sensor sensing a predetermined value of measured pressure.

Alternatively, or in combination with the pressure sensor, a position sensor may be provided for sensing as the physical parameter the orientation of the patient with respect to the horizontal. The position sensor may be a biocompatible version of what is shown in U.S. Pat. Nos. 4,942,668 and 5,900,909. For example, the control device may control the constriction device and/or stimulation device to change the constriction of the patient's wall portion in response to the position sensor sensing that the patient has assumed a substantially horizontal orientation, i.e. that the patient is lying down.

The above described sensors may be used in any of the embodiments of the invention, where applicable.

The control device may control the constriction device and/or stimulation device to change the constriction of the patient's wall portion in response to the time of day. For that purpose the control device may include a clock mechanism for controlling the constriction device and/or stimulation device to change the constriction of the patient's wall portion to increase or decrease the influence on the flow in the stomach during different time periods of the day. In case a sensor of any of the above-described types for sensing a physical or functional parameter is provided, either the clock mechanism is used for controlling the constriction device and/or stimulation device provided that the parameter sensed by the sensor does not override the clock mechanism, or the sensor is used for controlling the constriction device and/or stimulation device provided that the clock mechanism does not override the sensor. Suitably, the control device produces an indication, such as a sound signal or displayed information, in response to signals from the sensor.

The control device may comprise an implantable internal control unit that directly controls the constriction device and/or stimulation device in response to signals from the sensor. The control device may further comprise a wireless remote control adapted to set control parameters of the internal control unit from outside the patient without mechanically penetrating the patient. At least one of the control parameters, which is settable by the wireless remote control, is the physical or functional parameter. Suitably, the internal control unit includes the above mentioned clock mechanism, wherein the wireless remote control also is adapted to set the clock mechanism.

Alternatively, the control device may comprise an external control unit outside the patient's body for controlling the constriction device and/or stimulation device in response to signals from the sensor.

Constriction of Patient's Stomach

It should be understood that any embodiment or part of embodiment disclosed below in connection with constricting the patient's stomach could be used for the separate constriction device and separate stimulation device, where applicable.

Method step (a) may be performed in many different ways. Thus, step (a) may be performed by:
constricting the wall portion so that the through-flow area of the stomach assumes a size in the constricted state small enough to cause the constricted wall portion to contract to stop the flow in the stomach when step (b) is performed;
bending the wall portion;
clamping the wall portion between at least two elements positioned on different sides of the stomach;
clamping the stomach between an element and the bone or tissue of the patient;
rotating at least two elements positioned on different sides of the stomach; or
(6)—clamping the stomach between at least two articulated clamping elements positioned on different sides of the stomach.

In the above noted alternatives (1) to (6) of method step (a), the constriction of the wall portion of the stomach may be changed either mechanically or hydraulically. For many applications of the present invention, step (a) is suitably performed so that the through-flow area of the stomach assumes a size in the constricted state that is small enough to enable the stimulation during step (b) to contract the wall portion of the stomach to stop the flow in the stomach.

Where the constriction of the wall portion is hydraulically changed, the method of the invention may further comprise implanting in the patient a reservoir containing a predetermined amount of hydraulic fluid, and a constriction device engaging the wall portion and having an expandable/contractible cavity, wherein step (a) is performed by distributing hydraulic fluid from the reservoir to increase the volume of the cavity to constrict the wall portion, and by distributing hydraulic fluid from the cavity to the reservoir to decrease the volume of the cavity to release the wall portion. The cavity may be defined by a balloon of the constriction device that abuts the tissue wall portion of the patient's stomach, so that the patient's wall portion is constricted upon expansion of the cavity and released upon contraction of the cavity.

Alternatively, the cavity may be defined by a bellows that displaces a relatively large contraction element of the constriction device, for example a large balloon that abuts the wall portion, so that the patient's wall portion is constricted upon contraction of the bellows and released upon expansion of the bellows. Thus, a relatively small addition of hydraulic fluid to the bellows causes a relatively large increase in the constriction of the wall portion. Such a bellows may also be replaced by a suitably designed piston/cylinder mechanism.

Where the hydraulic means comprises a cavity in the constriction device, the following embodiments of the invention are conceivable.

1) The reservoir comprises first and second wall portions, and step (a) is performed by displacing the first and second wall portions relative to each other to change the volume of the reservoir, so that fluid is distributed from the reservoir to the cavity, or from the cavity to the reservoir.
  1a) At least one of a magnetic device, a hydraulic device or an electric control device displaces the first and second wall portions of the reservoir.
2) A pump is provided for pumping fluid between the reservoir and the cavity.
  2a) The pump comprises a first activation member for activating the pump to pump fluid from the reservoir to the cavity and a second activation member for activating the pump to pump fluid from the cavity to the reservoir.
    2a1) The first and second activation members are operable by manual manipulation thereof.
    2a2) At least one of the activation members operates when subjected to an external predetermined pressure.
    2a3) At least one of the first and second activating members is operable by magnetic means, hydraulic means, or electric control means.
  2b) A fluid conduit between the pump and the cavity is provided, wherein the reservoir forms part of the conduit. The conduit and pump are devoid of any non-return valve. The reservoir forms a fluid chamber with a variable volume, and the pump distributes fluid from the chamber to the cavity by a reduction in the volume of the chamber and withdraws fluid from the cavity by an expansion of the volume of the chamber. A motor is provided for driving the pump, wherein the pump comprises a movable wall of the reservoir for changing the volume of the chamber.

In all of the above noted embodiments 1 to 2b where the hydraulic means comprises an expandable cavity in the constriction device, the cavity can be exchanged by a cylinder/piston mechanism for adjusting the constriction device. In this case, hydraulic fluid is distributed between the reservoir and the cylinder/piston mechanism to adjust the constriction device.

3) The method further comprises implanting a reverse servo operatively connected to the hydraulic means. The term "reverse servo" is to be understood as a mechanism that transfers a strong force acting on a moving element having a short stroke into a weak force acting on another moving element having a long stroke; i.e., the reverse function of a normal servo mechanism. Thus, minor changes in the amount of fluid in a smaller reservoir could be transferred by the reverse servo into major changes in the amount of fluid in a larger reservoir.

Preferably, the reverse servo comprises an expandable servo reservoir containing servo fluid and a fluid supply reservoir hydraulically connected to the servo reservoir to form a closed conduit system for the servo fluid. The expandable servo reservoir has first and second wall portions, which are displaceable relative to each other in response to a change in the volume of the expandable servo reservoir.

In accordance with a first alternative, the first and second wall portions of the servo reservoir are operatively connected to the hydraulic means. The reverse servo distributes fluid between the fluid supply reservoir and the expandable servo reservoir to change the volume of the servo reservoir, whereby the hydraulic means is operated to adjust the constriction device.

In accordance with a second alternative, there is provided an implantable main reservoir containing a predetermined amount of hydraulic fluid, wherein the reverse servo is operated to distribute hydraulic fluid between the main reservoir and the hydraulic means to adjust the constriction device.

More specifically, the main reservoir is provided with first and second wall portions operatively connected to the first and second wall portions of the expandable servo reservoir, so that the volume of the main reservoir is changed when the volume of the expandable servo reservoir is changed. Thus, when the reverse servo distributes servo fluid between the fluid supply reservoir and the expandable servo reservoir to change the volume of the main reservoir, hydraulic fluid is distributed from the main reservoir to the hydraulic means, or from the hydraulic means to the main reservoir. Advantageously, the method comprises dimensioning the servo and main reservoirs, so that when the volume of the servo reservoir is changed by a relatively small amount of servo fluid, the volume of the main reservoir is changed by a relatively large amount of hydraulic fluid.

In both of the above-described alternatives, the fluid supply reservoir may have first and second wall portions, which are displaceable relative to each other to change the volume of the fluid supply reservoir to distribute servo fluid between the fluid supply reservoir and the expandable servo reservoir. The first and second wall portions of the fluid supply reservoir may be displaced relative to each other by manual manipulation, a magnetic device, a hydraulic device, or an electric control device to change the volume of the fluid supply reservoir to distribute servo fluid between the fluid supply reservoir and the expandable servo reservoir.

In all of the above noted embodiments 1 to 2b where the hydraulic means comprises an expandable cavity in the constriction device, or in embodiments where the hydraulic means includes a hydraulically operable mechanical construction, the reverse servo described above may be used. In a further embodiment of the invention, the hydraulic means include first and second hydraulically interconnected expandable/contractible reservoirs. The first reservoir is operatively connected to the constriction device, so that the constriction device changes the constriction of the patient's wall portion upon expansion or contraction of the first reservoir. By changing the volume of the second reservoir hydraulic fluid is distributed between the two reservoirs, so that the first reservoir is either expanded or contracted. This embodiment requires no non-return valve in the fluid communication conduits between the two reservoirs, which is beneficial to long-term operation of the hydraulic means.

Alternatively, the hydraulic means may include first and second hydraulically interconnected piston/cylinder mechanisms instead of the first and second reservoirs described above. The first piston/cylinder mechanism is operatively connected to the constriction device, so that the constriction device changes the constriction of the patient's wall portion upon operation of the first piston/cylinder mechanism. By operating the second piston/cylinder mechanism hydraulic fluid is distributed between the two piston/cylinder mechanisms, so that the first piston/cylinder mechanism adjusts the constriction device.

Where the constriction device does not include an expandable/contractible cavity, the constriction device may comprise at least two elongated clamping elements extending along the wall portion on different sides of the stomach. The hydraulic means, which may include the reverse servo described above, hydraulically moves the elongated clamping elements towards the stomach to constrict the wall portion of the stomach. For example, the constriction device may have hydraulic chambers in which the clamping elements slide back and forth, and the hydraulic means may also include a pump and an implantable reservoir containing hydraulic fluid. The pump distributes hydraulic fluid from the reservoir to the chambers to move the clamping elements against the wall portion, and distributes hydraulic fluid from the chambers to the reservoir to move the clamping elements away from the wall portion.

Energy Supply

It should be understood that any embodiment or part of embodiment disclosed below in connection with the power of the constriction and stimulation devices combined in the constriction/stimulation unit could be used for the separate constriction device and separate stimulation device, where applicable. Generally, method step (a) is performed by using the constriction device and step (b) is performed by using the stimulation device, wherein the method further comprises forming the constriction and stimulation devices in an operable constriction/stimulation unit.

In a simple form of the invention, the method comprises implanting a source of energy, such as a battery, rechargeable battery or accumulator, releasing energy from the source of energy and using the released energy in connection with the operation of the constriction/stimulation unit.

In a more sophisticated form of the invention, which is preferable, the method comprises transmitting wireless energy from outside the patient's body to inside the patient's body and using the transmitted wireless energy in connection with the operation of the constriction/stimulation unit.

Transmission of Wireless Energy

It should be understood that any embodiment or part of embodiment disclosed below in connection with wireless control or power of the constriction and stimulation devices combined in the constriction/stimulation unit could be used for the separate constriction device and separate stimulation device, where applicable. The wireless energy may be directly used in connection with the operation of the constriction/stimulation unit, as the wireless energy is being transmitted. For example, the wireless energy may be transmitted in the form of an electric, an electromagnetic or a magnetic field, or a combination thereof, or electromagnetic waves for direct power of the constriction/stimulation unit. For example, where an electric motor or pump operates the constriction device of the constriction/stimulation unit, wireless energy in the form of a magnetic or an electromagnetic field may be used for direct power of the motor or pump.

Thus, the motor or pump is running directly during transmission of the wireless energy. This may be achieved in two different ways: a) using a transforming device implanted in the patient to transform the wireless energy into energy of a different form, preferably electric energy, and powering the motor or pump with the transformed energy, or b) using the wirelessly transmitted energy to directly power the motor or pump. Preferably wireless energy in the form of an electromagnetic or magnetic field is used to directly influence specific components of the motor or pump to create kinetic energy. Such components may include coils integrated in the motor or pump.

The wireless energy is suitably transmitted in pulses or digital pulses, or a combination of pulses and digital pulses.

Preferably, the wireless energy is transmitted in at least one wireless signal, suitably a wave signal. The wave signal may comprise an electromagnetic wave signal including one of an infrared light signal, a visible light signal, an ultra violet light signal, a laser signal, a microwave signal, a radio wave signal, an x-ray radiation signal, and a gamma radiation signal. Alternatively, the wave signal may comprise a sound or an ultrasound wave signal. The wireless signal may be a digital or analogue signal, or a combination of a digital and analogue signal.

In accordance with a particular embodiment of the invention, the wireless energy is not for direct use in connection with the operation of the constriction/stimulation unit. In this embodiment the wireless energy comprises energy of a first form, which is transmitted into energy of a second form suited to operate the constriction/stimulation unit. Typically, the energy of the second form is different from the energy of the first form. For example, the wireless energy of the first form may comprise sound waves, whereas the energy of the second form may comprise electric energy. Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

Transforming Wireless Energy

It should be understood that any embodiment or part of embodiment disclosed below in connection with the control or energizing of the constriction and stimulation devices combined in the constriction/stimulation unit could be used for the separate constriction device and separate stimulation device, where applicable. In accordance with a particular embodiment of the invention, an implantable energy-transforming device is provided for transforming wireless energy of a first form transmitted by the energy-transmission device into energy of a second form, which typically is different from the energy of the first form. The constriction/stimulation unit is operable in response to the energy of the second form. For example, the wireless energy of the first form may comprise sound waves, whereas the energy of the second form may comprise electric energy. Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transforming device may function different from or similar to the energy-transmission device. Advantageously, the energy-transforming device comprises at least one element, such as at least one semiconductor, having a positive region and a negative region, when exposed to the energy of the first form transmitted by the energy-transmission device, wherein the element is capable of creating an energy field between the positive and negative regions, and the energy field produces the energy of the second form. More specifically, the element may comprise an electrical junction element, which is capable of inducing an electric field between the positive and negative regions when exposed to the energy of the first form transmitted by the energy-transmission device, whereby the energy of the second form comprises electric energy.

The energy of the first form may directly or indirectly be transformed into the energy of the second form. The method of the invention may comprise providing a motor for operating the constriction device and powering the motor with the energy of the second form. The constriction device may be operable to perform at least one reversible function and the method may comprise reversing the function by using the motor. For example, the method may comprise shifting the polarity of the energy of the second form to reverse the motor.

The motor may be directly powered with the transformed energy, as the energy of the second form is being transformed from the energy of the first form. Preferably, the constriction/stimulation unit is directly operated with the energy of the second form in a non-magnetic, non-thermal or non-mechanical manner.

Normally, the implanted constriction/stimulation unit comprises electric components that are energized with electrical energy. Therefore, the energy of the first form may be transformed into a direct current or pulsating direct current, or a combination of a direct current and pulsating direct current. Alternatively, the energy of the first form may be transformed into an alternating current or a combination of a direct and alternating current.

The method of the invention may comprise implanting in the patient an internal source of energy, and supplying energy from the internal source of energy for the operation of the constriction/stimulation unit. The method may further comprise implanting in the patient a switch operable to switch from an "off" mode, in which the internal source of energy is not in use, to an "on" mode, in which the internal source of energy supplies energy for the operation of the constriction/stimulation unit, and/or for energizing implanted electronic components of the constriction/stimulation unit. The switch may be operated by the energy of the first form or by the energy of the second form. The described switch arrangement reduces power consumption of the constriction/stimulation unit between operations.

The internal source of energy may store the energy of the second form. In this case, the internal source of energy suitably comprises an accumulator, such as at least one capacitor or at least one rechargeable battery, or a combination of at least one capacitor and at least one rechargeable battery. Where the internal source of energy is a rechargeable battery it may be charged only at times convenient for the patient, for example when the patient is sleeping. Alternatively, the internal source of energy may supply energy for the operation of the constriction/stimulation unit but not be used for storing the energy of the second form. In this alternative, the internal source of energy may be a battery and the switch described above may or may not be provided.

Suitably, the method of the invention may comprise implanting a stabilizer for stabilizing the energy of the second form. Where the energy of the second form comprises electric energy the stabilizer suitably comprises at least one capacitor.

The energy-transforming device may be designed for implantation subcutaneously in the abdomen, thorax or cephalic region of the patient. Alternatively, it may be designed for implantation in an orifice of the patient's body and under the mucosa or intramuscularly outside the mucosa of the orifice.

Control of Constriction/stimulation Unit

It should be understood that any embodiment or part of embodiment disclosed below in connection with the control of the constriction and stimulation devices combined in the constriction/stimulation unit could be used for the separate constriction device and separate stimulation device, where applicable. Although the constriction device of the constriction/stimulation unit may normally keep the patient's wall portion in the constricted state, in most applications using the present invention there will be daily adjustments of the constriction device. Therefore, in a preferred embodiment of the invention, the constriction device is adjustable to enable changing the constriction of the patient's wall portion as desired and the control device controls the constriction device to change the constriction of the wall portion.

The method of the invention suitably comprises operating the control device by the patient. In a simple form the control device comprises a manually operable switch for switching on and off the constriction/stimulation unit, and the method further comprises subcutaneously implanting the switch in the patient. It is preferable, however, that the control device comprises a hand-held wireless remote control operable by the patient from outside the patient's body to control the constriction/stimulation unit to adjust the stimulation intensity and/or adjust the constriction of the wall portion. The wireless remote control is suitably designed for application on the patient's body like a wristwatch.

In some applications of the invention, the constriction device of the constriction/stimulation unit may be designed to normally keep the patient's wall portion in the constricted state. I.e., after implantation the constriction device all the time keeps the wall portion constricted. In this case, the control device may be used when needed, conveniently by the patient, to control the stimulation device of the constriction/stimulation unit to stimulate the constricted tissue wall portion, preferably while adjusting the stimulation intensity, to cause contraction of the wall portion, so that the flow in the stomach is at least further restricted or stopped, and to control the stimulation device to cease the stimulation. More precisely, the method of the invention may comprise operating the control device by the patient to a) control the stimulation device in a first mode to stimulate the constricted wall portion to further restrict the flow in the stomach and control the stimulation device in a second mode to cease the stimulation of the wall portion to increase the flow in the stomach; or b) control the stimulation device in a first mode to stimulate the constricted wall portion to stop the flow in the stomach and control the stimulation device in a second mode to cease the stimulation of the wall portion to allow flow in the stomach.

Either the first mode or the second mode may be temporary.

The wireless remote control preferably transmits at least one wireless control signal for controlling the constriction/stimulation unit. The control signal may comprise a frequency, amplitude, phase modulated signal or a combination thereof, and may be an analogue or a digital signal, or a combination of an analogue and digital signal. The remote control may transmit an electromagnetic carrier wave signal for carrying the digital or analogue control signal. Also the carrier signal may comprise digital, analogue or a combination of digital and analogue signals.

Any of the above signals may comprise wave signals, such as a sound wave signal, an ultrasound wave signal, an electromagnetic wave signal, an infrared light signal, a visible light signal, an ultra violet light signal, a laser light signal, a micro wave signal, a radio wave signal, an x-ray radiation signal or a gamma radiation signal.

Alternatively, the control signal may comprise an electric or magnetic field, or a combined electric and magnetic field.

Operation of Constriction/stimulation Unit

It should be understood that any embodiment or part of embodiment for operating the combined stimulation device and constriction device, could be used, if applicable, for any one of the devices as a stand alone device. The method of the invention may comprise implanting in the patient an operation device, and operating the constriction/stimulation unit with the operation device. A magnet may be provided, wherein the method comprises using the magnet to activate the operation device from outside the patient's body. The operation device suitably comprises a motor which is powered with energy released from a source of energy, such as a battery. Although the constriction/stimulation unit in embodiments described above suitably is designed as a single piece, which is most practical for implantation, it should be noted that as an alternative the constriction device and stimulation device of the constriction/stimulation unit could be designed as separate pieces.

Laparoscopic Method

The present invention also provides a first method for controlling a flow of fluid in the stomach of a patient treated with VBG. The method comprises the steps of:
inserting a needle like tube into the cavity of the patients body,
filling the cavity with gas thereby expanding the abdominal cavity,
placing at least two laparoscopical trocars in the patient's body,
inserting a camera through one of the trocars into the cavity,
inserting a dissecting tool through any of the trocar and dissecting an area of at least one portion of the tissue wall of the stomach,
placing a constriction device and a stimulation device in the dissected area in operative engagement with the stomach,
using the constriction device to gently constrict the wall portion of the stomach to influence the flow in the stomach, and
using the stimulation device to stimulate the constricted wall portion to cause contraction of the wall portion to further influence the flow in the stomach.

The present invention also provides a second method for controlling a flow of fluid in the stomach of a patient treated with VBG. The method comprises the steps of:
inserting a needle like tube into a cavity of the patients body,
using the needle like tube to fill the cavity with gas thereby expanding the cavity,
placing at least two laparoscopical trocars in the patient's body,
inserting a camera through one of the trocars into the cavity,
inserting a dissecting tool through any of the trocar and dissecting an area of at least one portion of the tissue wall of the stomach,
placing a stimulation device in the dissected area in operative engagement with the stomach, and
using the stimulation device to stimulate the wall portion to cause contraction of the wall portion to influence the flow in the stomach.

The present invention also provides a third method for controlling a flow of fluid in the stomach of a patient treated with VBG. The method comprises the steps of:
inserting a needle like tube into a cavity of the patients body,
using the needle like tube to fill the cavity with gas thereby expanding the cavity,
placing at least two laparoscopical trocars in the patient's body,
inserting a camera through one of the trocars into the cavity,
inserting a dissecting tool through any of the trocar and dissecting an area of at least one portion of the tissue wall of the stomach,
placing a constriction device in the dissected area in operative engagement with the stomach,
using the constriction device to constrict the wall portion of the stomach to influence the flow in the stomach.

The present invention also provides a fourth method for controlling a flow of fluid in the stomach of a patient treated with VBG. The method comprises the steps of:
cutting the skin of the patient,
inserting a dissecting tool and dissecting an area of at least one portion of the tissue wall of the stomach,
placing a constriction device and a stimulation device in the dissected area in operative engagement with the stomach,
using the constriction device to gently constrict the wall portion of the stomach to influence the flow in the stomach, and
using the stimulation device to stimulate the constricted wall portion to cause contraction of the wall portion to further influence the flow in the stomach.

The present invention also provides a fifth method for controlling a flow of fluid in the stomach of a patient treated with VBG. The method comprises the steps of:
cutting the skin of the patient,
inserting a dissecting tool and dissecting an area of at least one portion of the tissue wall of the stomach,
placing a stimulation device in the dissected area in operative engagement with the stomach, and
using the stimulation device to stimulate the wall portion to cause contraction of the wall portion to influence the flow in the stomach.

The present invention also provides a sixth method for controlling a flow of fluid in the stomach of a patient treated with VBG. The method comprises the steps of:
cutting the skin of the patient,
inserting a dissecting tool and dissecting an area of at least one portion of the tissue wall of the stomach,
placing a constriction device in the dissected area in operative engagement with the stomach, and
using the constriction device to constrict the wall portion of the stomach to influence the flow in the stomach.

In all of the above-noted methods 1-6 the cavity may constitute the abdominal cavity.

The method further comprises implanting a powered operation device for operating the constriction device. The operation device may comprise a powered hydraulic operation device or an electrically powered operation device, such as an electric motor.

The method further comprises transmitting wireless energy for powering the operation device, and when desired to influence the flow in the patient's stomach, powering the operation device with the transmitted energy to operate the constriction device.

The method further comprises implanting a source of energy in the patient, providing an external source of energy, controlling the external source of energy to release wireless energy, transforming the wireless energy into storable energy, such as electric energy, non-invasively charging the implanted source of energy with the transformed energy, and controlling the implanted source of energy from outside the patient's body to release energy for use in connection with the operation of the constriction device and/or stimulation device. The wireless energy is transformed into a storable energy different from the wireless energy.

Alternatively, the method further comprises providing a source of energy outside the patient's body, controlling the external source of energy from outside the patient's body to release wireless energy, and using the released wireless energy for operating the constriction device and/or stimulation device. The wireless energy may be transformed into electrical energy inside the patient's body by an implanted energy-transforming device, wherein the electrical energy is used in connection with the operation of the constriction device and/or stimulation device. The electrical energy may be directly used in connection with the operation of the constriction device and/or stimulation device, as the transforming device transforms the wireless energy into the electrical energy. The external source of energy may be controlled from outside the patient's body to release non-magnetic wireless energy, wherein the released non-magnetic wireless energy is used for operating the constriction device and/or stimulation device. Alternatively, the external source of energy may be controlled from outside the patient's body to release electromagnetic wireless energy, wherein the released electromagnetic wireless energy is used for operating the constriction device and/or stimulation device.

Male Sexual Dysfunction

Another object of the present invention is to provide a method for treating a male impotent patient.

In accordance with this object of the present invention, there is provided a method for treating a male impotent patient comprising stimulating at least one penile portion of the patient's normal penile tissue or the prolongation thereof to cause contraction of the penile portion to at least restrict the blood flow leaving the penis, i.e., the venous blood flow, to achieve erection. In the following the term "penile portion" is to be understood as: the penile portion of the patient's normal penile tissue or the prolongation thereof.

Prolongation of the penile tissue includes but is not limited to the system filled with blood with blood such as the extension of corpus cavernosum (pl. corpora cavernosa) and blood vessels leading away from the penile area. To achieve erection preferable both corpus cavernosum or both exit vein systems from both corpus should be restricted. Therefore the terms is to be understood to include both one or two. One large restriction could be applied for both systems or one for each side.

In accordance with a main embodiment of the present invention, the method further comprises a) gently constricting the penile portion to restrict the blood flow leaving the penis, and b) stimulating the constricted penile portion to at least further restrict the blood flow leaving the penis to achieve erection.

The present invention provides an advantageous combination of the method steps (a) and (b), which results in a two-stage restriction of the blood flow in the patient's penile portion. Thus, applying a relatively weak force against the penile portion gently constricts the tissue wall of the penile portion and the constricted penile portion is stimulated to achieve the desired final restrict on the venous blood flow in the penile portion. The phrase "gently constricts a portion of the tissue wall" is to be understood as constricting the penile portion without substantially hampering the blood circulation in the tissue wall.

Preferably, step (b) is performed by intermittently and individually stimulating different areas of the penile portion. Such an intermittent and individual stimulation of different areas of the penile portion allows tissue of the penile portion to maintain over time substantially normal blood circulation.

The method of the present invention can be practiced on any place on an impotent patient's penile portion, which is a significant advance in the art, as compared with prior stimulation devices that are confined to electric stimulation of malfunctioning sphincters. Preferably, the constriction step (a) and stimulation step (b) are performed independently of each other. Steps (a) and (b) may be performed simultaneously. Optionally, step (b) may or may not be performed while step (a) is performed.

Initially, the constriction of the penile portion can be calibrated by stimulating the penile portion while adjusting the constriction of the penile portion until the desired restriction of the venous blood flow in the penile portion is obtained.

Flow Restriction

It should be understood that any embodiment or part of embodiment disclosed below in connection with flow restriction for constriction and stimulation devices combined in a constriction/stimulation unit could be used for the separate constriction device and separate stimulation device, where applicable.

In a principal embodiment of the invention, the penile portion is constricted, so that the venous blood flow in the penile portion at least is restricted and the constricted penile portion is stimulated to at least further restrict the venous blood flow in the penile portion. Specifically, the penile portion is constricted to a constricted state, in which the blood circulation in the constricted penile portion is substantially unrestricted and the venous blood flow in the penile portion is at least restricted, and the constricted penile portion is stimulated when it is in the constricted state to at least further restrict the venous blood flow in the penile portion.

The constriction step (a) and stimulation step (b) are suitably performed to constrict and stimulate the penile portion to an extent that depends on the flow restriction that is desired to be achieved in a specific application of the method of the invention. Thus, in accordance with a first flow restriction option, step (a) is performed by constricting the penile portion, so that the venous blood flow in the penile portion is restricted but not stopped, and step (b) is performed by stimulating the constricted penile portion to cause contraction thereof, so that the venous blood flow in the penile portion is further restricted but not stopped. The method may further comprise sensing a physical parameter of the patient and adjusting the intensity of the stimulation of the penile portion in response to the sensed parameter.

In accordance with a second flow restriction option, step (a) is performed by constricting the penile portion, so that the venous blood flow in the penile portion is restricted but not stopped, and step (b) is performed by stimulating the constricted penile portion to cause contraction thereof, so that the venous blood flow in the penile portion is stopped.

When using the method of the invention in accordance with the first or second options, the method may further comprise (c) ceaseing stimulating the penile portion to increase or allow the venous blood flow in the penile portion and (d) releasing the penile portion to restore the venous blood flow in the penile portion.

In accordance with a third flow restriction option, step (a) is performed by constricting the penile portion, so that the venous blood flow in the penile portion is substantially stopped, and step (b) is performed by stimulating the constricted penile portion to cause contraction thereof, so that the venous blood flow in the penile portion is completely stopped. The method may further comprise (c) ceaseing stimulating the penile portion to allow the venous blood flow in the penile portion and (d) releasing the penile portion to restore the venous blood flow in the penile portion.

Where the constricted penile portion is stimulated to contract, so that the venous blood flow in the penile portion is stopped, a first length of the constricted penile portion and a second length of the constricted penile portion, which is located downstream of the first length, are suitably simultaneously and cyclically stimulated, wherein the first length is progressively stimulated in the upstream direction of the blood flow and the second length is progressively stimulated in the downstream direction of the blood flow.

Furthermore, when using the method of the invention in accordance with the second and third options, the method may further comprise sensing a physical parameter of the patient or functional parameter of implanted components and adjusting the stimulation of the penile portion in response to the sensed parameter. For example, the intensity of the stimulation of the penile portion may be increased in response to a sensed pressure increase in the exit penile blood vessels, so that the venous blood flow in the penile portion remains stopped when a pressure increase occurs in the exit penile blood vessels. In particular, the method may comprise sensing a physical parameter of the patient's that relates to the pressure in the exit penile blood vessels, and controlling the stimulation of the penile portion in response to the sensed parameter. Any sensor for sensing a physical parameter of the patient, such as a pressure in the patient's body that relates to the pressure in the exit penile blood vessels may be provided, wherein the stimulation is controlled in response to signals from the sensor. Such a sensor may for example sense the pressure in the patient's abdomen, the pressure against the implanted constriction device or the pressure on the tissue wall of the penile portion.

In accordance with a fourth restriction option, step (a) is performed by constricting the penile portion, so that the venous blood flow in the penile portion is stopped. When needed, the penile portion is released to restore the venous blood flow in the penile portion. Step (b) is only performed by stimulating the constricted penile portion to cause contraction thereof, so that the venous blood flow in the penile portion remains stopped when a pressure increase occurs in the venous blood vessels. The method may further comprise sensing a physical parameter of the patient's body, such as a pressure in the patient's body that relates to the pressure in the exit penile blood vessels, and controlling the stimulation of the penile portion in response to the sensed parameter. Such a physical parameter may be a pressure in the patient's abdomen and the sensor may be a pressure sensor.

In some applications of the method of the invention, continuous stimulation may over time change the physical properties of the tissue so that the tissue might be injured. Also, the effect of a continuous stimulation of the tissue wall may decrease over time. Therefore, step (b) is preferably performed by intermittently and individually stimulating different areas of the penile portion so that the venous blood flow in the penile portion continues to be restricted as desired and each area of the penile portion essentially maintains its natural physical properties over time to prevent the area from being injured. Advantageously, each area of the penile portion is stimulated during successive time periods, each time period being short enough to maintain over time satisfactory blood circulation in the area. Thus, the areas are stimulated so that an area that currently is not stimulated will have time to restore substantially normal blood circulation before it is stimulated again.

To maintain satisfactory blood circulation in the tissue wall of the penile portion stimulation step (b) is suitably performed by stimulating one or more of different areas of the penile portion at a time, preferably by sequentially stimulating the different areas of the penile portion or by shifting the stimulation from one area to another over time. Preferably, stimulation step (b) is performed by cyclically propagating the stimulation of the areas along the penile portion, for example in accordance with a determined stimulation pattern.

The method of the invention may further comprise controlling, preferably by the patient, at least one of the constriction and stimulation of the penile portion from outside the patient's body.

Generally, the method of the invention comprises sensing a physical parameter of the patient and controlling, preferably automatically, at least one of the constriction and stimulation of the penile portion in response to the sensed parameter.

The constriction step (a) may be performed by constricting any penile portions of a series of penile portions of the penile portion, respectively, either in random or in accordance with a predetermined sequence. The stimulation step (b) may be performed by stimulating any of the constricted penile portions of the series of penile portions. Specifically, step (a) may be performed by constricting all of the penile portions of the series of penile portions, and step (b) may be performed by stimulating any constricted penile portions in random or in accordance with a predetermined sequence to close the exit penile blood vessels.

To summarize a few preferred embodiments see below:

In accordance with an alternative, step (a) is performed by constricting any penile portions of a series of penile portions, respectively. In accordance with an alternative, the penile portions of the series of penile portions are constricted in random or in accordance with a predetermined sequence.

In accordance with an alternative, step (b) is performed by stimulating any constricted penile portions of the series of penile portions. In accordance with an alternative, the penile portions of the series of penile portions are constricted in random or in accordance with a predetermined sequence, penile portion penile portion penile portion penile portion In accordance with an alternative, step (a) is performed by constricting any penile portions of a series of penile portions, respectively, wherein the penile portions of the series of penile portions are successively constricted without completely closing the exit penile blood vessels, and step (b) is performed by stimulating the constricted penile portions, so that the penile portions of the series of penile portions are further constricted. In accordance with an alternative, the penile portions of the series of penile portions are constricted in random or in accordance with a predetermined sequence.

In accordance with an alternative, step (a) is performed by constricting all of the penile portions of the series of penile portions, and step (b) is performed by stimulating any constricted penile portions so that the penile portions of the series of penile portions are further constricted.

In accordance with an alternative, the penile portions of the series of penile portions are further constricted by the stimulation device in random or in accordance with a predetermined sequence.

In accordance with an alternative for all applicable alternatives, step (a) and step (b) are performed independently of each other or in accordance with an alternative, step (a) and step (b) are performed simultaneously.

In any of the above noted embodiments step (b) may be performed by stimulating the penile portion with electric pulses.

Stimulation Modes

When stimulating neural or muscular tissue there is a risk of injuring or deteriorating the tissue over time if the stimulation is not properly performed. The method of the present invention is performed to reduce or even eliminate that risk. Thus, step (b) is performed by intermittently stimulating different areas of the penile portion so that at least two of the areas are stimulated at different points of time. I.e., the stimulation is shifted from one area to another area over time. In addition, step (b) is performed by intermittently stimulating the areas of the penile portion so that an area of the different areas that currently is not stimulated has time to restore substantially normal blood circulation before it is stimulated again. Furthermore, step (b) is performed by intermittently stimulating the areas during successive time periods, wherein each time period is short enough to maintain satisfactory blood circulation in the area until the laps of the time period. This gives the advantage that the method of the present invention provides continuous stimulation of the penile portion to achieve the desired flow control while essentially maintaining over time the natural physical properties of the penile tissue without risk of injuring the penile tissue.

Also, by physically changing the places of stimulation on the penile portion over time as described above it is possible to create an advantageous changing stimulation pattern on the penile portion, in order to achieve a desired flow control.

To achieve the desired reaction of the tissue wall during the stimulation thereof, step (b) may be performed by stimulating the penile portion with, preferably cyclically, varying stimulation intensity.

In a main embodiment of the invention, step (b) is performed by intermittently stimulating the penile portion with pulses, preferably in the form of pulse trains. The pulse trains can be configured in many different ways by varying pulse parameters. Thus, the pulse amplitudes of the pulses of the pulse trains, the off time periods between the individual pulses of each pulse train and the width and repetition frequency of each pulse may be varied. Also the off time periods between the pulse trains may be varied, wherein each off time period between the pulse trains is kept long enough to restore substantially normal blood circulation in each area of the penile portion, when the area is not stimulated during the off time periods. Furthermore, the repetition frequency of the pulses of the pulse trains and the length and number of pulses of each pulse train may be varied.

As mentioned above, for reasons of maintaining over time the effect of stimulation, it is preferable that different areas of the penile portion are intermittently and individually stimulated. In consequence, step (b) may be performed by stimulating one or more of the areas at a time with pulses, by cyclically propagating the stimulation of the areas with pulses along the penile portion, and/or by propagating the stimulation of the areas with pulses in accordance with a determined stimulation pattern. In case the off time periods between pulse trains that stimulate the respective area of the penile portion are varied, it is preferable that each off time period between the pulse trains is controlled to last long enough to restore substantially normal blood circulation in the area when the latter is not stimulated during the off time periods.

Electric Stimulation

In accordance with a preferred embodiment of the invention, step (b) is performed by electrically stimulating the penile portion, preferably with electric pulses to cause contraction of the penile portion. This embodiment is particularly suited for applications in which the patient's penile portion includes muscle fibers that react to electrical stimula. Thus, the penile portion that includes the muscle fibers is stimulated with such electric pulses, preferably in the form of electric pulse trains, when the penile portion is in the constricted state, to cause contraction of the penile portion. Of course, the configuration of the electric pulse trains may be similar to the above described pulse trains and different areas of the penile portion may be electrically stimulated in the same manner as described above.

In accordance with the preferred embodiment, the method of the invention comprises providing at least one, preferably a plurality of electrical elements, such as electrodes, engaging and stimulating the penile portion with electric pulses. Optionally, the electrical elements may be placed in a fixed orientation relative to one another. The method comprises electrically energizing the electrical elements, preferably by cyclically energizing each element with electric pulses. The electrical elements may be energized so that the electrical elements are energized one at a time in sequence, or so that a number or groups of the electrical elements are energized at a time. Also, groups of electrical elements may be sequentially energized, either randomly or in accordance with a predetermined pattern.

The method may further comprise applying the electrical elements on the patient's penile portion so that the electrical elements form any pattern of electrical elements, preferably an elongate pattern of electrical elements extending lengthwise along the penile portion and the elements abut the respective areas of the penile portion. The electrical elements may be successively energized along the elongate pattern of electrical elements in a direction opposite to or in the same direction as that of the flow in the patient's lumen. Optionally, the electrical elements may be successively energized along the elongate pattern of electrical elements from a position substantially at the center of the constricted penile portion towards both ends of the elongate pattern of electrical elements. The electrical elements may be energized so that energized electrical elements form two waves of energized electrical elements that simultaneously advance from the center of the constricted penile portion in two opposite directions towards both ends of the elongate pattern of electrical elements. Such waves of energized electrical elements can be repeated over and over again without harming the penile tissue and without moving blood in any direction in the exit penile blood vessels.

The elongate pattern of electrical elements may include one or more rows of electrical elements extending lengthwise along the penile portion. Each row of electrical elements may form a straight, helical or zig-zag path of electrical elements, or any form of path. The electrical elements may be energized so that the electrical elements currently energized form at least one group of adjacent energized electrical elements, wherein the elements in the group of energized electrical elements form a path of energized electrical elements extending at least in part around the patient's penile portion, preferably completely around the patient's penile portion. Alternatively, the elements in the group of energized electrical elements form two paths of energized electrical elements extending on mutual sides of the penile portion penile portion or more than two paths of energized electrical elements extending on different sides of the penile portion, preferably at least substantially transverse to the flow direction in the exit penile blood vessels.

In an embodiment of the invention, the electrical elements form a plurality of groups of elements, wherein the groups form a series of groups extending along the penile portion in the flow direction in the patient's lumen. The electrical elements of each group of electrical elements may form a path of elements extending at least in part around the penile portion. In a first alternative, the electrical elements of each group of electrical elements may form more than two paths of elements extending on different sides of the penile portion, preferably substantially transverse to the flow direction in the patient's lumen. The groups of electrical elements in the series of groups may be energized in random or in accordance with a predetermined pattern. Alternatively, the groups of electrical elements in the series of groups may be successively energized in a direction opposite to or in the same direction as that of the flow in the patient's lumen, or in both said directions starting from a position substantially at the center of the constricted penile portion. For example, groups of energized electrical elements may form advancing waves of energized electrical elements, as described above. I.e., the groups of electrical elements may be energized so that energized electrical elements form two waves of energized electrical elements that simultaneously advance from the center of the constricted penile portion in two opposite directions towards both ends of the elongate pattern of electrical elements.

Thermal Stimulation

In accordance with an embodiment of the invention, stimulation step (b) is performed by thermally stimulating the penile portion. Thus, the penile portion may be cooled, when the penile portion is constricted, to cause contraction of the penile portion. For example, the penile portion may be constricted to at least restrict the venous blood flow in the penile portion, and the constricted penile portion may be cooled to cause contraction thereof, so that the venous blood flow in the penile portion is at least further restricted, or further restricted but not stopped, or stopped. Alternatively, the penile portion may be heated, when the penile portion is constricted and contracted, to cause expansion of the penile portion. Where the penile portion includes a blood vessel, the blood vessel may be cooled to cause contraction thereof, or heated to cause expansion thereof. Where applicable, thermal stimulation may be practised in any of the embodiments of the present invention. Where applicable, thermal stimulation may be practised in any of the embodiments of the present invention, and the thermal stimulation may be controlled in response to various sensors, for example strain, motion or pressure sensors.

Constriction and Stimulation Devices

It should be understood that any embodiment or part of embodiment for the combined stimulation device and constriction device, could be used, where applicable, for any one of the devices as a stand alone device. Generally, the method of the invention comprises providing a constriction device that constricts the penile portion, a stimulation device that stimulates the constricted penile portion and a control device that controls the constriction device and/or the stimulation device. The method comprises operating the control device from outside the patient's body, preferably by using the control device to wirelessly control the constriction device and/or stimulation device. The wireless control is preferably performed in a non-magnetic manner, whereby implanted magnetic devices can be avoided. Suitably, the control device comprises a hand-held wireless remote control operated by the patient.

Alternatively, the control device comprises a manually operable switch for switching on and off the constriction device and/or stimulation device. In this case, the method comprises subcutaneously implanting the switch in the patient and manually operating the the implanted switch from outside the patient's body.

In an embodiment of the invention, the control device comprises a programmable internal control unit, such as a microprocessor, and the method comprises implanting in the patient the internal control unit and controlling by the internal control unit the constriction device and/or stimulation device. The control device may also comprise an external control unit outside the patient's body. In this case, the method comprises controlling by the external control unit the constriction device and/or stimulation device and, optionally, using the external control unit to program the implanted internal control unit. The internal control unit may be programmable for controlling the constriction device and/or stimulation device over time, for example in accordance with an activity schedule program.

The constriction of the penile portion can be calibrated by using the control device to control the stimulation device to stimulate the penile portion while controlling the constriction device to adjust the constriction of the penile portion until the desired restriction of the venous blood flow in the penile portion is obtained.

Sensor Controlled Constriction and/or Stimulation

It should be understood that any embodiment or part of embodiment disclosed below in connection with sensor control of the constriction and stimulation devices combined in the constriction/stimulation unit could be used for the separate constriction device and separate stimulation device, where applicable. In an embodiment of the invention, the method comprises implanting at least one sensor and controlling by the control device the constriction device and/or the stimulation device in response to signals from the sensor. Generally, the sensor directly or indirectly senses at least one physical parameter of the patient, functional parameter of the apparatus, or functional parameter of a medical implant in the patient.

Many different kinds of sensor for sensing physical parameters may be used. For example motion sensors for sensing organ motion, i.e. natural contractions, such as intestinal contractions, pressure sensors for sensing pressure in the penile tissue, strain sensors for sensing strain of the penile tissue, flow sensors for sensing fluid venous blood flow in the penile portion of the organ, spectro-photometrical sensors, or sensors for sensing the distribution of the stimulation on the stimulated penile tissue. Any conceivable sensors for sensing any other kind of useful physical parameter may be used.

Many different kinds of sensors that sense functional parameters of implanted components may also be used for the control of the constriction device and/or the stimulation device. For example sensors for sensing electric parameters of implanted electric components, or sensors for sensing the performance of implanted motors or the like.

The sensor may comprise a pressure sensor for sensing as the physical parameter a pressure in the patient's body that relates to the pressure in the exit penile blood vessels. In this case, the method suitably comprises operating the control device to control the constriction device to change the constriction of the patient's penile portion in response to the pressure sensor sensing a predetermined value of measured pressure.

The above described sensors may be used in any of the embodiments of the invention, where applicable.

The control device may comprise an implantable internal control unit that directly controls the constriction device and/or stimulation device in response to signals from the sensor. The control device may further comprise a wireless remote control adapted to set control parameters of the internal control unit from outside the patient without mechanically penetrating the patient. At least one of the control parameters, which is settable by the wireless remote control, is the physical or functional parameter Alternatively, the control device may comprise an external control unit outside the patient's body for controlling the constriction device and/or stimulation device in response to signals from the sensor.

Constriction of Penile Portion

It should be understood that any embodiment or part of embodiment disclosed below in connection with constricting the penile portion could be used for the separate constriction device and separate stimulation device, where applicable.

Method step (a) may be performed in many different ways. Thus, step (a) may be performed by:

(1)—constricting the penile portion so that the through-flow area of the blood vessel passageway assumes a size in the constricted state small enough to cause the constricted penile portion to contract to stop the venous blood flow in the penile portion when step (b) is performed;

(2)—bending the penile portion;

(3)—clamping the penile portion between at least two elements positioned on different sides of the penile portion;

(4)—clamping the penile portion between an element and the bone or tissue of the patient;

(5)—rotating at least two elements positioned on different sides of the penile portion; or (6)—clamping the penile portion between at least two articulated clamping elements positioned on different sides of the penile portion.

In the above noted alternatives (1) to (6) of method step (a), the constriction of the penile portion may be changed either mechanically or hydraulically. For many applications of the present invention, step (a) is suitably performed so that the through-flow area of the blood vessel passageway assumes a size in the constricted state that is small enough to enable the stimulation during step (b) to contract the penile portion to stop the venous blood flow in the penile portion.

Where the constriction of the penile portion is hydraulically changed, the method of the invention may further comprise implanting in the patient a reservoir containing a predetermined amount of hydraulic fluid, and a constriction device engaging the penile portion and having an expandable/contractible cavity, wherein step (a) is performed by distributing hydraulic fluid from the reservoir to increase the volume of the cavity to constrict the penile portion, and by distributing hydraulic fluid from the cavity to the reservoir to decrease the volume of the cavity to release the penile portion. The cavity may be defined by a balloon of the constriction device that abuts the tissue penile portion, so that the patient's penile portion is constricted upon expansion of the cavity and released upon contraction of the cavity.

Alternatively, the cavity may be defined by a bellows that displaces a relatively large contraction element of the constriction device, for example a large balloon that abuts the penile portion, so that the patient's penile portion is constricted upon contraction of the bellows and released upon expansion of the bellows. Thus, a relatively small addition of hydraulic fluid to the bellows causes a relatively large increase in the constriction of the penile portion. Such a bellows may also be replaced by a suitably designed piston/cylinder mechanism.

Where the hydraulic means comprises a cavity in the constriction device, the following embodiments of the invention are conceivable.

1) The reservoir comprises first and second wall portions, and step (a) is performed by displacing the first and second wall portions relative to each other to change the volume of the reservoir, so that fluid is distributed from the reservoir to the cavity, or from the cavity to the reservoir.

1a) At least one of a magnetic device, a hydraulic device or an electric control device displaces the first and second wall portions of the reservoir.

2) A pump is provided for pumping fluid between the reservoir and the cavity.

2*a*) The pump comprises a first activation member for activating the pump to pump fluid from the reservoir to the cavity and a second activation member for activating the pump to pump fluid from the cavity to the reservoir.

2*a*1) The first and second activation members are operable by manual manipulation thereof.

2*a*2) At least one of the activation members operates when subjected to an external predetermined pressure.

2*a*3) At least one of the first and second activating members is operable by magnetic means, hydraulic means, or electric control means.

2*b*) A fluid conduit between the pump and the cavity is provided, wherein the reservoir forms part of the conduit. The conduit and pump are devoid of any non-return valve. The reservoir forms a fluid chamber with a variable volume, and the pump distributes fluid from the chamber to the cavity by a reduction in the volume of the chamber and withdraws fluid from the cavity by an expansion of the volume of the chamber. A motor is provided for driving the pump, wherein the pump comprises a movable wall of the reservoir for changing the volume of the chamber.

In all of the above noted embodiments 1 to 2b where the hydraulic means comprises an expandable cavity in the constriction device, the cavity can be exchanged by a cylinder/piston mechanism for adjusting the constriction device. In this case, hydraulic fluid is distributed between the reservoir and the cylinder/piston mechanism to adjust the constriction device.

3) The method further comprises implanting a reverse servo operatively connected to the hydraulic means. The term "reverse servo" is to be understood as a mechanism that transfers a strong force acting on a moving element having a short stroke into a weak force acting on another moving element having a long stroke; i.e., the reverse function of a normal servo mechanism. Thus, minor changes in the amount of fluid in a smaller reservoir could be transferred by the reverse servo into major changes in the amount of fluid in a larger reservoir.

Preferably, the reverse servo comprises an expandable servo reservoir containing servo fluid and a fluid supply reservoir hydraulically connected to the servo reservoir to form a closed conduit system for the servo fluid. The expandable servo reservoir has first and second wall portions, which are displaceable relative to each other in response to a change in the volume of the expandable servo reservoir.

In accordance with a first alternative, the first and second wall portions of the servo reservoir are operatively connected to the hydraulic means. The reverse servo distributes fluid between the fluid supply reservoir and the expandable servo reservoir to change the volume of the servo reservoir, whereby the hydraulic means is operated to adjust the constriction device.

In accordance with a second alternative, there is provided an implantable main reservoir containing a predetermined amount of hydraulic fluid, wherein the reverse servo is operated to distribute hydraulic fluid between the main reservoir and the hydraulic means to adjust the constriction device. More specifically, the main reservoir is provided with first and second wall portions operatively connected to the first and second wall portions of the expandable servo reservoir, so that the volume of the main reservoir is changed when the volume of the expandable servo reservoir is changed. Thus, when the reverse servo distributes servo fluid between the fluid supply reservoir and the expandable servo reservoir to change the volume of the main reservoir, hydraulic fluid is distributed from the main reservoir to the hydraulic means, or from the hydraulic means to the main reservoir. Advantageously, the method comprises dimensioning the servo and main reservoirs, so that when the volume of the servo reservoir is changed by a relatively small amount of servo fluid, the volume of the main reservoir is changed by a relatively large amount of hydraulic fluid.

In both of the above-described alternatives, the fluid supply reservoir may have first and second wall portions, which are displaceable relative to each other to change the volume of the fluid supply reservoir to distribute servo fluid between the fluid supply reservoir and the expandable servo reservoir. The first and second wall portions of the fluid supply reservoir may be displaced relative to each other by manual manipulation, a magnetic device, a hydraulic device, or an electric control device to change the volume of the fluid supply reservoir to distribute servo fluid between the fluid supply reservoir and the expandable servo reservoir.

In all of the above noted embodiments 1 to 2b where the hydraulic means comprises an expandable cavity in the constriction device, or in embodiments where the hydraulic means includes a hydraulically operable mechanical construction, the reverse servo described above may be used. In a further embodiment of the invention, the hydraulic means include first and second hydraulically interconnected expandable/contractible reservoirs. The first reservoir is operatively connected to the constriction device, so that the constriction device changes the constriction of the patient's penile portion upon expansion or contraction of the first reservoir. By changing the volume of the second reservoir hydraulic fluid is distributed between the two reservoirs, so that the first reservoir is either expanded or contracted. This embodiment requires no non-return valve in the fluid communication conduits between the two reservoirs, which is beneficial to long-term operation of the hydraulic means.

Alternatively, the hydraulic means may include first and second hydraulically interconnected piston/cylinder mechanisms instead of the first and second reservoirs described above. The first piston/cylinder mechanism is operatively connected to the constriction device, so that the constriction device changes the constriction of the patient's penile portion upon operation of the first piston/cylinder mechanism. By operating the second piston/cylinder mechanism hydraulic fluid is distributed between the two piston/cylinder mechanisms, so that the first piston/cylinder mechanism adjusts the constriction device.

Where the constriction device does not include an expandable/contractible cavity, the constriction device may comprise at least two elongated clamping elements extending along the penile portion on different sides of the penile portion. The hydraulic means, which may include the reverse servo described above, hydraulically moves the elongated clamping elements towards the penile portion to constrict the penile portion. For example, the constriction device may have hydraulic chambers in which the clamping elements slide back and forth, and the hydraulic means may also include a pump and an implantable reservoir containing hydraulic fluid. The pump distributes hydraulic fluid from the reservoir to the chambers to move the clamping elements against the penile portion, and distributes hydraulic fluid from the chambers to the reservoir to move the clamping elements away from the penile portion.

Energy Supply

It should be understood that any embodiment or part of embodiment disclosed below in connection with the power of the constriction and stimulation devices combined in the constriction/stimulation unit could be used for the separate constriction device and separate stimulation device, where applicable.

Generally, method step (a) is performed by using the constriction device and step (b) is performed by using the stimulation device, wherein the method further comprises forming the constriction and stimulation devices in an operable constriction/stimulation unit.

In a simple form of the invention, the method comprises implanting a source of energy, such as a battery, rechargeable battery or accumulator, releasing energy from the source of energy and using the released energy in connection with the operation of the constriction/stimulation unit.

In a more sophisticated form of the invention, which is preferable, the method comprises transmitting wireless energy from outside the patient's body to inside the patient's body and using the transmitted wireless energy in connection with the operation of the constriction/stimulation unit.

Transmission of Wireless Energy

It should be understood that any embodiment or part of embodiment disclosed below in connection with wireless control or power of the constriction and stimulation devices combined in the constriction/stimulation unit could be used for the separate constriction device and separate stimulation device, where applicable.

The wireless energy may be directly used in connection with the operation of the constriction/stimulation unit, as the wireless energy is being transmitted. For example, the wireless energy may be transmitted in the form of an electric, an electromagnetic or a magnetic field, or a combination thereof, or electromagnetic waves for direct power of the constriction/stimulation unit. For example, where an electric motor or pump operates the constriction device of the constriction/stimulation unit, wireless energy in the form of a magnetic or an electromagnetic field may be used for direct power of the motor or pump.

Thus, the motor or pump is running directly during transmission of the wireless energy. This may be achieved in two different ways: a) using a transforming device implanted in the patient to transform the wireless energy into energy of a different form, preferably electric energy, and powering the motor or pump with the transformed energy, or b) using the wirelessly transmitted energy to directly power the motor or pump. Preferably wireless energy in the form of an electromagnetic or magnetic field is used to directly influence specific components of the motor or pump to create kinetic energy. Such components may include coils integrated in the motor or pump.

The wireless energy is suitably transmitted in pulses or digital pulses, or a combination of pulses and digital pulses.

Preferably, the wireless energy is transmitted in at least one wireless signal, suitably a wave signal. The wave signal may comprise an electromagnetic wave signal including one of an infrared light signal, a visible light signal, an ultra violet light signal, a laser signal, a microwave signal, a radio wave signal, an x-ray radiation signal, and a gamma radiation signal. Alternatively, the wave signal may comprise a sound or an ultrasound wave signal. The wireless signal may be a digital or analogue signal, or a combination of a digital and analogue signal.

In accordance with a particular embodiment of the invention, the wireless energy is not for direct use in connection with the operation of the constriction/stimulation unit. In this embodiment the wireless energy comprises energy of a first form, which is transmitted into energy of a second form suited to operate the constriction/stimulation unit. Typically, the energy of the second form is different from the energy of the first form. For example, the wireless energy of the first form may comprise sound waves, whereas the energy of the second form may comprise electric energy. Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

Transforming Wireless Energy

It should be understood that any embodiment or part of embodiment disclosed below in connection with the control or energizing of the constriction and stimulation devices combined in the constriction/stimulation unit could be used for the separate constriction device and separate stimulation device, where applicable.

In accordance with a particular embodiment of the invention, an implantable energy-transforming device is provided for transforming wireless energy of a first form transmitted by the energy-transmission device into energy of a second form, which typically is different from the energy of the first form. The constriction/stimulation unit is operable in response to the energy of the second form. For example, the wireless energy of the first form may comprise sound waves, whereas the energy of the second form may comprise electric energy. Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transforming device may function different from or similar to the energy-transmission device. Advantageously, the energy-transforming device comprises at least one element, such as at least one semiconductor, having a positive region and a negative region, when exposed to the energy of the first form transmitted by the energy-transmission device, wherein the element is capable of creating an energy field between the positive and negative regions, and the energy field produces the energy of the second form. More specifically, the element may comprise an electrical junction element, which is capable of inducing an electric field between the positive and negative regions when exposed to the energy of the first form transmitted by the energy-transmission device, whereby the energy of the second form comprises electric energy.

The energy of the first form may directly or indirectly be transformed into the energy of the second form. The method of the invention may comprise providing a motor for operating the constriction device and powering the motor with the energy of the second form. The constriction device may be operable to perform at least one reversible function and the method may comprise reversing the function by using the motor. For example, the method may comprise shifting the polarity of the energy of the second form to reverse the motor.

The motor may be directly powered with the transformed energy, as the energy of the second form is being transformed from the energy of the first form. Preferably, the constriction/ stimulation unit is directly operated with the energy of the second form in a non-magnetic, non-thermal or non-mechanical manner.

Normally, the implanted constriction/stimulation unit comprises electric components that are energized with electrical energy. Therefore, the energy of the first form may be transformed into a direct current or pulsating direct current, or a combination of a direct current and pulsating direct current. Alternatively, the energy of the first form may be transformed into an alternating current or a combination of a direct and alternating current.

The method of the invention may comprise implanting in the patient an internal source of energy, and supplying energy from the internal source of energy for the operation of the constriction/stimulation unit. The method may further comprise implanting in the patient a switch operable to switch from an "off" mode, in which the internal source of energy is not in use, to an "on" mode, in which the internal source of energy supplies energy for the operation of the constriction/stimulation unit, and/or for energizing implanted electronic components of the constriction/stimulation unit. The switch may be operated by the energy of the first form or by the energy of the second form. The described switch arrangement reduces power consumption of the constriction/stimulation unit between operations.

The internal source of energy may store the energy of the second form. In this case, the internal source of energy suitably comprises an accumulator, such as at least one capacitor or at least one rechargeable battery, or a combination of at least one capacitor and at least one rechargeable battery. Where the internal source of energy is a rechargeable battery it may be charged only at times convenient for the patient, for example when the patient is sleeping. Alternatively, the internal source of energy may supply energy for the operation of the constriction/stimulation unit but not be used for storing the energy of the second form. In this alternative, the internal source of energy may be a battery and the switch described above may or may not be provided.

Suitably, the method of the invention may comprise implanting a stabilizer for stabilizing the energy of the second form. Where the energy of the second form comprises electric energy the stabilizer suitably comprises at least one capacitor.

The energy-transforming device may be designed for implantation subcutaneously in the abdomen, thorax or cephalic region of the patient. Alternatively, it may be designed for implantation in an orifice of the patient's body and under the mucosa or intramuscularly outside the mucosa of the orifice.

Control of Constriction/Stimulation Unit

It should be understood that any embodiment or part of embodiment disclosed below in connection with the control of the constriction and stimulation devices combined in the constriction/stimulation unit could be used for the separate constriction device and separate stimulation device, where applicable.

Although the constriction device of the constriction/stimulation unit may normally keep the patient's penile portion in the constricted state, in most applications using the present invention there will be daily adjustments of the constriction device. Therefore, in a preferred embodiment of the invention, the constriction device is adjustable to enable changing the constriction of the patient's penile portion as desired and the control device controls the constriction device to change the constriction of the penile portion.

The method of the invention suitably comprises operating the control device by the patient. In a simple form the control device comprises a manually operable switch for switching on and off the constriction/stimulation unit, and the method further comprises subcutaneously implanting the switch in the patient. It is preferable, however, that the control device comprises a hand-held wireless remote control operable by the patient from outside the patient's body to control the constriction/stimulation unit to adjust the stimulation intensity and/or adjust the constriction of the penile portion. The wireless remote control is suitably designed for application on the patient's body like a wristwatch.

In some applications of the invention, the constriction device of the constriction/stimulation unit may be designed to normally keep the patient's penile portion in the constricted state. I.e., after implantation the constriction device all the time keeps the penile portion slightly constricted. In this case, the control device may be used when desired by the patient, to control the stimulation device of the constriction/stimulation unit to stimulate the constricted tissue penile portion, preferably while adjusting the stimulation intensity, to cause contraction of the penile portion, so that the venous blood flow in the penile portion is at least further restricted or stopped to achieve erection, and, later, to control the stimulation device to cease the stimulation. More precisely, the method of the invention may comprise operating the control device by the patient to a) control the stimulation device in a first mode to stimulate the constricted penile portion to further restrict the venous blood flow in the penile portion and control the stimulation device in a second mode to cease the stimulation of the penile portion to increase the venous blood flow in the penile portion; or b) control the stimulation device in a first mode to stimulate the constricted penile portion to stop the venous blood flow in the penile portion and control the stimulation device in a second mode to cease the stimulation of the penile portion to allow venous blood flow in the penile portion.

Either the first mode or the second mode may be temporary.

The wireless remote control preferably transmits at least one wireless control signal for controlling the constriction/stimulation unit. The control signal may comprise a frequency, amplitude, phase modulated signal or a combination thereof, and may be an analogue or a digital signal, or a combination of an analogue and digital signal. The remote control may transmit an electromagnetic carrier wave signal for carrying the digital or analogue control signal. Also the carrier signal may comprise digital, analogue or a combination of digital and analogue signals.

Any of the above signals may comprise wave signals, such as a sound wave signal, an ultrasound wave signal, an electromagnetic wave signal, an infrared light signal, a visible light signal, an ultra violet light signal, a laser light signal, a micro wave signal, a radio wave signal, an x-ray radiation signal or a gamma radiation signal.

Alternatively, the control signal may comprise an electric or magnetic field, or a combined electric and magnetic field.

Operation of Constriction/Stimulation Unit

It should be understood that any embodiment or part of embodiment for operating the combined stimulation device and constriction device, could be used, if applicable, for any one of the devices as a stand alone device.

The method of the invention may comprise implanting in the patient an operation device, and operating the constriction/stimulation unit with the operation device. A magnet may be provided, wherein the method comprises using the magnet to activate the operation device from outside the patient's body. The operation device suitably comprises a motor which is powered with energy released from a source of energy, such as a battery. Although the constriction/stimulation unit in embodiments described above suitably is designed as a single piece, which is most practical for implantation, it should be noted that as an alternative the constriction device and stimulation device of the constriction/stimulation unit could be designed as separate pieces.

Laparoscopic Method

The present invention also provides a first method for treating a male impotent patient, the method comprising the steps of:
inserting a needle like tube into a cavity of the patients body,
using the needle like tube to fill the cavity with gas thereby expanding the I cavity,
placing at least two laparoscopical trocars in the patient's body,
inserting a camera through one of the trocars into the cavity,
inserting a dissecting tool through any of the trocar and dissecting an area of at least one portion of the tissue wall of the penile portion,
placing a constriction device and a stimulation device in the dissected area in operative engagement with the penile portion,
using the constriction device to gently constrict the penile portion of the penile portion to restrict the venous blood flow in the penile portion, and
using the stimulation device to stimulate the constricted penile portion to cause contraction of the penile portion to further restrict the venous blood flow in the penile portion to achieve erection.

The present invention also provides a second method for treating a male impotent patient, the method comprising the steps of:
inserting a needle like tube into a cavity of the patients body,
using the needle like tube to fill the cavity with gas thereby expanding the cavity,
placing at least two laparoscopical trocars in the patient's body,
inserting a camera through one of the trocars into the cavity,
inserting a dissecting tool through any of the trocar and dissecting an area of at least one portion of the tissue wall of the penile portion,
placing a stimulation device in the dissected area in operative engagement with the penile portion, and
using the stimulation device to stimulate the penile portion to cause contraction of the penile portion to restrict the venous blood flow in the penile portion to achieve erection.

The present invention also provides a third method for treating a male impotent patient, the method comprising the steps of:
inserting a needle like tube into a cavity of the patients body,
using the needle like tube to fill the cavity with gas thereby expanding the cavity,
placing at least two laparoscopical trocars in the patient's body,
inserting a camera through one of the trocars into the cavity,
inserting a dissecting tool through any of the trocar and dissecting an area of at least one portion of the tissue wall of the penile portion,
placing a a constriction device in the dissected area in operative engagement with the penile portion,
using the constriction device to constrict the penile portion of the penile portion to restrict the venous blood flow in the penile portion to achieve erection.

The present invention also provides a fourth method for treating a male impotent patient, the method comprising the steps of:
cutting the skin of the patient,
inserting a dissecting tool and dissecting an area of at least one portion of the tissue wall of the penile portion,
placing a constriction device and a stimulation device in the dissected area in operative engagement with the penile portion,
using the constriction device to gently constrict the penile portion of the penile portion to restrict the venous blood flow in the penile portion, and
using the stimulation device to stimulate the constricted penile portion to cause contraction of the penile portion to further influence the venous blood flow in the penile portion to achieve erection.

The present invention also provides a fifth method for treating a male impotent patient. The method comprises the steps of:
cutting the skin of the patient,
inserting a dissecting tool and dissecting an area of at least one portion of the penile tissue wall,
placing a stimulation device in the dissected area in operative engagement with the penile portion, and
using the stimulation device to stimulate the penile portion to cause contraction of the penile portion to influence the venous blood flow in the penile portion.

The present invention also provides a sixth method for treating a male impotent patient, the method comprising the steps of:
cutting the skin of the patient,
inserting a dissecting tool and dissecting an area of at least one portion of the tissue wall of the penile portion,
placing a stimulation device in the dissected area in operative engagement with the penile portion, and
using the stimulation device to stimulate the penile portion to cause contraction of the penile portion to restrict the venous blood flow in the penile portion to achieve erection.

In all of the above-noted methods 1-3 the cavity may constitute at least one of an abdominal cavity, a cavity in the pelvic region, a cavity in the fat, muscle tissue and fibrotic tissue.

The method further comprises implanting a powered operation device for operating the constriction device. The operation device may comprise a powered hydraulic operation device or an electrically powered operation device, such as an electric motor.

The method further comprises transmitting wireless energy for powering the operation device, and when desired to influence the flow in the penile portion, powering the operation device with the transmitted energy to operate the constriction device.

Female Sexual Dysfunction (I)

Another object of the present invention is to provide a method for treating female sexual dysfunction which obviates at least some of the disadvantages in the prior art and which positively affects sexual stimuli and orgasm of a female patient.

In accordance with this object of the present invention, there is provided a method for treating sexual dysfunction of a female patient comprising stimulating at least one erectile portion of the patient's female erectile tissue to cause contraction of the erectile portion to at least restrict the blood flow leaving the erectile tissue, i.e., the venous blood flow, to obtain engorgement with blood of the female erectile tissue. In the following the term "erectile portion" is to be understood as the erectile portion of the patient's normal erectile tissue.

In accordance with a main embodiment of the present invention, the method further comprises gently constricting the erectile portion to restrict the blood flow leaving the erectile tissue, and stimulating the constricted erectile portion to at least further restrict the blood flow leaving the erectile tissue to obtain engorgement with blood of the female erectile tissue.

The present invention provides an advantageous combination of the method steps (a) and (b), which results in a two-stage restriction of the blood flow in the patient's erectile portion. Thus, applying a relatively weak force against the erectile portion gently constricts the tissue wall of the erectile portion and the constricted erectile portion is stimulated to achieve the desired final restrict on the venous blood flow in the erectile portion. The phrase "gently constricts a portion of the tissue wall" is to be understood as constricting the erectile portion without risking injuring the erectile tissue.

Preferably, step (b) is performed by intermittently and individually stimulating different areas of the erectile portion. Such an intermittent and individual stimulation of different areas of the erectile portion allows tissue of the erectile portion to maintain over time substantially normal blood circulation.

The method of the present invention can be practiced on any place on a female patient's erectile portion, which is a significant advance in the art. Preferably, the constriction step (a) and stimulation step (b) are performed independently of each other. Steps (a) and (b) may be performed simultaneously. Optionally, step (b) may or may not be performed while step (a) is performed.

Initially, the constriction of the erectile portion can be calibrated by stimulating the erectile portion while adjusting the constriction of the erectile portion until the desired restriction of the venous blood flow in the erectile portion is obtained.

Flow Restriction

It should be understood that any embodiment or part of embodiment disclosed below in connection with flow restriction for constriction and stimulation devices combined in a constriction/stimulation unit could be used for the separate constriction device and separate stimulation device, where applicable.

In a principal embodiment of the invention, the erectile portion is constricted, so that the venous blood flow in the erectile portion at least is restricted and the constricted erectile portion is stimulated to at least further restrict the venous blood flow in the erectile portion. Specifically, the erectile portion is constricted to a constricted state, in which the blood circulation in the constricted erectile portion is substantially unrestricted and the venous blood flow in the erectile portion is at least restricted, and the constricted erectile portion is stimulated when it is in the constricted state to at least further restrict the venous blood flow in the erectile portion.

The constriction step (a) and stimulation step (b) are suitably performed to constrict and stimulate the erectile portion to an extent that depends on the flow restriction that is desired to be achieved in a specific application of the method of the invention. Thus, in accordance with a first flow restriction option, step (a) is performed by constricting the erectile portion, so that the venous blood flow in the erectile portion is restricted but not stopped, and step (b) is performed by stimulating the constricted erectile portion to cause contraction thereof, so that the venous blood flow in the erectile portion is further restricted but not stopped. The method may further comprise sensing a physical parameter of the patient and adjusting the intensity of the stimulation of the erectile portion in response to the sensed parameter.

In accordance with a second flow restriction option, step (a) is performed by constricting the erectile portion, so that the venous blood flow in the erectile portion is restricted but not stopped, and step (b) is performed by stimulating the constricted erectile portion to cause contraction thereof, so that the venous blood flow in the erectile portion is stopped.

When using the method of the invention in accordance with the first or second options, the method may further comprise (c) ceaseing stimulating the erectile portion to increase or allow the venous blood flow in the erectile portion and (d) releasing the erectile portion to restore the venous blood flow in the erectile portion.

In accordance with a third flow restriction option, step (a) is performed by constricting the erectile portion, so that the venous blood flow in the erectile portion is substantially stopped, and step (b) is performed by stimulating the constricted erectile portion to cause contraction thereof, so that the venous blood flow in the erectile portion is completely stopped. The method may further comprise (c) ceaseing stimulating the erectile portion to allow the venous blood flow in the erectile portion and (d) releasing the erectile portion to restore the venous blood flow in the erectile portion.

Where the constricted erectile portion is stimulated to contract, so that the venous blood flow in the erectile portion is stopped, a first length of the constricted erectile portion and a second length of the constricted erectile portion, which is located downstream of the first length, are suitably simultaneously and cyclically stimulated, wherein the first length is progressively stimulated in the upstream direction of the blood flow and the second length is progressively stimulated in the downstream direction of the blood flow.

Furthermore, when using the method of the invention in accordance with the second and third options, the method may further comprise sensing a physical parameter of the patient or functional parameter of implanted components and adjusting the stimulation of the erectile portion in response to the sensed parameter. For example, the intensity of the stimulation of the erectile portion may be increased in response to a sensed pressure increase in the exit erectile tissue blood vessels, so that the venous blood flow in the erectile portion remains stopped when a pressure increase occurs in the exit erectile tissue blood vessels. In particular, the method may comprise sensing a physical parameter of the patient's that relates to the pressure in the exit erectile tissue blood vessels, and controlling the stimulation of the erectile portion in response to the sensed parameter. Any sensor for sensing a physical parameter of the patient, such as a pressure in the patient's body that relates to the pressure in the exit erectile tissue blood vessels may be provided, wherein the stimulation is controlled in response to signals from the sensor. Such a sensor may for example sense the pressure in the patient's abdomen, the pressure against the implanted constriction device or the pressure on the tissue wall of the erectile portion.

In accordance with a fourth restriction option, step (a) is performed by constricting the erectile portion, so that the venous blood flow in the erectile portion is stopped. When needed, the erectile portion is released to restore the venous blood flow in the erectile portion. Step (b) is only performed by stimulating the constricted erectile portion to cause contraction thereof, so that the venous blood flow in the erectile portion remains stopped when a pressure increase occurs in the venous blood vessels. The method may further comprise sensing a physical parameter of the patient's body, such as a pressure in the patient's body that relates to the pressure in the exit erectile tissue blood vessels, and controlling the stimulation of the erectile portion in response to the sensed parameter. Such a physical parameter may be a pressure in the patient's abdomen and the sensor may be a pressure sensor.

In some applications of the method of the invention, continuous stimulation may over time change the physical properties of the tissue so that the tissue might be injured. Also, the effect of a continuous stimulation of the tissue wall may decrease over time. Therefore, step (b) is preferably performed by intermittently and individually stimulating different areas of the erectile portion so that the venous blood flow in the erectile portion continues to be restricted as desired and each area of the erectile portion essentially maintains its natural physical properties over time to prevent the area from being injured. Advantageously, each area of the erectile portion is stimulated during successive time periods, each time period being short enough to maintain over time satisfactory blood circulation in the area. Thus, the areas are stimulated so that an area that currently is not stimulated will have time to restore substantially normal blood circulation before it is stimulated again.

To maintain satisfactory blood circulation in the tissue wall of the erectile portion stimulation step (b) is suitably performed by stimulating one or more of different areas of the erectile portion at a time, preferably by sequentially stimulating the different areas of the erectile portion or by shifting the stimulation from one area to another over time. Preferably, stimulation step (b) is performed by cyclically propagating the stimulation of the areas along the erectile portion, for example in accordance with a determined stimulation pattern.

The method of the invention may further comprise controlling, preferably by the patient, at least one of the constriction and stimulation of the erectile portion from outside the patient's body.

Generally, the method of the invention comprises sensing a physical parameter of the patient and controlling, preferably automatically, at least one of the constriction and stimulation of the erectile portion in response to the sensed parameter.

The constriction step (a) may be performed by constricting any erectile portions of a series of erectile portions of the erectile portion, respectively, either in random or in accordance with a predetermined sequence. The stimulation step (b) may be performed by stimulating any of the constricted erectile portions of the series of erectile portions. Specifically, step (a) may be performed by constricting all of the erectile portions of the series of erectile portions, and step (b) may be performed by stimulating any constricted erectile portions in random or in accordance with a predetermined sequence to close the exit erectile tissue blood vessels.

To Summarize a Few Preferred Embodiments See Below:

In accordance with an alternative, step (a) is performed by constricting any erectile portions of a series of erectile portions, respectively. In accordance with an alternative, the erectile portions of the series of erectile portions are constricted in random or in accordance with a predetermined sequence.

In accordance with an alternative, step (b) is performed by stimulating any constricted erectile portions of the series of erectile portions. In accordance with an alternative, the erectile portions of the series of erectile portions are constricted in random or in accordance with a predetermined sequence. In accordance with an alternative, step (a) is performed by constricting any erectile portions of a series of erectile portions of the, respectively, wherein the erectile portions of the series of erectile portions are successively constricted without completely closing the exit erectile tissue blood vessels, and step (b) is performed by stimulating the constricted erectile portions, so that the erectile portions of the series of erectile portions are further constricted. In accordance with an alternative, the erectile portions of the series of erectile portions are constricted in random or in accordance with a predetermined sequence.

In accordance with an alternative, step (a) is performed by constricting all of the erectile portions of the series of erectile portions, and step (b) is performed by stimulating any constricted erectile portions so that the erectile portions of the series of erectile portions are further constricted.

In accordance with an alternative, the erectile portions of the series of erectile portions are further constricted by the stimulation device in random or in accordance with a predetermined sequence.

In accordance with an alternative for all applicable alternatives, step (a) and step (b) are performed independently of each other or in accordance with an alternative, step (a) and step (b) are performed simultaneously.

In any of the above noted embodiments step (b) may be performed by stimulating the erectile portion with electric pulses.

Stimulation Modes

When stimulating neural or muscular tissue there is a risk of injuring or deteriorating the tissue over time if the stimulation is not properly performed. The method of the present invention is performed to reduce or even eliminate that risk. Thus, step (b) is performed by intermittently stimulating different areas of the erectile portion so that at least two of the areas are stimulated at different points of time. I.e., the stimulation is shifted from one area to another area over time. In addition, step (b) is performed by intermittently stimulating the areas of the erectile portion so that an area of the different areas that currently is not stimulated has time to restore substantially normal blood circulation before it is stimulated again. Furthermore, step (b) is performed by intermittently stimulating the areas during successive time periods, wherein each time period is short enough to maintain satisfactory blood circulation in the area until the laps of the time period. This gives the advantage that the method of the present invention provides continuous stimulation of the erectile portion to achieve the desired flow control while essentially maintaining over time the natural physical properties of the erectile portion without risk of injuring the erectile portion.

Also, by physically changing the places of stimulation on the erectile portion over time as described above it is possible to create an advantageous changing stimulation pattern on the erectile portion, in order to achieve a desired flow control.

To achieve the desired reaction of the tissue wall during the stimulation thereof, step (b) may be performed by stimulating the erectile portion with, preferably cyclically, varying stimulation intensity.

In a main embodiment of the invention, step (b) is performed by intermittently stimulating the erectile portion with pulses, preferably in the form of pulse trains. The pulse trains can be configured in many different ways by varying pulse parameters. Thus, the pulse amplitudes of the pulses of the pulse trains, the off time periods between the individual pulses of each pulse train and the width and repetition frequency of each pulse may be varied. Also the off time periods between the pulse trains may be varied, wherein each off time period between the pulse trains is kept long enough to restore substantially normal blood circulation in each area of the erectile portion, when the area is not stimulated during the off time periods. Furthermore, the repetition frequency of the pulses of the pulse trains and the length and number of pulses of each pulse train may be varied.

As mentioned above, for reasons of maintaining over time the effect of stimulation, it is preferable that different areas of the erectile portion are intermittently and individually stimulated. In consequence, step (b) may be performed by stimulating one or more of the areas at a time with pulses, by cyclically propagating the stimulation of the areas with pulses along the erectile portion, and/or by propagating the stimulation of the areas with pulses in accordance with a determined stimulation pattern. In case the off time periods between pulse trains that stimulate the respective area of the erectile portion are varied, it is preferable that each off time period between the pulse trains is controlled to last long enough to restore substantially normal blood circulation in the area when the latter is not stimulated during the off time periods.

Electric Stimulation

In accordance with a preferred embodiment of the invention, step (b) is performed by electrically stimulating the erectile portion, preferably with electric pulses to cause contraction of the erectile portion. This embodiment is particularly suited for applications in which the patient's erectile portion includes muscle fibers that react to electrical stimula. Thus, the erectile portion that includes the muscle fibers is stimulated with such electric pulses, preferably in the form of electric pulse trains, when the erectile portion is in the constricted state, to cause contraction of the erectile portion. Of course, the configuration of the electric pulse trains may be similar to the above described pulse trains and different areas of the erectile portion may be electrically stimulated in the same manner as described above.

In accordance with the preferred embodiment, the method of the invention comprises providing at least one, preferably a plurality of electrical elements, such as electrodes, engaging and stimulating the erectile portion with electric pulses. Optionally, the electrical elements may be placed in a fixed orientation relative to one another. The method comprises electrically energizing the electrical elements, preferably by cyclically energizing each element with electric pulses. The electrical elements may be energized so that the electrical elements are energized one at a time in sequence, or so that a number or groups of the electrical elements are energized at a time. Also, groups of electrical elements may be sequentially energized, either randomly or in accordance with a predetermined pattern.

The method may further comprise applying the electrical elements on the patient's erectile portion so that the electrical elements form any pattern of electrical elements, preferably an elongate pattern of electrical elements extending lengthwise along the erectile portion and the elements abut the respective areas of the erectile portion. The electrical elements may be successively energized along the elongate pattern of electrical elements in a direction opposite to or in the same direction as that of the flow in the patient's erectile blood vessels. Optionally, the electrical elements may be successively energized along the elongate pattern of electrical elements from a position substantially at the center of the constricted erectile portion towards both ends of the elongate pattern of electrical elements. The electrical elements may be energized so that energized electrical elements form two waves of energized electrical elements that simultaneously advance from the center of the constricted erectile portion in two opposite directions towards both ends of the elongate pattern of electrical elements. Such waves of energized electrical elements can be repeated over and over again without harming the erectile portion and without moving blood in any direction in the exit erectile tissue blood vessels.

The elongate pattern of electrical elements may include one or more rows of electrical elements extending lengthwise along the erectile portion. Each row of electrical elements may form a straight, helical or zig-zag path of electrical elements, or any form of path. The electrical elements may be energized so that the electrical elements currently energized form at least one group of adjacent energized electrical elements, wherein the elements in the group of energized electrical elements form a path of energized electrical elements extending at least in part around the patient's erectile portion, preferably completely around the patient's erectile portion. Alternatively, the elements in the group of energized electrical elements form two paths of energized electrical elements extending on mutual sides of the erectile portionerectile portion or more than two paths of energized electrical elements extending on different sides of the erectile portion, preferably at least substantially transverse to the flow direction in the exit erectile tissue blood vessels.

In an embodiment of the invention, the electrical elements form a plurality of groups of elements, wherein the groups form a series of groups extending along the erectile portion in the flow direction in the patient's lumen. The electrical elements of each group of electrical elements may form a path of elements extending at least in part around the erectile portion. In a first alternative, the electrical elements of each group of electrical elements may form more than two paths of elements extending on different sides of the erectile portion, preferably substantially transverse to the flow direction in the patient's lumen. The groups of electrical elements in the series of groups may be energized in random or in accordance with a predetermined pattern. Alternatively, the groups of electrical elements in the series of groups may be successively energized in a direction opposite to or in the same direction as that of the flow in the patient's lumen, or in both said directions starting from a position substantially at the center of the constricted erectile portion. For example, groups of energized electrical elements may form advancing waves of energized electrical elements, as described above. I.e., the groups of electrical elements may be energized so that energized electrical elements form two waves of energized electrical elements that simultaneously advance from the center of the constricted erectile portion in two opposite directions towards both ends of the elongate pattern of electrical elements.

Thermal Stimulation

In accordance with an embodiment of the invention, stimulation step (b) is performed by thermally stimulating the erectile portion. Thus, the erectile portion may be cooled, when the erectile portion is constricted, to cause contraction of the erectile portion. For example, the erectile portion may be constricted to at least restrict the venous blood flow in the erectile portion, and the constricted erectile portion may be cooled to cause contraction thereof, so that the venous blood flow in the erectile portion is at least further restricted, or further restricted but not stopped, or stopped. Alternatively, the erectile portion may be heated, when the erectile portion is constricted and contracted, to cause expansion of the erectile portion. Where applicable, thermal stimulation may be practised in any of the embodiments of the present invention, and the thermal stimulation may be controlled in response to various sensors, for example strain, motion or pressure sensors.

Constriction and Stimulation Devices

It should be understood that any embodiment or part of embodiment for the combined stimulation device and constriction device, could be used, where applicable, for any one of the devices as a stand alone device.

Generally, the method of the invention comprises providing a constriction device that constricts the erectile portion, a stimulation device that stimulates the constricted erectile portion and a control device that controls the constriction device and/or the stimulation device. The method comprises operating the control device from outside the patient's body, preferably by using the control device to wirelessly control the constriction device and/or stimulation device. The wireless control is preferably performed in a non-magnetic manner, whereby implanted magnetic devices can be avoided. Suitably, the control device comprises a hand-held wireless remote control operated by the patient.

Alternatively, the control device comprises a manually operable switch for switching on and off the constriction device and/or stimulation device. In this case, the method comprises subcutaneously implanting the switch in the patient and manually operating the the implanted switch from outside the patient's body.

In an embodiment of the invention, the control device comprises a programmable internal control unit, such as a microprocessor, and the method comprises implanting in the patient the internal control unit and controlling by the internal control unit the constriction device and/or stimulation device. The control device may also comprise an external control unit outside the patient's body. In this case, the method comprises controlling by the external control unit the constriction device and/or stimulation device and, optionally, using the external control unit to program the implanted internal control unit. The internal control unit may be programmable for controlling the constriction device and/or stimulation device over time, for example in accordance with an activity schedule program.

The constriction of the erectile portion can be calibrated by using the control device to control the stimulation device to stimulate the erectile portion while controlling the constriction device to adjust the constriction of the erectile portion until the desired restriction of the venous blood flow in the erectile portion is obtained.

Sensor Controlled Constriction and/or Stimulation

It should be understood that any embodiment or part of embodiment disclosed below in connection with sensor control of the constriction and stimulation devices combined in the constriction/stimulation unit could be used for the separate constriction device and separate stimulation device, where applicable. In an embodiment of the invention, the method comprises implanting at least one sensor and controlling by the control device the constriction device and/or the stimulation device in response to signals from the sensor. Generally, the sensor directly or indirectly senses at least one physical parameter of the patient, functional parameter of the apparatus, or functional parameter of a medical implant in the patient.

Many different kinds of sensor for sensing physical parameters may be used. For example motion sensors for sensing organ motion, i.e. natural contractions, pressure sensors for sensing pressure in the erectile tissue, strain sensors for sensing strain of the erectile tissue, flow sensors for sensing venous blood flow in the erectile portion, spectro-photometrical sensors, or sensors for sensing the distribution of the stimulation on the stimulated erectile tissue. Any conceivable sensors for sensing any other kind of useful physical parameter may be used.

Many different kinds of sensors that sense functional parameters of implanted components may also be used for the control of the constriction device and/or the stimulation device. For example sensors for sensing electric parameters of implanted electric components, or sensors for sensing the performance of implanted motors or the like.

The sensor may comprise a pressure sensor for sensing as the physical parameter a pressure in the patient's body that relates to the pressure in the exit erectile tissue blood vessels. In this case, the method suitably comprises operating the control device to control the constriction device to change the constriction of the patient's erectile portion in response to the pressure sensor sensing a predetermined value of measured pressure.

The above described sensors may be used in any of the embodiments of the invention, where applicable.

The control device may comprise an implantable internal control unit that directly controls the constriction device and/or stimulation device in response to signals from the sensor. The control device may further comprise a wireless remote control adapted to set control parameters of the internal control unit from outside the patient without mechanically penetrating the patient. At least one of the control parameters, which is settable by the wireless remote control, is the physical or functional parameter Alternatively, the control device may comprise an external control unit outside the patient's body for controlling the constriction device and/or stimulation device in response to signals from the sensor.

Constriction of Erectile Tissue Portion

It should be understood that any embodiment or part of embodiment disclosed below in connection with constricting the erectile portion could be used for the separate constriction device and separate stimulation device, where applicable.

Method step (a) may be performed in many different ways. Thus, step (a) may be performed by:
(1)—constricting the erectile portion so that the through-flow area of the blood vessel passageway assumes a size in the constricted state small enough to cause the constricted erectile portion to contract to stop the venous blood flow in the erectile portion when step (b) is performed;
(2)—bending the erectile portion;
(3)—clamping the erectile portion between at least two elements positioned on different sides of the erectile portion;
(4)—clamping the erectile portion between an element and the bone or tissue of the patient;
(5)—rotating at least two elements positioned on different sides of the erectile portion; or
(6)—clamping the erectile portion between at least two articulated clamping elements positioned on different sides of the erectile portion.

In the above noted alternatives (1) to (6) of method step (a), the constriction of the erectile portion may be changed either mechanically or hydraulically. For many applications of the present invention, step (a) is suitably performed so that the through-flow area of the blood vessel passageway assumes a size in the constricted state that is small enough to enable the stimulation during step (b) to contract the erectile portion to stop the venous blood flow in the erectile portion.

Where the constriction of the erectile portion is hydraulically changed, the method of the invention may further comprise implanting in the patient a reservoir containing a predetermined amount of hydraulic fluid, and a constriction device engaging the erectile portion and having an expandable/contractible cavity, wherein step (a) is performed by distributing hydraulic fluid from the reservoir to increase the volume of the cavity to constrict the erectile portion, and by distributing hydraulic fluid from the cavity to the reservoir to decrease the volume of the cavity to release the erectile portion. The cavity may be defined by a balloon of the constriction device that abuts the tissue erectile portion, so that the patient's erectile portion is constricted upon expansion of the cavity and released upon contraction of the cavity.

Alternatively, the cavity may be defined by a bellows that displaces a relatively large contraction element of the constriction device, for example a large balloon that abuts the erectile portion, so that the patient's erectile portion is constricted upon contraction of the bellows and released upon expansion of the bellows. Thus, a relatively small addition of hydraulic fluid to the bellows causes a relatively large increase in the constriction of the erectile portion. Such a bellows may also be replaced by a suitably designed piston/cylinder mechanism.

Where the hydraulic means comprises a cavity in the constriction device, the following embodiments of the invention are conceivable.

1) The reservoir comprises first and second wall portions, and step (a) is performed by displacing the first and second wall portions relative to each other to change the volume of the reservoir, so that fluid is distributed from the reservoir to the cavity, or from the cavity to the reservoir.

1a) At least one of a magnetic device, a hydraulic device or an electric control device displaces the first and second wall portions of the reservoir.

2) A pump is provided for pumping fluid between the reservoir and the cavity.

2a) The pump comprises a first activation member for activating the pump to pump fluid from the reservoir to the cavity and a second activation member for activating the pump to pump fluid from the cavity to the reservoir.

2a1) The first and second activation members are operable by manual manipulation thereof.

2a2) At least one of the activation members operates when subjected to an external predetermined pressure.

2a3) At least one of the first and second activating members is operable by magnetic means, hydraulic means, or electric control means.

2b) A fluid conduit between the pump and the cavity is provided, wherein the reservoir forms part of the conduit. The conduit and pump are devoid of any non-return valve. The reservoir forms a fluid chamber with a variable volume, and the pump distributes fluid from the chamber to the cavity by a reduction in the volume of the chamber and withdraws fluid from the cavity by an expansion of the volume of the chamber. A motor is provided for driving the pump, wherein the pump comprises a movable wall of the reservoir for changing the volume of the chamber.

In all of the above noted embodiments 1 to 2b where the hydraulic means comprises an expandable cavity in the constriction device, the cavity can be exchanged by a cylinder/piston mechanism for adjusting the constriction device. In this case, hydraulic fluid is distributed between the reservoir and the cylinder/piston mechanism to adjust the constriction device.

3) The method further comprises implanting a reverse servo operatively connected to the hydraulic means. The term "reverse servo" is to be understood as a mechanism that transfers a strong force acting on a moving element having a short stroke into a weak force acting on another moving element having a long stroke; i.e., the reverse function of a normal servo mechanism. Thus, minor changes in the amount of fluid in a smaller reservoir could be transferred by the reverse servo into major changes in the amount of fluid in a larger reservoir.

Preferably, the reverse servo comprises an expandable servo reservoir containing servo fluid and a fluid supply reservoir hydraulically connected to the servo reservoir to form a closed conduit system for the servo fluid. The expandable servo reservoir has first and second wall portions, which are displaceable relative to each other in response to a change in the volume of the expandable servo reservoir.

In accordance with a first alternative, the first and second wall portions of the servo reservoir are operatively connected to the hydraulic means. The reverse servo distributes fluid between the fluid supply reservoir and the expandable servo reservoir to change the volume of the servo reservoir, whereby the hydraulic means is operated to adjust the constriction device.

In accordance with a second alternative, there is provided an implantable main reservoir containing a predetermined amount of hydraulic fluid, wherein the reverse servo is operated to distribute hydraulic fluid between the main reservoir and the hydraulic means to adjust the constriction device. More specifically, the main reservoir is provided with first and second wall portions operatively connected to the first and second wall portions of the expandable servo reservoir, so that the volume of the main reservoir is changed when the volume of the expandable servo reservoir is changed. Thus, when the reverse servo distributes servo fluid between the fluid supply reservoir and the expandable servo reservoir to change the volume of the main reservoir, hydraulic fluid is distributed from the main reservoir to the hydraulic means, or from the hydraulic means to the main reservoir. Advantageously, the method comprises dimensioning the servo and main reservoirs, so that when the volume of the servo reservoir is changed by a relatively small amount of servo fluid, the volume of the main reservoir is changed by a relatively large amount of hydraulic fluid.

In both of the above-described alternatives, the fluid supply reservoir may have first and second wall portions, which are displaceable relative to each other to change the volume of the fluid supply reservoir to distribute servo fluid between the fluid supply reservoir and the expandable servo reservoir. The first and second wall portions of the fluid supply reservoir may be displaced relative to each other by manual manipulation, a magnetic device, a hydraulic device, or an electric control device to change the volume of the fluid supply reservoir to distribute servo fluid between the fluid supply reservoir and the expandable servo reservoir.

In all of the above noted embodiments 1 to 2b where the hydraulic means comprises an expandable cavity in the constriction device, or in embodiments where the hydraulic means includes a hydraulically operable mechanical construction, the reverse servo described above may be used. In a further embodiment of the invention, the hydraulic means include first and second hydraulically interconnected expandable/contractible reservoirs. The first reservoir is operatively connected to the constriction device, so that the constriction device changes the constriction of the patient's erectile portion upon expansion or contraction of the first reservoir. By changing the volume of the second reservoir hydraulic fluid is distributed between the two reservoirs, so that the first reservoir is either expanded or contracted. This embodiment requires no non-return valve in the fluid communication conduits between the two reservoirs, which is beneficial to long-term operation of the hydraulic means.

Alternatively, the hydraulic means may include first and second hydraulically interconnected piston/cylinder mechanisms instead of the first and second reservoirs described above. The first piston/cylinder mechanism is operatively connected to the constriction device, so that the constriction device changes the constriction of the patient's erectile portion upon operation of the first piston/cylinder mechanism. By operating the second piston/cylinder mechanism hydraulic fluid is distributed between the two piston/cylinder mechanisms, so that the first piston/cylinder mechanism adjusts the constriction device.

Where the constriction device does not include an expandable/contractible cavity, the constriction device may comprise at least two elongated clamping elements extending along the erectile portion on different sides of the erectile portion. The hydraulic means, which may include the reverse servo described above, hydraulically moves the elongated clamping elements towards the erectile portion to constrict the erectile portion. For example, the constriction device may have hydraulic chambers in which the clamping elements slide back and forth, and the hydraulic means may also include a pump and an implantable reservoir containing hydraulic fluid. The pump distributes hydraulic fluid from the reservoir to the chambers to move the clamping elements against the erectile portion, and distributes hydraulic fluid from the chambers to the reservoir to move the clamping elements away from the erectile portion.

Energy Supply

It should be understood that any embodiment or part of embodiment disclosed below in connection with the power of the constriction and stimulation devices combined in the constriction/stimulation unit could be used for the separate constriction device and separate stimulation device, where applicable.

Generally, method step (a) is performed by using the constriction device and step (b) is performed by using the stimulation device, wherein the method further comprises forming the constriction and stimulation devices in an operable constriction/stimulation unit.

In a simple form of the invention, the method comprises implanting a source of energy, such as a battery, rechargeable battery or accumulator, releasing energy from the source of energy and using the released energy in connection with the operation of the constriction/stimulation unit.

In a more sophisticated form of the invention, which is preferable, the method comprises transmitting wireless energy from outside the patient's body to inside the patient's body and using the transmitted wireless energy in connection with the operation of the constriction/stimulation unit.

Transmission of Wireless Energy

It should be understood that any embodiment or part of embodiment disclosed below in connection with wireless control or power of the constriction and stimulation devices combined in the constriction/stimulation unit could be used for the separate constriction device and separate stimulation device, where applicable.

The wireless energy may be directly used in connection with the operation of the constriction/stimulation unit, as the wireless energy is being transmitted. For example, the wireless energy may be transmitted in the form of an electric, an electromagnetic or a magnetic field, or a combination thereof, or electromagnetic waves for direct power of the constriction/stimulation unit. For example, where an electric motor or pump operates the constriction device of the constriction/stimulation unit, wireless energy in the form of a magnetic or an electromagnetic field may be used for direct power of the motor or pump.

Thus, the motor or pump is running directly during transmission of the wireless energy. This may be achieved in two different ways: a) using a transforming device implanted in the patient to transform the wireless energy into energy of a different form, preferably electric energy, and powering the motor or pump with the transformed energy, or b) using the wirelessly transmitted energy to directly power the motor or pump. Preferably wireless energy in the form of an electromagnetic or magnetic field is used to directly influence specific components of the motor or pump to create kinetic energy. Such components may include coils integrated in the motor or pump.

The wireless energy is suitably transmitted in pulses or digital pulses, or a combination of pulses and digital pulses.

Preferably, the wireless energy is transmitted in at least one wireless signal, suitably a wave signal. The wave signal may comprise an electromagnetic wave signal including one of an infrared light signal, a visible light signal, an ultra violet light signal, a laser signal, a microwave signal, a radio wave signal, an x-ray radiation signal, and a gamma radiation signal. Alternatively, the wave signal may comprise a sound or an ultrasound wave signal. The wireless signal may be a digital or analogue signal, or a combination of a digital and analogue signal.

In accordance with a particular embodiment of the invention, the wireless energy is not for direct use in connection with the operation of the constriction/stimulation unit. In this embodiment the wireless energy comprises energy of a first form, which is transmitted into energy of a second form suited to operate the constriction/stimulation unit. Typically, the energy of the second form is different from the energy of the first form. For example, the wireless energy of the first form may comprise sound waves, whereas the energy of the second form may comprise electric energy. Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

Transforming Wireless Energy

It should be understood that any embodiment or part of embodiment disclosed below in connection with the control or energizing of the constriction and stimulation devices combined in the constriction/stimulation unit could be used for the separate constriction device and separate stimulation device, where applicable.

In accordance with a particular embodiment of the invention, an implantable energy-transforming device is provided for transforming wireless energy of a first form transmitted by the energy-transmission device into energy of a second form, which typically is different from the energy of the first form. The constriction/stimulation unit is operable in response to the energy of the second form. For example, the wireless energy of the first form may comprise sound waves, whereas the energy of the second form may comprise electric energy. Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transforming device may function different from or similar to the energy-transmission device. Advantageously, the energy-transforming device comprises at least one element, such as at least one semiconductor, having a positive region and a negative region, when exposed to the energy of the first form transmitted by the energy-transmission device, wherein the element is capable of creating an energy field between the positive and negative regions, and the energy field produces the energy of the second form. More specifically, the element may comprise an electrical junction element, which is capable of inducing an electric field between the positive and negative regions when exposed to the energy of the first form transmitted by the energy-transmission device, whereby the energy of the second form comprises electric energy.

The energy of the first form may directly or indirectly be transformed into the energy of the second form. The method of the invention may comprise providing a motor for operating the constriction device and powering the motor with the energy of the second form. The constriction device may be operable to perform at least one reversible function and the method may comprise reversing the function by using the motor. For example, the method may comprise shifting the polarity of the energy of the second form to reverse the motor.

The motor may be directly powered with the transformed energy, as the energy of the second form is being transformed from the energy of the first form. Preferably, the constriction/stimulation unit is directly operated with the energy of the second form in a non-magnetic, non-thermal or non-mechanical manner.

Normally, the implanted constriction/stimulation unit comprises electric components that are energized with electrical energy. Therefore, the energy of the first form may be transformed into a direct current or pulsating direct current, or a combination of a direct current and pulsating direct current. Alternatively, the energy of the first form may be transformed into an alternating current or a combination of a direct and alternating current.

The method of the invention may comprise implanting in the patient an internal source of energy, and supplying energy from the internal source of energy for the operation of the constriction/stimulation unit. The method may further comprise implanting in the patient a switch operable to switch from an "off" mode, in which the internal source of energy is not in use, to an "on" mode, in which the internal source of energy supplies energy for the operation of the constriction/stimulation unit, and/or for energizing implanted electronic components of the constriction/stimulation unit. The switch may be operated by the energy of the first form or by the energy of the second form. The described switch arrangement reduces power consumption of the constriction/stimulation unit between operations.

The internal source of energy may store the energy of the second form. In this case, the internal source of energy suitably comprises an accumulator, such as at least one capacitor or at least one rechargeable battery, or a combination of at least one capacitor and at least one rechargeable battery. Where the internal source of energy is a rechargeable battery it may be charged only at times convenient for the patient, for example when the patient is sleeping. Alternatively, the internal source of energy may supply energy for the operation of the constriction/stimulation unit but not be used for storing the energy of the second form. In this alternative, the internal source of energy may be a battery and the switch described above may or may not be provided.

Suitably, the method of the invention may comprise implanting a stabilizer for stabilizing the energy of the second form. Where the energy of the second form comprises electric energy the stabilizer suitably comprises at least one capacitor.

The energy-transforming device may be designed for implantation subcutaneously in the abdomen, thorax or cephalic region of the patient. Alternatively, it may be designed for implantation in an orifice of the patient's body and under the mucosa or intramuscularly outside the mucosa of the orifice.

Control of Constriction/stimulation Unit

It should be understood that any embodiment or part of embodiment disclosed below in connection with the control of the constriction and stimulation devices combined in the constriction/stimulation unit could be used for the separate constriction device and separate stimulation device, where applicable.

Although the constriction device of the constriction/stimulation unit may normally keep the patient's erectile portion in the constricted state, in most applications using the present invention there will be adjustments of the constriction device. Therefore, in a preferred embodiment of the invention, the constriction device is adjustable to enable changing the constriction of the patient's erectile portion as desired and the control device controls the constriction device to change the constriction of the erectile portion.

The method of the invention suitably comprises operating the control device by the patient. In a simple form the control device comprises a manually operable switch for switching on and off the constriction/stimulation unit, and the method further comprises subcutaneously implanting the switch in the patient. It is preferable, however, that the control device comprises a hand-held wireless remote control operable by the patient from outside the patient's body to control the constriction/stimulation unit to adjust the stimulation intensity and/or adjust the constriction of the erectile portion. The wireless remote control is suitably designed for application on the patient's body like a wristwatch.

In some applications of the invention, the constriction device of the constriction/stimulation unit may be designed to normally keep the patient's erectile portion in the constricted state. I.e., after implantation the constriction device all the time keeps the erectile portion slightly constricted. In this case, the control device may be used when desired by the patient, to control the stimulation device of the constriction/stimulation unit to stimulate the constricted erectile portion, preferably while adjusting the stimulation intensity, to cause contraction of the erectile portion, so that the venous blood flow in the erectile portion is at least further restricted or stopped to obtain engorgement with blood of the female erectile tissue, and, later, to control the stimulation device to cease the stimulation. More precisely, the method of the invention may comprise operating the control device by the patient to a) control the stimulation device in a first mode to stimulate the constricted erectile portion to further restrict the venous blood flow in the erectile portion and control the stimulation device in a second mode to cease the stimulation of the erectile portion to increase the venous blood flow in the erectile portion; or b) control the stimulation device in a first mode to stimulate the constricted erectile portion to stop the venous blood flow in the erectile portion and control the stimulation device in a second mode to cease the stimulation of the erectile portion to allow venous blood flow in the erectile portion.

Either the first mode or the second mode may be temporary.

The wireless remote control preferably transmits at least one wireless control signal for controlling the constriction/stimulation unit. The control signal may comprise a frequency, amplitude, phase modulated signal or a combination thereof, and may be an analogue or a digital signal, or a combination of an analogue and digital signal. The remote control may transmit an electromagnetic carrier wave signal for carrying the digital or analogue control signal. Also the carrier signal may comprise digital, analogue or a combination of digital and analogue signals.

Any of the above signals may comprise wave signals, such as a sound wave signal, an ultrasound wave signal, an electromagnetic wave signal, an infrared light signal, a visible light signal, an ultra violet light signal, a laser light signal, a micro wave signal, a radio wave signal, an x-ray radiation signal or a gamma radiation signal.

Alternatively, the control signal may comprise an electric or magnetic field, or a combined electric and magnetic field.

Operation of Constriction/stimulation Unit

It should be understood that any embodiment or part of embodiment for operating the combined stimulation device and constriction device, could be used, if applicable, for any one of the devices as a stand alone device.

The method of the invention may comprise implanting in the patient an operation device, and operating the constriction/stimulation unit with the operation device. A magnet may be provided, wherein the method comprises using the magnet to activate the operation device from outside the patient's body. The operation device suitably comprises a motor which is powered with energy released from a source of energy, such as a battery. Although the constriction/stimulation unit in embodiments described above suitably is designed as a single piece, which is most practical for implantation, it should be noted that as an alternative the constriction device and stimulation device of the constriction/stimulation unit could be designed as separate pieces.

Laparoscopic Method

The present invention also provides a first method for treating sexual dysfunction of a female patient, the method comprising the steps of:
inserting a needle like tube into a cavity of the patients body,
using the needle like tube to fill the cavity with gas thereby expanding the cavity,
placing at least two laparoscopical trocars in the patient's body,
inserting a camera through one of the trocars into the cavity,
inserting a dissecting tool through any of the trocar and dissecting an area of at least one portion of the tissue wall of the erectile portion,
placing a constriction device and a stimulation device in the dissected area in operative engagement with the erectile portion,
using the constriction device to gently constrict the erectile portion of the erectile portion to restrict the venous blood flow in the erectile portion, and
using the stimulation device to stimulate the constricted erectile portion to cause contraction of the erectile portion to further restrict the venous blood flow in the erectile portion to obtain engorgement with blood of the female erectile tissue.

The present invention also provides a second method for treating sexual dysfunction of a female patient, the method comprising the steps of:
inserting a needle like tube into a cavity of the patients body,
using the needle like tube to fill the cavity with gas thereby expanding the cavity,
placing at least two laparoscopical trocars in the patient's body,
inserting a camera through one of the trocars into the cavity,
inserting a dissecting tool through any of the trocar and dissecting an area of at least one portion of the tissue wall of the erectile portion,
placing a stimulation device in the dissected area in operative engagement with the erectile portion, and
using the stimulation device to stimulate the erectile portion to cause contraction of the erectile portion to restrict the venous blood flow in the erectile portion to obtain engorgement with blood of the female erectile tissue.

The present invention also provides a third method for treating sexual dysfunction of a female patient, the method comprising the steps of:
inserting a needle like tube into a cavity of the patients body,
using the needle like tube to fill the cavity with gas thereby expanding the cavity,
placing at least two laparoscopical trocars in the patient's body,
inserting a camera through one of the trocars into the cavity,
inserting a dissecting tool through any of the trocar and dissecting an area of at least one portion of the tissue wall of the erectile portion,
placing a a constriction device in the dissected area in operative engagement with the erectile portion,
using the constriction device to constrict the erectile portion of the erectile portion to restrict the venous blood flow in the erectile portion to obtain engorgement with blood of the female erectile tissue.

The present invention also provides a fourth method for treating sexual dysfunction of a female patient, the method comprising the steps of:
cutting the skin of the patient,
inserting a dissecting tool and dissecting an area of at least one portion of the tissue wall of the erectile portion,
placing a constriction device and a stimulation device in the dissected area in operative engagement with the erectile portion,
using the constriction device to gently constrict the erectile portion of the erectile portion to restrict the venous blood flow in the erectile portion, and
using the stimulation device to stimulate the constricted erectile portion to cause contraction of the erectile portion to further influence the venous blood flow in the erectile portion to obtain engorgement with blood of the female erectile tissue.

The present invention also provides a fifth method for treating sexual dysfunction of a female patient. The method comprises the steps of:
cutting the skin of the patient,
inserting a dissecting tool and dissecting an area of at least one portion of the tissue wall of the erectile tissue, placing a stimulation device in the dissected area in operative engagement with the erectile tissue, and using the stimulation device to stimulate the erectile portion to cause contraction of the erectile portion to influence the venous blood flow in the erectile portion.

The present invention also provides a sixth method for treating sexual dysfunction of a female patient, the method comprising the steps of:

cutting the skin of the patient, inserting a dissecting tool and dissecting an area of at least one portion of the tissue wall of the erectile portion, placing a stimulation device in the dissected area in operative engagement with the erectile portion, and using the stimulation device to stimulate the erectile portion to cause contraction of the erectile portion to restrict the venous blood flow in the erectile portion to obtain engorgement with blood of the female erectile tissue.

In all of the above-noted methods 1-3 the cavity may constitute an abdominal cavity a cavity in the pelvic region, a cavity in human soft tissue, or muscle, or fat or fibrotic tissue.

The method further comprises implanting a powered operation device for operating the constriction device. The operation device may comprise a powered hydraulic operation device or an electrically powered operation device, such as an electric motor.

The method further comprises transmitting wireless energy for powering the operation device, and when desired to influence the flow in the erectile portion, powering the operation device with the transmitted energy to operate the constriction device.

Pregnancy Control

Egg Movement Control

An object of the present invention is to provide a method for controlling the movement of eggs in the uterine tubes of a female patient.

In accordance with this object of the present invention, there is provided a method for controlling a flow of eggs in an uterine tube of a female patient, the method comprising:

a) gently constricting at least one portion of the uterine tube wall to influence the flow of eggs in the uterine tube, using a constriction device, or b) stimulating at least one portion of the uterine tube wall to cause contraction of the uterine tube wall portion to further influence the flow of eggs in the uterine tube, using a stimulation device.

In accordance with the preferred object of the present invention, there is provided method for controlling a flow of eggs in a uterine tube of a female patient, the method comprising:

gently constricting at least one portion of the uterine tube wall to influence the flow of eggs in the uterine tube, using a constriction device, and stimulating at least one portion of the uterine tube wall to cause contraction of the uterine tube wall portion to further influence the flow of eggs in the uterine tube, using a stimulation device.

The present invention provides an advantageous combination of the method steps (a) and (b), which results in a two-stage influence on the flow of eggs in the uterine tube. Thus, applying a relatively weak force against the uterine tube wall portion gently constricts the uterine tube wall and the constricted wall portion is stimulated to achieve the desired final influence on the flow of eggs in the uterine tube. The phrase "gently constricts a portion of the uterine tube wall" is to be understood as constricting the uterine tube wall portion without substantially hampering the blood circulation in the uterine tube wall.

Preferably, step (b) is performed by intermittently and individually stimulating different areas of the uterine tube wall portion. Such an intermittent and individual stimulation of different areas of the uterine tube wall portion of the uterine tube wall allows tissue of the uterine tube wall portion to maintain over time substantially normal blood circulation.

Preferably, the constriction step (a) and stimulation step (b) are performed independently of each other. Steps (a) and (b) may be performed simultaneously. Optionally, step (b) may or may not be performed while step (a) is performed.

Initially, the constriction of the uterine tube wall portion can be calibrated by stimulating the uterine tube wall portion while adjusting the constriction of the uterine tube wall portion until the desired restriction of the flow of eggs in the uterine tube is obtained.

The term uterine tube of course also includes the two uterine tubes. The term eggs of course include one egg. Any embodiment or part of embodiment may be combined in several different casings. Preferable two constriction units, one power supply.

Flow Restriction

It should be understood that any embodiment or part of embodiment disclosed below in connection with flow restriction for the constriction and stimulation devices combined in the constriction/stimulation unit could be used for the separate constriction device and separate stimulation device, where applicable. The method of the present invention is well suited for restricting the flow of eggs in the uterine tube. Thus, in a principal embodiment of the invention, the uterine tube wall portion is constricted, so that the flow of eggs in the uterine tube at least is restricted and the constricted wall portion is stimulated to at least further restrict the flow of eggs in the uterine tube. Specifically, the uterine tube wall portion is constricted to a constricted state, in which the blood circulation in the constricted wall portion is substantially unrestricted and the flow of eggs in the uterine tube is at least restricted, and the constricted wall portion is stimulated when it is in the constricted state to at least further restrict the flow of eggs in the uterine tube.

The constriction step (a) and stimulation step (b) are suitably performed to constrict and stimulate the uterine tube wall portion to an extent that depends on the flow restriction that is desired to be achieved in a specific application of the method of the invention. Thus, in accordance with a first flow restriction option, step (a) is performed by constricting the uterine tube wall portion, so that the flow of eggs in the uterine tube is restricted but not stopped, and step (b) is performed by stimulating the constricted wall portion to cause contraction thereof, so that the flow of eggs in the uterine tube is further restricted but not stopped. The method may further comprise sensing a physical parameter of the patient and adjusting the intensity of the stimulation of the uterine tube wall portion in response to the sensed parameter.

In accordance with a second flow restriction option, step (a) is performed by constricting the uterine tube wall portion, so that the flow of eggs in the uterine tube is restricted but not stopped, and step (b) is performed by stimulating the constricted wall portion to cause contraction thereof, so that the flow of eggs in the uterine tube is stopped.

When using the method of the invention in accordance with the first or second options, the method may further comprise (c) ceaseing stimulating the uterine tube wall portion to increase or allow the flow of eggs in the uterine tube and (d) releasing the uterine tube wall portion to restore the flow of eggs in the uterine tube.

In accordance with a third flow restriction option, step (a) is performed by constricting the uterine tube wall portion, so that the flow of eggs in the uterine tube is substantially stopped, and step (b) is performed by stimulating the constricted wall portion to cause contraction thereof, so that the flow of eggs in the uterine tube is completely stopped. The method may further comprise (c) ceaseing stimulating the uterine tube wall portion to allow the flow of eggs in the uterine tube and (d) releasing the uterine tube wall portion to restore the flow of eggs in the uterine tube.

Where the constricted wall portion is stimulated to contract, so that the flow of eggs in the uterine tube is stopped, a first length of the constricted wall portion and a second length of the constricted wall portion, which is located downstream of the first length, are suitably simultaneously and cyclically stimulated, wherein the first length is progressively stimulated in the upstream direction of the uterine tube and the second length is progressively stimulated in the downstream direction of the uterine tube.

Furthermore, when using the method of the invention in accordance with the second and third options, the method may further comprise sensing a physical parameter of the patient or functional parameter of implanted components and adjusting the stimulation of the uterine tube wall portion in response to the sensed parameter. For example, the intensity of the stimulation of the uterine tube wall portion may be increased in response to a sensed pressure increase in the uterine tube, so that the flow of eggs in the uterine tube remains stopped when a pressure increase occurs in the uterine tube. In particular, the method may comprise sensing a physical parameter of the patient's that relates to the pressure in the uterine tube, and controlling the stimulation of the uterine tube wall portion in response to the sensed parameter. Any sensor for sensing a physical parameter of the patient, such as a pressure in the patient's body that relates to the pressure in the uterine tube may be provided, wherein the stimulation is controlled in response to signals from the sensor. Such a sensor may for example sense the pressure in the patient's abdomen, the pressure against the implanted constriction device or the pressure on the uterine tube wall. For example, a pressure sensor may be applied where the present invention is used for controlling flow of eggs of a female patient.

In accordance with a fourth restriction option, step (a) is performed by constricting the uterine tube wall portion, so that the flow of eggs in the uterine tube is stopped. When needed, the uterine tube wall portion is released to restore the flow of eggs in the uterine tube. Step (b) is only performed by stimulating the constricted wall portion to cause contraction thereof, so that the flow of eggs in the uterine tube remains stopped when a pressure increase occurs in the uterine tube. The method may further comprise sensing a physical parameter of the patient's body, such as a pressure in the patient's body that relates to the pressure in the uterine tube, and controlling the stimulation of the uterine tube wall portion in response to the sensed parameter. Such a physical parameter may be a pressure in the patient's abdomen and the sensor may be a pressure sensor.

In some applications of the method of the invention, continuous stimulation may over time change the physical properties of the tissue so that the tissue might be injured. Also, the effect of a continuous stimulation of the uterine tube wall may decrease over time. Therefore, step (b) is preferably performed by intermittently and individually stimulating different areas of the uterine tube wall portion so that the flow of eggs in the uterine tube continues to be restricted as desired and each area of the uterine tube wall portion essentially maintains its natural physical properties over time to prevent the area from being injured. Advantageously, each area of the uterine tube wall portion is stimulated during successive time periods, each time period being short enough to maintain over time satisfactory blood circulation in the area. Thus, the areas are stimulated so that an area that currently is not stimulated will have time to restore substantially normal blood circulation before it is stimulated again.

To maintain satisfactory blood circulation in the uterine tube wall stimulation step (b) is suitably performed by stimulating one or more of different areas of the uterine tube wall portion at a time, preferably by sequentially stimulating the different areas of the uterine tube wall portion or by shifting the stimulation from one area to another over time. Preferably, stimulation step (b) is performed by cyclically propagating the stimulation of the areas along the uterine tube wall portion, for example in accordance with a determined stimulation pattern.

The method of the invention may further comprise controlling, preferably by the patient, the constriction and/or stimulation of the uterine tube wall portion from outside the patient's body.

Generally, the method of the invention comprises sensing a physical parameter of the patient and controlling, preferably automatically, the constriction and/or stimulation of the uterine tube wall portion in response to the sensed parameter.

The constriction step (a) may be performed by constricting any uterine tube wall portions of a series of wall portions of the uterine tube, respectively, either in random or in accordance with a predetermined sequence. The stimulation step (b) may be performed by stimulating any of the constricted uterine tube wall portions of the series of uterine tube wall portions. Specifically, step (a) may be performed by constricting all of the uterine tube wall portions of the series of wall portions, and step (b) may be performed by stimulating any constricted uterine tube wall portions in random or in accordance with a predetermined sequence to close the uterine tube.

Moving Eggs in the Uterine Tube or Preventing the Movement of Eggs in the Uterine Tube in a Similar Way It should be understood that any embodiment or part of embodiment disclosed below in connection with moving eggs in the uterine tube, or preventing the movement of eggs in the uterine tube, for the constriction and stimulation devices combined in the constriction/stimulation unit could be used for the separate constriction device and separate stimulation device, where applicable. The method of the present invention can be practised for actively moving eggs in uterine tube. Thus, in the embodiments of the invention listed below, steps (a) and (b) are co-operated to move the eggs in the uterine tube.

1) Step (a) is performed by constricting the uterine tube wall portion to restrict the flow of eggs in the uterine tube, and step (b) is performed by stimulating the constricted wall portion to close the uterine tube either at an upstream end or a downstream end of the constricted uterine tube wall portion. The method further comprises (c) increasing the constriction of the uterine tube wall portion to move the eggs in the uterine tube.

2) Step (a) is performed by constricting the uterine tube wall portion to restrict the flow of eggs in the uterine tube, and step (b) is performed by progressively stimulating the constricted uterine tube wall portion to cause progressive contraction of the uterine tube wall portion to move the eggs in the uterine tube. The constricted uterine tube wall portion is progressively stimulated in the downstream or upstream direction of the uterine tube.

3) Step (a) is performed by varyingly constricting the uterine tube wall portion to vary the flow of eggs in the uterine tube, and step (b) is performed by progressively stimulating the constricted uterine tube wall portion to cause progressive contraction of the uterine tube wall portion to move the eggs in the uterine tube. The constricted uterine tube wall portion is progressively stimulated in the downstream or upstream direction of the uterine tube.

4) Step (a) is performed by varyingly constricting different areas of the uterine tube wall portion to cause progressive constriction of the uterine tube wall portion in the downstream or upstream direction of the uterine tube, and the constricted uterine tube wall portion is progressively stimulated to cause progressive contraction thereof in harmony with the progressive constriction of the uterine tube wall portion. The method may further comprise providing at least one elongated constriction element extending along the uterine tube wall portion, and controlling the elongated constriction element to progressively constrict the uterine tube wall portion in the downstream or upstream direction of the uterine tube. The elongated constriction element suitably comprises contact surfaces dimensioned to contact a length of uterine tube wall portion, and the method may further comprise providing a plurality of stimulation elements distributed along the contact surfaces, and controlling the stimulation elements to stimulate the different areas of the uterine tube wall portion along the length of the uterine tube wall portion.

5) Step (a) is performed by constricting any one of a series of wall portions of the uterine tube wall to at least restrict the flow of eggs in the uterine tube, and step (b) is performed by stimulating the constricted uterine tube wall portion to close the uterine tube. The method further comprises successively constricting the uterine tube wall portions of the series of uterine tube wall portions to move the eggs in the uterine tube in a peristaltic manner.

5a) In accordance with an alternative, the method further comprises providing at least one constriction element and at least one stimulation element positioned on the constriction element, moving the constriction element along the flow direction in the uterine tube to successively constrict the uterine tube wall portions of the series of uterine tube wall portions, and using the stimulation element to stimulate the uterine tube wall portion constricted by the constriction element to close the uterine tube. Suitably, the method further comprises cyclically moving the constriction element along the uterine tube wall portions of the series of uterine tube wall portions.

5b) In accordance with another alternative, the method further comprises providing a plurality of constriction elements and stimulation elements positioned on the constriction elements, moving each constriction element along the uterine tube to successively constrict the uterine tube wall portions of the series of uterine tube wall portions, and using the stimulation elements to stimulate the uterine tube wall portion constricted by any one of the constriction elements to close the uterine tube. Suitably, the method further comprises cyclically moving the constriction elements one after the other along the uterine tube wall portions of the series of uterine tube wall portions. Specifically, the method further comprises providing a rotor carrying the constriction elements, and rotating the rotor so that each constriction element cyclically constricts the uterine tube wall portions of the series of uterine tube wall portions. Each constriction element suitably comprises a roller that rolls on the uterine tube to constrict the latter.

6) Step (a) is performed by constricting any uterine tube wall portions of a series of uterine tube wall portions of the uterine tube wall, respectively, wherein the uterine tube wall portions of the series of uterine tube wall portions are successively constricted along the uterine tube to move the eggs in the uterine tube of the patient. The stimulation step (b) is performed by stimulating any constricted uterine tube wall portions of the series of uterine tube wall portions.

7) Step (a) is performed by constricting uterine tube wall portions of a series of uterine tube wall portions without completely closing the uterine tube, and step (b) is performed by stimulating the constricted uterine tube wall portions one after the other, so that the uterine tube wall portions of the series of uterine tube wall portions are successively contracted along the uterine tube to move the eggs in the uterine tube of the female patient.

8) Step (a) is performed by constricting the uterine tube wall portion at an upstream or downstream end thereof to close the uterine tube. The method further comprises (c) constricting the uterine tube wall portion between the upstream and downstream ends thereof, to move the eggs contained in the uterine tube wall portion between the upstream and downstream ends thereof downstream or upstream in the uterine tube. Optionally, the method further comprises stimulating the uterine tube wall portion between the upstream and downstream ends thereof, as (c) is performed.

8a) In accordance with an alternative, step (a) is performed by constricting the uterine tube wall portion at the upstream end thereof to restrict the flow of eggs in the uterine tube, and step (b) is performed by stimulating the constricted uterine tube wall portion at the upstream end to close the uterine tube, whereby the eggs contained in the uterine tube wall portion between the upstream and downstream ends thereof is moved downstream in the uterine tube, as step (c) is performed.

8b) In accordance with another alternative, step (a) is performed by constricting the uterine tube wall portion at the downstream end thereof to restrict the flow of eggs in the uterine tube, and step (b) is performed by stimulating the constricted uterine tube wall portion at the downstream end to close the uterine tube, whereby the eggs contained in the uterine tube wall portion between the upstream and downstream ends thereof is moved upstream in the uterine tube, as step (c) is performed.

To summarize a few prefered embodiments see below:

In accordance with an alternative, step (a) is performed by constricting any uterine tube wall portions of a series of uterine tube wall portions of the uterine tube wall, respectively. In accordance with an alternative, the uterine tube wall portions of the series of uterine tube wall portions are constricted in random or in accordance with a predetermined sequence. In accordance with an alternative, the uterine tube wall portions of the series of uterine tube wall portions are successively constricted along the uterine tube to move the eggs in the uterine tube of the patient or to prevent the eggs from moving in the uterine tube of the female patient.

In accordance with an alternative, step (b) is performed by stimulating any constricted uterine tube wall portions of the series of uterine tube wall portions. In accordance with an alternative, the uterine tube wall portions of the series of uterine tube wall portions are constricted in random or in accordance with a predetermined sequence. In accordance with an alternative, wherein the uterine tube wall portions of the series of uterine tube wall portions are successively constricted along the uterine tube to move the eggs in the uterine tube of the patient or to prevent the eggs from moving in the uterine tube of the patient.

In accordance with an alternative, step (a) is performed by constricting any uterine tube wall portions of a series of uterine tube wall portions of the uterine tube wall, respectively, wherein the uterine tube wall portions of the series of uterine tube wall portions are successively constricted without completely closing the uterine tube, and step (b) is performed by stimulating the constricted uterine tube wall portions, so that the uterine tube wall portions of the series of uterine tube wall portions are further constricted. In accordance with an alternative, the uterine tube wall portions of the series of uterine tube wall portions are constricted in random or in accordance with a predetermined sequence.

In accordance with an alternative, wherein the uterine tube wall portions of the series of uterine tube wall portions are successively constricted along the uterine tube to move the eggs in the uterine tube of the patient or to prevent the eggs from moving in the uterine tube of the patient.

In accordance with an alternative, step (a) is performed by constricting all of the uterine tube wall portions of the series of uterine tube wall portions, and step (b) is performed by stimulating any constricted uterine tube wall portions so that the uterine tube wall portions of the series of uterine tube wall portions are further constricted.

In accordance with an alternative, the uterine tube wall portions of the series of uterine tube wall portions are further constricted by the stimulation device in random or in accordance with a predetermined sequence.

In accordance with an alternative, the uterine tube wall portions of the series of uterine tube wall portions are successively further constricted by the stimulation device along the uterine tube to move the eggs in the uterine tube of the patient or to prevent the eggs from moving in the uterine tube of the patient.

In accordance with an alternative for all applicable alternatives, step (a) and step (b) are performed independently of each other or in accordance with an alternative, step (a) and step (b) are performed simultaneously.

In any of the above noted embodiments (1) to (8b), step (b) may be performed by stimulating the uterine tube wall portion with electric pulses.

Stimulation Modes

When stimulating muscular tissue there is a risk of injuring or deteriorating the tissue over time if the stimulation is not properly performed. The method of the present invention is performed to reduce or even eliminate that risk. Thus, step (b) is performed by intermittently stimulating different areas of the uterine tube wall portion so that at least two of the areas are stimulated at different points of time. I.e., the stimulation is shifted from one area to another area over time. In addition, step (b) is performed by intermittently stimulating the areas of the uterine tube wall portion so that an area of the different areas that currently is not stimulated has time to restore substantially normal blood circulation before it is stimulated again. Furthermore, step (b) is performed by intermittently stimulating the areas during successive time periods, wherein each time period is short enough to maintain satisfactory blood circulation in the area until the laps of the time period. This gives the advantage that the method of the present invention provides continuous stimulation of the uterine tube wall portion of the uterine tube to achieve the desired flow control while essentially maintaining over time the natural physical properties of the uterine tube without risk of injuring the uterine tube.

Also, by physically changing the places of stimulation on the uterine tube over time as described above it is possible to create an advantageous changing stimulation pattern on the uterine tube, in order to achieve a desired flow control.

To achieve the desired reaction of the uterine tube wall during the stimulation thereof, step (b) may be performed by stimulating the uterine tube wall portion with, preferably cyclically, varying stimulation intensity.

In a main embodiment of the invention, step (b) is performed by intermittently stimulating the uterine tube wall portion with pulses, preferably in the form of pulse trains. The pulse trains can be configured in many different ways by varying pulse parameters. Thus, the pulse amplitudes of the pulses of the pulse trains, the off time periods between the individual pulses of each pulse train and the width and repetition frequency of each pulse may be varied. Also the off time periods between the pulse trains may be varied, wherein each off time period between the pulse trains is kept long enough to restore substantially normal blood circulation in each area of the uterine tube wall portion, when the area is not stimulated during the off time periods. Furthermore, the repetition frequency of the pulses of the pulse trains and the length and number of pulses of each pulse train may be varied.

As mentioned above, for reasons of maintaining over time the effect of stimulation, it is preferable that different areas of the uterine tube wall portion are intermittently and individually stimulated. In consequence, step (b) may be performed by stimulating one or more of the areas at a time with pulses, by cyclically propagating the stimulation of the areas with pulses along the uterine tube wall portion, and/or by propagating the stimulation of the areas with pulses in accordance with a determined stimulation pattern. In case the off time periods between pulse trains that stimulate the respective area of the uterine tube wall portion are varied, it is preferable that each off time period between the pulse trains is controlled to last long enough to restore substantially normal blood circulation in the area when the latter is not stimulated during the off time periods.

Electric Stimulation

In accordance with a preferred embodiment of the invention, step (b) is performed by electrically stimulating the uterine tube wall portion, preferably with electric pulses to cause contraction of the uterine tube wall portion. This embodiment is particularly suited for applications in which the patient's wall portion includes muscle fibers that react to electrical stimula. Thus, the uterine tube wall portion that includes the muscle fibers is stimulated with such electric pulses, preferably in the form of electric pulse trains, when the uterine tube wall portion is in the constricted state, to cause contraction of the uterine tube wall portion. Of course, the configuration of the electric pulse trains may be similar to the above described pulse trains and different areas of the uterine tube wall portion may be electrically stimulated in the same manner as described above.

In accordance with the preferred embodiment, the method of the invention comprises providing at least one, preferably a plurality of electrical elements, such as electrodes, engaging and stimulating the uterine tube wall portion with electric pulses. Optionally, the electrical elements may be placed in a fixed orientation relative to one another. The method comprises electrically energizing the electrical elements, preferably by cyclically energizing each element with electric pulses. The electrical elements may be energized so that the electrical elements are energized one at a time in sequence, or so that a number or groups of the electrical elements are energized at a time. Also, groups of electrical elements may be sequentially energized, either randomly or in accordance with a predetermined pattern.

The method may further comprise applying the electrical elements on the patient's uterine tube wall portion so that the electrical elements form any pattern of electrical elements, preferably an elongate pattern of electrical elements extending lengthwise along the uterine tube wall portion and the elements abut the respective areas of the uterine tube wall portion. The electrical elements may be successively energized along the elongate pattern of electrical elements in a direction opposite to or in the same direction as that of the flow of eggs in the patient's uterine tube. Optionally, the electrical elements may be successively energized along the elongate pattern of electrical elements from a position substantially at the center of the constricted wall portion towards both ends of the elongate pattern of electrical elements. Where the uterine tube is to be kept closed for a relatively long time, the electrical elements may be energized so that energized electrical elements form two waves of energized electrical elements that simultaneously advance from the center of the constricted wall portion in two opposite directions towards both ends of the elongate pattern of electrical elements. Such waves of energized electrical elements can be repeated over and over again without harming the uterine tube and without moving fluid or gas in any direction in the uterine tube.

The elongate pattern of electrical elements may include one or more rows of electrical elements extending lengthwise along the uterine tube. Each row of electrical elements may form a straight, helical or zig-zag path of electrical elements, or any form of path. The electrical elements may be energized so that the electrical elements currently energized form at least one group of adjacent energized electrical elements, wherein the elements in the group of energized electrical elements form a path of energized electrical elements extending at least in part around the patient's uterine tube, preferably completely around the patient's uterine tube. Alternatively, the elements in the group of energized electrical elements form two paths of energized electrical elements extending on mutual sides of the patient's uterine tube or more than two paths of energized electrical elements extending on different sides of the patient's uterine tube, preferably at least substantially transverse to the flow direction in the uterine tube.

In an embodiment of the invention, the electrical elements form a plurality of groups of elements, wherein the groups form a series of groups extending along the patient's uterine tube in the flow direction in the patient's uterine tube. The electrical elements of each group of electrical elements may form a path of elements extending at least in part around the patient's uterine tube. In a first alternative, the electrical elements of each group of electrical elements may form more than two paths of elements extending on different sides of the patient's uterine tube, preferably substantially transverse to the flow direction in the patient's uterine tube. The groups of electrical elements in the series of groups may be energized in random or in accordance with a predetermined pattern. Alternatively, the groups of electrical elements in the series of groups may be successively energized in a direction opposite to or in the same direction as that of the flow of eggs in the patient's uterine tube, or in both said directions starting from a position substantially at the center of the constricted wall portion. For example, groups of energized electrical elements may form advancing waves of energized electrical elements, as described above. I.e., the groups of electrical elements may be energized so that energized electrical elements form two waves of energized electrical elements that simultaneously advance from the center of the constricted uterine tube wall portion in two opposite directions towards both ends of the elongate pattern of electrical elements.

Thermal Stimulation

In accordance with an embodiment of the invention, stimulation step (b) is performed by thermally stimulating the uterine tube wall portion. Thus, the uterine tube wall portion may be cooled, when the uterine tube wall portion is constricted, to cause contraction of the uterine tube wall portion. For example, the uterine tube wall portion may be constricted to at least restrict the flow of eggs in the uterine tube, and the constricted wall portion may be cooled to cause contraction thereof, so that the flow of eggs in the uterine tube is at least further restricted, or further restricted but not stopped, or stopped. Alternatively, the uterine tube wall portion may be heated, when the uterine tube wall portion is constricted and contracted, to cause expansion of the uterine tube wall portion. Where applicable, thermal stimulation may be practised in any of the embodiments of the present invention. Where applicable, thermal stimulation may be practised in any of the embodiments of the present invention, and the thermal stimulation may be controlled in response to various sensors, for example strain, motion or pressure sensors.

Constriction and Stimulation Devices

It should be understood that any embodiment or part of embodiment for the combined stimulation device and constriction device, could be used, if applicable, for any one of the devices as a stand alone device. Generally, the method of the invention comprises providing a constriction device that constricts the uterine tube wall portion, a stimulation device that stimulates the constricted uterine tube wall portion and a control device that controls the constriction device and/or the stimulation device. The method comprises operating the control device from outside the patient's body, preferably by using the control device to wirelessly control the constriction device and/or stimulation device. The wireless control is preferably performed in a non-magnetic manner, whereby implanted magnetic devices can be avoided. Suitably, the control device comprises a hand-held wireless remote control operated by the patient.

Alternatively, the control device comprises a manually operable switch for switching on and off the constriction device and/or stimulation device. In this case, the method comprises subcutaneously implanting the switch in the patient and manually operating the the implanted switch from outside the patient's body.

In an embodiment of the invention, the control device comprises a programmable internal control unit, such as a microprocessor, and the method comprises implanting in the patient the internal control unit and controlling by the internal control unit the constriction device and/or stimulation device. The control device may also comprise an external control unit outside the patient's body. In this case, the method comprises controlling by the external control unit the constriction device and/or stimulation device and, optionally, using the external control unit to program the implanted internal control unit. The internal control unit may be programmable for controlling the constriction device and/or stimulation device over time, for example in accordance with an activity schedule program.

The constriction of the uterine tube wall portion can be calibrated by using the control device to control the stimulation device to stimulate the uterine tube wall portion while controlling the constriction device to adjust the constriction of the uterine tube wall portion until the desired restriction of the flow of eggs in the uterine tube is obtained.

Sensor Controlled Constriction and/or Stimulation

It should be understood that any embodiment or part of embodiment disclosed below in connection with sensor control of the constriction and stimulation devices combined in the constriction/stimulation unit could be used for the separate constriction device and separate stimulation device, where applicable. In an embodiment of the invention, the method comprises implanting at least one sensor and controlling by the control device the constriction device and/or the stimulation device in response to signals from the sensor. Generally, the sensor directly or indirectly senses at least one physical parameter of the patient, functional parameter of the apparatus, or functional parameter of a medical implant in the patient.

Many different kinds of sensor for sensing physical parameters may be used. For example motion sensors for sensing organ motion, i.e. natural contractions, pressure sensors for sensing pressure in the uterine tube, strain sensors for sensing strain of the uterine tube, flow sensors for sensing fluid flow in the uterine tube, spectro-photometrical sensors, Ph-sensors for acidity or alkalinity of the fluid in the uterine tube, oxygen-sensors sensors for sensing the oxygen content of the fluid in the uterine tube or sensors for sensing the distribution of the stimulation on the stimulated uterine tube. Any conceivable sensors for sensing any other kind of useful physical parameter may be used.

Many different kinds of sensors that sense functional parameters of implanted components may also be used for the control of the constriction device and/or the stimulation device. For example sensors for sensing electric parameters of implanted electric components, or sensors for sensing the performance of implanted motors or the like.

The sensor may comprise a pressure sensor for sensing as the physical parameter a pressure in the patient's body that relates to the pressure in the uterine tube of the patient In this case, the method suitably comprises operating the control device to control the constriction device to change the constriction of the patient's uterine tube wall portion in response to the pressure sensor sensing a predetermined value of measured pressure.

Alternatively, or in combination with the pressure sensor, a position sensor may be provided for sensing as the physical parameter the orientation of the patient with respect to the horizontal. The position sensor may be a biocompatible version of what is shown in U.S. Pat. Nos. 4,942,668 and 5,900,909, these documents being incorporated hereby by reference. For example, the control device may control the constriction device and/or stimulation device to change the constriction of the patient's wall portion in response to the position sensor sensing that the patient has assumed a substantially horizontal orientation, i.e. that the patient is lying down.

The above described sensors may be used in any of the embodiments of the invention, where applicable.

The control device may control the constriction device and/or stimulation device to change the constriction of the patient's uterine tube wall portion in response to the time of day. For that purpose the control device may include a clock mechanism for controlling the constriction device and/or stimulation device to change the constriction of the patient's uterine tube wall portion to increase or decrease the influence on the flow of eggs in the uterine tube during different time periods of the day. In case a sensor of any of the above-described types for sensing a physical or functional parameter is provided, either the clock mechanism is used for controlling the constriction device and/or stimulation device provided that the parameter sensed by the sensor does not override the clock mechanism, or the sensor is used for controlling the constriction device and/or stimulation device provided that the clock mechanism does not override the sensor. Suitably, the control device produces an indication, such as a sound signal or displayed information, in response to signals from the sensor.

The control device may comprise an implantable internal control unit that directly controls the constriction device and/or stimulation device in response to signals from the sensor. The control device may further comprise a wireless remote control adapted to set control parameters of the internal control unit from outside the patient without mechanically penetrating the patient. At least one of the control parameters, which is settable by the wireless remote control, is the physical or functional parameter. Suitably, the internal control unit includes the above mentioned clock mechanism, wherein the wireless remote control also is adapted to set the clock mechanism.

Alternatively, the control device may comprise an external control unit outside the patient's body for controlling the constriction device and/or stimulation device in response to signals from the sensor.

Constriction of Patient's Uterine Tube

It should be understood that any embodiment or part of embodiment disclosed below in connection with constricting the patient's uterine tube could be used for the separate constriction device and separate stimulation device, where applicable. Method step (a) may be performed in many different ways. Thus, step (a) may be performed by:

(1)—constricting the uterine tube wall portion so that the through-flow area of the uterine tube assumes a size in the constricted state small enough to cause the constricted uterine tube wall portion to contract to stop the flow of eggs in the uterine tube when step (b) is performed;

(2)—bending the uterine tube wall portion;

(3)—clamping the uterine tube wall portion between at least two elements positioned on different sides of the uterine tube;

(4)—clamping the uterine tube between an element and the bone or tissue of the patient;

(5)—rotating at least two elements positioned on different sides of the uterine tube; or (6)—clamping the uterine tube between at least two articulated clamping elements positioned on different sides of the uterine tube.

In the above noted alternatives (1) to (6) of method step (a), the constriction of the uterine tube wall portion of the uterine tube may be changed either mechanically or hydraulically. For many applications of the present invention, step (a) is suitably performed so that the through-flow area of the uterine tube assumes a size in the constricted state that is small enough to enable the stimulation during step (b) to contract the uterine tube wall portion of the uterine tube to stop the flow of eggs in the uterine tube.

Where the constriction of the uterine tube wall portion is hydraulically changed, the method of the invention may further comprise implanting in the patient a reservoir containing a predetermined amount of hydraulic fluid, and a constriction device engaging the uterine tube wall portion and having an expandable/contractible cavity, wherein step (a) is performed by distributing hydraulic fluid from the reservoir to increase the volume of the cavity to constrict the uterine tube wall portion, and by distributing hydraulic fluid from the cavity to the reservoir to decrease the volume of the cavity to release the uterine tube wall portion. The cavity may be defined by a balloon of the constriction device that abuts the uterine tube wall portion of the patient's uterine tube, so that the patient's uterine tube wall portion is constricted upon expansion of the cavity and released upon contraction of the cavity.

Alternatively, the cavity may be defined by a bellows that displaces a relatively large contraction element of the constriction device, for example a large balloon that abuts the uterine tube wall portion, so that the patient's uterine tube wall portion is constricted upon contraction of the bellows and released upon expansion of the bellows. Thus, a relatively small addition of hydraulic fluid to the bellows causes a relatively large increase in the constriction of the uterine tube wall portion. Such a bellows may also be replaced by a suitably designed piston/cylinder mechanism.

Where the hydraulic means comprises a cavity in the constriction device, the following embodiments of the invention are conceivable.

1) The reservoir comprises first and second wall portions, and step (a) is performed by displacing the first and second wall portions relative to each other to change the volume of the reservoir, so that fluid is distributed from the reservoir to the cavity, or from the cavity to the reservoir.

1a) At least one of a magnetic device, a hydraulic device or an electric control device displaces the first and second wall portions of the reservoir.

2) A pump is provided for pumping fluid between the reservoir and the cavity.

2a) The pump comprises a first activation member for activating the pump to pump fluid from the reservoir to the cavity and a second activation member for activating the pump to pump fluid from the cavity to the reservoir.

2a1) The first and second activation members are operable by manual manipulation thereof.

2a2) At least one of the activation members operates when subjected to an external predetermined pressure.

2a3) At least one of the first and second activating members is operable by magnetic means, hydraulic means, or electric control means.

2b) A fluid conduit between the pump and the cavity is provided, wherein the reservoir forms part of the conduit. The conduit and pump are devoid of any non-return valve. The reservoir forms a fluid chamber with a variable volume, and the pump distributes fluid from the chamber to the cavity by a reduction in the volume of the chamber and withdraws fluid from the cavity by an expansion of the volume of the chamber. A motor is provided for driving the pump, wherein the pump comprises a movable wall of the reservoir for changing the volume of the chamber.

In all of the above noted embodiments 1 to 2b where the hydraulic means comprises an expandable cavity in the constriction device, the cavity can be exchanged by a cylinder/piston mechanism for adjusting the constriction device. In this case, hydraulic fluid is distributed between the reservoir and the cylinder/piston mechanism to adjust the constriction device.

3) The method further comprises implanting a reverse servo operatively connected to the hydraulic means. The term "reverse servo" is to be understood as a mechanism that transfers a strong force acting on a moving element having a short stroke into a weak force acting on another moving element having a long stroke; i.e., the reverse function of a normal servo mechanism. Thus, minor changes in the amount of fluid in a smaller reservoir could be transferred by the reverse servo into major changes in the amount of fluid in a larger reservoir.

Preferably, the reverse servo comprises an expandable servo reservoir containing servo fluid and a fluid supply reservoir hydraulically connected to the servo reservoir to form a closed conduit system for the servo fluid. The expandable servo reservoir has first and second wall portions, which are displaceable relative to each other in response to a change in the volume of the expandable servo reservoir.

In accordance with a first alternative, the first and second wall portions of the servo reservoir are operatively connected to the hydraulic means. The reverse servo distributes fluid between the fluid supply reservoir and the expandable servo reservoir to change the volume of the servo reservoir, whereby the hydraulic means is operated to adjust the constriction device.

In accordance with a second alternative, there is provided an implantable main reservoir containing a predetermined amount of hydraulic fluid, wherein the reverse servo is operated to distribute hydraulic fluid between the main reservoir and the hydraulic means to adjust the constriction device. More specifically, the main reservoir is provided with first and second wall portions operatively connected to the first and second wall portions of the expandable servo reservoir, so that the volume of the main reservoir is changed when the volume of the expandable servo reservoir is changed. Thus, when the reverse servo distributes servo fluid between the fluid supply reservoir and the expandable servo reservoir to change the volume of the main reservoir, hydraulic fluid is distributed from the main reservoir to the hydraulic means, or from the hydraulic means to the main reservoir. Advantageously, the method comprises dimensioning the servo and main reservoirs, so that when the volume of the servo reservoir is changed by a relatively small amount of servo fluid, the volume of the main reservoir is changed by a relatively large amount of hydraulic fluid.

In both of the above-described alternatives, the fluid supply reservoir may have first and second wall portions, which are displaceable relative to each other to change the volume of the fluid supply reservoir to distribute servo fluid between the fluid supply reservoir and the expandable servo reservoir. The first and second wall portions of the fluid supply reservoir may be displaced relative to each other by manual manipulation, a magnetic device, a hydraulic device, or an electric control device to change the volume of the fluid supply reservoir to distribute servo fluid between the fluid supply reservoir and the expandable servo reservoir.

In all of the above noted embodiments 1 to 2b where the hydraulic means comprises an expandable cavity in the constriction device, or in embodiments where the hydraulic means includes a hydraulically operable mechanical construction, the reverse servo described above may be used. In a further embodiment of the invention, the hydraulic means include first and second hydraulically interconnected expandable/contractible reservoirs. The first reservoir is operatively connected to the constriction device, so that the constriction device changes the constriction of the patient's wall portion upon expansion or contraction of the first reservoir. By changing the volume of the second reservoir hydraulic fluid is distributed between the two reservoirs, so that the first reservoir is either expanded or contracted. This embodiment requires no non-return valve in the fluid communication conduits between the two reservoirs, which is beneficial to long-term operation of the hydraulic means.

Alternatively, the hydraulic means may include first and second hydraulically interconnected piston/cylinder mechanisms instead of the first and second reservoirs described above. The first piston/cylinder mechanism is operatively connected to the constriction device, so that the constriction device changes the constriction of the patient's wall portion upon operation of the first piston/cylinder mechanism. By operating the second piston/cylinder mechanism hydraulic fluid is distributed between the two piston/cylinder mechanisms, so that the first piston/cylinder mechanism adjusts the constriction device.

Where the constriction device does not include an expandable/contractible cavity, the constriction device may comprise at least two elongated clamping elements extending along the uterine tube wall portion on different sides of the uterine tube. The hydraulic means, which may include the reverse servo described above, hydraulically moves the elongated clamping elements towards the uterine tube to constrict the uterine tube wall portion. For example, the constriction device may have hydraulic chambers in which the clamping elements slide back and forth, and the hydraulic means may also include a pump and an implantable reservoir containing hydraulic fluid. The pump distributes hydraulic fluid from the reservoir to the chambers to move the clamping elements against the uterine tube wall portion, and distributes hydraulic fluid from the chambers to the reservoir to move the clamping elements away from the uterine tube wall portion.

Energy Supply

It should be understood that any embodiment or part of embodiment disclosed below in connection with the power of the constriction and stimulation devices combined in the constriction/stimulation unit could be used for the separate constriction device and separate stimulation device, where applicable. Generally, method step (a) is performed by using the constriction device and step (b) is performed by using the stimulation device, wherein the method further comprises forming the constriction and stimulation devices in an operable constriction/stimulation unit.

In a simple form of the invention, the method comprises implanting a source of energy, such as a battery, rechargeable battery or accumulator, releasing energy from the source of energy and using the released energy in connection with the operation of the constriction/stimulation unit.

In a more sophisticated form of the invention, which is preferable, the method comprises transmitting wireless energy from outside the patient's body to inside the patient's body and using the transmitted wireless energy in connection with the operation of the constriction/stimulation unit.

Transmission of Wireless Energy

It should be understood that any embodiment or part of embodiment disclosed below in connection with wireless control or power of the constriction and stimulation devices combined in the constriction/stimulation unit could be used for the separate constriction device and separate stimulation device, where applicable. The wireless energy may be directly used in connection with the operation of the constriction/stimulation unit, as the wireless energy is being transmitted. For example, the wireless energy may be transmitted in the form of an electric, an electromagnetic or a magnetic field, or a combination thereof, or electromagnetic waves for direct power of the constriction/stimulation unit. For example, where an electric motor or pump operates the constriction device of the constriction/stimulation unit, wireless energy in the form of a magnetic or an electromagnetic field may be used for direct power of the motor or pump.

Thus, the motor or pump is running directly during transmission of the wireless energy. This may be achieved in two different ways: a) using a transforming device implanted in the patient to transform the wireless energy into energy of a different form, preferably electric energy, and powering the motor or pump with the transformed energy, or b) using the wirelessly transmitted energy to directly power the motor or pump. Preferably wireless energy in the form of an electromagnetic or magnetic field is used to directly influence specific components of the motor or pump to create kinetic energy. Such components may include coils integrated in the motor or pump.

The wireless energy is suitably transmitted in pulses or digital pulses, or a combination of pulses and digital pulses.

Preferably, the wireless energy is transmitted in at least one wireless signal, suitably a wave signal. The wave signal may comprise an electromagnetic wave signal including one of an infrared light signal, a visible light signal, an ultra violet light signal, a laser signal, a microwave signal, a radio wave signal, an x-ray radiation signal, and a gamma radiation signal. Alternatively, the wave signal may comprise a sound or an ultrasound wave signal. The wireless signal may be a digital or analogue signal, or a combination of a digital and analogue signal.

In accordance with a particular embodiment of the invention, the wireless energy is not for direct use in connection with the operation of the constriction/stimulation unit. In this embodiment the wireless energy comprises energy of a first form, which is transmitted into energy of a second form suited to operate the constriction/stimulation unit. Typically, the energy of the second form is different from the energy of the first form. For example, the wireless energy of the first form may comprise sound waves, whereas the energy of the second form may comprise electric energy. Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

Transforming Wireless Energy

It should be understood that any embodiment or part of embodiment disclosed below in connection with the control or energizing of the constriction and stimulation devices combined in the constriction/stimulation unit could be used for the separate constriction device and separate stimulation device, where applicable. In accordance with a particular embodiment of the invention, an implantable energy-transforming device is provided for transforming wireless energy of a first form transmitted by the energy-transmission device into energy of a second form, which typically is different from the energy of the first form. The constriction/stimulation unit is operable in response to the energy of the second form. For example, the wireless energy of the first form may comprise sound waves, whereas the energy of the second form may comprise electric energy. Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transforming device may function different from or similar to the energy-transmission device. Advantageously, the energy-transforming device comprises at least one element, such as at least one semiconductor, having a positive region and a negative region, when exposed to the energy of the first form transmitted by the energy-transmission device, wherein the element is capable of creating an energy field between the positive and negative regions, and the energy field produces the energy of the second form. More specifically, the element may comprise an electrical junction element, which is capable of inducing an electric field between the positive and negative regions when exposed to the energy of the first form transmitted by the energy-transmission device, whereby the energy of the second form comprises electric energy.

The energy of the first form may directly or indirectly be transformed into the energy of the second form. The method of the invention may comprise providing a motor for operating the constriction device and powering the motor with the energy of the second form. The constriction device may be operable to perform at least one reversible function and the method may comprise reversing the function by using the motor. For example, the method may comprise shifting the polarity of the energy of the second form to reverse the motor.

The motor may be directly powered with the transformed energy, as the energy of the second form is being transformed from the energy of the first form. Preferably, the constriction/stimulation unit is directly operated with the energy of the second form in a non-magnetic, non-thermal or non-mechanical manner.

Normally, the implanted constriction/stimulation unit comprises electric components that are energized with electrical energy. Therefore, the energy of the first form may be transformed into a direct current or pulsating direct current, or a combination of a direct current and pulsating direct current. Alternatively, the energy of the first form may be transformed into an alternating current or a combination of a direct and alternating current.

The method of the invention may comprise implanting in the patient an internal source of energy, and supplying energy from the internal source of energy for the operation of the constriction/stimulation unit. The method may further comprise implanting in the patient a switch operable to switch from an "off" mode, in which the internal source of energy is not in use, to an "on" mode, in which the internal source of energy supplies energy for the operation of the constriction/stimulation unit, and/or for energizing implanted electronic components of the constriction/stimulation unit. The switch may be operated by the energy of the first form or by the energy of the second form. The described switch arrangement reduces power consumption of the constriction/stimulation unit between operations.

The internal source of energy may store the energy of the second form. In this case, the internal source of energy suitably comprises an accumulator, such as at least one capacitor or at least one rechargeable battery, or a combination of at least one capacitor and at least one rechargeable battery. Where the internal source of energy is a rechargeable battery it may be charged only at times convenient for the patient, for example when the patient is sleeping. Alternatively, the internal source of energy may supply energy for the operation of the constriction/stimulation unit but not be used for storing the energy of the second form. In this alternative, the internal source of energy may be a battery and the switch described above may or may not be provided.

Suitably, the method of the invention may comprise implanting a stabilizer for stabilizing the energy of the second form. Where the energy of the second form comprises electric energy the stabilizer suitably comprises at least one capacitor.

The energy-transforming device may be designed for implantation subcutaneously in the abdomen, thorax or cephalic region of the patient. Alternatively, it may be designed for implantation in an orifice of the patient's body and under the mucosa or intramuscularly outside the mucosa of the orifice.

Control of Constriction/Stimulation Unit

It should be understood that any embodiment or part of embodiment disclosed below in connection with the control of the constriction and stimulation devices combined in the constriction/stimulation unit could be used for the separate constriction device and separate stimulation device, where applicable. Although the constriction device of the constriction/stimulation unit may normally keep the patient's wall portion in the constricted state, in most applications using the present invention there will be daily adjustments of the constriction device. Therefore, in a preferred embodiment of the invention, the constriction device is adjustable to enable changing the constriction of the patient's uterine tube wall portion as desired and the control device controls the constriction device to change the constriction of the uterine tube wall portion.

The method of the invention suitably comprises operating the control device by the patient. In a simple form the control device comprises a manually operable switch for switching on and off the constriction/stimulation unit, and the method further comprises subcutaneously implanting the switch in the patient. It is preferable, however, that the control device comprises a hand-held wireless remote control operable by the patient from outside the patient's body to control the constriction/stimulation unit to adjust the stimulation intensity and/or adjust the constriction of the uterine tube wall portion. The wireless remote control is suitably designed for application on the patient's body like a wristwatch.

In some applications of the invention, the constriction device of the constriction/stimulation unit may be designed to normally keep the patient's uterine tube wall portion in the constricted state. I.e., after implantation the constriction device all the time keeps the uterine tube wall portion constricted. In this case, the control device may be used when needed, conveniently by the patient, to control the stimulation device of the constriction/stimulation unit to stimulate the constricted uterine tube wall portion, preferably while adjusting the stimulation intensity, to cause contraction of the uterine tube wall portion, so that the flow of eggs in the uterine tube is at least further restricted or stopped, and to control the stimulation device to cease the stimulation. More precisely, the method of the invention may comprise operating the control device by the patient to a) control the stimulation device in a first mode to stimulate the constricted wall portion to further restrict the flow of eggs in the uterine tube and control the stimulation device in a second mode to cease the stimulation of the uterine tube wall portion to increase the flow of eggs in the uterine tube; or b) control the stimulation device in a first mode to stimulate the constricted wall portion to stop the flow of eggs in the uterine tube and control the stimulation device in a second mode to cease the stimulation of the uterine tube wall portion to allow flow in the uterine tube.

Either the first mode or the second mode may be temporary.

The wireless remote control preferably transmits at least one wireless control signal for controlling the constriction/stimulation unit. The control signal may comprise a frequency, amplitude, phase modulated signal or a combination thereof, and may be an analogue or a digital signal, or a combination of an analogue and digital signal. The remote control may transmit an electromagnetic carrier wave signal for carrying the digital or analogue control signal. Also the carrier signal may comprise digital, analogue or a combination of digital and analogue signals.

Any of the above signals may comprise wave signals, such as a sound wave signal, an ultrasound wave signal, an electromagnetic wave signal, an infrared light signal, a visible light signal, an ultra violet light signal, a laser light signal, a micro wave signal, a radio wave signal, an x-ray radiation signal or a gamma radiation signal.

Alternatively, the control signal may comprise an electric or magnetic field, or a combined electric and magnetic field.

Operation of Constriction/Stimulation Unit

It should be understood that any embodiment or part of embodiment for operating the combined stimulation device and constriction device, could be used, if applicable, for any one of the devices as a stand alone device. The method of the invention may comprise implanting in the patient an operation device, and operating the constriction/stimulation unit with the operation device. A magnet may be provided, wherein the method comprises using the magnet to activate the operation device from outside the patient's body. The operation device suitably comprises a motor which is powered with energy released from a source of energy, such as a battery. Although the constriction/stimulation unit in embodiments described above suitably is designed as a single piece, which is most practical for implantation, it should be noted that as an alternative the constriction device and stimulation device of the constriction/stimulation unit could be designed as separate pieces.

Laparoscopic Method

The present invention also provides a first method for controlling a flow of eggs in a uterine tube formed by a uterine tube wall of a patient. The method comprises the steps of:
inserting a needle like tube into the cavity of the patients body,
filling the cavity with gas thereby expanding the cavity,
placing at least two laparoscopic trocars in the patient's body,
inserting a camera through one of the trocars into the cavity,
inserting a dissecting tool through any of the trocar and dissecting an area of at least one portion of the uterine tube wall,
placing a constriction device and a stimulation device in the dissected area in operative engagement with the uterine tube,
using the constriction device to gently constrict the uterine tube wall portion of the uterine tube to influence the flow of eggs in the uterine tube, and
using the stimulation device to stimulate the constricted wall portion to cause contraction of the uterine tube wall portion to further influence the flow of eggs in the uterine tube.

The present invention also provides a second method for controlling a flow of eggs in a uterine tube formed by a uterine tube wall of a patient. The method comprises the steps of:
inserting a needle like tube into a cavity of the patients body,
using the needle like tube to fill the cavity with gas thereby expanding the cavity,
placing at least two laparoscopic trocars in the patient's body,
inserting a camera through one of the trocars into the cavity,
inserting a dissecting tool through any of the trocar and dissecting an area of at least one portion of the uterine tube wall,
placing a stimulation device in the dissected area in operative engagement with the uterine tube, and
using the stimulation device to stimulate the uterine tube wall portion to cause contraction of the uterine tube wall portion to influence the flow of eggs in the uterine tube.

The present invention also provides a third method for controlling a flow of eggs in a uterine tube formed by a uterine tube wall of a patient. The method comprises the steps of:
inserting a needle like tube into a cavity of the patients body,
using the needle like tube to fill the cavity with gas thereby expanding the cavity,
placing at least two laparoscopic trocars in the patient's body,
inserting a camera through one of the trocars into the cavity,
inserting a dissecting tool through any of the trocar and dissecting an area of at least one portion of the uterine tube wall,
placing a constriction device in the dissected area in operative engagement with the uterine tube,
using the constriction device to constrict the uterine tube wall portion of the uterine tube to influence the flow of eggs in the uterine tube.

The present invention also provides a fourth method for controlling a flow of eggs in a uterine tube formed by a uterine tube wall of a patient. The method comprises the steps of:
cutting the skin of the patient,
inserting a dissecting tool and dissecting an area of at least one portion of the uterine tube wall,
placing a constriction device and a stimulation device in the dissected area in operative engagement with the uterine tube,
using the constriction device to gently constrict the uterine tube wall portion of the uterine tube to influence the flow of eggs in the uterine tube, and
using the stimulation device to stimulate the constricted wall portion to cause contraction of the uterine tube wall portion to further influence the flow of eggs in the uterine tube.

The present invention also provides a fifth method for controlling a flow of eggs in a uterine tube formed by a uterine tube wall of a patient. The method comprises the steps of:
cutting the skin of the patient,
inserting a dissecting tool and dissecting an area of at least one portion of the uterine tube wall,
placing a stimulation device in the dissected area in operative engagement with the uterine tube, and
using the stimulation device to stimulate the uterine tube wall portion to cause contraction of the uterine tube wall portion to influence the flow of eggs in the uterine tube.

The present invention also provides a sixth method for controlling a flow of eggs in a uterine tube formed by a uterine tube wall of a patient. The method comprises the steps of:
cutting the skin of the patient,
inserting a dissecting tool and dissecting an area of at least one portion of the uterine tube wall,
placing a constriction device in the dissected area in operative engagement with the uterine tube, and
using the constriction device to constrict the uterine tube wall portion to influence the flow of eggs in the uterine tube.

In all of the above presented methods 1-6 above the cavity may constitute at least one of an abdominal cavity, a cavity in the pelvic region, a retroperitoneal cavity, a cavity in human soft tissue such as muscle, fat and fibrotic tissue.

The method further comprises implanting a powered operation device for operating the constriction device. The operation device may comprise a powered hydraulic operation device or an electrically powered operation device, such as an electric motor.

The method further comprises transmitting wireless energy for powering the operation device, and when desired to influence the flow of eggs in the patient's uterine tube, powering the operation device with the transmitted energy to operate the constriction device.

Sperm Movement Control

Another object of the present invention is to provide a method for controlling the movement of sperms in the uterine tubes of a female patient.

In accordance with this object of the present invention, there is provided a method for controlling a flow of sperms in an uterine tube of a female patient, the method comprising:
a) gently constricting at least one portion of the uterine tube wall to influence the flow of sperms in the uterine tube, using a constriction device, or
b) stimulating at least one portion of the uterine tube wall to cause contraction of the uterine tube wall portion to further influence the flow of sperms in the uterine tube, using a stimulation device.

In accordance with the preferred object of the present invention, there is provided method for controlling a flow of sperms in a uterine tube of a female patient, the method comprising:
gently constricting at least one portion of the uterine tube wall to influence the flow of sperms in the uterine tube, using a constriction device, and
stimulating at least one portion of the uterine tube wall to cause contraction of the uterine tube wall portion to further influence the flow of sperms in the uterine tube, using a stimulation device.

The present invention provides an advantageous combination of the method steps (a) and (b), which results in a two-stage influence on the flow of sperms in the uterine tube. Thus, applying a relatively weak force against the uterine tube wall portion gently constricts the uterine tube wall and the constricted wall portion is stimulated to achieve the desired final influence on the flow of sperms in the uterine tube. The phrase "gently constricts a portion of the uterine tube wall" is to be understood as constricting the uterine tube wall portion without substantially hampering the blood circulation in the uterine tube wall.

Preferably, step (b) is performed by intermittently and individually stimulating different areas of the uterine tube wall portion. Such an intermittent and individual stimulation of different areas of the uterine tube wall portion of the uterine tube allows tissue of the uterine tube wall portion to maintain over time substantially normal blood circulation.

Preferably, the constriction step (a) and stimulation step (b) are performed independently of each other. Steps (a) and (b) may be performed simultaneously. Optionally, step (b) may or may not be performed while step (a) is performed.

Initially, the constriction of the uterine tube wall portion can be calibrated by stimulating the uterine tube wall portion while adjusting the constriction of the uterine tube wall portion until the desired restriction of the flow of sperms in the uterine tube is obtained.

The term uterine tube of course also includes the two uterine tubes. The term sperms of course include one sperm.

Any embodiment or part of embodiment may be combined in several different casings. Preferable two constriction units, one power supply.

Flow Restriction

It should be understood that any embodiment or part of embodiment disclosed below in connection with flow restriction for the constriction and stimulation devices combined in the constriction/stimulation unit could be used for the separate constriction device and separate stimulation device, where applicable. The method of the present invention is well suited for restricting the flow of sperms in the uterine tube. Thus, in a principal embodiment of the invention, the uterine tube wall portion is constricted, so that the flow of sperms in the uterine tube at least is restricted and the constricted wall portion is stimulated to at least further restrict the flow of sperms in the uterine tube. Specifically, the uterine tube wall portion is constricted to a constricted state, in which the blood circulation in the constricted wall portion is substantially unrestricted and the flow of sperms in the uterine tube is at least restricted, and the constricted wall portion is stimulated when it is in the constricted state to at least further restrict the flow of sperms in the uterine tube.

The constriction step (a) and stimulation step (b) are suitably performed to constrict and stimulate the uterine tube wall portion to an extent that depends on the flow restriction that is desired to be achieved in a specific application of the method of the invention. Thus, in accordance with a first flow restriction option, step (a) is performed by constricting the uterine tube wall portion, so that the flow of sperms in the uterine tube is restricted but not stopped, and step (b) is performed by stimulating the constricted wall portion to cause contraction thereof, so that the flow of sperms in the uterine tube is further restricted but not stopped. The method may further comprise sensing a physical parameter of the patient and adjusting the intensity of the stimulation of the uterine tube wall portion in response to the sensed parameter.

In accordance with a second flow restriction option, step (a) is performed by constricting the uterine tube wall portion, so that the flow of sperms in the uterine tube is restricted but not stopped, and step (b) is performed by stimulating the constricted wall portion to cause contraction thereof, so that the flow of sperms in the uterine tube is stopped.

When using the method of the invention in accordance with the first or second options, the method may further comprise (c) ceaseing stimulating the uterine tube wall portion to increase or allow the flow of sperms in the uterine tube and (d) releasing the uterine tube wall portion to restore the flow of sperms in the uterine tube.

In accordance with a third flow restriction option, step (a) is performed by constricting the uterine tube wall portion, so that the flow of sperms in the uterine tube is substantially stopped, and step (b) is performed by stimulating the constricted wall portion to cause contraction thereof, so that the flow of sperms in the uterine tube is completely stopped. The method may further comprise (c) ceaseing stimulating the uterine tube wall portion to allow the flow of sperms in the uterine tube and (d) releasing the uterine tube wall portion to restore the flow of sperms in the uterine tube.

Where the constricted wall portion is stimulated to contract, so that the flow of sperms in the uterine tube is stopped, a first length of the constricted wall portion and a second length of the constricted wall portion, which is located downstream of the first length, are suitably simultaneously and cyclically stimulated, wherein the first length is progressively stimulated in the upstream direction of the uterine tube and the second length is progressively stimulated in the downstream direction of the uterine tube.

Furthermore, when using the method of the invention in accordance with the second and third options, the method may further comprise sensing a physical parameter of the patient or functional parameter of implanted components and adjusting the stimulation of the uterine tube wall portion in response to the sensed parameter. For example, the intensity of the stimulation of the uterine tube wall portion may be increased in response to a sensed pressure increase in the uterine tube, so that the flow of sperms in the uterine tube remains stopped when a pressure increase occurs in the uterine tube. In particular, the method may comprise sensing a physical parameter of the patient's that relates to the pressure in the uterine tube, and controlling the stimulation of the uterine tube wall portion in response to the sensed parameter. Any sensor for sensing a physical parameter of the patient, such as a pressure in the patient's body that relates to the pressure in the uterine tube may be provided, wherein the stimulation is controlled in response to signals from the sensor. Such a sensor may for example sense the pressure in the patient's abdomen, the pressure against the implanted constriction device or the pressure on the uterine tube wall. For example, a pressure sensor may be applied where the present invention is used for controlling flow of sperms of a female patient.

In accordance with a fourth restriction option, step (a) is performed by constricting the uterine tube wall portion, so that the flow of sperms in the uterine tube is stopped. When needed, the uterine tube wall portion is released to restore the flow of sperms in the uterine tube. Step (b) is only performed by stimulating the constricted wall portion to cause contraction thereof, so that the flow of sperms in the uterine tube remains stopped when a pressure increase occurs in the uterine tube. The method may further comprise sensing a physical parameter of the patient's body, such as a pressure in the patient's body that relates to the pressure in the uterine tube, and controlling the stimulation of the uterine tube wall portion in response to the sensed parameter. Such a physical parameter may be a pressure in the patient's abdomen and the sensor may be a pressure sensor.

In some applications of the method of the invention, continuous stimulation may over time change the physical properties of the tissue so that the tissue might be injured. Also, the effect of a continuous stimulation of the uterine tube wall may decrease over time. Therefore, step (b) is preferably performed by intermittently and individually stimulating different areas of the uterine tube wall portion so that the flow of sperms in the uterine tube continues to be restricted as desired and each area of the uterine tube wall portion essentially maintains its natural physical properties over time to prevent the area from being injured. Advantageously, each area of the uterine tube wall portion is stimulated during successive time periods, each time period being short enough to maintain over time satisfactory blood circulation in the area. Thus, the areas are stimulated so that an area that currently is not stimulated will have time to restore substantially normal blood circulation before it is stimulated again.

To maintain satisfactory blood circulation in the uterine tube wall stimulation step (b) is suitably performed by stimulating one or more of different areas of the uterine tube wall portion at a time, preferably by sequentially stimulating the different areas of the uterine tube wall portion or by shifting the stimulation from one area to another over time. Preferably, stimulation step (b) is performed by cyclically propagating the stimulation of the areas along the uterine tube wall portion, for example in accordance with a determined stimulation pattern.

The method of the invention may further comprise controlling, preferably by the patient, the constriction and/or stimulation of the uterine tube wall portion from outside the patient's body.

Generally, the method of the invention comprises sensing a physical parameter of the patient and controlling, preferably automatically, the constriction and/or stimulation of the uterine tube wall portion in response to the sensed parameter.

The constriction step (a) may be performed by constricting any uterine tube wall portions of a series of wall portions of the uterine tube, respectively, either in random or in accordance with a predetermined sequence. The stimulation step (b) may be performed by stimulating any of the constricted uterine tube wall portions of the series of uterine tube wall portions. Specifically, step (a) may be performed by constricting all of the uterine tube wall portions of the series of wall portions, and step (b) may be performed by stimulating any constricted uterine tube wall portions in random or in accordance with a predetermined sequence to close the uterine tube.

Moving Sperms in the Uterine Tube or Preventing the Movement of Sperms in the Uterine Tube in a Similar Way It should be understood that any embodiment or part of embodiment disclosed below in connection with moving sperms in the uterine tube, or preventing the movement of sperms in the uterine tube, for the constriction and stimulation devices combined in the constriction/stimulation unit could be used for the separate constriction device and separate stimulation device, where applicable. The method of the present invention can be practised for actively moving the sperms in uterine tube. Thus, in the embodiments of the invention listed below, steps (a) and (b) are co-operated to move the sperms in the uterine tube.

1) Step (a) is performed by constricting the uterine tube wall portion to restrict the flow of sperms in the uterine tube, and step (b) is performed by stimulating the constricted wall portion to close the uterine tube either at an upstream end or a downstream end of the constricted uterine tube wall portion. The method further comprises (c) increasing the constriction of the uterine tube wall portion to move the sperms in the uterine tube.

2) Step (a) is performed by constricting the uterine tube wall portion to restrict the flow of sperms in the uterine tube, and step (b) is performed by progressively stimulating the constricted uterine tube wall portion to cause progressive contraction of the uterine tube wall portion to move the sperms in the uterine tube. The constricted uterine tube wall portion is progressively stimulated in the downstream or upstream direction of the uterine tube.

3) Step (a) is performed by varyingly constricting the uterine tube wall portion to vary the flow of sperms in the uterine tube, and step (b) is performed by progressively stimulating the constricted uterine tube wall portion to cause progressive contraction of the uterine tube wall portion to move the sperms in the uterine tube. The constricted uterine tube wall portion is progressively stimulated in the downstream or upstream direction of the uterine tube.

4) Step (a) is performed by varyingly constricting different areas of the uterine tube wall portion to cause progressive constriction of the uterine tube wall portion in the downstream or upstream direction of the uterine tube, and the constricted uterine tube wall portion is progressively stimulated to cause progressive contraction thereof in harmony with the progressive constriction of the uterine tube wall portion. The method may further comprise providing at least one elongated constriction element extending along the uterine tube wall portion, and controlling the elongated constriction element to progressively constrict the uterine tube wall portion in the downstream or upstream direction of the uterine tube. The elongated constriction element suitably comprises contact surfaces dimensioned to contact a length of uterine tube wall portion, and the method may further comprise providing a plurality of stimulation elements distributed along the contact surfaces, and controlling the stimulation elements to stimulate the different areas of the uterine tube wall portion along the length of the uterine tube wall portion.

5) Step (a) is performed by constricting any one of a series of wall portions of the uterine tube wall to at least restrict the flow of sperms in the uterine tube, and step (b) is performed by stimulating the constricted uterine tube wall portion to close the uterine tube. The method further comprises successively constricting the uterine tube wall portions of the series of uterine tube wall portions to move the sperms in the uterine tube in a peristaltic manner.

5a) In accordance with an alternative, the method further comprises providing at least one constriction element and at least one stimulation element positioned on the constriction element, moving the constriction element along the flow direction in the uterine tube to successively constrict the uterine tube wall portions of the series of uterine tube wall portions, and using the stimulation element to stimulate the uterine tube wall portion constricted by the constriction element to close the uterine tube. Suitably, the method further comprises cyclically moving the constriction element along the uterine tube wall portions of the series of uterine tube wall portions.

5b) In accordance with another alternative, the method further comprises providing a plurality of constriction elements and stimulation elements positioned on the constriction elements, moving each constriction element along the uterine tube to successively constrict the uterine tube wall portions of the series of uterine tube wall portions, and using the stimulation elements to stimulate the uterine tube wall portion constricted by any one of the constriction elements to close the uterine tube. Suitably, the method further comprises cyclically moving the constriction elements one after the other along the uterine tube wall portions of the series of uterine tube wall portions. Specifically, the method further comprises providing a rotor carrying the constriction elements, and rotating the rotor so that each constriction element cyclically constricts the uterine tube wall portions of the series of uterine tube wall portions. Each constriction element suitably comprises a roller that rolls on the uterine tube to constrict the latter.

6) Step (a) is performed by constricting any uterine tube wall portions of a series of uterine tube wall portions of the uterine tube wall, respectively, wherein the uterine tube wall portions of the series of uterine tube wall portions are successively constricted along the uterine tube to move the sperms in the uterine tube of the patient. The stimulation step (b) is performed by stimulating any constricted uterine tube wall portions of the series of uterine tube wall portions.

7) Step (a) is performed by constricting uterine tube wall portions of a series of uterine tube wall portions without completely closing the uterine tube, and step (b) is performed by stimulating the constricted uterine tube wall portions one after the other, so that the uterine tube wall portions of the series of uterine tube wall portions are successively contracted along the uterine tube to move the sperms in the uterine tube of the female patient.

8) Step (a) is performed by constricting the uterine tube wall portion at an upstream or downstream end thereof to close the uterine tube. The method further comprises (c) constricting the uterine tube wall portion between the upstream and downstream ends thereof, to move the sperms sperms contained in the uterine tube wall portion between the upstream and downstream ends thereof downstream or upstream in the uterine tube. Optionally, the method further comprises stimulating the uterine tube wall portion between the upstream and downstream ends thereof, as (c) is performed.

8a) In accordance with an alternative, step (a) is performed by constricting the uterine tube wall portion at the upstream end thereof to restrict the flow of sperms in the uterine tube, and step (b) is performed by stimulating the constricted uterine tube wall portion at the upstream end to close the uterine tube, whereby the sperms contained in the uterine tube wall portion between the upstream and downstream ends thereof is moved downstream in the uterine tube, as step (c) is performed.

8b) In accordance with another alternative, step (a) is performed by constricting the uterine tube wall portion at the downstream end thereof to restrict the flow of sperms in the uterine tube, and step (b) is performed by stimulating the constricted uterine tube wall portion at the downstream end to close the uterine tube, whereby the sperms contained in the uterine tube wall portion between the upstream and downstream ends thereof is moved upstream in the uterine tube, as step (c) is performed.

To summarize a few prefered embodiments see below:

In accordance with an alternative, step (a) is performed by constricting any uterine tube wall portions of a series of uterine tube wall portions of the uterine tube wall, respectively. In accordance with an alternative, the uterine tube wall portions of the series of uterine tube wall portions are constricted in random or in accordance with a predetermined sequence. In accordance with an alternative, the uterine tube wall portions of the series of uterine tube wall portions are successively constricted along the uterine tube to move the sperms in the uterine tube of the patient or to prevent the sperms from moving in the uterine tube of the female patient.

In accordance with an alternative, step (b) is performed by stimulating any constricted uterine tube wall portions of the series of uterine tube wall portions. In accordance with an alternative, the uterine tube wall portions of the series of uterine tube wall portions are constricted in random or in accordance with a predetermined sequence. In accordance with an alternative, wherein the uterine tube wall portions of the series of uterine tube wall portions are successively constricted along the uterine tube to move the sperms in the uterine tube of the patient or to prevent the sperms from moving in the uterine tube of the patient.

In accordance with an alternative, step (a) is performed by constricting any uterine tube wall portions of a series of uterine tube wall portions of the uterine tube wall, respectively, wherein the uterine tube wall portions of the series of uterine tube wall portions are successively constricted without completely closing the uterine tube, and step (b) is performed by stimulating the constricted uterine tube wall portions, so that the uterine tube wall portions of the series of uterine tube wall portions are further constricted. In accordance with an alternative, the uterine tube wall portions of the series of uterine tube wall portions are constricted in random or in accordance with a predetermined sequence.

In accordance with an alternative, wherein the uterine tube wall portions of the series of uterine tube wall portions are successively constricted along the uterine tube to move the sperms in the uterine tube of the patient or to prevent the sperms from moving in the uterine tube of the patient.

In accordance with an alternative, step (a) is performed by constricting all of the uterine tube wall portions of the series of uterine tube wall portions, and step (b) is performed by stimulating any constricted uterine tube wall portions so that the uterine tube wall portions of the series of uterine tube wall portions are further constricted.

In accordance with an alternative, the uterine tube wall portions of the series of uterine tube wall portions are further constricted by the stimulation device in random or in accordance with a predetermined sequence.

In accordance with an alternative, the uterine tube wall portions of the series of uterine tube wall portions are successively further constricted by the stimulation device along the uterine tube to move the sperms in the uterine tube of the patient or to prevent the sperms from moving in the uterine tube of the patient.

In accordance with an alternative for all applicable alternatives, step (a) and step (b) are performed independently of each other or in accordance with an alternative, step (a) and step (b) are performed simultaneously.

In any of the above noted embodiments (1) to (8b), step (b) may be performed by stimulating the uterine tube wall portion with electric pulses.

Stimulation Modes

When stimulating muscular tissue there is a risk of injuring or deteriorating the tissue over time if the stimulation is not properly performed. The method of the present invention is performed to reduce or even eliminate that risk. Thus, step (b) is performed by intermittently stimulating different areas of the uterine tube wall portion so that at least two of the areas are stimulated at different points of time. I.e., the stimulation is shifted from one area to another area over time. In addition, step (b) is performed by intermittently stimulating the areas of the uterine tube wall portion so that an area of the different areas that currently is not stimulated has time to restore substantially normal blood circulation before it is stimulated again. Furthermore, step (b) is performed by intermittently stimulating the areas during successive time periods, wherein each time period is short enough to maintain satisfactory blood circulation in the area until the laps of the time period. This gives the advantage that the method of the present invention provides continuous stimulation of the uterine tube wall portion of the uterine tube to achieve the desired flow control while essentially maintaining over time the natural physical properties of the uterine tube without risk of injuring the uterine tube.

Also, by physically changing the places of stimulation on the uterine tube over time as described above it is possible to create an advantageous changing stimulation pattern on the uterine tube, in order to achieve a desired flow control.

To achieve the desired reaction of the uterine tube wall during the stimulation thereof, step (b) may be performed by stimulating the uterine tube wall portion with, preferably cyclically, varying stimulation intensity.

In a main embodiment of the invention, step (b) is performed by intermittently stimulating the uterine tube wall portion with pulses, preferably in the form of pulse trains. The pulse trains can be configured in many different ways by varying pulse parameters. Thus, the pulse amplitudes of the pulses of the pulse trains, the off time periods between the individual pulses of each pulse train and the width and repetition frequency of each pulse may be varied. Also the off time periods between the pulse trains may be varied, wherein each off time period between the pulse trains is kept long enough to restore substantially normal blood circulation in each area of the uterine tube wall portion, when the area is not stimulated during the off time periods. Furthermore, the repetition frequency of the pulses of the pulse trains and the length and number of pulses of each pulse train may be varied.

As mentioned above, for reasons of maintaining over time the effect of stimulation, it is preferable that different areas of the uterine tube wall portion are intermittently and individually stimulated. In consequence, step (b) may be performed by stimulating one or more of the areas at a time with pulses, by cyclically propagating the stimulation of the areas with pulses along the uterine tube wall portion, and/or by propagating the stimulation of the areas with pulses in accordance with a determined stimulation pattern. In case the off time periods between pulse trains that stimulate the respective area of the uterine tube wall portion are varied, it is preferable that each off time period between the pulse trains is controlled to last long enough to restore substantially normal blood circulation in the area when the latter is not stimulated during the off time periods.

Electric Stimulation

In accordance with a preferred embodiment of the invention, step (b) is performed by electrically stimulating the uterine tube wall portion, preferably with electric pulses to cause contraction of the uterine tube wall portion. This embodiment is particularly suited for applications in which the patient's wall portion includes muscle fibers that react to electrical stimula. Thus, the uterine tube wall portion that includes the muscle fibers is stimulated with such electric pulses, preferably in the form of electric pulse trains, when the uterine tube wall portion is in the constricted state, to cause contraction of the uterine tube wall portion. Of course, the configuration of the electric pulse trains may be similar to the above described pulse trains and different areas of the uterine tube wall portion may be electrically stimulated in the same manner as described above.

In accordance with the preferred embodiment, the method of the invention comprises providing at least one, preferably a plurality of electrical elements, such as electrodes, engaging and stimulating the uterine tube wall portion with electric pulses. Optionally, the electrical elements may be placed in a fixed orientation relative to one another. The method comprises electrically energizing the electrical elements, preferably by cyclically energizing each element with electric pulses. The electrical elements may be energized so that the electrical elements are energized one at a time in sequence, or so that a number or groups of the electrical elements are energized at a time. Also, groups of electrical elements may be sequentially energized, either randomly or in accordance with a predetermined pattern.

The method may further comprise applying the electrical elements on the patient's uterine tube wall portion so that the electrical elements form any pattern of electrical elements, preferably an elongate pattern of electrical elements extending lengthwise along the uterine tube wall portion and the elements abut the respective areas of the uterine tube wall portion. The electrical elements may be successively energized along the elongate pattern of electrical elements in a direction opposite to or in the same direction as that of the flow of sperms in the patient's uterine tube. Optionally, the electrical elements may be successively energized along the elongate pattern of electrical elements from a position substantially at the center of the constricted wall portion towards both ends of the elongate pattern of electrical elements. Where the uterine tube is to be kept closed for a relatively long time, the electrical elements may be energized so that energized electrical elements form two waves of energized electrical elements that simultaneously advance from the center of the constricted wall portion in two opposite directions towards both ends of the elongate pattern of electrical elements. Such waves of energized electrical elements can be repeated over and over again without harming the uterine tube and without moving fluid or gas in any direction in the uterine tube.

The elongate pattern of electrical elements may include one or more rows of electrical elements extending lengthwise along the uterine tube. Each row of electrical elements may form a straight, helical or zig-zag path of electrical elements, or any form of path. The electrical elements may be energized so that the electrical elements currently energized form at least one group of adjacent energized electrical elements, wherein the elements in the group of energized electrical elements form a path of energized electrical elements extending at least in part around the patient's uterine tube, preferably completely around the patient's uterine tube. Alternatively, the elements in the group of energized electrical elements form two paths of energized electrical elements extending on mutual sides of the patient's uterine tube or more than two paths of energized electrical elements extending on different sides of the patient's uterine tube, preferably at least substantially transverse to the flow direction in the uterine tube.

In an embodiment of the invention, the electrical elements form a plurality of groups of elements, wherein the groups form a series of groups extending along the patient's uterine tube in the flow direction in the patient's uterine tube. The electrical elements of each group of electrical elements may form a path of elements extending at least in part around the patient's uterine tube. In a first alternative, the electrical elements of each group of electrical elements may form more than two paths of elements extending on different sides of the patient's uterine tube, preferably substantially transverse to the flow direction in the patient's uterine tube. The groups of electrical elements in the series of groups may be energized in random or in accordance with a predetermined pattern. Alternatively, the groups of electrical elements in the series of groups may be successively energized in a direction opposite to or in the same direction as that of the flow of sperms in the patient's uterine tube, or in both said directions starting from a position substantially at the center of the constricted wall portion. For example, groups of energized electrical elements may form advancing waves of energized electrical elements, as described above. I.e., the groups of electrical elements may be energized so that energized electrical elements form two waves of energized electrical elements that simultaneously advance from the center of the constricted uterine tube wall portion in two opposite directions towards both ends of the elongate pattern of electrical elements.

Thermal Stimulation

In accordance with an embodiment of the invention, stimulation step (b) is performed by thermally stimulating the uterine tube wall portion. Thus, the uterine tube wall portion may be cooled, when the uterine tube wall portion is constricted, to cause contraction of the uterine tube wall portion. For example, the uterine tube wall portion may be constricted to at least restrict the flow of sperms in the uterine tube, and the constricted wall portion may be cooled to cause contraction thereof, so that the flow of sperms in the uterine tube is at least further restricted, or further restricted but not stopped, or stopped. Alternatively, the uterine tube wall portion may be heated, when the uterine tube wall portion is constricted and contracted, to cause expansion of the uterine tube wall portion. Where applicable, thermal stimulation may be practised in any of the embodiments of the present invention. Where applicable, thermal stimulation may be practised in any of the embodiments of the present invention, and the thermal stimulation may be controlled in response to various sensors, for example strain, motion or pressure sensors.

Constriction and Stimulation Devices

It should be understood that any embodiment or part of embodiment for the combined stimulation device and constriction device, could be used, if applicable, for any one of the devices as a stand alone device. Generally, the method of the invention comprises providing a constriction device that constricts the uterine tube wall portion, a stimulation device that stimulates the constricted uterine tube wall portion and a control device that controls the constriction device and/or the stimulation device. The method comprises operating the control device from outside the patient's body, preferably by using the control device to wirelessly control the constriction device and/or stimulation device. The wireless control is preferably performed in a non-magnetic manner, whereby implanted magnetic devices can be avoided. Suitably, the control device comprises a hand-held wireless remote control operated by the patient.

Alternatively, the control device comprises a manually operable switch for switching on and off the constriction device and/or stimulation device. In this case, the method comprises subcutaneously implanting the switch in the patient and manually operating the the implanted switch from outside the patient's body.

In an embodiment of the invention, the control device comprises a programmable internal control unit, such as a microprocessor, and the method comprises implanting in the patient the internal control unit and controlling by the internal control unit the constriction device and/or stimulation device. The control device may also comprise an external control unit outside the patient's body. In this case, the method comprises controlling by the external control unit the constriction device and/or stimulation device and, optionally, using the external control unit to program the implanted internal control unit. The internal control unit may be programmable for controlling the constriction device and/or stimulation device over time, for example in accordance with an activity schedule program.

The constriction of the uterine tube wall portion can be calibrated by using the control device to control the stimulation device to stimulate the uterine tube wall portion while controlling the constriction device to adjust the constriction of the uterine tube wall portion until the desired restriction of the flow of sperms in the uterine tube is obtained.

Sensor Controlled Constriction and/or Stimulation

It should be understood that any embodiment or part of embodiment disclosed below in connection with sensor control of the constriction and stimulation devices combined in the constriction/stimulation unit could be used for the separate constriction device and separate stimulation device, where applicable. In an embodiment of the invention, the method comprises implanting at least one sensor and controlling by the control device the constriction device and/or the stimulation device in response to signals from the sensor. Generally, the sensor directly or indirectly senses at least one physical parameter of the patient, functional parameter of the apparatus, or functional parameter of a medical implant in the patient.

Many different kinds of sensor for sensing physical parameters may be used. For example motion sensors for sensing organ motion, i.e. natural contractions, pressure sensors for sensing pressure in the uterine tube, strain sensors for sensing strain of the uterine tube, flow sensors for sensing fluid flow in the uterine tube, spectro-photometrical sensors, Ph-sensors for acidity or alkalinity of the fluid in the uterine tube, oxygen-sensors sensors for sensing the oxygen content of the fluid in the uterine tube or sensors for sensing the distribution of the stimulation on the stimulated uterine tube. Any conceivable sensors for sensing any other kind of useful physical parameter may be used.

Many different kinds of sensors that sense functional parameters of implanted components may also be used for the control of the constriction device and/or the stimulation device. For example sensors for sensing electric parameters of implanted electric components, or sensors for sensing the performance of implanted motors or the like.

The sensor may comprise a pressure sensor for sensing as the physical parameter a pressure in the patient's body that relates to the pressure in the uterine tube of the patient In this case, the method suitably comprises operating the control device to control the constriction device to change the constriction of the patient's uterine tube wall portion in response to the pressure sensor sensing a predetermined value of measured pressure.

Alternatively, or in combination with the pressure sensor, a position sensor may be provided for sensing as the physical parameter the orientation of the patient with respect to the horizontal. The position sensor may be a biocompatible version of what is shown in U.S. Pat. Nos. 4,942,668 and 5,900,909, these documents being incorporated hereby by reference. For example, the control device may control the constriction device and/or stimulation device to change the constriction of the patient's wall portion in response to the position sensor sensing that the patient has assumed a substantially horizontal orientation, i.e. that the patient is lying down.

The above described sensors may be used in any of the embodiments of the invention, where applicable.

The control device may control the constriction device and/or stimulation device to change the constriction of the patient's uterine tube wall portion in response to the time of day. For that purpose the control device may include a clock mechanism for controlling the constriction device and/or stimulation device to change the constriction of the patient's uterine tube wall portion to increase or decrease the influence on the flow of sperms in the uterine tube during different time periods of the day. In case a sensor of any of the above-described types for sensing a physical or functional parameter is provided, either the clock mechanism is used for controlling the constriction device and/or stimulation device provided that the parameter sensed by the sensor does not override the clock mechanism, or the sensor is used for controlling the constriction device and/or stimulation device provided that the clock mechanism does not override the sensor. Suitably, the control device produces an indication, such as a sound signal or displayed information, in response to signals from the sensor.

The control device may comprise an implantable internal control unit that directly controls the constriction device and/or stimulation device in response to signals from the sensor. The control device may further comprise a wireless remote control adapted to set control parameters of the internal control unit from outside the patient without mechanically penetrating the patient. At least one of the control parameters, which is settable by the wireless remote control, is the physical or functional parameter. Suitably, the internal control unit includes the above mentioned clock mechanism, wherein the wireless remote control also is adapted to set the clock mechanism.

Alternatively, the control device may comprise an external control unit outside the patient's body for controlling the constriction device and/or stimulation device in response to signals from the sensor.

Constriction of Patient's Uterine Tube

It should be understood that any embodiment or part of embodiment disclosed below in connection with constricting the patient's uterine tube could be used for the separate constriction device and separate stimulation device, where applicable. Method step (a) may be performed in many different ways. Thus, step (a) may be performed by:
(1)—constricting the uterine tube wall portion so that the through-flow area of the uterine tube assumes a size in the constricted state small enough to cause the constricted uterine tube wall portion to contract to stop the flow of sperms in the uterine tube when step (b) is performed;
(2)—bending the uterine tube wall portion;
(3)—clamping the uterine tube wall portion between at least two elements positioned on different sides of the uterine tube;
(4)—clamping the uterine tube between an element and the bone or tissue of the patient;
(5)—rotating at least two elements positioned on different sides of the uterine tube; or
(6)—clamping the uterine tube between at least two articulated clamping elements positioned on different sides of the uterine tube.

In the above noted alternatives (1) to (6) of method step (a), the constriction of the uterine tube wall portion of the uterine tube may be changed either mechanically or hydraulically. For many applications of the present invention, step (a) is suitably performed so that the through-flow area of the uterine tube assumes a size in the constricted state that is small enough to enable the stimulation during step (b) to contract the uterine tube wall portion of the uterine tube to stop the flow of sperms in the uterine tube.

Where the constriction of the uterine tube wall portion is hydraulically changed, the method of the invention may further comprise implanting in the patient a reservoir containing a predetermined amount of hydraulic fluid, and a constriction device engaging the uterine tube wall portion and having an expandable/contractible cavity, wherein step (a) is performed by distributing hydraulic fluid from the reservoir to increase the volume of the cavity to constrict the uterine tube wall portion, and by distributing hydraulic fluid from the cavity to the reservoir to decrease the volume of the cavity to release the uterine tube wall portion. The cavity may be defined by a balloon of the constriction device that abuts the uterine tube wall portion of the patient's uterine tube, so that the patient's uterine tube wall portion is constricted upon expansion of the cavity and released upon contraction of the cavity.

Alternatively, the cavity may be defined by a bellows that displaces a relatively large contraction element of the constriction device, for example a large balloon that abuts the uterine tube wall portion, so that the patient's uterine tube wall portion is constricted upon contraction of the bellows and released upon expansion of the bellows. Thus, a relatively small addition of hydraulic fluid to the bellows causes a relatively large increase in the constriction of the uterine tube wall portion. Such a bellows may also be replaced by a suitably designed piston/cylinder mechanism.

Where the hydraulic means comprises a cavity in the constriction device, the following embodiments of the invention are conceivable.

The reservoir comprises first and second wall portions, and step (a) is performed by displacing the first and second wall portions relative to each other to change the volume of the reservoir, so that fluid is distributed from the reservoir to the cavity, or from the cavity to the reservoir.

1a) At least one of a magnetic device, a hydraulic device or an electric control device displaces the first and second wall portions of the reservoir.

2) A pump is provided for pumping fluid between the reservoir and the cavity.

2a) The pump comprises a first activation member for activating the pump to pump fluid from the reservoir to the cavity and a second activation member for activating the pump to pump fluid from the cavity to the reservoir.

2a1) The first and second activation members are operable by manual manipulation thereof.

2a2) At least one of the activation members operates when subjected to an external predetermined pressure.

2a3) At least one of the first and second activating members is operable by magnetic means, hydraulic means, or electric control means.

2b) A fluid conduit between the pump and the cavity is provided, wherein the reservoir forms part of the conduit. The conduit and pump are devoid of any non-return valve. The reservoir forms a fluid chamber with a variable volume, and the pump distributes fluid from the chamber to the cavity by a reduction in the volume of the chamber and withdraws fluid from the cavity by an expansion of the volume of the chamber. A motor is provided for driving the pump, wherein the pump comprises a movable wall of the reservoir for changing the volume of the chamber.

In all of the above noted embodiments 1 to 2b where the hydraulic means comprises an expandable cavity in the constriction device, the cavity can be exchanged by a cylinder/piston mechanism for adjusting the constriction device. In this case, hydraulic fluid is distributed between the reservoir and the cylinder/piston mechanism to adjust the constriction device.

3) The method further comprises implanting a reverse servo operatively connected to the hydraulic means. The term "reverse servo" is to be understood as a mechanism that transfers a strong force acting on a moving element having a short stroke into a weak force acting on another moving element having a long stroke; i.e., the reverse function of a normal servo mechanism. Thus, minor changes in the amount of fluid in a smaller reservoir could be transferred by the reverse servo into major changes in the amount of fluid in a larger reservoir.

Preferably, the reverse servo comprises an expandable servo reservoir containing servo fluid and a fluid supply reservoir hydraulically connected to the servo reservoir to form a closed conduit system for the servo fluid. The expandable servo reservoir has first and second wall portions, which are displaceable relative to each other in response to a change in the volume of the expandable servo reservoir.

In accordance with a first alternative, the first and second wall portions of the servo reservoir are operatively connected to the hydraulic means. The reverse servo distributes fluid between the fluid supply reservoir and the expandable servo reservoir to change the volume of the servo reservoir, whereby the hydraulic means is operated to adjust the constriction device.

In accordance with a second alternative, there is provided an implantable main reservoir containing a predetermined amount of hydraulic fluid, wherein the reverse servo is operated to distribute hydraulic fluid between the main reservoir and the hydraulic means to adjust the constriction device. More specifically, the main reservoir is provided with first and second wall portions operatively connected to the first and second wall portions of the expandable servo reservoir, so that the volume of the main reservoir is changed when the volume of the expandable servo reservoir is changed. Thus, when the reverse servo distributes servo fluid between the fluid supply reservoir and the expandable servo reservoir to change the volume of the main reservoir, hydraulic fluid is distributed from the main reservoir to the hydraulic means, or from the hydraulic means to the main reservoir. Advantageously, the method comprises dimensioning the servo and main reservoirs, so that when the volume of the servo reservoir is changed by a relatively small amount of servo fluid, the volume of the main reservoir is changed by a relatively large amount of hydraulic fluid.

In both of the above-described alternatives, the fluid supply reservoir may have first and second wall portions, which are displaceable relative to each other to change the volume of the fluid supply reservoir to distribute servo fluid between the fluid supply reservoir and the expandable servo reservoir. The first and second wall portions of the fluid supply reservoir may be displaced relative to each other by manual manipulation, a magnetic device, a hydraulic device, or an electric control device to change the volume of the fluid supply reservoir to distribute servo fluid between the fluid supply reservoir and the expandable servo reservoir.

In all of the above noted embodiments 1 to 2b where the hydraulic means comprises an expandable cavity in the constriction device, or in embodiments where the hydraulic means includes a hydraulically operable mechanical construction, the reverse servo described above may be used. In a further embodiment of the invention, the hydraulic means include first and second hydraulically interconnected expandable/contractible reservoirs. The first reservoir is operatively connected to the constriction device, so that the constriction device changes the constriction of the patient's wall portion upon expansion or contraction of the first reservoir. By changing the volume of the second reservoir hydraulic fluid is distributed between the two reservoirs, so that the first reservoir is either expanded or contracted. This embodiment requires no non-return valve in the fluid communication conduits between the two reservoirs, which is beneficial to long-term operation of the hydraulic means.

Alternatively, the hydraulic means may include first and second hydraulically interconnected piston/cylinder mechanisms instead of the first and second reservoirs described above. The first piston/cylinder mechanism is operatively connected to the constriction device, so that the constriction device changes the constriction of the patient's wall portion upon operation of the first piston/cylinder mechanism. By operating the second piston/cylinder mechanism hydraulic fluid is distributed between the two piston/cylinder mechanisms, so that the first piston/cylinder mechanism adjusts the constriction device.

Where the constriction device does not include an expandable/contractible cavity, the constriction device may comprise at least two elongated clamping elements extending along the uterine tube wall portion on different sides of the uterine tube. The hydraulic means, which may include the reverse servo described above, hydraulically moves the elongated clamping elements towards the uterine tube to constrict the uterine tube wall portion. For example, the constriction device may have hydraulic chambers in which the clamping elements slide back and forth, and the hydraulic means may also include a pump and an implantable reservoir containing hydraulic fluid. The pump distributes hydraulic fluid from the reservoir to the chambers to move the clamping elements against the uterine tube wall portion, and distributes hydraulic fluid from the chambers to the reservoir to move the clamping elements away from the uterine tube wall portion.

Energy Supply

It should be understood that any embodiment or part of embodiment disclosed below in connection with the power of the constriction and stimulation devices combined in the constriction/stimulation unit could be used for the separate constriction device and separate stimulation device, where applicable. Generally, method step (a) is performed by using the constriction device and step (b) is performed by using the stimulation device, wherein the method further comprises forming the constriction and stimulation devices in an operable constriction/stimulation unit.

In a simple form of the invention, the method comprises implanting a source of energy, such as a battery, rechargeable battery or accumulator, releasing energy from the source of energy and using the released energy in connection with the operation of the constriction/stimulation unit.

In a more sophisticated form of the invention, which is preferable, the method comprises transmitting wireless energy from outside the patient's body to inside the patient's body and using the transmitted wireless energy in connection with the operation of the constriction/stimulation unit.

Transmission of Wireless Energy

It should be understood that any embodiment or part of embodiment disclosed below in connection with wireless control or power of the constriction and stimulation devices combined in the constriction/stimulation unit could be used for the separate constriction device and separate stimulation device, where applicable. The wireless energy may be directly used in connection with the operation of the constriction/stimulation unit, as the wireless energy is being transmitted. For example, the wireless energy may be transmitted in the form of an electric, an electromagnetic or a magnetic field, or a combination thereof, or electromagnetic waves for direct power of the constriction/stimulation unit. For example, where an electric motor or pump operates the constriction device of the constriction/stimulation unit, wireless energy in the form of a magnetic or an electromagnetic field may be used for direct power of the motor or pump.

Thus, the motor or pump is running directly during transmission of the wireless energy. This may be achieved in two different ways: a) using a transforming device implanted in the patient to transform the wireless energy into energy of a different form, preferably electric energy, and powering the motor or pump with the transformed energy, or b) using the wirelessly transmitted energy to directly power the motor or pump. Preferably wireless energy in the form of an electromagnetic or magnetic field is used to directly influence specific components of the motor or pump to create kinetic energy. Such components may include coils integrated in the motor or pump.

The wireless energy is suitably transmitted in pulses or digital pulses, or a combination of pulses and digital pulses.

Preferably, the wireless energy is transmitted in at least one wireless signal, suitably a wave signal. The wave signal may comprise an electromagnetic wave signal including one of an infrared light signal, a visible light signal, an ultra violet light signal, a laser signal, a microwave signal, a radio wave signal, an x-ray radiation signal, and a gamma radiation signal. Alternatively, the wave signal may comprise a sound or an ultrasound wave signal. The wireless signal may be a digital or analogue signal, or a combination of a digital and analogue signal.

In accordance with a particular embodiment of the invention, the wireless energy is not for direct use in connection with the operation of the constriction/stimulation unit. In this embodiment the wireless energy comprises energy of a first form, which is transmitted into energy of a second form suited to operate the constriction/stimulation unit. Typically, the energy of the second form is different from the energy of the first form. For example, the wireless energy of the first form may comprise sound waves, whereas the energy of the second form may comprise electric energy. Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

Transforming Wireless Energy

It should be understood that any embodiment or part of embodiment disclosed below in connection with the control or energizing of the constriction and stimulation devices combined in the constriction/stimulation unit could be used for the separate constriction device and separate stimulation device, where applicable. In accordance with a particular embodiment of the invention, an implantable energy-transforming device is provided for transforming wireless energy of a first form transmitted by the energy-transmission device into energy of a second form, which typically is different from the energy of the first form. The constriction/stimulation unit is operable in response to the energy of the second form. For example, the wireless energy of the first form may comprise sound waves, whereas the energy of the second form may comprise electric energy. Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transforming device may function different from or similar to the energy-transmission device. Advantageously, the energy-transforming device comprises at least one element, such as at least one semiconductor, having a positive region and a negative region, when exposed to the energy of the first form transmitted by the energy-transmission device, wherein the element is capable of creating an energy field between the positive and negative regions, and the energy field produces the energy of the second form. More specifically, the element may comprise an electrical junction element, which is capable of inducing an electric field between the positive and negative regions when exposed to the energy of the first form transmitted by the energy-transmission device, whereby the energy of the second form comprises electric energy.

The energy of the first form may directly or indirectly be transformed into the energy of the second form. The method of the invention may comprise providing a motor for operating the constriction device and powering the motor with the energy of the second form. The constriction device may be operable to perform at least one reversible function and the method may comprise reversing the function by using the motor. For example, the method may comprise shifting the polarity of the energy of the second form to reverse the motor.

The motor may be directly powered with the transformed energy, as the energy of the second form is being transformed from the energy of the first form. Preferably, the constriction/stimulation unit is directly operated with the energy of the second form in a non-magnetic, non-thermal or non-mechanical manner.

Normally, the implanted constriction/stimulation unit comprises electric components that are energized with electrical energy. Therefore, the energy of the first form may be transformed into a direct current or pulsating direct current, or a combination of a direct current and pulsating direct current. Alternatively, the energy of the first form may be transformed into an alternating current or a combination of a direct and alternating current.

The method of the invention may comprise implanting in the patient an internal source of energy, and supplying energy from the internal source of energy for the operation of the constriction/stimulation unit. The method may further comprise implanting in the patient a switch operable to switch from an "off" mode, in which the internal source of energy is not in use, to an "on" mode, in which the internal source of energy supplies energy for the operation of the constriction/stimulation unit, and/or for energizing implanted electronic components of the constriction/stimulation unit. The switch may be operated by the energy of the first form or by the energy of the second form. The described switch arrangement reduces power consumption of the constriction/stimulation unit between operations.

The internal source of energy may store the energy of the second form. In this case, the internal source of energy suitably comprises an accumulator, such as at least one capacitor or at least one rechargeable battery, or a combination of at least one capacitor and at least one rechargeable battery. Where the internal source of energy is a rechargeable battery it may be charged only at times convenient for the patient, for example when the patient is sleeping. Alternatively, the internal source of energy may supply energy for the operation of the constriction/stimulation unit but not be used for storing the energy of the second form. In this alternative, the internal source of energy may be a battery and the switch described above may or may not be provided.

Suitably, the method of the invention may comprise implanting a stabilizer for stabilizing the energy of the second form. Where the energy of the second form comprises electric energy the stabilizer suitably comprises at least one capacitor.

The energy-transforming device may be designed for implantation subcutaneously in the abdomen, thorax or cephalic region of the patient. Alternatively, it may be designed for implantation in an orifice of the patient's body and under the mucosa or intramuscularly outside the mucosa of the orifice.

Control of Constriction/Stimulation Unit

It should be understood that any embodiment or part of embodiment disclosed below in connection with the control of the constriction and stimulation devices combined in the constriction/stimulation unit could be used for the separate constriction device and separate stimulation device, where applicable. Although the constriction device of the constriction/stimulation unit may normally keep the patient's wall portion in the constricted state, in most applications using the present invention there will be daily adjustments of the constriction device. Therefore, in a preferred embodiment of the invention, the constriction device is adjustable to enable changing the constriction of the patient's uterine tube wall portion as desired and the control device controls the constriction device to change the constriction of the uterine tube wall portion.

The method of the invention suitably comprises operating the control device by the patient. In a simple form the control device comprises a manually operable switch for switching on and off the constriction/stimulation unit, and the method further comprises subcutaneously implanting the switch in the patient. It is preferable, however, that the control device comprises a hand-held wireless remote control operable by the patient from outside the patient's body to control the constriction/stimulation unit to adjust the stimulation intensity and/or adjust the constriction of the uterine tube wall portion. The wireless remote control is suitably designed for application on the patient's body like a wristwatch.

In some applications of the invention, the constriction device of the constriction/stimulation unit may be designed to normally keep the patient's uterine tube wall portion in the constricted state. I.e., after implantation the constriction device all the time keeps the uterine tube wall portion constricted. In this case, the control device may be used when needed, conveniently by the patient, to control the stimulation device of the constriction/stimulation unit to stimulate the constricted uterine tube wall portion, preferably while adjusting the stimulation intensity, to cause contraction of the uterine tube wall portion, so that the flow of sperms in the uterine tube is at least further restricted or stopped, and to control the stimulation device to cease the stimulation. More precisely, the method of the invention may comprise operating the control device by the patient to control the stimulation device in a first mode to stimulate the constricted wall portion to further restrict the flow of sperms in the uterine tube and control the stimulation device in a second mode to cease the stimulation of the uterine tube wall portion to increase the flow of sperms in the uterine tube; or control the stimulation device in a first mode to stimulate the constricted wall portion to stop the flow of sperms in the uterine tube and control the stimulation device in a second mode to cease the stimulation of the uterine tube wall portion to allow flow in the uterine tube.

Either the first mode or the second mode may be temporary.

The wireless remote control preferably transmits at least one wireless control signal for controlling the constriction/stimulation unit. The control signal may comprise a frequency, amplitude, phase modulated signal or a combination thereof, and may be an analogue or a digital signal, or a combination of an analogue and digital signal. The remote control may transmit an electromagnetic carrier wave signal for carrying the digital or analogue control signal. Also the carrier signal may comprise digital, analogue or a combination of digital and analogue signals.

Any of the above signals may comprise wave signals, such as a sound wave signal, an ultrasound wave signal, an electromagnetic wave signal, an infrared light signal, a visible light signal, an ultra violet light signal, a laser light signal, a micro wave signal, a radio wave signal, an x-ray radiation signal or a gamma radiation signal.

Alternatively, the control signal may comprise an electric or magnetic field, or a combined electric and magnetic field.

Operation of Constriction/Stimulation Unit

It should be understood that any embodiment or part of embodiment for operating the combined stimulation device and constriction device, could be used, if applicable, for any one of the devices as a stand alone device. The method of the invention may comprise implanting in the patient an operation device, and operating the constriction/stimulation unit with the operation device. A magnet may be provided, wherein the method comprises using the magnet to activate the operation device from outside the patient's body. The operation device suitably comprises a motor which is powered with energy released from a source of energy, such as a battery. Although the constriction/stimulation unit in embodiments described above suitably is designed as a single piece, which is most practical for implantation, it should be noted that as an alternative the constriction device and stimulation device of the constriction/stimulation unit could be designed as separate pieces.

Laparoscopic Method

The present invention also provides a first method for controlling a flow of sperms in a uterine tube formed by a uterine tube wall of a patient. The method comprises the steps of:
inserting a needle like tube into the cavity of the patients body,
filling the cavity with gas thereby expanding the cavity,
placing at least two laparoscopic trocars in the patient's body,
inserting a camera through one of the trocars into the cavity,
inserting a dissecting tool through any of the trocar and dissecting an area of at least one portion of the uterine tube wall,
placing a constriction device and a stimulation device in the dissected area in operative engagement with the uterine tube,
using the constriction device to gently constrict the uterine tube wall portion of the uterine tube to influence the flow of sperms in the uterine tube, and
using the stimulation device to stimulate the constricted wall portion to cause contraction of the uterine tube wall portion to further influence the flow of sperms in the uterine tube.

The present invention also provides a second method for controlling a flow of sperms in a uterine tube formed by a uterine tube wall of a patient. The method comprises the steps of:
inserting a needle like tube into a cavity of the patients body,
using the needle like tube to fill the cavity with gas thereby expanding the cavity,
placing at least two laparoscopic trocars in the patient's body,
inserting a camera through one of the trocars into the cavity,
inserting a dissecting tool through any of the trocar and dissecting an area of at least one portion of the uterine tube wall,
placing a stimulation device in the dissected area in operative engagement with the uterine tube, and
using the stimulation device to stimulate the uterine tube wall portion to cause contraction of the uterine tube wall portion to influence the flow of sperms in the uterine tube.

The present invention also provides a third method for controlling a flow of sperms in a uterine tube formed by a uterine tube wall of a patient. The method comprises the steps of:
inserting a needle like tube into a cavity of the patients body,
using the needle like tube to fill the cavity with gas thereby expanding the cavity,
placing at least two laparoscopic trocars in the patient's body,
inserting a camera through one of the trocars into the cavity,
inserting a dissecting tool through any of the trocar and dissecting an area of at least one portion of the uterine tube wall,
placing a constriction device in the dissected area in operative engagement with the uterine tube,
using the constriction device to constrict the uterine tube wall portion of the uterine tube to influence the flow of sperms in the uterine tube.

The present invention also provides a fourth method for controlling a flow of sperms in a uterine tube formed by a uterine tube wall of a patient. The method comprises the steps of:
cutting the skin of the patient,
inserting a dissecting tool and dissecting an area of at least one portion of the uterine tube wall,
placing a constriction device and a stimulation device in the dissected area in operative engagement with the uterine tube,
using the constriction device to gently constrict the uterine tube wall portion of the uterine tube to influence the flow of sperms in the uterine tube, and
using the stimulation device to stimulate the constricted wall portion to cause contraction of the uterine tube wall portion to further influence the flow of sperms in the uterine tube.

The present invention also provides a fifth method for controlling a flow of sperms in a uterine tube formed by a uterine tube wall of a patient. The method comprises the steps of:
cutting the skin of the patient,
inserting a dissecting tool and dissecting an area of at least one portion of the uterine tube wall,
placing a stimulation device in the dissected area in operative engagement with the uterine tube, and
using the stimulation device to stimulate the uterine tube wall portion to cause contraction of the uterine tube wall portion to influence the flow of sperms in the uterine tube.

The present invention also provides a sixth method for controlling a flow of sperms in a uterine tube formed by a uterine tube wall of a patient. The method comprises the steps of:
cutting the skin of the patient,
inserting a dissecting tool and dissecting an area of at least one portion of the uterine tube wall,
placing a constriction device in the dissected area in operative engagement with the uterine tube, and
using the constriction device to constrict the uterine tube wall portion to influence the flow of sperms in the uterine tube.

In all of the above presented methods 1-6 above the cavity may constitute at least one of an abdominal cavity, a cavity in the pelvic region, a retroperitoneal cavity, a cavity in human soft tissue such as muscle, fat and fibrotic tissue.

The method further comprises implanting a powered operation device for operating the constriction device. The operation device may comprise a powered hydraulic operation device or an electrically powered operation device, such as an electric motor.

The method further comprises transmitting wireless energy for powering the operation device, and when desired to influence the flow of sperms in the patient's uterine tube, powering the operation device with the transmitted energy to operate the constriction device.

Blood Flow Control

Another object of the present invention is to provide a method for controlling the flow of blood and/or other bodily matter in blood vessels and to obviate at least some of the disadvantages of the prior art.

In accordance with this object of the present invention, there is provided a method for controlling the flow of blood and/or other bodily matter in a blood vessel, the method comprising:
a) gently constricting a portion of the wall to influence the flow in the blood vessel, and
b) stimulating the constricted wall portion to cause contraction of the at least one portion of the wall to further influence the flow in the blood vessel.

The present invention provides an advantageous combination of the method steps (a) and (b), which results in a two-stage influence on the flow of blood and/or other bodily matter in the blood vessel. Thus, applying a relatively weak force against the at least one portion of the wall gently constricts the wall of the blood vessel and the constricted wall portion is stimulated to achieve the desired final influence on the flow in the blood vessel. The phrase "gently constricts a portion of the wall of the blood vessel" is to be understood as constricting the at least one portion of the wall without substantially hampering the blood circulation in the wall of the blood vessel.

Alternatively the method comprises:
gently constricting at least one portion of the tissue wall to influence the flow in the lumen, or
stimulating at least one portion of the tissue wall to cause contraction of the wall portion to further influence the flow in the lumen.

It should be understood that any embodiment or part of embodiment disclosed below in this application for the constriction and stimulation devices combined in the constriction/stimulation unit could be used for the separate constriction device and separate stimulation device, where applicable.

Preferably, step (b) is performed by intermittently and individually stimulating different areas of the wall portion. Such an intermittent and individual stimulation of different areas of the at least one portion of the wall of the blood vessel allows tissue of the at least one portion of the wall to maintain over time substantially normal blood circulation.

The method of the present invention can be practiced on any place on any kind of blood vessels. Preferably, the constriction step (a) and stimulation step (b) are performed independently of each other. Steps (a) and (b) may be performed simultaneously. Optionally, step (b) may or may not be performed while step (a) is performed.

Initially, the constriction of the at least one portion of the wall can be calibrated by stimulating the at least one portion of the wall while adjusting the constriction of the at least one portion of the wall until the desired restriction of the flow in the blood vessel is obtained.

Flow Restriction

The method of the present invention is well suited for restricting the flow of blood and/or other bodily matter in the blood vessel. Thus, in a principal embodiment of the invention, the at least one portion of the wall is constricted, so that the flow in the blood vessel at least is restricted and the constricted wall portion is stimulated to at least further restrict the flow in the blood vessel. Specifically, the at least one portion of the wall is constricted to a constricted state, in which the blood circulation in the constricted wall portion is substantially unrestricted and the flow in the blood vessel is at least restricted, and the constricted wall portion is stimulated when it is in the constricted state to at least further restrict the flow in the blood vessel.

Specifically, the constriction device is adapted to constrict the wall portion to a constricted state in which the blood circulation in the constricted wall portion is substantially unrestricted and the flow in the blood vessel is at least restricted, and the control device controls the stimulation device to cause an increase of the tonus of the blood vessel, so that the flow in the blood vessel is at least further restricted when the wall portion is kept by the constriction device in the constricted state.

The constriction step (a) and stimulation step (b) are suitably performed to constrict and stimulate the at least one portion of the wall to an extent that depends on the flow restriction that is desired to be achieved in a specific application of the method of the invention. Thus, in accordance with a first flow restriction option, step (a) is performed by constricting the wall portion, so that the flow in the blood vessel is restricted but not stopped, and step (b) is performed by stimulating the constricted wall portion to cause contraction thereof, so that the flow in the blood vessel is further restricted but not stopped. The method may further comprise sensing a physical parameter of the patient and adjusting the intensity of the stimulation of the at least one portion of the wall in response to the sensed parameter.

In accordance with a second flow restriction option, step (a) is performed by constricting the wall portion, so that the flow in the blood vessel is restricted but not stopped, and step (b) is performed by stimulating the constricted wall portion to cause contraction thereof, so that the flow in the blood vessel is stopped.

When using the method of the invention in accordance with the first or second options, the method may further comprise (c) ceaseing stimulating the at least one portion of the wall to increase or allow the flow in the blood vessel and (d) releasing the at least one portion of the wall to restore the flow in the blood vessel.

In accordance with a third flow restriction option, step (a) is performed by constricting the wall portion, so that the flow in the blood vessel is substantially stopped, and step (b) is performed by stimulating the constricted wall portion to cause contraction thereof, so that the flow in the blood vessel is completely stopped. The method may further comprise (c) ceaseing stimulating the at least one portion of the wall to allow the flow in the blood vessel and (d) releasing the at least one portion of the wall to restore the flow in the blood vessel.

Where the constricted wall portion is stimulated to contract, so that the flow in the blood vessel is stopped, a first length of the constricted wall portion and a second length of the constricted wall portion, which is located downstream of the first length, are suitably simultaneously and cyclically stimulated, wherein the first length is progressively stimulated in the upstream direction of the blood vessel and the second length is progressively stimulated in the downstream direction of the blood vessel.

Furthermore, when using the method of the invention in accordance with the second and third options, the method may further comprise sensing a physical parameter of the patient or functional parameter of implanted components and adjusting the stimulation of the at least one portion of the wall in response to the sensed parameter. For example, the intensity of the stimulation of the at least one portion of the wall may be increased in response to a sensed pressure increase in the blood vessel, so that the flow in the blood vessel remains stopped when a pressure increase occurs in the blood vessel.

In particular, the method may comprise sensing a physical parameter of the patient's that relates to the pressure in the blood vessel, and controlling the stimulation of the at least one portion of the wall in response to the sensed parameter. Any sensor for sensing a physical parameter of the patient, such as a pressure in the patient's body that relates to the pressure in the blood vessel may be provided, wherein the stimulation is controlled in response to signals from the sensor. Such a sensor may for example the pressure against the implanted constriction device or the pressure on the wall of the blood vessel.

In accordance with a fourth restriction option, step (a) is performed by constricting the wall portion, so that the flow in the blood vessel is stopped. When needed, the at least one portion of the wall is released to restore the flow in the blood vessel. Step (b) is only performed by stimulating the constricted wall portion to cause contraction thereof, so that the flow in the blood vessel remains stopped when a pressure increase occurs in the blood vessel. The method may further comprise sensing a physical parameter of the patient's body, such as a pressure in the patient's body that relates to the pressure in the blood vessel, and controlling the stimulation of the at least one portion of the wall in response to the sensed parameter. Such a physical parameter may be a pressure in the patient's abdomen and the sensor may be a pressure sensor.

In some applications of the method of the invention, continuous stimulation may over time change the physical properties of the tissue so that the tissue might be injured. Also, the effect of a continuous stimulation of the wall of the blood vessel may decrease over time. Therefore, step (b) is preferably performed by intermittently and individually stimulating different areas of the at least one portion of the wall so that the flow in the blood vessel continues to be restricted as desired and each area of the at least one portion of the wall essentially maintains its natural physical properties over time to prevent the area from being injured. Advantageously, each area of the at least one portion of the wall is stimulated during successive time periods, each time period being short enough to maintain over time satisfactory blood circulation in the area. Thus, the areas are stimulated so that an area that currently is not stimulated will have time to restore substantially normal blood circulation before it is stimulated again.

To maintain satisfactory blood circulation in the wall of the blood vessel of the patient's blood vessel stimulation step (b) is suitably performed by stimulating one or more of different areas of the at least one portion of the wall at a time, preferably by sequentially stimulating the different areas of the at least one portion of the wall or by shifting the stimulation from one area to another over time. Preferably, stimulation step (b) is performed by cyclically propagating the stimulation of the areas along the wall portion, for example in accordance with a determined stimulation pattern.

The method of the invention may further comprise controlling, preferably by the patient, the constriction and/or stimulation of the at least one portion of the wall from outside the patient's body.

Generally, the method of the invention comprises sensing a physical parameter of the patient and controlling, preferably automatically, the constriction and/or stimulation of the at least one portion of the wall in response to the sensed parameter.

The constriction step (a) may be performed by constricting any wall portions of a series of wall portions of the blood vessel's wall of the blood vessel, respectively, either in random or in accordance with a predetermined sequence. The stimulation step (b) may be performed by stimulating any of the constricted wall portions of the series of wall portions. Specifically, step (a) may be performed by constricting all of the wall portions of the series of wall portions, and step (b) may be performed by stimulating any constricted wall portions in random or in accordance with a predetermined sequence to close the blood vessel.

Moving Blood and/or Other Bodily Matter in Blood Vessel or Preventing the Movement of Blood and/or Other Bodily Matters in the Lumen in a Similar Way The method of the present invention can be practised for actively moving the blood and/or other bodily matter in blood vessel of a patient's blood vessel. Thus, in the embodiments of the invention listed below, steps (a) and (b) are co-operated to move the blood and/or other bodily matter in the blood vessel.

1) Step (a) is performed by constricting the at least one portion of the wall to restrict the flow in the blood vessel, and step (b) is performed by stimulating the constricted wall portion to close the blood vessel either at an upstream end or a downstream end of the constricted wall portion. The method further comprises (c) increasing the constriction of the at least one portion of the wall to move the blood and/or other bodily matter in the blood vessel.

2) Step (a) is performed by constricting the at least one portion of the wall to restrict the flow in the blood vessel, and step (b) is performed by progressively stimulating the constricted wall portion to cause progressive contraction of the at least one portion of the wall to move the blood and/or other bodily matter in the blood vessel. The constricted wall portion is progressively stimulated in the downstream or upstream direction of the blood vessel.

3) Step (a) is performed by varyingly constricting the at least one portion of the wall to vary the flow in the blood vessel, and step (b) is performed by progressively stimulating the constricted wall portion to cause progressive contraction of the at least one portion of the wall to move the blood and/or other bodily matter in the blood vessel. The constricted wall portion is progressively stimulated in the downstream or upstream direction of the blood vessel.

4) Step (a) is performed by varyingly constricting different areas of the at least one portion of the wall to cause progressive constriction of the at least one portion of the wall in the downstream or upstream direction of the blood vessel, and the constricted wall portion is progressively stimulated to cause progressive contraction thereof in harmony with the progressive constriction of the wall portion. The method may further comprise providing at least one elongated constriction element extending along the wall portion, and controlling the elongated constriction element to progressively constrict the at least one portion of the wall in the downstream or upstream direction of the blood vessel. The elongated constriction element suitably comprises contact surfaces dimensioned to contact a length of wall portion, and the method may further comprise providing a plurality of stimulation elements distributed along the contact surfaces, and controlling the stimulation elements to stimulate the different areas of the at least one portion of the wall along the length of the wall portion.

5) Step (a) is performed by constricting any one of a series of wall portions of the wall of the blood vessel to at least restrict the flow in the blood vessel, and step (b) is performed by stimulating the constricted wall portion to close the blood vessel. The method further comprises successively constricting the wall portions of the series of wall portions to move the blood and/or other bodily matter in the blood vessel in a peristaltic manner.

5a) In accordance with an alternative, the method further comprises providing at least one constriction element and at least one stimulation element positioned on the constriction element, moving the constriction element along the blood vessel in the flow direction in the blood vessel to successively constrict the wall portions of the series of wall portions, and using the stimulation element to stimulate the at least one portion of the wall constricted by the constriction element to close the blood vessel. Suitably, the method further comprises cyclically moving the constriction element along the wall portions of the series of wall portions.

5b) In accordance with another alternative, the method further comprises providing a plurality of constriction elements and stimulation elements positioned on the constriction elements, moving each constriction element along the blood vessel to successively constrict the wall portions of the series of wall portions, and using the stimulation elements to stimulate the at least one portion of the wall constricted by any one of the constriction elements to close the blood vessel. Suitably, the method further comprises cyclically moving the constriction elements one after the other along the wall portions of the series of wall portions. Specifically, the method further comprises providing a rotor carrying the constriction elements, and rotating the rotor so that each constriction element cyclically constricts the wall portions of the series of wall portions. Each constriction element suitably comprises a roller that rolls on the blood vessel to constrict the latter.

6) Step (a) is performed by constricting any wall portions of a series of wall portions of the blood vessel's wall of the blood vessel, respectively, wherein the wall portions of the series of wall portions are successively constricted along the blood vessel to move the blood and/or other bodily matter in the blood vessel of the patient's blood vessel. The stimulation step (b) is performed by stimulating any constricted wall portions of the series of wall portions.

7) Step (a) is performed by constricting wall portions of a series of wall portions without completely closing the blood vessel, and step (b) is performed by stimulating the constricted wall portions one after the other, so that the wall portions of the series of wall portions are successively contracted along the blood vessel to move the blood and/or other bodily matter in the blood vessel of the patient's blood vessel.

8) Step (a) is performed by constricting the at least one portion of the wall at an upstream or downstream end thereof to close the blood vessel. The method further comprises (c) constricting the at least one portion of the wall between the upstream and downstream ends thereof, to move the blood or other bodily matter contained in the at least one portion of the wall between the upstream and downstream ends thereof downstream or upstream in the blood vessel. Optionally, the method further comprises stimulating the at least one portion of the wall between the upstream and downstream ends thereof, as (c) is performed.

8a) In accordance with an alternative, step (a) is performed by constricting the at least one portion of the wall at the upstream end thereof to restrict the flow in the blood vessel, and step (b) is performed by stimulating the constricted wall portion at the upstream end to close the blood vessel, whereby the blood and/or other bodily matter contained in the at least one portion of the wall between the upstream and downstream ends thereof is moved downstream in the blood vessel, as step (c) is performed.

8b) In accordance with another alternative, step (a) is performed by constricting the at least one portion of the wall at the downstream end thereof to restrict the flow in the blood vessel, and step (b) is performed by stimulating the constricted wall portion at the downstream end to close the blood vessel, whereby the blood and/or other bodily matter contained in the at least one portion of the wall between the upstream and downstream ends thereof is moved upstream in the blood vessel, as step (c) is performed.

Where the blood vessel is in shape, such as the small intestines, a particularly long wall portion of the blood vessel may be surgically prepared to extend in zigzag with adjacent walls stitched together by two parallel rows of stitches and with the adjacent walls cut through between the two rows of stitches. As a result, the blood vessel of this long wall portion of the blood vessel can be significantly expanded. In this case, a considerably larger volume of blood is moved in the blood vessel each time step (a) and/or step (b) is performed.

In any of the above noted embodiments (1) to (8b), step (b) may be performed by stimulating the at least one portion of the wall with electric pulses.

Stimulation Modes

When stimulating tissue there is a risk of injuring or deteriorating the tissue over time if the stimulation is not properly performed. The method of the present invention is performed to reduce or even eliminate that risk. Thus, step (b) is performed by intermittently stimulating different areas of the at least one portion of the wall so that at least two of the areas are stimulated at different points of time. I.e., the stimulation is shifted from one area to another area over time. In addition, step (b) is performed by intermittently stimulating the areas of the at least one portion of the wall so that an area of the different areas that currently is not stimulated has time to restore substantially normal blood circulation before it is stimulated again. Furthermore, step (b) is performed by intermittently stimulating the areas during successive time periods, wherein each time period is short enough to maintain satisfactory blood circulation in the area until the laps of the time period. This gives the advantage that the method of the present invention provides continuous stimulation of the at least one portion of the wall of the blood vessel to achieve the desired flow control while essentially maintaining over time the natural physical properties of the blood vessel without risk of injuring the blood vessel.

Also, by physically changing the places of stimulation on the blood vessel over time as described above it is possible to create an advantageous changing stimulation pattern on the blood vessel, in order to achieve a desired flow control.

To achieve the desired reaction of the wall of the blood vessel during the stimulation thereof, step (b) may be performed by stimulating the at least one portion of the wall with, preferably cyclically, varying stimulation intensity.

In a main embodiment of the invention, step (b) is performed by intermittently stimulating the at least one portion of the wall with pulses, preferably in the form of pulse trains. The pulse trains can be configured in many different ways by varying pulse parameters. Thus, the pulse amplitudes of the pulses of the pulse trains, the off time periods between the individual pulses of each pulse train and the width and repetition frequency of each pulse may be varied. Also the off time periods between the pulse trains may be varied, wherein each off time period between the pulse trains is kept long enough to restore substantially normal blood circulation in each area of the wall portion, when the area is not stimulated during the off time periods. Furthermore, the repetition frequency of the pulses of the pulse trains and the length and number of pulses of each pulse train may be varied.

As mentioned above, for reasons of maintaining over time the effect of stimulation, it is preferable that different areas of the at least one portion of the wall are intermittently and individually stimulated. In consequence, step (b) may be performed by stimulating one or more of the areas at a time with pulses, by cyclically propagating the stimulation of the areas with pulses along the wall portion, and/or by propagating the stimulation of the areas with pulses in accordance with a determined stimulation pattern. In case the off time periods between pulse trains that stimulate the respective area of the at least one portion of the wall are varied, it is preferable that each off time period between the pulse trains is controlled to last long enough to restore substantially normal blood circulation in the area when the latter is not stimulated during the off time periods.

Electric Stimulation

In accordance with a preferred embodiment of the invention, step (b) is performed by electrically stimulating the wall portion, preferably with electric pulses to cause contraction of the wall portion. Thus, the at least one portion of the wall is stimulated with such electric pulses, preferably in the form of electric pulse trains, when the at least one portion of the wall is in the constricted state, to cause contraction of the wall portion. Of course, the configuration of the electric pulse trains may be similar to the above described pulse trains and different areas of the at least one portion of the wall may be electrically stimulated in the same manner as described above.

In accordance with the preferred embodiment, the method of the invention comprises providing at least one, preferably a plurality of electrical elements, such as electrodes, engaging and stimulating the at least one portion of the wall with electric pulses. Optionally, the electrical elements may be placed in a fixed orientation relative to one another. The method comprises electrically energizing the electrical elements, preferably by cyclically energizing each element with electric pulses. The electrical elements may be energized so that the electrical elements are energized one at a time in sequence, or so that a number or groups of the electrical elements are energized at a time. Also, groups of electrical elements may be sequentially energized, either randomly or in accordance with a predetermined pattern.

The method may further comprise applying the electrical elements on the patient's wall portion so that the electrical elements form any pattern of electrical elements, preferably an elongate pattern of electrical elements extending lengthwise along the at least one portion of the wall and the elements abut the respective areas of the wall portion. The electrical elements may be successively energized along the elongate pattern of electrical elements in a direction opposite to or in the same direction as that of the flow in the patient's blood vessel. Optionally, the electrical elements may be successively energized along the elongate pattern of electrical elements from a position substantially at the center of the constricted wall portion towards both ends of the elongate pattern of electrical elements. Where the blood vessel is to be kept closed for a relatively long time, the electrical elements may be energized so that energized electrical elements form two waves of energized electrical elements that simultaneously advance from the center of the constricted wall portion in two opposite directions towards both ends of the elongate pattern of electrical elements. Such waves of energized electrical elements can be repeated over and over again without harming the blood vessel and without moving blood or gas in any direction in the blood vessel.

The elongate pattern of electrical elements may include one or more rows of electrical elements extending lengthwise along the blood vessel. Each row of electrical elements may form a straight, helical or zig-zag path of electrical elements, or any form of path. The electrical elements may be energized so that the electrical elements currently energized form at least one group of adjacent energized electrical elements, wherein the elements in the group of energized electrical elements form a path of energized electrical elements extending at least in part around the patient's blood vessel, preferably completely around the patient's blood vessel. Alternatively, the elements in the group of energized electrical elements form two paths of energized electrical elements extending on mutual sides of the patient's blood vessel or more than two paths of energized electrical elements extending on different sides of the patient's blood vessel, preferably at least substantially transverse to the flow direction in the blood vessel.

In an embodiment of the invention, the electrical elements form a plurality of groups of elements, wherein the groups form a series of groups extending along the patient's blood vessel in the flow direction in the patient's blood vessel. The electrical elements of each group of electrical elements may form a path of elements extending at least in part around the patient's blood vessel. In a first alternative, the electrical elements of each group of electrical elements may form more than two paths of elements extending on different sides of the patient's blood vessel, preferably substantially transverse to the flow direction in the patient's blood vessel. The groups of electrical elements in the series of groups may be energized in random or in accordance with a predetermined pattern. Alternatively, the groups of electrical elements in the series of groups may be successively energized in a direction opposite to or in the same direction as that of the flow in the patient's blood vessel, or in both said directions starting from a position substantially at the center of the constricted wall portion. For example, groups of energized electrical elements may form advancing waves of energized electrical elements, as described above. I.e., the groups of electrical elements may be energized so that energized electrical elements form two waves of energized electrical elements that simultaneously advance from the center of the constricted wall portion in two opposite directions towards both ends of the elongate pattern of electrical elements.

Thermal Stimulation

In accordance with an embodiment of the invention, stimulation step (b) is performed by thermally stimulating the wall portion. Thus, the at least one portion of the wall may be cooled, when the at least one portion of the wall is constricted, to cause contraction of the wall portion. For example, the at least one portion of the wall may be constricted to at least restrict the flow in the blood vessel, and the constricted wall portion may be cooled to cause contraction thereof, so that the flow in the blood vessel is at least further restricted, or further restricted but not stopped, or stopped. Alternatively, the at least one portion of the wall may be heated, when the at least one portion of the wall is constricted and contracted, to cause expansion of the wall portion. Where the at least one portion of the wall includes a blood vessel, the blood vessel may be cooled to cause contraction thereof, or heated to cause expansion thereof. Where applicable, thermal stimulation may be practised in any of the embodiments of the present invention. Where applicable, thermal stimulation may be practised in any of the embodiments of the present invention, and the thermal stimulation may be controlled in response to various sensors, for example strain, motion or pressure sensors.

Constriction and Stimulation Devices

Generally, the method of the invention comprises providing a constriction device that constricts the wall portion, a stimulation device that stimulates the constricted wall portion and a control device that controls the constriction device and/or the stimulation device. The method comprises operating the control device from outside the patient's body, preferably by using the control device to wirelessly control the constriction device and/or stimulation device. The wireless control is preferably performed in a non-magnetic manner, whereby implanted magnetic devices can be avoided. Suitably, the control device comprises a hand-held wireless remote control operated by the patient.

Alternatively, the control device comprises a manually operable switch for switching on and off the constriction device and/or stimulation device. In this case, the method comprises subcutaneously implanting the switch in the patient and manually operating the the implanted switch from outside the patient's body.

In an embodiment of the invention, the control device comprises a programmable internal control unit, such as a microprocessor, and the method comprises implanting in the patient the internal control unit and controlling by the internal control unit the constriction device and/or stimulation device. The control device may also comprise an external control unit outside the patient's body. In this case, the method comprises controlling by the external control unit the constriction device and/or stimulation device and, optionally, using the external control unit to program the implanted internal control unit. The internal control unit may be programmable for controlling the constriction device and/or stimulation device over time, for example in accordance with an activity schedule program.

The constriction of the at least one portion of the wall can be calibrated by using the control device to control the stimulation device to stimulate the at least one portion of the wall while controlling the constriction device to adjust the constriction of the at least one portion of the wall until the desired restriction of the flow in the blood vessel is obtained.

Sensor Controlled Constriction and/or Stimulation

In an embodiment of the invention, the method comprises implanting at least one sensor and controlling by the control device the constriction device and/or the stimulation device in response to signals from the sensor. Generally, the sensor directly or indirectly senses at least one physical parameter of the patient, functional parameter of the apparatus, or functional parameter of a medical implant in the patient.

Many different kinds of sensor for sensing physical parameters may be used. For example motion sensors for sensing blood vessel motion, i.e. natural contractions, pressure sensors for sensing pressure in the blood vessel, strain sensors for sensing strain of the blood vessel, flow sensors for sensing blood flow in the blood vessel, spectro-photometrical sensors, Ph-sensors for acidity or alkalinity of the blood in the blood vessel, oxygen-sensors sensors for sensing the oxygen content of the blood in the blood vessel, or sensors for sensing the distribution of the stimulation on the stimulated blood vessel. Any conceivable sensor for sensing any kind of useful physical parameter may be used.

Many different kinds of sensors that sense functional parameters of implanted components may also be used for the control of the constriction device and/or the stimulation device. For example sensors for sensing electric parameters of implanted electric components, or sensors for sensing the performance of implanted motors or the like.

The sensor may comprise a pressure sensor for sensing as the physical parameter a pressure in the patient's body that relates to the pressure in the blood vessel of the patient's blood vessel. In this case, the method suitably comprises operating the control device to control the constriction device to change the constriction of the patient's wall portion in response to the pressure sensor sensing a predetermined value of measured pressure.

Alternatively, or in combination with the pressure sensor, a position sensor may be provided for sensing as the physical parameter the orientation of the patient with respect to the horizontal. The position sensor may be a biocompatible version of what is shown in U.S. Pat. Nos. 4,942,668 and 5,900,909. For example, the control device may control the constriction device and/or stimulation device to change the constriction of the patient's wall portion in response to the position sensor sensing that the patient has assumed a substantially horizontal orientation, i.e. that the patient is lying down.

The above described sensors may be used in any of the embodiments of the invention, where applicable.

The control device may control the constriction device and/or stimulation device to change the constriction of the patient's wall portion in response to the time of day. For that purpose the control device may include a clock mechanism for controlling the constriction device and/or stimulation device to change the constriction of the patient's wall portion to increase or decrease the influence on the flow in the blood vessel during different time periods of the day. In case a sensor of any of the above-described types for sensing a physical or functional parameter is provided, either the clock mechanism is used for controlling the constriction device and/or stimulation device provided that the parameter sensed by the sensor does not override the clock mechanism, or the sensor is used for controlling the constriction device and/or stimulation device provided that the clock mechanism does not override the sensor. Suitably, the control device produces an indication, such as a sound signal or displayed information, in response to signals from the sensor.

The control device may comprise an implantable internal control unit that directly controls the constriction device and/or stimulation device in response to signals from the sensor. The control device may further comprise a wireless remote control adapted to set control parameters of the internal control unit from outside the patient without mechanically penetrating the patient. At least one of the control parameters, which is settable by the wireless remote control, is the physical or functional parameter. Suitably, the internal control unit includes the above mentioned clock mechanism, wherein the wireless remote control also is adapted to set the clock mechanism.

Alternatively, the control device may comprise an external control unit outside the patient's body for controlling the constriction device and/or stimulation device in response to signals from the sensor.

Constriction of Patient's Blood Vessel

Method step (a) may be performed in many different ways. Thus, step (a) may be performed by:
(1)—constricting the at least one portion of the wall so that the through-flow area of the blood vessel assumes a size in the constricted state small enough to cause the constricted wall portion to contract to stop the flow in the blood vessel when step (b) is performed;
(2)—bending the wall portion;
(3)—clamping the at least one portion of the wall between at least two elements positioned on different sides of the blood vessel;

(4)—clamping the blood vessel between an element and the bone or tissue of the patient;

(5)—rotating at least two elements positioned on different sides of the blood vessel; or (6)—clamping the blood vessel between at least two articulated clamping elements positioned on different sides of the blood vessel.

In the above noted alternatives (1) to (6) of method step (a), the constriction of the at least one portion of the wall of the blood vessel may be changed either mechanically or hydraulically. For many applications of the present invention, step (a) is suitably performed so that the through-flow area of the blood vessel assumes a size in the constricted state that is small enough to enable the stimulation during step (b) to contract the at least one portion of the wall of the blood vessel to stop the flow in the blood vessel.

Where the constriction of the at least one portion of the wall is hydraulically changed, the method of the invention may further comprise implanting in the patient a reservoir containing a predetermined amount of hydraulic blood, and a constriction device engaging the at least one portion of the wall and having an expandable/contractible cavity, wherein step (a) is performed by distributing hydraulic blood from the reservoir to increase the volume of the cavity to constrict the wall portion, and by distributing hydraulic blood from the cavity to the reservoir to decrease the volume of the cavity to release the wall portion. The cavity may be defined by a balloon of the constriction device that abuts the wall of the blood vessel portion of the patient's blood vessel, so that the patient's wall portion is constricted upon expansion of the cavity and released upon contraction of the cavity.

Alternatively, the cavity may be defined by a bellows that displaces a relatively large contraction element of the constriction device, for example a large balloon that abuts the wall portion, so that the patient's wall portion is constricted upon contraction of the bellows and released upon expansion of the bellows. Thus, a relatively small addition of hydraulic blood to the bellows causes a relatively large increase in the constriction of the wall portion. Such a bellows may also be replaced by a suitably designed piston/cylinder mechanism.

Where the hydraulic means comprises a cavity in the constriction device, the following embodiments of the invention are conceivable.

1) The reservoir comprises first and second wall portions, and step (a) is performed by displacing the first and second wall portions relative to each other to change the volume of the reservoir, so that blood is distributed from the reservoir to the cavity, or from the cavity to the reservoir.

1a) At least one of a magnetic device, a hydraulic device or an electric control device displaces the first and second wall portions of the reservoir.

2) A pump is provided for pumping blood between the reservoir and the cavity.

2a) The pump comprises a first activation member for activating the pump to pump blood from the reservoir to the cavity and a second activation member for activating the pump to pump blood from the cavity to the reservoir.

2a1) The first and second activation members are operable by manual manipulation thereof.

2a2) At least one of the activation members operates when subjected to an external predetermined pressure.

2a3) At least one of the first and second activating members is operable by magnetic means, hydraulic means, or electric control means.

2b) A blood conduit between the pump and the cavity is provided, wherein the reservoir forms part of the conduit. The conduit and pump are devoid of any non-return valve. The reservoir forms a blood chamber with a variable volume, and the pump distributes blood from the chamber to the cavity by a reduction in the volume of the chamber and withdraws blood from the cavity by an expansion of the volume of the chamber. A motor is provided for driving the pump, wherein the pump comprises a movable wall of the reservoir for changing the volume of the chamber.

In all of the above noted embodiments 1 to 2b where the hydraulic means comprises an expandable cavity in the constriction device, the cavity can be exchanged by a cylinder/piston mechanism for adjusting the constriction device. In this case, hydraulic blood is distributed between the reservoir and the cylinder/piston mechanism to adjust the constriction device.

3) The method further comprises implanting a reverse servo operatively connected to the hydraulic means. The term "reverse servo" is to be understood as a mechanism that transfers a strong force acting on a moving element having a short stroke into a weak force acting on another moving element having a long stroke; i.e., the reverse function of a normal servo mechanism. Thus, minor changes in the amount of blood in a smaller reservoir could be transferred by the reverse servo into major changes in the amount of blood in a larger reservoir.

Preferably, the reverse servo comprises an expandable servo reservoir containing servo blood and a blood supply reservoir hydraulically connected to the servo reservoir to form a closed conduit system for the servo blood. The expandable servo reservoir has first and second wall portions, which are displaceable relative to each other in response to a change in the volume of the expandable servo reservoir.

In accordance with a first alternative, the first and second wall portions of the servo reservoir are operatively connected to the hydraulic means. The reverse servo distributes blood between the blood supply reservoir and the expandable servo reservoir to change the volume of the servo reservoir, whereby the hydraulic means is operated to adjust the constriction device.

In accordance with a second alternative, there is provided an implantable main reservoir containing a predetermined amount of hydraulic blood, wherein the reverse servo is operated to distribute hydraulic blood between the main reservoir and the hydraulic means to adjust the constriction device. More specifically, the main reservoir is provided with first and second wall portions operatively connected to the first and second wall portions of the expandable servo reservoir, so that the volume of the main reservoir is changed when the volume of the expandable servo reservoir is changed. Thus, when the reverse servo distributes servo blood between the blood supply reservoir and the expandable servo reservoir to change the volume of the main reservoir, hydraulic blood is distributed from the main reservoir to the hydraulic means, or from the hydraulic means to the main reservoir. Advantageously, the method comprises dimensioning the servo and main reservoirs, so that when the volume of the servo reservoir is changed by a relatively small amount of servo blood, the volume of the main reservoir is changed by a relatively large amount of hydraulic blood.

In both of the above-described alternatives, the blood supply reservoir may have first and second wall portions, which are displaceable relative to each other to change the volume of the blood supply reservoir to distribute servo blood between the blood supply reservoir and the expandable servo reservoir. The first and second wall portions of the blood supply reservoir may be displaced relative to each other by manual manipulation, a magnetic device, a hydraulic device, or an electric control device to change the volume of the blood supply reservoir to distribute servo blood between the blood supply reservoir and the expandable servo reservoir.

In all of the above noted embodiments 1 to 2b where the hydraulic means comprises an expandable cavity in the constriction device, or in embodiments where the hydraulic means includes a hydraulically operable mechanical construction, the reverse servo described above may be used. In a further embodiment of the invention, the hydraulic means include first and second hydraulically interconnected expandable/contractible reservoirs. The first reservoir is operatively connected to the constriction device, so that the constriction device changes the constriction of the patient's wall portion upon expansion or contraction of the first reservoir. By changing the volume of the second reservoir hydraulic blood is distributed between the two reservoirs, so that the first reservoir is either expanded or contracted. This embodiment requires no non-return valve in the blood communication conduits between the two reservoirs, which is beneficial to long-term operation of the hydraulic means.

Alternatively, the hydraulic means may include first and second hydraulically interconnected piston/cylinder mechanisms instead of the first and second reservoirs described above. The first piston/cylinder mechanism is operatively connected to the constriction device, so that the constriction device changes the constriction of the patient's wall portion upon operation of the first piston/cylinder mechanism. By operating the second piston/cylinder mechanism hydraulic blood is distributed between the two piston/cylinder mechanisms, so that the first piston/cylinder mechanism adjusts the constriction device.

Where the constriction device does not include an expandable/contractible cavity, the constriction device may comprise at least two elongated clamping elements extending along the at least one portion of the wall on different sides of the blood vessel. The hydraulic means, which may include the reverse servo described above, hydraulically moves the elongated clamping elements towards the blood vessel to constrict the at least one portion of the wall of the blood vessel. For example, the constriction device may have hydraulic chambers in which the clamping elements slide back and forth, and the hydraulic means may also include a pump and an implantable reservoir containing hydraulic blood. The pump distributes hydraulic blood from the reservoir to the chambers to move the clamping elements against the wall portion, and distributes hydraulic blood from the chambers to the reservoir to move the clamping elements away from the wall portion.

Energy Supply

Generally, method step (a) is performed by using the constriction device and step (b) is performed by using the stimulation device, wherein the method further comprises forming the constriction and stimulation devices in an operable constriction/stimulation unit.

In a simple form of the invention, the method comprises implanting a source of energy, such as a battery, rechargeable battery or accumulator, releasing energy from the source of energy and using the released energy in connection with the operation of the constriction/stimulation unit.

In a more sophisticated form of the invention, which is preferable, the method comprises transmitting wireless energy from outside the patient's body to inside the patient's body and using the transmitted wireless energy in connection with the operation of the constriction/stimulation unit.

Transmission of Wireless Energy

The wireless energy may be directly used in connection with the operation of the constriction/stimulation unit, as the wireless energy is being transmitted. For example, the wireless energy may be transmitted in the form of an electric, an electromagnetic or a magnetic field, or a combination thereof, or electromagnetic waves for direct power of the constriction/stimulation unit. For example, where an electric motor or pump operates the constriction device of the constriction/stimulation unit, wireless energy in the form of a magnetic or an electromagnetic field may be used for direct power of the motor or pump.

Thus, the motor or pump is running directly during transmission of the wireless energy. This may be achieved in two different ways: a) using a transforming device implanted in the patient to transform the wireless energy into energy of a different form, preferably electric energy, and powering the motor or pump with the transformed energy, or b) using the wirelessly transmitted energy to directly power the motor or pump. Preferably wireless energy in the form of an electromagnetic or magnetic field is used to directly influence specific components of the motor or pump to create kinetic energy. Such components may include coils integrated in the motor or pump.

The wireless energy is suitably transmitted in pulses or digital pulses, or a combination of pulses and digital pulses.

Preferably, the wireless energy is transmitted in at least one wireless signal, suitably a wave signal. The wave signal may comprise an electromagnetic wave signal including one of an infrared light signal, a visible light signal, an ultra violet light signal, a laser signal, a microwave signal, a radio wave signal, an x-ray radiation signal, and a gamma radiation signal. Alternatively, the wave signal may comprise a sound or an ultrasound wave signal. The wireless signal may be a digital or analogue signal, or a combination of a digital and analogue signal.

In accordance with a particular embodiment of the invention, the wireless energy is not for direct use in connection with the operation of the constriction/stimulation unit. In this embodiment the wireless energy comprises energy of a first form, which is transmitted into energy of a second form suited to operate the constriction/stimulation unit. Typically, the energy of the second form is different from the energy of the first form. For example, the wireless energy of the first form may comprise sound waves, whereas the energy of the second form may comprise electric energy. Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

Transforming Wireless Energy

In accordance with a particular embodiment of the invention, an implantable energy-transforming device is provided for transforming wireless energy of a first form transmitted by the energy-transmission device into energy of a second form, which typically is different from the energy of the first form. The constriction/stimulation unit is operable in response to the energy of the second form. For example, the wireless energy of the first form may comprise sound waves, whereas the energy of the second form may comprise electric energy. Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transforming device may function different from or similar to the energy-transmission device. Advantageously, the energy-transforming device comprises at least one element, such as at least one semiconductor, having a positive region and a negative region, when exposed to the energy of the first form transmitted by the energy-transmission device, wherein the element is capable of creating an energy field between the positive and negative regions, and the energy field produces the energy of the second form. More specifically, the element may comprise an electrical junction element, which is capable of inducing an electric field between the positive and negative regions when exposed to the energy of the first form transmitted by the energy-transmission device, whereby the energy of the second form comprises electric energy.

The energy of the first form may directly or indirectly be transformed into the energy of the second form. The method of the invention may comprise providing a motor for operating the constriction device and powering the motor with the energy of the second form. The constriction device may be operable to perform at least one reversible function and the method may comprise reversing the function by using the motor. For example, the method may comprise shifting the polarity of the energy of the second form to reverse the motor.

The motor may be directly powered with the transformed energy, as the energy of the second form is being transformed from the energy of the first form. Preferably, the constriction/stimulation unit is directly operated with the energy of the second form in a non-magnetic, non-thermal or non-mechanical manner.

Normally, the implanted constriction/stimulation unit comprises electric components that are energized with electrical energy. Therefore, the energy of the first form may be transformed into a direct current or pulsating direct current, or a combination of a direct current and pulsating direct current. Alternatively, the energy of the first form may be transformed into an alternating current or a combination of a direct and alternating current.

The method of the invention may comprise implanting in the patient an internal source of energy, and supplying energy from the internal source of energy for the operation of the constriction/stimulation unit. The method may further comprise implanting in the patient a switch operable to switch from an "off" mode, in which the internal source of energy is not in use, to an "on" mode, in which the internal source of energy supplies energy for the operation of the constriction/stimulation unit, and/or for energizing implanted electronic components of the constriction/stimulation unit. The switch may be operated by the energy of the first form or by the energy of the second form. The described switch arrangement reduces power consumption of the constriction/stimulation unit between operations.

The internal source of energy may store the energy of the second form. In this case, the internal source of energy suitably comprises an accumulator, such as at least one capacitor or at least one rechargeable battery, or a combination of at least one capacitor and at least one rechargeable battery. Where the internal source of energy is a rechargeable battery it may be charged only at times convenient for the patient, for example when the patient is sleeping. Alternatively, the internal source of energy may supply energy for the operation of the constriction/stimulation unit but not be used for storing the energy of the second form. In this alternative, the internal source of energy may be a battery and the switch described above may or may not be provided.

Suitably, the method of the invention may comprise implanting a stabilizer for stabilizing the energy of the second form. Where the energy of the second form comprises electric energy the stabilizer suitably comprises at least one capacitor.

The energy-transforming device may be designed for implantation subcutaneously in the abdomen, thorax or cephalic region of the patient. Alternatively, it may be designed for implantation in an orifice of the patient's body and under the mucosa or intramuscularly outside the mucosa of the orifice.

Control of Constriction/Stimulation Unit

Although the constriction device of the constriction/stimulation unit may normally keep the patient's wall portion in the constricted state, in most applications using the present invention there will be daily adjustments of the constriction device. Therefore, in a preferred embodiment of the invention, the constriction device is adjustable to enable changing the constriction of the patient's wall portion as desired and the control device controls the constriction device to change the constriction of the wall portion.

The method of the invention suitably comprises operating the control device by the patient. In a simple form the control device comprises a manually operable switch for switching on and off the constriction/stimulation unit, and the method further comprises subcutaneously implanting the switch in the patient. It is preferable, however, that the control device comprises a hand-held wireless remote control operable by the patient from outside the patient's body to control the constriction/stimulation unit to adjust the stimulation intensity and/or adjust the constriction of the wall portion. The wireless remote control is suitably designed for application on the patient's body like a wristwatch.

In some applications of the invention, the constriction device of the constriction/stimulation unit may be designed to normally keep the patient's wall portion in the constricted state. I.e., after implantation the constriction device all the time keeps the at least one portion of the wall constricted. In this case, the control device may be used when needed, conveniently by the patient, to control the stimulation device of the constriction/stimulation unit to stimulate the constricted wall of the blood vessel portion, preferably while adjusting the stimulation intensity, to cause contraction of the wall portion, so that the flow in the blood vessel is at least further restricted or stopped, and to control the stimulation device to cease the stimulation. More precisely, the method of the invention may comprise operating the control device by the patient to a) control the stimulation device in a first mode to stimulate the constricted wall portion to further restrict the flow in the blood vessel and control the stimulation device in a second mode to cease the stimulation of the at least one portion of the wall to increase the flow in the blood vessel; or b) control the stimulation device in a first mode to stimulate the constricted wall portion to stop the flow in the blood vessel and control the stimulation device in a second mode to cease the stimulation of the at least one portion of the wall to allow flow in the blood vessel.

Either the first mode or the second mode may be temporary.

The wireless remote control preferably transmits at least one wireless control signal for controlling the constriction/stimulation unit. The control signal may comprise a frequency, amplitude, phase modulated signal or a combination thereof, and may be an analogue or a digital signal, or a combination of an analogue and digital signal. The remote control may transmit an electromagnetic carrier wave signal for carrying the digital or analogue control signal. Also the carrier signal may comprise digital, analogue or a combination of digital and analogue signals.

Any of the above signals may comprise wave signals, such as a sound wave signal, an ultrasound wave signal, an electromagnetic wave signal, an infrared light signal, a visible light signal, an ultra violet light signal, a laser light signal, a micro wave signal, a radio wave signal, an x-ray radiation signal or a gamma radiation signal.

Alternatively, the control signal may comprise an electric or magnetic field, or a combined electric and magnetic field.

Operation of Constriction/Stimulation Unit

The method of the invention may comprise implanting in the patient an operation device, and operating the constriction/stimulation unit with the operation device. A magnet may be provided, wherein the method comprises using the magnet to activate the operation device from outside the patient's body. The operation device suitably comprises a motor which is powered with energy released from a source of energy, such as a battery. Although the constriction/stimulation unit in embodiments described above suitably is designed as a single piece, which is most practical for implantation, it should be noted that as an alternative the constriction device and stimulation device of the constriction/stimulation unit could be designed as separate pieces.

Laparoscopic Method

First: The method for controlling a flow of blood and/or other bodily matter in a blood vessel, the method comprising the steps of:
inserting a needle like tube into a cavity of the patients body,
using the needle like tube to fill the cavity with gas thereby expanding the cavity,
placing at least two laparoscopical trocars in the patient's body,
inserting a camera through one of the trocars into the cavity,
inserting a dissecting tool through any of the trocar and dissecting an area of at least one portion of the wall of the blood vessel,
placing a constriction device and a stimulation device in the dissected area in operative engagement with the blood vessel,
using the constriction device to gently constrict the at least one portion of the wall of the blood vessel to influence the flow in the blood vessel, and
using the stimulation device to stimulate the constricted wall portion to cause contraction of the at least one portion of the wall to further influence the flow in the blood vessel.

Second: The method for controlling a flow of blood in a blood vessel, the method comprising the steps of:
inserting a needle like tube into a cavity of the patients body,
using the needle like tube to fill the cavity with gas thereby expanding the cavity,
placing at least two laparoscopical trocars in the patient's body,
inserting a camera through one of the trocars into the cavity,
inserting a dissecting tool through any of the trocar and dissecting an area of at least one wall portion of a blood vessel,
placing a flow influence device comprising, a stimulation device in the dissected area in operative engagement with the blood vessel, and p0 using the stimulation device to stimulate the wall portion of the blood vessel to cause contraction of the wall portion to influence the flow in the blood vessel.

Third: The method for controlling a flow of blood in a blood vessel, the method comprising the steps of:
inserting a needle like tube into a cavity of the patients body,
using the needle like tube to fill the cavity with gas thereby expanding the cavity,
placing at least two laparoscopical trocars in the patient's body,
inserting a camera through one of the trocars into the cavity,
inserting a dissecting tool through any of the trocar and dissecting an area of at least one wall portion of the blood vessel,
placing a flow influence device comprising, a constriction device in the dissected area in operative engagement with the blood vessel,
using the constriction device to constrict the wall portion of the blood vessel to influence the flow in the lumen.

Fourth: The method for controlling a flow blood in a lumen formed by a tissue wall of a patient's blood vessel, the method comprising the steps of:
cutting the skin of the patient,
inserting a dissecting tool and dissecting an area of at least one portion of the tissue wall of the blood vessel,
placing a flow influence device comprising, a constriction device and a stimulation device in the dissected area in operative engagement with the blood vessel,
using the constriction device to gently constrict the wall portion of the organ to influence the flow in the lumen of the blood vessel, and
using the stimulation device to stimulate the constricted wall portion to cause contraction of the wall portion of the blood vessel to further influence the flow in the lumen.

Fifth: The method for controlling a flow of blood in a lumen formed by a tissue wall of a patient's blood vessel, the method comprising the steps of:
cutting the skin of the patient,
inserting a dissecting tool and dissecting an area of at least one portion of the tissue wall of the blood vessel,
placing a flow influence device comprising, a stimulation device in the dissected area in operative engagement with the blood vessel, and
using the stimulation device to stimulate the wall portion to cause contraction of the wall portion of the blood vessel to influence the flow in the lumen.

Sixth: The method for controlling a flow of blood in a lumen formed by a tissue wall of a patient's blood vessel, the method comprising the steps of:
cutting the skin of the patient,
inserting a dissecting tool and dissecting an area of at least one portion of the tissue wall of the blood vessel,
placing a flow influence device comprising, a constriction device in the dissected area in operative engagement with the blood vessel, and
using the constriction device to constrict the wall portion of the blood vessel to influence the flow in the lumen.

The method further comprises implanting a powered operation device for operating the constriction device. The operation device may comprise a powered hydraulic operation device or an electrically powered operation device, such as an electric motor.

The method further comprises transmitting wireless energy for powering the operation device, and when desired to influence the flow in the patient's blood vessel, powering the operation device with the transmitted energy to operate the constriction device.

The method further comprises implanting a source of energy in the patient, providing an external source of energy, controlling the external source of energy to release wireless energy, transforming the wireless energy into storable energy, such as electric energy, non-invasively charging the implanted source of energy with the transformed energy, and controlling the implanted source of energy from outside the patient's body to release energy for use in connection with the operation of the constriction device and/or stimulation device. The wireless energy is transformed into a storable energy different from the wireless energy.

Alternatively, the method further comprises providing a source of energy outside the patient's body, controlling the external source of energy from outside the patient's body to release wireless energy, and using the released wireless energy for operating the constriction device and/or stimulation device. The wireless energy may be transformed into electrical energy inside the patient's body by an implanted energy-transforming device, wherein the electrical energy is used in connection with the operation of the constriction device and/or stimulation device. The electrical energy may be directly used in connection with the operation of the constriction device and/or stimulation device, as the transforming device transforms the wireless energy into the electrical energy. The external source of energy may be controlled from outside the patient's body to release non-magnetic wireless energy, wherein the released non-magnetic wireless energy is used for operating the constriction device and/or stimulation device. Alternatively, the external source of energy may be controlled from outside the patient's body to release electromagnetic wireless energy, wherein the released electromagnetic wireless energy is used for operating the constriction device and/or stimulation device.

The above-described methods of the present invention may be practised for treating dysfunctions of a blood vessel of a human being. The above-described methods of the present invention may be practised for controlling blood flow in a blood vessel. The above-described method is suited for treating dysfunctions of a blood vessel of a human being or animal. For example, for treating locally high blood pressure in the lungs. It is also suited for treating dysfunctions in the distribution of the blood flow of a patient.

Where the method is practiced for controlling the blood flow in a blood vessel of a patient, the method comprises a) gently constricting at least one portion of the wall of the blood vessel of the patient's blood vessel to influence the blood flow in the blood vessel, and stimulating the constricted wall of the blood vessel portion to cause contraction thereof to further influence the blood flow in the blood vessel.

Aneurysm

Another object of the present invention is to overcome or at least reduce some of the problems associated with existing treatments of aneurysm.

In accordance with this object of the present invention, there is provided a method for treating a vascular aneurysm of a blood vessel in a human or mammal patient. The method comprises: a) gently constricting a portion of the tissue wall of the blood vessel extending along the aneurysm to reduce the bulge of the blood vessel caused by the aneurysm, and b) stimulating the constricted wall portion of the blood vessel tissue wall to cause contraction of the wall portion to further reduce the bulge of the blood vessel and strengthen the blood vessel tissue wall.

The present invention provides an advantageous combination of constriction and stimulation, which results in a two-stage reduction of the bulge of the blood vessel caused by the aneurysm. Thus, the constriction phase of the method may gently constrict the tissue wall by applying a relatively weak force against the wall portion, and the stimulation phase of the method may stimulate the constricted wall portion to achieve the desired final reduction of the bulge, as well as stabilizing, treating, and monitoring the condition of the blood vessel. The phrase "gently constricting a portion of the tissue wall" is to be understood as constricting the wall portion without injuring the blood vessel tissue.

Preferably, the stimulation step (b) is performed in a fashion adapted to stimulate different areas of the wall portion as the constricting step (a) is performed to constrict the wall portion, and preferably the areas of the wall portion are intermittently and individually stimulated. This intermittent and individual stimulation of different areas of the wall portion of the blood vessel allows tissue of the wall portion to maintain normal condition during the constriction and stimulation phases.

For the treatment of aneurysms, it is particularly preferred that the method supports and preferably also strengthens the blood vessel. A combination of stimulation and constriction is applied to stimulate the healing of the vessel, preferably resulting in the reduction or disappearence of the aneurysm.

The constricting step (a) and stimulating step (b) may be carried out simultaneously and/or independently of each other. Alternatively, step (b) may not be performed while step (a) is performed. Initially, the reduction of the bulge of the blood vessel may be calibrated by stimulating the constricted wall portion while adjusting the constriction of the wall portion until the desired reduction of the bulge caused by the aneurysm is obtained.

In a method according to an embodiment of the invention, a physical parameter of the patient is sensed and the intensity of the stimulation of the wall portion is adjusted in response to the sensed parameter. For example, the intensity of the stimulation of the wall portion may be increased in response to a sensed pressure decrease in the blood vessel or bulge reduction of the aneurysm, so that the blood flow is stopped, for example in an acute situation, i.e. a rupture of the anaeurysm. The intensity of the stimulation of the wall portion may be increased, so that the reduction of the bulge of the blood vessel is maintained when a pressure increase occurs in the blood vessel. Any physical parameter of the patient, such as a pressure in the patient's body, for example the pressure in the patient's abdomen, that relates to the pressure in the blood vessel may be sensed and the intensity of the stimulation of the wall portion may be adjusted in response to the sensed parameter.

For example, a pressure sensor may be applied where the present invention is used for monitoring, and react to variations in the systolic or diastolic pressure of the patient. In the stabilization, treatment and monitoring of an anaeurysm, it is conceived that a pressure sensor is provided to account for the variations in pressure and thereby provide a more gentle and physiological support and treatment. It is also conceived that a sensor is provided to follow the healing or worsening of the condition, as well as for alerting when pathological changes occur, and preferably indicate any changes in that direction.

In a particular embodiment of the method of the invention, the method comprises detecting a sudden reduction of pressure indicative of a bursting aneurysm, where such sudden pressure reduction ellicits a signal, and the method includes a step of stopping the blood flow in response to such signal. A complete stop of the blood flow to a part of the body, e.g. the lower limbs in the case of an aneurysm on the Y-bifurcation extending to the legs, is of course only an acute measure, preventing death from internal haemorrhage.

In another embodiment of the invention, the method comprises detecting a change in a parameter indicative of a pathological change in the aneurysm, e.g. a change in pressure, temperature, conductivity, pH or other parameter, indicating a worsening condition or an imminent burst of the anaeurysm.

In the above embodiment, the method comprises, in addition to said detecting step, transmitting an alarm signal when the measured value of the above parameter deviates for a set range or threshold value.

The method of the invention further comprises providing a constriction device for performing the constricting step (a), a stimulation device for performing the stimulating step (b) and a control device for controlling the constriction device and/or stimulation device The constriction device may include a plurality of separate constriction elements adapted to constrict any wall portions of a series of wall portions of the blood vessel's tissue wall, respectively. The control device may control the constriction device to activate the constriction elements in random or in accordance with a predetermined sequence. In this case, the stimulation device includes stimulation elements positioned on the constriction elements, wherein the control device controls the stimulation device to activate the stimulation elements to stimulate any wall portions of the series of wall portions constricted by said constriction elements to contract the blood vessel to support or stimulate the walls of a blood vessel, or in acute situations even close the it's lumen.

Alternatively, in a method according to an embodiment of the invention, the control device controls the constriction device to activate the constriction elements to constrict all of the wall portions of the series of wall portions, and controls the stimulation device to activate the stimulation elements to stimulate any constricted wall portions in random or in accordance with a predetermined sequence. The design of the constriction device in the form of a plurality of separate constriction elements makes possible to counteract growth of hard fibrosis where the constriction device is implanted.

Stimulation

When stimulating neural or muscular tissue there is a risk of injuring or deteriorating the tissue over time, if the stimulation is not properly performed. The method of the present invention is designed to reduce or even eliminate that risk. Thus, in accordance with an embodiment of the method according to the present invention, the control device controls the stimulation device to intermittently stimulate different areas of the wall portion of the blood vessel, such that at least two of the areas are stimulated at different points of time that is, the stimulation is shifted from one area to another area over time. In addition, the control device controls the stimulation device, such that an area of the different areas that currently is not stimulated has time to restore substantially normal blood circulation before the stimulation device stimulates the area again. Furthermore, the control device controls the stimulation device to stimulate each area during successive time periods, wherein each time period is short enough to maintain satisfactory blood circulation in the area until the lapse of the time period. This gives the advantage that the apparatus of the present invention enables continuous stimulation of the wall portion of the blood vessel to achieve the desired flow control, while essentially maintaining over time the natural physical properties of the blood vessel without risking injuring the blood vessel.

Also, by physically changing the places of stimulation on the blood vessel over time as described above it is possible to create an advantageous changing stimulation pattern on the blood vessel, in order to achieve a desired flow control and preferably a positive influence on the health an regeneration of tissue.

In a method according to an embodiment of the invention, the control device may control the stimulation device to stimulate one or more of the areas of the wall portion at a time, for example by sequentially stimulating the different areas. Furthermore, the control device may control the stimulation device to cyclically propagate the stimulation of the areas along the wall portion, preferably in accordance with a determined stimulation pattern. To achieve the desired reaction of the tissue wall during the stimulation thereof, the control device may control the stimulation device to, preferably cyclically, vary the intensity of the stimulation of the wall portion.

In a preferred embodiment of the invention, the control device controls the stimulation device to intermittently stimulate the areas of the wall portion with pulses that preferably form pulse trains. At least a first area and a second area of the areas of the wall portion may be repeatedly stimulated with a first pulse train and a second pulse train, respectively, such that the first and second pulse trains over time are shifted relative to each other. For example, the first area may be stimulated with the first pulse train, while the second area is not stimulated with said second pulse train, and vice versa. Alternatively, the first and second pulse trains may be shifted relative to each other, such that the first and second pulse trains at least partially overlap each other.

The pulse trains can be configured in many different ways. Thus, the control device may control the stimulation device to vary the amplitudes of the pulses of the pulse trains, the duty cycle of the individual pulses of each pulse train, the width of each pulse of the pulse trains, the length of each pulse train, the repetition frequency of the pulses of the pulse trains, the repetition frequency of the pulse trains, the number of pulses of each pulse train, and/or the off time periods between the pulse trains. Several pulse trains of different configurations may be employed to achieve the desired effect.

In case the control device controls the stimulation device to vary the off time periods between pulse trains that stimulate the respective area of the wall portion, it is also possible to control each off time period between pulse trains to last long enough to restore substantially normal blood circulation in the area when the latter is not stimulated during the off time periods.

Electric Stimulation

In accordance with a preferred embodiment of the method according to the invention, the stimulation device is an electrically powered stimulation device that electrically stimulates the tissue wall portion of the patient's bodily blood vessel, preferably with electric pulses. This embodiment is particularly suited for applications in which the wall portion includes muscle fibers that react to electrical stimula. In this embodiment, the control device controls the stimulation device to stimulate the wall portion with electric pulses preferably in the form of electric pulse trains, when the wall portion is in the constricted state, to cause contraction of the wall portion. Of course, the configuration of the electric pulse trains may be similar to the above described pulse trains and the control device may control the stimulation device to electrically stimulate the different areas of the wall of the blood vessel in the same manner as described above.

In a method according to an embodiment of the invention, the electric stimulation device suitably comprises at least one, preferably a plurality of electrical elements, such as electrodes, for engaging and stimulating the wall portion with electric pulses. Optionally, the electrical elements may be placed in a fixed orientation relative to one another. The control device controls the electric stimulation device to electrically energize the electrical elements, one at a time, or groups of electrical elements at a time. Preferably, the control device controls the electric stimulation device to cyclically energize each element with electric pulses. Optionally, the control device may control the stimulation device to energize the electrical elements, such that the electrical elements are energized one at a time in sequence, or such that a number or groups of the electrical elements are energized at the same time. Also, groups of electrical elements may be sequentially energized, either randomly or in accordance with a predetermined pattern.

The electrical elements may form any pattern of electrical elements. Preferably, the electrical elements form an elongate pattern of electrical elements, wherein the electrical elements are applicable on the patient's wall of the blood vessel, such that the elongate pattern of electrical elements extends lengthwise along the wall of the blood vessel, and the elements abut the respective areas of the wall portion. The elongate pattern of electrical elements may include one or more rows of electrical elements extending lengthwise along the wall of the blood vessel. Each row of electrical elements may form a straight, helical or zig-zag path of electrical elements, or any form of path. The control device may control the stimulation device to successively energize the electrical elements longitudinally along the elongate pattern of electrical elements in a direction opposite to, or in the same direction as that of, the flow in the lumen of a blood vessel.

Optionally, the method may comprise steps where the control device controls the stimulation device to successively energize the electrical elements from a position substantially at the center of the constricted wall portion towards both ends of the elongate pattern of electrical elements. Where the lumen of the blood vessel, for example a blood vessel in the case of a rupture, is to be kept closed for a relatively long time, the control device may control the stimulation device to energize the electrical elements, such that energized electrical elements form two waves of energized electrical elements that simultaneously advance from the center of the constricted wall portion in two opposite directions towards both ends of the elongate pattern of electrical elements. Such waves of energized electrical elements can be repeated over and over again without harming the blood vessel and without moving fluid in any direction in the lumen of the blood vessel.

In a method according to an embodiment of the invention, the control device suitably controls the stimulation device to energize the electrical elements, such that the electrical elements currently energized form at least one group of adjacent energized electrical elements. In accordance with a first alternative, the elements in the group of energized electrical elements form one path of energized electrical elements. The path of energized electrical elements may extend at least in part around the patient's blood vessel. In a second alternative, the elements of the group of energized electrical elements may form two paths of energized electrical elements extending on mutual sides of the patient's blood vessel, preferably substantially transverse to the flow direction in the blood vessel. In a third alternative, the elements of the group of energized electrical elements may form more than two paths of energized electrical elements extending on different sides of the patient's blood vessel, preferably substantially transverse to the flow direction.

In accordance with a preferred embodiment of the invention, the electrical elements form a plurality of groups of elements, wherein the groups form a series of groups extending along the blood vessel in the direction of flow. The electrical elements of each group of electrical elements may form a path of elements extending at least in part around the patient's blood vessel. In a first alternative, the electrical elements of each group of electrical elements may form more than two paths of elements extending on different sides of the blood vessel, preferably substantially transverse to the flow direction said vessel. The control device may control the stimulation device to energize the groups of electrical elements in the series of groups in random, or in accordance with a predetermined pattern. Alternatively, the control device may control the stimulation device to successively energize the groups of electrical elements in the series of groups in a direction opposite to, or in the same direction as that of, the flow in the blood vessel, or in both said directions starting from a position substantially at the center of the constricted wall portion. For example, groups of energized electrical elements may form advancing waves of energized electrical elements, as described above; that is, the control device may control the stimulation device to energize the groups of electrical elements, such that energized electrical elements form two waves of energized electrical elements that simultaneously advance from the center of the constricted wall portion in two opposite directions towards both ends of the elongate pattern of electrical elements.

A structure may be provided for holding the electrical elements in a fixed orientation. Although the structure may be separate from the constriction device, it is preferable that the structure is integrated in the constriction device, which is a practical design and facilitates implantation of the constriction and stimulation devices. Where the electrical elements form an elongate pattern of electrical elements, the structure may be applicable on the patient's blood vessel such that the elongate pattern of electrical elements extends along the blood vessel in the same direction as that of the flow in blood vessel and the elements abut the respective areas of the wall portion of the blood vessel.

Thermal Stimulation

In another embodiment of the invention, the stimulation device thermally stimulates the wall portion of the blood vessel. Thus, the control device may control the stimulation device to cool the wall portion, when the wall portion is constricted, to cause contraction of the wall portion. Alternatively, the control device may control the stimulation device to heat the wall portion, when the wall portion is constricted and contracted, to cause expansion of the wall portion. The control device may control the stimulation device to cool the blood vessel to cause contraction thereof, or heat the blood vessel to cause expansion thereof. Where applicable, thermal stimulation may be practised in any of the embodiments of the present invention, and the thermal stimulation may be controlled in response to various sensors, for example strain, motion or pressure sensors.

Sensor Controlled Constriction and/or Stimulation

As mentioned above, the method may comprise the use of at least one implantable sensor, wherein the control device controls the constriction device and/or the stimulation device in response to signals from the sensor. Generally, the sensor directly or indirectly senses at least one physical parameter of the patient, or at least one functional parameter of the apparatus, or at least one functional parameter of a medical implant in the patient.

Many different kinds of sensor for sensing physical parameters may be used. For example pressure sensors for sensing pressure in the blood vessel, strain sensors for sensing strain of the blood vessel, flow sensors for sensing fluid flow in the lumen of the blood vessel, spectro-photometrical sensors, Ph-sensors for sensing acidity or alkalinity of the fluid in the lumen of the blood vessel, oxygen-sensors sensors for sensing the oxygen content of the fluid in the blood vessel or walls thereof, or sensors for sensing the distribution of the stimulation on the stimulated blood vessel. Any conceivable sensors for sensing any other kind of useful physical parameter may be used.

Many different kinds of sensors that sense functional parameters of the apparatus may also be used for the control of the constriction device and/or the stimulation device in methods according to the invention. For example sensors for sensing electric parameters of implanted electric components of the apparatus, or sensors for sensing the performance of implanted motors of the apparatus.

The sensor may comprise a pressure sensor for sensing as the physical parameter a pressure in the patient's body that relates to the pressure in the blood vessel, wherein the control device controls the constriction device and/or stimulation device to change the constriction of the wall portion in response to the pressure sensor sensing a predetermined value of measured pressure.

Alternatively, or in combination with the pressure sensor, a position sensor may be provided for sensing as the physical parameter the orientation of the patient with respect to the horizontal. The position sensor may be a biocompatible version of what is shown in U.S. Pat. Nos. 4,942,668 and 5,900,909. For example, the control device may control the constriction device and/or stimulation device to change the constriction of the patient's wall portion in response to the position sensor sensing that the patient has assumed a substantially horizontal orientation, i.e. that the patient is lying down.

The above described sensors may be used in any of the embodiments of the invention, where applicable.

In a method according to an embodiment of the invention, the control device may control the constriction device and/or stimulation device to change the constriction of the patient's wall portion in response to the time of day. For that purpose the control device may include a clock mechanism for controlling the constriction device and/or stimulation device to change the constriction of the wall portion to increase or decrease the influence on the flow in the vessel during different time periods of the day. In case a sensor of any of the above-described types for sensing a physical or functional parameter is provided, either the clock mechanism is used for controlling the constriction device and/or stimulation device provided that the parameter sensed by the sensor does not override the clock mechanism, or the sensor is used for controlling the constriction device and/or stimulation device provided that the clock mechanism does not override the sensor. Suitably, the control device produces an indication, such as a sound signal or displayed information, in response to signals from the sensor.

The control device may comprise an implantable internal control unit that directly controls the constriction device and/or stimulation device in response to signals from the sensor. The control device may further comprise a wireless remote control adapted to set control parameters of the internal control unit from outside the patient without mechanically penetrating the patient. At least one of the control parameters, which is settable by the wireless remote control, is the physical or functional parameter. Suitably, the internal control unit includes the above mentioned clock mechanism, wherein the wireless remote control also is adapted to set the clock mechanism.

Alternatively, the control device may comprise an external control unit outside the patient's body for controlling the constriction device and/or stimulation device in response to signals from the sensor.

Adjustable Constriction

In several alternative embodiments of the invention, the degree of constriction is adjustable. In these embodiments, there is an operation device for operating the adjustable constriction device to change the constriction of the patient's tissue wall portion, and the constriction and stimulation devices form a constriction/stimulation unit.

Preferably, the constriction and stimulation devices of the constriction/stimulation unit are integrated in a single piece suitable for implantation. The constriction device of the unit comprises contact surfaces dimensioned to contact a length of a tissue wall portion of a patient's blood vessel, and the stimulation device of the unit comprises a plurality of stimulation elements provided on and distributed along the contact surfaces. When the control device controls the stimulation device to stimulate the wall portion, the stimulation elements stimulate different areas of the wall portion along the length of the wall portion. The stimulation elements preferably comprise electric elements, as described above, for stimulating the wall portion with electric pulses. However, in most applications of the present invention, other kinds of stimulations, such as thermal stimulation, could be suitable to employ.

The operation device operates the adjustable constriction device of the constriction/stimulation unit in a manner that depends on the design of the constriction device, as will be explained by the following examples of embodiments.

The constriction device comprises at least two elongated clamping elements having the contact surfaces and extending along the wall portion on different sides of the blood vessel, and the operation device operates the clamping elements to clamp the wall portion between the clamping elements to constrict the wall portion of the blood vessel.

The constriction device comprises one elongate clamping element having the contact surfaces and extending along the wall portion on one side of the blood vessel, and the operation device operates the clamping element to clamp the wall portion between the clamping element and the bone or tissue of the patient to constrict the wall portion.

The constriction device comprises at least two engagement elements having the contact surfaces and positioned on different sides of the blood vessel, and the operation device rotates the engagement elements, such that the engagement elements engage and constrict the wall portion of the blood vessel.

The constriction device comprises at least two articulated clamping elements having the contact surfaces and positioned on different sides of the blood vessel, and the operation device moves the clamping elements towards each other to clamp the wall portion of the blood vessel between the clamping elements, to constrict the wall portion.

The constriction device comprises at least two separate clamping elements having the contact surfaces, at least one of the clamping elements being pivoted, such that it may turn in a plane in which the loop of the constriction member extends, and the operation device turns the pivoted clamping element to change the size of the constriction opening.

The constriction device comprises at least one elongated constriction member having the contact surfaces, and forming means for forming the constriction member into at least a substantially closed loop around the blood vessel, wherein the loop defines a constriction opening. The operation device operates the constriction member in the loop to change the size of the constriction opening.

6a) The elongated constriction member comprises a belt having the contact surfaces, and the operation device operates the belt to change the longitudinal extension of the belt in the loop to change the size of the constriction opening. The forming means may form the constriction member or belt into a loop having at least one predetermined size.

6b) The elongated constriction member is operable to change the size of the constriction opening, such that the outer circumferential confinement surface of the constriction device is changed, or, alternatively, is unchanged.

6c) The elongated constriction member is elastic and varies in thickness as seen in a cross-section there through, and is operable to turn around the longitudinal extension of the constriction member.

6d) The elongated constriction member comprises two substantially or partly semi-circular frame elements having the contact surfaces and hinged together, such that the semi-circular elements are swingable relative to each other from a fully open state in which they substantially or partly form a circle to a fully folded state in which they substantially form a semi-circle.

In the above noted embodiments (1) to (6d), it is important that the constriction device is designed to constrict said length of the tissue wall portion of the patient's blood vessel. For this purpose, the constriction device may include two or more of the described constriction elements/members to be applied in a row along said length of the wall portion, wherein said row extends in the direction of flow in the blood vessel. Preferably, such constriction elements/members are non-inflatable and mechanically operable or adjustable. An example of a non-inflatable constriction element is a cylinder, arranged around a blood vessel and supporting the same. Preferably said cylinder is elastic, and more preferably it is part of a device incorporating one or more of the functions of constriction, stimulation and monitoring described herein.

In the above noted embodiments (1) to (6d), the operation device may either mechanically or hydraulically adjust the constriction device of the constriction/stimulation unit. Also, the operation device may comprise an electrically powered operation device for operating the constriction device. For many applications of the present invention, the operation device suitably operates the constriction device, such that the through-flow area of the aneurysm assumes a size in the constricted state that enables the stimulation device to contract the wall portion such that the flow in the lumen is stopped, which may be a life-saving action in acute situations.

Mechanical Operation

Where the operation device mechanically operates the constriction device of the constriction/stimulation unit, it may be non-inflatable. Furthermore, the operation device may comprise a servo system, which may include a gearbox. The term "servo system" encompasses the normal definition of a servo mechanism, i.e., an automatic device that controls large amounts of power by means of very small amounts of power, but may alternatively or additionally encompass the definition of a mechanism that transfers a weak force acting on a moving element having a long stroke into a strong force acting on another moving element having a short stroke. Preferably, the operation device operates the constriction device in a non-magnetic and/or non-manual manner. A motor may be operatively connected to the operation device. The operation device may be operable to perform at least one reversible function and the motor may be capable of reversing the function.

Hydraulic Operation

Where the operation device hydraulically operates the constriction device of the constriction/stimulation unit, it includes hydraulic means for adjusting the constriction device.

In an embodiment of the invention, the hydraulic means comprises a reservoir and an expandable/contractible cavity in the constriction device, wherein the operation device distributes hydraulic fluid from the reservoir to expand the cavity, and distributes hydraulic fluid from the cavity to the reservoir to contract the cavity. The cavity may be defined by a balloon of the constriction device that abuts the tissue wall portion of the patient's blood vessel, so that the patient's wall portion is constricted upon expansion of the cavity and released upon contraction of the cavity.

Alternatively, the cavity may be defined by a bellows that displaces a relatively large contraction element of the constriction device, for example a large balloon that abuts the wall portion, so that the patient's wall portion is constricted upon contraction of the bellows and released upon expansion of the bellows. Thus, a relatively small addition of hydraulic fluid to the bellows causes a relatively large increase in the constriction of the wall portion. Such a bellows may also be replaced by a suitably designed piston/cylinder mechanism.

Where the hydraulic means comprises a cavity in the constriction device, the apparatus of the invention can be designed in accordance with the options listed below.

The reservoir comprises first and second wall portions, and the operation device displaces the first and second wall portions relative to each other to change the volume of the reservoir, such that fluid is distributed from the reservoir to the cavity, or from the cavity to the reservoir.

1a) The first and second wall portions of the reservoir are displaceable relative to each other by at least one of a magnetic device, a hydraulic device or an electric control device.

2) The operation device comprises a pump for pumping fluid between the reservoir and the cavity.

2a) The pump comprises a first activation member for activating the pump to pump fluid from the reservoir to the cavity and a second activation member for activating the pump to pump fluid from the cavity to the reservoir.

2a1) The first and second activation members are operable by manual manipulation thereof.

2a2) At least one of the activation members operates when subjected to an external predetermined pressure.

2a3) At least one of the first and second activating members is operable by magnetic means, hydraulic means, or electric control means.

2b) The apparatus comprises a fluid conduit between the pump and the cavity, wherein the reservoir forms part of the conduit. The conduit and pump are devoid of any non-return valve. The reservoir forms a fluid chamber with a variable volume, and the pump distributes fluid from the chamber to the cavity by a reduction in the volume of the chamber and withdraws fluid from the cavity by an expansion of the volume of the chamber. The apparatus further comprises a motor for driving the pump, wherein the pump comprises a movable wall of the reservoir for changing the volume of the chamber.

In all of the above noted embodiments 1 to 2b where the hydraulic means comprises an expandable cavity in the constriction device, the cavity can be exchanged by a cylinder/piston mechanism for adjusting the constriction device. In this case, the operation device distributes hydraulic fluid between the reservoir and the cylinder/piston mechanism to adjust the constriction device.

In a special embodiment of the invention, the operation device comprises a reverse servo operatively connected to the hydraulic means. The term "reverse servo" is to be understood as a mechanism that transfers a strong force acting on a moving element having a short stroke into a weak force acting on another moving element having a long stroke; i.e., the reverse function of a normal servo mechanism. Thus, minor changes in the amount of fluid in a smaller reservoir could be transferred by the reverse servo into major changes in the amount of fluid in a larger reservoir. The reverse servo is particularly suited for manual operation thereof.

Preferably, the reverse servo comprises an expandable servo reservoir containing servo fluid and a fluid supply reservoir hydraulically connected to the servo reservoir to form a closed conduit system for the servo fluid. The expandable servo reservoir has first and second wall portions, which are displaceable relative to each other in response to a change in the volume of the expandable servo reservoir.

In accordance with a first alternative, the first and second wall portions of the servo reservoir are operatively connected to the hydraulic means. The reverse servo distributes fluid between the fluid supply reservoir and the expandable servo reservoir to change the volume of the servo reservoir, whereby the hydraulic means is operated to adjust the constriction device.

In accordance with a second alternative, there is provided an implantable main reservoir containing a predetermined amount of hydraulic fluid, wherein the reverse servo is operable to distribute hydraulic fluid between the main reservoir and the hydraulic means to adjust the constriction device. More specifically, the main reservoir is provided with first and second wall portions operatively connected to the first and second wall portions of the expandable servo reservoir, such that the volume of the main reservoir is changed when the volume of the expandable servo reservoir is changed. Thus, when the reverse servo distributes servo fluid between the fluid supply reservoir and the expandable servo reservoir to change the volume of the main reservoir, hydraulic fluid is distributed from the main reservoir to the hydraulic means, or from the hydraulic means to the main reservoir. Advantageously, the servo and main reservoirs are dimensioned, such that when the volume of the servo reservoir is changed by a relatively small amount of servo fluid, the volume of the main reservoir is changed by a relatively large amount of hydraulic fluid.

In both of the above-described alternatives, the fluid supply reservoir may have first and second wall portions, which are displaceable relative to each other to change the volume of the fluid supply reservoir to distribute servo fluid between the fluid supply reservoir and the expandable servo reservoir. The first and second wall portions of the fluid supply reservoir may be displaceable relative to each other by manual manipulation, a magnetic device, a hydraulic device, or an electric control device to change the volume of the fluid supply reservoir to distribute servo fluid between the fluid supply reservoir and the expandable servo reservoir.

In all of the above noted embodiments 1 to 2b where the hydraulic means comprises an expandable cavity in the constriction device, or in embodiments where the hydraulic means comprises a hydraulically operable mechanical construction, the operation device may include the reverse servo described above. In a further embodiment of the invention, the hydraulic means include first and second hydraulically interconnected expandable/contractible reservoirs. The first reservoir is operatively connected to the constriction device, such that the constriction device changes the constriction of the patient's wall portion upon expansion or contraction of the first reservoir. By changing the volume of the second reservoir hydraulic fluid is distributed between the two reservoirs, so that the first reservoir is either expanded or contracted. This embodiment requires no non-return valve in the fluid communication conduits between the two reservoirs, which is beneficial to long-term operation of the hydraulic means.

Alternatively, the hydraulic means may include first and second hydraulically interconnected piston/cylinder mechanisms instead of the first and second reservoirs described above. The first piston/cylinder mechanism is operatively connected to the constriction device, such that the constriction device changes the constriction of the patient's wall portion upon operation of the first piston/cylinder mechanism. By operating the second piston/cylinder mechanism hydraulic fluid is distributed between the two piston/cylinder mechanisms, so that the first piston/cylinder mechanism adjusts the constriction device.

Where the constriction device does not include an expandable/contractible cavity, the constriction device may comprise at least two elongated clamping elements having the above-mentioned contact surfaces and extending along the wall portion on different sides of the blood vessel. The hydraulic means, which may include the reverse servo described above, hydraulically moves the elongated clamping elements towards the wall portion to constrict the wall portion. For example, the constriction device may have hydraulic chambers in which the clamping elements slide back and forth. Further, the hydraulic means may also include a pump and an implantable reservoir containing hydraulic fluid. The pump distributes hydraulic fluid from the reservoir to the chambers to move the clamping elements against the wall portion, and distributes hydraulic fluid from the chambers to the reservoir to move the clamping elements away from the wall portion.

Design of the Control Device

In a method according to an embodiment of the invention, the control device suitably controls the constriction/stimulation unit from outside the patient's body. Preferably, the control device is operable by the patient. For example, the control device may comprise a manually operable switch for switching on and off the constriction/stimulation unit, wherein the switch is adapted for subcutaneous implantation in the patient to be manually or magnetically operated from outside the patient's body. Alternatively, the control device may comprise a hand-held wireless remote control, which is conveniently operable by the patient to switch on and off the constriction/stimulation unit. The wireless remote control may also be designed for application on the patient's body like a wristwatch. Such a wristwatch type of remote control may emit a control signal that follows the patient's body to implanted signal responsive means of the apparatus.

Where the control device wirelessly controls the constriction/stimulation unit from outside the patient's body, the wireless control function is preferably performed in a non-magnetic manner, i.e., the control device controls the constriction device of the constriction/stimulation unit in a non-magnetic manner. The patient may use the remote control to control the constriction/stimulation unit to adjust the stimulation intensity and/or adjust the constriction of the wall portion. The wireless remote control may comprise at least one external signal transmitter or transceiver and at least one internal signal receiver or transceiver implantable in the patient.

The wireless remote control preferably transmits at least one wireless control signal for controlling the constriction/stimulation unit. The control signal may comprise a frequency, amplitude, phase modulated signal or a combination thereof, and may be an analogue or a digital signal, or a combination of an analogue and digital signal. The remote control may transmit an electromagnetic carrier wave signal for carrying the digital or analogue control signal. Also the carrier signal may comprise digital, analogue or a combination of digital and analogue signals.

Any of the above control signals may comprise wave signals, for example a sound wave signal, an ultrasound wave signal, an electromagnetic wave signal, an infrared light signal, a visible light signal, an ultra violet light signal, a laser light signal, a microwave signal, a radio wave signal, an x-ray radiation signal or a gamma radiation signal. Alternatively, the control signal may comprise an electric or magnetic field, or a combined electric and magnetic field.

As mentioned above, the control signal may follow the patient's body to implanted signal responsive means of the apparatus.

In a method according to an embodiment of the invention, the control device may include a programmable internal control unit, such as a microprocessor, implantable in the patient for controlling the constriction/stimulation unit. The control device may further include an external control unit intended to be outside the patient's body, wherein the internal control unit is programmable by the external control unit. For example, the internal control unit may be programmable for controlling the constriction/stimulation unit over time, suitably in accordance with an activity schedule program. The apparatus of the invention may comprise an external data communicator and an implantable internal data communicator communicating with the external data communicator, wherein the internal communicator feeds data related to the constriction/stimulation unit back to the external data communicator or the external data communicator feeds data to the internal data communicator.

Source of Energy

The present invention also presents a solution for supplying energy for use in connection with the operation of the constriction/stimulation unit. Thus, in a broad sense, the present invention provides an apparatus for treating a vascular aneurysm of a blood vessel, supporting the walls thereof, and stimulating the walls, wherein the apparatus comprises an implantable constriction device for gently constricting a portion of the tissue wall to influence the flow in the lumen of the blood vessel, a stimulation device for intermittently and individually stimulating different areas of the wall portion, as the constriction device constricts the wall portion, to cause contraction of the wall portion to further strengthen the blood vessel, wherein the constriction and stimulation devices form an operable constriction/stimulation unit, a source of energy, and a control device operable from outside the patient's body to control the source of energy to release energy for use in connection with the operation of the constriction/stimulation unit. In a simple form of the invention, the source of energy, such as a battery or accumulator, is implantable in the patient's body.

Transmission of Wireless Energy

In a more sophisticated form of the invention, which is preferable, the source of energy is external to the patient's body and the control device controls the external source of energy to release wireless energy. In this sophisticated form of the invention, the apparatus comprises an energy-transmission device that transmits the released wireless energy from outside the patient's body to inside the patient's body. Among many things the wireless energy may comprise electromagnetic energy, an electric field, an electromagnetic field or a magnetic field, or a combination thereof, or electromagnetic waves. The energy-transmission device may transmit wireless energy for direct use in connection with the operation of the constriction/stimulation unit, as the wireless energy is being transmitted. For example, where an electric motor or pump operates the constriction device, wireless energy in the form of a magnetic or an electromagnetic field may be used for direct power of the motor or pump.

Thus, the motor or pump is running directly during transmission of the wireless energy. This may be achieved in two different ways: a) using a transforming device implanted in the patient to transform the wireless energy into energy of a different form, preferably electric energy, and powering the motor or pump with the transformed energy, or b) using the wirelessly transmitted energy to directly power the motor or pump. Preferably wireless energy in the form of an electromagnetic or magnetic field is used to directly influence specific components of the motor or pump to create kinetic energy for driving the motor or pump. Such components may include coils integrated in the motor or pump, or materials influenced by magnetic fields, or permanent magnets, wherein the magnetic or electromagnetic field influences the coils to generate a current for driving the motor or pump, or influences the material or permanent magnets to create kinetic energy for driving the motor or pump.

Preferably, the energy-transmission device transmits energy by at least one wireless signal, suitably a wave signal. The wave signal may comprise an electromagnetic wave signal including one of an infrared light signal, a visible light signal, an ultra violet light signal, a laser signal, a microwave signal, a radio wave signal, an x-ray radiation signal, and a gamma radiation signal. Alternatively, the wave signal may comprise a sound or ultrasound wave signal. The wireless signal may be a digital or analogue signal, or a combination of a digital and analogue signal.

Transforming Wireless Energy

In accordance with a particular embodiment of the invention, an implantable energy-transforming device is provided for transforming wireless energy of a first form transmitted by the energy-transmission device into energy of a second form, which typically is different from the energy of the first form. The constriction/stimulation unit is operable in response to the energy of the second form. For example, the wireless energy of the first form may comprise sound waves, whereas the energy of the second form may comprise electric energy. In this case, the energy-transforming device may include a piezo-electric element for transforming the sound waves into electric energy. Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transforming device may function differently from or similar to the energy-transmission device. In a special embodiment, the energy-transforming device comprises at least one element, such as at least one semiconductor, having a positive region and a negative region, when exposed to the energy of the first form transmitted by the energy-transmission device, wherein the element is capable of creating an energy field between the positive and negative regions, and the energy field produces the energy of the second form. More specifically, the element may comprise an electrical junction element, which is capable of inducing an electric field between the positive and negative regions when exposed to the energy of the first form transmitted by the energy-transmission device, whereby the energy of the second form comprises electric energy.

The energy-transforming device may transform the energy of the first form directly or indirectly into the energy of the second form. An implantable motor or pump for operating the constriction device of the constriction/stimulation unit may be provided, wherein the motor or pump is powered by the energy of the second form. The constriction device may be operable to perform at least one reversible function and the motor may be capable of reversing the function. For example, the control device may shift polarity of the energy of the second form to reverse the motor.

The energy-transforming device may directly power the motor or pump with the transformed energy, as the energy of the second form is being transformed from the energy of the first form. Preferably, the energy-transforming device directly operates the constriction/stimulation unit with the energy of the second form in a non-magnetic, non-thermal or non-mechanical manner.

Normally, the constriction/stimulation unit comprises electric components that are energized with electrical energy. Other implantable electric components of the apparatus may be at least one voltage level guard or at least one constant current guard. Therefore, the energy-transforming device may transform the energy of the first form into a direct current or pulsating direct current, or a combination of a direct current and pulsating direct current. Alternatively, the energy-transforming device may transform the energy of the first form into an alternating current or a combination of a direct and alternating current.

In a method according to an embodiment of the invention, the apparatus of the invention may comprise an internal source of energy implantable in the patient for supplying energy for the operation of the constriction/stimulation unit. The apparatus may further comprise an implantable switch operable to switch from an "off" mode, in which the internal source of energy is not in use, to an "on" mode, in which the internal source of energy supplies energy for the operation of the constriction/stimulation unit, and/or for energizing implanted electronic components of the apparatus. The switch may be operable by the energy of the first form transmitted by the energy-transmission device or by the energy of the second form supplied by the energy-transforming device. The described switch arrangement reduces power consumption of the apparatus between operations.

The internal source of energy may store the energy of the second form supplied by the energy-transforming device. In this case, the internal source of energy suitably comprises an accumulator, such as at least one capacitor or at least one rechargeable battery, or a combination of at least one capacitor and at least one rechargeable battery. Where the internal source of energy is a rechargeable battery it may be charged only at times convenient for the patient, for example when the patient is sleeping. Alternatively, the internal source of energy may supply energy for the operation of the constriction/stimulation unit but not be used for storing the energy of the second form. In this alternative, the internal source of energy may be a battery and the switch described above may or may not be provided.

Suitably, the apparatus comprises an implantable stabilizer for stabilizing the energy of the second form. Where the energy of the second form is electric energy the stabilizer suitably comprises at least one capacitor.

The energy-transforming device may be designed for implantation subcutaneously in the abdomen, thorax or cephalic region of the patient. Alternatively, it may be designed for implantation in an orifice of the patient's body and under the mucosa or intramuscularly outside the mucosa of the orifice.

Although the constriction/stimulation unit in the embodiments described above is designed as a single piece, which is most practical for implantation, it should be noted that as an alternative the constriction device and stimulation device could be designed as separate pieces. Any one of the constriction and stimulation units described above may alternatively be replaced by two or more separate constriction/stimulation elements, which are controlled independently of one another.

Male Contraception

Another object of the present invention is to provide a male contraception method for obtaining a time-limited sterility of a male mammalian individual.

In accordance with this object of the present invention, there is provided a male contraception method, comprising influencing the flow of sperms in the lumen of a male patient's vas deferens so that any sperm is prevented from flowing from the vas deferens to the male patient's urethra, when the patient is sexually active.

In an embodiment of the invention, the method comprises restricting the lumen of the vas deferens in the region downstream the ampulla, so that any sperm is prevented from flowing in the vas deferens lumen.

As a result, the method of the present invention provides a reliable temporary sterilization by shielding of sperms compartmentalized in the ampulla, whereby the apparatus immediately may exert its contraceptive effect.

The method may further comprise providing a constriction device configured to constrict the vas deference, and operating the constriction device to constrict the vas deferens to restrict the vas deferens lumen so that any sperm is prevented from flowing in the vas deferens lumen.

Alternatively or in combination, the method may further comprise providing a stimulation device configured to stimulate the vas deference, and operating the stimulation device to constrict the vas deferens to restrict the vas deferens lumen so that any sperm is prevented from flowing in the vas deferens lumen.

In this context, restricting the vas deferens lumen means that the lumen is occluded or movements are created to prevent flow in the lumen in a manner to prevent sperms to reach the urethra by operating on vas deferens from the outside. The terms "vas deferens" may include one vas deferens or both vasa deferentia. When explaining the inventive methods of restricting of vas deferens according to the invention also other terms like "lumen" or "tissue portion" or "body vas deferens" are used, but such terms shall be regarded as functional synonyms and interchangeable with "vas deferens".

The term "ampulla" refers to the enlargement of vas deference close to where it meets the seminal vesicle. The term "downstream the ampulla" refers to a location after the ampulla in the direction of the urethra and the seminal vesicle. Consequently, "upstream the ampulla" would refer to a location on the vas deference before the ampulla in the direction towards the testicle. That the restriction device is adapted to restrict vas deference in this specific region preferably means that it is designed to be accommodated in this region of the body.

In another embodiment of the invention, the method comprises
gently constricting at least one portion of the tissue wall of vas deferens to influence the flow in the vas deferens, or
stimulating at least one portion of the tissue wall of vas deferens to cause contraction of the wall portion to further influence the flow in the vas deferens.

In accordance with a most beneficial embodiment of the invention, the method comprises gently constricting the tissue wall portion to influence the flow in the vas deferens, and stimulating the constricted wall portion to cause contraction of the wall portion of vas deferens to further influence the flow in the vas deferens.

The present invention provides an advantageous combination of the method steps (a) and (b), which results in a two-stage influence on the flow of fluids and/or other bodily matter in the vas deferens. Thus, applying a relatively weak force against the wall portion gently constricts the tissue wall and the constricted wall portion is stimulated to achieve the desired final influence on the flow in the lumen. The phrase "gently constricts a portion of the tissue wall" is to be understood as constricting the wall portion without substantially hampering the blood circulation in the tissue wall.

Preferably, step (b) is performed by intermittently and individually stimulating different areas of the wall portion. Such an intermittent and individual stimulation of different areas of the wall portion of vas deferens allows tissue of the wall portion to maintain over time substantially normal blood circulation.

The method of the present invention can be practiced on any place on any kind of bodily organs, in particular, but not limited to, tubular bodily organs, which is a significant advance in the art, as compared with prior stimulation devices that are confined to electric stimulation of malfunctioning sphincters. Preferably, the constriction step (a) and stimulation step (b) are performed independently of each other. Steps (a) and (b) may be performed simultaneously. Optionally, step (b) may or may not be performed while step (a) is performed.

Initially, the constriction of the wall portion can be calibrated by stimulating the wall portion while adjusting the constriction of the wall portion until the desired restriction of the flow in the lumen is obtained.

Flow Restriction

It should be understood that any embodiment or part of embodiment disclosed below in connection with flow restriction for the constriction and stimulation devices combined in the constriction/stimulation unit could be used for the separate constriction device and separate stimulation device, where applicable. The method of the present invention is well suited for restricting the flow of fluids and/or other bodily matter in the lumen of a bodily organ. Thus, in a principal embodiment of the invention, the wall portion is constricted, so that the flow in the lumen at least is restricted and the constricted wall portion is stimulated to at least further restrict the flow in the lumen. Specifically, the wall portion is constricted to a constricted state, in which the blood circulation in the constricted wall portion is substantially unrestricted and the flow in the lumen is at least restricted, and the constricted wall portion is stimulated when it is in the constricted state to at least further restrict the flow in the lumen.

The constriction step (a) and stimulation step (b) are suitably performed to constrict and stimulate the wall portion to an extent that depends on the flow restriction that is desired to be achieved in a specific application of the method of the invention. Thus, in accordance with a first flow restriction option, step (a) is performed by constricting the wall portion, so that the flow in the lumen is restricted but not stopped, and step (b) is performed by stimulating the constricted wall portion to cause contraction thereof, so that the flow in the lumen is further restricted but not stopped. The method may further comprise sensing a physical parameter of the patient and adjusting the intensity of the stimulation of the wall portion in response to the sensed parameter.

In accordance with a second flow restriction option, step (a) is performed by constricting the wall portion, so that the flow in the lumen is restricted but not stopped, and step (b) is performed by stimulating the constricted wall portion to cause contraction thereof, so that the flow in the lumen is stopped. first or second options, the method may further comprise (c) ceaseing stimulating the wall portion to increase or allow the flow in the lumen and (d) releasing the wall portion to restore the flow in the lumen.

In accordance with a third flow restriction option, step (a) is performed by constricting the wall portion, so that the flow in the lumen is substantially stopped, and step (b) is performed by stimulating the constricted wall portion to cause contraction thereof, so that the flow in the lumen is completely stopped. The method may further comprise (c) ceaseing stimulating the wall portion to allow the flow in the lumen and (d) releasing the wall portion to restore the flow in the lumen.

Where the constricted wall portion is stimulated to contract, so that the flow in the lumen is stopped, a first length of the constricted wall portion and a second length of the constricted wall portion, which is located downstream of the first length, are suitably simultaneously and cyclically stimulated, wherein the first length is progressively stimulated in the upstream direction of the lumen and the second length is progressively stimulated in the downstream direction of the lumen.

Furthermore, when using the method of the invention in accordance with the second and third options, the method may further comprise sensing a physical parameter of the patient or functional parameter of implanted components and adjusting the stimulation of the wall portion in response to the sensed parameter. For example, the intensity of the stimulation of the wall portion may be increased in response to a sensed pressure increase in the lumen, so that the flow in the lumen remains stopped when a pressure increase occurs in the lumen. In particular, the method may comprise sensing a physical parameter of the patient's that relates to the pressure in the lumen, and controlling the stimulation of the wall portion in response to the sensed parameter. Any sensor for sensing a physical parameter of the patient, such as a pressure in the patient's body that relates to the pressure in the lumen may be provided, wherein the stimulation is controlled in response to signals from the sensor. Such a sensor may for example sense the pressure in the patient's abdomen, the pressure against the implanted constriction device or the pressure on the tissue wall of the bodily organ.

In accordance with a fourth restriction option, step (a) is performed by constricting the wall portion, so that the flow in the lumen is stopped. When needed, the wall portion is released to restore the flow in the lumen. Step (b) is only performed by stimulating the constricted wall portion to cause contraction thereof, so that the flow in the lumen remains stopped when a pressure increase occurs in the lumen. The method may further comprise sensing a physical parameter of the patient's body, such as a pressure in the patient's body that relates to the pressure in the lumen, and controlling the stimulation of the wall portion in response to the sensed parameter. Such a physical parameter may be a pressure in the patient's abdomen and the sensor may be a pressure sensor.

In some applications of the method of the invention, continuous stimulation may over time change the physical properties of the tissue so that the tissue might be injured. Also, the effect of a continuous stimulation of the tissue wall may decrease over time. Therefore, step (b) is preferably performed by intermittently and individually stimulating different areas of the wall portion so that the flow in the lumen continues to be restricted as desired and each area of the wall portion essentially maintains its natural physical properties over time to prevent the area from being injured. Advantageously, each area of the wall portion is stimulated during successive time periods, each time period being short enough to maintain over time satisfactory blood circulation in the area. Thus, the areas are stimulated so that an area that currently is not stimulated will have time to restore substantially normal blood circulation before it is stimulated again.

To maintain satisfactory blood circulation in the tissue wall of the patient's organ stimulation step (b) is suitably performed by stimulating one or more of different areas of the wall portion at a time, preferably by sequentially stimulating the different areas of the wall portion or by shifting the stimulation from one area to another over time. Preferably, stimulation step (b) is performed by cyclically propagating the stimulation of the areas along the wall portion, for example in accordance with a determined stimulation pattern.

The method of the invention may further comprise controlling, preferably by the patient, the constriction and/or stimulation of the wall portion from outside the patient's body.

Generally, the method of the invention comprises sensing a physical parameter of the patient and controlling, preferably automatically, the constriction and/or stimulation of the wall portion in response to the sensed parameter.

The constriction step (a) may be performed by constricting any wall portions of a series of wall portions of the organ's tissue wall, respectively, either in random or in accordance with a predetermined sequence. The stimulation step (b) may be performed by stimulating any of the constricted wall portions of the series of wall portions. Specifically, step (a) may be performed by constricting all of the wall portions of the series of wall portions, and step (b) may be performed by stimulating any constricted wall portions in random or in accordance with a predetermined sequence to close the organ's lumen.

Moving Sperms in the Lumen or Preventing the Movement of Sperms in the Lumen in a Similar Way It should be understood that any embodiment or part of embodiment disclosed below in connection with moving sperms in the lumen, or preventing the move of sperms in the lumen, for the constriction and stimulation devices combined in the constriction/stimulation unit could be used for the separate constriction device and separate stimulation device, where applicable. The method of the present invention can be practised for actively moving the fluid and/or other bodily matter in lumen of a patient's organ. Thus, in the embodiments of the invention listed below, steps (a) and (b) are co-operated to move the fluid and/or other bodily matter in the lumen.

1) Step (a) is performed by constricting the wall portion to restrict the flow in the lumen, and step (b) is performed by stimulating the constricted wall portion to close the lumen either at an upstream end or a downstream end of the constricted wall portion. The method further comprises (c) increasing the constriction of the wall portion to move the fluid and/or other bodily matter in the lumen.

2) Step (a) is performed by constricting the wall portion to restrict the flow in the lumen, and step (b) is performed by progressively stimulating the constricted wall portion to cause progressive contraction of the wall portion to move the fluid and/or other bodily matter in the lumen. The constricted wall portion is progressively stimulated in the downstream or upstream direction of the lumen.

3) Step (a) is performed by varyingly constricting the wall portion to vary the flow in the lumen, and step (b) is performed by progressively stimulating the constricted wall portion to cause progressive contraction of the wall portion to move the fluid and/or other bodily matter in the lumen. The constricted wall portion is progressively stimulated in the downstream or upstream direction of the lumen.

4) Step (a) is performed by varyingly constricting different areas of the wall portion to cause progressive constriction of the wall portion in the downstream or upstream direction of the lumen, and the constricted wall portion is progressively stimulated to cause progressive contraction thereof in harmony with the progressive constriction of the wall portion. The method may further comprise providing at least one elongated constriction element extending along the wall portion, and controlling the elongated constriction element to progressively constrict the wall portion in the downstream or upstream direction of the lumen. The elongated constriction element suitably comprises contact surfaces dimensioned to contact a length of wall portion, and the method may further comprise providing a plurality of stimulation elements distributed along the contact surfaces, and controlling the stimulation elements to stimulate the different areas of the wall portion along the length of the wall portion.

5) Step (a) is performed by constricting any one of a series of wall portions of the tissue wall to at least restrict the flow in the lumen, and step (b) is performed by stimulating the constricted wall portion to close the lumen. The method further comprises successively constricting the wall portions of the series of wall portions to move the fluid and/or other bodily matter in the lumen in a peristaltic manner.

5a) In accordance with an alternative, the method further comprises providing at least one constriction element and at least one stimulation element positioned on the constriction element, moving the constriction element along the organ in the flow direction in the lumen to successively constrict the wall portions of the series of wall portions, and using the stimulation element to stimulate the wall portion constricted by the constriction element to close the lumen. Suitably, the method further comprises cyclically moving the constriction element along the wall portions of the series of wall portions.

5b) In accordance with another alternative, the method further comprises providing a plurality of constriction elements and stimulation elements positioned on the constriction elements, moving each constriction element along the organ to successively constrict the wall portions of the series of wall portions, and using the stimulation elements to stimulate the wall portion constricted by any one of the constriction elements to close the lumen. Suitably, the method further comprises cyclically moving the constriction elements one after the other along the wall portions of the series of wall portions. Specifically, the method further comprises providing a rotor carrying the constriction elements, and rotating the rotor so that each constriction element cyclically constricts the wall portions of the series of wall portions. Each constriction element suitably comprises a roller that rolls on the organ to constrict the latter.

6) Step (a) is performed by constricting any wall portions of a series of wall portions of the organ's tissue wall, respectively, wherein the wall portions of the series of wall portions are successively constricted along the organ to move the fluid and/or other bodily matter in the lumen of the patient's organ. The stimulation step (b) is performed by stimulating any constricted wall portions of the series of wall portions.

7) Step (a) is performed by constricting wall portions of a series of wall portions without completely closing the organ's lumen, and step (b) is performed by stimulating the constricted wall portions one after the other, so that the wall portions of the series of wall portions are successively contracted along the organ to move the fluid and/or other bodily matter in the lumen of the patient's organ.

8) Step (a) is performed by constricting the wall portion at an upstream or downstream end thereof to close the lumen. The method further comprises (c) constricting the wall portion between the upstream and downstream ends thereof, to move the fluid or other bodily matter contained in the wall portion between the upstream and downstream ends thereof downstream or upstream in the lumen. Optionally, the method further comprises stimulating the wall portion between the upstream and downstream ends thereof, as (c) is performed.

8a) In accordance with an alternative, step (a) is performed by constricting the wall portion at the upstream end thereof to restrict the flow in the lumen, and step (b) is performed by stimulating the constricted wall portion at the upstream end to close the lumen, whereby the fluid and/or other bodily matter contained in the wall portion between the upstream and downstream ends thereof is moved downstream in the lumen, as step (c) is performed.

8b) In accordance with another alternative, step (a) is performed by constricting the wall portion at the downstream end thereof to restrict the flow in the lumen, and step (b) is performed by stimulating the constricted wall portion at the downstream end to close the lumen, whereby the fluid and/or other bodily matter contained in the wall portion between the upstream and downstream ends thereof is moved upstream in the lumen, as step (c) is performed.

In accordance with an alternative, step (a) and step (b) are performed independently of each other or simultaneously.

In any of the above noted embodiments (1) to (8b), step (b) may be performed by stimulating the wall portion with electric pulses.

To summerize a few prefered embodiments see below:

In accordance with an alternative, step (a) is performed by constricting any wall portions of a series of wall portions of the organ's tissue wall, respectively. In accordance with an alternative, the wall portions of the series of wall portions are constricted in random or in accordance with a predetermined sequence. In accordance with an alternative, the wall portions of the series of wall portions are successively constricted along the organ to move the fluid and/or other bodily matter in the lumen of the patient's organ or to prevent the fluid and/or other bodily matter to move in the lumen of the patient's organ.

In accordance with an alternative, step (b) is performed by stimulating any constricted wall portions of the series of wall portions. In accordance with an alternative, the wall portions of the series of wall portions are constricted in random or in accordance with a predetermined sequence. In accordance with an alternative, wherein the wall portions of the series of wall portions are successively constricted along the organ to move the fluid and/or other bodily matter in the lumen of the patient's organ or to prevent the fluid and/or other bodily matter to move in the lumen of the patient's organ.

In accordance with an alternative, step (a) is performed by constricting any wall portions of a series of wall portions of the organ's tissue wall, respectively, wherein the wall portions of the series of wall portions are succesively constricted without completely closing the organ's lumen, and step (b) is performed by stimulating the constricted wall portions, so that the wall portions of the series of wall portions are further constricted. In accordance with an alternative, the wall portions of the series of wall portions are constricted in random or in accordance with a predetermined sequence.

In accordance with an alternative, wherein the wall portions of the series of wall portions are successively constricted along the organ to move the fluid and/or other bodily matter in the lumen of the patient's organ or to prevent the fluid and/or other bodily matter to move in the lumen of the patient's organ.

In accordance with an alternative, step (a) is performed by constricting all of the wall portions of the series of wall portions, and step (b) is performed by stimulating any constricted wall portions so that the wall portions of the series of wall portions are further constricted.

In accordance with an alternative, the wall portions of the series of wall portions are further constricted by the stimulation device in random or in accordance with a predetermined sequence.

In accordance with an alternative, the wall portions of the series of wall portions are successively further constricted by the stimulation device along the organ to move the fluid and/or other bodily matter in the lumen of the patient's organ or to prevent the fluid and/or other bodily matter to move in the lumen of the patient's organ.

A method for controlling a flow of sperms in an vas deferens of a female patient, the method comprising:

applying influence on at least one portion of the vas deferens wall of a vas deferens portion, and controlling the influence to influence the flow of sperms in the vas deferens portion.

A method, wherein the step of influencing comprises stimulating the vas deferens wall portion to cause contraction of the vas deferens wall portion to influence the flow of sperms in the vas deferens.

A method, wherein the step of influencing comprises constricting the wall portion of the vas deferens wall to constrict the vas deferens wall portion, to cause contraction of the vas deferens wall portion to influence the flow of sperms in the vas deferens.

A method, wherein the step of contracting the vas deferens wall portion comprising contracting any wall portions of a series of wall portions of the vas deferens's wall, respectively, wherein the vas deferens wall portions of the series of wall portions are contracted in random or in accordance with a predetermined sequence.

The method further comprising, the vas deferens wall portions of the series of wall portions are successively contracted along the vas deferens to move the sperms in the vas deferens or to prevent the sperms to move in the vas deferens.

The method, further comprising contracting the vas deferens wall portions of the series of wall portions at least two at a time at positions spaced apart on the vas deferens, thus creating a closed space in the lumen of the vas deferens, wherein one contracted wall portion is placed proximal and one wall portion is placed distal on the vas deferens, the further method comprising the steps of;

opening and closing said closed space or varying the position of said closed space.

The method, further comprising two or more closed spaces, the further method comprising the steps of;

opening and closing said closed spaces according, to a predetermined sequence, or varying the position of said closed spaces along the vas deferens, according to a predetermined sequence, to prevent any sperm to pass all the contracted wall portions for a period exceeding 3-5 days.

Stimulation Modes

When stimulating neural or muscular tissue there is a risk of injuring or deteriorating the tissue over time if the stimulation is not properly performed. The method of the present invention is performed to reduce or even eliminate that risk. Thus, step (b) is performed by intermittently stimulating different areas of the wall portion so that at least two of the areas are stimulated at different points of time. I.e., the stimulation is shifted from one area to another area over time. In addition, step (b) is performed by intermittently stimulating the areas of the wall portion so that an area of the different areas that currently is not stimulated has time to restore substantially normal blood circulation before it is stimulated again. Furthermore, step (b) is performed by intermittently stimulating the areas during successive time periods, wherein each time period is short enough to maintain satisfactory blood circulation in the area until the laps of the time period. This gives the advantage that the method of the present invention provides continuous stimulation of the wall portion of the organ to achieve the desired flow control while essentially maintaining over time the natural physical properties of the organ without risk of injuring the organ.

Also, by physically changing the places of stimulation on the organ over time as described above it is possible to create an advantageous changing stimulation pattern on the organ, in order to achieve a desired flow control.

To achieve the desired reaction of the tissue wall during the stimulation thereof, step (b) may be performed by stimulating the wall portion with, preferably cyclically, varying stimulation intensity.

In a main embodiment of the invention, step (b) is performed by intermittently stimulating the wall portion with pulses, preferably in the form of pulse trains. The pulse trains can be configured in many different ways by varying pulse parameters. Thus, the pulse amplitudes of the pulses of the pulse train, the off time periods between the individual pulses of each pulse train and the width and repetition frequency of each pulse may be varied. Also the off time periods between the pulse trains may be varied, wherein each off time period between the pulse trains is kept long enough to restore substantially normal blood circulation in each area of the wall portion, when the area is not stimulated during the off time periods. Furthermore, the repetition frequency of the pulses of the pulse trains and the length and number of pulses of each pulse train may be varied.

As mentioned above, for reasons of maintaining over time the effect of stimulation, it is preferable that different areas of the wall portion are intermittently and individually stimulated. In consequence, step (b) may be performed by stimulating one or more of the areas at a time with pulses, by cyclically propagating the stimulation of the areas with pulses along the wall portion, and/or by propagating the stimulation of the areas with pulses in accordance with a determined stimulation pattern. In case the off time periods between pulse trains that stimulate the respective area of the wall portion are varied, it is preferable that each off time period between the pulse trains is controlled to last long enough to restore substantially normal blood circulation in the area when the latter is not stimulated during the off time periods.

Electric Stimulation

In accordance with a preferred embodiment of the invention, step (b) is performed by electrically stimulating the wall portion, preferably with electric pulses to cause contraction of the wall portion. This embodiment is particularly suited for applications in which the patient's wall portion includes muscle fibers that react to electrical stimula. Thus, the wall portion that includes the muscle fibers is stimulated with such electric pulses, preferably in the form of electric pulse trains, when the wall portion is in the constricted state, to cause contraction of the wall portion. Of course, the configuration of the electric pulse trains may be similar to the above described pulse trains and different areas of the wall portion may be electrically stimulated in the same manner as described above.

In accordance with the preferred embodiment, the method of the invention comprises providing at least one, preferably a plurality of electrical elements, such as electrodes, engaging and stimulating the wall portion with electric pulses. Optionally, the electrical elements may be placed in a fixed orientation relative to one another. The method comprises electrically energizing the electrical elements, preferably by cyclically energizing each element with electric pulses. The electrical elements may be energized so that the electrical elements are energized one at a time in sequence, or so that a number or groups of the electrical elements are energized at a time. Also, groups of electrical elements may be sequentially energized, either randomly or in accordance with a predetermined pattern.

The method may further comprise applying the electrical elements on the patient's wall portion so that the electrical elements form any pattern of electrical elements, preferably an elongate pattern of electrical elements extending lengthwise along the wall portion and the elements abut the respective areas of the wall portion. The electrical elements may be successively energized along the elongate pattern of electrical elements in a direction opposite to or in the same direction as that of the flow in the patient's lumen. Optionally, the electrical elements may be successively energized along the elongate pattern of electrical elements from a position substantially at the center of the constricted wall portion towards both ends of the elongate pattern of electrical elements. Where the lumen of the organ is to be kept closed for a relatively long time, the electrical elements may be energized so that energized electrical elements form two waves of energized electrical elements that simultaneously advance from the center of the constricted wall portion in two opposite directions towards both ends of the elongate pattern of electrical elements. Such waves of energized electrical elements can be repeated over and over again without harming the organ and without moving fluid or gas in any direction in the lumen of the organ.

The elongate pattern of electrical elements may include one or more rows of electrical elements extending lengthwise along the organ. Each row of electrical elements may form a straight, helical or zig-zag path of electrical elements, or any form of path. The electrical elements may be energized so that the electrical elements currently energized form at least one group of adjacent energized electrical elements, wherein the elements in the group of energized electrical elements form a path of energized electrical elements extending at least in part around the patient's organ, preferably completely around the patient's organ. Alternatively, the elements in the group of energized electrical elements form two paths of energized electrical elements extending on mutual sides of the patient's organ or more than two paths of energized electrical elements extending on different sides of the patient's organ, preferably at least substantially transverse to the flow direction in the lumen of the organ.

In an embodiment of the invention, the electrical elements form a plurality of groups of elements, wherein the groups form a series of groups extending along the patient's organ in the flow direction in the patient's lumen. The electrical elements of each group of electrical elements may form a path of elements extending at least in part around the patient's organ. In a first alternative, the electrical elements of each group of electrical elements may form more than two paths of elements extending on different sides of the patient's organ, preferably substantially transverse to the flow direction in the patient's lumen. The groups of electrical elements in the series of groups may be energized in random or in accordance with a predetermined pattern. Alternatively, the groups of electrical elements in the series of groups may be successively energized in a direction opposite to or in the same direction as that of the flow in the patient's lumen, or in both said directions starting from a position substantially at the center of the constricted wall portion. For example, groups of energized electrical elements may form advancing waves of energized electrical elements, as described above. I.e., the groups of electrical elements may be energized so that energized electrical elements form two waves of energized electrical elements that simultaneously advance from the center of the constricted wall portion in two opposite directions towards both ends of the elongate pattern of electrical elements.

Thermal Stimulation

In accordance with an embodiment of the invention, stimulation step (b) is performed by thermally stimulating the wall portion. Thus, the wall portion may be cooled, when the wall portion is constricted, to cause contraction of the wall portion. For example, the wall portion may be constricted to at least restrict the flow in the lumen, and the constricted wall portion may be cooled to cause contraction thereof, so that the flow in the lumen is at least further restricted, or further restricted but not stopped, or stopped. Alternatively, the wall portion may be heated, when the wall portion is constricted and contracted, to cause expansion of the wall portion. Where the wall portion includes a blood vessel, the blood vessel may be cooled to cause contraction thereof, or heated to cause expansion thereof. Where applicable, thermal stimulation may be practised in any of the embodiments of the present invention. Where applicable, thermal stimulation may be practised in any of the embodiments of the present invention, and the thermal stimulation may be controlled in response to various sensors, for example strain, motion or pressure sensors.

A male contraception method is further provided. The method comprises influencing the flow of sperms in the lumen of a male patient's vas deferens so that any sperm is prevented from flowing from the vas deferens to the male patient's urethra, when the patient is sexually active.

According to one embodiment the method, the flow influencing step comprises restricting the lumen of the vas deferens in the region downstream the ampulla, so that any sperm is prevented from flowing in the vas deferens lumen.

According to another embodiment the method further comprises providing a constriction device configured to constrict the vas deference, and operating the constriction device to constrict the vas deferens to restrict the vas deferens lumen so that any sperm is prevented from flowing in the vas deferens lumen.

According to yet another embodiment the method further comprises providing a stimulation device configured to stimulate the vas deference, and operating the stimulation device to constrict the vas deferens to restrict the vas deferens lumen so that any sperm is prevented from flowing in the vas deferens lumen.

The flow influencing steps could comprise the steps of: a) gently constricting at least one portion of a tissue wall of vas deferens to influence the flow in the vas deferens, using a constriction device, or stimulating at least one portion of the tissue wall of vas deferens to cause contraction of the wall portion of vas deferens, to influence the flow in the vas deferens, using a stimulation device.

The step of gently constricting at least one portion of a tissue wall of vas deferens could be performed so that the flow in the vas deferens at least is restricted or such that the flow in the vas deferens at least is restricted.

According to one embodiment the flow influencing step comprises the steps of: gently constricting the tissue wall portion of vas deferens to influence the flow in the lumen, and stimulating the constricted wall portion of vas deferens to cause contraction of the wall portion to further influence the flow in the lumen.

According to yet another embodiment the step of gently constricting at least one portion of a tissue wall of vas deferens could be performed by constricting the wall portion, so that the flow in the vas deferens is restricted but not stopped, and by stimulating the constricted wall portion to cause contraction thereof, so that the flow in the vas deferens is stopped.

According to yet another embodiment the step of gently constricting at least one portion of a tissue wall of vas deferens could be performed by constricting the wall portion, so that the flow in the vas deferens is stopped, and stimulating the constricted wall portion to cause contraction thereof, so that the flow in the vas deferens remains stopped when a pressure increase occurs in the vas deferens. The steps (a) and (b) could further be co-operated to move a flow of sperms appearing in the vas deferens.

According to yet another embodiment the step of gently constricting at least one portion of a tissue wall of vas deferens could be performed by constricting the wall portion to restrict the flow in the vas deferens in the vas deferens, and by progressively stimulating the constricted wall portion to cause progressive contraction of the wall portion to move any sperm appearing in the vas deferens lumen.

The method of controlling a flow of fluid in the vas deferens of a male patient could comprise the steps of: inserting a needle like tube into a cavity of the patients body, using the needle like tube to fill the cavity with gas thereby expanding the cavity, placing at least two laparoscopic trocars in the patient's body, inserting a camera through one of the trocars into the cavity, inserting a dissecting tool through any of the trocar and dissecting an area of at least one portion of the tissue wall of vas deferens, placing a constriction device and a stimulation device in the dissected area in operative engagement with vas deferens, using the constriction device to gently constrict the wall portion of the vas deferens to influence the flow in the vas deferens, and using the stimulation device to stimulate the constricted wall portion to cause contraction of the wall portion to further influence the flow in the vas deferens.

The method for controlling a flow of fluid in the vas deferens of a male patient could further comprise the steps of: inserting a needle like tube into a cavity of the patients body, using the needle like tube to fill the cavity with gas thereby expanding the cavity, placing at least two laparoscopic trocars in the patient's body, inserting a camera through one of the trocars into the cavity, inserting a dissecting tool through any of the trocar and dissecting an area of at least one portion of the tissue wall of vas deferens, placing a stimulation device in the dissected area in operative engagement with vas deferens, and using the stimulation device to stimulate the wall portion to cause contraction of the wall portion to influence the flow in the vas deferens.

The method of controlling a flow of fluid in the vas deferens of a male patient could comprise the steps of: inserting a needle like tube into a cavity of the patients body, using the needle like tube to fill the cavity with gas thereby expanding the cavity, placing at least two laparoscopic trocars in the patient's body, inserting a camera through one of the trocars into the cavity, inserting a dissecting tool through any of the trocar and dissecting an area of at least one portion of the tissue wall of vas deferens, placing a constriction device in the dissected area in operative engagement with vas deferens, using the constriction device to constrict the wall portion of the vas deferens to influence the flow in the vas deferens.

The method of controlling a flow of fluid in the vas deferens of a male patient could comprise the steps of: cutting the skin of the patient, inserting a dissecting tool and dissecting an area of at least one portion of the tissue wall of vas deferens, placing a constriction device and a stimulation device in the dissected area in operative engagement with vas deferens, using the constriction device to gently constrict the wall portion of vas deferens to influence the flow in the vas deferens, and using the stimulation device to stimulate the constricted wall portion to cause contraction of the wall portion to further influence the flow in the vas deferens.

The method of controlling a flow of fluid in the vas deferens of a male patient could comprise the steps of: cutting the skin of the patient, inserting a dissecting tool and dissecting an area of at least one portion of the tissue wall of vas deferens, placing a stimulation device in the dissected area in operative engagement with vas deferens, and using the stimulation device to stimulate the wall portion to cause contraction of the wall portion to influence the flow in the vas deferens.

The method of controlling a flow of fluid in the vas deferens of a male patient could comprise the steps of: cutting the skin of the patient, inserting a dissecting tool and dissecting an area of at least one portion of the tissue wall of vas deferens, placing a a constriction device in the dissected area in operative engagement with vas deferens, and using the constriction device to constrict the wall portion of vas deferens to influence the flow in the lumen.

The cavity in any of the methods could constitute at least one of an abdominal cavity, a cavity in the pelvic region, a cavity subperitoneally, a cavity in scrotum, a cavity downstream the vas deferens ampulla close to the prostate, a cavity in human soft tissue, muscle, fat and/or fibrotic tissue.

According to one embodiment the step of placing the device could involve the step of placing it in operative engagement with vas deferens or it's prolongation downstream the ampulla close to the prostate gland, that's to say downstream the ampulla where the sperm are collected and ready to be released into urethra at the level of the prostate gland, thus achieving a short term stop in sperm release into urethra during ejaculation without affecting release from the prostate gland.

Gallstones

Another object of the present invention is to provide a method for enhancing the movement of gallstones from the bile ducts to the duodenum, so as to at least substantially or even completely eliminate the blockage and pain associated with gallstones. One major purpose of the invention is to enable the transport of gallstones to the duodenum as this relieves the symptoms. Gallstones that reach the duodenum are secreted together with feces.

In accordance with this object of the present invention, there is provided a method for enhancing the movement of gallstones in a patient suffering from gallstone trouble, the method comprising:
gently constricting a portion of the wall of the biliary duct to influence the movement of bile and/or gallstones in the biliary duct, or
stimulating a portion of the wall of the biliary duct to cause contraction of the wall portion to influence the movement of bile and/or gallstones in the biliary duct.

There is also provided a method for enhancing the movement of gallstones in a patient suffering from gallstone trouble, the method comprising:
gently constricting a portion of the wall to influence the movement of bile and/or gallstones in the biliary duct, and b) stimulating the constricted wall portion to cause contraction of the wall portion to further influence the movement of bile and/or gallstones in the biliary duct.

The present invention provides an advantageous combination of the method steps (a) and (b), which results in a two-stage influence on the movement of bile and/or gallstones in the lumen of a biliary duct. Thus, applying a relatively weak force against the wall portion gently constricts the tissue wall and the constricted wall portion is stimulated to achieve the desired final influence on the movement of bile and/or gallstones in the biliary duct. The phrase "gently constricts a portion of the tissue wall" is to be understood as constricting the wall portion without substantially hampering the blood circulation in the tissue wall.

Preferably, step (b) is performed by intermittently and individually stimulating different areas of the wall portion. Such an intermittent and individual stimulation of different areas of the wall portion of the biliary duct allows tissue of the wall portion to maintain over time substantially normal blood circulation.

It should be understood that any embodiment or part of embodiment disclosed below in this application for the constriction and stimulation devices combined in the constriction/stimulation unit could be used for the separate constriction device and separate stimulation device, where applicable.

The method of the present invention can be practiced anywhere along the biliary ducts, for example on the hepatic ducts, the common bile duct or the cystic ducts or any of the sphincters associated with these ducts. Preferably, the constriction step (a) and stimulation step (b) are performed independently of each other. Steps (a) and (b) may be performed simultaneously. Optionally, step (b) may or may not be performed while step (a) is performed.

Initially, the constriction of the wall portion can be calibrated by stimulating the wall portion while adjusting the constriction of the wall portion until the desired restriction of the movement of bile and/or gallstones in the biliary duct is obtained.

Flow Restriction

There may be of importance to be able to restrict flow of bile and/or gallstones in the biliary duct or even completely close the biliary duct. For example when surgery on the biliary duct is to be performed. The method of the present invention is well suited for such a situation. Thus, in a principal embodiment of the invention, the wall portion is constricted, so that the movement of bile and/or gallstones in the biliary duct at least is restricted and the constricted wall portion is stimulated to at least further restrict the movement of bile and/or gallstones. Specifically, the wall portion is constricted to a constricted state, in which the blood circulation in the constricted wall portion is substantially unrestricted and the movement of bile and/or gallstones in the biliary duct is at least restricted, and the constricted wall portion is stimulated when it is in the constricted state to at least further restrict the movement of bile and/or gallstones in the biliary duct.

The constriction step (a) and stimulation step (b) are suitably performed to constrict and stimulate the wall portion to an extent that depends on the flow restriction that is desired to be achieved in a specific application of the method of the invention. Thus, in accordance with a first flow restriction option, step (a) is performed by constricting the wall portion, so that the movement of bile and/or gallstones in the biliary duct is restricted but not stopped, and step (b) is performed by stimulating the constricted wall portion to cause contraction thereof, so that the movement of bile and/or gallstones in the biliary duct is further restricted but not stopped. The method may further comprise sensing a physical parameter of the patient and adjusting the intensity of the stimulation of the wall portion in response to the sensed parameter.

In accordance with a second flow restriction option, step (a) is performed by constricting the wall portion, so that the movement of bile and/or gallstones in the biliary duct is restricted but not stopped, and step (b) is performed by stimulating the constricted wall portion to cause contraction thereof, so that the movement of bile and/or gallstones in the biliary duct is stopped.

When using the method of the invention in accordance with the first or second options, the method may further comprise (c) ceaseing stimulating the wall portion to increase or allow the movement of bile and/or gallstones in the biliary duct and (d) releasing the wall portion to restore the movement of bile and/or gallstones in the biliary duct.

In accordance with a third flow restriction option, step (a) is performed by constricting the wall portion, so that the movement of bile and/or gallstones in the biliary duct is substantially stopped, and step (b) is performed by stimulating the constricted wall portion to cause contraction thereof, so that the movement of bile and/or gallstones in the biliary duct is completely stopped. The method may further comprise (c) ceaseing stimulating the wall portion to allow the movement of bile and/or gallstones in the biliary duct and (d) releasing the wall portion to restore the movement of bile and/or gallstones in the biliary duct.

Where the constricted wall portion is stimulated to contract, so that the movement of bile and/or gallstones in the biliary duct is stopped, a first length of the constricted wall portion and a second length of the constricted wall portion, which is located downstream of the first length, are suitably simultaneously and cyclically stimulated, wherein the first length is progressively stimulated in the upstream direction of the lumen and the second length is progressively stimulated in the downstream direction of the lumen.

Furthermore, when using the method of the invention in accordance with the second and third options, the method may further comprise sensing a physical parameter of the patient or functional parameter of implanted components and adjusting the stimulation of the wall portion in response to the sensed parameter. For example, the intensity of the stimulation of the wall portion may be increased in response to a sensed pressure increase in the lumen, so that the movement of bile and/or gallstones in the biliary duct remains stopped when a pressure increase occurs in the lumen. In particular, the method may comprise sensing a physical parameter of the patient's that relates to the pressure in the lumen, and controlling the stimulation of the wall portion in response to the sensed parameter. Any sensor for sensing a physical parameter of the patient, such as a pressure in the patient's body that relates to the pressure in the lumen may be provided, wherein the stimulation is controlled in response to signals from the sensor. Such a sensor may for example sense the pressure in the patient's abdomen, the pressure against the implanted constriction device or the pressure on the tissue wall of the biliary duct.

In accordance with a fourth restriction option, step (a) is performed by constricting the wall portion, so that the movement of bile and/or gallstones in the biliary duct is stopped. When needed, the wall portion is released to restore the movement of bile and/or gallstones in the biliary duct. Step (b) is only performed by stimulating the constricted wall portion to cause contraction thereof, so that the movement of bile and/or gallstones in the biliary duct remains stopped when a pressure increase occurs in the lumen. The method may further comprise sensing a physical parameter of the patient's body, such as a pressure in the patient's body that relates to the pressure in the lumen, and controlling the stimulation of the wall portion in response to the sensed parameter. Such a physical parameter may be a pressure in the patient's abdomen and the sensor may be a pressure sensor.

In some applications of the method of the invention, continuous stimulation may over time change the physical properties of the tissue so that the tissue might be injured. Also, the effect of a continuous stimulation of the tissue wall may decrease over time. Therefore, step (b) is preferably performed by intermittently and individually stimulating different areas of the wall portion so that the movement of bile and/or gallstones in the biliary duct continues to be restricted as desired and each area of the wall portion essentially maintains its natural physical properties over time to prevent the area from being injured. Advantageously, each area of the wall portion is stimulated during successive time periods, each time period being short enough to maintain over time satisfactory blood circulation in the area. Thus, the areas are stimulated so that an area that currently is not stimulated will have time to restore substantially normal blood circulation before it is stimulated again.

To maintain satisfactory blood circulation in the tissue wall of the patient's biliary duct stimulation step (b) is suitably performed by stimulating one or more of different areas of the wall portion at a time, preferably by sequentially stimulating the different areas of the wall portion or by shifting the stimulation from one area to another over time. Preferably, stimulation step (b) is performed by cyclically propagating the stimulation of the areas along the wall portion, for example in accordance with a determined stimulation pattern.

The method of the invention may further comprise controlling, preferably by the patient, the constriction and/or stimulation of the wall portion from outside the patient's body.

Generally, the method of the invention comprises sensing a physical parameter of the patient and controlling, preferably automatically, the constriction and/or stimulation of the wall portion in response to the sensed parameter.

The constriction step (a) may be performed by constricting any wall portions of a series of wall portions of the tissue wall of the biliary duct, respectively, either in random or in accordance with a predetermined sequence. The stimulation step (b) may be performed by stimulating any of the constricted wall portions of the series of wall portions. Specifically, step (a) may be performed by constricting all of the wall portions of the series of wall portions, and step (b) may be performed by stimulating any constricted wall portions in random or in accordance with a predetermined sequence to close the biliary duct.

Moving Bile and/or Gall Stones in the Biliary Duct

Importantly, the method of the present invention can be practised for actively moving the bile and/or gallstones in lumen of a patient's biliary duct. Specifically, the method of the invention is useful for releasing a gallstone, which is lodged in the biliary duct and cannot move downstream. Thus, in the embodiments of the invention listed below, steps (a) and (b) are co-operated to move the bile and/or gall stones in the lumen.

1) Step (a) is performed by constricting the wall portion to restrict the movement of bile and/or gallstones in the biliary duct, and step (b) is performed by stimulating the constricted wall portion to close the lumen either at an upstream end or a downstream end of the constricted wall portion. The method further comprises (c) increasing the constriction of the wall portion to move the bile and/or gall stones in the lumen.

2) Step (a) is performed by constricting the wall portion to restrict the movement of bile and/or gallstones in the biliary duct, and step (b) is performed by progressively stimulating the constricted wall portion to cause progressive contraction of the wall portion to move the bile and/or gall stones in the lumen. The constricted wall portion is progressively stimulated in the downstream or upstream direction of the lumen.

3) Step (a) is performed by varyingly constricting the wall portion to vary the movement of bile and/or gallstones in the biliary duct, and step (b) is performed by progressively stimulating the constricted wall portion to cause progressive contraction of the wall portion to move the bile and/or gall stones in the lumen. The constricted wall portion is progressively stimulated in the downstream or upstream direction of the lumen.

4) Step (a) is performed by varyingly constricting different areas of the wall portion to cause progressive constriction of the wall portion in the downstream or upstream direction of the lumen, and the constricted wall portion is progressively stimulated to cause progressive contraction thereof in harmony with the progressive constriction of the wall portion. The method may further comprise providing at least one elongated constriction element extending along the wall portion, and controlling the elongated constriction element to progressively constrict the wall portion in the downstream or upstream direction of the lumen. The elongated constriction element suitably comprises contact surfaces dimensioned to contact a length of wall portion, and the method may further comprise providing a plurality of stimulation elements distributed along the contact surfaces, and controlling the stimulation elements to stimulate the different areas of the wall portion along the length of the wall portion.

5) Step (a) is performed by constricting any one of a series of wall portions of the tissue wall to at least restrict the movement of bile and/or gallstones in the biliary duct, and step (b) is performed by stimulating the constricted wall portion to close the lumen. The method further comprises successively constricting the wall portions of the series of wall portions to move the bile and/or gall stones in the lumen in a peristaltic manner.

5a) In accordance with an alternative, the method further comprises providing at least one constriction element and at least one stimulation element positioned on the constriction element, moving the constriction element along the organ in the flow direction in the lumen to successively constrict the wall portions of the series of wall portions, and using the stimulation element to stimulate the wall portion constricted by the constriction element to close the lumen. Suitably, the method further comprises cyclically moving the constriction element along the wall portions of the series of wall portions.

5b) In accordance with another alternative, the method further comprises providing a plurality of constriction elements and stimulation elements positioned on the constriction elements, moving each constriction element along the biliary duct to successively constrict the wall portions of the series of wall portions, and using the stimulation elements to stimulate the wall portion constricted by any one of the constriction elements to close the lumen. Suitably, the method further comprises cyclically moving the constriction elements one after the other along the wall portions of the series of wall portions. Specifically, the method further comprises providing a rotor carrying the constriction elements, and rotating the rotor so that each constriction element cyclically constricts the wall portions of the series of wall portions. Each constriction element suitably comprises a roller that rolls on the biliary duct to constrict the latter.

6) Step (a) is performed by constricting any wall portions of a series of wall portions of the tissue wall of the organ, respectively, wherein the wall portions of the series of wall portions are successively constricted along the biliary duct to move the bile and/or gall stones in the lumen of the patient's biliary duct. The stimulation step (b) is performed by stimulating any constricted wall portions of the series of wall portions.

7) Step (a) is performed by constricting wall portions of a series of wall portions without completely closing the biliary duct, and step (b) is performed by stimulating the constricted wall portions one after the other, so that the wall portions of the series of wall portions are successively contracted along the biliary duct to move the bile and/or gall stones in the lumen of the patient's biliary duct.

8) Step (a) is performed by constricting the wall portion at an upstream or downstream end thereof to close the lumen. The method further comprises (c) constricting the wall portion between the upstream and downstream ends thereof, to move the bile and/or gallstones contained in the wall portion between the upstream and downstream ends thereof downstream or upstream in the biliary duct. Optionally, the method further comprises stimulating the wall portion between the upstream and downstream ends thereof, as (c) is performed.

8a) In accordance with an alternative, step (a) is performed by constricting the wall portion at the upstream end thereof to restrict the movement of bile and/or gallstones in the biliary duct, and step (b) is performed by stimulating the constricted wall portion at the upstream end to close the biliary duct, whereby the bile and/or gall stones contained in the wall portion between the upstream and downstream ends thereof is moved downstream in the biliary duct, as step (c) is performed.

8b) In accordance with another alternative, step (a) is performed by constricting the wall portion at the downstream end thereof to restrict the movement of bile and/or gallstones in the biliary duct, and step (b) is performed by stimulating the constricted wall portion at the downstream end to close the biliary duct, whereby the bile and/or gall stones contained in the wall portion between the upstream and downstream ends thereof is moved upstream in the biliary duct, as step (c) is performed. This can be used to release gallstones that are stuck in the biliary ducts. These gallstones are subsequently moved downstream, towards the duodenum.

As the biliary duct is tubular in shape, a particularly long wall portion of the biliary duct may be surgically prepared to extend in zigzag with adjacent walls stitched together by two parallel rows of stitches and with the adjacent walls cut through between the two rows of stitches. As a result, the lumen of this long wall portion of the biliary duct can be significantly expanded. In this case, a considerably larger volume of fluid is moved in the biliary duct each time step (a) and/or step (b) is performed.

In any of the above noted embodiments (1) to (8b), step (b) may be performed by stimulating the wall portion with electric pulses.

Importantly, in any of the embodiments above, movement of bile and/or gallstones can be carried out with electric stimulation only. Thus, in such an embodiment, there is no constriction device.

Stimulation Modes

When stimulating neural or muscular tissue there is a risk of injuring or deteriorating the tissue over time if the stimulation is not properly performed. The method of the present invention is performed to reduce or even eliminate that risk. Thus, step (b) is performed by intermittently stimulating different areas of the wall portion so that at least two of the areas are stimulated at different points of time. I.e., the stimulation is shifted from one area to another area over time. In addition, step (b) is performed by intermittently stimulating the areas of the wall portion so that an area of the different areas that currently is not stimulated has time to restore substantially normal blood circulation before it is stimulated again. Furthermore, step (b) is performed by intermittently stimulating the areas during successive time periods, wherein each time period is short enough to maintain satisfactory blood circulation in the area until the laps of the time period. This gives the advantage that the method of the present invention provides continuous stimulation of the wall portion of the biliary duct to achieve the desired flow control while essentially maintaining over time the natural physical properties of the biliary duct without risk of injuring the biliary duct.

Also, by physically changing the places of stimulation on the biliary duct over time as described above it is possible to create an advantageous changing stimulation pattern on the biliary duct, in order to achieve a desired flow control.

To achieve the desired reaction of the tissue wall during the stimulation thereof, step (b) may be performed by stimulating the wall portion with, preferably cyclically, varying stimulation intensity.

In a main embodiment of the invention, step (b) is performed by intermittently stimulating the wall portion with pulses, preferably in the form of pulse trains. The pulse trains can be configured in many different ways by varying pulse parameters. Thus, the pulse amplitudes of the pulses of the pulse trains, the off time periods between the individual pulses of each pulse train and the width and repetition frequency of each pulse may be varied. Also the off time periods between the pulse trains may be varied, wherein each off time period between the pulse trains is kept long enough to restore substantially normal blood circulation in each area of the wall portion, when the area is not stimulated during the off time periods. Furthermore, the repetition frequency of the pulses of the pulse trains and the length and number of pulses of each pulse train may be varied.

As mentioned above, for reasons of maintaining over time the effect of stimulation, it is preferable that different areas of the wall portion are intermittently and individually stimulated. In consequence, step (b) may be performed by stimulating one or more of the areas at a time with pulses, by cyclically propagating the stimulation of the areas with pulses along the wall portion, and/or by propagating the stimulation of the areas with pulses in accordance with a determined stimulation pattern. In case the off time periods between pulse trains that stimulate the respective area of the wall portion are varied, it is preferable that each off time period between the pulse trains is controlled to last long enough to restore substantially normal blood circulation in the area when the latter is not stimulated during the off time periods.

Electric Stimulation

In accordance with a preferred embodiment of the invention, step (b) is performed by electrically stimulating the wall portion, preferably with electric pulses to cause contraction of the wall portion. This embodiment is particularly suited for applications in which the patient's wall portion includes muscle fibers that react to electrical stimula. Thus, the wall portion that includes the muscle fibers is stimulated with such electric pulses, preferably in the form of electric pulse trains, when the wall portion is in the constricted state, to cause contraction of the wall portion. Of course, the configuration of the electric pulse trains may be similar to the above described pulse trains and different areas of the wall portion may be electrically stimulated in the same manner as described above.

In accordance with the preferred embodiment, the method of the invention comprises providing at least one, preferably a plurality of electrical elements, such as electrodes, engaging and stimulating the wall portion with electric pulses. Optionally, the electrical elements may be placed in a fixed orientation relative to one another. The method comprises electrically energizing the electrical elements, preferably by cyclically energizing each element with electric pulses. The electrical elements may be energized so that the electrical elements are energized one at a time in sequence, or so that a number or groups of the electrical elements are energized at a time. Also, groups of electrical elements may be sequentially energized, either randomly or in accordance with a predetermined pattern.

The method may further comprise applying the electrical elements on the patient's wall portion so that the electrical elements form any pattern of electrical elements, preferably an elongate pattern of electrical elements extending lengthwise along the wall portion and the elements abut the respective areas of the wall portion. The electrical elements may be successively energized along the elongate pattern of electrical elements in a direction opposite to or in the same direction as that of the flow in the patient's biliary duct. Optionally, the electrical elements may be successively energized along the elongate pattern of electrical elements from a position substantially at the center of the constricted wall portion towards both ends of the elongate pattern of electrical elements. Where the lumen of the biliary duct is to be kept closed for a relatively long time, the electrical elements may be energized so that energized electrical elements form two waves of energized electrical elements that simultaneously advance from the center of the constricted wall portion in two opposite directions towards both ends of the elongate pattern of electrical elements. Such waves of energized electrical elements can be repeated over and over again without harming the biliary duct and without moving matter in any direction in the lumen of the biliary duct.

The elongate pattern of electrical elements may include one or more rows of electrical elements extending lengthwise along the biliary duct. Each row of electrical elements may form a straight, helical or zig-zag path of electrical elements, or any form of path. The electrical elements may be energized so that the electrical elements currently energized form at least one group of adjacent energized electrical elements, wherein the elements in the group of energized electrical elements form a path of energized electrical elements extending at least in part around the patient's biliary duct, preferably completely around the patient's biliary duct. Alternatively, the elements in the group of energized electrical elements form two paths of energized electrical elements extending on mutual sides of the patient's biliary duct or more than two paths of energized electrical elements extending on different sides of the patient's biliary duct, preferably at least substantially transverse to the flow direction in the lumen of the biliary duct.

In an embodiment of the invention, the electrical elements form a plurality of groups of elements, wherein the groups form a series of groups extending along the patient's biliary duct in the flow direction in the patient's biliary duct. The electrical elements of each group of electrical elements may form a path of elements extending at least in part around the patient's biliary duct. In a first alternative, the electrical elements of each group of electrical elements may form more than two paths of elements extending on different sides of the patient's biliary duct, preferably substantially transverse to the flow direction in the patient's biliary duct. The groups of electrical elements in the series of groups may be energized in random or in accordance with a predetermined pattern. Alternatively, the groups of electrical elements in the series of groups may be successively energized in a direction opposite to or in the same direction as that of the flow in the patient's biliary duct, or in both said directions starting from a position substantially at the center of the constricted wall portion. For example, groups of energized electrical elements may form advancing waves of energized electrical elements, as described above. I.e., the groups of electrical elements may be energized so that energized electrical elements form two waves of energized electrical elements that simultaneously advance from the center of the constricted wall portion in two opposite directions towards both ends of the elongate pattern of electrical elements.

Laparoscopic Method

The present invention also provides alternative laparoscopic methods.

First, there is provided a method for controlling movement of bile and/or gallstones in a biliary duct, the method comprising the steps of:
inserting a needle like tube into the abdomen of the patients body,
filling the abdomen with gas thereby expanding the abdominal cavity,
placing at least two laparoscopical trocars in the patient's body,
inserting a camera through one of the trocars into the abdomen,
inserting a dissecting tool through any of the trocar and dissecting an area of at least one portion of the tissue wall of the biliary duct,
placing a constriction device and a stimulation device in the dissected area in operative engagement with the biliary duct,
using the constriction device to gently constrict the wall portion of the biliary duct to influence the movement of bile and/or gallstones in the biliary duct, and
using the stimulation device to stimulate the constricted wall portion to cause contraction of the wall portion to further influence the movement of bile and/or gallstones in the biliary duct.

Second, there is provided a method for controlling movement of bile and/or gallstones in a biliary duct, the method comprising the steps of:
inserting a needle like tube into a cavity of the patients body,
using the needle like tube to fill the cavity with gas thereby expanding the cavity,
placing at least two laparoscopical trocars in the patient's body,
inserting a camera through one of the trocars into the cavity,
inserting a dissecting tool through any of the trocar and dissecting an area of at least one wall portion of a biliary duct,
placing a flow influence device comprising, a stimulation device in the dissected area in operative engagement with the biliary duct, and
using the stimulation device to stimulate the wall portion of the biliary duct to cause contraction of the wall portion to influence the movement of bile and/or gallstones in the biliary duct.

Third, there is provided a method for controlling movement of bile and/or gallstones in a biliary duct, the method comprising the steps of:
inserting a needle like tube into a cavity of the patients body,
using the needle like tube to fill the cavity with gas thereby expanding the cavity,
placing at least two laparoscopical trocars in the patient's body,
inserting a camera through one of the trocars into the cavity,
inserting a dissecting tool through any of the trocar and dissecting an area of at least one wall portion of the biliary duct,
placing a flow influence device comprising, a constriction device in the dissected area in operative engagement with the biliary duct,
using the constriction device to constrict the wall portion of the biliary duct to influence the movement of bile and/or gallstones in the lumen.

Fourth, there is provided a method for controlling movement of bile and/or gallstones in a lumen formed by a tissue wall of a patient's biliary duct, the method comprising the steps of:
cutting the skin of the patient,
inserting a dissecting tool and dissecting an area of at least one portion of the tissue wall of the biliary duct,
placing a flow influence device comprising, a constriction device and a stimulation device in the dissected area in operative engagement with the biliary duct,
using the constriction device to gently constrict the wall portion of the organ to influence the movement of bile and/or gallstones in the lumen of the biliary duct, and
using the stimulation device to stimulate the constricted wall portion to cause contraction of the wall portion of the biliary duct to further influence the movement of bile and/or gallstones in the lumen.

Fifth, there is provided a method for controlling movement of bile and/or gallstones in a lumen formed by a tissue wall of a patient's biliary duct, the method comprising the steps of:
cutting the skin of the patient,
inserting a dissecting tool and dissecting an area of at least one portion of the tissue wall of the biliary duct,
placing a flow influence device comprising, a stimulation device in the dissected area in operative engagement with the biliary duct, and
using the stimulation device to stimulate the wall portion to cause contraction of the wall portion of the biliary duct to influence the movement of bile and/or gallstones in the lumen.

Sixth, there is provided a method for controlling movement of bile and/or gallstones in a lumen formed by a tissue wall of a patient's biliary duct, the method comprising the steps of:
cutting the skin of the patient,
inserting a dissecting tool and dissecting an area of at least one portion of the tissue wall of the biliary duct,
placing a flow influence device comprising, a constriction device in the dissected area in operative engagement with the biliary duct, and
using the constriction device to constrict the wall portion of the biliary duct to influence the movement of bile and/or gallstones in the lumen.

Pregnancy Promotion

Another object of the present invention is to provide a pregnancy promotion method.

In accordance with this object of the present invention, there is provided a method of promoting pregnancy of a female patient, comprising the steps of restricting the lumen of an oviduct of the patient to accumulate at least one egg released from the ovary in the oviduct for a predetermined period of time, and ceasing restricting the oviduct lumen to admit the egg in the oviduct to be transported to the uterus.

For practicing the method, an implanted restriction device is used to restrict the oviduct lumen and to cease restricting the oviduct lumen, typically after the oviduct lumen having accumulated the egg up to three days to achieve right timing for pregnancy.

The restriction device may be adapted to be adjusted from outside the patients body to restrict or not restrict the oviduct lumen, preferably non-invasively adjusted from outside the patients body. It may also be adjusted by manual manipulation, electrical or magnetic power or hydraulic power. The hydraulic power may comprise at least one subcutaneously placed reservoir controlled by the patient. Preferably, the restriction device is reversibly adjustable.

The method further comprises ceasing restricting the oviduct lumen when convenient for the patient to increase the likelihood for getting pregnant. The predetermined period of time is chosen in the interval of 0 to 2 days repeated every month until pregnancy is achieved. Preferably, the predetermined period is between 8 and 12 hours.

Flow Restriction

The restriction device for practicing the method of the invention could be designed to include hydraulic, mechanical or stimulation means, or combination of such means. Such a designed restriction device could be used in such a manner that the oviduct lumen is restricted over time at different places on the oviduct. More than two different places on the oviduct could be involved in such shifting restrictions of the oviduct lumen. This would allow the oviduct to recover at any one of the different places on the oviduct while the oviduct lumen is restricted at another place on the oviduct, so that the oviduct does not run the risk of being injured over a longer period of time.

When the restriction of the oviduct lumen is shifted between different places on the oviduct, especially when the place of the lumenal restriction is displaced upstream of the oviduct towards the ovary, it may be convenient to use a moving device for practicing the method of the invention, to avoid any egg being squeezed in the restricted oviduct lumen at an upstream located place on the oviduct and to avoid any egg being released by mistake for further downstream transportation when the restriction of the oviduct lumen ceases. The moving device may be adapted to affect the oviduct wall such that an egg appearing in the oviduct is caused to move. This could be performed by any of the above mentioned restriction devices, but may also be performed by a specially designed separate device. In one embodiment the moving device is designed to generate vibrations.

The moving device may be configured to provide peristaltic like wave movement of the oviduct wall in the direction towards the ovary. Such peristaltic wave like movements in the upstream direction towards the ovary may stop flow of any egg towards the uterus without fully restricting the oviduct lumen to allow any sperm to pass. Alternatively, the moving device may provide peristaltic like wave movements of the oviduct wall towards the uterus to cause movement of any egg downstream to the uterus.

Where the restriction device includes a stimulation device it could both 1) restrict the oviduct lumen by stimulation and 2) also create peristaltic wave like movements of the oviduct wall in the upstream direction to stop egg flow without fully restricting the oviduct lumen or cause movement of the egg in the downstream direction to the uterus.

Preferably, such a stimulation device is configured to stimulate different areas of a wall portion of the oviduct wall as the wall portion is constricted, and the stimulation device is controlled to intermittently and individually stimulate the areas of the wall portion. This intermittent and individual stimulation of different areas of the wall portion of the oviduct allows tissue of the wall portion to maintain substantially normal blood circulation during the performance of the method of the invention.

Movement of the Egg in the Oviduct Lumen

In one embodiment the method comprises constricting a wall portion of the oviduct to restrict or vary the flow in the oviduct, and controlling the stimulation device to progressively stimulate the constricted wall portion, in the downstream or upstream direction of the oviduct, to cause progressive contraction of the wall portion to move the egg downstream in the oviduct or to prevent further transportation of the egg to the uterus.

Sensor

The stimulation device may be controlled to change the stimulation of the wall portion of the oviduct in response to a sensed physical parameter of the patient. For example, the stimulation device may be controlled to increase the intensity of the stimulation of the wall portion in response to a sensed pressure increase in the oviduct lumen, such that the flow in the oviduct lumen remains stopped. Any sensor for sensing a physical parameter of the patient, such as a pressure in the patient's body that relates to the pressure in the oviduct lumen may be provided, wherein the stimulation device is controlled in response to signals from the sensor. Such a sensor may for example sense the pressure in the patient's abdomen, the pressure against the implanted restriction device device or the pressure on the tissue wall of the oviduct. For example, a hormone level sensor may be used for controlling flow of eggs in the oviduct lumen.

From time to time, the place where the oviduct lumen is restricted is preferably displaced along the oviduct from one place to another in the direction from the ovary towards the uterus. For example, three different places on the oviduct may share a time period of three days with one day per each place where the oviduct lumen is restricted, whereby the risk of injuring the oviduct is decreased or even eliminated, Peristaltic Like Wave Oviduct Wall Movements In an embodiment of the invention, the method comprises only partly restricting the oviduct lumen so that a sperm is able to pass in the oviduct lumen, creating peristaltic wave like movements of a part of the oviduct wall to prevent an egg released from the ovary from being transported in the oviduct lumen to the uterus, accumulating the egg in the oviduct lumen for a predetermined period of time, whereby a sperm appearing in the oviduct lumen is able to reach the egg during the time the egg is accumulated, and ceasing restricting the oviduct lumen to release the egg, so that the egg is allowed to be transported in the oviduct lumen to the uterus.

Restriction Embodiment

In an embodiment, the method comprises providing a hydraulic restriction device including a reservoir for distributing gas or fluid to or from the restriction device, and placing the reservoir subcutaneously to be reached by the patients hand for moving fluid manually to or from the restriction device. Preferably, two or more reservoirs could be provided for restricting the oviduct lumen at different places thereof, starting with a place closest to the ovary.

Embodiments of the Method According to the Present Invention

In a first general embodiment, the method comprises the following steps:
restricting an oviduct lumen of the patient postoperatively to accumulate at least one egg released from the ovary in the oviduct lumen for a predetermined period of time,
ceasing restricting the oviduct lumen to admit any egg appearing in the oviduct lumen to be transported to the uterus, and
controlling the restricting and ceasing restricting steps from outside the patients body.
In this first and other methods the predetermined period of time is in the interval of 0 to 2 days, preferably 8 to 12 hours.
In a second embodiment, the method comprises the steps of:
inserting a needle like tube into the abdomen of the patients body,
using the tube like needle like to fill the abdomen with gas thereby expanding the abdominal cavity,
placing at least two laparoscopic trocars in the patient's body,
inserting a camera through one of the trocars into the abdomen,
inserting at least one dissecting tool through a trocar and dissecting an area of at least one portion of the two oviducts of the patient,
placing two restriction devices on the two oviducts, respectively,
adjusting the restriction devices after the operation at a time convenient to get pregnant,
controlling the adjusting step from outside the patients body, and
post-operatively restricting and releasing the two oviduct lumens to increase the likelihood of getting pregnant.
In both the first and second embodiments, the restricting step may comprise:
restricting the oviduct lumen at a first place of the oviduct to accumulate at least one egg released from the ovary in the oviduct lumen for a predetermined period of time,
restricting the oviduct lumen at a second place of the oviduct,
ceasing restricting the oviduct lumen at the first place of the oviduct, and
allowing the oviduct shorter restriction periods at each restriction place.
The method may further comprise the steps of:
ceasing restricting the oviduct lumen at the second place of the oviduct, allowing transport of the egg down to the uterus.
The method may also comprise the steps of:
restricting a third part of the oviduct lumen
ceasing restricting the oviduct lumen at the second place of the oviduct,
allowing the oviduct shorter restriction periods at each restriction place.
The method may also comprise the steps of:
ceasing restricting the oviduct lumen at the third place of the oviduct,
allowing transport of the egg down to the uterus
The method may also comprise the steps of:
restricting a fourth part of the oviduct lumen
ceasing restricting the oviduct lumen at the third place of the oviduct,
allowing the oviduct shorter restriction periods at each restriction place.

The method may also comprise the steps of:
ceasing restricting the oviduct lumen at the fourth place of the oviduct,
allowing transport of the egg down to the uterus
In both these methods normally if the restriction of the oviduct lumen at the first place of the oviduct is closer to the ovary this allows the oviduct lumen at the second place to be restricted without interferring with any accumulated egg.
Normally these methods are performed to restrict the oviduct lumen at more than two places on the oviduct and the restriction places are varied while keeping the oviduct lumen closed at at least one restriction place when restriction of the oviduct lumen is desired.
In a third embodiment, the method comprises:
restricting the oviduct lumen at places on the oviduct in consecutive order starting at
a place on the oviduct closest to the ovary,
then restricting the oviduct lumen at any new place on the oviduct one step closer to the uterus, and
overlapping in time the restriction of the oviduct lumen at more than one place on the oviduct to restrict the oviduct lumen without interferring with any egg accumulated in the oviduct lumen.
The method may of course comprise only postoperatively varying the restriction places on the oviduct independently of order, to allow the oviduct to recover or to avoid any damage from the restriction of the oviduct while the oviduct lumen is kept restricted.
In a fourth embodiment, the method comprises the following steps:
causing a peristaltic like restriction wave movement of a portion of the oviduct wall to prevent at least one egg appearing in the oviduct lumen from being transported in the oviduct lumen to the uterus while only partly restricting the oviduct lumen,
accumulating the egg in the oviduct lumen for a predetermined period of time,
allowing a sperm to reach the egg during the time the egg is accumulated, and
post-operatively controlling from the outside the human body the oviduct wall wave movement to cease, whereby the egg is released and is transported to the uterus.
In a fifth embodiment, the method comprises the steps of:
inserting a tube like needle into the abdomen of the patients body,
using the tube like needle like to fill the abdomen with gas thereby expanding the abdominal cavity,
placing at least two laparoscopic trocars in the patient's body,
inserting a camera through one of the trocars into the abdomen,
inserting at least one dissecting tool through a trocar and dissecting an area of at least one portion of the two oviducts of the patient,
placing two restriction devices on the two oviducts, respectively,
finishing the operation and withdrawing the instruments after eventual suturing, and thereafter postoperatively:
controlling from outside the patient's body the restriction devices to restrict the oviduct lumens at a time relevant to achieve pregnancy,
controlling the restriction devices to cause peristaltic like wave movements of portions of the oviduct walls towards the ovary to prevent an egg appearing in the oviduct lumen from being transported to the uterus for a predetermined period of time without fully restricting the oviduct lumen,
accumulating any egg released from the ovary in at least one of the oviduct lumens, allowing any sperm appearing in the oviduct lumen to reach the egg during the time the egg is accumulated, and controlling from outside the patient's body the restriction devices to cease the peristaltic like wave movements to release the egg in any of the oviduct lumens to allow the egg to be transported in a normal way to the uterus.

Movement Method in a sixth embodiment, the method comprises the following steps:

restricting a first part of an oviduct lumen of the patient to accumulate at least one egg released from the ovary in the oviduct lumen for a predetermined period of time, moving the accumulated egg by an implanted movement device away in the oviduct lumen towards the ovary from the restriction area, allowing a second part of the oviduct lumen closer to the ovary to be restricted without interfering with any accumulated egg ceasing restricting the first part of the oviduct lumen, repeating restricting the first part of the oviduct lumen, ceasing restricting the second part of the oviduct lumen, and p0 allowing the oviduct to recover between restriction intervals.

Preferably, the method according to the sixth embodiment further comprises:

repeating moving any accumulated egg by the movement device away in the oviduct lumen towards the ovary from the restricted first part of the oviduct lumen, allowing a second part of the oviduct lumen closer to the ovary to be restricted without interfering with any accumulated egg, repeating ceasing restricting the first part of the oviduct lumen, repeating all the preceding steps to allow the oviduct to recover between restriction intervals.

The movement device may comprise a vibrating device to generate vibration of at least a part of the wall of the oviduct, so that any accumulated egg is caused to move, and the movement action on the egg is repeated. The movement device may comprise a mechanical device, a hydraulic device or a stimulation device, or a combination of such devices.

Pregnancy Inhibition

Another object of the present invention is to provide a pregnancy inhibition method.

In accordance with this object, there is provided a method for avoiding pregnancy of a female patient, comprising the steps of restricting the lumen of an oviduct of the patient to accumulate at least one egg released from the ovary in the oviduct for a predetermined period of time, and ceasing restricting the oviduct lumen to admit the egg in the oviduct to be transported to the uterus.

For practicing the method, an implanted restriction device is used to restrict the oviduct lumen to accumulate any egg released from the ovary into the oviduct lumen, and to cease restricting the oviduct lumen, when desired.

The restriction device may be adapted to be adjusted from outside the patients body to restrict or not restrict the oviduct lumen, preferably non-invasively adjusted from outside the patients body. It may also be adjusted by manual manipulation, electrical or magnetic power or hydraulic power. The hydraulic power may comprise at least one subcutaneously placed reservoir controlled by the patient. Preferably, the restriction device is reversibly adjustable.

The method further comprises accumulating any egg released from the ovary in the oviduct for a predetermined period of time, and ceasing restricting the oviduct lumen when convenient for the patient to avoid pregnancy. The predetermined period of time is chosen in the interval of 1 to 30 days. Preferably, the predetermined period is more than 30 days.

Flow Restriction

The restriction device for practicing the method of the invention could be designed to include hydraulic, mechanical or stimulation means, or combination of such means. Such a designed restriction device could be used in such a manner that the oviduct lumen is restricted over time at different places on the oviduct. More than two different places on the oviduct could be involved in such shifting restrictions of the oviduct lumen. This would allow the oviduct to recover at any one of the different places on the oviduct while the oviduct lumen is restricted at another place on the oviduct, so that the oviduct does not run the risk of being injured over a longer period of time.

When the restriction of the oviduct lumen is shifted between different places on the oviduct, especially when the place of the lumenal restriction is displaced upstream of the oviduct towards the ovary, it may be convenient to use a moving device for practicing the method of the invention, to avoid any egg being squeezed in the restricted oviduct lumen at an upstream located place on the oviduct and to avoid any egg being released by mistake for further downstream transportation when the restriction of the oviduct lumen ceases. The moving device may be adapted to affect the oviduct wall such that an egg appearing in the oviduct is caused to move. This could be performed by any of the above mentioned restriction devices, but may also be performed by a specially designed separate device. In one embodiment the moving device is designed to generate vibrations.

The moving device may be configured to provide peristaltic like wave movement of the oviduct wall in the direction towards the ovary. Such peristaltic wave like movements in the upstream direction towards the ovary may stop flow of any egg towards the uterus, preferably by completely closing the oviduct lumen to stop any sperm to pass. Alternatively, the moving device may provide peristaltic like wave movements of the oviduct wall towards the uterus to cause movement of any egg downstream to the uterus, when there is no pregnancy risk.

Where the restriction device includes a stimulation device it could both 1) restrict the oviduct lumen by stimulation and 2) also create peristaltic wave like movements of the oviduct wall in the upstream direction to stop egg flow without fully restricting the oviduct lumen or cause movement of the egg in the downstream direction to the uterus.

Preferably, such a stimulation device is configured to stimulate different areas of a wall portion of the oviduct wall as the wall portion is constricted, and the stimulation device is controlled to intermittently and individually stimulate the areas of the wall portion. This intermittent and individual stimulation of different areas of the wall portion of the oviduct allows tissue of the wall portion to maintain substantially normal blood circulation during the performance of the method of the invention.

Movement of the Egg in the Oviduct Lumen

In an embodiment the method comprises constricting a wall portion of the oviduct to restrict or vary the flow in the oviduct lumen, and controlling the stimulation device to progressively stimulate the constricted wall portion, in the downstream or upstream direction of the oviduct, to cause progressive contraction of the wall portion to move the egg downstream in the oviduct lumenor to prevent further transportation of the egg to the uterus.

Embodiments of the Method According to the Present Invention

In a first general embodiment, the method comprises the following steps:
restricting an oviduct lumen of the patient postoperatively to accumulate at least one egg released from the ovary in the oviduct lumen for a predetermined period of time,
ceasing restricting the oviduct lumen to admit any egg appearing in the oviduct lumen to be transported to the uterus, and
controlling the restricting and ceasing restricting steps from outside the patients body.

In this first and other embodiments of the method, the predetermined period of time is in the interval of 2 to 30 days, or is more than 30 days.

In a second embodiment, the method comprises the steps of:
inserting a needle like tube into the abdomen of the patients body,
using the tube like needle like to fill the abdomen with gas thereby expanding the abdominal cavity,
placing at least two laparoscopic trocars in the patient's body,
inserting a camera through one of the trocars into the abdomen,
inserting at least one dissecting tool through a trocar and dissecting an area of at least one portion of the two oviducts of the patient,
placing two restriction devices on the two oviducts, respectively,
adjusting the restriction devices after the operation at a time convenient to avoid pregnancy,
controlling the adjusting step from outside the patients body, and
post-operatively restricting the two oviduct lumens to avoid pregnancy.

In both the first and second embodiments, the restricting step may comprise:
restricting the oviduct lumen at a first place of the oviduct to accumulate at least one egg released from the ovary in the oviduct lumen for a predetermined period of time,
restricting the oviduct lumen at a second place of the oviduct,
ceasing restricting the oviduct lumen at the first place of the oviduct, and
allowing the oviduct shorter restriction periods at each restriction place.

The method may further comprise the steps of:
ceasing restricting the oviduct lumen at the second place of the oviduct, allowing transport of the egg down to the uterus.

The method may also comprise the steps of:
restricting a third part of the oviduct lumen
ceasing restricting the oviduct lumen at the second place of the oviduct,
allowing the oviduct shorter restriction periods at each restriction place.

The method may also comprise the steps of:
ceasing restricting the oviduct lumen at the third place of the oviduct,
allowing transport of the egg down to the uterus The method may also comprise the steps of:
restricting a fourth part of the oviduct lumen
ceasing restricting the oviduct lumen at the third place of the oviduct,
allowing the oviduct shorter restriction periods at each restriction place.

The method may also comprise the steps of:
ceasing restricting the oviduct lumen at the fourth place of the oviduct,
allowing transport of the egg down to the uterus In both these methods normally if the restriction of the oviduct lumen at the first place of the oviduct is closer to the ovary this allows the oviduct lumen at the second place to be restricted without interferring with any accumulated egg.

Normally these methods are performed to restrict the oviduct lumen at more than two places on the oviduct and the restriction places are varied while keeping the oviduct lumen closed at at least one restriction place when restriction of the oviduct lumen is desired.

In a third embodiment, the method comprises:
restricting the oviduct lumen at places on the oviduct in consecutive order starting at a place on the oviduct closest to the ovary,
then restricting the oviduct lumen at any new place on the oviduct one step closer to the uterus, and
overlapping in time the restriction of the oviduct lumen at more than one place on the oviduct to restrict the oviduct lumen without interferring with any egg accumulated in the oviduct lumen.

The method may of course comprise only postoperatively varying the restriction places on the oviduct independently of order, to allow the oviduct to recover or to avoid any damage from the restriction of the oviduct while the oviduct lumen is kept restricted.

In a fourth embodiment, the method comprises the following steps:
causing a peristaltic like restriction wave movement of a portion of the oviduct wall to prevent at least one egg appearing in the oviduct lumen from being transported in the oviduct lumen to the uterus while restricting the oviduct lumen at all times,
accumulating the egg in the oviduct lumen for a predetermined period of time,
preventing any sperm to reach the egg during the time the egg is accumulated, and
post-operatively controlling from the outside the human body the oviduct wall wave movement to cease, whereby the egg is released and is transported to the uterus.

In a fifth embodiment, the method comprises the steps of:
inserting a tube like needle into the abdomen of the patients body,
using the tube like needle like to fill the abdomen with gas thereby expanding the abdominal cavity,
placing at least two laparoscopic trocars in the patient's body,
inserting a camera through one of the trocars into the abdomen,
inserting at least one dissecting tool through a trocar and dissecting an area of at least one portion of the two oviducts of the patient,
placing two restriction devices on the two oviducts, respectively,
finishing the operation and withdrawing the instruments after eventual suturing, and thereafter postoperatively:
controlling from outside the patient's body the restriction devices to restrict the oviduct lumens at a time relevant to avoid pregnancy, controlling the restriction devices to cause peristaltic like wave movements of portions of the oviduct walls towards the ovary to prevent an egg appearing in the oviduct lumen from being transported to the uterus for a predetermined period of time, accumulating any egg released from the ovary in at least one of the oviduct lumens, preventing any sperm from reaching the egg during the time the egg is accumulated, and controlling from outside the patient's body the restriction devices to cease the peristaltic like wave movements to release the egg in any of the oviduct lumens to allow the egg to be transported in a normal way to the uterus, when the risk of pregnancy is low.

The method may further comprise providing a hydraulic restriction device including a reservoir for distributing gas or fluid to or from the restriction device, and placing the reservoir subcutaneously to be reached by the patients hand for moving fluid manually to or from the restriction device. Preferably, two or more reservoirs could be provided for restricting the oviduct lumen at different places thereof, starting with a place closest to the ovary.

In a sixth embodiment, the method comprises the following steps:

restricting a first part of an oviduct lumen of the patient to accumulate at least one egg released from the ovary in the oviduct lumen for a predetermined period of time, moving the accumulated egg by an implanted movement device away in the oviduct lumen towards the ovary from the restriction area, allowing a second part of the oviduct lumen closer to the ovary to be restricted without interferring with any accumulated egg ceasing restricting the first part of the oviduct lumen, repeating restricting the first part of the oviduct lumen, ceasing restricting the second part of the oviduct lumen, and allowing the oviduct to recover between restriction intervals.

These steps are preferably followed by;

repeating moving any accumulated egg by the movement device away in the oviduct towards the ovary from the restricted first area, repeating restricting a second part of the oviduct closer to the ovary without interferring with any accumulated egg, Preferably, the method according to the sixth embodiment further comprises:

repeating moving any accumulated egg by the movement device away in the oviduct lumen towards the ovary from the restricted first part of the oviduct lumen, allowing a second part of the oviduct lumen closer to the ovary to be restricted without interferring with any accumulated egg, repeating ceasing restricting the first part of the oviduct lumen, repeating all the preceding steps to allow the oviduct to recover between restriction intervals.

Preferably, the method further comprises varying the restriction places on the oviduct between three or more places on the oviduct while always keeping the oviduct lumen closed.

The movement device may comprise a vibrating device to generate vibration of at least a part of the wall of the oviduct, so that any accumulated egg is caused to move, and the movement action on the egg is repeated. The movement device may comprise a mechanical device, a hydraulic device or a stimulation device, or a combination of such devices.

Female Sexual Dysfunction (II)

Another object of the present invention to obviate at least some of the disadvantages in the prior art and provide a new dimension to treat female sexual dysfunction positively affecting sexual stimuli and orgasm.

In accordance with this object there is provided a female sexual dysfunction treatment method, comprising providing a stimulation device configured to stimulate a female patient's erectile tissue, implanting the stimulation device in the patient's body, and operating the stimulation device from outside the patient's body to stimulate the erectile tissue so that the erectile blood flow passageway is affected to increase the amount of blood in the female erectile tissue to obtain engorgement with blood of the female erectile tissue.

One advantage of the present invention is that the likelihood to get orgasm will increase by the stimulation device. Another advantage of the present invention is that the sexual response to sexual stimuli will increase.

There is also provided an operation method for implanting the stimulation device.

The operation method comprises the steps of: a) creating an opening in the skin or vaginal wall of a female patient, b) dissecting at least one area of the female erectile tissue, c) placing the stimulation device within said area, and d) post-operatively operating on patient command the stimulation device to stimulate the female erectile tissue to obtain engorgement with blood of the female erectile tissue.

The operation method further comprises post-operatively and non-invasively controlling the stimulation device from outside the body.

The operation method further comprises e) placing a power source for powering the stimulation device within the body, and f) placing a control unit for performing step d) and a rechargeable battery for powering the control unit remote from the stimulation device.

Step (c) may include placing in the patient's body an integrated unit comprising the stimulation device and power source.

Step (c) may also include placing electrical electrodes and an electrical wire connected to the power source.

Step (a) may further comprise:

inserting a tube or needle into the patients body, filling the body through the tube or needle with a gas and thereby expanding a cavity within the female patients body, inserting at least two laparoscopic trocars into said cavity, inserting at least one camera trough at least one laparoscopic trocar, and inserting at least one dissecting tool through at least one laparoscopic trocar.

Definitions

The term "female erectile tissue" refers to both 1) tissue of the female sexual organs that before or during sexual intercourse are filled with blood including, but not limited to, the corpora cavernosa and the vestibular bulbs, 2) extensions of said tissue, including but not limited to erectile blood flow passageways including both arterial or venous blood vessels, and in relevant cases only, and 3) the surrounding tissues including relevant muscle tissue to affect the blood flow passage way described above, including affecting and increasing the arterial blood flow reaching said female erectile tissue.

The term "free flow" as used throughout the description and the terms denotes a fluid passageway unaffected by any artificial stimulations in any direction, such as valves or return valves.

The term "tissue" as used throughout the description and the claims denotes a cellular organizational level intermediate between cells and a complete organism. Hence, a tissue is an ensemble of cells, not necessarily identical, but from the same origin, that together carry out a specific function. For example tissue includes bone.

In general terms the present invention relates to methods for treating a sexual dysfunctional female patient which comprises providing a stimulation device for stimulating the erectile tissues of a female patient. In accordance with the invention stimulation can be performed by stimulating so as to affect blood passageways to or from the erectile tissues. The present invention also relates to the accomplishment of stimulation directly on the corpus cavernosa and thereby affects stimulation of glands assisting with their secretion of fluids associated with natural engorgement In a first aspect there is provided an apparatus for treating a sexual dysfunctional female patient, comprising a stimulation device adapted to stimulate an erectile blood flow passageway to increase the amount of blood in the female erectile tissue and thereby obtaining engorgement with blood of the female erectile tissue by affecting said erectile blood flow passageway.

In an embodiment the method comprises using the stimulation device to restrict venous blood flow leaving the female erectile tissue.

In an embodiment the method comprises engaging by the stimulation device at least one venous blood vessel leading from the female erectile tissue, corpus cavernosum, vestibular bulbs or a muscle affecting such blood flow that drains the female erectile tissue, and operating the stimulation device to stimulate venous blood vessel or muscle to temporarily and at least partially restrict the erectile blood flow in the venous blood vessel.

In an embodiment the method comprises providing two or more post-operatively and non-invasively adjustable stimulation devices.

In an embodiment the method comprises generating an alarm signal in response to the lapse of a predetermined time period during which the stimulation device has been operating.

In an embodiment the method comprises operating the stimulation device to stimulate the erectile tissue to increase the arterial blood flow reaching the female erectile tissue to obtain engorgement with blood of the female erectile tissue, wherein the stimulation device is operated to stimulate at least one artery to enlarge the cross-sectional area of the blood flow passageway in the artery. The stimulation device may be configured to stimulate the artery by heating the artery.

In an embodiment the method comprises operating the stimulation device to stimulate a muscle related to the arterial blood flow reaching the female erectile tissue, wherein the stimulation device is operated to stimulate the muscle to cause relaxation of the muscle to increase the arterial blood flow.

In an embodiment the method comprises operating the stimulation device to stimulate a muscle related to the venous blood flow leaving the female erectile tissue, wherein the stimulation device is operated to stimulate the muscle to cause contraction of the muscle to restrict the erectile venous blood flow.

Female Sexual Dysfunction (III)

Another object of the present invention to obviate at least some of the disadvantages in the prior art and provide a new dimension to treat female sexual dysfunction positively affecting sexual stimuli and orgasm.

In accordance with this object there is provided a female sexual dysfunction treatment method, comprising a) increasing the amount of blood in the female erectile tissue to obtain engorgement with blood of the female erectile tissue.

Preferably, step (a) is performed by providing an adjustable restriction device configured to restrict the venous blood flow leaving the female erectile tissue, implanting the restriction device in the patient's body, and operating the restriction device from outside the patient's body to constrict at least one venous blood vessel, which drains the female erectile tissue, to temporarily and at least partially restrict the venous blood flow leaving the female erectile tissue to obtain engorgement with blood of the female erectile tissue, or to constrict the female erectile tissue to temporarily and at least partially restrict the venous blood flow leaving the female erectile tissue to obtain engorgement with blood of the female erectile tissue.

In an embodiment the method comprises providing a restriction device configured to constrict at least one venous blood vessel or corpus cavernosum or vestibular bulbs that drains the female erectile tissue, and is adapted to temporarily and at least partially restrict the venous blood flow leaving the female erectile tissue. Preferably, two or more post-operatively and non-invasively adjustable restriction devices operated.

There is also provided an operation method for implanting the stimulation device.

The operation method comprises the steps of: a) creating an opening in the skin or vaginal wall of a female patient, b) dissecting at least one area of the female erectile tissue, c) placing the restriction device within said area, and d) postoperatively operating on patient command the restriction device to restrict the female erectile tissue to obtain engorgement with blood of the female erectile tissue.

The operation method further comprises post-operatively and non-invasively controlling the stimulation device from outside the body.

The operation method further comprises e) placing a power source within the body, wherein step (e) comprises the step of placing a control unit and a rechargeable battery remote from the stimulation device.

Step (c) may include placing an integrated unit comprising the restriction device and power source.

Step (c) may also include placing electrical electrodes and an electrical wire connected to the power source.

Step (a) may further comprise:
inserting a tube or needle into the patients body,
filling the body through the tube or needle with a gas and thereby expanding a cavity within the female patients body,
inserting at least two laparoscopic trocars into said cavity,
inserting at least one camera trough at least one laparoscopic trocar, and
inserting at least one dissecting tool through at least one laparoscopic trocar.

Definitions

The term "female erectile tissue" refers to 1) tissue of the female sexual organs that before or during sexual intercourse are filled with blood including, but not limited to, the corpora cavernosa of the clitoris and the vestibular bulbs. 2) extensions of said tissue, including but not limited to blood vessels and the surrounding tissues.

The term "free flow" refers to a fluid passageway without any restrictions in any direction, such as valves or return valves.

The term "tissue" refers to all human tissue, including bone.

Intestinal Disorder (I)

"Artificial Reservoir"

Another object of the present invention is to provide a method for treating a patient having a disorder related to the patient's intestine.

Internal Reservoir with Implantable Flow Control Device

In accordance with this object, there is provide a method for treating a patient having a disorder related to the patient's intestine, comprising providing an artificial or artificially modified reservoir, implanting the reservoir in the patient's body, and receiving and temporarily collecting therein intestinal contents. The method further comprises emptying the reservoir while remaining within the patient's body. The method further comprises implanting in the patient's body an at least partly artificial flow control device and controlling by the control device the flow of intestinal contents from the reservoir.

The internal reservoir will substantially extend the time period before the patient feels a need to excrete feces. Rather than using an external bag for that purpose which has to be attached, removed and cleaned, the internal reservoir remains within the patient's body. By combining such internal reservoir with an appropriate flow control device for emptying the reservoir, the patient's living circumstances are substantially improved.

Reservoir Formed from Intestine or Human Tissue

According to a first general embodiment, the reservoir may be formed from at least one bent portion of the patient's intestine. More specifically, laterally adjacent sections of the intestine are cut open along their mutual contact line and the resulting upper halves and lower halves thereof are then interconnected so as to form the reservoir. The interconnection can advantageously be made with staplers, possibly including bonding with a biocompatible glue, but sewing is likewise an option. Alternatively, the reservoir may also be formed from surgically modified and connected human tissue.

Isolated Lateral Arrangement of Reservoir

The reservoir may be laterally connected to the intestine by means of a single passage through which the intestinal contents are fed in both ways, i.e. from the intestine into the reservoir and, when the reservoir is emptied, in the reverse direction from the reservoir back to the intestine and further out of the body. Accordingly, there is provided a passage in fluid communication with the reservoir and connected to a surgically created lateral opening in a wall of the patient's intestine, wherein said passage transfers intestinal contents to and from the reservoir.

Through-Flow Arrangement of Reservoir

Instead of a single passage, two passage may be provided, a first passage leading feces to the reservoir and a second passage different from the first passage leading the feces from the reservoir when the reservoir is emptied.

Accordingly a first passage is provided in fluid communication with the reservoir and connected to a surgically created first opening of the patient's intestine, wherein said first passage transfers intestinal contents to the reservoir, and a second passage is provided in fluid communication with the reservoir, wherein said second passage transfers intestinal contents from the reservoir.

The second passage must not necessarily redirect the feces back to the intestine, it may as well be surgically connected to a surgically created stoma or to the patient's rectum or anus or to tissue adjacent the patient's anus.

On the other hand, rather than directly connecting the second passage to the stoma or anus, the second open end portion may be connected to a healthy portion of the patient's small intestine or of the patient's large intestine. Since the small intestine and large intestine have different diameters and wall thickness, the structure of the second open end portion can be substantially different in these cases. The healthy portion of the intestine may then be connected to the patient's rectum or anus or to tissue adjacent the patient's anus or to use that portion for creating a stomy.

Lateral Attachment

In particular, the second passage may be surgically connected to a second surgically created opening of the patient's intestine, this not being restricted to a connection to a cross-sectional opening. More specifically, the second passage is connected to a lateral opening in the wall of the patient's intestine. Similarly, it is preferred that also the first passage is connected to a lateral opening in the wall of the patient's intestine. Lateral attachment of the passage or passages between the intestine and the reservoir has the advantage that the forces resulting from the peristaltic waves moving along the intestine have less impact on the connection. In frontal connections, i.e. where the reservoir is attached to a cross-sectional opening of the intestine, the peristaltic waves tend to pull the intestine away from the connection, this requiring special securing measures.

In order to connect the reservoir to the intestine, the first passage is preferably bonded and/or sewn and or stapled to the intestine, this applying to both a cross-sectional and a lateral attachment.

Valve as Part of the Flow Control Device

As a main element of the flow control device for controlling flow from the reservoir, in particular for emptying the reservoir, there may be provided one or more valve and/or pump.

Exit Valve

For instance, the at least one valve may include an exit valve preventing intestinal contents flow from the reservoir in its closed position. Preferably, the exit valve is a normally closed valve so that no energy is needed to keep the valve closed during the system's inactive periods.

Entry Valve in Addition to Exit Valve

In addition, the flow control device may comprise an entry valve allowing intestinal contents to flow towards the reservoir in its open position. This can be advantageous particularly during the emptying of the reservoir, when the entry valve should be closed. Therefore, the entry valve is preferably a normally open valve. Accordingly, the exit valve and the entry valve preferably cooperate so that when one of the two valves is closed, the respective other valve is open, and vice versa.

Valve Arrangement (Internal, Intersecting, Outside)

The valves can be arranged in many different ways, depending on the type of valve. For instance, at least one of the valve or valves, respectively, can be permanently implanted inside the patient's intestine. Or, where at least one of the valve or valves, respectively, has an upstream open end and has a downstream open end in fluid connection with the upstream open end, the upstream open end can be connected to a surgically created opening of the patient's intestine and the downstream open end can be connected to either one of a surgically created opening of the patient's intestine, a surgically created stoma, the patient's anus or tissue adjacent the patient's anus. Alternatively, at least one of the valve or valves, respectively, may be implanted inside the patient's body outside a section of the patient's intestine and may comprise at least one element acting on the intestine section from the outside thereof so as to act on and, in particular, prevent intestinal contents flow through the intestine section. This latter valve arrangement is advantageous inasmuch its installment does not require any surgery on the respective part of the intestine.

Valve Types

As regards the various valve types that may be employed, the at least one valve may e.g. comprise a central opening which is normally closed by resilient means that can be urged apart mechanically by inserting a conduit through the central opening so as to open the central opening of the valve. In the simplest embodiment, the valve may be opened by mechanical force, such as by inserting a tube from outside the patient's body through the valve. The valve in this case can be a simple non-return valve.

According to a more complex alternative, the at least one valve may comprise a compartment with a variable volume adapted to open and close the valve by changing the compartment's volume. Advantageously, the at least one valve comprises at least one passage for filling and emptying the compartment with hydraulic fluid. The compartment preferably has at least one flexible wall defining an opening for the intestine or a conduit of the reservoir to pass through, the opening being adapted to close upon increase of the compartment's volume.

According to another alternative, the at least one valve may be a flap valve permanently implanted inside the patient's intestine. The flap valve may for instance comprise a rotatable disc.

According to a very specific alternative, in which the at least one valve is implanted inside the patient's body outside a section of the patient's intestine to act on the intestine section from the outside thereof, the valve may comprise at least one electrical stimulation device adapted to electrically stimulate muscle or neural tissue of an intestine section so as to cause at least partial contraction of the intestine section. This is a very gender way of constricting the intestine. The stimulation device preferably comprises at least one electrode adapted to apply electric pulses to the intestine section.

It is particularly advantageous to make use of a stimulation device to stimulate different portions of the intestine section over time. Thus, different portions of the intestine section can be constricted by stimulation at different times in any predetermined stimulation pattern, thereby giving the intestine portions currently not stimulated time to recover and, thus, improving the blood circulation in the respective intestine section.

Furthermore, the stimulation device can specifically stimulate, over time, the different portions of the intestine section in a wave like manner in a direction opposite to natural intestinal contents flow. As a result, the valve counteracts the natural intestinal contents flow, thereby improving the valve's closing function.

Alternatively, or preferably in addition to the stimulation device, the at least one valve may comprise a constriction device implanted in the patient's body for at least partly constricting the intestine section mechanically from outside the intestine section. Where the stimulation device is combined with the constriction device, the stimulation device and the constriction device preferably act on the same intestine section. In that case, it is advantageous if the constriction device in its normal condition constricts the intestine section only partly, in order not to damage the intestine over time. Complete constriction and, thus, closing of the intestine may then be obtained by additionally stimulating the intestine section in a manner as described before.

In addition, when constriction of the intestine section caused by the constriction device is released, the stimulation device may be used to pump intestinal contents along the intestine section by, over time, stimulating different portions of the intestine section in a wave like manner in a direction of natural intestinal contents flow. In this situation, the valve may incorporate the additional function of a pump for actively supporting the discharge of feces from the human body.

Pump as Part of the Implantable Flow Control Device

Where the flow control device comprises a pump for emptying the reservoir, a variety of different types of pumps may be employed.

For instance, the pump may empty the reservoir by squeezing the reservoir, if the reservoir has a flexible wall that allows for squeezing.

In particular, the pump and the reservoir can be separate from each other and the pump can be implanted in the patient's body separate from but in close proximity to the reservoir so as to act on the reservoir from the outside thereof. For instance, the reservoir may have a flexible wall and the pump may comprise a movable piston, with a front end of the piston adapted to act on the flexible wall of the reservoir from the outside thereof upon advancement of the piston.

Alternatively, the pump and the reservoir can be fixedly connected to one another. For instance, the reservoir may be formed by a bellow, said bellow having an end wall closing the bellow at one end thereof and said end wall making part of the pump such that a volume of the bellow is reduced upon advancement of said end wall. Preferably, the bellow is made of a resilient material so as to urge the bellow into a normally expanded position.

In another alternative where the pump and the reservoir are fixedly connected to one another, the pump comprises a movable piston with a front end of the piston extending into the reservoir such that a volume of the reservoir can be reduced upon advancement of the piston. Preferably, the pump and the reservoir are comprised in a common housing so that they can be implanted as a unit. Furthermore, it is advantageous if the piston is spring loaded so as to urge the piston into a normally retracted position.

As a further alternative, the pump may be permanently arranged inside the reservoir.

As a still further alternative, the pump and the reservoir can be provided separate from each other with the pump being implanted inside the patient's body outside the patient's intestine. Similarly to the very specific valve alternative described above, according to this alternative the pump comprises at least one electrical stimulation device adapted to electrically stimulate muscle or neural tissue of an intestine section so as to cause at least partial contraction of the intestine section. Again, the stimulation device preferably comprises at least one electrode applying electric pulses to the intestine section. Furthermore, the stimulation device may stimulate different portions of the intestine section over time so as to pump intestinal contents along the intestine section by, over time, stimulating the different portions of the intestine section in a wave like manner in the direction of natural intestinal contents flow.

Also, the pump may comprise a constriction device similar to the valve alternative described earlier for at least partly constricting the intestine section mechanically, whereby the constriction device is preferably adapted to pump intestinal contents along the intestine section by, over time, constricting different portions of an intestine section in a wave like manner in the direction of natural intestinal contents flow.

Again, the stimulation device may be combined with the constriction device so as to pump the intestinal contents along the intestine section by, over time, stimulating the different portions of the intestine section in a wave like manner in a direction of natural intestinal contents flow, when constriction of the intestine section caused by the constriction device is released at the respective portions.

Finally, the pump may also be constituted by a manually drivable pump and may comprise an actuator for manually driving the pump. The actuator in this case is preferably arranged for subcutaneous implantation so as to be operable from outside the patient's body.

Motor

Where the valves or pump or any other element of the flow control device is not or not only manually drivable, at least one motor can be provided for automatically driving one or more of the elements of the flow control device. The motor is preferably driven by electric or electromagnetic energy.

A motor in the sense of the present invention is a device that transforms energy other than mechanical energy into mechanical energy. While a pump in the sense of the present invention is a device for advancing liquid or pasty material, a pump may at the same time be a motor in certain circumstances, such as where the transformation of energy into mechanical energy causes advancement of the liquid or pasty material without any intervening mechanical means such as a piston, bellow or the like.

For instance, the at least one motor can be arranged for driving at least one of the valve or valves, respectively, between its closed and open position. Also, the at least one motor can be arranged for driving the pump.

A manually operable switch may be provided for activating the at least one motor and be subcutaneously implanted so as to be operable from outside the patient's body.

Energy Source

An energy source may be provided for supplying energy directly or indirectly to at least one energy consuming part of the system. Preferably, the energy source includes a battery or an accumulator, such as one or more of a rechargeable battery and a capacitor, as an energy storage means. The energy storage means is advantageously adapted for being implanted inside the patient's body.

Wireless Energy Transmission

Energy is preferably transmitted wirelessly. Thus, where the energy source is provided for supplying energy directly or indirectly to at least one energy consuming part of the system, the energy source may comprise a wireless energy transmitter adapted to wirelessly transmit energy from outside the patient's body to the at least one energy consuming part. Alternatively, where the energy source includes a battery or an accumulator, in particular one which is implanted in the patient's body, the energy source may comprise a wireless energy transmitter adapted to wirelessly transmit energy from outside the patient's body to the energy storage means.

Energy Transmission Feedback

A feedback subsystem, which can make part of a control device described subsequently, can advantageously be provided to wirelessly send feedback information related to the energy to be stored in the accumulator from inside the human body to the outside thereof. The feedback information is then used for adjusting the amount of wireless energy transmitted by the energy transmitter. Such feedback information may relate to an energy balance which is defined as the balance between an amount of wireless energy received inside the human body and an amount of energy consumed by the at least one energy consuming part. Alternatively, the feedback information may relate to an energy balance which is defined as the balance between a rate of wireless energy received inside the human body and a rate of energy consumed by the at least one energy consuming part.

Also, the transmission of energy from the energy storage means to the at least one energy consuming part may be performed wirelessly by means of an accordingly adapted wireless energy transmitter.

Preferably, in order to reduce the number of parts and possibly increase the system's efficiency, the energy consuming part can be adapted to directly transform the wirelessly transmitted energy into kinetic energy. Otherwise, it will be necessary to provide an implantable energy transforming device for transforming the wireless energy, preferably into electric energy. In this case, it is further preferred to set up the system such that the energy consuming part is driven with the electric energy, as said energy transforming device transforms the wireless energy into the electric energy.

The energy transmitter can be adapted to generate an electromagnetic field, a magnetic field or an electrical field. The wireless energy may be transmitted by the energy transmission device by at least one wireless signal. More specifically, the energy transmitter may be adapted to transmit the energy by at least one wireless energy signal, which may comprise an electromagnetic wave signal, including at least one of an infrared light signal, a visible light signal, an ultra violet light signal, a laser signal, a microwave signal, an X-ray radiation signal, and a gamma radiation signal. Also, the wireless energy signal may comprise a sound or ultrasound wave signal. Furthermore, the wireless energy signal may comprise a digital or analog signal or a combination thereof.

Galvanic Energy Transmission

Where energy is not transmitted wirelessly, galvanic coupling elements should be provided at least between the energy source and the motor for transmitting energy to the motor in contacting fashion.

Control Unit

It is advantageous to provide a control unit adapted to directly or indirectly control one or more elements of the system, such as for controlling opening of the exit valve and/or closing of the entry valve, in particular in a manner such that when one of the two valves is closed, the respective other valve is open, and vice versa. The control unit can also be adapted to control actuation of the pump.

The control unit is preferably operable by the patient, e.g. particularly in order to empty the reservoir.

At least part of the control unit may be adapted to be implantable in the patient's body. For instance, a manually operable switch may be provided for activating the control unit, the switch preferably being arranged for subcutaneous implantation so as to be operable from outside the patient's body. Also, the control unit may comprise a first part adapted for implantation in the patient's body and a second part adapted to cooperate with the first part from outside the patient's body. In this case, the control unit can be adapted to transmit data from the external second part of the control unit to the implanted first part of the control unit in the same manner as energy is transmitted to the at least one energy consuming part.

That is, the second part of the control unit may be adapted to wirelessly transmit a control signal to the implantable first part of the control unit for controlling the at least one energy consuming part from outside the patient's body. Also, the implantable first part of the control unit may be programmable via the second part of the control unit. Furthermore, the implantable first part of the control unit may be adapted to transmit a feedback signal to the second part of the control unit.

Sensor

Furthermore, a physical parameter sensor adapted to directly or indirectly sense a physical parameter of the patient can be provided. The physical parameter sensor may be adapted to sense at least one of the following physical parameters of the patient: a pressure within the reservoir, a pressure within the patient's intestine, an expansion of the reservoir, a distension of an intestinal wall of the patient's intestine, a movement of the intestinal wall.

Similarly, a functional parameter sensor adapted to directly or indirectly sense a functional parameter of the system can be provided, wherein the functional parameter sensor may be adapted to sense at least one of the following functional parameters of the system: a pressure against a part of the system such as the reservoir, a distension of a part of the system such as a wall of the reservoir, an electrical parameter such as voltage, current or energy balance, a position or movement of a movable part of the system.

Preferably, an indicator is coupled to the sensor or sensors, the indicator being adapted to provide a signal when a sensor senses a value for the parameter beyond a predetermined threshold value. The sensor signal may comprise at least one of the following types of signals: a sound signal, a visual signal.

Intestinal Contents Collecting Device (with "External" Pump)

As mentioned before, an intestinal contents collecting device may be temporarily applied from outside the patient's body when the reservoir is to be emptied. The collecting device may comprise a front open end applied towards the exit valve so as to provide a flow passage from the exit valve towards the collecting device. More specifically, the collecting device front open end is preferably applied to the exit valve so as to open the valve and thereby provide said flow passage towards the collecting device. Where the exit valve is normally closed by resilient means, said front open end is inserted through the central opening of the exit valve so as to urge apart the resilient means normally closing the central opening.

The collecting device preferably comprises a suction pump, which may comprise a piston-cylinder-arrangement. The suction pump may be driven manually, in particular where it is intended for use as a back-up pump for a situation where the pump of the flow control device is out of operation. However, preferably a motor is connected to the suction pump for driving the pump automatically.

Reservoir Formed from Intestine

The reservoir of the system described above may be made from the patient's intestine. A respective surgical method of treating the patient would comprise the steps of:
cutting the patient's skin and abdominal wall,
dissecting an area of the patient's intestine,
cutting the patient's intestine along a mutual contact line of laterally adjacent sections of a bent portion thereof and connecting by suturing and/or stapling the resulting upper and lower halves of the intestine so as to form a reservoir,
implanting a flow control device so as to permanently reside inside the patient's body and adapted to control flow of intestinal contents from the reservoir to outside the patient's body, and
thereafter, permanently closing the abdominal wall and skin.

A respective laparoscopic surgical method of treating the patient would comprise the steps of:
making a small opening in the patient's skin and abdominal wall,
introducing a needle in the abdominal cavity,
inflating the abdominal cavity with gas,
inserting at least one trocar into the cavity,
introducing a camera through the trocar, inserting at least one dissecting instrument preferably through a second trocar,
dissecting an area of the intestine,
cutting the patient's intestine along a mutual contact line of laterally adjacent sections of a bent portion thereof and
connecting by suturing and/or stapling the resulting upper and lower halves of the intestine so as to form a reservoir,
implanting a flow control device so as to permanently reside inside the patient's body and adapted to control flow of intestinal contents from the reservoir to outside the patient's body,
extracting the instruments, camera and trocar, and in relation thereto
suturing, if necessary, the abdominal wall and permanently closing the skin.

As also mentioned before, the system may be surgically connected to a surgically created stoma or to the patient's rectum or anus or to tissue adjacent the patient's anus. This would require, where a stomy is involved, the following additional steps:
cutting the patient's skin and abdominal wall so as to create an opening for an intestinal stomy,
dissecting the area of the opening,
dividing the intestine downstream of the reservoir so as to maintain an upstream natural intestine section still connected to the reservoir with a cross-sectional opening at the downstream end thereof,
dissecting the mesentery of the upstream natural intestine section in the area of the cross-sectional opening at the downstream end thereof to prepare for creating the intestinal stomy,
advancing the upstream natural intestine section through the abdominal wall and skin and
suturing the upstream natural intestine section in the area of the cross-sectional opening to the skin with the intestinal mucosa turned inside out, thereby achieving the intestinal stomy.

Where the system may be surgically connected to a the patient's anus or to tissue adjacent the patient's anus, this would require the following additional steps:
dividing the intestine so as to create an upstream natural intestine section having a cross-sectional opening at the downstream end thereof and a downstream natural intestine section leading to the patient's anus,
dissecting the area of the patient's anus and surgically separating the downstream natural intestine section from the patient's anus, whereas the steps of dividing the intestine and separating the intestine section leading to the patient's anus can alternatively be carried out in reversed order,
dissecting the mesentery of the upstream natural intestine section in the area of the cross-sectional opening at the downstream end thereof to prepare for connecting the upstream natural intestine section to the patient's anus or tissue adjacent the patient's anus,
advancing the downstream end of the upstream natural intestine section through the patient's anus, and
suturing the cross-sectional opening of the upstream natural intestine section to the patient's anus or tissue adjacent the patient's anus.

In line with the very specific valve embodiment described previously, the method may further involve the step of implanting at least one electrical stimulation device in the vicinity of an intestine section so as to allow for at least partial contraction of the intestine section by means of electrical stimulation of muscle or neural tissue with the aid of the electrical stimulation device. Preferably, electric pulses are applied to the intestine section by means of the stimulation device.

Preferably the stimulation device is implanted along the intestine section so as to be able to stimulate different portions of the intestine section over time. More specifically, the stimulation device may be implanted to pump intestinal contents along the intestine section by, over time, stimulating the different portions of the intestine section in a wave like manner.

Also, a constriction device may be implanted so as to allow for at least partial mechanical constriction of the intestine section by means of the constriction device. The constriction device may advantageously combined with the stimulation device so as to allow for adding further constriction of the intestine section by stimulating the intestine section with stimulation pulses. In particular, this may be used for pumping intestinal contents along the intestine section by, over time, stimulating the different portions of the intestine section in a wave like manner, when constriction of the intestine section caused by the constriction device is released.

Artificial Reservoir

While the reservoir may be made from the patient's intestine in the manner as described earlier, an artificial reservoir made from non-biologic material may as well be used. In this case, a surgical method of treating a patient may comprise the steps of:

cutting the patient's skin and abdominal wall,
dissecting an area of the patient's intestine,
surgically creating an opening in the dissected intestinal area,
affixing to the opening a reservoir so as to receive and temporarily collect therein intestinal contents from the patient's intestine,
implanting a flow control device so as to permanently reside inside the patient's body and adapted to control flow of intestinal contents from the reservoir to outside the patient's body, and
suturing the abdominal wall and skin.

A respective laparoscopic surgical method of treating a patient may comprise the steps of:

making a small opening in the patient's skin and abdominal wall,
introducing a needle in the abdominal cavity,
inflating the abdominal cavity with gas,
inserting at least one trocar into the cavity,
introducing a camera through the trocar,
inserting at least one dissecting instrument preferably through a second trocar,
dissecting an area of the intestine,
surgically creating an opening in the dissected intestinal area,
affixing to the opening an artificial reservoir so as to receive and temporarily collect therein intestinal contents from the patient's intestine and
implanting a flow control device so as to permanently reside inside the patient's body and be adapted to control flow of intestinal contents from the reservoir to outside the patient's body,
connecting the intestine to the artificial reservoir with securing means,
extracting the instruments, camera and trocar, and in relation thereto
suturing, if necessary, the abdominal wall and permanently closing the skin.

In the afore described embodiments the reservoir is attached to an opening of the intestine, which opening may be a lateral opening created in the intestinal wall so as to allow intestinal content to flow to the reservoir and, possibly, also from the reservoir back to the intestine through the same opening. However, the opening may as well be a cross-sectional opening of the intestine, which can be obtained by dividing the intestine. In the latter case of a connecting the reservoir to a cross-sectional opening of the intestine, a respective surgical method of treating a patient would comprise the steps of:

cutting the patient's skin and abdominal wall,
dissecting an area of the patient's intestine,
dissecting a portion of the dissected intestinal area such that intestinal mesentery connected thereto is opened in such a way that supply of blood through the mesentery to the dissected intestinal area is maintained as much as possible on both sides of the dissected portion,
dividing the patient's intestine in the dissected portion so as to create an upstream part of the intestine with a first intestinal opening and a downstream part of the intestine with a second intestinal opening with the mesentery still maintaining a tissue connection between the upstream and downstream intestine parts,
affixing to the first intestinal opening an artificial reservoir so as to receive and temporarily collect therein intestinal contents from the patient's intestine,
affixing the reservoir to the second intestinal opening so as to allow for discharging intestinal contents from the reservoir through the second intestinal opening,
implanting a flow control device so as to permanently reside inside the patient's body and be adapted to control flow of intestinal contents from the reservoir through the downstream intestine part, and
suturing the abdominal wall and skin.

A corresponding laparoscopic surgical method of treating a patient comprises the steps of:

making a small opening in the patient's skin and abdominal wall,
introducing a needle in the abdominal cavity,
inflating the abdominal cavity with gas,
inserting at least one trocar into the cavity,
introducing a camera through the trocar,
inserting at least one dissecting instrument preferable through at least a second trocar,
dissecting an area of the intestine,
dissecting a portion of the dissected intestinal area such that intestinal mesentery connected thereto is opened in such a way that supply of blood through the mesentery to the dissected intestinal area is maintained as much as possible on both sides of the dissected portion,
dividing the patient's intestine in the dissected portion so as to create an upstream part of the intestine with a first intestinal opening and a downstream part of the intestine with a second intestinal opening with the mesentery still maintaining a tissue connection between the upstream and downstream intestine parts,
affixing to the first intestinal opening an artificial reservoir so as to receive and temporarily collect therein intestinal contents from the patient's intestine,
affixing the reservoir to the second intestinal opening so as to allow for discharging intestinal contents from the reservoir through the second intestinal opening,
implanting a flow control device so as to permanently reside inside the patient's body and be adapted to control flow of intestinal contents from the reservoir to the downstream intestine part,
connecting the intestine to the artificial reservoir with securing means,
extracting the instruments, camera and trocar, and in relation thereto
suturing, if necessary, the abdominal wall and permanently closing the skin.

Depending on where the intestine is divided, the "second" cross-sectional intestinal opening is created either in the patient's small intestine or in the patient's large intestine.

Where the downstream part of the intestine is to be attached to a surgically created stomy, this may involve the following additional steps:
cutting the patient's skin and abdominal wall to create an opening for an intestinal stomy,
dissecting the area of the opening,
dividing the downstream intestine part so as to create at the downstream end of the downstream intestine part a third opening,
dissecting the mesentery of the downstream intestine part in the area of the third opening to prepare for creating the intestinal stomy,
advancing the downstream intestine part through the abdominal wall and skin and
suturing the third opening to the skin with the intestinal mucosa turned inside out, thereby achieving the intestinal stomy.

Where the downstream part of the intestine is to be attached to the patient's anus or tissue adjacent the patient's anus, rather than to a surgically created stomy, this may involve the following additional steps:
dividing the intestine so as to create an upstream natural intestine section having a cross-sectional opening at the downstream end thereof and a downstream natural intestine section leading to the patient's anus,
dissecting the area of the patient's anus and surgically separating the downstream natural intestine section from the patient's anus, whereas the steps of dividing the intestine and separating the intestine section leading to the patient's anus can alternatively be carried out in reversed order,
dissecting the mesentery of the upstream natural intestine section in the area of the cross-sectional opening at the downstream end thereof to prepare for connecting the upstream natural intestine section to the patient's anus or tissue adjacent the patient's anus,
advancing the downstream end of the upstream natural intestine section through the patient's anus, and
suturing the cross-sectional opening of the upstream natural intestine section to the patient's anus or tissue adjacent the patient's anus.

Exit Valve

Where the flow control device comprises an exit valve preventing intestinal contents to flow through the valve in its closed position, the step of implanting the flow control device may comprise:
cutting at least one portion of the patient's intestine so as to create at least one artificial opening in the intestine downstream of the reservoir,
affixing the exit valve to the artificial intestinal opening, and
connecting the exit valve to a pre-existing opening in the patient's body.

The step of connecting the exit valve to a pre-existing opening in the patient's body may comprise either one of affixing the exit valve to the patient's anus or tissue adjacent the patient's anus, to a portion of the patient's intestine leading to the patient's anus, or—after surgically creating an artificial stoma in the patient's abdominal wall and skin—to the surgically created stoma stoma. Alternatively, the exit valve may be connected to a portion of the patient's intestine and that portion of the patient's intestine may be used to create the stomy.

Lateral Connection (of Reservoir, Pump or Valve) to Intestine

It was described before how the reservoir may be attached between two cross-sectional openings of a divided intestine. It is, however, also possible to surgically create an opening in the dissected intestinal area by cutting the artificial intestinal opening into a lateral wall of the intestine so as to create a lateral artificial intestinal opening, and attach the reservoir to the lateral opening. In this case, the intestine is preferably permanently closed downstream of the lateral artificial intestinal opening.

By-Pass Connection

Where two lateral artificial intestinal openings are cut at different locations of the intestine's lateral wall, the intestine may further be cut between the two locations and the cut ends permanently closed or the intestine may simply be permanently closed between the two locations, e.g. by suturing and/or stapling, wherein the reservoir is affixed in flow connection intermediate the two artificial intestinal openings.

End-Connection (of Reservoir or Exit Valve; Sleeve/Bulge Connector)

Where the step of surgically creating an opening in the dissected intestinal area comprises cutting the artificial intestine completely in a crosswise direction so as to create at least one artificial opening in the intestine, the step of affixing to the opening may comprise:
connecting a conduit to a section of the intestine by inserting an end of the conduit into the artificial intestinal opening, and
placing a flexible sleeve so as to extend over the intestine and conduit such that at least part of the intestine is located intermediate the sleeve and the outer surface of the conduit.

Where the flexible sleeve is mounted on the outer surface of the conduit so as to be foldable upon itself, the step of placing the flexible sleeve so as to extend over the intestine and conduit may comprise folding the flexible sleeve upon itself such that at least part of the intestine is located intermediate the folded sleeve.

Alternatively, or in addition, where the step of surgically creating an opening in the dissected intestinal area comprises cutting the artificial intestine completely in a crosswise direction so as to create at least one artificial opening in the intestine, the step of affixing to the opening may comprise:
connecting a conduit having a bulge formed on the outside thereof to a section of the intestine by inserting an end of the conduit into the artificial intestinal opening so that the intestine extends over the bulge from one side of the bulge, and
advancing a blocking ring over the intestine towards the bulge from the respective other side of the bulge such that the intestine is located intermediate the conduit's outer surface and the blocking ring.

The afore-mentioned conduits with a sleeve or with a bulge serve to improve the strength of the connection against forces which result from the peristaltic movement of the intestine and tend to pull on the intestine. The conduit may also combine a sleeve and a bulge. The conduit may lead to or from the reservoir or may make part of the valve or pump.

External/Internal Arrangement of Exit Valve

Where the flow control device comprises an exit valve preventing intestinal contents flow through the valve in its closed position, the step of implanting the flow control device may comprise either placing the exit valve outside and adjacent to a section of the intestine downstream of the reservoir so as to allow acting on said intestine section from the outside thereof by means of the exit valve, or affixing the exit valve within a section of the intestine downstream of the reservoir so as to allow closing said intestine section by means of the exit valve when the valve is in its closed position.

Bond and Suture Connection

The step of affixing to the opening preferably comprises bonding, possibly further including suturing and/or stapling, an element to the intestine so as to surround and close the artificial intestinal opening.

Pump

Where the flow control device comprises a pump for emptying the reservoir, the step of implanting the flow control device may comprise implanting the pump in the patient's abdomen either separate from but in close proximity to the reservoir so that it can act on the reservoir from the outside thereof, or fixedly connected to the reservoir. Alternatively, the pump may be implanted in the reservoir so that it can act on the intestinal contents in the reservoir from the inside the reservoir.

Manual Drive

Where the flow control device comprises an actuator for manually driving the pump, such actuator is preferably implanted subcutaneously so as to be operable from outside the patient's body.

Motor/Pump

As mentioned before, at least one motor and/or a pump may be implanted for automatically driving one or more elements of the flow control device.

Switch

Where the motor and/or pump comprises a manually operable switch for activating the motor and/or pump, the switch is preferably implanted subcutaneously so as to be operable from outside the patient's body.

Energy Source/Energy Transmission

As mentioned before, an energy source, possibly comprising an energy storage means, may be implanted inside the patient's body for supplying at least one energy consuming part with energy.

Furthermore, an energy transforming device for transforming wireless energy into electric energy may also be implanted. Alternatively or in addition thereto, galvanic coupling elements may be implanted for transmitting energy to the energy consuming part in contacting fashion.

Control Unit

Also, as mentioned before, at least a part of a control unit may be implanted to directly or indirectly control one or more elements of the flow control device.

Where the control unit comprises a manually operable switch for activating the control unit, the switch is preferably implanted subcutaneously so as to be operable from outside the patient's body.

Sensor

As mentioned before, one or more physical and/or functional parameter sensors may be implanted to directly or indirectly sense physical and/or functional parameters inside the patient and in the system implanted inside the patient. Where the sensor is a pressure sensor, it may be placed in the reservoir or intestine so as to sense the pressure within the reservoir or intestine, respectively. Where the sensor is a tension sensor, it may be placed in contact with the reservoir or intestine so as to sense an expansion of the reservoir or intestine, respectively. Where the sensor is a movement sensor, it may be placed in contact with the intestine so as to sense movement of the intestine. The functional sensor may be adapted to measure at least one of the following functional parameters of the system: an electrical parameter such as voltage, current or energy balance or a stimulation parameter in relation to the system.

Use

Once the system according to the invention has been properly installed, the flow control device can be used for emptying the reservoir implanted in the patient.

Exit and Entry Valve

More specifically, where the flow control device comprises an exit valve preventing intestinal contents flow from the reservoir in its closed position, the method of use comprises the steps of opening the exit valve and then emptying the reservoir. Where in addition to the exit valve an entry valve is provided allowing intestinal contents to flow towards the reservoir in its open position, the method further comprises the step of closing the entry valve before emptying the reservoir.

According to one embodiment, the patient's intestine will be constricted by means of the exit valve so as to prevent intestinal contents flow through the constricted intestine section while the reservoir is not to be emptied. In addition, the patient's intestine may be constricted by means of the entry valve so as to prevent intestinal contents flow through the constricted intestine section while the reservoir is to be emptied.

As mentioned before, the step of constricting may comprise the step of electrically stimulating muscle or neural tissue of the intestine section to cause at least partial contraction of the intestine section, preferably by applying electric pulses to the intestine section. More preferably, different portions of the intestine section may be stimulated over time. This specifically allows for stimulating, over time, the different portions of the intestine section in a wave like manner in a direction opposite to natural intestinal contents flow, thereby supporting the closing function of the valve.

As mentioned before, constriction may also be achieved by mechanically constricting the intestine section at least partly. Where this is combined with electrically stimulation, it is preferred that the steps of mechanically constricting and electrically stimulating are performed on the same intestine section. More specifically, in order to empty the reservoir intestinal contents along the intestine section can be pumped by, over time, electrically stimulating different portions of the intestine section in a wave like manner in a direction of natural intestinal contents flow, when said mechanical constriction of the intestine section is released.

Where a valve, in particular the exit valve, comprises a hydraulic compartment, the method of use may involve the step of filling or emptying the compartment with hydraulic fluid in order to change its open-closed-state.

As mentioned before, in a simple embodiment, a conduit may be inserted from outside the patient's body into the intestine, thereby mechanically urging the exit valve to open, when emptying of the reservoir is desired.

Pump

Emptying the reservoir by means of a pump may involve the step of acting on a wall of the reservoir by means of the pump so as to reduce the reservoir's volume, thereby emptying the reservoir.

Where the pump and the reservoir are separate from each other and where the pump is furthermore implanted inside the patient's body outside the patient's intestine and comprises at least one electrical stimulation device, the method of use may comprise the steps of electrically stimulating muscle or neural tissue of an intestine section by means of the stimulation device so as to cause at least partial contraction of the intestine section, preferably by applying electric pulses to the intestine section. Again, the step of emptying the reservoir may comprise pumping intestinal contents along the intestine section by, over time, stimulating the different portions of the intestine section in a wave like manner in a direction of natural intestinal contents flow.

The intestinal contents may likewise be pumped along the intestine section by, over time, constricting different portions of an intestine section in a wave like manner in the direction of natural intestinal contents flow by means of a constriction device which is adapted to at least partly constrict the intestine section mechanically. Where the stimulation device is combined with such constriction device, pumping of the intestinal contents along the intestine section by, over time, stimulating the different portions of the intestine section in a wave like manner in a direction of natural intestinal contents flow may be performed, while constriction of the intestine section caused by the constriction device is released at the respective portions.

The pump may be activated by manually operating a subcutaneously arranged actuator from outside the patient's body.

Where a conduit is inserted from outside the patient's body into the intestine, thereby mechanically urging the exit valve to open when emptying the reservoir and where such conduit provides a flow passage to an external collecting device comprising a suction pump, the method of use further comprises the step of emptying the reservoir by means of the suction pump.

Motor

The suction pump may preferably be driven by means of a motor. Also, at least the exit valve is preferably driven between its closed and open positions by means of at least one motor implanted in the patient's body. Similarly, the pump is preferably driven by means of a motor implanted in the patient's body.

In either case, the motor is preferably activated from outside the patient's body by operating a subcutaneously arranged switch.

Energy

As mentioned before, energy may be transmitted from outside the patient's body to at least one implanted energy consuming part of the system, preferably in the form of wireless energy. This may involve the following additional steps:
transforming the wirelessly transmitted energy into electric energy by means of an energy transforming device,
storing the transformed energy in an energy storage means, and
supplying the stored energy from the energy storage means to at least one implanted energy consuming part of the system.

Again, energy may be supplied wirelessly from the storage means to the energy consuming part.

Preferably, at least part of the wirelessly transmitted energy is transformed into electric energy and used for the energy consuming part of the system as said part of the wirelessly transmitted energy is transformed into the electric energy.

Control

Where a first part of a control unit for controlling at least one energy consuming part of the system is implanted inside the patient's body, the method of use may further comprise the step of using the external second part of the control unit to transmit data to the implanted first part of the control unit. Preferably, the data are transmitted to the implanted first part of the control unit in the same manner as energy is transmitted to the implanted energy consuming part. More particularly, the data are preferably transmitted wirelessly to the implanted first part of the control unit. This may involve a wireless control signal.

For instance, the implanted first part of the control unit can be programmed via the external second part of the control unit. Furthermore, a feedback signal may be transmitted from the implanted first part of the control unit to the external second part of the control unit.

Sensor

Where one or more of the afore-mentioned sensors are provided, the method of use may comprise the step of sensing a physical parameter in the patient's body and/or a functional parameter of the system in the patient's body, such as one or more of the following parameters: a pressure within the reservoir, a pressure within the patient's intestine, an expansion of the reservoir, a distension of an intestinal wall of the patient's intestine, a pressure against a part of the system such as the reservoir, a distension of a part of the system such as a wall of the reservoir, an electrical parameter such as voltage, current or energy balance, a position or movement of a movable part of the system, any stimulation parameter in relation to the system.

A signal, such as a sound signal or a visual signal, may be provided when a value for the physical parameter sensed is beyond a predetermined threshold value.

Intestinal Disorder (II)

"Artificial Intestine Section with Wirelessly Charged Accumulator"

Another object of the present invention is to provide a method for treating a patient having a disorder related to the patient's intestine.

In accordance with this object, there is provided an intestinal disorder treatment method for treating a patient having a disorder related to the patient's intestine. The method comprises
surgically creating at least one opening in the patient's intestine,
providing an artificial intestine section having a first open end portion and a second open end portion in fluid communication with one another,
connecting at least the first open end portion of the artificial intestine section to the surgically created opening in the patient's intestine,
implanting an accumulator for accumulating energy,
wirelessly charging the accumulator with energy, and
supplying energy from the accumulator directly or indirectly to at least one energy consuming part of the artificial intestine section.

Lateral Connection to Intestine

Preferably, at least the first open end portion and possibly also the second open end portion of the artificial intestine section are connected to a lateral opening surgically created in a wall of the patient's intestine. Thus, rather than connecting the artificial intestine section to the cross-sectional end of the patient's intestine, it is connected to a lateral opening in the patient's intestinal wall, and for this purpose the respective open end portion of the artificial intestine section is specifically designed.

By connecting the artificial intestine section laterally to the intestine, forces caused by the peristaltic movement of the intestine and acting on the artificial intestine section of the intestine are largely avoided. More specifically, where the artificial intestine section is connected to the cross-sectional opening of the intestine, the peristaltic waves of the intestine tend to pull the intestine off of the connection between the intestine and the artificial intestine section. As compared to this, where the artificial intestine section is attached to an opening in the lateral wall of the intestine, the peristaltic waves pass the artificial intestine section substantially without any impact on the connection between the intestinal wall and the artificial intestine section.

Structure of Lateral Attachment

In order to securely attach the artificial intestine section to the lateral opening, at least the first open end portion may comprise a shoulder portion formed around the end portion for lateral connection to the patient's intestinal wall. Preferably, at least a part of the shoulder portion extends laterally from the artificial intestine section by 3 mm to 20 mm. Furthermore, the shoulder portion preferably has a curved cross section, so as to generally conform to the intestinal wall when laterally attached thereto. An open end portion adapted in this way can advantageously be attached to the intestinal wall from the outside thereof.

The shoulder portion may be split into an upper and a lower shoulder portion with a gap between the upper and lower shoulder portions for accommodating intestinal wall tissue therein. The lower shoulder portion, if suitably adapted, can then be placed inside the patient's intestine through the surgically created lateral wall opening, whereas the upper shoulder portion will be placed outside the intestinal wall.

In order to allow the lateral wall opening to be easily stretched over the lower shoulder portion when the lower shoulder portion is advanced there through and yet in order to have a large contact area between the intestinal wall and the shoulder portion, the upper shoulder portion may be made larger than the lower shoulder portion. Thus, the surface area of the upper shoulder portion contacting the intestinal wall is also larger than the surface area of the lower shoulder portion contacting the intestinal wall.

The open end portion for lateral connection to the patient's intestinal wall may be connected to the patient's intestinal wall by gluing. For instance, it may have a particular rough surface structure for the glue to better adhere. Also, the open end portion may be connected to the patient's intestinal wall by sewing. For instance, a certain area of the shoulder portion may be perforated for stitching through the perforations or may be made from a material which is easy to penetrate with a needle. Similarly, the open end portion may specifically be connected to the patient's intestinal wall by stapling.

Frontal Connection to Intestine

While it is generally preferred to connect the first and possibly also the second open end portion of the artificial intestine section laterally to an opening in the patient's intestinal wall, it is as well possible to adapt the open end portion to be connected to a cross-sectional opening surgically created in the patient's intestine.

Structure of Frontal Attachment (Bulge/Sleeve)

In this case, the open end portion of the artificial intestine section preferably includes a conduit having an outer surface with at least one bulge extending outwardly from the conduit's outer surface in a circumferential direction of the conduit about at least a part of the conduit's circumference, and a blocking ring loosely fitting over the outer surface of the conduit with a clearance between the outer surface and the blocking ring for mounting intestinal tissue within the clearance, said blocking ring having an inner cross sectional diameter which is smaller than or substantially identical to an outer cross sectional diameter of the at least one bulge so as to prevent the blocking ring from slipping over the bulge when intestinal tissue is mounted within the clearance.

The artificial intestine section may then be affixed to the cross-sectional opening of the intestine part by inserting the artificial intestine section having a bulge formed on the outside thereof into the cross-sectional opening of the intestine part so that the intestine part extends over the bulge from one side of the bulge and advancing a blocking ring over the intestine part towards the bulge from the respective other side of the bulge such that the intestine part is located intermediate the outer surface of the artificial intestine section and the blocking ring.

Alternatively, the open end portion may include a conduit having an outer surface and a flexible sleeve adapted to axially extend and closely fit around at least part of said outer surface of the conduit. The flexible sleeve can be mounted on said outer surface either folded or rolled upon itself or so as to be foldable upon itself. In either case, the open end portion of the artificial intestine section may then be affixed to the cross-sectional opening of the intestine part by inserting the open end portion of the artificial intestine section into the cross-sectional opening of the intestine part and placing the flexible sleeve so as to extend over both the intestine part and open end portion of the artificial intestine section such that the intestine part is located intermediate the sleeve and the outer surface of the artificial intestine section.

Where the flexible sleeve is mounted on the outer surface of the open end portion of the artificial intestine piece so as to be foldable upon itself, the step of placing the flexible sleeve so as to extend over both the intestine part and open end portion of the artificial intestine section comprises folding the flexible sleeve upon itself such that the intestine part is located intermediate the folded sleeve.

The bulge and sleeve may also be provided on one conduit so as to be used in combination.

The afore-mentioned conduit of the artificial intestine section with a sleeve or with a bulge serve to improve the strength of the connection against axial forces which may e.g. result from the peristaltic movement of the intestine and tend to pull on the intestine.

Furthermore, the conduit of the open end portion preferably comprises a multilayer material. For instance, it is advantageous when the open end portion comprises a porous ingrowth layer that allows ingrowth of living tissue. The ingrowth layer may have a net-like structure and is most preferably made from Dacron®.

Through-Flow Arrangement

Straight Connection/By-Pass Connection

According to the afore-described structures of the first and second open end portions of the artificial intestine section, it is possible to connect both the first and second open end portions to a surgically created cross-sectional opening in the patient's intestine, so as to form an intermediate intestine section, or to connect both the first and second open end portions to a surgically created lateral opening in a wall of the patient's intestine, so as to form a by-pass intestine section.

Stoma/Anus Connection

Alternatively, the second open end portion may be connected to an surgically created stoma or to the patient's rectum or anus or to tissue adjacent the patient's anus, so as to form an intestine end section.

Downstream Connection to Residual Intestine

Further alternatively, the second open end portion may be connected to a portion of the patient's small intestine or to a portion of the patient's large intestine, as the case may be, and this portion of the patient's intestine may then lead to the surgically created stoma or to the patient's rectum or anus or to tissue adjacent the patient's anus.

Material

Preferably, at least the first open end portion is made from a biocompatible material. The biocompatible material of the open end portion may comprise at least one material of the following group of materials: titanium, stainless steel, ceramics, biocompatible polymer material. More specifically, the biocompatible polymer material may comprise at least one polymer of the following group of polymers: polytetrafluoroethylene, silicone, polyurethane, expanded polytetrafluoroethylene (ePTFE).

Intest. Content Interacting Device as an Energy Consuming Part

The at least one energy consuming part of the artificial intestine section comprises at least one element adapted to directly or indirectly interact with intestinal contents contained in the artificial intestine section between the first and second open end portions thereof.

Flow Control Device as an Energy Consuming Part

In a more advanced alternative, the at least one element may include a flow control device adapted to control flow of intestinal contents from the artificial intestine section through the second open end portion. The flow control device is preferably adapted to prevent flow of intestinal contents from the artificial intestine section through the second open end portion.

Exit Valve as Flow Control Device

The flow control device preferably includes at least one valve, including an exit valve preventing intestinal contents flow through the second open end portion in its closed position. Preferably, the exit valve is a normally closed valve so that no energy is needed to keep the valve closed during the system's inactive periods.

Entry Valve as an Additional Part of the Flow Control Device

In addition, the flow control device may include an entry valve allowing intestinal contents to flow towards the reservoir in its open position. This can be advantageous particularly during the emptying of the reservoir, when the entry valve should be closed. Therefore, the entry valve is preferably a normally open valve. Accordingly, the exit valve and the entry valve are preferably adapted to cooperate such that when one of the two valves is closed, the respective other valve is open, and vice versa.

Valve Types

As regards the various valve types that may be employed, the at least one valve may e.g. include a compartment with a variable volume adapted to open and close the valve by changing the compartment's volume. Advantageously, the at least one valve includes at least one passage for filling and emptying the compartment with hydraulic fluid. The compartment preferably has at least one flexible wall defining an opening for a conduit to pass through, the opening being adapted to close upon increase of the compartment's volume.

According to a different alternative, the at least one valve may be a flap valve. The flap valve may for instance comprise a rotatable disc.

Extra Valve Separate from Artificial Intestine Piece

While the valve or valves preferably make an integral part of the artificial intestine section, the artificial intestine section may further include one or more extra valves adapted to control flow of intestinal contents in a natural section of the patient's intestine upstream and/or downstream the artificial intestine section. The extra valve may be rigidly connected to the artificial section but may as well form a completely separate part. The extra valve is implanted inside the patient's body outside a section of the patient's natural intestine and includes at least one element acting on the natural intestine section from the outside thereof so as to prevent intestinal contents flow through the natural intestine section. This valve arrangement does not require any surgery on the respective part of the natural intestine when the valve is implanted.

The extra valve may include at least one electrical stimulation device adapted to electrically stimulate muscle or neural tissue of an intestine section so as to cause at least partial contraction of the natural intestine section. This is a very gender way of constricting the intestine. The stimulation device preferably includes at least one electrode adapted to apply electric pulses to the natural intestine section.

It is particularly advantageous to make use of a stimulation device which is adapted to stimulate different portions of the intestine section over time. Thus, different portions of the intestine section can be constricted by stimulation at different times in any predetermined stimulation pattern, thereby giving the intestine portions currently not stimulated time to recover and, thus, improving the blood circulation in the respective intestine section.

Furthermore, the stimulation device can specifically be adapted to stimulate, over time, the different portions of the intestine section in a wave like manner in a direction opposite to natural intestinal contents flow. As a result, the valve counteracts the natural intestinal contents flow, thereby improving the valve's closing function.

Alternatively, or preferably in addition to the stimulation device, the at least one valve may include a constriction device implanted in the patient's body for at least partly constricting the natural intestine section mechanically from outside the natural intestine section. Where the stimulation device is combined with the constriction device, the stimulation device and the constriction device preferably act on the same intestine section. In that case, it is advantageous if the constriction device in its normal condition constricts the natural intestine section only partly, in order not to damage the intestine over time. Complete constriction and, thus, closing of the intestine may then be obtained by additionally stimulating the natural intestine section in a manner as described before.

In addition, when constriction of the intestine section caused by the constriction device is released, the stimulation device may, if accordingly adapted, be used to pump intestinal contents along the natural intestine section by, over time, stimulating the different portions of the natural intestine section in a wave like manner in a direction of natural intestinal contents flow. In this situation, the valve may incorporate the additional function of a pump for actively supporting the discharge of feces from the human body.

Pump as an Energy Consuming Part

The at least one energy consuming part of the artificial intestine section may include a pump for advancing intestinal contents through the second open end portion to outside the artificial intestine section.

Pump with Reservoir

In addition to the pump, the artificial intestine section may include a reservoir between the first and second open end portions for receiving and temporarily collecting therein intestinal contents supplied through the first open end portion. In this case, the pump is preferably adapted for emptying the reservoir through the second open end portion. A variety of different structures may be realized.

For instance, the reservoir may be formed by a bellow, said bellow having an end wall closing the bellow at one end thereof. The end wall may then make part of the pump such that a volume of the bellow is reduced upon advancement of said end wall. Preferably, bellow is made of a resilient material so as to urge the bellow into a normally expanded position.

In another embodiment, the pump may include a movable piston, with a front end of the piston extending into the reservoir such that a volume of the reservoir is reduced upon advancement of the piston. Preferably, the piston is spring loaded so as to urge the piston into a normally retracted position.

Alternatively, the pump may be permanently arranged inside the reservoir.

In a further alternative, the reservoir may have a flexible wall and the pump is adapted for emptying the reservoir by squeezing the reservoir. In this case, the pump may e.g. include a constriction device adapted to alternately constrict and release sections of the reservoir so as to pump intestinal contents along the reservoir by, over time, constricting different sections of the reservoir in a wave like manner. More specifically, the reservoir may have a tube-like form and a roller pump may be used as the pump acting on the tube-like reservoir from the outside thereof.

Motor as an Energy Consuming Part

Where the valves or pump or any other energy consuming part of the artificial intestine section is not or not only manually drivable, the artificial intestine section may comprise at least one motor arranged for automatically driving at least one energy consuming part of the artificial intestine section. The motor is preferably arranged to be driven by electric or electromagnetic energy.

A motor in the sense of the present invention is a device that transforms energy other than mechanical energy into mechanical energy. While a pump in the sense of the present invention is a device for advancing liquid or pasty material, a pump may at the same time be a motor in certain circumstances, such as where the transformation of energy into mechanical energy causes advancement of the liquid or pasty material without any intervening mechanical means such as a piston, bellow or the like.

For instance, the at least one motor can be arranged for driving at least one of the valve or valves, respectively, between its closed and open position. Also, the at least one motor can be arranged for driving the pump.

A manually operable switch may be provided for activating the at least one motor, the switch being preferably arranged for subcutaneous implantation so as to be operable from outside the patient's body.

Energy Transmission

Where energy is not transmitted wirelessly, galvanic coupling elements may be provided at least between the accumulator and the energy consuming part, in particular the motor, for transmitting energy to the motor in contacting fashion.

The energy may alternatively be transmitted wirelessly from the accumulator to the motor. Thus, the energy source may comprise a wireless energy transmitter adapted to wirelessly transmit energy from the accumulator to the energy consuming part.

Preferably, in order to reduce the number of parts and possibly increase the system's efficiency, the energy consuming part, in particular the motor, can be adapted to directly transform the wirelessly transmitted energy from the accumulator into kinetic energy. In the alternative, the energy consuming part will have to include a transforming device for transforming the wirelessly transmitted energy from the accumulator into electric energy.

Similarly, the system preferably includes an implantable energy transforming device for transforming the wirelessly transmitted energy from outside the patient's body into energy to be stored in the accumulator, and a wireless energy transmitter adapted to wirelessly transmit energy from outside the patient's body to said implantable energy transforming device.

It is further preferred to set up the system such that the energy consuming part is driven with the electric energy, as said energy transforming device transforms the wireless energy into the electric energy.

The energy transmitter can be adapted to generate an electromagnetic field, a magnetic field or an electrical field. The wireless energy may be transmitted by the energy transmission device by at least one wireless signal. More specifically, the energy transmitter may be adapted to transmit the energy by at least one wireless energy signal, which may comprise an electromagnetic wave signal, including at least one of an infrared light signal, a visible light signal, an ultra violet light signal, a laser signal, a microwave signal, an X-ray radiation signal, and a gamma radiation signal. Also, the wireless energy signal may comprise a sound or ultrasound wave signal. Furthermore, the wireless energy signal may comprise a digital or analog signal or a combination thereof.

Energy Transmission Feedback

A feedback subsystem, which can make part of a control device described subsequently, can advantageously be provided to wirelessly send feedback information related to the energy to be stored in the accumulator from inside the human body to the outside thereof. The feedback information is then used for adjusting the amount of wireless energy transmitted by the energy transmitter. Such feedback information may relate to an energy balance which is defined as the balance between an amount of wireless energy received inside the human body and an amount of energy consumed by the at least one energy consuming part. Alternatively, the feedback information may relate to an energy balance which is defined as the balance between a rate of wireless energy received inside the human body and a rate of energy consumed by the at least one energy consuming part.

Accumulator

The accumulator preferably comprises a rechargeable battery. It may alternatively or in addition comprise a capacitor. The accumulator may be implanted inside the patient's body either fixedly connected to the artificial intestine section or distant to the artificial intestine section.

Primary Energy Source

A primary energy source may be provided for charging the accumulator with energy from outside the patient's body. The primary energy source is preferably adapted to be mounted on the patient's body.

Control Unit

It is advantageous to provide a control unit adapted to directly or indirectly control one or more elements of the system, such as for controlling opening of the exit valve and/or closing of the entry valve, in particular in a manner such that when one of the two valves is closed, the respective other valve is open, and vice versa. The control unit can also be adapted to control actuation of the pump.

The control unit is preferably operable by the patient, e.g. particularly in order to empty the reservoir.

At least part of the control unit may be adapted to be implantable in the patient's body. For instance, a manually operable switch may be provided for activating the control unit, the switch preferably being arranged for subcutaneous implantation so as to be operable from outside the patient's body. Also, the control unit may comprise a first part adapted for implantation in the patient's body and a second part adapted to cooperate with the first part from outside the patient's body. In this case, the control unit can be adapted to transmit data from the external second part of the control unit to the implanted first part of the control unit in the same manner as energy is transmitted by said wireless energy transmitter from outside the patient's body to said implantable energy transforming device.

That is, the second part of the control unit may be adapted to wirelessly transmit a control signal to the implantable first part of the control unit for controlling the at least one energy consuming part from outside the patient's body. Also, the implantable first part of the control unit may be programmable via the second part of the control unit. Furthermore, the implantable first part of the control unit may be adapted to transmit a feedback signal to the second part of the control unit.

Sensor

Furthermore, a physical parameter sensor adapted to directly or indirectly sense a physical parameter of the patient can be provided. The physical parameter sensor may be adapted to sense at least one of the following physical parameters of the patient: a pressure within the artificial intestine section, a pressure within the patient's natural intestine, an expansion of the artificial intestine section, a distension of an intestinal wall of the patient's natural intestine, a movement of the patient's intestinal wall.

Similarly, a functional parameter sensor adapted to directly or indirectly sense a functional parameter of the system can be provided, wherein the functional parameter sensor may be adapted to sense at least one of the following functional parameters of the system: a pressure against a part of the system such as the artificial intestine section, a distension of a part of the system such as a wall of the artificial intestine section, an electrical parameter such as voltage, current or energy balance, a position or movement of a movable part of the system.

Preferably, an indicator is coupled to the sensor or sensors, the indicator being adapted to provide a signal when a sensor senses a value for the parameter beyond a predetermined threshold value. The sensor signal may comprise at least one of the following types of signals: a sound signal, a visual signal.

Method of Treatment (Implantation)

Specifically, there is provided a surgical method for treating a patient according to the invention, comprising the steps of:
cutting the patient's skin and abdominal wall,
dissecting an area of the patient's intestine,
surgically creating at least one opening in the dissected intestinal area so as to create an artificial intestinal opening,
providing an artificial intestine section having a first open end portion and a second open end portion in flow communication with one another and affixing the first open end portion to the artificial intestinal opening so as to be in flow communication therewith,
providing an accumulator adapted to be charged wirelessly with energy from outside the patient's body and arranging the accumulator inside the patient's body so as to allow for supplying energy directly or indirectly from the accumulator to at least one energy consuming part of said artificial intestine section, and
suturing the abdominal wall and skin.

A corresponding laparoscopic surgical method of treating a patient comprises the steps of:
making a small opening in the patient's skin and abdominal wall,
introducing a needle in the abdominal cavity, inflating the abdominal cavity with gas,
inserting at least one trocar into the cavity,
introducing a camera through the trocar,
inserting at least one dissecting instrument preferably through a second trocar,
dissecting an area of the intestine,
surgically creating at least one opening in the dissected intestinal area so as to create an artificial intestinal opening,
providing an artificial intestine section having a first open end portion and a second open end portion in flow communication with one another and affixing the first open end portion to the artificial intestinal opening so as to be in flow communication therewith,
providing an accumulator adapted to be charged wirelessly with energy from outside the patient's body and arranging the accumulator inside the patient's body so as to allow for supplying energy directly or indirectly from the accumulator to at least one energy consuming part of said artificial intestine section, and
extracting the instruments, camera and trocar, and in relation thereto
suturing, if necessary, the abdominal wall and permanently closing the skin.

Where the accumulator is provided fixedly connected to the artificial intestine section, it may be arranged inside the patient's body along with the artificial intestine section. Alternatively, where the accumulator is provided separate from the artificial intestine section, it may be implanted inside the patient's body distant to the artificial intestine section.

Where energy is not transferred wirelessly from the accumulator to the energy consuming part of the artificial intestine section, the accumulator may be galvanically coupled to the artificial intestine section for transmitting the energy to the at least one energy consuming part of the artificial intestine section in contacting fashion.

Dividing the Intestine

The method of implantation may involve dividing the intestine so as to obtain one or two cross-sectional opening of the intestine. The method of implantation may then comprise the following additional steps:
dissecting a portion of the dissected intestinal area downstream of the intestinal opening to be created, such that intestinal mesentery connected to the dissected portion is opened in such a way that supply of blood through the mesentery to the dissected intestinal area is maintained as far as possible on both sides of the dissected portion, and
dividing the patient's intestine in the dissected portion so as to create an upstream part of the intestine with an artificial intestinal opening being formed as a cross-sectional opening at the downstream side thereof and a downstream part of the intestine with an artificial intestinal opening being formed as a cross-sectional opening at the upstream side thereof, wherein the mesentery maintains a tissue connection between the upstream and downstream intestine parts.

Frontal Connection at Upstream End

At least the first open end portion of the artificial intestine section can then be affixed to the cross-sectional downstream opening of the upstream intestine part so as to be in flow communication therewith.

Frontal Connection at Downstream End

Also, the second open end portion of the artificial intestine section can be affixed to the cross-sectional upstream opening of the downstream intestine part so as to be in flow communication therewith.

Frontal Connection at Both Ends

Where the artificial intestine piece is to be connected to both cross-sectional openings of the divided intestine, the method may comprise the two afore-mentioned steps in combination, i.e. affixing the first open end portion of the artificial intestine section to the cross-sectional downstream opening of the upstream intestine part so as to be in flow communication therewith and affixing the second open end portion of the artificial intestine section to the cross-sectional upstream opening of the downstream intestine part so as to be in flow communication therewith.

Frontal Connection Upstream, Lateral Connection Downstream

Alternatively, the second open end portion of the artificial intestine section may be connected to a lateral opening in the wall of the downstream intestine part, in which case the method of implantation may comprise the following steps:

closing the cross-sectional opening at the downstream side of the upstream intestine part, surgically creating an opening in a wall of the upstream intestine part so as to create a lateral intestinal opening therein, affixing the first open end portion of the artificial intestine section to the lateral intestinal opening of the upstream intestine part so as to be in flow communication therewith and affixing the second open end portion of the artificial intestine section to the cross-sectional upstream opening of the downstream intestine part so as to be in flow communication therewith.

Sleeve/Bulge Connector for Frontal Connection

The step of affixing the open end portion of the artificial intestine section to the cross-sectional opening of the intestine part preferably comprises:

inserting the open end portion of the artificial intestine section into the cross-sectional opening of the intestine part, and placing a flexible sleeve so as to extend over both the intestine part and open end portion of the artificial intestine section such that the intestine part is located intermediate the sleeve and the outer surface of the artificial intestine section.

Where the flexible sleeve is mounted on the outer surface of the open end portion of the artificial intestine piece so as to be foldable upon itself and wherein the step of placing the flexible sleeve so as to extend over both the intestine part and open end portion of the artificial intestine section comprises folding the flexible sleeve upon itself such that the intestine part is located intermediate the folded sleeve.

Alternatively, or in addition, the step of affixing the open end portion of the artificial intestine section to the cross-sectional opening of the intestine part comprises:

inserting the artificial intestine section having a bulge formed on the outside thereof into the cross-sectional opening of the intestine part so that the intestine part extends over the bulge from one side of the bulge, and advancing a blocking ring over the intestine part towards the bulge from the respective other side of the bulge such that the intestine part is located intermediate the outer surface of the artificial intestine section and the blocking ring.

The afore-mentioned open end portion of the artificial intestine section with a sleeve or with a bulge serve to improve the strength of the connection against axial forces which may e.g. result from the peristaltic movement of the intestine and tend to pull on the intestine. The open end portion of the artificial intestine section may also combine a sleeve and a bulge.

Lateral Connection Upstream, Frontal Connection Downstream

It has been described above that the second open end portion of the artificial intestine section may be connected to a lateral opening in the wall of the downstream intestine part while the first open end portion is connected to a cross-sectional opening of the upstream intestine part. The connection can alternatively be made vice versa, in which case the method of implantation may comprise the following steps:

closing the cross-sectional opening at the upstream side of the downstream intestine part, surgically creating an opening in a wall of the downstream intestine part so as to create a lateral intestinal opening therein, affixing the second open end portion of the artificial intestine section to the lateral intestinal opening of the downstream intestine part so as to be in flow communication therewith and affixing the first open end portion of the artificial intestine section to the cross-sectional downstream opening of the upstream intestine part so as to be in flow communication therewith.

Lateral Connection at Both Ends

Of course, it is also possible and even preferred to connect both open end portions of the artificial intestine piece to lateral openings in the intestinal wall, in which case the method of implantation may comprise the following steps:

closing the cross-sectional opening at the downstream side of the upstream intestine part, surgically creating an opening in a wall of the upstream intestine part so as to create a lateral intestinal opening therein, affixing the first open end portion of the artificial intestine section to the lateral intestinal opening of the upstream intestine part so as to be in flow communication therewith closing the cross-sectional opening at the upstream side of the downstream intestine part, surgically creating an opening in a wall of the downstream intestine part so as to create a lateral intestinal opening therein and affixing the second open end portion of the artificial intestine section to the lateral intestinal opening of the downstream intestine part so as to be in flow communication therewith.

Lateral Connection at Both Ends without Dividing Intestine

It is also possible to connect both open end portions of the artificial intestine piece to lateral openings in the intestinal wall without dividing the intestine, in which case the step of surgically creating at least one opening in the dissected intestinal area comprises the steps of surgically creating a first opening in a wall of the intestine so as to create a first lateral intestinal opening and surgically creating a second opening in the wall of the intestine at a location downstream of the first opening so as to create a second lateral intestinal opening, and the method of implantation then further comprises the steps of:

permanently closing the patient's intestine at a location between the first and second lateral intestinal openings so as to form an upstream intestinal part upstream said permanent closure and a downstream intestinal part downstream said permanent closure, affixing the first open end portion of the artificial intestine section to the first lateral intestinal opening and affixing the second open end portion of the artificial intestine section to the second lateral intestinal opening.

Structure of Lateral Attachment

Where the open end portion of the artificial intestine section is to be affixed to a lateral intestinal opening so as to be in flow communication therewith, this may comprise the step of connecting the afore-mentioned shoulder portion, which is formed around the open end portion, to the patient's intestinal wall so as to surround the lateral intestinal opening. In particular, the step of affixing the open end portion to the intestine may comprise attaching the shoulder portion to the patient's outer intestinal wall.

Alternatively, where the shoulder portion is split into an upper and a lower shoulder portion with a gap between the upper and lower shoulder portions, the step of affixing the open end portion of the artificial intestine section to the lateral intestinal opening comprises placing the lower shoulder portion inside the patient's intestine and the upper shoulder portion outside the patient's intestine such that intestinal wall tissue is accommodated in the gap.

The step of affixing the open end portion of the artificial intestine section to the lateral intestinal opening may comprise gluing, sewing and/or stapling the open end portion to the patient's intestinal wall.

Exit Through Stoma

As mentioned before, the downstream intestinal part may be connected to a surgically created stomy or to the patient's rectum or anus or to tissue adjacent the patient's anus. In the case of a connection to a stomy, this would involve the following steps:

cutting the patient's skin and abdominal wall so as to create an opening for an intestinal stomy,
dissecting the area of the stomy opening,
dividing the intestine at a location downstream of the artificial intestine section so as to create an upstream natural intestine section having a cross-sectional opening at the downstream end thereof and a downstream natural intestine section,
dissecting the mesentery of the upstream natural intestine section in the area of the cross-sectional opening thereof to prepare for creating the intestinal stomy,
advancing the downstream end of the upstream natural intestine section through the abdominal wall and skin, and
suturing the cross-sectional opening of the upstream natural intestine section to the skin with the intestinal mucosa turned inside out, thereby achieving the intestinal stomy.

Exit Through Anus

In the case of a connection to the patient's anus or to tissue adjacent the patient's anus, this would involve the following steps:

dividing the intestine at a location downstream of the artificial intestine section so as to create an upstream natural intestine section having a cross-sectional opening at the downstream end thereof and a downstream natural intestine section leading to the patient's anus,
dissecting the area of the patient's anus and surgically separating the downstream natural intestine section from the patient's anus, whereas the steps of dividing the intestine and separating the intestine section leading to the patient's anus can alternatively be carried out in reversed order,
dissecting the mesentery of the upstream natural intestine section in the area of the cross-sectional opening at the downstream end thereof to prepare for connecting the upstream natural intestine section to the patient's anus or tissue adjacent the patient's anus,
advancing the downstream end of the upstream natural intestine section through the patient's anus, and
suturing the cross-sectional opening of the upstream natural intestine section to the patient's anus or tissue adjacent the patient's anus.

Depending upon the circumstances, the step of dividing the intestine so as to form the upstream natural intestine section may be performed either on the patient's small intestine or on the patient's large intestine.

Intest. Content Interacting Device as an Energy Consuming Part (Flow Control Device/Exit Valve/Entry Valve/Pump/Reservoir)

As mentioned before, the artificial intestine section or system may include at least one energy consuming part adapted to directly or indirectly interact with intestinal contents contained in the artificial intestine section between the first and second open end portions thereof. This element will be implanted along with the artificial intestine section. As also mentioned before, the energy consuming part may comprise a flow control device adapted to control flow of intestinal contents from the artificial intestine section through the second open end portion.

Again, the flow control device may comprise an exit valve preventing intestinal contents flow through the second open end portion in its closed position and may additionally comprise an entry valve allowing intestinal contents to flow through the first open end portion into the artificial intestine section in its open position.

Alternatively or in addition, as also mentioned before, the flow control device may include a pump for advancing intestinal contents through the second open end portion to outside the artificial intestine section.

If a reservoir is provided between the first and second open end portions for receiving and temporarily collecting therein intestinal contents supplied through the first open end portion, the pump may be adapted to empty the reservoir through the second open end portion.

Furthermore, where the pump comprises a manually operable switch for activating the pump, the method of implantation may further comprise the step of implanting the switch subcutaneously so as to be operable from outside the patient's body.

Motor

Again, at least one motor may be implanted along with the artificial intestine section and may be arranged for automatically driving one or more energy consuming part of the flow control device. Where the motor comprises a manually operable switch for activating the motor, the method of implantation may further comprise the step of implanting the switch subcutaneously so as to be operable from outside the patient's body.

Energy Transmission

Where energy is transmitted wirelessly, for instance from outside the patient's body to inside the patient's body either to an energy consuming part and/or more specifically to be stored in the accumulator or from the accumulator to the energy consuming part, it may further be necessary to implant an energy transforming device for transforming the wireless energy into electric energy. Alternatively or in addition, galvanic coupling elements may be implanted, e.g. for transmitting energy to the energy consuming part in contacting fashion from the implanted energy source.

Accumulator

Preferably, at least one rechargeable battery is provided as the accumulator. Alternatively or in addition thereto, at least one capacitor may be provided as the accumulator.

Control Unit

Furthermore, as mentioned previously, at least a part of a control unit may be implanted inside the patient's body adapted to directly or indirectly control one or more of the elements that have also been implanted in the patient's body. Where the control unit comprises a manually operable switch for activating the control unit, the method of implantation may further comprise the step of implanting said switch subcutaneously so as to be operable from outside the patient's body.

Sensor

As mentioned before, one or more physical and/or functional parameter sensors may be implanted to directly or indirectly sense physical and/or functional parameters inside the patient and in the system implanted inside the patient. Where the sensor is a pressure sensor, it may be placed in the artificial intestine section or the patient's natural intestine so as to sense the pressure within the artificial intestine section or patient's natural intestine, respectively. Where the sensor is a tension sensor, it may be placed in contact with the artificial intestine section or the patient's natural intestine so as to sense an expansion of the artificial intestine section or patient's natural intestine, respectively. Where the sensor is a movement sensor, it may be placed in contact with the artificial intestine section or the patient's natural intestine so as to sense movement of the artificial intestine section or patient's natural intestine, respectively. The functional sensor may be adapted to measure at least one of the following functional parameters: an electrical parameter such as voltage, current or energy balance or a stimulation parameter in relation to the system.

Use

Once the system described above has been properly installed and where the at least one energy consuming part of the artificial intestine section comprises at least one element adapted to directly or indirectly interact with intestinal contents contained in the artificial intestine section between the first and second open end portions thereof, the at least one element may be activated so as to interact with the intestinal contents.

Exit and Entry Valve

Where the at least one element comprises an exit valve preventing intestinal contents flow from the artificial intestine section through the second open end portion in its closed position, the method of use may further comprise the steps of opening the exit valve and then removing intestinal contents from the artificial intestine section. Furthermore, where the at least one element further comprises an entry valve allowing intestinal contents to flow through the first open end portion into the artificial intestine section in its open position, the method may further comprise the step of closing the entry valve before removing intestinal contents from the artificial intestine section.

Pump

Where the at least one element interacting with intestinal contents inside the artificial intestine piece comprises a pump, the method of use may further comprise the step of advancing intestinal contents from the artificial intestine section through the second open end portion thereof to outside the artificial intestine section by means of the pump. The pump may be activated by manually operating a subcutaneously arranged actuator from outside the patient's body.

Pump with Reservoir

More specifically, if the artificial intestine section comprises a reservoir between the first and second open end portions for receiving and temporarily collecting therein intestinal contents supplied through the first open end portion, the step of advancing intestinal contents to outside the intestine section may comprise operating the pump so as to empty the reservoir.

Where the reservoir is formed by a bellow, said bellow having an end wall closing the bellow at one end thereof and said end wall making part of the pump, the step of advancing the intestinal contents to outside the intestine section may comprise advancing the end wall so as to reduce a volume of the bellow.

Where the pump comprises a movable piston with a front end of the piston extending into the reservoir, the step of advancing the intestinal contents to outside the intestine section may comprise advancing the piston so as to reduce a volume of the reservoir.

Where the reservoir has a flexible wall, the step of advancing the intestinal contents to outside the intestine section may comprise squeezing the reservoir by means of the pump. For instance, the pump may include a constriction device, in which case the step of advancing the intestinal contents to outside the intestine section may comprise alternately constricting and releasing sections of the reservoir so as to pump the intestinal contents along the reservoir by, over time, constricting different sections of the reservoir in a wave like manner. More specifically, the reservoir may have a tube-like form and the pump can be a roller pump acting on the tube-like reservoir from the outside thereof.

Motor

Furthermore, where the at least one element interacting with intestinal contents inside the artificial intestine piece comprises a motor, the method of use may further comprise the step of driving at least the exit valve between its closed and open positions and/or driving at least the pump by means of the motor. In either case, the motor is preferably activated by manually operating a subcutaneously arranged actuator from outside the patient's body.

Energy

Again, energy is to be transmitted wirelessly from outside the patient's body to the accumulator. Therefore, upon charging the accumulator with energy, the method of use involves the following steps:

transmitting the energy wirelessly from outside the patient's body, transforming the wirelessly transmitted energy into energy to be stored in the accumulator by means of an energy transforming device implanted in the patient's body, and charging the accumulator with at least part of the transformed energy.

The method of use may then further involve the step of supplying energy from the accumulator to at least one implanted energy consuming part of the system, preferably wirelessly.

More preferably, at least part of the wirelessly transmitted energy is transformed into electric energy and used for the energy consuming part of the system, as said part of the wirelessly transmitted energy is transformed into the electric energy.

As mentioned before, the wireless energy can advantageously be transmitted by means of an electromagnetic field, a magnetic field or an electrical field. More specifically, the energy may be transmitted by at least one wireless energy signal, which may comprise an electromagnetic wave signal, including at least one of an infrared light signal, a visible light signal, an ultra violet light signal, a laser signal, a microwave signal, an X-ray radiation signal, and a gamma radiation signal. Also, the wireless energy signal may comprise a sound or ultrasound wave signal. Furthermore, the wireless energy signal may comprise a digital or analog signal or a combination thereof.

Control

Where a first part of a control unit for controlling at least one energy consuming part of the system is implanted inside the patient's body, the method of use may further comprise the step of using the external second part of the control unit to transmit data to the implanted first part of the control unit. Preferably, the data are transmitted to the implanted first part of the control unit in the same manner as energy is transmitted to the implanted energy consuming part. More particularly, the data are preferably transmitted wirelessly to the implanted first part of the control unit. This may involve a wireless control signal.

For instance, the implanted first part of the control unit can be programmed via the external second part of the control unit. Furthermore, a feedback signal may be transmitted from the implanted first part of the control unit to the external second part of the control unit.

Sensor

Where one or more of the afore-mentioned sensors are provided, the method of use may comprise the step of sensing a physical parameter in the patient's body and/or a functional parameter of the artificial intestine piece or system in the patient's body, such as one or more of the following parameters: a pressure within the artificial intestine section, a pressure within the patient's natural intestine, an expansion of the artificial intestine section, a distension of an intestinal wall of the patient's natural intestine, a movement of the patient's intestinal wall, a pressure against a part of the system such as the artificial intestine section, a distension of a part of the system such as a wall of the artificial intestine section, an electrical parameter such as voltage, current or energy balance, a position or movement of a movable part of the system.

A signal, such as a sound signal or a visual signal, may be provided when a value for the physical parameter sensed is beyond a predetermined threshold value.

Intestinal Disorder (III)

"Artificial Intestine Section"

Another object of the present invention is to provide a method for treating a patient having a disorder related to the patient's intestine.

In accordance with this object, there is provided an intestinal disorder treatment method for treating a patient having a disorder related to the patient's intestine. The method comprises surgically creating at least one opening in the patient's intestine, providing an artificial intestine section having a first open end portion and a second open end portion in fluid communication with one another, and connecting at least the first open end portion of the artificial intestine section to the surgically created opening in the patient's intestine.

Thus, rather than connecting the artificial intestine section to the cross-sectional end of the patient's intestine, it will be connected to a lateral opening in the patient's intestinal wall, and for this purpose the respective end portion of the artificial intestine section is specifically designed.

By connecting the artificial intestine section laterally to the intestine, forces caused by the peristaltic movement of the intestine and acting on the artificial intestine section of the intestine are largely avoided. More specifically, where the artificial intestine section is connected to the cross-sectional opening of the intestine, the peristaltic waves of the intestine tend to pull the intestine off of the connection between the intestine and the artificial intestine section. As compared to this, where the artificial intestine section is attached to an opening in the lateral wall of the intestine, the peristaltic waves pass the artificial intestine section substantially without any impact on the connection between the intestinal wall and the artificial intestine section.

The second open end portion of the artificial intestine section may be connected to a surgically created stomy or to the patient's rectum or anus or to tissue adjacent the patient's anus. Alternatively, since direct contact of the artificial intestine section with the patient's skin may cause inflammation and might not be acceptable on the long run for many reasons, it is likewise possible to design the second open end portion of the artificial intestine section so as to be connected to a portion of the large intestine or to a portion of the small intestine, as the case may be, and to connect that portion to the patient's rectum or anus or to tissue adjacent the patient's anus or to use that portion for creating a stomy.

By-Pass Arrangement

Alternatively, both the first and second open end portions can be connected to a surgically created lateral opening in a wall of the patient's intestine.

Structure of Attachment

In order to securely attach the artificial intestine section to the lateral opening, at least the first open end portion may comprise a shoulder portion formed around the end portion for lateral connection to the patient's intestinal wall. Preferably, at least a part of the shoulder portion extends laterally from the artificial intestine section by 3 mm to 20 mm. Furthermore, the shoulder portion preferably has a curved cross section, so as to generally conform to the intestinal wall when laterally attached thereto. An open end portion adapted in this way can advantageously be attached to the intestinal wall from the outside thereof.

The shoulder portion may be split into an upper and a lower shoulder portion with a gap between the upper and lower shoulder portions for accommodating intestinal wall tissue therein. The lower shoulder portion, if suitably adapted, can then be placed inside the patient's intestine through the surgically created lateral wall opening, whereas the upper shoulder portion will be placed outside the intestinal wall.

In order to allow the lateral wall opening to be easily stretched over the lower shoulder portion when the lower shoulder portion is advanced there through and yet in order to have a large contact area between the intestinal wall and the shoulder portion, the upper shoulder portion may be made larger than the lower shoulder portion. Thus, the surface area of the upper shoulder portion contacting the intestinal wall is also larger than the surface area of the lower shoulder portion contacting the intestinal wall.

The open end portion for lateral connection to the patient's intestinal wall may be connected to the patient's intestinal wall by gluing. For instance, it may have a particular rough surface structure for the glue to better adhere. Also, the open end portion may be connected to the patient's intestinal wall by sewing. For instance, a certain area of the shoulder portion may be perforated for stitching through the perforations or may be made from a material which is easy to penetrate with a needle. Similarly, the open end portion may specifically be connected to the patient's intestinal wall by stapling.

Preferably, at least the first open end portion is made from a biocompatible material. The biocompatible material of the open end portion may comprise at least one material of the following group of materials: titanium, stainless steel, ceramics, biocompatible polymer material. More specifically, the biocompatible polymer material may comprise at least one polymer of the following group of polymers: polytetrafluoroethylene, silicone, polyurethane, expanded polytetrafluoroethylene (ePTFE).

Also, at least the first open end portion preferably comprises a multilayer material. For instance, it is advantageous when the open end portion comprises a porous ingrowth layer that allows ingrowth of living tissue. The ingrowth layer may have a net-like structure and is most preferably made from Dacron®.

Intestinal Content Interacting Device within Artificial Intestine Section

In a preferred embodiment, the artificial intestine section is adapted to directly or indirectly interact with intestinal contents contained in the artificial intestine section between the first and second open end portions thereof.

Reservoir

In its simplest form, the at least one element of the artificial intestine section comprises an artificial reservoir between the first and second open end portions for receiving and temporarily collecting therein intestinal contents supplied through the first open end portion.

Flow Control Device

In a more advanced embodiment, the at least one element may comprise, possibly in addition to the reservoir, a flow control device adapted to control flow of intestinal contents from the artificial intestine section through the second open end portion. The flow control device is preferably adapted to prevent flow of intestinal contents from the artificial intestine section through the second open end portion.

Exit Valve as Flow Control Device

The flow control device preferably comprises at least one valve, including an exit valve preventing intestinal contents flow through the second open end portion in its closed position. Preferably, the exit valve is a normally closed valve so that no energy is needed to keep the valve closed during the system's inactive periods.

Entry Valve as an Additional Part of the Flow Control Device

In addition, the flow control device may comprise an entry valve allowing intestinal contents to flow towards the reservoir in its open position. This can be advantageous particularly during the emptying of the reservoir, when the entry valve should be closed. Therefore, the entry valve is preferably a normally open valve. Accordingly, the exit valve and the entry valve are preferably adapted to cooperate such that when one of the two valves is closed, the respective other valve is open, and vice versa.

Valve Types

As regards the various valve types that may be employed, the at least one valve may e.g. comprise a central opening which is normally closed by resilient means that can be urged apart mechanically by inserting a conduit through the central opening so as to open the central opening of the valve. In the simplest embodiment, the valve may be opened by mechanical force, such as by inserting a tube from outside the patient's body through the valve. The valve in this case can be a simple non-return valve.

According to a more complex alternative, the at least one valve may comprise a compartment with a variable volume adapted to open and close the valve by changing the compartment's volume. Advantageously, the at least one valve comprises at least one passage for filling and emptying the compartment with hydraulic fluid. The compartment preferably has at least one flexible wall defining an opening for the intestine or a conduit of the reservoir to pass through, the opening being adapted to close upon increase of the compartment's volume.

According to a different alternative, the at least one valve may be a flap valve permanently implanted inside the patient's intestine. The flap valve may for instance comprise a rotatable disc.

Extra Valve Separate from Artificial Intestine Piece

While the valve or valves preferably make an integral part of the artificial intestine section, the artificial intestine section may further include one or more extra valves adapted to control flow of intestinal contents in a natural section of the patient's intestine upstream and/or downstream the artificial intestine section. The extra valve may be rigidly connected to the artificial section but may as well form a completely separate part. The extra valve is implanted inside the patient's body outside a section of the patient's natural intestine and includes at least one element acting on the natural intestine section from the outside thereof so as to prevent intestinal contents flow through the natural intestine section. This valve arrangement does not require any surgery on the respective part of the natural intestine when the valve is implanted.

The extra valve may include at least one electrical stimulation device adapted to electrically stimulate muscle or neural tissue of an intestine section so as to cause at least partial contraction of the natural intestine section. This is a very gender way of constricting the intestine. The stimulation device preferably includes at least one electrode adapted to apply electric pulses to the natural intestine section.

It is particularly advantageous to make use of a stimulation device which is adapted to stimulate different portions of the intestine section over time. Thus, different portions of the intestine section can be constricted by stimulation at different times in any predetermined stimulation pattern, thereby giving the intestine portions currently not stimulated time to recover and, thus, improving the blood circulation in the respective intestine section.

Furthermore, the stimulation device can specifically be adapted to stimulate, over time, the different portions of the intestine section in a wave like manner in a direction opposite to natural intestinal contents flow. As a result, the valve counteracts the natural intestinal contents flow, thereby improving the valve's closing function.

Alternatively, or preferably in addition to the stimulation device, the at least one valve may comprise a constriction device implanted in the patient's body for at least partly constricting the natural intestine section mechanically from outside the natural intestine section. Where the stimulation device is combined with the constriction device, the stimulation device and the constriction device preferably act on the same intestine section. In that case, it is advantageous if the constriction device in its normal condition constricts the natural intestine section only partly, in order not to damage the intestine over time. Complete constriction and, thus, closing of the intestine may then be obtained by additionally stimulating the natural intestine section in a manner as described before.

In addition, when constriction of the intestine section caused by the constriction device is released, the stimulation device may, if accordingly adapted, be used to pump intestinal contents along the natural intestine section by, over time, stimulating the different portions of the natural intestine section in a wave like manner in a direction of natural intestinal contents flow. In this situation, the valve may incorporate the additional function of a pump for actively supporting the discharge of feces from the human body.

Pump as Part of the Implantable Flow Control Device

The flow control device may comprise a pump for advancing intestinal contents through the second open end portion to outside the artificial intestine section. Where the artificial intestine section comprises a reservoir, the pump may be adapted for emptying the reservoir. A variety of different structures may be realized.

For instance, the reservoir may be formed by a bellow, said bellow having an end wall closing the bellow at one end thereof. The end wall may then make part of the pump such that a volume of the bellow is reduced upon advancement of said end wall. Preferably, bellow is made of a resilient material so as to urge the bellow into a normally expanded position.

In another alternative, the pump may comprise a movable piston, with a front end of the piston extending into the reservoir such that a volume of the reservoir is reduced upon advancement of the piston. Preferably, the piston is spring loaded so as to urge the piston into a normally retracted position.

Alternatively, the pump may be adapted for being permanently arranged inside the reservoir.

In a further alternative, the reservoir may have a flexible wall and the pump is adapted for emptying the reservoir by squeezing the reservoir. In this case, the pump may e.g. include a constriction device adapted to alternately constrict and release sections of the reservoir so as to pump intestinal contents along the reservoir by, over time, constricting different sections of the reservoir in a wave like manner. More specifically, the reservoir may have a tube-like form and a roller pump may be used as the pump acting on the tube-like reservoir from the outside thereof.

Motor

Where the valves or pump or any other element of the flow control device is not or not only manually drivable, at least one motor can be provided for automatically driving at least one energy consuming part of the flow control device. The motor is preferably arranged to be driven by electric or electromagnetic energy.

A motor in the sense of the present invention is a device that transforms energy other than mechanical energy into mechanical energy. While a pump in the sense of the present invention is a device for advancing liquid or pasty material, a pump may at the same time be a motor in certain circumstances, such as where the transformation of energy into mechanical energy causes advancement of the liquid or pasty material without any intervening mechanical means such as a piston, bellow or the like.

For instance, the at least one motor can be arranged for driving at least one of the valve or valves, respectively, between its closed and open position. Also, the at least one motor can be arranged for driving the pump.

A manually operable switch may be provided for activating the at least one motor, the switch being preferably arranged for subcutaneous implantation so as to be operable from outside the patient's body.

Energy Source

The artificial intestine section may be combined with further components to form a system. The further components may be integrated in the artificial intestine section to be implanted along therewith or may be separate from the artificial intestine section to be implanted separately or not to be implanted at all.

The system may for instance comprise an energy source for supplying energy directly or indirectly to at least one energy consuming part of the system. Preferably, the energy source includes a battery or an accumulator, such as one or more of a rechargeable battery and a capacitor, as an energy storage means. The energy storage means is advantageously adapted for being implanted inside the patient's body, more preferably as a part of the artificial intestine section.

Wireless Energy Transmission

Energy is preferably transmitted wirelessly. Thus, where the energy source is provided for supplying energy directly or indirectly to at least one energy consuming part of the system, the energy source may comprise a wireless energy transmitter adapted to wirelessly transmit energy from outside the patient's body to the at least one energy consuming part. Alternatively, where the energy source includes a battery or an accumulator, in particular one which is implanted in the patient's body, the energy source may comprise a wireless energy transmitter adapted to wirelessly transmit energy from outside the patient's body to the energy storage means.

Energy Transmission Feedback

A feedback subsystem, which can make part of a control device described subsequently, can advantageously be provided to wirelessly send feedback information related to the energy to be stored in the accumulator from inside the human body to the outside thereof. The feedback information is then used for adjusting the amount of wireless energy transmitted by the energy transmitter. Such feedback information may relate to an energy balance which is defined as the balance between an amount of wireless energy received inside the human body and an amount of energy consumed by the at least one energy consuming part. Alternatively, the feedback information may relate to an energy balance which is defined as the balance between a rate of wireless energy received inside the human body and a rate of energy consumed by the at least one energy consuming part.

Also, the transmission of energy from the energy storage means to the at least one energy consuming part may be performed wirelessly by means of an accordingly adapted wireless energy transmitter.

Preferably, in order to reduce the number of parts and possibly increase the system's efficiency, the energy consuming part can be adapted to directly transform the wirelessly transmitted energy into kinetic energy. Otherwise, it will be necessary to provide an implantable energy transforming device for transforming the wireless energy, preferably into electric energy. In this case, it is further preferred to set up the system such that the energy consuming part is driven with the electric energy, as said energy transforming device transforms the wireless energy into the electric energy.

The energy transmitter can be adapted to generate an electromagnetic field, a magnetic field or an electrical field. The wireless energy may be transmitted by the energy transmission device by at least one wireless signal. More specifically, the energy transmitter may be adapted to transmit the energy by at least one wireless energy signal, which may comprise an electromagnetic wave signal, including at least one of an infrared light signal, a visible light signal, an ultra violet light signal, a laser signal, a microwave signal, an X-ray radiation signal, and a gamma radiation signal. Also, the wireless energy signal may comprise a sound or ultrasound wave signal. Furthermore, the wireless energy signal may comprise a digital or analog signal or a combination thereof.

Galvanic Energy Transmission

Where energy is not transmitted wirelessly, galvanic coupling elements should be provided at least between the energy source and the motor for transmitting energy to the motor in contacting fashion.

Control Unit

It is advantageous to provide a control unit adapted to directly or indirectly control one or more elements of the system, such as for controlling opening of the exit valve and/or closing of the entry valve, in particular in a manner such that when one of the two valves is closed, the respective other valve is open, and vice versa. The control unit can also be adapted to control actuation of the pump.

The control unit is preferably operable by the patient, e.g. particularly in order to empty the reservoir.

At least part of the control unit may be adapted to be implantable in the patient's body. For instance, a manually operable switch may be provided for activating the control unit, the switch preferably being arranged for subcutaneous implantation so as to be operable from outside the patient's body. Also, the control unit may comprise a first part adapted for implantation in the patient's body and a second part adapted to cooperate with the first part from outside the patient's body. In this case, the control unit can be adapted to transmit data from the external second part of the control unit to the implanted first part of the control unit in the same manner as energy is transmitted to the at least one energy consuming part.

That is, the second part of the control unit may be adapted to wirelessly transmit a control signal to the implantable first part of the control unit for controlling the at least one energy consuming part from outside the patient's body. Also, the implantable first part of the control unit may be programmable via the second part of the control unit. Furthermore, the implantable first part of the control unit may be adapted to transmit a feedback signal to the second part of the control unit.

Sensor

Furthermore, a physical parameter sensor adapted to directly or indirectly sense a physical parameter of the patient can be provided. The physical parameter sensor may be adapted to sense at least one of the following physical parameters of the patient: a pressure within the artificial intestine section, a pressure within the patient's intestine, an expansion of the artificial intestine section, a distension of an intestinal wall of the patient's intestine, a movement of the intestinal wall.

Similarly, a functional parameter sensor adapted to directly or indirectly sense a functional parameter of the system can be provided, wherein the functional parameter sensor may be adapted to sense at least one of the following functional parameters of the system: a pressure against a part of the system such as the artificial intestine section, a distension of a part of the system such as a wall of the artificial intestine section, an electrical parameter such as voltage, current or energy balance, a position or movement of a movable part of the system.

Preferably, an indicator is coupled to the sensor or sensors, the indicator being adapted to provide a signal when a sensor senses a value for the parameter beyond a predetermined threshold value. The sensor signal may comprise at least one of the following types of signals: a sound signal, a visual signal.

Intestinal Contents Collecting Device (with "External" Pump)

Where the artificial intestine piece comprises a reservoir, in a simple way, an intestinal contents collecting device may used to be temporarily applied from outside the patient's body when the reservoir is to be emptied. According to a preferred alternative, the collecting device may comprise a front open end to be applied towards the exit valve so as to provide a flow passage from the exit valve towards the collecting device. More specifically, the collecting device front open end is preferably applied to the exit valve so as to open the valve and thereby provide said flow passage towards the collecting device. Where the exit valve is normally closed by resilient means, said front open end is inserted through the central opening of the exit valve so as to urge apart the resilient means normally closing the central opening.

The collecting device preferably comprises a suction pump, which may comprise a piston-cylinder-arrangement. The suction pump may be adapted to be driven manually, in particular where it is intended for use as a back-up pump for a situation where the pump of the flow control device is out of operation. However, preferably a motor is connected to the suction pump for driving the pump automatically.

Method of Treatment (Implantation)

Specifically, there is provided a surgical method for treating a patient according to the invention, comprising the steps of:
cutting the patient's skin and abdominal wall,
dissecting an area of the patient's intestine,
surgically creating at least one opening in a wall of the dissected intestinal area so as to create an artificial lateral intestinal opening,
providing an artificial intestine section having a first open end portion and a second open end portion in flow communication with one another and affixing the first open end portion to the lateral intestinal opening so as to be in flow communication therewith, and
suturing the abdominal wall and skin.

A corresponding laparoscopic surgical method of treating a patient would comprise the steps of:
making a small opening in the patient's skin and abdominal wall,
introducing a needle in the abdominal cavity,
inflating the abdominal cavity with gas,
inserting at least one trocar into the cavity,
introducing a camera through the trocar,
inserting at least one dissecting instrument preferably through a second trocar,
dissecting an area of the intestine,
surgically creating at least one opening in a wall of the dissected intestinal area so as to create an artificial lateral intestinal opening,
providing an artificial intestine section having a first open end portion and a second open end portion in flow communication with one another and affixing the first open end portion to the lateral intestinal opening so as to be in flow communication therewith,
extracting the instruments, camera and trocar, and in relation thereto
suturing, if necessary, the abdominal wall and permanently closing the skin.

Closing the Intestine by Sewing

The dissected portion may be permanently closed at a location downstream of the lateral intestinal opening so as to create an upstream part of the intestine including the lateral intestinal opening and a downstream part of the intestine, and the second open end portion of the artificial intestine section may be affixed to the downstream intestinal part, preferably again to a lateral opening in the wall of the downstream intestinal part. The downstream intestinal part may be connected to a surgically created stomy or to the patient's rectum or anus or to tissue adjacent the patient's anus. The step of permanently closing the patient's intestine preferably comprises sewing and/or stapling the intestinal wall so as to form a dead end.

Dividing the Intestine

The patient's intestine may alternatively be divided and the artificial intestine piece may be placed between the resulting upstream and downstream intestinal parts. This would require the following steps:
dissecting a portion of the dissected intestinal area downstream of the lateral intestinal opening such that intestinal mesentery connected to the dissected portion is opened in such a way that supply of blood through the mesentery to the dissected intestinal area is maintained as far as possible on both sides of the dissected portion,
dividing the patient's intestine in the dissected portion so as to create an upstream part of the intestine with the lateral intestinal opening and a downstream part of the intestine, said downstream intestine part being separate from the upstream intestine part and having a cross-sectional opening at the upstream side thereof, wherein the mesentery maintains a tissue connection between the upstream and downstream intestine parts,
affixing the second open end portion of the artificial intestine section to the downstream intestine part, and
permanently closing the upstream intestine part at a location downstream of the lateral intestinal opening.

Lateral Front and Lateral End Connection (By-Pass)

As mentioned before, preferably not only the first open end but also the second open end of the artificial intestine section are connected to a lateral opening in the patient's intestinal walls. This would involve the following steps to be performed on the downstream intestinal part:

surgically creating an opening in a wall of the downstream intestinal part at an upstream end thereof so as to create a second artificial lateral intestinal opening, and affixing the second open end portion of the artificial intestine section to the second lateral intestinal opening so as to be in flow communication therewith.

The step of permanently closing the patient's intestine may then comprise sewing the intestinal wall with two rows of sutures or staples and cutting and dividing the intestine between the sutures or staples so as to form two dead ends.

Alternatively, where the method of implanting the artificial intestine section involves dividing the patient's intestine, the step of affixing the second open end portion of the artificial intestine section to the downstream intestinal part may comprise the steps of:

surgically creating an opening in a wall of the downstream intestinal part at an upstream end thereof so as to create a second artificial lateral intestinal opening, affixing the second open end portion of the artificial intestine section to the second lateral intestinal opening so as to be in flow communication therewith, and permanently closing the cross-sectional opening at the upstream side of the downstream intestine part at a location upstream of the second lateral intestinal opening, e.g. by sewing and/or stapling.

Lateral Front Connection and Straight End Connection

However, the second open end portion of the artificial intestine section can likewise be affixed to a cross-sectional upstream opening of the downstream intestinal part of the divided intestine so as to be in flow communication therewith.

Sleeve/Bulge Connector

The step of affixing the second open end portion of the artificial intestine section to a cross-sectional upstream opening of the downstream intestine part preferably comprises:

inserting the second open end portion of the artificial intestine section into the upstream opening of the downstream intestine part, and placing a flexible sleeve so as to extend over both the downstream intestine part and second open end portion of the artificial intestine section such that the downstream intestine part is located intermediate the sleeve and the outer surface of the artificial intestine section.

Where the flexible sleeve is mounted on the outer surface of the second open end portion of the artificial intestine piece so as to be foldable upon itself, the step of placing the flexible sleeve so as to extend over both the downstream intestine part and second open end portion of the artificial intestine section comprises folding the flexible sleeve upon itself such that the downstream intestine part is located intermediate the folded sleeve.

Alternatively, or in addition, the step of affixing the second open end portion of the artificial intestine section to the cross-sectional upstream opening of the downstream intestine part may comprise:

inserting the artificial intestine section having a bulge formed on the outside thereof into the upstream opening of the downstream intestine part so that the downstream intestine part extends over the bulge from one side of the bulge, and advancing a blocking ring over the downstream intestine part towards the bulge from the respective other side of the bulge such that the downstream intestine part is located intermediate the outer surface of the artificial intestine section and the blocking ring.

The afore-mentioned second open end portion of the artificial intestine section with a sleeve or with a bulge serve to improve the strength of the connection against axial forces which may e.g. result from the peristaltic movement of the intestine and tend to pull on the intestine. The second open end portion of the artificial intestine section may also combine a sleeve and a bulge.

Exit Through Stoma

As mentioned before, the downstream intestinal part may be connected to a surgically created stomy or to the patient's rectum or anus or to tissue adjacent the patient's anus. In the case of a connection to a stomy, this would involve the following steps:

cutting the patient's skin and abdominal wall so as to create an opening for an intestinal stomy, dissecting the area of the stomy opening, dividing the intestine at a location downstream of the artificial intestine piece so as to create an upstream natural intestine section having a cross-sectional opening at the downstream end thereof and a downstream natural intestine section, dissecting the mesentery of the upstream natural intestine section in the area of the cross-sectional opening thereof to prepare for creating the intestinal stomy, advancing the downstream end of the upstream natural intestine section through the abdominal wall and skin, and suturing the cross-sectional opening of the upstream natural intestine section to the skin with the intestinal mucosa turned inside out, thereby achieving the intestinal stomy.

Exit Through Anus

In the case of a connection to the patient's anus or to tissue adjacent the patient's anus, this would involve the following steps:

dividing the intestine at a location downstream of the artificial intestine piece so as to create an upstream natural intestine section having a cross-sectional opening at the downstream end thereof and a downstream natural intestine section leading to the patient's anus, dissecting the area of the patient's anus and surgically separating the downstream natural intestine section from the patient's anus, whereas the steps of dividing the intestine and separating the intestine section leading to the patient's anus can alternatively be carried out in reversed order, dissecting the mesentery of the upstream natural intestine section in the area of the cross-sectional opening at the downstream end thereof to prepare for connecting the upstream natural intestine section to the patient's anus or tissue adjacent the patient's anus, advancing the downstream end of the upstream natural intestine section through the patient's anus, and suturing the cross-sectional opening of the upstream natural intestine section to the patient's anus or tissue adjacent the patient's anus.

Depending upon the circumstances, the step of dividing the intestine so as to form the upstream natural intestine section may be performed either on the patient's small intestine or on the patient's large intestine.

Structure of Attachment

Where the first open end portion of the artificial intestine section and possibly also the second open end portion are to be affixed to the lateral intestinal opening so as to be in flow communication therewith, this may comprise the step of connecting the afore-mentioned shoulder portion, which is formed around the open end portion, to the patient's intestinal wall so as to surround the lateral intestinal opening. In particular, the step of affixing the open end portion to the intestine may comprise attaching the shoulder portion to the patient's outer intestinal wall.

Alternatively, where the shoulder portion is split into an upper and a lower shoulder portion with a gap between the upper and lower shoulder portions, the step of affixing the open end portion of the artificial intestine section to the lateral intestinal opening may comprise placing the lower shoulder portion inside the patient's intestine and the upper shoulder portion outside the patient's intestine such that the intestinal wall tissue is accommodated in the gap.

The step of affixing the open end portion of the artificial intestine section to the lateral intestinal opening may comprise gluing, sewing and/or stapling the open end portion to the patient's intestinal wall.

As a material for the first open end portion at least one biocompatible material from the following group of materials may be selected: titanium, stainless steel, ceramics, biocompatible polymer material, wherein the biocompatible polymer is preferably selected from the following group of polymers: polytetrafluoroethylene, silicone, polyurethane, expanded polytetrafluoroethylene (ePTFE).

More specifically, a multilayer material may be selected for the first open end, in particular one having a porous ingrowth layer allowing ingrowth of living tissue. The ingrowth layer is preferably chosen to have a net-like structure.

Intestinal Content Interacting Device within Artificial Intestine Piece/Reservoir/Flow Control Device As mentioned before, the artificial intestine section or system may comprise at least one element adapted to directly or indirectly interact with intestinal contents contained in the artificial intestine section between the first and second open end portions thereof. This element will be implanted along with the artificial intestine section. As also mentioned before, the element may comprise a reservoir for receiving and temporarily collecting therein intestinal contents supplied through the first open end portion and/or a flow control device adapted to control flow of intestinal contents from the artificial intestine section through the second open end portion.

Again, the flow control device may comprise an exit valve preventing intestinal contents flow through the second open end portion in its closed position and may additionally comprise an entry valve allowing intestinal contents to flow through the first open end portion into the artificial intestine section in its open position.

Alternatively or in addition, as also mentioned before, the flow control device may comprise a pump for advancing intestinal contents through the second open end portion to outside the artificial intestine section. Where the pump comprises a manually operable switch for activating the pump, the method of implantation may further comprise the step of implanting the switch subcutaneously so as to be operable from outside the patient's body.

Motor

Again, at least one motor may be implanted in the patient's body either separately or, more preferably, integrally with the artificial intestine section and may be arranged for automatically driving one or more energy consuming part of the flow control device. Where the motor comprises a manually operable switch for activating the motor, the method of implantation may further comprise the step of implanting the switch subcutaneously so as to be operable from outside the patient's body.

Energy Source/Energy Transmission

The method of implantation may further comprise the step of implanting inside the patient's body an energy source, possibly comprising energy storage means such as a battery or an accumulator as described before, for supplying at least one of the energy consuming parts with energy.

Where energy is transmitted wirelessly, for instance from outside the patient's body to inside the patient's body either to an energy consuming part and/or to the accumulator or from the accumulator to the energy consuming part, it may further be necessary to implant an energy transforming device for transforming the wireless energy into electric energy. Alternatively or in addition, galvanic coupling elements may be implanted, e.g. for transmitting energy to the energy consuming part in contacting fashion from outside the patient's body and/or from the implanted energy source.

Control Unit

Furthermore, as mentioned previously, at least a part of a control unit may be implanted inside the patient's body adapted to directly or indirectly control one or more of the elements that have also been implanted in the patient's body. Where the control unit comprises a manually operable switch for activating the control unit, the method of implantation may further comprise the step of implanting said switch subcutaneously so as to be operable from outside the patient's body.

Sensor

As mentioned before, one or more physical and/or functional parameter sensors may be implanted to directly or indirectly sense physical and/or functional parameters inside the patient and in the system implanted inside the patient. Where the sensor is a pressure sensor, it may be placed in the artificial intestine section or the patient's natural intestine so as to sense the pressure within the artificial intestine section or patient's natural intestine, respectively. Where the sensor is a tension sensor, it may be placed in contact with the artificial intestine section or the patient's intestine so as to sense an expansion of the artificial intestine section or patient's natural intestine, respectively. Where the sensor is a movement sensor, it may be placed in contact with the artificial intestine section or the patient's natural intestine so as to sense movement of the artificial intestine section or patient's natural intestine, respectively. The functional sensor may be adapted to measure at least one of the following functional parameters of the system: an electrical parameter such as voltage, current or energy balance or a stimulation parameter in relation to the system.

Use

Once the artificial intestine section or system according to the invention has been properly installed, the flow control device can be used for emptying the reservoir implanted in the patient.

Accordingly, a method of treating a patient by means of the artificial intestine section which comprises at least one element adapted to directly or indirectly interact with intestinal contents contained in the artificial intestine section may comprise the step of actuating the at least one element so as to interact with the intestinal contents contained in the artificial intestine section between the first and second open end portions thereof.

Exit and Entry Valve

Where the at least one element comprises an exit valve preventing intestinal contents flow from the artificial intestine section through the second open end portion in its closed position, the method may further comprise the steps of opening the exit valve and then removing intestinal contents from the artificial intestine section. Furthermore, where the at least one element further comprises an entry valve allowing intestinal contents to flow through the first open end portion into the artificial intestine section in its open position, the method may further comprise the step of closing the entry valve before removing intestinal contents from the artificial intestine section.

In particular, the method of use may comprise the step of inserting a conduit from outside the patient's body into the artificial intestine section, thereby mechanically urging the exit valve to open.

Pump

Where the at least one element interacting with intestinal contents inside the artificial intestine piece comprises a pump, the method of use may further comprise the step of advancing intestinal contents from the artificial intestine section through the second open end portion thereof to outside the artificial intestine section by means of the pump. The pump may be activated by manually operating a subcutaneously arranged actuator from outside the patient's body.

Alternatively, a flow passage may be provided to extend from the artificial intestine section to an external collecting device and intestinal contents may then be removed from the artificial intestine section by means of a suction pump.

Motor

The suction pump is preferably driven by means of a motor.

Furthermore, where the at least one element interacting with intestinal contents inside the artificial intestine piece comprises a motor, the method of use may further comprise the step of driving at least the exit valve between its closed and open positions and/or driving at least the pump by means of the motor. In either case, the motor is preferably activated by manually operating a subcutaneously arranged actuator from outside the patient's body.

Energy

As mentioned before, energy may be transmitted from outside the patient's body to at least one implanted energy consuming part of the system, preferably in the form of wireless energy. This may involve the following additional steps:
transforming the wirelessly transmitted energy into electric energy by means of an energy transforming device,
storing the transformed energy in an energy storage means, and
supplying the stored energy from the energy storage means to at least one implanted energy consuming part of the system.

Again, energy may be transmitted wirelessly from the storage means to the energy consuming part.

Preferably, at least part of the wirelessly transmitted energy is transformed into electric energy and used for the energy consuming part of the system, as said part of the wirelessly transmitted energy is transformed into the electric energy.

Control

Where a first part of a control unit for controlling at least one energy consuming part of the system is implanted inside the patient's body, the method of use may further comprise the step of using the external second part of the control unit to transmit data to the implanted first part of the control unit. Preferably, the data are transmitted to the implanted first part of the control unit in the same manner as energy is transmitted to the implanted energy consuming part. More particularly, the data are preferably transmitted wirelessly to the For instance, the implanted first part of the control unit can be programmed via the external second part of the control unit. Furthermore, a feedback signal may be transmitted from the implanted first part of the control unit to the external second part of the control unit.

Sensor

Where one or more of the afore-mentioned sensors are provided, the method of use may comprise the step of sensing a physical parameter in the patient's body and/or a functional parameter of the artificial intestine piece or system in the patient's body, such as one or more of the following parameters: a pressure within the artificial intestine section, a pressure within the patient's natural intestine, an expansion of the artificial intestine section, a distension of an intestinal wall of the patient's natural intestine, a movement of the patient's intestinal wall, a pressure against a part of the system such as the artificial intestine section, a distension of a part of the system such as a wall of the artificial intestine section, an electrical parameter such as voltage, current or energy balance, a position or movement of a movable part of the system.

A signal, such as a sound signal or a visual signal, may be provided when a value for the physical parameter sensed is beyond a predetermined threshold value.

Intestinal Disorder (IV)

"Intestinal Pump"

Another object of the present invention is to provide a method for treating a patient having a disorder related to the passageway of the patient's intestines.

In accordance with this object, there is provided a method for treating a patient having a disorder related to the passageway of the intestines. The method comprises the steps of:
constricting a selected portion of the patient's intestines to at least substantially reduce the volume of the passageway of the intestines along the selected portion, so that intestinal contents is displaced through the passageway of the intestines in the downstream direction thereof,
releasing the selected portion to increase the volume of the passageway of the intestines along the selected portion, so that intestinal contents in the passageway of the intestines upstream of the selected portion enters the selected portion, and
repeating steps (a) and (b) an optional number of times.

Where the selected portion of the intestines ends at the patient's anus, the method further comprises performing steps (a) and (b) to discharge intestinal contents through the anus. Alternatively, the method further comprises surgically modifying the patient's intestines to end at a stoma, and performing steps (a) and (b) to discharge intestinal contents through the stoma.

The method steps (a) and (b) can be performed in accordance with several alternatives, as will be described in the following.

Alternative 1. Step (a) is performed by initially constricting the selected portion partially to close the passageway of the intestines at an upstream end of the selected portion and then constricting the entire selected portion, and step (b) is performed by initially fully releasing the selected portion except at a downstream end thereof and then releasing the selected portion at the downstream end.

Alternative 2. Step (a) is performed by:
partially constricting the selected portion to at least substantially decrease the cross-sectional area of the passageway of the intestines at an upstream end of the selected portion,
electrically stimulating muscle or neural tissue of the constricted selected portion at the upstream end to cause contraction of the constricted selected portion to close the passageway of the intestines at the upstream end of the selected portion, and
then constricting the entire selected portion.

Step (b) is performed by initially fully releasing the selected portion except at a downstream end thereof and then releasing the selected portion at the downstream end.

Alternative 3. Step (a) is performed by:
partially constricting the selected portion to at least substantially decrease the cross-sectional area of the passageway of the intestines at an upstream end of the selected portion, electrically stimulating muscle or neural tissue of the constricted selected portion at the upstream end to cause contraction of the constricted selected portion to close the passageway of the intestines at the upstream end of the selected portion,
at least partially constricting the entire selected portion, and
then successively stimulating the selected portion from the upstream end to a downstream end thereof to cause progressive contraction of the selected portion, so that intestinal contents is displaced in the passageway of the intestines in a peristaltic manner.

Step (b) is performed by ceasing stimulating the selected portion and fully releasing the selected portion except at a downstream end thereof, and then releasing the selected portion at the downstream end.

Alternative 4. Step (a) is performed by:
partially constricting the selected portion to at least substantially decrease the cross-sectional area of the passageway of the intestines along the entire selected portion, and
successively stimulating the constricted portion from an upstream end to a downstream end thereof to cause progressive contraction of the selected portion, so that intestinal contents is displaced in the passageway of the intestines in a peristaltic manner.

Alternative 5. Step (a) is performed by successively constricting portions of a series of selected portions of the intestines so that intestinal contents is displaced downstream in the passageway of the intestines in a peristaltic manner.

Alternative 6. Step (a) is performed by:
successively constricting portions of a series of selected portions of the intestines so that each constricted portion at least substantially decreases the cross-sectional area of the passageway of the intestines, and
electrically stimulating each constricted portion to cause contraction of the constricted intestinal portion to close the passageway of the intestines, whereby intestinal contents is displaced downstream in the passageway of the intestines in a peristaltic manner.

Alternative 7. Step (a) is performed by progressively constricting the selected portion so that intestinal contents is displaced downstream in the passageway of the intestines in a peristaltic manner.

Alternative 8. Step (a) is performed by:
electrically stimulating the selected portion to cause contraction thereof, and
progressively constricting the contracted selected portion so that intestinal contents is displaced downstream in the passageway of the intestines in a peristaltic manner.

An apparatus for practicing the method of the invention includes a pump for implantation in the patient, wherein the pump is operable on at least one selected portion of the intestines to pump intestinal contents through the passageway of the intestines. The pump includes a constriction device adapted to alternately constrict the selected portion to at least substantially reduce the volume of the passageway of the intestines along the selected portion and release the selected portion to increase the volume of the passageway of the intestines along the selected portion, such that intestinal contents is displaced through the passageway of the intestines.

For a patient where the selected portion of the intestines ends at the patient's anus, the pump is adapted to pump intestinal contents out from the patient's body through the anus. This solution differs from the prior art according to U.S. Pat. No. 6,752,754 discussed above, in that the pump of the present apparatus operates on the patient's intestine, i.e., the constriction device of the pump constricts the intestine to displace intestinal contents therein.

For an ileostomy, a jejunostomy, a colostomy or a rectostomy patient, where the patient's intestines are surgically modified ending in a stoma, the pump is adapted to pump intestinal contents out from the patient's body through the stoma.

The apparatus may include an artificial intestinal piece adapted to be surgically joined to the patient's intestines to form part of the passageway of the intestines and to form at least part of the selected portion of the intestines to be constricted by the constriction device. The constriction device may operate only on the artificial intestinal piece to minimize the risk of injuring the intestines. When the pump is not in operation, the constriction device can firmly constrict the artificial intestinal piece to completely close the passageway of the intestines. Alternatively, there may be provided at least one implantable releasable closure adapted to engage the artificial intestinal piece to close the passageway of the intestines, or at least partially constrict the selected portion, when the pump is not in operation, and to release the selected portion to open the passageway of the intestines when the pump is in operation.

The artificial intestinal piece may be integrated with the patient's intestines between two ends thereof. Specifically, the artificial intestinal piece may be joined directly or indirectly to the patient's anus, whereby the pump can pump intestinal contents out from the patient's body through the anus. This solution differs from the prior art according to U.S. Pat. No. 6,752,754 discussed above, in that the pump of the present invention operates on the artificial intestinal piece, i.e., the constriction device of the pump constricts the artificial intestinal piece to displace intestinal contents therein. Alternatively, the artificial intestinal piece may be adapted to end in a stoma, whereby the pump can to pump intestinal contents out from the patient's body through the stoma.

To keep the pump fixed in a desired position in the patient's abdomen, an engagement device may be attached to the pump, the engagement device being adapted to attach the pump to tissue related to the patient's abdominal cavity, such as the abdominal wall.

To externally protect the intestines, an elastic protective tubing may be provided to at least partially cover the selected portion of the intestines, so that the constriction device of the pump constricts both the protective tubing and the selected portion.

An implantable support may be provided to support the selected portion of the intestines as the constriction device constricts the selected portion. Alternatively, the constriction device may be adapted to constrict the selected portion against a tissue or a bone of the patient's body.

The apparatus may further include a control device for controlling the pump to operate the constriction device to alternately constrict and release the selected portion, such that intestinal contents is moved through the passageway of the intestines. The control device is suitably operable by the patient and preferably includes a wireless remote control.

Electric Stimulation of the Intestines

An electric stimulation device may be provided for electrically stimulating muscle or neural tissue of the selected portion of the intestines to cause at least partial contraction of the selected portion. Using such a stimulation device as a complement to the constriction device enables a particularly careful treatment of the patient's intestines so that the risk of injuring the intestines over time is minimized, as will be evident from the embodiments of the invention described below.

The stimulation device may include at least one electrode adapted to stimulate muscle or neural tissue of the selected portion of the intestinal tissue with electric pulses. Preferably, the stimulation device includes a plurality of electrodes separate from or integrated with the constriction device, wherein the electrodes form a series of electrodes along the selected portion of the intestines. The electric pulses may be positive and/or negative, preferably combined positive and negative pulses. The desired stimulation effect is achieved by varying different pulse parameters, such as the pulse amplitude, the off time period between successive pulses, the pulse duration and the pulse repetition frequency. A pulse amplitude of about 5 mA and a pulse duration of about 300 µs are suited for neural stimulation, whereas a pulse amplitude of about 20 mA and a pulse duration of about 30 µs are suited for muscular stimulation. The pulse repetition frequency suitably is about 10 Hz.

The control device advantageously controls the stimulation device to variably energize the electrodes along the selected portion, for example in accordance with a preset scheme, to cause partial contractions of the selected portion that over time change their positions on the selected portion, whereby parts of the intestines that currently are not stimulated can restore substantially normal blood circulation before they are stimulated again. A number or groups of the electrodes may be progressively energized in a direction upstream or downstream of the intestines. Alternatively, the electrodes may be energized one at a time in sequence or groups of the electrodes may be sequentially energized, either randomly or in accordance with a predetermined pattern.

Pump Design

In accordance with a simple alternative, the constriction device of the pump includes a first constriction element for constricting and releasing the selected portion at an upstream end thereof, and a second constriction element for constricting and releasing the selected portion between the upstream and downstream ends thereof. In this embodiment, the control device controls the first and second constriction elements to alternately constrict and release the selected portion independently of one another.

For the operation of the pump, the control device controls the upstream first constriction element to constrict the selected portion to close the passageway of the intestines at the upstream end of the selected portion, and controls the second constriction element to constrict the selected portion between the upstream and downstream ends thereof to move intestinal contents contained in the selected portion downstream in the passageway of the intestines.

The control device also controls the first and second constriction elements to release the selected portion to allow intestinal contents in the passageway of the intestines upstream of the selected portion to enter the selected portion.

When the pump is not in operation, the stimulation device described above is used for cooperation with any of the constriction elements to close the passageway of the intestines. Thus, the first and second constriction elements are adapted to be maintained in a rest position, in which at least one of the constriction elements gently constricts the selected portion to at least substantially decrease the cross-sectional area of the passageway of the intestines, and the control device controls the stimulation device to stimulate the selected portion where the constriction element constricts the selected portion to close the passageway of the intestines. The phrase "gently constrict the selected portion" is to be understood as constricting the portion of the intestines without substantially hampering the blood circulation in intestinal tissue. The rest position allows for sufficient blood circulation in the blood vessels of the selected portion of the intestines, such that the intestinal tissues of the selected portion maintain their integrity following long exposure to the constriction element that constricts the selected portion.

The stimulation device may also be used for cooperation with any of the constriction elements when the pump is in operation. In this case, the stimulation device includes at least one electrode. Preferably, the stimulation device includes a plurality of electrodes forming a series of electrodes along a surface of at least one of the constriction elements of the constriction device, wherein the surface contacts the selected portion of the intestines. The electrodes stimulate muscle or neural tissue of the selected portion with electric pulses where one of the first constriction element and the second constriction element constricts the selected portion.

For the operation of the pump where the constriction elements and the stimulation device cooperate, the control device controls the upstream first constriction element to gently constrict the selected portion to at least substantially decrease the cross-sectional area of the passageway of the intestines at the upstream end of the selected portion, controls the stimulation device to stimulate the selected portion where the first constriction element constricts the selected portion to cause contraction of the selected portion to close the passageway of the intestines at the upstream end of the selected portion, and controls the second constriction element to constrict the selected portion between the upstream and downstream ends thereof to move intestinal contents contained in the selected portion downstream in the passageway of the intestines.

Optionally, the stimulation device may cooperate with the second constriction element by electrically stimulating the selected portion where the second constriction element constricts the selected portion to reduce the volume of the passageway of the intestines. Specifically, the control device may control the stimulation device to successively stimulate the selected portion where the second constriction element constricts the selected portion, such that the selected portion constricted by the second constriction element is progressively contracted. As a result, the intestinal contents is displaced in the passageway of the intestines in a peristaltic manner. Alternatively, the constriction device may include only a single elongated constriction element, wherein the control device controls the stimulation device to successively stimulate the selected portion where the constriction element constricts the selected portion, such that the selected portion constricted by the constriction element is progressively contracted, whereby intestinal contents is displaced in the passageway of the intestines in a peristaltic manner.

In accordance with a more sophisticated alternative, the constriction device of the pump includes a first constriction element for constricting and releasing the selected portion at an upstream end thereof, a second constriction element for constricting and releasing the selected portion at a downstream end thereof, and a third constriction element for constricting and releasing the selected portion between the upstream and downstream ends thereof. In this embodiment, the control device controls the first, second and third constriction elements to alternately constrict and release the selected portion independently of one another.

For the operation of the pump, the control device controls the upstream first constriction element to constrict the selected portion to close the passageway of the intestines at the upstream end of the selected portion, controls the downstream second constriction element to release the selected portion, and controls the third constriction element to constrict the selected portion between the upstream and downstream ends thereof to move intestinal contents contained in the selected portion downstream in the passageway of the intestines.

The control device also controls the downstream second constriction element to constrict the selected portion to close the passageway of the intestines at the downstream end of the selected portion, controls the upstream first constriction element to release the selected portion, and controls the third constriction element to release the selected portion between the upstream and downstream ends thereof to allow intestinal contents in the passageway of the intestines upstream of the selected portion to enter the selected portion.

When the pump is not in operation, the stimulation device described above is used for cooperation with any of the constriction elements to close the passageway of the intestines, as described above in connection with the simple embodiment of the invention. Thus, the first, second and third constriction elements are adapted to be maintained in a rest position, in which at least one of the constriction elements gently constricts the selected portion to at least substantially decrease the cross-sectional area of the passageway of the intestines, and the control device controls the stimulation device to stimulate the selected portion where the constriction element constricts the selected portion to close the passageway of the intestines.

The stimulation device may also be used for cooperation with any of the first, second and third constriction elements when the pump is in operation. In this case, the stimulation device includes a plurality of electrodes forming a series of electrodes along a surface of at least one of the constriction elements of the constriction device, wherein the surface contacts the selected portion of the intestines. The electrodes stimulate muscle or neural tissue of the selected portion with electric pulses where one of the first constriction element and the second constriction element constricts the selected portion, and/or where the third constriction element constricts the selected portion.

For the operation of the pump where the constriction elements and the stimulation device cooperate, the control device controls the upstream first constriction element to gently constrict the selected portion to at least substantially decrease the cross-sectional area of the passageway of the intestines at the upstream end of the selected portion, controls the stimulation device to electrically stimulate the selected portion where the first constriction element constricts the selected portion to cause contraction of the selected portion to close the passageway of the intestines at the upstream end of the selected portion, controls the downstream second constriction element to release the selected portion, and controls the third constriction element to constrict the selected portion between the upstream and downstream ends thereof to move intestinal contents contained in the selected portion downstream in the passageway of the intestines.

Optionally, the stimulation device may cooperate with the third constriction element by electrically stimulating the selected portion where the third constriction element constricts the selected portion to reduce the volume of the passageway of the intestines. Specifically, the control device may control the stimulation device to successively stimulate the selected portion where the third constriction element constricts the selected portion, such that the selected portion constricted by the third constriction element is progressively contracted. As a result, intestinal contents is displaced in the passageway of the intestines in a peristaltic manner.

Furthermore, the control device controls the downstream second constriction element to gently constrict the selected portion to at least substantially decrease the cross-sectional area of the passageway of the intestines at the downstream end of the selected portion, controls the stimulation device to stimulate the selected portion where the second constriction element constricts the selected portion to cause contraction of the selected portion to close the passageway of the intestines at the downstream end of the selected portion, controls the upstream first constriction element to release the selected portion, and controls the third constriction element to release the selected portion between the upstream and downstream ends thereof to allow intestinal contents in the passageway of the intestines upstream of the selected portion to enter the selected portion.

In accordance with another alternative of the apparatus, which includes the stimulation device, the constriction device includes a first constriction element for constricting and releasing the selected portion at an upstream end thereof, and a second constriction element for constricting and releasing the selected portion at a downstream end thereof, wherein said control device controls said first and second constriction elements to alternately constrict and release the selected portion independently of each other. In this embodiment, the stimulation device is adapted to electrically stimulate the selected portion between the upstream and downstream ends thereof to cause contraction of the selected portion to reduce the volume of the passageway of the intestines.

For the operation of the pump, the control device controls the upstream first constriction element to constrict the selected portion to close the passageway of the intestines at the upstream end of the selected portion, controls the downstream second constriction element to release the selected portion, and controls the stimulation device to successively stimulate the selected portion between the upstream and downstream ends thereof to cause progressive contraction of the selected portion, so that intestinal contents is displaced in the passageway of the intestines in a peristaltic manner.

Optionally, the control device may control the upstream first constriction element to gently constrict the selected portion to at least substantially decrease the cross-sectional area of the passageway of the intestines at the upstream end of the selected portion, and control the stimulation device to stimulate the selected portion where the first constriction element constricts the selected portion to cause contraction of the selected portion to close the passageway of the intestines at the upstream end of the selected portion.

Furthermore, the control device controls the downstream second constriction element to constrict the selected portion to close the passageway of the intestines at the downstream end of the selected portion, controls the upstream first constriction element to release the selected portion, and controls the stimulation device to cease stimulating the selected portion between the upstream and downstream ends thereof to allow intestinal contents in the passageway of the intestines upstream of the selected portion to enter the selected portion.

Optionally, the control device may control the downstream second constriction element to gently constrict the selected portion to at least substantially decrease the cross-sectional area of the passageway of the intestines at the downstream end of the selected portion, and control the stimulation device to stimulate the selected portion where the second constriction element constricts the selected portion to cause contraction of the selected portion to close the passageway of the intestines at the downstream end of the selected portion.

In accordance with another alternative of the apparatus, the constriction device is adapted to constrict any portions of a series of selected portions of the intestines to close the passageway of the intestines, and the control device controls the constriction device to successively constrict the selected portions of the series of selected portions to move intestinal contents downstream in the passageway of the intestines in a peristaltic manner. Specifically, the constriction device includes a plurality of constriction elements, each of which is movable along the intestines to successively constrict the selected portions of the series of selected portions, wherein the control device controls the constriction device to cyclically move the constriction elements one after the other along the selected portions of the series of selected portions. (Alternatively, the constriction device may include only one single constriction element.) Preferably, the constriction device includes a rotor carrying the constriction elements, and the control device controls the rotor to rotate, such that each constriction element cyclically constricts the selected portions of the series of selected portions. Each constriction element suitably includes a roller for rolling on the intestines to constrict the selected portions thereof.

Optionally, the stimulation device described above may be used for cooperation with the constriction device to successively constrict and contract the selected portions of the series of selected portions. Thus, the constriction device constricts any portions of the series of selected portions to at least substantially decrease the cross-sectional area of the passageway of the intestines and the stimulation device electrically stimulates the selected portion constricted by the constriction device to close the passageway of the intestines. The control device controls the constriction device to successively constrict the selected portions of the series of selected portions to move intestinal contents in the passageway of the intestines in a peristaltic manner, while controlling the stimulation device to successively stimulate the selected portions to cause successive contractions thereof in harmony with the successive constrictions of the selected portions performed by the constriction device. Specifically, the stimulation device includes one or more electrodes positioned on the constriction elements of the constriction device and adapted to stimulate intestinal tissue with electric pulses. A plurality of such electrodes may be distributed along a surface in relation to each constriction element, wherein the surface contacts the intestines as the constriction element constricts any one of the selected portions. The control device controls the constriction device to cyclically move the constriction elements one after the other along the selected portions of the series of selected portions, while controlling the stimulation device to energize the electrodes.

In accordance with another alternative of the apparatus, the constriction device includes at least one elongated constriction element extending along the intestines, preferably two elongated elements extending along the intestines at opposite sides thereof. The control device controls the constriction device, such that the elongated constriction elements co-operate with each other to progressively constrict the selected portion to move intestinal contents in the passageway of the intestines. The elongated constriction elements comprise contact surfaces dimensioned for contacting a length of the selected portion of the intestines at opposite sides thereof.

The contact surfaces are suitably convex, wherein the control device controls the constriction device, such that the convex contact surfaces of the constriction elements rolls on and progressively constricts the selected portion of the intestines. Each constriction element is adapted to change between a constriction state, in which the convex surface is capable of rolling along and constricting the selected portion of the intestines, and a release state, in which the convex surface is released from the selected portion of the intestines.

Optionally, the stimulation device described above may be used for cooperation with the elongated constriction elements. Thus, the control device may control the stimulation device to stimulate the selected portion as the elongated constriction element progressively constricts the selected portion. The electrodes of the stimulation device are suitably longitudinally distributed on a surface of the elongated constriction element that contacts the selected portion of the intestines, wherein the control device controls the stimulation device to energize the electrodes successively along the elongated constriction element to cause progressive contraction of the selected portion of the intestines.

In accordance with another alternative of the apparatus, said constriction device is adapted to radially expand at least a section of the selected portion of the intestines to form an expanded chamber of the passageway of the intestines along the selected portion, and to axially constrict the expanded section of the selected portion to at least substantially reduce the volume of the chamber, such that intestinal contents is displaced through the passageway of the intestines. In operation, the control device controls the constriction device to axially constrict and release the expanded section of the selected portion, so that intestinal contents is displaced through the passageway of the intestines. The constriction device is adjustable between a rest position, in which it does not expand the section of the selected portion, and an expansion position, in which it expands the section of the selected portion. Suitably, the constriction device is provided with a material that allows growth of fibrotic tissue for externally joining the expansion device with the wall of the selected portion of the intestines, whereby the expansion device pulls the wall of the selected portion radially outwardly, when it is in its expansion position, to form the expanded section of the selected portion.

Optionally, the stimulation device described above may be used for electrically stimulating the expanded section of the selected portion, when the constriction device is in its expansion position, to cause axial contraction of the expanded section of the selected portion. The electrodes of the stimulation device suitably form at least one series of electrodes extending around the expanded section of the selected portion of the intestines.

Separate Closure

There may be provided at least one implantable releasable closure adapted to engage the selected portion of the intestines to close the passageway of the intestines, or at least partially constrict the selected portion, when the pump is not in operation, and to release the selected portion to open the passageway of the intestines when the pump is in operation. Preferably, the closure at least partially constricts the selected portion to at least substantially decrease the cross-sectional area of the passageway of the intestines, when the pump is not in operation, and the stimulation device described above is provided to electrically stimulate muscle or neural tissue of the intestines to cause contraction of the intestines where the closure constricts the intestines to completely close the passageway of the intestines. The electrodes of the stimulation device, which are separate from or integrated with the closure, are suitably distributed along a surface of the closure that contacts the intestines. The control device controls the closure and the stimulation device to co-operate, to allow for sufficient blood circulation in the blood vessels of the constricted intestines, such that intestinal tissues maintain their integrity following long exposure to the closure, when the pump is not in operation. Where the pump includes an elongated constriction element provided with electrodes of the stimulation device, as described above, the control device may variably energize the electrodes, in order to always allow for sufficient blood circulation in the blood vessels of the constricted intestine, where the pump operates.

Closing the Passageway of the Patient's Intestines by the Pump

Instead of providing the separate closure described above, the constriction device of the pump can be maintained in a rest position, in which it keeps the selected portion at least partially constricted, when the pump is not in operation. When the constriction device is in this rest position, it constricts the selected portion no more than to allow for sufficient blood circulation in the blood vessels of the constricted intestines, such that intestinal tissues maintain their integrity following long exposure to the constriction device. Furthermore, the constriction device constricts the intestines to at least substantially decrease the cross-sectional area of the passageway of the intestines, when the constriction device is in the rest position, and the stimulation device described above is provided to electrically stimulate the intestines where the constriction device constricts the intestines, to cause contraction of the intestines to completely close the passageway of the intestines. Preferably, the control device controls the stimulation device, to variably energize the electrodes of the stimulation device along the selected portion, to cause partial contractions of the selected portion that over time change their positions on the selected portion, whereby parts of the intestines that currently are not stimulated can restore substantially normal blood circulation before they are stimulated again.

Artificial Intestinal Piece

An artificial intestinal piece may be surgically joined to the patient's intestines to form part of the passageway of the intestines and to form at least part of the selected portion of the intestines to be constricted by the constriction device. A significant advantage of this embodiment is that a constriction device of the various pump designs described above can be used for operating only on the artificial intestinal piece, not on the sensitive intestines. When the pump is not in operation, the constriction device can constrict the artificial intestinal piece to completely close the passageway of the intestines.

The artificial intestinal piece may be integrated with the patient's intestines between two ends thereof, for example, where a piece of the rectum has been removed due to cancer. Alternatively, the artificial intestinal piece may be joined directly or indirectly to the patient's anus.

Where the artificial intestinal piece is implanted in an ileostomy, a jejunostomy, a colostomy or a rectostomy patient, the constriction device constricts the artificial intestinal piece in order to discharge intestinal contents through a stoma located downstream of the artificial intestinal piece. Alternatively, the artificial intestinal piece may end at such a stoma.

Manually Operable Pump

A subcutaneously implantable actuator operatively connected to the constriction device of the pump may be provided, wherein the actuator is manually actuatable for operating the constriction device.

The constriction device may be hydraulically operable, and the actuator may be hydraulically connected to the hydraulically operable constriction device. The actuator preferably includes a manually compressible resilient reservoir for hydraulic fluid used for operating the constriction device.

Suitably, there is provided a reverse servo hydraulically interconnecting the reservoir and the hydraulically operable constriction device. The term "reverse servo" is to be understood as a mechanism that transfers a strong force acting on a moving element having a short stroke into a weak force acting on another moving element having a long stroke; i.e., the reverse function of a normal servo mechanism. Thus, minor changes in the amount of fluid in a smaller reservoir, which in this case can be hydraulically connected to the resilient reservoir of the actuator, could be transferred by the reverse servo into major changes in the amount of fluid in a larger reservoir, which in this case can be hydraulically connected to the constriction device. The reverse servo is particularly suited for manual operation thereof.

The reservoir is hydraulically connected to the hydraulically operable constriction device, such that when the reservoir is manually compressed the constriction device constricts the selected portion between the upstream and downstream ends thereof to move intestinal contents contained in the selected portion downstream in the passageway of the intestines. When the resilient reservoir is manually released and restores its uncompressed shape, the constriction device releases the selected portion between the upstream and downstream ends thereof to allow intestinal contents in the passageway of the intestines upstream of the selected portion to enter the selected portion.

The hydraulically operable constriction device includes a constriction element and a hydraulic bellows device that operates the constriction element to constrict the selected portion between the upstream and downstream ends thereof, when the bellows device is expanded. The compressible resilient reservoir is hydraulically connected to the bellows device, such that the bellows device is expanded when the reservoir is manually compressed and retracted, when the reservoir is manually released and restores its uncompressed shape. Thus, the bellows device operates the constriction element to release the selected portion between the upstream and downstream ends, when the bellows device is retracted.

In a specific alternative of the hydraulically operable constriction device, the constriction device includes a first hydraulically operable sub-device for constricting and releasing the selected portion at an upstream end thereof, a second hydraulically operable sub-device for constricting and releasing the selected portion at a downstream end thereof, and a third hydraulically operable sub-device for constricting and releasing the selected portion between the upstream and downstream ends thereof. The reservoir is hydraulically connected to the first, second and third sub-devices, such that when the reservoir is manually compressed, the upstream first sub-device constricts the selected portion to close the passageway of the intestines at the upstream end of the selected portion, the downstream second sub-device releases the selected portion, and the third sub-device constricts the selected portion between the upstream and downstream ends thereof to move intestinal contents contained in the selected portion downstream in the passageway of the intestines. When the resilient reservoir is manually released and restores its uncompressed shape, the downstream second sub-device constricts the selected portion to close the passageway of the intestines at the downstream end of the selected portion, the upstream second sub-device releases the selected portion, and the third sub-device releases the selected portion between the upstream and downstream ends thereof to allow intestinal contents in the passageway of the intestines upstream of the selected portion to enter the selected portion.

The first sub-device of the constriction device includes a first constriction element and a first hydraulic bellows device that operates the first constriction element to constrict the selected portion at the upstream end when the first bellows device is expanded, the second sub-device of the constriction device comprises a second constriction element and a second hydraulic bellows device that operates the second constriction element to release the selected portion at the downstream end when the second bellows device is expanded, and the third sub-device of the constriction device comprises a third constriction element and a third hydraulic bellows device that operates the third constriction element to constrict the selected portion between the upstream and downstream ends when the third bellows device is expanded. The compressible resilient reservoir is hydraulically connected to the first, second and third bellows devices, such that the bellows devices are expanded when the reservoir is manually compressed and retracted when the reservoir is manually released and restores its uncompressed shape. Thus, the first bellows device operates the first constriction element to release the selected portion at the upstream end when the first bellows device is retracted, the second bellows device operates the second constriction element to constrict the selected portion at the downstream end when the second bellows device is retracted, and the third bellows device operates the third constriction element to release the selected portion between the upstream and downstream ends when the third bellows device is retracted.

Where applicable, the pumps disclosed in this specification may be manually operable by using hydraulic means as described above.

Powered Pump

In an embodiment of the invention, the pump is powered. The control device may include a manually operable switch for starting and stopping the powered pump, wherein the switch is adapted for subcutaneous implantation in the patient. Alternatively, the control device may include a wireless remote control, suitably operated by the patient holding it, for controlling the pump, i.e., to start and stop.

A wireless energy transmitter may be provided for transmitting wireless energy from outside the patient's body into the patient's body for powering the pump. The energy transmitter may transmit wireless energy for directly powering the pump, as the wireless energy is being transmitted. Among many things, the wireless energy may comprise electromagnetic energy, such as an electric, an electromagnetic or a magnetic field, or a combination thereof, or electromagnetic waves for direct power of the pump. For example, where the pump includes an electric pump, wireless energy in the form of a magnetic or an electromagnetic field may be used for direct power of the electric pump.

Thus, the electric pump runs directly during transmission of the wireless energy. This may be achieved in two different ways: a) using an energy-transforming device implanted in the patient to transform the wireless energy into energy of a different form, preferably electric energy, and powering the pump with the transformed energy, or b) using the wirelessly transmitted energy to directly power the pump. Preferably wireless energy in the form of an electromagnetic or magnetic field is used to directly influence specific components of the pump to create kinetic energy. Such components may include coils integrated in the pump.

Alternatively, an accumulator, such as a capacitor or a rechargeable battery, may be provided for storing the electric energy produced by the energy-transforming device, wherein the control device controls the accumulator to release energy for powering the pump. An implantable charge meter for measuring the charge of the accumulator may be provided and the control device may produce an indication in response to the charge meter.

Sensor

An implantable sensor may be provided for directly or indirectly sensing a physical parameter of the patient or a functional parameter of the apparatus. Regarding the physical parameter, the control device may produce an indication, such as, a sound signal or displayed information in response to the sensor sensing a value of the physical parameter exceeding a threshold value, when the pump is not in operation. The physical parameter may be the volume of the intestinal contents in the selected portion of the intestines, the distension of the intestinal wall, or the pressure in the selected portion of the intestines.

Regarding the functional parameter of the apparatus, the control device may produce an indication, such as an alarm, a sound signal or displayed information in response to the sensor sensing a value of the functional parameter exceeding a threshold value, when the pump is in operation.

Communication

There may be provided an external data communicator intended to be outside the patient's body, and an internal data communicator implantable in the patient for communicating with the external communicator. The internal data communicator feeds data related to the patient back to the external data communicator, and/or the external data communicator feeds data to the internal data communicator.

In another embodiment of the invention, there is provided a method for treating a patient having a disorder related to the passageway of the intestines. This method comprises the steps of:

providing a pump including a constriction device engaging a selected portion of the intestines to constrict and release the selected portion, controlling the pump to operate the constriction device to alternately constrict the selected portion to at least substantially reduce the volume of the passageway of the intestines along the selected portion and release the selected portion to increase the volume of the passageway of the intestines along the selected portion, so that intestinal contents is displaced through the passageway of the intestines.

This method further comprises providing at least one releasable closure engaging the patient's intestines, and using the closure to at least substantially close the passageway of the intestines, when the pump is not in operation, and to release the intestines, when the pump is in operation. The closure may be used to constrict the intestines to close the passageway of the intestines.

Alternatively, the closure may be used to constrict the intestines to at least substantially decrease the cross-sectional area of the passageway of the intestines, wherein the method further comprises electrically stimulating muscle or neural tissue of the intestines to cause contraction of the intestines where the closure constricts the intestines to close the passageway of the intestines. In this case, the method suitably comprises coordinating the operation of the closure and the electric stimulation of the intestines, to allow for sufficient blood circulation in the blood vessels of the constricted intestines, so that intestinal tissues maintain their integrity following long exposure to the closure, when the pump is not in operation.

The present invention also provides a method (I) for using an apparatus as described above to treat a patient having a disorder related to the passageway of the intestines. This method (I) comprises the steps of:

providing an apparatus as described above, inserting a needle like tube into the abdomen of the patients body, supplying gas through the tube to fill the abdomen with gas, thereby expanding the abdominal cavity, placing at least two laparoscopical trocars in the patient's body, inserting through one of the trocars a camera into the abdomen, selecting a portion of the patient's intestines, inserting a dissecting tool through one of the trocars and dissecting an area of the selected portion, placing the pump of the apparatus in the dissected area in operative engagement with the selected portion of the intestines, and using the pump to pump intestinal contents through the passageway of the intestines.

The method (I) may further comprise cutting an opening through the patient's skin and abdominal wall and passing the patient's intestine through the opening creating a stoma, and selecting the portion of the patient's intestines in the vicinity of the stoma, wherein the pump is used for discharging the intestinal contents through the stoma.

The present invention provides another method (II) for using an apparatus as described above to treat a patient having a disorder related to the passageway of the intestines. This method (II) comprises the steps of:

providing an apparatus as described above, cutting an opening through the patient's skin and abdominal wall, selecting a portion of the patient's intestines, inserting a dissecting tool through the opening and dissecting an area of the selected portion, placing the pump of the apparatus in the dissected area in operative engagement with the selected portion of the intestines, and using the pump to pump intestinal contents through the passageway of the intestines.

The present invention provides yet another method (III) for using an apparatus as described above to treat a patient having a disorder related to the passageway of the intestines. This method (III) comprises the steps of:

cutting an opening through the patient's skin and abdominal wall and passing a portion of the patient's intestines through the opening creating a stoma, cutting the intestines to separate a short piece of the intestines forming the stoma from the remaining part of the intestines while keeping blood vessels of the mesentery connected to the short piece of the intestines, to ensure blood supply to the short piece of the intestines, dissecting an area at the short piece of the intestines, placing an artificial intestinal piece in the dissected area, and surgically joining it to the short piece of the intestines and to the remaining part of the intestines to form a continuous passageway of the intestines through the remaining part of the intestines, the artificial intestinal piece and the short piece of the intestines, the artificial intestinal piece forming a selected portion of the patient's intestines, providing an apparatus as described above, placing the pump of the apparatus in operative engagement with the artificial intestinal piece, and using the pump to pump intestinal contents through the passageway of the intestines and out of the stoma.

The above methods (I), (II) and (III) may further comprise subcutaneously implanting a manually operable switch for starting and stopping the pump.

In accordance with the above methods (I), (II) and (III), the constriction device of the pump is put in operative engagement with the selected portion of the intestines, and the pump is controlled to operate the constriction device to alternately constrict the selected portion to at least substantially reduce the volume of the passageway of the intestines along the selected portion, and release the selected portion to increase the volume of the passageway of the intestines along the selected portion, so that intestinal contents is displaced through the passageway of the intestines.

The methods (I), (II) and (III) further comprise implanting at least one releasable closure in operative engagement with the selected portion of the intestines, and using the releasable closure to close the passageway of the intestines when the pump is not in operation and to release the intestines when the pump is in operation.

The methods (I), (II) and (III) further comprise implanting an electrically powered operation device, such as an electric motor, for operating the releasable closure. Alternatively, the operation device includes a hydraulic operation device.

The methods (I), (II) and (III) further comprise transmitting wireless energy for powering the operation device, and when desired to pump intestinal contents through the passageway of the intestines, powering the operation device with the transmitted energy to operate the closure to release the selected portion of the intestines.

The methods (I), (II) and (III) further comprise implanting a source of energy in the patient, providing an external source of energy, controlling the external source of energy to release wireless energy, transforming the wireless energy into storable energy, non-invasively charging the implanted source of energy with the transformed energy, and controlling the implanted source of energy from outside the patient's body to release energy for use in connection with the operation of the pump and/or releasable closure. The patient's intestines may be surgically modified to end in a stoma, and when desired to discharge intestinal contents out from the patient's body, the implanted source of energy is controlled to supply energy for operating the releasable closure to temporarily release the selected portion of the intestines and the pump is used to pump intestinal contents in the passageway of the intestines out from the body through the stoma. The wireless energy may be transformed into a storable energy, such as electric energy, different than the wireless energy, wherein the storable energy is used for operating the pump and/or releasable closure.

Alternatively, the methods (I), (II) and (III) further comprise providing an external source of energy outside the patient's body, controlling the external source of energy from outside the patient's body to release wireless energy, and using the released wireless energy for operating the pump and/or releasable closure. For example, the external source of energy may be controlled to release wireless energy directly operating the pump and/or releasable closure. The external source of energy may be controlled to release non-magnetic wireless energy, wherein the released non-magnetic wireless energy is used for operating the pump and/or releasable closure. Alternatively, the external source of energy may be controlled to release electromagnetic wireless energy, wherein the released electromagnetic wireless energy is used for operating the pump and/or releasable closure.

The wireless energy may be transformed into electrical energy inside the patient's body by an implanted energy-transforming device, wherein the electrical energy is used in connection with the operation of the pump and/or releasable closure. The electrical energy may be directly used in connection with the operation of the pump and/or releasable closure. For example, the pump and/or releasable closure may be directly operated with the electrical energy, as the energy-transforming device transforms the wireless energy into the electrical energy.

The methods (I), (II) and (III) further comprise controlling the releasable closure to:

at least partially restrict the passageway of the intestines in the selected portion to prevent intestinal contents from passing therethrough, or release the intestines to allow intestinal contents to be pumped therethrough by using the pump.

Step (a) may be performed by controlling the releasable closure to partially restrict the passageway of the intestines in the selected portion and electrically stimulating the selected portion of the intestines to cause contraction thereof to further restrict the passageway of the intestines to prevent intestinal contents from passing therethrough.

The present invention provides yet another method for using an apparatus, as described above, to treat a patient having a disorder related to the passageway of the intestines. This method comprises:

providing a wireless remote control adapted to control the pump from outside the patient's body, and operating the wireless remote control by the patient to start the pump, when the patient wants to defecate, and stop the pump when the patient has finished defecating.

A surgical method of treating a patient is further provided, the method comprises the steps of: cutting the patient's skin and abdominal wall, dissecting an area of the patient's intestine, surgically creating an opening in the dissected intestinal area, affixing to the opening a reservoir so as to receive and temporarily collect therein intestinal contents from the patient's intestine, involving introducing a conduit into said opening, further involving covering at least partly the intestine introduced onto the conduit with a sleeve, implanting a flow control device so as to permanently reside inside the patient's body and adapted to control flow of intestinal contents from the reservoir to outside the patient's body, and suturing the abdominal wall and skin.

A laparoscopic surgical method of treating a patient is further provided, the method comprises the steps of: making a small opening in the patient's skin and abdominal wall, introducing a needle in the abdominal cavity, inflating the abdominal cavity with gas, inserting at least one trocar into the cavity, introducing a camera through the trocar, inserting at least one dissecting instrument preferably through a second trocar, dissecting an area of the intestine, surgically creating an opening in the dissected intestinal area, affixing to the opening an artificial reservoir so as to receive and temporarily collect therein intestinal contents from the patient's intestine, involving, introducing a conduit into said opening, further involving covering at least partly the intestine introduced onto the conduit with a sleeve, implanting a flow control device so as to permanently reside inside the patient's body and be adapted to control flow of intestinal contents from the reservoir to outside the patient's body, connecting the intestine to the artificial reservoir with securing means, extracting the instruments, camera and trocar, and in relation thereto, and suturing, if necessary, the abdominal wall and permanently closing the skin.

A surgical method of treating a patient is further provided, the method comprises the steps of: cutting the patient's skin and abdominal wall, dissecting an area of the patient's intestine, dissecting a portion of the dissected intestinal area such that intestinal mesentery connected thereto is opened in such a way that supply of blood through the mesentery to the dissected intestinal area is maintained as much as possible on both sides of the dissected portion, dividing the patient's intestine in the dissected portion so as to create an upstream part of the intestine with a first intestinal opening and a downstream part of the intestine with a second intestinal opening with the mesentery still maintaining a tissue connection between the upstream and downstream intestine parts, affixing to the first intestinal opening an artificial reservoir so as to receive and temporarily collect therein intestinal contents from the patient's intestine, involving introducing a conduit into said opening, further involving covering at least partly the intestine introduced onto the conduit with a sleeve, affixing the reservoir to the second intestinal opening so as to allow for discharging intestinal contents from the reservoir through the second intestinal opening, involving introducing a conduit into said opening, further involving covering at least partly the intestine introduced onto the conduit with a sleeve, implanting a flow control device so as to permanently reside inside the patient's body and be adapted to control flow of intestinal contents from the reservoir through the downstream intestine part, and suturing the abdominal wall and skin.

A laparoscopic surgical method of treating a patient is further provided, the method comprising the steps of: making a small opening in the patient's skin and abdominal wall, introducing a needle in the abdominal cavity, inflating the abdominal cavity with gas, inserting at least one trocar into the cavity, introducing a camera through the trocar, inserting at least one dissecting instrument preferable through at least a second trocar, dissecting an area of the intestine, dissecting a portion of the dissected intestinal area such that intestinal mesentery connected thereto is opened in such a way that supply of blood through the mesentery to the dissected intestinal area is maintained as much as possible on both sides of the dissected portion, dividing the patient's intestine in the dissected portion so as to create an upstream part of the intestine with a first intestinal opening and a downstream part of the intestine with a second intestinal opening with the mesentery still maintaining a tissue connection between the upstream and downstream intestine parts, affixing to the first intestinal opening an artificial reservoir so as to receive and temporarily collect therein intestinal contents from the patient's intestine, involving introducing a conduit into said opening, further involving covering at least partly the intestine introduced onto the conduit with a sleeve, affixing the reservoir to the second intestinal opening so as to allow for discharging intestinal contents from the reservoir through the second intestinal opening, involving introducing a conduit into said opening, further involving covering at least partly the intestine introduced onto the conduit with a sleeve, implanting a flow control device so as to permanently reside inside the patient's body and be adapted to control flow of intestinal contents from the reservoir to the downstream intestine part, connecting the intestine to the artificial reservoir with securing means, extracting the instruments, camera and trocar, and in relation thereto suturing, if necessary, the abdominal wall and permanently closing the skin.

In the embodiments where the method comprises the step of affixing the open end portion of the artificial intestine section to the cross-sectional opening of the intestine part comprises the method could comprise the steps of inserting the open end portion of the artificial intestine section into the cross-sectional opening of the intestine part, and placing a flexible sleeve so as to extend over both the intestine part and open end portion of the artificial intestine section such that the intestine part is located intermediate the sleeve and the outer surface of the artificial intestine section, wherein the sleeve is adapted to increase the strength of the connection between the intestine section and the patient's intestine against axial forces resulting from peristaltic movements of the intestine which tend to pull on the intestine, when said artificial intestine section is long term implanted.

The sleeve according to any of the embodiments herein could be made of a non-resorbable material for long term implantation in a patient, preferably being more than one year. In embodiments where the intestine is adapted to heal using only natural parts, the sleeve may comprise a resorbable non-polymer material.

According to one embodiment of the system, the pump could further comprise a mounting device adapted to be mounted to the peritoneum. The mounting device could be adapted to pass through the peritoneal wall and hold said intestinal section, comprising a flange intended for placement outside the peritoneum. The mounting device could be adapted to hold sutures and staplers passing through the peritoneal wall, when implanted, to hold said artificial intestine section.

In embodiments comprising implantation of a flow control device the method could comprise the steps of: implanting an upstream flow control device outside the intestine on a upstream part, in relation to the intestinal opening, so as to permanently reside inside the patient's body and be adapted to control flow of intestinal contents in the intestine to the reservoir. The intestinal opening could be created in the patient's small intestine or in the patient's large intestine.

In embodiments where the method comprises implantation of a flow control device the method could comprise the steps of: implanting a downstream flow control device outside the intestine on a down-stream part, in relation to the intestinal opening, so as to permanently reside inside the patient's body and be adapted to control flow of intestinal contents from the reservoir to the downstream intestine part. The intestinal opening could be created in the patient's small intestine or in the patient's large intestine. The downstream flow control device could comprise an exit valve, affixing the exit valve to a portion of the patient's intestine leading to a pre-existing opening in the patient's body including the patient's anus, or to a surgically created an intestinal stomy in the patient's abdominal wall and skin.

Aneurysm

In accordance with one embodiment a stimulation device for treating a vascular aneurysm of a human or mammal patient is provided. The stimulation device comprises an implantable electrode adapted to be placed in close connection to the aneurysm, and is adapted to provide an electrical stimulation pulse on a wall portion of the aneurysm. Hereby an efficient treatment of the aneurysm can be provided.

In accordance with one embodiment one or several electrode(s) is/are adapted to stimulate multiple stimulation points.

In accordance with one embodiment at least two electrodes are provided and groups of stimulation points individually stimulated.

In accordance with one embodiment a device for delivering electrical stimulation pulse at different time intervals is provided.

In a preferred embodiment, the system comprises at least one switch implantable in the patient for manually and non-invasively controlling the device.

In another preferred embodiment, the system comprises a wireless remote control for non-invasively controlling the device.

In a preferred embodiment, the system comprises a hydraulic operation device for operating the device.

In one embodiment, the system comprises comprising a motor or a pump for operating the device.

The invention also extends to methods for implanting the device and to a computer program product adapted to control the device.

Any feature in any of the four combinations of features in the combination embodiments described below may be used in any combination and furthermore in combination with any other feature or embodiment described in any of the other figures or figure text or descriptions in this application.

First combination embodiments includes electrical stimulation comprising:

A medical device including a stimulation device for treating a vascular aneurysm of a human or mammal patient comprising:

at least one implantable electrode adapted to placed in close connection to the aneurysm, the at least one electrode being adapted to provide an electrical stimulation pulse on a wall portion of the aneurysm.

At least one electrode is adapted to stimulate multiple stimulation points. Alternatively at least two electrodes are provided and wherein groups of stimulation points are controllable to be individually stimulated.

A pulse generator adapted to generate positive and negative electrical stimulation pulses.

Electrical stimulation pulses, which may have a constant current and preferable the stimulation device deliver the electrical stimulation pulse as pulse train stimulation with breaks to allow the vessel to rest.

A stimulation device that deliver the electrical stimulation pulses at different time intervals.

A device preferable delivering the electrical stimulation pulse as a pulse width modulated stimulation pulse.

A stimulation device preferable deliver the electrical stimulation pulse during the systolic phase.

A stimulation device further comprising a monitoring system for detecting an expansion of the aneurysm. Also to avoid any fast expansion and burst leading to death.

If so said monitoring system may increase intensity and or position of the stimulation, when detecting an expansion of the aneurysm.

A method of treating an aneurysm of a mammal patient by providing the medical device according to any feature disclosed herein, comprising the steps of:

inserting a needle or a tube like instrument into the patient's abdominal cavity, using the needle or tube like instrument to fill a part of the patient's body with gas and thereby expanding said abdominal cavity, placing at least two laparoscopic trocars in said cavity, inserting a camera through one of the laparoscopic trocars into said cavity, inserting at least one dissecting tool through one of said at least two laparoscopic trocars, dissecting an area of an aneurysm of a blood vessel, placing said medical device, comprising a stimulation device, onto said the aneurysmic blood vessel, and stimulating said aneurysm to increase the tonus of the aneurysm wall.

An alternative method of treating an aneurysm of a mammal patient by providing the medical device including any feature disclosed herein, comprising the steps of:

inserting a needle or a tube like instrument into the patient's thoraxial cavity, using the needle or tube like instrument to fill a part of the patient's body with gas and thereby expanding said thoraxial cavity, placing at least two laparoscopic trocars in said cavity, inserting a camera through one of the laparoscopic trocars into said cavity, inserting at least one dissecting tool through one of said at least two laparoscopic trocars, dissecting an area of an aneurysm of a blood vessel, placing said medical device, comprising a stimulation device, onto said the aneurysmic blood vessel, and stimulating said aneurysm to increase the tonus of the aneurysm wall.

An alternative method of treating an aneurysm of a mammal patient by providing the medical device including any feature disclosed herein, said method comprising the steps of:
cutting the skin in the abdominal or thoraxial wall of said mammal patient,
dissecting an area of the aneurysm,
placing said medical device, comprising a stimulation device, onto said aneurysm, and
stimulating said aneurysm to increase the tonus of the aneurysm wall.

A method of treating an aneurysm of a mammal patient by providing the medical device including any feature disclosed herein, said method comprising the steps of:
cutting the skin of said mammal patient,
dissecting an area of the aneurysm,
placing said medical device, comprising a stimulation device, onto said aneurysm, and
stimulating said aneurysm to increase the tonus of the aneurysm wall.

Additionally a computer program product comprising computer program segments that when executed on a computer causes the computer to generate a pattern of signals for an implantable electrode adapted to placed in close connection to an aneurysm, the at least one electrode being adapted to provide an electrical stimulation pulse on a wall portion of the aneurysm.

A device including a digital storage medium comprising the computer program product.

Second combination embodiments includes a hydraulic system putting pressure on the aneurysm comprising:

A device for treating an aneurysm of a human or mammal patient comprising:
An implantable member adapted to hold fluid, wherein said member is adapted to be placed in connection with a blood vessel having the aneurysm, the member being adapted to exercise a pressure on the aneurysm of said blood vessel.

A device preferable adapted to prevent or reduce an expansion of said aneurysm.

A device adapted to be postoperatively adjusted. The device is normally non-invasively adjustable.

A device preferable adapted to perform self adjustments of the pressure applied onto said aneurysm within a predetermined treatment interval.

A device normally comprising a control unit and a sensor, the control unit being adapted to control pressure adjustments of based on a signal generated by the sensor.

The sensor may comprise any type of sensor. Preferable a pressure regulator is adapted to regulate the pressure in the member, wherein the pressure regulator preferable is adapted to even out the difference in pressure in the implantable member during the systolic and diastolic phase for reducing the pressure difference or providing a substantially even outside pressure on the aneurysm. The pressure regulator may comprise pressure tank.

A implantable member which is alternatively Y-shaped, wherein the implantable Y-shaped member normally is adapted to be placed at the Aorta Bifurcation A pressure regulator in one embodiment comprises an expandable first reservoir.

The expandable first reservoir preferable is spring loaded.

A device wherein the pressure regulator in a preferred embodiment comprises a pump.

A device further comprising a second reservoir and a pump adapted to move liquid between the first and second reservoirs.

A device wherein preferable said first reservoir has a predetermined optimal pressure regulation volume treatment interval and wherein said pump is adapted to pump liquid from the first to the second reservoir to keep said first reservoir within said regulation interval, when said aneurysm expands and to pump liquid from said implantable member into said first reservoir.

A device preferable provides a pressure equal or less than the diastolic blood pressure of a treated patient.

A device preferable adapted to increase the pressure on the blood vessel when the aneurysm expands.

A device comprising a control device adapted to increase the pressure on the blood vessel when the aneurysm expands more than a predetermined value, preferable during a time period.

A control unit adapted to control the expansion of said aneurysm by controlling the pressure applied on the blood vessel when the aneurysm expands.

A device preferable further comprising a sensor for sensing an expansion of the aneurysm.

A device preferable further comprising a volume control unit adapted to directly or indirectly control the volume in the implantable member based on a signal generated by the sensor for controlling an expansion of the aneurysm, wherein normally said volume control unit controls the volume in the implantable member based on a signal indicative of: flow of fluid from said implantable member or pressure in said fluid filled in said implantable member.

A device wherein the implantable member is divided into a plurality of sub-reservoirs.

A device wherein the sub-reservoirs are provided axially along the blood vessel or radially along the blood vessel.

A device wherein preferable at least one reservoir is located above said aneurysm and one reservoir is located below said aneurysm.

A device further comprising a logic circuitry for determining when the aneurysm is expanding based on the signal from the sensor.

A device further comprising an electrical pulse generator adapted to provide electrical signals for stimulation of the aneurysm wall via electrodes located on the inside of the implantable member.

A control unit adapted to vary to position of the electrical stimulation signals for stimulation of the aneurysm.

A method of treating an aneurysm of a mammal patient by providing the medical device according to any feature disclosed herein, comprising the steps of:
inserting a needle or a tube like instrument into the patient's abdominal cavity,
using the needle or tube like instrument to fill a part of the patient's body with gas and thereby expanding said abdominal cavity,
placing at least two laparoscopic trocars in said cavity,
inserting a camera through one of the laparoscopic trocars into said cavity,
inserting at least one dissecting tool through one of said at least two laparoscopic trocars,
dissecting an area of an aneurysm of a blood vessel,
placing the device onto said the aneurysmic blood vessel, and adjusting the pressure the device exerts onto said aneurysm.

An alternative method of treating an aneurysm of a mammal patient by providing the medical device including any feature disclosed herein, comprising the steps of:

inserting a needle or a tube like instrument into the patient's thoraxial cavity, using the needle or tube like instrument to fill a part of the patient's body with gas and thereby expanding said thoraxial cavity, placing at least two laparoscopic trocars in said cavity, inserting a camera through one of the laparoscopic trocars into said cavity, inserting at least one dissecting tool through one of said at least two laparoscopic trocars, dissecting an area of an aneurysm of a blood vessel, placing the device onto said the aneurysmic blood vessel, and adjusting the pressure said device exerts onto said aneurysm.

An alternative method of treating an aneurysm of a mammal patient by providing the medical device including any feature disclosed herein, said method comprising the steps of:

cutting the skin in the abdominal or thoraxial wall of said mammal patient, dissecting an area of the aneurysm, placing said device onto said aneurysm, and starting the stimulation device and adapted to adjust adjust any parameter related to said stimulation.

adjusting the pressure said device exerts onto said aneurysm.

adjusting the pressure said device exerts onto said aneurysm.

A computer program product comprising computer program segments that when executed on a computer causes the computer to control the pressure applied by an implantable member adapted to hold fluid and adapted to be placed in connection with a blood vessel having an aneurysm. A digital storage medium comprising the computer program product.

Third combination embodiments includes a mechanical system putting pressure on the aneurysm including any feature in any combination, comprising:

A device for treating a vascular aneurysm of a human or mammal patient comprising:

An implantable member adapted to be placed in connection with a blood vessel having an aneurysm for providing a pressure from outside the blood vessel, the device being adapted to be adjusted postoperatively.

A device preferable adapted to prevent or reduce an expansion of said aneurysm.

A device adapted to monitor an expansion of said aneurysm.

The device is preferable adjustable non-invasively.

A device adapted to perform self adjustments of the pressure applied onto said aneurysm within a predetermined treatment interval.

A device comprising an control unit and a sensor, wherein the control unit is adapted to control the pressure applied onto said aneurysm based on said signal generated by the sensor.

A device, wherein the surface of the member facing the blood vessel is adapted to exercise pressure on the blood vessel.

A device, wherein the pressure on the blood vessel is mechanically exercised.

A, wherein the mechanically exercised pressure is controlled hydraulically.

A device, wherein mechanical pressure on the blood vessel is directly or indirectly exercised by a motor or a pump.

A, wherein the implantable member is generally cylindrical

A device, wherein the implantable member comprises a number of segments being individually adjustable.

A device, wherein the implantable member is a Y-shaped member

A device, wherein the implantable Y-shaped member is adapted to be placed at the Aorta Bifurcation.

A pressure regulating system adapted to even out the difference in pressure in the implantable reservoir in the systolic and diastolic phase to reduce the differences or to achieve a substantially even pressure affecting said aneurysm from the outside of said blood vessel.

A device, wherein the implantable member is an elastic member.

A device, wherein the elastic member is a band.

A device, wherein the elastic member is adapted to apply a pressure onto said aneurysm and has an expansion interval wherein the pressure applied is substantially constant or within an interval for treating and reducing expansion of the aneurysm.

A device, wherein the implantable member is spring loaded.

A device according to claim 1, wherein the implantable member is hydraulically operated.

A device, wherein the implantable member is pneumatically operated

A device, wherein the implantable member is adapted to exert an essentially constant pressure or a pressure reducing the pressure difference, caused by the changes in blood pressure in said blood vessel, on the aneurysm.

A device, wherein the provided pressure is equal or less than the diastolic blood pressure of a treated patient.

A device further comprising a control unit adapted to increase the pressure on the blood vessel when the aneurysm expands.

A device comprising a control device adapted to increase the pressure on the blood vessel when the aneurysm expands more than a predetermined value.

A device comprising a control device adapted to increase the pressure on the blood vessel when the aneurysm expands more than a predetermined value during a time period.

A device, further comprising a sensor or a measuring device for sensing an expansion of the aneurysm.

A device, further comprising logic circuitry for determining when the aneurysm is expanding based on a signal from a sensor or measuring device.

A device, further comprising an electrical pulse generator adapted to provide stimulation of the aneurysm wall via electrodes located on the inside of the implantable member.

A method of treating an aneurysm of a mammal patient by providing the medical device according to any feature disclosed herein, comprising the steps of:

inserting a needle or a tube like instrument into the patient's abdominal cavity, using the needle or tube like instrument to fill a part of the patient's body with gas and thereby expanding said abdominal cavity, placing at least two laparoscopic trocars in said cavity, inserting a camera through one of the laparoscopic trocars into said cavity, inserting at least one dissecting tool through one of said at least two laparoscopic trocars, dissecting an area of an aneurysm of a blood vessel, placing the device onto said the aneurysmic blood vessel, and adjusting the pressure the device exerts onto said aneurysm.

An alternative method of treating an aneurysm of a mammal patient by providing the medical device including any feature disclosed herein, comprising the steps of:

inserting a needle or a tube like instrument into the patient's thoraxial cavity, using the needle or tube like instrument to fill a part of the patient's body with gas and thereby expanding said thoraxial cavity, placing at least two laparoscopic trocars in said cavity, inserting a camera through one of the laparoscopic trocars into said cavity, inserting at least one dissecting tool through one of said at least two laparoscopic trocars, dissecting an area of an aneurysm of a blood vessel, placing the device onto said the aneurysmic blood vessel, and adjusting the pressure said device exerts onto said aneurysm.

An alternative method of treating an aneurysm of a mammal patient by providing the medical device including any feature disclosed herein, said method comprising the steps of:

cutting the skin in the abdominal or thoraxial wall of said mammal patient, dissecting an area of the aneurysm, placing said device onto said aneurysm, and starting the stimulation device and adapted to adjust adjust any parameter related to said stimulation.

adjusting the pressure said device exerts onto said aneurysm.

adjusting the pressure said device exerts onto said aneurysm.

A computer program product comprising computer program segments that when executed on a computer causes the computer to control the pressure applied by an implantable member adapted to be placed in connection with a blood vessel having an aneurysm.

A digital storage medium comprising the computer program product.

Fourth combination embodiments includes a monitoring/sensor system putting pressure on the aneurysm including any feature in any combination, comprising:

A device for monitoring an aneurysm of a human or mammal patient comprising:

A sensor placed in relation to a wall portion of the aneurysm for generating a signal corresponding to a parameter related to the aneurysm or the treatment of the aneurism.

A device, wherein the parameter corresponds to the size of the aneurysm.

A device, wherein the parameter corresponds to the diameter of the aneurysm.

A device wherein the sensor is a gauge sensor.

A device wherein the parameter corresponds to a pressure.

A device wherein the pressure corresponds to a pressure from a hydraulic cuff provided around the aneurysm.

A device wherein the pressure corresponds to a pressure from a mechanical implantable member provided around the aneurysm.

A device wherein the pressure corresponds to a pressure in a blood vessel.

A device wherein the sensor is adapted to measure the pressure exerted on an implantable member provided around the aneurysm.

A device wherein the sensor is adapted to measure the volume of a hydraulic implantable member.

A method of treating an aneurysm of a mammal patient by providing the medical device, comprising the steps of:

inserting a needle or a tube like instrument into the patient's abdominal cavity, using the needle or tube like instrument to fill a part of the patient's body with gas and thereby expanding said abdominal cavity, placing at least two laparoscopic trocars in said cavity, inserting a camera through one of the laparoscopic trocars into said cavity, inserting at least one dissecting tool through one of said at least two laparoscopic trocars, dissecting an area of an aneurysm of a blood vessel, placing the device onto said the aneurysmic blood vessel, and monitoring the expansion of the aneurysm by measuring the expansion the aneurysm exerts onto the device.

A method of treating an aneurysm of a mammal patient by providing the medical device, comprising the steps of:

inserting a needle or a tube like instrument into the patient's thoraxial cavity, using the needle or tube like instrument to fill a part of the patient's body with gas and thereby expanding said thoraxial cavity, placing at least two laparoscopic trocars in said cavity, inserting a camera through one of the laparoscopic trocars into said cavity, inserting at least one dissecting tool through one of said at least two laparoscopic trocars, dissecting an area of an aneurysm of a blood vessel, placing the device onto said the aneurysmic blood vessel, and monitoring the expansion of the aneurysm by measuring the expansion the aneurysm exerts onto the device.

A method of treating an aneurysm of a mammal patient by providing the medical device, said method comprising the steps of:

cutting the skin in the abdominal or thoraxial wall of said mammal patient, dissecting an area of the aneurysm, placing said device onto said aneurysm, and monitoring the expansion of the aneurysm by measuring the expansion the aneurysm exerts onto the device.

A method of treating an aneurysm of a mammal patient by providing the medical device, said method comprising the steps of:

cutting the skin of said mammal patient, dissecting an area of the aneurysm, placing said device onto said aneurysm, and monitoring the expansion of the aneurysm by measuring the expansion the aneurysm exerts onto the device.

Please note that any embodiment, of a device or system, or part of embodiment as well as any method or part of method could be combined in any way. All examples herein should be seen as part of the general description and therefore possible to combine in any way in general terms.

BRIEF DESCRIPTION OF THE DRAWINGS

FIGS. 1F, 1G and 1H illustrate different states of operation of a modification of the general embodiment.

FIGS. 1I, 1K and 1L illustrate an alternative mode of operation of the modification of the general embodiment.

FIG. 11A is a longitudinal cross-section of an embodiment of an apparatus used for practicing the method of the invention, where the apparatus includes a thermal stimulation device and the apparatus is constricting a tissue wall of a patient's organ.

FIG. 11B is the same embodiment of FIG. 11A with the thermal stimulation device activated.

FIG. 13C shows a modification of the embodiment of FIG. 13B.

FIG. 30A is a schematic view of a hydraulically operable inflatable constriction device for used for practicing the method of the invention.

FIG. 30B is the same embodiment shown in FIG. 30A with the constriction device inflated.

FIGS. 31A, 31B, 31C and 31D are block diagrams illustrating four different principles for hydraulic operation of the constriction device shown in FIG. 30A.

FIGS. 76-89 schematically show various embodiments of the system for wirelessly powering the apparatus shown in FIG. 74.

FIGS. 90A to 90D illustrate an apparatus for use with the method according to the invention when implanted in a male patient for contraception.

FIG. 92 illustrates an apparatus used for practicing the method of the invention where the apparatus is applied on the common bile duct.

FIG. 93A illustrates a pregnancy promotion apparatus used for practicing the method of the invention applied on the oviducts of a female patient, wherein the apparatus is in a non-restricting operating state.

FIG. 93B is a view similar to that of FIG. 93A, but wherein the apparatus is in a restricting operating state.

FIGS. 107A and 107B show a specific embodiment, wherein the pump and the reservoir are comprised in a common housing and the pump comprises a moveable piston with a front end of the piston extending into the reservoir such that a volume of the reservoir is reduced upon advancement of the piston. The piston is spring loaded so as to urge the piston into a normally retracted position. Furthermore, entry and exit valves are provided in this embodiment, here being realized as flap valves. The flap valves are controlled so that one valve is open while the other one is closed.

In FIG. 108A the bellows of the exit valve are expanded to compress the intestine at the downstream side of the reservoir, whereas in FIG. 108B the intestine is closed by means of the bellows of the entry valve upstream of the reservoir so that the reservoir can be emptied by advancing the piston of the pump.

Figure 111A:
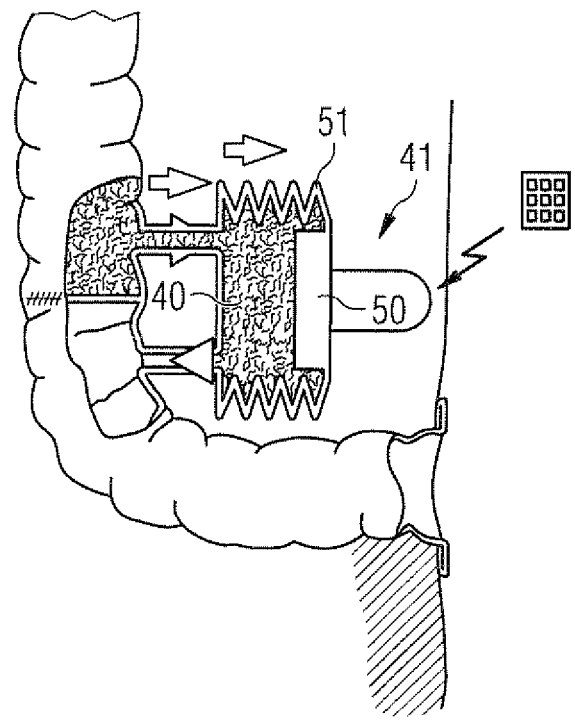
FIGS. 111A and 111B show a structure similar to the one of FIGS. 110A to 110C, however, with the pump and the reservoir being fixedly connected to one another. The reservoir is formed by a bellow having an end wall closing the bellow at one end thereof. The end wall makes part of the pump such that a volume of the bellow can be reduced upon advancement of the end wall. The bellow is made of a resilient material so as to urge the bellow into a normally extended position.
Figure 111B:
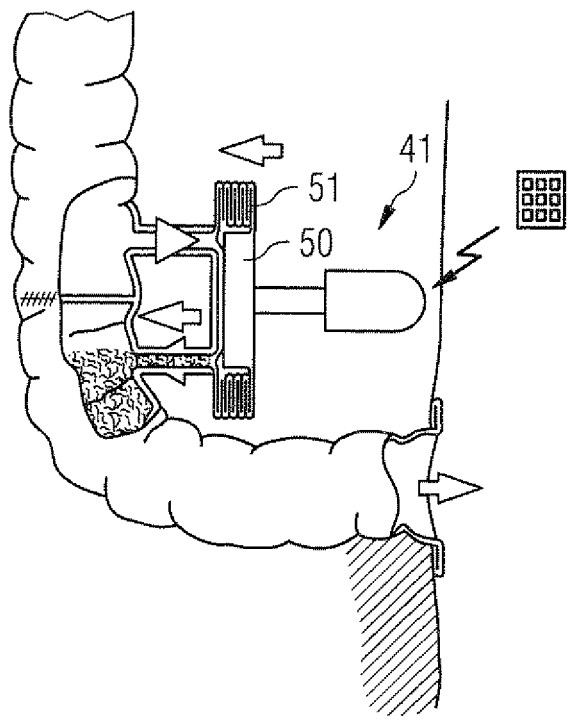
Figure 113A:
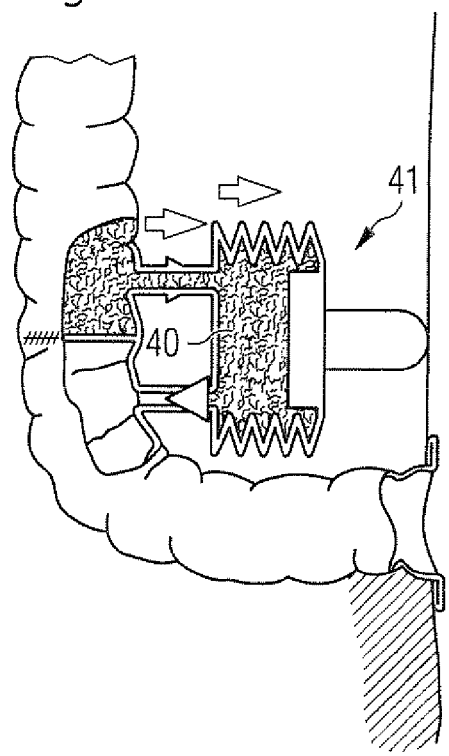
Figure 113B:
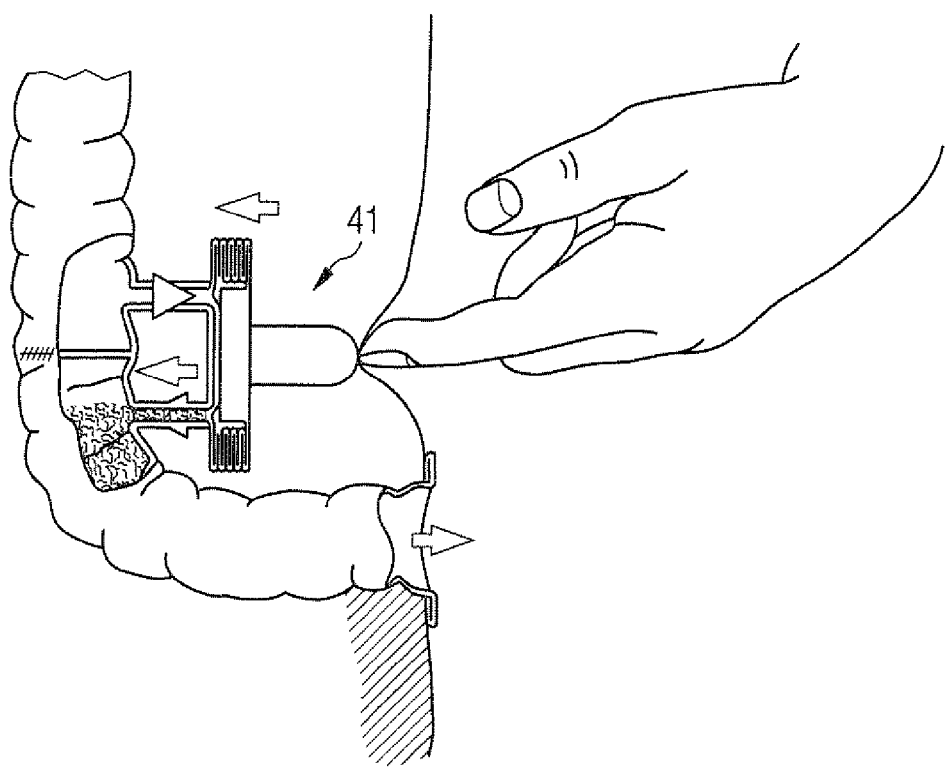

FIGS. 113A and 113B likewise show a variant to the system shown in FIGS. 111A and 111B. While in the system of FIGS. 111A, 111B the pump is automatically driven, such as by an integrated motor, and activated via remote control, the system in FIGS. 113A and 113B is again manually operable in that the manually operable pump is mounted subcutaneously.

Figure 114A:
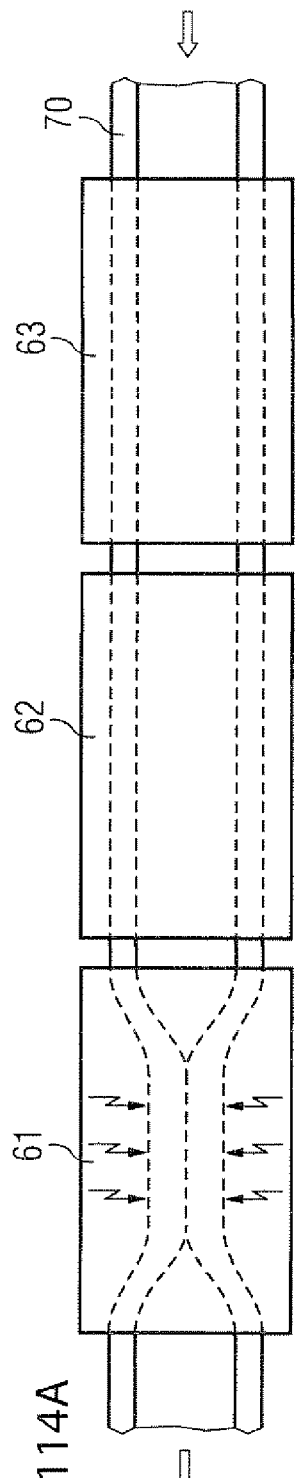
Figure 114B:
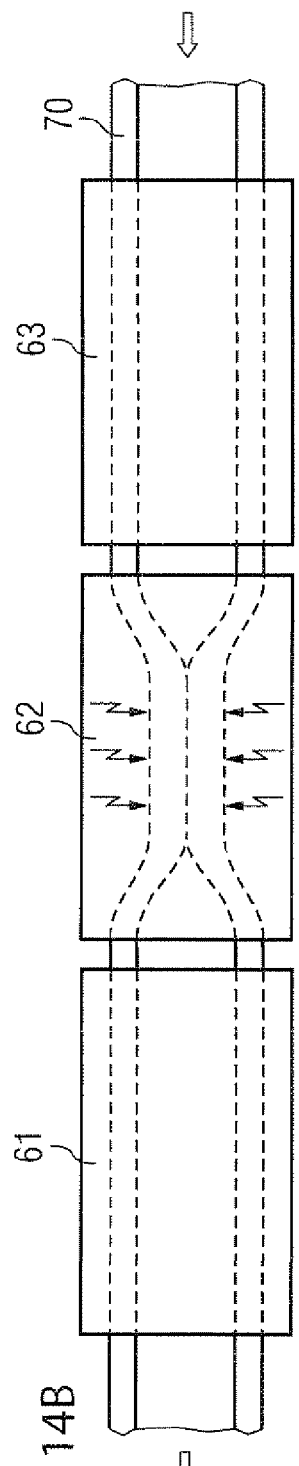
Figure 114C:
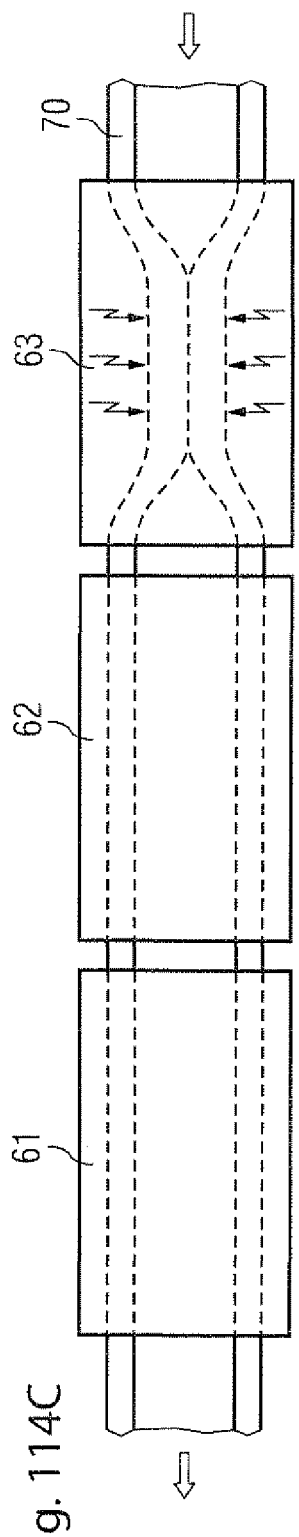

FIGS. 114A to 114C show a plurality of cooperating valves implanted inside the patient's body and outside the patient's intestine. Each of the valves comprises an electrical stimulation device adapted to electrically stimulate muscle or neural tissue of an intestine section so as to cause at least partial contraction of the intestine section. For that purpose, the stimulation device comprises at least one electrode adapted to apply electric pulses to the intestine section. While instead of the three stimulation devices shown, a single stimulation device would be sufficient for opening and closing the intestine, the arrangement of the plurality of stimulation devices is adapted to stimulate different portions of the intestine section over time. The function of the three stimulation devices may also be combined in one integral unit. The direction of natural intestinal contents flow is indicated by arrows. The different portions of the intestine section in a wavelike manner may be made in a direction opposite to the natural intestinal contents flow, as shown in FIGS. 114A to 114C, so as to close the intestine section. The stimulation in the wavelike manner may also be made in the direction of natural intestinal contents flow to support emptying of the intestine or reservoir.

Figure 108A:
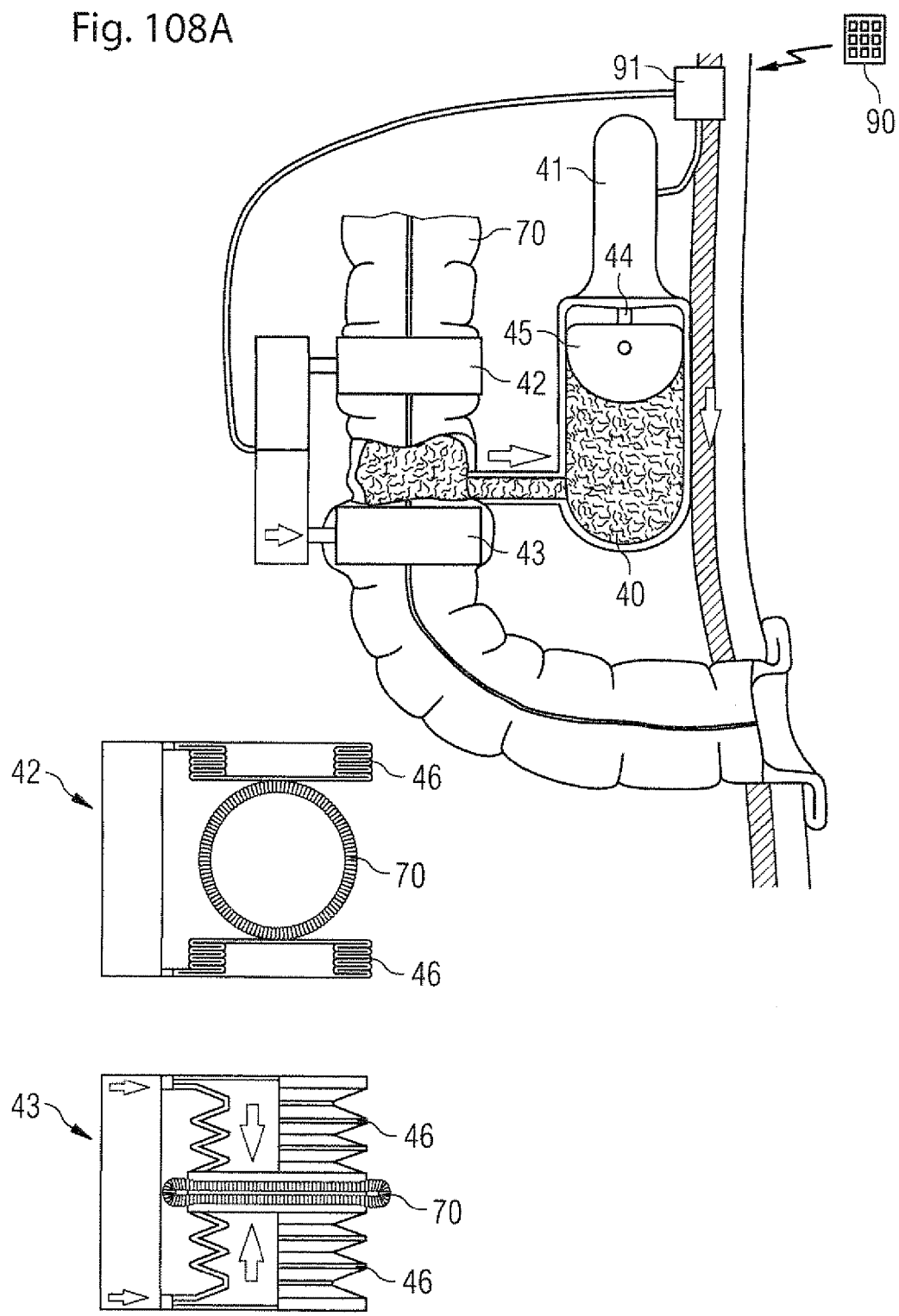
FIGS. 108A and 108B show a system similar to the one of FIGS. 107A and 107B, and FIGS. 106A and B, with a single opening in the reservoir connected to the intestine. However, here the entry and exit valves comprise bellows acting on the intestine from the outside so as to close the intestine by compression.
Figure 108B:
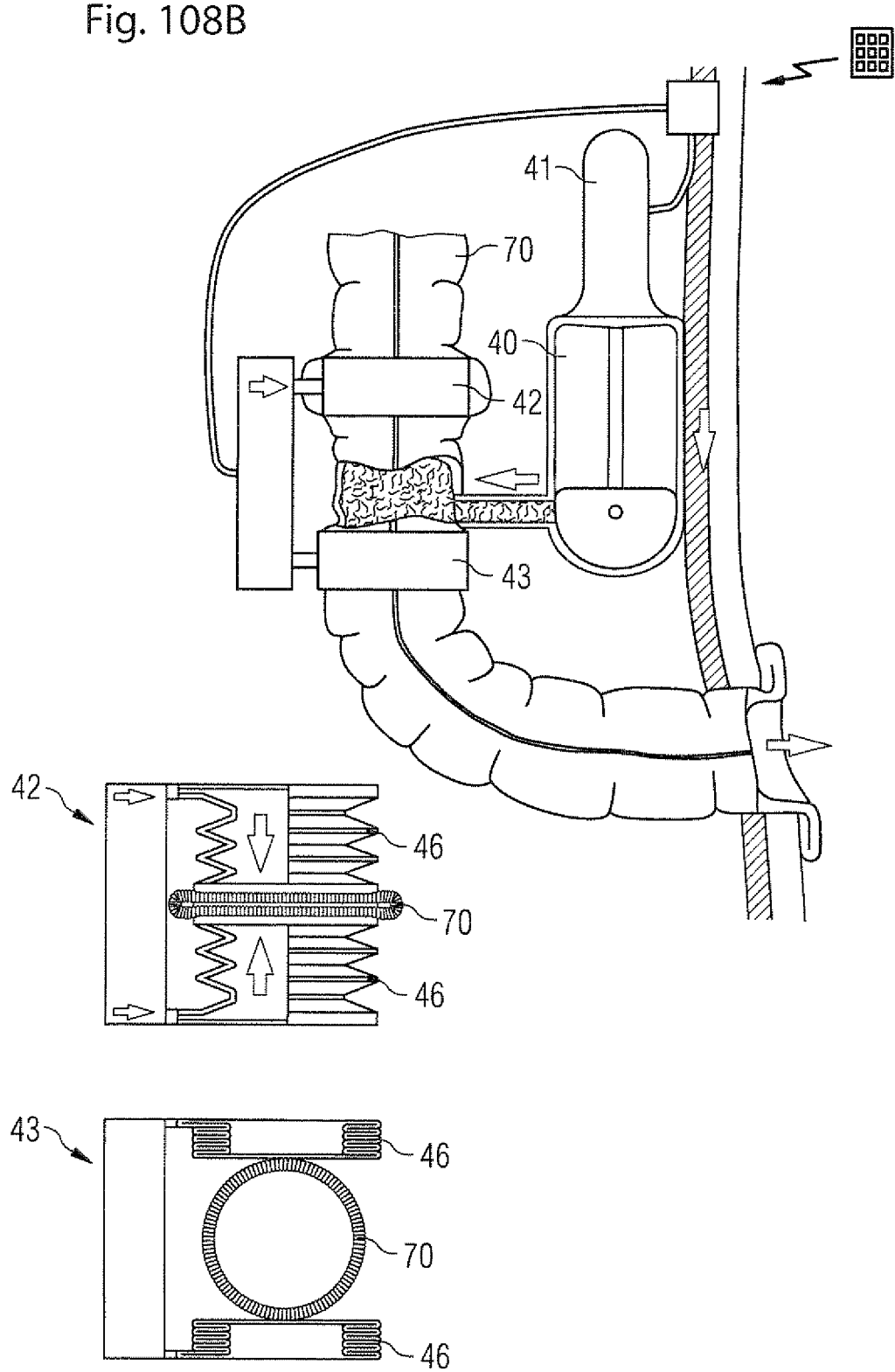
Figure 115A:
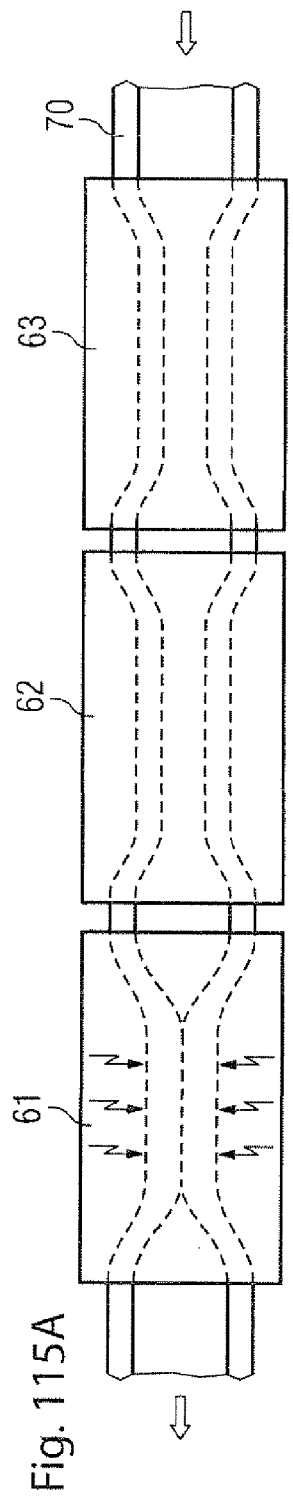
Figure 115B:
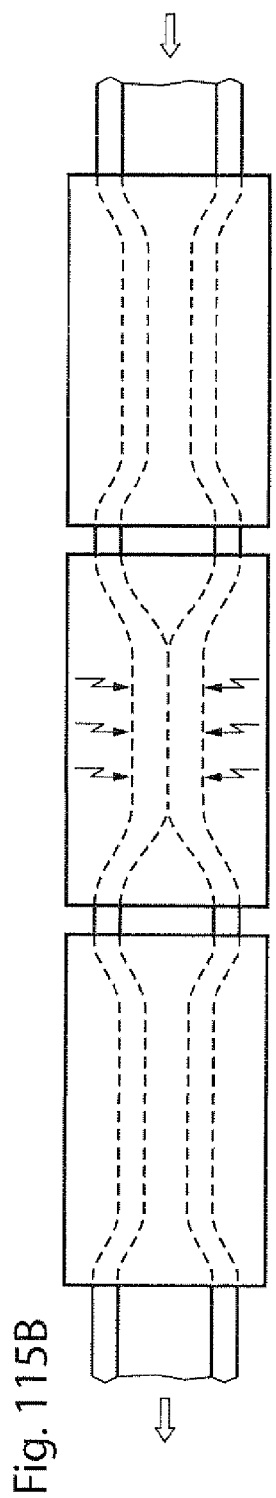
Figure 115C:
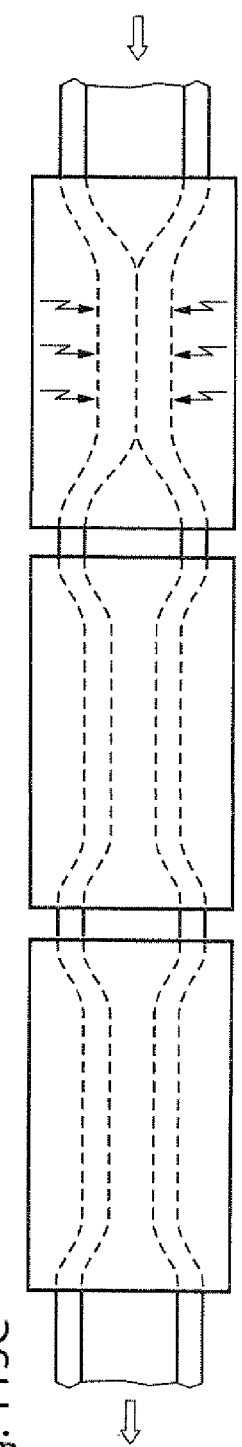

FIGS. 115A to 115C show the stimulation devices of FIGS. 114A to 114C in combination with constriction devices, such as the bellow valves described in relation to FIGS. 108A and 108B, for at least partly constricting the intestine section mechanically. Complete constriction is obtained by additional electrical stimulation of the respective intestine sections. The constriction devices may be released in order to allow intestinal contents to flow through.

Figure 116A:
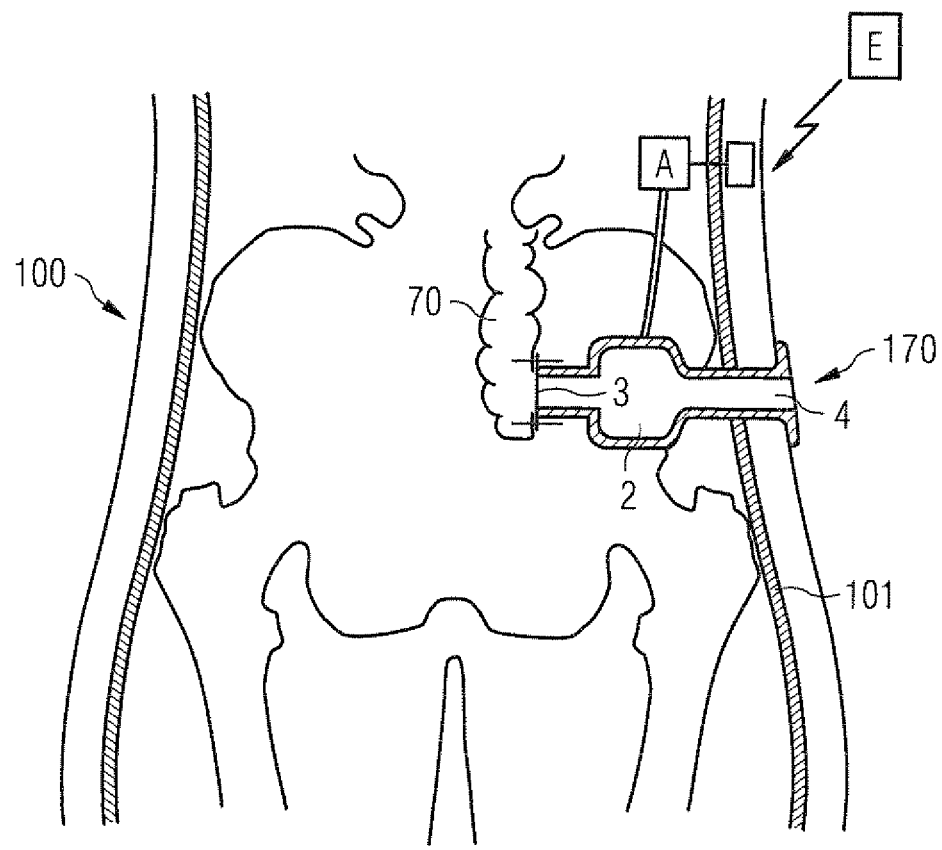

FIG. 116a shows a system according to the present invention with an artificial intestine section being implanted inside a patient's body and having a first open end portion connected to a surgically created opening in the patient's intestine, more specifically to a lateral opening in a wall of the patient's intestine. The second open end portion exits the patient's abdominal wall forming a stomy. The artificial intestine section is here shown as a black box and includes at least one energy consuming part, such as one or more valves, a pump and/or any other flow control device, a motor for driving the same, possibly in connection with a reservoir. An accumulator is implanted along with the artificial intestine section and can be wirelessly charged from outside the patient's body. The energy is here galvanically transmitted from the accumulator to the artificial intestine section.

Figure 116B:
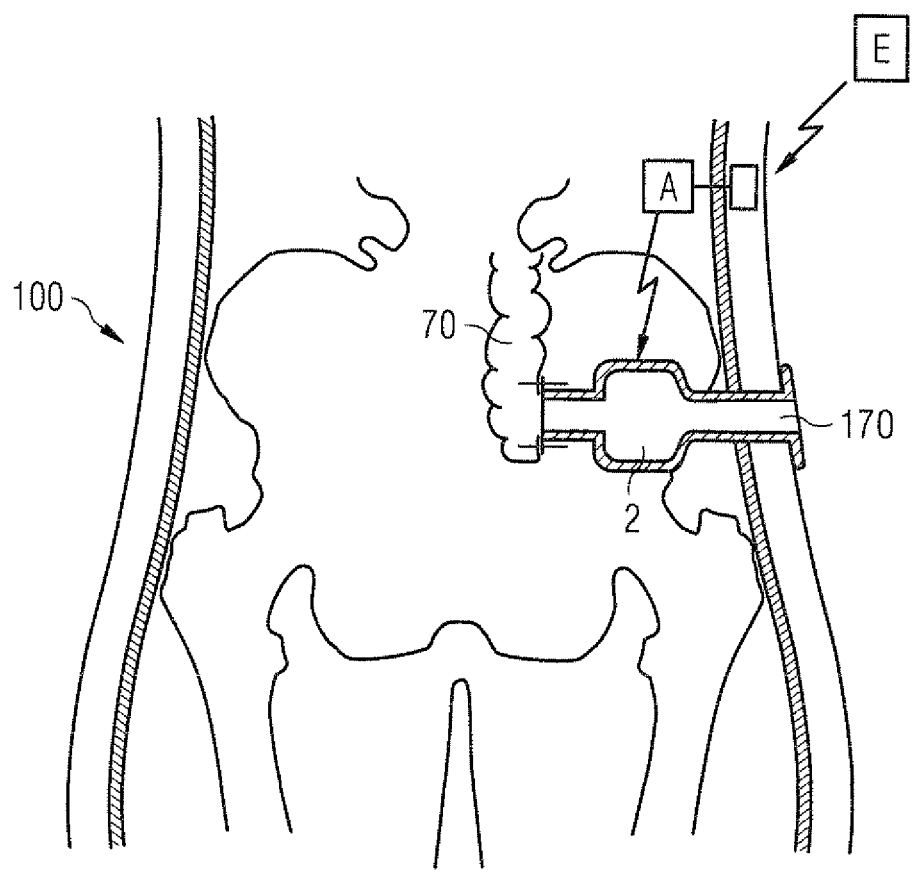

FIG. 116B shows a system corresponding to the one shown in FIG. 1, however, with the energy being transmitted wirelessly from the accumulator to the artificial intestine section.

Figure 116C:
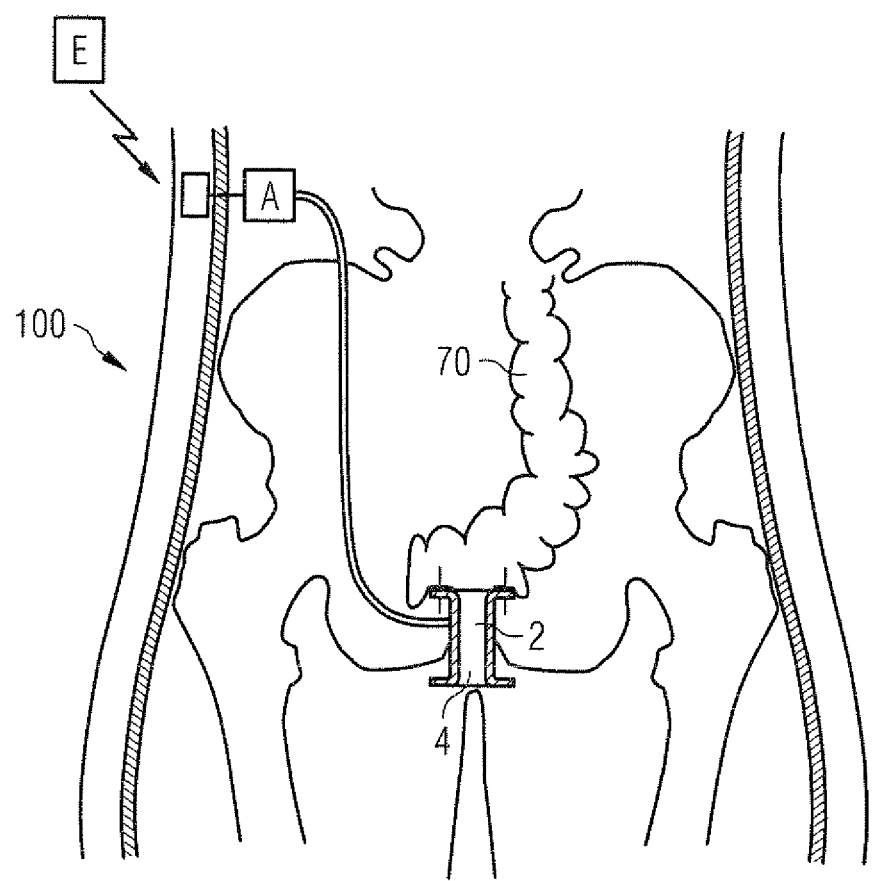

FIG. 116C shows a system corresponding to the one shown in FIG. 1, however, with the second open end portion of the artificial intestine section exiting the patient's anus.

Figure 117:
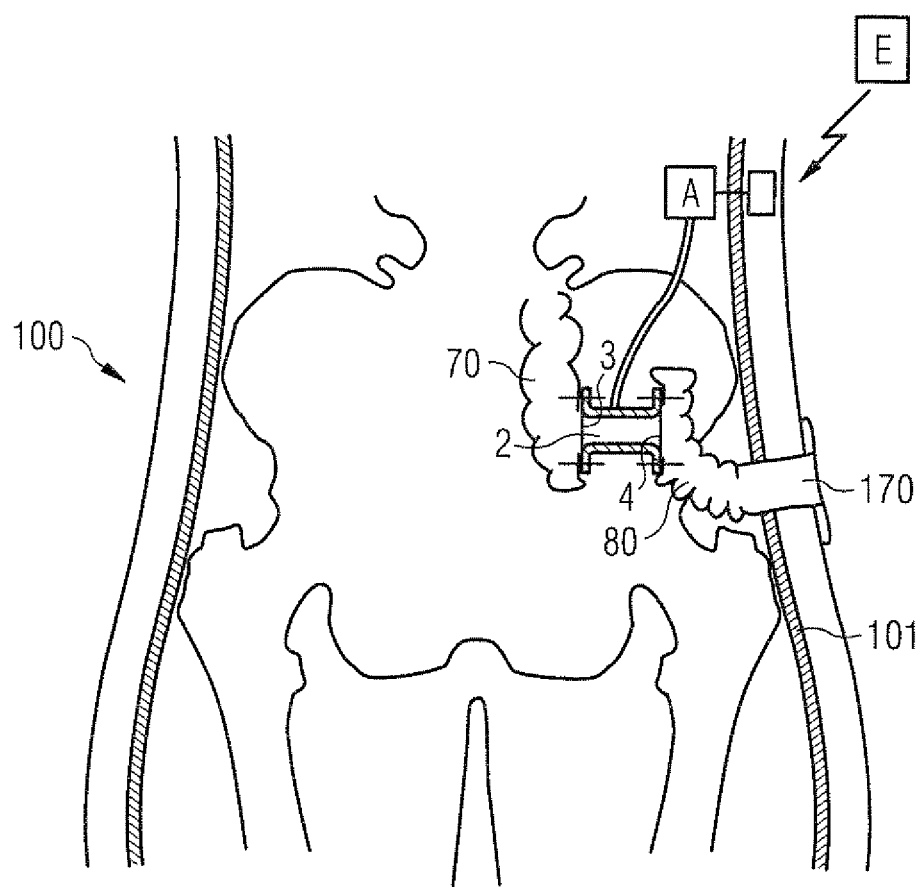

FIG. 117 shows a system where both the first and second open end portions of the artificial intestine section are attached to surgically created lateral openings in a wall of the patient's small and/or large intestine. The downstream part of the intestine exits the patient's abdominal wall forming a surgically created stomy. The downstream part of the intestine may as well exit through the patient's anus.

Figure 118:
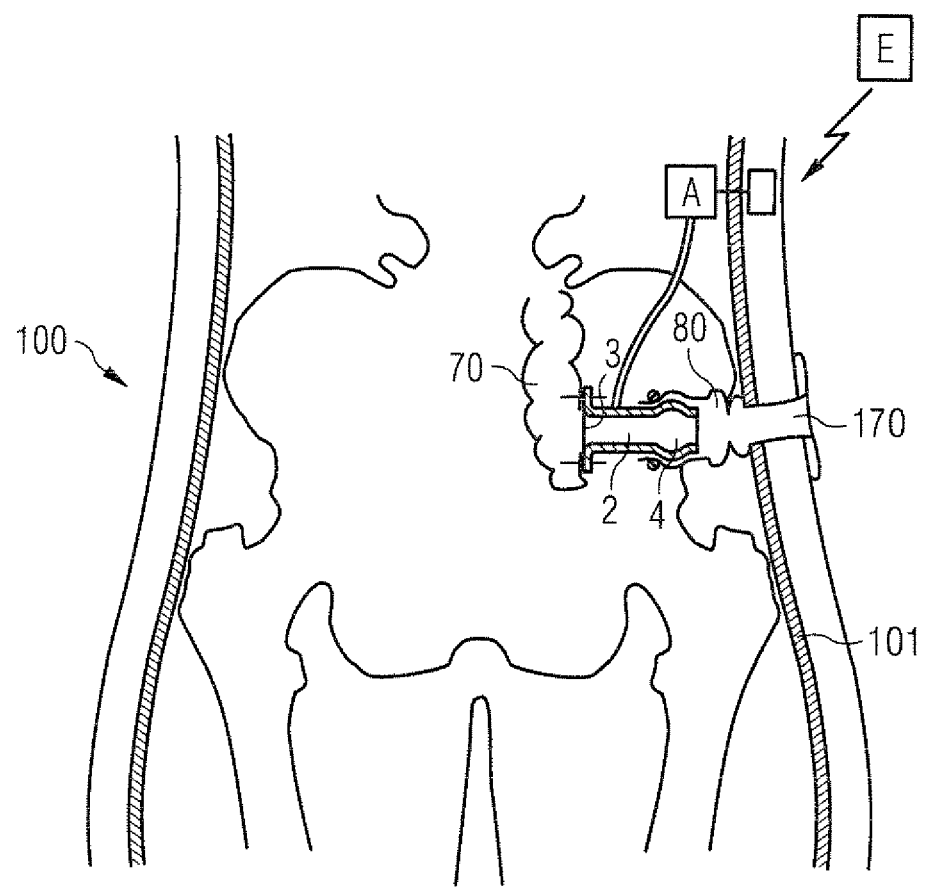

FIG. 118 shows a similar system with the difference that the second open end portion is connected to a cross-sectional opening of the patient's intestine, further leading to the surgically created stomy. The downstream part of the intestine may as well exit through the patient's anus.

Figure 119:
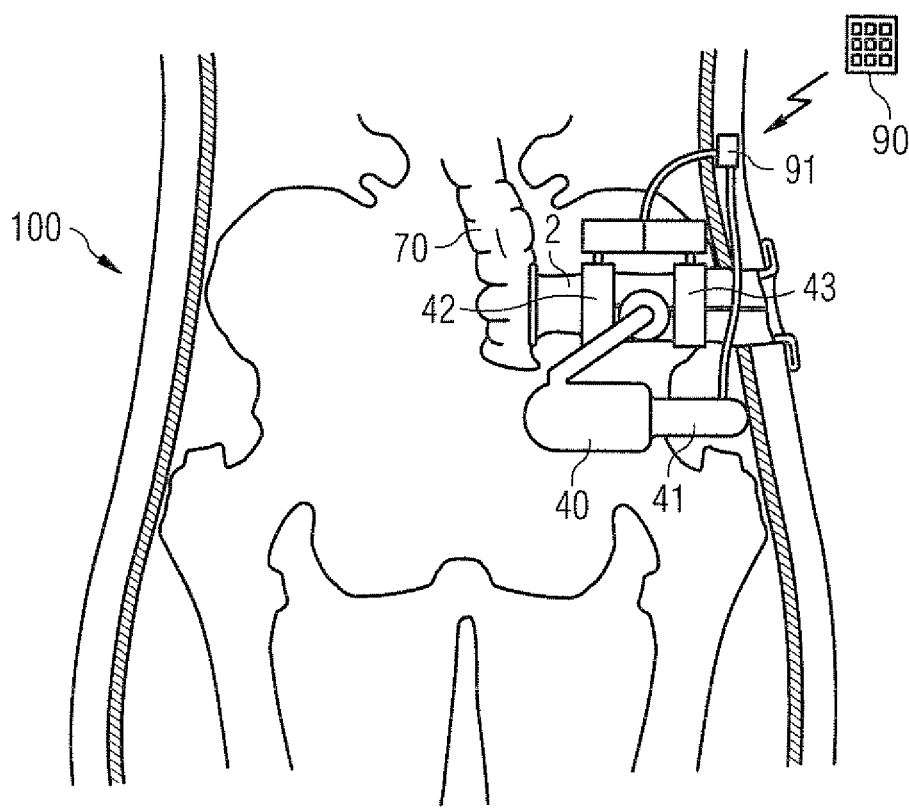

FIG. 119 shows an embodiment of the artificial intestine section with an artificial reservoir and an entry valve and exit valve arranged upstream and downstream of the reservoir. The reservoir is mounted with a pump in a common housing and the pump and the entry and exit valves are controlled by means of a control device, of which a part is implanted inside the patient's body. Data are transmitted wirelessly between the external part and implanted part of the control unit. In addition, energy is wirelessly transmitted to the artificial intestine section or to an accumulator also implanted in the patient's body and galvanically connected here to the valves and pump.

Figure 120B:
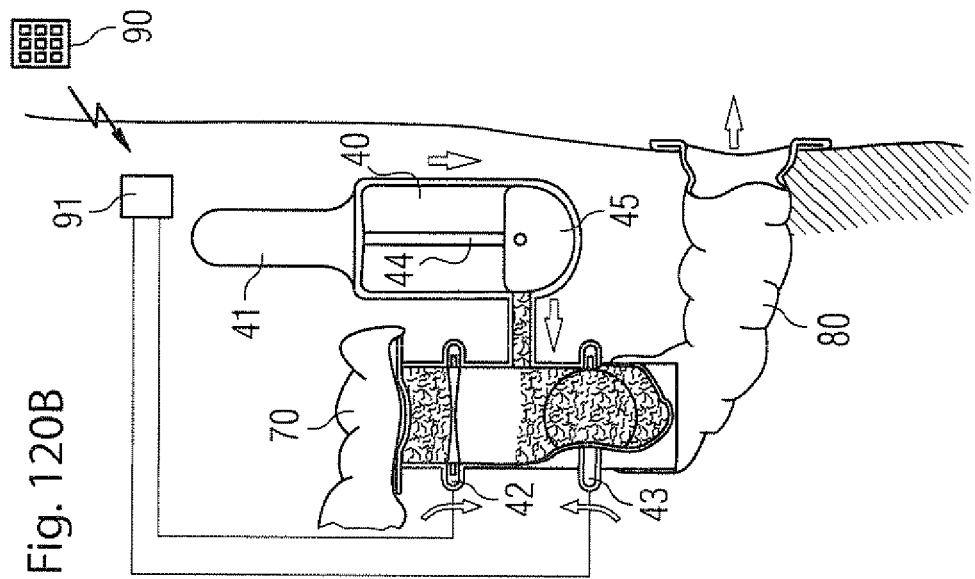
Figure 120A:
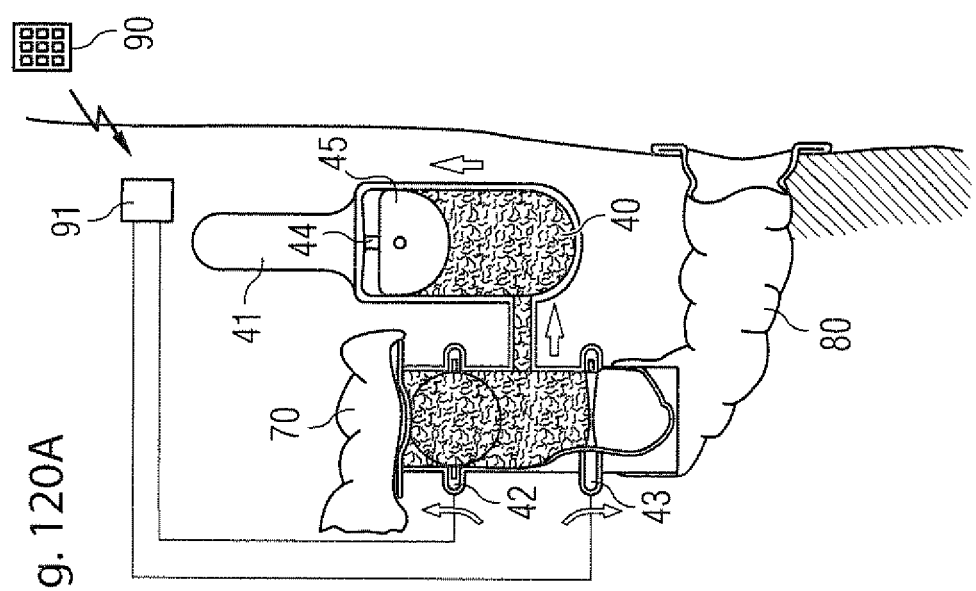

FIGS. 120A and 120B show a first embodiment of the structure of FIG. 119 in more detail. The pump comprises a moveable piston with a front end of the piston extending into the reservoir such that a volume of the reservoir is reduced upon advancement of the piston. The piston is spring loaded so as to urge the piston into a normally retracted position. Furthermore, entry and exit valves are here realized as flap valves. The flap valves are controlled so that one valve is open while the other one is closed.

Figure 8A:
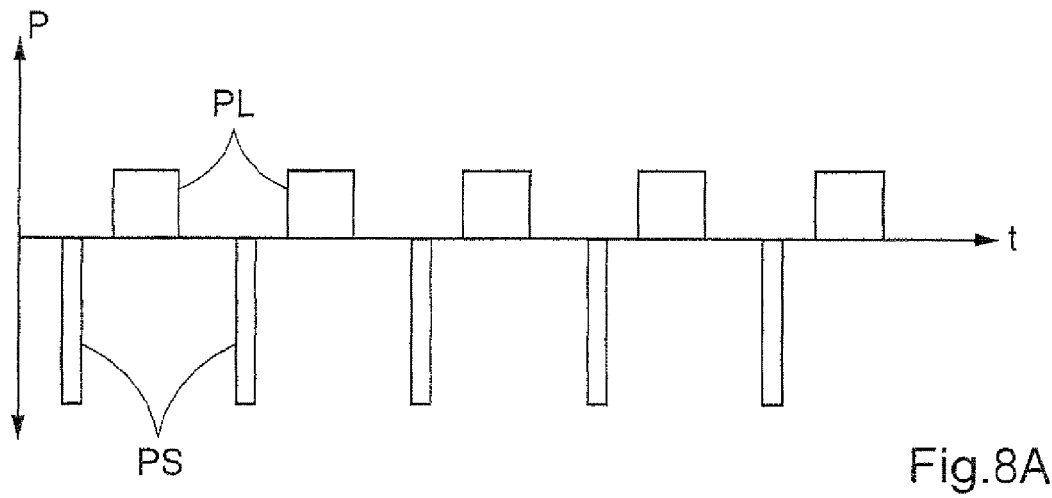
FIG. 8A is a pulse/time diagram showing electric stimulation pulses generated by the apparatus used for practicing the method of the invention, wherein the electric pulses are for stimulating a tissue wall of a patient's organ.
Figure 121A:
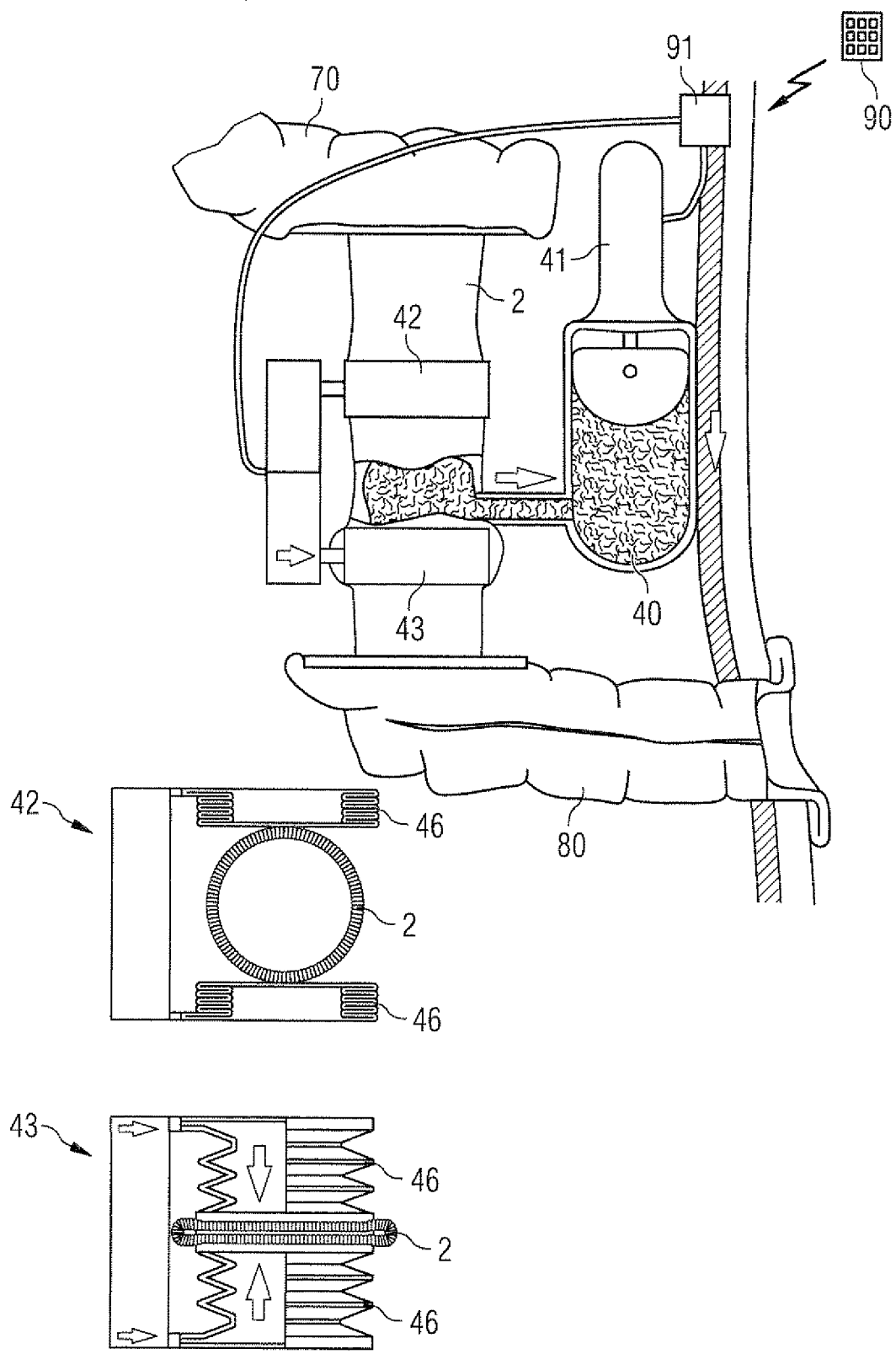
Figure 121B:
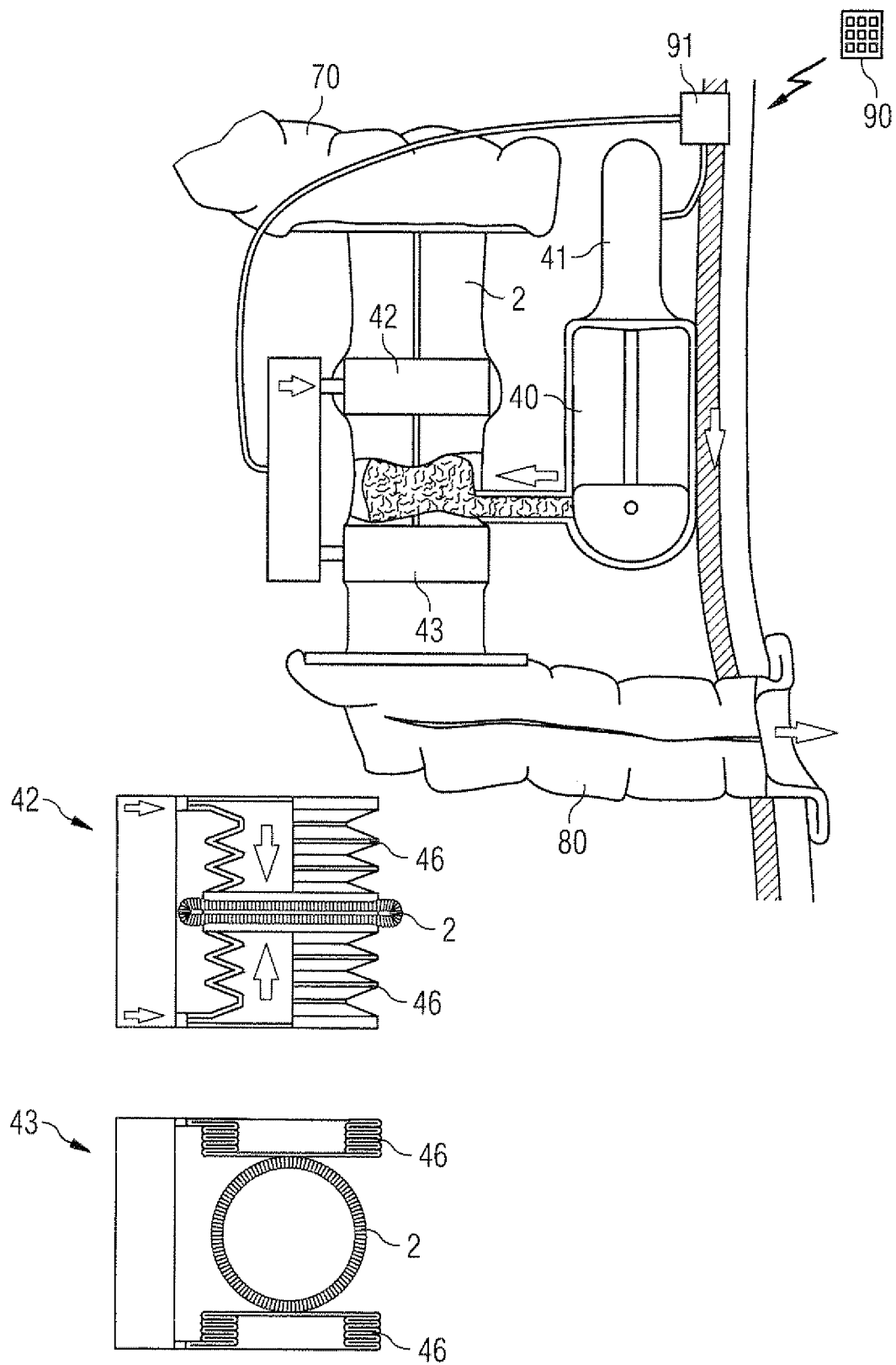

FIGS. 121A and 121B show a system similar to the one of FIGS. 120A and 120B. However, here the entry and exit valves comprise bellows acting on the intestine from the outside so as to close the intestine by compression. In FIG. 8A the bellows of the exit valve are expanded to compress the artificial intestine section at the downstream side of the reservoir, whereas in FIG. 121B the artificial intestine section is closed by means of the bellows of the entry valve upstream of the reservoir so that the reservoir can be emptied by advancing the piston of the pump.

Figure 122:
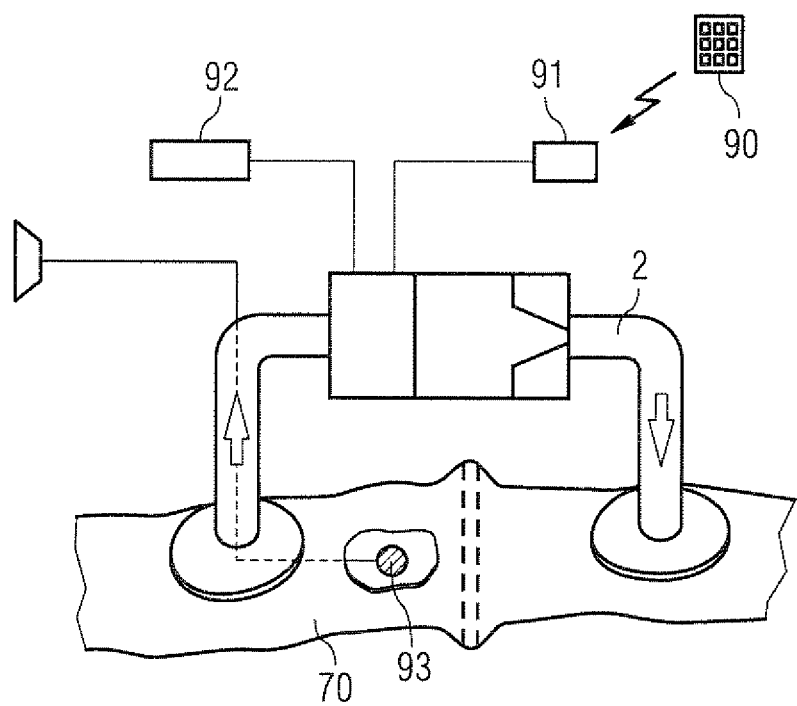

FIG. 122 shows an embodiment schematically, wherein the artificial intestine section by-passes a section of the patient's intestine, the intestine being closed by sewing so as to direct intestinal content towards the artificial intestine section. The enlarged area of the artificial intestine section represents any kind of element acting on the intestinal contents within the artificial intestine section, such as a reservoir, one or more valves, a pump or any other flow control device, possibly including a motor, and the like. Furthermore, a battery implantable in the patient's body and preferably rechargeable provides the artificial intestine section with energy. The artificial intestine section is wirelessly controlled and the battery, if rechargeable, wirelessly charged. A sensor implanted on or within the intestine delivers data on the physical conditions within the intestine for controlling the artificial intestine section.

FIGS. 123A to 123C show an embodiment, where the artificial intestine section comprises a reservoir with a flexible wall. A pump is implanted in the patient's body separate but in close proximity to the reservoir and is used to empty the reservoir. The pump is actuated by means of a subcutaneously implanted, manually operable switch.

Figure 124A:
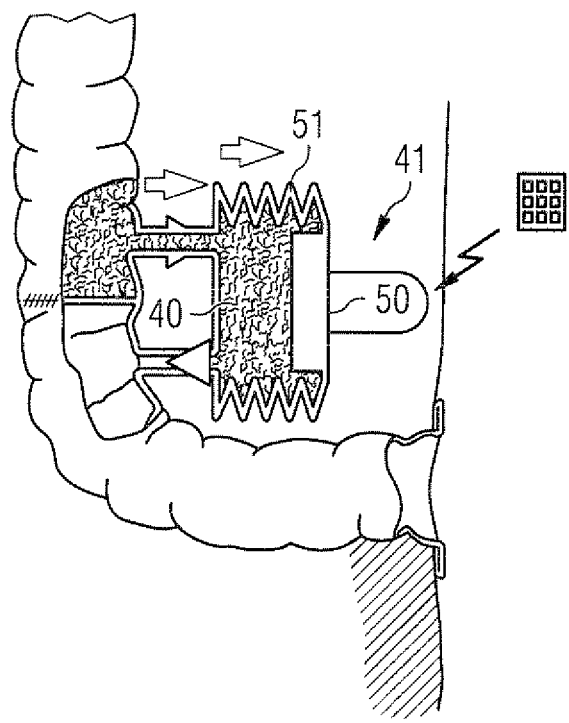
Figure 124B:
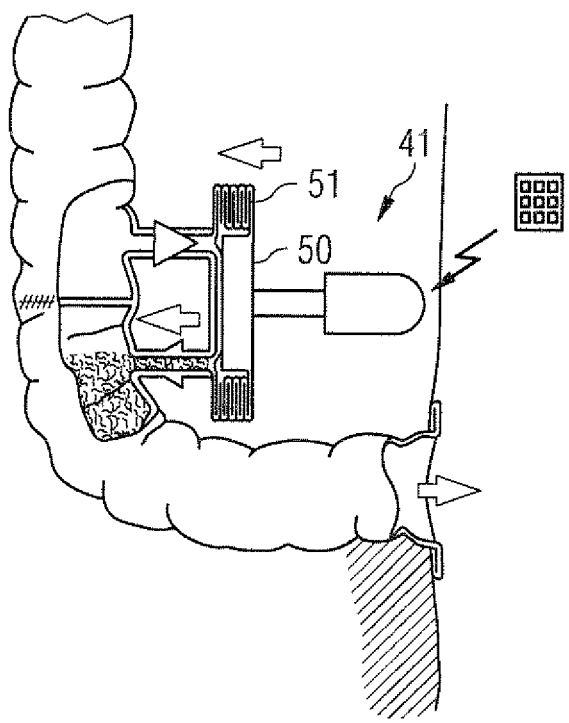
Figure 125A:
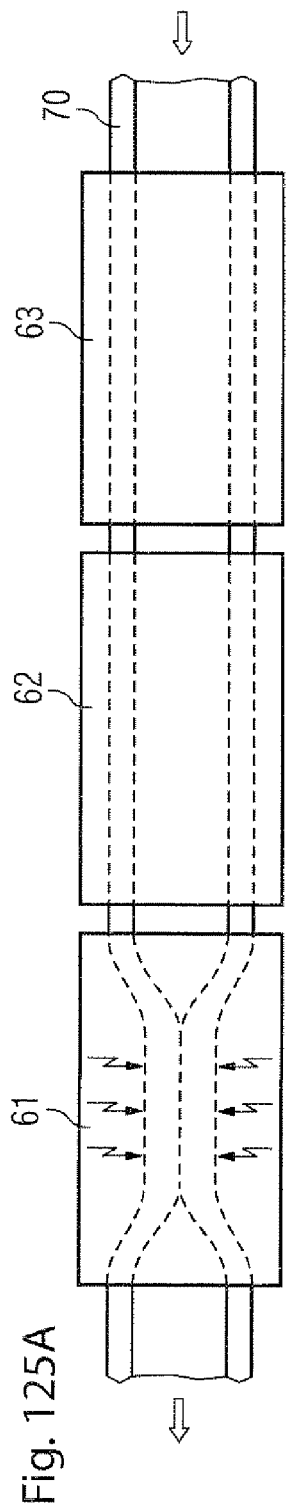
Figure 125B:
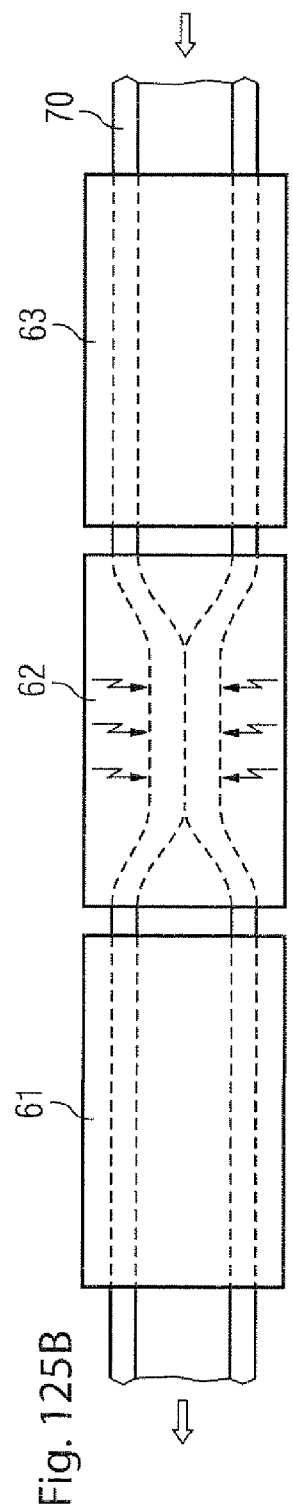
Figure 125C:
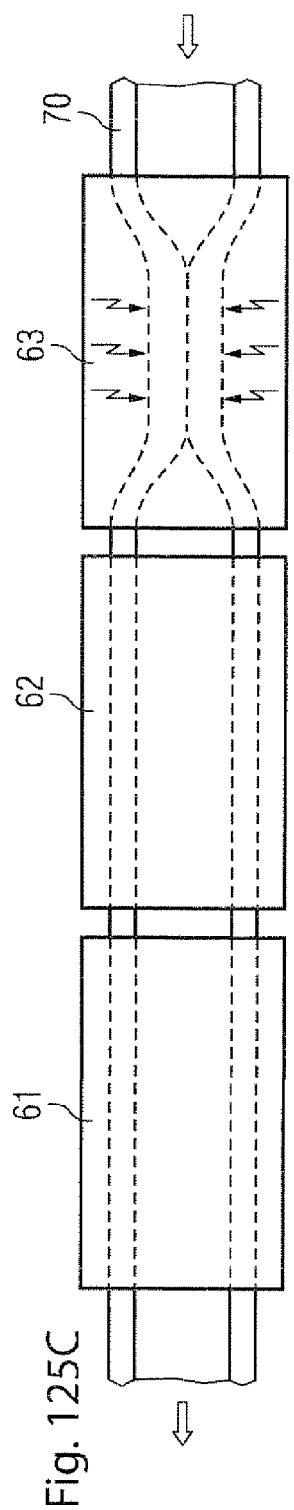

FIGS. 124A and 124B show a structure similar to the one of FIGS. 123A to 123C, however, with the pump and the reservoir being fixedly connected to one another. The reservoir is formed by a bellow having an end wall closing the bellow at one end thereof. The end wall makes part of the pump such that a volume of the bellow can be reduced upon advancement of the end wall. The bellow is made of a resilient material so as to urge the bellow into a normally extended position FIGS. 125A to 125C show a plurality of cooperating valves implanted inside the patient's body and outside the patient's intestine. These can be positioned behind and/or in front of the artificial intestine piece along the patient's natural intestine. Each of the valves comprises an electrical stimulation device adapted to electrically stimulate muscle or neural tissue of an intestine section so as to cause at least partial contraction of the intestine section. For that purpose, the stimulation device comprises at least one electrode adapted to apply electric pulses to the intestine section. While instead of the three stimulation devices shown, a single stimulation device would be sufficient for opening and closing the intestine, the arrangement of the plurality of stimulation devices is adapted to stimulate different portions of the intestine section over time. The function of the three stimulation devices may also be combined in one integral unit. The direction of natural intestinal contents flow is indicated by arrows. The different portions of the intestine section in a wavelike manner may be made in a direction opposite to the natural intestinal contents flow, as shown in FIGS. 125A to 125C, so as to close the intestine section. The stimulation in the wavelike manner may also be made in the direction of natural intestinal contents flow to support emptying of the intestine or reservoir.

Figure 126A:
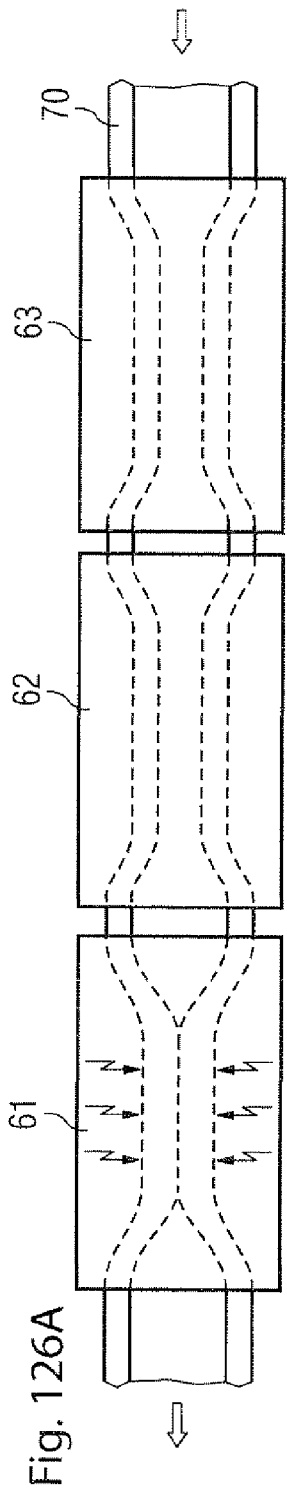
Figure 126B:
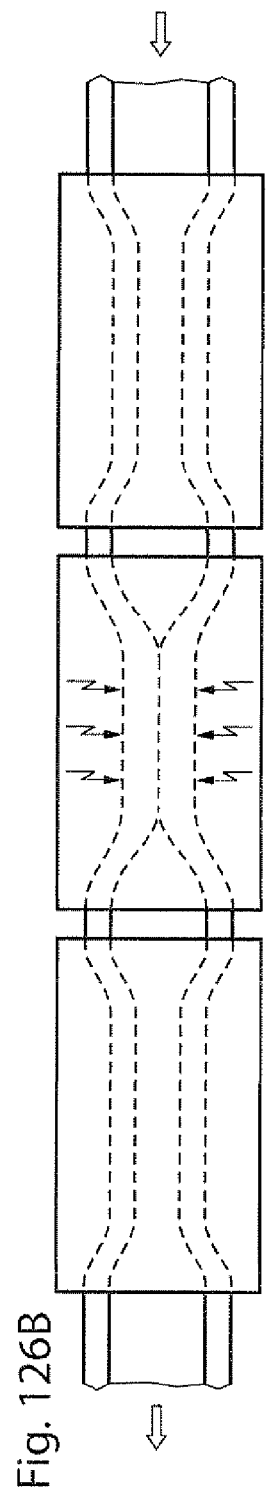
Figure 126C:
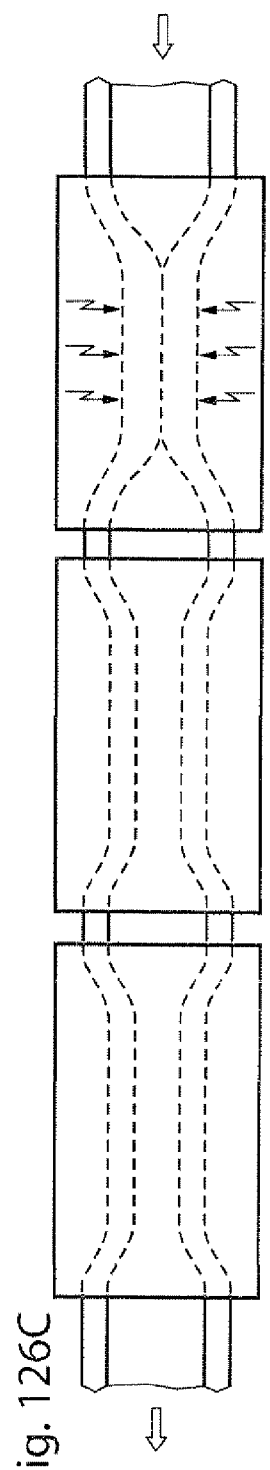

FIGS. 126A to 126C show the stimulation devices of FIGS. 125A to 125C in combination with constriction devices, such as the bellow valves described in relation to FIGS. 121A and 121B, for at least partly constricting the intestine section mechanically. Complete constriction is obtained by additional electrical stimulation of the respective intestine sections. The constriction devices may be released in order to allow intestinal contents to flow through.

Figure 127A:
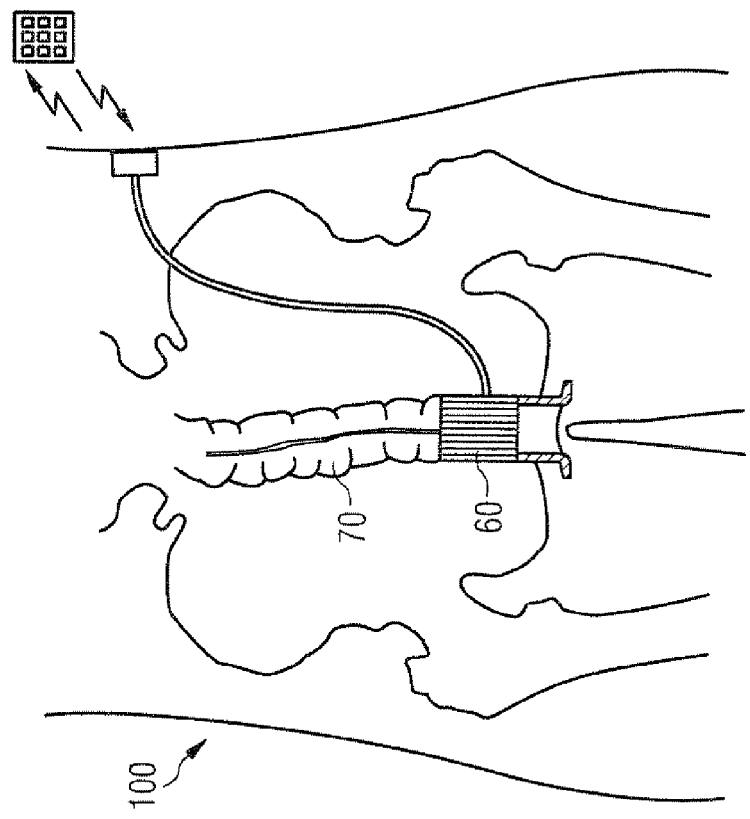
Figure 127B:
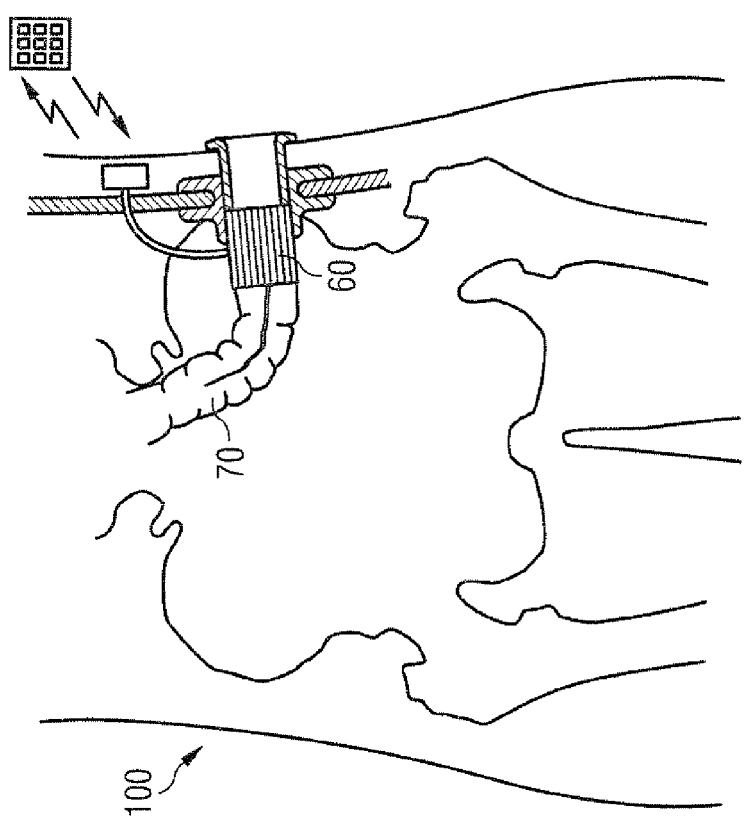

FIGS. 127A and 127B show a system comprising the artificial intestine section connected to a cross-sectional opening of the patient's intestine and having a valve as shown in FIG. 125 or 126 arranged around the patient's intestine upstream of the artificial intestine section. Energy and/or data is transmitted wirelessly.

Figure 128:
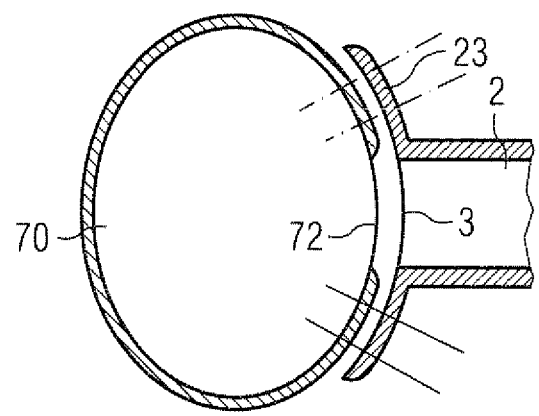

FIG. 128 shows the structure of an open end portion of the artificial intestine section for attaching the artificial intestine section to a lateral opening in the patient's intestine by means of a shoulder portion formed around the end portion. The end portion is sewn to the intestine and may additionally or alternatively be stapled and/or glued to the intestine.

Figure 129:
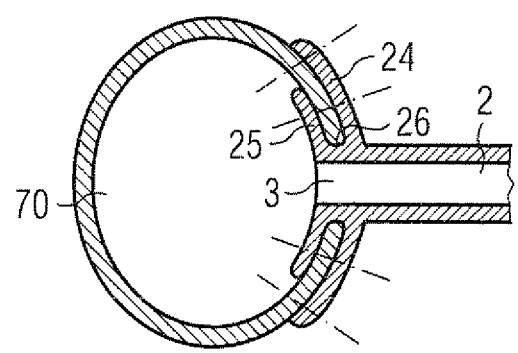

FIG. 129 shows an improved structure for lateral attachment to the intestine, wherein the shoulder portion is split into an upper and a lower shoulder portion forming a gap to accommodate intestinal wall tissue therein. The surface area of the upper shoulder portion is larger than the surface area of the lower shoulder portion.

Figure 130:
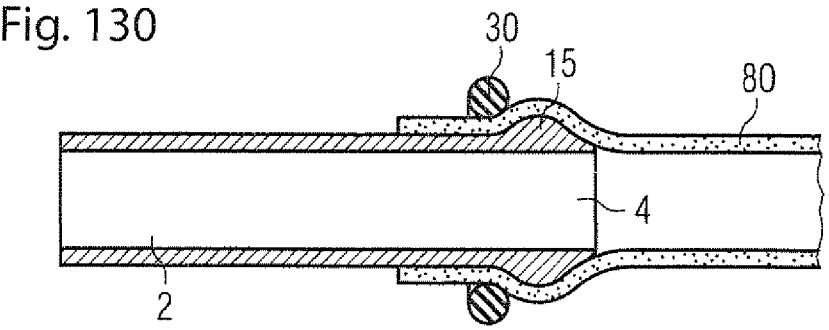

FIG. 130 shows an enlarged view of a ring-and-bulge connection by which the artificial intestine section and the patient's downstream intestinal part are connected, as shown in FIG. 118.

Figure 131A:
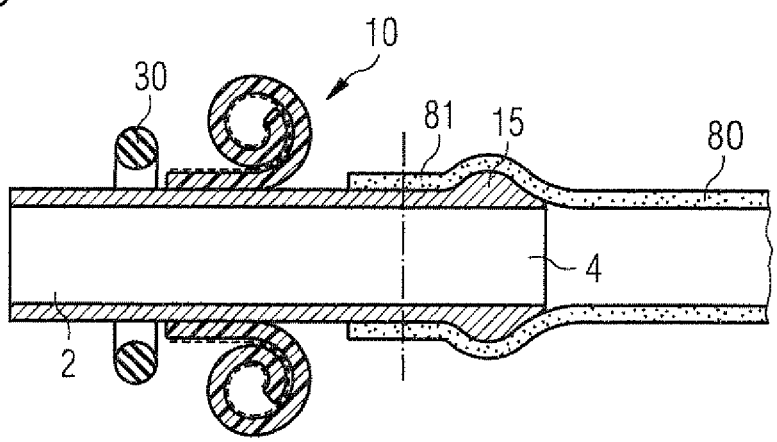
Figure 131B:
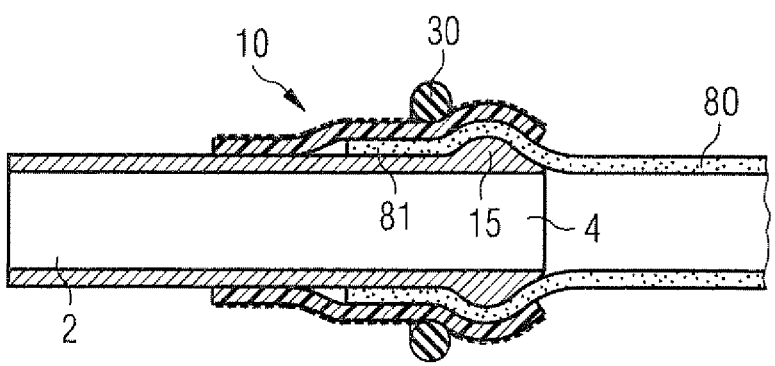

FIGS. 131A and 131B show the ring-and-bulge connection of FIG. 130 in combination with a sleeve. The sleeve is rolled upon itself and can be unrolled such that a part of the intestine is located intermediate the sleeve and the conduit. Thereafter, the ring is pushed over the sleeve against the bulge.

Figure 132A:
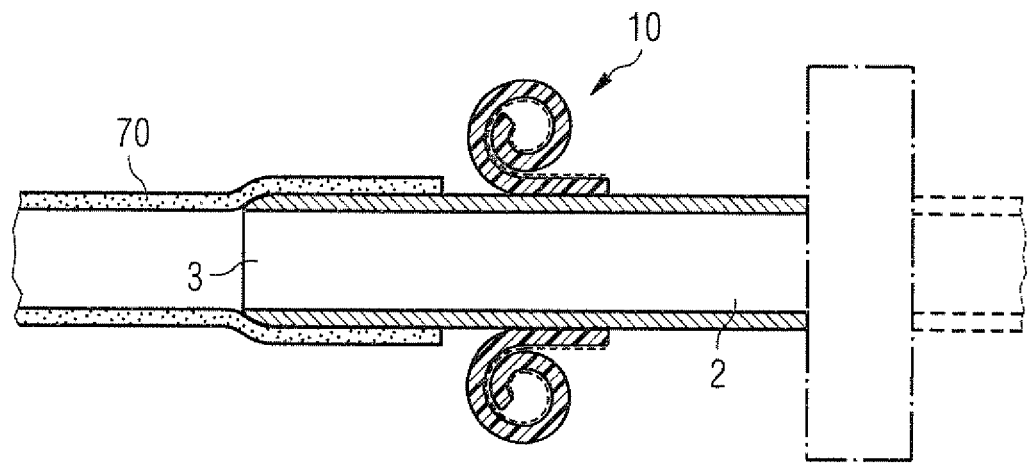
Figure 132B:
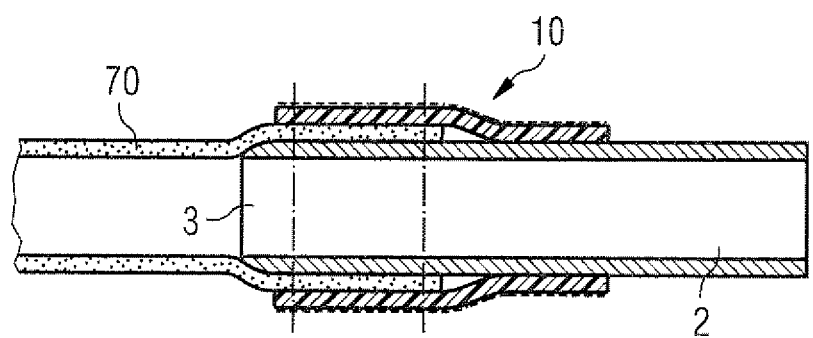

FIGS. 132A and 132B show a connection of the artificial intestine section to a cross-sectional opening of the patient's intestine similar to the connection shown in FIGS. 131A and 131B, however, without the bulge and the ring.

Figure 133A:
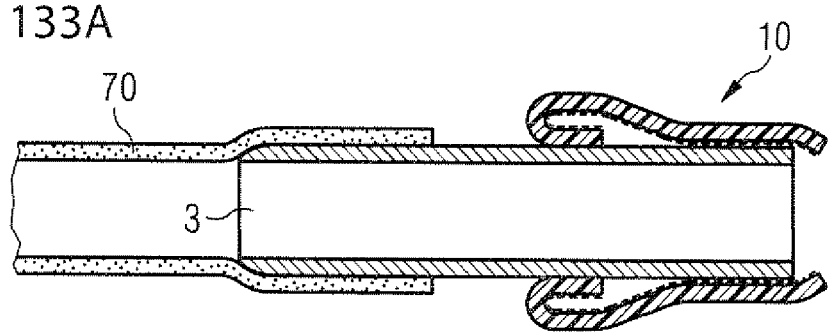
Figure 133B:
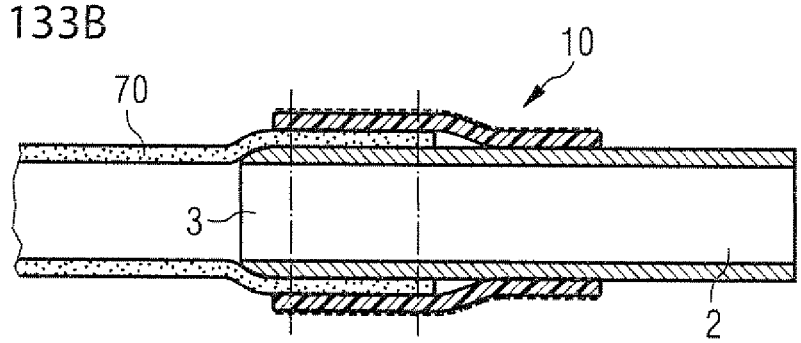

FIGS. 133A and 133B show an alternative to the connection in FIGS. 132A and 132B. Instead of unrolling the sleeve, it is simply pulled over the intestine.

Figure 134A:
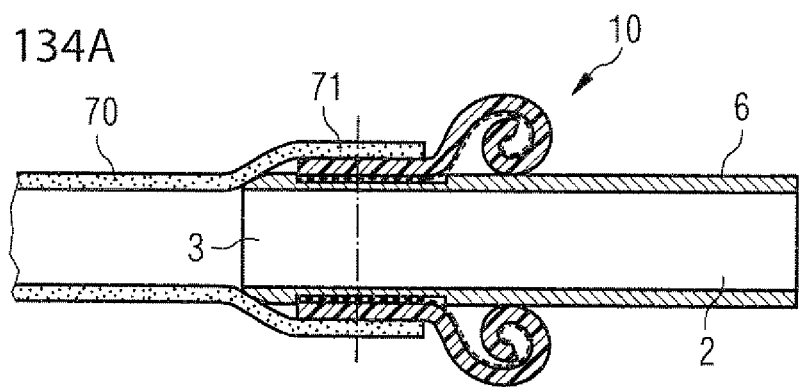
Figure 134B:
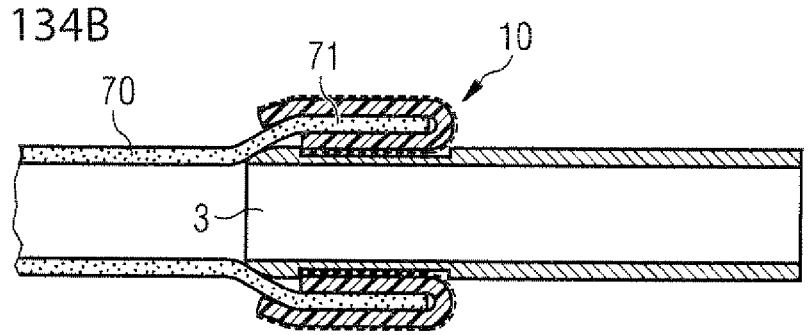

FIGS. 134A and 134B show another sleeve connection. Here, the sleeve is mounted on the outer surface of the open end portion so as to be foldable upon itself. By folding the flexible sleeve upon itself, a part of the intestine is located intermediate the folded sleeve.

Figure 135:
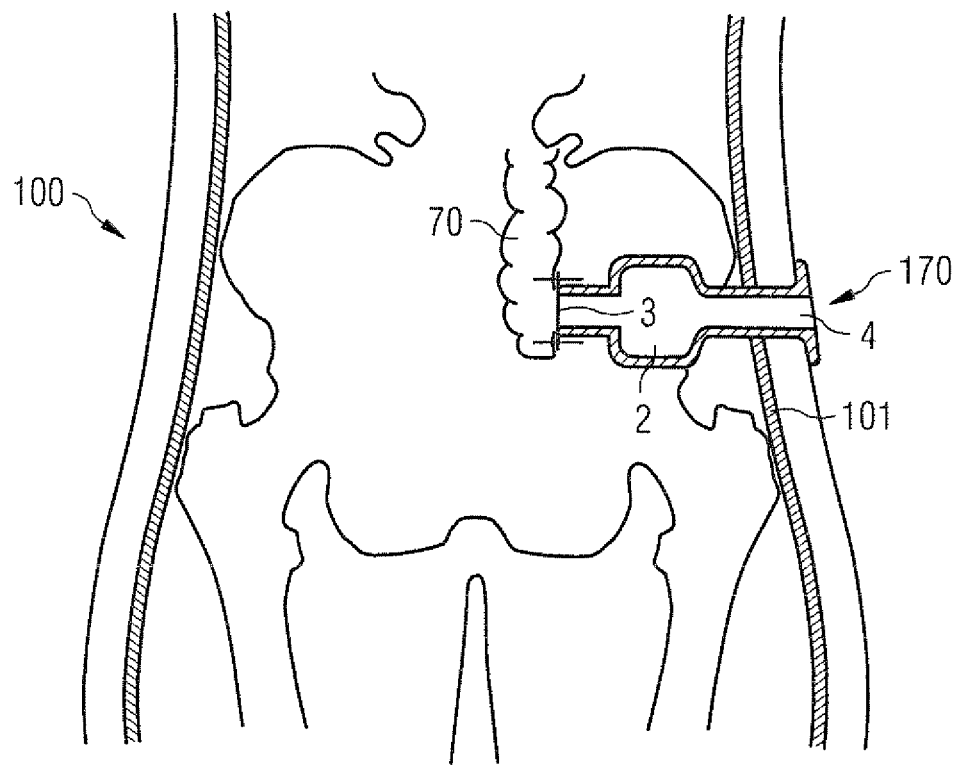

FIG. 135 shows a system according to the present invention with an artificial intestine section being implanted inside a patient's body and having a first open end portion connected to a surgically created lateral opening in a wall of the patient's intestine. The second open end portion exits the patient's abdominal wall forming a stomy. The artificial intestine section is here shown as a black box and may include an artificial reservoir for intestinal contents, a motor, one or more valves, a pump and/or any other flow control device.

Figure 136:
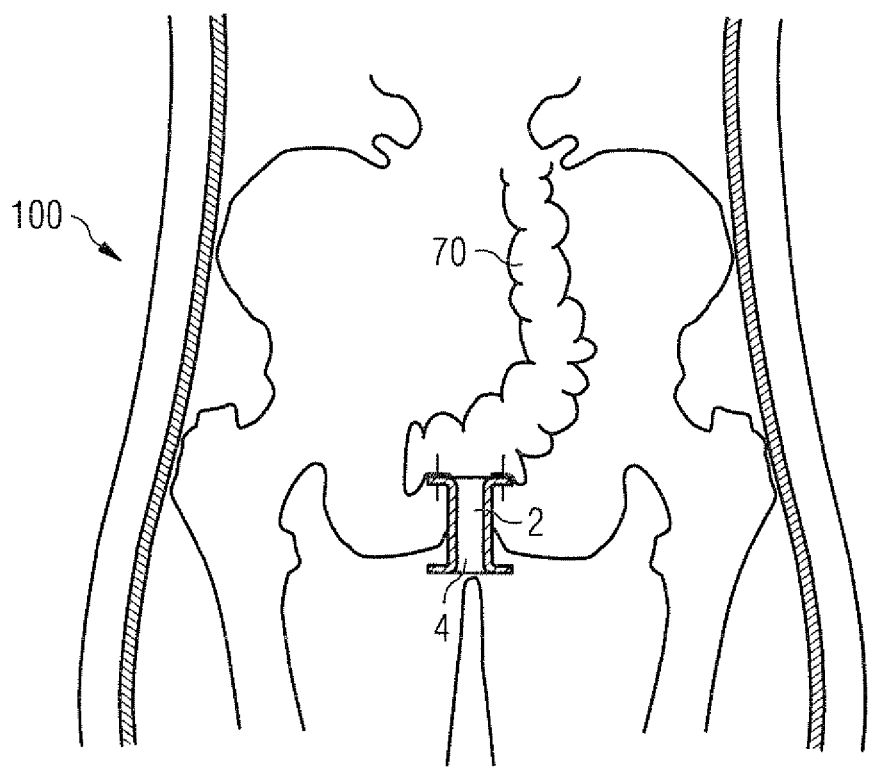

The system shown in FIG. 136 corresponds to the one shown in FIG. 135, however, with the second open end portion of the artificial intestine section exiting the patient's anus.

Figure 137:
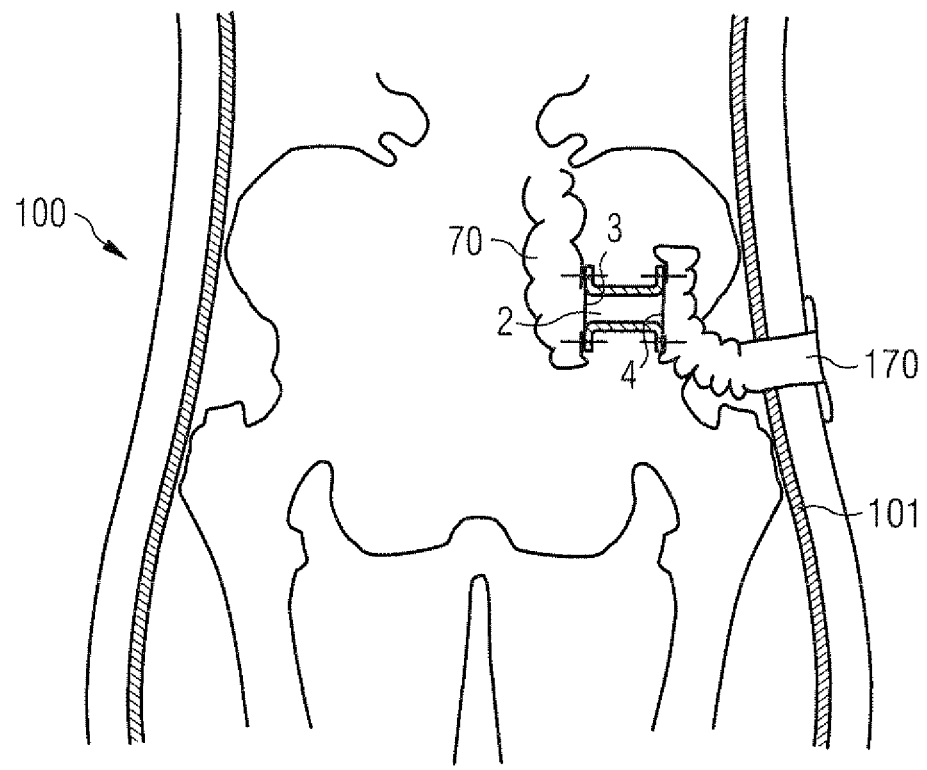

FIG. 137 shows a system where both the first and second open end portions of the artificial intestine section are attached to surgically created lateral openings in a wall of the patient's small and/or large intestine. The downstream part of the intestine exits the patient's abdominal wall forming a surgically created stomy. The downstream part of the intestine may as well exit through the patient's anus.

Figure 138:
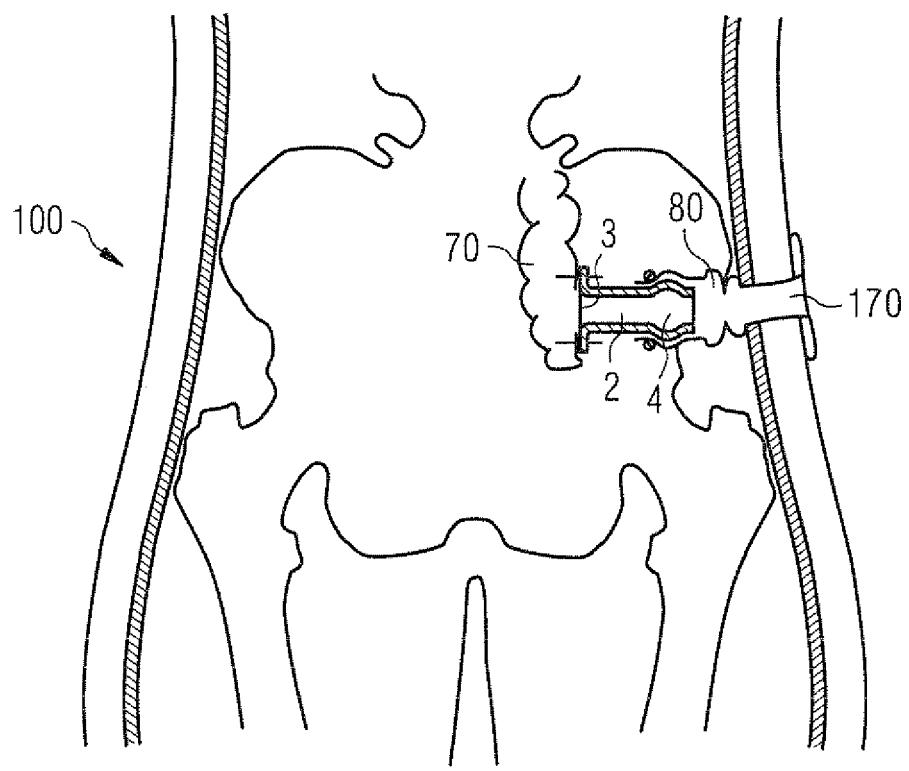

FIG. 138 shows a similar system with the difference that the second open end portion is connected to a cross-sectional opening of the patient's intestine, further leading to the surgically created stomy. The downstream part of the intestine may as well exit through the patient's anus.

Figure 139:
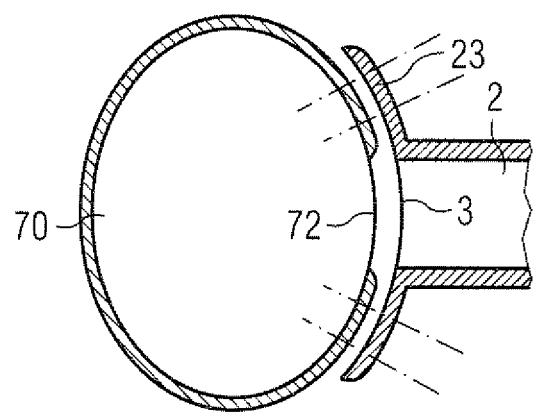

FIG. 139 shows the structure of the first open end portion of the artificial intestine section for attaching the artificial intestine section to the lateral opening in the patient's intestine by means of a shoulder portion formed around the end portion. The end portion is sewn to the intestine and may additionally or alternatively be stapled and/or glued to the intestine.

Figure 140:
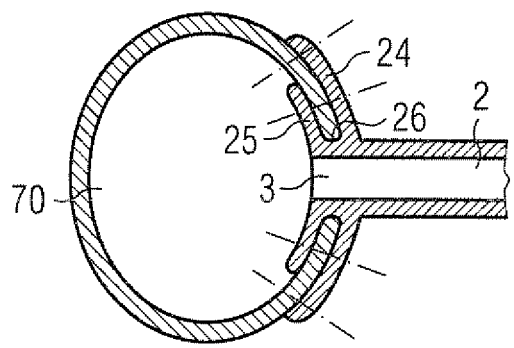

FIG. 140 shows an improved structure for lateral attachment to the intestine, wherein the shoulder portion is split into an upper and a lower shoulder portion forming a gap to accommodate intestinal wall tissue therein. The surface area of the upper shoulder portion is larger than the surface area of the lower shoulder portion.

Figure 141:
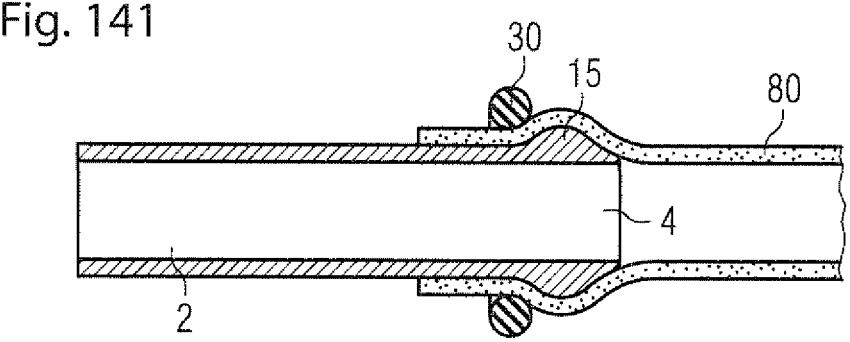

FIG. 141 shows an enlarged view of a ring-and-bulge connection by which the artificial intestine section and the patient's downstream intestinal part are connected, as shown in FIG. 138.

Figure 142A:
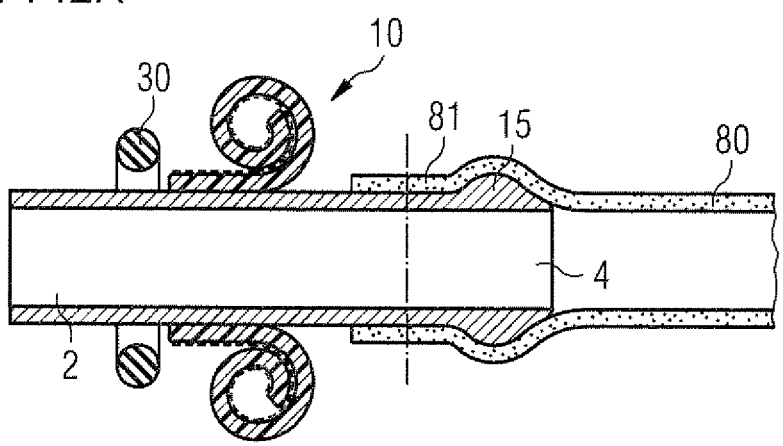
Figure 142B:
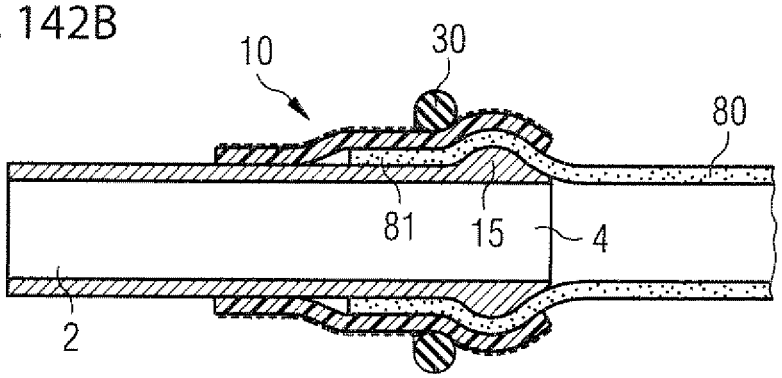

FIGS. 142A and 142B show the ring-and-bulge connection of FIG. 141 in combination with a sleeve. The sleeve is rolled upon itself and can be unrolled such that a part of the intestine is located intermediate the sleeve and the conduit. Thereafter, the ring is pushed over the sleeve against the bulge.

Figure 143A:
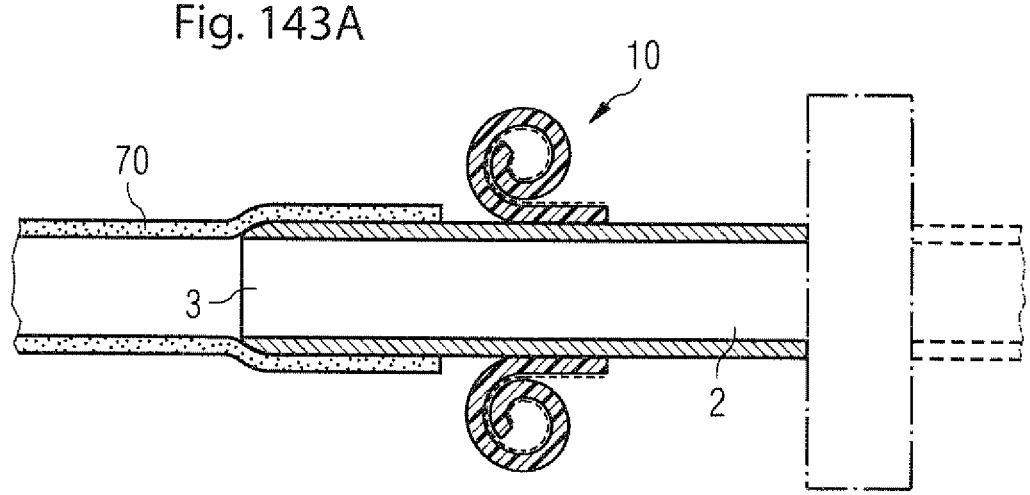
Figure 143B:
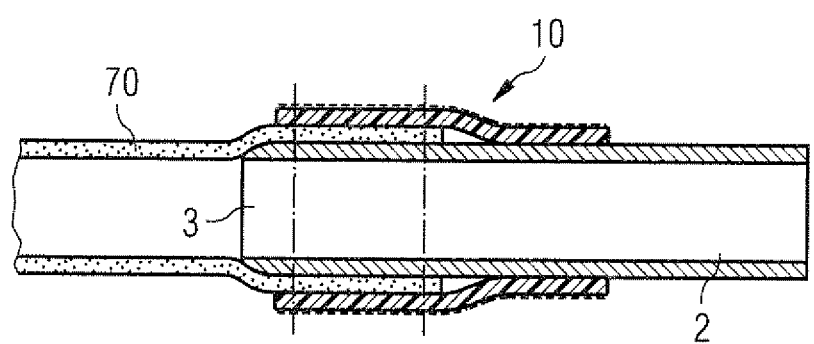

FIGS. 143A and 143B show a connection of the artificial intestine section to the cross-sectional opening of the patient's intestine similar to the connection shown in FIGS. 142A and 142B, however, without the bulge and the ring.

Figure 144A:
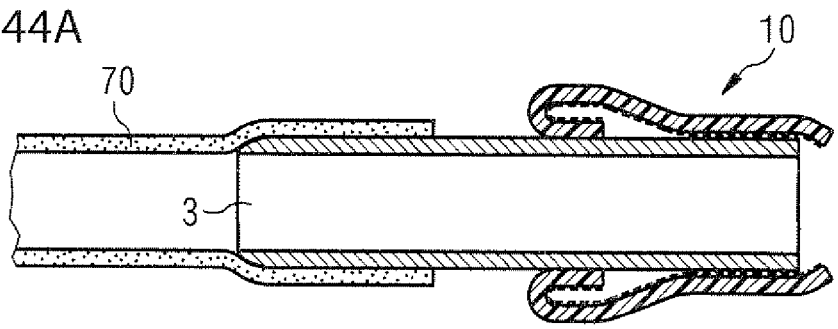
Figure 144B:
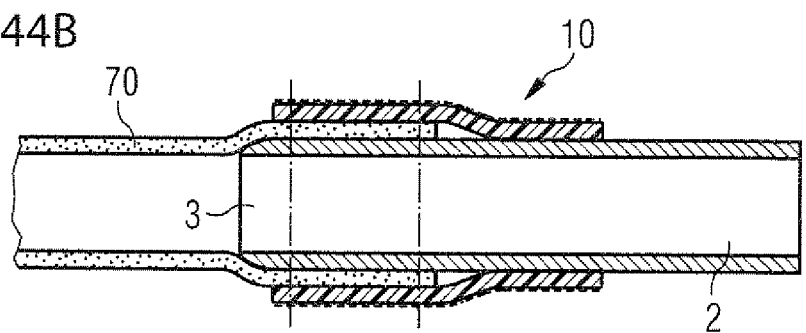

FIGS. 144A and 144B show an alternative to the connection in FIG. 143A and 143B. Instead of unrolling the sleeve, it is simply pulled over the intestine.

Figure 145A:
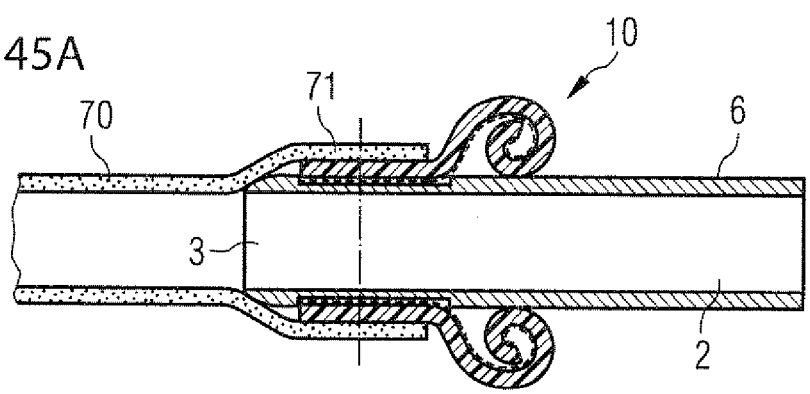
Figure 145B:
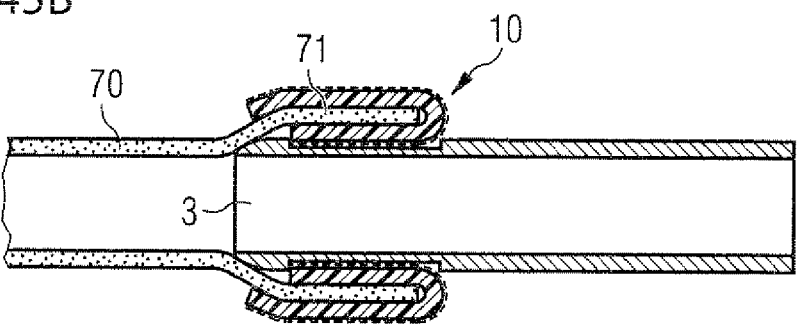

FIGS. 145A and 145B show another sleeve connection. Here, the sleeve is mounted on the outer surface of the open end portion so as to be foldable upon itself. By folding the flexible sleeve upon itself, a part of the intestine is located intermediate the folded sleeve.

Figure 146:
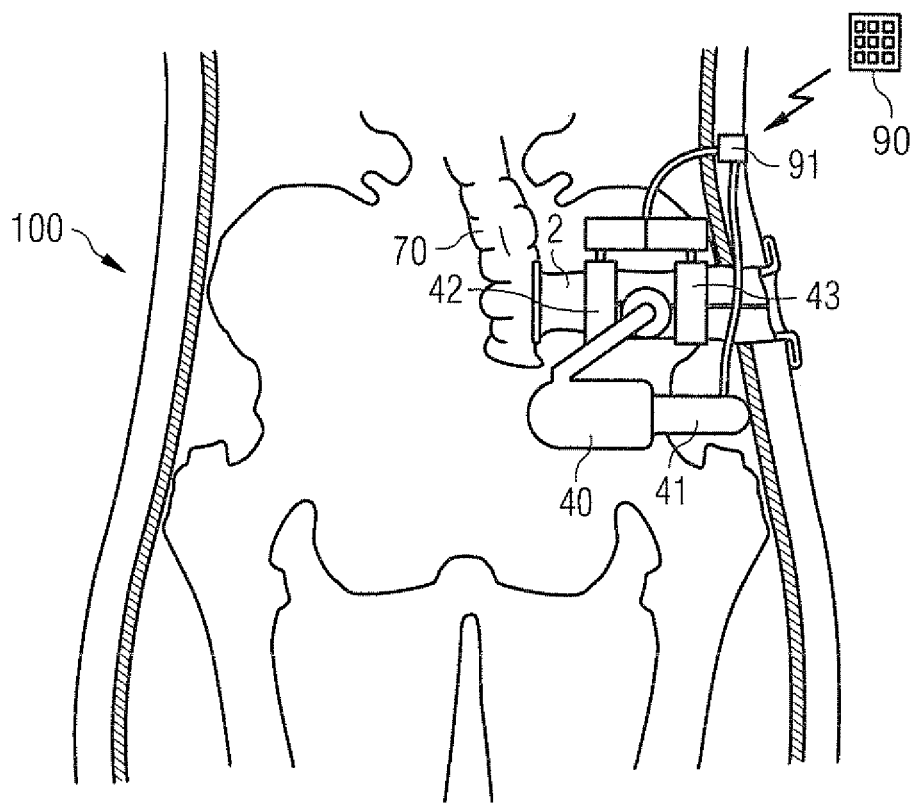

FIG. 146 shows an embodiment of the artificial intestine section with an artificial reservoir and an entry valve and exit valve arranged upstream and downstream of the reservoir. The reservoir is mounted with a pump in a common housing and the pump and the entry and exit valves are controlled by means of a control device, of which a part is implanted inside the patient's body. Data are transmitted wirelessly between the external part and implanted part of the control unit. In addition, energy is wirelessly transmitted to the artificial intestine section or to an accumulator also implanted in the patient's body and galvanically connected here to the valves and pump.

Figure 147A:
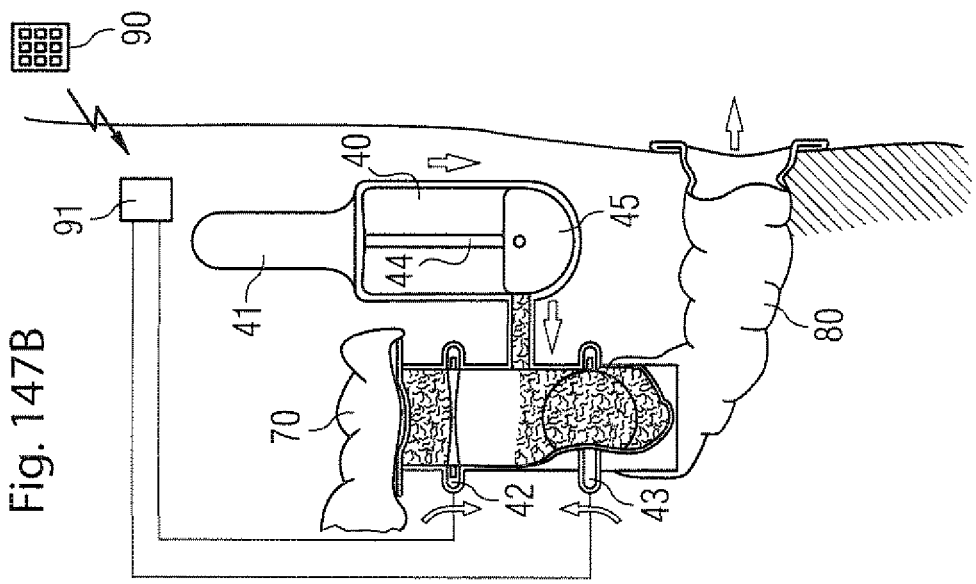
Figure 147B:
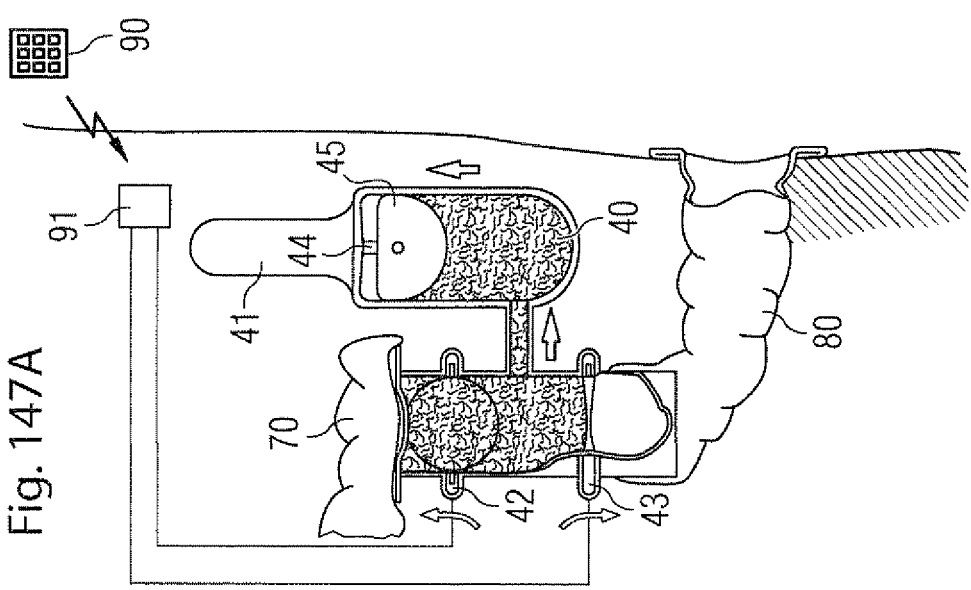

FIGS. 147A and 147B show a first embodiment of the structure of FIG. 146 in more detail. The pump comprises a moveable piston with a front end of the piston extending into the reservoir such that a volume of the reservoir is reduced upon advancement of the piston. The piston is spring loaded so as to urge the piston into a normally retracted position. Furthermore, entry and exit valves are here realized as flap valves. The flap valves are controlled so that one valve is open while the other one is closed.

Figure 148A:
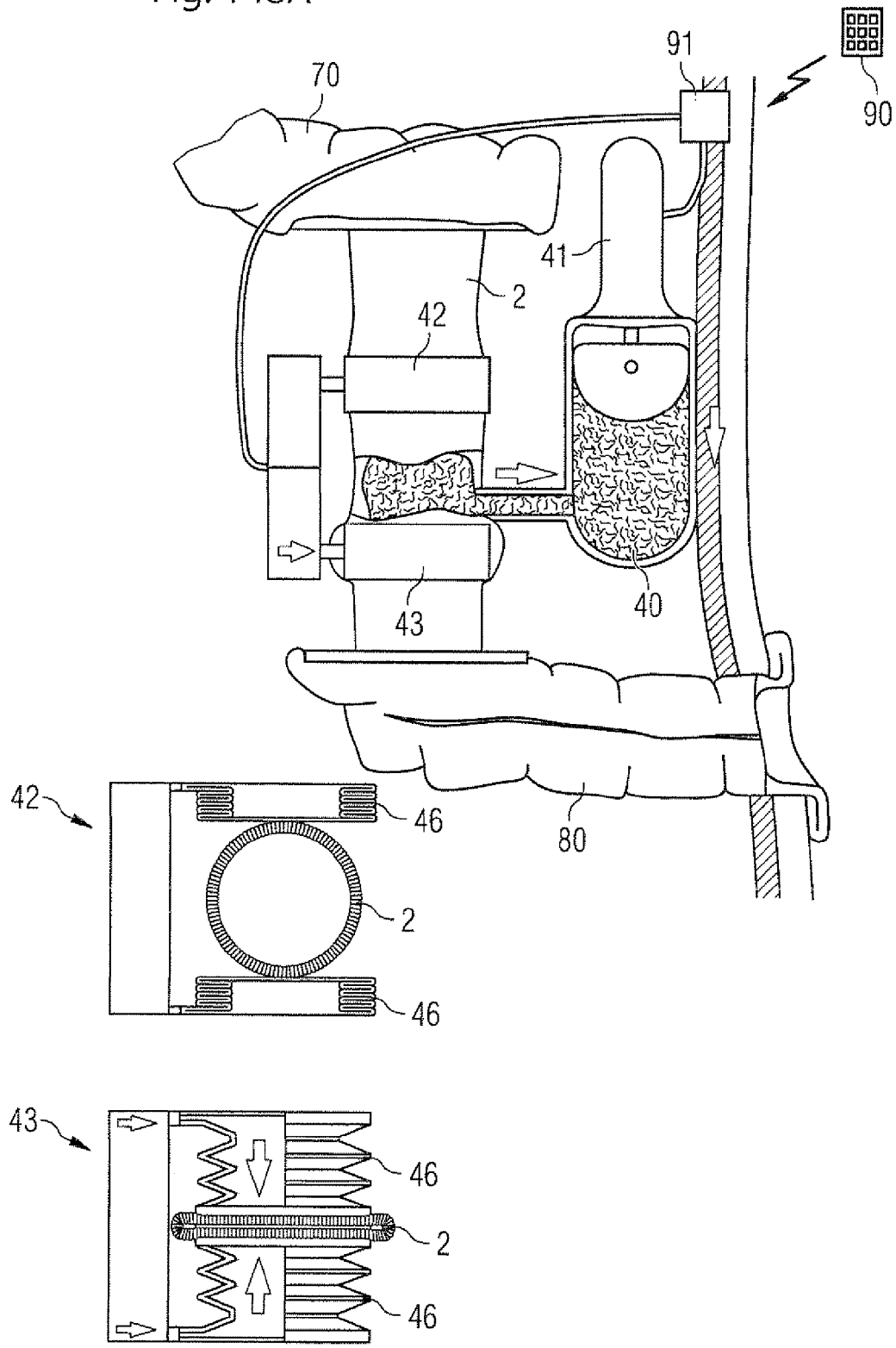
Figure 148B:
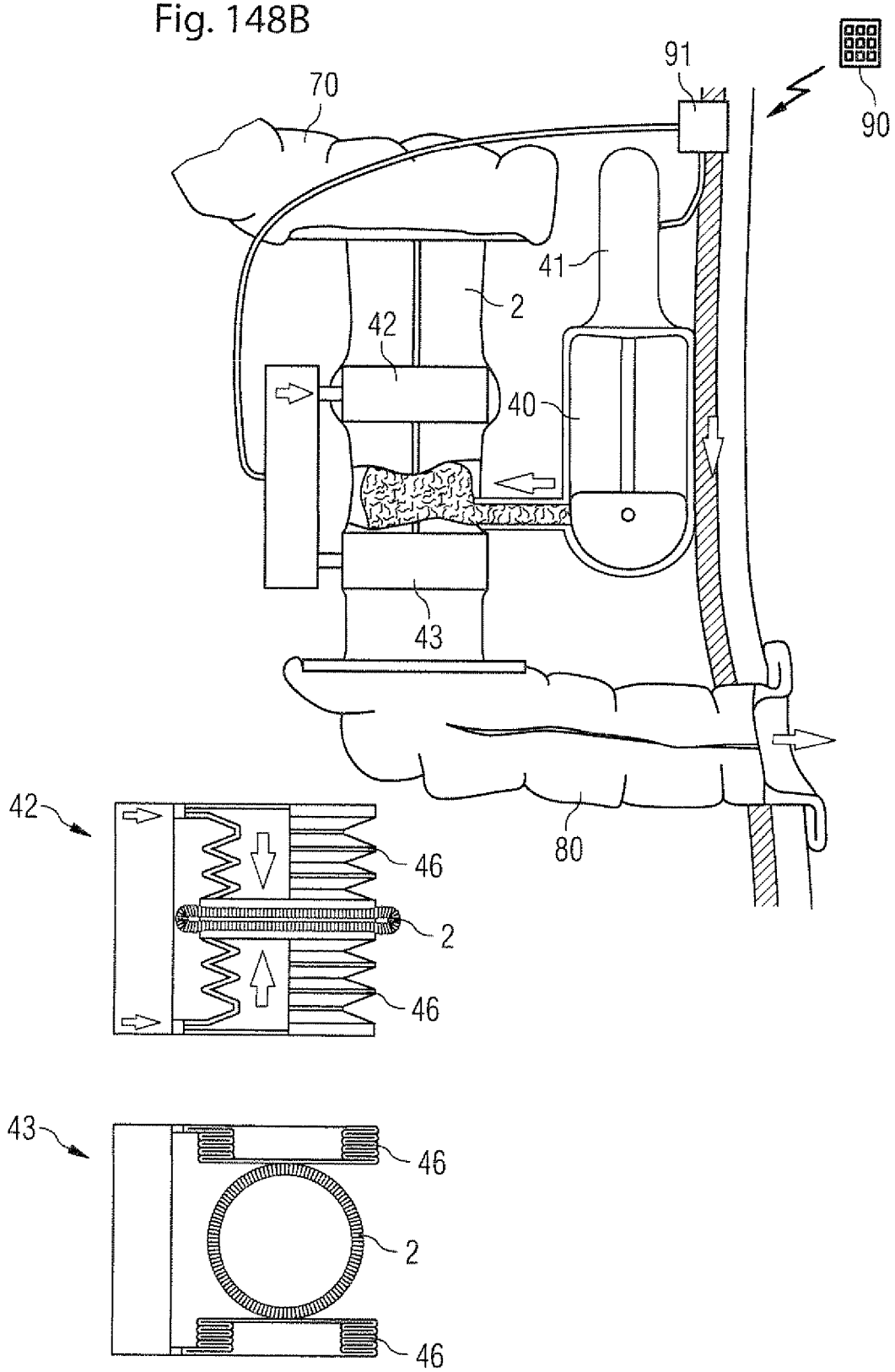

FIGS. 148A and 148B show a system similar to the one of FIGS. 147A and 147B. However, here the entry and exit valves comprise bellows acting on the intestine from the outside so as to close the intestine by compression. In FIG. 148A the bellows of the exit valve are expanded to compress the artificial intestine section at the downstream side of the reservoir, whereas in FIG. 148B the artificial intestine section is closed by means of the bellows of the entry valve upstream of the reservoir so that the reservoir can be emptied by advancing the piston of the pump.

Figure 149:
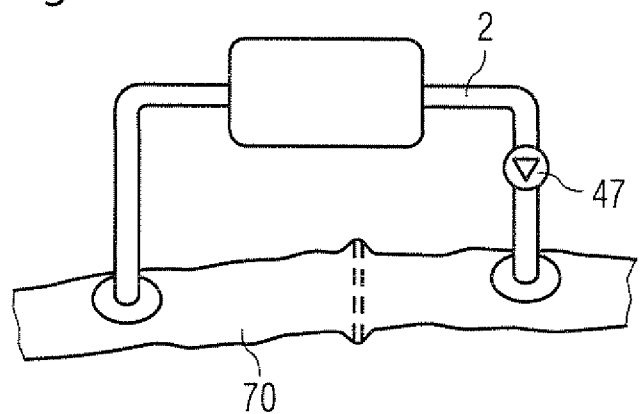

FIG. 149 shows an embodiment schematically, wherein the artificial intestine section by-passes a section of the patient's intestine, the intestine being closed by sewing so as to direct intestinal content towards the artificial intestine section. An exit valve is provided for controlling the flow of intestinal contents from the artificial intestine section. The enlarged area of the artificial intestine section represents any kind of element acting on the intestinal contents within the artificial intestine section, such as a reservoir, one or more valves, a pump or any other flow control device, possibly including a motor, and the like.

Figure 150:
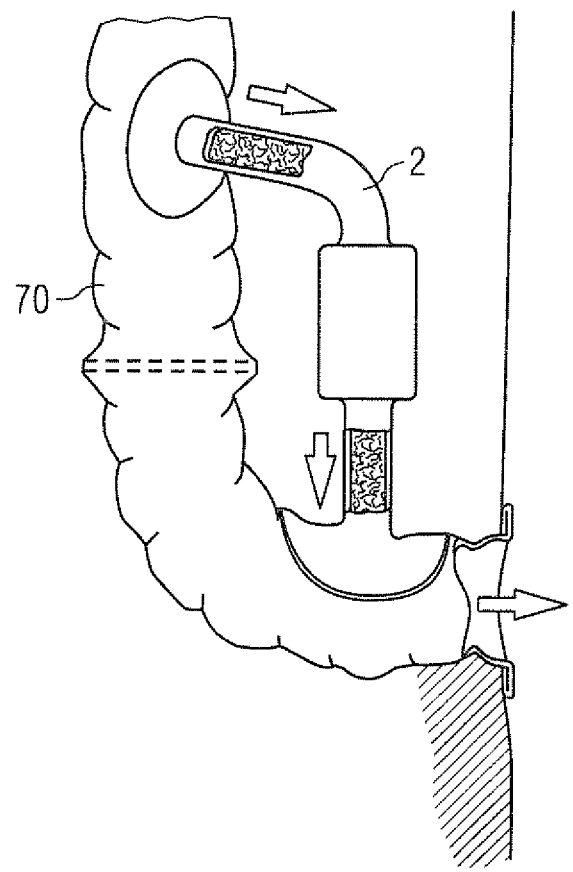

FIG. 150 shows a by-passing artificial intestine section in action, further leading to a surgically created stoma. A pump or valve may be contained in the artificial intestine section.

Figure 151:
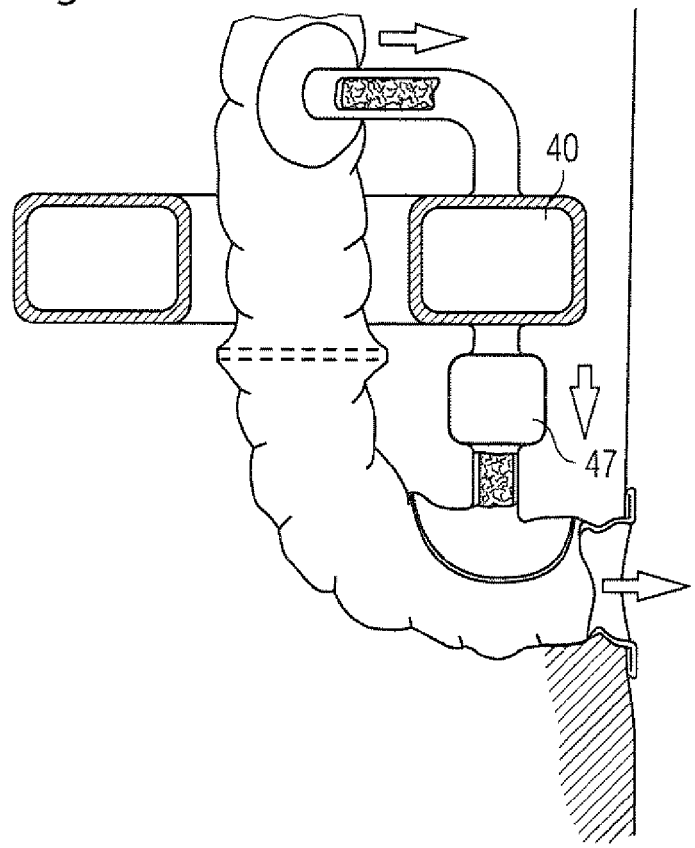

FIG. 151 shows the artificial intestine section of FIG. 150 with a large reservoir and an exit valve downstream the reservoir.

Figure 152:
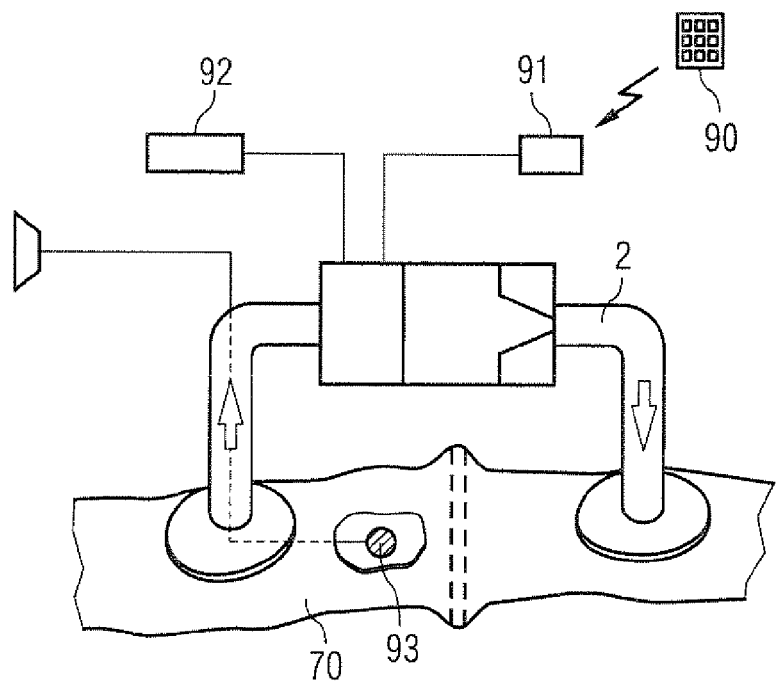

FIG. 152 shows the by-passing artificial intestine section including a pump and a valve incorporated therein. Furthermore, a battery implantable in the patient's body and preferably rechargeable provides the artificial intestine section with energy. The artificial intestine section is wirelessly controlled and the battery, if rechargeable, wirelessly charged. A sensor implanted on or within the intestine delivers data on the physical conditions within the intestine for controlling the artificial intestine section.

Figure 153C:
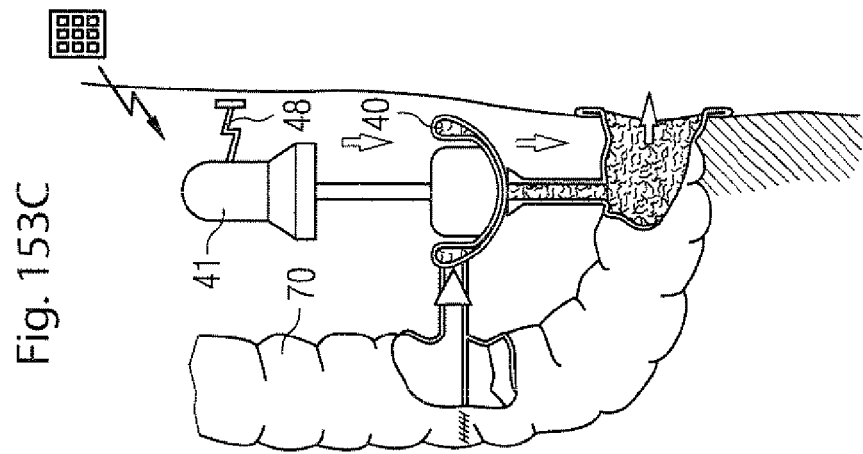
Figure 153B:
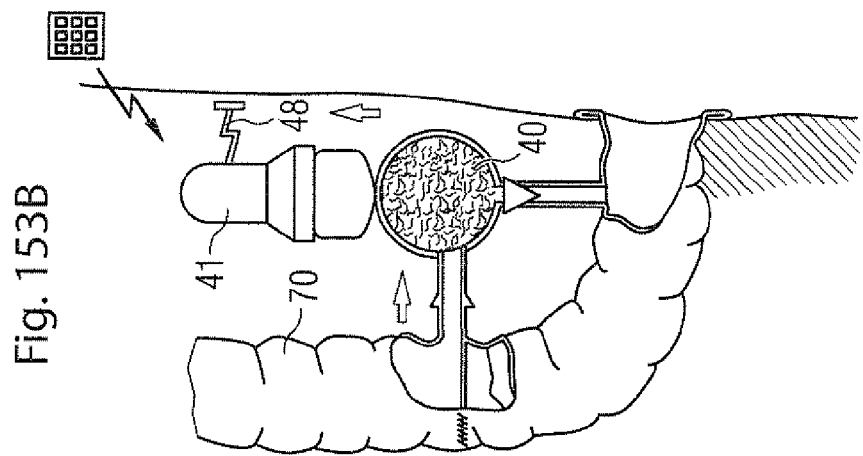
Figure 153A:
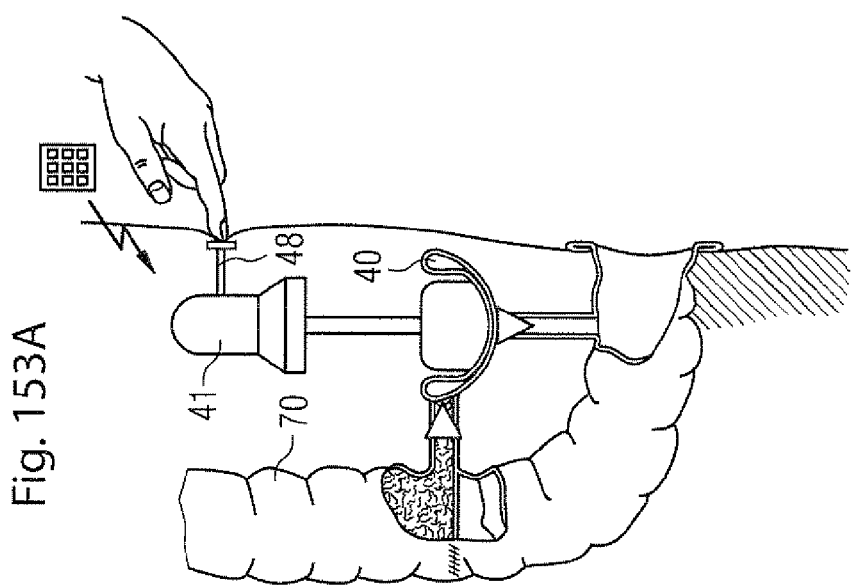

FIGS. 153A to 153C show an embodiment, where the artificial intestine section comprises a reservoir with a flexible wall. A pump is implanted in the patient's body separate but in close proximity to the reservoir and is used to empty the reservoir. The pump is actuated by means of a subcutaneously implanted, manually operable switch.

Figure 153D:
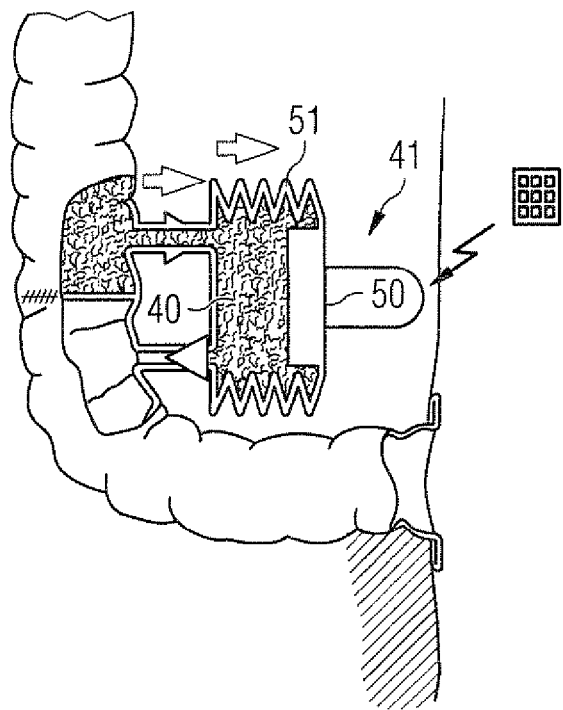
Figure 153E:
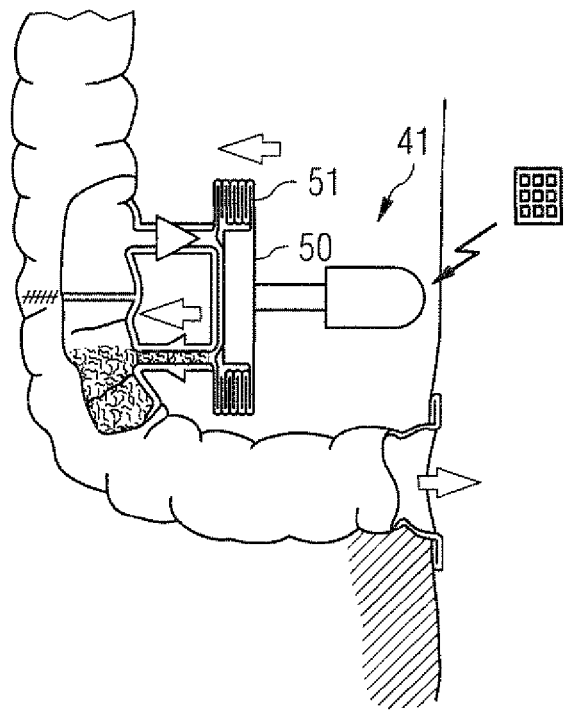
Figure 154A:
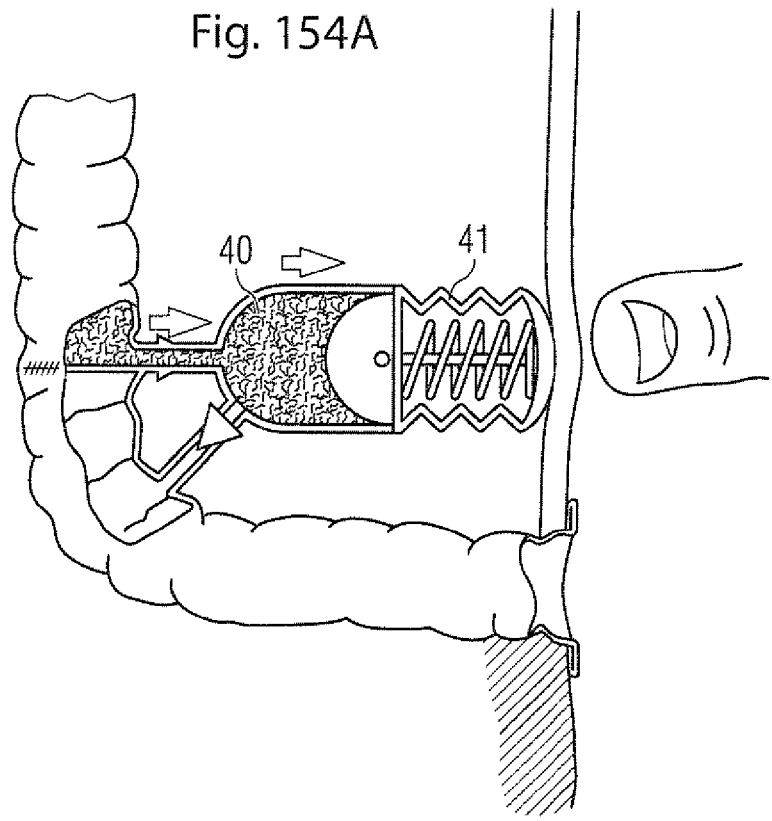
Figure 154B:
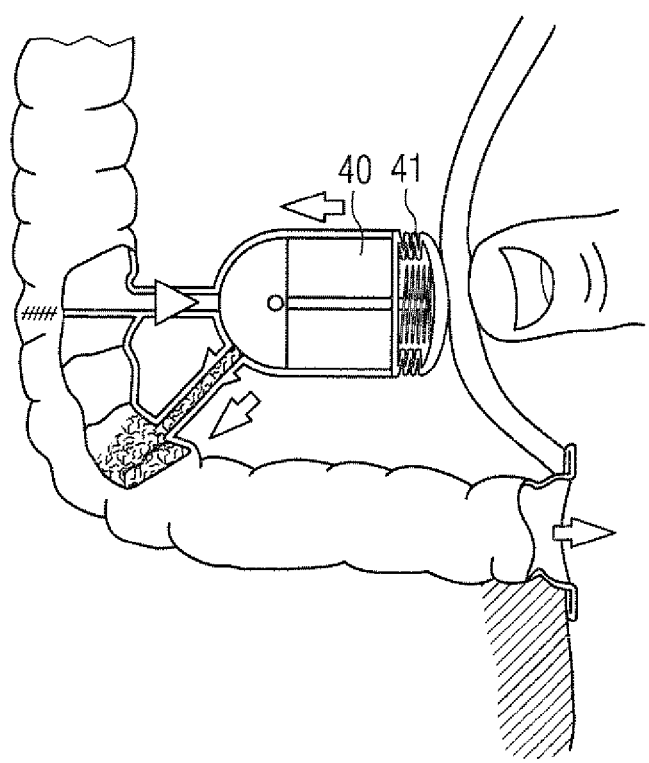

FIGS. 153D and 153E show a structure similar to the one of FIGS. 153A to 153C, however, with the pump and the reservoir being fixedly connected to one another. The reservoir is formed by a bellow having an end wall closing the bellow at one end thereof. The end wall makes part of the pump such that a volume of the bellow can be reduced upon advancement of the end wall. The bellow is made of a resilient material so as to urge the bellow into a normally extended position FIGS. 154A and 154B show a variant to FIGS. 153D and 153E. Here, the pump and reservoir are integrally combined. The pump is manually operable and subcutaneously mounted so as to be operable from the outside of the patient's body.

Figure 155A:
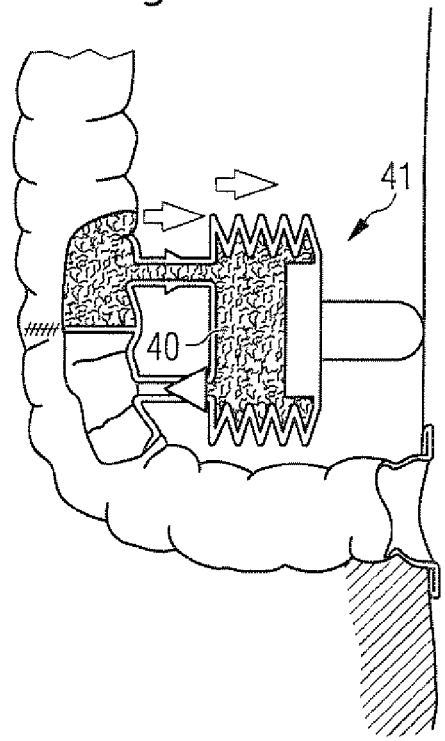
Figure 155B:
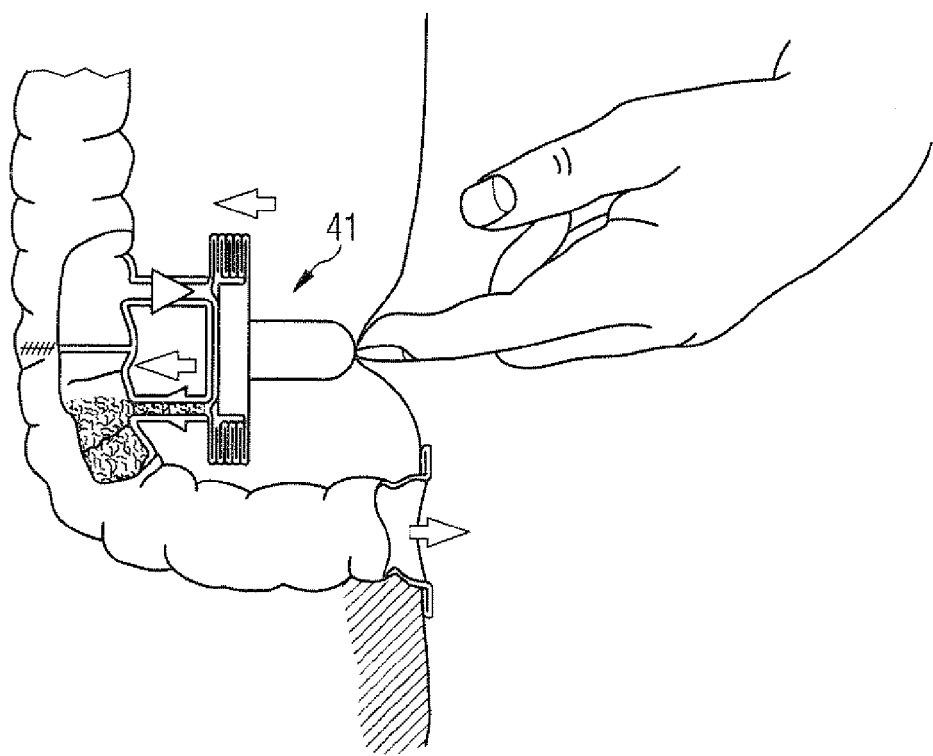

FIGS. 155A and 155B likewise show a variant to the system shown in FIGS. 153D and 153E. While in the system of FIGS. 153D, 153E the pump is automatically driven, such as by an integrated motor, and activated via remote control, the system in FIGS. 155A and 155B is again manually operable in that the manually operable pump is mounted subcutaneously.

FIGS. 160A to 160C show a plurality of cooperating valves implanted inside the patient's body and outside the patient's intestine. These can be positioned behind and/or in front of the artificial intestine piece along the patient's natural intestine. Each of the valves comprises an electrical stimulation device adapted to electrically stimulate muscle or neural tissue of an intestine section so as to cause at least partial contraction of the intestine section. For that purpose, the stimulation device comprises at least one electrode adapted to apply electric pulses to the intestine section. While instead of the three stimulation devices shown, a single stimulation device would be sufficient for opening and closing the intestine, the arrangement of the plurality of stimulation devices is adapted to stimulate different portions of the intestine section over time. The function of the three stimulation devices may also be combined in one integral unit. The direction of natural intestinal contents flow is indicated by arrows. The different portions of the intestine section in a wavelike manner may be made in a direction opposite to the natural intestinal contents flow, as shown in FIGS. 160A to 160C, so as to close the intestine section. The stimulation in the wavelike manner may also be made in the direction of natural intestinal contents flow to support emptying of the intestine or reservoir.

FIGS. 161A to 161C show the stimulation devices of FIGS. 160A to 160C in combination with constriction devices, such as the bellow valves described in relation to FIGS. 148A and 148B, for at least partly constricting the intestine section mechanically. Complete constriction is obtained by additional electrical stimulation of the respective intestine sections. The constriction devices may be released in order to allow intestinal contents to flow through.

Figure 162:
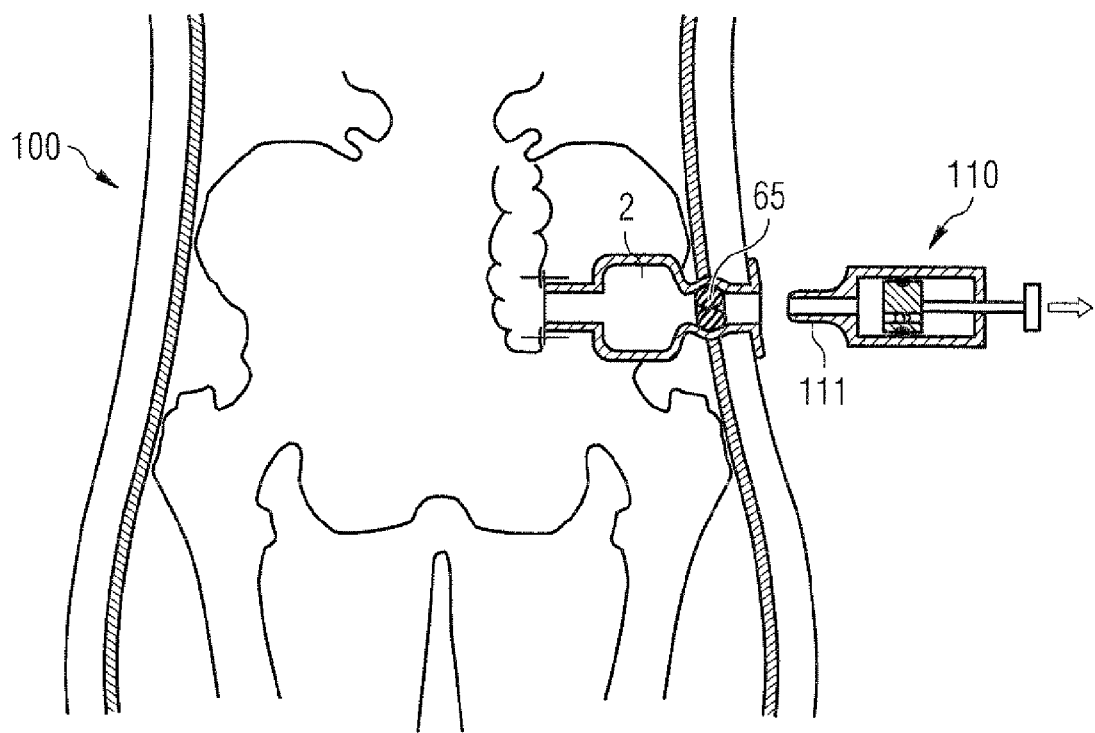

FIG. 162 shows a system similar to the system of FIG. 135, however, with a flow control device in the form of an exit valve being implanted within the artificial intestine section. An external manually driven suction pump is used for emptying the artificial intestine section, wherein a conduit on the front end of the pump is inserted from outside the patient's body into the intestine, thereby mechanically urging the exit valve to open.

Figure 163A:
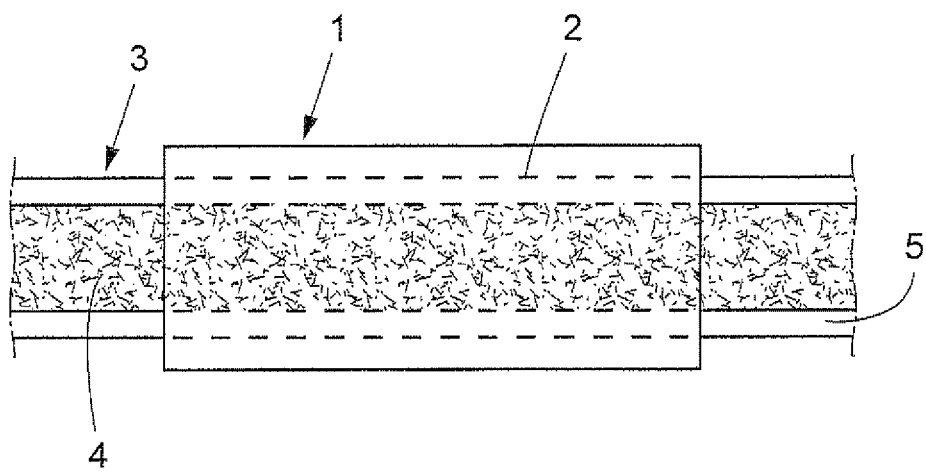
Figure 163B:
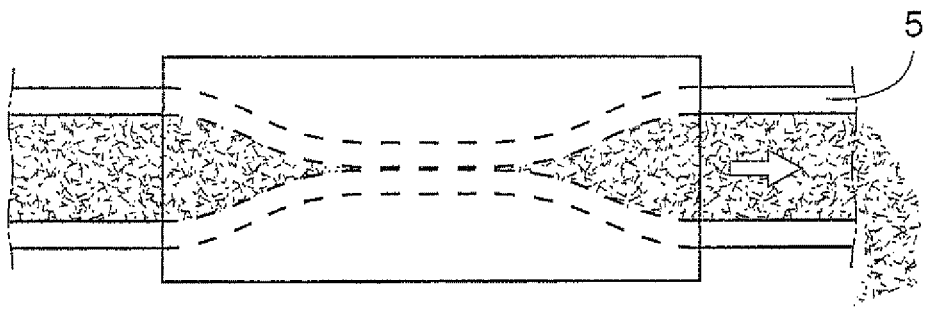

FIGS. 163A and 163B schematically illustrate different stages of operation of a general apparatus according to the present invention, wherein a pump of the apparatus is applied on a patient's intestines.

Figure 164A:
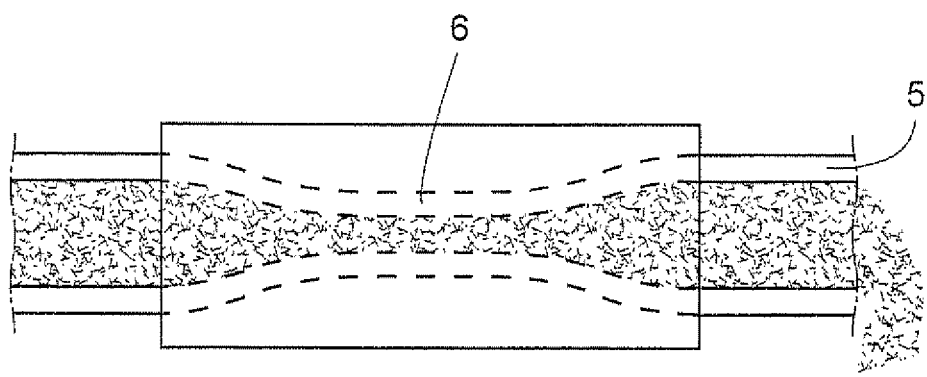
Figure 164B:
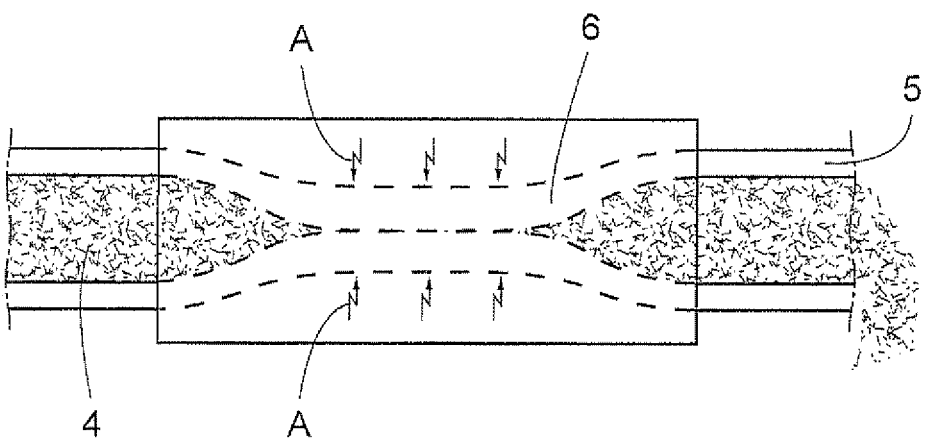

FIGS. 164A and 164B schematically illustrate different stages of operation of the general apparatus of FIGS. 163A and 163B also including an electric stimulation device.

FIGS. 165A, 165B and 165C schematically illustrate different stages of operation of an embodiment of the present invention, wherein a peristaltic pump is applied on a patient's intestines.

Figure 166A:
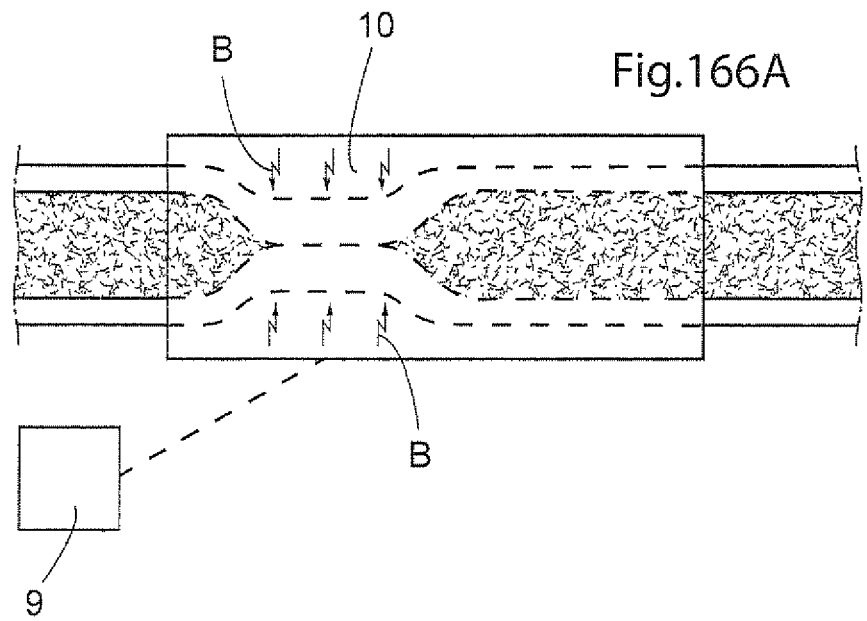
Figure 166B:
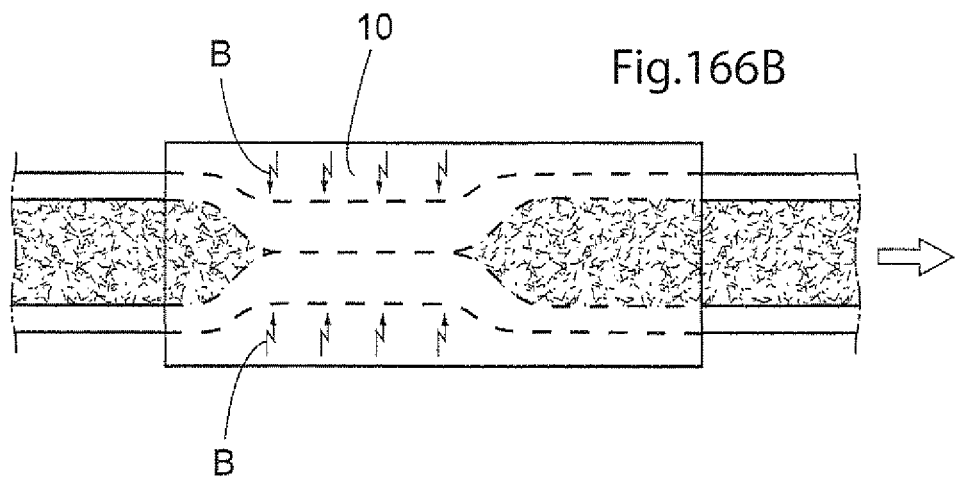
Figure 166C:
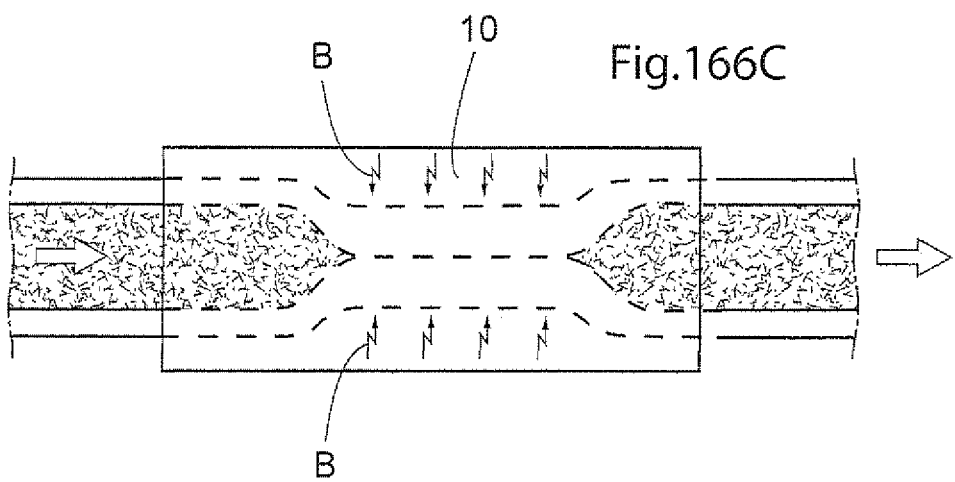

FIGS. 166A, 166B and 166C schematically illustrate the embodiment of FIGS. 165A-165C also including an electric stimulation device.

Figure 167A:
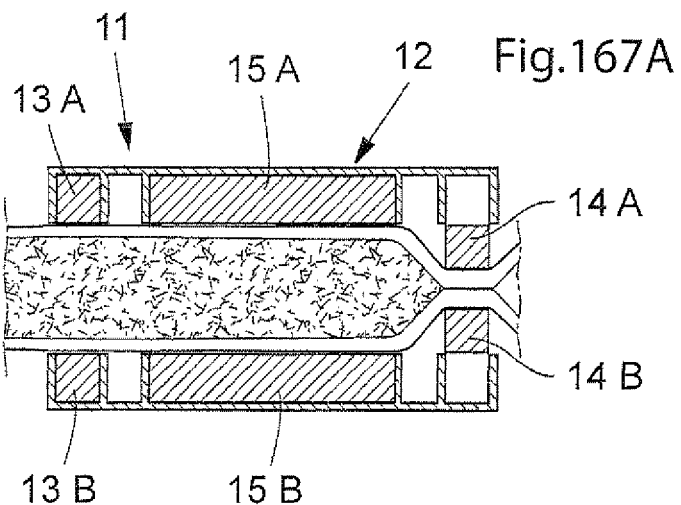
Figure 167B:
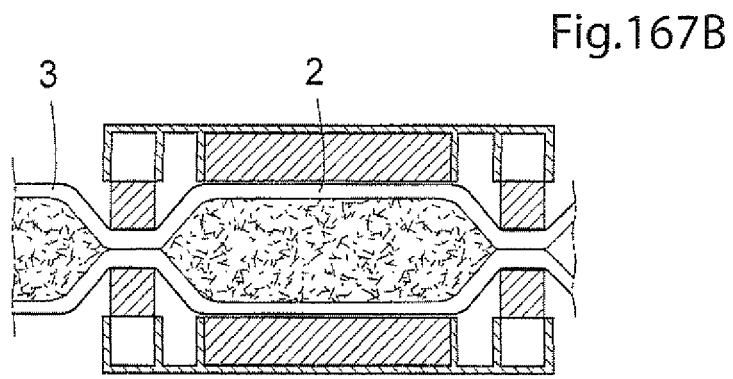
Figure 167C:
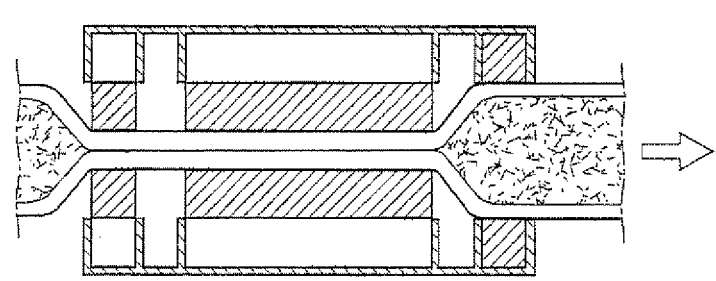

FIGS. 167A, 167B and 167C are longitudinal cross-sections of an embodiment of the invention showing different stages of operation, wherein a pump includes a constriction device that radially constricts a patient's intestines.

Figure 168A:
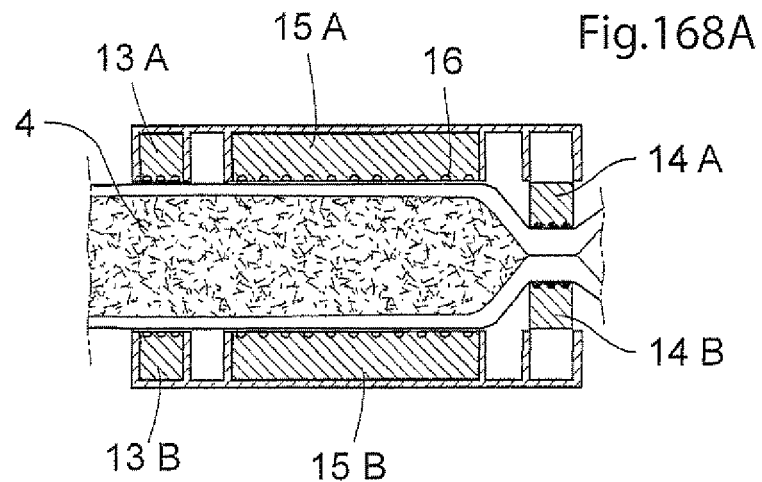
Figure 168B:
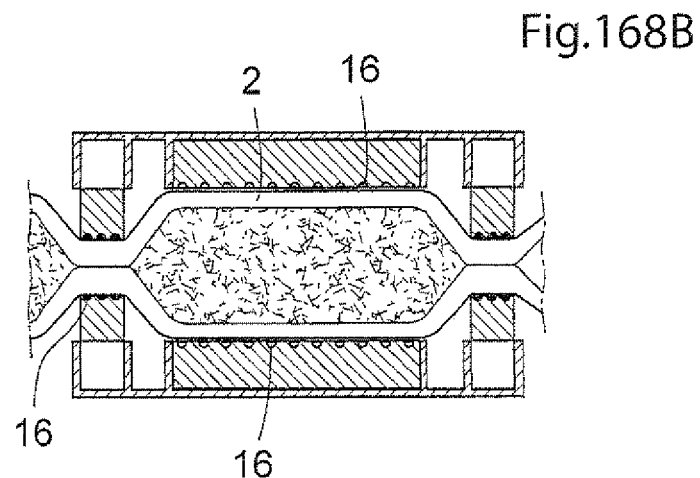
Figure 168C:
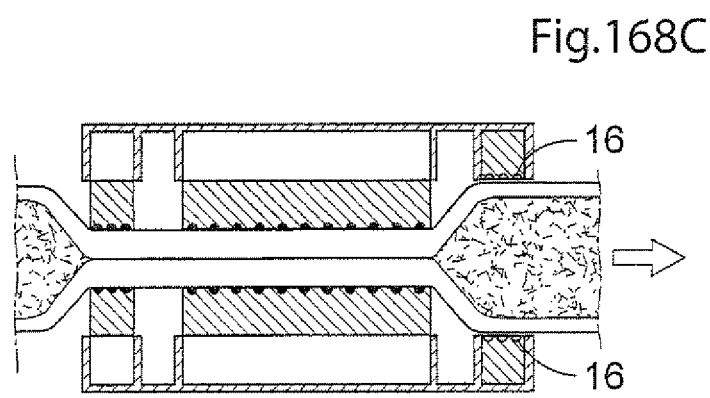

FIGS. 168A, 168B and 168C are longitudinal cross-sections of a modification of the embodiment of FIGS. 167A-167C, including an electric stimulation device.

Figure 169:
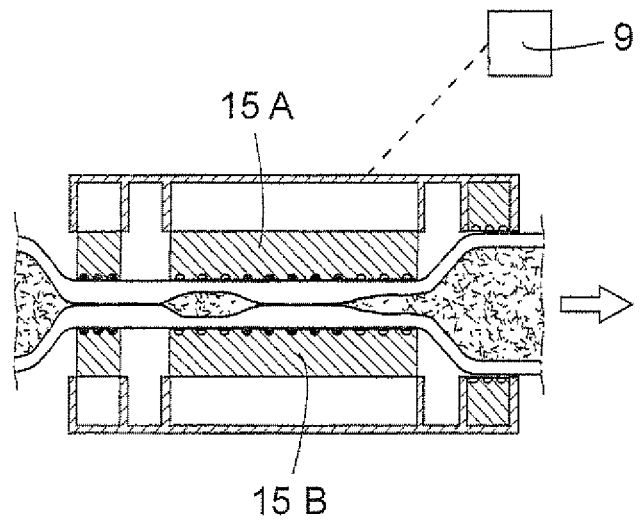

FIG. 169 shows the same embodiment as that of FIG. 168C illustrating a modified operation of the stimulation device.

Figure 170:
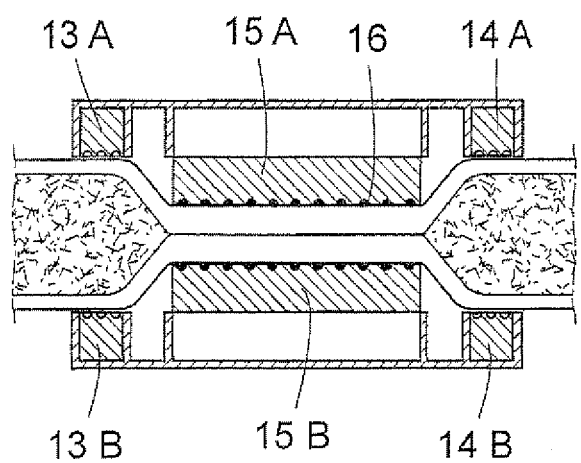

FIG. 170 shows the embodiment of FIG. 168A when the pump is not in operation.

FIGS. 171A, 171B, 171C and 171D illustrate a modified operation of the stimulation device of the embodiment according to FIG. 168A when the pump is not in operation.

Figure 172A:
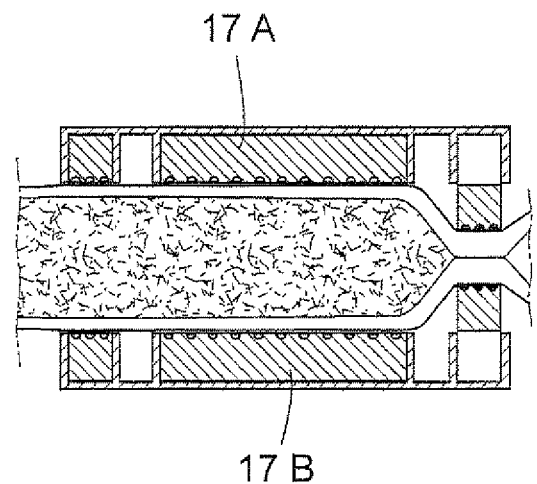
Figure 172B:
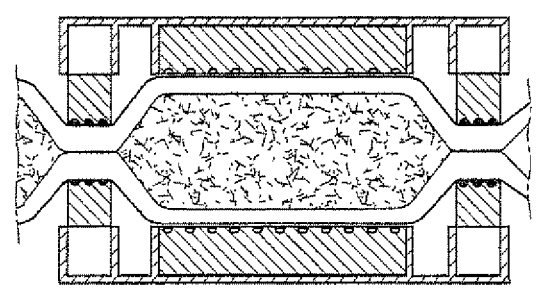
Figure 172C:
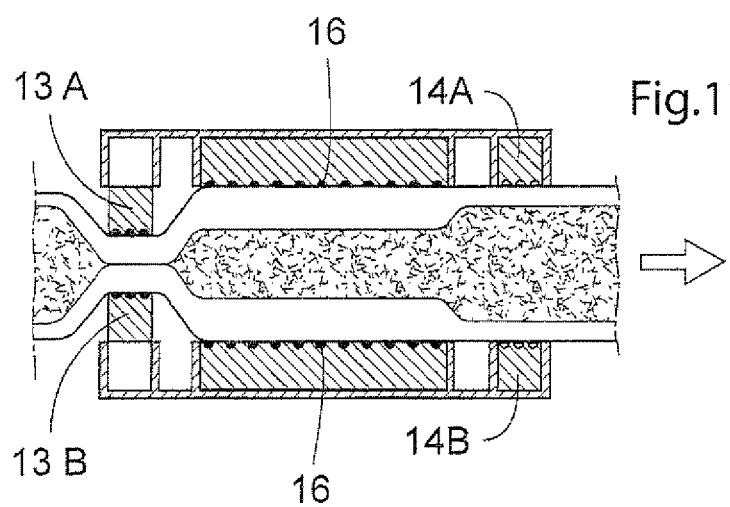

FIGS. 172A, 172B and 172C are longitudinal cross-sections of another embodiment of the invention including an electric stimulation device and showing different stages of operation.

Figure 173B:
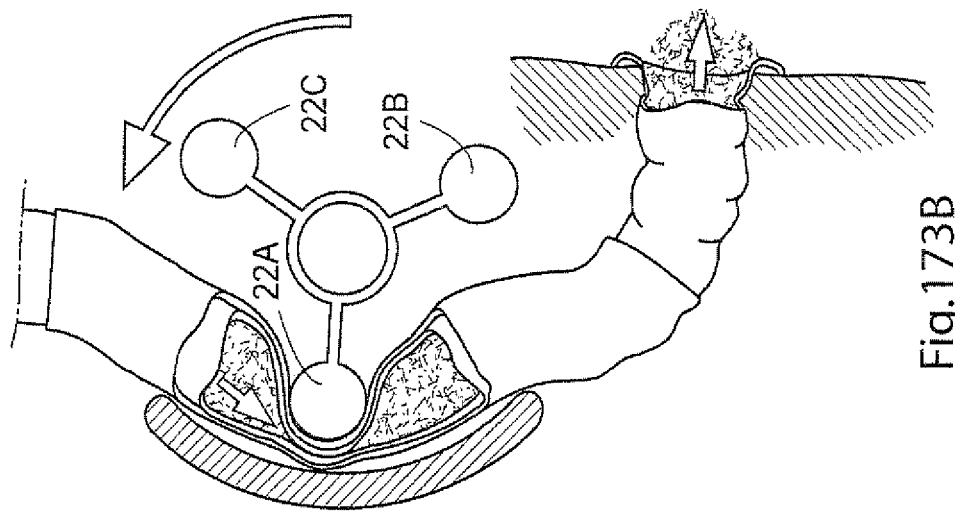
Figure 173A:
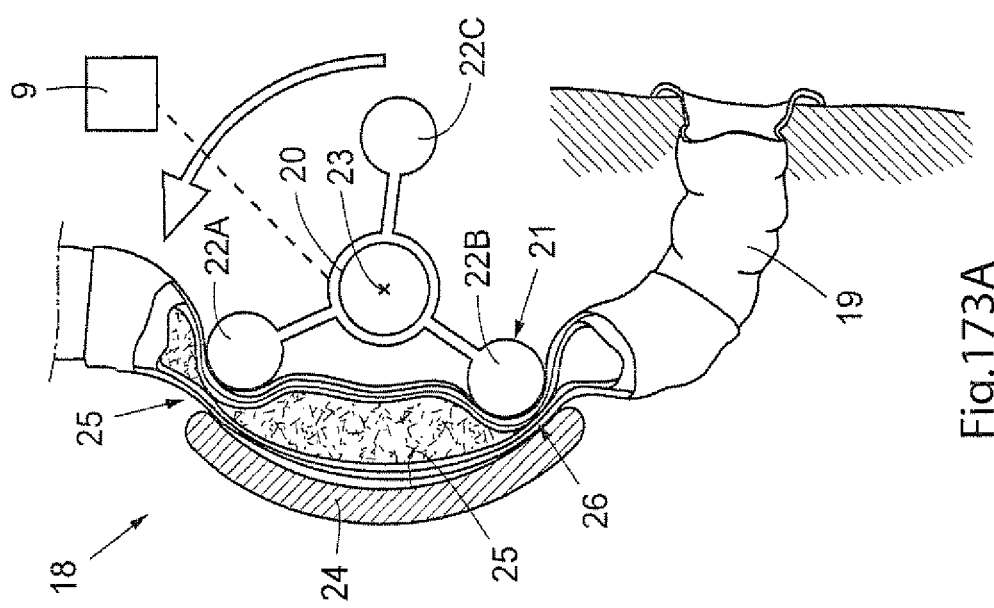

FIGS. 173A and 173B are views of another embodiment of the invention showing different stages of operation, wherein a rotary peristaltic pump is applied on a patient's small intestines.

FIGS. 174A and 174B are views of a modification of the embodiment of FIGS. 173A and 173B, also including an electric stimulation device.

FIGS. 175A through 175D are longitudinal cross-sections of another embodiment of the invention showing different stages of operation, wherein another type of peristaltic pump is applied on a patient's small intestines.

FIGS. 176A through 176D are longitudinal cross-sections of a modification of the embodiment of FIGS. 175A-175D, including an electric stimulation device.

Figure 177A:
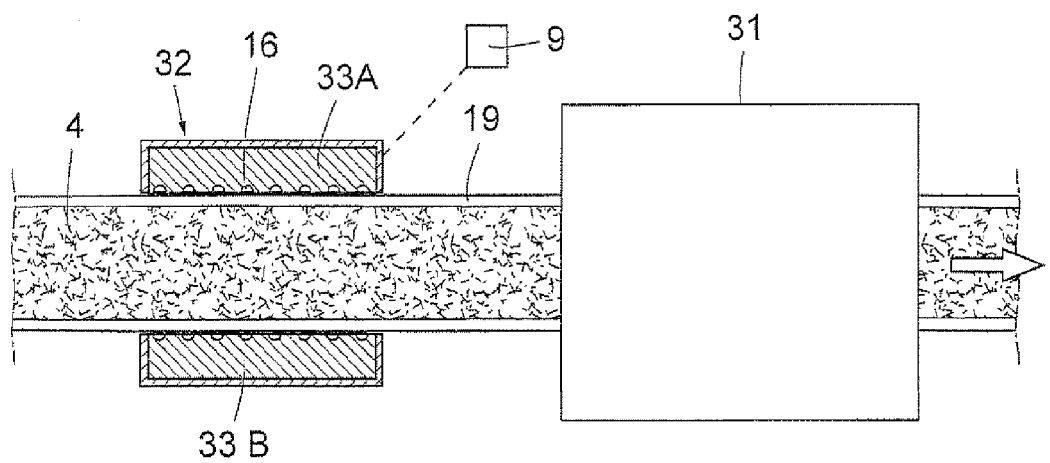
Figure 177B:
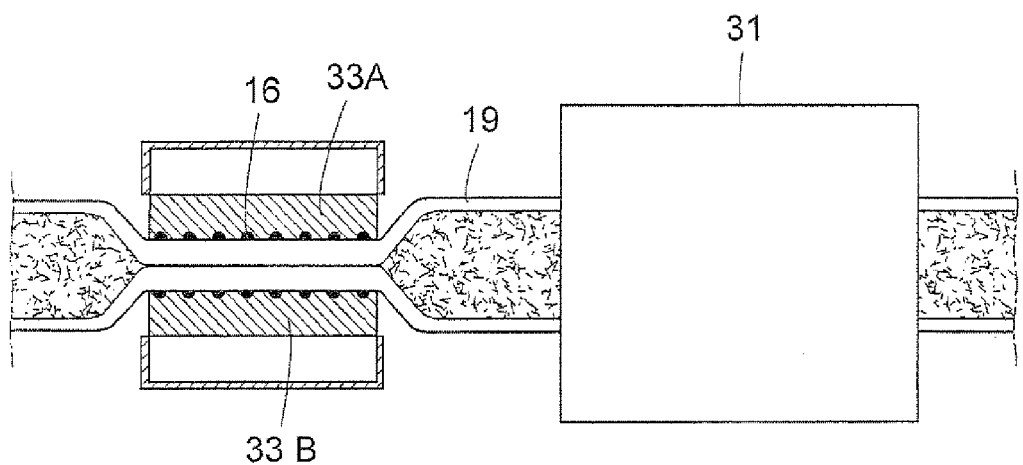

FIGS. 177A and 177B show different stages of operation of another embodiment of the invention including a separate intestinal closure.

Figure 178A:
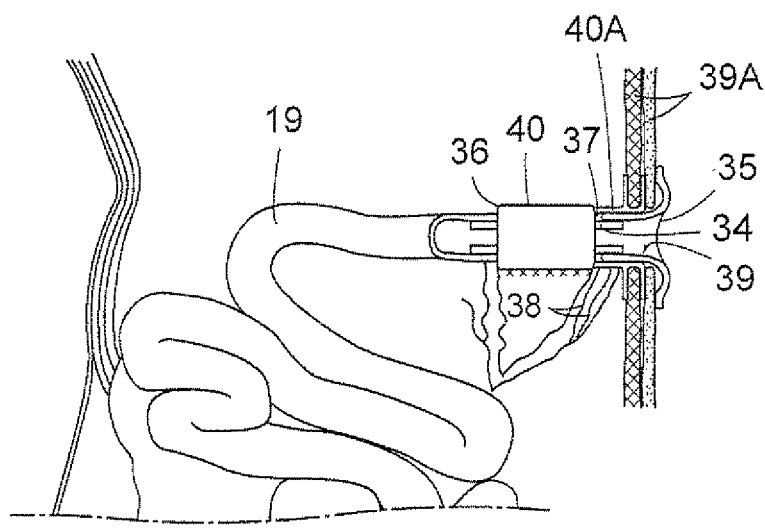

FIG. 178A shows another embodiment of the invention including an artificial intestinal piece implanted in a colostomy patient, wherein a pump operates on the artificial intestinal piece.

Figure 178B:
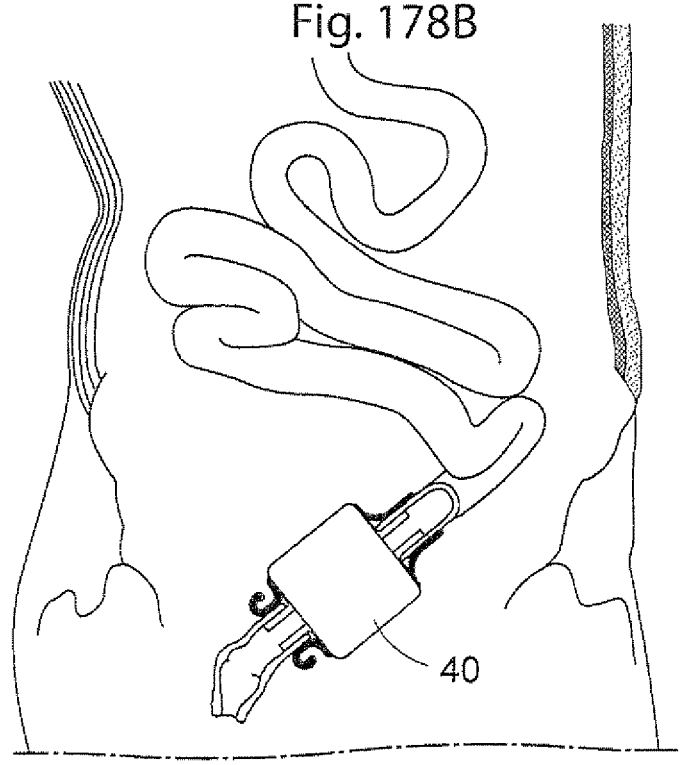

FIG. 178B shows the artificial intestinal piece of FIG. 178A joined to the patient's anus.

Figure 179:
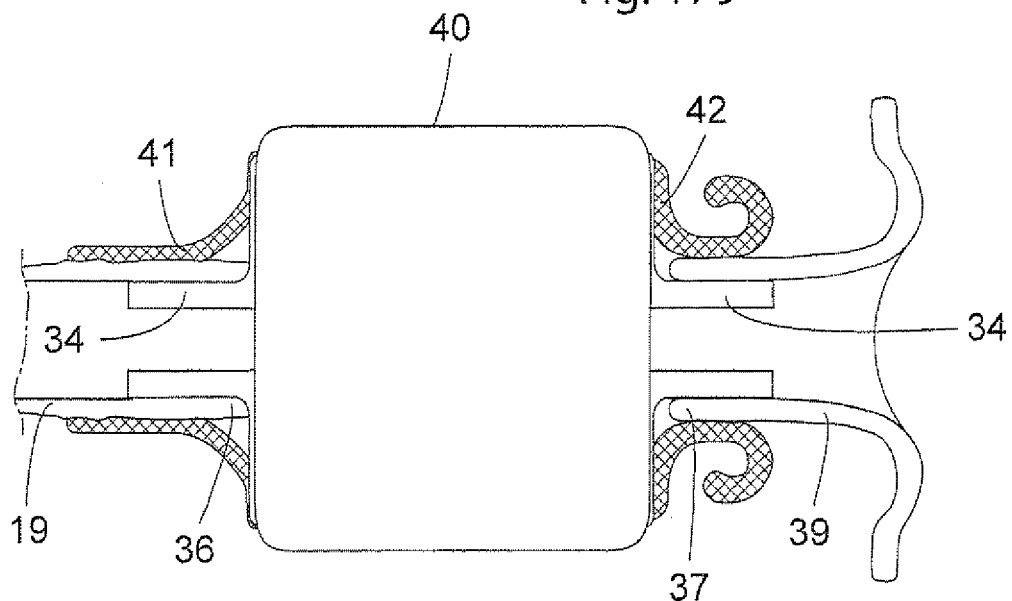

FIG. 179 shows an enlarged detail of the embodiment of FIG. 178.

Figure 180:
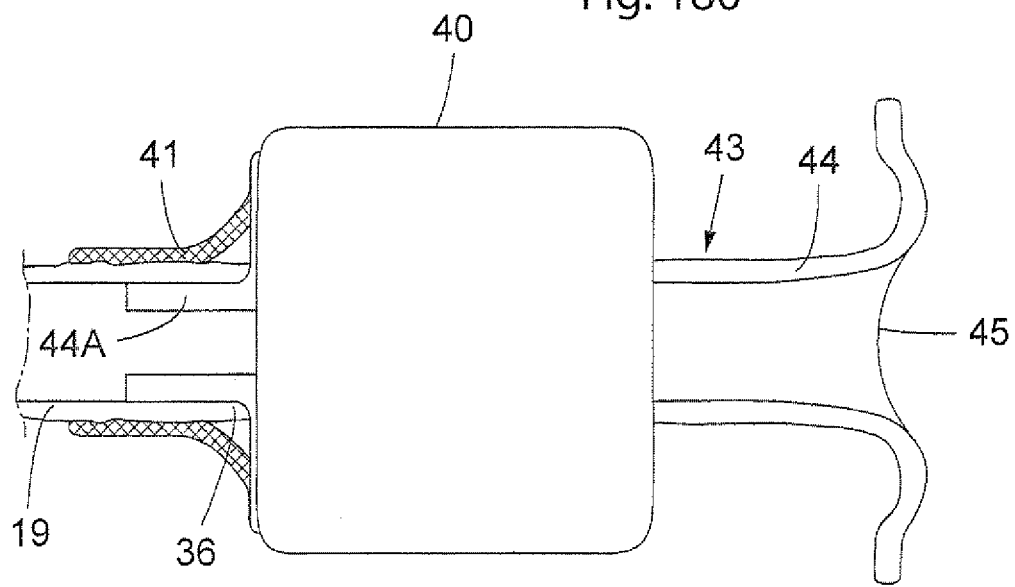

FIG. 180 shows a modification of the embodiment of FIG. 179.

FIGS. 181A, 181B, 181C and 181D schematically illustrate different stages of operation of another embodiment of the invention, wherein a pump includes a constriction device that axially constricts a patient's intestines.

Figure 181A:
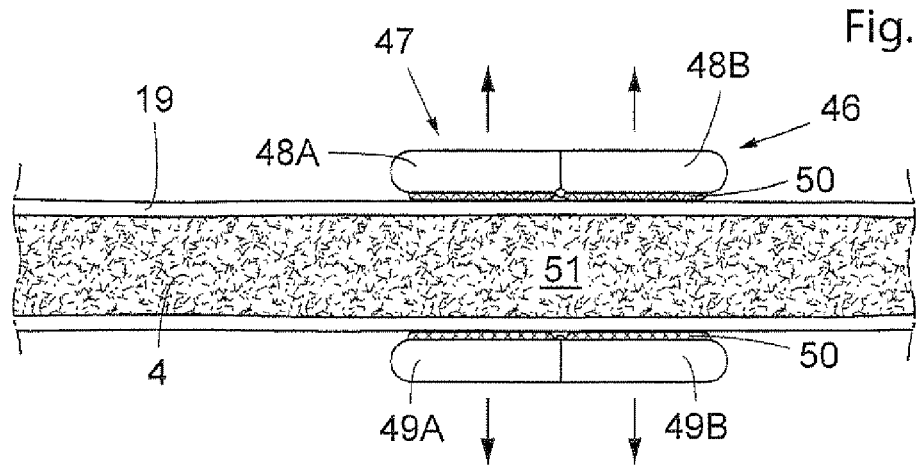
Figure 181B:
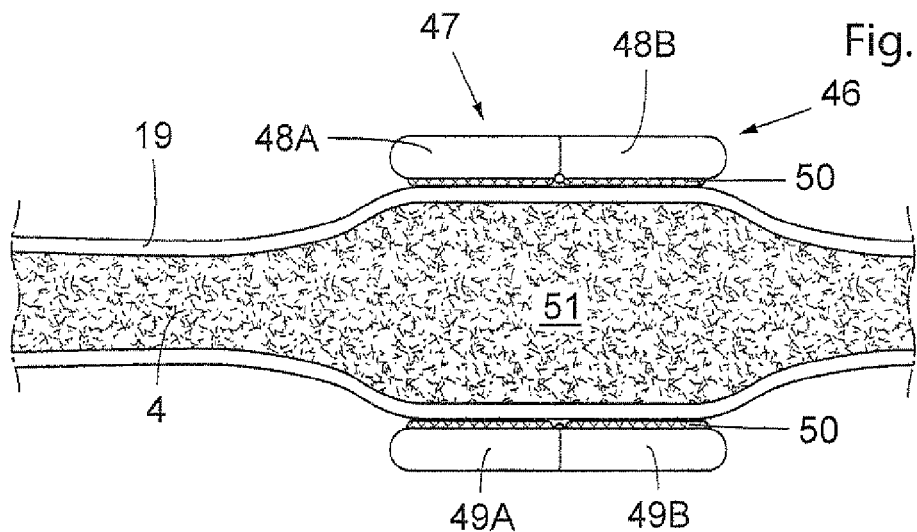
Figure 181C:
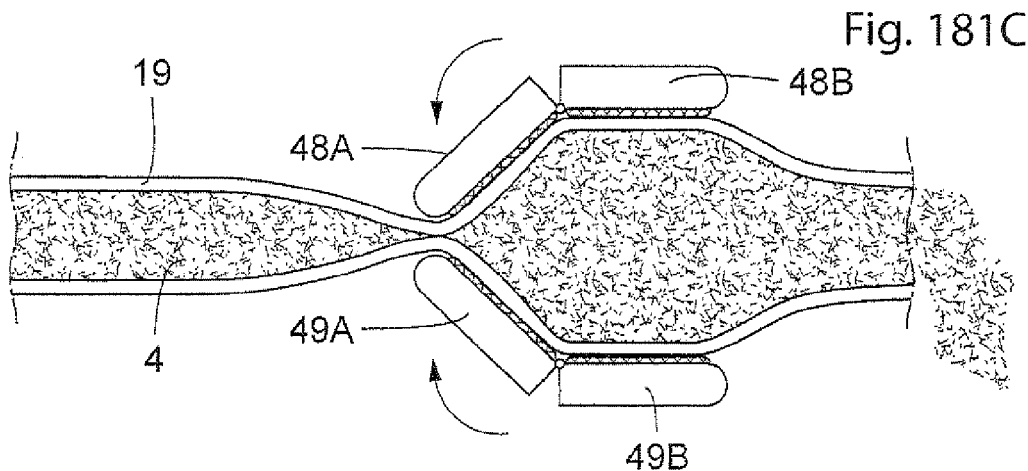
Figure 181D:
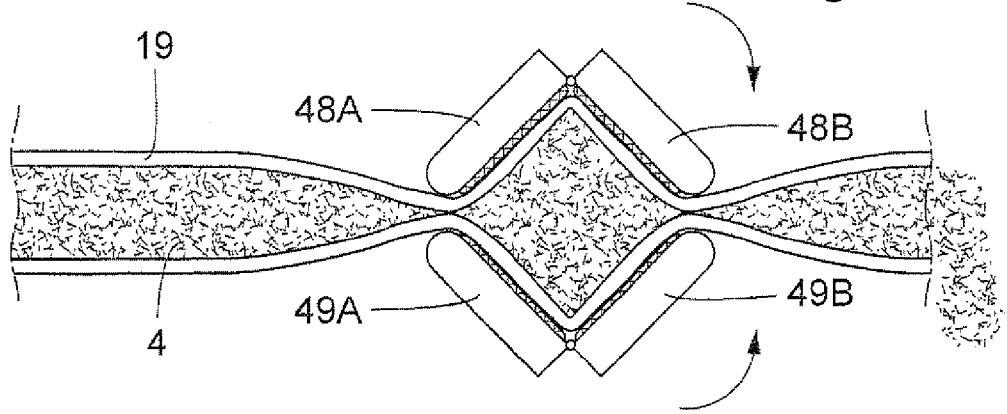
Figure 181E:
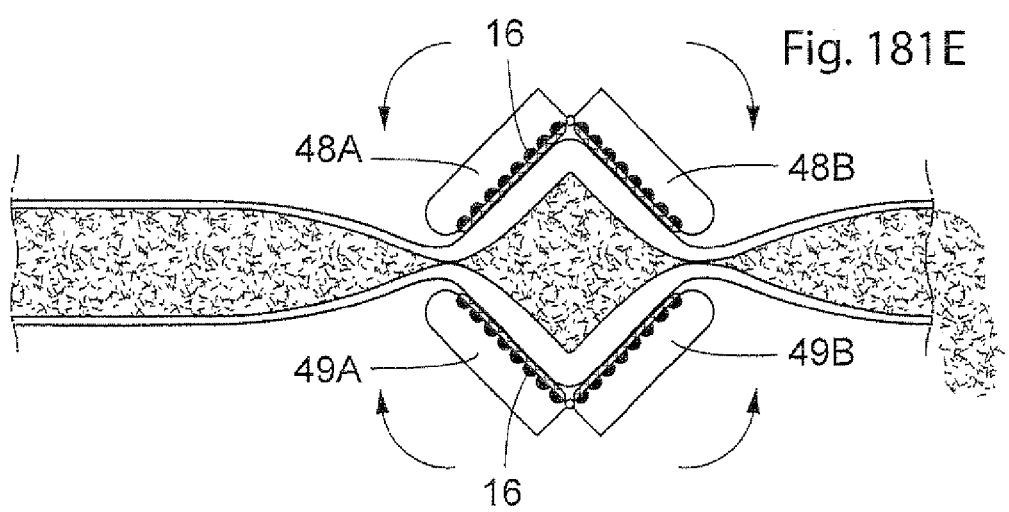

FIG. 181E illustrates the embodiment of FIG. 181D also including an electric stimulation device.

Figure 182:
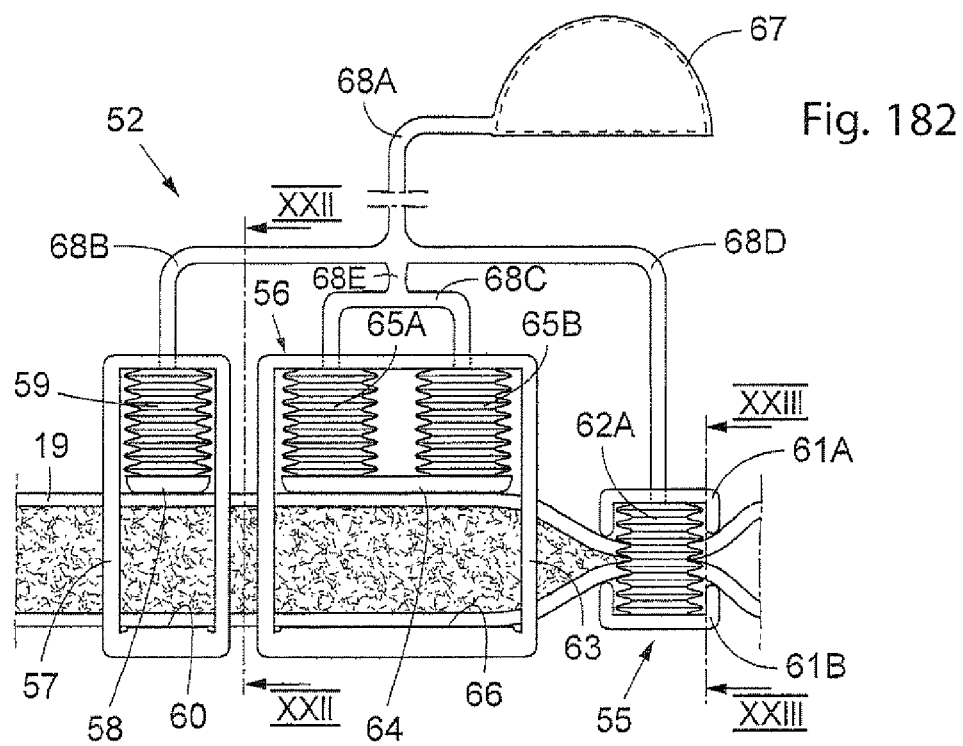

FIG. 182 is a side view of another embodiment of the invention, wherein a pump includes a hydraulically operable constriction device applied on a patient's intestines in a first stage of operation.

Figure 183:
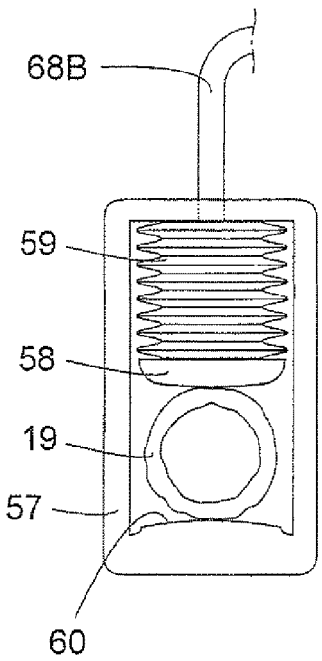
Figure 184:
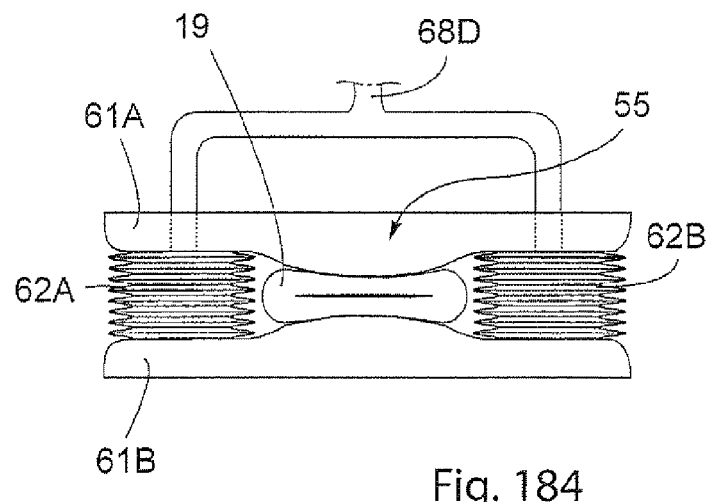

FIGS. 183 and 184 are views taken along section lines XXII-XXII and XXIII-XXIII, respectively, in FIG. 182.

Figure 185:
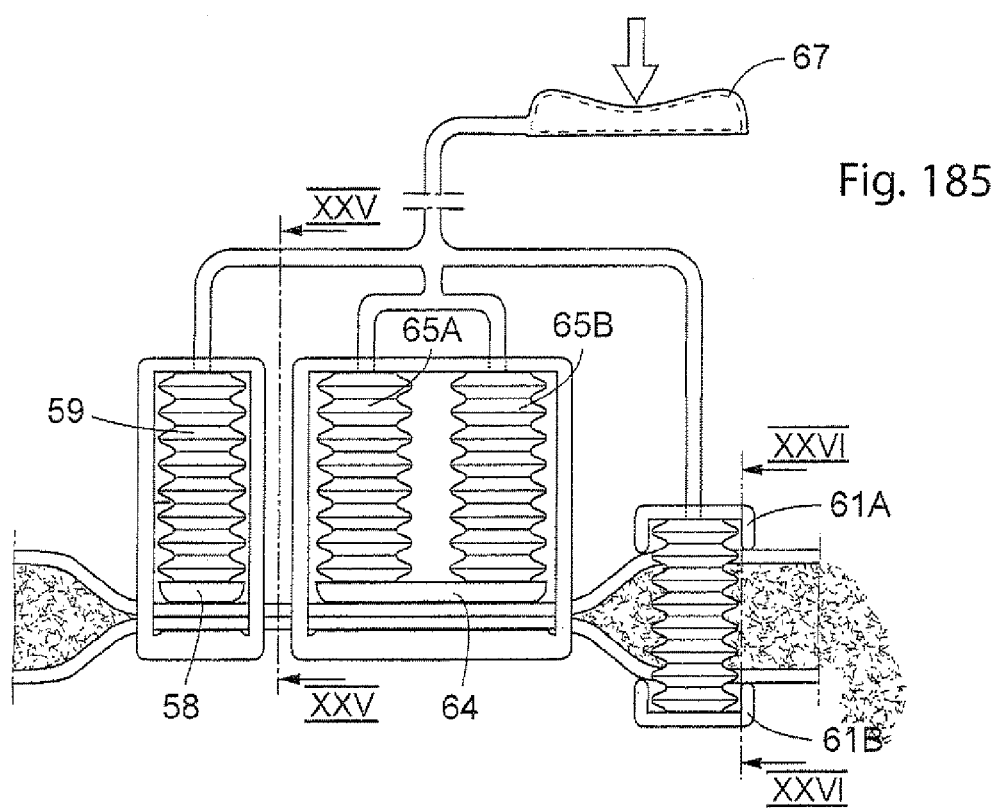

FIG. 185 is a side view of the embodiment of FIG. 182 with the constriction device in a second stage of operation.

Figure 186:
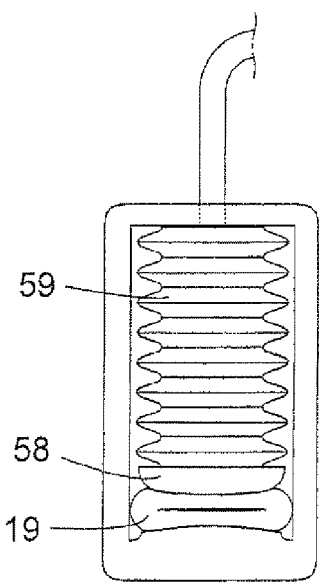
Figure 187:
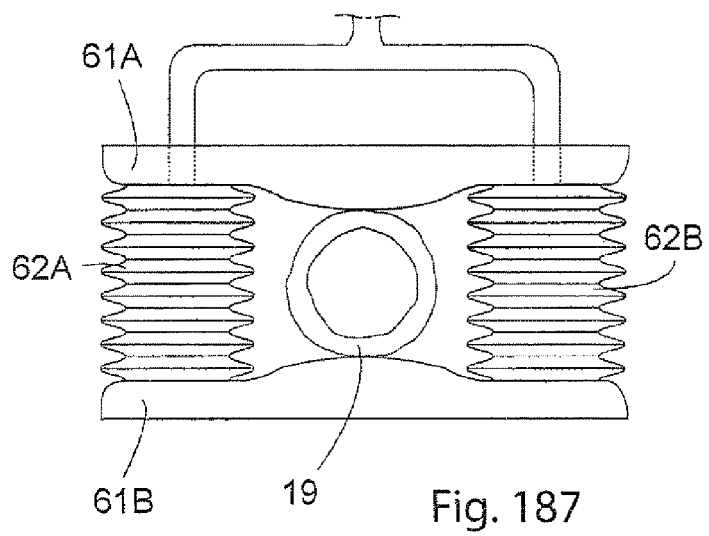

FIGS. 186 and 187 are views taken along section lines XXV-XXV and XXVI-XXVI, respectively, in FIG. 185.

Figure 188A:
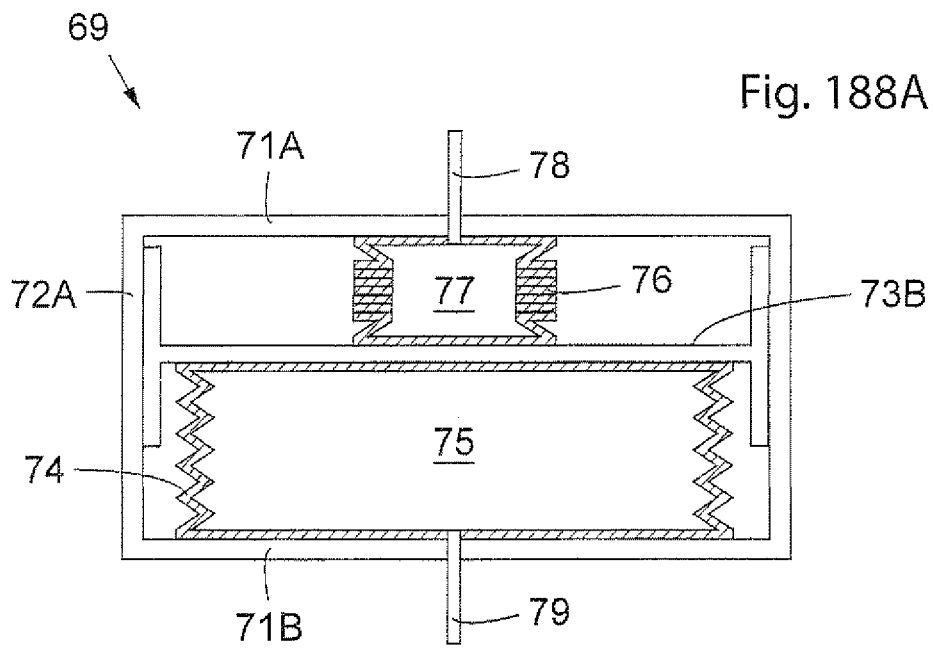
Figure 188B:
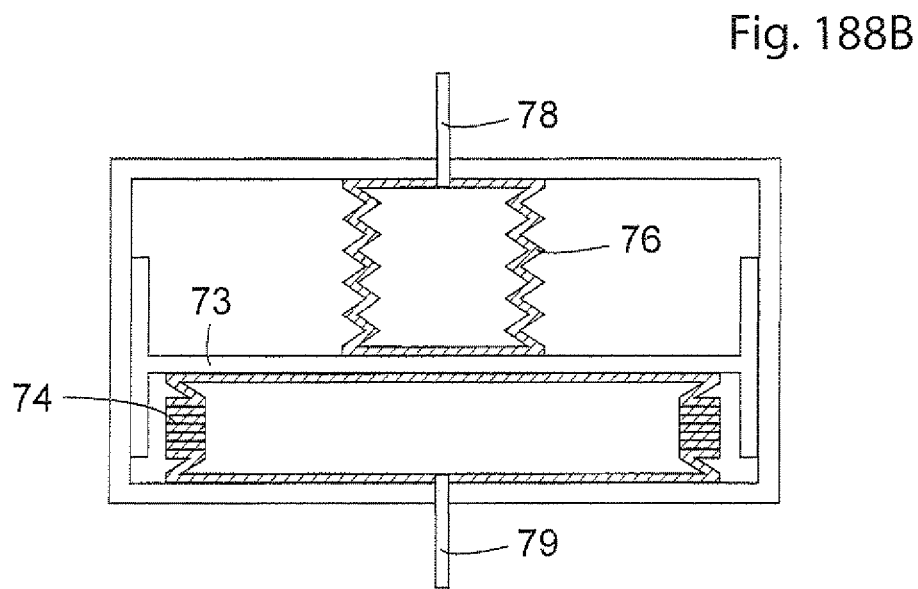

FIGS. 188A and 188B show different stages of operation of a hydraulic reverse servo suited for connection with the hydraulic constriction device of FIGS. 182-187.

Figure 189A:
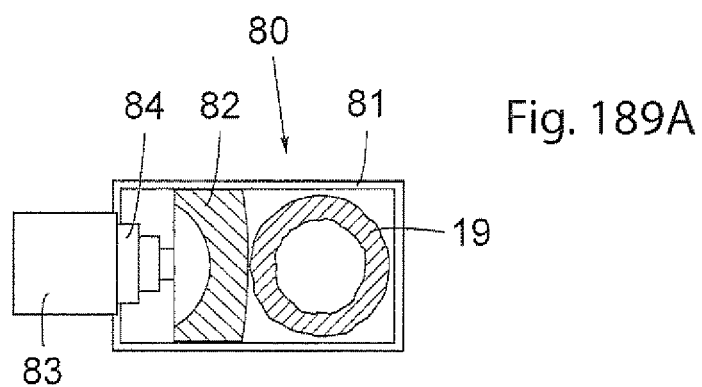
Figure 189B:
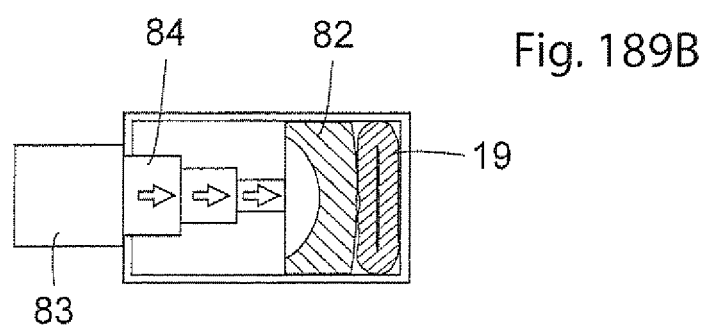

FIGS. 189A and 189B show different stages of operation of a mechanically operated constriction device suited for use in some of the embodiments of the present invention.

Figure 189C:
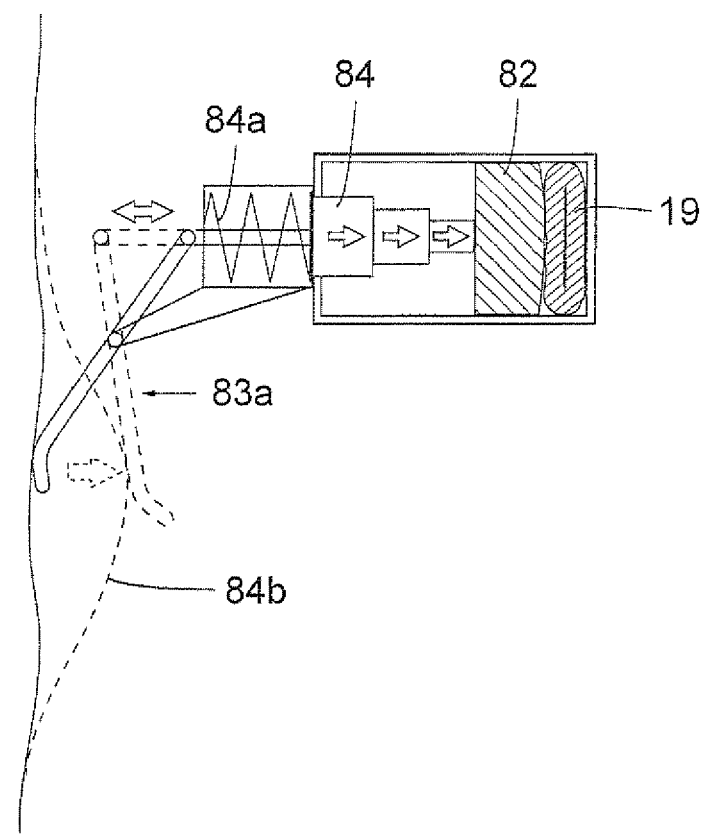

FIG. 189C is a modification of the embodiment of FIGS. 189A and 189B.

Figure 190:
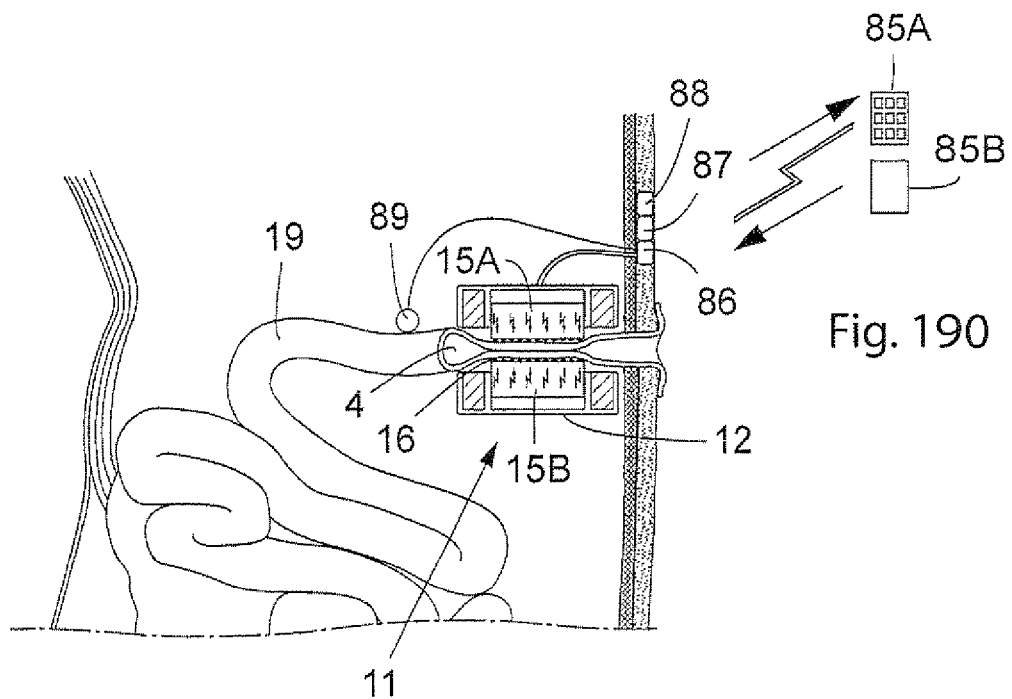

FIG. 190 illustrates the pump of the embodiment of FIGS. 168A and 168B applied on the small intestines of a colostomy patient.

Figure 191:
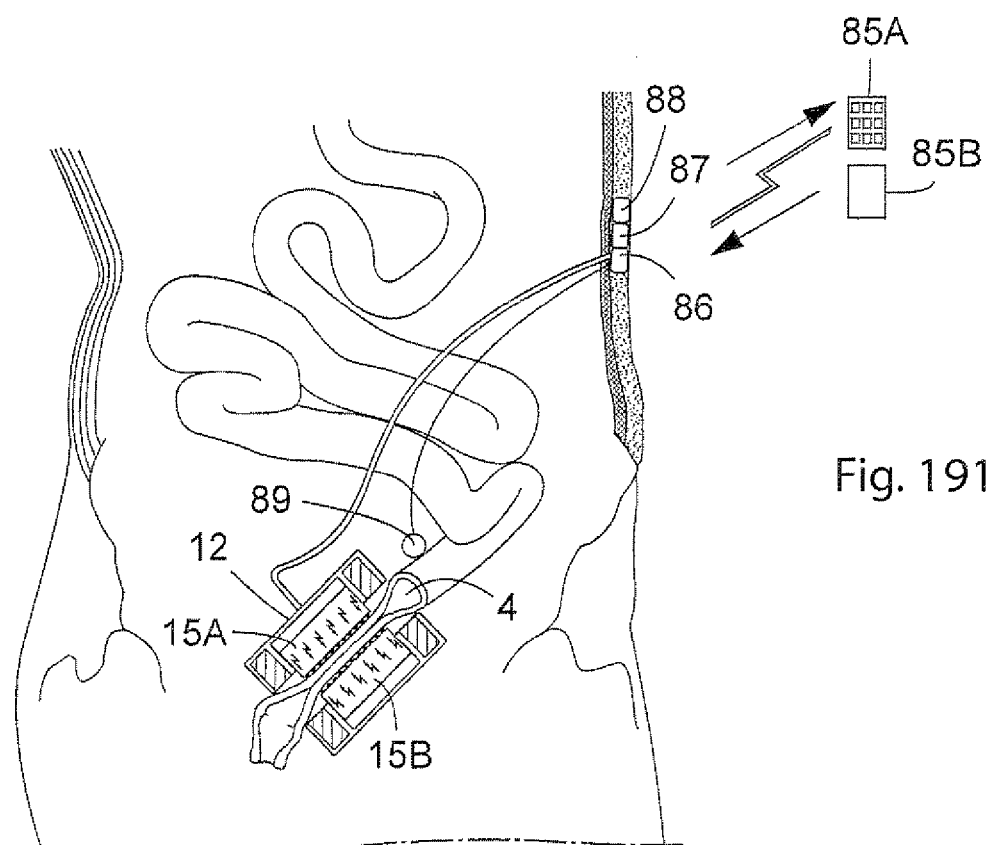

FIG. 191 illustrates the pump of the embodiment of FIGS. 168A and 168B applied on a colostomy patient's small intestines ending at the patient's anus.

Figure 192A:
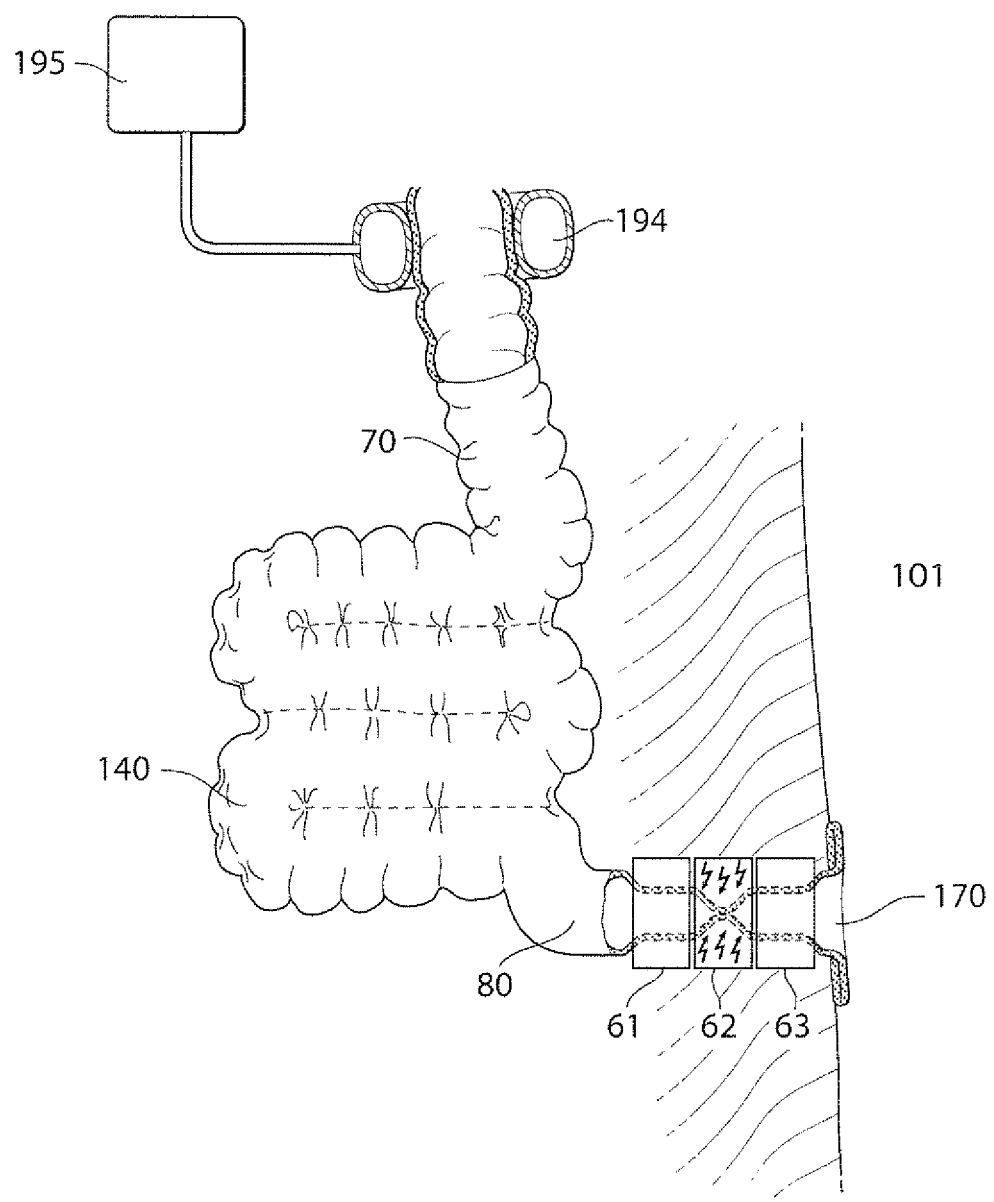

FIG. 192A shows a surgically modified section of a human intestine forming an intestinal reservoir with a deactivated entry valve in front and an activated exit valve behind the intestinal reservoir.

Figure 192B:
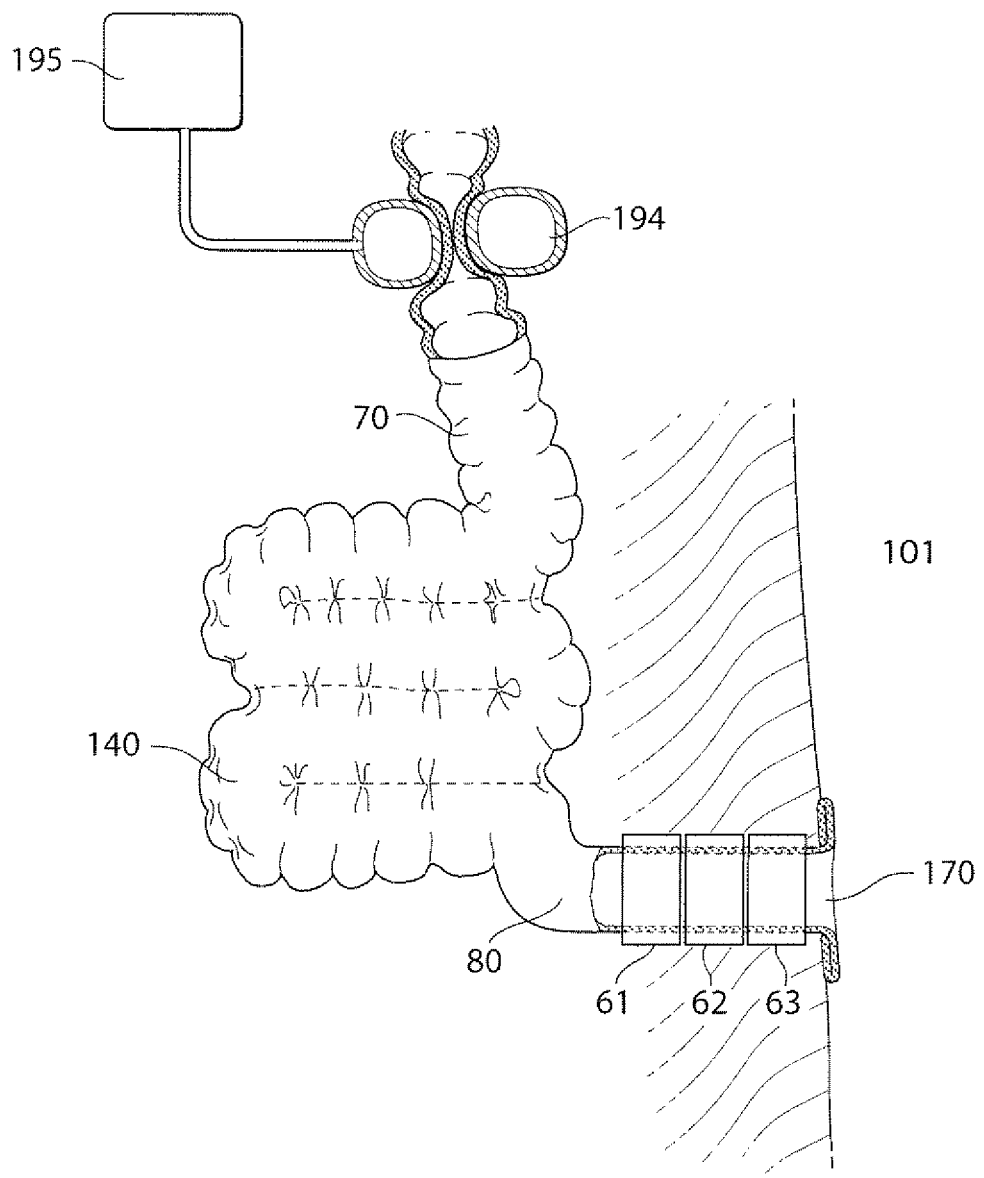

FIG. 192B shows the intestinal reservoir of FIG. 192A with the entry valve activated and the exit valve deactivated.

Figure 193A:
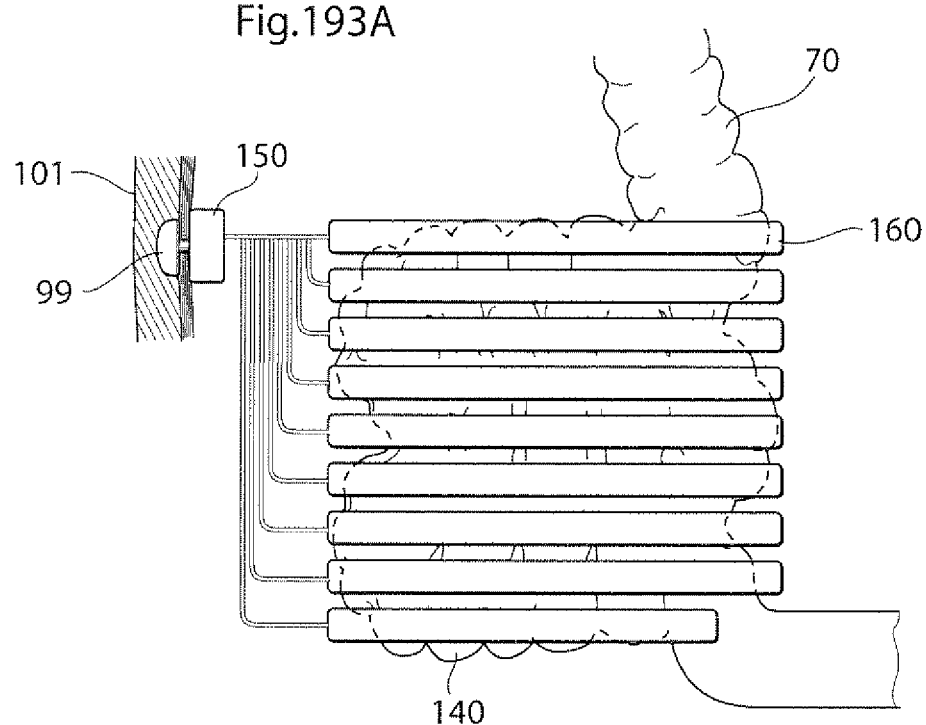

FIG. 193A shows a plan view of an electrical type pump for emptying the intestinal reservoir of FIG. 192B with a plurality of rod-like electrical stimulation devices placed side by side adjacent the intestinal reservoir.

Figure 193B:
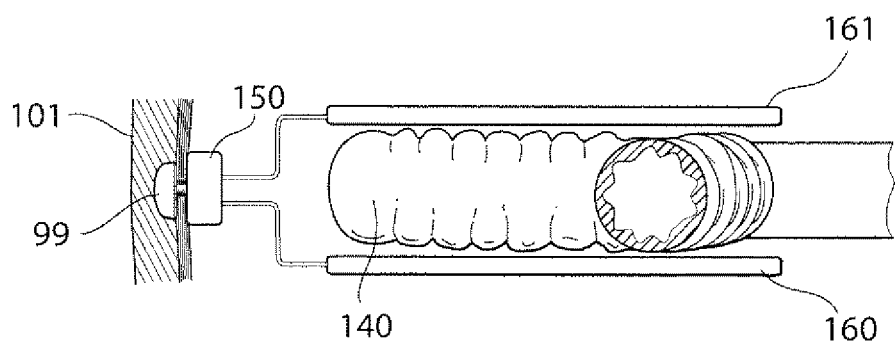

FIG. 193B shows a side view of the electrical type pump of FIG. 193A.

Figure 194A:
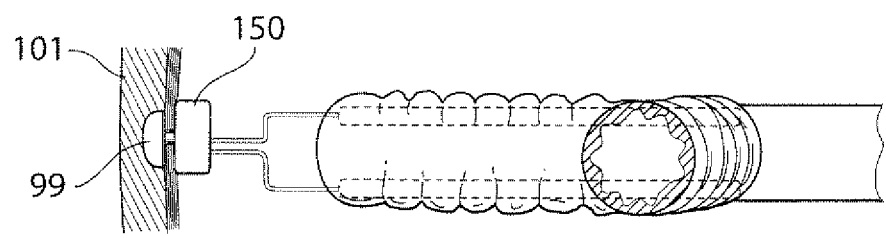

FIG. 194A shows a side view of a variant of the electrical type pump of FIG. 193B with the plurality of rod-like electrical stimulation devices placed side by side in folds formed by the wall of the intestinal reservoir.

Figure 194B:
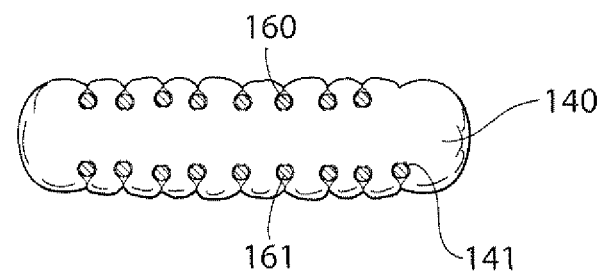

FIG. 194B shows the variant of the electrical type pump of FIG. 194A in a different, cross-sectional side view.

Figure 195A:
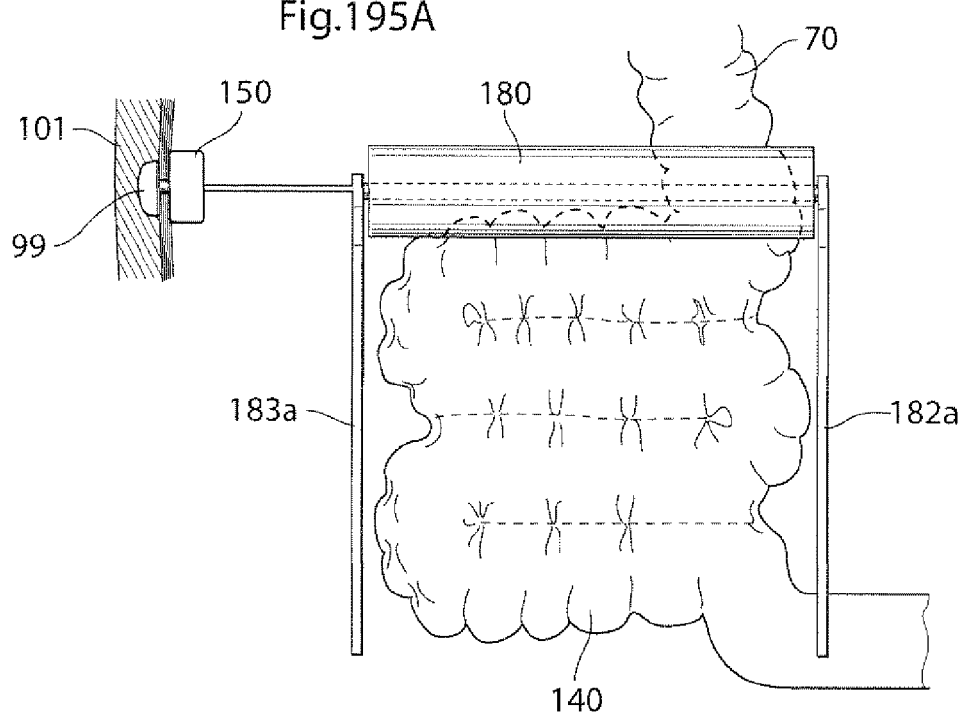

FIG. 195A shows a plan view of a mechanical type pump for emptying the intestinal reservoir of FIG. 192B.

Figure 195B:
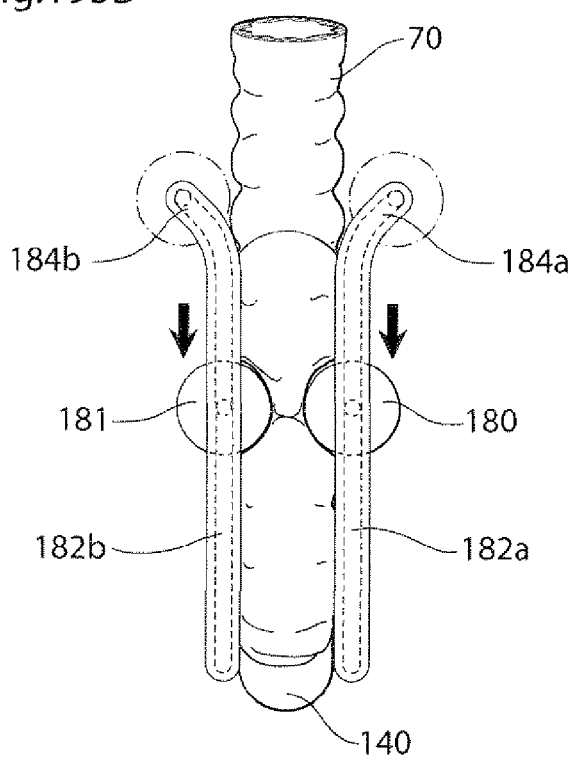

FIG. 195B shows a side view of the mechanical type pump of FIG. 195A.

Figure 196A:
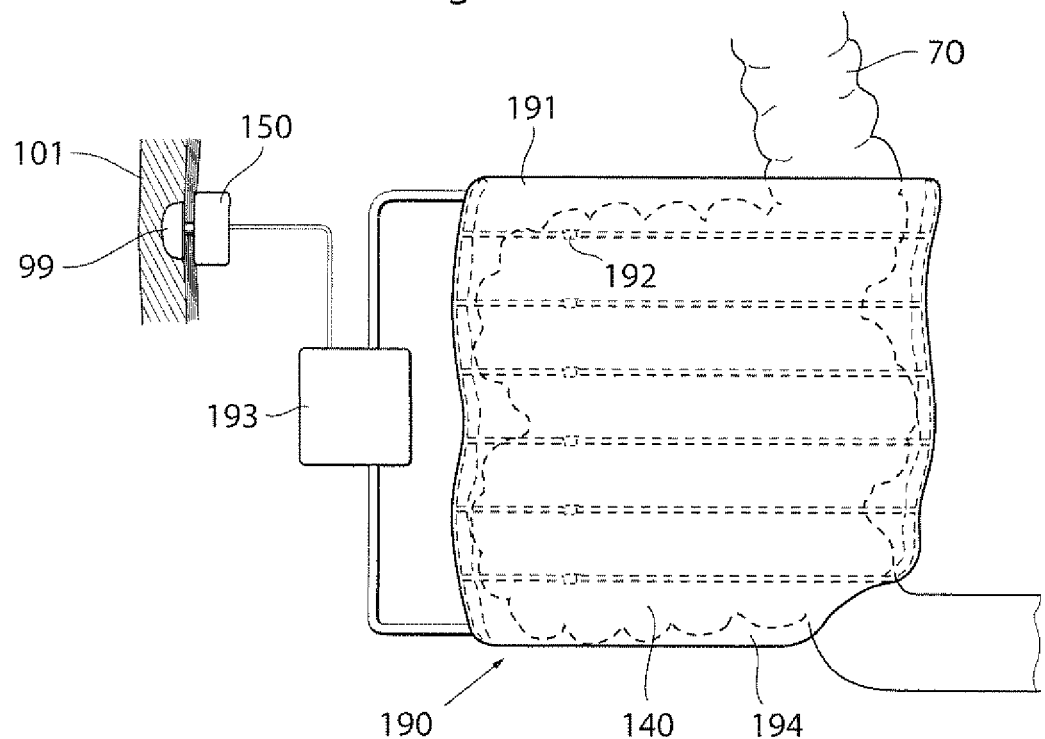

FIG. 196A shows a plan view of a hydraulic type pump for emptying the intestinal reservoir of FIG. 192B.

Figure 196B:
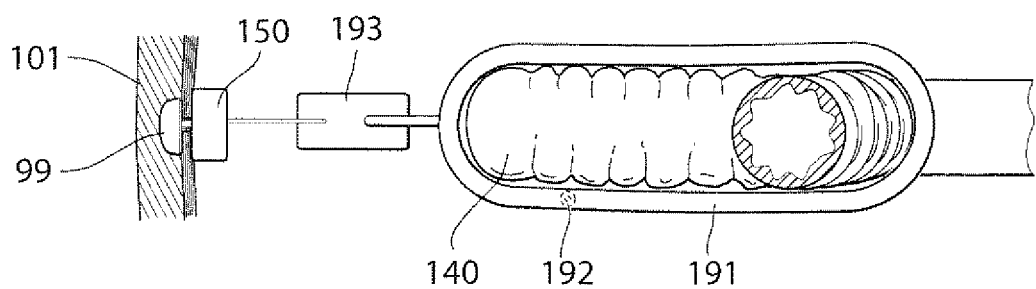

FIG. 196B shows a side view of the hydraulic type pump of FIG. 196A.

Figure 197A:
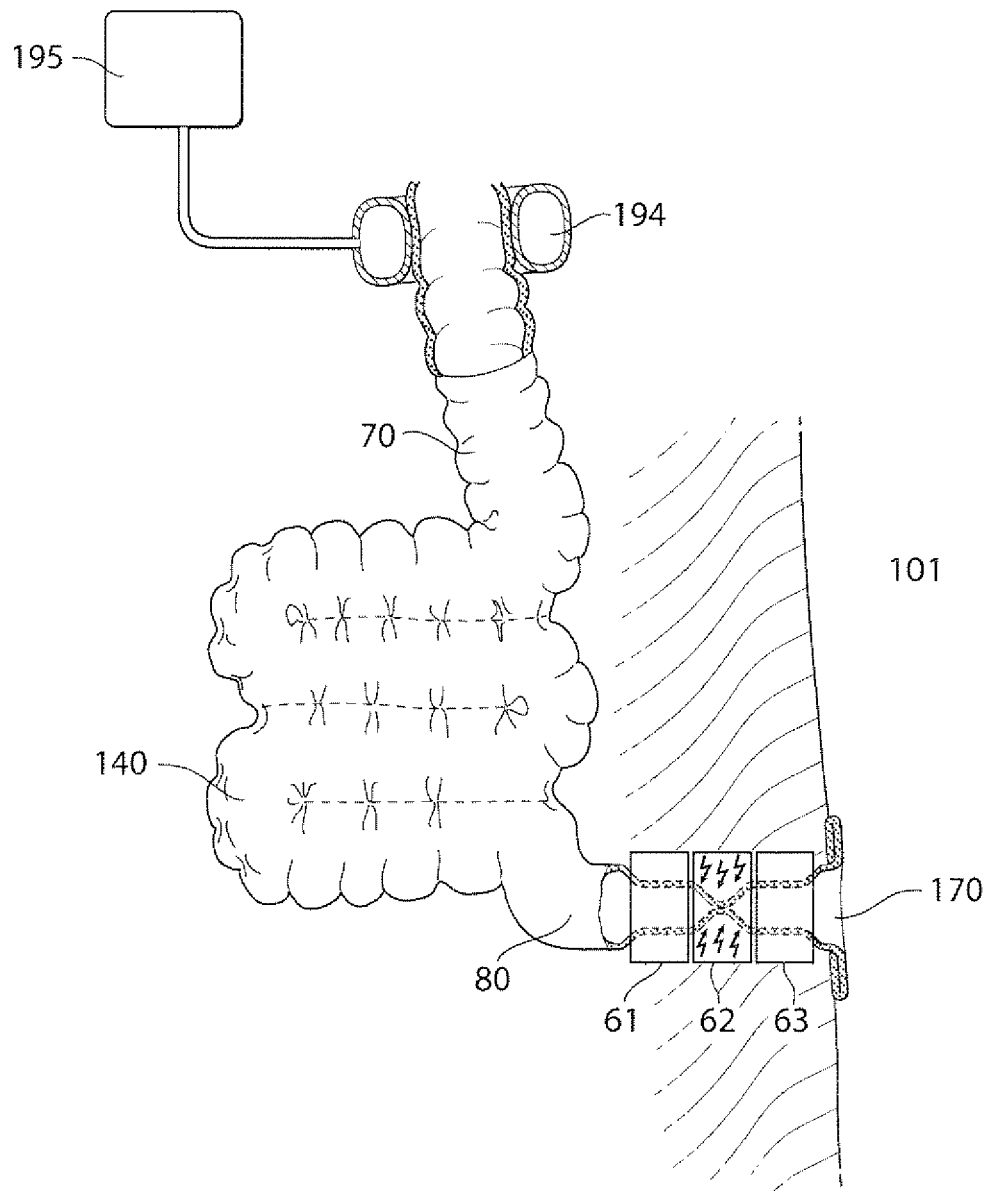

FIG. 197A shows a surgically modified section of a human intestine forming an intestinal reservoir with a deactivated entry valve in front and an activated exit valve behind the intestinal reservoir.

Figure 197B:
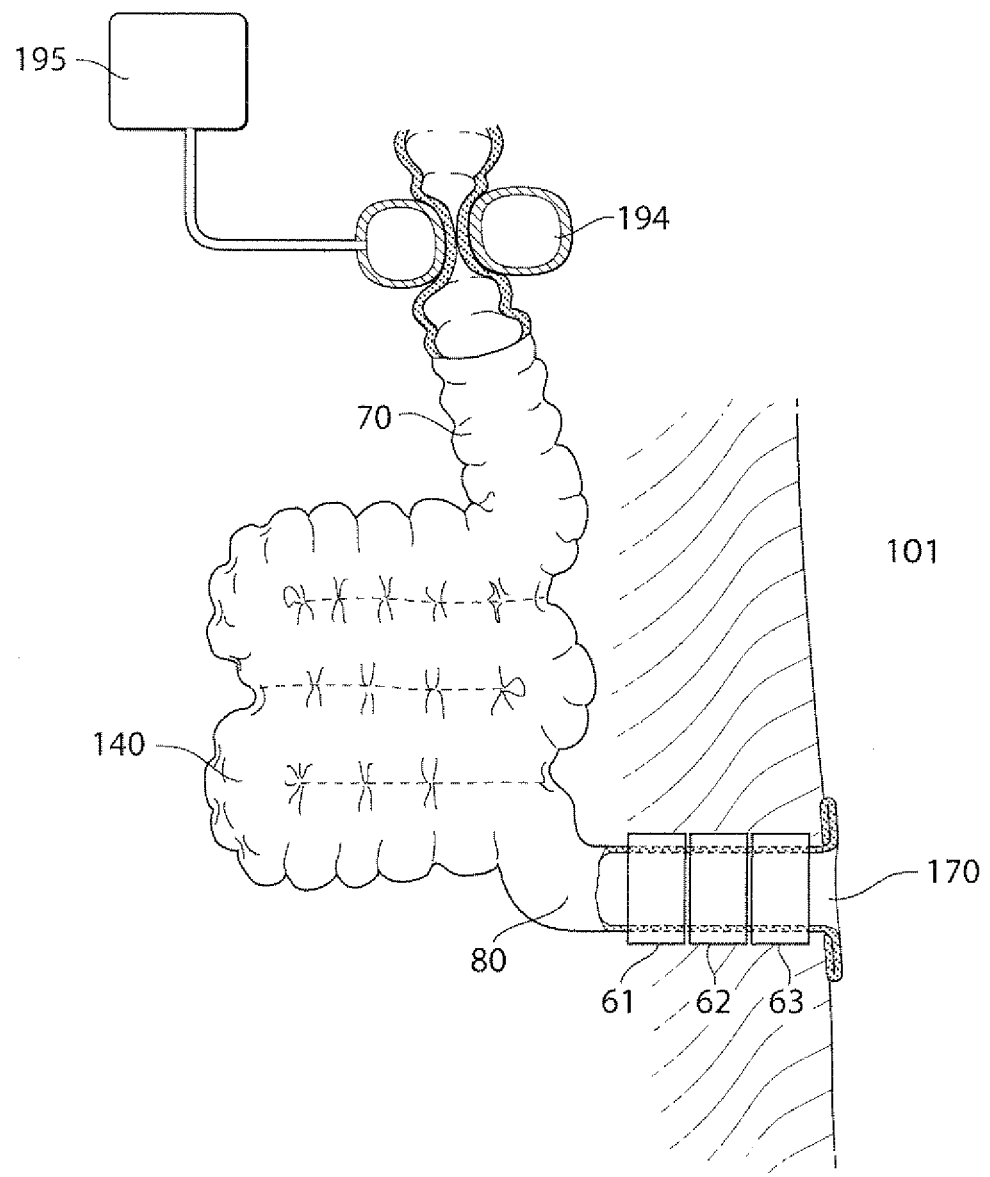

FIG. 197B shows the intestinal reservoir of FIG. 197A with the entry valve activated and the exit valve deactivated.

Figure 198A:
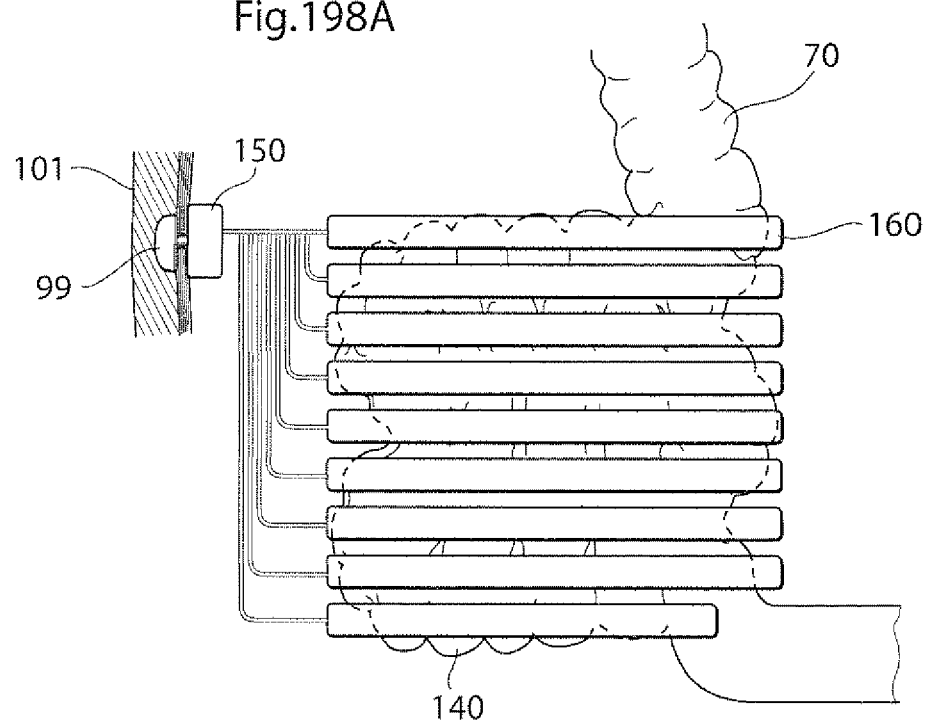

FIG. 198A shows a plan view of an electrical type pump for emptying the intestinal reservoir of FIG. 197B with a plurality of rod-like electrical stimulation devices placed side by side adjacent the intestinal reservoir.

Figure 198B:
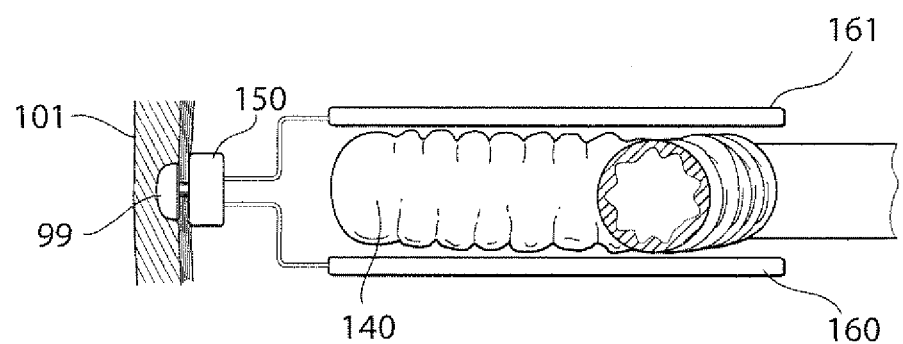

FIG. 198B shows a side view of the electrical type pump of FIG. 198A.

Figure 199A:
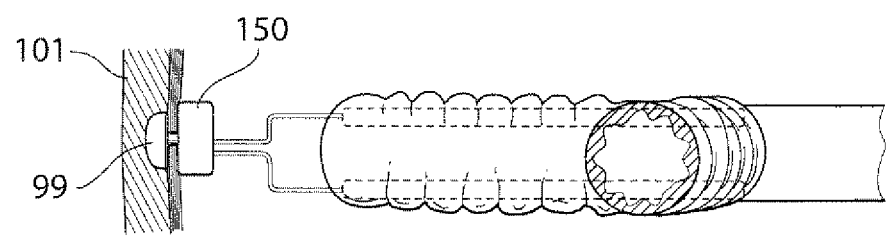

FIG. 199A shows a side view of a variant of the electrical type pump of FIG. 198B with the plurality of rod-like electrical stimulation devices placed side by side in folds formed by the wall of the intestinal reservoir.

Figure 199B:
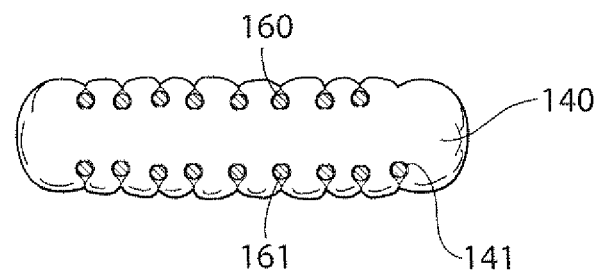

FIG. 199B shows the variant of the electrical type pump of FIG. 199A in a different, cross-sectional side view.

Figure 200A:
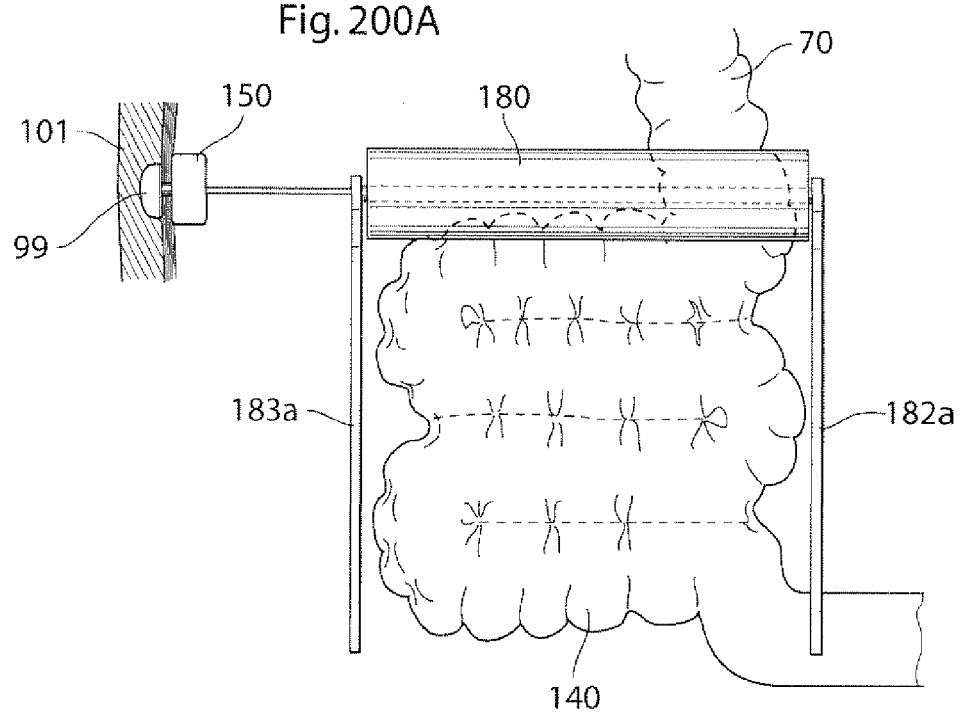

FIG. 200A shows a plan view of a mechanical type pump for emptying the intestinal reservoir of FIG. 197B.

Figure 200B:
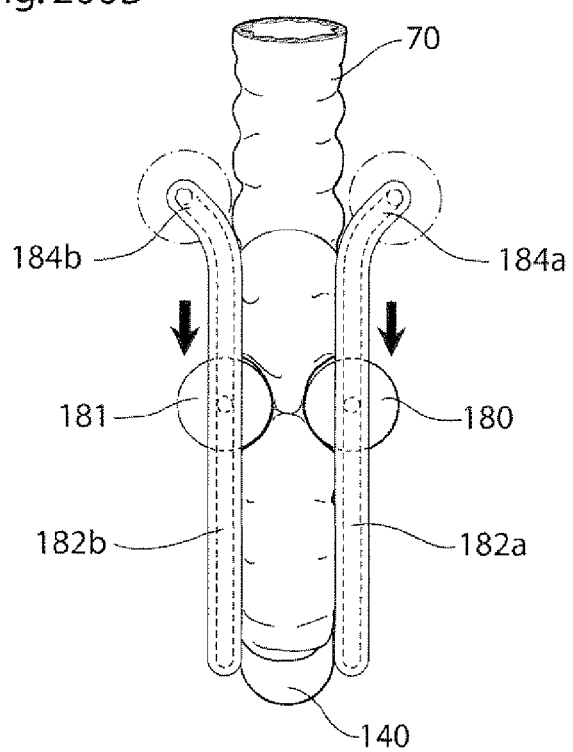

FIG. 200B shows a side view of the mechanical type pump of FIG. 200A.

Figure 201A:
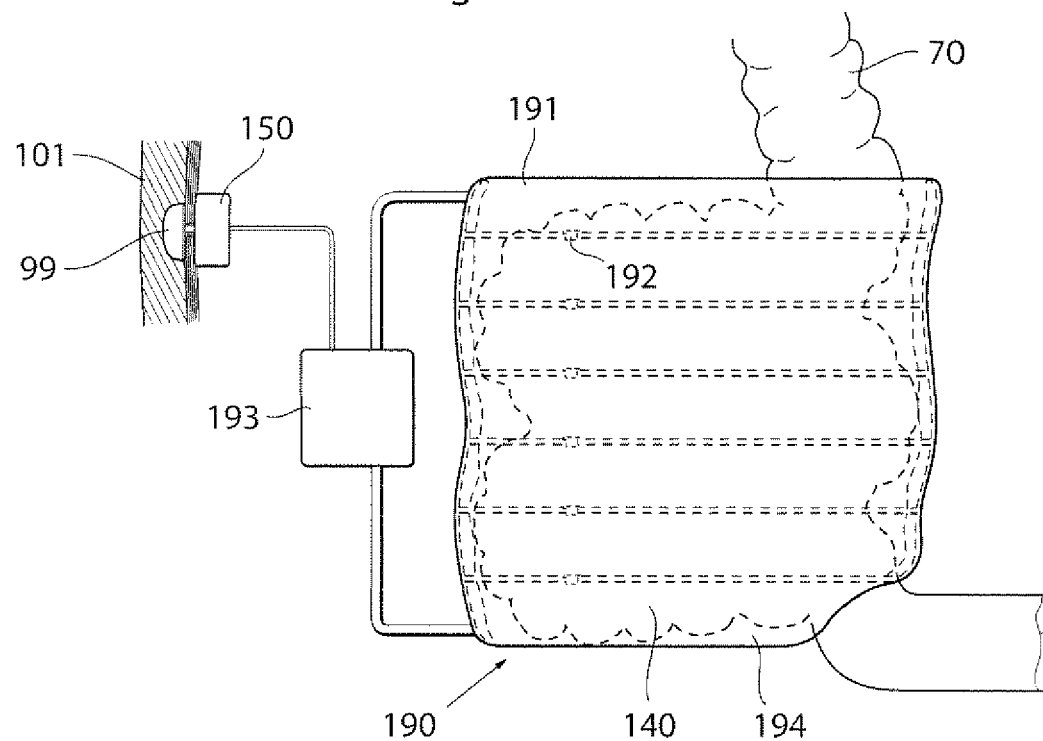

FIG. 201A shows a plan view of a hydraulic type pump for emptying the intestinal reservoir of FIG. 197B.

Figure 201B:
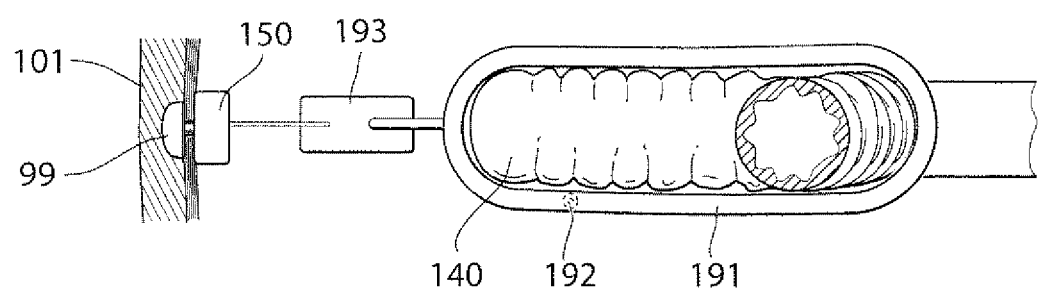

FIG. 201B shows a side view of the hydraulic type pump of FIG. 201A.

Figure 202:
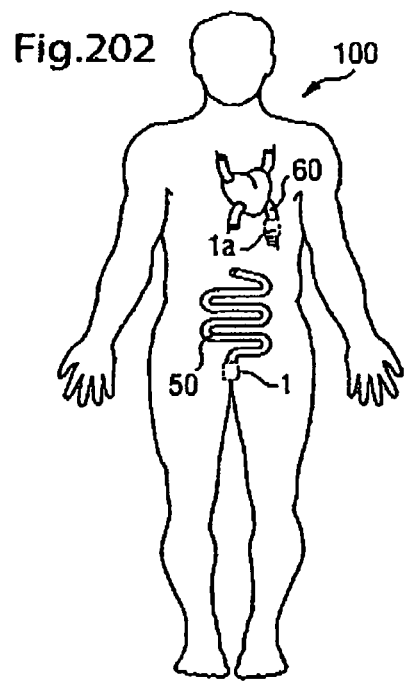

FIG. 202 shows an exemplary view of a patient with one tissue connector connected to the patient's aorta and another tissue connector connected to the end of the patient's large bowel.

Figure 203A:
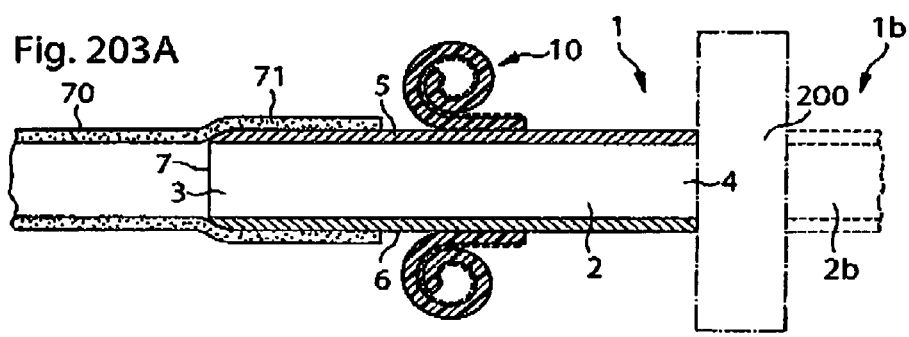
Figure 203B:
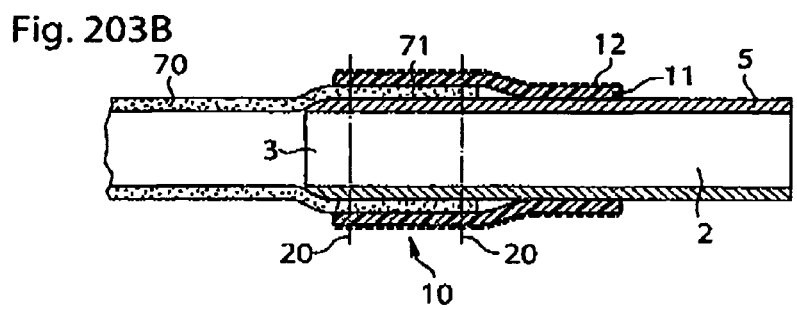

FIGS. 203a and 203b show a cross-section of a first embodiment of the tissue connector in the state of mounting and in the connected state.

Figure 204A:
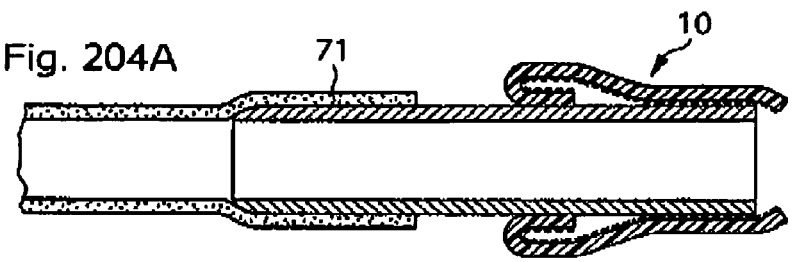
Figure 204B:
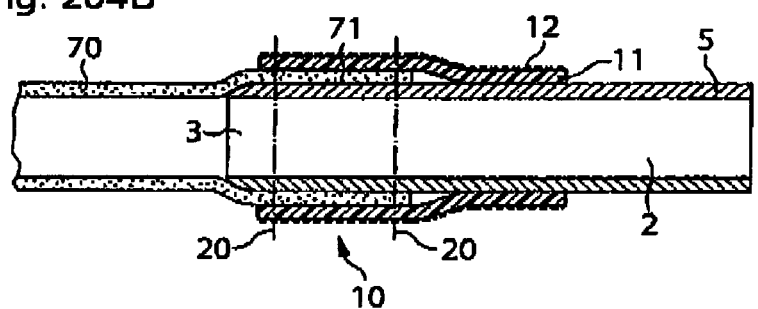

FIGS. 204a and 204b show a cross-section of an alternative of the first embodiment of the tissue connector in the state of mounting and in the connected state.

Figure 205:
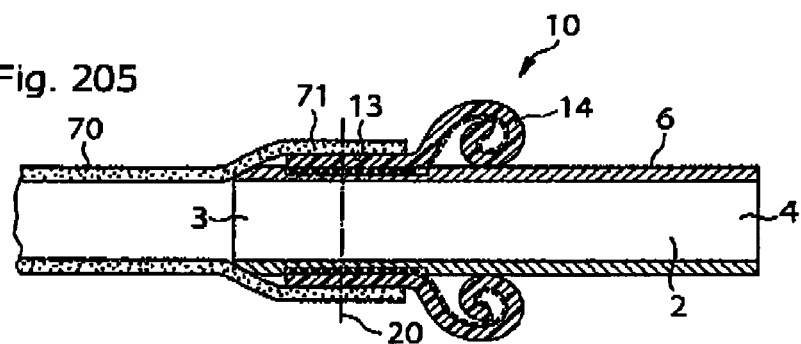
Figure 206:
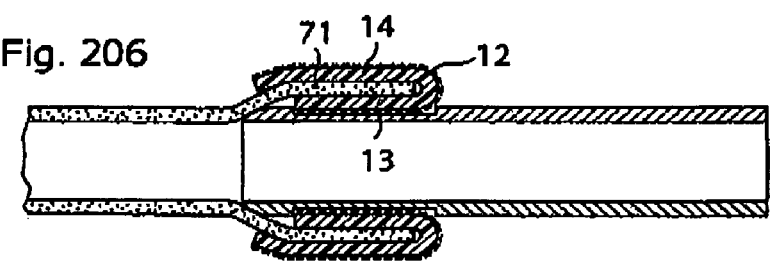

FIGS. 205 and 206 show a second embodiment of the tissue connector in the state mounting and in the connected state.

Figure 207:
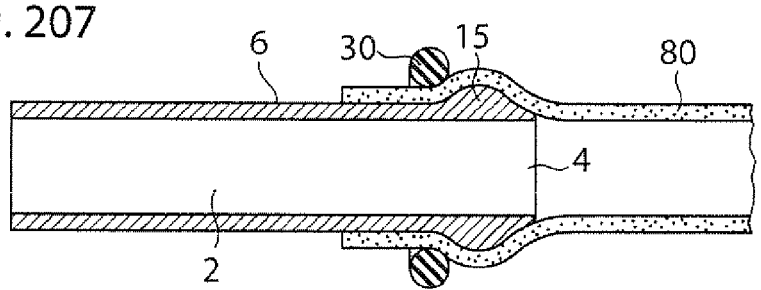

FIG. 207 shows an alternative for mounting living tissue on a free end of the tissue connector.

Figure 208A:
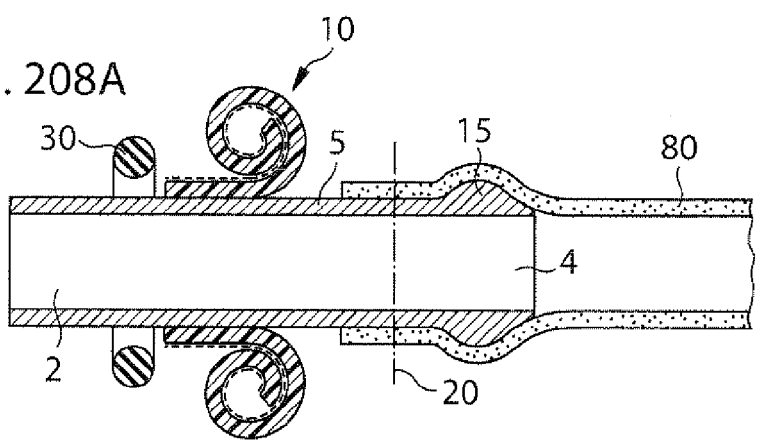
Figure 208B:
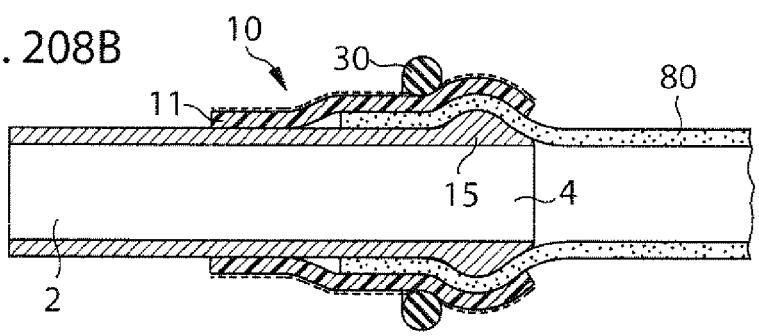

FIGS. 208a and 208b show a combination of an embodiment similar to the one shown in FIGS. 203a and 203b with additional mounting means as shown in FIG. 207.

Figure 209:
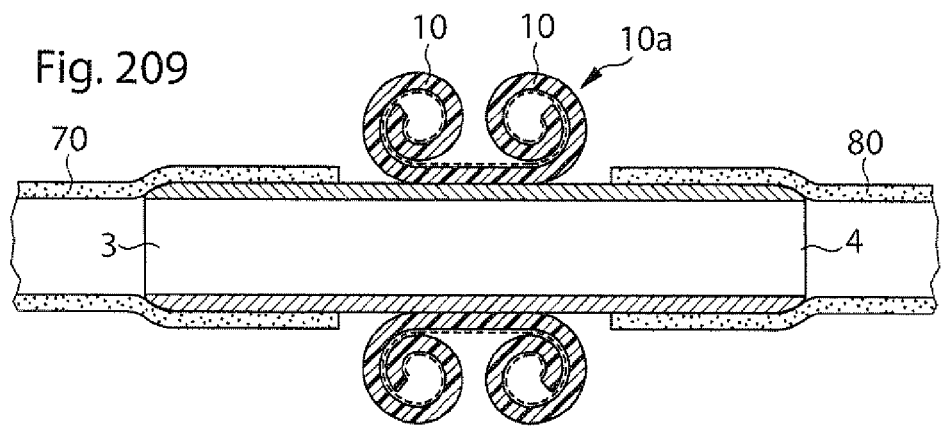

FIG. 209 shows a specific embodiment of a tissue connector with two ends thereof connected to living tissue.

Figure 210:
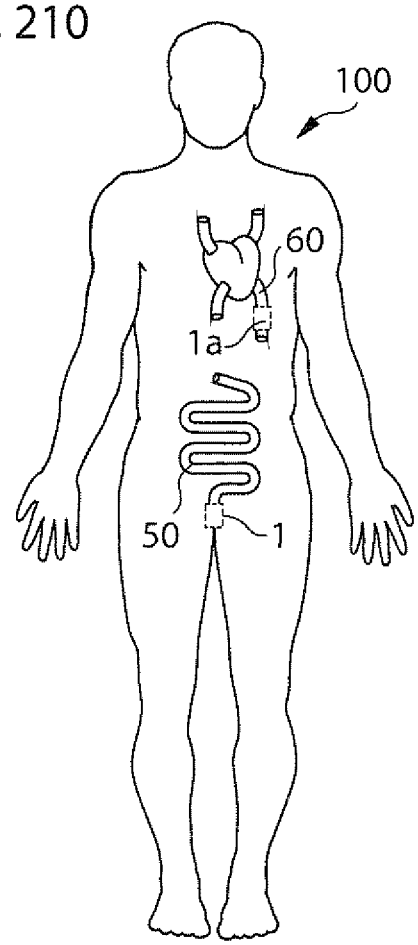

FIG. 210 shows an exemplary view of a patient with one tissue connector connected to the patient's aorta and another tissue connector connected to the end of the patient's large bowel.

Figure 211:
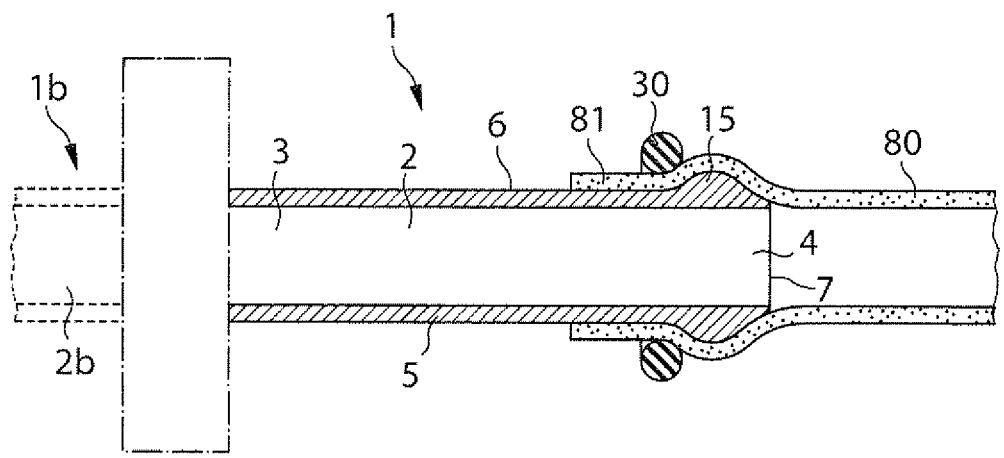

FIG. 211 shows a cross section of a first embodiment of the tissue connector in a state connected to living tissue.

Figure 212:
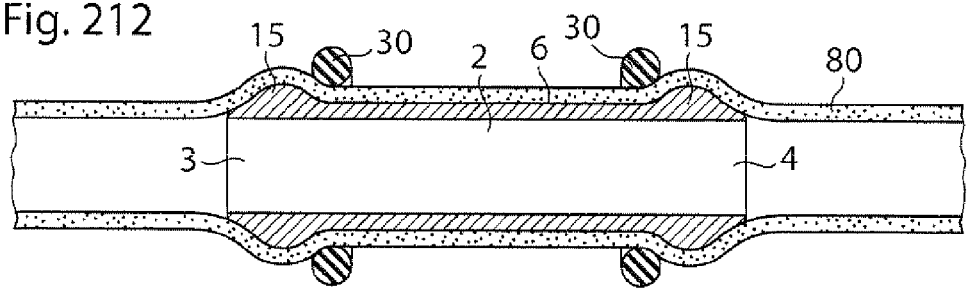

FIG. 212 shows a second embodiment of the tissue connector with two connecting ends.

Figure 213:
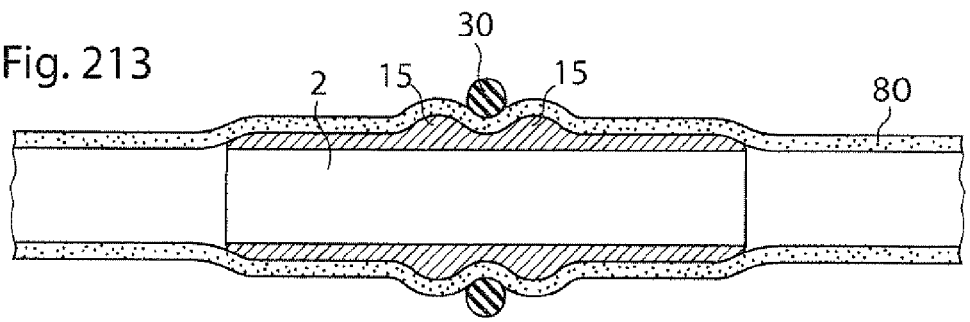

FIG. 213 shows a third embodiment of the tissue connector as an alternative to the second embodiment.

Figure 214A:
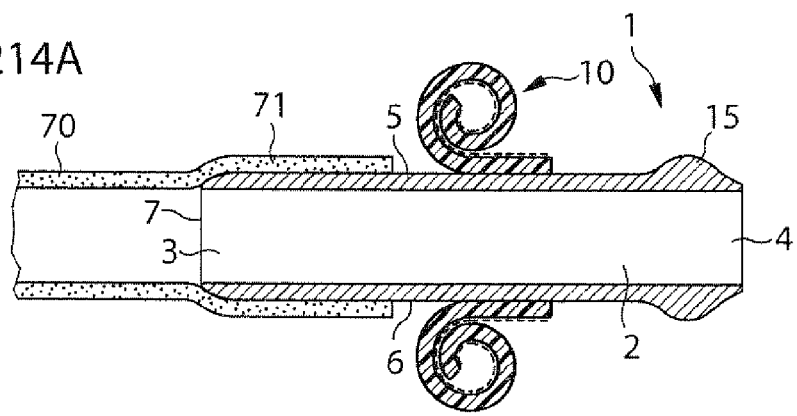
Figure 214B:
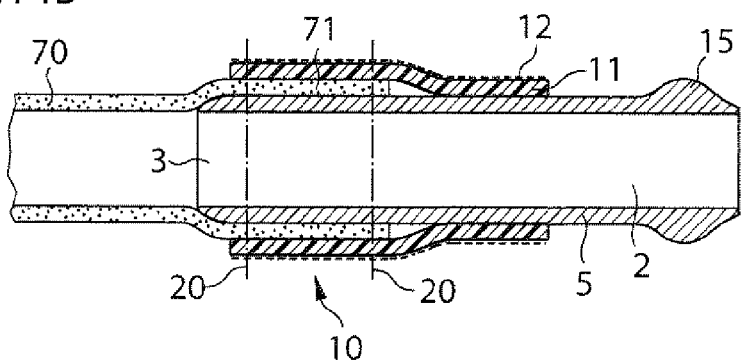

FIGS. 214a and 214b show an alternative for mounting living tissue on a free end of the tissue connector.

Figure 215A:
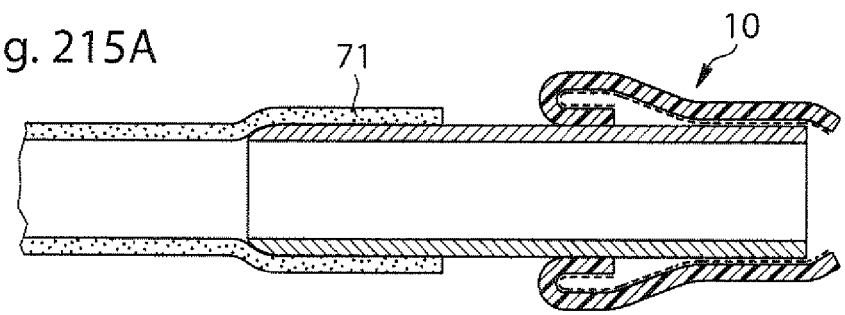
Figure 215B:
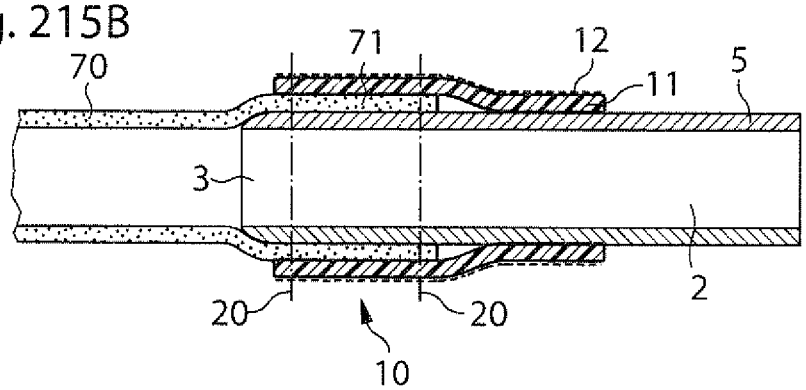

FIGS. 215a and 215b show another alternative for mounting living tissue on a free end of the tissue connector.

Figure 216A:
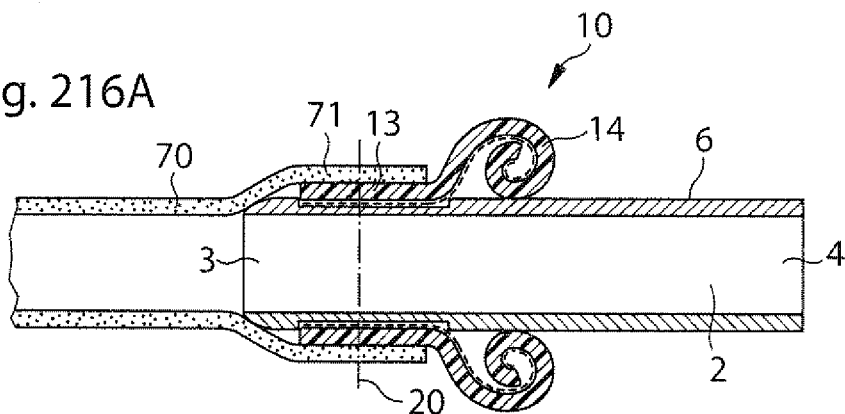
Figure 216B:
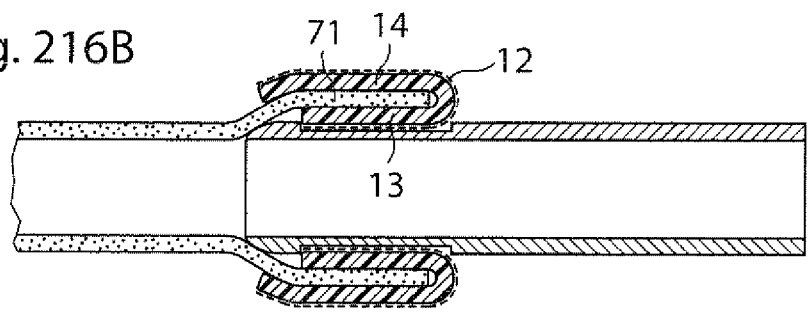

FIGS. 216a and 216b show a further alternative for mounting living tissue on a free end of the tissue connector.

Figure 217A:
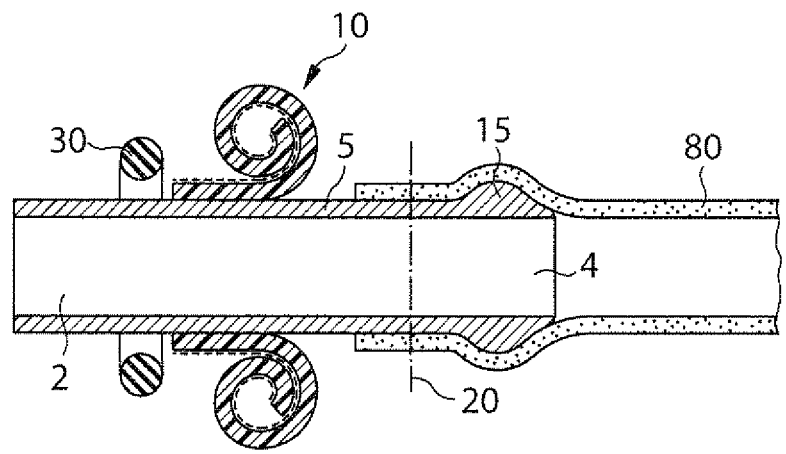
Figure 217B:
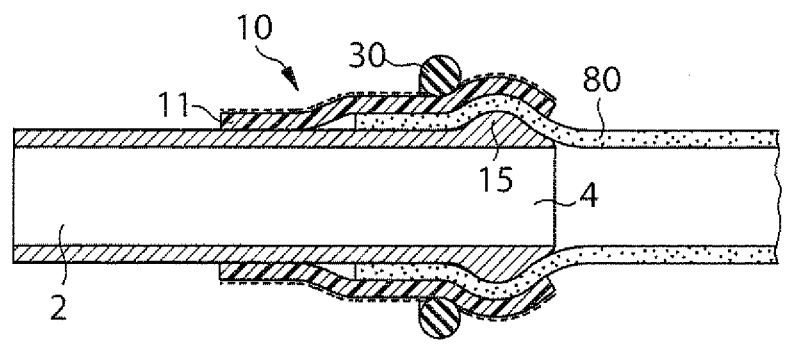

FIGS. 217a and 217b show a combination of an embodiment similar to the one shown in FIG. 211 with additional mounting means as shown in FIGS. 214a and 214b.

Figure 218:
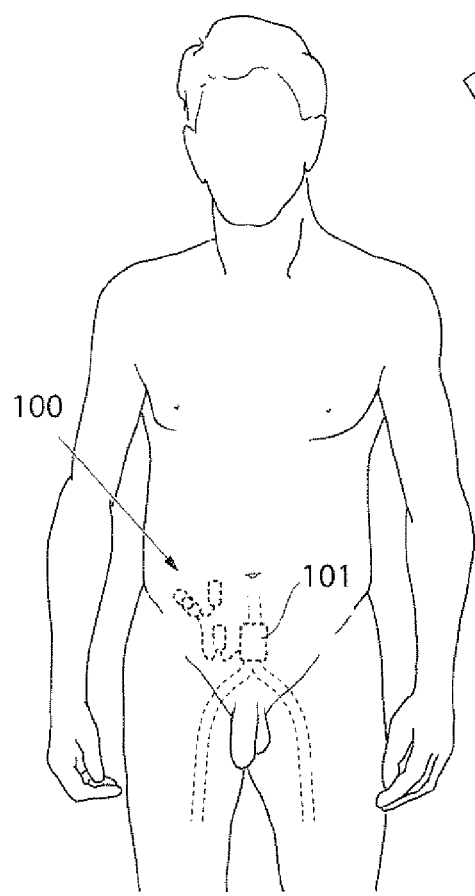

FIG. 218 is general view of a human body having a device for treating aneurysm implanted.

Figure 219:
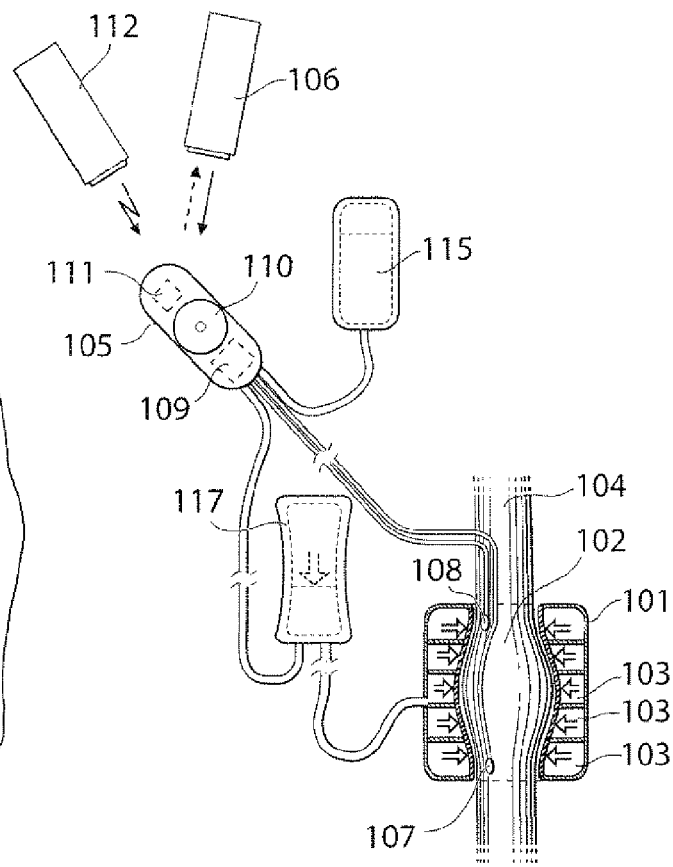

FIG. 219 is a view illustrating a device for treating aneurysm with associated equipment.

Figure 220:
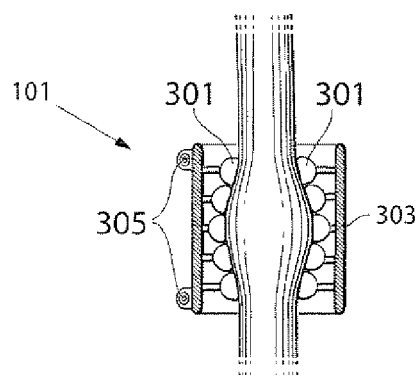

FIG. 220 is a view illustrating a mechanical device for treating aneurysm.

Figure 221:
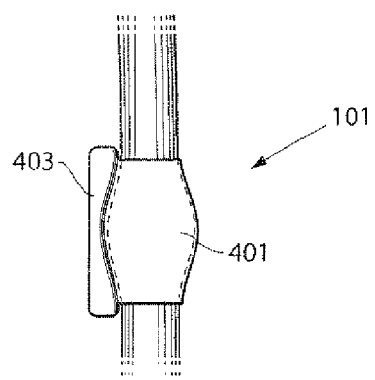

FIG. 221 is a view illustrating a mechanical device for treating aneurysm.

Figure 222:
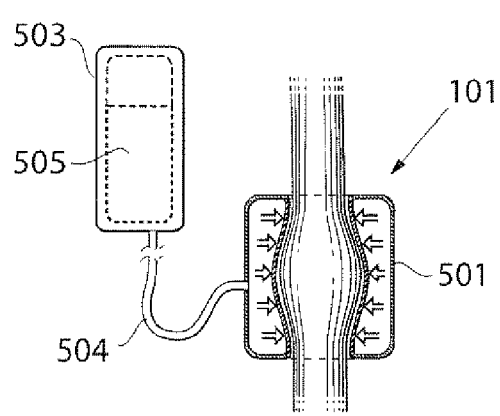

FIG. 222 is a view illustrating a hydraulic device for treating aneurysm.

Figure 223:
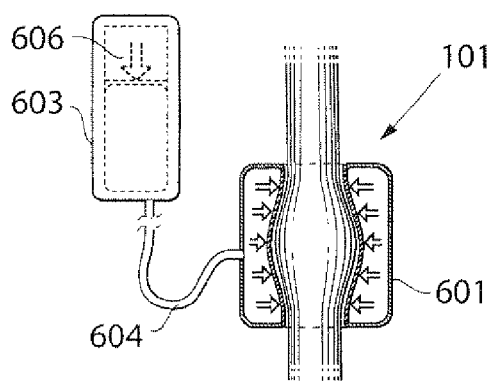

FIG. 223 is a view illustrating a hydraulic device for treating aneurysm.

Figure 224:
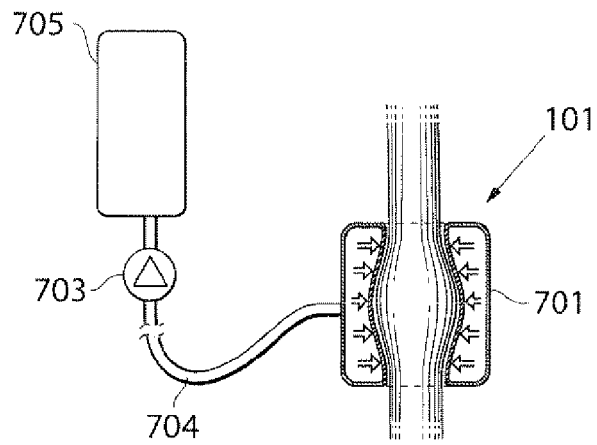

FIG. 224 is a view illustrating a hydraulic device for treating aneurysm.

Figure 225:
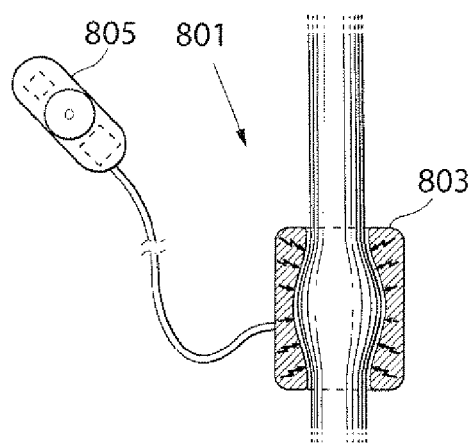

FIG. 225 is a view illustrating a stimulation device for treating a vascular aneurysm of a human or mammal patient.

Figure 226:
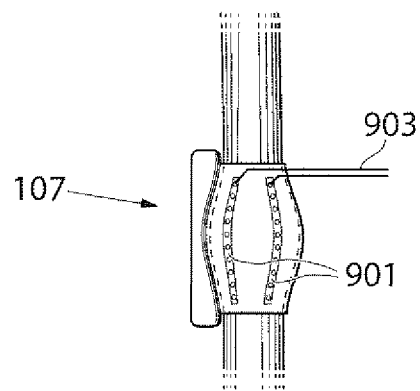

FIG. 226 is a view illustrating a sensor used when treating or monitoring a vascular aneurysm of a human or mammal patient.

Figure 227:
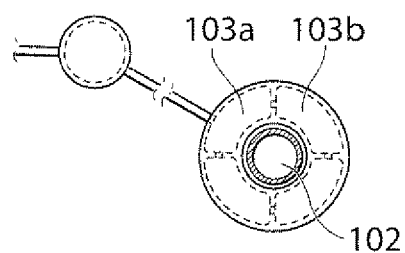

FIG. 227 is a view from above of a device for treating aneurysm implanted around a blood vessel.

Figure 228:
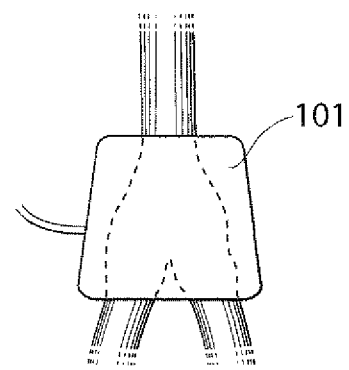

FIG. 228 is a view of a device for treating aneurysm having a Y-shape.

Figure 229:
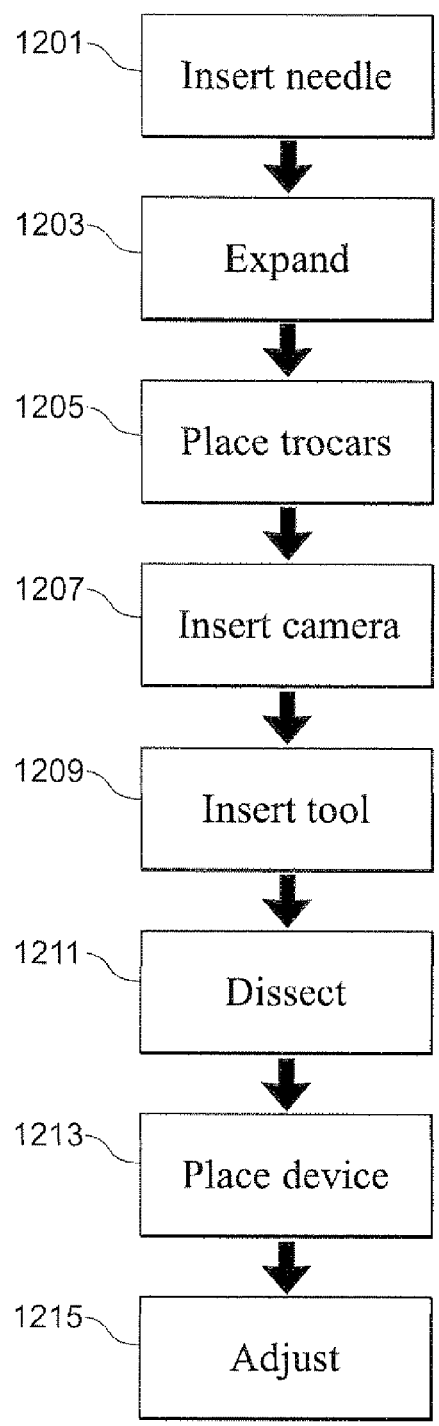

FIG. 229 is a flowchart illustrating steps performed when implanting a device for treating or monitoring an aneurysm in accordance with one embodiment.

Figure 230:
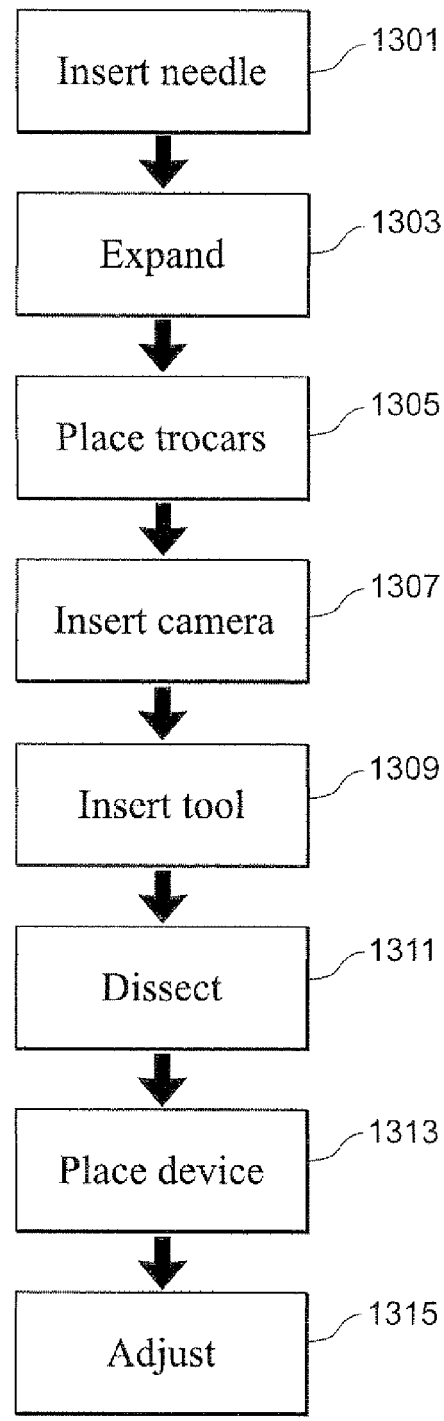

FIG. 230 is a flowchart illustrating steps performed when implanting a device for treating or monitoring an aneurysm in accordance with one embodiment.

FIG. 231 is a flowchart illustrating steps performed when implanting a device for treating or monitoring an aneurysm in accordance with one embodiment.

FIG. 232 is a flowchart illustrating steps performed when implanting a device for treating or monitoring an aneurysm in accordance with one embodiment.

Figure 233:
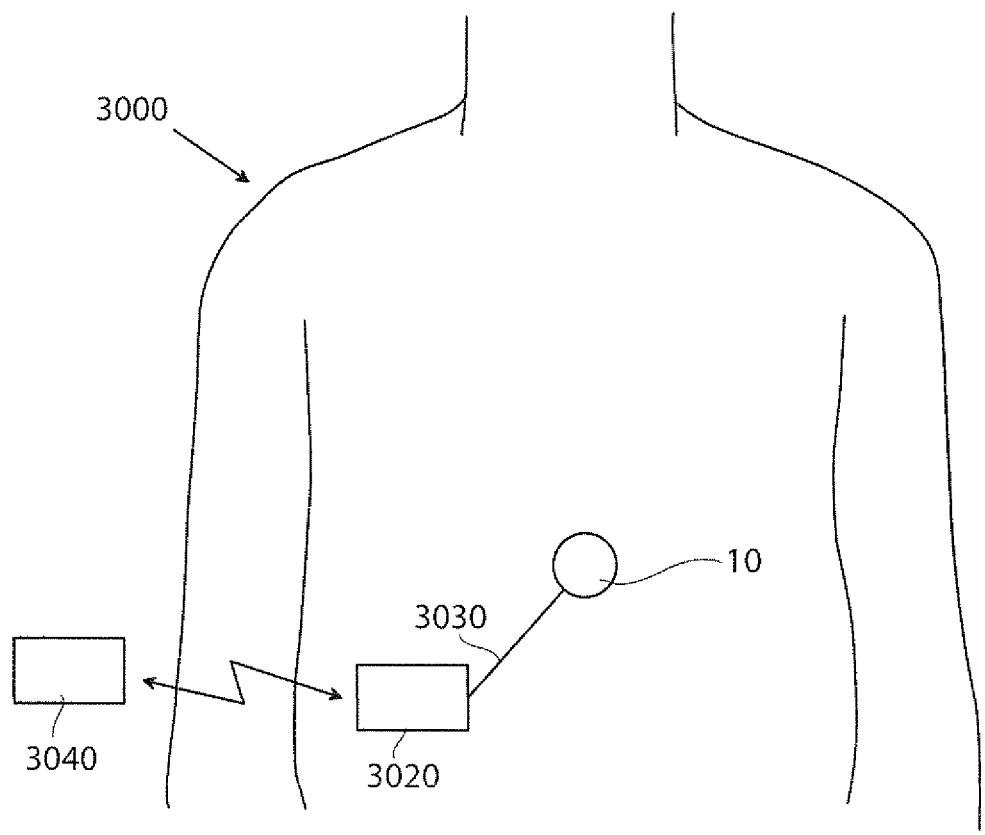

FIG. 233 illustrates a system for treating a disease, wherein the system includes a device of the invention implanted in a patient.

FIG. 234-248 schematically show various embodiments of the system for wirelessly powering the device shown in FIG. 233.

Figure 249:
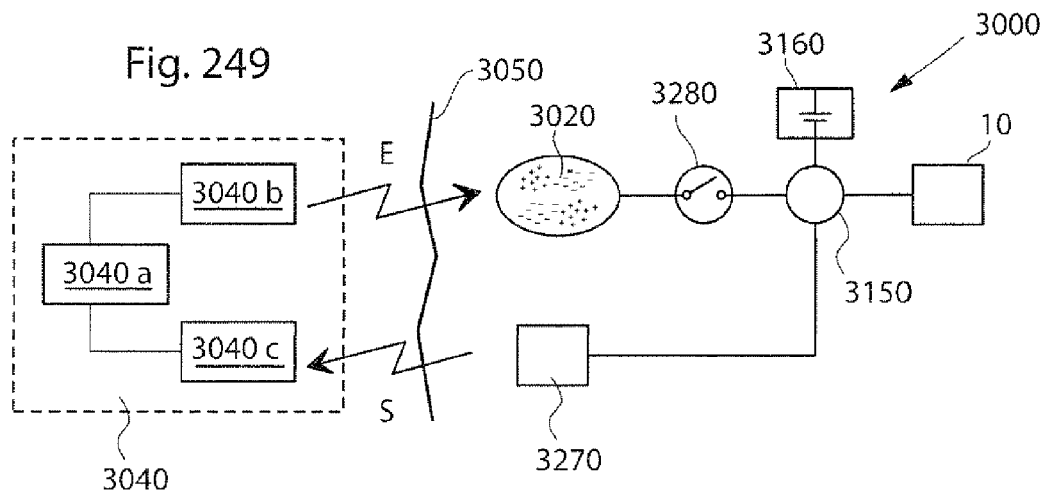

FIG. 249 is a schematic block diagram illustrating an arrangement for supplying an accurate amount of energy used for the operation of the device shown in FIG. 233.

Figure 250:
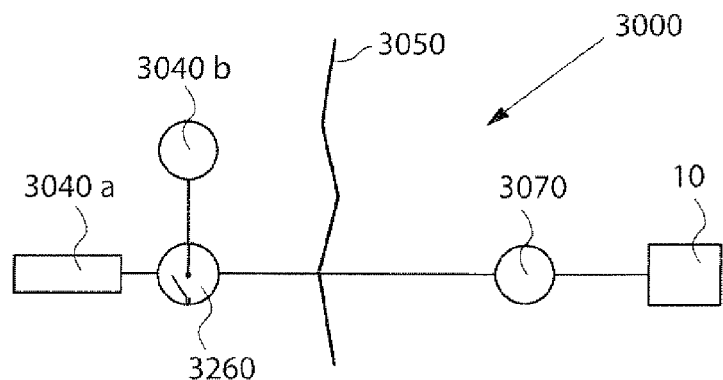

FIG. 250 schematically shows an embodiment of the system, in which the device is operated with wire bound energy.

Figure 251:
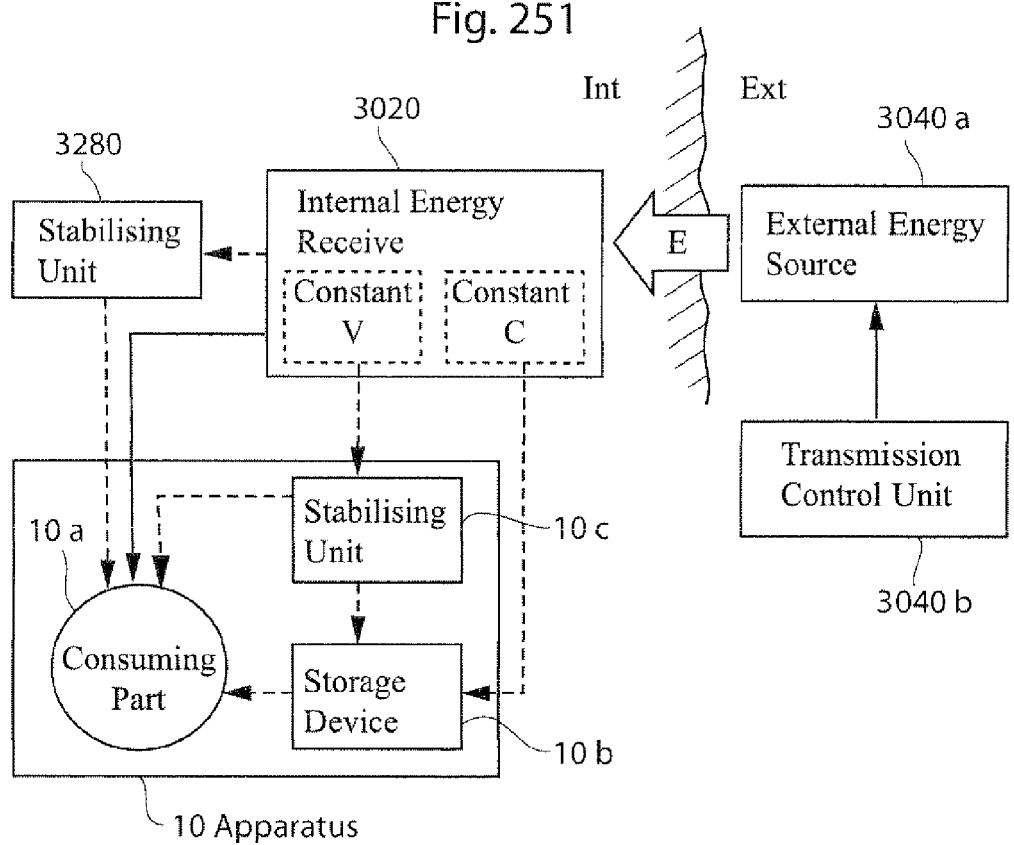

FIG. 251 is a more detailed block diagram of an arrangement for controlling the transmission of wireless energy used for the operation of the device shown in FIG. 233.

Figure 252:
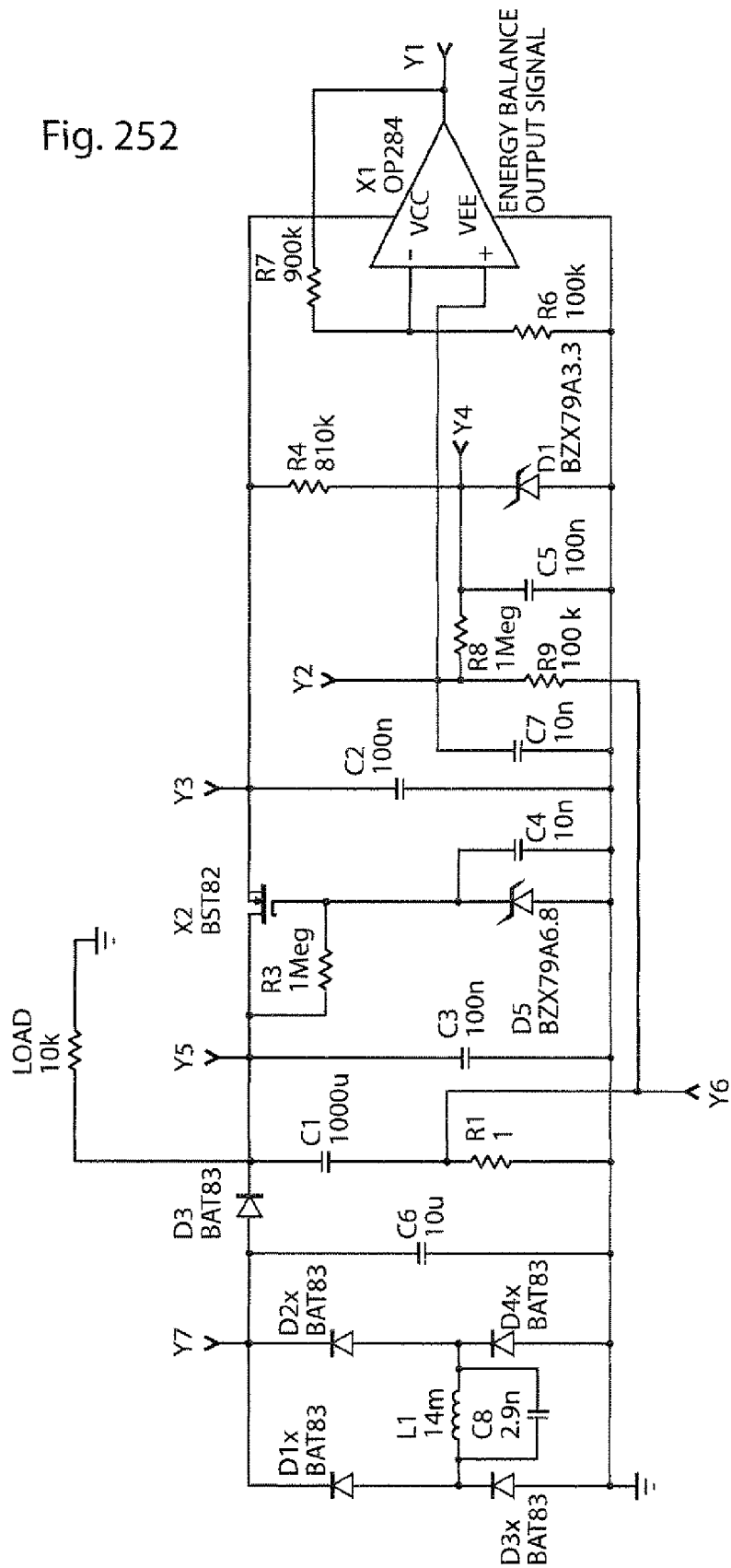

FIG. 252 is a circuit for the arrangement shown in FIG. 251, according to a possible implementation example.

FIGS. 253-259 show various ways of arranging hydraulic or pneumatic powering of a device implanted in a patient.

DETAILED DESCRIPTION OF THE INVENTION

Referring to the drawing figures, like reference numerals designate identical or corresponding elements throughout the several figures. Where applicable, the term "organ" used below includes (but not limited to) the esophagus, stomach, intestines, urine bladder, urethra, ureter, renal pelvis, blood vessels, aorta, corpus cavernosum, exit veins of erectile tissue, uterine tube, vas deferens and bile duct.

Figure 1A:
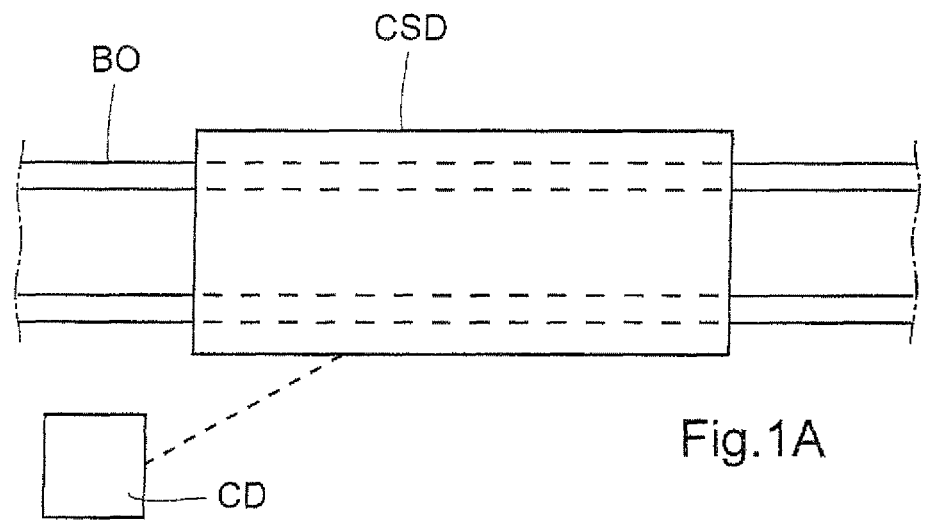
FIGS. 1A, 1B, 1C, 1D and 1E schematically illustrate different states of operation of a general embodiment of an apparatus used for practicing the method according to the present invention.
Figure 1B:
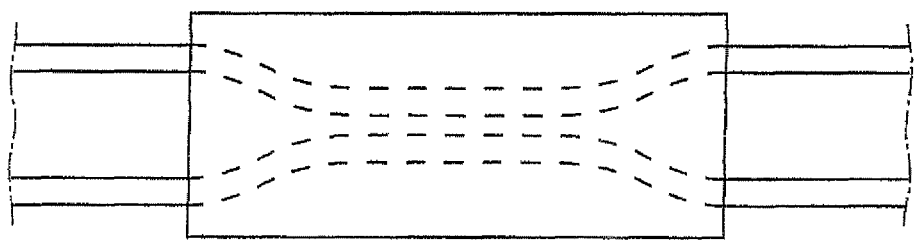
Figure 1C:
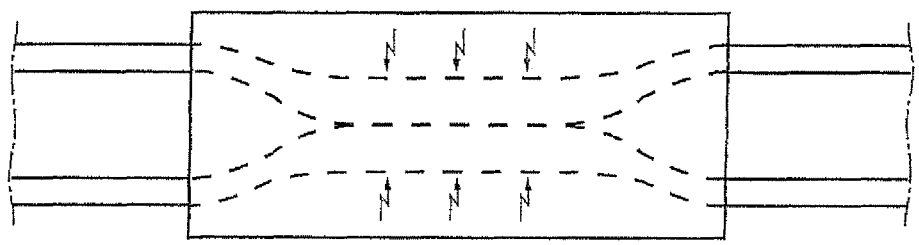

FIGS. 1A, 1B and 1C schematically illustrate different states of operation of a generally designed apparatus used for practicing the method of the present invention, when the apparatus is applied on a wall portion of a bodily organ designated BO. The apparatus includes a constriction device and a stimulation device, which are designated CSD, and a control device designated CD for controlling the constriction and stimulation devices CSD. FIG. 1A shows the apparatus in an inactivation state, in which the constriction device does not constrict the organ BO and the stimulation device does not stimulate the organ BO. FIG. 1B shows the apparatus in a constriction state, in which the control device CD controls the constriction device to gently constrict the wall portion of the organ BO to a constricted state, in which the blood circulation in the constricted wall portion is substantially unrestricted and the flow in the lumen of the wall portion is restricted. FIG. 1C shows the apparatus in a stimulation state, in which the control device CD controls the stimulation device to stimulate different areas of the constricted wall portion, so that the wall portion of the organ BO contracts (thickens) and closes the lumen.

Figure 1D:
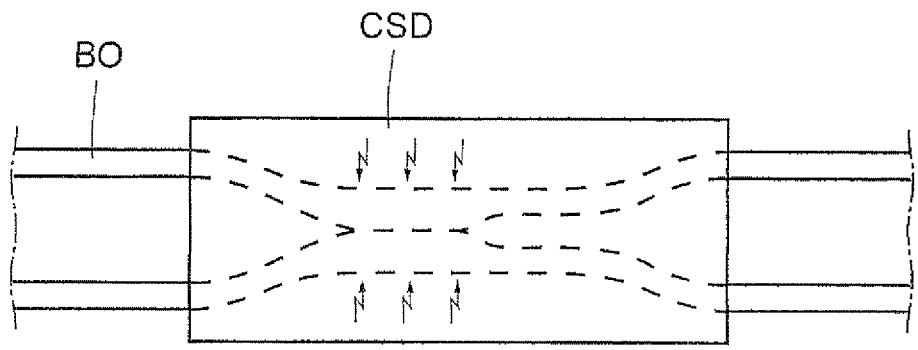
Figure 1E:
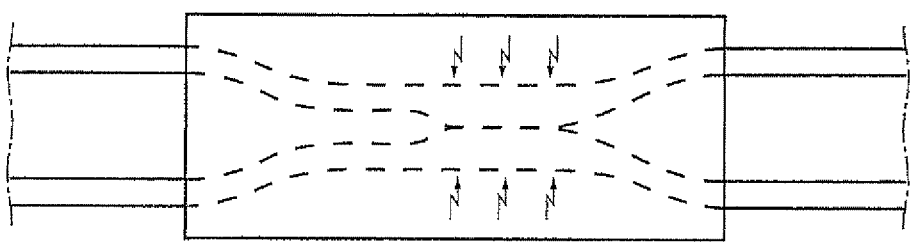

FIGS. 1D and 1E show how the stimulation of the constricted wall portion can be cyclically varied between a first stimulation mode, in which the left area of the wall portion (see FIG. 1D) is stimulated while the right area of the wall portion is not stimulated, and a second stimulation mode, in which the right area of the wall portion (see FIG. 1E) is stimulated while the left area of the wall portion is not stimulated, in order to maintain over time satisfactory blood circulation in the constricted wall portion.

It should be noted that the stimulation modes shown in FIGS. 1D and 1E only constitute a principle example of how the constricted wall portion of the organ BO may be stimulated. Thus, more than two different areas of the constricted wall portion may be simultaneously stimulated in cycles or successively stimulated. Also, groups of different areas of the constricted wall portion may be successively stimulated.

FIGS. 1F, 1G and 1H illustrate different states of operation of a modification of the general embodiment shown in FIGS. 1A-1E, wherein the constriction and stimulation devices CSD include several separate constriction/stimulation elements, here three elements CSDE1, CSDE2 and CSDE3. FIG. 1F shows how the element CSDE1 in a first state of operation is activated to both constrict and stimulate the organ BO, so that the lumen of the organ BO is closed, whereas the other two elements CSDE2 and CSDE3 are inactivated. FIG. 1G shows how the element CSDE2 in a second following state of operation is activated, so that the lumen of the organ BO is closed, whereas the other two elements CSDE1 and CSDE3 are inactivated. FIG. 1H shows how the element CSDE3 in a following third state of operation is activated, so that the lumen of the organ BO is closed, whereas the other two elements CSDE1 and CSDE2 are inactivated. By shifting between the first, second and third states of operation, either randomly or in accordance with a predetermined sequence, different portions of the organ can by temporarily constricted and stimulated while maintaining the lumen of the organ closed, whereby the risk of injuring the organ is minimized. It is also possible to activate the elements CSDE1-CSDE3 successively along the lumen of the organ to move fluids and/or other bodily matter in the lumen.

FIGS. 1I, 1K and 1L illustrate an alternative mode of operation of the modification of the general embodiment. Thus, FIG. 1I shows how the element CSDE1 in a first state of operation is activated to both constrict and stimulate the organ BO, so that the lumen of the organ BO is closed, whereas the other two elements CSDE2 and CSDE3 are activated to constrict but not stimulate the organ BO, so that the lumen of the organ BO is not completely closed where the elements CSDE2 and CSDE3 engage the organ BO. FIG. 1K shows how the element CSDE2 in a second following state of operation is activated to both constrict and stimulate the organ BO, so that the lumen of the organ BO is closed, whereas the other two elements CSDE1 and CSDE3 are activated to constrict but not stimulate the organ BO, so that the lumen of the organ BO is not completely closed where the elements CSDE1 and CSDE3 engage the organ BO. FIG. 1L shows how the element CSDE3 in a following third state of operation is activated to both constrict and stimulate the organ BO, so that the lumen of the organ BO is closed, whereas the other two elements CSDE1 and CSDE2 are activated to constrict but not stimulate the organ BO, so that the lumen of the organ BO is not completely closed where the elements CSDE1 and CSDE2 engage the organ BO. By shifting between the first, second and third states of operation, either randomly or in accordance with a predetermined sequence, different portions of the organ can by temporarily stimulated while maintaining the lumen of the organ closed, whereby the risk of injuring the organ is reduced. It is also possible to activate the stimulation of the elements CSDE1-CSDE3 successively along the lumen of the organ BO to move fluids and/or other bodily matter in the lumen.

Figure 3:
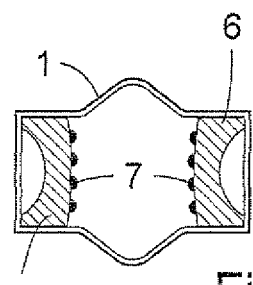
FIG. 3 is a cross-section along line II-II in FIG. 2.
Figure 2:
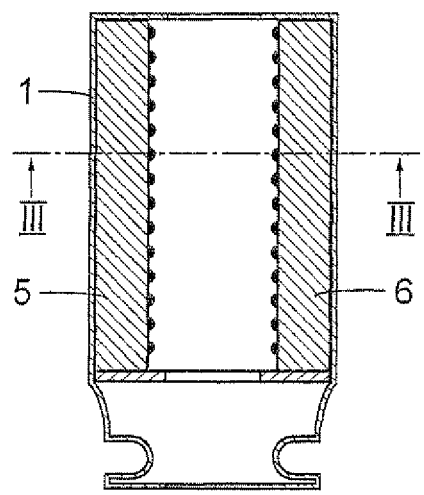
FIG. 2 is a longitudinal cross-section of an embodiment of the apparatus of FIG. 1 including a constriction device and an electric stimulation device.
Figure 4:
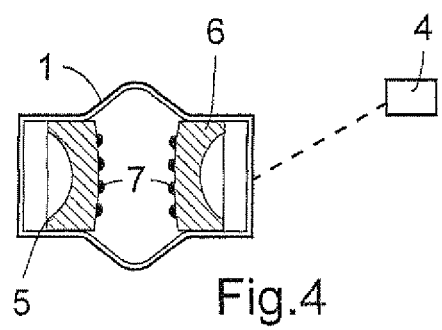
FIG. 4 is the same cross-section shown in FIG. 3 but with the apparatus in a different state of operation.

FIGS. 2-4 show basic components of an embodiment of the apparatus according to FIGS. 1A-1C for controlling a flow of fluid and/or other bodily matter in a lumen formed by a tissue wall of a patient's organ. The apparatus includes a tubular housing 1 with open ends, a constriction device 2 arranged in the housing 1, a stimulation device 3 integrated in the constriction device 2, and a control device 4 (indicated in FIG. 4) for controlling the constriction and stimulation devices 2 and 3. The constriction device 2 has two elongate clamping elements 5, 6, which are radially movable in the tubular housing 1 towards and away from each other between retracted positions, see FIG. 3, and clamping positions, see FIG. 4. The stimulation device 3 includes a multiplicity of electrical elements 7 positioned on the clamping elements 5, 6, so that the electrical elements 7 on one of the clamping elements 5, 6 face the electrical elements 7 on the other clamping element. Thus, in this embodiment the constriction and stimulation devices form a constriction/stimulation unit, in which the constriction and stimulation devices are integrated in a single piece.

The constriction and stimulation devices may also be separate from each other. In this case, a structure may be provided for holding the electrical elements 7 in a fixed orientation relative to one another. Alternatively, the electrical elements 7 may include electrodes that are separately attached to the wall portion of the patient's organ.

Figure 5A:
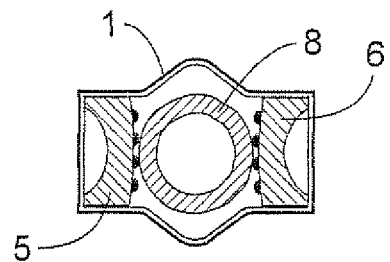
FIGS. 5A, 5B and 5C are cross-sections of the embodiment of FIG. 2 showing different states of operations with the apparatus applied on a tissue wall of a patient's organ.
Figure 5B:
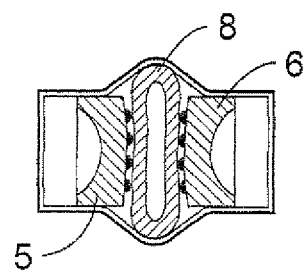
Figure 5C:
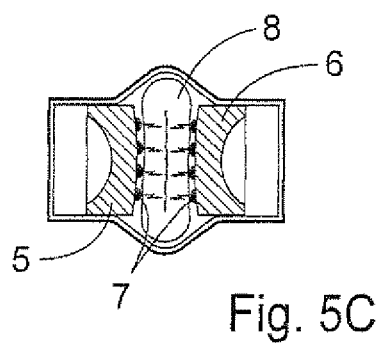

FIGS. 5A-5C illustrate in principle the function of the apparatus of FIG. 2 when the apparatus is applied on a portion 8 of a tubular tissue wall of a patient's organ. Thus, FIG. 5A shows the apparatus in a non-clamping state, in which the clamping elements 5, 6 are in their retracted positions and the wall portion 8 extends through the open ends of the housing 1 without being constricted by the clamping elements 5, 6. FIG. 5B shows the apparatus in a clamping state, in which the clamping elements 5, 6 have been moved from their retracted positions to their clamping positions, in which the clamping elements 5, 6 gently constrict the wall portion 8 to a constricted state, in which the blood circulation in the constricted wall portion 8 is substantially unrestricted and the flow in the lumen of the wall portion 8 is restricted. FIG. 5C shows the apparatus in a stimulation state, in which the clamping elements 5, 6 constrict the wall portion 8 and the electrical elements 7 of the stimulation device 3 electrically stimulate different areas of the wall portion 8, so that the wall portion 8 contracts (thickens) and closes the lumen.

When the apparatus is in its stimulation state, it is important to stimulate the different areas of the wall portion 8 in a manner so that they essentially maintains their natural physical properties over time to prevent the areas from being injured. Consequently, the control device 4 controls the stimulation device 3 to intermittently stimulate each area of the wall portion 8 during successive time periods, wherein each time period is short enough to maintain over time satisfactory blood circulation in the area. Furthermore, the control device 4 controls the stimulation of the areas of the wall portion 8, so that each area that currently is not stimulated restores substantially normal blood circulation before it is stimulated again. To maintain over time the effect of stimulation, i.e., to keep the lumen closed by maintaining the wall portion 8 contracted, the control device 4 controls the stimulation device 3 to stimulate one or more of the areas at a time and to shift the stimulation from one area to another over time. The control device 4 may control the stimulation device 3 to cyclically propagate the stimulation of the areas along the tubular wall portion 8, for example in accordance with a determined stimulation pattern. To achieve the desired reaction of the tissue wall during the stimulation thereof, the control device may control the stimulation device to, preferably cyclically, vary the intensity of the stimulation of the wall portion 8.

In the embodiment of FIGS. 2-4, the electrical elements 7 form a series of fourteen groups of electrical elements 7 extending longitudinally along each elongate clamping element 5 and 6, respectively, see FIG. 2. The electrical elements 7 of each group of electrical elements 7 form a first path of four electrical elements 7 positioned in a row on clamping element 5 and extending tranverse thereto and a second path of four electrical elements 7 positioned in a row on clamping element 6 and extending tranverse thereto. Thus, the two paths of electrical elements 7 extend on mutual sides of the patient's organ. The control device 4 controls the stimulation device 3 to successively energize the groups of electrical elements 7 in the series of groups in a direction opposite to or, alternatively, in the same direction as that of the flow in the patient's lumen. Of course, the number of electrical elements 7 of each path of electrical elements 7 can be greater or smaller than four, and several parallel rows electrical elements 7 can form each path of electrical elements 7.

Figure 6A:
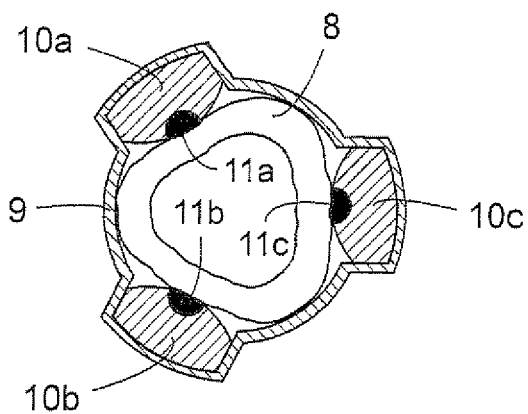
FIGS. 6A, 6B and 6C are cross-sections of a modification of the embodiment of FIG. 2 showing different states of operations with the apparatus applied on a tissue wall of a patient's organ.
Figure 6B:
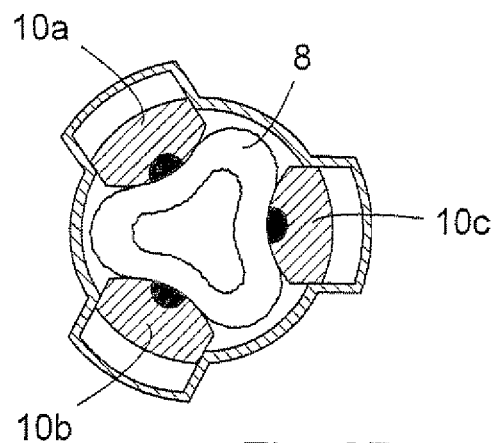
Figure 6C:
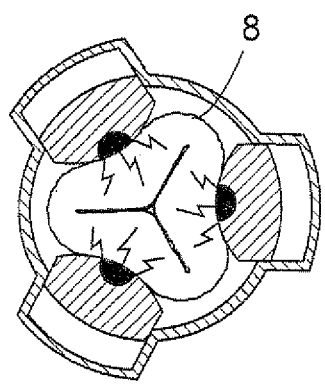

FIGS. 6A-6C show another embodiment of an apparatus used for practicing the method of the invention including a tubular housing 9 and three elongate clamping elements 10a, 10b, 10c, which are radially movable in the tubular housing 9 towards and away from a central axis thereof between retracted positions, see FIG. 6A, and clamping positions, see FIG. 6B. The three clamping elements 10a-10c are symmetrically disposed around the central axis of the housing 9. The stimulation device of this embodiment includes electrical elements 11a, 11b, 11c that form a series of groups of elements extending longitudinally along the elongate clamping elements 10a-10c, wherein the electrical elements 11a-11c of each group of electrical elements form a path of three electrical elements 11a, 11b and 11c extending circumferentially around the central axis of the housing 9. The three electrical elements 11a-11c of each group are positioned on the three clamping elements 10a-10c, respectively. Thus, the path of three electrical elements 11a-11c extends around the patient's organ. Of course, the number of electrical elements 11a-11c of each path of electrical elements can be greater than three, and several parallel rows electrical elements 11a-11c can form each path of electrical elements.

Figure 7A:
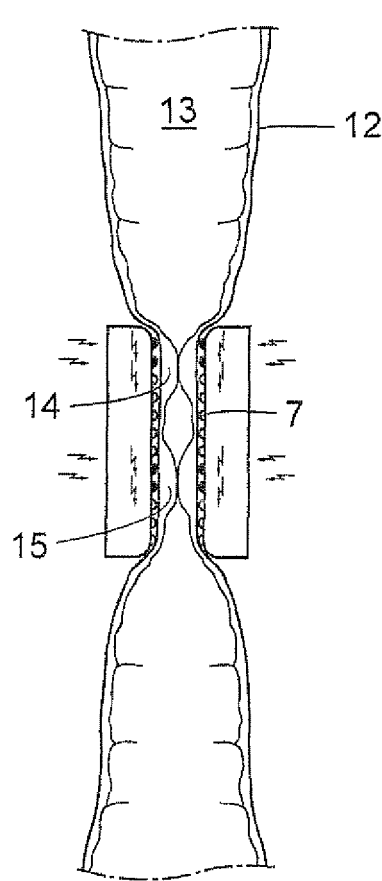
FIGS. 7A and 7B show different steps of an electric stimulation mode performed by the apparatus of FIG. 2 while the apparatus is constricting a tissue wall of a patient's organ.
Figure 7B:
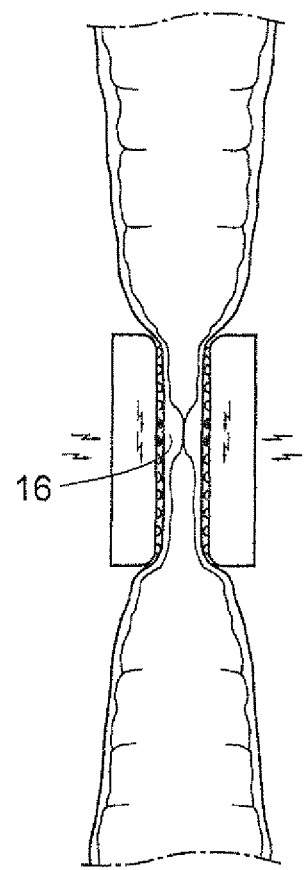

FIGS. 7A and 7B show different steps of an electric stimulation mode performed by the apparatus of FIG. 2 while the clamping elements 5, 6 of the apparatus are constricting a portion of a tubular tissue wall of a patient's organ 12 to restrict the flow in the lumen 13 of the organ 12. For the sake of clarity only the clamping elements 5, 6 of the constriction device 2 are shown in FIGS. 7A, 7B. Thus, FIG. 7A illustrates how energized electrical elements 7 of groups of electrical elements electrically stimulate a first portion 14 and a second portion 15 of the tubular wall to contract and close the lumen 13. FIG. 7B illustrates how energized electrical elements 7 of other groups of electrical elements electrically stimulate a third portion 16 of the tubular wall different from the first and second portions to contract and close the lumen 13, while the electrical stimulation of the first and second portions 14, 15 of the tubular wall has been ceased, so that substantially normal blood circulation in the first and second portions is restored. In this manner, the electric stimulation of the constricted tubular wall is shifted over time from one portion of the tubular wall to another to insure recurrent restoration of blood circulation in the constricted tubular wall.

The control device 4 controls the stimulation device 3 to energize the electrical elements 7 with electric biphasic pulses, i.e., combined positive and negative pulses. The desired stimulation effect is achieved by varying different pulse parameters. Thus, the control device 4 controls the stimulation device 3 to vary the pulse amplitude (voltage), the off time period between successive pulses, the pulse duration and the pulse repetition frequency. The pulse current should be between 1 to 30 mA. For neural stimulation, a pulse current of about 5 mA and a pulse duration of about 300 μs are suitable, whereas a pulse current of about 20 mA and a pulse duration of about 30 μs are suitable for muscular stimulation. The pulse repetition frequency suitably is about 10 Hz. For example, as illustrated in the Pulse/time diagram P/t of FIG. 8A, a pulse combination including a negative pulse PS of short duration and high amplitude (voltage), and a positive pulse PL of long duration and low amplitude following the negative pulse may be cyclically repeated to form a pulse train of such pulse combinations. The energy content of the negative pulse PS should be substantially equal to the energy content of the positive pulse PL.

Figure 8B:
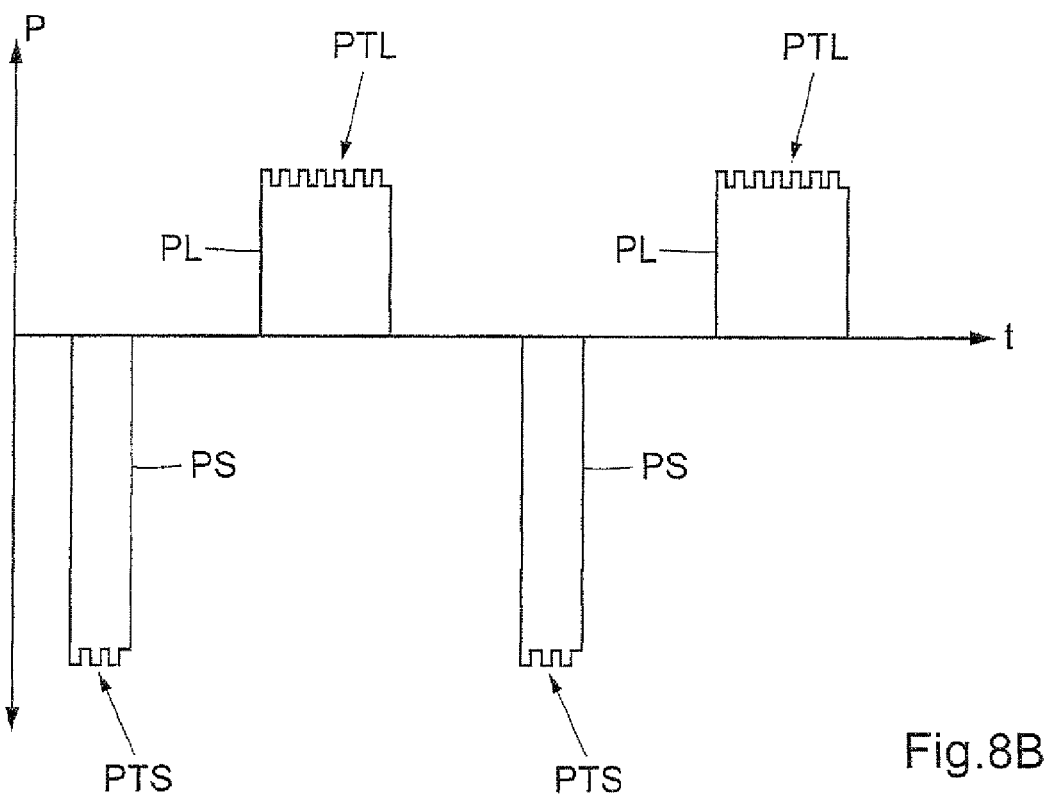
FIG. 8B is pulse/time diagram showing a modification of the electric stimulation shown in FIG. 8A, in which pulses of mixed frequencies and/or amplitudes are employed.

FIG. 8B is a pulse/time diagram showing a modification of the electric stimulation shown in FIG. 8A. Thus, the pulse combination of FIG. 8A is mixed with a pulse train combination having a first relatively long pulse train PTL of high frequency/low amplitude pulses, appearing simultaneously with the positive pulse PL of the pulse combination of FIG. 8A, and a second relatively short pulse train PTS of high frequency/low amplitude appearing simultaneously with the negative pulse PS of the pulse combination shown in FIG. 8A. As a result, the high frequency/low amplitudes pulse trains PTL and PTS are superimposed on the positive and negative pulses PL and PS of FIG. 8A, as illustrated in FIG. 8B. The pulse configuration of FIG. 8B, and variations thereof, is beneficial to use in connection with the stimulation of particular human organs, in order to achieve the desired stimulation effect.

Figure 9A:
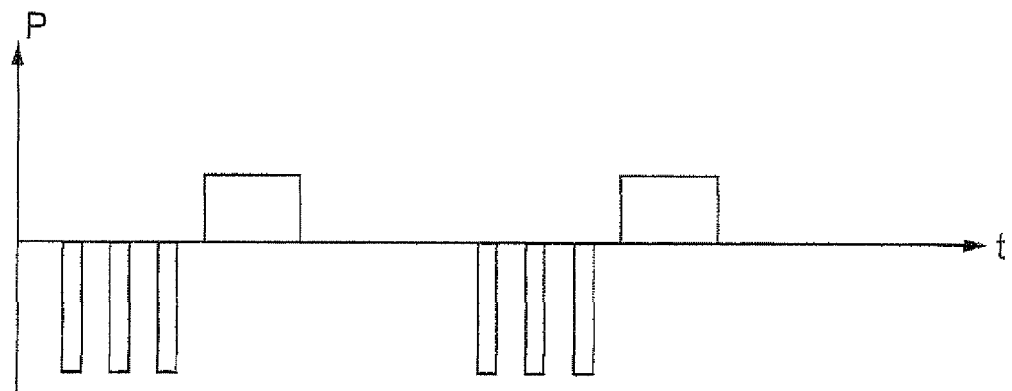
FIGS. 9A and 9B show two pulse/time diagrams, respectively, representing electric stimulation of two different areas of the tissue wall with pulses forming pulse trains.

Preferably, the electric pulses form pulse trains, as illustrated in the Pulse/time diagrams P/t of FIGS. 9A, 9B, 9C and 9D. The Pulse/time diagram P/t of FIG. 9A represents an individual area of the wall portion of the patient's tubular organ which is stimulated with a pulse train 18A. The pulse train 18A includes three initial negative pulses, each of which is of short duration and high amplitude (voltage), and one positive pulse of long duration and low amplitude following the negative pulses. After a delay to enable the area of the organ to restore substantially normal blood circulation the pulse train 18A is repeated.

Figure 9B:
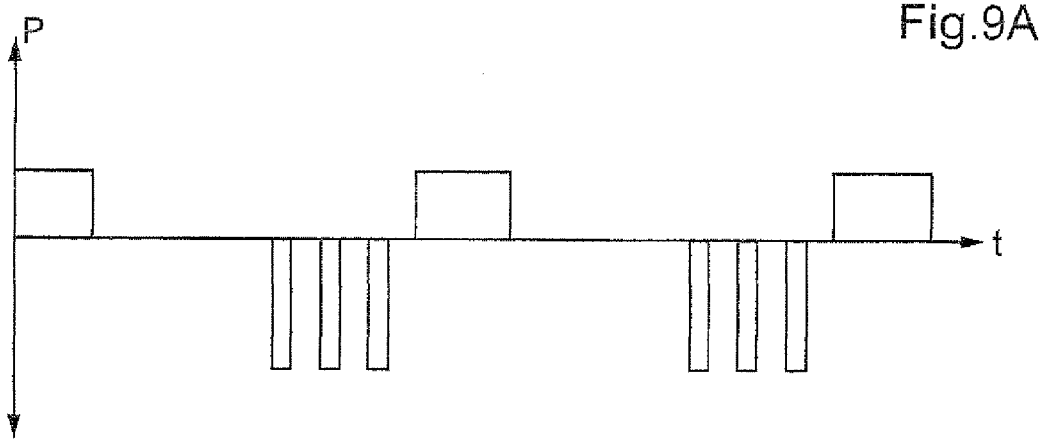

The Pulse/time diagram P/t of FIG. 9B represents another individual area of the wall portion, which is stimulated with a pulse train 18B having the same configuration as the pulse train 18A. The pulse trains 18A and 18B are shifted relative to each other, so that they partially overlap one another to ensure that the constricted wall portion always is stimulated to contract as desired.

Figure 10A:
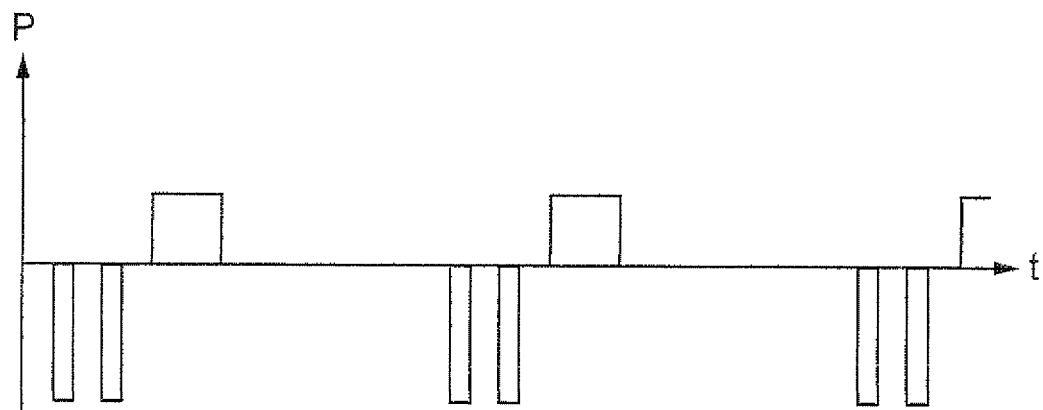
FIGS. 10A and 10B show the pulse/time diagrams of FIGS. 9A and 9B with modified pulse trains.
Figure 10B:
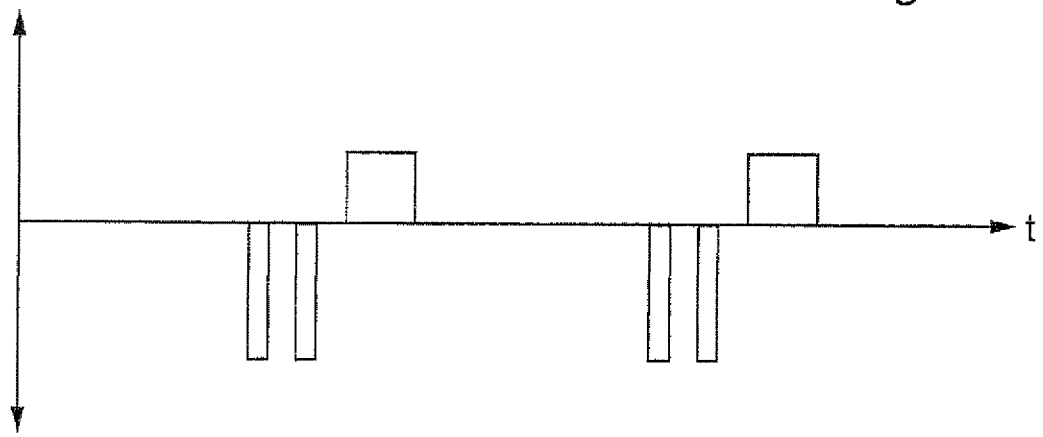

The pulse/time diagrams P/t of FIGS. 10A and 10B represent two different areas of the wall portion, which are stimulated with cyclically repeated pulse trains 18C and 18D, respectively, having the same configuration. Each pulse train 18C, 18D includes two initial negative pulses, each of which is of short duration and high amplitude (voltage), and one positive pulse of long duration and low amplitude following the two negative pulses. In this case, the pulse trains 18C and 18D are shifted relative to each other, so that they do not overlap each other. Thus, the off time period between adjacent pulse trains 18C is longer than the duration of pulse train 18D and the off time period between adjacent pulse trains 18D is longer than the duration of pulse train 18C.

The pulse trains 18A, 18B, 18C and 18D can be configured in many different ways. Thus, the control device 4 can control the stimulation device 2 to vary the length of each pulse train, the repetition frequency of the pulse trains, the number of pulses of each pulse train, and/or the off time periods between the pulse trains. Typically, the control device 4 controls each off time period between the pulse trains to last long enough to restore substantially normal blood circulation in the area that just has been stimulated before that area again is stimulated with electric pulses.

FIGS. 11A and 11B show another embodiment of an apparatus used for practicing the method of the invention that controls blood flow in a blood vessel 19. The apparatus of FIGS. 11A and 11B includes a constriction device with two clamping elements 20a and 20b, a stimulation device in the form of two thermal stimulation elements 21a and 21b integrated in the clamping elements 20a, 20b, respectively, and a control device 4 for controlling the clamping elements 20a, 20b and stimulation elements 21a, 21b. The clamping elements 20a and 20b are movable towards and away from each other in the same manner as described above in connection with the embodiment according to FIGS. 5A-5C. The thermal stimulation elements 21a and 21b, which may include Pertier elements, are positioned on the clamping elements 20a, 20b, so that the thermal elements 21a are facing the thermal elements 21b. FIG. 11A shows how the clamping elements 20a, 20b constrict the blood vessel 19, so that the blood flow is restricted. FIG. 11B shows how the control device 4 controls the thermal stimulation elements 21a, 21b to cool the wall of the blood vessel 19, so that the wall contracts and closes the blood vessel 19. To release the blood vessel 19, the control device 4 controls the thermal stimulation elements 21 a, 21 b to heat the wall of the blood vessel 19, so that the wall expands.

Figure 12A:
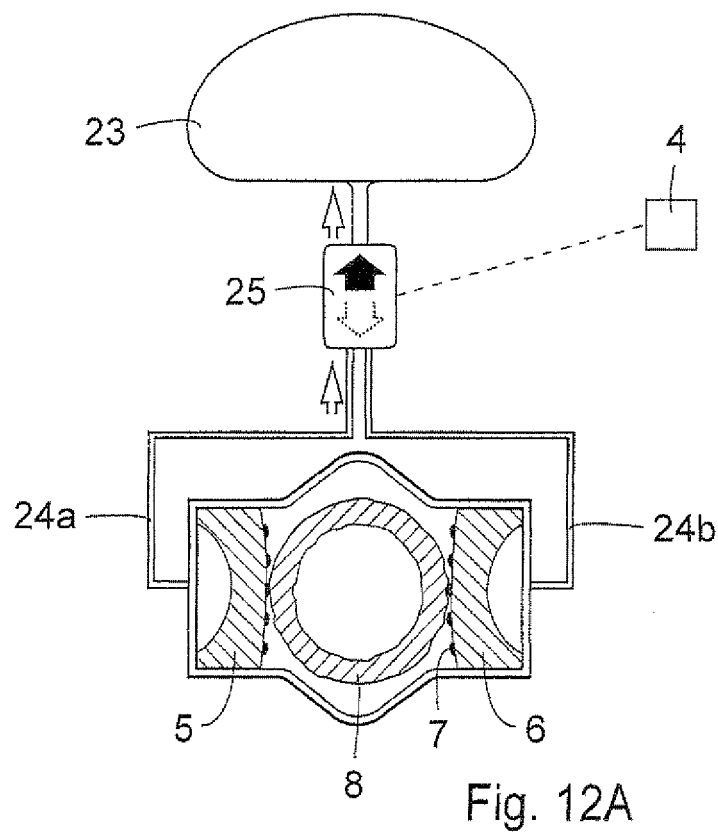
FIG. 12A is a schematic view of hydraulic operation means suited for operating the constriction device of the embodiments of FIGS. 2-11
Figure 12B:
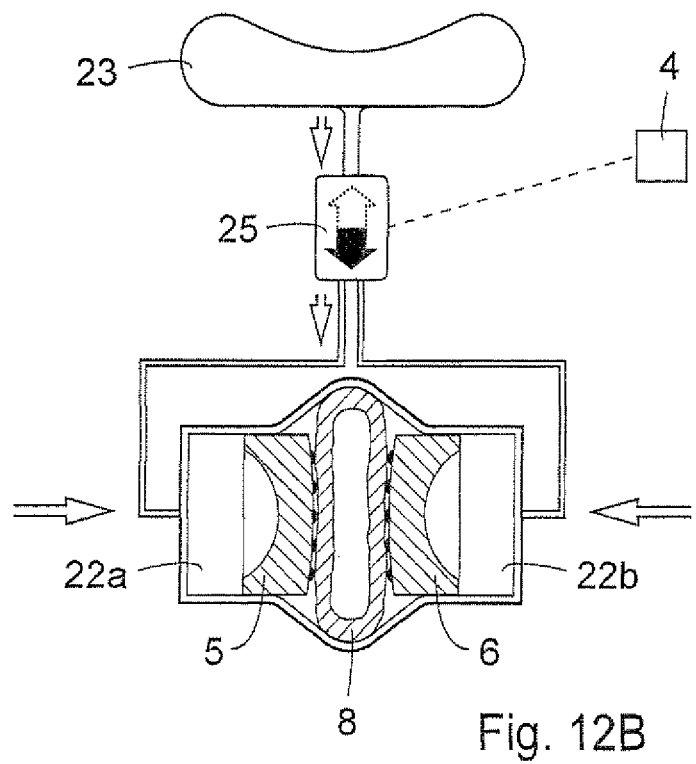
FIG. 12B shows the embodiment of FIG. 12A with the constriction device constricting a tissue wall of a patient's organ.

FIGS. 12A and 12B show hydraulic operation means suited for operating the constriction device of the embodiments described above. Specifically, FIGS. 12A and 12B show the apparatus of FIG. 2 provided with such means for hydraulic operation of the constriction device 2. (The stimulation device is not shown.) Thus, the housing 1 forms two hydraulic chambers 22a and 22b, in which the two clamping elements 5,6 are slidable back and forth relative to the tubular tissue wall portion 8 of a patient's organ. The hydraulic operation means include an expandable reservoir 23, such as an elastic balloon, containing hydraulic fluid, conduits 24a and 24b between the reservoir 23 and the hydraulic chambers 22a, 22b, and a two-way pump 25 for pumping the hydraulic fluid in the conduits 24a, 24b. The control device 4 controls the pump 25 to pump hydraulic fluid from the reservoir 23 to the chambers 22a, 22b to move the clamping elements 5, 6 against the wall portion 8, whereby the tubular wall portion 8 is constricted, see FIG. 12B, and to pump hydraulic fluid from the chambers 22a, 22b to the reservoir 23 to move the clamping elements 5, 6 away from the wall portion 8, whereby the tubular wall 8 is released, see FIG. 12A.

Alternatively, the embodiment of FIGS. 12A and 12B may be manually operated by applying suitable manually operable hydraulic means for distributing the hydraulic fluid between the expandable reservoir 23 and the hydraulic chambers 22a, 22b. In this case the pump 25 is omitted.

Figure 13A:
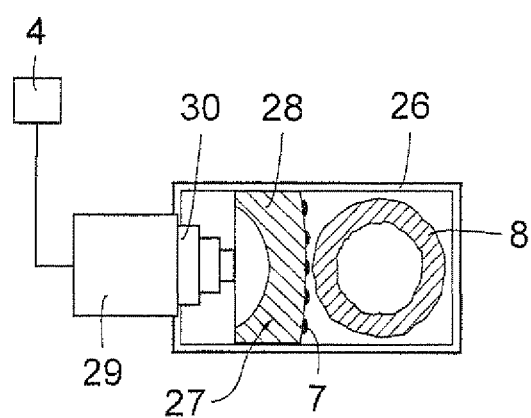
FIG. 13A is a schematic view of mechanical operation means suited for operating the constriction device of the embodiments of FIGS. 2-11.
Figure 13B:
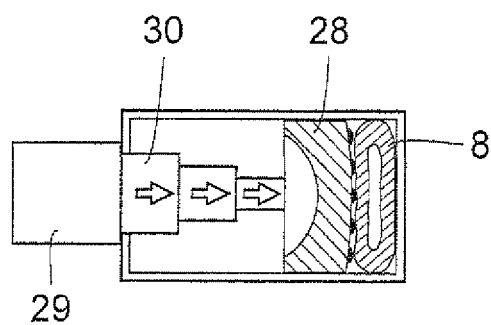
FIG. 13B shows the embodiment of FIG. 13A with the constriction device constricting a tissue wall of a patient's organ.

FIGS. 13A and 13B schematically show another embodiment of an apparatus used for practicing the method of the invention. The apparatus of FIGS. 13A and 13B comprises an open ended tubular housing 26 applied on the tubular tissue wall portion 8 of a patient's organ, a constriction device 27 arranged in the housing 26 and a control device 4 for controlling the constriction device 27. A stimulation device (not shown) as described above is also provided in the housing 26. The constriction device 27 includes a clamping element 28, which is radially movable in the tubular housing 26 towards and away from the tubular wall portion 8 between a retracted position, see FIG. 13A, and a clamping position, see FIG. 13B, in which the clamping element 28 gently constricts the tubular wall portion 8. Mechanical operation means for mechanically operating the clamping element 28 includes an electric motor 29 attached to the housing 26 and a telescopic device 30, which is driven by the motor 29 and operatively connected to the clamping element 28. The control device 4 controls the electric motor 29 to expand the telescopic device 30 to move the clamping element 28 against the wall portion 8, whereby the tubular wall portion 8 is constricted, see FIG. 13B, and controls the motor 29 to retract the telescopic device 30 to move the clamping element 28 away from the wall portion 8, whereby the wall portion 8 is released, see FIG. 13A.

Alternatively, the motor 29 may be omitted and the telescopic device 30 be modified for manual operation, as shown in FIG. 13C. Thus, a spring 30a may be provided acting to keep the telescopic device 30 expanded to force the clamping element 28 against the wall portion 8. The mechanical operation means may include a subcutaneously implanted lever mechanism 29a that is operatively connected to the telescopic device 30. The patient may push the lever mechanism 29a through the skin to pull the telescopic device 30 against the action of the spring 30a to the retracted position of the telescopic device 30, as indicated in phantom lines. When the patient releases the lever mechanism 29a, the spring 30a expands the telescopic device 30, whereby clamping element 28 is forced against the wall portion 8.

The mechanical operation means as described above in connection with FIGS. 13A, 13B and 13C may also be implemented in the embodiments according to FIGS. 1-11.

Figure 14:
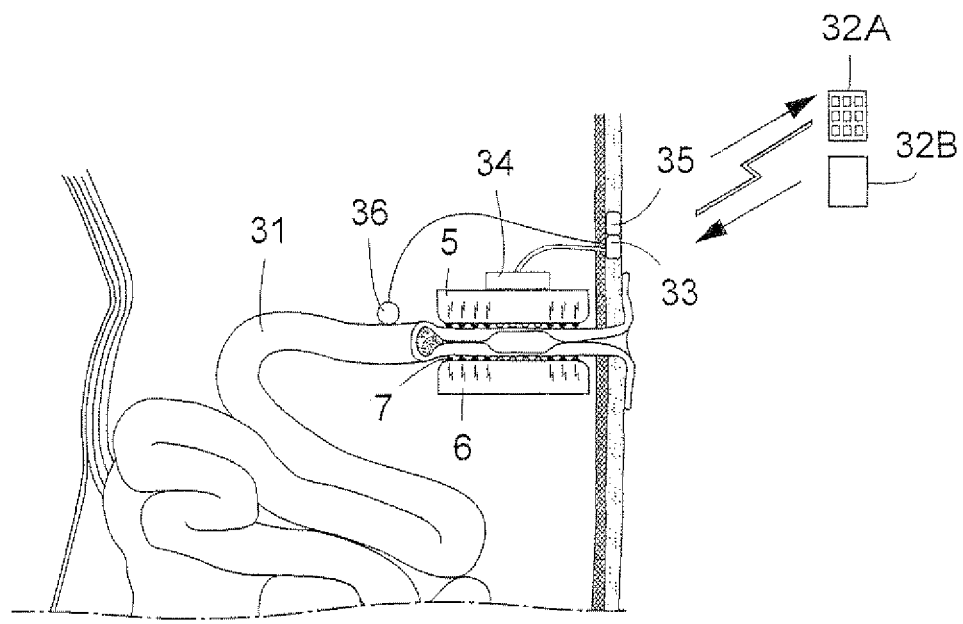
FIG. 14A illustrates an apparatus used for practicing the method of the invention where the apparatus is applied on the small intestines of a colostomy patient having a stoma opening in the abdomen.
FIG. 14B illustrates an apparatus used for practicing the method of the invention where the apparatus is applied on the small intestines of a colostomy patient having the small intestines ending at the patient's anus.
Figure 14:
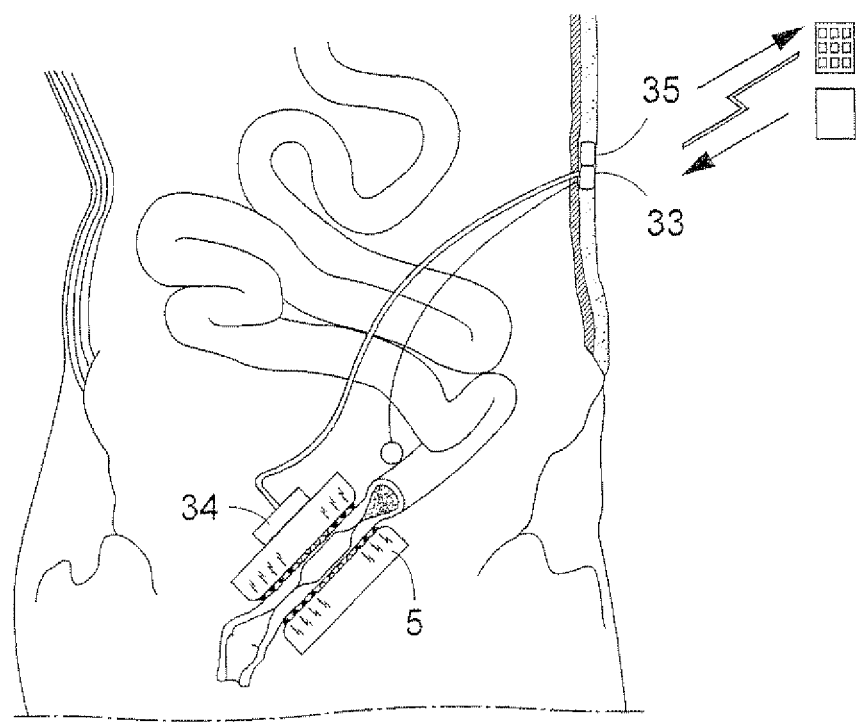

FIG. 14A illustrates the apparatus of FIG. 2 applied on the intestines 31 of a colostomy patient having a stoma in the abdomen. The clamping elements 5, 6 of the constriction device 2 constrict the intestines 31 and the stimulation device 3 is energized to close the intestinal passageway. (For the sake of clarity, the housing is not shown and the clamping elements 5, 6 are exaggerated.) In this embodiment, a control device includes an external control unit in the form of a hand-held wireless remote control 32, and an implanted internal control unit 33, which may include a microprocessor, for controlling the constriction and stimulation devices. The remote control 32 is operable by the patient to control the internal control unit 33 to switch on and off the constriction device and/or the stimulation device. Alternatively, however, the remote control 32 may be replaced by a subcutaneously implanted push button that is manually switched by the patient between "on" and "off". Such a manually operable push button may also be provided in combination with the remote control 32 as an emergency button to allow the patient to stop the operation of the apparatus in case of emergency or malfunction.

The internal control unit 33 controls an implanted operation device 34 to move the clamping elements 5, 6. An implanted source of energy 35, such as a rechargeable battery, powers the operation device 34. The internal control unit 33, which may be implanted subcutaneously or in the abdomen, also works as en energy receiver, i.e., for transforming wireless energy into electric energy and charging the implanted source of energy 35 (rechargeable battery) with the electric energy.

An implanted sensor 36 senses a physical parameter of the patient, such as the pressure in the intestines, or a parameter that relates to the pressure in the intestines, wherein the internal control unit 33 controls the constriction device 2 and/or the stimulation device 3 in response to signals from the sensor 36. In this embodiment the sensor 36 is a pressure sensor, wherein the internal control unit 33 controls the constriction device and/or stimulation device to change the constriction of the patient's intestines 31 in response to the pressure sensor 36 sensing a predetermined value of measured pressure. For example, the control unit 33 may control the constriction device and/or stimulation device to increase the constriction of the patient's intestines 31 in response to the pressure sensor sensing an increased pressure. Alternatively or in combination, the remote control 32 controls the constriction device and/or stimulation device in response to signals from the sensor 36. The remote control 32 may be equipped with means for producing an indication, such as a sound signal or displayed information, in response to signals from the sensor 36, in the same manner as the internal control unit 33.

The remote control 32 may be equipped with means for producing an indication, such as a sound signal or displayed information, in response to signals from the sensor 36. When the patient's attention is taken by such an indication indicating an increased pressure exceeding a threshold value, he or she may use the remote control to control the constriction device and stimulation device to pump feces through the patient's stoma.

FIG. 14B shows an embodiment which is similar to the embodiment of FIG. 14A except that the constriction device is applied on the small intestines of a colostomy patient having the small intestines surgically connected to the patient's anus.

Figure 15:
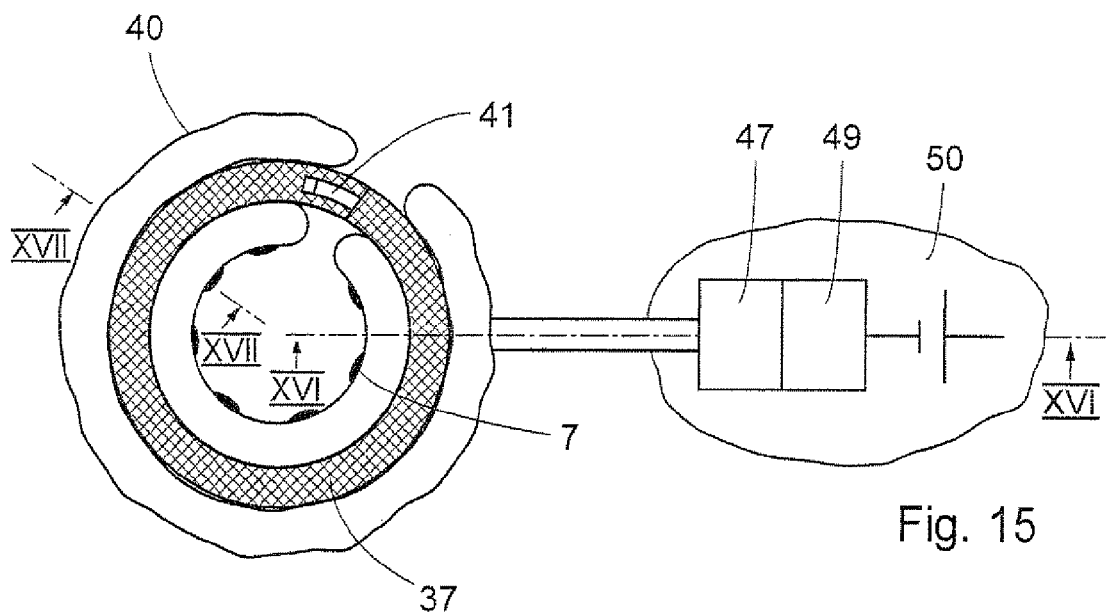
FIG. 15 is a schematic sectional view of a mechanically operable non-inflatable constriction device used for practicing the method of the invention.
Figure 16:
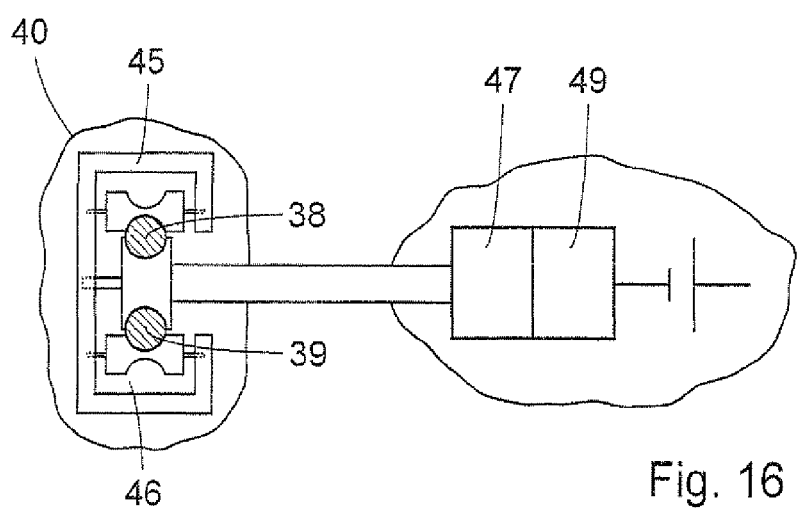
FIGS. 16 and 17 are cross-sectional views taken along the lines XVI-XVI and XVII-XVII, respectively, of FIG. 15.
Figure 17:
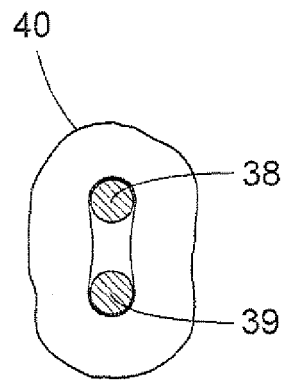

FIGS. 15-17 show another embodiment of an apparatus used for practicing the method of the invention. The apparatus of FIGS. 15-17 includes a mechanically operable constriction device having an elongated constriction member in the form of a circular resilient core 37 with two overlapping end portions 38,39. The core 37 defines a substantially circular restriction opening and is enclosed in an elastic soft hose 40 except at a releasable and lockable joint 41 of the core 37, which when released enables application of the core 37 with its hose 40 around a portion of a tubular tissue wall of a patient. The materials of all of these elements are bio-compatible so that the patient' body will not reject them. An operation device 42 for mechanically operating the longitudinal extension of the core 37 to change the size of the restriction opening comprises a drive wheel 43 in frictional engagement with the overlapping end portions 38,39 of the core 37. The drive wheel 43 is journalled on a holder 44 placed in the hose 40 and provided with two counter pressure rollers 45,46 pressing the respective end portions 38, 39 of the core 37 against the drive wheel 43 to increase the frictional engagement there between. An electric motor 47 of the operation device is connected to the drive wheel 43 via a long flexible drive shaft 48 and is moulded together with a remote controlled power supply unit 49 in a body 50 of silicone rubber. The length of the flexible drive shaft 48 is selected so that the body 50 can be placed in a desired position in the patient's body, suitably in the abdomen.

The power supply unit 49 can be controlled to power the electric motor 47 to turn the drive wheel 43 in one direction to reduce the diameter of the core 37, so that the wall portion is constricted, or to turn the drive wheel 43 in the opposite direction to increase the diameter of the core 37, so that the wall portion is released.

In accordance with a first alternative, a rack gear may be formed on one of the end portions 38,39 of the core 37 and the drive wheel 43 may be replaced by a drive gear wheel connected to the other end portion of the core 37 and in mesh with the rack gear.

In accordance with a second alternative, the operation device 42 may be designed as a worm-driven hose clamp, i.e., one of the end portions 38, 39 of the core 37 may be provided with threads and the other end portion of the core 37 may be provided with a worm, the threads of which interacts with the threads of said one end portion of the core 37. The threads of such a worm may also interact with threads provided on both end portions 38, 39 of the core 37. In this alternative, the electric motor 47 turns the worm in one direction to reduce the diameter of the core 37, so that the wall portion is constricted, or turn the worm in the opposite direction to increase the diameter of the core 37, so that the wall portion is released in one direction to reduce the diameter of the core 37, so that the wall portion is constricted, or turns the clamping screw in the opposite direction to increase the diameter of the core 37, so that the wall portion is released.

Figure 18:
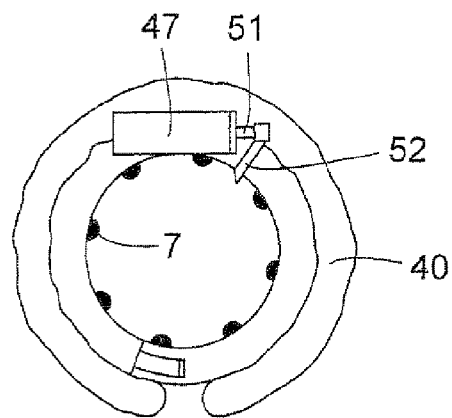
FIG. 18 schematically shows an alternative design of the embodiment of FIG. 15.

FIG. 18 shows a constriction device which is identical to the constriction device shown in FIGS. 15-17, except that the motor 47 is encapsulated in the hose 40 so that it is fixed to the core 37 and has a short drive shaft 51, and that the motor 47 is positioned relative to the core 37 such that the drive shaft 51 extends substantially tangentially to the circular core 37. There is an angular gearing 52 connecting the drive shaft 51 to the drive wheel 43.

Figure 19:
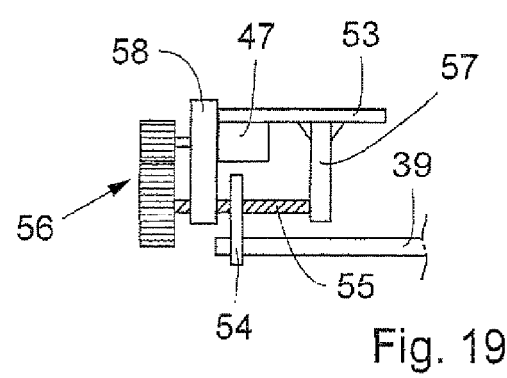
FIG. 19 schematically illustrates a motor arrangement for the embodiment according to FIG. 18.

FIG. 19 shows a suitable alternative arrangement for the motor 47 in the embodiment of FIG. 17, comprising a first clamping member 53 secured to one end portion of the core 37 and a second clamping member 54 secured to the other end portion 39 of the core 37. The motor 47 is secured to the first clamping member 53 and is operatively connected to a worm 55 via a gear transmission 56. The worm 55 is journalled at its opposite ends on holders 57 and 58, which are rigidly secured to the clamping member 53 and the motor 47, respectively. The second clamping member 54 has a pinion in mesh with the worm 55. When the motor 47 is powered the worm 55 rotates and will thereby pull the end portion 39 of the core 37 in one or the opposite longitudinal direction, so that the diameter of the substantially circular core 37 is either increased or decreased. The motor 47, worm gear 55, gear transmission 56 and second clamping member 54 constitute a servo system of the type that transfers a weak force acting on a moving element having a long stroke into a strong force acting on another moving element having a short stroke.

Figure 20:
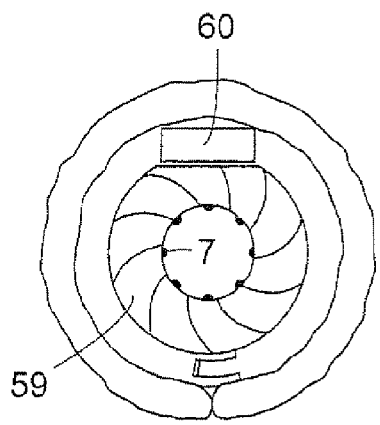
FIGS. 20 and 21 are schematic sectional views of two alternative designs of non-inflatable constriction devices used for practicing the method of the invention.

FIG. 20 shows another embodiment of an apparatus used for practicing the method of the invention. The apparatus of FIG. 20 includes a constriction device having a plurality of arcuate lamellae 59 arranged like the conventional adjustable aperture mechanism of a camera. A motor 60 operates the lamellae 59 to change the size of a restriction opening defined by the lamellae 59.

Figure 21:
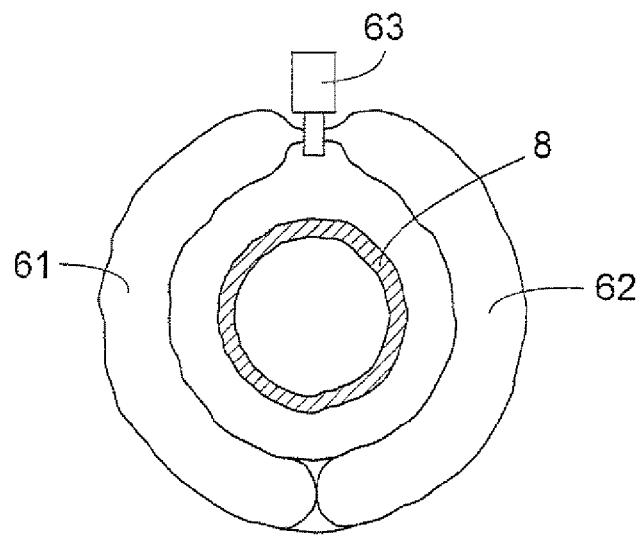
Figure 22:
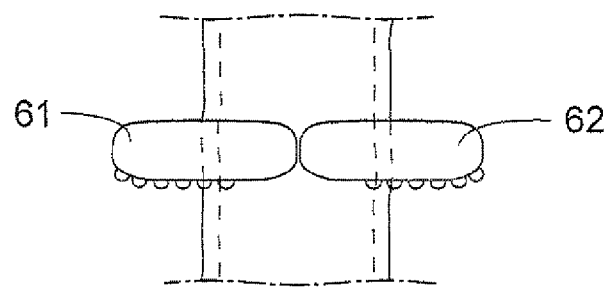
FIGS. 22 and 23 illustrate a fully open and a reduced constriction opening, respectively, of the embodiment of FIG. 21.
Figure 23:
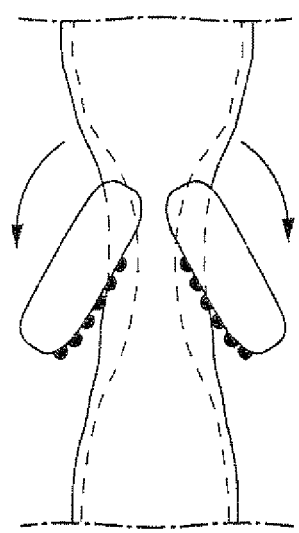
Figure 24:
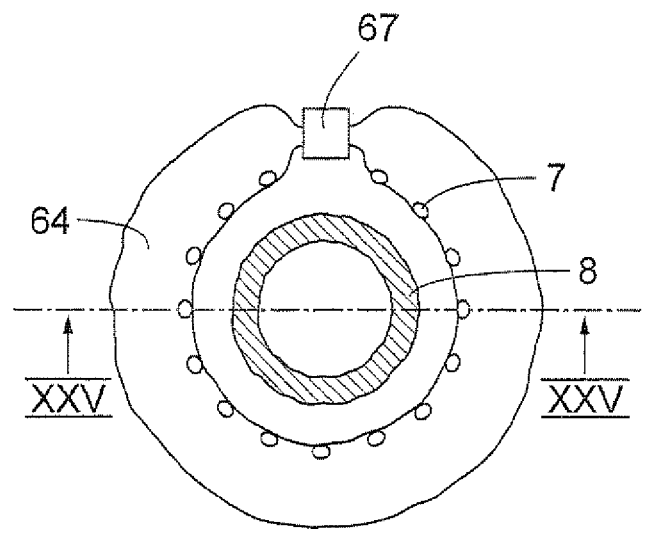
FIG. 24 is a schematic view of a further alternative design of a non-inflatable constriction device used for practicing the method of the invention.
Figure 25:
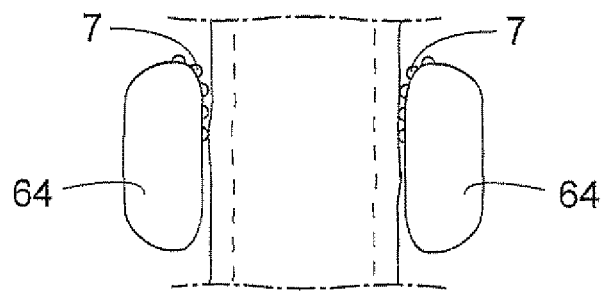
FIGS. 25 and 26 illustrate a fully open and a reduced constriction opening, respectively, of the embodiment of FIG. 24.
Figure 26:
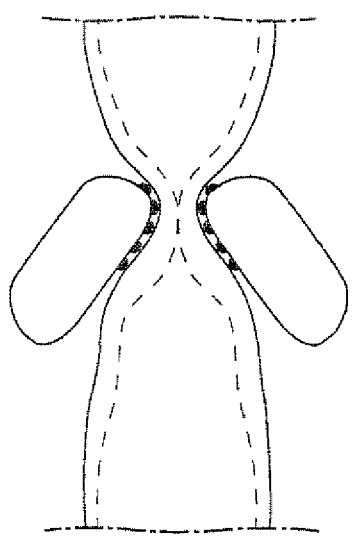

FIGS. 21-23 show another embodiment of an apparatus used for practicing the method of the invention. The apparatus of FIGS. 21-23 includes a constriction device having two semi-circular elements 61 and 62, which are hinged together. The semi-circular elements 61,62 are swingable relative to each other between a fully open state in which they substantially form a circle, illustrated in FIG. 23 and an angular state, in which the size of the restriction opening defined by the semi-circular elements 61, 62 is reduced, illustrated in FIG. 24. A motor 63 operates the semi-circular elements 61, 62 to swing them relative to each other.

FIGS. 24-28 show another embodiment of an apparatus used for practicing the method of the invention. The apparatus of FIGS. 24-28 includes a constriction device having an elastic belt 64, which forms a circle and has a substantially oval cross-section. A motor 67 operates the belt 64 to turn around the longitudinal extension thereof between a fully open state, in which the inner broader side of the belt 64 forms a substantially cylindrical surface, illustrated in FIG. 25, and a reduced open state, in which the inner broader side of the belt 64 forms a substantially conical surface, illustrated in FIG. 26.

Figure 27:
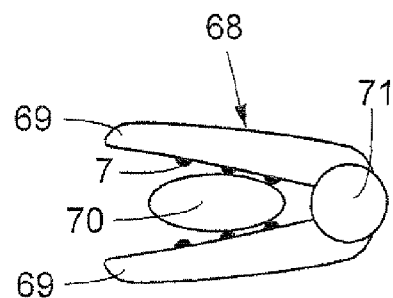
FIG. 27 is a schematic view of another alternative design of a non-inflatable constriction device used for practicing the method of the invention.

FIG. 27 shows another embodiment of an apparatus used for practicing the method of the invention. The apparatus of FIG. 27 includes a constriction device 68 having two rigid articulated clamping elements 69 positioned on opposite sides of a portion of a tubular tissue wall 70 of a patient. An operation device 71 turns the clamping elements 69 toward each other to clamp the wall portion 70 between the clamping elements 69 to thereby contract the wall portion, and turns the clamping elements 69 away from each other to release the wall portion from the clamping elements 69.

Figure 28:
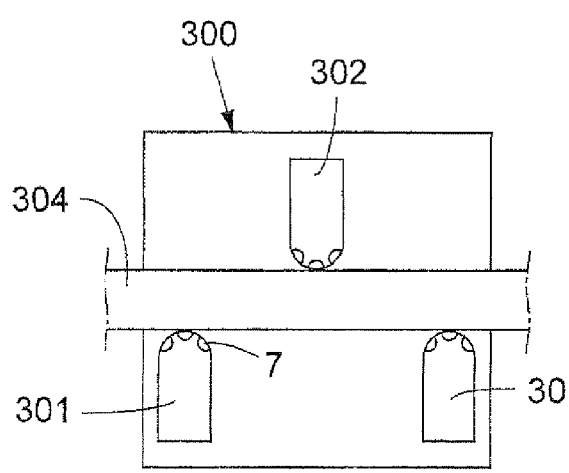
FIGS. 28 and 29 are schematic sectional views, respectively, of yet another alternative design of a non-inflatable constriction device used for practicing the method of the invention.
Figure 29:
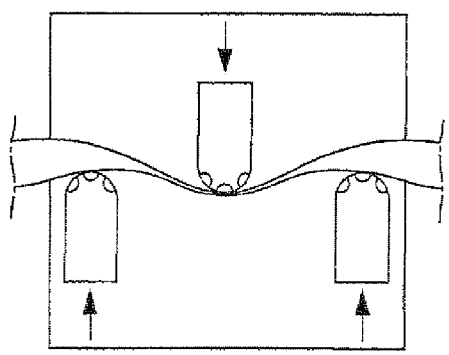

FIGS. 28 and 29 show another embodiment of an apparatus used for practicing the method of the invention. The apparatus of FIGS. 28 and 29 include a constriction device 300 having three bending members 301, 302 and 303 displaced relative to one another in a row along a portion of a tubular tissue wall 304 of a patient's organ and positioned alternately on opposite sides of the tubular wall 304. (Alternatively, each member 301, 302 and 303 may take the shape of an hour-glass.) An operation device (not shown) moves the two outer members 301, 303 laterally against the tubular wall 304 in one direction and the intermediate member 302 against the tubular wall 304 in the opposite direction to bend the tubular wall 304 to thereby constrict the tubular wall portion 304, see FIG. 29. To release the wall portion 304 the operation device moves the members 301-303 away from the tubular wall portion 304 to the position shown in FIG. 28.

FIGS. 30A and 30B show another embodiment of an apparatus used for practicing the method of the invention. The apparatus of FIGS. 30A and 30B include a hydraulically operable elongated constriction device in the form of a band 72 having an expandable/contractible cavity 73, which is in fluid communication with an adjustable reservoir 74 containing hydraulic fluid. FIG. 30A illustrates when the band is in a non-constriction state, whereas FIG. 30B illustrates when the band is in a constriction state, in which the cavity 73 is expanded by hydraulic fluid supplied by the reservoir 74.

FIGS. 31A, 31B, 31C and 31D are block diagrams of three differently operated hydraulic constriction devices used for practicing the method of the invention. FIG. 31A shows the band 72 of FIG. 30A, the cavity 73 of which is in fluid communication with a reservoir 75. FIG. 31B shows the embodiment of FIG. 30A, in which the cavity 73 of the band 72 is in fluid communication with the reservoir 74 via an operation device in the form of a two-way pump 76. FIG. 31C shows an operation device in the form of a reverse servo system with a first closed system controlling a second system. The reverse servo system comprises an adjustable fluid supply reservoir 77 and an adjustable servo reservoir 78. The servo reservoir 78 controls a larger adjustable reservoir 79 which in connection with the band 72 applied around a portion of tubular tissue wall of a patient's organ varies the volume of the cavity 73 of the band 72, which in turn varies the constriction of the wall portion. FIG. 31D shows an embodiment identical to the embodiment of FIG. 31C, except that the larger reservoir 79 is omitted. Instead, the servo reservoir 78 is in fluid communication with the cavity of the band 72.

In all of the above embodiments according to FIGS. 12A through 30B, stimulation devices may be provided to form constriction/stimulation units, in which the stimulation devices include a multiplicity of electrical elements 7 (indicated in FIGS. 12A-15, 18, 20-23, 26-31B) positioned on the constriction devices.

Figure 32:
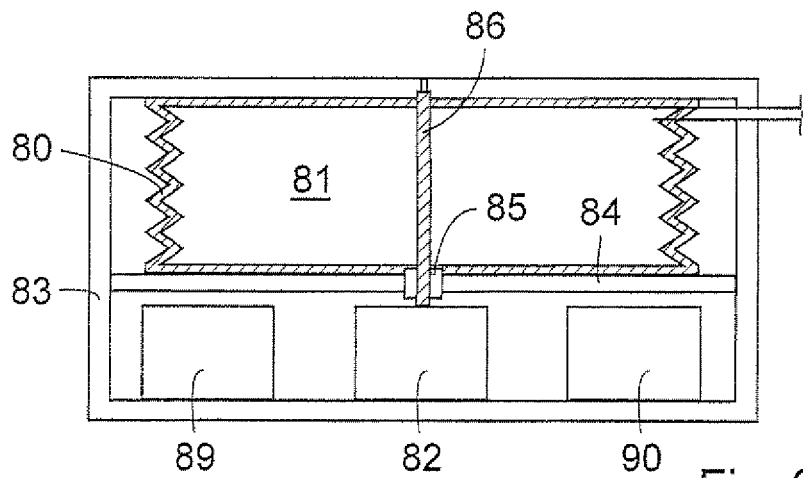
FIG. 32 is a cross-sectional view of a reservoir having a variable volume controlled by a remote control motor.

FIG. 32 is a cross-sectional view of a fluid supply device including a bellows reservoir 80 defining a chamber 81, the size of which is variable by an operation device comprising a remote controlled electric motor 82. The reservoir 80 and the motor 82 are placed in a housing 83. Moving a large wall 84 varies the chamber 81. The wall 84 is secured to a nut 85, which is threaded on a rotatable spindle 86. The spindle 86 is rotated by the motor 82. A battery 89 placed in the housing 83 powers the motor 82. A signal receiver 90 for controlling the motor 82 is also placed in the housing 83. Alternatively, the battery 89 and the signal receiver 90 may be mounted in a separate place. The motor 82 may also be powered with energy transferred from transmitted signals.

Where applicable, the fluid supply device of FIG. 32 may be used for supplying hydraulic fluid for the operation of the constriction devices described in this specification. For example, the fluid supply device of FIG. 32 may be substituted for the reservoir 74 in the embodiment according to FIG. 30A.

Figure 33A:
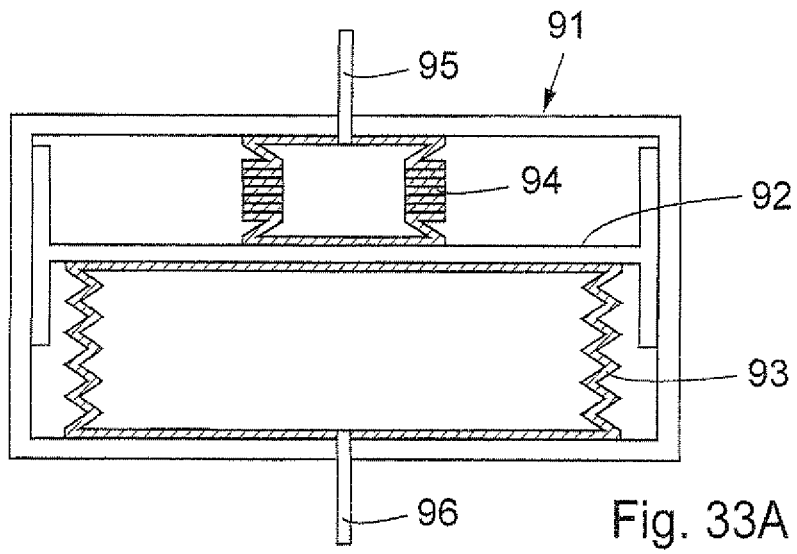
FIGS. 33A and 33B are perspective views of a reverse servo in accordance with a particular embodiment of the hydraulic operation principle shown in FIG. 31C.
Figure 33B:
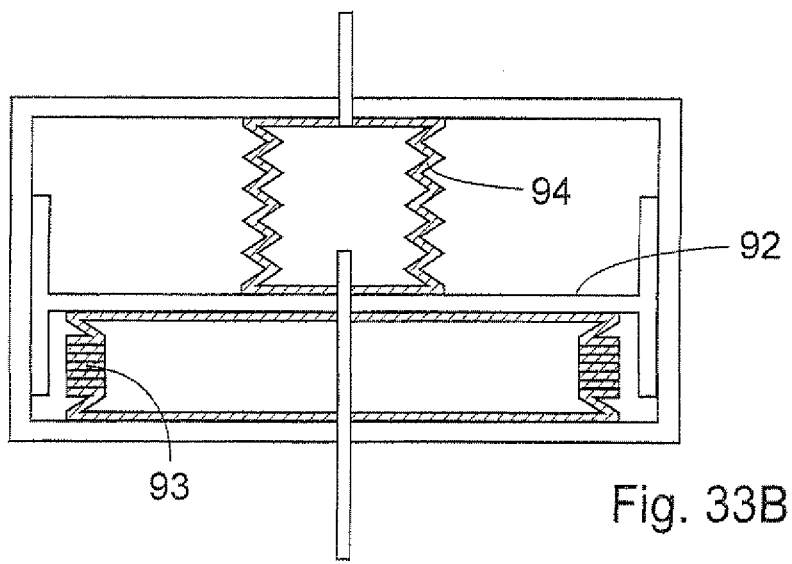

FIGS. 33A and 33B show a reverse servo used for practicing the method of the invention. The reverse servo includes a rectangular housing 91 and an intermediate wall 92, which is movable in the housing 91. A relatively large, substantially cylindrical bellows reservoir 93 is arranged in the housing 91 and is joined to the movable intermediate wall 92. Another cylindrical bellows reservoir 94, which is substantially smaller than reservoir 93, is arranged in the housing 91 at the other side of the intermediate wall 92 and is also joined to the wall 92. The small bellows reservoir 94 has a fluid supply pipe 95 and the large bellows reservoir 93 has a fluid supply pipe 96.

Referring to FIG. 33A, when a small amount of hydraulic fluid is conducted through the supply pipe 95 into the small bellows reservoir 94, the small bellows reservoir 94 expands and pushes the movable intermediate wall 92 towards the large bellows reservoir 93. As a result, the large bellows reservoir 93 is contracted by the intermediate wall 92, whereby a large amount of hydraulic fluid is forced out of the large bellows reservoir 93 through the supply pipe 96, see FIG. 33B.

For example, the reverse servo of FIGS. 33A and 33B may be used in the embodiment of FIG. 31c, wherein the small bellows reservoir 94 corresponds to the small servo reservoir 78 and the large bellows reservoir 93 corresponds to the large reservoir 79. Also, the reverse servo of FIGS. 33A and 33B may be used in the embodiment of FIGS. 30A and 30B, wherein the small bellows reservoir 94 is connected to the adjustable reservoir 74 and the large bellows reservoir 93 is connected to the cavity 73 of the band 72.

Figure 34:
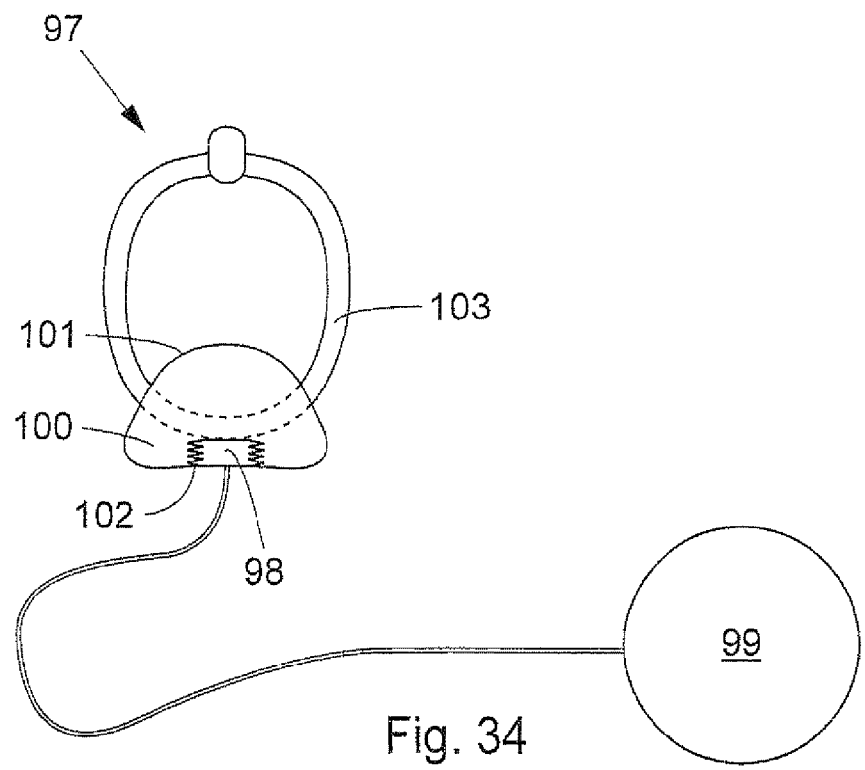
FIG. 34 is a schematic view of another hydraulically operable constriction device for practicing the method according to the present invention.

FIG. 34 schematically shows a hydraulically operable constriction device 97, which is similar to the embodiment shown in FIG. 30A, except that the hydraulic system is designed differently. Thus, the constriction device 97 includes a relatively small inflatable cavity 98, which is in fluid communication with a reservoir 99 containing hydraulic fluid, and a relatively large cavity 100, which is displaceable by small cavity 98. Small cavity 98 is adapted to displace large cavity 100 to constrict the patient's tubular wall portion when small cavity 98 is inflated and to displace large cavity 100 to release the wall portion when small cavity 98 is deflated. Thus, a relatively small addition of hydraulic fluid from reservoir 99 to small cavity 98 causes a relatively large increase in the constriction of the wall portion.

Large cavity 100 is defined by a contraction element in the form of a big balloon 101, which may be connected to an injection port (not shown) for calibration of the volume of large cavity 100. Adding fluid to or withdrawing fluid from the injection port with the aid of a syringe calibrates the volume of balloon 101. Small cavity 98 is defined by a small bellows 102 attached to an annular frame 103 of constriction device 97 and at the opposite end is attached to balloon 101.

Figure 35A:
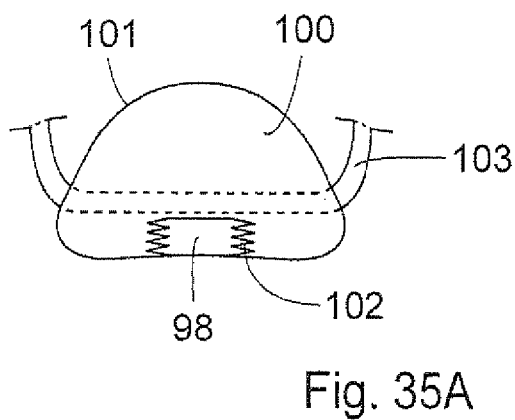
FIG. 35A illustrates the constriction device of FIG. 34 in a constricted state.
Figure 35B:
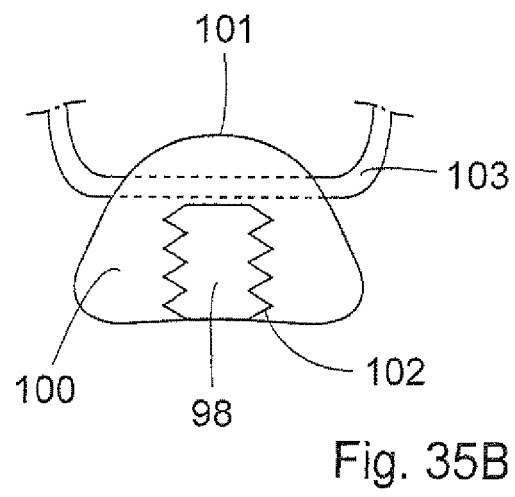
FIG. 35B illustrates the constriction device of FIG. 34 in a released state.
Figure 36:
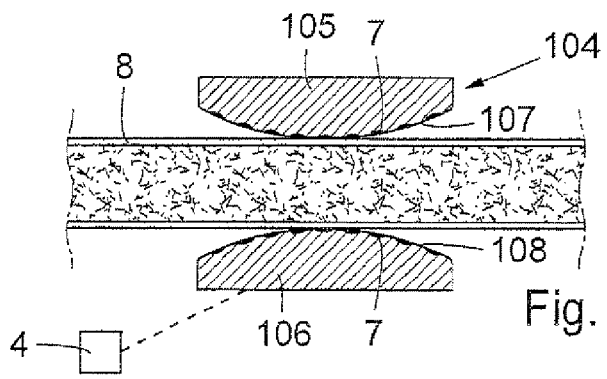
FIGS. 36A-36E schematically illustrate different operation stages of an embodiment of the invention, in which a constriction device and a stimulation device used for practicing the method of the invention co-operate to move the fluid and/or other bodily matter in the lumen of a patient's organ.
Figure 36:
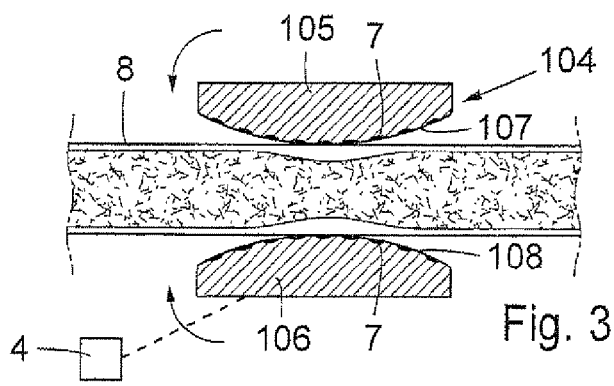
Figure 36:
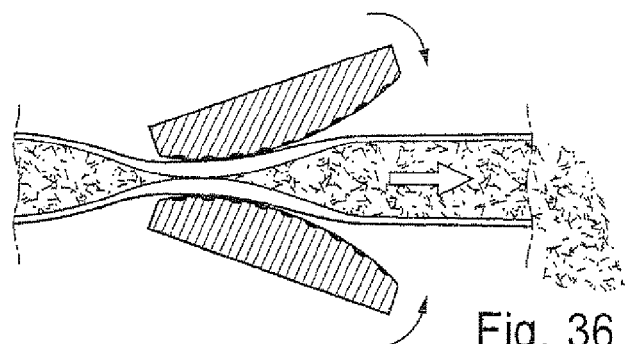
Figure 36:
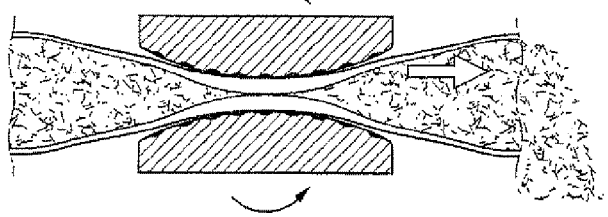
Figure 36:
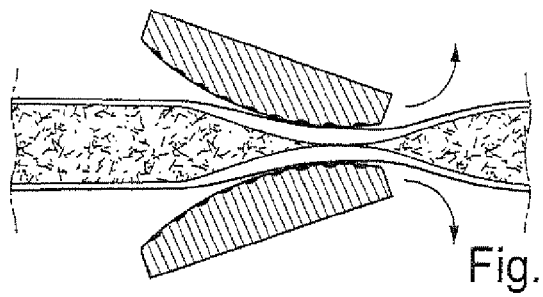

FIGS. 35A and 35B schematically illustrate the operation of constriction device 97, when annular frame 103 is applied around the tubular wall portion of the patient's organ. Referring to FIG. 35A, when small cavity 98 is deflated bellows 102 pulls balloon 101 inwardly into annular frame 103, so that constriction device 97 constricts the wall portion. Referring to FIG. 34B, when small cavity 98 is inflated bellows 102 pulls balloon 101 out of annular frame 103, so that constriction device 97 releases the wall portion.

As mentioned above, the constriction device and stimulation device can co-operate to actively move the fluid and/or other bodily matter in the lumen of a patient's organ. This can be practised by use of the constriction/stimulation unit according to FIG. 2. Thus, in accordance with a first cooperation option, the clamping elements 5, 6 of the constriction device constricts the wall portion 8 without completely closing the lumen, and the control device 4 controls the electrical elements 7 to progressively stimulate the constricted wall portion in the downstream or upstream direction of the lumen to cause progressive contraction of the wall portion 8 to move the fluid and/or other bodily matter in the lumen.

In accordance with a second cooperation option, the constriction device constricts the wall portion so that the flow in the lumen is restricted, and the control device 4 controls a few electrical elements 7 at one end of the elongate clamping elements 5, 6 to stimulate the constricted wall portion 8 to close the lumen either at an upstream end or a downstream end of the wall portion 8. With the lumen closed in this manner, the control device 4 controls the constriction device to increase the constriction of the wall portion, whereby the fluid and/or other bodily matter in the lumen is moved downstream or upstream of the wall portion 8.

Alternatively, the control device 4 controls the stimulation device to stimulate the constricted wall portion 8 while the constriction device varies the constriction of the different areas of the wall portion, so that the wall portion 8 is progressively constricted in the downstream or upstream direction of the lumen. FIGS. 36A-36E show different operation stages of such an alternative embodiment. Thus, a constriction device 104 used for practicing the method of the invention includes two elongate constriction elements 105, 106 having convex surfaces 107, 108 that abut a length of the wall portion 8 on mutual sides thereof. A multiplicity of electrical elements 7 (such as electrodes) are positioned on the convex surfaces 107, 108. The control device 4 controls the electrical elements 7 during operation of the constriction device 104 to stimulate the wall portion 8 and controls the elongate constriction elements 105, 106 to move relative to the tubular wall portion 8 so that the constriction elements 105, 106 progressively constrict the wall portion 8, as appears from FIGS. 36A to 36D.

Thus, in an initial position of the constriction elements 105, 106 shown in FIG. 36A, the wall portion is not constricted by the constriction elements 105, 106 and the electrical elements 7 are not energized. Starting from this initial position, the control device 4 controls the constriction elements 105, 106 to swing the left ends of the constriction elements 105, 106 toward the wall portion (indicated by arrows) to constrict the tubular wall portion 8, see FIG. 36B, while energizing the electrical elements 7, so that the electrical elements 7 that contact the wall portion 8 contract the latter. FIG. 36C shows how the lumen of the tubular wall portion 8 is completely closed by the thickened wall portion 8. Then, as shown in FIG. 36C, the control device 4 controls the constriction elements 105, 106 to move so that their right ends are moving towards each other (indicated by arrows), while the convex surfaces 107, 108 of the constriction elements 105, 106 are rolling on each other with the contracted wall portion 8 between them, see FIG. 36D. As a result, the bodily matter in the lumen of the organ is forced to the right (indicated by a white arrow). When the constriction elements 105, 106 have rolled on each other to the position shown in FIG. 36E, the control device 4 controls the right ends of the constriction elements 105, 106 to move away from each other (indicated by arrows in FIG. 36E) to the initial position shown in FIG. 36A. The operation stages described according to FIGS. 36A to 36E can be cyclically repeated a number of times until the desired amount of bodily matter has been moved in the lumen of the organ in a peristaltic manner.

Alternatively, only one of the constriction elements 105, 106 can be provided with a convex surface, whereas the other constriction element has a plane surface that abuts the wall portion. It is also possible to use a single constriction element with a convex surface that presses the tubular portion 8 of the organ against a bone of the patient.

In the embodiment according to FIGS. 36A to 36E, the control device 4 may control the electrical elements 7 to progressively stimulate the constricted wall portion 8 to cause progressive contraction thereof in harmony with the movement of the elongate constriction elements 105, 106, as the convex surfaces 107, 108 of the constriction elements 105, 106 are rolling on each other.

Figure 37:
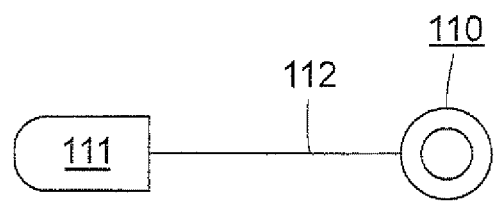
FIGS. 37 to 49 are schematic block diagrams illustrating twelve embodiments, respectively, of an apparatus used for practicing the method of the invention, wherein wireless energy is transmitted from outside a patient's body to energy consuming components of the apparatus implanted in the patient.

FIG. 37 schematically shows a general embodiment of the apparatus of the invention, in which energy is transferred to energy consuming components of the apparatus implanted in the patient.

The apparatus of FIG. 37 comprises an implanted constriction/stimulation unit 109, which is operable to gently constrict a portion of a tubular tissue wall of a patient's organ and to stimulate different areas of the constricted portion to cause contraction of the wall portion. The constriction device of the constriction/stimulation unit 110 is capable of performing a reversible function, i.e., to constrict and release the wall portion, so that the constriction/stimulation unit 110 works as an artificial sphincter.

A source of energy 111 is adapted to supply energy consuming components of the constriction/stimulation unit 110 with energy via a power supply line 112. A wireless remote control or a subcutaneously implanted switch operable by the patient to switch on or off the supply of energy from the source of energy may be provided. The source of energy may be an implantable permanent or rechargeable battery, or be included in an external energy-transmission device, which may be operable directly by the patient or be controlled by a remote control operable by the patient to transmit wireless energy to the energy consuming components of the constriction/stimulation unit. Alternatively, the source of energy may comprise a combination of an implantable rechargeable battery, an external energy-transmission device and an implantable energy-transforming device for transforming wireless energy transmitted by the external energy-transmission device into electric energy for the charge of the implantable rechargeable battery.

Figure 38:
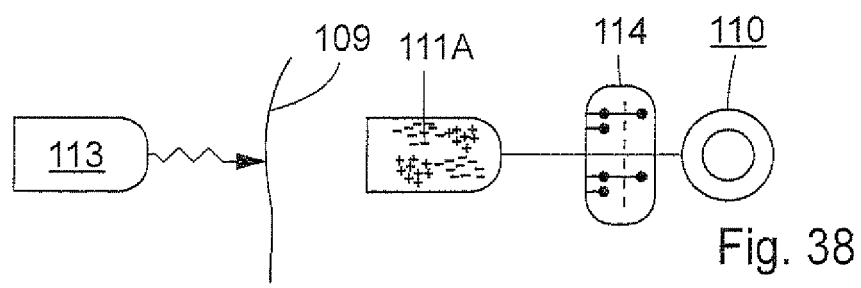

FIG. 38 shows a special embodiment of the general embodiment of FIG. 37 having some parts implanted in a patient and other parts located outside the patient's body. Thus, in FIG. 38 all parts placed to the right of the patient's skin 109 are implanted and all parts placed to the left of the skin 109 are located outside the patient's body. An implanted energy-transforming device 111A of the apparatus is adapted to supply energy consuming components of the constriction/stimulation unit 110 with energy via the power supply line 112. An external energy-transmission device 113 of the apparatus includes a wireless remote control transmitting a wireless signal, which is received by a signal receiver incorporated in the implanted energy-transforming device 111A. The implanted energy-transforming device 111A transforms energy from the signal into electric energy which is supplied via the power supply line 112 to the constriction/stimulation unit 110.

The apparatus of FIG. 3 (may also include an implanted rechargeable battery for energizing energy consuming implanted components of the apparatus. In this case, the implanted energy-transforming device 111A also charges the battery with electric energy, as the energy-transforming device transforms energy from the signal into the electric energy.

A reversing device in the form of an electric switch 114, such as a microprocessor, is implanted in the patient for reversing the constriction device of the constriction/stimulation unit 110. The wireless remote control of the external energy-transmission device 113 transmits a wireless signal that carries energy and the implanted energy-transforming device 111A transforms the wireless energy into a current for operating the switch 114. When the polarity of the current is shifted by the energy-transforming device 111A the switch 114 reverses the function performed by the constriction device of the constriction/stimulation unit 110.

Figure 39:
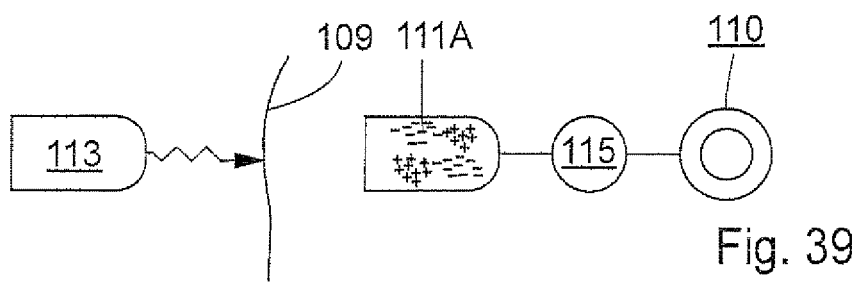

FIG. 39 shows another embodiment of the invention including the energy-transforming device 111A, the constriction/stimulation unit 110 and an operation device in the form of a motor 115 for operating the constriction device of the constriction/stimulation unit 110. The motor 115 is powered with energy from the energy-transforming device 111A, as the remote control of the external energy-transmission device 113 transmits a wireless signal to the receiver of the energy-transforming device 111A.

Figure 40:
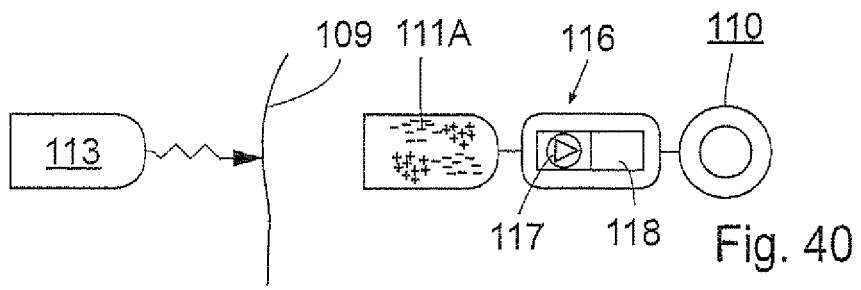

FIG. 40 shows yet another embodiment of the invention including the energy-transforming device 111A, the constriction/stimulation unit 110 and an assembly 116 including a motor/pump unit 117 and a fluid reservoir 118. In this case the constriction device of the constriction/stimulation unit 110 is hydraulically operated, i.e., hydraulic fluid is pumped by the motor/pump unit 117 from the reservoir 118 to the constriction/stimulation unit 110 to constrict the wall portion, and hydraulic fluid is pumped by the motor/pump unit 117 back from the constriction/stimulation unit 110 to the reservoir 118 to release the wall portion. The implanted energy-transforming device 111A transforms wireless energy into a current, for powering the motor/pump unit 117.

Figure 41:
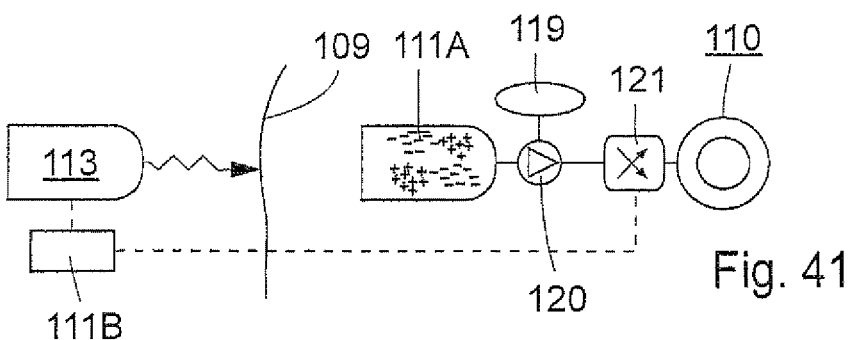

FIG. 41 shows another embodiment of an apparatus used for practicing the method of the invention. The apparatus of FIG. 41 comprises the external energy-transmission device 113 that controls the control unit 122 to reverse the motor 115 when needed, the constriction/stimulation unit 110, the constriction device of which is hydraulically operated, and the implanted energy-transforming device 111A, and further comprises an implanted hydraulic fluid reservoir 119, an implanted motor/pump unit 120, an implanted reversing device in the form of a hydraulic valve shifting device 121 and a separate external wireless remote control 111B. The motor of the motor/pump unit 120 is an electric motor. In response to a control signal from the wireless remote control of the external energy-transmission device 113, the implanted energy-transforming device 111A powers the motor/pump unit 120 with energy from the energy carried by the control signal, whereby the motor/pump unit 120 distributes hydraulic fluid between the reservoir 119 and the constriction device of the constriction/stimulation unit 110. The remote control 111B controls the shifting device 121 to shift the hydraulic fluid flow direction between one direction in which the fluid is pumped by the motor/pump unit 120 from the reservoir 119 to the constriction device of the constriction/stimulation unit 110 to constrict the wall portion, and another opposite direction in which the fluid is pumped by the motor/pump unit 120 back from the constriction device of the constriction/stimulation unit 110 to the reservoir 119 to release the wall portion.

Figure 42:
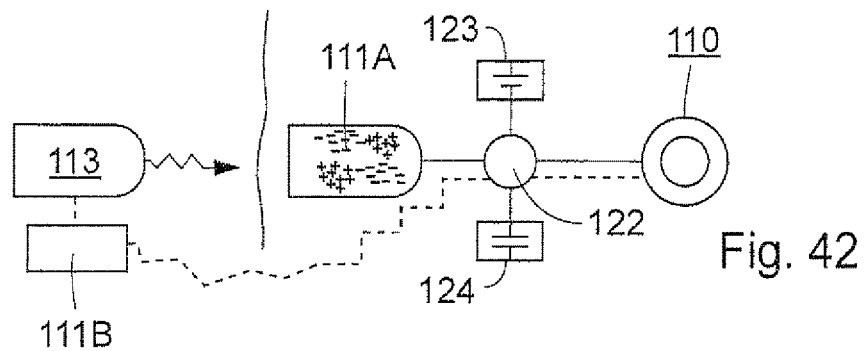

FIG. 42 shows an embodiment of the invention including the energy-transforming device 111A and the constriction/stimulation unit 110. A control unit 122, an accumulator 123 and a capacitor 124 are also implanted in the patient. A separate external wireless remote control 111B controls the control unit 122. The control unit 122 controls the energy-transforming device 111A to store electric energy in the accumulator 123, which supplies energy to the constriction/stimulation unit 110. In response to a control signal from the wireless remote control 111B, the control unit 122 either releases electric energy from the accumulator 123 and transfers the released energy via power lines, or directly transfers electric energy from the energy-transforming device 111A via the capacitor 124, which stabilizes the electric current, for the operation of the constriction/stimulation unit 110.

In accordance with one alternative, the capacitor 124 in the apparatus of FIG. 42 may be omitted. In accordance with another alternative, the accumulator 123 in this apparatus may be omitted.

Figure 43:
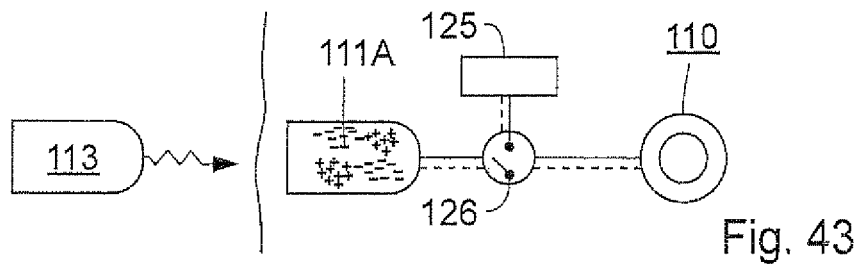

FIG. 43 shows an embodiment of the invention including the energy-transforming device 111A, the constriction/stimulation unit 110. A battery 125 for supplying energy for the operation of the constriction/stimulation unit 110 and an electric switch 126 for switching the operation of the constriction/stimulation unit 110 are also implanted in the patient. The switch 126 is operated by the energy supplied by the energy-transforming device 111A to switch from an off mode, in which the battery 125 is not in use, to an on mode, in which the battery 125 supplies energy for the operation of the constriction/stimulation unit 110.

Figure 44:
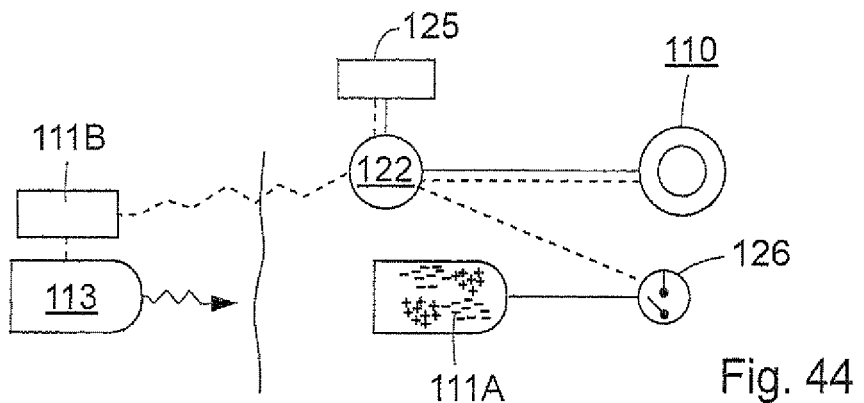

FIG. 44 shows an apparatus identical to that of FIG. 43, except that a control unit 122 also is implanted in the patient. A separate external wireless remote control 111B controls the control unit 122. In this case, the switch 126 is operated by the energy supplied by the energy-transforming device 111A to switch from an off mode, in which the wireless remote control 111B is prevented from controlling the control unit 122 and the battery 125 is not in use, to a standby mode, in which the remote control 111B is permitted to control the control unit 122 to release electric energy from the battery 125 for the operation of the constriction/stimulation unit 110.

Figure 45:
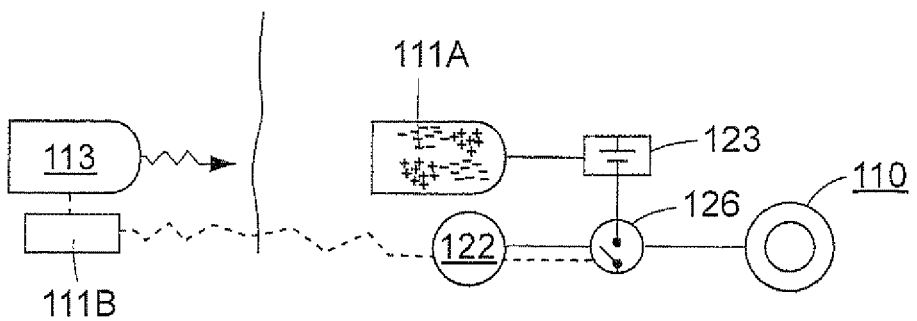

FIG. 45 shows an apparatus identical to that of FIG. 44, except that the accumulator 123 is substituted for the battery 125 and the implanted components are interconnected differently. In this case, the accumulator 123 stores energy from the energy-transforming device 111A. In response to a control signal from the wireless remote control 111B, the implanted control unit 122 controls the switch 126 to switch from an off mode, in which the accumulator 123 is not in use, to an on mode, in which the accumulator 123 supplies energy for the operation of the constriction/stimulation unit 110.

Figure 46:
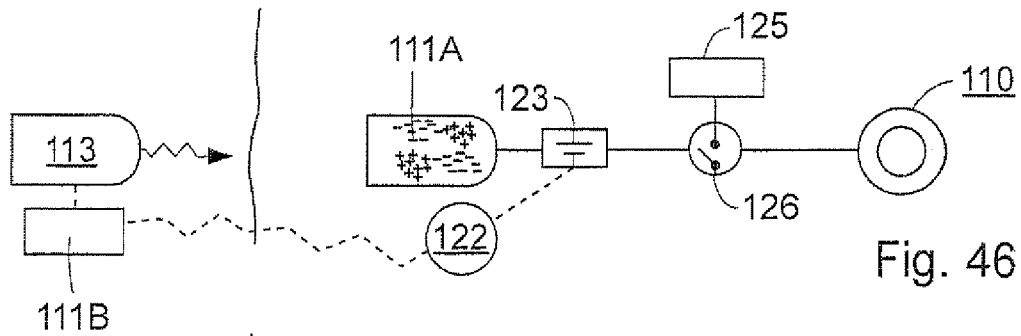

FIG. 46 shows an apparatus identical to that of FIG. 45, except that the battery 125 also is implanted in the patient and the implanted components are interconnected differently. In response to a control signal from the wireless remote control 111B, the implanted control unit 122 controls the accumulator 123, which may be a capacitor, to deliver energy for operating the switch 126 to switch from an off mode, in which the battery 125 is not in use, to an on mode, in which the battery 125 supplies electric energy for the operation of the constriction/stimulation unit 110.

Alternatively, the switch 126 may be operated by energy supplied by the accumulator 123 to switch from an off mode, in which the wireless remote control 111B is prevented from controlling the battery 125 to supply electric energy and the battery 125 is not in use, to a standby mode, in which the wireless remote control 111B is permitted to control the battery 125 to supply electric energy for the operation of the constriction/stimulation unit 110.

Figure 47:
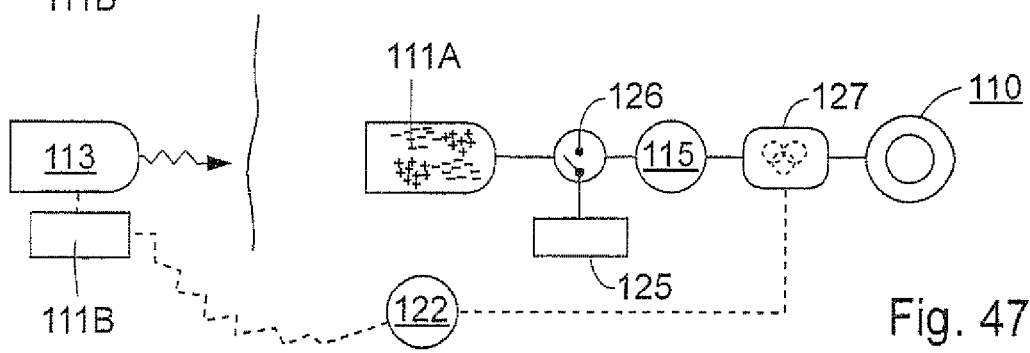

FIG. 47 shows an apparatus identical to that of FIG. 43, except that a motor 115, a mechanical reversing device in the form of a gearbox 127 and a control unit 122 for controlling the gearbox 127 also are implanted in the patient. A separate external wireless remote control 111B controls the implanted control unit 122 to control the gearbox 127 to reverse the function performed by the constriction device (mechanically operated) of the constriction/stimulation unit 110.

Figure 48:
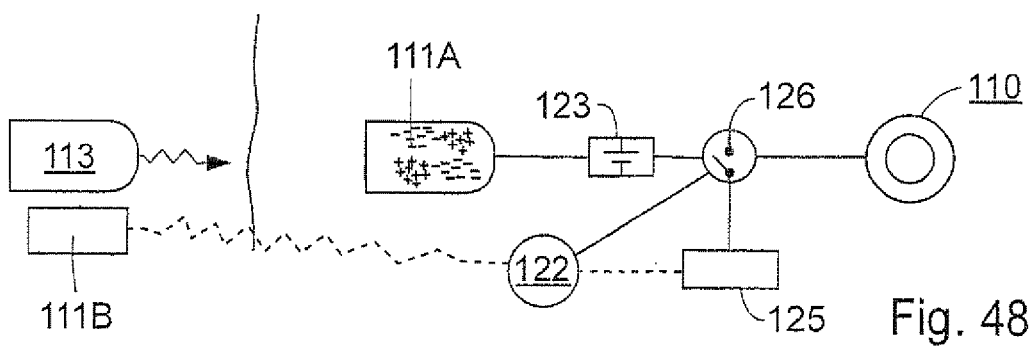

FIG. 48 shows an apparatus identical to that of FIG. 46 except that the implanted components are interconnected differently. Thus, in this case the battery 125 powers the control unit 122 when the accumulator 123, suitably a capacitor, activates the switch 126 to switch to an on mode. When the switch 126 is in its on mode the control unit 122 is permitted to control the battery 125 to supply, or not supply, energy for the operation of the constriction/stimulation unit 110.

Figure 49:
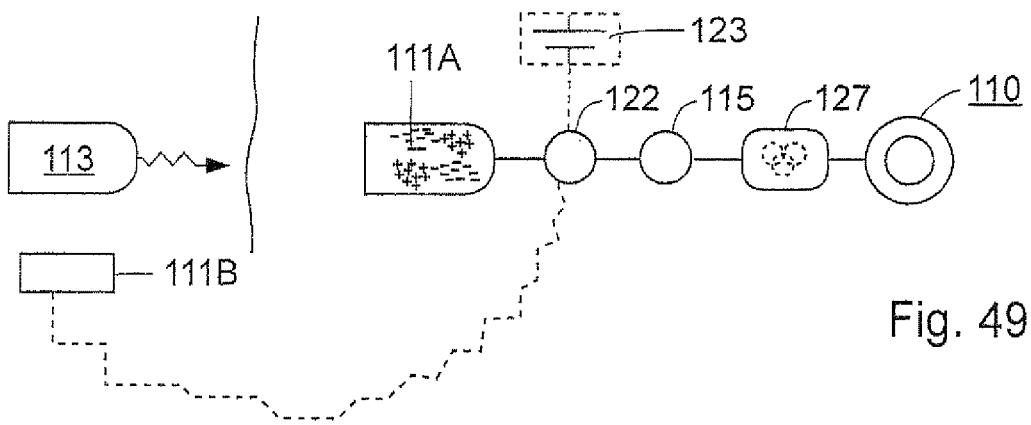

FIG. 49 shows an embodiment of the invention identical to that of FIG. 39, except that a gearbox 127 that connects the motor 115 to the constriction/stimulation unit 110, and a control unit 122 that controls the energy-transforming device 111A to power the motor 115 also are implanted in the patient. There is a separate external wireless remote control 111B that controls the control unit 122 to reverse the motor 115 when needed.

Optionally, the accumulator 123 shown in FIG. 42 may be provided in the embodiment of FIG. 49, wherein the implanted control unit 122 controls the energy-transforming device 111A to store the transformed energy in the accumulator 123. In response to a control signal from the wireless remote control 111B, the control unit 122 controls the accumulator 123 to supply energy for the operation of the constriction/stimulation unit 110.

Any of the apparatuses of FIGS. 36-49 can be used for practicing the method of the invention.

Those skilled in the art will realise that the above various embodiments according to FIGS. 38-49 could be combined in many different ways. For example, the energy operated switch 114 could be incorporated in any of the embodiments of FIGS. 39, 42-49, the hydraulic shifting device 121 could be incorporated in the embodiment of FIG. 40, and the gearbox 127 could be incorporated in the embodiment of FIG. 39. The switch 114 may be of a type that includes electronic components, for example a microprocessor, or a FGPA (Field Programmable Gate Array) designed for switching. Alternatively, however, the energy operated switch 114 may be replaced by a subcutaneously implanted push button that is manually switched by the patient between "on" and "off".

Alternatively, a permanent or rechargeable battery may be substituted for the energy-transforming devices 111A of the embodiments shown in FIGS. 38-49.

Figure 50:
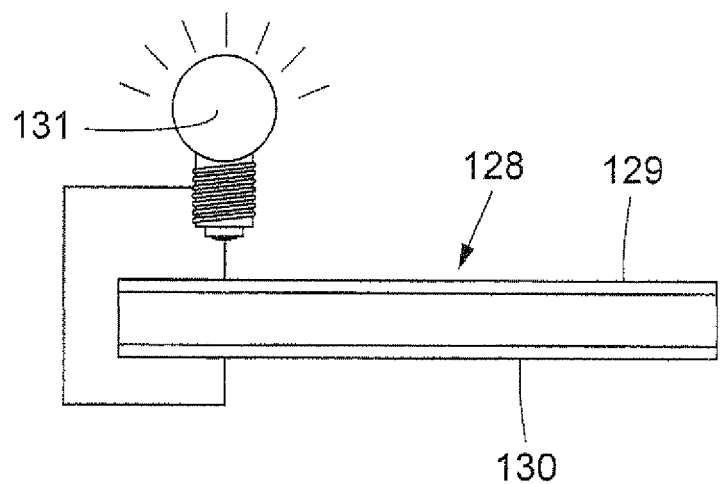
FIG. 50 illustrates an energy-transforming device in the form of an electrical junction element used for practicing the method of the invention.

FIG. 50 shows the energy-transforming device in the form of an electrical junction element 128 for use in any of the above embodiments according to FIGS. 37-49. The element 128 is a flat p-n junction element comprising a p-type semiconductor layer 129 and an n-type semiconductor layer 130 sandwiched together. A light bulb 131 is electrically connected to opposite sides of the element 128 to illustrate how the generated current is obtained. The output of current from such a p-n junction element 128 is correlated to the temperature. See the formula below.

$$I = I0(\exp(qV/kT) - 1)$$

where
I is the external current flow,
I0 is the reverse saturation current,
q is the fundamental electronic charge of $1.602 \times 10\text{-}19$ coulombs,
V is the applied voltage,
k is the Boltzmann constant, and
T is the absolute temperature.

Under large negative applied voltage (reverse bias), the exponential term becomes negligible compared to 1.0, and I is approximately −I0. I0 is strongly dependent on the temperature of the junction and hence on the intrinsic-carrier concentration. I0 is larger for materials with smaller bandgaps than for those with larger bandgaps. The rectifier action of the diode, that is, its restriction of current flow to only one direction, is in this particular embodiment the key to the operation of the p-n junction element 128.

The alternative way to design a p-n junction element is to deposit a thin layer of semiconductor onto a supporting material which does not absorb the kind of energy utilized in the respective embodiments. For use with wirelessly transmitted energy in terms of light waves, glass could be a suitable material. Various materials may be used in the semiconductor layers such as but not limited to cadmium telluride, copper-indium-diselenide and silicon. It is also possible to use a multilayer structure with several layers of p and n-type materials to improve efficiency.

The electric energy generated by the p-n junction element 128 could be of the same type as generated by solar cells, in which the negative and positive fields create a direct current. Alternatively, the negative and positive semiconductor layers may change polarity following the transmitted waves, thereby generating the alternating current.

The p-n junction element 128 is designed to make it suited for implantation. Thus, all the external surfaces of the element 128 in contact with the human body are made of a biocompatible material. The p-n junction semiconductors are designed to operate optimally at a body temperature of 37° C. because the current output, which should be more than 1 µA, is significantly depending on temperature as shown above. Since both the skin and subcutis absorb energy, the relation between the sensitivity or working area of the element 128 and the intensity or strength of the wireless energy-transmission is considered. The p-n junction element 128 preferably is designed flat and small. Alternatively, if the element 128 is made in larger sizes it should be flexible, in order to adapt to the patient's body movements. The volume of the element 128 should be kept less than 2000 cm$^3$.

Figure 51:
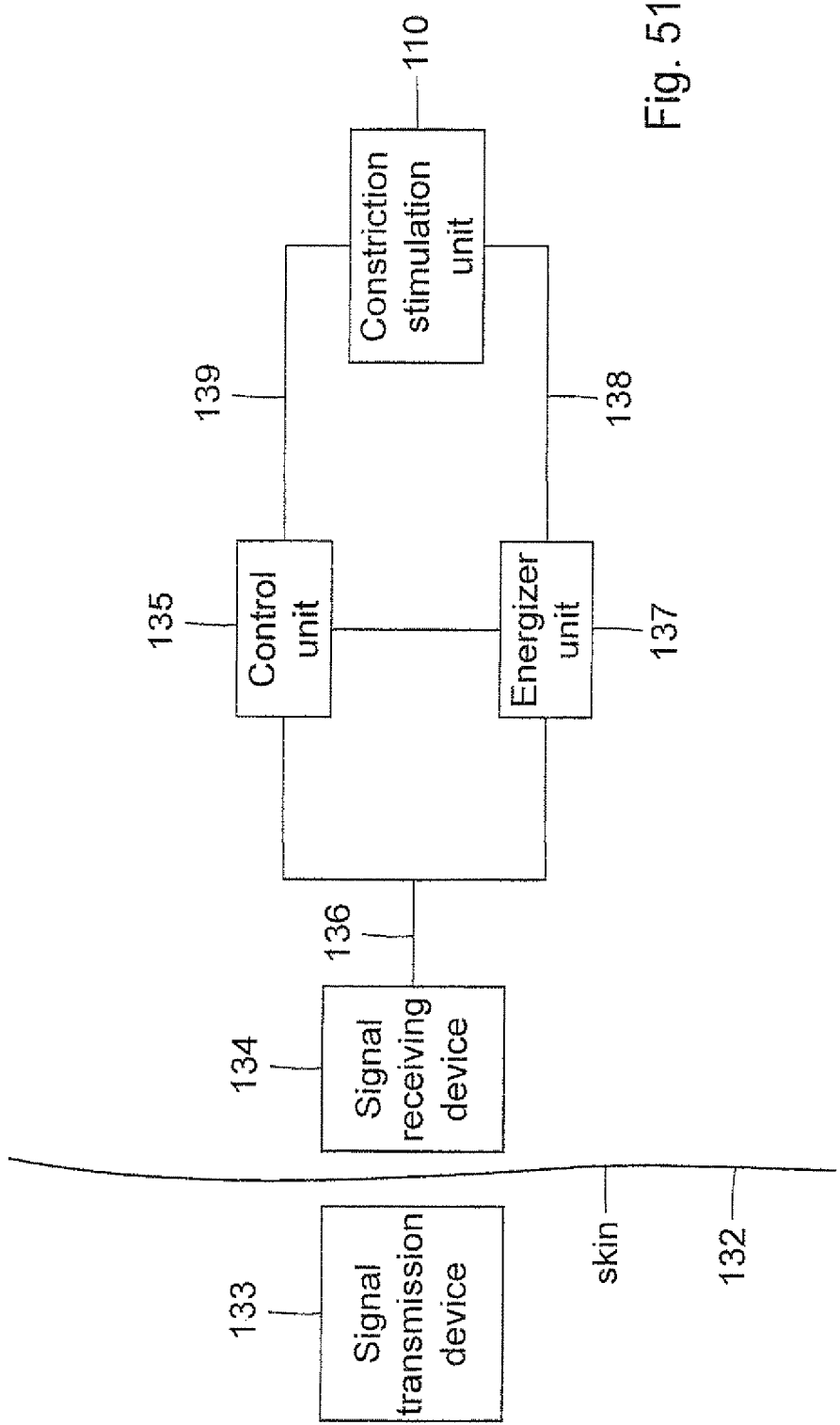
FIG. 51 is a block diagram illustrating control components used for practicing the method of the invention.

FIG. 51 shows basic parts of a remote control used for practicing the method of the invention. The remote control controls the constriction/stimulation unit 110. In this case, the stimulation device of the constriction/stimulation unit stimulates the wall portion of the patient's organ with electric pulses. The remote control is based on wireless transmission of electromagnetic wave signals, often of high frequencies in the order of 100 kHz-1 gHz, through the skin 132 of the patient. In FIG. 51, all parts placed to the left of the skin 132 are located outside the patient's body and all parts placed to the right of the skin 132 are implanted.

An external signal-transmission device 133 is to be positioned close to a signal-receiving device 134 implanted close to the skin 132. As an alternative, the signal-receiving device 134 may be placed for example inside the abdomen of the patient. The signal-receiving device 134 comprises a coil, approximately 1-100 mm, preferably 25 mm in diameter, wound with a very thin wire and tuned with a capacitor to a specific high frequency. A small coil is chosen if it is to be implanted under the skin of the patient and a large coil is chosen if it is to be implanted in the abdomen of the patient. The signal transmission device 133 comprises a coil having about the same size as the coil of the signal-receiving device 134 but wound with a thick wire that can handle the larger currents that is necessary. The coil of the signal transmission device 133 is tuned to the same specific high frequency as the coil of the signal-receiving device 134.

The signal-transmission device 133 is adapted to send digital information via the power amplifier and signal-receiving device 134 to an implanted control unit 135. To avoid that accidental random high frequency fields trigger control commands, digital signal codes are used. A conventional keypad placed on the signal transmission device 133 is used to order the signal transmission device 133 to send digital signals for the control of the constriction/stimulation unit. The signal transmission device 133 starts a command by generating a high frequency signal. After a short time, when the signal has energized the implanted parts of the control system, commands are sent to operate the constriction device of the constriction/stimulation unit 110 in predefined steps. The commands are sent as digital packets in the form illustrated below.

| Start pattern, 8 bits | Command, 8 bits | Count, 8 bits | Checksum, 8 bits |
| --- | --- | --- | --- |

The commands are sent continuously during a rather long time period (e.g. about 30 seconds or more). When a new constriction or release step is desired the Count byte is increased by one to allow the implanted control unit 135 to decode and understand that another step is demanded by the signal transmission device 133. If any part of the digital packet is erroneous, its content is simply ignored.

Through a line 136, an implanted energizer unit 137 draws energy from the high frequency electromagnetic wave signals received by the signal-receiving device 134. The energizer unit 137 stores the energy in a source of energy, such as a large capacitor, powers the control unit 135 and powers the constriction/stimulation unit 110 via a line 138.

The control unit 135 comprises a demodulator and a microprocessor. The demodulator demodulates digital signals sent from the signal transmission device 133. The microprocessor receives the digital packet, decodes it and sends a control signal via a signal line 139 to control the constriction device of the constriction/stimulation unit 110 to either constrict or release the wall portion of the patient's organ depending on the received command code.

Figure 52:
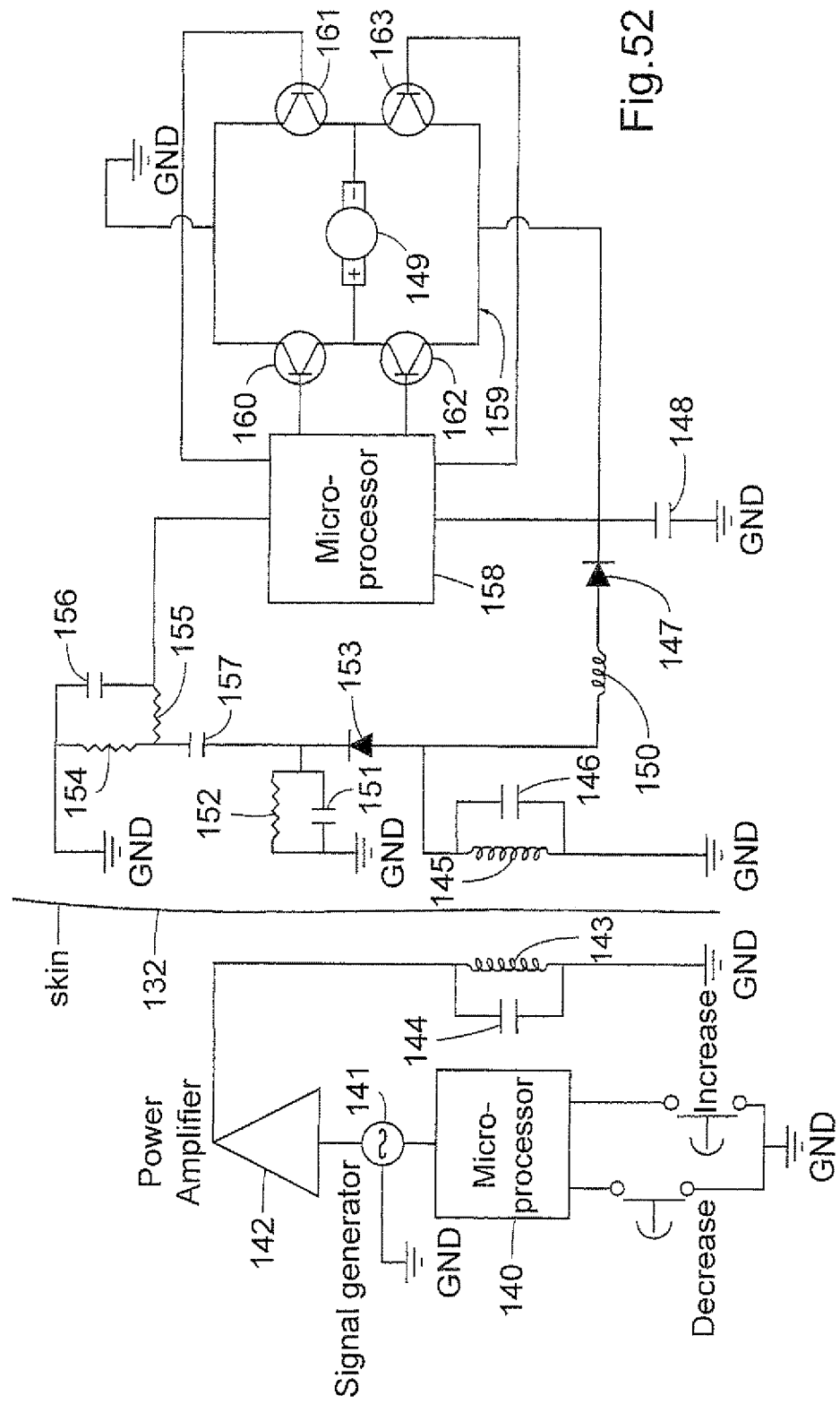
FIG. 52 is a schematic view of exemplary circuitry of an embodiment of the invention, in which wireless energy is transformed into a current.

FIG. 52 shows a circuitry of an embodiment of the invention, in which wireless energy is transformed into a current. External components of the circuitry include a microprocessor 140, a signal generator 141 and a power amplifier 142 connected thereto. The microprocessor 140 is adapted to switch the signal generator 141 on/off and to modulate signals generated by the signal generator 141 with digital commands. The power amplifier 142 amplifies the signals and sends them to an external signal-transmitting antenna 143. The antenna 143 is connected in parallel with a capacitor 144 to form a resonant circuit tuned to the frequency generated by the signal generator 141.

Implanted components of the circuitry include a signal receiving antenna coil 145 and a capacitor 146 forming together a resonant circuit that is tuned to the same frequency as the transmitting antenna 143. The signal receiving antenna coil 145 induces a current from the received high frequency electromagnetic waves and a rectifying diode 147 rectifies the induced current, which charges a storage capacitor 148. The storage capacitor 148 powers a motor 149 for driving the constriction device of the constriction/stimulation unit 110. A coil 150 connected between the antenna coil 145 and the diode 147 prevents the capacitor 148 and the diode 147 from loading the circuit of the signal-receiving antenna 145 at higher frequencies. Thus, the coil 150 makes it possible to charge the capacitor 148 and to transmit digital information using amplitude modulation.

A capacitor 151 and a resistor 152 connected in parallel and a diode 153 forms a detector used to detect amplitude modulated digital information. A filter circuit is formed by a resistor 154 connected in series with a resistor 155 connected in series with a capacitor 156 connected in series with the resistor 154 via ground, and a capacitor 157, one terminal of which is connected between the resistors 154,155 and the other terminal of which is connected between the diode 153 and the circuit formed by the capacitor 151 and resistor 152. The filter circuit is used to filter out undesired low and high frequencies. The detected and filtered signals are fed to an implanted microprocessor 158 that decodes the digital information and controls the motor 149 via an H-bridge 159 comprising transistors 160,161,162 and 163. The motor 149 can be driven in two opposite directions by the H-bridge 159.

The microprocessor 158 also monitors the amount of stored energy in the storage capacitor 148. Before sending signals to activate the motor 149, the microprocessor 158 checks whether the energy stored in the storage capacitor 148 is enough. If the stored energy is not enough to perform the requested operation, the microprocessor 158 waits for the received signals to charge the storage capacitor 148 before activating the motor 149.

Alternatively, the energy stored in the storage capacitor 148 may only be used for powering a switch, and the energy for powering the motor 149 may be obtained from another implanted energy source of relatively high capacity, for example a battery. In this case the switch is adapted to connect the battery to the motor 149 in an on mode when the switch is powered by the storage capacitor 148 and to keep the battery disconnected from the motor 149 in a standby mode when the switch is not powered.

Figure 53A:
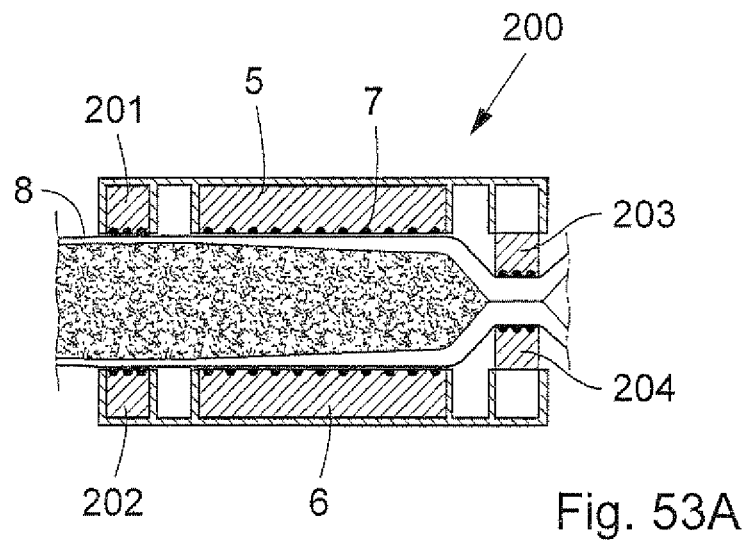
FIGS. 53A-53C schematically illustrate different operation stages of another embodiment of the invention of the type shown in FIG. 2 used for practicing the method of the invention, wherein a constriction device and a stimulation device co-operate to move the fluid and/or other bodily matter in the lumen of a patient's organ.
Figure 53B:
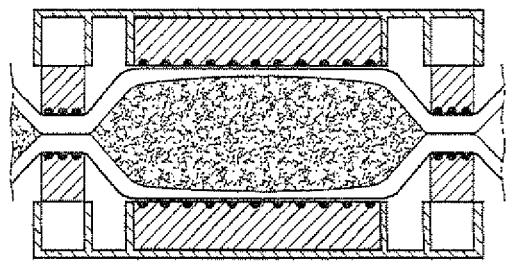
Figure 53C:
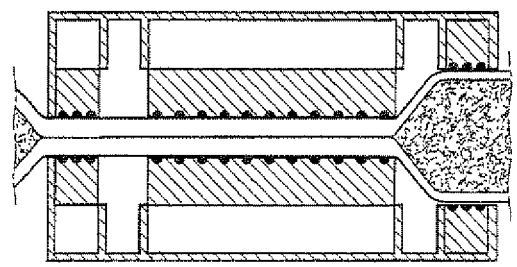

FIGS. 53A-53C show an apparatus used for practicing the method of the invention which is similar to the apparatus of FIG. 2, except that the constriction/stimulation unit, here denoted by reference numeral 200, is provided with additional clamping elements. The apparatus of FIGS. 53A-53C is suited for actively moving the fluid and/or other bodily matter in the lumen of a patient's organ. Thus, the constriction/stimulation unit 200 also includes a first pair of short clamping elements 201 and 202, and a second pair of short clamping elements 203 and 204, wherein the first and second pairs of clamping elements are positioned at mutual sides of the elongate clamping elements 5,6. The two short clamping elements 201, 202 of the first pair are radially movable towards and away from each other between retracted positions (FIG. 53A) and clamping positions (FIGS. 53B and 53C), and the two short clamping elements 203, 204 of the second pair are radially movable towards and away from each other between retracted positions (FIG. 53C) and clamping positions (FIGS. 53A and 53B). The stimulation device 3 also includes electrical elements 7 positioned on the short clamping elements 201-204, so that the electrical elements 7 on one of the short clamping elements 201 and 203, respectively, of each pair of short elements face the electrical elements 7 on the other short clamping element 202 and 204, respectively, of each pair of short elements.

The constriction/stimulation unit 200 is applied on a wall portion 8 of a tubular tissue wall of a patient's organ, so that the short clamping elements 201, 202 are positioned at an upstream end of the wall portion 8, whereas the short clamping elements 203, 204 202 are positioned at a downstream end of the wall portion 8. In FIGS. 53A to 53C the upstream end of the wall portion 8 is to the left and the downstream end of the wall portion 8 is to the right.

The control device 4 controls the pair of short clamping elements 201, 202, the pair of elongate clamping elements 5, 6 and the pair of short elements 203, 204 to constrict and release the wall portion 8 independently of one another. The control device also controls the electrical elements 7 on a clamping element that is constricting the wall portion to stimulate the constricted wall portion 8 with electric pulses to cause contraction of the wall portion 8, so that the lumen of the wall portion 8 is closed.

FIGS. 53A-53C illustrate how the control device 4 controls the operation of the constriction/stimulation unit 200 to cyclically move fluid and/or other bodily matter downstream in the lumen of the wall portion 8. Thus, in FIG. 53A the short clamping elements 201, 202 and the elongate clamping elements 5, 6 are in their retracted positions, whereas the short clamping elements 203, 204 are in their clamping positions while the electrical elements 7 on elements 203, 204 electrically stimulate the wall portion 8. The electrical stimulation causes the wall portion 8 at the elements 203, 204 to thicken, whereby the lumen is closed. FIG. 53B illustrates how also the short clamping elements 201, 202 have been moved radially inwardly to their clamping positions while the electrical elements 7 on elements 201, 202 electrically stimulate the wall portion 8, whereby a volume of bodily matter is trapped in the lumen between the upstream and downstream ends of the wall portion 8. FIG. 53C illustrates how initially the short clamping elements 203, 204 have been moved radially outwardly to their retracted positions, and then the elongate clamping elements 5, 6 have been moved radially inwardly to their clamping positions while the electrical elements 7 on elements 5, 6 electrically stimulate the wall portion 8. As a result, the bodily matter in the lumen between the upstream and downstream ends of the wall portion 8 has been moved downstream in the lumen as indicated by an arrow. Then, the control device 4 controls the constriction/stimulation unit 200 to assume the state shown in FIG. 53A, whereby bodily matter may flow into and fill the lumen between the upstream and downstream ends of the wall portion 8, so that the cycle of the operation is completed.

Alternatively, the operation cycle of the constriction/stimulation unit 200 described above may be reversed, in order to move bodily matter upstream in the lumen. In this case the control device 4 controls the short clamping elements 203, 204 to constrict the wall portion 8 at the downstream end thereof to restrict the flow in the lumen and controls the electric elements 7 to stimulate the constricted wall portion 8 with electric pulses at the downstream end to close the lumen. With the lumen closed at the downstream end of the constricted wall portion 8 and the short clamping elements 201, 202 in their retracted positions, as shown in FIG. 53A, the control device 4 controls the elongate clamping elements 5, 6 to constrict the wall portion 8 between the upstream and downstream ends thereof. As a result, the fluid and/or other bodily matter contained in the wall portion 8 between the upstream and downstream ends thereof is moved upstream in the lumen.

Although FIGS. 53A-53C disclose pairs of clamping elements, it should be noted that it is conceivable to design the constriction/stimulation unit 200 with only a single short clamping element 201, a single elongate clamping element 5 and a single short clamping element 203. In this case the bottom of the tubular wall portion 8 is supported by stationary elements of the constriction/stimulation unit 200 opposite to the clamping elements 201, 5, 203.

Figure 54A:
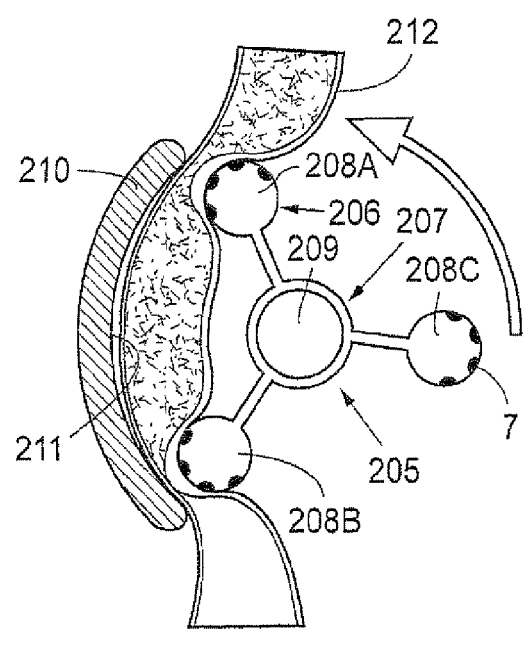
FIGS. 54A-54B schematically illustrate different operation stages of another apparatus of the type shown in FIGS. 36A-36E used for practicing the method of the invention, wherein a constriction device and a stimulation device co-operate to move the fluid and/or other bodily matter in the lumen of a patient's organ.
Figure 54B:
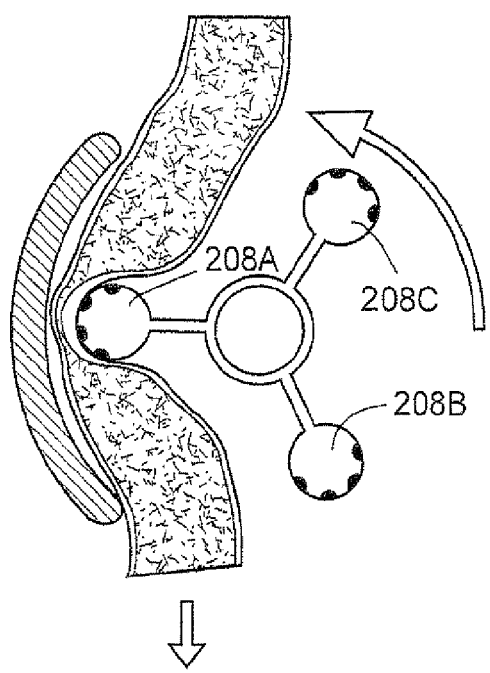

FIGS. 54A and 54B schematically show another apparatus used for practicing the method of the invention, in particular for actively moving the fluid and/or other bodily matter in the lumen of a patient's tubular organ. The apparatus of FIGS. 54A and 54B includes a constriction/stimulation unit 205, the constriction device 206 of which has a rotor 207, which carries three cylindrical constriction elements 208A, 208B and 208C positioned equidistantly from the axis 209 of the rotor 207. The constriction elements 208A-208C may be designed as rollers. Each cylindrical element 208A-208C is provided with electrical elements 7. A stationary elongate support element 210 is positioned spaced from but close to the rotor 207 and has a part cylindrical surface 211 concentric with the axis 209 of the rotor 207. The constriction/stimulation unit 205 is applied on a patient's tubular organ 212, so that the organ 212 extends between the support element 210 and the rotor 207.

The control device 4 controls the rotor 207 of the constriction device to rotate so that the constriction elements 208A-208C successively constrict wall portions of a series of wall portions of the tubular organ 212 against the elongate support element 210. The electrical elements 7 of the constriction elements 208A-208C stimulate the constricted wall portions with electric pulses so that the wall portions thicken and close the lumen of the organ 212. FIG. 54A illustrates how the constriction element 208A has started to constrict the wall of the organ 212 and how the lumen of the organ 212 is closed with the aid of the electrical elements 7 on the constriction element 208A, whereas the constriction element 208B is about to release the organ 212. FIG. 54B illustrates how the constriction element 208A has advanced about halfway along the elongate support element 210 and moved the bodily matter in the lumen in a direction indicated by an arrow. The constriction element 208B has released the organ 212, whereas the constriction element 208C is about to engage the organ 212. Thus, the control device 4 controls the rotor 207 to cyclically move the constriction elements 208A-208C one after the other along the elongate support element 210 while constricting the wall portions of the organ 212, so that the bodily matter in the organ 212 is moved in a peristaltic manner.

Figure 55A:
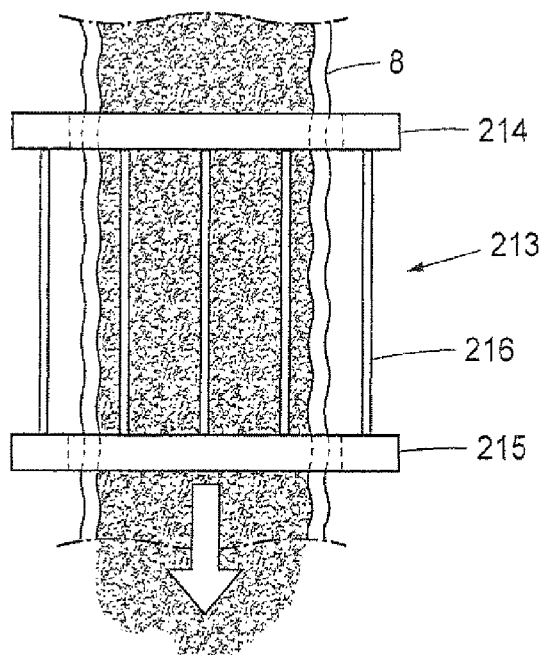
FIG. 55A is a schematic view of another mechanically operable non-inflatable constriction device used for practicing the method of the invention.
Figure 55B:
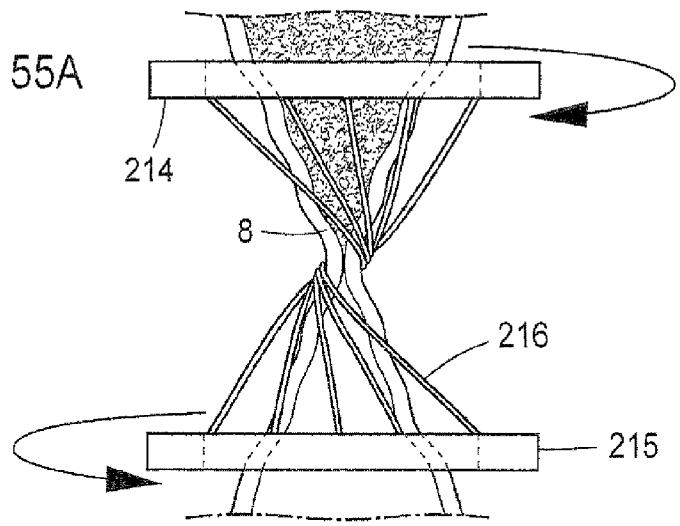
FIG. 55B shows the constriction device of FIG. 55A in a constricted state.
Figure 55:
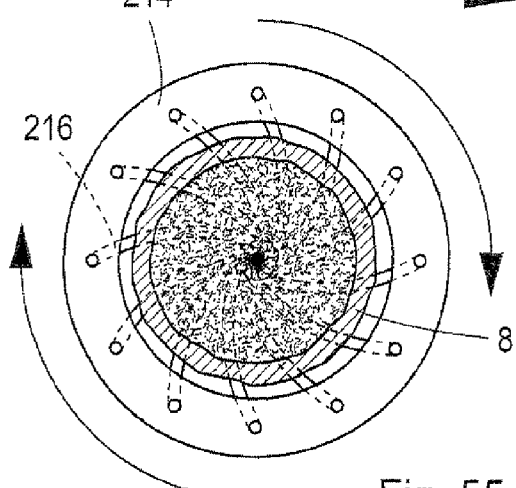
FIG. 55C is an end view of the embodiment of FIG. 55B.

FIGS. 55A, 55B and 55C show another mechanically operable constriction device 213 used for practicing the method of the invention. Referring to FIG. 55A, the constriction device 213 includes a first ring-shaped holder 214 applied on a tubular organ 8 of a patient and a second ring-shaped holder 215 also applied on the organ 8 spaced apart from holder 214. There are elastic strings 216 (here twelve strings) that extend in parallel along the tubular organ 8 and interconnect the two holders 213, 214 without contacting the organ 8. FIG. 55A illustrate an inactivated state of the constriction device 213 in which the organ 8 is not constricted.

Referring to FIGS. 55B and 55C, when organ 8 is to be constricted the ring-shaped holders 213 and 214 are rotated by an operation means (not shown) in opposite directions, whereby the elastic strings 216 constrict the organ 8 in a manner that appears from FIGS. 55B and 55C. For the sake of clarity, only five strings 216 are shown in FIG. 55B.

In accordance with the present invention, electrodes for electrically stimulating the organ 8 to cause contraction of the wall of the organ 8 are attached to the strings 216 (not shown in FIGS. 55A-55C).

Figure 56:
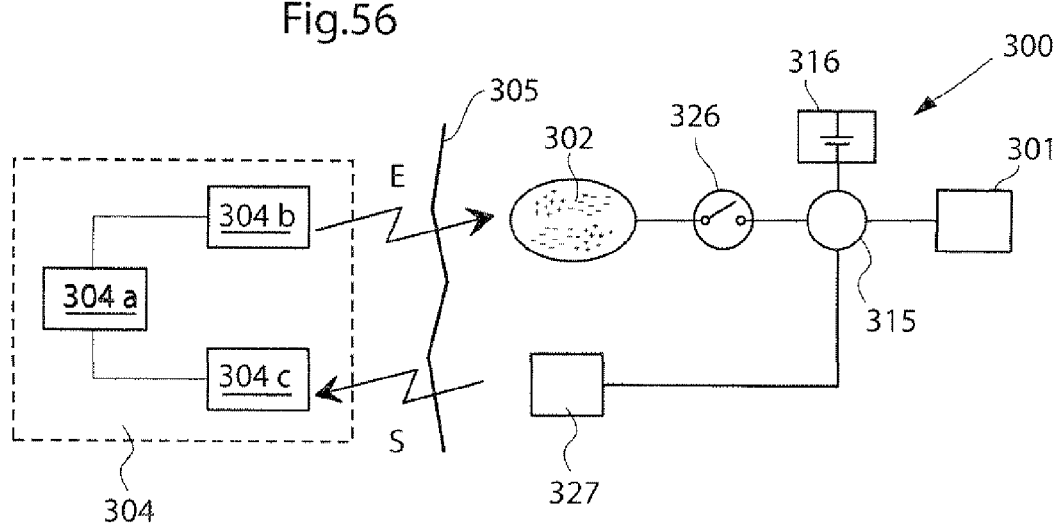
FIG. 56 is a schematic block diagram illustrating an arrangement for supplying an accurate amount of wireless energy used for the operation of the constriction/stimulation unit as described above.

FIG. 56 schematically illustrates an arrangement capable of sending information from inside the patient's body to the outside thereof to give information related to at least one functional parameter of the apparatus, and/or related to a physical parameter of the patient, in order to supply an accurate amount of energy to an implanted internal energy receiver 302 connected to energy consuming components of an implanted constriction/stimulation unit 301 of the apparatus. Such an energy receiver 302 may include a source of energy and/or an energy-transforming device. Briefly described, wireless energy is transmitted from an external source of energy 304a located outside the patient and is received by the internal energy receiver 302 located inside the patient. The internal energy receiver is adapted to directly or indirectly supply received energy to the energy consuming components of the constriction/stimulation unit 301 via a switch 326. An energy balance is determined between the energy received by the internal energy receiver 302 and the energy used for the constriction/stimulation unit 301, and the transmission of wireless energy is then controlled based on the determined energy balance. The energy balance thus provides an accurate indication of the correct amount of energy needed, which is sufficient to operate the constriction/stimulation unit 301 properly, but without causing undue temperature rise.

In FIG. 56 the patient's skin is indicated by a vertical line 305. Here, the energy receiver comprises an energy-transforming device 302 located inside the patient, preferably just beneath the patient's skin 305. Generally speaking, the implanted energy-transforming device 302 may be placed in the abdomen, thorax, muscle fascia (e.g. in the abdominal wall), subcutaneously, or at any other suitable location. The implanted energy-transforming device 302 is adapted to receive wireless energy E transmitted from the external source of energy 304a provided in an external energy-transmission device 304 located outside the patient's skin 305 in the vicinity of the implanted energy-transforming device 302.

As is well known in the art, the wireless energy E may generally be transferred by means of any suitable Transcutaneous Energy Transfer (TET) device, such as a device including a primary coil arranged in the external source of energy 304a and an adjacent secondary coil arranged in the implanted energy-transforming device 302. When an electric current is fed through the primary coil, energy in the form of a voltage is induced in the secondary coil which can be used to power the implanted energy consuming components, e.g. after storing the incoming energy in an implanted source of energy, such as a rechargeable battery or a capacitor. However, the present invention is generally not limited to any particular energy transfer technique, TET devices or energy sources, and any kind of wireless energy may be used.

The amount of energy received by the implanted energy receiver may be compared with the energy used by the implanted components of the apparatus. The term "energy used" is then understood to include also energy stored by implanted components of the apparatus. A control device includes an external control unit 304b that controls the external source of energy 304a based on the determined energy balance to regulate the amount of transferred energy. In order to transfer the correct amount of energy, the energy balance and the required amount of energy is determined by means of a determination device including an implanted internal control unit 315 connected between the switch 326 and the constriction/stimulation unit 301. The internal control unit 315 may thus be arranged to receive various measurements obtained by suitable sensors or the like, not shown, measuring certain characteristics of the constriction/stimulation unit 301, somehow reflecting the required amount of energy needed for proper operation of the constriction/stimulation unit 301. Moreover, the current condition of the patient may also be detected by means of suitable measuring devices or sensors, in order to provide parameters reflecting the patient's condition. Hence, such characteristics and/or parameters may be related to the current state of the constriction/stimulation unit 301, such as power consumption, operational mode and temperature, as well as the patient's condition reflected by parameters such as: body temperature, blood pressure, heartbeats and breathing. Other kinds of physical parameters of the patient and functional parameters of the device are described elsewhere.

Furthermore, a source of energy in the form of an accumulator 316 may optionally be connected to the implanted energy-transforming device 302 via the control unit 315 for accumulating received energy for later use by the constriction/stimulation unit 301. Alternatively or additionally, characteristics of such an accumulator, also reflecting the required amount of energy, may be measured as well. The accumulator may be replaced by a rechargeable battery, and the measured characteristics may be related to the current state of the battery, any electrical parameter such as energy consumption voltage, temperature, etc. In order to provide sufficient voltage and current to the constriction/stimulation unit 301, and also to avoid excessive heating, it is clearly understood that the battery should be charged optimally by receiving a correct amount of energy from the implanted energy-transforming device 302, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit 315. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 315 of the determination device is adapted to determine the energy balance and/or the currently required amount of energy, (either energy per time unit or accumulated energy) based on measurements made by the above-mentioned sensors or measuring devices of the apparatus, or the patient, or an implanted source of energy if used, or any combination thereof. The internal control unit 315 is further connected to an internal signal transmitter 327, arranged to transmit a control signal reflecting the determined required amount of energy, to an external signal receiver 304c connected to the external control unit 304b. The amount of energy transmitted from the external source of energy 304a may then be regulated in response to the received control signal.

Alternatively, the determination device may include the external control unit 304b. In this alternative, sensor measurements can be transmitted directly to the external control unit 304b wherein the energy balance and/or the currently required amount of energy can be determined by the external control unit 304b, thus integrating the above-described function of the internal control unit 315 in the external control unit 304b. In that case, the internal control unit 315 can be omitted and the sensor measurements are supplied directly to the internal signal transmitter 327 which sends the measurements over to the external signal receiver 304c and the external control unit 304b. The energy balance and the currently required amount of energy can then be determined by the external control unit 304b based on those sensor measurements.

Hence, the present solution according to the arrangement of FIG. 56 employs the feed back of information indicating the required energy, which is more efficient than previous solutions because it is based on the actual use of energy that is compared to the received energy, e.g. with respect to the amount of energy, the energy difference, or the energy receiving rate as compared to the energy rate used by implanted energy consuming components. The apparatus may use the received energy either for consuming or for storing the energy in an implanted source of energy or the like. The different parameters discussed above would thus be used if relevant and needed and then as a tool for determining the actual energy balance. However, such parameters may also be needed per se for any actions taken internally to specifically operate the apparatus.

The internal signal transmitter 327 and the external signal receiver 304c may be implemented as separate units using suitable signal transfer means, such as radio, IR (Infrared) or ultrasonic signals. Alternatively, the internal signal transmitter 327 and the external signal receiver 304c may be integrated in the implanted energy-transforming device 302 and the external source of energy 304a, respectively, so as to convey control signals in a reverse direction relative to the energy transfer, basically using the same transmission technique. The control signals may be modulated with respect to frequency, phase or amplitude.

Thus, the feedback information may be transferred either by a separate communication system including receivers and transmitters or may be integrated in the energy system. Such an integrated information feedback and energy system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off. In implementing this system in the arrangement of FIG. 17, the switch 326 is either separate and controlled by the internal control unit 315, or integrated in the internal control unit 315. It should be understood that the switch 326 should be interpreted in its broadest embodiment. This means a transistor, MCU, MCPU, ASIC FPGA or a DA converter or any other electronic component or circuit that may switch the power on and off.

To conclude, the energy supply arrangement illustrated in FIG. 56 may operate basically in the following manner. The energy balance is first determined by the internal control unit 315 of the determination device. A control signal reflecting the required amount of energy is also created by the internal control unit 315, and the control signal is transmitted from the internal signal transmitter 327 to the external signal receiver 304c. Alternatively, the energy balance can be determined by the external control unit 304b instead depending on the implementation, as mentioned above. In that case, the control signal may carry measurement results from various sensors. The amount of energy emitted from the external source of energy 304a can then be regulated by the external control unit 304b, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external source of energy 304a, such as voltage, current, amplitude, wave frequency and pulse characteristics. This system may also be used to obtain information about the coupling factors between the coils in a TET system even to calibrate the system both to find an optimal place for the external coil in relation to the internal coil and to optimize energy transfer. Simply comparing in this case the amount of energy transferred with the amount of energy received. For example if the external coil is moved the coupling factor may vary and correctly displayed movements could cause the external coil to find the optimal place for energy transfer. Preferably, the external coil is adapted to calibrate the amount of transferred energy to achieve the feedback information in the determination device, before the coupling factor is maximized.

This coupling factor information may also be used as a feedback during energy transfer. In such a case, the energy system of the present invention comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factor between the first and second coils. The energy transmitter may regulate the transmitted energy in response to the obtained coupling factor.

Figure 57:
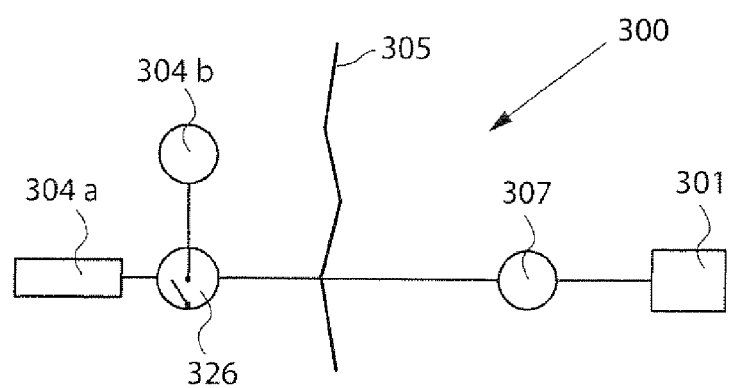
FIG. 57 schematically shows an embodiment of the invention, in which the apparatus is operated with wire bound energy.

With reference to FIG. 57, although wireless transfer of energy for operating the apparatus has been described above to enable non-invasive operation, it will be appreciated that the apparatus can be operated with wire bound energy as well. Such an example is shown in FIG. 57, wherein an external switch 326 is interconnected between the external source of energy 304a and an operation device, such as an electric motor 307 operating the constriction/stimulation unit 301. An external control unit 304b controls the operation of the external switch 326 to effect proper operation of the constriction/stimulation unit 301.

Figure 58:
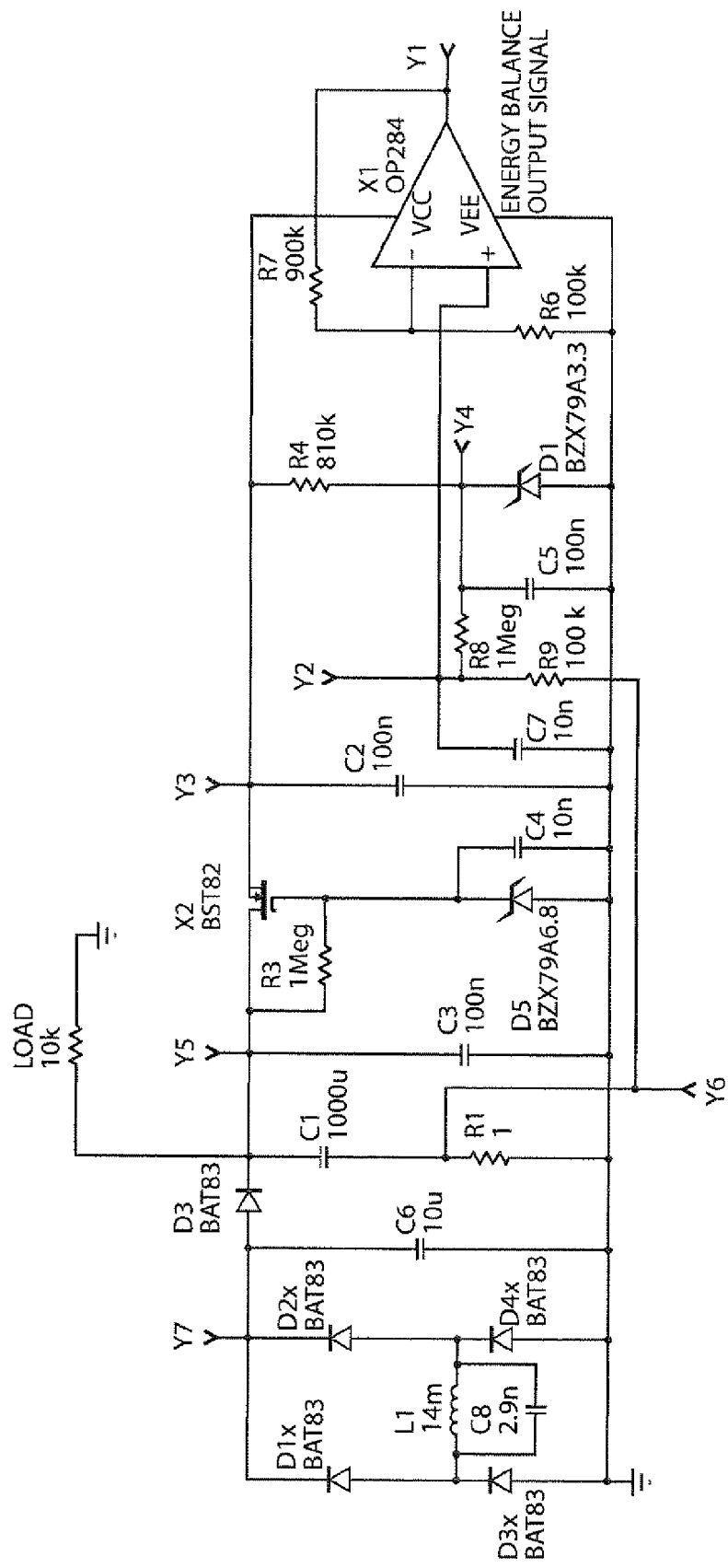
FIG. 58 is a more detailed block diagram of an arrangement for controlling the transmission of wireless energy used for the operation of the constriction/stimulation unit as described above.

FIG. 58 illustrates different embodiments for how received energy can be supplied to and used by the constriction/stimulation unit 301. Similar to the example of FIG. 56, an internal energy receiver 302 receives wireless energy E from an external source of energy 304a which is controlled by a transmission control unit 304b. The internal energy receiver 302 may comprise a constant voltage circuit, indicated as a dashed box "constant V" in FIG. 58, for supplying energy at constant voltage to the constriction/stimulation unit 301. The internal energy receiver 302 may further comprise a constant current circuit, indicated as a dashed box "constant C" in the figure, for supplying energy at constant current to the constriction/stimulation unit 301.

The constriction/stimulation unit 301 comprises an energy consuming part 301a, which may be a motor, pump, restriction device, or any other medical appliance that requires energy for its electrical operation. The constriction/stimulation unit 301 may further comprise an energy storage device 301b for storing energy supplied from the internal energy receiver 302. Thus, the supplied energy may be directly consumed by the energy consuming part 301a, or stored by the energy storage device 301b, or the supplied energy may be partly consumed and partly stored. The constriction/stimulation unit 301 may further comprise an energy stabilizing unit 301c for stabilizing the energy supplied from the internal energy receiver 302. Thus, the energy may be supplied in a fluctuating manner such that it may be necessary to stabilize the energy before consumed or stored.

The energy supplied from the internal energy receiver 302 may further be accumulated and/or stabilized by a separate energy stabilizing unit 328 located outside the constriction/stimulation unit 301, before being consumed and/or stored by the constriction/stimulation unit 301. Alternatively, the energy stabilizing unit 328 may be integrated in the internal energy receiver 302. In either case, the energy stabilizing unit 328 may comprise a constant voltage circuit and/or a constant current circuit.

It should be noted that FIG. 56 and FIG. 58 illustrate some possible but non-limiting implementation options regarding how the various shown functional components and elements can be arranged and connected to each other. However, the skilled person will readily appreciate that many variations and modifications can be made within the scope of the present invention.

Figure 59:
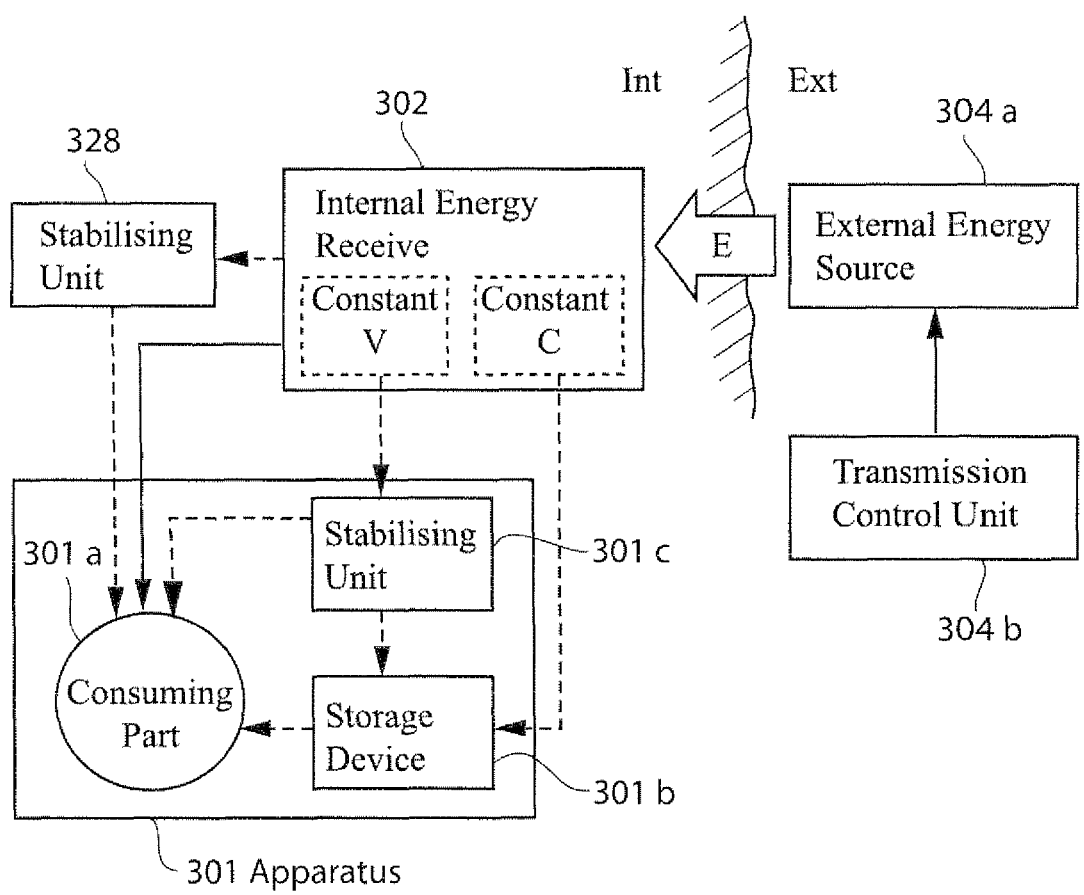
FIG. 59 is a circuit for the arrangement shown in FIG. 19, according to a possible implementation example.

FIG. 59 schematically shows an energy balance measuring circuit of one of the proposed designs of the apparatus for controlling transmission of wireless energy, or energy balance. The circuit has an output signal centered on 2.5V and proportionally related to the energy imbalance. The derivative of this signal shows if the value goes up and down and how fast such a change takes place. If the amount of received energy is lower than the energy used by implanted components of the apparatus, more energy is transferred and thus charged into the source of energy. The output signal from the circuit is typically fed to an ND converter and converted into a digital format. The digital information can then be sent to the external energy-transmission device allowing it to adjust the level of the transmitted energy. Another possibility is to have a completely analog system that uses comparators comparing the energy balance level with certain maximum and minimum thresholds sending information to external energy-transmission device if the balance drifts out of the max/min window.

The schematic FIG. 59 shows a circuit implementation for a system that transfers energy to the implanted energy components of the apparatus from outside of the patient's body using inductive energy transfer. An inductive energy transfer system typically uses an external transmitting coil and an internal receiving coil. The receiving coil, L1, is included in the schematic FIG. 59; the transmitting parts of the system are excluded.

The implementation of the general concept of energy balance and the way the information is transmitted to the external energy transmitter can of course be implemented in numerous different ways. The schematic FIG. 20 and the above described method of evaluating and transmitting the information should only be regarded as examples of how to implement the control system.

Circuit Details

In FIG. 59 the symbols Y1, Y2, Y3 and so on symbolize test points within the circuit. The components in the diagram and their respective values are values that work in this particular implementation which of course is only one of an infinite number of possible design solutions.

Energy to power the circuit is received by the energy receiving coil L1. Energy to implanted components is transmitted in this particular case at a frequency of 25 kHz. The energy balance output signal is present at test point Y1.

The embodiments described in connection with FIGS. 56, 58 and 59 identify a general method of the present invention for controlling transmission of wireless energy to implanted energy consuming components of the apparatus. Such a method will be defined in general terms in the following.

A method is thus provided for controlling transmission of wireless energy supplied to implanted energy consuming components of an apparatus as described above. The wireless energy E is transmitted from an external source of energy located outside the patient and is received by an internal energy receiver located inside the patient, the internal energy receiver being connected to the implanted energy consuming components of the apparatus for directly or indirectly supplying received energy thereto. An energy balance is determined between the energy received by the internal energy receiver and the energy used for the operation of the implanted parts of the apparatus. The transmission of wireless energy E from the external source of energy is then controlled based on the determined energy balance.

The wireless energy may be transmitted inductively from a primary coil in the external source of energy to a secondary coil in the internal energy receiver. A change in the energy balance may be detected to control the transmission of wireless energy based on the detected energy balance change. A difference may also be detected between energy received by the internal energy receiver and energy used for the operation of the implanted parts of the apparatus, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the operation of the implanted parts of the apparatus be consumed to operate the implanted parts of the apparatus and/or stored in at least one implanted energy storage device of the apparatus.

When electrical and/or physical parameters of the implanted parts of the apparatus and/or physical parameters of the patient are determined, the energy may be transmitted for consumption and storage according to a transmission rate per time unit which is determined based on said parameters. The total amount of transmitted energy may also be determined based on said parameters.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or current related to the energy balance.

The transmission of wireless energy from the external source of energy may be controlled by applying to the external source of energy electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

The circuit formed by the first electric circuit and the external source of energy may have a first characteristic time period or first time constant, and when effectively varying the transmitted energy, such frequency time period may be in the range of the first characteristic time period or time constant or shorter.

A constriction device can be arranged to delay the movement of the bodily matter in a lumen of the organ for a predetermined amount of time. This can be achieved in many different ways, of which two will be described below.

Figure 60:
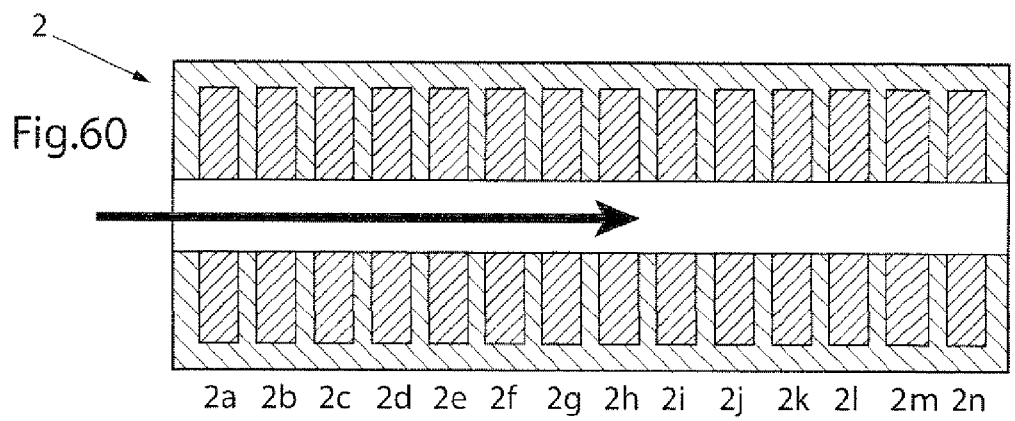
FIG. 60 is a sectional view through a constriction device.
Figure 61A:
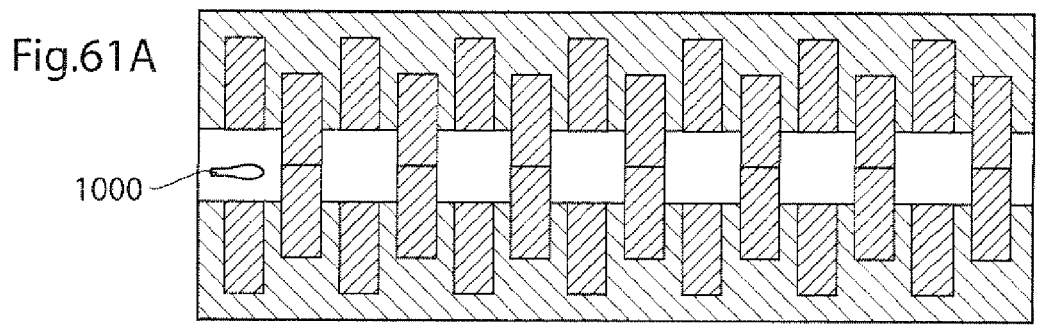
FIG. 61A-C illustrates the constriction device of FIG. 60 in different interrupting stages.

FIG. 60 is a sectional view through a constriction device 2 adapted to restrict or stop the flow through a luminal organ. The general flow direction is illustrated by an arrow. The constriction device comprises an array of constriction elements 2a-2m, each arranged to restrict or close a part of the luminal organ. The constriction device illustrated in FIG. 56 is in an open or non-operative position wherein the flow is uninterrupted FIG. 61A illustrates the constriction device of FIG. 60 in a first interrupting stage, wherein every other constriction element is in a closed position. A bodily matter, generally designated 1000, is allowed to enter the space formed by the first, non-closed constriction element. It is stopped there by the second constriction element, which is in a closed position. This operative state can remain for a desired period of time, such as one day.

Figure 61B:
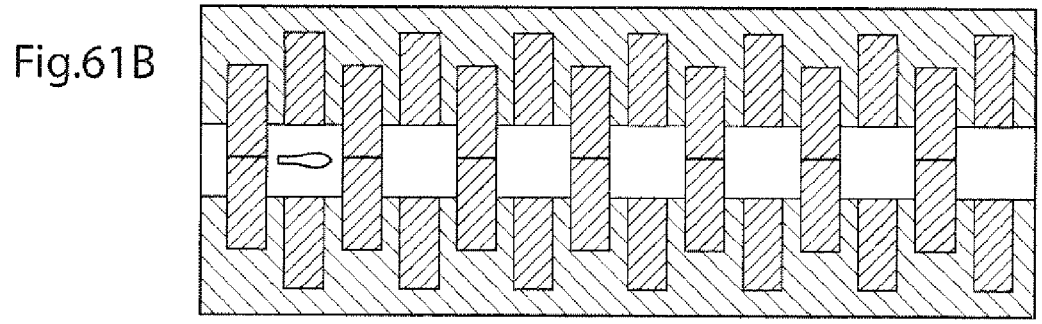

FIG. 61B illustrates the constriction device of FIG. 60 in a second interrupting stage, wherein every constriction element that was closed in the first interrupting stage is in an open position and vice versa. The bodily matter is then allowed to enter the space formed by the second, non-closed constriction element. It is stopped there by the third constriction element, which is in a closed position. This operative state can remain for a desired period of time, such as one day.

FIG. 61A illustrates the constriction device of FIG. 60 in a third interrupting stage, wherein every other constriction element is in a closed position, exactly as in the first interrupting stage. The bodily matter shown in FIGS. 61A and 61B, is allowed to enter the space formed by the third, non-closed constriction element. It is stopped there by the fourth constriction element, which is in a closed position. This operative state can remain for a desired period of time, such as one day.

Repeating this process, the movement of a bodily matter can be delayed for a desired period of time until it reaches the other end of the constriction device. Since the life of a bodily matter is less than about five days, delaying a bodily matter in this way will ensure that it does not reach an egg in the luminal organ and thereby the constriction device functions to prevent any flow of bodily matter. By altering the constricted area of the luminal organ, this will not be harmed like if the same area were constricted for a longer period of time.

Figure 61C:
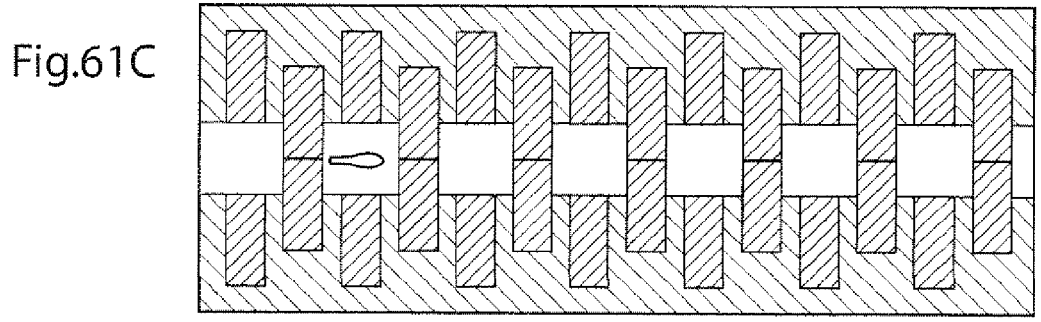
Figure 62A:
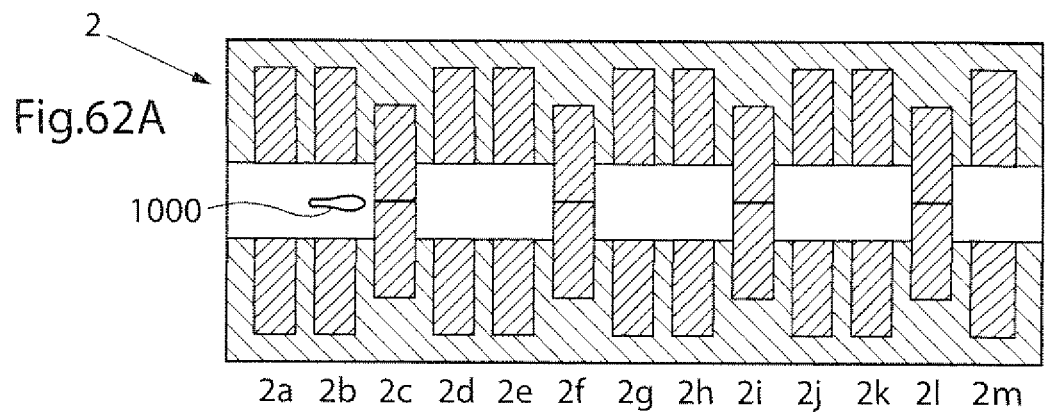
FIG. 62A-D show a second embodiment of a constriction device.
Figure 62B:
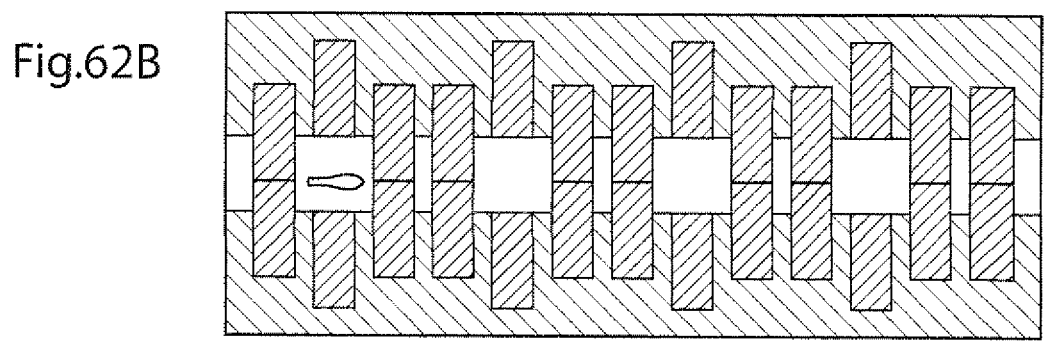
Figure 62C:
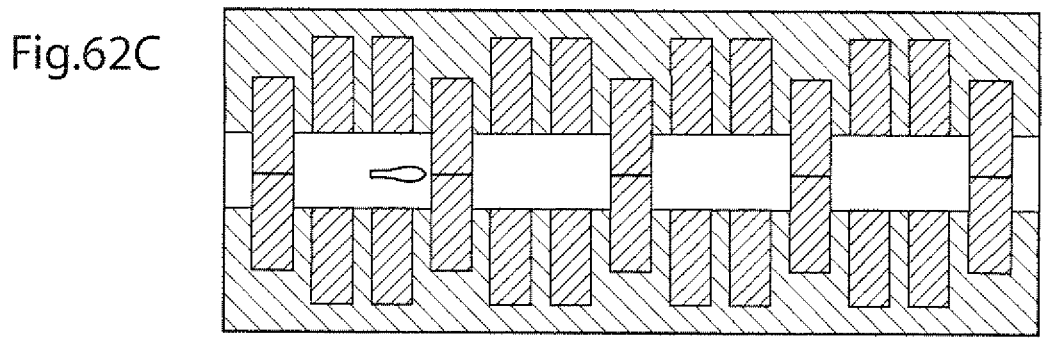
Figure 62D:
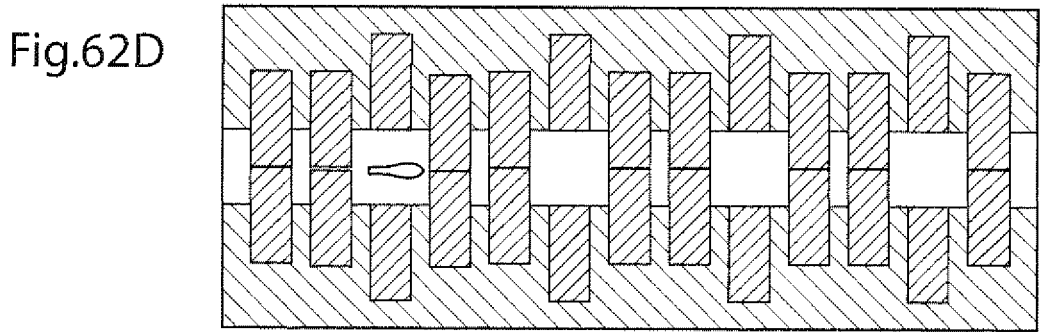

FIGS. 62A-D show a second embodiment of a constriction device. This operates in a way similar to the first embodiment of a constriction device shown in FIGS. 61A-C. However, in this embodiment, two consecutive constriction elements are in an open position at a time when allowing progress of the bodily matter.

FIG. 63A-E disclose one particular embodiment of the invention using a pump for a luminal organ to pump such bodily matter in the luminal organ. The principle is simple; more than one restriction device is supplied on the outside of the organ to restrict the same from the outside thereof. The restriction device may comprise any one of or a combination of; a stimulation device, a mechanical or hydraulic restriction device. One first restriction is applied and restricted. At least one further restriction is then applied. Preferably the restriction applies slowly to not cause any unnecessary movement of any bodily matter backwards. The further restrictions preferably has a longer restricted area. Thereafter all the restrictions are rapidly released causing suction both from the proximal and distal side. As long as the restriction is applied slowly and released fast any other way to apply the restriction may alternatively work.

Figure 63A:
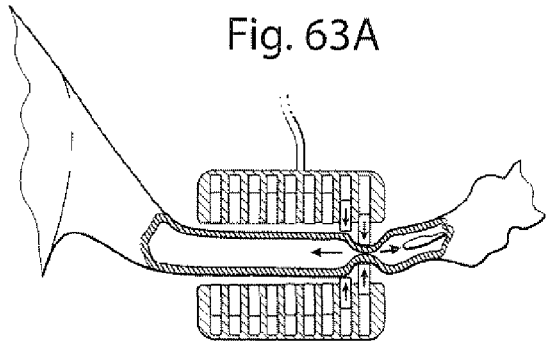
FIG. 63A-E disclose one particular embodiment of the invention using pump to such bodily matter in the lumenal organ.
Figure 63B:
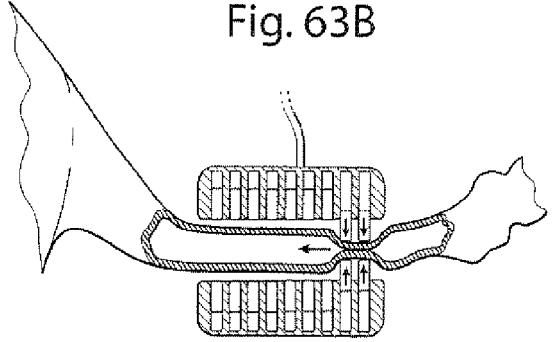
Figure 63C:
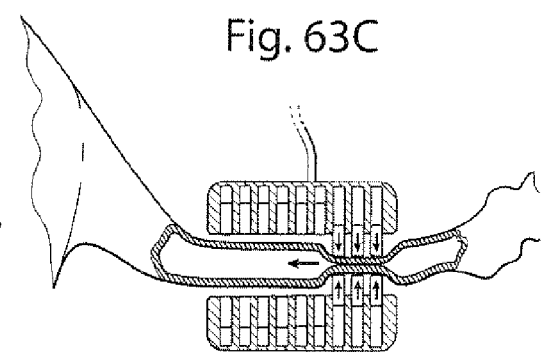
Figure 63D:
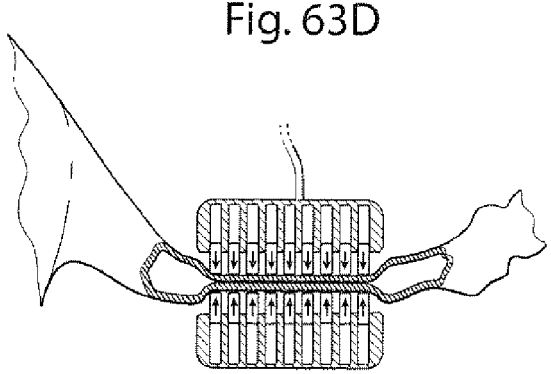
Figure 63E:
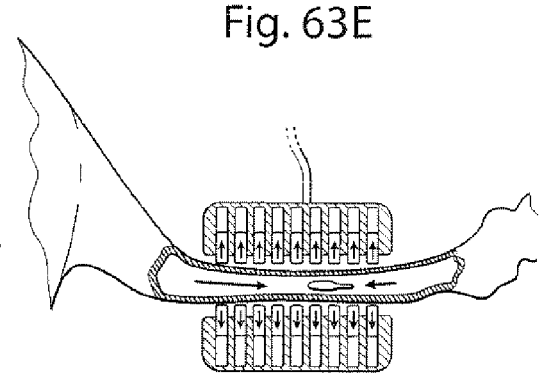

FIG. 63A disclose an applied restriction on the luminal organ with a restriction device 2. FIG. 63B-D disclose further applied restrictions. FIG. 63E disclose a rapid release of all the restriction areas at the same time thus creating a suction from both sides or if one restriction most distal or most proximal is not released sucking from only one side.

Intestinal Dysfunction

Figure 64A:
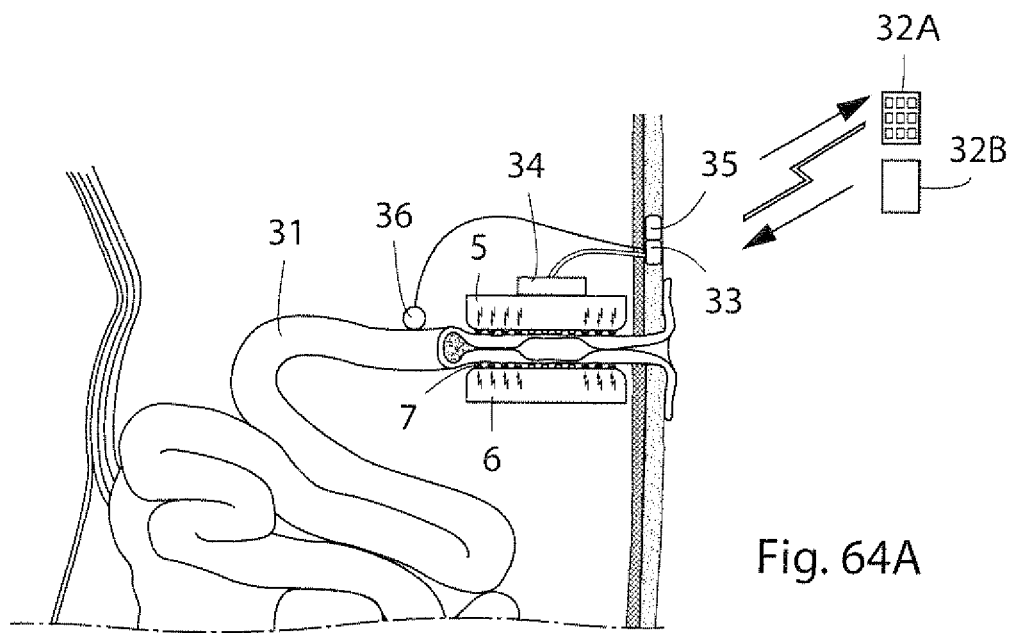
FIG. 64A illustrates an apparatus used for practicing the method of the invention where the apparatus is applied on the small intestines of a colostomy patient having a stoma opening in the abdomen.

FIG. 64A illustrates the apparatus of FIG. 2 applied on the intestines 31 of a stoma colostomy patient having a stoma in the abdomen. The with the clamping elements 5, 6 of the constriction device 2 constricting the intestines 31 and the stimulation device 3 is energized to close the fecal intestinal passageway. (For the sake of clarity, the housing is not shown and the clamping elements 5, 6 are exaggerated.) In this embodiment, a control device includes an external control unit in the form of a hand-held wireless remote control 32, and an implanted internal control unit 33, which may include a microprocessor, for controlling the constriction and stimulation devices. The remote control 32 is operable by the patient to control the internal control unit 33 to switch on and off the constriction device and/or the stimulation device. Alternatively, however, the remote control 32 may be replaced by a subcutaneously implanted push button that is manually switched by the patient between "on" and "off". Such a manually operable push button may also be provided in combination with the remote control 32 as an emergency button to allow the patient to stop the operation of the apparatus in case of emergency or malfunction.

The internal control unit 33 controls an implanted operation device 34 to move the clamping elements 5, 6. An implanted source of energy 35, such as a rechargeable battery, powers the operation device 34. The internal control unit 33, which may be implanted subcutaneously or in the abdomen, also works as en energy receiver, i.e., for transforming wireless energy into electric energy and charging the implanted source of energy 35 (rechargeable battery) with the electric energy.

An implanted sensor 36 senses a physical parameter of the patient, such as the pressure in the intestines, or a parameter that relates to the pressure in the intestines, wherein the internal control unit 33 controls the constriction device 2 and/or the stimulation device 3 in response to signals from the sensor 36. In this embodiment the sensor 36 is a pressure sensor, wherein the internal control unit 33 controls the constriction device and/or stimulation device to change the constriction of the patient's intestines 31 in response to the pressure sensor 36 sensing a predetermined value of measured pressure. For example, the control unit 33 may control the constriction device and/or stimulation device to increase the constriction of the patient's intestines 31 in response to the pressure sensor sensing an increased pressure. Alternatively or in combination, the remote control 32 controls the constriction device and/or stimulation device in response to signals from the sensor 36. The remote control 32 may be equipped with means for producing an indication, such as a sound signal or displayed information, in response to signals from the sensor 36, in the same manner as the internal control unit 33.

The remote control 32 may be equipped with means for producing an indication, such as a sound signal or displayed information, in response to signals from the sensor 36. When the patient's attention is taken by such an indication indicating an increased pressure exceeding a threshold value, he or she may use the remote control to control the constriction device and stimulation device to pump feces through the patient's stoma.

Figure 64B:
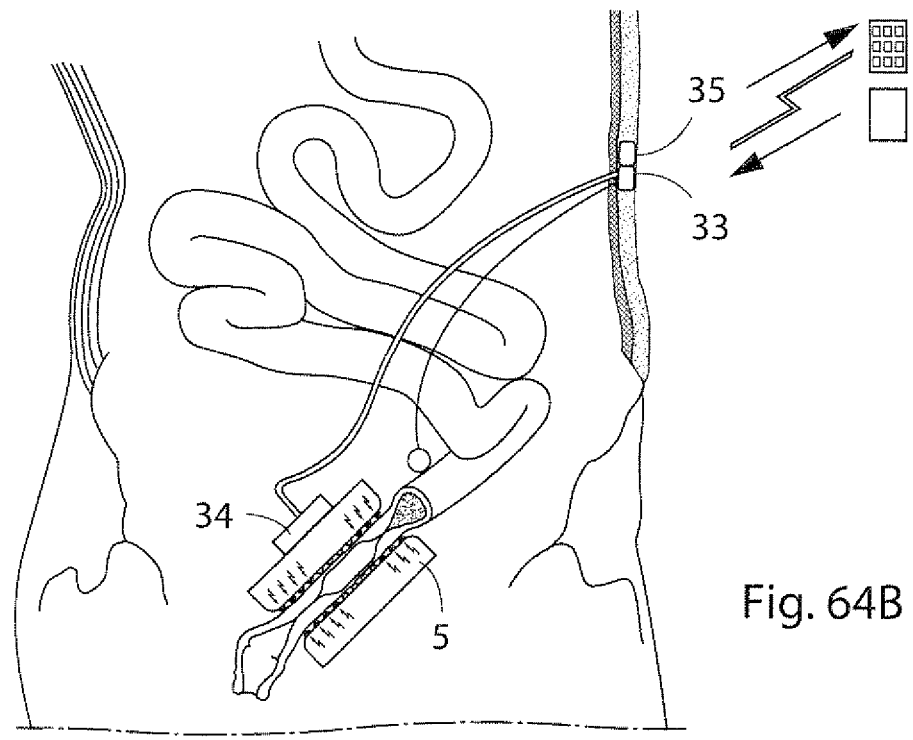
FIG. 64B illustrates an apparatus used for practicing the method of the invention where the apparatus is applied on the small intestines of a colostomy patient having the small intestines ending at the patient's anus.

FIG. 64B shows an embodiment which is similar to the embodiment of FIG. 64A except that the constriction device is applied on the small intestines of a colostomy patient having the small intestines surgically connected to the patient's anus.

Urinary Dysfunction

Figure 65A:
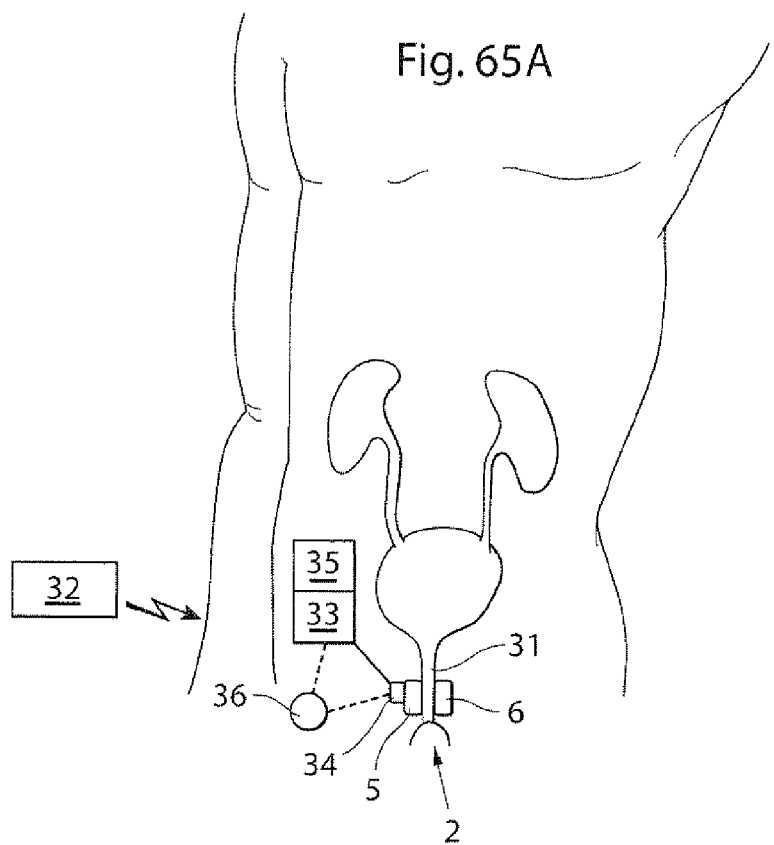
FIG. 65A illustrates the apparatus of the invention applied on the urethra of a urinary incontinent patient.

FIG. 65A illustrates the embodiment of FIG. 2 applied on the urethra 31 of a urinary stress and overflow incontinent patient with the clamping elements 5, 6 of the constriction device 2 constricting the urethra 31 and the stimulation device 3 energized to close the urinary passageway. (For the sake of clarity, the housing is not shown and the clamping elements 5, 6 are exaggerated.) In this embodiment, a control device includes an external control unit in the form of a hand-held wireless remote control 32, and an implanted internal control unit 33, which may include a microprocessor, for controlling the constriction and stimulation devices. The remote control 32 is operable by the patient to control the internal control unit 33 to switch on and off the constriction device and/or the stimulation device. Alternatively, however, the remote control 32 may be replaced by a subcutaneously implanted push button that is manually switched by the patient between "on" and "off". Such a manually operable push button may also be provided in combination with the remote control 32 as an emergency button to allow the patient to stop the operation of the apparatus in case of emergency or malfunction.

The internal control unit 33 controls an implanted operation device 34 to move the clamping elements 5, 6. An implanted source of energy 35, such as a rechargeable battery, powers the operation device 34. The internal control unit 33, which may be implanted subcutaneously or in the abdomen, also works as en energy receiver, i.e., for transforming wireless energy into electric energy and charging the implanted source of energy 35 (rechargeable battery) with the electric energy.

An implanted sensor 36 senses a physical parameter of the patient, such as the pressure in the bladder, or a parameter that relates to the pressure in the bladder, wherein the internal control unit 33 controls the constriction device 2 and/or the stimulation device 3 in response to signals from the sensor 36. In this embodiment the sensor 36 is a pressure sensor, wherein the internal control unit 33 controls the constriction device and/or stimulation device to change the constriction of the patient's urethra 31 in response to the pressure sensor 36 sensing a predetermined value of measured pressure. For example, the control unit 33 may control the constriction device and/or stimulation device to increase the constriction of the patient's urethra 31 in response to the pressure sensor sensing an increased pressure. Alternatively or in combination, the remote control 32 controls the constriction device and/or stimulation device in response to signals from the sensor 36, in the same manner as the internal control unit 33.

The remote control 32 may be equipped with means for producing an indication, such as a sound signal or displayed information, in response to signals from the sensor 36. When the patient's attention is taken by such an indication indicating an increased pressure exceeding a threshold value, or when the patient desires to urinate, he or she may use the remote control to control the constriction device and stimulation device to pump urine through the urethra.

Figure 65B:
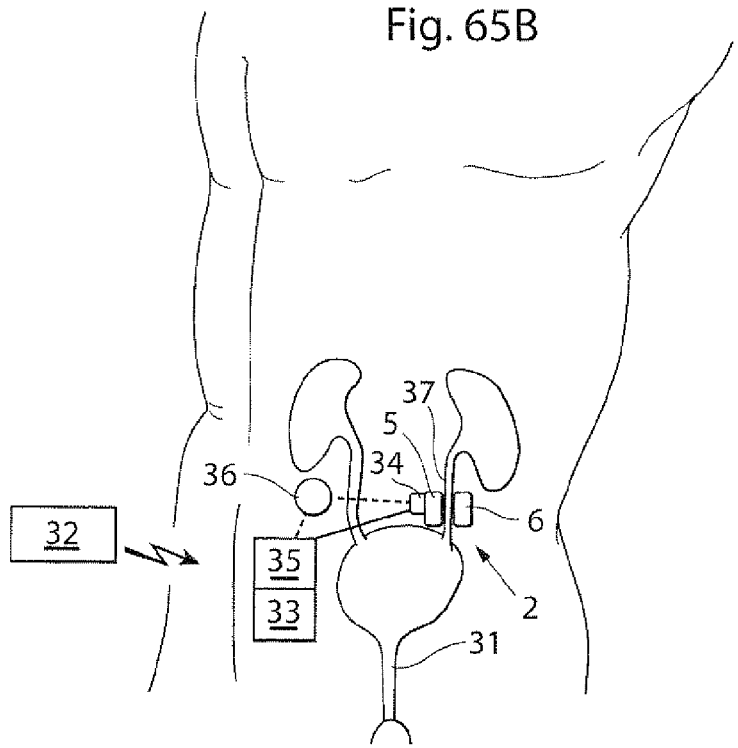
FIG. 65B illustrates the apparatus of the invention applied on the ureter of a urinary incontinent patient.

The embodiment of FIG. 65B is similar to that of FIG. 65A, except that the constriction device is applied to an urether 37 instead of the urethra. This embodiment is in other aspects similar or identical to the embodiment described above with reference to FIG. 65A. It will be appreciated that more than one constriction device can be used, e.g., one constriction device on each of the two ureters.

The embodiment of FIG. 65B is similar to that of FIG. 65A, except that but shows the constriction device is applied to an urether 37 instead of the urethra. This embodiment is in other aspects similar or identical to the embodiment described above with reference to FIG. 65A. It will be appreciated that more than one constriction device can be used, e.g., one constriction device on each of the two ureters.

Figure 65C:
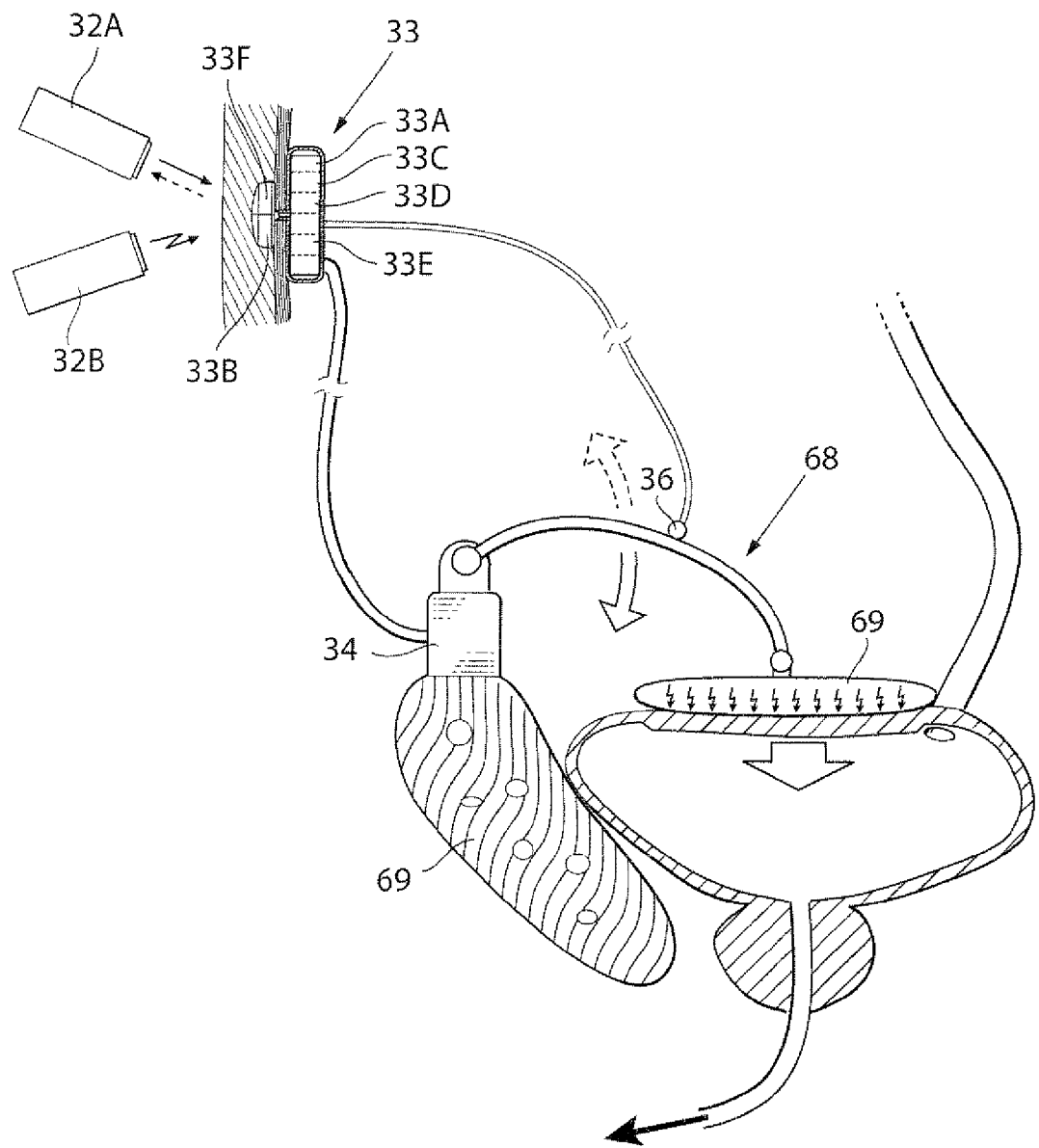
FIG. 65C illustrates the apparatus of the invention applied on the urinary bladder of a patient.

FIG. 65C illustrates a constriction device 68 similar to the embodiment of FIG. 27 applied on the urinary bladder of a patient suffering from urinary dysfunction, i.e., disability to empty the bladder. The clamping elements 69 of the constriction device 68 are positioned on different sides of the bladder. In this embodiment, the control device includes an external control unit in the form of a hand-held wireless remote control 32A and an implanted internal control unit 33, which may include a microprocessor 33A, for controlling the constriction and stimulation devices. There is an external energy transmitter 32B that transmits wireless energy. The remote control 32A and the energy transmitter 32B may be separate devices, as shown in FIG. 65C, or may be integrated in a single hand-held device. The remote control 32A is operable by the patient to control the internal control unit 33 to switch on and off the constriction device and/or the stimulation device. The internal control unit 33 also includes a push button 33B that can be used by the patient to manually switch "on" and "off" the operation of the constriction and/or stimulation devices. The button also serves as an emergency button to allow the patient to stop the operation of the apparatus in case of emergency or malfunction.

The internal control unit 33 controls a hydraulic operation device 34 to move the clamping elements 69. An injection port 33F integrated in the push button 33B is provided to calibrate the amount of hydraulic fluid in hydraulic components of the hydraulic operation device. The internal control unit 33 also includes a source of energy 33C, such as a rechargeable battery, for powering the operation device 34, and an energy receiver 33D for transforming wireless energy transmitted by the external energy transmitter 32B into electric energy and charging the implanted source of energy 33C (rechargeable battery) with the electric energy.

An implanted sensor 36 applied on the constriction device (here on the clamping element 69) senses a physical parameter of the patient, such as the pressure in the bladder, or a parameter that relates to the pressure in the bladder. the internal control unit 33 includes a signal transmitter 33E that sends an alarm signal to the external remote control 32A in response to signals from the sensor 36 indicating a predetermined value of measured pressure.

The remote control 32 may be equipped with means for producing an indication, such as a sound signal or displayed information, in response to received signals such as alarm signals. When the patient's attention is taken by such an indication indicating an increased pressure exceeding a threshold value, or when the patient desires to urinate, he or she may conveniently use the remote control 32A or the push button 33B to activate the operation device 34 to empty the bladder.

Figure 65D:
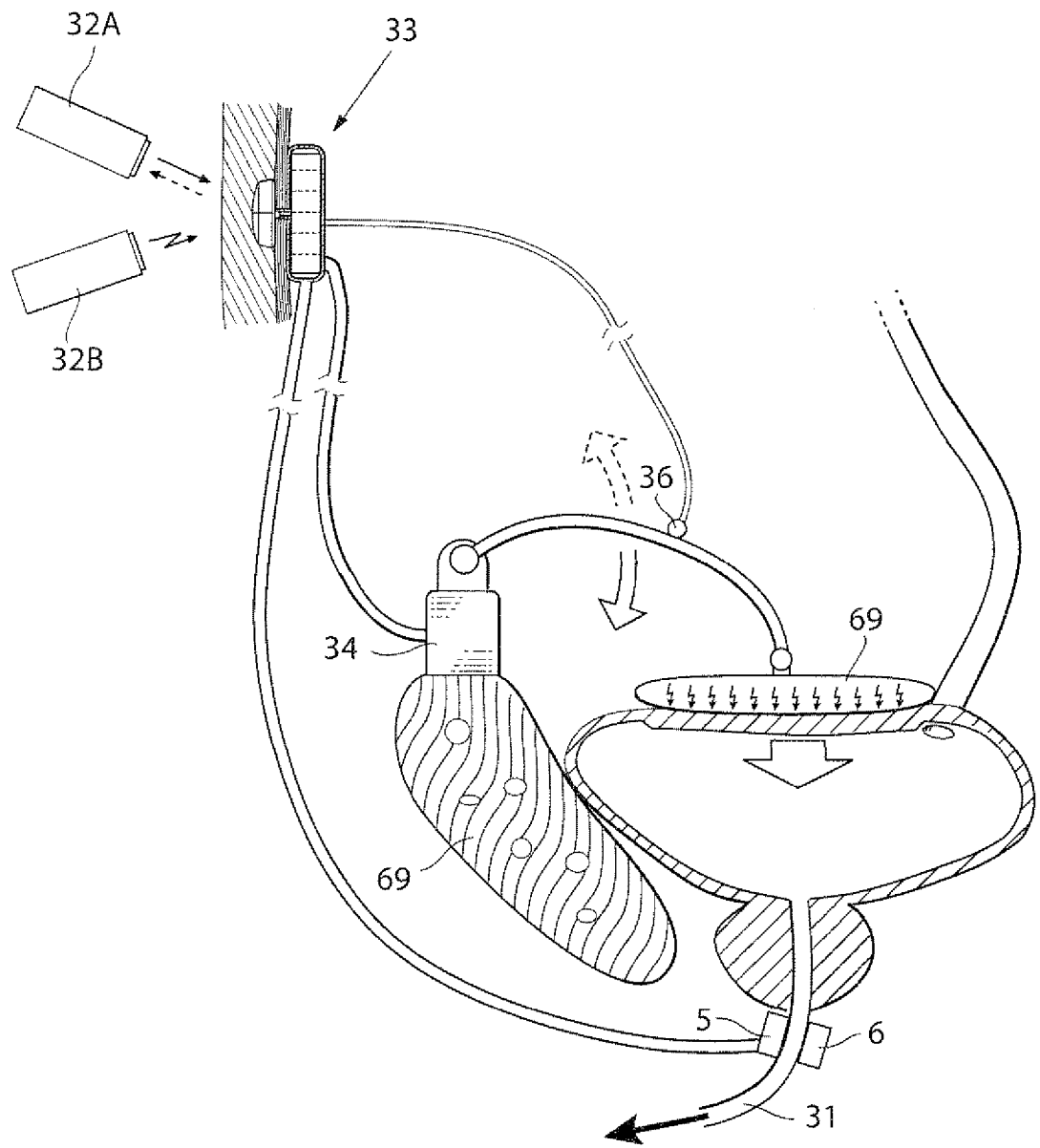
FIG. 65D illustrates the embodiment of FIG. 65C combined with the embodiment shown in FIG. 65A.

The embodiment of FIG. 65D is similar to that of FIG. 65C, except that the clamping elements 5, 6 of the constriction device 2 shown in FIG. 65A is applied on the urethra 31. The embodiment of FIG. 65D is suited to treat patients who are incontinent as well as disabled to empty the bladder.

The skilled person understands that the embodiments of FIGS. 65A-65D could be combined in many different ways as desired. For example, as shown in FIG. 65B, another constriction device may be applied on the patient's urether 37 in the embodiment of FIG. 65C.

Obesity

Figure 66A:
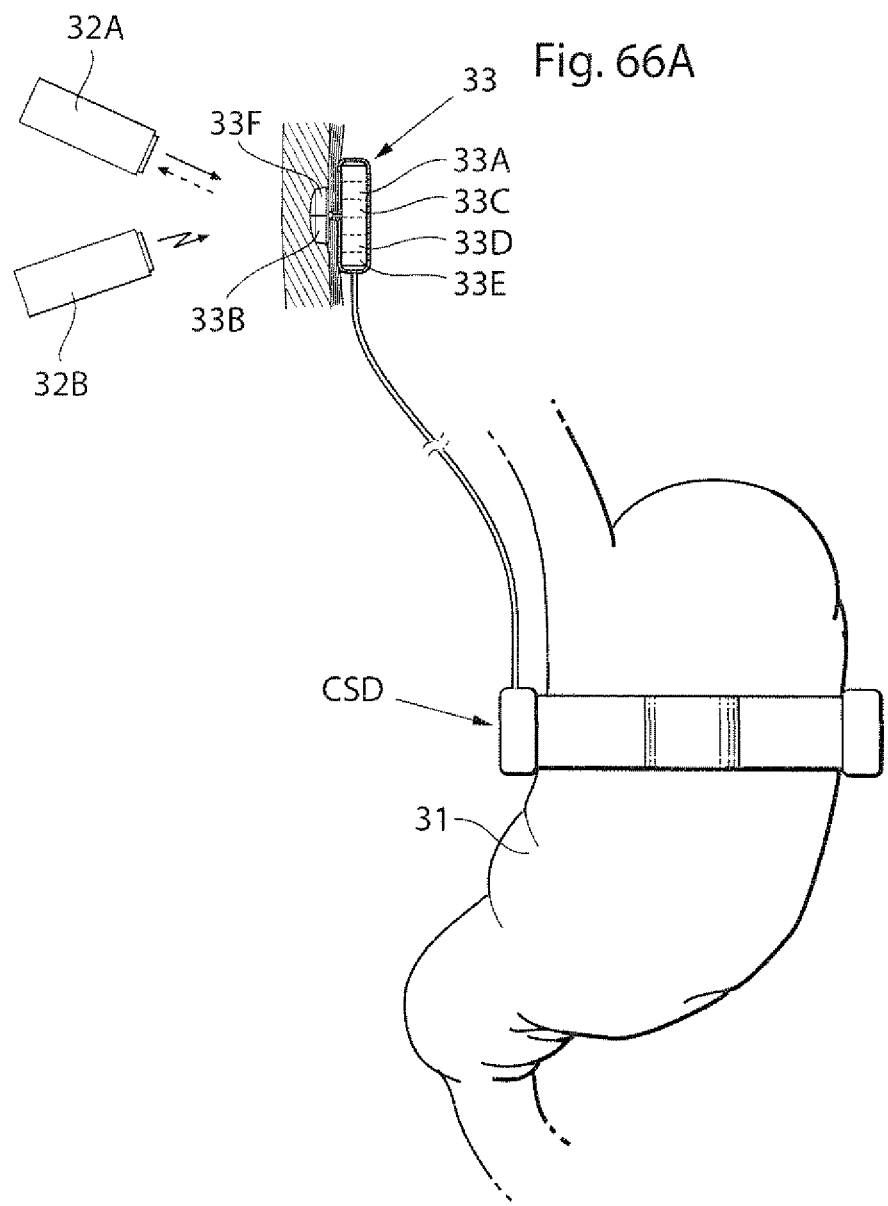
FIG. 66A illustrates a constriction/stimulation unit of an apparatus for practicing the method of the invention applied on the stomach of an obese patient surgically modified by AGB (Adjustable Gastric Banding).
Figure 66B:
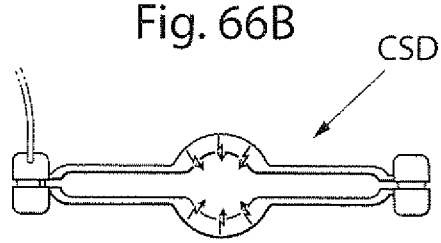
FIG. 66B is a side view of the constriction/stimulation unit used in the embodiment shown in FIG. 66A.

FIG. 66A schematically illustrates the stomach 31 of an obese patient surgically modified by AGB. A constriction/stimulation unit CSD designed as a hydraulically adjustable clamp (similar to the unit 68 shown in FIG. 27) is applied around the stomach 31 The clamp-shaped unit CSD clamps the stomach 31, so that the stomach is flattened, except at the middle of the stomach, where the clamp-shaped unit CSD is enlarged to form an opening defined by two opposed semi-circles of the clamp-shaped unit CSD, see FIG. 66B. This opening defined by said semi-circles permits a food passageway to form in the stomach.

There is a wireless remote control 32A and an implanted internal control unit 33, which may include a microprocessor 33A, for controlling the unit CSD, and an external energy transmitter 32A that transmits wireless energy. In this embodiment the remote control 32A and the energy transmitter 32B are separate devices. However, they may be integrated in a single hand-held device. The remote control 32 is operable by a nurse or doctor to program the microprocessor to properly control the constriction/stimulation unit CSD to suit the individual patients. In addition, the constriction/stimulation unit CSD may be controlled by a subcutaneously implanted push button that can be used by the patient to temporarily switch off the operation of the constriction/stimulation unit CSD in case of emergency, or malfunction of the apparatus.

An injection port 33F integrated in the push button 33B is provided to calibrate the amount of hydraulic fluid in hydraulic components of the adjustable hydraulic clamp of unit CSD. The internal control unit 33 also includes a source of energy 33C, such as a rechargeable battery, for powering the unit CSD, and an energy receiver 33D for transforming wireless energy transmitted by the external energy transmitter 32B into electric energy and charging the implanted source of energy 33C (rechargeable battery) with the electric energy.

An implanted sensor (not shown) senses a physical parameter of the patient, such as the pressure in the stomach, or a parameter that relates to the pressure in the stomach. The internal control unit 33 controls the constriction/stimulation unit CSD to reduce or even close the food passageway in response to signals from the sensor indicating flow of food into the stomach, i.e., when the patient has started to eat. After the lapse of a preset period of time, when the patient feels satiety, the internal control unit 33 controls the constriction/stimulation device CSD to open up the food passageway to allow food collected in the upper part of the stomach to pass through the food passageway. Alternatively or in combination, the remote control 32 controls the constriction/stimulation unit CSD in response to signals from the sensor, in the same manner as the internal control unit 33.

The internal control unit 33 may include a signal transmitter that can send an alarm signal to the external remote control 32 in response to signals from the sensor 36 indicating a harmful high pressure in the stomach. The remote control 32 may be equipped with means for producing an indication, such as a sound signal or displayed information, in response to received alarm signals. When the patient's attention is taken by such an alarm signal, he or she may use the push button mentioned above to temporarily switch off the operation of the constriction/stimulation unit CSD to fully open up the food passageway.

Figure 67:
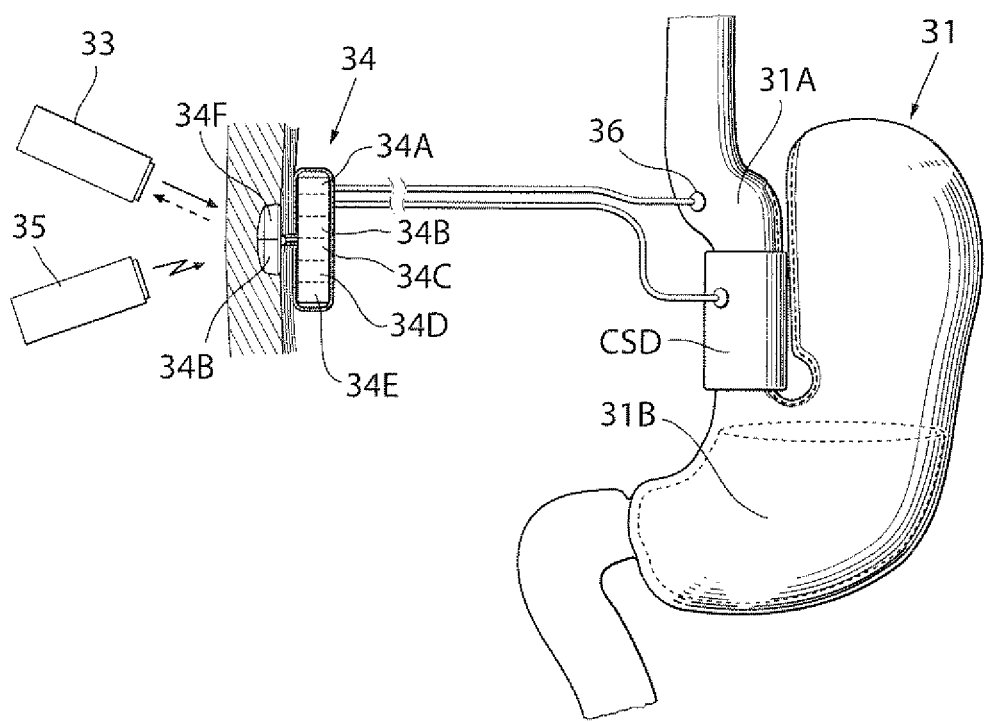
FIG. 67 illustrates a constriction/stimulation unit of an apparatus for practicing the method of the invention applied on the stomach of an obese patient surgically modified by VBG (Vertical Banded Gastroplasty).

FIG. 67 schematically illustrates the stomach 31 of an obese patient treated by VBG (Vertical Banded Gastroplasty). which is a recognized type of bariatric surgery. VBG is currently normally performed with laparoscopic surgery, introducing a camera and other instruments into the abdominal cavity. The stomach is then normally stapled by the instruments in two steps to achieve a stapled circular opening right through both layers of the stomach followed by a vertical stapling of at least two vertical rows of staples. The staples compartmentalize the stomach 31 into a smaller proximal compartment 31A adjacent the esophagus 32 and a larger distal compartment 31B, wherein the smaller proximal compartment 31A communicates with the larger distal compartment 31B through a relatively small outlet opening. The smaller proximal compartment 31A forms a prolongation of the oesophagus 32 at an upper part of the stomach. In this case the stomach 31 has been divided in between the vertical rows of staples 32.

A constriction/stimulation unit CSD in the form of a sleeve is applied on the stomach around the "prolongation of the oesophagus". Of course, the constriction/stimulation unit CSD may be selected from any one of the various constriction and stimulation devices here disclosed. A control device includes an external control unit in the form of a hand-held wireless remote control 33 and a subcutaneously implanted internal control unit 34, which may include a microprocessor 34A, for controlling and programming the operation of the constriction/stimulation unit CSD. There is an external energy transmitter 35 that transmits wireless energy. The remote control 33 and the energy transmitter 35 may be separate devices, as shown in FIG. 67, or may be integrated in a single hand-held device. The remote control 33 is operable by a nurse or doctor to program the microprocessor 34A to properly control the constriction/stimulation unit CSD to suit the individual patients. The internal control unit 34 also includes an emergency push button 34B that can be used by the patient to temporarily switch off the operation of the constriction/stimulation unit CSD in case of emergency, or malfunction of the apparatus. Where the constriction device of the constriction/stimulation unit CSD is hydraulically operated, an injection port 34F is provided integrated in the push button 34B to calibrate the amount of hydraulic fluid in hydraulic components of the hydraulic system serving the constriction device.

The internal control unit 34 also includes a source of energy 34C, such as a rechargeable battery, for powering the constriction/stimulation unit CSD, and an energy receiver 34D for transforming wireless energy transmitted by the external energy transmitter 35 into electric energy and charging the implanted source of energy 34C (rechargeable battery) with the electric energy.

An implanted sensor 36 connected to the internal control unit 34 and applied on the smaller proximal compartment 31A senses a physical parameter of the patient, such as the pressure in the compartment 31A, or a parameter that relates to the pressure in the compartment 31A. The internal control unit 34 controls the constriction/stimulation unit CSD to reduce or even close the food passageway extending from the smaller proximal compartment 31A to the larger distal compartment 31B in response to signals from the sensor 36 indicating flow of food into the smaller compartment, i.e., when the patient has started to eat. After the lapse of a preset period of time, when the patient feels satiety, the internal control unit 34 controls the constriction/stimulation unit CSD to open up the food passageway to allow food collected in the smaller compartment 31A to pass into the larger compartment 31B. Alternatively or in combination, the remote control 33 controls the constriction/stimulation unit CSD in response to signals from the sensor 36, in the same manner as the internal control unit 34.

The internal control unit 34 also includes a signal transmitter 34E that can send an alarm signal to the external remote control 33 in response to signals from the sensor 36 indicating a harmful high pressure in the smaller apartment 31A. The remote control 33 may be equipped with means for producing an indication, such as a sound signal or displayed information, in response to received alarm signals. When the patient's attention is taken by such an alarm signal, he or she may use the push button 34B to temporarily switch off the operation of the constriction/stimulation unit CSD to fully open up the food passageway.

Sexual Dysfunction

Figure 68A:
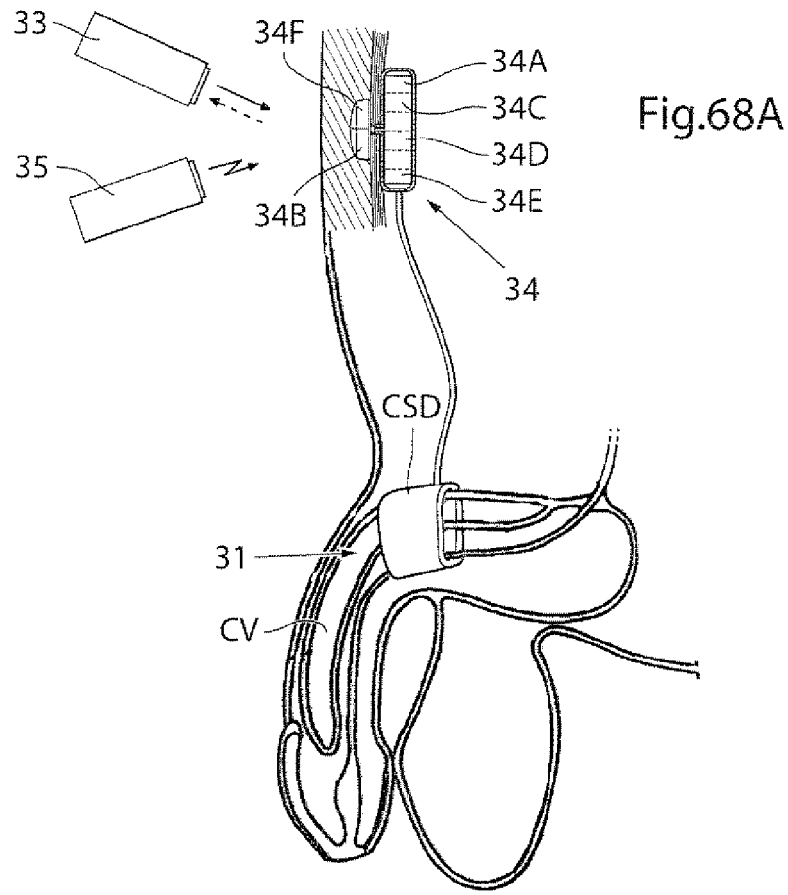
FIG. 68A illustrates an apparatus used for practicing the method of the invention applied around the corpus cavernosum of an impotent patient.

FIG. 68A illustrates an apparatus for practicing the method of the invention applied on a male impotent patient. A constriction/stimulation unit CSD in the form of a sleeve is applied around the corpus cavernosum CV in the penile portion 31 of the patient. Of course, the constriction/stimulation unit CSD may be selected from any one of the various constriction and stimulation devices here disclosed. A control device includes an external control unit in the form of a hand-held wireless remote control 33 and a subcutaneously implanted internal control unit 34, which may include a microprocessor 34A, for controlling and programming the operation of the constriction/stimulation unit CSD. There is an external energy transmitter 35 that transmits wireless energy. The remote control 33 and the energy transmitter 35 may be separate devices, as shown in FIG. 68A, or may be integrated in a single hand-held device. The remote control 33 is operable to program the microprocessor 34A to properly control the constriction/stimulation unit CSD to suit the individual patients. The internal control unit 34 also includes an emergency push button 34B that can be used by the patient to temporarily switch off the operation of the constriction/stimulation unit CSD in case of malfunction of the apparatus. Where the constriction device of the constriction/stimulation unit CSD is hydraulically operated, an injection port 34F is provided integrated in the push button 34B to calibrate the amount of hydraulic fluid in hydraulic components of the hydraulic system serving the constriction device.

The internal control unit 34 also includes a source of energy 34C, such as a rechargeable battery, for powering the constriction/stimulation unit CSD, and an energy receiver 34D for transforming wireless energy transmitted by the external energy transmitter 35 into electric energy and charging the implanted source of energy 34C (rechargeable battery) with the electric energy.

An implanted sensor 36 connected to the internal control unit 34 and applied on the penile portion 31 senses a physical parameter of the patient, such as the pressure in the penile portion 31, or a parameter that relates to the pressure in the penile portion 31. The internal control unit 34 controls the constriction/stimulation unit CSD to increase or decrease the restriction of the blood flow leaving the penis in response to signals from the sensor 36. When the control unit 34 receives signals from the sensor indicating a pressure that exceeds a predetermined high pressure in the penile portion as a result of ejaculation, the internal control unit 34 controls the constriction/stimulation unit CSD to release the penile portion to restore the exit penile blood flow. Alternatively or in combination, the remote control 33 controls the constriction/stimulation unit CSD in response to signals from the sensor 36, in the same manner as the internal control unit 34.

The internal control unit 34 also includes a signal transmitter 34E that can send an alarm signal to the external remote control 33 in response to signals from the sensor 36 indicating a too high pressure in the penile portion 31 that can be harmful to the patient. The remote control 33 may be equipped with means for producing an indication, such as a sound signal or displayed information, in response to received alarm signals. When the patient's attention is taken by such an alarm signal, he may use the push button 34B to quickly switch off the operation of the constriction/stimulation unit CSD to fully release the penile portion.

Figure 68B:
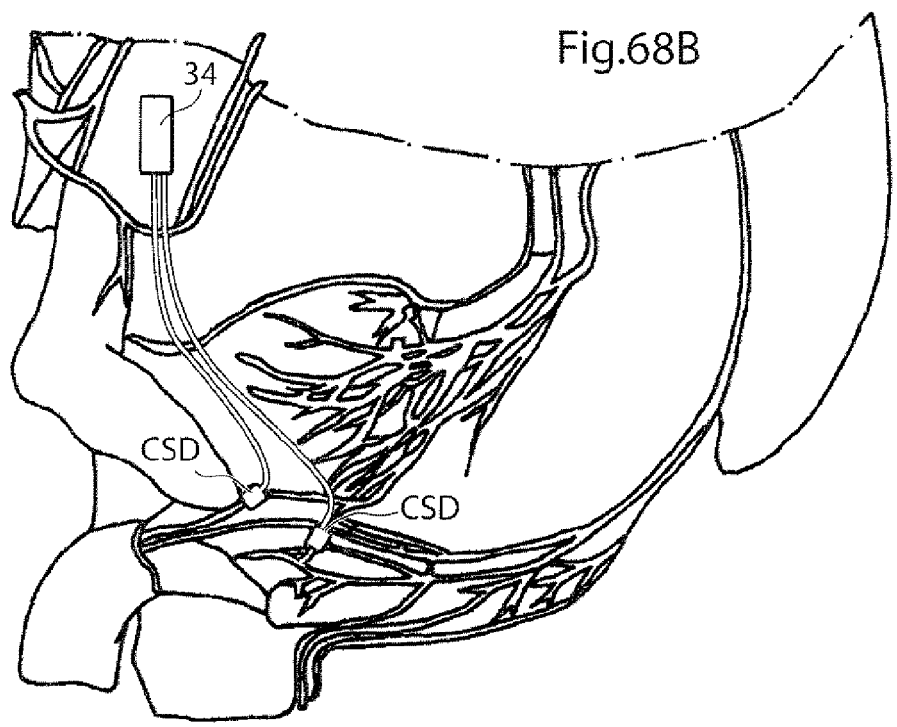
FIG. 68B illustrates an apparatus used for practicing the method of the invention having two constriction/stimulation units applied around respective exit veins from the patient's penis.

FIG. 68B shows an embodiment which is similar to the embodiment of FIG. 68A except that the apparatus includes two constriction/stimulation units CSD which are applied around respective exit veins from the patient's penis.

Of course, the constriction and stimulation devices of the constriction/stimulation units shown in FIGS. 68A and 68B may be replaced by any one of the constriction and stimulation devices described in the various embodiments of the present invention.

Figure 69A:
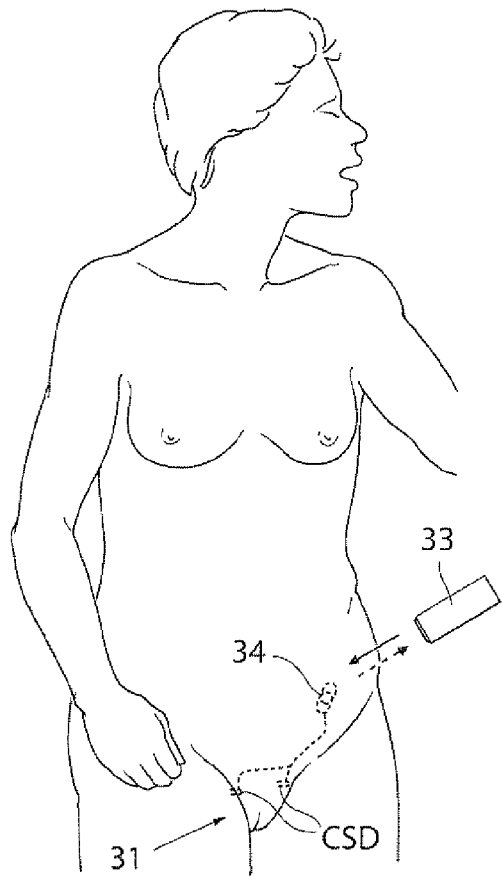
FIG. 69A illustrates an apparatus used for practicing the method of the invention implanted in the body of a female patient suffering from sexual dysfunction.

FIG. 69A illustrates an apparatus for practicing the method of the invention applied on a female patient suffering from sexual dysfunction. A constriction/stimulation unit CSD in the form of a sleeve is applied around the corpus cavernosum CV in the erectile portion 31 of the patient. Of course, the constriction/stimulation unit CSD may be selected from any one of the various constriction and stimulation devices here disclosed. A control device includes an external control unit in the form of a hand-held wireless remote control 33 and a subcutaneously implanted internal control unit 34, which may include a microprocessor 34A, for controlling and programming the operation of the constriction/stimulation unit CSD. There is an external energy transmitter 35 that transmits wireless energy. The remote control 33 and the energy transmitter 35 may be separate devices, as shown in FIG. 69A, or may be integrated in a single hand-held device. The remote control 33 is operable to program the microprocessor 34A to properly control the constriction/stimulation unit CSD to suit the individual patients. The internal control unit 34 also includes an emergency push button 34B that can be used by the patient to temporarily switch off the operation of the constriction/stimulation unit CSD in case of malfunction of the apparatus. Where the constriction device of the constriction/stimulation unit CSD is hydraulically operated, an injection port 34F is provided integrated in the push button 34B to calibrate the amount of hydraulic fluid in hydraulic components of the hydraulic system serving the constriction device.

The internal control unit 34 also includes a source of energy 34C, such as a rechargeable battery, for powering the constriction/stimulation unit CSD, and an energy receiver 34D for transforming wireless energy transmitted by the external energy transmitter 35 into electric energy and charging the implanted source of energy 34C (rechargeable battery) with the electric energy.

An implanted sensor 36 connected to the internal control unit 34 and applied on the erectile portion 31 senses a physical parameter of the patient, such as the pressure in the erectile portion 31, or a parameter that relates to the pressure in the erectile portion 31. The internal control unit 34 controls the constriction/stimulation unit CSD to increase or decrease the restriction of the blood flow leaving the erectile tissue in response to signals from the sensor 36. When the control unit 34 receives signals from the sensor indicating a pressure that exceeds a predetermined high pressure in the erectile portion as a result of orgasm, the internal control unit 34 controls the constriction/stimulation unit CSD to release the erectile portion to restore the exit erectile tissue blood flow. Alternatively or in combination, the remote control 33 controls the constriction/stimulation unit CSD in response to signals from the sensor 36, in the same manner as the internal control unit 34.

The internal control unit 34 also includes a signal transmitter 34E that can send an alarm signal to the external remote control 33 in response to signals from the sensor 36 indicating a too high pressure in the erectile portion 31 that can be harmful to the patient. The remote control 33 may be equipped with means for producing an indication, such as a sound signal or displayed information, in response to received alarm signals. When the patient's attention is taken by such an alarm signal, he may use the push button 34B to quickly switch off the operation of the constriction/stimulation unit CSD to fully release the erectile portion.

Figure 69B:
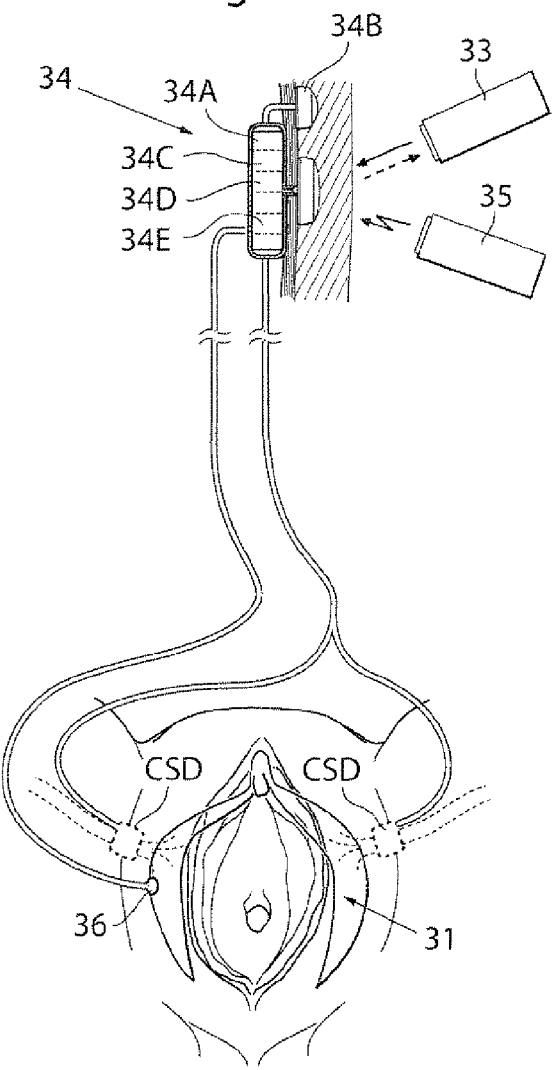
FIG. 69B illustrates the apparatus shown in FIG. 69A having two constriction/stimulation units applied around respective exit veins of the patient's erectile tissue.
Figure 69C:
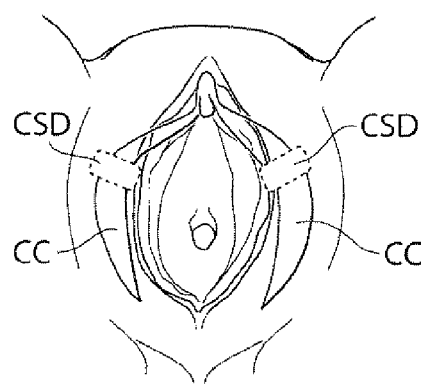
FIG. 69C illustrates the apparatus shown in FIG. 69A having two constriction/stimulation units applied around respective corpora cavernosa of the patient's erectile tissue.

FIG. 69B shows an embodiment which is similar to the embodiment of FIG. 69A except that the apparatus includes two constriction/stimulation units CSD which are applied around respective exit veins from the patient's erectile tissue.

Of course, the constriction and stimulation devices of the constriction/stimulation units shown in FIGS. 69A and 69B may be replaced by any one of the constriction and stimulation devices described in the various embodiments of the present invention.

Pregnancy Control

Egg Movement Control

Figure 70:
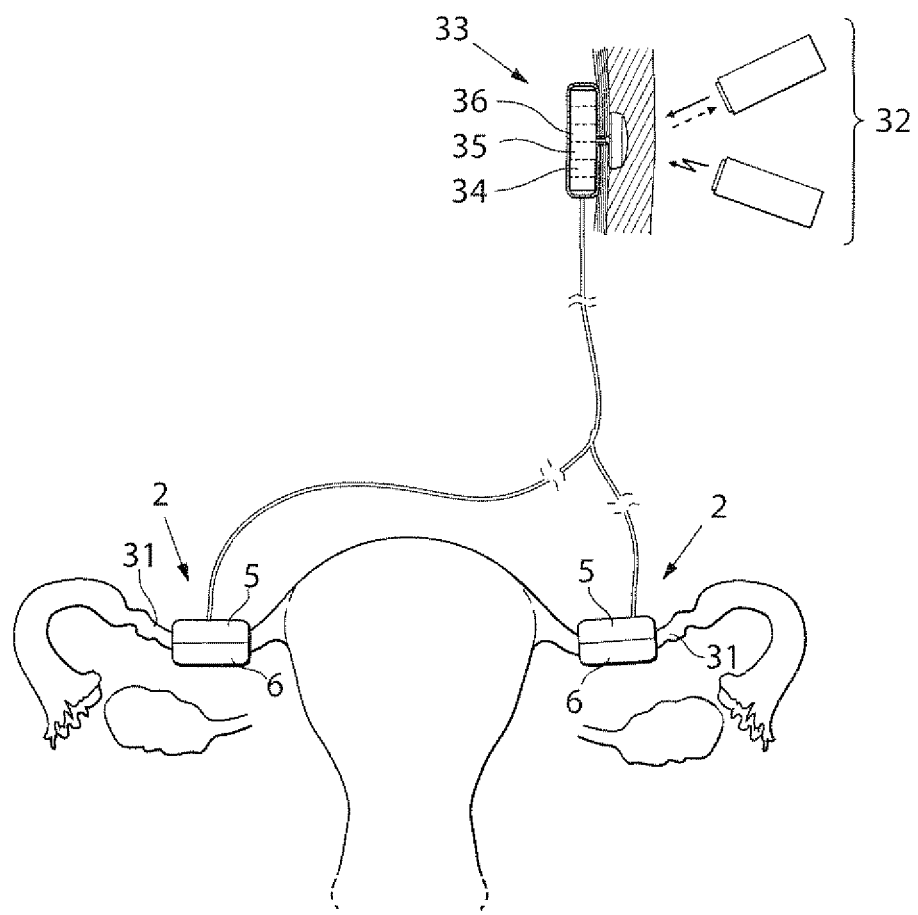
FIG. 70 Illustrates a female uterus and the connecting uterine tubes, with the apparatus and energy supply unit in place.

FIG. 70 illustrates the embodiment of FIG. 2 applied on the uterine tube of a patient. The clamping elements 5, 6 of the constriction device 2 constrict the uterine tubes 31 and the stimulation device 3 is energized to close the uterine tube. (For the sake of clarity, the housing is not shown and the clamping elements 5, 6 are exaggerated.) In this embodiment, a control device includes an external control unit in the form of a hand-held wireless remote control 32, and an implanted internal control unit 33, which may include a microprocessor, for controlling the constriction and stimulation devices. The remote control 32 is operable by the patient to control the internal control unit 33 to switch on and off the constriction device and/or the stimulation device. Alternatively, however, the remote control 32 may be replaced by a subcutaneously implanted push button that is manually switched by the patient between "on" and "off". Such a manually operable push button may also be provided in combination with the remote control 32 as an emergency button to allow the patient to stop the operation of the apparatus in case of emergency or malfunction.

The internal control unit 33 controls an implanted operation device 34 to move the clamping elements 5, 6. An implanted source of energy 35, such as a rechargeable battery, powers the operation device 34. The internal control unit 33, which may be implanted subcutaneously or in the abdomen, also works as en energy receiver, i.e., for transforming wireless energy into electric energy and charging the implanted source of energy 35 (rechargeable battery) with the electric energy.

An implanted sensor 36 senses a physical parameter of the patient, such as the pressure in the uterine tubes, or a parameter that relates to the pressure in the uterine tubes, wherein the internal control unit 33 controls the constriction device 2 and/or the stimulation device 3 in response to signals from the sensor 36. In this embodiment the sensor 36 is a pressure sensor, wherein the internal control unit 33 controls the constriction device and/or stimulation device to change the constriction of the patient's intestines 31 in response to the pressure sensor 36 sensing a predetermined value of measured pressure. For example, the control unit 33 may control the constriction device and/or stimulation device to increase the constriction of the patient's uterine tubes 31 in response to the pressure sensor sensing an increased pressure. Alternatively or in combination, the remote control 32 controls the constriction device and/or stimulation device in response to signals from the sensor 36, in the same manner as the internal control unit 33.

The remote control 32 may be equipped with means for producing an indication, such as a sound signal or displayed information, in response to signals from the sensor 36. When the patient's attention is taken by such an indication indicating an increased pressure exceeding a threshold value, he or she may use the remote control to control the constriction device and stimulation device to pump eggs through the patient's uterine tubes.

Of course, the constriction device 2 shown in FIG. 70 may be replaced by any one of the constriction devices described in the various embodiments of the present invention, where applicable.

Sperm Movement Control

Figure 71:
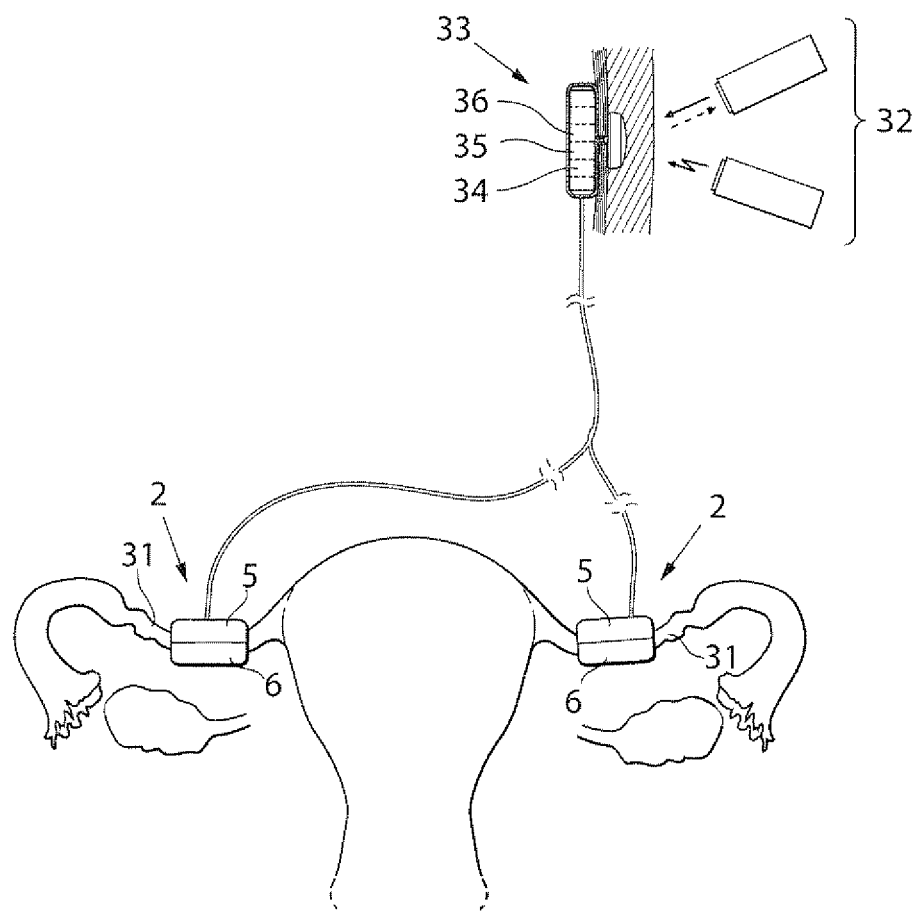
FIG. 71 Illustrates a female uterus and the connecting uterine tubes, with the apparatus and energy supply unit in place.

FIG. 71A illustrates a constriction/stimulation unit 36 applied on the uterine tube of a patient. FIGS. 71B and 71C show different positions of unit 36 on the uterine tubes. There is a wireless remote control 32A and an implanted internal control unit 33, which may include a microprocessor 33A, for controlling the unit 36, and an external energy transmitter 32B that transmits wireless energy. In this embodiment the remote control 32A and the energy transmitter 32B are separate devices. However, they may be integrated in a single hand-held device. The remote control 32 is operable by a nurse or doctor to program the microprocessor to properly control the constriction/stimulation unit 36 to suit the individual patients. In addition, the constriction/stimulation unit 36 may be controlled by a subcutaneously implanted push button that can be used by the patient to temporarily switch off the operation of the constriction/stimulation unit 36 in case of emergency, or malfunction of the apparatus.

The internal control unit 33 also includes a source of energy 33C, such as a rechargeable battery, for powering the unit 36, and an energy receiver 33D for transforming wireless energy transmitted by the external energy transmitter 32B into electric energy and charging the implanted source of energy 33C (rechargeable battery) with the electric energy.

An implanted sensor (not shown) senses a physical parameter of the patient, such as the pressure in the uterine tubes, or a parameter that relates to the pressure in the uterine tubes, wherein the internal control unit 33 controls unit 36 in response to signals from the sensor. In this embodiment the sensor is a pressure sensor, wherein the internal control unit 33 controls unit 36 to change the constriction of the patient's uterine tube 31 in response to the pressure sensor sensing a predetermined value of measured pressure. For example, the control unit 33 may control unit 36 to increase the constriction of the patient's uterine tubes 31 in response to the pressure sensor sensing an increased pressure. Alternatively or in combination, the remote control 32A controls unit 36 in response to signals from the sensor, in the same manner as the internal control unit 33.

The remote control 32 may be equipped with means for producing an indication, such as a sound signal or displayed information, in response to signals from the sensor 36. When the patient's attention is taken by such an indication indicating an increased pressure exceeding a threshold value, she may use the remote control 32A to pump sperms through the uterine tubes towards the ovary. If pregnancy is desired. Otherwise, she may control the pump to pump in the opposite direction to avoid pregnancy.

Of course, the constriction/stimulation unit 36 shown in FIGS. 71A-C may be replaced by any one of the constriction/stimulation units described in the various embodiments of the present invention, where applicable.

Blood Flow Control

Figure 72A:
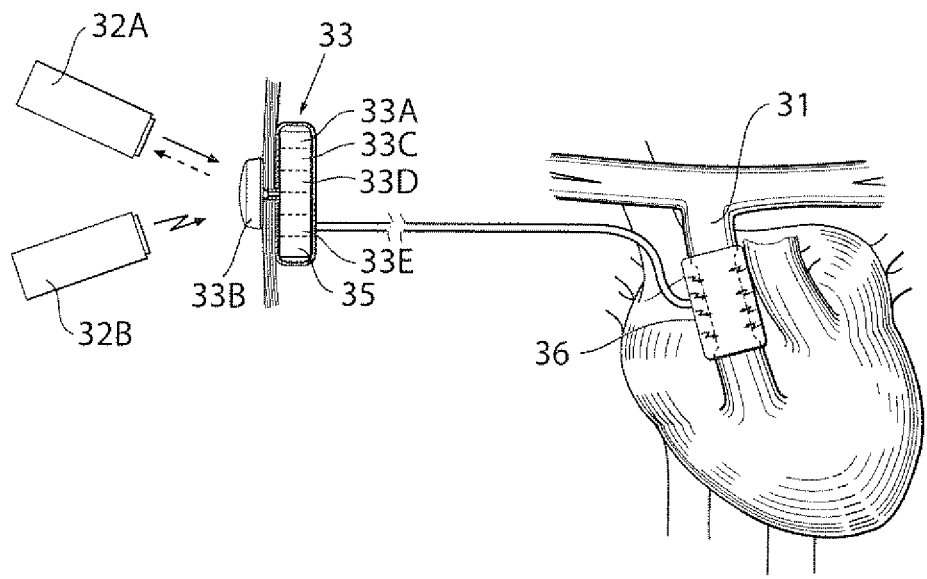
FIG. 72A schematically shows an embodiment of a system for controlling a flow of blood with wireless control.

FIG. 72A illustrates a constriction/stimulation device applied on a blood vessel a patient suffering from pulmonary hypertension. A restriction device is applied on the pulmonary artery in this case the trunk as disclosed. The combination of gently constricting and stimulating will cause a restriction to reduce blood pressure. In this embodiment, the control device includes an external control unit in the form of a hand-held wireless remote control 32A and an implanted internal control unit 33, which may include a microprocessor 33A, for controlling the constriction and stimulation devices. There is an external energy transmitter 32A that transmits wireless energy. The remote control 32A and the energy transmitter 32B may be separate devices, as shown in FIG. 72, or may be integrated in a single hand-held device. The remote control 32A is operable by the patient to control the internal control unit 33 to switch on and off the constriction device and/or the stimulation device. The internal control unit 33 also includes a push button 33B that can be used by the patient to manually switch "on" and "off" the operation of the constriction and/or stimulation devices. The button also serves as an emergency button to allow the patient to stop the operation of the apparatus in case of emergency or malfunction. Preferably the control unit controls the device automatically after input from a sensor.

The internal control unit 33 controls the constriction/stimulation device. The internal control unit 33 also includes a source of energy 33C, such as a rechargeable battery, for powering the operation device 34, and an energy receiver 33D for transforming wireless energy transmitted by the external energy transmitter 32B into electric energy and charging the implanted source of energy 33C (rechargeable battery) with the electric energy.

An implanted sensor 36 applied on the constriction device senses a physical parameter of the patient, such as the pressure in the vessel, or a parameter that relates to the pressure in the vessel. The internal control unit 33 includes a signal transmitter 33E that sends an alarm signal to the external remote control 32A in response to signals from the sensor 36 indicating a predetermined value of measured pressure.

The remote control 32 may be equipped with means for producing an indication, such as a sound signal or displayed information, in response to received signals such as alarm signals. When the patient's attention is taken by such an indication indicating an increased pressure exceeding a threshold value, or when the patient desires to urinate, he or she may conveniently use the remote control 32A or the push button 33B to activate the operation device 34 to empty the bladder.

Figure 72B:
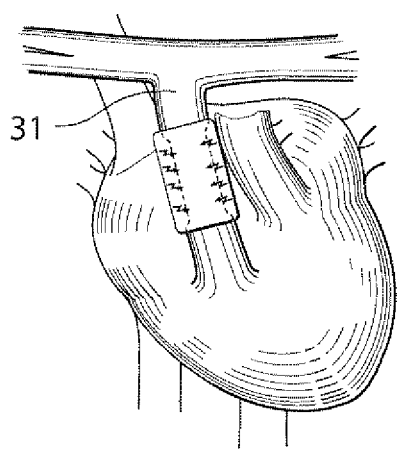
FIGS. 72B and 72C show different positions for a constriction device comprised in a system for controlling a flow of blood.
Figure 72C:
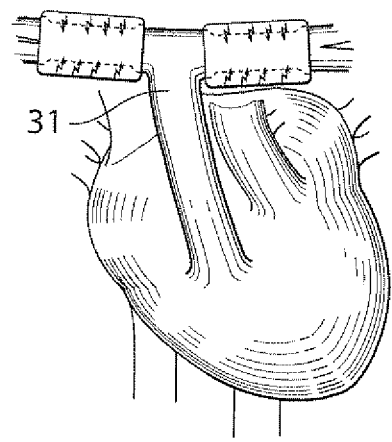

A comparison, FIG. 72B illustrates the position of one single constriction/stimulation device while FIG. 72C illustrates the positions of two constriction/stimulation device. To reduce the pressure to the lung the pulmonary artery could be restricted before the bifurcation to the two lungs or after the same.

Aneurysm

Figure 73:
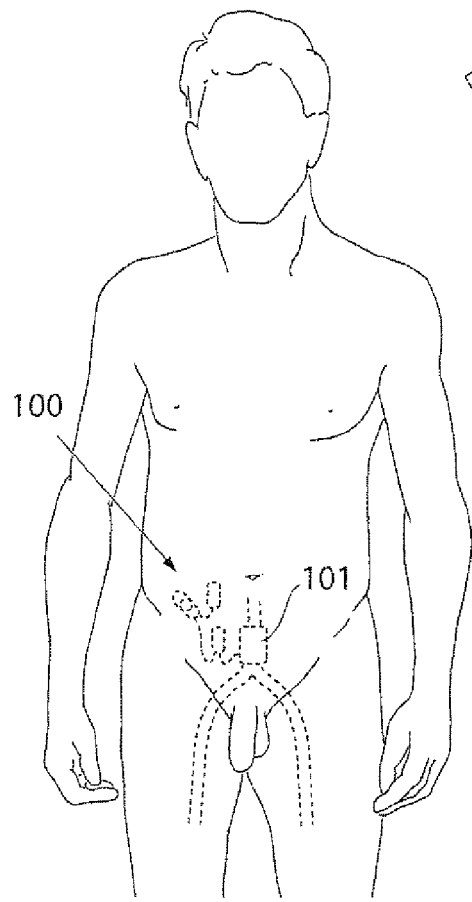
FIG. 73 is a schematic general view of a human being having a cuff implanted for treating an aneurysm located on the aorta in the abdomen close to the Y-bifurcation extending to the legs.

FIG. 73 shows a general view of a human 100 having a cuff 101 implanted for treating an aneurysm. In FIG. 73 the treated aneurysm is located on the aorta in the abdomen close to the Y-bifurcation extending to the legs. The cuff 101 can be designed in various ways but is generally formed as an implantable member adapted to be placed in connection with a blood vessel having said vascular aneurysm, and adapted to exert a pressure on said aneurysm from the outside of said blood vessel. In particular the pressure exerted on the blood vessel is essentially uniform from all direction and adapted to hinder the blood vessel to expand in all directions thereby acting to prevent the blood vessel from bursting. The pressure can in accordance with one embodiment be essentially equal to or lower than the diastolic blood pressure of the treated patient. The cuff 101 can be made in any suitable material such as an elastic material adapted for implantation in a human or mammal body.

The cuff 101 can exercise the pressure in a number of different ways. In accordance with one embodiment of the present invention the pressure applied on the blood vessel can be mechanical and adjustable by means of an adjustable screw or a similar means in order to apply a pressure on the blood vessel. The cuff 101 can also be formed by a spring loaded member and operated in a suitable manner such as hydraulically or pneumatically In FIG. 74A a cuff 101 in accordance with one embodiment of the present invention is shown in more detail. The cuff 101 comprises a number of segments 103 each adjustable and possible to tailor fit a particular aneurysm 102 of a blood vessel 104 to be treated. Each segment 103 can be adjusted either as a whole or individually. The segments 103 can be controlled and adjusted mechanically by an adjustable screw or similar or adapted to be filled with a fluid. For example, the segments can be provided axially along the blood vessel and also radially along the blood vessel forming a matrix of sub-segments that constitutes the cuff 101. In particular one segment can be located above and one below the aneurysm along the blood vessel.

The adjustment can be controlled by an electronic control unit 105 adapted to receive and transmit signals from a transmitter/receiver 106 located outside the body of a treated patient. The electronic control unit can also comprise a chargeable battery 111 chargeable from the outside by an external charger unit 112. The electronic control unit can comprise an electrical pulse generator 109 for generating electrical pulses as is described in more detail below.

The electronic control unit 105 can further be connected to or comprise a hydraulic pump 110 associated with a reservoir 115 containing of a fluid used to regulate the pressure of the cuff 101. The pump is thus adapted to pump the hydraulic fluid in or out from the cuff 101 in order to adjust the pressure applied in the aneurysm. The control mechanism used for keeping the pressure in the cuff 101 can comprise a pressure tank 117.

The cuff 101 can be shaped in any desirable form to enable treatment of an aneurysm wherever it is located. In accordance with one embodiment the cuff 101 is provided with at least one sensor 107 adapted to sense the pressure from the blood vessel that the cuff is surrounding.

The sensor(s) 107 used to generate a signal indicative of one or many parameters related to the aneurysm and the device 101 used for treating the aneurysm can for example be a gauge sensor. The sensor 107 can be adapted to generate sensor signals used for monitoring parameters including but not limited to the pressure in a hydraulic cuff, the pressure of a mechanical cuff, the pressure of a pneumatic cuff, the pressure in a blood vessel, the shape of the blood vessel in particular a parameter related to the diameter of the aneurysm.

By sensing the pressure from the blood vessel the cuff can be controlled to apply a correct pressure on the blood vessel thereby keeping the form of the blood vessel essentially constant. For example the pressure may vary over time as a result of changes in the wall of the blood vessel of surrounding tissue. Also the pressure will change as a function of the phase in which the heart is working. In other words the pressure will be different in a systolic phase as compared to a diastolic phase. By using a pressure sensor the pressure applied by the cuff 101 can be adapted to react to changes in the sensed pressure and apply a corresponding counter pressure. The sensor signals generated by the sensor(s) 107 of the cuff can also be used to trigger an alarm in response to the sensor signal indicating an expansion of the aneurysm. In response to an alarm signal being generated the cuff can be automatically controlled to exercise a counter pressure on the blood vessel to counter or limit the expansion of the aneurysm.

In yet another embodiment, electrodes 108 can be provided in the cuff. The electrodes can be connected to the electrical pulse generator, which is adapted to generate electrical pulses for stimulating the wall of the aneurysm. The purpose of the electrical stimulation is to increase the tonus of the wall of the aneurysm.

In accordance with one embodiment the electrical stimulation device used for treating a vascular aneurysm of a human or mammal patient is connected to electrodes adapted to stimulate the wall of the aneurysm at multiple stimulation points. The multiple stimulation groups may further be blood vesselized in different stimulation groups which can stimulated independently of each other. In accordance with one embodiment the electrical stimulation is performed with positive and or negative voltage stimulation pulses. In one embodiment the current used for stimulation of the aneurysm wall is kept essentially constant.

The sequence of electrical pulses used to stimulation the wall of the aneurysm can be applied with a predetermined periodicity having periods of no stimulation therein between during which periods without stimulation the wall of the aneurysm is allowed to rest. The electrical stimulation signal can also be Pulse Width Modulated to control the energy applied. In accordance with one embodiment the electrical stimulation is applied during the systolic phase to increase the tonus of the wall of the aneurysm. The systolic phase can be detected by the sensors 107 used to sense the pressure of the aneurysm as described above.

In accordance with one embodiment the stimulation can be controlled to be applied with a temporarily increased intensity and position during emergency situations when the aneurysm is detected to rapidly expands, to limit the expansion of said aneurysm.

The shape of the cuff 101 can as stated above be tailor made to suit the location where an aneurysm is to be treated. In FIG. 74C, a cuff 101 is seen from above in a direction aligned with a treated blood vessel. As can be seen in FIG. 74C each segment 3 can be sub-divided into a number of sub segments 103a, 103b . . . together forming a closed loop around the treated aneurysm. In case the aneurysm is located in the aorta bifurcation region the cuff 101 can be Y-shaped as is shown in FIG. 74B.

Figure 74A:
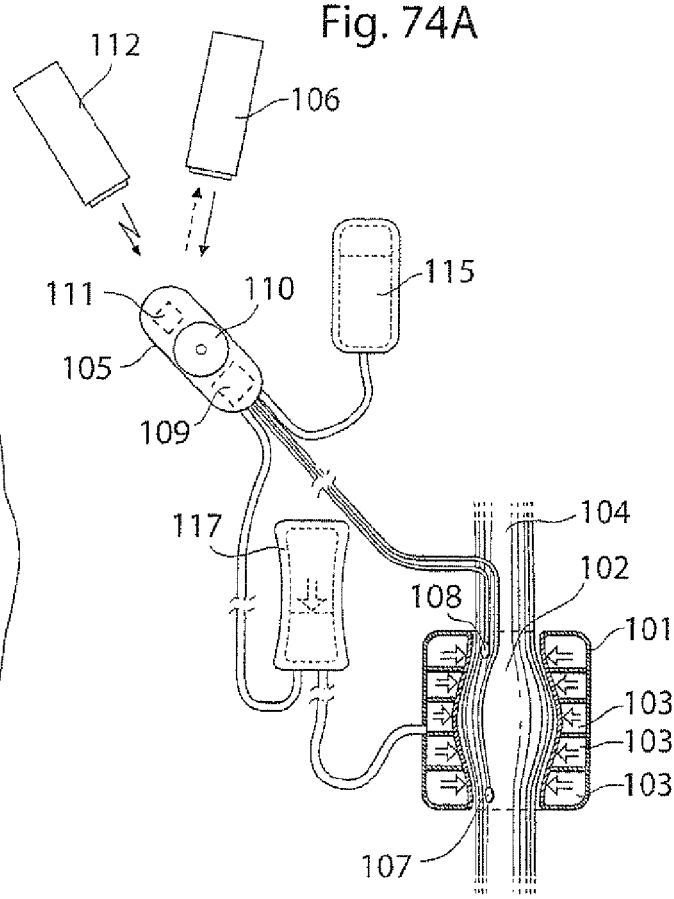
FIG. 74A shows a schematic detail of the apparatus indicated in FIG. 73.
Figure 74B:
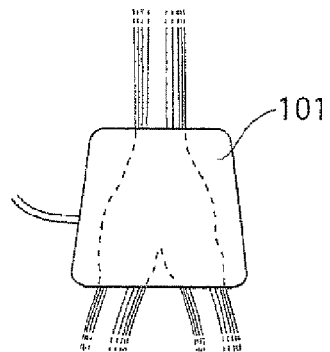
FIG. 74B shows a detail of the cuff when placed on the Y-bifurcation.
Figure 74C:
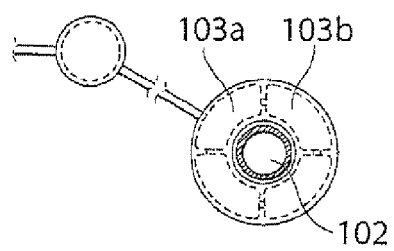
FIG. 74C shows a cross-sectional view of the cuff in FIG. 73B.

Of course, the constriction device 101 shown in FIGS. 74A-74C may be replaced by any one of the constriction devices described in the various embodiments of the present invention, where applicable.

Figure 75:
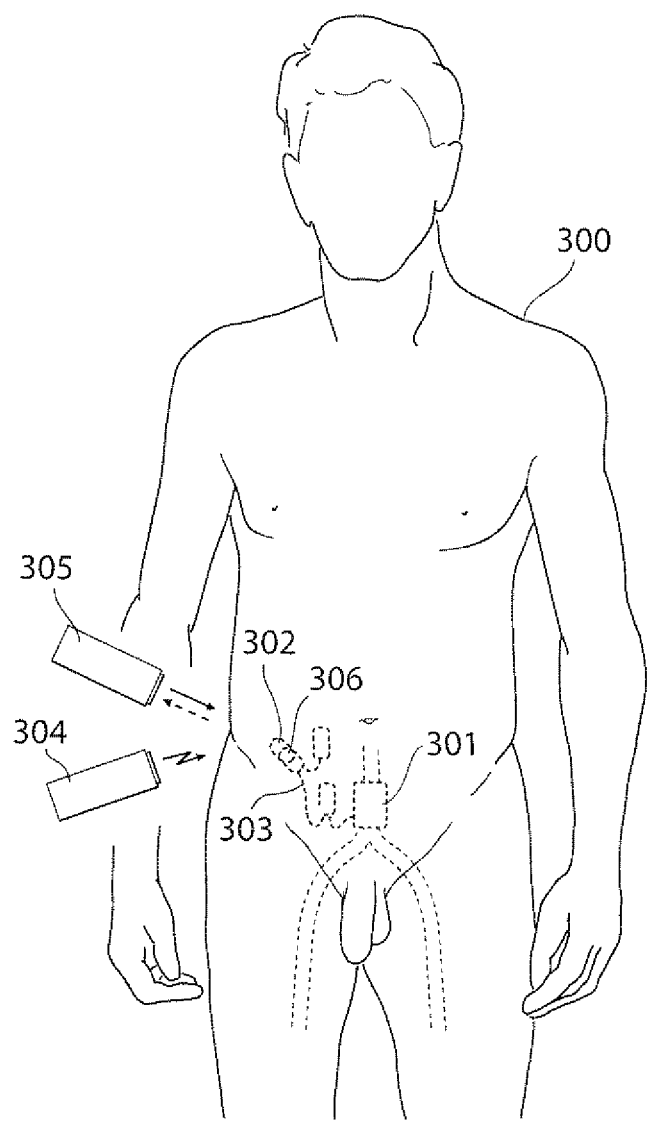
FIG. 75 illustrates a system for treating, stabilizing or monitoring an aneurysm, wherein the system includes an apparatus for use in a method according to an embodiment of the invention implanted in a patient.

FIG. 75 illustrates a system for treating a disease comprising a constriction/stimulation unit 301 for practicing any one of the methods of the present invention disclosed herein. Unit 301 is placed in the abdomen of a patient 300. An implanted energy-transforming device 302 is adapted to supply energy consuming components of unit 301 with energy via a power supply line 303. An external energy-transmission device 304 for non-invasively energizing unit 301 transmits energy by at least one wireless energy signal. The implanted energy-transforming device 302 transforms energy from the wireless energy signal into electric energy which is supplied via the power supply line 303. The system may also include a transmitter/receiver 305 located outside the body of a treated patient. This transmitter/receiver communicates with an electronic control unit 306 adapted to receive and transmit signals from said transmitter/receiver 305. The system can also comprise a chargeable battery (not shown) chargeable from the outside by an external charger unit, same or different from the external energy-transmission device 304. The system can also comprise an electrical pulse generator (not shown) for generating electrical pulses as is described in more detail below.

The wireless energy signal may include a wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal. Alternatively, the wireless energy signal may include an electric or magnetic field, or a combined electric and magnetic field.

The wireless energy-transmission device 304 may transmit a carrier signal for carrying the wireless energy signal. Such a carrier signal may include digital, analogue or a combination of digital and analogue signals. In this case, the wireless energy signal includes an analogue or a digital signal, or a combination of an analogue and digital signal.

Generally speaking, the energy-transforming device 302 is provided for transforming wireless energy of a first form transmitted by the energy-transmission device 304 into energy of a second form, which typically is different from the energy of the first form. The implanted apparatus 301 is operable in response to the energy of the second form. The energy-transforming device 302 may directly power unit 301 with the second form energy, as the energy-transforming device 302 transforms the first form energy transmitted by the energy-transmission device 304 into the second form energy. The system may further include an implantable accumulator, wherein the second form energy is used at least partly to charge the accumulator.

Alternatively, the wireless energy transmitted by the energy-transmission device 304 may be used to directly power unit 301, as the wireless energy is being transmitted by the energy-transmission device 304. Where the system comprises an operation device for operating unit 301, as will be described below, the wireless energy transmitted by the energy-transmission device 304 may be used to directly power the operation device to create kinetic energy for the operation of unit 301.

The wireless energy of the first form may comprise sound waves and the energy-transforming device 302 may include a piezo-electric element for transforming the sound waves into electric energy. The energy of the second form may comprise electric energy in the form of a direct current or pulsating direct current, or a combination of a direct current and pulsating direct current, or an alternating current or a combination of a direct and alternating current. Normally, unit 301 comprises electric components that are energized with electrical energy. Other implantable electric components of the system may be at least one voltage level guard or at least one constant current guard connected with the electric components of unit 301.

Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transmission device may be controlled from outside the patient's body to release electromagnetic wireless energy, and the released electromagnetic wireless energy is used for operating unit 301. Alternatively, the energy-transmission device is controlled from outside the patient's body to release non-magnetic wireless energy, and the released non-magnetic wireless energy is used for operating unit 301.

The external energy-transmission device 304 also includes a wireless remote control having an external signal transmitter for transmitting a wireless control signal for non-invasively controlling unit 301. The control signal is received by an implanted signal receiver which may be incorporated in the implanted energy-transforming device 302 or be separate there from.

The wireless control signal may include a frequency, amplitude, or phase modulated signal or a combination thereof. Alternatively, the wireless control signal includes an analogue or a digital signal, or a combination of an analogue and digital signal. Alternatively, the wireless control signal comprises an electric or magnetic field, or a combined electric and magnetic field.

The wireless remote control may transmit a carrier signal for carrying the wireless control signal. Such a carrier signal may include digital, analogue or a combination of digital and analogue signals. Where the control signal includes an analogue or a digital signal, or a combination of an analogue and digital signal, the wireless remote control preferably transmits an electromagnetic carrier wave signal for carrying the digital or analogue control signals.

FIG. 76 illustrates the system of FIG. 75 in the form of a more generalized block diagram showing unit 301, the energy-transforming device 302 powering unit 301 via power supply line 303, and the external energy-transmission device 304, The patient's skin 305, generally shown by a vertical line, separates the interior of the patient to the right of the line from the exterior to the left of the line.

FIG. 77 shows an embodiment of the invention identical to that of FIG. 76, except that a reversing device in the form of an electric switch 306 operable for example by polarized energy also is implanted in the patient for reversing unit 301. When the switch is operated by polarized energy the wireless remote control of the external energy-transmission device 304 transmits a wireless signal that carries polarized energy and the implanted energy-transforming device 302 transforms the wireless polarized energy into a polarized current for operating the electric switch 306. When the polarity of the current is shifted by the implanted energy-transforming device 302 the electric switch 306 reverses the function performed by unit 301.

FIG. 78A shows an embodiment of the invention identical to that of FIG. 76, except that an operation device 307 implanted in the patient for operating unit 301 is provided between the implanted energy-transforming device 302 and unit 301. This operation device can be in the form of a motor 307, such as an electric servomotor. The motor 307 is powered with energy from the implanted energy-transforming device 302, as the remote control of the external energy-transmission device 304 transmits a wireless signal to the receiver of the implanted energy-transforming device 302.

FIG. 78B shows an embodiment of the invention identical to that of FIG. 76, except that it also comprises an operation device is in the form of an assembly 308 including a motor/pump unit 309 and a fluid reservoir 310 is implanted in the patient. In this case unit 301 is hydraulically operated, i.e. hydraulic fluid is pumped by the motor/pump unit 309 from the fluid reservoir 310 through a conduit 311 to unit 301 to operate unit 301, and hydraulic fluid is pumped by the motor/pump unit 309 back from unit 301 to the fluid reservoir 310 to return unit 301 to a starting position. The implanted energy-transforming device 302 transforms wireless energy into a current, for example a polarized current, for powering the motor/pump unit 309 via an electric power supply line 312.

Instead of a hydraulically operated unit 301, it is also envisaged that the operation device comprises a pneumatic operation device. In this case, the hydraulic fluid can be pressurized air to be used for regulation and the fluid reservoir is replaced by an air chamber.

In all of these embodiments the energy-transforming device 302 may include a rechargeable accumulator like a battery or a capacitor to be charged by the wireless energy and supplies energy for any energy consuming part of the system.

As an alternative, the wireless remote control described above may be replaced by manual control of any implanted part to make contact with by the patient's hand most likely indirect, for example a press button placed under the skin.

FIG. 79 shows an embodiment of the invention comprising the external energy-transmission device 304 with its wireless remote control, unit 301, in this case hydraulically operated, and the implanted energy-transforming device 302, and further comprising a hydraulic fluid reservoir 313, a motor/pump unit 309 and an reversing device in the form of a hydraulic valve shifting device 314, all implanted in the patient. Of course the hydraulic operation could easily be performed by just changing the pumping direction and the hydraulic valve may therefore be omitted. The remote control may be a device separated from the external energy-transmission device or included in the same. The motor of the motor/pump unit 309 is an electric motor. In response to a control signal from the wireless remote control of the external energy-transmission device 304, the implanted energy-transforming device 302 powers the motor/pump unit 309 with energy from the energy carried by the control signal, whereby the motor/pump unit 309 distributes hydraulic fluid between the hydraulic fluid reservoir 313 and unit 301. The remote control of the external energy-transmission device 304 controls the hydraulic valve shifting device 314 to shift the hydraulic fluid flow direction between one direction in which the fluid is pumped by the motor/pump unit 309 from the hydraulic fluid reservoir 313 to unit 301 to operate unit 301, and another opposite direction in which the fluid is pumped by the motor/pump unit 309 back from unit 301 to the hydraulic fluid reservoir 313 to return unit 301 to a starting position.

FIG. 80 shows an embodiment of the invention comprising the external energy-transmission device 304 with its wireless remote control, unit 301, the implanted energy-transforming device 302, an implanted internal control unit 315 controlled by the wireless remote control of the external energy-transmission device 304, an implanted accumulator 316 and an implanted capacitor 317. The internal control unit 315 arranges storage of electric energy received from the implanted energy-transforming device 302 in the accumulator 316, which supplies energy to unit 301. In response to a control signal from the wireless remote control of the external energy-transmission device 304, the internal control unit 315 either releases electric energy from the accumulator 316 and transfers the released energy via power lines 318 and 319, or directly transfers electric energy from the implanted energy-transforming device 302 via a power line 320, the capacitor 317, which stabilizes the electric current, a power line 321 and the power line 319, for the operation of unit 301.

The internal control unit is preferably programmable from outside the patient's body. In a preferred embodiment, the internal control unit is programmed to regulate unit 301 according to a pre-programmed time-schedule or to input from any sensor sensing any possible physical parameter of the patient or any functional parameter of the system.

In accordance with an alternative, the capacitor 317 in the embodiment of FIG. 80 may be omitted. In accordance with another alternative, the accumulator 316 in this embodiment may be omitted.

FIG. 81 shows an embodiment of the invention identical to that of FIG. 76, except that a battery 322 for supplying energy for the operation of unit 301 and an electric switch 323 for switching the operation of unit 301 also are implanted in the patient. The electric switch 323 may be controlled by the remote control and may also be operated by the energy supplied by the implanted energy-transforming device 302 to switch from an off mode, in which the battery 322 is not in use, to an on mode, in which the battery 322 supplies energy for the operation of unit 301.

FIG. 82 shows an embodiment of the invention identical to that of FIG. 80, except that an internal control unit 315 controllable by the wireless remote control of the external energy-transmission device 304 also is implanted in the patient. In this case, the electric switch 323 is operated by the energy supplied by the implanted energy-transforming device 302 to switch from an off mode, in which the wireless remote control is prevented from controlling the internal control unit 315 and the battery is not in use, to a standby mode, in which the remote control is permitted to control the internal control unit 315 to release electric energy from the battery 322 for the operation of unit 301.

Figure 83:
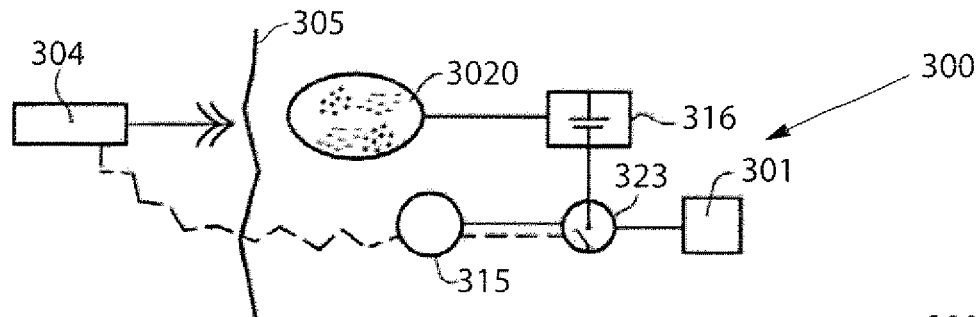

FIG. 83 shows an embodiment of the invention identical to that of FIG. 82, except that an accumulator 316 is substituted for the battery 322 and the implanted components are interconnected differently. In this case, the accumulator 316 stores energy from the implanted energy-transforming device 302. In response to a control signal from the wireless remote control of the external energy-transmission device 304, the internal control unit 315 controls the electric switch 323 to switch from an off mode, in which the accumulator 316 is not in use, to an on mode, in which the accumulator 316 supplies energy for the operation of unit 301. The accumulator may be combined with or replaced by a capacitor.

Figure 84:
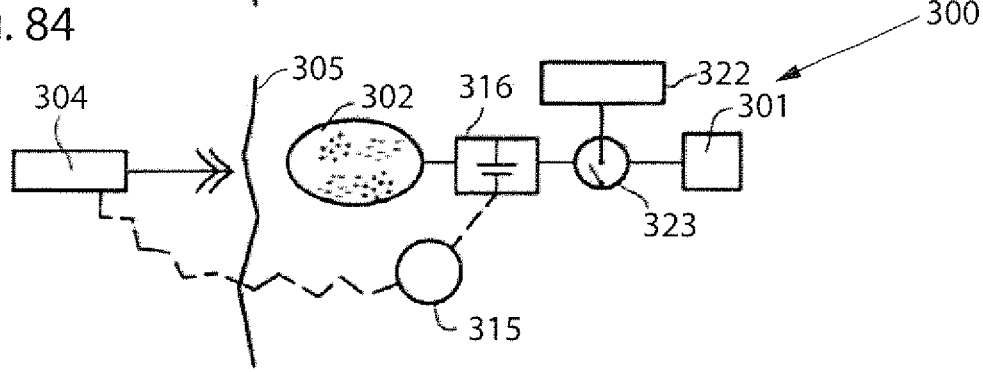

FIG. 84 shows an embodiment of the invention identical to that of FIG. 82, except that a battery 322 also is implanted in the patient and the implanted components are interconnected differently. In response to a control signal from the wireless remote control of the external energy-transmission device 304, the internal control unit 315 controls the accumulator 316 to deliver energy for operating the electric switch 323 to switch from an off mode, in which the battery 322 is not in use, to an on mode, in which the battery 322 supplies electric energy for the operation of unit 301.

Alternatively, the electric switch 323 may be operated by energy supplied by the accumulator 316 to switch from an off mode, in which the wireless remote control is prevented from controlling the battery 322 to supply electric energy and is not in use, to a standby mode, in which the wireless remote control is permitted to control the battery 322 to supply electric energy for the operation of unit 301.

It should be understood that the switch 323 and all other switches in this application should be interpreted in its broadest embodiment. This means a transistor, MCU, MCPU, ASIC, FPGA or a DA converter or any other electronic component or circuit that may switch the power on and off. Preferably the switch is controlled from outside the body, or alternatively by an implanted internal control unit.

Figure 85:
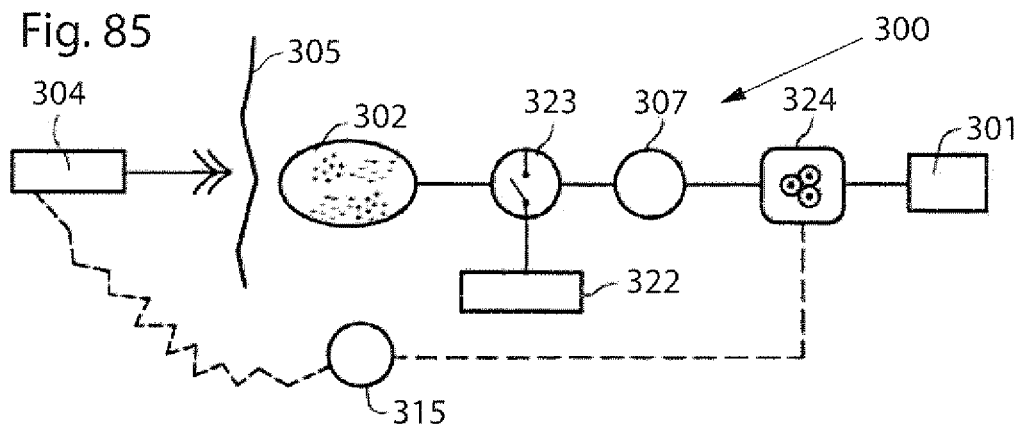

FIG. 85 shows an embodiment of the invention identical to that of FIG. 81, except that a motor 307, a mechanical reversing device in the form of a gear box 324, and an internal control unit 315 for controlling the gear box 324 also are implanted in the patient. The internal control unit 315 controls the gear box 324 to reverse the function performed by unit 301 (mechanically operated). Even simpler is to switch the direction of the motor electronically. The gear box interpreted in its broadest embodiment may stand for a servo arrangement saving force for the operation device in favour of longer stroke to act.

Figure 86:
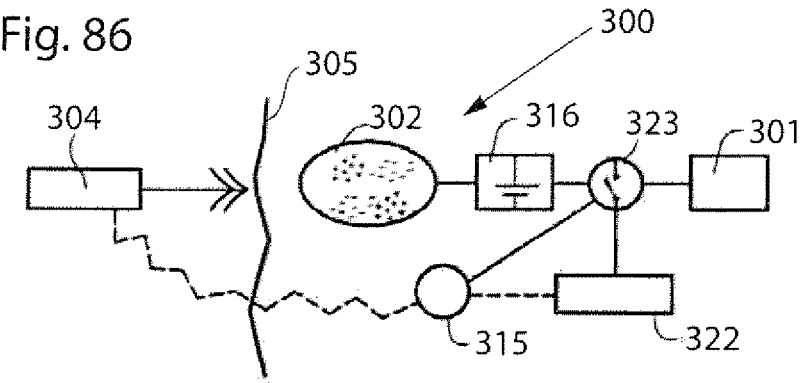

FIG. 86 shows an embodiment of the invention identical to that of FIG. 84 except that the implanted components are interconnected differently. Thus, in this case the internal control unit 315 is powered by the battery 322 when the accumulator 316, suitably a capacitor, activates the electric switch 323 to switch to an on mode. When the electric switch 323 is in its on mode the internal control unit 315 is permitted to control the battery 322 to supply, or not supply, energy for the operation of unit 301.

Figure 87:
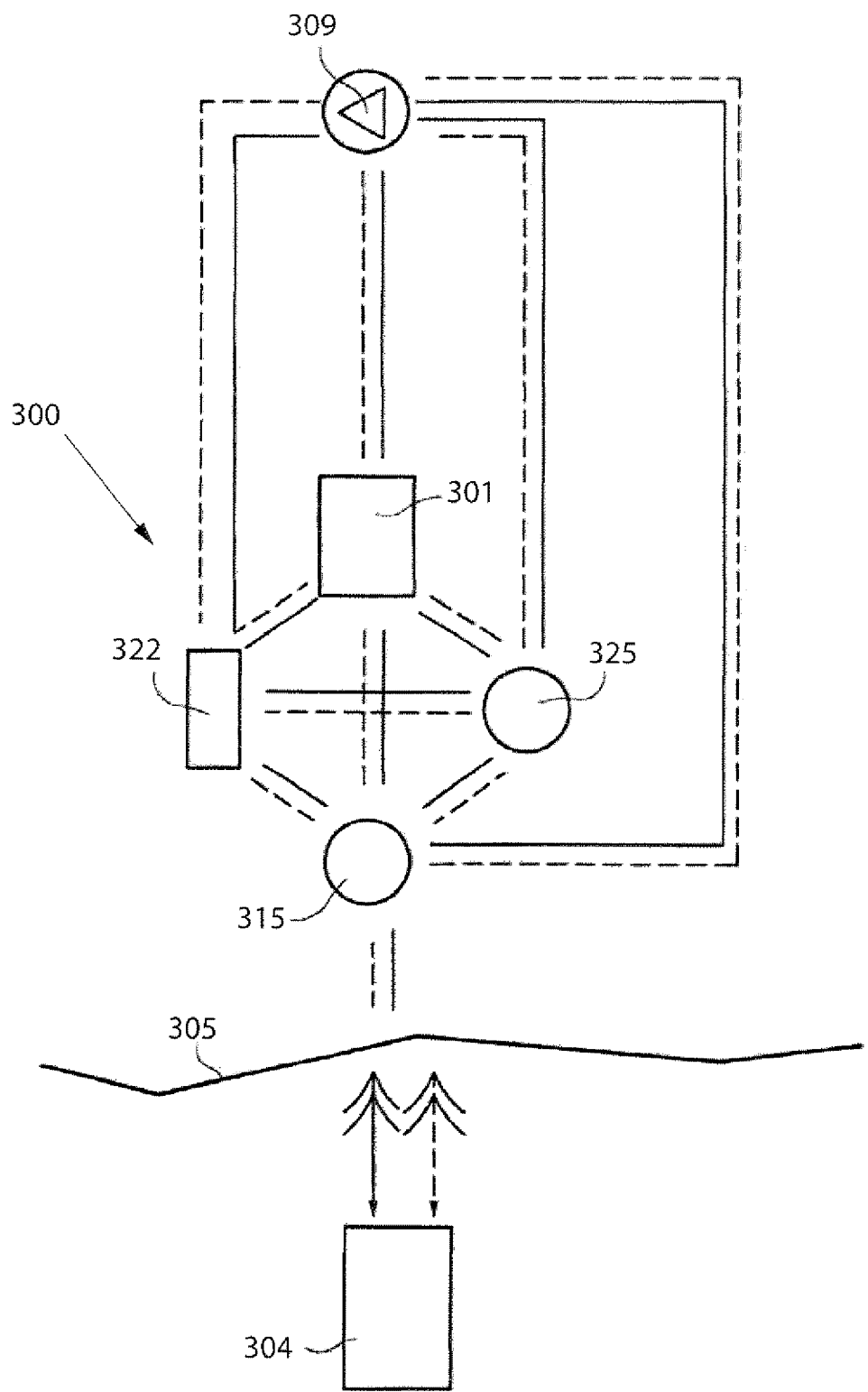

FIG. 87 schematically shows conceivable combinations of implanted components of unit 301 for achieving various communication options. Basically, there are unit 301, the internal control unit 315, motor or pump unit 309, and the external energy-transmission device 304 including the external wireless remote control. As already described above the wireless remote control transmits a control signal which is received by the internal control unit 315, which in turn controls the various implanted components of unit 301.

A feedback device, preferably comprising a sensor or measuring device 325, may be implanted in the patient for sensing a physical parameter of the patient. The physical parameter may be at least one selected from the group consisting of pressure, volume, diameter, stretching, elongation, extension, movement, bending, elasticity, muscle contraction, nerve impulse, body temperature, blood pressure, blood flow, heartbeats and breathing. The sensor may sense any of the above physical parameters. For example, the sensor may be a pressure or motility sensor. Alternatively, the sensor 325 may be arranged to sense a functional parameter. The functional parameter may be correlated to the transfer of energy for charging an implanted energy source and may further include at least one selected from the group of parameters consisting of; electricity, pressure, volume, diameter, stretch, elongation, extension, movement, bending, elasticity, temperature and flow.

The feedback may be sent to the internal control unit or out to an external control unit preferably via the internal control unit. Feedback may be sent out from the body via the energy transfer system or a separate communication system with receiver and transmitters.

The internal control unit 315, or alternatively the external wireless remote control of the external energy-transmission device 304, may control unit 301 in response to signals from the sensor 325. A transceiver may be combined with the sensor 325 for sending information on the sensed physical parameter to the external wireless remote control. The wireless remote control may comprise a signal transmitter or transceiver and the internal control unit 315 may comprise a signal receiver or transceiver. Alternatively, the wireless remote control may comprise a signal receiver or transceiver and the internal control unit 315 may comprise a signal transmitter or transceiver. The above transceivers, transmitters and receivers may be used for sending information or data related to unit 301 from inside the patient's body to the outside thereof.

Where the motor/pump unit 309 and battery 322 for powering the motor/pump unit 309 are implanted, information related to the charging of the battery 322 may be fed back. To be more precise, when charging a battery or accumulator with energy feed back information related to said charging process is sent and the energy supply is changed accordingly.

Figure 88:
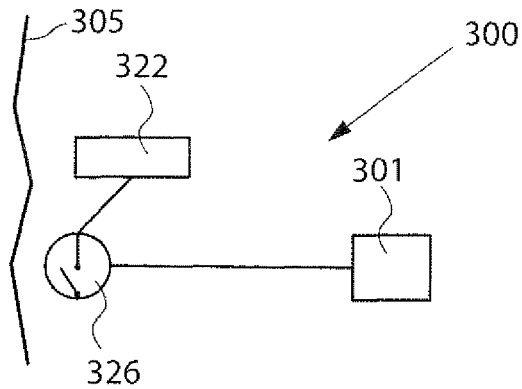

FIG. 88 shows an alternative embodiment wherein unit 301 is regulated from outside the patient's body. The system 300 comprises a battery 322 connected to unit 301 via a subcutaneous electric switch 326. Thus, the regulation of unit 301 is performed non-invasively by manually pressing the subcutaneous switch, whereby the operation of unit 301 is switched on and off. It will be appreciated that the shown embodiment is a simplification and that additional components, such as an internal control unit or any other part disclosed in the present application can be added to the system. Two subcutaneous switches may also be used. In the preferred embodiment one implanted switch sends information to the internal control unit to perform a certain predetermined performance and when the patient press the switch again the performance is reversed.

Figure 89:
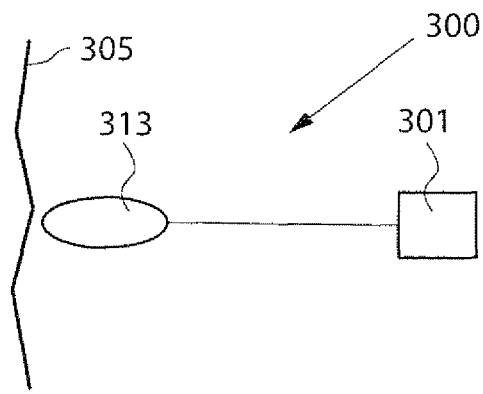

FIG. 89 shows an alternative embodiment, wherein the system 300 comprises a hydraulic fluid reservoir 313 hydraulically connected to unit 301. Non-invasive regulation is performed by manually pressing the hydraulic reservoir connected to unit 301.

The system may include an external data communicator and an implantable internal data communicator communicating with the external data communicator. The internal communicator feeds data related to unit 301 or the patient to the external data communicator and/or the external data communicator feeds data to the internal data communicator.

Male Contraception

FIG. 90A illustrates the embodiment of FIG. 2 applied on vas deferens for male contraception. With reference to FIGS. 90A and 89B an apparatus for male contraception is now described. FIG. 90A shows a restriction of vas deferens (vasa deferentia) with the controller. FIG. 90B depicts only the restriction devices of the invention. FIG. 90A shows the apparatus having with two restriction devices 660A and 660B in arrangement with the two vas deferens to perform restriction of these lumens to prevent from that sperms are transported through the vas deferens. Restriction devices 660A and 660B operates either to constrict vas deference, to stimulate vas deference, or the combination thereof. The restriction devices are operatively connected to the controller 600 having a control device 650 that is subcutaneously implanted.

The control device has an energy source 651 for supplying energy consuming parts of the apparatus with energy. The energy source is supplied with wireless energy from an external energizer unit 620. The controller further includes an external remote control unit 630 capable of communicating with the control device 650 and an internal control unit 640. The control device further has an external part 652 for including functions needed for external operation such as an injection port for supply of hydraulic fluid when the constriction is hydraulically operated and an activation/deactivation button for operating the restriction.

Figure 90D:
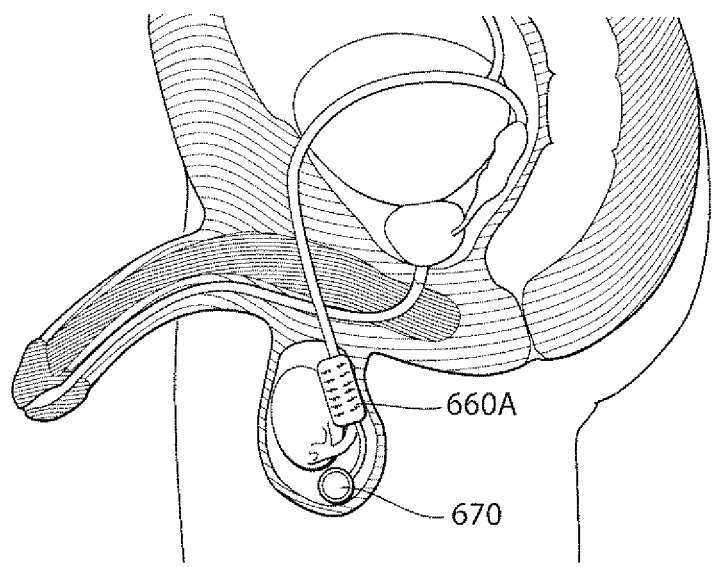

FIG. 90C shows the same apparatus as in FIG. 90B without the control device. FIG. 90D shows a manually operated embodiment of the contraception device. A manually operable pump 670 located in the scrotum hydraulically operates on the restriction device 660A to restrict vas deferens.

The cavity in the method according to any of the embodiments could constitute at least one of an abdominal cavity, a cavity in the pelvic region, a cavity subperitoneally, a cavity in scrotum, a cavity downstream the vas deferens ampulla close to the prostate, a cavity in human soft tissue, muscle, fat and/or fibrotic tissue.

The step of placing a device according to any of the embodiments herein could involve placing it in operative engagement with vas deferens or it's prolongation downstream the ampulla close to the prostate gland, that's to say downstream the ampulla where the sperm are collected and ready to be released into urethra at the level of the prostate gland, thus achieving a short term stop in sperm release into urethra during ejaculation without affecting release from the prostate gland.

Figure 91A:
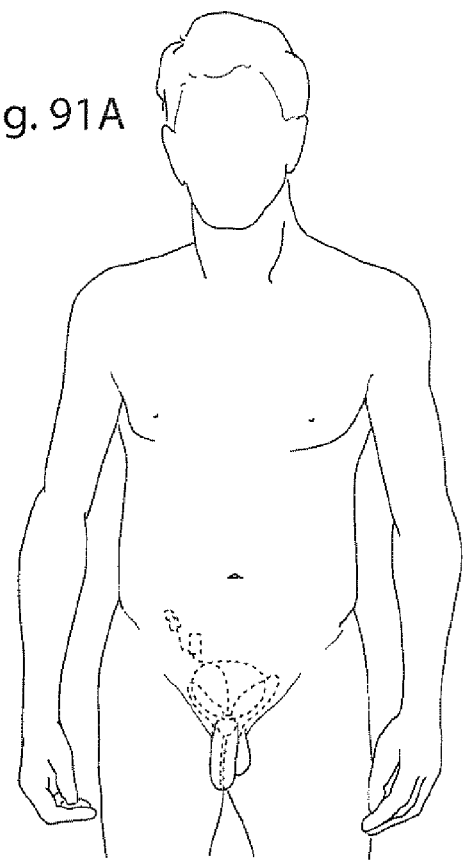
FIGS. 91A to 91F illustrate another apparatus for use with the method according to the invention when implanted in a male patient for contraception.
Figure 91B:
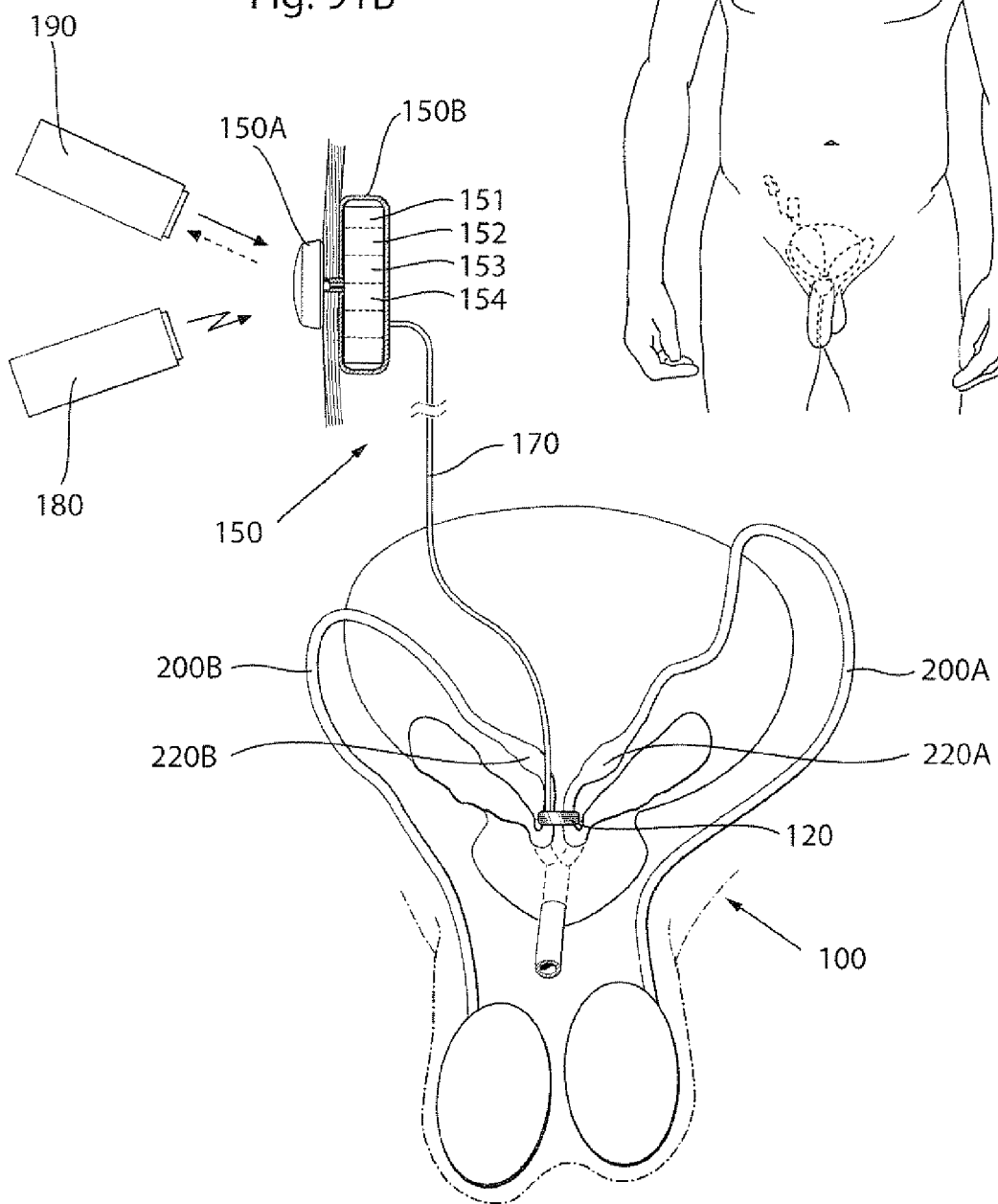

FIG. 91A is a schematic view of another apparatus for male contraception for practicing the method of the invention, as illustrated in FIG. 91B. The apparatus 100 of FIG. 91B shows restriction of vas deferens 200A, 200B (vasa deferentia) downstream the ampulla of vas deferens 220A, 220B. The apparatus thereby is operable to temporarily prevent from reaching urethra and provide time-limited sterility. The apparatus 100 has a restriction device 120 adapted to constrict vas deferens mechanically or hydraulically and a control device 150 for controlling the operation of the restriction device as it is operated with a schematically illustrated operation device 170. The control device 150 is subcutaneously located and includes an external part and an internal part. An energizer unit (energy transmission device) 180 is capable to supply the device with wireless transmitted energy to an energy transforming device 151 connected to an energy source 152 for supplying energy consuming parts of the apparatus with energy. An external remote control unit 190 is capable of communicating with the control device 150 internal control unit 153 of the control device. The external part 150A of the control device 150 includes functions needed for external operation such as an injection port for supply of hydraulic fluid when the constriction is hydraulically operated and an activation/deactivation button for operating the restriction device. The internal part of the control device 150B can include a number of functions needed to control and operate the restriction device 120. In a hydraulically operated restriction device 120 the control device 150 can include a pump 154 operable on a reservoir for hydraulic fluid (not shown), whereby transportation of fluid from the reservoir activates the restriction device to restrict vas deferens and transportation back to the reservoir deactivates the restriction device to release vas deferens.

Figure 91C:
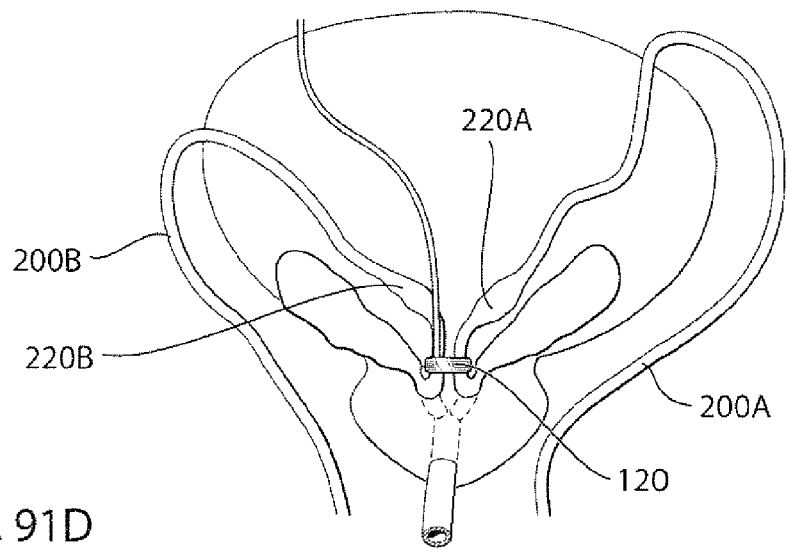
Figure 91D:
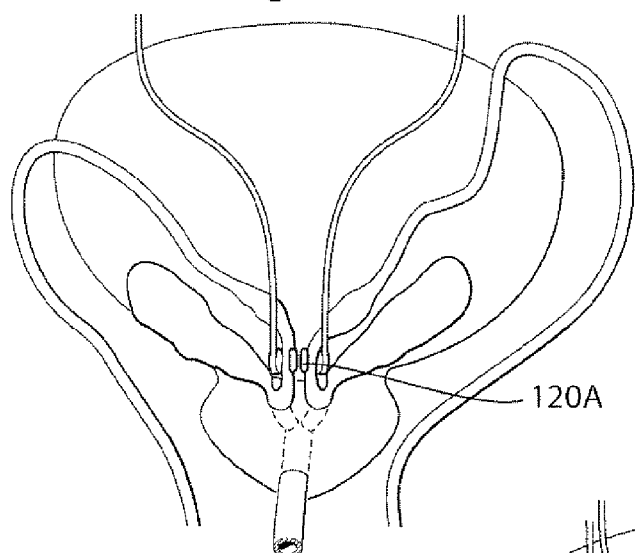
Figure 91E:
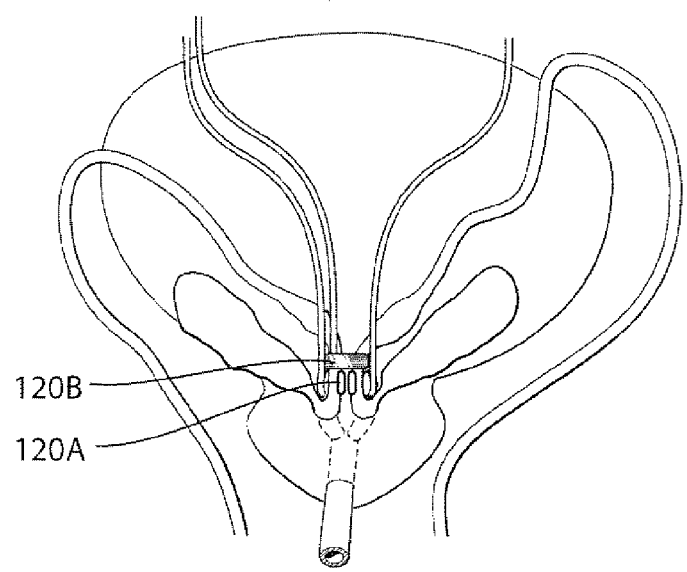
Figure 91F:
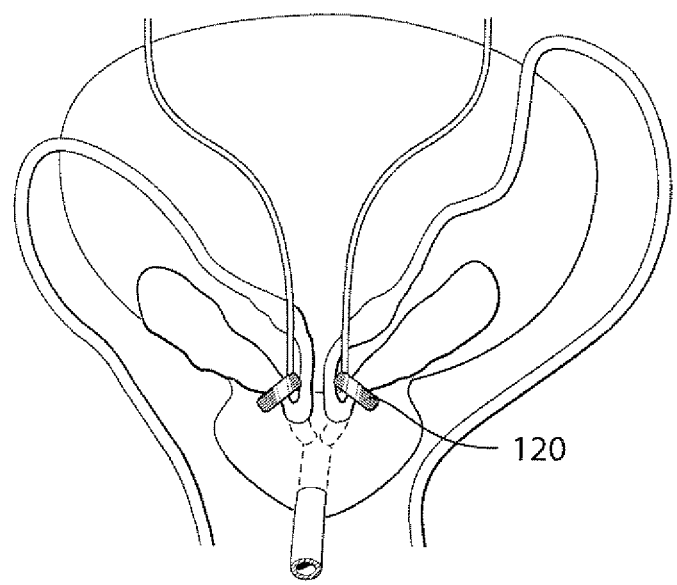

FIG. 91C shows the apparatus of FIG. 91B without any control device. The restriction device 120 is of the same type as in FIG. 91B, but it is here adapted to restrict both vas deferens and the outlet ducts of the seminal vesicles. FIG. 91D shows an apparatus of FIG. 91B or 91C with a modified restriction device 120A operating with a stimulation device on both vas deferens. The stimulation device is here represented a by set of electrodes. FIG. 91E shows an apparatus of FIG. 91B or 91C with a restriction device comprising a stimulation device 120A and a constriction device 120B controlled by the control device to restrict both vas deference by their combined actions. In One embodiment the constriction device 120B is manually operated with a pump that operates on a reservoir to perform a constriction on vas deferens while the stimulation device operated by the control device stimulates vas deference to obtaining the sperm transport blocking effect. FIG. 91F shows another variant of the apparatus of FIG. 91B, wherein the restriction device 120 includes two constriction devices each adapted to constrict a vas deference and an outlet duct of a seminal vesicle, respectively in order to both stop the flow of sperms and seminal fluid.

Figure 91G:
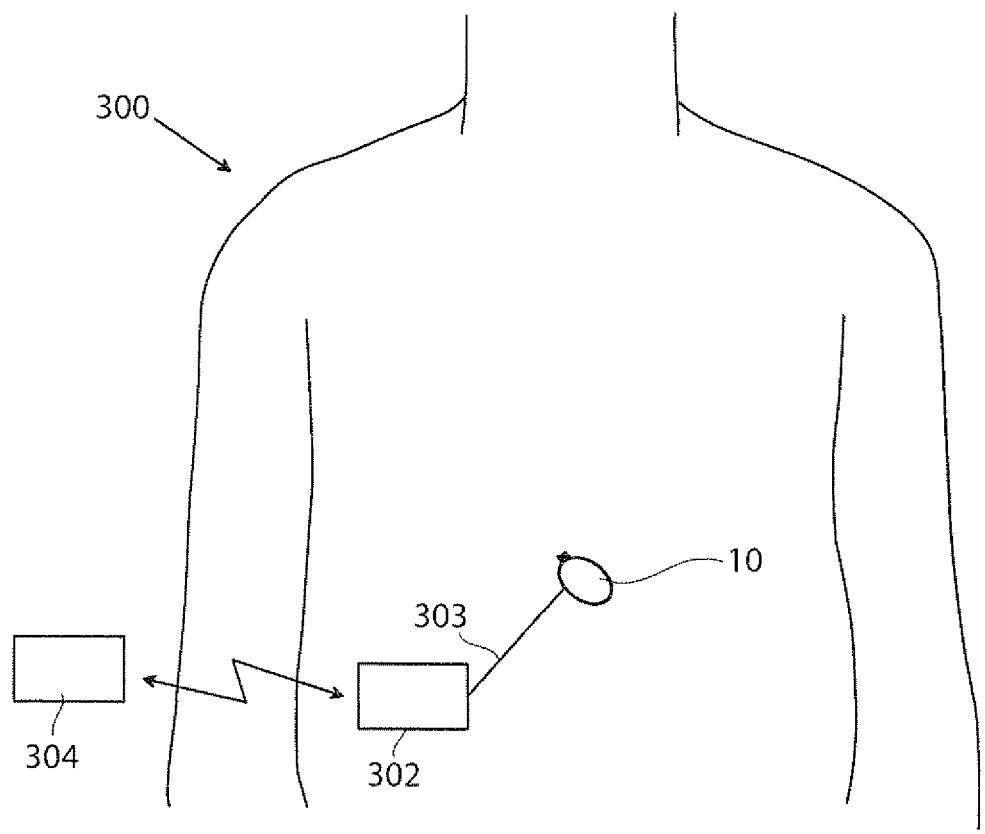
FIG. 91G illustrates a system controlling an apparatus of any one of FIGS. 91A to 91F implanted in a patient.

FIG. 91G illustrates a system for treating a disease comprising an apparatus 10 of the present invention placed in the abdomen of a patient. An implanted energy-transforming device 302 is adapted to supply energy consuming components of the apparatus with energy via a power supply line 303. An external energy-transmission device 304 for non-invasively energizing the apparatus 10 transmits energy by at least one wireless energy signal. The implanted energy-transforming device 302 transforms energy from the wireless energy signal into electric energy which is supplied via the power supply line 303.

The wireless energy signal may include a wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal. Alternatively, the wireless energy signal may include an electric or magnetic field, or a combined electric and magnetic field.

The wireless energy-transmission device 304 may transmit a carrier signal for carrying the wireless energy signal. Such a carrier signal may include digital, analogue or a combination of digital and analogue signals. In this case, the wireless energy signal includes an analogue or a digital signal, or a combination of an analogue and digital signal.

Generally speaking, the energy-transforming device 302 is provided for transforming wireless energy of a first form transmitted by the energy-transmission device 304 into energy of a second form, which typically is different from the energy of the first form. The implanted apparatus 10 is operable in response to the energy of the second form. The energy-transforming device 302 may directly power the apparatus with the second form energy, as the energy-transforming device 302 transforms the first form energy transmitted by the energy-transmission device 304 into the second form energy. The system may further include an implantable accumulator, wherein the second form energy is used at least partly to charge the accumulator.

Alternatively, the wireless energy transmitted by the energy-transmission device 304 may be used to directly power the apparatus, as the wireless energy is being transmitted by the energy-transmission device 304. Where the system comprises an operation device for operating the apparatus, as will be described below, the wireless energy transmitted by the energy-transmission device 304 may be used to directly power the operation device to create kinetic energy for the operation of the apparatus.

The wireless energy of the first form may comprise sound waves and the energy-transforming device 302 may include a piezo-electric element for transforming the sound waves into electric energy. The energy of the second form may comprise electric energy in the form of a direct current or pulsating direct current, or a combination of a direct current and pulsating direct current, or an alternating current or a combination of a direct and alternating current. Normally, the apparatus comprises electric components that are energized with electrical energy. Other implantable electric components of the system may be at least one voltage level guard or at least one constant current guard connected with the electric components of the apparatus.

Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transmission device may be controlled from outside the patient's body to release electromagnetic wireless energy, and the released electromagnetic wireless energy is used for operating the apparatus. Alternatively, the energy-transmission device is controlled from outside the patient's body to release non-magnetic wireless energy, and the released non-magnetic wireless energy is used for operating the apparatus.

The external energy-transmission device 304 also includes a wireless remote control having an external signal transmitter for transmitting a wireless control signal for non-invasively controlling the apparatus. The control signal is received by an implanted signal receiver which may be incorporated in the implanted energy-transforming device 302 or be separate there from.

The wireless control signal may include a frequency, amplitude, or phase modulated signal or a combination thereof. Alternatively, the wireless control signal includes an analogue or a digital signal, or a combination of an analogue and digital signal. Alternatively, the wireless control signal comprises an electric or magnetic field, or a combined electric and magnetic field.

The wireless remote control may transmit a carrier signal for carrying the wireless control signal. Such a carrier signal may include digital, analogue or a combination of digital and analogue signals. Where the control signal includes an analogue or a digital signal, or a combination of an analogue and digital signal, the wireless remote control preferably transmits an electromagnetic carrier wave signal for carrying the digital or analogue control signals.

Gallstones

FIG. 92 illustrates the embodiment of FIG. 2 applied on the common bile duct 31 of a gallstone patient. The clamping elements 5, 6 of the constriction device 2 constrict the common bile duct 31 and the stimulation device 3 is energized to close the common bile duct. (For the sake of clarity, the housing is not shown and the clamping elements 5, 6 are exaggerated.) In this embodiment, a control device includes an external control unit in the form of a hand-held wireless remote control 32. The remote control 32 is operable by the patient to control the internal control unit 33 to switch on and off the constriction device and/or the stimulation device. Alternatively, however, the remote control 32 may be replaced by a subcutaneously implanted push button that is manually switched by the patient between "on" and "off". Such a manually operable push button may also be provided in combination with the remote control 32 as an emergency button to allow the patient to stop the operation of the apparatus in case of emergency or malfunction.

The internal control unit 33 controls an implanted operation device 34 to move the clamping elements 5, 6. An implanted source of energy 35, such as a rechargeable battery, powers the operation device 34. The internal control unit 33, which may be implanted subcutaneously or in the abdomen, also works as en energy receiver, i.e., for transforming wireless energy into electric energy and charging the implanted source of energy 35 (rechargeable battery) with the electric energy.

An implanted sensor 36 senses a physical parameter of the patient, such as the pressure in the common bile duct, or a parameter that relates to the pressure in the intestines, wherein the internal control unit 33 controls the constriction device 2 and/or the stimulation device 3 in response to signals from the sensor 36. In this embodiment the sensor 36 is a pressure sensor, wherein the internal control unit 33 controls the constriction device and/or stimulation device to change the constriction of the patient's intestines 31 in response to the pressure sensor 36 sensing a predetermined value of measured pressure. For example, the control unit 33 may control the constriction device and/or stimulation device to increase the constriction of the patient's common bile duct 31 in response to the pressure sensor sensing an increased pressure.

Alternatively or in combination, the remote control 32 controls the constriction device and/or stimulation device in response to signals from the sensor 36. The remote control 32 may be equipped with means for producing an indication, such as a sound signal or displayed information, in response to signals from the sensor 36, in the same manner as the internal control unit 33.

The remote control 32 may be equipped with means for producing an indication, such as a sound signal or displayed information, in response to signals from the sensor 36.

Of course, the constriction device 2 shown in FIG. 92 may be replaced by any one of the devices described in the various embodiments of the present invention, where applicable.

Pregnancy Promotion

FIGS. 93A and 93B illustrates a pregnancy promotion device for practicing the present invention applied on the oviducts 31a, 31b of a female patient. Clamping elements 5, 6 of a restriction or constriction device 2 constrict the oviducts 31a, 31b. (For the sake of clarity, the housing is not shown and the clamping elements 5, 6 are exaggerated.) In this embodiment, a control device includes a subcutaneously implanted push button that is manually switched by the patient between "on" and "off". Such a manually operable push button may also be provided in combination with a remote control as an emergency button to allow the patient to stop the operation of the device in case of emergency or malfunction. Such a remote control will be described below with reference to FIGS. 95A and 95B.

Figure 94A:
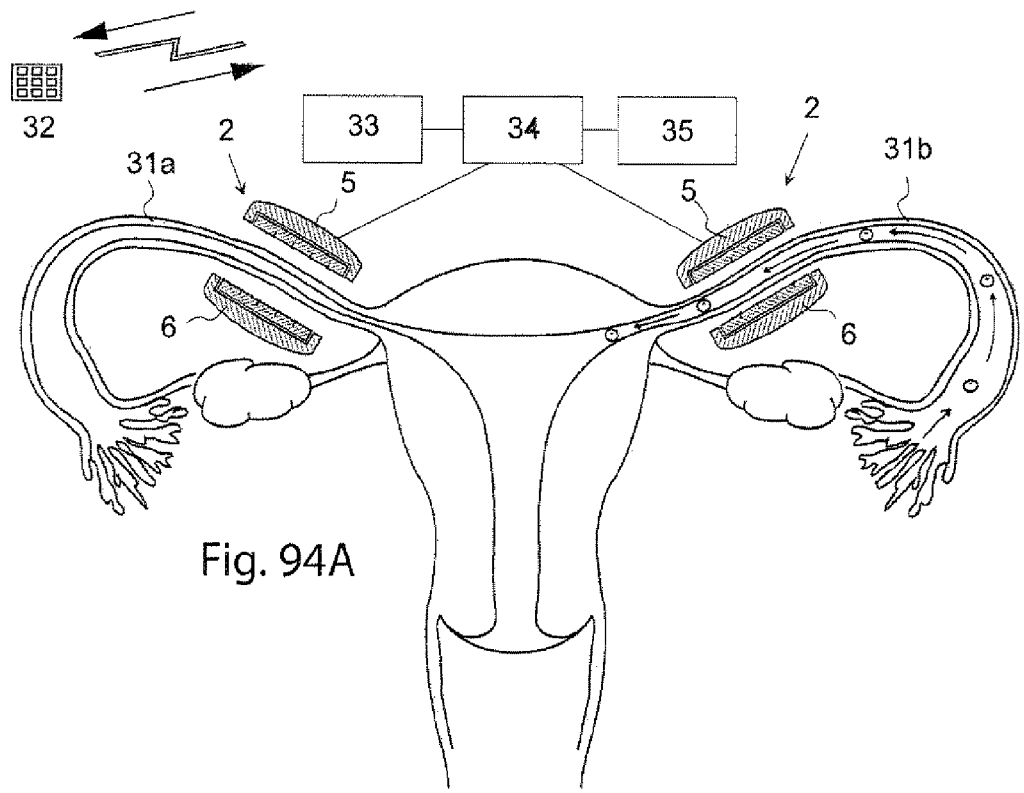
FIG. 94A illustrates the embodiment of FIG. 93A with remote control applied on the oviducts of a female patient, wherein the apparatus is in a non-restricting operating state.
Figure 94B:
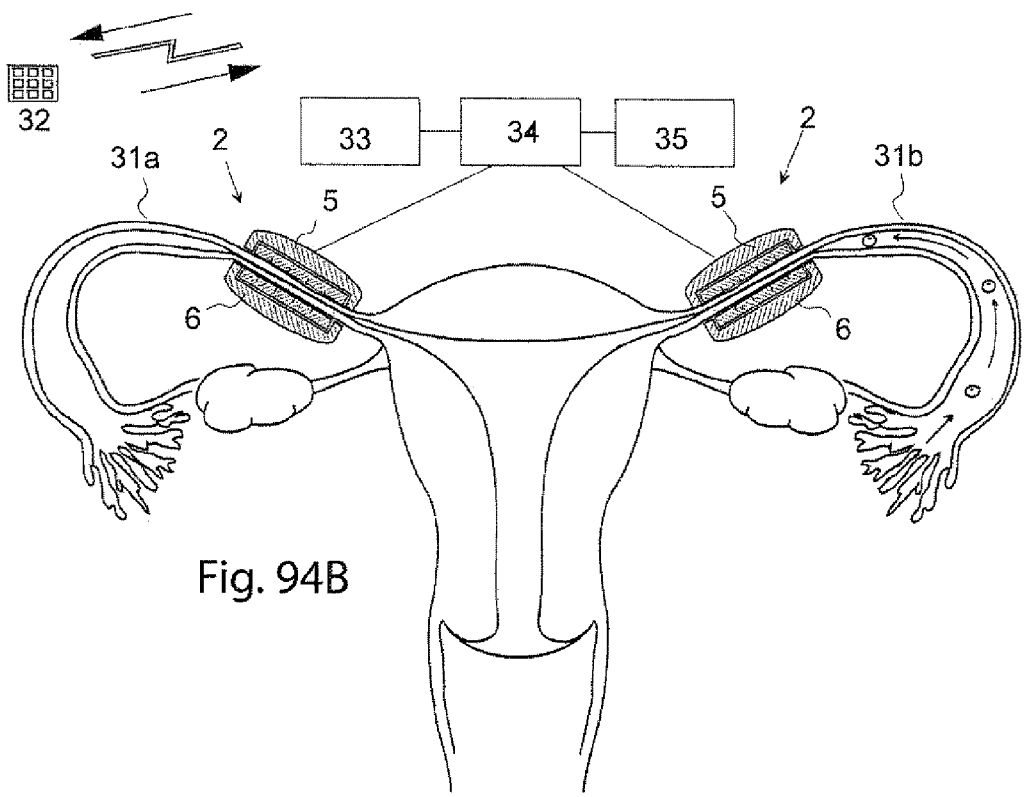
FIG. 94B is a view similar to that of FIG. 94A, but wherein the apparatus is in a restricting operating state.

FIGS. 94A and 94B illustrates an alternative embodiment applied on the oviducts 31a, 31b of a female patient. The clamping elements 5, 6 of the constriction device 2 constrict the oviducts 31a, 31b. (For the sake of clarity, the housing is not shown and the clamping elements 5, 6 are exaggerated.) In this embodiment, a control device includes an external control unit in the form of a hand-held wireless remote control 32, and an implanted internal control unit 33, which may include a microprocessor, for controlling the constriction and stimulation devices. The remote control 32 is operable by the patient to control the internal control unit 33 to switch on and off the device.

The internal control unit 33 controls an implanted operation device 34 to move the clamping elements 5, 6. An implanted source of energy 35, such as a rechargeable battery, powers the operation device 34. The internal control unit 33, which may be implanted subcutaneously or in the abdomen, may also work as en energy receiver, i.e., for transforming wireless energy into electric energy and charging the implanted source of energy 35 (rechargeable battery) with the electric energy.

An implanted sensor 36 senses a physical parameter of the patient, such as the temperature, wherein the internal control unit 33 controls the constriction device 2 and/or the stimulation device 3 in response to signals from the sensor 36. In this embodiment the sensor 36 is a hormone level sensor, wherein the internal control unit 33 controls the constriction device and/or stimulation device to change the constriction of the patient's oviduct 31 in response to the sensor 36 sensing a predetermined value of measured value. For example, the control unit 33 may control the constriction device and/or stimulation device to increase the constriction of the patient's oviduct 31 in response to the sensor sensing an increased or decreased hormone level. Alternatively or in combination, the remote control 32 controls the constriction device and/or a stimulation device in response to signals from the sensor 36, in the same manner as the internal control unit 33.

The remote control 32 may be equipped with means for producing an indication, such as a sound signal or displayed information, in response to signals from the sensor 36. When the patient's attention is taken by such an indication indicating a release of the oviduct based on said sensor input. The patient may use the remote control to control the constriction device or stimulation device to pump eggs through the oviducts of the patient.

Pregnancy Inhibition

Figure 95A:
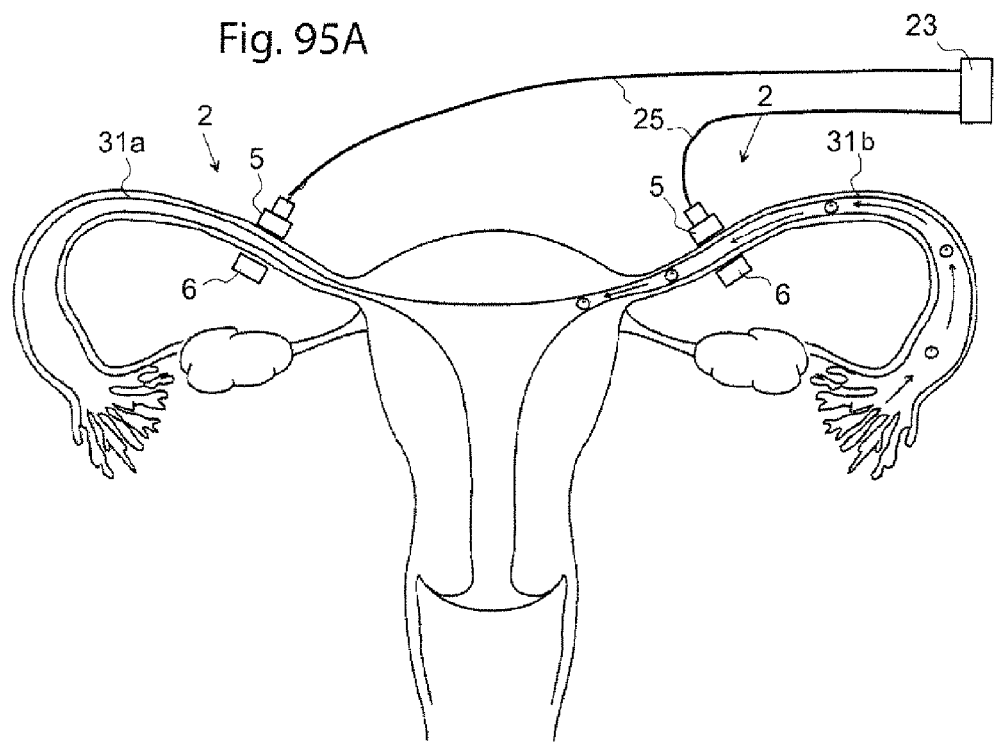
FIG. 95A illustrates a pregnancy inhibition apparatus used for practicing the method of the invention applied on the oviducts of a female patient, wherein the apparatus is in a non-restricting operating state.
Figure 95B:
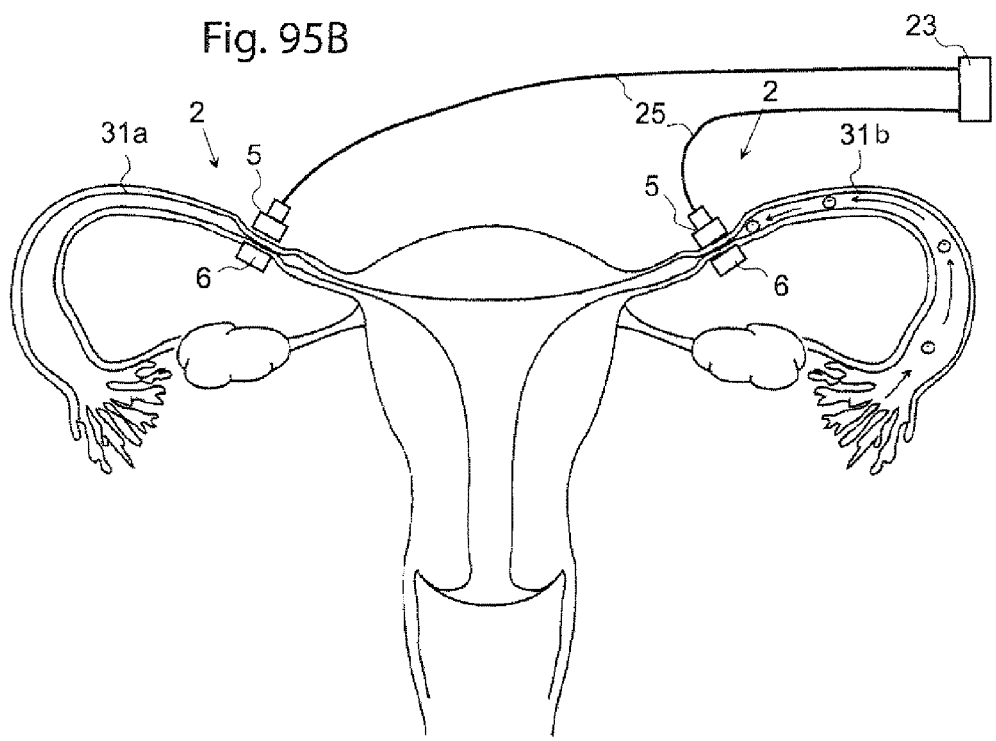
FIG. 95B is a view similar to that of FIG. 95A, but wherein the apparatus is in a restricting operating state.

FIGS. 95A and 95B illustrates a pregnancy inhibition system for practicing the present invention applied on the oviducts 31a, 31b of a female patient. Clamping elements 5, 6 of a restriction or constriction device 2 constrict the oviducts 31a, 31b. (For the sake of clarity, the housing is not shown and the clamping elements 5, 6 are exaggerated.) In this embodiment, a control device includes a subcutaneously implanted push button that is manually switched by the patient between "on" and "off". Such a manually operable push button may also be provided in combination with a remote control as an emergency button to allow the patient to stop the operation of the system in case of emergency or malfunction. Such a remote control will be described below with reference to FIGS. 96 and 97.

Figure 96:
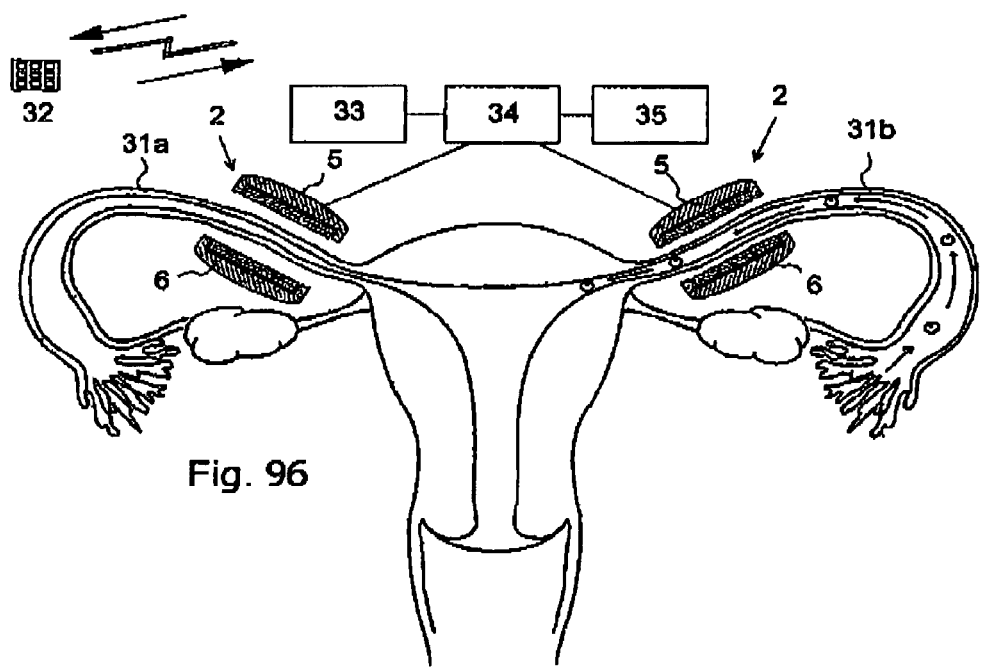
FIG. 96A illustrates the embodiment of FIG. 95A with remote control applied on the oviducts of the female patient, wherein the apparatus is in a non-restricting operating state.
Figure 97:
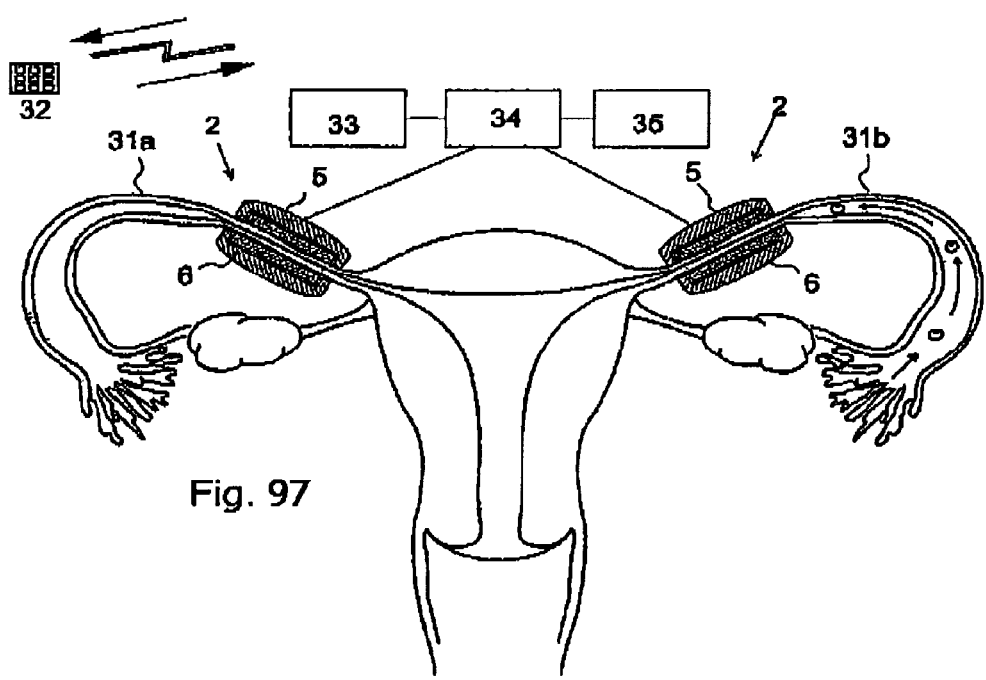
FIG. 97 is a view similar to that of FIG. 96A, but wherein the apparatus is in a restricting operating state.

FIGS. 96 and 97 illustrates an alternative embodiment applied on the oviducts 31a, 31b of a female patient. The clamping elements 5, 6 of the constriction device 2 constrict the oviducts 31a, 31b. (For the sake of clarity, the housing is not shown and the clamping elements 5, 6 are exaggerated.) In this embodiment, a control device includes an external control unit in the form of a hand-held wireless remote control 32, and an implanted internal control unit 33, which may include a microprocessor, for controlling the constriction and stimulation devices. The remote control 32 is operable by the patient to control the internal control unit 33 to switch on and off the restriction device.

The internal control unit 33 controls an implanted operation device 34 to move the clamping elements 5, 6. An implanted source of energy 35, such as a rechargeable battery, powers the operation device 34. The internal control unit 33, which may be implanted subcutaneously or in the abdomen, may also work as en energy receiver, i.e., for transforming wireless energy into electric energy and charging the implanted source of energy 35 (rechargeable battery) with the electric energy.

An implanted sensor 36 senses a physical parameter of the patient, such as the temperature, wherein the internal control unit 33 controls the constriction device 2 and/or the stimulation device 3 in response to signals from the sensor 36. In this embodiment the sensor 36 is a hormone level sensor, wherein the internal control unit 33 controls the constriction device and/or stimulation device to change the constriction of the patient's oviduct 31 in response to the sensor 36 sensing a predetermined value of measured value. For example, the control unit 33 may control the constriction device and/or stimulation device to increase the constriction of the patient's oviduct 31 in response to the sensor sensing an increased or decreased hormone level. Alternatively or in combination, the remote control 32 controls the constriction device and/or a stimulation device in response to signals from the sensor 36, in the same manner as the internal control unit 33.

The remote control 32 may be equipped with means for producing an indication, such as a sound signal or displayed information, in response to signals from the sensor 36. When the patient's attention is taken by such an indication indicating a release of the oviduct based on said sensor input. The patient may use the remote control to control the constriction device or stimulation device to pump eggs through the oviducts of the patient.

FIG. 97 is intentionally omitted.

Female Sexual Dysfunction (II)

Figure 98A:
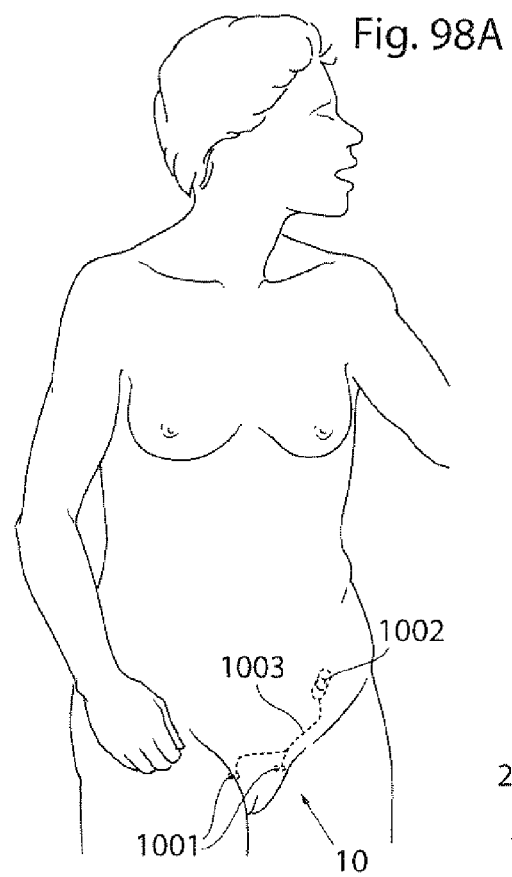
FIGS. 98A-98C illustrate a female sexual dysfunction apparatus used for practicing the method of the invention, wherein the apparatus includes a stimulation device implanted in the patient.

FIG. 98A schematically illustrates an implanted female sexual dysfunction treatment apparatus 10 for practicing the present invention and a subcutaneously implanted control device 1002.

Figure 98B:
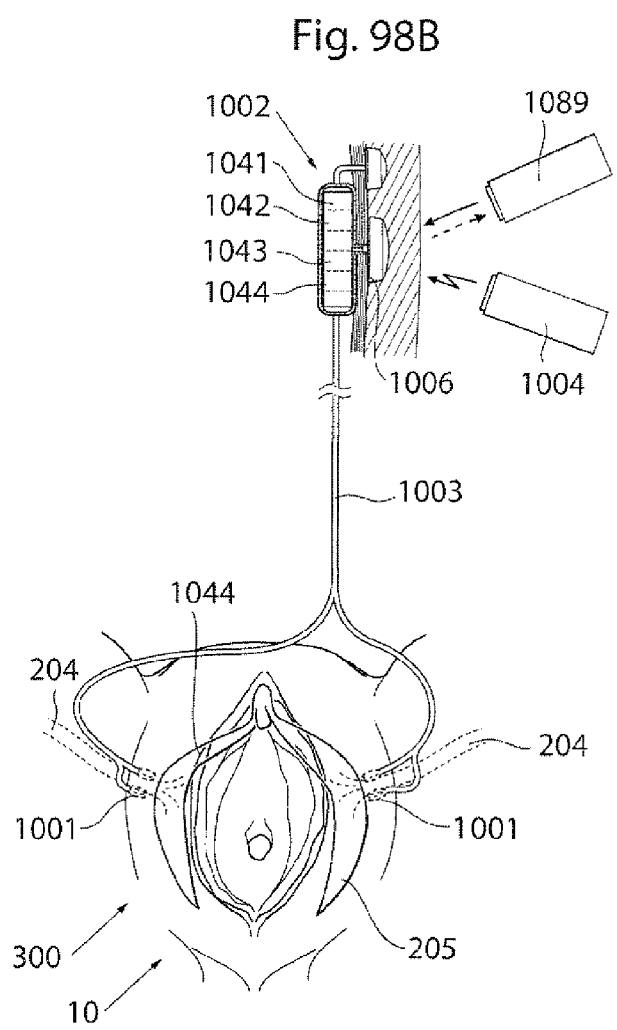

FIG. 98B is detailed illustration of the apparatus 10. The stimulation device 1001, here illustrated as electrodes operable to stimulate the veins, is implanted to stimulate veins 204 of the female erectile tissue 205 of the patient. It is connected to the control device 1002 device trough a power supply line 1003. An external energy-transmission device 1004 for energizing the apparatus transmits energy by at least one wireless energy signal. The system can be controlled with a remote control 1099. Also a subcutaneous control switch 1006 can be used to control the apparatus.

In one embodiment a sensor 1044 measures at least one physiological or functional parameter. The location of the sensor 1044 is adapted to the circumstances, e.g. which parameter that should be measured. The control device 1002 can comprise at least one item selected from the group consisting of; an internal control unit 1041 for communication, an internal energy source 1042, a sensor control unit 1043, and an energy transforming device for transforming wireless energy from the energy transmission device 1004. If a non-rechargeable battery is used the energy-transforming device 1044 may be omitted but the other mentioned items may be used as suitable.

In general, any item, or combinations of items, described and suited therefore, may be connected to the stimulation device and a senor contacting the female organ via the connection line 1003. If e.g. the apparatus 10 is electrically operated it may be suitable to connect it to a source of electrical energy 1042 via the connection line 1003 which in this case may be an electrical conduit. The control unit 1041 may be connected to the source of electrical energy 1042.

Figure 98C:
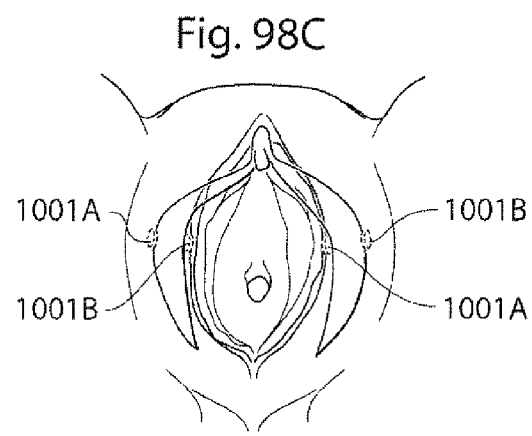

FIG. 98B shows the stimulation device as operating on the veins of corpora cavernosa without the other parts of the apparatus. FIG. 98C demonstrates an alternative apparatus wherein the stimulation device is represented by two different units 1001 each operating on corpora cavernosa for its direct stimulation to obtain an engorgement effect.

Female Sexual Dysfunction (III)

Figure 99A:
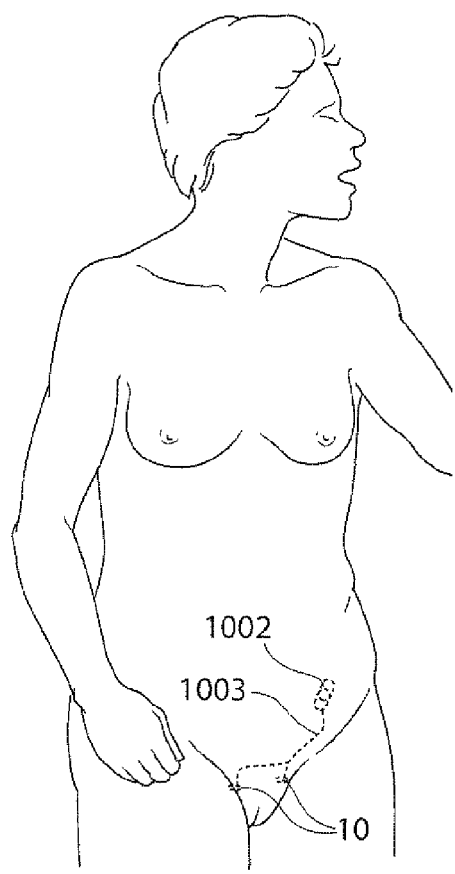
FIGS. 99A-99D illustrate a female sexual dysfunction apparatus used for practicing the method of the invention, wherein the apparatus includes a restriction device implanted in the patient.

FIG. 99A illustrates an implanted female sexual dysfunction apparatus 10 for practicing the present invention. An implanted energy-transforming device 1002 is adapted to supply energy consuming components of the apparatus with energy via a power supply line 1003. An external energy-transmission device 1004 for non-invasively energizing the apparatus 10 transmits energy by at least one wireless energy signal. The implanted energy-transforming device 1002 transforms energy from the wireless energy signal into electric energy which is supplied via the power supply line 1003.

The wireless energy signal may include a wave signal selected from the following: a sound wave signal, an ultra-sound wave signal, an electromagnetic wave signal, an infrared light signal, a visible light signal, an ultra violet light signal, a laser light signal, a micro wave signal, a radio wave signal, an x-ray radiation signal and a gamma radiation signal. Alternatively, the wireless energy signal may include an electric or magnetic field, or a combined electric and magnetic field.

The wireless energy-transmission device 1004 may transmit a carrier signal for carrying the wireless energy signal. Such a carrier signal may include digital, analogue or a combination of digital and analogue signals. In this case, the wireless energy signal includes an analogue or a digital signal, or a combination of an analogue and digital signal.

Generally speaking, the energy-transforming device 1002 is provided for transforming wireless energy of a first form transmitted by the energy-transmission device 1004 into energy of a second form, which typically is different from the energy of the first form. The implanted apparatus 10 is operable in response to the energy of the second form. The energy-transforming device 1002 may directly power the apparatus with the second form energy, as the energy-transforming device 1002 transforms the first form energy transmitted by the energy-transmission device 1004 into the second form of energy. The system may further include an implantable accumulator, wherein the second form of energy is used at least partly to charge the accumulator.

Alternatively, the wireless energy transmitted by the energy-transmission device 1004 may be used to directly power the apparatus, as the wireless energy is being transmitted by the energy-transmission device 1004. Where the system comprises an operation device for operating the apparatus, as will be described below, the wireless energy transmitted by the energy-transmission device 1004 may be used to directly power the operation device to create kinetic energy for the operation of the apparatus.

The wireless energy of the first form may comprise sound waves and the energy-transforming device 1002 may include a piezo-electric element for transforming the sound waves into electric energy. The energy of the second form may comprise electric energy in the form of a direct current or pulsating direct current, or a combination of a direct current and pulsating direct current, or an alternating current or a combination of a direct and alternating current. Normally, the apparatus comprises electric components that are energized with electrical energy. Other implantable electric components of the system may be at least one voltage level guard or at least one constant current guard connected with the electric components of the apparatus.

Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transmission device may be controlled from outside the patient's body to release electromagnetic wireless energy, and the released electromagnetic wireless energy is used for operating the apparatus. Alternatively, the energy-transmission device is controlled from outside the patient's body to release non-magnetic wireless energy, and the released non-magnetic wireless energy is used for operating the apparatus.

The external energy-transmission device 1004 also includes a wireless remote control having an external signal transmitter for transmitting a wireless control signal for non-invasively controlling the apparatus. The control signal is received by an implanted signal receiver which may be incorporated in the implanted energy-transforming device 1002 or be separate.

The wireless control signal may include a frequency, amplitude, or phase modulated signal or a combination thereof. Alternatively, the wireless control signal includes an analogue or a digital signal, or a combination of an analogue and digital signal. Alternatively, the wireless control signal comprises an electric or magnetic field, or a combined electric and magnetic field.

The wireless remote control may transmit a carrier signal for carrying the wireless control signal. Such a carrier signal may include digital, analogue or a combination of digital and analogue signals. Where the control signal includes an analogue or a digital signal, or a combination of an analogue and digital signal, the wireless remote control preferably transmits an electromagnetic carrier wave signal for carrying the digital or analogue control signals.

Figure 99B:
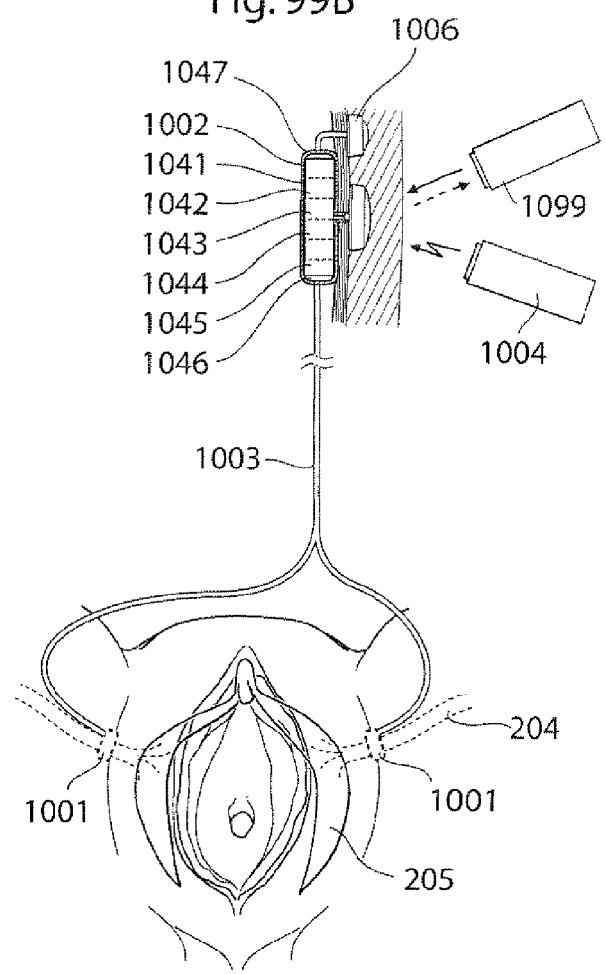

FIG. 99B illustrates in more detail the adjustable restriction device 1001, implanted on veins draining female erectile tissue. The energy transforming device 1002 may in another embodiment comprise a battery to supply energy to the device. The battery supply may of course be placed both remote to and incorporated in the device. The wireless energy-transmission device 1004 will be omitted if only a non-rechargeable battery is used. The system can be controlled with a remote control. In addition to the wireless remote control 1099, a subcutaneous control switch 1006 can be used to control the apparatus. The switch 1006 may in an alternative embodiment comprise a small hydraulic control reservoir. In such a case an injection port may be provided specially for calibrating the system with fluid.

The energy-transforming device 1002 may comprise at least one item selected from the group consisting of; a control unit 1041, a battery 1042, a sensor 1043, a motor 1044, a pump 1045, a reservoir 1046. The item 1047 may be an injection port. The items being selected depending on the circumstances, e.g. if the apparatus is electrically, hydraulically, pneumatically or mechanically operated.

Where a non-rechargeable battery is used, the items 1041 to 1047 may be used as suitable, and be connected to the apparatus 10 and sensor 1043 as suitable. If e.g. the apparatus 10 is hydraulically operated it may e.g. be suitable to use a control unit 1041, a pump 1045 and/or a reservoir 1046.

In general, any item, or combinations of items, described and suited therefore, may be connected to the apparatus 10 via the power supply line 1003. The actual item, or combinations of items, being chosen depending on the circumstances, e.g. if the apparatus 10 is electrically, hydraulically, pneumatically or mechanically operated.

If e.g. the apparatus 10 is mechanically operated it may be connected to a motor 1044 via the power supply line 1003 which in this case may be a wire or bowden cable. A control unit 1041 may be connected to the motor 1044.

If e.g. the apparatus 10 is electrically operated it may be suitable to connect it to a source of electrical energy 1002 or 1042 via the power supply line 1003 which in this case may be an electrical conduit. A control unit 1041 may be connected to the source of electrical energy 1002 or 1042.

A control unit may be provided both for controlling and communicating with the implant and out from the body. The control unit may receive input from any sensor, specially a pressure sensor. Any type of sensor may be supplied. A motor or pump may be provided depending if the device is hydraulically or mechanically restricting. A reservoir may be provided if the device is hydraulic. The restriction device may comprise any hydraulic device or mechanical device or stimulation device alone or in any combination as described in the present application. The stimulation device may comprise both thermal stimulation or electrical stimulation. Although the device has specific placements on the drawings it should be understood that the placement may vary a lot within the female genital area, preferable placed in the area of the female erectile tissue. The implant preferably includes intelligence in forms of a FPGA or MCU or ASIC or any other circuit, component or memory.

Figure 99C:
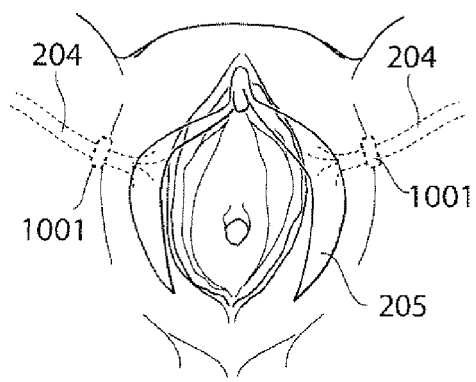

FIG. 99C illustrates the adjustable restriction device 1001, implanted in the female erectile tissue of the patient to constrict the two vein systems 204 that normally drain the female erectile tissue 205 of blood. More restriction devices may be provided.

Figure 99D:
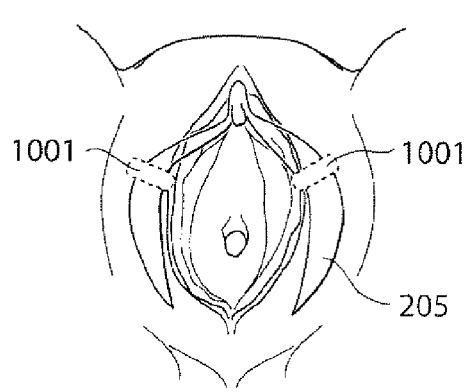

FIG. 99D illustrates the adjustable restriction device 1001, implanted directly on the female erectile tissue 205 of the patient, for example the two corpus cavernosum and/or vestibular bulbs.

Intestinal Disorder

"Artificial Reservoir"

Figure 100A:
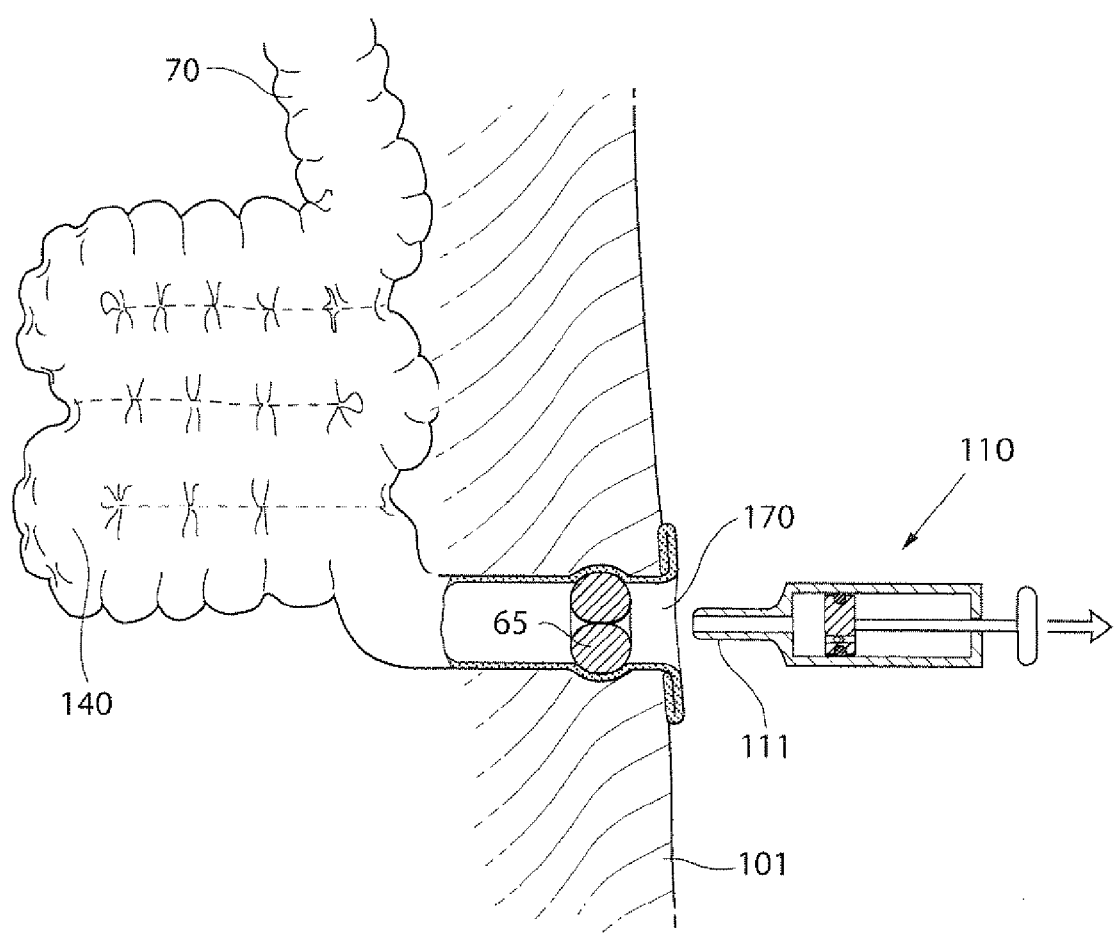
FIG. 100A shows a system according to the present invention, wherein the reservoir is formed by a plurality of bent portions of human intestine, with laterally adjacent sections thereof being cut open along their mutual contact line and the resulting upper halfs and lower halfs thereof being interconnected so as to form a reservoir. The flow control device consists of one exit valve implanted within the intestine, and the intestine exits the patients abdominal wall through a surgically created stomy. An external manually driven suction pump is used for emptying the reservoir, wherein a conduit on the front end of the pump is inserted from outside the patient's body into the intestine, thereby mechanically urging the exit valve to open. Accordingly, the structure of the exit valve is resilient so as to close automatically.

FIG. 100a shows a system according to the present invention, wherein the reservoir 140 is formed by a plurality of bent portions of human intestine 70, with laterally adjacent sections thereof being cut open along their mutual contact line and the resulting upper halfs and lower halfs thereof being interconnected so as to form a reservoir 140. The flow control device consists of one exit valve 65 implanted within the intestine 70, and the intestine 70 exits the patients abdominal wall 101 through a surgically created stomy 170. An external manually driven suction pump 110 is used for emptying the reservoir 140, wherein a conduit 111 on the front end of the pump 110 is inserted from outside the patient's body into the intestine 70, thereby mechanically urging the exit valve 65 to open. Accordingly, the structure of the exit valve 65 is resilient so as to close automatically.

Figure 100B:
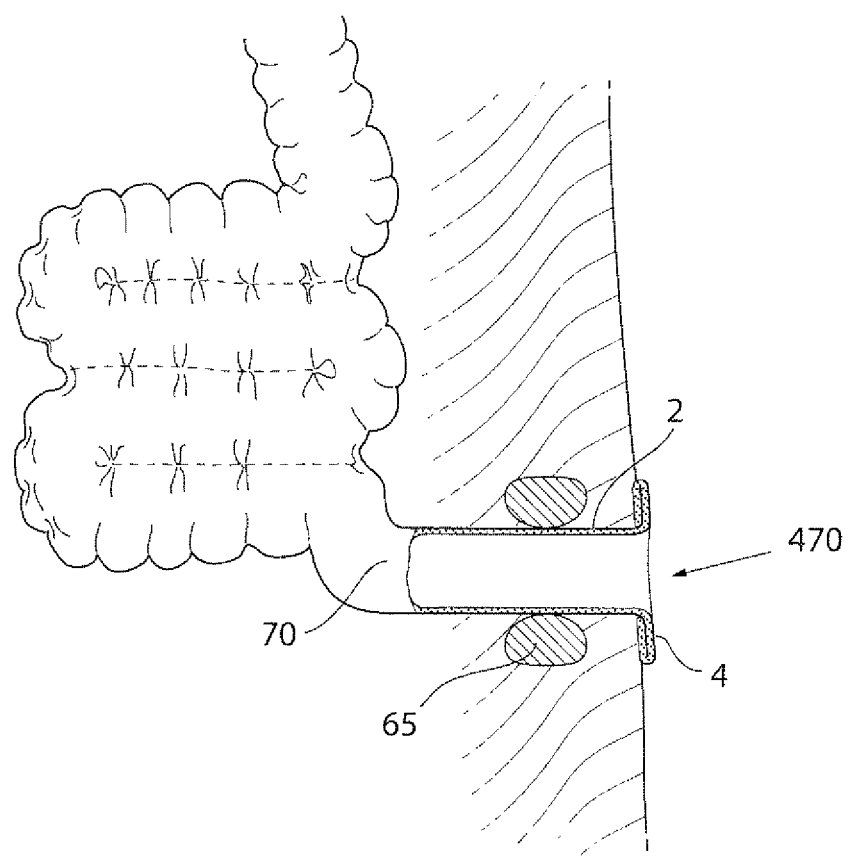
FIG. 100B shows a variant of FIG. 100A, wherein the exit valve is placed outside of the intestine.

FIG. 100b shows an embodiment wherein the reservoir 140 is formed by a plurality of bent portions of human intestine 70, with laterally adjacent sections thereof being cut open along their mutual contact line and the resulting upper halfs and lower halfs thereof being interconnected so as to form a reservoir 140. The flow control device consists of one exit valve 65 implanted on the outside of the intestine 70.

Figure 101A:
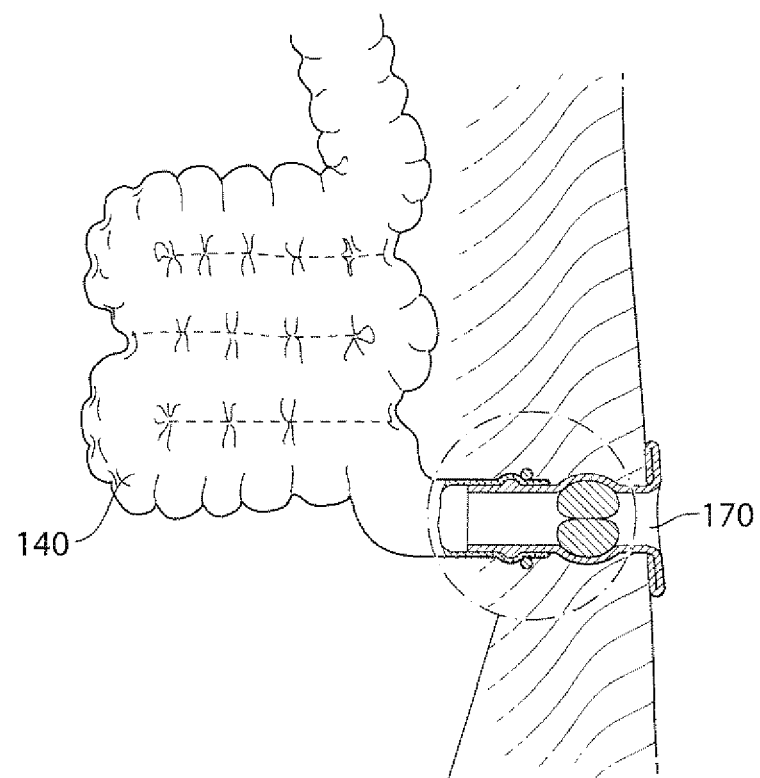
FIG. 101A shows a variant to FIG. 100A. Instead of being implanted inside the patient's intestine, the exit valve makes part of an artificial intestine section, one end of which forms the stomy opening and the other end of which is affixed by means of a ring-and-bulge connector to the cross-sectional opening of the intestine.
Figure 101B:
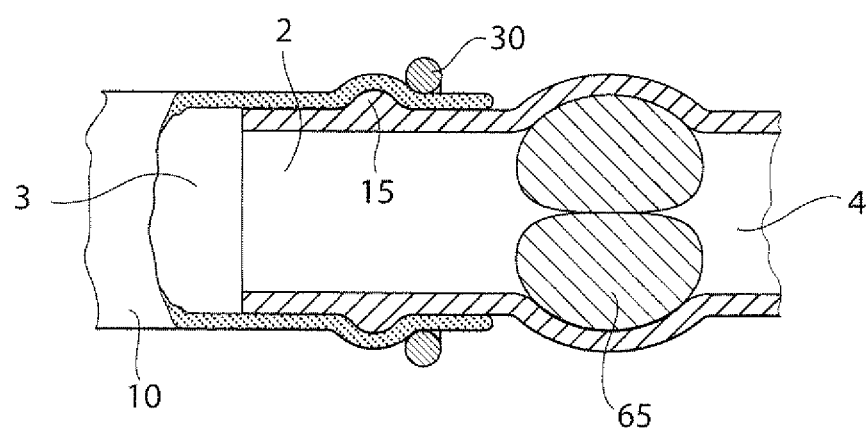
FIG. 101B shows an enlarged view of the ring-and-bulge connection between the artificial intestine section and the patient's intestine.
Figure 101C:
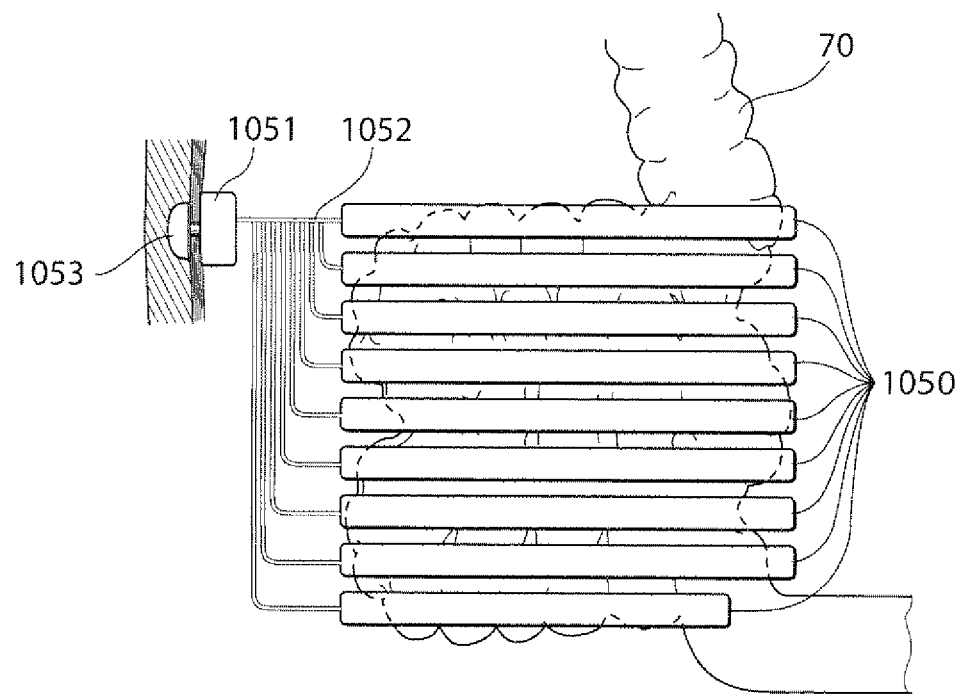
FIG. 101C shows an embodiment where an electrical flow control device is placed outside the reservoir.

FIG. 101c shows the embodiment wherein the reservoir 140 is formed by a plurality of bent portions of human intestine 70, in a frontal view. The reservoir is adapted to be emptied by means of electric stimulation delivered by electrical stimulation electrodes 1050 connected to a control unit 1051 by electrical leads 1052. The control unit 1051 is herein adapted to be implanted, and a switch 1053 for operating the control unit could be subcutaneously implanted such that it can be operated by the patient. The electrodes are according to the embodiment shown adapted to be sequentially activated top-down such that the reservoir intake is closed when the electrode at the top is activated; thereafter the electrodes are activated sequentially to empty the reservoir.

Figure 101D:
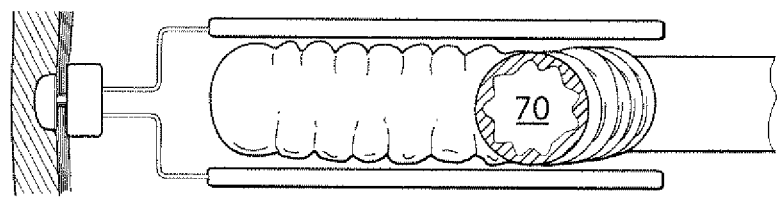
FIG. 101D shows the device according to FIG. 101C in a top view.

FIG. 101d shows the reservoir adapted to be emptied using electric stimulation according to FIG. 101c, in a top view.

Figure 101E:
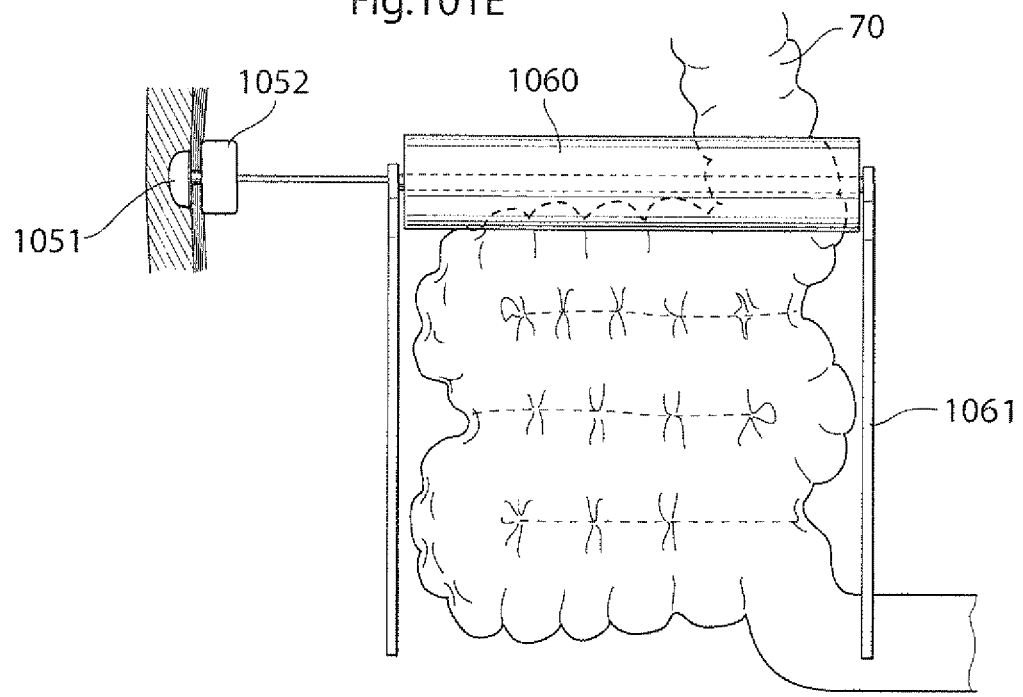
FIG. 101E shows an embodiment where a mechanical flow control device is placed outside the reservoir.

FIG. 101e shows an embodiment wherein the reservoir 140 is formed by a plurality of bent portions of human intestine 70, in a frontal view. The reservoir is adapted to be emptied by means of a mechanical element 1060 being a roller 1060 adapted to roll over the reservoir in the direction from the top portion to the bottom portion, compressing the reservoir and thereby emptying the reservoir. The rollers are guided by guide rails 1061 controlling the movement of the rollers 1060. The emptying device is controlled by an implantable control unit 1051 which is connected to the emptying device by an electrical lead 1052. A switch 1053 for operating the control unit could be subcutaneously implanted such that it can be operated by the patient.

Figure 101F:
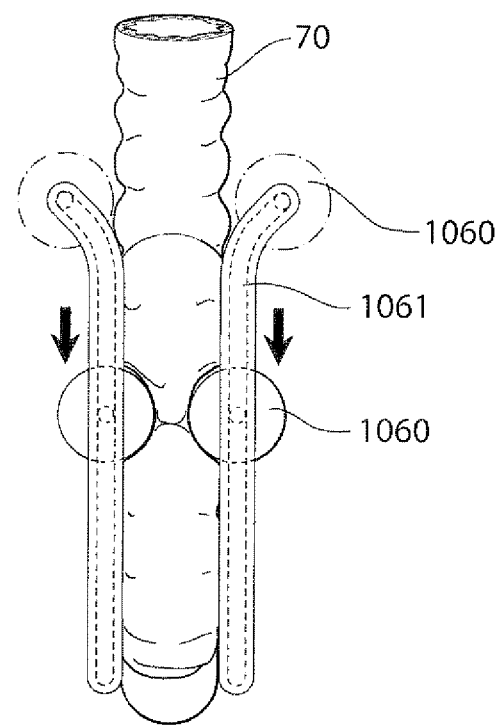
FIG. 101F shows the device according to FIG. 101E in a top view.

FIG. 101f shows the reservoir adapted to be emptied using a mechanical element 1060 according to FIG. 101e, in a top view.

Figure 101G:
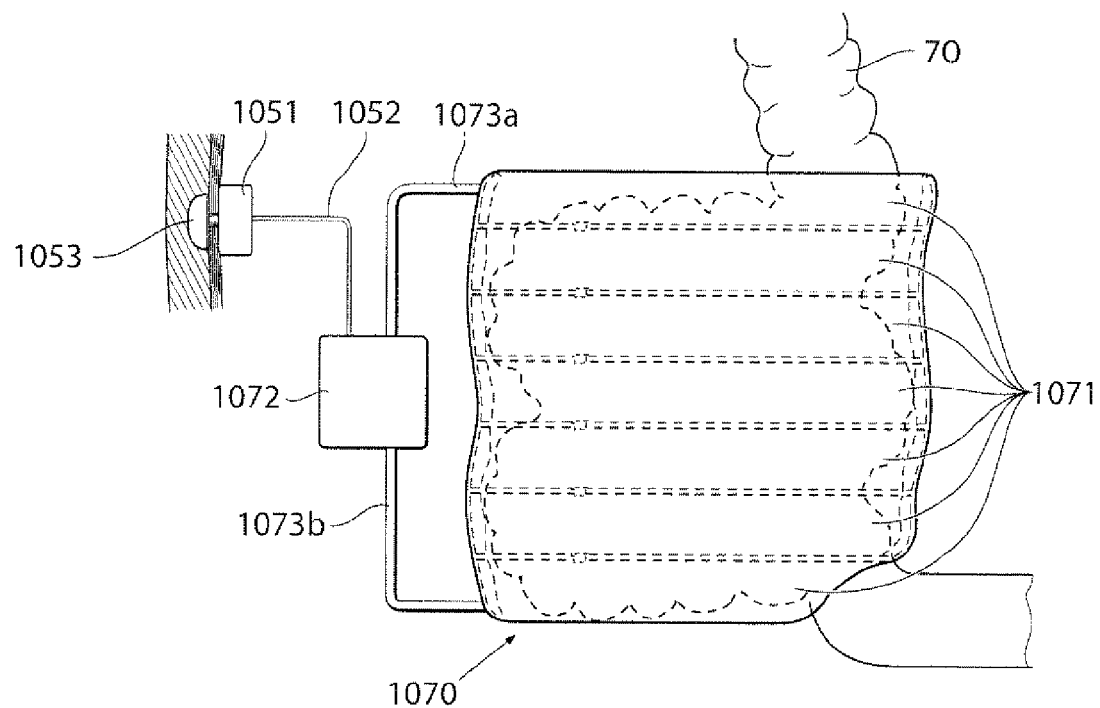
FIG. 101G shows an embodiment where a hydraulic flow control device is placed outside the reservoir.

FIG. 101g shows an embodiment wherein the reservoir 140 is formed by a plurality of bent portions of human intestine 70, in a frontal view. The reservoir is adapted to be emptied by means of a hydraulic emptying device 1070 comprising an inflatable device adapted to be filled by a hydraulic fluid in the direction from the top portion to the bottom portion, compressing the reservoir and thereby emptying the reservoir. The inflatable device comprises a plurality of sections 1071 adapted to be sequentially filled by a hydraulic fluid. The hydraulic device 1070 is controlled by an implantable control unit 1051 which is connected to a fluid reservoir 1072 comprising a pump by an electrical lead 1052. The pump is adapted to pump fluid from the fluid reservoir 1072 through a conduit 1073a into the inflatable device. A switch 1053 for operating the control unit could be subcutaneously implanted such that it can be operated by the patient.

Figure 101H:
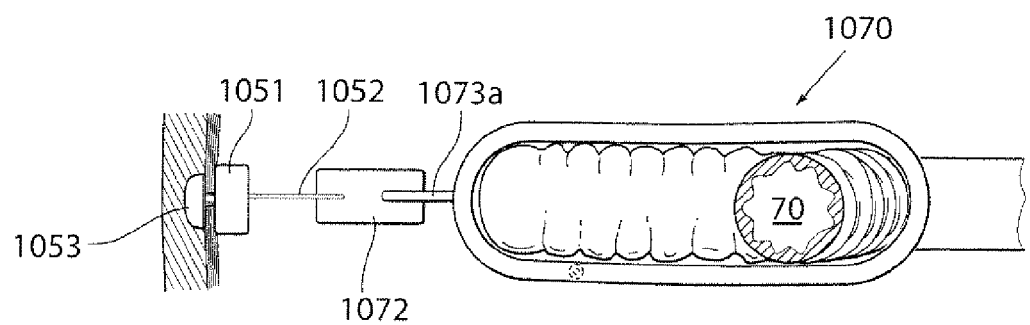
FIG. 101H shows the device according to FIG. 101G in a top view.

FIG. 101h shows the reservoir adapted to be emptied using a hydraulic device 1070 according to FIG. 101g, in a top view.

FIG. 101e shows a variant to FIG. 1. Instead of being implanted inside the patient's intestine 70, the exit valve 65 makes part of an artificial intestine section 2, one end 4 of which forms the stomy opening 170 and the other end 3 of which is affixed by means of a ring-and-bulge connector 15, 30 to the cross-sectional opening of the intestine 70.

FIG. 101b shows an enlarged view of the ring-and-bulge connection 15, 30 between the artificial intestine section 2 and the patient's intestine 70.

Figure 102A:
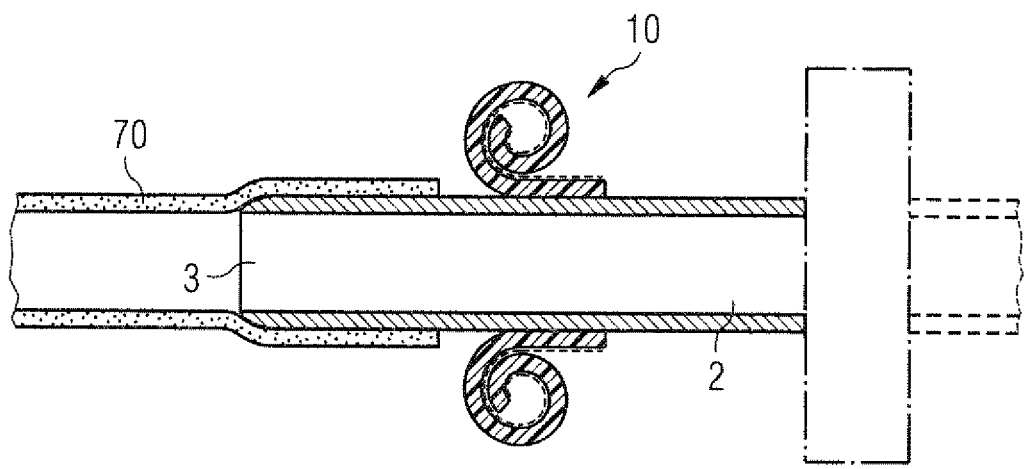
FIGS. 102A and 102B show an alternative to the ring-and-bulge connection. Here, the artificial intestine section comprises a conduit and a flexible sleeve which axially extends and closely fits around the outer surface of the conduit. The sleeve is rolled upon itself and can be unrolled such that a part of the intestine is located intermediate the sleeve and the conduit.
Figure 102B:
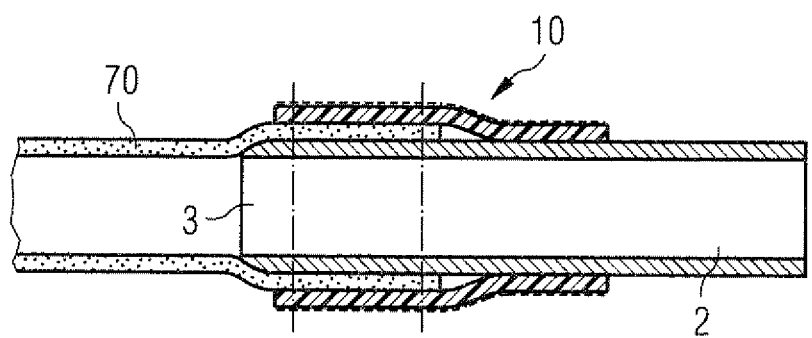

FIGS. 102A and 102B show an alternative to the ring-and-bulge connection of FIG. 2A. Here, the artificial intestine section 2 comprises a conduit and a flexible sleeve 10 which axially extends and closely fits around the outer surface 6 of the conduit 2. The sleeve 10 is rolled upon itself and can be unrolled such that a part 71 of the intestine 70 is located intermediate the sleeve 10 and the conduit 2.

Figure 103A:
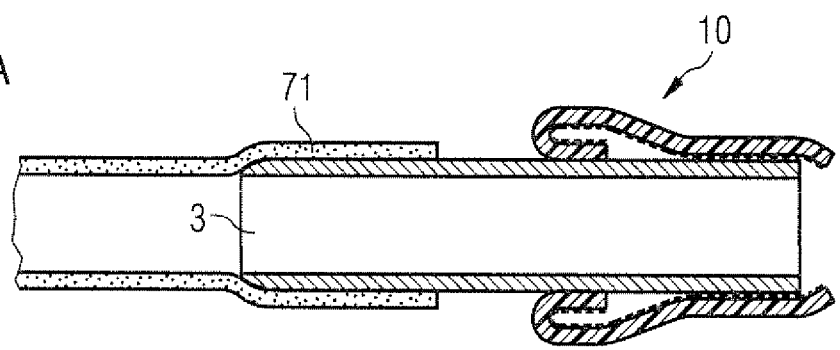
FIGS. 103A and 103B show an alternative to the connection in FIGS. 102A and 102B. Instead of unrolling the sleeve, it is simply pulled over the intestine.
Figure 103B:
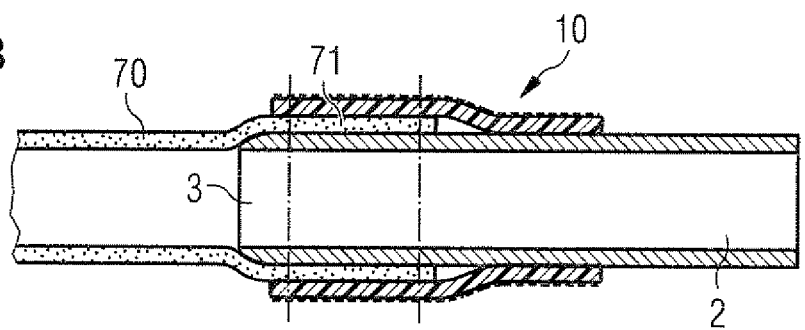

FIGS. 103A and 103B show an alternative to the connection in FIGS. 102A and 102B. Instead of unrolling the sleeve 10, it is simply pulled over the intestine 71.

Figure 103C:
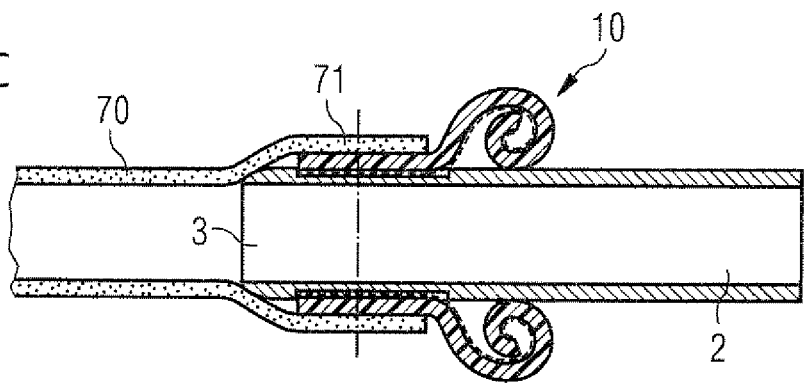
FIGS. 103C and 103D show another sleeve connection. Here, the sleeve is mounted on the outer surface of the conduit so as be foldable upon itself. By folding the flexible sleeve upon itself, a part of the intestine is located intermediate the folded sleeve.
Figure 103D:
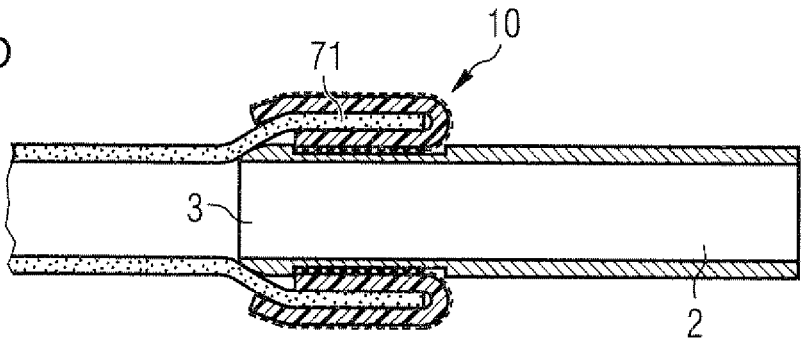

FIGS. 103C and 103D show another sleeve connection. Here, the sleeve 10 is mounted on the outer surface of the conduit 2 so as be foldable upon itself. By folding the flexible sleeve 10 upon itself, a part 71 of the intestine 70 is located intermediate the folded sleeve 10.

Figure 104A:
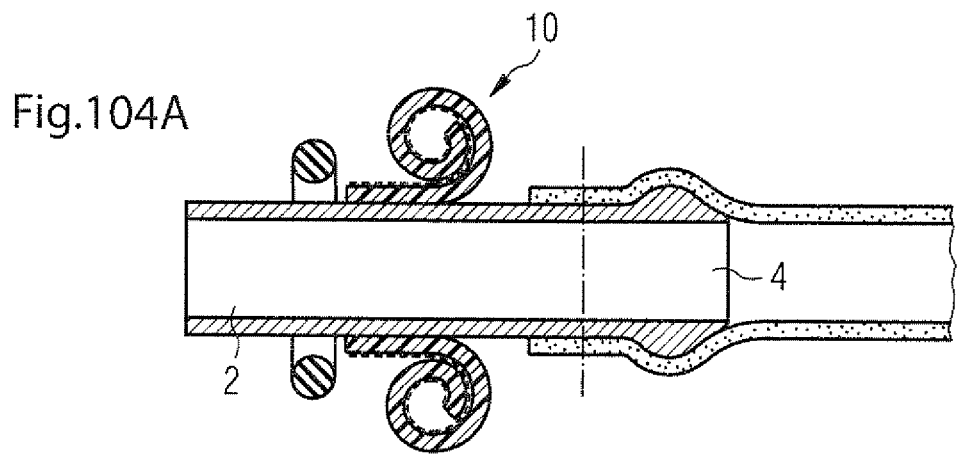
FIGS. 104A and 104B show a combined connection comprising both the function of the ring-and-bulge connection and the function of the sleeve connection of FIGS. 102A and 102B. Combinations of the ring-and-bulge connection with the sleeve connections of FIGS. 103A, 103B or 103C, 103D are likewise possible.
Figure 104B:
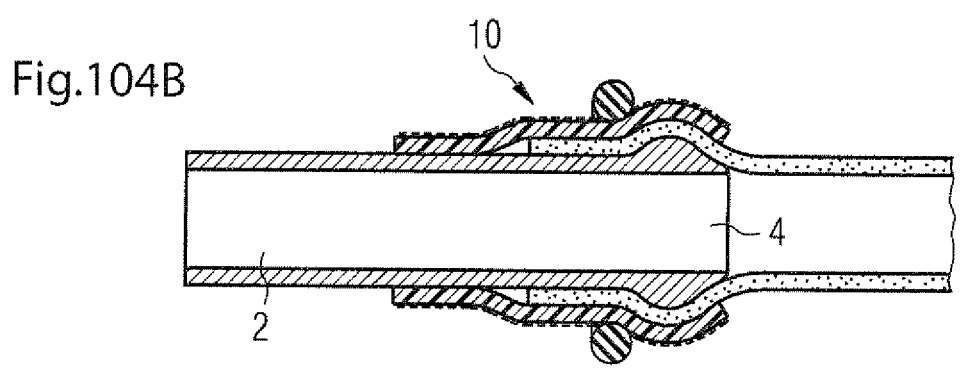

FIGS. 104A and 104B show a combined connection comprising both the function of the ring-and-bulge connection and the function of the sleeve connection of FIGS. 102A and 102B. Combinations of the ring-and-bulge connection with the sleeve connections of FIG. 103A, 103B or 103C, 103D are likewise possible.

Figure 105:
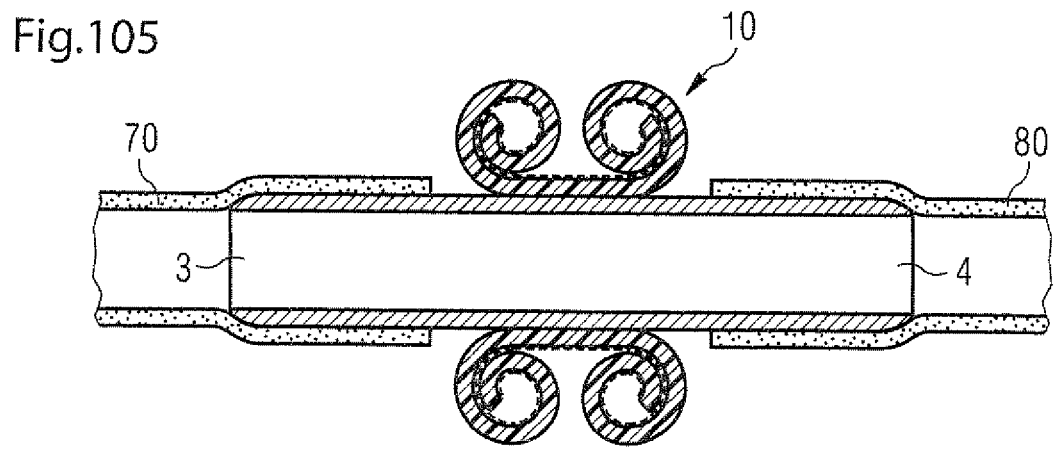
FIG. 105 generally shows that the artificial intestine section may be affixed with both open ends to cross-sectional openings created in the patient's intestine, intended for cases where the downstream open end portion of the artificial intestine section is not intended to form a stomy or anus. The artificial intestine section here is shown without any internal components and may comprise a reservoir for intestinal contents, one or more valves, a pump and/or any other flow control device. The connection of the open end portions of the artificial intestine section to the patient's intestine is shown in FIG. 105 to be made by sleeve connections, here involving a single sleeve.

FIG. 105 generally shows that the artificial intestine section may be affixed with both open ends 3, 4 to cross-sectional openings created in the patient's intestine 70, 80, intended for cases where the downstream open end portion of the artificial intestine section is not intended to form a stomy or anus. The artificial intestine section here is shown without any internal components and may comprise a reservoir for intestinal contents, one or more valves, a pump and/or any other flow control device. The connection of the open end portions of the artificial intestine section to the patient's intestine is shown in FIG. 105 to be made by sleeve connections, here involving a single sleeve 10.

Figure 106A:
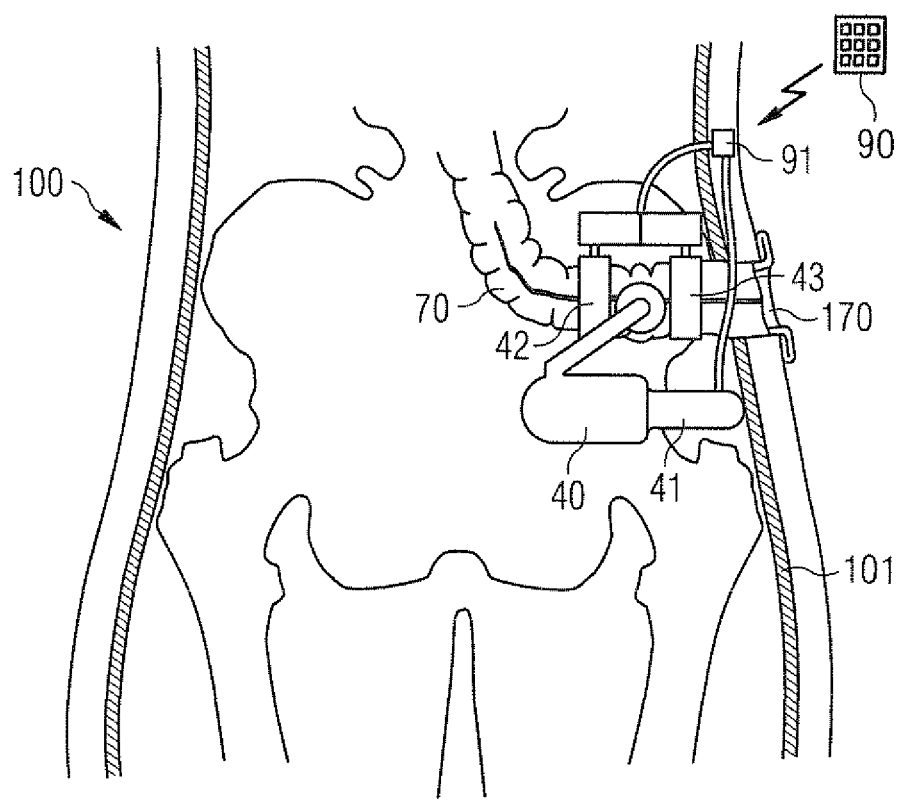
FIG. 106A shows an embodiment with an artificial reservoir connected to a lateral opening in the patient's intestine wall, a single opening of the reservoir. An entry valve and an exit valve are arranged at the patient's intestine upstream and downstream of the reservoir. A stomy exiting the patient's abdominal wall has been surgically created from the patient's small or large intestine. The reservoir is mounted with a pump in a common housing and the pump and the entry and exit valves are controlled by means of a control device, of which a part is implanted inside the patient's body. Data are transmitted wirelessly between the external part and the implanted part of the control unit. In addition, energy is wirelessly transmitted to an accumulator also implanted in the patient's body and galvanically connected here to the valves and pump.

FIG. 106A shows an embodiment with an artificial reservoir 40 connected to a lateral opening in the patient's intestine wall. An entry valve 42 and an exit valve 43 are arranged at the patient's intestine upstream and downstream of the reservoir 40. A stomy 170 exiting the patient's abdominal wall 101 has been surgically created from the patient's small or large intestine. The reservoir 40 is mounted with a pump 41 in a common housing and the pump 41 and the entry and exit valves 42, 43 are controlled by means of a control device, of which a part 91 is implanted inside the patient's body 100. Data are transmitted wirelessly between the external part 90 and the implanted part 91 of the control unit. In addition, energy is wirelessly transmitted to an accumulator also implanted in the patient's body and galvanically connected here to the valves and pump.

Figure 106B:
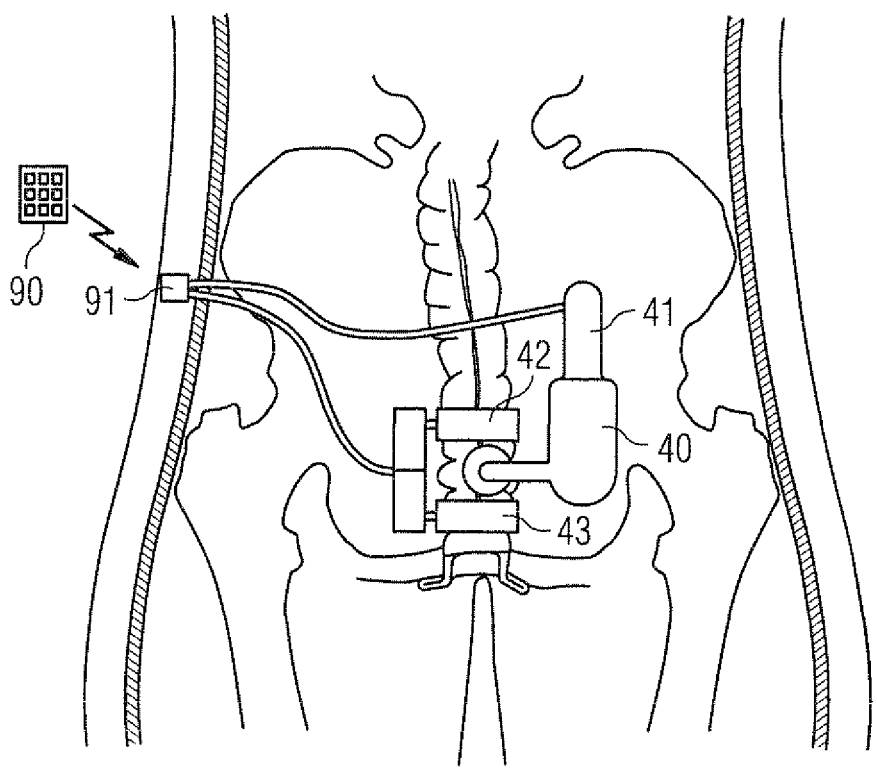
FIG. 106B shows the system of FIG. 106A connected to the patient's anus rather than to a surgically created stomy.

FIG. 106B shows the system of FIG. 106A connected to the patient's anus rather than to a surgically created stomy.

FIGS. 107A and 107B show a specific embodiment, wherein the pump 41 and the reservoir 40 are comprised in a common housing and the pump 41 comprises a movable piston 44 with a front end 45 of the piston 44 extending into the reservoir 40 such that a volume of the reservoir 40 is reduced upon advancement of the piston 44. The piston 44 is spring loaded so as to urge the piston 44 into a normally retracted position. Furthermore, entry and exit valves 42, 43 are provided in this embodiment, here being realized as flap valves. The flap valves are controlled so that one valve is open while the other one is closed.

FIGS. 108A and 108B show a system similar to the one of FIGS. 107A and 107B. However, here the entry and exit valves 42, 43 comprise bellows 46 acting on the intestine 70 from the outside so as to close the intestine 70 by compression. In FIG. 108A the bellows 46 of the exit valve 43 are expanded to compress the intestine 70 at the downstream side of the reservoir 40, whereas in FIG. 108B the intestine 70 is closed by means of the bellows 46 of the entry valve 42 upstream of the reservoir 40 so that the reservoir 40 can be emptied by advancing the piston 44 of the pump 41.

Figure 109:
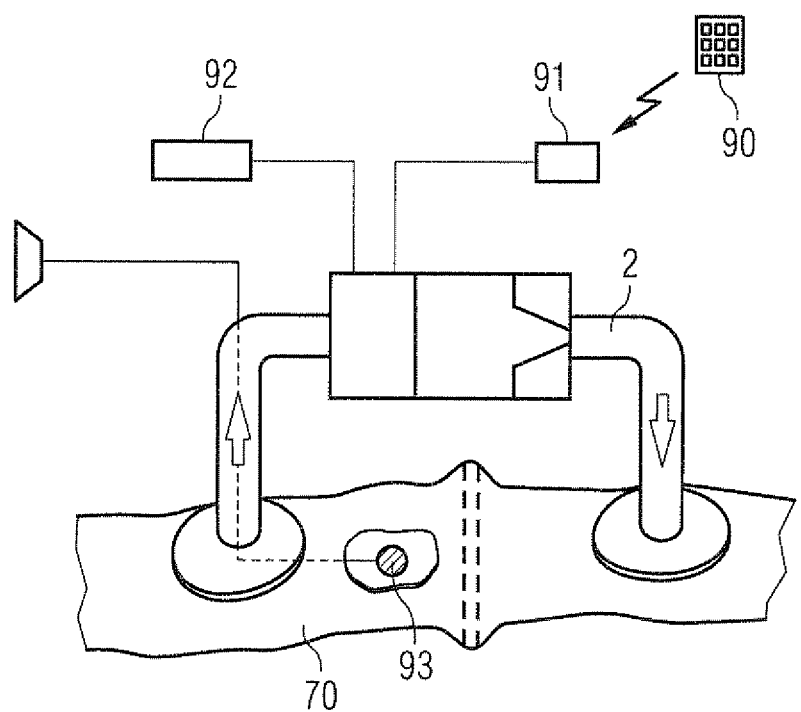
FIG. 109 shows an embodiment schematically, wherein the artificial intestine section by-passes a section of the patient's intestine, the intestine being closed by sewing so as to direct intestinal content towards the artificial intestine section. The enlarged area of the artificial intestine section represents any kind of element acting on the intestinal contents within the artificial intestine section, such as a reservoir, one or more valves, a pump or any other flow control device, possibly including a motor, and the like. Furthermore, a battery implantable in the patient's body and preferably rechargeable provides the artificial intestine section with energy. The artificial intestine section is wirelessly controlled and the battery, if rechargeable, wirelessly charged. A sensor implanted on or within the intestine delivers data on the physical conditions within the intestine for controlling the artificial intestine section.

FIG. 109 shows an embodiment schematically, wherein the artificial intestine section 2 by-passes a section of the patient's intestine 70, the intestine 70 being closed by sewing so as to direct intestinal content towards the artificial intestine section 2. The enlarged area of the artificial intestine section represents any kind of element acting on the intestinal contents within the artificial intestine section, such as a reservoir, one or more valves, a pump or any other flow control device, possibly including a motor, and the like. Furthermore, a battery 92 implantable in the patient's body and preferably rechargeable provides the artificial intestine section 2 with energy. The artificial intestine section 2 is wirelessly controlled and the battery 92, if rechargeable, wirelessly charged. A sensor 93 implanted on or within the intestine 70 delivers data on the physical conditions within the intestine 70 for controlling the artificial intestine section 2.

Figure 110C:
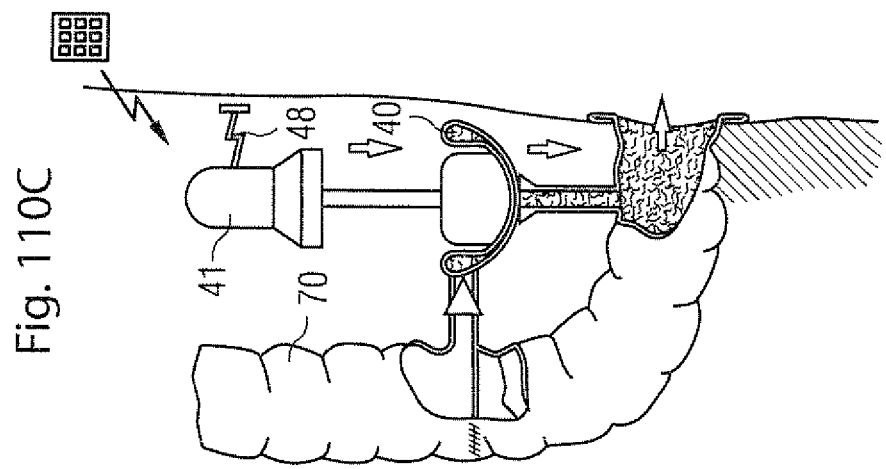
FIGS. 110A to 110C show a specific embodiment, wherein the artificial reservoir by-passes a section of the patient's intestine. The reservoir has a flexible wall and a pump implanted in the patient's body separate but in close proximity to the reservoir is used to empty the reservoir. The pump is actuated by means of a subcutaneously implanted, manually operable switch.
Figure 110B:
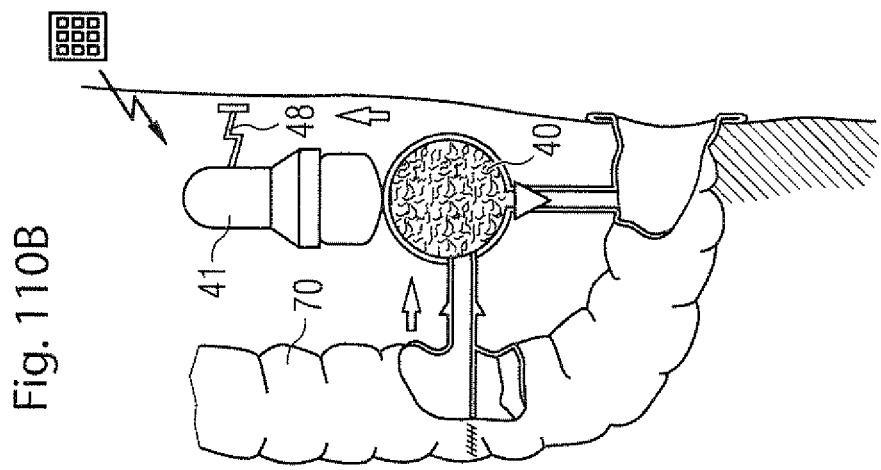
Figure 110A:
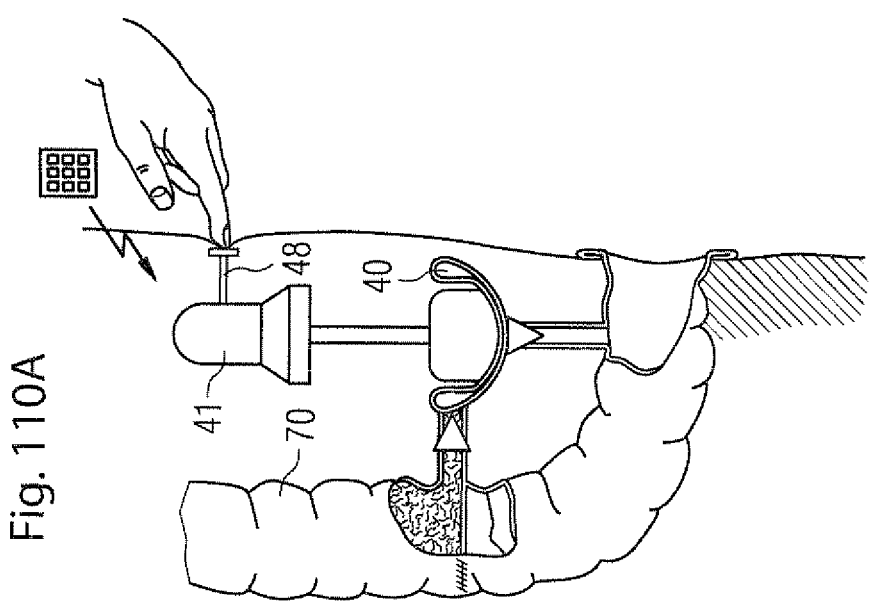

FIGS. 110A to 110C show a specific embodiment, wherein the artificial reservoir 40 by-passes a section of the patient's intestine 70. The reservoir 40 has a flexible wall and a pump 41 implanted in the patient's body separate but in close proximity to the reservoir 40 is used to empty the reservoir 40. The pump 41 is actuated by means of a subcutaneously implanted, manually operable switch 48.

FIGS. 111A and 111B show a structure similar to the one of FIGS. 110A to 110C, however, with the pump 41 and the reservoir 40 being fixedly connected to one another. The reservoir 40 is formed by a bellow 51 having an end wall 50 closing the bellow 51 at one end thereof. The end wall 50 makes part of the pump 41 such that a volume of the bellow 51 can be reduced upon advancement of the end wall 50. The bellow 51 is made of a resilient material so as to urge the bellow 51 into a normally extended position.

Figure 112A:
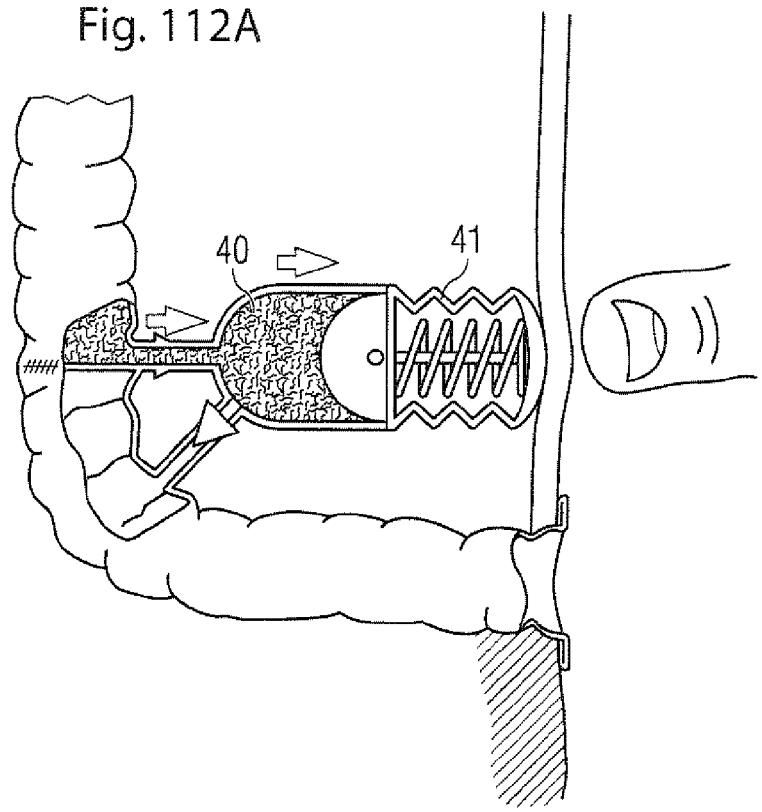
FIGS. 112A and 112B show a variant to FIGS. 111A and 111B. Here, the pump and reservoir are integrally combined. The pump is manually operable and subcutaneously mounted so as to be operable from the outside of the patient's body.
Figure 112B:
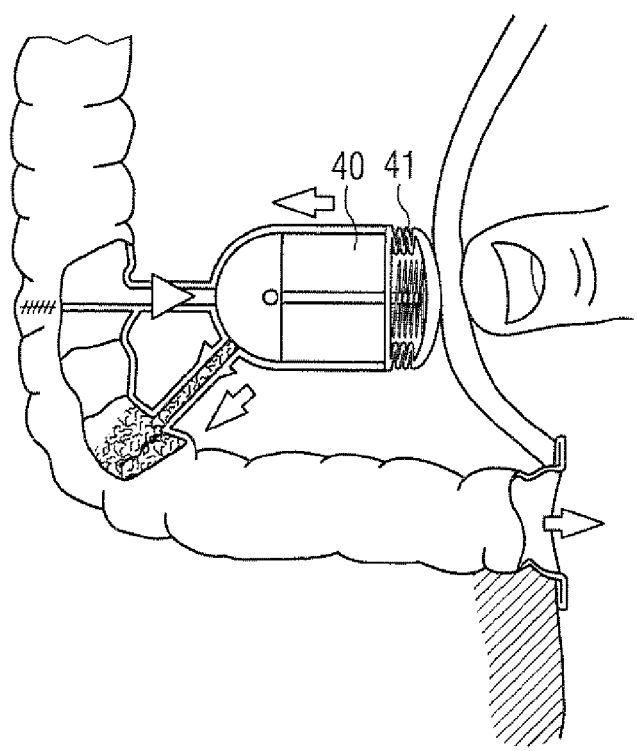

FIGS. 112A and 112B show a variant to FIGS. 111A and 111B. Here, the pump 41 and reservoir 40 are integrally combined. The pump 41 is manually operable and subcutaneously mounted so as to be operable from the outside of the patient's body.

FIGS. 113A and 113B likewise show a variant to the system shown in FIGS. 111A and 111B. While in the system of FIGS. 111A, 111B the pump 41 is automatically driven, such as by an integrated motor, and activated via remote control, the system in FIGS. 113A and 113B is again manually operable in that the manually operable pump 41 is mounted subcutaneously.

FIGS. 114A to 114C show a plurality of cooperating valves 61, 62, 63 implanted inside the patient's body and outside the patient's intestine 70. Each of the valves 61, 62, 63 comprises an electrical stimulation device adapted to electrically stimulate muscle or neural tissue of an intestine section so as to cause at least partial contraction of the intestine section. For that purpose, the stimulation device comprises at least one electrode adapted to apply electric pulses to the intestine section. While instead of the three stimulation devices shown, a single stimulation device would be sufficient for opening and closing the intestine, the arrangement of the plurality of stimulation devices is adapted to stimulate different portions of the intestine section over time. The function of the three stimulation devices may also be combined in one integral unit. The direction of natural intestinal contents flow is indicated by arrows. The different portions of the intestine section in a wavelike manner may be made in a direction opposite to the natural intestinal contents flow, as shown in FIGS. 114A to 114C, so as to close the intestine section. The stimulation in the wavelike manner may also be made in the direction of natural intestinal contents flow to support emptying of the intestine or reservoir.

FIGS. 115A to 115C show the stimulation devices of FIGS. 114A to 114C in combination with constriction devices, such as the bellow valves described in relation to FIGS. 108A and 108B, for at least partly constricting the intestine section mechanically. Complete constriction is obtained by additional electrical stimulation of the respective intestine sections. The constriction devices may be released in order to allow intestinal contents to flow through.

According to one embodiment a first and second passage is adapted to connect to a divided intestinal portion such that intestinal mesentery connected thereto is opened in such a way that supply of blood through the mesentery to the dissected intestinal area is maintained on both sides of the divided intestinal portion. The upstream part of the intestine with a first intestinal opening and a downstream part of the intestine with a second intestinal opening with the mesentery still maintaining a tissue connection between the upstream and downstream intestine parts and the connection of the first and second passage are adapted to take such mesentery in account to allow free blood supply, when implanted.

A holding device could be adapted to hold a suture or stapler mounted through the peritoneal wall. The holding device could be a T-shaped or a device having a pop-rivet design, exemplified as 150a and 150b of FIG. 97b, where the holding device has a pop-rivet design adapted to be fixated to the peritoneum or the muscular tissue of the abdomen.

The system could according to one embodiment comprise a constriction device for at least partly constricting the intestine section mechanically or hydraulically.

The term bonded should throughout the application comprise suturing and stapling.

The mounting of the holding device to the peritoneum could prevent large movements and movement forces acting on the connection between the intestine section and the patient's intestine against forces resulting from peristaltic movements and movement of the human body.

In embodiments comprising a sleeve connection, the sleeve could be adapted to increase the strength of the connection between the intestine section and the patient's intestine against axial forces resulting from peristaltic movements of the intestine which tend to pull on the intestine, comprising resorbable non-polymeric material.

According to one embodiment, the second open end portion could be adapted to be connected to the patient's rectum or anus or to tissue adjacent the patient's anus or to an artificial stoma, so as to form an intestine end section, so as to form an intestine end section.

The flow control device could according to one embodiment comprise at least one valve, including an exit valve preventing intestinal contents flow through the second open end portion in its closed position, wherein the exit valve is a normally closed valve.

In embodiments where the system comprises a shoulder portion or holding device, the shoulder portion or holding device could comprise at least one biocompatible material selected from the following group of materials: titanium, stainless steel, ceramics, biocompatible polymer, other biocompatible polymer material. The shoulder portion could be adapted to be connected to the patient's intestinal wall by sewing or stapling.

The system could comprise an artificial intestine section which could comprise a holding device adapted to be mounted to the peritoneum, when implanted, to prevent large movements and movement forces acting on the connection between the intestine section and the patient's intestine against forces resulting from peristaltic movements and movement of the human body.

The shoulder portion of the system could be split into an upper and a lower shoulder portion with a gap between the upper and lower shoulder portions adapted to accommodate intestinal wall tissue therein, wherein the lower shoulder portion is adapted to being placed inside the patient's intestine through a surgically created lateral opening in the intestinal wall and wherein the upper shoulder portion is adapted to being placed outside the intestinal wall.

Intestinal Disorder

"Artificial Intestine Section with Wirelessly Charged Accumulator"

FIG. 116a shows a system according to the present invention with an artificial intestine section being implanted inside a patient's body and having a first open end portion connected to a surgically created opening in the patient's intestine, more specifically to a lateral opening in a wall of the patient's intestine. The second open end portion exits the patient's abdominal wall forming a stomy. The artificial intestine section is here shown as a black box and includes at least one energy consuming part, such as one or more valves, a pump and/or any other flow control device, a motor for driving the same, possibly in connection with a reservoir. An accumulator is implanted along with the artificial intestine section and can be wirelessly charged from outside the patient's body. The energy is here galvanically transmitted from the accumulator to the artificial intestine section.

FIG. 116b shows a system corresponding to the one shown in FIG. 116a, however, with the energy being transmitted wirelessly from the accumulator to the artificial intestine section.

FIG. 116c shows a system corresponding to the one shown in FIG. 116a, however, with the second open end portion of the artificial intestine section exiting the patient's anus.

FIG. 117 shows a system where both the first and second open end portions of the artificial intestine section are attached to surgically created lateral openings in a wall of the patient's small and/or large intestine. The downstream part of the intestine exits the patient's abdominal wall forming a surgically created stomy. The downstream part of the intestine may as well exit through the patient's anus.

FIG. 118 shows a similar system with the difference that the second open end portion is connected to a cross-sectional opening of the patient's intestine, further leading to the surgically created stomy. The downstream part of the intestine may as well exit through the patient's anus.

FIG. 119 shows an embodiment of the artificial intestine section with an artificial reservoir and an entry valve and exit valve arranged upstream and downstream of the reservoir. The reservoir is mounted with a pump in a common housing and the pump and the entry and exit valves are controlled by means of a control device, of which a part is implanted inside the patient's body. Data are transmitted wirelessly between the external part and implanted part of the control unit. In addition, energy is wirelessly transmitted to the artificial intestine section or to an accumulator also implanted in the patient's body and galvanically connected here to the valves and pump.

FIGS. 120A and 120B show a first embodiment of the structure of FIG. 6 in more detail. The pump comprises a movable piston with a front end of the piston extending into the reservoir such that a volume of the reservoir is reduced upon advancement of the piston. The piston is spring loaded so as to urge the piston into a normally retracted position. Furthermore, entry and exit valves are here realized as flap valves. The flap valves are controlled so that one valve is open while the other one is closed.

FIGS. 121A and 121B show a system similar to the one of FIGS. 120A and 120B. However, here the entry and exit valves comprise bellows acting on the intestine from the outside so as to close the intestine by compression. In FIG. 8A the bellows of the exit valve are expanded to compress the artificial intestine section at the downstream side of the reservoir, whereas in FIG. 121B the artificial intestine section is closed by means of the bellows of the entry valve upstream of the reservoir so that the reservoir can be emptied by advancing the piston of the pump.

FIG. 122 shows an embodiment schematically, wherein the artificial intestine section by-passes a section of the patient's intestine, the intestine being closed by sewing so as to direct intestinal content towards the artificial intestine section. The enlarged area of the artificial intestine section represents any kind of element acting on the intestinal contents within the artificial intestine section, such as a reservoir, one or more valves, a pump or any other flow control device, possibly including a motor, and the like. Furthermore, a battery implantable in the patient's body and preferably rechargeable provides the artificial intestine section with energy. The artificial intestine section is wirelessly controlled and the battery, if rechargeable, wirelessly charged. A sensor implanted on or within the intestine delivers data on the physical conditions within the intestine for controlling the artificial intestine section.

FIGS. 123A to 123C show an embodiment, where the artificial intestine section comprises a reservoir with a flexible wall. A pump is implanted in the patient's body separate but in close proximity to the reservoir and is used to empty the reservoir. The pump is actuated by means of a subcutaneously implanted, manually operable switch.

FIGS. 124A and 124B show a structure similar to the one of FIGS. 123A to 123C, however, with the pump and the reservoir being fixedly connected to one another. The reservoir is formed by a bellow having an end wall closing the bellow at one end thereof. The end wall makes part of the pump such that a volume of the bellow can be reduced upon advancement of the end wall. The bellow is made of a resilient material so as to urge the bellow into a normally extended position.

FIGS. 125A to 125C show a plurality of cooperating valves implanted inside the patient's body and outside the patient's intestine. These can be positioned behind and/or in front of the artificial intestine piece along the patient's natural intestine. Each of the valves comprises an electrical stimulation device adapted to electrically stimulate muscle or neural tissue of an intestine section so as to cause at least partial contraction of the intestine section. For that purpose, the stimulation device comprises at least one electrode adapted to apply electric pulses to the intestine section. While instead of the three stimulation devices shown, a single stimulation device would be sufficient for opening and closing the intestine, the arrangement of the plurality of stimulation devices is adapted to stimulate different portions of the intestine section over time. The function of the three stimulation devices may also be combined in one integral unit. The direction of natural intestinal contents flow is indicated by arrows. The different portions of the intestine section in a wavelike manner may be made in a direction opposite to the natural intestinal contents flow, as shown in FIGS. 125A to 125C, so as to close the intestine section. The stimulation in the wavelike manner may also be made in the direction of natural intestinal contents flow to support emptying of the intestine or reservoir.

FIGS. 126A to 126C show the stimulation devices of FIGS. 125A to 125C in combination with constriction devices, such as the bellow valves described in relation to FIGS. 121A and 121B, for at least partly constricting the intestine section mechanically. Complete constriction is obtained by additional electrical stimulation of the respective intestine sections. The constriction devices may be released in order to allow intestinal contents to flow through.

FIGS. 127A and 127B show a system comprising the artificial intestine section connected to a cross-sectional opening of the patient's intestine and having a valve as shown in FIG. 125 or 126 arranged around the patient's intestine upstream of the artificial intestine section. Energy and/or data is transmitted wirelessly.

FIG. 128 shows the structure of an open end portion of the artificial intestine section for attaching the artificial intestine section to a lateral opening in the patient's intestine by means of a shoulder portion formed around the end portion. The end portion is sewn to the intestine and may additionally or alternatively be stapled and/or glued to the intestine.

FIG. 129 shows an improved structure for lateral attachment to the intestine, wherein the shoulder portion is split into an upper and a lower shoulder portion forming a gap to accommodate intestinal wall tissue therein. The surface area of the upper shoulder portion is larger than the surface area of the lower shoulder portion.

FIG. 130 shows an enlarged view of a ring-and-bulge connection by which the artificial intestine section and the patient's downstream intestinal part are connected, as shown in FIG. 118.

FIGS. 131A and 131B show the ring-and-bulge connection of FIG. 130 in combination with a sleeve. The sleeve is rolled upon itself and can be unrolled such that a part of the intestine is located intermediate the sleeve and the conduit. Thereafter, the ring is pushed over the sleeve against the bulge.

FIGS. 132A and 132B show a connection of the artificial intestine section to a cross-sectional opening of the patient's intestine similar to the connection shown in FIGS. 131A and 131B, however, without the bulge and the ring.

FIGS. 133A and 133B show an alternative to the connection in FIGS. 19A and 19B. Instead of unrolling the sleeve, it is simply pulled over the intestine.

FIGS. 134A and 134B show another sleeve connection. Here, the sleeve is mounted on the outer surface of the open end portion so as to be foldable upon itself. By folding the flexible sleeve upon itself, a part of the intestine is located intermediate the folded sleeve.

According to one embodiment a first and second passage is adapted to connect to a divided intestinal portion such that intestinal mesentery connected thereto is opened in such a way that supply of blood through the mesentery to the dissected intestinal area is maintained on both sides of the divided intestinal portion. The upstream part of the intestine with a first intestinal opening and a downstream part of the intestine with a second intestinal opening with the mesentery still maintaining a tissue connection between the upstream and downstream intestine parts and the connection of the first and second passage are adapted to take such mesentery in account to allow free blood supply, when implanted.

A holding device could be adapted to hold a suture or stapler mounted through the peritoneal wall. The holding device could be a T-shaped or a device having a pop-rivet design, exemplified as 150a and 150b of FIG. 97b, where the holding device has a pop-rivet design adapted to be fixated to the peritoneum or the muscular tissue of the abdomen.

The system could according to one embodiment comprise a constriction device for at least partly constricting the intestine section mechanically or hydraulically.

The term bonded should throughout the application comprise suturing and stapling.

The mounting of the holding device to the peritoneum could prevent large movements and movement forces acting on the connection between the intestine section and the patient's intestine against forces resulting from peristaltic movements and movement of the human body.

In embodiments comprising a sleeve connection, the sleeve could be adapted to increase the strength of the connection between the intestine section and the patient's intestine against axial forces resulting from peristaltic movements of the intestine which tend to pull on the intestine, comprising resorbable non-polymeric material.

According to one embodiment, the second open end portion could be adapted to be connected to the patient's rectum or anus or to tissue adjacent the patient's anus or to an artificial stoma, so as to form an intestine end section, so as to form an intestine end section.

The flow control device could according to one embodiment comprise at least one valve, including an exit valve preventing intestinal contents flow through the second open end portion in its closed position, wherein the exit valve is a normally closed valve.

In embodiments where the system comprises a shoulder portion or holding device, the shoulder portion or holding device could comprise at least one biocompatible material selected from the following group of materials: titanium, stainless steel, ceramics, biocompatible polymer, other biocompatible polymer material. The shoulder portion could be adapted to be connected to the patient's intestinal wall by sewing or stapling.

The system could comprise an artificial intestine section which could comprise a holding device adapted to be mounted to the peritoneum, when implanted, to prevent large movements and movement forces acting on the connection between the intestine section and the patient's intestine against forces resulting from peristaltic movements and movement of the human body.

The shoulder portion of the system could be split into an upper and a lower shoulder portion with a gap between the upper and lower shoulder portions adapted to accommodate intestinal wall tissue therein, wherein the lower shoulder portion is adapted to being placed inside the patient's intestine through a surgically created lateral opening in the intestinal wall and wherein the upper shoulder portion is adapted to being placed outside the intestinal wall.

Intestinal Disorder

"Artificial Intestine Section" Intestine—By-Pass Flow Control

FIG. 135 shows a system according to the present invention with an artificial intestine section being implanted inside a patient's body and having a first open end portion connected to a surgically created lateral opening in a wall of the patient's intestine. The second open end portion exits the patient's abdominal wall forming a stomy. The artificial intestine section is here shown as a black box and may include an artificial reservoir for intestinal contents, a motor, one or more valves, a pump and/or any other flow control device.

The system shown in FIG. 136 corresponds to the one shown in FIG. 1, however, with the second open end portion of the artificial intestine section exiting the patient's anus.

FIG. 137 shows a system where both the first and second open end portions of the artificial intestine section are attached to surgically created lateral openings in a wall of the patient's small and/or large intestine. The downstream part of the intestine exits the patient's abdominal wall forming a surgically created stomy. The downstream part of the intestine may as well exit through the patient's anus.

FIG. 138 shows a similar system with the difference that the second open end portion is connected to a cross-sectional opening of the patient's intestine, further leading to the surgically created stomy. The downstream part of the intestine may as well exit through the patient's anus.

FIG. 139 shows the structure of the first open end portion of the artificial intestine section for attaching the artificial intestine section to the lateral opening in the patient's intestine by means of a shoulder portion formed around the end portion. The end portion is sewn to the intestine and may additionally or alternatively be stapled and/or glued to the intestine.

FIG. 140 shows an improved structure for lateral attachment to the intestine, wherein the shoulder portion is split into an upper and a lower shoulder portion forming a gap to accommodate intestinal wall tissue therein. The surface area of the upper shoulder portion is larger than the surface area of the lower shoulder portion.

FIG. 141 shows an enlarged view of a ring-and-bulge connection by which the artificial intestine section and the patient's downstream intestinal part are connected, as shown in FIG. 138.

FIGS. 142A and 142B show the ring-and-bulge connection of FIG. 141 in combination with a sleeve. The sleeve is rolled upon itself and can be unrolled such that a part of the intestine is located intermediate the sleeve and the conduit. Thereafter, the ring is pushed over the sleeve against the bulge.

FIGS. 143A and 143B show a connection of the artificial intestine section to the cross-sectional opening of the patient's intestine similar to the connection shown in FIGS. 142A and 142B, however, without the bulge and the ring.

FIGS. 144A and 144B show an alternative to the connection in FIGS. 9A and 9B. Instead of unrolling the sleeve, it is simply pulled over the intestine.

FIGS. 145A and 145B show another sleeve connection. Here, the sleeve is mounted on the outer surface of the open end portion so as to be foldable upon itself. By folding the flexible sleeve upon itself, a part of the intestine is located intermediate the folded sleeve.

FIG. 146 shows an embodiment of the artificial intestine section with an artificial reservoir and an entry valve and exit valve arranged upstream and downstream of the reservoir. The reservoir is mounted with a pump in a common housing and the pump and the entry and exit valves are controlled by means of a control device, of which a part is implanted inside the patient's body. Data are transmitted wirelessly between the external part and implanted part of the control unit. In addition, energy is wirelessly transmitted to the artificial intestine section or to an accumulator also implanted in the patient's body and galvanically connected here to the valves and pump.

FIGS. 147A and 147B show a first embodiment of the structure of FIG. 146 in more detail. The pump comprises a movable piston with a front end of the piston extending into the reservoir such that a volume of the reservoir is reduced upon advancement of the piston. The piston is spring loaded so as to urge the piston into a normally retracted position. Furthermore, entry and exit valves are here realized as flap valves. The flap valves are controlled so that one valve is open while the other one is closed.

FIGS. 148A and 148B show a system similar to the one of FIGS. 147A and 147B. However, here the entry and exit valves comprise bellows acting on the intestine from the outside so as to close the intestine by compression. In FIG. 148A the bellows of the exit valve are expanded to compress the artificial intestine section at the downstream side of the reservoir, whereas in FIG. 148B the artificial intestine section is closed by means of the bellows of the entry valve upstream of the reservoir so that the reservoir can be emptied by advancing the piston of the pump.

FIG. 149 shows an embodiment schematically, wherein the artificial intestine section by-passes a section of the patient's intestine, the intestine being closed by sewing so as to direct intestinal content towards the artificial intestine section. An exit valve is provided for controlling the flow of intestinal contents from the artificial intestine section. The enlarged area of the artificial intestine section represents any kind of element acting on the intestinal contents within the artificial intestine section, such as a reservoir, one or more valves, a pump or any other flow control device, possibly including a motor, and the like.

FIG. 150 shows a by-passing artificial intestine section in action, further leading to a surgically created stoma. A pump or valve may be contained in the artificial intestine section.

FIG. 151 shows the artificial intestine section of FIG. 150 with a large reservoir and an exit valve downstream the reservoir.

FIG. 152 shows the by-passing artificial intestine section including a pump and a valve incorporated therein. Furthermore, a battery implantable in the patient's body and preferably rechargeable provides the artificial intestine section with energy. The artificial intestine section is wirelessly controlled and the battery, if rechargeable, wirelessly charged. A sensor implanted on or within the intestine delivers data on the physical conditions within the intestine for controlling the artificial intestine section.

FIGS. 153A to 153C show an embodiment, where the artificial intestine section comprises a reservoir with a flexible wall. A pump is implanted in the patient's body separate but in close proximity to the reservoir and is used to empty the reservoir. The pump is actuated by means of a subcutaneously implanted, manually operable switch.

FIGS. 153D and 153E show a structure similar to the one of FIGS. 153A to 153C, however, with the pump and the reservoir being fixedly connected to one another. The reservoir is formed by a bellow having an end wall closing the bellow at one end thereof. The end wall makes part of the pump such that a volume of the bellow can be reduced upon advancement of the end wall. The bellow is made of a resilient material so as to urge the bellow into a normally extended position.

FIGS. 154A and 154B show a variant to FIGS. 153A and 153B. Here, the pump and reservoir are integrally combined.

The pump is manually operable and subcutaneously mounted so as to be operable from the outside of the patient's body.

FIGS. 155A and 155B likewise show a variant to the system shown in FIGS. 153A and 153B. While in the system of FIGS. 153D, 153E the pump is automatically driven, such as by an integrated motor, and activated via remote control, the system in FIGS. 155A and 155B is again manually operable in that the manually operable pump is mounted subcutaneously.

FIGS. 160A to 160C show a plurality of cooperating valves implanted inside the patient's body and outside the patient's intestine. These can be positioned behind and/or in front of the artificial intestine piece along the patient's natural intestine. Each of the valves comprises an electrical stimulation device adapted to electrically stimulate muscle or neural tissue of an intestine section so as to cause at least partial contraction of the intestine section. For that purpose, the stimulation device comprises at least one electrode adapted to apply electric pulses to the intestine section. While instead of the three stimulation devices shown, a single stimulation device would be sufficient for opening and closing the intestine, the arrangement of the plurality of stimulation devices is adapted to stimulate different portions of the intestine section over time. The function of the three stimulation devices may also be combined in one integral unit. The direction of natural intestinal contents flow is indicated by arrows. The different portions of the intestine section in a wavelike manner may be made in a direction opposite to the natural intestinal contents flow, as shown in FIGS. 160A to 160C, so as to close the intestine section. The stimulation in the wavelike manner may also be made in the direction of natural intestinal contents flow to support emptying of the intestine or reservoir.

FIGS. 161A to 161C show the stimulation devices of FIGS. 160A to 160C in combination with constriction devices, such as the bellow valves described in relation to FIGS. 161A and 161B, for at least partly constricting the intestine section mechanically. Complete constriction is obtained by additional electrical stimulation of the respective intestine sections. The constriction devices may be released in order to allow intestinal contents to flow through.

FIG. 162 shows a system similar to the system of FIG. 135, however, with a flow control device in the form of an exit valve being implanted within the artificial intestine section. An external manually driven suction pump is used for emptying the artificial intestine section, wherein a conduit on the front end of the pump is inserted from outside the patient's body into the intestine, thereby mechanically urging the exit valve to open.

The system could include a first intestinal passage way in flow communication with the reservoir arranged for transferring intestinal contents to the reservoir, and a second intestinal passage way in flow communication with the reservoir, said second passage way being arranged for transferring intestinal contents from the reservoir.

The system may further comprise a pump for emptying said reservoir, wherein the second passage way is adapted to being surgically connected to a surgically created stoma and wherein said pump is adapted to pump intestinal contents out through said stoma or being surgically connected to the patient's anus or to tissue adjacent the patient's anus and wherein said pump is adapted to pump intestinal contents out through the patient's anus or to tissue adjacent the patient's anus.

The pump may be adapted to pump intestinal contents into to the small intestine and out from said reservoir or to pump into the large intestine and out from said reservoir.

The second passage way may include the large intestine or large intestine or an artificial intestinal piece.

The reservoir has an upstream part of the reservoir with a first open end and a downstream part of the reservoir with a second open end, wherein the downstream part is adapted to be advanced through the abdominal wall and skin and, thereby achieving an intestinal stomy or, wherein the downstream intestinal part is adapted to be connected to the patient's anus or tissue adjacent the patient's anus or, wherein the second open end is adapted to being connected to an artificial intestinal piece.

The artificial intestinal piece may comprise a valve for controlling the flow of intestinal contents and adapted to be connected to the patient's small intestine or large intestine.

The system may comprise a holding device adapted to be mounted to the peritoneum, when implanted, to prevent large movements and movement forces acting on the connection between the intestine section and the patient's intestine against forces resulting from peristaltic movements and movement of the human body.

The holding device may be adapted to hold a suture or stapler mounted through the peritoneal wall or comprise a part intended for placement outside the peritoneum, when implanted, adapted to pass through the peritoneal wall and hold said intestinal section.

The holding device may also comprise a flange intended for placement outside the peritoneum, when implanted, to hold said artificial intestine section.

According to one embodiment, the artificial intestine section has both the first and second open end portions adapted to be connected to a surgically created lateral opening in a wall of the patient's intestine or wherein the first and second open end portions are connected differently, one to a surgically created lateral opening of the intestine and one to a surgically created divided cross-sectional opening.

According to another embodiment the artificial intestine section comprises a holding device adapted to be mounted to the peritoneum, when implanted, to prevent large movements and movement forces acting on the connection between the intestine section and the patient's intestine against forces resulting from peristaltic movements and movement of the human body.

According to one embodiment the artificial reservoir is a reservoir for receiving and temporarily collecting intestinal contents supplied through the first open end portion, is adapted to be emptied to move intestinal contents out through the second open end portion.

According to one embodiment the system comprises an extra valve comprising at least one of; at least one electrical stimulation device adapted to electrically stimulate muscle or neural tissue of the natural intestine section so as to cause at least partial contraction of the natural intestine section and one hydraulic or mechanic constriction device to restrict the natural intestine section.

According to one embodiment the system comprises a flow control device comprising at least one valve, wherein the at least one motor is arranged for driving at least one of the valve or valves, respectively, between closed and open positions.

According to one embodiment the system comprises a pump for moving intestinal contents in the artificial section, wherein the at least one motor is arranged for driving the pump.

According to one embodiment the system comprises a manually operable switch for activating the at least one motor, the switch being arranged for subcutaneous implantation so as to be operable from outside the patient's body.

According to one embodiment the system comprises a holding device adapted to pass through the peritoneal wall and hold said intestinal section, comprising a flange intended for placement outside the peritoneum or the holding device being adapted to hold sutures and staplers passing through the peritoneal wall, when implanted, to hold said artificial intestine section.

According to one embodiment the system comprises an energy source comprising an implantable accumulator, wherein the accumulator comprises one or more of a rechargeable battery and a capacitor.

According to one embodiment the system comprises the energy source comprises a wireless energy transmitter adapted to wirelessly transmit energy from outside the patient's body to the at least one energy consuming part, wherein the system further comprising a feedback subsystem adapted to wirelessly send feedback information related to the energy to be stored in the accumulator from inside the human body to the outside thereof, wherein the system is adapted to use the feedback information for adjusting the amount of wireless energy transmitted by the energy transmitter.

Intestinal Disorder
"Intestinal Pump"

FIG. 163A schematically shows a general embodiment of the apparatus according to the present invention for treating a patient suffering from a disorder related to the passageway of the patient's intestines, such as constipation or anal incontinence. The apparatus includes a pump 1 externally applied on a selected portion 2 of the patient's intestines 3, such as a portion of the large intestine. The pump 1 includes a constriction device for constricting the selected portion 2 to displace intestinal contents therein. In operation, the apparatus cyclically changes between a first stage of operation, in which the constriction device does not constrict the selected portion 2 to allow intestinal contents to fill the selected portion 2, as illustrated in FIG. 163A, and a second stage of operation, in which the constriction device constricts the selected portion 2 to at least substantially reduce the volume of the passageway of the intestines 4 along the selected portion 2, so that the selected portion 2 of the tubular intestine 3 is at least partially flattened. As a result, intestinal contents is displaced out of the selected portion 2 downstream in the intestine 3 and discharges through an open end 5 of the intestine 3, as illustrated in FIG. 163B. When the apparatus changes from the second stage of operation (FIG. 163B) to the first stage of operation (FIG. 163A), the constriction device of the pump 1 releases the selected portion 2 to allow intestinal contents to enter the selected portion 2, whereby the volume of the passageway of the intestines 4 along the selected portion 2 is increased as intestinal contents fills the selected portion 2.

The apparatus of FIG. 163A may be provided with an electric stimulation device for electrically stimulating muscle or neural tissue of the selected portion 2 to cause contraction of the intestinal wall 6, so that the intestinal wall 6 thickens. When operating the apparatus provided with such a stimulation device, the apparatus cyclically performs a sequence of three stages of operation, namely a first stage of operation, in which the constriction device of the pump 1 does not constrict the selected portion 2 to allow intestinal contents to fill the selected portion 2, as illustrated in FIG. 163A, a second stage of operation, in which the constriction device constricts the selected portion 2 so that the latter is partially flattened, as illustrated in FIG. 164A, whereby some intestinal contents is displaced downstream in the intestine 3 and discharges through the open end 5, and a third stage of operation, in which the electric stimulation device stimulates the constricted selected portion 2 with electric pulses (indicated by arrows A in FIG. 164B) to thicken the intestinal wall 6 to completely close the passageway of the intestines 4, whereby more intestinal contents is displaced downstream in the intestine 3 and discharges through the open end 5, see FIG. 164B. The use of the electric stimulation device for accomplishing complete closing of the passageway of the intestines 4 enables the constriction device of the pump 1 to partially constrict the selected portion 2 without substantially hampering the blood circulation in the intestinal tissue.

FIGS. 165A, 165B and 165C schematically illustrate an embodiment of the invention, which is similar to the general embodiment according to FIGS. 163A and 163B, except that the apparatus includes a peristaltic type of pump 7. The peristaltic pump 7 includes a constriction device that provides a limited constriction 8 of the selected portion 2 extending along a part of the selected portion 2, see FIG. 165A. A control device 9 is provided for controlling the constriction device of the peristaltic pump 7 to displace the constriction 8 in the downstream direction (from left to right in FIGS. 165A-165C) to move intestinal contents forwards in the passageway of the intestines 4, as illustrated in FIGS. 165A through 165C. When the constriction 8 has been displaced to the right end of the selected portion 2 and intestinal contents has entered and refilled the selected portion 2 upstream of the constriction 8, the control device 9 controls the constriction device of the peristaltic pump 7 to release the selected portion 2 at its right end and to apply the constriction 8 at the left end of the selected portion 2, as illustrated in FIG. 165A, whereby the above described operation can be repeated.

FIGS. 166A, 166B and 166C schematically illustrate an embodiment of the invention, which is similar to the embodiment according to FIGS. 165A, 165B and 165C, except that the apparatus of the embodiment of FIGS. 165A-165C also includes an electric stimulation device having the same purpose as the electric stimulation device described above in connection with the embodiment according to FIGS. 164A and 164B. In the embodiment of FIGS. 166A-166C, a limited constriction 10 of the selected portion 2 is provided by the combination of two measures. Thus, in accordance with a first measure, the constriction device of the peristaltic pump 7 constricts a part of the selected portion 2 so that the latter partially flattens but does not close the passageway of the intestines 4. In accordance with a following second measure, the electric stimulation device stimulates the constricted part of the selected portion 2 with electric pulses (indicated by arrows B in FIGS. 165A-165C) to thicken the intestinal wall to completely close the passageway of the intestines, whereby the constriction 10 is created. The control device 9 controls the constriction device and stimulation device to displace the constriction 10 in the same manner as described above for the corresponding constriction 8 according to the embodiment of FIGS. 165A-165C.

FIGS. 167A, 167B and 167C show an embodiment of the invention, in which the apparatus includes a pump 11 having a constriction device 12 designed to constrict, i.e., flatten a selected portion 2 of the patient's intestines 3. Thus, the constriction device 12 includes an upstream first pair of short constriction elements 13A and 13B, a downstream second pair of short constriction elements 14A and 14B, and a third pair of elongate constriction elements 15A and 15B positioned between the first and second short element pairs. The two short constriction elements 13A,13B of the first pair are radially movable towards and away from each other between retracted positions (FIG. 167A) and constricting positions (FIGS. 167B and 167C), the two short constriction elements 14A, 14B of the second pair are radially movable towards and away from each other between retracted positions (FIG. 167C) and constricting positions (FIGS. 167A and 167B), and the two elongate constriction elements 167A, 167B of the third pair are radially movable towards and away from each other between retracted positions (FIGS. 167A and 167B) and constricting positions (FIG. 167C). The pump 11 is applied on to the selected portion 2 so that the two constriction elements of each pair of constriction elements are positioned at opposite sides of the selected portion 2, the short constriction elements 13A, 13B being positioned at an upstream end of the selected portion 2, and the short constriction elements 14A, 14B being positioned at a downstream end of the selected portion 2.

The control device 9 controls the pair of short constriction elements 13A, 13B, the pair of elongate constriction elements 15A, 15B and the pair of short elements 14A, 14B to constrict and release the selected portion 2 independently of one another. FIGS. 167A-167C illustrate how the control device 9 controls the operation of the pump 11 to cyclically displace intestinal contents in the downstream direction of the passageway of the intestines 4. Thus, in FIG. 167A the short constriction elements 13A, 13B and the elongate constriction elements 15A, 15B are in their retracted positions, whereas the short constriction elements 14A, 14B are in their constricting positions. FIG. 167B illustrates how the short constriction elements 13A, 13B have also been moved radially inwardly to their constricting positions, whereby a volume of intestinal contents is trapped in the passageway of the intestines 4 between the upstream and downstream ends of the selected portion 2. FIG. 167C illustrates how the short constriction elements 14A, 14B initially have been moved radially outwardly to their retracted positions, and then the elongate constriction elements 15A, 15B have been moved radially inwardly to their constricting positions. As a result, the intestinal contents in the passageway of the intestines 4 between the upstream and downstream ends of the selected portion 2 has been moved downstream in the passageway of the intestines 4, as indicated by an arrow. Then, the control device 9 controls the constriction device 12 to assume the state shown in FIG. 167A to allow intestinal contents to enter and fill the passageway of the intestines between the upstream and downstream ends of the selected portion 2, whereby the pumping cycle is completed.

Although FIGS. 167A-167C disclose pairs of constriction elements, it should be noted that it is conceivable to design the constriction device 12 with only a single short constriction element 13A, a single elongate constriction element 15A and a single short constriction element 14A. In such a case, the selected portion 2 of the intestine 3 is supported by stationary elements of the constriction device 12 positioned at the side of the selected portion 2 which is opposite to the constriction elements 13A, 14A and 15A.

FIGS. 168A, 168B and 168C show an embodiment of the invention, which is similar to the embodiment according to FIGS. 167A, 167B and 167C, except that the apparatus according to FIGS. 168A-168C also includes an electric stimulation device having the same purpose as the electric stimulation device described above in connection with the embodiment according to FIGS. 164A and 164B. The stimulation device according to FIGS. 168A-168C includes rows of electrodes 16 positioned on the constriction elements 13A, 13B, 14A, 14B, 15A and 15B and adapted to stimulate muscle or neural tissue of the selected portion of the intestinal tissue with electric pulses. In FIGS. 168A-168C, inactivated electrodes 16 are indicated by unfilled rings, whereas activated electrodes 16 are indicated by black round spots. In this embodiment, the constriction device and stimulation device cooperate to avoid hampering the blood circulation in the intestinal tissue. Thus, the two constriction elements of each pair of constriction elements are adapted to constrict the selected portion no more than to almost close the passageway of the intestines. The final complete closure of the passageway of the intestines is achieved by the electrodes 16 stimulating the constricted selected portion 2 with electric pulses, so that the intestinal wall thickens and completely closes the passageway of the intestines.

In operation of the apparatus according to FIGS. 168A-168C, the control device 9 controls the constriction elements 13A-15B to move in the same sequence as described above in connection with the embodiment according to FIGS. 167A-167C. The control device 9 also controls the electrodes 16 to electrically stimulate the intestinal tissue where any one of the constriction elements 13A-15A constricts the selected portion 2.

FIG. 169 shows the same embodiment as that of FIG. 168C illustrating a modified operation of the electrodes 16 on the elongate constriction elements 15A and 15B. Thus, the control device 9 controls the electrodes 16 to successively stimulate the selected portion 2 where the elongate constriction elements 15A, 15B constrict the selected portion 2, so that the constricted selected portion is progressively contracted in the downstream direction. As a result, intestinal contents is displaced downstream in the passageway of the intestines in a peristaltic manner. Alternatively, the electrodes 16 may successively stimulate the selected portion 2 to progressively contract the portion 2 in the upstream direction.

FIG. 170 shows the embodiment of FIG. 168A when the pump 11 is not in operation and the constriction elements 13A-15B are maintained in a rest position. Thus, the short upstream and downstream constriction elements 13A, 13B, 14A and 14B are kept in their retracted positions, whereas the elongate constriction elements 15A,15B gently constrict the selected portion to at least substantially decrease the cross-sectional area of the passageway of the intestines. The control device 9 controls all of the electrodes 16 on the constriction elements 15A, 15B to electrically stimulate the constricted selected portion 2 to thicken the intestinal wall so that the passageway of the intestines is kept completely closed. Alternatively, only a part of the constricted portion may be stimulated at a time.

Figure 171A:
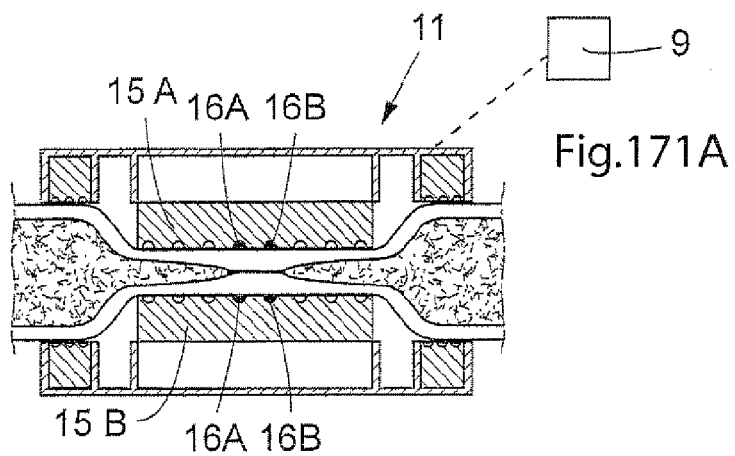

FIGS. 171A, 171B, 171C and 171D illustrate a modified operation of the electrodes 16 of the embodiment according to FIG. 168A when the pump 11 is not in operation. Referring to FIG. 171A, there are eight electrodes positioned in a row along constriction element 15A and eight electrodes positioned in a row along constriction element 15B. The control device 9 activates the electrodes in the two rows of electrodes in accordance with a preset scheme to cause partial contractions of the selected portion 2 that over time change their positions on the selected portion, whereby parts of the intestines that currently are not stimulated can restore substantially normal blood circulation before they are stimulated again. Starting from the electrodes positioned in the middle of the elongate constriction elements 15A, 15B, the electrodes are progressively activated in the direction upstream and the direction downstream of the intestines.

Figure 171B:
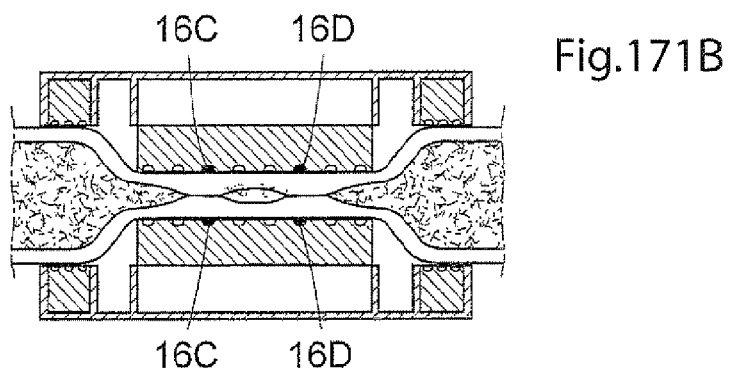
Figure 171C:
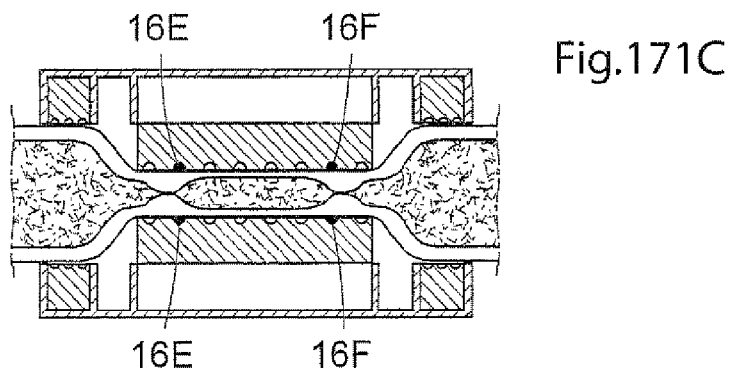
Figure 171D:
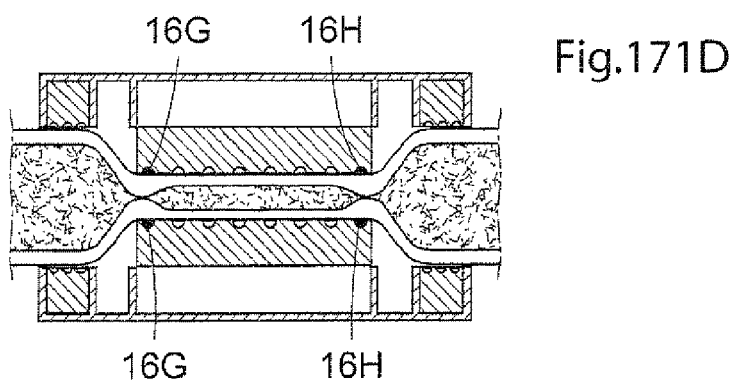

Thus, the control device 9 activates two pairs of adjacent electrodes 16A and 16B positioned centrally in the two rows of electrodes to thicken the intestinal wall along a short distance of the selected portion 2 to close the passageway of the intestines in the middle of the selected portion 2. Referring to FIG. 171B, after the laps of a predetermined time period, in the order of seconds, a next pair of electrodes 16C to the left of the electrode pair 16A and a next pair of electrodes 16D to the right of the electrode pair 16B are activated, whereas the electrodes 16A and 16B are inactivated. As a result, the intestinal wall is thickened at two different positions spaced from the middle of the selected portion 2. Referring to FIG. 9C, after the laps of another predetermined time period, a next pair of electrodes 16E to the left of the electrode pair 16C and a next pair of electrodes 16F to the right of the electrode pair 16D are activated, whereas the electrodes 16C and 16D are inactivated. As a result, the intestinal wall is thickened at two positions spaced farther from the middle of the selected portion 2. Referring to FIG. 171D, after the laps of yet another predetermined time period, a next pair of electrodes 16G to the left of the electrode pair 16E and a next pair of electrodes 16H to the right of the electrode pair 16F are activated, whereas the electrodes 16E and 16F are inactivated. Then, the above described stimulation operation according to FIGS. 171A-171D is cyclically repeated until the pump 11 is to be operated.

FIGS. 172A, 172B and 172C show an embodiment of the invention, which is similar to the embodiment according to FIGS. 168A, 168B and 168C, except that the movable elongate constriction elements 15A and 15B are replaced by two elongate stationary elements 17A and 17B. The stimulation device of this embodiment includes rows of electrodes 16 positioned on the stationary elements 17A, 17B and adapted to electrically stimulate the intestinal wall of the selected portion 2 to reduce the volume of the passageway of the intestines 4 between the upstream and downstream ends of the selected portion 2. Thus, FIG. 172C illustrates how the short constriction elements 14A, 14B initially have been moved radially outwardly to their retracted positions, and then the electrodes 16 have been activated to cause contraction of the intestinal wall so that the volume of the passageway of the intestines between the upstream and downstream ends of the selected portion 2 is reduced, whereby intestinal contents is moved downstream in the passageway of the intestines 4 as indicated by an arrow. For the sake of clarity, the thickness of the intestinal wall subjected to electric stimulation by the electrodes 16 is exaggerated in FIG. 172C.

FIGS. 173A and 173B are views of another embodiment of the invention showing different stages of operation, wherein a rotary peristaltic pump 18 is applied on the small intestines 19 of a colostomy patient near the stoma. The peristaltic pump 18 includes a rotor 20 carrying a constriction device 21 in the form of three cylindrical constriction elements 22A, 22B and 22C positioned equidistantly from the axis 23 of the rotor 20. The constriction elements 22A-22C may be designed as rollers. A stationary elongate support element 24 is positioned spaced from but close to the rotor 20 and has a part cylindrical surface 25 concentric with the axis 23 of the rotor 20. The pump 18 is applied on the small intestines 19, so that the intestine 19 extends between the support element 24 and the rotor 20.

The control device 9 controls the rotor 20 to rotate so that the constriction elements 22A-22C successively constrict portions of a series of selected portions of the intestines 19 against the elongate support element 24. FIG. 173A illustrates how the constriction element 22A constricts intestines 19 at a first portion 25 and closes the passageway of intestines 4, whereas the constriction element 22B is about to release intestine 19 at a second portion 26 downstream of the first portion 25. FIG. 173B illustrates how the constriction element 22A has advanced about halfway along the elongate support element 24 and displaced the intestinal contents in the passageway of the intestines so that some intestinal contents discharges through the stoma. The constriction element 22B has released intestines 19, whereas the constriction element 22C is about to engage intestines 19. Thus, the control device 9 controls the rotor 20 to cyclically move the constriction elements 22A-22C one after the other along the elongate support element 24 while constricting the selected portions of intestines 19, so that intestinal contents in the passageway of intestines 4 is displaced in a peristaltic manner. The same constriction principle may also be practiced by other mechanical constriction devices that do not include a rotor.

FIGS. 174A and 174B show an embodiment of the invention, which is similar to the embodiment according to FIGS. 173A and 173B, except that the apparatus of the embodiment of FIGS. 174A-174B also includes an electric stimulation device having the same purpose as the electric stimulation device described above in connection with the embodiment according to FIGS. 166A-166C. The stimulation device according to FIGS. 174A-174B includes electrodes 16 provided on the constriction elements 22A-22C. In this embodiment, the rotor 20 is spaced somewhat farther from the stationary elongate support element 23, as compared with the embodiment according to FIGS. 173A and 173B, so that the constriction elements 22A-22C do not completely close the passageway of the intestines by mechanical action, as they constrict intestine 19 during rotation of the rotor 20. Complete closure of the passageway of intestines 4 is accomplished by activation of the electrodes 16. The same combined constriction and stimulation principle may also be practiced by other mechanical constriction devices that do not include a rotor.

Thus, when any one of the constriction elements 22A-22C constricts a portion of intestines 19, its associated electrodes 16 electrically stimulate the constricted portion with electric pulses so that the intestinal wall of the constricted portion thickens and closes the passageway of intestines 4.

FIGS. 175A through 175D are longitudinal cross-sections of another embodiment of the invention showing different stages of operation, wherein another type of peristaltic pump 27 is applied on a selected portion of the patient's intestines 19. The pump 27 comprises a constriction device 28 including two elongate constriction elements 29A and 29B having convex surfaces 30A and 30B that abut a length of the selected portion on mutual sides thereof. The control device 9 controls the elongate constriction elements 29A, 29B to move relative to the selected portion so that the constriction elements 29A, 29B progressively constrict the selected portion, as shown in FIGS. 175A to 175D.

Figure 175A:
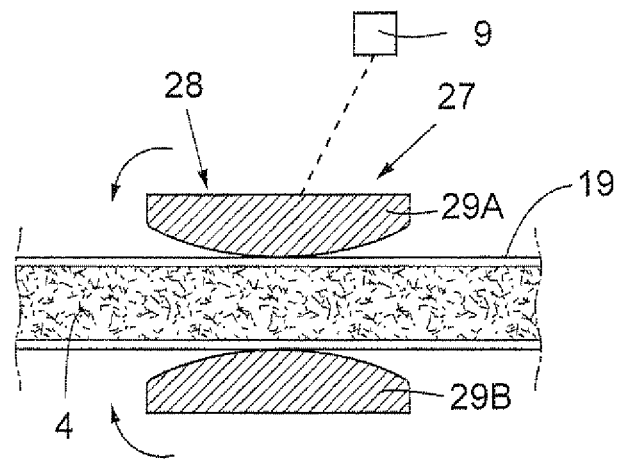
Figure 175B:
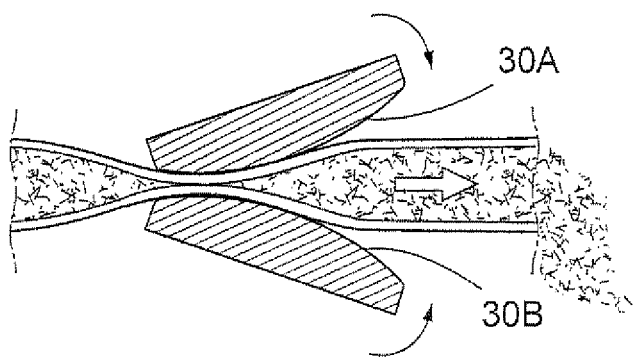
Figure 175C:
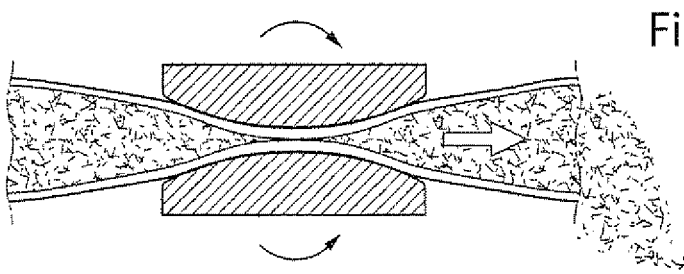
Figure 175D:
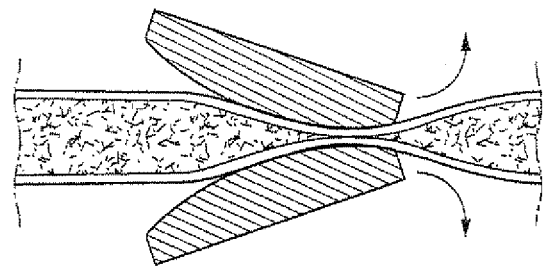

Thus, in an initial position of the constriction elements 29A, 29B shown in FIG. 175A, the selected portion is not constricted by the constriction elements 29A, 29B. Starting from this initial position, the control device 9 controls the constriction elements 29A, 29B to swing the left ends of the constriction elements 29A, 29B toward the selected portion (indicated by arrows) to constrict the selected portion of intestines 19, see FIG. 175A. FIG. 175B shows how the passageway of intestines 4 is completely closed by the constricted selected portion. Then, as shown in FIG. 175B, the control device 9 controls the constriction elements 29A, 29B to move so that their right ends move towards each other (indicated by arrows), while the convex surfaces 30A, 30B of the constriction elements 29A, 29B are rolling on each other with the constricted selected portion between them, see FIG. 175C. As a result, intestinal contents in intestines 19 is forced to the right (indicated by a white arrow). When the constriction elements 29A, 29B have rolled on each other to the position shown in FIG. 175D, the control device 9 controls the constriction elements 29A, 29B to move their right ends away from each other (indicated by arrows in FIG. 175D) to the initial position shown in FIG. 175A. The operation stages shown in FIGS. 175A to 175D can be cyclically repeated a number of times until the desired amount of intestinal contents has been displaced in the passageway of the intestines in a peristaltic manner. This embodiment is particularly suited for use in a stoma patient. Thus, the peristaltic pump 27 is applied on the patient's intestines close to the patient's stoma.

Alternatively, only one of the constriction elements 29A, 29B can be provided with a convex surface, whereas the other constriction element has a plane surface that abuts the selected portion. It is also possible to use a single constriction element with a convex surface that presses the selected portion of the intestine 19 against a bone of the patient.

FIGS. 176A through 176D show an embodiment of the invention, which is similar to the embodiment according to FIGS. 175A-175D, except that the apparatus of the embodiment of FIGS. 176A-176D also includes an electric stimulation device having the same purpose as the electric stimulation device described above in connection with the embodiment according to FIGS. 166A-166C. The stimulation device includes electrodes 16 positioned on the convex surfaces 30A, 30B. In the embodiment of FIGS. 176A-176D, the constriction elements 29A and 29B are spaced somewhat farther from each other, as compared with the embodiment according to FIGS. 175A-175D, so that the constriction elements 29A, 29B do not completely close the passageway of the intestines 4 by mechanical action, as they constrict the intestine 19 during operation. Complete closure of the passageway of the intestines 4 is accomplished by activation of the electrodes 16.

Figure 176A:
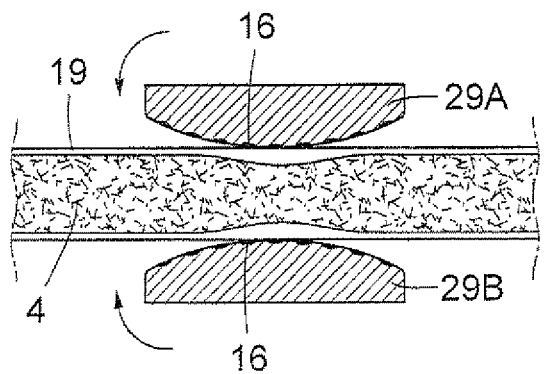
Figure 176B:
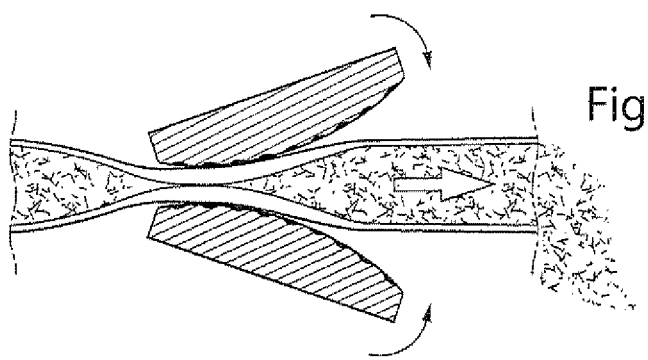
Figure 176C:
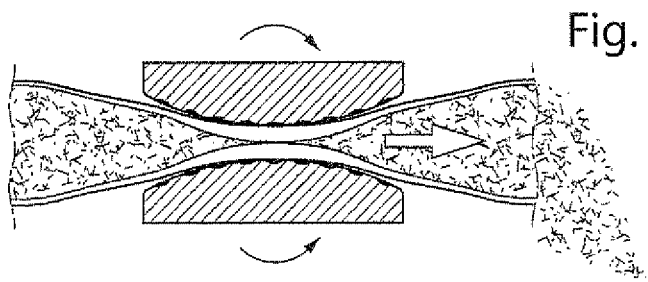
Figure 176D:
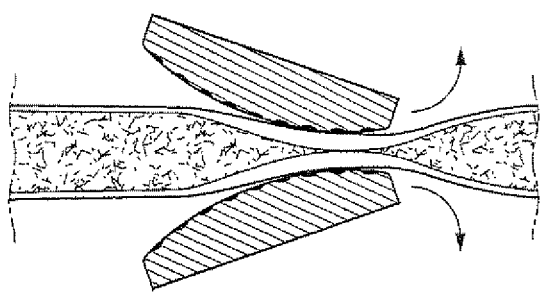

Thus, with the constriction elements 29A, 29B in the initial position shown in FIG. 176A, the control device 9 controls the constriction elements 29A, 29B to swing the left ends thereof toward the selected portion of the intestines 19 (indicated by arrows) to constrict the selected portion, while controlling the electrodes 16 to electrically stimulate the intestine 19 to cause contraction and thickening of the intestinal wall. FIG. 176B shows how the passageway of the intestines 4 is completely closed by the combination of the mechanical constriction of the intestine 19 by the constriction elements 29A, 29 B and the electric stimulation of the intestine 19 by the electrodes 16. FIGS. 176C and 176D shows operation stages that correspond to the operation stages of FIGS. 175C and 175D described above.

In the embodiment according to FIGS. 176A to 176D, the control device 9 may control the electrodes 16 to progressively stimulate the constricted selected portion to cause progressive contraction thereof in harmony with the movement of the elongate constriction elements 29A 29B, as the convex surfaces 30A, 30B of the constriction elements 29A, 29B are rolling on each other.

FIGS. 177A and 177B show different stages of operation of another embodiment of the invention, in which the apparatus includes a separate pump 31 and a separate releasable closure 32 applied on a selected portion of a patient's intestine 19. The pump 31 is of the type described above, which includes a constriction device that alternately constricts and releases the selected portion of the intestines 19, such that intestinal contents is displaced through the passageway of the intestines 4. The closure 32 includes two elongate constriction elements 33A and 33B, which are positioned at opposite sides of the selected portion. The constriction elements 33A, 33B are radially movable towards and away from each other between retracted positions (FIG. 177A), in which the selected portion of the intestine 19 is released when the pump 31 is in operation, and constricting positions, in which the constriction elements 33A, 33B constrict the selected portion to close the passageway of the intestines when the pump is not in operation.

There is a stimulation device including rows of electrodes 16 positioned on the constriction elements 33A, 33B for stimulating muscle or neural tissue of the selected portion of the intestine 19 with electric pulses to cause contraction of the intestinal wall. FIG. 177A illustrates the electrodes 16 by unfilled rings indicating inactivated electrodes and FIG. 177B illustrates the electrodes 16 by black round spots indicating activated electrodes. The constriction elements 33A, 33B and electrodes 16 cooperate to avoid hampering the blood circulation in the intestinal tissue, when the closure 32 closes the passageway of the intestines 4. Thus, the constriction elements 33A, 33B at least partially constrict the selected portion to at least substantially decrease the cross-sectional area of the passageway of the intestines 4, when the pump 31 is not in operation (FIG. 177B), and the electrodes electrically stimulate muscle or neural tissue of the intestines to cause contraction of the intestines, so that the intestinal wall thickens, to completely close the passageway of the intestines 4. The electrodes may be activated in accordance with the preset scheme described above in connection with the embodiment of FIGS. 171A-171D, or in accordance with any other determined pattern or scheme that causes variation of the stimulation of the intestine.

FIG. 178A shows another embodiment of the invention including an artificial intestinal piece 34 implanted in a colostomy patient provided with a stoma 35. The small intestines 19 is surgically cut to form an upstream open end 36 thereof and a downstream open end 37 of a short separated piece 39 of the small intestines 19 that forms the stoma 35. The short piece 39 of the intestines 19 extends through a surgically created opening in the patient's abdominal wall 39A. The artificial intestinal piece 34 is surgically joined to and integrated with the patient's small intestines 19 between the upstream end 36 and downstream end 37. Blood vessels 38 of a portion of the patient's mesentery supply blood to the separate piece 39 of the intestines that forms the stoma 35. The artificial intestinal piece 34 is provided with a pump 40, which includes a constriction device that only operates on the artificial intestinal piece 34. A holder 40A attached to the pump 40 is secured to the abdominal wall 39A at the opening thereof. The constriction device of pump 40 alternately constricts and releases the artificial intestinal piece 34, which may include an elastic tubing, so that intestinal contents is discharged through the patient's stoma 35. The constriction device of pump 40 may be selected from any one of the various constriction devices described in the embodiments of the present application. In the embodiment of FIG. 178A, the constriction device may constrict the artificial intestinal piece 34 to normally keep the passageway thereof closed, when the pump 40 is not in operation. Also, any kind of pump that is capable of constricting the small intestines may be used in the embodiment of FIG. 178A.

The artificial intestinal piece 34 or 43 described above may alternatively be joined directly or indirectly to the patient's anus, as illustrated in FIG. 178B.

FIG. 179 is an enlarged view of the artificial intestinal piece 34 and the pump 40 showing how the intestinal piece 34 with the pump 40 is sealed to the intestines 19 at the upstream and downstream ends 36, 37 thereof. Thus, a fabric tubular net 41 is applied on the intestines 19 at the upstream end 36 thereof and is attached to the pump 40. Another fabric tubular net 42 is applied on the separate piece 39 of the intestines 19 and is attached to the pump 40. The tubular net 42 has not been fully applied on the separate piece 39 to illustrate how the net 42 is rolled on the piece 39. Initially the fabric nets 41 and 42 are sutured to the intestines, normally with absorbable sutures. The tubular nets 41, 42 promote ingrowth of fibrotic tissue that seals the intestines 19 to the artificial intestinal piece 34. Another material such as PTFE, silicone or polyurethane may be applied externally on the tubular nets 41, 42.

FIG. 180 shows a modification of the embodiment of FIG. 179, which includes an artificial intestinal piece 43 having a tubular portion 44 that extends from the pump 40 at the downstream side thereof and forms a stoma 45. Another tubular portion 44A of the artificial intestinal piece 43 extends from the pump 40 at the upstream end thereof. With this modification there is only need for surgically joining and sealing the tubular portion 44A of the artificial intestinal piece 43 to the patient's small intestines 19.

FIGS. 181A, 181B, 181C and 181D schematically illustrate different stages of operation of another embodiment of the invention, wherein a pump 46 includes a constriction device 47 that axially constricts a patient's intestines 19. Referring to FIG. 181A, the constriction device 47 includes a first pair of constriction elements 48A and 48B hinged to each other and a second pair of constriction elements 49A and 49B hinged to each other. The two pairs of constriction elements 48A, 48b and 49A, 49B are joined to a selected portion of the intestines 19 at opposite sides thereof by means of a material 50 that allows ingrowth of fibrotic tissue. FIG. 181B shows how the first pair of constriction elements 48A, 48B and the second pair of constriction elements 49A, 49B have been moved away from each other to radially expand the selected portion of intestines 19 to form an expanded chamber 51 of the passageway of intestines 4. FIG. 181C shows how the constriction elements 48A and 49B are turned towards each other to radially and axially constrict the selected portion of intestines 19, whereby the volume of the chamber 51 is reduced causing intestinal contents to displace through the passageway of the intestines and out of intestines 19. FIG. 181D shows how also the constriction elements 48B and 49B of the second pair are turned towards each other, to axially constrict the expanded selected portion to further reduce the volume of the chamber 51, whereby more intestinal contents is displaced through the passageway of intestines 4 and out of intestines 19.

FIG. 181E illustrates the embodiment of FIG. 181D including an electric stimulation device having the same purpose as the electric stimulation device described above in connection with the embodiment according to FIGS. 166A-166C. The stimulation device of FIG. 181E includes electrodes 16 positioned on the constriction elements 48A, 48B, 49A and 49B. The electrodes 16 electrically stimulate the intestines 19 to cause contraction and thickening of the intestinal wall at the same time as the constriction elements 48A, 48B, 49A and 49B axially constricts the intestines 19.

FIGS. 182-185 show another embodiment of the invention, wherein a manually operable pump 52 includes a hydraulically operated constriction device 53 applied on a selected portion of the patient's intestines 19. The constriction device 53 includes a first sub-device 54 for constricting and releasing the selected portion at an upstream end thereof, a second sub-device 55 for constricting and releasing the selected portion at a downstream end thereof, and a third sub-device 56 for constricting and releasing the selected portion between the upstream and downstream ends thereof. The first sub-device 54 includes a frame 57, a constriction element 58 movable relative to the frame 57 and a hydraulic bellows 59 connected between the frame 57 and the constriction element 58. A support surface 60 of the frame 57 supports the intestine 19, so that the constriction element 58 can constrict the intestine 19 against the support surface 60, see FIG. 183. The second sub-device 55 includes two constriction elements 61A and 61B positioned at opposite sides of the intestine 19 and two bellows 62A and 62B also positioned at opposite sides of the intestine 19 and interconnecting the constriction elements 61A, 61B, see FIG. 184. The third sub-device 56 is designed similar to the first sub-device 54 and includes a frame 63, an elongate constriction element 64 movable relative to the frame 63 and two hydraulic bellows 65A and 65B connected between the frame 63 and the elongate constriction element 64. A support surface 66 of the frame 63 supports the intestine 19. The bellows 59, 65A, 65B, 62A, 62B are dimensioned, such that when they are fully expanded, the volume of the bellows 59 is equal to the volume of the two bellows 62A and 62B, whereas the volume of the two bellows 65A and 65B is larger than the volume of the bellows 59 and larger than the volume of the bellows 62A and 62B.

An actuator in the form of a manually compressible elastic reservoir 67 containing a volume of hydraulic fluid is subcutaneously implantable in the patient's body and hydraulically connected to the respective bellows 59, 65A, 65B, 62A and 62B via hydraulic conduits 68A, 68B, 68C, 68D and 68E of equal size. Conduit 68C branches hydraulic fluid supplied through the single conduit 68E to the two bellows 65A and 65B. FIGS. 182-184 show the pump 52 in an inactivated state, in which the reservoir 67 is uncompressed, whereby all of the bellows 59, 65A, 65B, 62A, 62B are retracted. As a result, the sub-device 55 constricts the intestine 19 at the downstream end of the selected portion (see FIG. 184), whereas the sub-devices 54 and 56 release the intestine 19.

FIGS. 185-187 show the pump 52 in an activated state, in which the patient manually compresses the reservoir 67 to distribute hydraulic fluid from the reservoir 67 to the bellows 59, 65A, 65B, 62A, 62B. As a result, the bellows 59 expands so that the short constriction element 58 constricts the intestine 19 and closes the passageway of the intestines 4 at the upstream end of the selected portion of the intestine 19 (see FIG. 186), the two bellows 62A, 62B expand so that the short constriction elements 61A, 61B release the intestine 19 and open the passageway of the intestines 4 at the downstream end of the selected portion (see FIG. 187), and the two bellows 65A, 65B expand so that the elongate constriction elements 64 constrict the selected portion between the upstream and downstream ends thereof, whereby intestinal contents is displaced in the passageway of the intestines 4. Since the bellows 59 has a smaller volume when expanded than the combined volume of the two bellows 65A, 65B and hydraulic fluid is supplied to the bellows 65A, 65B via the single conduit 68E, the bellows 59 expands more quickly than the bellows 65A, 65B, when the reservoir 67 is compressed. (This difference in the rate of expansion may alternatively be achieved by designing bellows 59 with a smaller volume than the volume of each one of bellows 65A and 65B, and connecting bellows 65A to conduit 68B and bellows 65B to conduit 68D.) Consequently, the constriction element 58 closes the passageway of the intestines 4 at the upstream end of the selected portion of the intestine 19 well before the elongate constriction element 64 fully constricts the intestines, whereby a significant amount of intestinal contents in the selected portion of the intestine 19 is forced downstream in the passageway of the intestines as the constriction element 64 constricts the intestine 19. When the patient ceases to compress the reservoir 67, the reservoir resumes its uncompressed shape sucking hydraulic fluid from the bellows 59, 65A, 65B, 62A, 62B, whereby the bellows 59, 65A, 65B, 62A, 62B retract and the pump 52 returns to the inactivated state shown in FIG. 182.

The hydraulic operation means of the constriction device according to FIGS. 182-184 described above may also be implemented in the constriction devices of the embodiments according to FIGS. 1-10C and in the closure of the embodiment according to FIGS. 177A, 177B.

FIGS. 188A and 188B show a hydraulic reverse servo 69 suited for use in the embodiment of FIGS. 182-187. The reverse servo 69 includes a rectangular housing 70 with two parallel long sidewalls 71A and 71B and two parallel short sidewalls 72A and 72B. A movable wall 73 parallel with the long sidewalls 71A, 71B slides on the short sidewalls 72A, 72B between the long sidewalls 71A, 71B. A relatively large, substantially cylindrical bellows reservoir 74 defining a chamber 75 extends between and is joined to the movable intermediate wall 73 and the long sidewall 71B, and a relatively small, substantially cylindrical bellows reservoir 76 defining a chamber 77, which is substantially smaller than the chamber 75 of the large reservoir 74, extends between and is joined to the movable wall 73 and the long sidewall 71A. The small bellows reservoir 76 has a fluid supply pipe 78 for connection to the compressible reservoir 67 through the conduit 68A and the large bellows reservoir 74 has a fluid supply pipe 79 for connection to the bellows 59, 65A, 65B, 62A, 62B through the conduits 68B-68D.

Referring to FIG. 188A, when the patient compresses the reservoir 67, a small amount of hydraulic fluid is conducted from the reservoir 67 through the supply pipe 78 into the chamber 77 of the small bellows reservoir 76, so that the small bellows reservoir 76 expands and pushes the movable intermediate wall 73 towards the long sidewall 71B. As a result, the large bellows reservoir 74 is contracted by the intermediate wall 73 against the long sidewall 71B, whereby a large amount of hydraulic fluid is forced out of the chamber 75 of the large bellows reservoir 74 through the supply pipe 79 and further through the conduits 68B-68D into the bellows 59, 65A, 65B, 62A, 62B of the pump 52, see FIG. 188B.

FIGS. 189A and 189B show a mechanically operated constriction device 80, which may be implemented in the embodiments according to FIGS. 163-172C and 177A, 177B. The constriction device 80 includes an open ended tubular housing 81 applied on a selected portion of a patient's intestine 19, and a constriction element 82, which is radially movable in the tubular housing 81 towards and away from the intestine 19 between a released position, see FIG. 189A, and a constricted position, see FIG. 189B, in which the constriction element 82 constricts the selected portion of the intestines 19. Mechanical operation means for mechanically operating the constriction element 82 includes an electric motor 83 attached to the housing 81 and a telescopic device 84, which is driven by the motor 83 and operatively connected to the constriction element 82. When the motor 83 is powered, it expands the telescopic device 30 so that the constriction element 82 constricts the intestine 19 and closes the passageway of the intestines 4, see FIG. 28B. When the constriction element 82 is to release the intestine 19, the electric motor 83 is reversed so that the telescopic device 84 retracts the constriction element 82 to the position shown in FIG. 189A, whereby the intestine 19 is released and the passageway of the intestines 4 is open.

Alternatively, the mechanical operation means may include a subcutaneously implanted actuator operatively connected to clamping element 82, wherein the actuator is manually operated by the patient, as shown in FIG. 189C. Thus, the motor 83 is replaced by a spring 84a acting to keep the telescopic device 84 expanded to force the clamping element 82 against the intestine 19. The actuator includes a lever mechanism 83a that is operatively connected to the telescopic device 84. The patient may push through the skin the lever mechanism 83a to pull the telescopic device 84 against the action of the spring 84a to the retracted position of the telescopic device 84, as indicated in phantom lines. When the patient releases the lever mechanism 83a, the spring 84a expands the telescopic device 84, whereby clamping element 82 is forced back against the intestine 19.

The mechanical operation means, as described above in connection with FIGS. 189A, 189B and 189C, may also be implemented in the embodiments according to FIGS. 163A-172C and 177A-180.

FIG. 190 illustrates the pump 11 of the embodiment of FIGS. 168A and 168B applied on the intestines of a stoma patient, wherein the constriction elements 15A, 15B of the constriction device 12 constrict the intestines 19 and the electrodes 16 are energized to close the passageway of the intestines 4. A control device includes an external control unit in the form of a wireless remote control 85A, and an implanted internal control unit 86, which may include a microprocessor, for controlling the pump 11. The remote control 85A is operable by the patient to control the internal control unit 86 to switch on and off the pump 11. A separate wireless energy transmitter 85B, which alternatively may be integrated with the remote control 85A, is adapted to transmit wireless energy from outside the patient's body to an implanted energy-transforming device 87 that transforms the transmitted wireless energy into electric energy. An implanted rechargeable battery 88 for powering the pump 11 and for energizing the electrodes 16 stores the electric energy produced by the energy-transforming device 87. The control unit 86, energy-transforming device 87 and battery 88 are implanted as a package in the patient's fat layer between the skin and the abdominal wall. The pump 11 may also be directly powered with the electric energy, as the energy-transforming device 87 transforms the wireless energy transmitted by the wireless energy transmitter 85B into the electric energy. The wireless energy may comprise electromagnetic waves emitted by a coil of the energy transmitter 85B, wherein a corresponding coil of the energy-transforming device 87 transforms the electromagnetic waves into a current.

An implanted sensor 89 senses a physical parameter of the patient, such as the volume of the intestinal contents in the selected portion of the intestines or the distension of or the pressure in the intestines 19. The remote control 85A is adapted to produce an indication, such as a sound signal or displayed information, in response to the sensor sensing a value of the physical parameter exceeding a threshold value, when the pump 11 is not in operation. This indication should pay attention to the patient when it is time to defecate.

FIG. 191 illustrates the pump 11 of the embodiment of FIGS. 168A and 168B applied on a colostomy patient's small intestines 19 surgically connected to the patient's anus.

A general method for controlling transmission of wireless energy to implanted energy consuming components of the apparatus of the present invention will be defined in general terms in the following.

A method is thus provided for controlling transmission of wireless energy supplied to implanted energy consuming components of an apparatus as described above. The wireless energy E is transmitted from an external source of energy located outside the patient and is received by an internal energy receiver located inside the patient, the internal energy receiver being connected to the implanted energy consuming components of the apparatus for directly or indirectly supplying received energy thereto. An energy balance is determined between the energy received by the internal energy receiver and the energy used for the operation of the implanted parts of the apparatus. The transmission of wireless energy E from the external source of energy is then controlled based on the determined energy balance.

The wireless energy may be transmitted inductively from a primary coil in the external source of energy to a secondary coil in the internal energy receiver. A change in the energy balance may be detected to control the transmission of wireless energy based on the detected energy balance change. A difference may also be detected between energy received by the internal energy receiver and energy used for the operation of the implanted parts of the apparatus, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the operation of the implanted parts of the apparatus be consumed to operate the implanted parts of the apparatus and/or stored in at least one implanted energy storage device of the apparatus.

When electrical and/or physical parameters of the implanted parts of the apparatus and/or physical parameters of the patient are determined, the energy may be transmitted for consumption and storage according to a transmission rate per time unit which is determined based on said parameters. The total amount of transmitted energy may also be determined based on said parameters.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/ or stored energy, the derivative may be determined for a monitored voltage and/or current related to the energy balance.

The transmission of wireless energy from the external source of energy may be controlled by applying to the external source of energy electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

The circuit formed by the first electric circuit and the external source of energy may have a first characteristic time period or first time constant, and when effectively varying the transmitted energy, such frequency time period may be in the range of the first characteristic time period or time constant or shorter.

The embodiments also identify general features for controlling transmission of wireless energy to implanted energy consuming components of the apparatus of the present invention. Such features of the apparatus will be defined in general terms in the following.

In its broadest sense, the apparatus comprises a control device for controlling the transmission of wireless energy from an energy-transmission device, and an implantable internal energy receiver for receiving the transmitted wireless energy, the internal energy receiver being connected to implantable energy consuming components of the apparatus for directly or indirectly supplying received energy thereto. The apparatus further comprises a determination device adapted to determine an energy balance between the energy received by the internal energy receiver and the energy used for the implantable energy consuming components of the apparatus, wherein the control device controls the transmission of wireless energy from the external energy-transmission device, based on the energy balance determined by the determination device.

Further, the apparatus of the invention may comprise any of the following features:

A primary coil in the external source of energy adapted to transmit the wireless energy inductively to a secondary coil in the internal energy receiver.

The determination device is adapted to detect a change in the energy balance, and the control device controls the transmission of wireless energy based on the detected energy balance change.

The determination device is adapted to detect a difference between energy received by the internal energy receiver and energy used for the implantable energy consuming components of the apparatus, and the control device controls the transmission of wireless energy based on the detected energy difference.

The control device controls the external energy-transmission device to decrease the amount of transmitted wireless energy if the detected energy balance change implies that the energy balance is increasing, or vice versa, wherein the decrease/increase of energy transmission corresponds to a detected change rate.

The control device controls the external energy-transmission device to decrease the amount of transmitted wireless energy if the detected energy difference implies that the received energy is greater than the used energy, or vice versa, wherein the decrease/increase of energy transmission corresponds to the magnitude of said detected energy difference.

The energy used for implanted parts of the apparatus is consumed to operate the implanted parts, and/or stored in at least one energy storage device of the apparatus.

Where electrical and/or physical parameters of the apparatus and/or physical parameters of the patient are determined, the energy-transmission device transmits the energy for consumption and storage according to a transmission rate per time unit which is determined by the determination device based on said parameters. The determination device also determines the total amount of transmitted energy based on said parameters.

When a difference is detected between the total amount of energy received by the internal energy receiver and the total amount of consumed and/or stored energy, and the detected difference is related to the integral over time of at least one measured electrical parameter related to the energy balance, the determination device determines the integral for a monitored voltage and/or current related to the energy balance.

When the derivative is determined over time of a measured electrical parameter related to the amount of consumed and/or stored energy, the determination device determines the derivative for a monitored voltage and/or current related to the energy balance.

The energy-transmission device comprises a coil placed externally to the human body, and an electric circuit is provided to power the external coil with electrical pulses to transmit the wireless energy. The electrical pulses have leading and trailing edges, and the electric circuit is adapted to vary first time intervals between successive leading and trailing edges and/or second time intervals between successive trailing and leading edges of the electrical pulses to vary the power of the transmitted wireless energy. As a result, the energy receiver receiving the transmitted wireless energy has a varied power.

The electric circuit is adapted to deliver the electrical pulses to remain unchanged except varying the first and/or second time intervals.

The electric circuit has a time constant and is adapted to vary the first and second time intervals only in the range of the first time constant, so that when the lengths of the first and/or second time intervals are varied, the transmitted power over the coil is varied.

The electric circuit is adapted to deliver the electrical pulses to be varied by only varying the lengths of first time intervals between successive leading and trailing edges of the electrical pulses.

The electric circuit is adapted to supplying a train of two or more electrical pulses in a row, said train having a first electrical pulse at the start of the pulse train and having a second electrical pulse at the end of the pulse train, and the lengths of the second time intervals between successive trailing edge of the second electrical pulse in a first pulse train and leading edge of the first electrical pulse of a second pulse train are varied by the first electronic circuit.

The electric circuit is adapted to provide the electrical pulses as pulses having a substantially constant height and/or amplitude and/or intensity and/or voltage and/or current and/or frequency.

The electric circuit has a time constant, and is adapted to vary the first and second time intervals only in the range of the first time constant, so that when the lengths of the first and/or second time intervals are varied, the transmitted power over the first coil are varied.

The electric circuit is adapted to provide the electrical pulses varying the lengths of the first and/or the second time intervals only within a range that includes the first time constant or that is located relatively close to the first time constant, compared to the magnitude of the first time constant.

FIG. 192a shows a system, wherein the reservoir 140 is formed by a plurality of bent portions of human intestine 70, with laterally adjacent sections thereof being cut open along their mutual contact line and the resulting upper halves and lower halves thereof being interconnected so as to form walls of a reservoir 140. The interconnection can advantageously be made with staplers, possibly including bonding with a biocompatible glue, but sewing is likewise an option.

At the exit of the reservoir 140, cooperating exit valves 61, 62, 63 are provided along a non-modified terminate section 80 of the patient's natural intestine 70. The terminate section 80 exits the patient's abdominal wall 101 through a surgically created stomy 170. The valves 61, 62, 63 each comprise an electrical stimulation device adapted to electrically stimulate muscle or neural tissue of the intestine 70 so as to cause at least partial contraction of the intestine. Electrical stimulation is achieved by applying electrical pulses to the intestine section 80. Each of the valves 61, 62, 63 further comprises at least one constriction device. As shown in FIG. 192a, the constriction devices of the valves 61, 62, 63 only partly constrict the patient's intestine 70, whereas the electrical stimulation devices of the valves are adapted to further constrict the respective sections so that flow through the terminate section is completely prevented. In FIG. 192a the electrical stimulation device of the valve 62 completely constricts this respective section of the patient's intestine. Closing is preferably achieved by stimulating the different sections in a wave-like manner in a direction opposite to the natural intestine contents flow. Since the electrical stimulation always occurs for a short time period on each section of the intestine, the valves 61, 62, 63 allow for gentle constriction of the intestine's terminate section 80 at the exit of the reservoir, so that the exit is normally kept closed.

Instead of the electrical stimulation devices combined with the constriction devices, the valve at the exit of the reservoir 140 may be formed only by one or possibly more constriction devices.

In the situation shown in FIG. 192a, in which the valves 61, 62, 63 close the exit of the reservoir 140, an entry valve in the form of a cuff 194 at the entrance of the reservoir 140 is open to allow intestinal contents to flow into the reservoir 140. In this embodiment, the cuff 194 is a hydraulic device which is connected to a hydraulic reservoir 195 supplying the cuff 194 with hydraulic fluid when the entry valve is to be closed. The pump and control for filling and emptying the hydraulic reservoir 195 are not specifically shown and are synchronized with the functions of the other valves of the system.

When the reservoir 140 is to be emptied, the valves 61, 62, 63 are opened to release the patient's intestine 70 at the exit of the reservoir as shown in FIG. 192b. At the same time, the cuff 194 is supplied with hydraulic fluid so as to completely constrict the intestine 70 at the entrance of the reservoir 140. In this manner, the reservoir 140 can be emptied without additional intestinal contents flowing into the reservoir 140. Advantageously, the valves 61, 62, 63 may support emptying of the reservoir 140 constricting the different sections of the terminate section 80 in a wave-like manner in the direction towards the stomy 170. Alternatively, an exit valve may be provided adapted to be arranged downstream from the reservoir 140 so as to receive a conduit inserted from outside the patient's body into the patient's intestine, thereby mechanically urging the exit valve to open when emptying of the reservoir 140 is desired. Such conduit provides a flow passage to an external collecting device comprising a suction pump adapted to empty the reservoir.

In the following, different embodiments of the system for emptying the reservoir 140 are described.

As shown in FIG. 193A, the reservoir 140 may be emptied by means of stimulation devices 160 which are adapted to electrically stimulate muscle or neural tissue of the reservoir so as to cause at least partial contraction of the reservoir 140. This is a very gentle way of constricting the tissue. A second set of stimulation devices 161 is arranged at the opposite side of the reservoir 140 as shown in FIG. 101b. In this embodiment, the stimulation devices 160, 161 are thus arranged substantially in two planes at opposite sides of the reservoir 140. The stimulation devices 160, 161 preferably comprise at least one electrode adapted to apply electric pulses to the reservoir 140. The stimulation devices 160, 161 have a longitudinal shape so as to span over the reservoir 140 when arranged side by side as shown in FIG. 101a. The overall spanned area would typically be larger than 10 cm×10 cm in plan view.

As shown in FIG. 193A, the stimulation devices 160 have a longitudinal or rod-like shape so as to substantially cover the width of the reservoir 140. They may each comprise one longitudinal electrode, or they may each comprise several electrodes that are arranged in series on each stimulation device 160 and can preferably be controlled individually. In another embodiment, the stimulation devices 160 may be plate-like members having a larger width than those shown in the embodiment of FIG. 193A, resulting in a decreased number of stimulation devices. Furthermore, instead of arranging the stimulation devices separately side by side, they may also be combined in one integral unit, such as a plate, on one or each opposing side of the reservoir. In case that the stimulation device or devices have an enlarged width, a plurality of electrodes may be arranged in parallel on the stimulation devices. The plate-like or rod-like stimulation devices may be embedded in a flexible web to facilitate implantation and relative fixation of adjacent stimulation devices.

In another preferred embodiment, the stimulation devices 160, 161 are embedded in surgically created folds or invaginations 141 in the intestinal wall of the reservoir 140, as shown in FIGS. 194A, 194B. By providing invaginations 141 in the reservoir 140, the stimulation devices 160, 161 are substantially surrounded by tissue of the reservoir 140 and thus contact surface is increased. Stimulation of the reservoir 140 can thus be improved. Furthermore, by this way of implantation, surrounding tissue in the abdominal cavity is not contacted by the electrodes and thus not influenced by the stimulation. Fixation of the stimulation devices 160, 161 is also improved, thus enabling the stimulation devices 160, 161 to be precisely located over long time. In this embodiment, the stimulation devices 160, 161 necessarily follow the movement of the wall of the reservoir 140, in particular the stimulation devices 160, 161 approach while intestinal contents are released from the reservoir 140.

The stimulation devices 160, 161 are specifically adapted to stimulate, over time, the different portions of the reservoir 140 in a consecutive or wave-like manner in a direction towards the exit valve 61, 62, 63 or stomy 170 (or anus) to cause the reservoir 140 to be emptied. Thus, different portions of the reservoir 140 can be constricted by stimulation at different times in any predetermined stimulation pattern. This allows for adapting the arrangement of the stimulation devices 160, 161 and their mode of operation to the individual form of the reservoir 140. This functionality is further enhanced where each of the stimulation devices carries 160, 161 a plurality of electrodes that are controlled individually or in groups.

Emptying of the reservoir 140 can be activated by the patient pushing a subcutaneously arranged, manually operable actuator 99 in the abdominal wall 101 connected to an energy storage means and/or controller 150. The stimulation devices 160, 161 are controlled and/or supplied with energy by means of the energy storage means and/or controller 150.

When the cuff 194 is closed during emptying the reservoir, all stimulation devices 160, 161 may stimulate the reservoir 140 at the same time or, as mentioned before, in a consecutive or wave-like manner, to cause the entire reservoir to constrict. Since the cuff 194 is closed, the content of the reservoir 140 is urged to flow in the direction towards the stomy 170 (or anus).

Alternatively, or even in addition to the electrical stimulation device 160, 161, a constriction device may be provided implanted in the patient's body for constricting the reservoir 140 mechanically or hydraulically from outside the intestinal wall of the reservoir 140. Examples of mechanical and hydraulic constriction devices will be described in more detail hereinafter in relation to FIGS. 195A, 195B and FIGS. 196A, 196B. Where the stimulation device is combined with the constriction device, the stimulation device and the constriction device preferably act on the portion of the same reservoir 140. In that case, it is advantageous if the constriction device constricts the portion of the reservoir 140 only partly, in order not to damage the intestine. Further constriction is achieved by simultaneous electrical stimulation.

In addition, when constriction of the reservoir 140 caused by the constriction device is released, the stimulation device may, if accordingly adapted, be used to pump intestinal contents towards the exit of the reservoir 140 by, over time, stimulating different portions of the intestinal wall of the reservoir 140 in a wave like manner in a direction of natural intestinal contents flow. In this way, filling of the reservoir 140 is supported, since intestinal contents do not remain in the area of the entrance of the reservoir 140 but are transported in the direction towards the exit.

FIGS. 195A, 195B show an embodiment comprising mechanically acting members in the form of rollers 180, 181 for emptying the reservoir 140. The rollers 180, 181 are arranged on opposite sides of the reservoir 140 and have a length spanning the entire width of the reservoir 140. They are each guided by two tracks 182a, 183a and 182b, 183b, respectively, and are driven by a motor integrated in the rollers (not shown) which preferably comprises a servo drive. The servo drive reduces the force required to move the rollers 180, 181. The tracks 182a, 183a, 182b, 183b are arranged in pairs on opposite sides of the reservoir 140. As shown in FIG. 195B, the tracks have bent end portions 184a, 184b directed away from the reservoir 140 so as to allow the rollers 180, 181 to assume an inactive position in which they do not constrict the reservoir 140. Upon emptying, the rollers 180, 181 are driven along the tracks in the direction of the arrows, thereby coming closer to each other and constricting the reservoir 140. The rollers are further driven along the length of the reservoir in their proximate position guided by the tracks and mechanically squeeze intestinal contents in the direction towards the exit of the reservoir 140. When the rollers 180, 181 have reached their final position and the reservoir 140 is emptied, they are returned to their initial inactive position at the end portions 184a, 184b of the tracks. Instead of rollers on each side of the reservoir 140, it can be sufficient to provide one or more rollers only on one side of the reservoir 140 and place a counteracting plate on the respective other side of the reservoir 140.

In a further embodiment shown in FIGS. 196A, 196A, emptying of the reservoir 140 is carried out by means of a hydraulically acting member 190 acting on the intestinal wall of the reservoir 140 from the outside thereof. The hydraulically acting member 190 is connected to an artificial reservoir 193 supplying the hydraulically acting member 190 with hydraulic fluid and having a sufficient size to contain hydraulic fluid corresponding to the volume of the reservoir 140. The artificial reservoir 193 has a flexible wall to allow the hydraulic fluid to be drawn off from the artificial reservoir 193. The hydraulically acting member 190 is of flexible material and may be tube-like or bag-like so as to accommodate the reservoir 140 therein. As shown in FIG. 104*b*, the reservoir 140 is surrounded by the hydraulically acting member 190. The hydraulically acting member 190 is divided into a plurality of chambers, wherein a first chamber 191 and a last chamber 194 are connected to the artificial reservoir 193 by hydraulic pipes. The chambers are interconnected by connections 192, which may be simple holes acting as a throttle or which may include a valve.

Upon activating emptying of the reservoir 140 by pushing the button 99, hydraulic fluid is supplied to the first chamber 191. The subsequent chambers are supplied with hydraulic fluid through connections 192 thus causing the hydraulically acting member 190 to be filled from the first chamber 191 to the last chamber 194. The filling of the chambers occurs sequentially, with the next following chamber starting to fill before the foregoing chamber is filled completely. In this manner, intestinal contents are hydraulically squeezed out in the direction towards the exit of the reservoir 140. When the hydraulically acting member 190 is completely filled with hydraulic fluid, the reservoir 140 completely constricted. The hydraulic fluid is then retracted from the hydraulically acting member 190 to the artificial reservoir 193 using negative pressure so as to allow the reservoir 140 to fill up again.

In another embodiment, each chamber may have a separate connection to the artificial reservoir 193 in order to be able to be filled individually. The reservoir 140 may be emptied by consecutively filling two adjacent chambers, i.e. filling the first and second chamber, then emptying the first chamber while filling the third chamber, then emptying the second chamber while filling the fourth chamber, and so forth. In this manner intestinal contents are squeezed towards the exit of the reservoir 140.

Alternatively, instead of applying a negative pressure for evacuating the chambers, at least one valve, preferably two valves, may be provided (not shown) between the hydraulically acting member 190 and the artificial reservoir 193 which, when in an appropriate operational position, allows hydraulic fluid to passively flow from the chambers back into the artificial reservoir 193 when the reservoir 140 fills with intestinal contents and which, when in an appropriate other position, allows hydraulic fluid to be pumped from the artificial reservoir into the chambers.

As in all embodiments, emptying of the reservoir 140 is coordinated with the opening and closing of the entry and exit valves 194, 61, 62, 63.

FIG. 197*a* shows a reservoir 140 formed from human intestine 70. A plurality of bent portions of the human's intestine 70 is cut open along the mutual contact lines of laterally adjacent sections thereof. The resulting upper halves and lower halves are interconnected so as to form the walls of the intestinal reservoir 140. The interconnection can advantageously be made with staplers, possibly including bonding with a biocompatible glue, but sewing is likewise an option.

At the exit of the intestinal reservoir 140, an exit valve comprising a plurality of valve sections 61, 62, 63 is provided along and encloses a non-modified terminate section 80 of the patient's intestine. The non-modified terminate section 80 is passed through the patient's abdominal wall 101 and forms a surgically created stoma 170. The non-modified terminate section 80 could like-wise lead to the patient's rectum or anus. The valve sections 61, 62, 63 each comprise an electrical stimulation device adapted to electrically stimulate muscle or neutral tissue of the intestine's terminate section 80 so as to cause at least partial contraction of the terminate section. Electrical stimulation is achieved by applying electrical pulses to the terminate section 80 by means of electrodes (not shown). Each of the valve sections 61, 62, 63 further comprises at least one constriction device.

In FIG. 197A the constriction devices of all three valve sections 61, 62, 63 are activated. As can be seen, the constriction devices 61, 62, 63 only partly constrict the intestine's terminate section 80 so that blood circulation in the tissue of the intestinal wall is not negatively affected thereby. The electrical stimulation devices of the valve sections 61, 62, 63 are adapted to further constrict the terminate section 80 so that flow through the terminate section 80 is completely prevented. However, only one electrical stimulation device is activated at a time. In the situation shown in FIG. 197A, the central valve section 62 is currently activated so as to stimulate and thereby completely constrict the corresponding section of the intestine's terminate section 80. While instead of the three stimulation devices shown, a single stimulation device would be sufficient for opening and closing the intestine, the arrangement of the plurality of stimulation devices allows to stimulate different sections of the intestine's terminate section 80 over time. The function of the three stimulation devices may also be combined in one integral unit. Since the electrical stimulation in each valve section 61, 62, 63 always occurs for a short time period only, the respective other, non-stimulated sections of the intestine's terminate section 80 have time to recover from a previous constriction so that sufficient blood flow within the intestinal wall is ensured. All in all, the valve sections 61, 62, 63 allow for gentle constriction of the intestine's terminate section 80 at the exit of the reservoir when keeping the exit normally closed. Most preferably, closing is achieved by stimulating different sections of the intestine's terminate section 80 in a wave-like manner in a direction opposite to the natural intestine contents flow.

However, instead of combining electrical stimulation devices with a constriction device, the valve at the exit of the reservoir 140 may only be formed by one or a plurality of constriction devices. The constriction device is preferably of the hydraulic type, such as in the form of pressure cuffs, but may also be of the mechanical type. The constriction device is not described here in more detail, and may correspond to the entry valve 194 provided at the entry of the reservoir 140. The entry valve 194 here has the form of a hydraulic cuff. While the valve sections 61, 62, 63 of the exit valve are provided to normally close the exit of the intestinal reservoir 140 in order to keep intestinal contents inside the reservoir 140, the entry valve 194 is normally open to allow intestinal contents to flow into the reservoir 140.

The cuff of the entry valve 194 can be filled with a hydraulic fluid from an artificial hydraulic reservoir 195 so as to completely constrict the intestine 70 in front of the reservoir 140. This way, backflow of intestinal contents into the intestine 70 may effectively be prevented, when emptying of the reservoir is desired. At the same time, the valve sections 61, 62, 63 of the exit valve are opened to allow emptying of the intestinal reservoir 140. This is shown in FIG. 197B. As can be seen, the partial constriction of the terminal section 80 by means of the constriction devices has been released. Also, electrical stimulation pulses are no longer applied. However, it can be advantageous to support the emptying process by constricting the different sections of the intestine's terminate section 80 in a wave-like manner in a direction towards the stoma 170 by means of the valve sections 61, 62, 63 of the exit valve.

In the following, different embodiments of a system for emptying the intestinal reservoir 140 are described.

As shown in FIG. 198A, the reservoir 140 may be emptied by means of an electrical stimulation type pump comprising electrical stimulation devices 160 which are adapted to electrically stimulate muscle or neural tissue of the intestinal reservoir 140 so as to cause at least partial contraction of the reservoir 140. This is a very gentle way of constricting the tissue of the intestinal reservoir 140. A second set of electrical stimulation devices 161 is arranged on the opposite side of the reservoir 140, as can be seen in FIG. 198B. Thus, the stimulation devices 160, 161 are arranged substantially in two planes at opposite sides of the reservoir 140. The stimulation devices 160, 161 have a longitudinal shape so as to span over the reservoir 140 when arranged side by side as shown in FIG. 198A.

As shown in FIG. 198A, the stimulation devices 160, 161 each have a longitudinal or rod-like shape substantially spanning the entire width of the reservoir 140. The length is 10 cm or longer, depending on the size of the intestinal reservoir. The overall spanned area would typically be larger than 10 cm×10 cm in plan view. The stimulation devices 160, 161 may each comprise a row of electrodes arranged along the length thereof and adapted to apply electric pulses to the intestinal wall of the reservoir 140. Alternatively, each stimulation device may substantially consist of only one longitudinal electrode. Preferably, the electrodes can be controlled individually.

In another embodiment, not shown, the stimulation devices 160, 161 may form plate-like members having a larger width than those shown in FIG. 198A, resulting in a decreased number of stimulation devices. In an even further embodiment, likewise not shown, instead of arranging the stimulation devices separately side by side, they may be combined in an integral unit, such as a plate, on one side or on opposing sides of the intestinal reservoir. In case that the stimulation device or devices form plate-like members with an enlarged width, a plurality of electrode rows may be arranged in parallel on the stimulation devices. The plate-like or rod-like stimulation devices may be embedded in a flexible web (not shown) to facilitate implantation and relative fixation of adjacent stimulation devices.

Emptying of the intestinal reservoir 140 can be activated by the patient pressing a manually operable actuator 99 subcutaneously implanted in the patient's abdominal wall 101 in the form of a switch. The actuator 99 is connected to a combined energy storage means and controller device 150. The stimulation devices 160, 161 are controlled and supplied with energy via the energy storage means and controller device 150. The device is connected to the electrical stimulation devices 160, 161 via individual lines.

Under the control of the device 150, different portions of the intestinal wall of the reservoir 140 are stimulated at different times in a predetermined stimulation pattern by means of the electrical stimulation devices 160, 161 and, thus, different sections of the intestinal reservoir 140 are constricted by such stimulation. The stimulation devices 160, 161 are specifically adapted to stimulate, over time, respectively adjacent portions of the intestinal wall of the reservoir 140 in a consecutive or wave-like manner in a direction towards the stoma 170 (or rectum/anus) to cause the reservoir 140 to be emptied. This structure allows for adapting the arrangement of the stimulation devices 160, 161 and their mode of operation to the individual form of the intestinal reservoir 140. This functionality is further enhanced where each of the stimulation devices carries 160, 161 a plurality of electrodes that are controlled individually or in groups.

As stated before, the entry valve 194 is preferably closed during the emptying of the reservoir. This is particularly important in case that all stimulation devices 160, 161 are activated simultaneously so as to constrict all sections of the reservoir 140 at the same time. Since the exit valve 194 is closed, intestinal contents cannot flow back from the reservoir into the patient's intestine but are urged towards the exit of the reservoir. An entry valve is not specifically needed when the electrical stimulation devices are activated in a consecutive or wave-like manner, as mentioned before, in.

In another embodiment shown in FIG. 199A and 199B, the stimulation devices 160, 161 are specifically provided for being embedded in folds or invaginations 141 surgically created in the intestinal wall of the reservoir 140. By providing the invaginations 141 in the reservoir 140, the simulation devices 160, 161 are substantially surrounded by tissue of the reservoir 140 and, thus, contact area is increased. Stimulation of the reservoir 140 can thus be improved. Furthermore, surrounding tissue in the abdominal cavity is not contacted by the electrodes of the stimulation devices and, thus, not influenced by the stimulation process. Fixation of the stimulation devices 160, 161 is also improved, thereby ensuring that the stimulation devices 160, 161 are precisely located over long time. The stimulation devices 160, 161 necessarily follow all movements of the intestinal wall of the reservoir 140.

Alternatively, or even in addition to the electrical stimulation type pump, a constriction type pump may be implanted in the patient's body for constricting the reservoir 140 mechanically or hydraulically from outside the intestinal wall of the reservoir 140. Examples of mechanical and hydraulic constriction type pumps will be described in more detail hereinafter in relation to FIGS. 200A, 200B and FIGS. 201A, 201B. Where the stimulation type pump is combined with a constriction type pump, the two pumps preferably act on the same portion of the reservoir 140. In that case, it is advantageous if the constriction type pump constricts the respective portion of the reservoir 140 only partly, in order not to damage the intestine, whereas further constriction is achieved by simultaneous electrical stimulation of the same portion.

In addition, when constriction of the reservoir 140 caused by the constriction type pump is released, the stimulation type pump may, if accordingly adapted, be used to pump intestinal contents towards the exit of the reservoir 140 by, over time, stimulating different portions of the intestinal wall of the reservoir 140 in a wave-like manner in a direction of natural intestinal contents flow. In this way, filling of the reservoir 140 is supported, since intestinal contents do not remain in the area of the entrance of the reservoir 140 but are transported in the direction towards the exit.

FIGS. 200A, 200B show an embodiment of a mechanical type pump comprising mechanically acting members in the form of rollers 180, 181 for emptying the reservoir 140. The rollers 180, 181 are arranged on opposite sides of the reservoir 140 and have a length spanning the entire width of the reservoir 140, i.e. 10 cm or more. The rollers are each guided by two tracks 182*a*, 183*a* and 182*b*, 183*b*, respectively, and are driven by a motor integrated in the rollers (not shown) which preferably comprises a servo drive. The servo drive reduces the force required to move the rollers 180, 181, so that a relatively small motor can be used in exchange for a longer emptying process. The tracks 182*a*, 183*a*, 182*b*, 183*b* are arranged in pairs on opposite sides of the reservoir 140. As can be seen from FIG. 4B, the tracks have bent end portions 184*a*, 184*b* directed away from the reservoir 140 so that the rollers 180, 181 can assume an inactive position in which they do not constrict the reservoir 140. When emptying of the reservoir is desired, the rollers 180, 181 are driven along the tracks in the direction of the arrows, thereby approaching each other and constricting the reservoir 140. When the rollers are further guided by the tracks along the length of the reservoir in their proximate position, they mechanically squeeze intestinal contents in the direction towards and out of the exit of the reservoir 140. When the rollers 180, 181 have reached their final position and the reservoir 140 is emptied, they are returned to their initial inactive position at the end portions 184*a*, 184*b* of the tracks. Instead of rollers on each side of the reservoir 140, it can be sufficient to provide one or more rollers only on one side of the reservoir 140 and place a counteracting plate on the respective opposite side of the reservoir 140.

Again, emptying of the intestinal reservoir 140 can be activated by the patient pressing the manually operable actuator 99 subcutaneously implanted in the patient's abdominal wall 101, the actuator 99 being connected to the combined energy storage means and controller device 150. Energy is supplied from the device 150 to the motor or motors inside the rollers 180, 181.

FIGS. 201A, 201B show an embodiment of a hydraulic type pump comprising a hydraulically acting member 190 adapted to act on the intestinal wall of the reservoir 140 from the outside thereof. The hydraulically acting member 190 is connected to an artificial reservoir 193 supplying the hydraulically acting member 190 with hydraulic fluid. The artificial reservoir 193 is of a size sufficiently large to accommodate hydraulic fluid in an amount corresponding to the volume of the intestinal reservoir 140. The artificial reservoir 193 has a flexible wall to allow the hydraulic fluid to be drawn off from and to be filled back into the artificial reservoir 193. The hydraulically acting member 190 is of flexible material and may be tube-like or bag-like so as to accommodate therein the intestinal reservoir 140. As shown in FIG. 201B, the reservoir 140 is surrounded by the hydraulically acting member 190. The hydraulically acting member 190 is divided into a plurality of chambers, wherein a first chamber 191 and a last chamber 194 are connected to the artificial reservoir 193 by hydraulic conduits. The chambers are interconnected via connections 192, which may be simple holes acting as a throttle or may include one or more valves that are preferably automatically controlled.

Upon activation of the system by the patient using the subcutaneous actuator 99, emptying of the intestinal reservoir 140 is started by supplying hydraulic fluid from the artificial reservoir 193 to the first chamber 191. The next following chambers are supplied with the hydraulic fluid through the connections 192, thereby causing the hydraulically acting member 190 to be filled slowly from the first chamber 191 to the last chamber 194. The filling of the chambers occurs sequentially, with the next following chamber starting to fill before the foregoing chamber is filled completely. In this manner, intestinal contents are hydraulically squeezed out in the direction towards the exit of the reservoir 140. When the hydraulically acting member 190 is completely filled with hydraulic fluid, the reservoir 140 is completely constricted. The hydraulic fluid is then withdrawn from the chambers of the hydraulically acting member 190 back into the artificial reservoir 193 using negative pressure. The intestinal reservoir 140 may then start to fill up with intestinal contents again.

Again, this process is controlled by the device 150, which is connected to the artificial reservoir 193. Connected to or integrally formed with the artificial reservoir 193 is an electrically driven pump (not shown) for pumping the hydraulic fluid into and withdrawing the hydraulic fluid from the hydraulically acting member. The electrically driven pump is supplied with energy from the combined energy storage means and control device 150.

In another embodiment, each chamber of the hydraulically acting member 190 may have separate fluid connection to the artificial reservoir 193 in order to be able to be filled individually. The intestinal reservoir 140 may be emptied by consecutively filling two adjacent chambers of the hydraulically acting member 190, i.e. first filling the first and second chamber, then emptying the first chamber while filling the third chamber, then emptying the second chamber while filling the fourth chamber, and so forth. In this manner intestinal contents are squeezed towards and out of the exit of the intestinal reservoir 140.

Alternatively, instead of applying a negative pressure for evacuating the chambers, at least one valve, preferably two valves, may be provided (not shown) between the hydraulically acting member 190 and the artificial reservoir 193 which, when in an appropriate operational position, allows the hydraulic fluid to passively flow from the hydraulically acting member back into the artificial reservoir 193 when the intestinal reservoir 140 fills with intestinal contents and which, when in an appropriate other position, prevents the hydraulic fluid to flow from the hydraulically acting member back into the artificial reservoir when the intestinal reservoir is being emptied.

As in all embodiments, emptying of the reservoir 140 is coordinated with the opening and closing of the entry valve 194 and exit valves 61, 62, 63.

Energy Transmission

An energy source may be provided for supplying energy directly or indirectly to at least one energy consuming part of the system, in particular for driving the pump or the motor of the pump. Preferably, the energy source includes a battery or an accumulator, such as one or more of a rechargeable battery and a capacitor, as an energy storage means. The energy storage means is advantageously adapted for being implanted inside the patient's body, as in the case of the afore mentioned combined energy storage means and control device 150.

Energy is preferably transmitted wirelessly. Thus, where the energy source is provided for supplying energy directly or indirectly to at least one energy consuming part of the system, the energy source may comprise a wireless energy transmitter adapted to wirelessly transmit energy from outside the patient's body to the at least one energy consuming part. Alternatively, where the energy source includes a battery or an accumulator, in particular one which is implanted in the patient's body, the energy source may comprise a wireless energy transmitter adapted to wirelessly transmit energy from outside the patient's body to the energy storage means.

Where energy is not transmitted wirelessly, galvanic coupling elements may be provided at least between the accumulator and the energy consuming part, in particular the motor, for transmitting energy to the motor in contacting fashion.

Preferably, in order to reduce the number of parts and possibly increase the system's efficiency, the energy consuming part, in particular the motor, can be adapted to directly transform the wirelessly transmitted energy from the accumulator into kinetic energy. In the alternative, the energy consuming part will have to comprise a transforming device for transforming the wirelessly transmitted energy from the accumulator into electric energy.

Similarly, the system preferably comprises an implantable energy transforming device for transforming the wirelessly transmitted energy from outside the patient's body into energy to be stored in the accumulator of the implanted system and further comprises a wireless energy transmitter adapted to wirelessly transmit energy from outside the patient's body to said implantable energy transforming device.

It is further preferred to set up the system such that the energy consuming part is driven with the electric energy, as said energy transforming device transforms the wireless energy into the electric energy.

The energy transmitter can be adapted to generate an electromagnetic field, a magnetic field or an electrical field. The wireless energy may be transmitted by the energy transmission device by at least one wireless signal. More specifically, the energy transmitter may be adapted to transmit the energy by at least one wireless energy signal, which may comprise an electromagnetic wave signal, including at least one of an infrared light signal, a visible light signal, an ultra violet light signal, a laser signal, a microwave signal, an X-ray radiation signal, and a gamma radiation signal. Also, the wireless energy signal may comprise a sound or ultrasound wave signal. Furthermore, the wireless energy signal may comprise a digital or analog signal or a combination thereof.

Primary Energy Source

A primary energy source may be provided for charging the energy storage means with energy from outside the patient's body. The primary energy source is preferably adapted to being mounted on the patient's body.

Energy Transmission Feedback

A feedback subsystem, which can make part of a control device described subsequently, can advantageously be provided to wirelessly send feedback information related to the energy to be stored in the energy storage means from inside the human body to the outside thereof. The feedback information is then used for adjusting the amount of wireless energy transmitted by the energy transmitter. Such feedback information may relate to an energy balance which is defined as the balance between an amount of wireless energy received inside the human body and an amount of energy consumed by the at least one energy consuming part. Alternatively, the feedback information may relate to an energy balance which is defined as the balance between a rate of wireless energy received inside the human body and a rate of energy consumed by an energy consuming part.

Control Unit

It is advantageous to provide a control unit adapted to directly or indirectly control one or more elements of the system, such as for controlling opening of the exit valve and/or closing of the entry valve in combination with the pump, in particular in a manner such that when one of the two valves is closed, the respective other valve is open, and vice versa.

At least part of the control unit may be adapted to be implantable in the patient's body. For instance, as described before, a manually operable actuator 99 in the form of a switch may be provided for activating the control unit, the switch preferably being arranged for subcutaneous implantation so as to be operable from outside the patient's body. Alternatively, the control unit may comprise a first part adapted for implantation in the patient's body and a second part adapted to cooperate with the first part from outside the patient's body. In this case, the control unit can be adapted to transmit data from the external second part of the control unit to the implanted first part of the control unit in the same manner as energy is transmitted by said wireless energy transmitter from outside the patient's body to said implantable energy transforming device.

That is, the second part of the control unit may be adapted to wirelessly transmit a control signal to the implantable first part of the control unit for controlling the at least one energy consuming part from outside the patient's body. Also, the implantable first part of the control unit may be programmable via the second part of the control unit. Furthermore, the implantable first part of the control unit may be adapted to transmit a feedback signal to the second part of the control unit.

Sensor

Furthermore, a physical parameter sensor adapted to directly or indirectly sense a physical parameter of the patient can be provided. The physical parameter sensor may be adapted to sense at least one of the following physical parameters of the patient: a pressure within the artificial intestine section, a pressure within the patient's natural intestine, an expansion of the artificial intestine section, a distension of an intestinal wall of the patient's natural intestine, a movement of the patient's intestinal wall.

Similarly, a functional parameter sensor adapted to directly or indirectly sense a functional parameter of the system can be provided, wherein the functional parameter sensor may be adapted to sense at least one of the following functional parameters of the system: a pressure against a part of the system such as the artificial intestine section, a distension of a part of the system such as a wall of the artificial intestine section, an electrical parameter such as voltage, current or energy balance, a position or movement of a movable part of the system.

Preferably, an indicator is coupled to the sensor or sensors, the indicator being adapted to provide a signal when a sensor senses a value for the parameter beyond a predetermined threshold value. The sensor signal may comprise at least one of the following types of signals: a sound signal, a visual signal.

Method of Treatment (Implantation)

The invention does not only relate to the system described above, but also to a method of implanting the system or at least components thereof within the patient's body.

As mentioned before, the reservoir of the system is made from the patient's intestine. A respective surgical method of treating the patient therefore comprises the steps of:

cutting the patient's skin and abdominal wall, dissecting an area of the patient's intestine, cutting the patient's intestine along a mutual contact line of laterally adjacent sections of a bent portion thereof and connecting by suturing and/or stapling the resulting upper and lower halves of the intestine so as to form an intestinal wall of a reservoir, implanting at least a pump as part of a flow control device so as to permanently reside inside the patient's body and to act on said intestinal wall so as to reduce the reservoir's volume in order to empty intestinal contents from the reservoir to outside the patient's body, and thereafter, permanently closing the abdominal wall and skin.

A respective laparoscopic surgical method of treating the patient comprises the steps of:

making a small opening in the patient's skin and abdominal wall, introducing a needle in the abdominal cavity, inflating the abdominal cavity with gas,
inserting at least one trocar into the cavity,
introducing a camera through the trocar,
inserting at least one dissecting instrument preferably through a second trocar,
dissecting an area of the intestine,
cutting the patient's intestine along a mutual contact line of laterally adjacent sections of a bent portion thereof and connecting by suturing and/or stapling the resulting upper and lower halves of the intestine so as to form an intestinal wall of a reservoir,
implanting at least a pump as part of a flow control device so as to permanently reside inside the patient's body and to act on said intestinal wall so as to reduce the reservoir's volume in order to empty intestinal contents from the reservoir to outside the patient's body,
extracting the instruments, camera and trocar, and in relation thereto
suturing, if necessary, the abdominal wall and permanently closing the skin.

As also mentioned before, the system may be surgically connected to a surgically created stoma or to the patient's rectum or anus or to tissue adjacent the patient's anus. This would require, where a stoma is involved, the following additional steps:

cutting the patient's skin and abdominal wall so as to create an opening for an intestinal stoma,
dissecting the area of the opening,
dividing the intestine downstream of the reservoir so as to maintain an upstream natural intestine section still connected to the reservoir with a cross-sectional opening at the downstream end thereof,
dissecting the mesentery of the upstream natural intestine section in the area of the cross-sectional opening at the downstream end thereof to prepare for creating the intestinal stoma,
advancing the upstream natural intestine section through the abdominal wall and skin and
suturing the upstream natural intestine section in the area of the cross-sectional opening to the skin with the intestinal mucosa turned inside out, thereby achieving the intestinal stoma.

Where the system may be surgically connected to a the patient's anus or to tissue adjacent the patient's anus, this would require the following additional steps:

dividing the intestine so as to create an upstream natural intestine section having a cross-sectional opening at the downstream end thereof and a downstream natural intestine section leading to the patient's anus,
dissecting the area of the patient's anus and surgically separating the downstream natural intestine section from the patient's anus, whereas the steps of dividing the intestine and separating the intestine section leading to the patient's anus can alternatively be carried out in reversed order,
dissecting the mesentery of the upstream natural intestine section in the area of the cross-sectional opening at the downstream end thereof to prepare for connecting the upstream natural intestine section to the patient's anus or tissue adjacent the patient's anus,
advancing the downstream end of the upstream natural intestine section through the patient's anus, and
suturing the cross-sectional opening of the upstream natural intestine section to the patient's anus or tissue adjacent the patient's anus.

In context with the implantation of an electrical stimulation type pump described previously, the method may further involve the step of implanting at least one electrical stimulation device in the vicinity of the intestinal reservoir so as to allow for at least partial contraction of the intestinal reservoir by means of electrical stimulation of muscle or neural tissue with the aid of the electrical stimulation device. Preferably, electric pulses are applied to the intestine section by means of the stimulation device.

According to a preferred embodiment, as also mentioned before, folds are surgically created from the intestinal wall of the reservoir and components of the electrical stimulation type pump are implanted in the folds. The open side of the folds is preferably closed by sewing, bonding and/or stapling the tissue of the intestinal wall together so as to form bags in which the electrical stimulation devices of the pump are placed either after or preferably before the closing of the folds. While the electrical stimulation devices are preferably longitudinal, they may likewise have any other shape, whereby the folds or bags are surgically formed from the intestinal wall so as to accommodate therein the individual stimulation devices.

Preferably, a plurality of electrical stimulation devices is implanted side by side along the intestinal wall of the reservoir so as to be able to stimulate different portions of the intestinal wall over time. More specifically, the stimulation devices may be implanted to pump intestinal contents along the intestinal reservoir by, over time, stimulating the different portions of the intestinal wall consecutively or, preferably, in a wave like manner.

Alternatively, or in addition to the electrical stimulation type pump, a constriction type pump, such as a mechanical pump or a hydraulic pump, may be implanted so as to allow for at least partial mechanical or hydraulic constriction of the intestinal reservoir by means of the constriction type pump. The constriction type pump may advantageously be combined with the electrical stimulation type pump so as to allow for adding further constriction of the intestinal reservoir by stimulating sections of the intestinal reservoir with electric pulses. In particular, this may be used for pumping intestinal contents along the intestinal reservoir by, over time, stimulating the different portions of the intestine section in a wavelike manner, when constriction of the intestine section caused by the constriction device is released.

Exit and Entry Valve

Where an exit valve is provided in addition to the at least one pump for preventing intestinal contents to exit the intestinal reservoir unintentionally, the method of implantation preferably comprises the additional step of placing the exit valve outside and adjacent to a section of the intestine downstream of the intestinal reservoir so as to allow acting on said intestine section from the outside thereof by means of the exit valve.

Similarly, where an entry valve is provided for preventing backflow of intestinal contents from the reservoir when the intestinal reservoir is being emptied, the method of implantation may further comprise the additional step of placing the entry valve outside and adjacent to a section of the intestine upstream of the intestinal reservoir so as to allow acting on said intestine section from the outside thereof by means of the entry valve.

Sleeve

FIG. 202 schematically shows a body 100 of a patient with a first tissue connector 1 connected to the end of the patient's large bowel 50 and a second tissue connector 1*a* interconnecting two pieces of the patient's aorta 60. The tissue connector 1 may either connect the large bowel 50 to the patient's anus or to an artificial anus which may include an excrements collecting container. The tissue connector 1*a* may include between its two ends a heart valve, a blood pump, a drug delivery device or the like.

The tissue connectors 1 and 1*a* shown in FIG. 202 represent only a few of many different possible locations and applications of the tissue connector within the human's or, alternatively, an animal's body. Further examples of possible applications have already been outlined further above.

FIGS. 203*a* and 203*b* show a first embodiment of the tissue connector 1 in the state of mounting the tissue connector to a tubular part of living tissue 70. The tissue connector 1 comprises a conduit 2 with a first end 3 and a second end 4. In FIG. 203*a*, the first end 3 of the conduit 2 has already been inserted into an end portion of living tissue 70. The inner cross section of the conduit 2 is selected to approximately match the inner cross section of the tubular living tissue 70 so as not to obstruct any flow of material. The thickness of the wall 5 of the conduit, which is typically circular, is chosen to provide sufficient strength so that it does not collapse under the forces that will act upon the conduit during use, while providing sufficient flexibility where needed. On the other hand, the thickness should not be chosen too large since the living tissue will have to be stretched over the outer surface 6 of the conduit 2 without damage and without excessively affecting blood circulation within the end portion 71 of the living tissue 70.

The wall 5 of conduit 2 is tapered towards its leading edge 7. In addition, the leading edge 7 is rounded. These two measures prevent damage to the living tissue 70 when the conduit 2 is inserted into the end portion 71 of the living tissue 70.

The second end 4 may serve and be adapted to be connected to an implantable medical device, an implantable reservoir, an implantable pump, an implantable motor or a combination of the afore mentioned items (generally designated with 200). It may also be connected to any other implantable device 200. The implantable device 200 may even form a part of the tissue connector 1, either integrally or attached thereto.

The implantable device 200 may also be a medical device replacing one or more of the patient's organs, such as an artificial urine bladder, a fecal excrement's collecting container, an artificial urethra, an artificial heart, an artificial esophagus, an artificial trachea or the like. Alternatively, the second end 4 of the conduit 2 may be connected to a biological implant obtained from a third party's body, such as a urine bladder, an intestine, a urethra, a ureter, a kidney, a bowel, a heart, an esophagus, a trachea, a blood vessel or the like.

The device 200 may also comprise a flow restrictor for partial or complete restriction of flow through the conduit. This can be suitable e.g. in the case where the tissue connector is located at the end of the patient's large bowel.

The device 200 may also be placed between the tissue connector 1 and a second tissue connector 1 b with conduit 2*b*, as is indicated in FIG. 203*a* by dotted lines. This arrangement is practical where the device 200 has to be placed at a location within one of the patient's organs, such as in a blood vessel, in which case the blood vessel would be divided and the device 200 placed between the two tissue connectors 1 and 1*b* connected to the respective free ends of the divided blood vessel. As an example, the device 200 could include a flow restrictor, such as an artificial heart valve, or a drug delivery reservoir.

Apart from the conduit 2 and the optional device 200, the tissue connector 1 of the embodiment shown in FIG. 203*a* has a flexible sleeve 10 axially extending and closely fitted around a part of the outer surface 6 of the conduit 2. The flexible sleeve 10 may be delivered separately from the conduit 2 and placed over the conduit's outer surface 6 shortly before implantation into the patient's body. However, it is preferred to provide the conduit 2 with the flexible sleeve 10 as a unitary item, the flexible sleeve 10 preferably fixed to the outer surface 6 by means of bonding, welding and/or clamping. In the case of bonding, it can be advisable to pretreat the outer surface 6 e.g. with a primer, depending upon the material combination to be bonded together.

In FIG. 203*a*, the flexible sleeve 10 is rolled upon itself and can be unrolled over the portion 71 of living tissue 70 so as to cover, seal and protect that portion 71 on the first end 3 of the conduit 2, as is shown in FIG. 203*b*. The tissue portion 71 and the overlapping part 11 of flexible sleeve 10 are fixed to the first end 3 of the conduit 2 by suturing threads 20 therethrough and through the wall 5 of the conduit 2, as is indicated in FIG. 203*b* by dotted lines.

The flexible sleeve 10 is a multilayer material comprising a porous ingrowth layer to allow ingrowth of living tissue. For that, it has a netlike structure. On top of the ingrowth layer 11 there is provided a support layer 12. The support layer 12 may have one or more of various functions. One possible function is to provide support to the ingrowth layer 11 so as to ease handling and/or prevent fussing of the ingrowth layer. Also, the support layer 12 may provide some tension, thereby exerting a compressive force in a radial direction so as to slightly clamp the tissue portion 71 against the outer surface 6 of the conduit 2. For that, the support layer should have an appropriate elasticity. Finally, the support layer may provide protection for the tissue portion 71.

Preferably, the support layer should be porous so that exchange between the tissue portion 71 and the surrounding area within the patient's body is possible. This is an important aspect for the ingrowth of living tissue material into the ingrowth layer 11. Expanded polytetrafluoroethylene (ePTFE) is particularly suitable, as it is flexible, inert and can be made with any desired porosity. Other biocompatible polymers, such as polyurethane and the like, are suitable as well.

FIGS. 204*a* and 204*b* show an alternative of the first embodiment of the tissue connector which differs from the connector shown in FIGS. 203*a* and 203*b* solely by the fact that the flexible sleeve 10 is not rolled upon itself but, instead, folded upon itself. By unfolding the folded sleeve 10, it can be placed over the tissue portion 71 in the same manner as discussed above in relation to FIGS. 203*a*, 203*b*, as is shown in FIG. 204*b*.

FIGS. 206*a* and 205*b* show a second embodiment of a tissue connector where the flexible sleeve 10 is arranged such that it is foldable upon itself. More particularly, the first end 3 of the conduit 2 is inserted in the tissue portion 71 of living tissue 70 to an extent that it overlaps a first portion 13 of the flexible sleeve 10. The remaining portion 14 of the flexible sleeve 10 not being covered by the tissue portion 71 is rolled upon itself and can be unrolled so as to cover the tissue portion 71. As a result shown in FIG. 206*b*, the flexible sleeve 10 is folded upon itself with the tissue portion 71 placed intermediate the folded sleeve 10.

Different to the embodiments described before, suturing the tissue portion 71 to the wall 5 of the conduit 2 is carried out before the tissue portion 71 is covered with the remaining part 14 of the flexible sleeve 10. The remaining part 14 thereby seals any penetration holes caused by the suturing.

In an alternative of the second embodiment, not shown, the first end 3 of the conduit 2 will be inserted in the tissue portion 71 only so far that the tissue portion 71 does not overlap with the flexible sleeve 10. Thus, after unrolling the flexible sleeve 10, only a part of the folded sleeve 10 will cover the tissue portion 71.

Furthermore, also not shown, the remaining part 14 of the sleeve 10 is not necessarily rolled upon itself, as shown in FIG. 206a, but may lay flat against the outer surface 6 of the conduit 2, similar to the embodiment shown in FIG. 204a.

As will be recognized, the portion 13 of the flexible sleeve 10 is arranged in a circumferential groove provided in the outer surface 6 of the conduit 2. It is advantageous when the depth of the groove corresponds to the thickness of the flexible sleeve 10. This will facilitate introducing the first end 3 of the conduit 2 into the living tissue 70.

FIG. 207 shows a possibility of fixing the conduit 2, such as the conduit's second end 4, to a tubular part of living tissue 80 or to a hose that belongs or leads to a medical device, reservoir, or the like. Accordingly, at least one bulge 15 extends outwardly from the conduit's outer surface 6 in a circumferential direction of the conduit 2 about at least a part of the conduit's circumference. Furthermore, at least one blocking ring 30 loosely fitting over the outer surface 6 of the conduit 2 with a clearance between the outer surface 6 and the blocking ring 30 is provided for mounting the tubular living tissue 80 (or alternatively the hose) within the clearance. The blocking ring has an inner cross-sectional diameter which is about the same as the outer cross-sectional diameter of the bulge 15. This prevents the blocking ring from slipping over the bulge when the living tissue 80, as shown in FIG. 207, is mounted within the clearance.

When an axial force tends to pull the tubular living tissue 80 from the outer surface 6 of the conduit 2, the blocking ring 30 will move with the tubular tissue 80, thereby compressing the tubular tissue 80 against the bulge 15, so as to prevent any further slippage of the tubular tissue 80 over the bulge 15. This is a self-enhancing effect.

This kind of locking mechanism can be combined with any of the aforementioned embodiments of the tissue connector. Of these variants, only one shall exemplary be described in the following in relation to FIGS. 208a and 208b. The embodiment shown in FIGS. 208a and 208b substantially correspond to the embodiment of FIGS. 203a and 203b, where the flexible sleeve 10 is rolled upon itself and then unrolled to cover the tubular tissue 80 which, in this case, is pulled over the second end 4 of the conduit 2 sufficiently far so as to extend also over the bulge 15. After the flexible sleeve 10 has been unrolled over the tubular tissue 80, the blocking ring 30 is pushed over the flexible sleeve against the bulge 15. After a while, the threads 20 sutured to the tubular tissue 80 and the wall 5 of the conduit 2 (FIG. 6a) will have been absorbed by the patient's body and, about during the same time, living tissue will have formed in and connect the tubular tissue 80 to the ingrowth layer 11 of the flexible sleeve 10. Therefore, as the tubular tissue 80 tends to be pulled off of the second end 4 of the conduit 2, the blocking ring 30 will also be moved, press the tubular tissue 80 and the flexible sleeve 10 against the bulge 15 and thereby prohibit any further slippage of the tubular tissue 80 over the bulge 15. The friction coefficient between the blocking ring 30 and the outer surface of the flexible sleeve should be higher than the friction coefficient which the conduit's outer surface 6 has in relation to the tubular tissue 80.

Note that the flexible sleeve 10 in its unrolled state as shown in FIG. 6b must not necessarily extend over the bulge 15 but can end a distance away from the bulge. In that situation, the blocking ring 30 would not clamp the sleeve 10 against the bulge 15.

The afore mentioned embodiments have mainly been described in relation to a tissue connector of which only one of the two ends is intended to be connected to tubular living tissue. However, as has also been mentioned before, there are various applications where the tissue connector may connect two pieces of tubular living tissue, such as when bridging two pieces of identical tubular living tissue or connecting tubular living tissue with tissue of a biological transplant. For that, the second end 4 of the tissue connector's conduit 2 can be designed according to any of the aforementioned embodiments. FIG. 209 gives just an example of how such tissue connector could be designed. Accordingly, two flexible sleeves 10 are integrally formed to form a single flexible sleeve 10a, with each of the sleeves 10 being rolled upon itself, similar to the embodiment shown in FIG. 2a. The two flexible sleeves 10 can, of course, be provided separately. Furthermore, a bulge 15 and a blocking ring 30 can be provided at one or both of the conduit's ends 3 and 4. Also, a medical device, flow restrictor or the like can be incorporated intermediate the two ends 3 and 4.

Bulge

FIG. 210 schematically shows a body 100 of a patient with a first tissue connector 1 connected to the end of the patient's large bowel 50 and a second tissue connector 1a interconnecting two pieces of the patient's aorta 60. The tissue connector 1 may either connect the large bowel 50 to the patient's anus or to an artificial anus which may include an excrements collecting container. The tissue connector 1a may include between its two ends a heart valve, a blood pump, a drug delivery device or the like.

The tissue connectors 1 and 1a shown in FIG. 201 represent only a few of many different possible locations and applications of the tissue connector within the human's or, alternatively, an animal's body. Further examples of possible applications have already been outlined further above.

FIG. 211 shows a first embodiment of the tissue connector 1 connected to a tubular part of living tissue 80. The tissue connector 1 comprises a conduit 2 with a first end 3 and a second end 4. The second end 4 of the conduit 2 has already been inserted into an end portion of living tissue 80. The inner cross section of the conduit 2 is selected to approximately match the inner cross section of the tubular living tissue 80 so as not to obstruct any flow of material. The thickness of the wall 5 of the conduit, which is typically circular, is chosen to provide sufficient strength so that it does not collapse under the forces that will act upon the conduit during use, while providing sufficient flexibility where needed. On the other hand, the thickness should not be chosen too large since the living tissue will have to be stretched over the outer surface 6 of the conduit 2 without damage and without excessively affecting blood circulation within the end portion 81 of the living tissue 80.

The wall 5 of conduit 2 is tapered towards its leading edge 7. In addition, the leading edge 7 is rounded. These two measures prevent damage to the living tissue 80 when the conduit 2 is inserted into the end portion 81 of the living tissue 80.

The first end 3 may serve and be adapted to be connected to an implantable medical device, an implantable reservoir, an implantable pump, an implantable motor or a combination of the afore mentioned items (generally designated with 200). It may also be connected to any other implantable device 200. The implantable device 200 may even form a part of the tissue connector 1, either integrally or attached thereto.

The implantable device 200 may also be a medical device replacing one or more of the patient's organs, such as an artificial urine bladder, a fecal excrement's collecting container, an artificial urethra, an artificial heart, an artificial esophagus, an artificial trachea or the like. Alternatively, the first end 3 of the conduit 2 may be connected to a biological implant obtained from a third party's body, such as a urine bladder, an intestine, a urethra, a ureter, a kidney, a bowel, a heart, an esophagus, a trachea, a blood vessel or the like.

The device 200 may also comprise a flow restrictor for partial or complete restriction of flow through the conduit. This can be suitable e.g. in the case where the tissue connector is located at the end of the patient's large bowel.

The device 200 may also be placed between the tissue connector 1 and a second tissue connector 1b with conduit 2b, as is indicated in FIG. 211 by dotted lines. This arrangement is practical where the device 200 has to be placed at a location within one of the patient's organs, such as in a blood vessel, in which case the blood vessel would be divided and the device 200 placed between the two tissue connectors 1 and 1b connected to the respective free ends of the divided blood vessel. As an example, the device 200 could include a flow restrictor, such as an artificial heart valve, or a drug delivery reservoir.

Apart from the conduit 2 and the optional device 200, the tissue connector 1 of the embodiment shown in FIG. 211 has a bulge 15 that extends outwardly from the conduit's outer surface 6 in a circumferential direction of the conduit 2 about at least a part of the conduit's circumference. Furthermore, at least one blocking ring 30 loosely fitting over the outer surface 6 of the conduit 2 with a clearance between the outer surface 6 and the blocking ring 30 is provided for mounting the tubular living tissue 80 within the clearance. The blocking ring has an inner cross-sectional diameter which is about the same as the outer cross-sectional diameter of the bulge 15. This prevents the blocking ring from slipping over the bulge when the living tissue 80, as shown in FIG. 211, is mounted within the clearance.

When an axial force tends to pull the tubular living tissue 80 from the outer surface 6 of the conduit 2, the blocking ring 30 will move with the tubular tissue 80, thereby compressing the tubular tissue 80 against the bulge 15, so as to prevent any further slippage of the tubular tissue 80 over the bulge 15. This is a self-enhancing effect. Preferably, the blocking ring in this and in the subsequently described embodiments is made from a material that has a friction coefficient in relation to living human (outer) mucosa tissue that is higher than a friction coefficient which the conduit's outer surface has in relation to living human (inner) serosa tissue.

FIG. 212 shows a second embodiment of the tissue connector 1 comprising the conduit 2 with each of its first and second ends 3 and 4 having a circumferential bulge 15. Between the two bulges 15 two blocking rings 30 are arranged. Tubular living tissue 80 has been pulled over the conduit 2 and through the blocking rings 30, and the blocking rings 30 have then been pushed into a position closest to the bulges 15. Therefore, when stretching forces are applied to the tubular tissue 80 in the one or the other direction, depending upon the direction one of the two blocking rings 30 will move towards the associated bulge 15, thereby clamping the tissue 80 between the blocking ring 30 and the bulge 15 and prohibiting any further slippage of the tissue 80 off the conduit 2.

The embodiment shown in FIG. 212 is particularly suitable to strengthen weak sections in a tubular part of living tissue or to seal a porous section, such as a porous section of the patient's intestine.

The same tissue connector as shown in FIG. 212 may also be used to connect two separate ends of tubular tissue or to connect one end of tubular tissue with another end of a hose or the like that may lead e.g. to an implantable medical device or to an exit port, such as an artificial body exit.

FIG. 213 shows a third embodiment that can be used as an alternative to the embodiment previously discussed in relation to FIG. 212. Again, the conduit 2 has two bulges 15 to prevent the tubular tissue 80 from slipping off of the conduit. However, in this embodiment the bulges 15 are arranged in close proximity to one another so that a single blocking ring 30 located between the two bulges 15 in an axial direction of the conduit will be sufficient to cooperate with one or the other of the two bulges 15 depending upon the direction of the stretching force acting upon the tissue 80.

FIGS. 214a and 214b show an alternative for mounting living tissue on the free end 3 of the tissue connector 1 to either another part of living tissue 70 or to a hose. Apart from the conduit 2 and the bulge 15 at the second end of the conduit 2, the tissue connector 1 of the embodiment shown in FIG. 5a has a flexible sleeve 10 axially extending and closely fitted around a part of the outer surface 6 of the conduit 2. The flexible sleeve 10 may be delivered separately from the conduit 2 and placed over the conduit's outer surface 6 shortly before implantation into the patient's body. However, it is preferred to provide the conduit 2 with the flexible sleeve 10 as a unitary item, the flexible sleeve 10 preferably fixed to the outer surface 6 by means of bonding, welding and/or clamping. In the case of bonding, it can be advisable to pretreat the outer surface 6 e.g. with a primer, depending upon the material combination to be bonded together.

In FIG. 214a, the flexible sleeve 10 is rolled upon itself and can be unrolled over the portion 71 of living tissue 70 so as to cover, seal and protect that portion 71 on the first end 3 of the conduit 2, as is shown in FIG. 214b. The tissue portion 71 and the overlapping part 11 of flexible sleeve 10 are fixed to the first end 3 of the conduit 2 by suturing threads 20 therethrough and through the wall 5 of the conduit 2, as is indicated in FIG. 214b by dotted lines.

The flexible sleeve 10 is a multilayer material comprising a porous ingrowth layer to allow ingrowth of living tissue. For that, it has a netlike structure. On top of the ingrowth layer 11 there is provided a support layer 12. The support layer 12 may have one ore more of various functions. One possible function is to provide support to the ingrowth layer 11 so as to ease handling and/or prevent fussing of the ingrowth layer. Also, the support layer 12 may provide some tension, thereby exerting a compressive force in a radial direction so as to slightly clamp the tissue portion 71 against the outer surface 6 of the conduit 2. For that, the support layer should have an appropriate elasticity. Finally, the support layer may provide protection for the tissue portion 71.

Preferably, the support layer should be porous so that exchange between the tissue portion 71 and the surrounding area within the patient's body is possible. This is an important aspect for the ingrowth of living tissue material into the ingrowth layer 11. Expanded polytetrafluoroethylene (ePTFE) is particularly suitable, as it is flexible, inert and can be made with any desired porosity. Other biocompatible polymers, such as polyurethane and the like, are suitable as well.

FIGS. 215a and 215b show an alternative which differs from the connector shown in FIGS. 5a and 5b solely by the fact that the flexible sleeve 10 is not rolled upon itself but, instead, folded upon itself. By unfolding the folded sleeve 10, it can be placed over the tissue portion 71 in the same manner as discussed above in relation to FIGS. 214a, 214b, as is shown in FIG. 215b.

FIGS. 216a and 216b show another alternative where the flexible sleeve 10 is arranged such that it is foldable upon itself. More particularly, the first end 3 of the conduit 2 is inserted in the tissue portion 71 of living tissue 70 to an extent that it overlaps a first portion 13 of the flexible sleeve 10. The remaining portion 14 of the flexible sleeve 10 not being covered by the tissue portion 71 is rolled upon itself and can be unrolled so as to cover the tissue portion 71. As a result shown in FIG. 216b, the flexible sleeve 10 is folded upon itself with the tissue portion 71 placed intermediate the folded sleeve 10.

Different to the alternatives described before, suturing the tissue portion 71 to the wall 5 of the conduit 2 is carried out before the tissue portion 71 is covered with the remaining part 14 of the flexible sleeve 10. The remaining part 14 thereby seals any penetration holes caused by the suturing.

In an even further alternative, not shown, the first end 3 of the conduit 2 will be inserted in the tissue portion 71 only so far that the tissue portion 71 does not overlap with the flexible sleeve 10. Thus, after unrolling the flexible sleeve 10, only a part of the folded sleeve 10 will cover the tissue portion 71.

Furthermore, also not shown, the remaining part 14 of the sleeve 10 is not necessarily rolled upon itself, as shown in FIG. 216*a*, but may lay flat against the outer surface 6 of the conduit 2, similar to the embodiment shown in FIG. 215*a*.

As will be recognized, the portion 13 of the flexible sleeve 10 is arranged in a circumferential groove provided in the outer surface 6 of the conduit 2. It is advantageous when the depth of the groove corresponds to the thickness of the flexible sleeve 10. This will facilitate introducing the first end 3 of the conduit 2 into the living tissue 70.

Any of the described flexible sleeve connections can be combined with the bulge locking ring locking mechanism. Of these variants, only one shall exemplary be described in the following in relation to FIGS. 217*a* and 217*b*. The embodiment shown in FIGS. 217*a* and 217*b* substantially correspond to the embodiment of FIGS. 216*a* and 216*b*, where the flexible sleeve 10 is rolled upon itself and then unrolled to cover the tubular tissue 80 which, in this case, is pulled over the second end 4 of the conduit 2 sufficiently far so as to extend also over the bulge 15. After the flexible sleeve 10 has been unrolled over the tubular tissue 80, the blocking ring 30 is pushed over the flexible sleeve against the bulge 15. After a while, the threads 20 sutured to the tubular tissue 80 and the wall 5 of the conduit 2 (FIG. 217*a*) will have been absorbed by the patient's body and, about during the same time, living tissue will have formed in and connect the tubular tissue 80 to the ingrowth layer 11 of the flexible sleeve 10. Therefore, as the tubular tissue 80 tends to be pulled off of the second end 4 of the conduit 2, the blocking ring 30 will also be moved, press the tubular tissue 80 and the flexible sleeve 10 against the bulge 15 and thereby prohibit any further slippage of the tubular tissue 80 over the bulge 15. The friction coefficient between the blocking ring 30 and the outer surface of the flexible sleeve should be higher than the friction coefficient which the conduit's outer surface 6 has in relation to the tubular tissue 80.

Note that the flexible sleeve 10 in its unrolled state as shown in FIG. 215*b* must not necessarily extend over the bulge 15 but can end a distance away from the bulge. In that situation, the blocking ring 30 would not clamp the sleeve 10 against the bulge 15 but only the living tissue 80.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

Aneurysm

In FIG. 218 a general view of a human 100 having a member, in particular a cuff 101, implanted for treating an aneurism is shown. In FIG. 218 the treated aneurism is located on the aorta in the abdomen close to the Y-bifurcation extending to the legs. The cuff 101 can be designed in various ways but is generally formed as an implantable member adapted to be placed in connection with a blood vessel having said vascular aneurism, and adapted to exert a pressure on said aneurism from the outside of said blood vessel. In particular the pressure exerted on the blood vessel is essentially uniform from all direction and adapted to hinder the blood vessel to expand in all directions thereby acting to prevent the blood vessel from bursting. The pressure can in accordance with one embodiment be essentially equal to or lower than the diastolic blood pressure of the treated patient. The cuff 101 can be made in any suitable material such as an elastic material adapted for implantation in a human or mammal body.

The cuff 101 can exercise the pressure in a number of different ways. In accordance with one embodiment of the present invention the pressure applied on the blood vessel can be mechanical and adjustable by means of an adjustable screw or a similar means in order to apply a pressure on the blood vessel. The cuff 101 can also be formed by a spring loaded member and operated in a suitable manner such as hydraulically or pneumatically.

In FIG. 219 a cuff 101 in accordance with one embodiment of the present invention is shown in more detail. The cuff 101 comprises a number of segments 103 each adjustable and possible to tailor to fit a particular aneurism 102 of a blood vessel 104 to be treated. Each segment 103 can be adjusted either as a whole or individually. The segments 103 can be controlled and adjusted mechanically by an adjustable screw or similar or adapted to be filled with a fluid. For example, the segments can be provided axially along the blood vessel and also radially along the blood vessel forming a matrix of subsegments that constitutes the cuff 101. In particular one segment can be located above and one below the aneurysm along the blood vessel.

The adjustment can be controlled by an electronic control unit 105 adapted to receive and transmit signals from a transmitter/receiver 106 located outside the body of a treated patient. The electronic control unit can also comprise a chargeable battery 111 chargeable from the outside by an external charger unit 112. The electronic control unit can comprise an electrical pulse generator 109 for generating electrical pulses as is described in more detail below.

The electronic control unit 105, such as a microprocessor or a MCU or a FPGA or a ASIC and can further be connected to or comprise a hydraulic pump 110 associated with a reservoir 115 containing of a fluid used to regulate the pressure of the cuff 101. The pump is thus adapted to pump the hydraulic fluid in or out from the cuff 101 in order to adjust the pressure applied in the aneurism. The control mechanism used for keeping the pressure in the cuff 101 can comprise a pressure tank 117.

In a preferred embodiment the pressure tank 117 is adapted to be able to change its volume still keeping substantially the same pressure, thus keeping the same pressure onto the aneurysm although some expansion of size of the aneurysm may occur. However, if the expansion goes too far the pressure tank may come out of range to keep the pressure constant and with some kind of volume detection in the pressure tank the pump 110 is then able to move fluid out from the pressure tank into the reservoir 115 to again be within pressure range in the pressure tank. The pressure tank is also able to even out the systolic pulses supplied to the aneurysmic wall The cuff 101 can be shaped in any desirable form to enable treatment of an aneurism wherever it is located. In accordance with one embodiment the cuff 101 is provided with at least one sensor 107 adapted to sense the pressure from the blood vessel that the cuff is surrounding.

The sensor(s) 107 used to generate a signal indicative of one or many parameters related to the aneurism and the device 101 used for treating the aneurism can for example be a gauge sensor. The sensor 107 can be adapted to generate sensor signals used for monitoring parameters including but not limited to the pressure in a hydraulic cuff, the pressure of a mechanical cuff, the pressure of a pneumatic cuff, the pressure in a blood vessel, the shape of the blood vessel in particular a parameter related to the diameter of the aneurysm.

An alternative or complement to the remote placed transmitter 106 is a switch (part of 105), preferable subcutaneously placed, such a switch may be mechanical or electrical, such as a microprocessor or a MCU or a FPGA or a ASIC, or the switch may comprise a small hydraulic control reservoir.

The restriction device may comprise any hydraulic device or mechanical device or stimulation device alone or monitoring/sensor device in any combination as described in the present application. The stimulation device may comprise both thermal stimulation or electrical stimulation. If a hydraulic system is used the hydraulic pump may in a system comprise an injection port (part of 110) for the injection of hydraulic fluid, preferable for calibration of hydraulic fluid. A subcutaneously place switch may also be used as well as an feedback alarm system connected to the sensor/monitoring system.

Although the device has specific placements on the drawings it should be understood that the placement might vary.

Any combination of features or embodiments may comprise from any source within this application. Any embodiment in any combination that is disclosed in this application, specially, but not limited to, in FIG. 218-259, may be used.

In FIG. 220 a view illustrating a mechanical cuff 101 is shown. The cuff can for example comprise an elastic material 301 kept in place by a suitable compressing device. The cuff 101 in accordance with one embodiment of the present invention comprises an elastic material in the form of a number of gel filled pads 301. The pads 301 can be shaped in a suitable manner and in particular formed to absorb the geometrical shape of the aneurysm. This can for example be achieved by providing pads with different tilting angles. The elastic material 301 can be kept in place by at least one adjustable fastening member 303. The fastening member 303 can for example be adjusted by a screw 305 or a similar device. By adjusting the fastening member 303 the pressure applied on the aneurysm can be controlled.

In FIG. 221, a view illustrating a mechanical cuff 101 is shown. The cuff can for example comprise an elastic band 401. The band 401 can be adjusted by an adjustor 403 to provide a higher or smaller pressure on the aneurysm.

In FIG. 222, a view illustrating a hydraulic cuff 101 is shown. The cuff can for example comprise implantable member 501 adapted to hold fluid. The member 501 is adapted to be placed in connection with a blood vessel having an aneurysm. The member can exercise a pressure on the aneurysm the blood vessel in response to the conditions of the fluid of the member 501. By filling the member with a fluid pressure can be applied onto the aneurysm in order to prevent or reduce an expansion the aneurysm when implanted in a patient thereby enabling postoperative treatment of the aneurysm. Further the treatment can be adjusted postoperatively by regulating the pressure using an implanted pressure regulator 503. The pressure regulator can for example be formed by a pressure tank 503 implanted in the patient interconnected via a hose 504 with the member 501. The pressure tank can comprise an expandable reservoir 505 for storing superfluous fluid.

In FIG. 223, a view illustrating a hydraulic cuff 101 is shown. The cuff can for example comprise implantable member 601 adapted to hold fluid. The member 601 is adapted to be placed in connection with a blood vessel having an aneurysm. The member can exercise a pressure on the aneurysm the blood vessel in response to the conditions of the fluid of the member 601. By filling the member with a fluid pressure can be applied onto the aneurysm in order to prevent or reduce an expansion the aneurysm when implanted in a patient thereby enabling postoperative treatment of the aneurysm. Further the treatment can be adjusted postoperatively by regulating the pressure using an implanted pressure regulator 603. The pressure regulator can for example be formed by a spring loaded tank 603 implanted in the patient interconnected via a hose 604 with the member 601. The spring 606 used to control the pressure of the tank and thereby indirectly the pressure applied by the cuff 101 on the aneurysm can be an adjustable spring in order to control the pressure.

In FIG. 224, a view illustrating a hydraulic cuff 101 is shown. The cuff can for example comprise implantable member 701 adapted to hold fluid. The member 601 is adapted to be placed in connection with a blood vessel having an aneurysm. The member can exercise a pressure on the aneurysm the blood vessel in response to the conditions of the fluid of the member 701. By filling the member with a fluid pressure can be applied onto the aneurysm in order to prevent or reduce an expansion the aneurysm when implanted in a patient thereby enabling postoperative treatment of the aneurysm. Further the treatment can be adjusted postoperatively by regulating the pressure using an implanted pressure regulator 703. The pressure regulator can for example be formed by a pump 703 implanted in the patient on a hose 704 interconnecting a tank 705 with the member 701. The pump 703 is used to control the pressure of the member 703 by pumping fluid in and out of the member 701 and thereby controlling the pressure applied by the cuff 101 on the aneurysm.

By sensing the pressure from the blood vessel the cuff can be controlled to apply a correct pressure on the blood vessel thereby keeping the form of the blood vessel essentially constant. For example the pressure may vary over time as a result of changes in the wall of the blood vessel of surrounding tissue. Also the pressure will change as a function of the phase in which the heart is working. In other words the pressure will be different in a systolic phase as compared to a diastolic phase. By using a pressure sensor the pressure applied by the cuff 101 can be adapted to react to changes in the sensed pressure and apply a corresponding counter pressure. The sensor signals generated by the sensor(s) 107 of the cuff can also be used to trigger an alarm in response to the sensor signal indicating an expansion of the aneurism. In response to an alarm signal being generated the cuff can be automatically controlled to exercise a counter pressure on the blood vessel to counter or limit the expansion of the aneurism.

In yet another embodiment, electrodes 108 can be provided in the cuff. The electrodes can be connected to the electrical pulse generator, which is adapted to generate electrical pulses for stimulating the wall of the aneurism. The purpose of the electrical stimulation is to increase the tonus of the wall of the aneurism.

In FIG. 225, a stimulation device 801 for treating a vascular aneurysm of a human or mammal patient is shown. The device 801 comprises at least one implantable electrode 803 adapted to be placed in close connection to the aneurysm. The electrode is adapted to provide an electrical stimulation pulse on a wall portion of the aneurysm. The electrical stimulation pulse can for example be generated by a pulse generator 805. The pulse generator can be implanted in the patient.

In accordance with one embodiment the electrical stimulation device used for treating a vascular aneurysm of a human or mammal patient is connected to electrodes adapted to stimulate the wall of the aneurism at multiple stimulation points. The multiple stimulation groups may further be organized in different stimulation groups which can stimulated independently of each other. In accordance with one embodiment the electrical stimulation is performed with positive and or negative voltage stimulation pulses. In one embodiment the current used for stimulation of the aneurysm wall is kept essentially constant.

The sequence of electrical pulses used to stimulation the wall of the aneurysm can be applied with a predetermined periodicity having periods of no stimulation therein between during which periods without stimulation the wall of the aneurysm is allowed to rest. The electrical stimulation signal can also be Pulse Width Modulated to control the energy applied. In accordance with one embodiment the electrical stimulation is applied during the systolic phase to increase the tonus of the wall of the aneurysm. The systolic phase can be detected by the sensors 107 used to sense the pressure of the aneurysm as described above.

In accordance with one embodiment the stimulation can be controlled to be applied with a temporarily increased intensity and position during emergency situations when the aneurysm is detected to rapidly expands, to limit the expansion of said aneurysm.

In order to provide input for controlling the pressure and or to monitor the aneurysm a device 107 can be provided. In FIG. 226 a view illustrating a sensor 901 used when treating or monitoring a vascular aneurysm of a human or mammal patient is shown. The sensor 901 is placed in relation to a wall portion of the aneurysm for generating a signal corresponding to a parameter related to the aneurysm or the treatment of the aneurism. The signal generated by the sensor can be a signal corresponding to the size of the aneurysm and is accessible via a signal output 903. For example the signal can be indicative of the diameter of the aneurysm. In accordance with one embodiment of the he sensor is a gauge sensor. The sensor 901 can also be adapted to generate any output related to monitoring or treatment of the aneurysm. For example the sensor can be adapted to sense the resistance, capacitance, pressure, volume extension, flexure of a member in contact with the aneurysm.

The shape of the cuff 101 can as stated above be tailor made to suit the location where an aneurysm is to be treated. In FIG. 227, a cuff 101 is seen from above in a direction aligned with a treated blood vessel. As can be seen in FIG. 220 each segment 3 can be sub-divided into a number of sub segments 103a, 103b . . . together forming a closed loop around the treated aneurysm. In case the aneurysm is located in the aorta bifurcation region the cuff 101 can be Y-shaped as is shown in FIG. 228.

The device as described herein can be implanted in a patient using some suitable surgical procedure as depicted in FIG. 229. For example, the device can be implanted by inserting a needle or a tube like instrument into the patient's abdominal cavity, step 1201. Next in a step 1203 a part of the patient's body with gas using the needle or tube like instrument thereby expanding said abdominal cavity. Next in a step 1205 at least two laparoscopic trocars are placed in the cavity. Thereupon in a step 1207 a camera is inserted through one of the laparoscopic trocars into the cavity. Next in a step 1209 at least one dissecting tool is inserted through one of said at least two laparoscopic trocars. An area of an aneurysm of a blood vessel is then dissected in a step 1211. The device is then placed onto the aneurysmic blood vessel in a step 1213, and the pressure that the device exerts onto the aneurysm is adjusted in a step 1215.

In accordance with one embodiment of the present invention the device can be implanted by a procedure depicted in FIG. 230. First in a step 1301 a needle or a tube like instrument is inserted into the patient's thoraxial cavity. Next, in a step 1303 a part of the patient's body with gas using the needle or tube like instrument to fill and thereby expanding the thoraxial cavity. Thereupon at least two laparoscopic trocars are placed in said cavity in a step 1305 Thereupon in a step 1307 a camera is inserted through one of the laparoscopic trocars into the cavity. Next in a step 1309 at least one dissecting tool is inserted through one of said at least two laparoscopic trocars. An area of an aneurysm of a blood vessel is then dissected in a step 1311. The device is then placed onto the aneurysmic blood vessel in a step 1313, and the pressure that the device exerts onto the aneurysm is adjusted in a step 1315.

In accordance with one embodiment of the present invention the device can be implanted by a procedure depicted in FIG. 231. First in a step 1401, the skin in the abdominal or thoraxial wall of the mammal patient is cut. Next, in a step 1403 an area of the aneurysm is dissected. Next, the device is then placed onto the aneurysmic blood vessel in a step 1405, and the pressure that the device exerts onto the aneurysm is adjusted in a step 1407.

In accordance with one embodiment of the present invention the device can be implanted by a procedure depicted in FIG. 232. First in a step 1501, the skin of the mammal patient is cut. Next, in a step 1503 an area of the aneurysm is dissected. Next, the device is then placed onto the aneurysmic blood vessel in a step 1505, and the pressure that the device exerts onto the aneurysm is adjusted in a step 1507.

FIG. 233 illustrates a system for treating a disease comprising a device 10 of the present invention placed in the abdomen of a patient. An implanted energy-transforming device 3020 is adapted to supply energy consuming components of the device with energy via a power supply line 3030. An external energy-transmission device 3040 for non-invasively energizing the device 10 transmits energy by at least one wireless energy signal. The implanted energy-transforming device 10020 transforms energy from the wireless energy signal into electric energy which is supplied via the power supply line 3030.

In one embodiment at least one battery may be a part of or replace the energy transforming device 3020 to supply energy to the device 10 over a power supply line 3030. In one embodiment the battery is not rechargeable. In an alternative embodiment the battery is rechargeable. The battery supply may of course be placed both remote to and incorporated in the device.

The wireless energy signal may include a wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal. Alternatively, the wireless energy signal may include an electric or magnetic field, or a combined electric and magnetic field.

The wireless energy-transmission device 3040 may transmit a carrier signal for carrying the wireless energy signal. Such a carrier signal may include digital, analogue or a combination of digital and analogue signals. In this case, the wireless energy signal includes an analogue or a digital signal, or a combination of an analogue and digital signal.

Generally speaking, the energy-transforming device 3020 is provided for transforming wireless energy of a first form transmitted by the energy-transmission device 3040 into energy of a second form, which typically is different from the energy of the first form. The implanted device 10 is operable in response to the energy of the second form. The energy-transforming device 3020 may directly power the device with the second form energy, as the energy-transforming device 3020 transforms the first form energy transmitted by the energy-transmission device 3040 into the second form energy. The system may further include an implantable accumulator, wherein the second form energy is used at least partly to charge the accumulator.

Alternatively, the wireless energy transmitted by the energy-transmission device 3040 may be used to directly power the device, as the wireless energy is being transmitted by the energy-transmission device 3040. Where the system comprises an operation device for operating the device, as will be described below, the wireless energy transmitted by the energy-transmission device 1004 may be used to directly power the operation device to create kinetic energy for the operation of the device.

The wireless energy of the first form may comprise sound waves and the energy-transforming device 3020 may include a piezo-electric element for transforming the sound waves into electric energy. The energy of the second form may comprise electric energy in the form of a direct current or pulsating direct current, or a combination of a direct current and pulsating direct current, or an alternating current or a combination of a direct and alternating current. Normally, the device comprises electric components that are energized with electrical energy. Other implantable electric components of the system may be at least one voltage level guard or at least one constant current guard connected with the electric components of the device.

Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transmission device may be controlled from outside the patient's body to release electromagnetic wireless energy, and the released electromagnetic wireless energy is used for operating the device. Alternatively, the energy-transmission device is controlled from outside the patient's body to release non-magnetic wireless energy, and the released non-magnetic wireless energy is used for operating the device.

The external energy-transmission device 3040 also includes a wireless remote control having an external signal transmitter for transmitting a wireless control signal for non-invasively controlling the device. The control signal is received by an implanted signal receiver which may be incorporated in the implanted energy-transforming device 3020 or be separate there from.

The wireless control signal may include a frequency, amplitude, or phase modulated signal or a combination thereof. Alternatively, the wireless control signal includes an analogue or a digital signal, or a combination of an analogue and digital signal. Alternatively, the wireless control signal comprises an electric or magnetic field, or a combined electric and magnetic field.

The wireless remote control may transmit a carrier signal for carrying the wireless control signal. Such a carrier signal may include digital, analogue or a combination of digital and analogue signals. Where the control signal includes an analogue or a digital signal, or a combination of an analogue and digital signal, the wireless remote control preferably transmits an electromagnetic carrier wave signal for carrying the digital or analogue control signals.

FIG. 233 illustrates the system of FIG. 232 in the form of a more generalized block diagram showing the device 10, the energy-transforming device 3020 powering the device 10 via power supply line 3030, and the external energy-transmission device 3040, The patient's skin 3050, generally shown by a vertical line, separates the interior of the patient to the right of the line from the exterior to the left of the line.

FIG. 234 shows an embodiment of the invention identical to that of FIG. 233, except that a reversing device in the form of an electric switch 3060 operable for example by polarized energy also is implanted in the patient for reversing the device 10. When the switch is operated by polarized energy the wireless remote control of the external energy-transmission device 3040 transmits a wireless signal that carries polarized energy and the implanted energy-transforming device 3020 transforms the wireless polarized energy into a polarized current for operating the electric switch 3060. When the polarity of the current is shifted by the implanted energy-transforming device 3020 the electric switch 3060 reverses the function performed by the device 10.

FIG. 235 shows an embodiment of the invention identical to that of FIG. 233, except that an operation device 3070 implanted in the patient for operating the device 10 is provided between the implanted energy-transforming device 3020 and the device 10. This operation device can be in the form of a motor 3070, such as an electric servomotor. The motor 3070 is powered with energy from the implanted energy-transforming device 3020, as the remote control of the external energy-transmission device 3040 transmits a wireless signal to the receiver of the implanted energy-transforming device 3020.

FIG. 236 shows an embodiment of the invention identical to that of FIG. 233, except that it also comprises an operation device is in the form of an assembly 3080 including a motor/pump unit 3090 and a fluid reservoir 3100 is implanted in the patient. In this case the device 10 is hydraulically operated, i.e. hydraulic fluid is pumped by the motor/pump unit 3090 from the fluid reservoir 3100 through a conduit 3110 to the device 10 to operate the device, and hydraulic fluid is pumped by the motor/pump unit 3090 back from the device 10 to the fluid reservoir 3100 to return the device to a starting position. The implanted energy-transforming device 1002 transforms wireless energy into a current, for example a polarized current, for powering the motor/pump unit 1009 via an electric power supply line 3120.

Instead of a hydraulically operated device 10, it is also envisaged that the operation device comprises a pneumatic operation device. In this case, the hydraulic fluid can be pressurized air to be used for regulation and the fluid reservoir is replaced by an air chamber.

In all of these embodiments the energy-transforming device 3020 may include a rechargeable accumulator like a battery or a capacitor to be charged by the wireless energy and supplies energy for any energy consuming part of the system.

As an alternative, the wireless remote control described above may be replaced by manual control of any implanted part to make contact with by the patient's hand most likely indirect, for example a press button placed under the skin.

Figure 238:
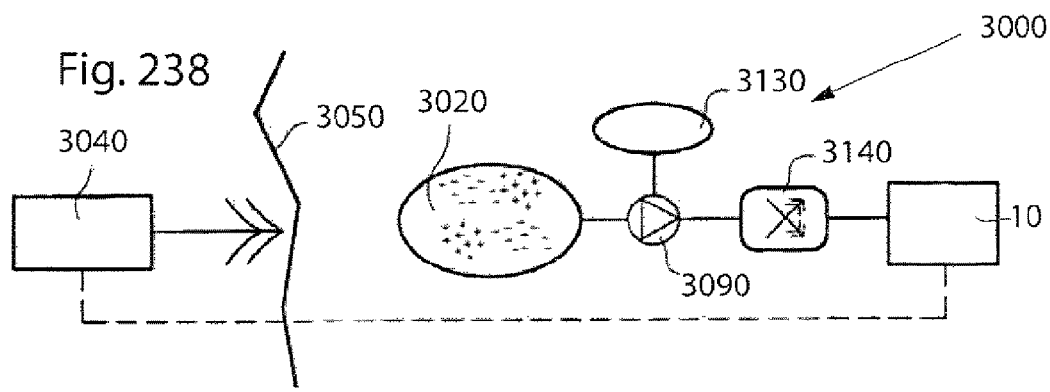

FIG. 238 shows an embodiment of the invention comprising the external energy-transmission device 3040 with its wireless remote control, the device 10, in this case hydraulically operated, and the implanted energy-transforming device 3020, and further comprising a hydraulic fluid reservoir 3130, a motor/pump unit 3090 and an reversing device in the form of a hydraulic valve shifting device 3140, all implanted in the patient. Of course the hydraulic operation could easily be performed by just changing the pumping direction and the hydraulic valve may therefore be omitted. The remote control may be a device separated from the external energy-transmission device or included in the same. The motor of the motor/pump unit 3090 is an electric motor. In response to a control signal from the wireless remote control of the external energy-transmission device 3040, the implanted energy-transforming device 3020 powers the motor/pump unit 3090 with energy from the energy carried by the control signal, whereby the motor/pump unit 3090 distributes hydraulic fluid between the hydraulic fluid reservoir 3130 and the device 10. The remote control of the external energy-transmission device 3040 controls the hydraulic valve shifting device 3140 to shift the hydraulic fluid flow direction between one direction in which the fluid is pumped by the motor/pump unit 3090 from the hydraulic fluid reservoir 3130 to the device 10 to operate the device, and another opposite direction in which the fluid is pumped by the motor/pump unit 3090 back from the device 10 to the hydraulic fluid reservoir 3130 to return the device to a starting position.

Figure 239:
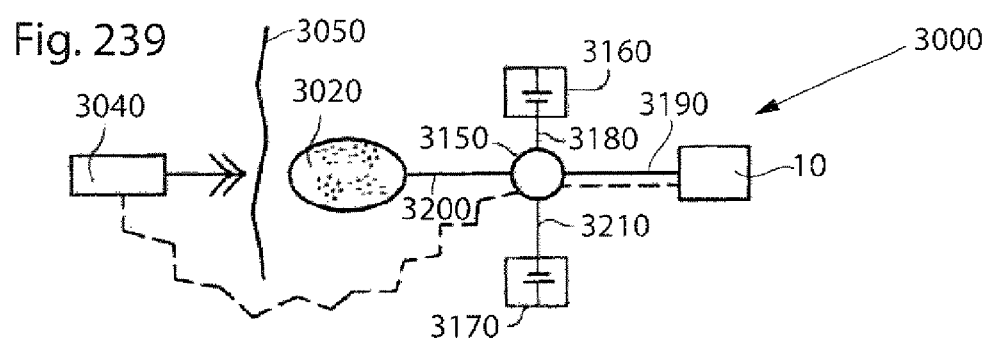

FIG. 239 shows an embodiment of the invention comprising the external energy-transmission device 1004 with its wireless remote control, the device 10, the implanted energy-transforming device 3020, an implanted internal control unit 3150 controlled by the wireless remote control of the external energy-transmission device 3040, an implanted accumulator 3160 and an implanted capacitor 3170. The internal control unit 1015 arranges storage of electric energy received from the implanted energy-transforming device 3020 in the accumulator 3160, which supplies energy to the device 10. In response to a control signal from the wireless remote control of the external energy-transmission device 3040, the internal control unit 3150 either releases electric energy from the accumulator 3160 and transfers the released energy via power lines 3180 and 3190, or directly transfers electric energy from the implanted energy-transforming device 3020 via a power line 3200, the capacitor 3170, which stabilizes the electric current, a power line 3210 and the power line 3190, for the operation of the device 10.

The internal control unit is preferably programmable from outside the patient's body. In a preferred embodiment, the internal control unit is programmed to regulate the device 10 according to a pre-programmed time-schedule or to input from any sensor sensing any possible physical parameter of the patient or any functional parameter of the system.

In accordance with an alternative, the capacitor 3170 in the embodiment of FIG. 224 may be omitted. In accordance with another alternative, the accumulator 3160 in this embodiment may be omitted.

Figure 240:
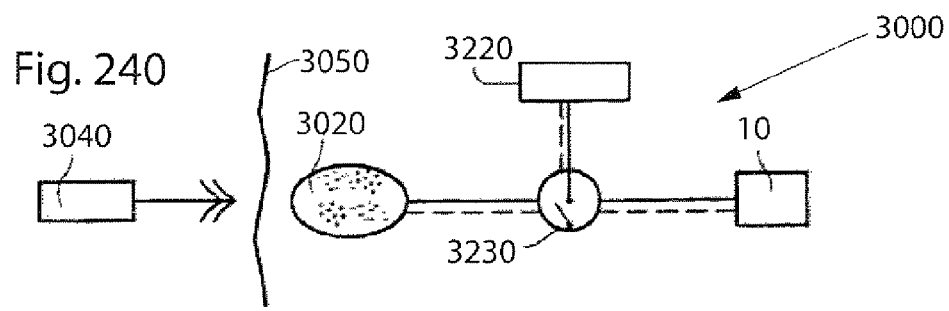

FIG. 240 shows an embodiment of the invention identical to that of FIG. 234, except that a battery 3220 for supplying energy for the operation of the device 10 and an electric switch 3230 for switching the operation of the device 10 also are implanted in the patient. The electric switch 3230 may be controlled by the remote control and may also be operated by the energy supplied by the implanted energy-transforming device 3020 to switch from an off mode, in which the battery 3220 is not in use, to an on mode, in which the battery 3220 supplies energy for the operation of the device 10.

Figure 241:
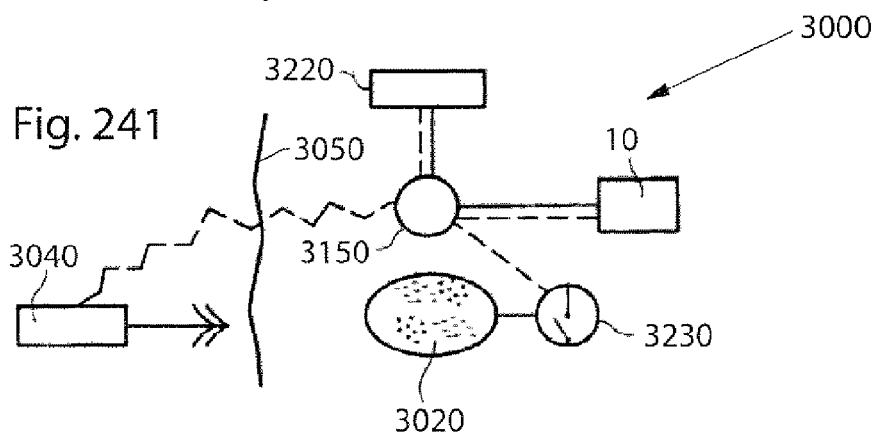

FIG. 241 shows an embodiment of the invention identical to that of FIG. 240, except that an internal control unit 3150 controllable by the wireless remote control of the external energy-transmission device 3040 also is implanted in the patient. In this case, the electric switch 3230 is operated by the energy supplied by the implanted energy-transforming device 3020 to switch from an off mode, in which the wireless remote control is prevented from controlling the internal control unit 3150 and the battery is not in use, to a standby mode, in which the remote control is permitted to control the internal control unit 3150 to release electric energy from the battery 3220 for the operation of the device 10.

Figure 242:
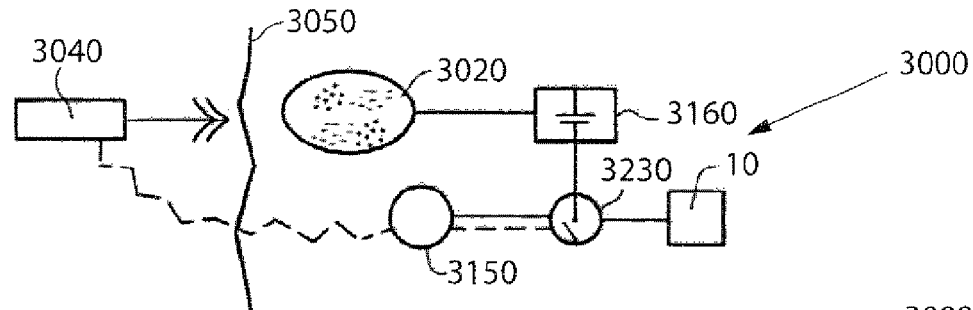

FIG. 242 shows an embodiment of the invention identical to that of FIG. 241, except that an accumulator 3160 is substituted for the battery 3220 and the implanted components are interconnected differently. In this case, the accumulator 3160 stores energy from the implanted energy-transforming device 3020. In response to a control signal from the wireless remote control of the external energy-transmission device 3040, the internal control unit 3150 controls the electric switch 3230 to switch from an off mode, in which the accumulator 3160 is not in use, to an on mode, in which the accumulator 3160 supplies energy for the operation of the device 10. The accumulator may be combined with or replaced by a capacitor.

Figure 243:
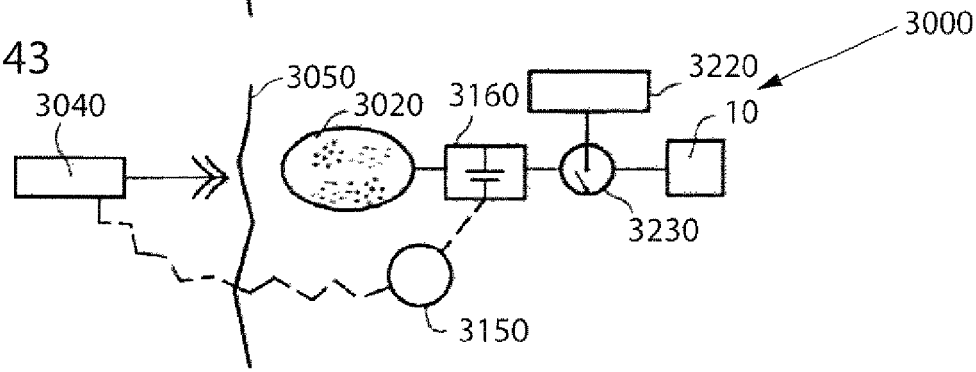

FIG. 243 shows an embodiment of the invention identical to that of FIG. 242, except that a battery 3220 also is implanted in the patient and the implanted components are interconnected differently. In response to a control signal from the wireless remote control of the external energy-transmission device 3040, the internal control unit 3150 controls the accumulator 3160 to deliver energy for operating the electric switch 3230 to switch from an off mode, in which the battery 3220 is not in use, to an on mode, in which the battery 3220 supplies electric energy for the operation of the device 10.

Alternatively, the electric switch 3230 may be operated by energy supplied by the accumulator 3160 to switch from an off mode, in which the wireless remote control is prevented from controlling the battery 3220 to supply electric energy and is not in use, to a standby mode, in which the wireless remote control is permitted to control the battery 3220 to supply electric energy for the operation of the device 10.

It should be understood that the switch 3230 and all other switches in this application should be interpreted in its broadest embodiment. This means a transistor, MCU, MCPU, ASIC, FPGA or a DA converter or any other electronic component or circuit that may switch the power on and off. Preferably the switch is controlled from outside the body, or alternatively by an implanted internal control unit.

Figure 244:
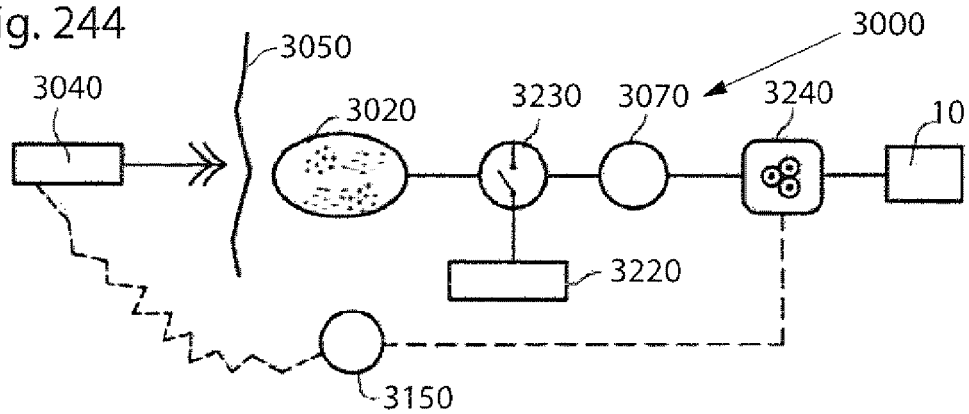

FIG. 244 shows an embodiment of the invention identical to that of FIG. 240, except that a motor 3070, a mechanical reversing device in the form of a gear box 3240, and an internal control unit 3150 for controlling the gear box 3240 also are implanted in the patient. The internal control unit 3150 controls the gear box 3240 to reverse the function performed by the device 10 (mechanically operated). Even simpler is to switch the direction of the motor electronically. The gear box interpreted in its broadest embodiment may stand for a servo arrangement saving force for the operation device in favor of longer stroke to act.

Figure 245:
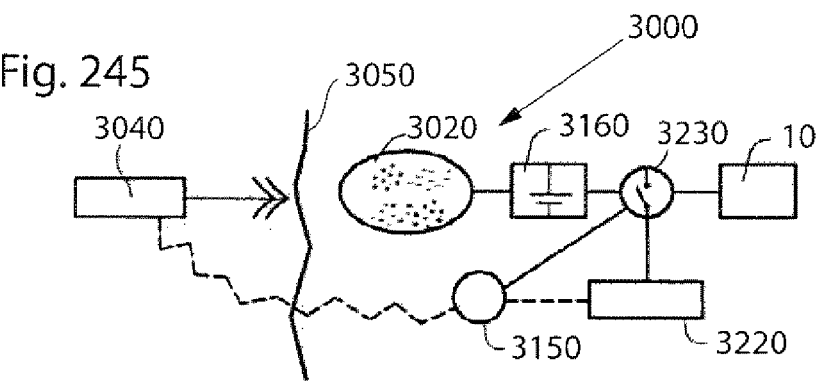

FIG. 245 shows an embodiment of the invention identical to that of FIG. 241 except that the implanted components are interconnected differently. Thus, in this case the internal control unit 3150 is powered by the battery 3220 when the accumulator 3160, suitably a capacitor, activates the electric switch 3230 to switch to an on mode. When the electric switch 3230 is in its on mode the internal control unit 3150 is permitted to control the battery 3220 to supply, or not supply, energy for the operation of the device 10.

Figure 246:
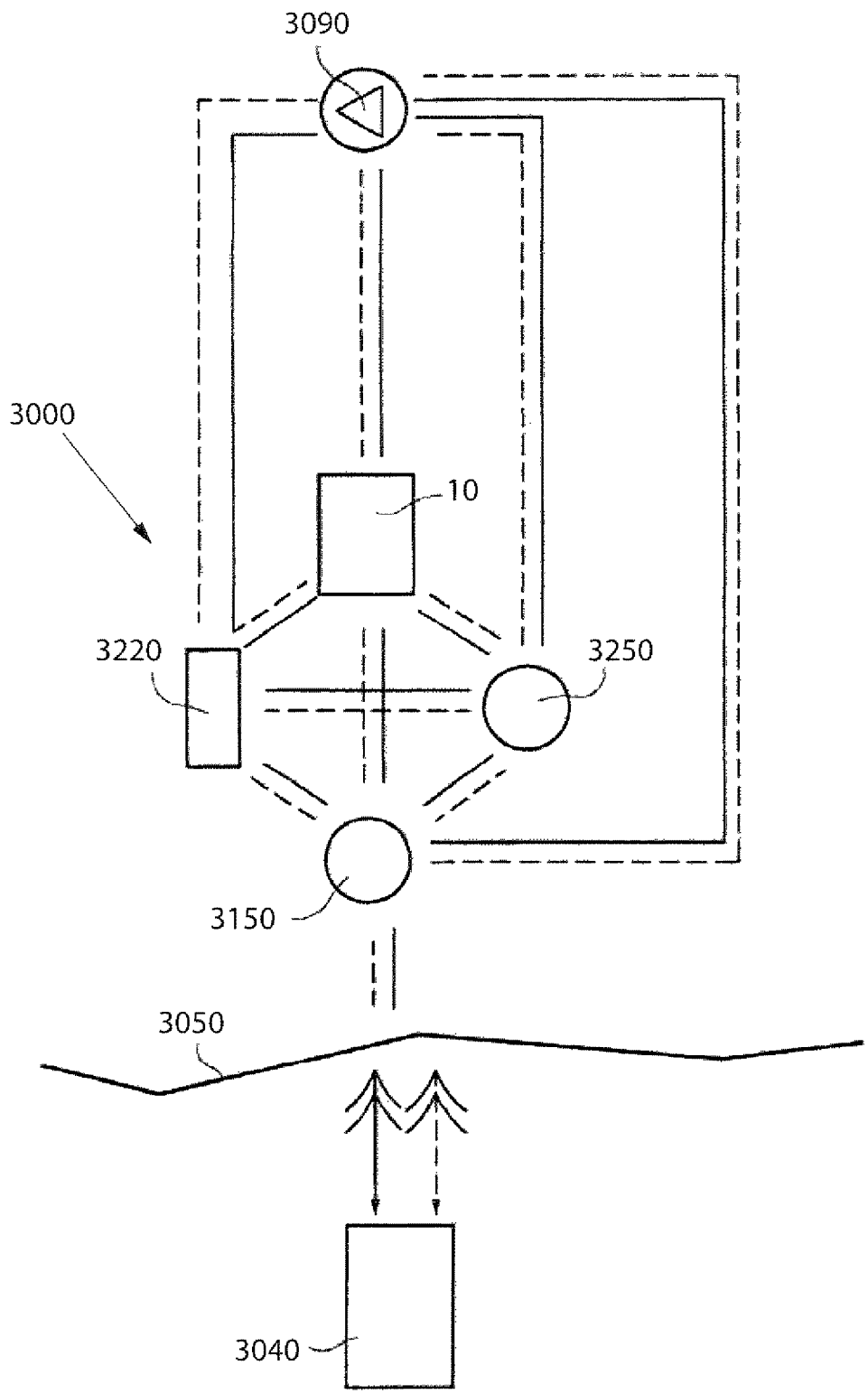

FIG. 246 schematically shows conceivable combinations of implanted components of the device for achieving various communication options. Basically, there are the device 10, the internal control unit 3150, motor or pump unit 3090, and the external energy-transmission device 3040 including the external wireless remote control. As already described above the wireless remote control transmits a control signal which is received by the internal control unit 3150, which in turn controls the various implanted components of the device.

A feedback device, preferably comprising a sensor or measuring device 3250, may be implanted in the patient for sensing a physical parameter of the patient. The physical parameter may be at least one selected from the group consisting of pressure, volume, diameter, stretching, elongation, extension, movement, bending, elasticity, muscle contraction, nerve impulse, body temperature, blood pressure, blood flow, heartbeats and breathing. The sensor may sense any of the above physical parameters. For example, the sensor may be a pressure or motility sensor. Alternatively, the sensor 3250 may be arranged to sense a functional parameter. The functional parameter may be correlated to the transfer of energy for charging an implanted energy source and may further include at least one selected from the group of parameters consisting of; electricity, any electrical parameter, pressure, volume, diameter, stretch, elongation, extension, movement, bending, elasticity, temperature and flow.

The feedback may be sent to the internal control unit or out to an external control unit preferably via the internal control unit. Feedback may be sent out from the body via the energy transfer system or a separate communication system with receiver and transmitters.

The internal control unit 3150, or alternatively the external wireless remote control of the external energy-transmission device 3040, may control the device 10 in response to signals from the sensor 3250. A transceiver may be combined with the sensor 3250 for sending information on the sensed physical parameter to the external wireless remote control. The wireless remote control may comprise a signal transmitter or transceiver and the internal control unit 3150 may comprise a signal receiver or transceiver. Alternatively, the wireless remote control may comprise a signal receiver or transceiver and the internal control unit 3150 may comprise a signal transmitter or transceiver. The above transceivers, transmitters and receivers may be used for sending information or data related to the device 10 from inside the patient's body to the outside thereof.

Where the motor/pump unit 3090 and battery 3220 for powering the motor/pump unit 3090 are implanted, information related to the charging of the battery 3220 may be fed back. To be more precise, when charging a battery or accumulator with energy feedback information related to said charging process is sent and the energy supply is changed accordingly.

Figure 247:
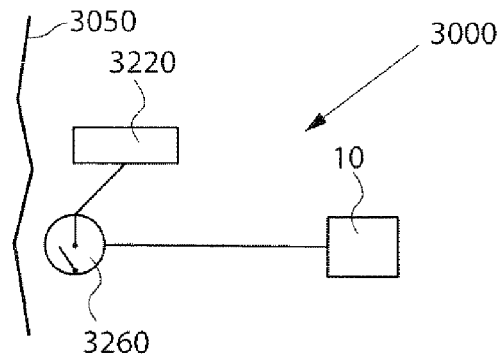

FIG. 247 shows an alternative embodiment wherein the device 10 is regulated from outside the patient's body. The system 3000 comprises a battery 3220 connected to the device 10 via a subcutaneous electric switch 3260. Thus, the regulation of the device 10 is performed non-invasively by manually pressing the subcutaneous switch, whereby the operation of the device 10 is switched on and off. It will be appreciated that the shown embodiment is a simplification and that additional components, such as an internal control unit or any other part disclosed in the present application can be added to the system. Two subcutaneous switches may also be used. In the preferred embodiment one implanted switch sends information to the internal control unit to perform a certain predetermined performance and when the patient press the switch again the performance is reversed.

Figure 248:
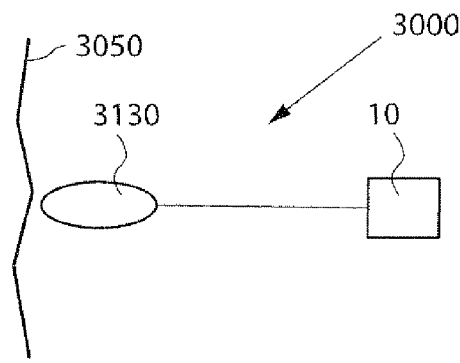

FIG. 248 shows an alternative embodiment, wherein the system 3000 comprises a hydraulic fluid reservoir 3130 hydraulically connected to the device. Non-invasive regulation is performed by manually pressing the hydraulic reservoir connected to the device.

The system may include an external data communicator and an implantable internal data communicator communicating with the external data communicator. The internal communicator feeds data related to the device or the patient to the external data communicator and/or the external data communicator feeds data to the internal data communicator.

FIG. 249 schematically illustrates an arrangement of the system that is capable of sending information from inside the patient's body to the outside thereof to give feedback information related to at least one functional parameter of the device or system, or related to a physical parameter of the patient, in order to supply an accurate amount of energy to an implanted internal energy receiver 3020 connected to implanted energy consuming components of the device 10. Such an energy receiver 3020 may include an energy source and/or an energy-transforming device. Briefly described, wireless energy is transmitted from an external energy source 3040*a* located outside the patient and is received by the internal energy receiver 3020 located inside the patient. The internal energy receiver is adapted to directly or indirectly supply received energy to the energy consuming components of the device 10 via a switch 3260. An energy balance is determined between the energy received by the internal energy receiver 3020 and the energy used for the device 10, and the transmission of wireless energy is then controlled based on the determined energy balance. The energy balance thus provides an accurate indication of the correct amount of energy needed, which is sufficient to operate the device 10 properly, but without causing undue temperature rise.

In FIG. 249 the patient's skin is indicated by a vertical line 3050. Here, the energy receiver comprises an energy-transforming device 1002 located inside the patient, preferably just beneath the patient's skin 3050. Generally speaking, the implanted energy-transforming device 1002 may be placed in the abdomen, thorax, muscle fascia (e.g. in the abdominal wall), subcutaneously, or at any other suitable location. The implanted energy-transforming device 3020 is adapted to receive wireless energy E transmitted from the external energy-source 3040*a* provided in an external energy-transmission device 3040 located outside the patient's skin 3050 in the vicinity of the implanted energy-transforming device 3020.

As is well known in the art, the wireless energy E may generally be transferred by means of any suitable Transcutaneous Energy Transfer (TET) device, such as a device including a primary coil arranged in the external energy source 1004*a* and an adjacent secondary coil arranged in the implanted energy-transforming device 3020. When an electric current is fed through the primary coil, energy in the form of a voltage is induced in the secondary coil which can be used to power the implanted energy consuming components of the device, e.g. after storing the incoming energy in an implanted energy source, such as a rechargeable battery or a capacitor. However, the present invention is generally not limited to any particular energy transfer technique, TET devices or energy sources, and any kind of wireless energy may be used.

The amount of energy received by the implanted energy receiver may be compared with the energy used by the implanted components of the device. The term "energy used" is then understood to include also energy stored by implanted components of the device. A control device includes an external control unit 3040*b* that controls the external energy source 3040*a* based on the determined energy balance to regulate the amount of transferred energy. In order to transfer the correct amount of energy, the energy balance and the required amount of energy is determined by means of a determination device including an implanted internal control unit 3150 connected between the switch 3260 and the device 10. The internal control unit 3150 may thus be arranged to receive various measurements obtained by suitable sensors or the like, not shown, measuring certain characteristics of the device 10, somehow reflecting the required amount of energy needed for proper operation of the device 10. Moreover, the current condition of the patient may also be detected by means of suitable measuring devices or sensors, in order to provide parameters reflecting the patient's condition. Hence, such characteristics and/or parameters may be related to the current state of the device 10, such as power consumption, operational mode and temperature, as well as the patient's condition reflected by parameters such as; body temperature, blood pressure, heartbeats and breathing. Other kinds of physical parameters of the patient and functional parameters of the device are described elsewhere.

Furthermore, an energy source in the form of an accumulator 3160 may optionally be connected to the implanted energy-transforming device 3020 via the control unit 3150 for accumulating received energy for later use by the device 10. Alternatively or additionally, characteristics of such an accumulator, also reflecting the required amount of energy, may be measured as well. The accumulator may be replaced by a rechargeable battery, and the measured characteristics may be related to the current state of the battery, any electrical parameter such as energy consumption voltage, temperature, etc. In order to provide sufficient voltage and current to the device 10, and also to avoid excessive heating, it is clearly understood that the battery should be charged optimally by receiving a correct amount of energy from the implanted energy-transforming device 3020, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit 3150. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 3150 of the determination device is adapted to determine the energy balance and/or the currently required amount of energy, (either energy per time unit or accumulated energy) based on measurements made by the above-mentioned sensors or measuring devices of the device 10, or the patient, or an implanted energy source if used, or any combination thereof. The internal control unit 3150 is further connected to an internal signal transmitter 3270, arranged to transmit a control signal reflecting the determined required amount of energy, to an external signal receiver 3040c connected to the external control unit 3040b. The amount of energy transmitted from the external energy source 3040a may then be regulated in response to the received control signal.

Alternatively, the determination device may include the external control unit 3040b. In this alternative, sensor measurements can be transmitted directly to the external control unit 3040b wherein the energy balance and/or the currently required amount of energy can be determined by the external control unit 3040b, thus integrating the above-described function of the internal control unit 3150 in the external control unit 3040b. In that case, the internal control unit 3150 can be omitted and the sensor measurements are supplied directly to the internal signal transmitter 3270 which sends the measurements over to the external signal receiver 3040c and the external control unit 3040b. The energy balance and the currently required amount of energy can then be determined by the external control unit 3040b based on those sensor measurements.

Hence, the present solution according to the arrangement of FIG. 249 employs the feedback of information indicating the required energy, which is more efficient than previous solutions because it is based on the actual use of energy that is compared to the received energy, e.g. with respect to the amount of energy, the energy difference, or the energy receiving rate as compared to the energy rate used by implanted energy consuming components of the device. The device may use the received energy either for consuming or for storing the energy in an implanted energy source or the like. The different parameters discussed above would thus be used if relevant and needed and then as a tool for determining the actual energy balance. However, such parameters may also be needed per se for any actions taken internally to specifically operate the device.

The internal signal transmitter 3270 and the external signal receiver 3040c may be implemented as separate units using suitable signal transfer means, such as radio, IR (Infrared) or ultrasonic signals. Alternatively, the internal signal transmitter 3270 and the external signal receiver 3040c may be integrated in the implanted energy-transforming device 3020 and the external energy source 3040a, respectively, so as to convey control signals in a reverse direction relative to the energy transfer, basically using the same transmission technique. The control signals may be modulated with respect to frequency, phase or amplitude.

Thus, the feedback information may be transferred either by a separate communication system including receivers and transmitters or may be integrated in the energy system. In accordance with the present invention, such an integrated information feedback and energy system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off. In implementing this system in the arrangement of FIG. 249, the switch 3260 is either separate and controlled by the internal control unit 3150, or integrated in the internal control unit 3150. It should be understood that the switch 3260 should be interpreted in its broadest embodiment. This means a transistor, MCU, MCPU, ASIC FPGA or a DA converter or any other electronic component or circuit that may switch the power on and off.

To conclude, the energy supply arrangement illustrated in FIG. 249 may operate basically in the following manner. The energy balance is first determined by the internal control unit 3150 of the determination device. A control signal reflecting the required amount of energy is also created by the internal control unit 3150, and the control signal is transmitted from the internal signal transmitter 3270 to the external signal receiver 3040c. Alternatively, the energy balance can be determined by the external control unit 3040b instead depending on the implementation, as mentioned above. In that case, the control signal may carry measurement results from various sensors. The amount of energy emitted from the external energy source 1004a can then be regulated by the external control unit 3040b, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 3040a, such as voltage, current, amplitude, wave frequency and pulse characteristics.

This system may also be used to obtain information about the coupling factors between the coils in a TET system even to calibrate the system both to find an optimal place for the external coil in relation to the internal coil and to optimize energy transfer. Simply comparing in this case the amount of energy transferred with the amount of energy received. For example if the external coil is moved the coupling factor may vary and correctly displayed movements could cause the external coil to find the optimal place for energy transfer. Preferably, the external coil is adapted to calibrate the amount of transferred energy to achieve the feedback information in the determination device, before the coupling factor is maximized.

This coupling factor information may also be used as a feedback during energy transfer. In such a case, the energy system of the present invention comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factor between the first and second coils. The energy transmitter may regulate the transmitted energy in response to the obtained coupling factor.

With reference to FIG. 250, although wireless transfer of energy for operating the device has been described above to enable non-invasive operation, it will be appreciated that the device can be operated with wire bound energy as well. Such an example is shown in FIG. 250, wherein an external switch 3260 is interconnected between the external energy source 3040a and an operation device, such as an electric motor 3070 operating the device 10. An external control unit 3040b controls the operation of the external switch 3260 to effect proper operation of the device 10.

FIG. 251 illustrates different embodiments for how received energy can be supplied to and used by the device 10. Similar to the example of FIG. 249, an internal energy receiver 3020 receives wireless energy E from an external energy source 3040a which is controlled by a transmission control unit 3040b. The internal energy receiver 3020 may comprise a constant voltage circuit, indicated as a dashed box "constant V" in the figure, for supplying energy at constant voltage to the device 10. The internal energy receiver 3020 may further comprise a constant current circuit, indicated as a dashed box "constant C" in the figure, for supplying energy at constant current to the device 10.

The device 10 comprises an energy consuming part 10a, which may be a motor, pump, restriction device, or any other medical appliance that requires energy for its electrical operation. The device 10 may further comprise an energy storage device 10b for storing energy supplied from the internal energy receiver 3020. Thus, the supplied energy may be directly consumed by the energy consuming part 10a, or stored by the energy storage device 10b, or the supplied energy may be partly consumed and partly stored. The device 10 may further comprise an energy stabilizing unit 10c for stabilizing the energy supplied from the internal energy receiver 3020. Thus, the energy may be supplied in a fluctuating manner such that it may be necessary to stabilize the energy before consumed or stored.

The energy supplied from the internal energy receiver 3020 may further be accumulated and/or stabilized by a separate energy stabilizing unit 3280 located outside the device 10, before being consumed and/or stored by the device 10. Alternatively, the energy stabilizing unit 3280 may be integrated in the internal energy receiver 3020. In either case, the energy stabilizing unit 3280 may comprise a constant voltage circuit and/or a constant current circuit.

It should be noted that FIG. 249 and FIG. 251 illustrate some possible but non-limiting implementation options regarding how the various shown functional components and elements can be arranged and connected to each other. However, the skilled person will readily appreciate that many variations and modifications can be made within the scope of the present invention.

FIG. 252 schematically shows an energy balance measuring circuit of one of the proposed designs of the system for controlling transmission of wireless energy, or energy balance control system. The circuit has an output signal centered on 2.5V and proportionally related to the energy imbalance. The derivative of this signal shows if the value goes up and down and how fast such a change takes place. If the amount of received energy is lower than the energy used by implanted components of the device, more energy is transferred and thus charged into the energy source. The output signal from the circuit is typically feed to an A/D converter and converted into a digital format. The digital information can then be sent to the external energy-transmission device allowing it to adjust the level of the transmitted energy. Another possibility is to have a completely analog system that uses comparators comparing the energy balance level with certain maximum and minimum thresholds sending information to external energy-transmission device if the balance drifts out of the max/min window.

The schematic FIG. 252 shows a circuit implementation for a system that transfers energy to the implanted energy components of the device of the present invention from outside of the patient's body using inductive energy transfer. An inductive energy transfer system typically uses an external transmitting coil and an internal receiving coil. The receiving coil, L1, is included in the schematic FIG. 235; the transmitting parts of the system are excluded.

The implementation of the general concept of energy balance and the way the information is transmitted to the external energy transmitter can of course be implemented in numerous different ways. The schematic FIG. 252 and the above described method of evaluating and transmitting the information should only be regarded as examples of how to implement the control system.

Circuit Details

In FIG. 252 the symbols Y1, Y2, Y3 and so on symbolize test points within the circuit. The components in the diagram and their respective values are values that work in this particular implementation which of course is only one of an infinite number of possible design solutions.

Energy to power the circuit is received by the energy receiving coil L1. Energy to implanted components is transmitted in this particular case at a frequency of 25 kHz. The energy balance output signal is present at test point Y1.

Those skilled in the art will realize that the above various embodiments of the system could be combined in many different ways. For example, the electric switch 3060 of FIG. 235 could be incorporated in any of the embodiments of FIGS. 238-244, the hydraulic valve shifting device 3140 of FIG. 238 could be incorporated in the embodiment of FIG. 237, and the gear box 3240 could be incorporated in the embodiment of FIG. 236. Please observe that the switch simply could mean any electronic circuit or component.

The embodiments described in connection with FIGS. 249, 251 and 252 identify a method and a system for controlling transmission of wireless energy to implanted energy consuming components of an electrically operable device. Such a method and system will be defined in general terms in the following.

A method is thus provided for controlling transmission of wireless energy supplied to implanted energy consuming components of a device as described above. The wireless energy E is transmitted from an external energy source located outside the patient and is received by an internal energy receiver located inside the patient, the internal energy receiver being connected to the implanted energy consuming components of the device for directly or indirectly supplying received energy thereto. An energy balance is determined between the energy received by the internal energy receiver and the energy used for the device. The transmission of wireless energy E from the external energy source is then controlled based on the determined energy balance.

The wireless energy may be transmitted inductively from a primary coil in the external energy source to a secondary coil in the internal energy receiver. A change in the energy balance may be detected to control the transmission of wireless energy based on the detected energy balance change. A difference may also be detected between energy received by the internal energy receiver and energy used for the medical device, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the medical device may be consumed to operate the medical device, and/or stored in at least one energy storage device of the medical device.

When electrical and/or physical parameters of the medical device and/or physical parameters of the patient are determined, the energy may be transmitted for consumption and storage according to a transmission rate per time unit which is determined based on said parameters. The total amount of transmitted energy may also be determined based on said parameters.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or current related to the energy balance.

The transmission of wireless energy from the external energy source may be controlled by applying to the external energy source electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

The circuit formed by the first electric circuit and the external energy source may have a first characteristic time period or first time constant, and when effectively varying the transmitted energy, such frequency time period may be in the range of the first characteristic time period or time constant or shorter.

A system comprising a device as described above is thus also provided for controlling transmission of wireless energy supplied to implanted energy consuming components of the device. In its broadest sense, the system comprises a control device for controlling the transmission of wireless energy from an energy-transmission device, and an implantable internal energy receiver for receiving the transmitted wireless energy, the internal energy receiver being connected to implantable energy consuming components of the device for directly or indirectly supplying received energy thereto. The system further comprises a determination device adapted to determine an energy balance between the energy received by the internal energy receiver and the energy used for the implantable energy consuming components of the device, wherein the control device controls the transmission of wireless energy from the external energy-transmission device, based on the energy balance determined by the determination device.

Further, the system may comprise any of the following:
A primary coil in the external energy source adapted to transmit the wireless energy inductively to a secondary coil in the internal energy receiver.
The determination device is adapted to detect a change in the energy balance, and the control device controls the transmission of wireless energy based on the detected energy balance change
The determination device is adapted to detect a difference between energy received by the internal energy receiver and energy used for the implantable energy consuming components of the device, and the control device controls the transmission of wireless energy based on the detected energy difference.
The control device controls the external energy-transmission device to decrease the amount of transmitted wireless energy if the detected energy balance change implies that the energy balance is increasing, or vice versa, wherein the decrease/increase of energy transmission corresponds to a detected change rate.
The control device controls the external energy-transmission device to decrease the amount of transmitted wireless energy if the detected energy difference implies that the received energy is greater than the used energy, or vice versa, wherein the decrease/increase of energy transmission corresponds to the magnitude of said detected energy difference.
The energy used for the device is consumed to operate the device, and/or stored in at least one energy storage device of the device.
Where electrical and/or physical parameters of the device and/or physical parameters of the patient are determined, the energy-transmission device transmits the energy for consumption and storage according to a transmission rate per time unit which is determined by the determination device based on said parameters. The determination device also determines the total amount of transmitted energy based on said parameters.
When a difference is detected between the total amount of energy received by the internal energy receiver and the total amount of consumed and/or stored energy, and the detected difference is related to the integral over time of at least one measured electrical parameter related to the energy balance, the determination device determines the integral for a monitored voltage and/or current related to the energy balance.
When the derivative is determined over time of a measured electrical parameter related to the amount of consumed and/or stored energy, the determination device determines the derivative for a monitored voltage and/or current related to the energy balance.
The energy-transmission device comprises a coil placed externally to the human body, and an electric circuit is provided to power the external coil with electrical pulses to transmit the wireless energy. The electrical pulses have leading and trailing edges, and the electric circuit is adapted to vary first time intervals between successive leading and trailing edges and/or second time intervals between successive trailing and leading edges of the electrical pulses to vary the power of the transmitted wireless energy. As a result, the energy receiver receiving the transmitted wireless energy has a varied power.
The electric circuit is adapted to deliver the electrical pulses to remain unchanged except varying the first and/or second time intervals.
The electric circuit has a time constant and is adapted to vary the first and second time intervals only in the range of the first time constant, so that when the lengths of the first and/or second time intervals are varied, the transmitted power over the coil is varied.
The electric circuit is adapted to deliver the electrical pulses to be varied by only varying the lengths of first time intervals between successive leading and trailing edges of the electrical pulses.
The electric circuit is adapted to supplying a train of two or more electrical pulses in a row, said train having a first electrical pulse at the start of the pulse train and having a second electrical pulse at the end of the pulse train, and the lengths of the second time intervals between successive trailing edge of the second electrical pulse in a first pulse train and leading edge of the first electrical pulse of a second pulse train are varied by the first electronic circuit.
The electric circuit is adapted to provide the electrical pulses as pulses having a substantially constant height and/or amplitude and/or intensity and/or voltage and/or current and/or frequency.
The electric circuit has a time constant, and is adapted to vary the first and second time intervals only in the range of the first time constant, so that when the lengths of the first and/or second time intervals are varied, the transmitted power over the first coil are varied.
The electric circuit is adapted to provide the electrical pulses varying the lengths of the first and/or the second time intervals only within a range that includes the first time constant or that is located relatively close to the first time constant, compared to the magnitude of the first time constant.

FIGS. 253-256 show in more detail block diagrams of four different ways of hydraulically or pneumatically powering an implanted device according to the invention.

Figure 253:
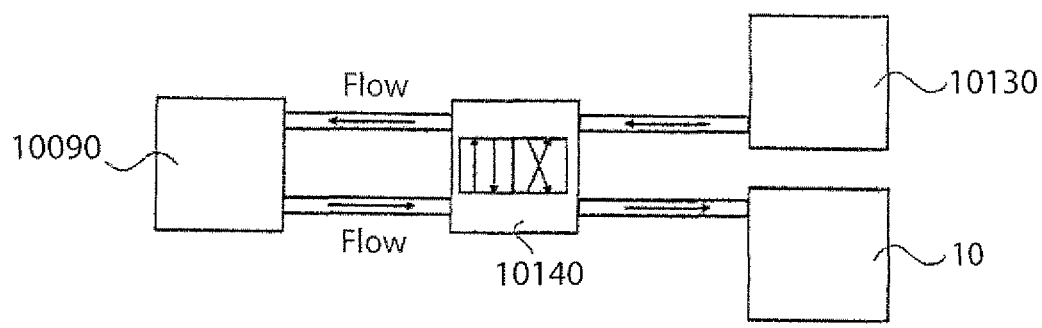

FIG. 253 shows a system as described above with. The system comprises an implanted device 10 and further a separate regulation reservoir 10130, a one way pump 10090 and an alternate valve 10140.

Figure 254:

FIG. 254 shows the device 10 and a fluid reservoir 10130. By moving the wall of the regulation reservoir or changing the size of the same in any other different way, the adjustment of the device may be performed without any valve, just free passage of fluid any time by moving the reservoir wall.

Figure 255:
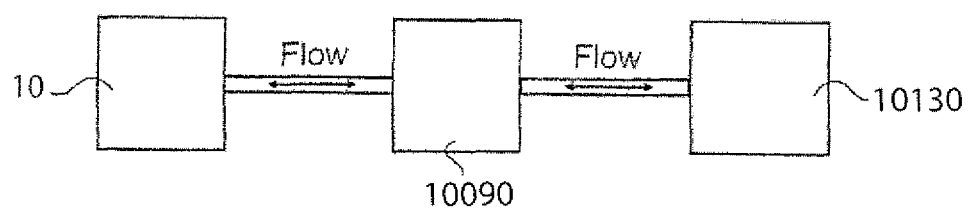

FIG. 255 shows the device 10, a two way pump 10090 and the regulation reservoir 10130.

Figure 256:
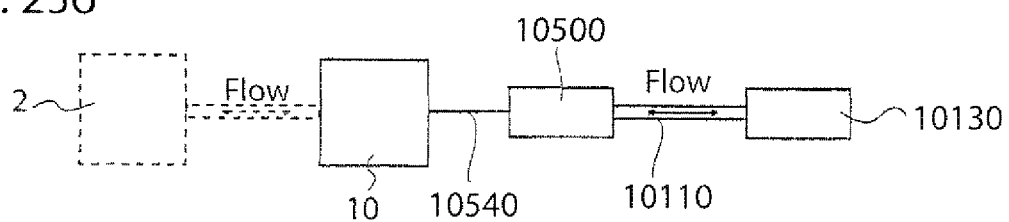

FIG. 256 shows a block diagram of a reversed servo system with a first closed system controlling a second closed system. The servo system comprises a regulation reservoir 10130 and a servo reservoir 10500. The servo reservoir 10500 mechanically controls an implanted device 10 via a mechanical interconnection 10540. The device has an expandable/contactable cavity. This cavity is preferably expanded or contracted by supplying hydraulic fluid from the larger adjustable reservoir 10520 in fluid connection with the device 10. Alternatively, the cavity contains compressible gas, which can be compressed and expanded under the control of the servo reservoir 10500.

The servo reservoir 10500 can also be part of the device itself.

Figure 257A:
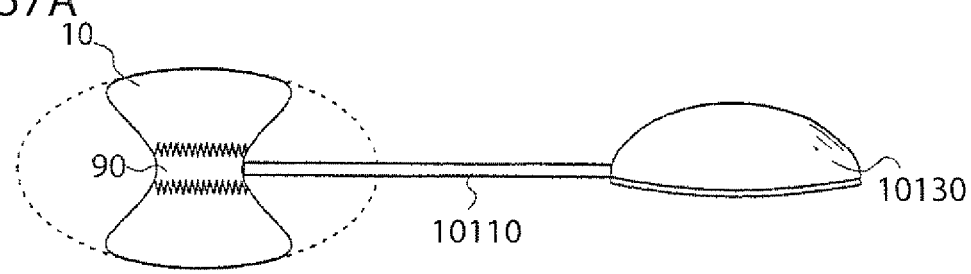
Figure 257B:
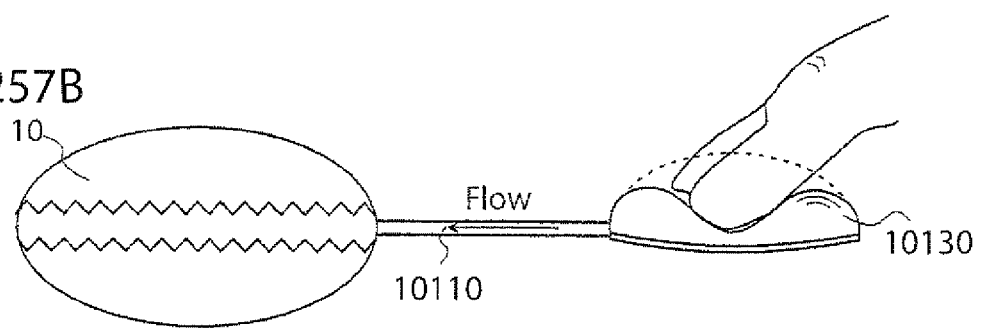
Figure 257C:
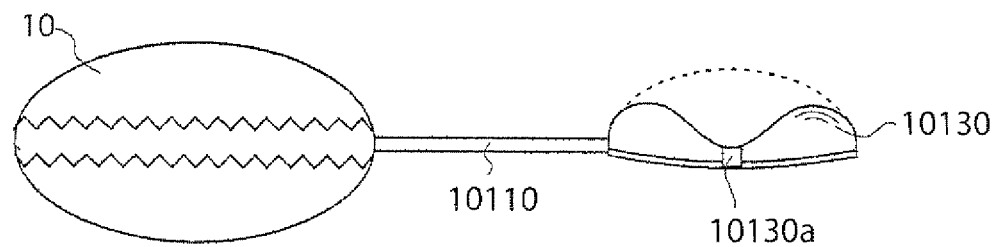
Figure 258:
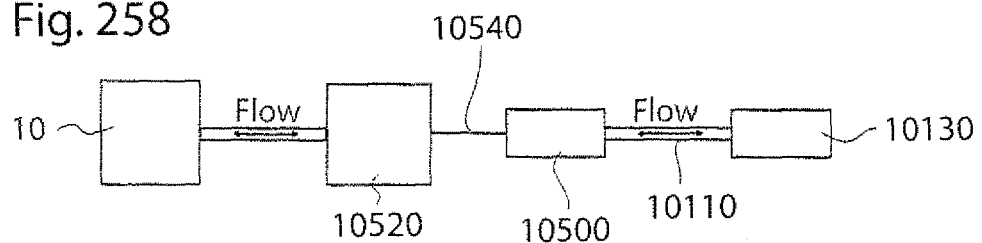

In one embodiment, the regulation reservoir is placed subcutaneous under the patient's skin and is operated by pushing the outer surface thereof by means of a finger. This system is illustrated in FIGS. 257*a-c*. In FIG. 257*a*, a flexible subcutaneous regulation reservoir 10130 is shown connected to a bulge shaped servo reservoir 10500 by means of a conduit 10110. This bellow shaped servo reservoir 10500 is comprised in a flexible device 10. In the state shown in FIG. 257*a*, the servo reservoir 10500 contains a minimum of fluid and most fluid is found in the regulation reservoir 10130. Due to the mechanical interconnection between the servo reservoir 10500 and the device 10, the outer shape of the device 10 is contracted, i.e., it occupies less than its maximum volume. This maximum volume is shown with dashed lines in the figure.

FIG. 257*b* shows a state wherein a user, such as the patient in with the device is implanted, presses the regulation reservoir 10130 so that fluid contained therein is brought to flow through the conduit 10110 and into the servo reservoir 10500, which, thanks to its bellow shape, expands longitudinally. This expansion in turn expands the device 10 so that it occupies its maximum volume, thereby stretching the stomach wall (not shown), which it contacts.

The regulation reservoir 10130 is preferably provided with means 10130*a* for keeping its shape after compression. This means, which is schematically shown in FIG. 257*c*, will thus keep the device 10 in a stretched position also when the user releases the regulation reservoir. In this way, the regulation reservoir essentially operates as an on/off switch for the system.

An alternative embodiment of hydraulic or pneumatic operation will now be described with reference to FIGS. 258 and 259*a-c*. The block diagram shown in FIG. 258 comprises with a first closed system controlling a second closed system. The first system comprises a regulation reservoir 10130 and a servo reservoir 10500. The servo reservoir 10500 mechanically controls a larger adjustable reservoir 10520 via a mechanical interconnection 10540. An implanted device 10 having an expandable/contactable cavity is in turn controlled by the larger adjustable reservoir 10520 by supply of hydraulic fluid from the larger adjustable reservoir 10520 in fluid connection with the device 10.

Figure 259A:
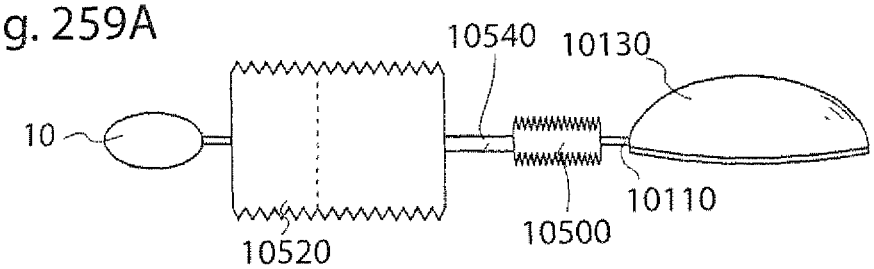
Figure 259B:
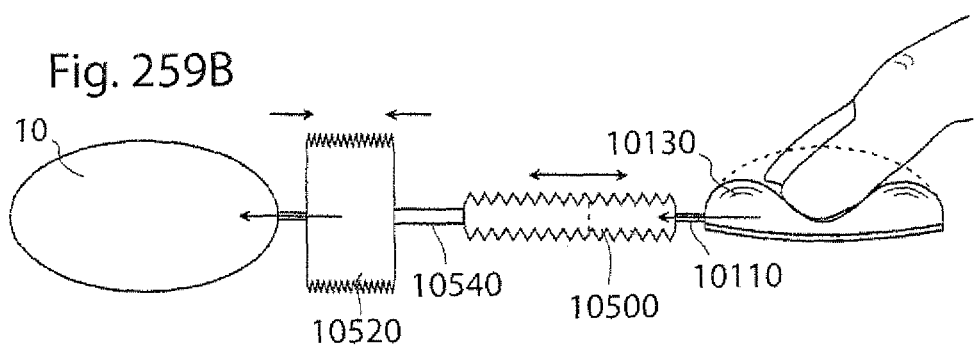
Figure 259C:
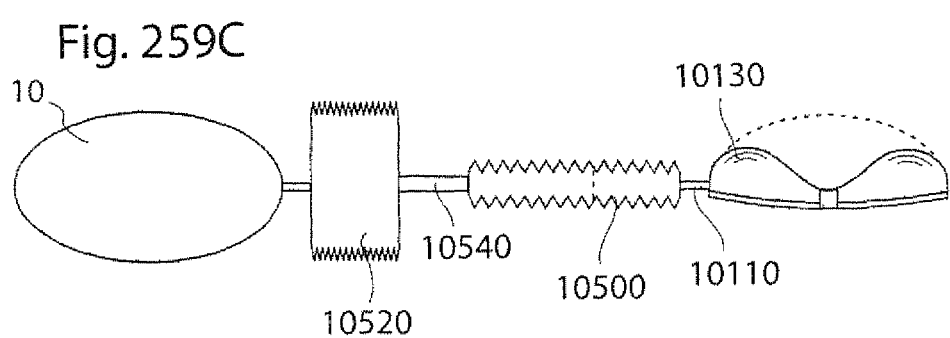

An example of this embodiment will now be described with reference to FIG. 259*a-c*. Like in the previous embodiment, the regulation reservoir is placed subcutaneous under the patient's skin and is operated by pushing the outer surface thereof by means of a finger. The regulation reservoir 10130 is in fluid connection with a bellow shaped servo reservoir 10500 by means of a conduit 10110. In the first closed system 10130, 10110, 10500 shown in FIG. 259*a*, the servo reservoir 10500 contains a minimum of fluid and most fluid is found in the regulation reservoir 10130.

The servo reservoir 10500 is mechanically connected to a larger adjustable reservoir 10520, in this example also having a bellow shape but with a larger diameter than the servo reservoir 10500. The larger adjustable reservoir 1052 is in fluid connection with the device 10. This means that when a user pushes the regulation reservoir 10130, thereby displacing fluid from the regulation reservoir 10130 to the servo reservoir 10500, the expansion of the servo reservoir 10500 will displace a larger volume of fluid from the larger adjustable reservoir 10520 to the device 10. In other words, in this reversed servo, a small volume in the regulation reservoir is compressed with a higher force and this creates a movement of a larger total area with less force per area unit.

Like in the previous embodiment described above with reference to FIGS. 257*a-c*, the regulation reservoir 10130 is preferably provided with means 10130*a* for keeping its shape after compression. This means, which is schematically shown in the figure, will thus keep the device 10 in a stretched position also when the user releases the regulation reservoir. In this way, the regulation reservoir essentially operates as an on/off switch for the system.

Please note that any embodiment, of a device or system, or part of embodiment as well as any method or part of method could be combined in any way. All examples herein should be seen as part of the general description and therefore possible to combine in any way in general terms.

What is claimed is:

1. A method for controlling a flow of fluid and/or other bodily matter in a lumen formed by a tissue wall of a patient's organ, the method comprising the steps of:
   inserting a needle like tube into a cavity of the patient's body,
   using the needle like tube to fill the cavity with gas thereby expanding the cavity,
   placing at least two trocars in the patient's body,
   inserting a camera through one of the trocars into the cavity,
   inserting a dissecting tool through any of the trocars and dissecting an area of at least one portion of the tissue wall of the patient's organ,
   placing a constriction device and a stimulation device in the dissected area in operative engagement with the patient's organ,
   using the constriction device to gently constrict the at least one portion of the tissue wall portion of the patient's organ to influence the flow in the lumen, and
   using the stimulation device to stimulate the constricted at least one portion of the tissue wall portion of the patient's organ to cause contraction of the wall portion to further influence the flow in the lumen.

2. The method according to claim 1, wherein the constriction is performed by constricting the at least one portion of the tissue wall portion of the patient's organ, so that the flow in the lumen is restricted but not stopped, and the stimulation is performed by stimulating the constricted at least one portion of the tissue wall portion of the patient's organ to cause contraction thereof, so that the flow in the lumen is further restricted but not stopped.

3. The method according to claim 1, wherein the constriction is performed by constricting the at least one portion of the tissue wall portion of the patient's organ, so that the flow in the lumen is restricted but not stopped, and the stimulation is performed by stimulating the constricted wall portion to cause contraction thereof, so that the flow in the lumen is stopped.

4. The method according to claim 1, wherein the constriction is performed by constricting the at least one portion of the tissue wall portion of the patient's organ, so that the flow in the lumen is stopped, and the stimulation is performed by stimulating the constricted wall portion of the patient's organ to cause contraction thereof, so that the flow in the lumen remains stopped when a pressure increase occurs in the lumen.

5. The method according to claim 1, wherein the constriction and the stimulation are co-operated to move the fluid and/or other bodily matter in the lumen.

6. The method according to claim 5, wherein the constriction is performed by constricting the at least one portion of the tissue wall portion of the patient's organ to restrict the flow in the lumen, and the stimulation is performed by progressively stimulating the constricted at least one portion of the tissue wall portion of the patient's organ to cause progressive contraction of the wall portion to move the fluid and/or other bodily matter in the lumen.

7. A method for controlling a flow of fluid in a food passageway formed by a tissue wall of a patient's stomach, the method comprising the steps of:
   inserting a needle like tube into a cavity of the patient's body,
   using the needle like tube to fill the cavity with gas thereby expanding the cavity,
   placing at least two laparoscopical trocars in the patient's body,
   inserting a camera through one of the trocars into the cavity,
   inserting a dissecting tool through any of the trocars and dissecting an area of at least one portion of the tissue wall of the patient's stomach,
   placing a constriction device and a stimulation device in the dissected area in operative engagement with the patient's stomach,
   using the constriction device to gently constrict the at least one portion of the tissue wall portion of the patient's stomach to influence the flow in the food passageway, and
   using the stimulation device to stimulate the constricted at least one portion of the tissue wall portion of the patient's stomach to cause contraction of the wall portion to further influence the flow in the food passageway.

8. A method for controlling a flow of fluid in a food passageway formed by a tissue wall of the stomach of a patient treated with VBG, the method comprising the steps of:
   inserting a needle like tube into a cavity of the patient's body,
   using the needle like tube to fill the cavity with gas thereby expanding the cavity,
   placing at least two laparoscopical trocars in the patient's body,
   inserting a camera through one of the trocars into the cavity,
   inserting a dissecting tool through any of the trocars and dissecting an area of at least one portion of the tissue wall of the patient's stomach,
   placing a constriction device and a stimulation device in the dissected area in operative engagement with the patient's stomach,
   using the constriction device to gently constrict the at least one portion of the tissue wall portion of the patient's stomach to influence the flow in the food passageway, and
   using the stimulation device to stimulate the constricted at least one portion of the tissue wall portion of the patient's stomach to cause contraction of the wall portion to further influence the flow in the food passageway.

9. A method for treating a male impotent patient having a penile portion, the method comprising the steps of:
   inserting a needle like tube into a cavity of the patient's body,
   using the needle like tube to fill the cavity with gas thereby expanding the cavity,
   placing at least two laparoscopical trocars in the patient's body,
   inserting a camera through one of the trocars into the cavity,
   inserting a dissecting tool through any of the trocar and dissecting an area of at least one portion of a tissue wall of the male impotent patient's penile portion,
   placing a constriction device and a stimulation device in the dissected area in operative engagement with the male impotent patient's penile portion,
   using the constriction device to gently constrict the at least one portion of the tissue wall of the male impotent patient's penile portion of the male impotent patient's penile portion to restrict the venous blood flow in the penile portion, and
   using the stimulation device to stimulate the constricted at least one portion of the tissue wall of the male impotent patient's penile portion of the male impotent patient's penile portion to cause contraction of the male impotent patient's penile portion to further restrict the venous blood flow in the penile portion to achieve erection.

10. A method for treating sexual dysfunction of a female patient having an erectile portion, the method comprising the steps of:
    inserting a needle like tube into a cavity of the patient's body,
    using the needle like tube to fill the cavity with gas thereby expanding the cavity,
    placing at least two laparoscopical trocars in the patient's body,
    inserting a camera through one of the trocars into the cavity,
    inserting a dissecting tool through any of the trocars and dissecting an area of at least one portion of a tissue wall of the patient's erectile portion,
    placing a constriction device and a stimulation device in the dissected area in operative engagement with the patient's erectile portion,
    using the constriction device to gently constrict the at least one portion of the erectile portion of the patient's erectile portion to restrict the venous blood flow in the erectile portion, and
    using the stimulation device to stimulate the constricted at least one portion of the patient's erectile portion to cause contraction of the patient's erectile portion to further restrict the venous blood flow in the erectile portion to obtain engorgement with blood of the female erectile tissue.

11. A method for controlling a flow of eggs in a uterine tube formed by a uterine tube wall of a patient's uterine tube, the method comprising the steps of:
    inserting a needle like tube into a cavity of the patient's body,
    using the needle like tube to fill the cavity with gas thereby expanding the cavity,
    placing at least two laparoscopical trocars in the patient's body,
    inserting a camera through one of the trocars into the cavity,
    inserting a dissecting tool through any of the trocars and dissecting an area of at least one portion of the uterine tube wall of the patient's uterine tube,
    placing a constriction device and a stimulation device in the dissected area in operative engagement with the patient's uterine tube,
    using the constriction device to gently constrict the at least one portion of the uterine tube wall portion of the patient's uterine tube to influence the flow of eggs in the uterine tube, and
    using the stimulation device to stimulate the constricted at least one portion of the uterine tube wall portion of the patient's uterine tube to cause contraction of the uterine tube wall portion to further influence the flow of eggs in the uterine tube.

12. A method for controlling a flow of sperms in a uterine tube formed by a uterine tube wall of a patient's uterine tube, the method comprising the steps of:
- inserting a needle like tube into a cavity of the patient's body,
- using the needle like tube to fill the cavity with gas thereby expanding the cavity,
- placing at least two laparoscopic trocars in the patient's body,
- inserting a camera through one of the trocars into the cavity,
- inserting a dissecting tool through any of the trocar and dissecting an area of at least one portion of the uterine tube wall of the patient's the uterine tube,
- placing a constriction device and a stimulation device in the dissected area in operative engagement with the patient's uterine tube,
- using the constriction device to gently constrict the at least one portion of the uterine tube wall portion of the patient's uterine tube to influence the flow of sperms in the uterine tube, and
- using the stimulation device to stimulate the constricted at least one portion of the uterine tube wall portion of the patient's uterine tube to cause contraction of the uterine tube wall portion to further influence the flow of sperms in the uterine tube.

13. A method for controlling a flow of blood and/or other bodily matter in a patient's blood vessel, the method comprising the steps of:
- inserting a needle like tube into a cavity of the patient's body,
- using the needle like tube to fill the cavity with gas thereby expanding the cavity,
- placing at least two laparoscopical trocars in the patient's body,
- inserting a camera through one of the trocars into the cavity,
- inserting a dissecting tool through any of the trocars and dissecting an area of at least one portion of the wall of the patient's blood vessel,
- placing a constriction device and a stimulation device in the dissected area in operative engagement with the patient's blood vessel,
- using the constriction device to gently constrict the at least one portion of the wall of the patient's blood vessel to influence the flow in the blood vessel, and
- using the stimulation device to stimulate the constricted at least one wall portion of the patient's blood vessel to cause contraction of the at least one portion of the wall to further influence the flow in the blood vessel.

14. A method for treating a vascular aneurysm of a blood vessel in a human or mammal patient, the method comprising the steps of:
- inserting a needle like tube into a cavity of the patient's body,
- using the needle like tube to fill the cavity with gas thereby expanding the abdominal cavity,
- placing at least two laparoscopical trocars in the patient's body,
- inserting a camera through one of the trocars into the cavity,
- inserting a dissecting tool through any of the trocars and dissecting an area of at least one portion of the tissue wall of the patient's blood vessel,
- placing a constriction device and a stimulation device in the dissected area in operative engagement with the patient's blood vessel,
- using the constriction device to gently constrict the at least one portion of the tissue wall portion of the patient's blood vessel extending along the aneurysm to reduce the bulge of the blood vessel caused by the aneurysm, and
- using the stimulation device to stimulate the constricted at least one portion of the tissue wall portion of the patient's blood vessel to cause contraction of the wall portion to further reduce the bulge of the blood vessel and strengthen the blood vessel tissue wall.

15. A method for controlling a flow of fluid in the vas deferens of a male patient, the method comprising the steps of:
- inserting a needle like tube into a cavity of the patient's body,
- using the needle like tube to fill the cavity with gas thereby expanding the cavity,
- placing at least two laparoscopical trocars in the patient's body,
- inserting a camera through one of the trocars into the cavity,
- inserting a dissecting tool through any of the trocars and dissecting an area of at least one portion of the tissue wall of the patient's vas deferens,
- placing a constriction device and a stimulation device in the dissected area in operative engagement with the patient's vas deferens,
- using the constriction device to gently constrict the at least one portion of the tissue wall portion of the patient's vas deferens to influence the flow in the vas deferens, and
- using the stimulation device to stimulate the constricted at least one portion of the tissue wall portion of the patient's vas deferens to cause contraction of the wall portion to further influence the flow in the vas deferens.

16. A method for enhancing the movement of gallstones in the biliary duct of a patient suffering from gallstone trouble, the method comprising the steps of:
- inserting a needle like tube into the abdomen of the patient's body,
- using the needle like tube to fill the abdomen with gas thereby expanding the abdominal cavity,
- placing at least two laparoscopical trocars in the patient's body,
- inserting a camera through one of the trocars into the abdomen,
- a dissecting tool through any of the trocars and dissecting an area of at least one portion of the tissue wall of the patient's biliary duct,
- placing a constriction device and a stimulation device in the dissected area in operative engagement with the patient's biliary duct,
- using the constriction device to gently constrict the at least one portion of the tissue wall portion of the patient's biliary duct to influence the movement of bile and/or gallstones in the biliary duct, and
- using the stimulation device to stimulate the constricted at least one portion of the tissue wall portion of the patient's biliary duct to cause contraction of the wall portion to further influence the movement of bile and/or gallstones in the biliary duct.

17. A method for promoting pregnancy of a female patient, comprising the steps of:
- restricting a lumen of an oviduct of the patient to accumulate at least one egg released from an ovary in the oviduct for a predetermined period of time, and ceasing restricting the oviduct lumen to admit the at least one egg in the oviduct to be transported to the uterus, when convenient for the patient to increase the likelihood for getting pregnant, providing a constriction device configured to constrict a wall portion of the oviduct to at least partly temporarily restrict or vary the flow in the oviduct and a stimulation device configured to stimulate the constricted wall portion of the oviduct to further affect the temporary restriction or further vary the flow in the oviduct, and controlling the stimulation device to progressively stimulate the constricted wall portion, in the downstream or upstream direction of the oviduct, to cause progressive contraction of the wall portion to move the at least one egg downstream in the oviduct or to temporarily prevent further transportation of the at least one egg to the uterus, increasing the likelihood for sperm meeting the egg.

18. The method according to claim 17, further comprising only partly restricting the oviduct lumen so that a sperm is able to pass in the oviduct lumen, creating peristaltic wave like movements of a part of the oviduct wall to prevent the at least one egg released from the ovary from being transported in the oviduct lumen to the uterus, accumulating the at least one egg in the oviduct lumen for a predetermined period of time, whereby the sperm appearing in the oviduct lumen is able to reach the egg during the time the at least one egg is accumulated, and ceasing restricting the oviduct lumen to release the egg, so that the egg is allowed to be transported in the oviduct lumen to the uterus.

19. The method according to claim 17, wherein the restricting step is performed postoperatively, further comprising controlling the restricting and ceasing restricting steps from outside the patient's body.

20. A method for promoting pregnancy of a female patient, comprising the steps of:
performing an operation comprising the steps of:
inserting a needle like tube into the abdomen of the patient's body,
using the needle like tube to fill the abdomen with gas thereby expanding the abdominal cavity,
placing at least two laparoscopic trocars in the patient's body,
inserting a camera through one of the trocars into the abdomen,
inserting at least one dissecting tool through a trocar and dissecting an area of at least one portion of the two oviducts of the patient, and
placing two restriction devices on two oviduct lumens, respectively, and
placing a stimulation device to the oviducts,
the restriction devices being, after the operation at a time convenient to get pregnant, adjustable from outside the patient's body,
to restrict and release the two oviduct lumens to increase the likelihood of getting pregnant, and configured to
restrict temporarily each of the oviduct lumens at places in consecutive order starting at places on each oviduct closest to the ovary, then restricting each oviduct lumen at any new place on each oviduct closer to the uterus, and
the stimulation device being configured to stimulate the restricted places of the oviduct lumens to further affect the restriction or further vary the flow in the oviduct, and
being controllable to progressively stimulate the constricted wall portion, in the downstream or upstream direction of the oviduct, to cause progressive contraction of the wall portion to promote further transportation of n egg to the uterus or at least temporarily prevent the egg being transported to increase the likelihood for the egg to meet a sperm.

21. The method of claim 20, wherein the restricting step comprises
restricting the oviduct lumen at a first place of the oviduct to accumulate at least one egg released from the ovary in the oviduct lumen for a predetermined period of time,
restricting the oviduct lumen at a second place of the oviduct,
ceasing restricting the oviduct lumen at the first place of the oviduct, and
allowing the oviduct shorter restriction periods at each restriction place.

22. The method of claim 21, further comprising the step of:
ceasing restricting the oviduct lumen at the second place of the oviduct, allowing transport of the egg down to the uterus.

23. The method of claim 21, further comprising the steps of:
restricting the oviduct lumen at a third place of the oviduct,
ceasing restricting the oviduct lumen at the second place of the oviduct,
allowing the oviduct shorter restriction periods at each restriction place.

24. The method of claim 23, further comprising the step of:
ceasing restricting the oviduct lumen at the third place of the oviduct,
allowing transport of the egg down to the uterus.

25. The method of claim 23, further comprising the steps of:
restricting the oviduct lumen at a fourth place of the oviduct,
ceasing restricting the oviduct lumen at the third place of the oviduct,
allowing the oviduct shorter restriction periods at each restriction place.

26. The method of claim 25, further comprising the step of:
ceasing restricting the oviduct lumen at the fourth place of the oviduct,
allowing transport of the egg down to the uterus.

27. The method of claim 20, further comprising:
restricting each oviduct lumen at places on each oviduct in consecutive order starting at a place on each oviduct closest to the ovary,
then restricting the oviduct lumen at any new place on each oviduct closer to the uterus, and
overlapping in time the restriction of the oviduct lumen at more than one place on the oviduct to restrict the oviduct lumen without interfering with any egg accumulated in the oviduct lumen.

28. The method of claim 27, further comprising only postoperatively varying the restriction places on the oviduct independently of order, to allow the oviduct to recover or to avoid any damage from the restriction of the oviduct while the oviduct lumen is kept restricted.

29. The method of claim 20, further comprising the following steps:
causing a peristaltic like restriction wave movement of a portion of the oviduct wall to prevent at least one egg appearing in the oviduct lumen from being transported in the oviduct lumen to the uterus while only partly restricting the oviduct lumen,
accumulating the egg in the oviduct lumen for a predetermined period of time, allowing a sperm to reach the egg during the time the egg is accumulated, and post-operatively controlling from the outside the human body the oviduct wall wave movement to cease, whereby the egg is released and is transported to the uterus.

31. A method for promoting pregnancy of a female patient, comprising:

restricting a lumen of an oviduct of the patient at places on the oviduct in consecutive order, wherein the restricting starts at a place on an oviduct closest to the ovary, and then restricting the oviduct lumen at a new place on the oviduct closer to the uterus, wherein a restriction of the oviduct lumen at one place partially overlaps in time another restriction of the oviduct lumen at a second place on the oviduct lumen to restrict the oviduct lumen without interfering with any egg accumulated in the oviduct lumen.

30. A method for promoting pregnancy of a female patient, comprising the steps of:

performing an operation comprising the steps of:

inserting a tube like needle into the abdomen of the patient's body, using the tube like needle like to fill the abdomen with gas thereby expanding the abdominal cavity, placing at least two laparoscopic trocars in the patient's body, inserting a camera through one of the trocars into the abdomen, inserting at least one dissecting tool through one of the trocars and dissecting an area of at least one portion of two oviducts of the patient, placing two restriction devices on the two oviducts, respectively, finishing the operation and withdrawing the needle, trocars, camera, and dissecting tool after eventual suturing, and thereafter, the restriction devices being adapted to be post operatively controlled from outside the patient's body to restrict the oviduct lumens at a time relevant to achieve pregnancy, to cause peristaltic like wave movements of portions of the two oviduct walls towards at least one of the patient's two ovaries to prevent an egg appearing in one of the two oviduct lumens containing the egg from being transported to the uterus for a predetermined period of time without fully restricting the oviduct lumen, whereby any egg released from either of the two ovaries is accumulated in at least one of the oviduct lumens, and whereby any sperm appearing in the at least one oviduct lumen is allowed to reach the egg during the time the egg is accumulated in the at least one oviduct lumen, and to cease the peristaltic like wave movements to release the egg in the at least one oviduct lumen to thereby allow the egg to be transported to the patient's uterus.

32. A method for promoting pregnancy of a female patient, comprising the following steps:

causing a peristaltic like restriction wave movement of a portion of an oviduct lumen wall to prevent an egg appearing in the oviduct lumen from being transported in the oviduct lumen to the uterus while only partly restricting the oviduct lumen, accumulating an egg in the oviduct lumen for a predetermined period of time, allowing a sperm to reach the egg during the time the egg is accumulated, and post-operatively controlling from the outside the human body the oviduct wall wave movement to cease, whereby the egg is released and is transported to the uterus.

33. A method for promoting pregnancy of a female patient, comprising the following steps:

restricting a first part of an oviduct lumen of the patient to accumulate at least one an egg released from an ovary in the oviduct lumen for a predetermined period of time, moving the accumulated egg by an implanted movement device away in the oviduct lumen towards the ovary from a restriction area, allowing a second part of the oviduct lumen closer to the ovary to be restricted without interfering with any accumulated egg, ceasing restricting the first part of the oviduct lumen, repeating restricting the first part of the oviduct lumen, ceasing restricting the second part of the oviduct lumen, and allowing the oviduct to recover between restriction intervals.

* * * * *